US012698266B2

(12) United States Patent
Garcia Fortanet et al.

(10) Patent No.: US 12,698,266 B2
(45) Date of Patent: Aug. 4, 2026

(54) TRPML MODULATORS

(71) Applicant: Casma Therapeutics, Inc., Boston, MA (US)

(72) Inventors: Jorge Garcia Fortanet, Wilmington, MA (US); Jeffrey Owen Saunders, Lincoln, MA (US); Harit Umesh Vora, North Andover, MA (US); Jian Lin, Acton, MA (US); Andrew Thomas Maynard, Winchester, MA (US); Erik Lee Meredith, Hudson, MA (US)

(73) Assignee: Casma Therapeutics, Inc., Boston, MA (US)

( * ) Notice: Subject to any disclaimer, the term of this patent is extended or adjusted under 35 U.S.C. 154(b) by 743 days.

(21) Appl. No.: 17/786,607

(22) PCT Filed: Dec. 18, 2020

(86) PCT No.: PCT/US2020/065851

§ 371 (c)(1),
(2) Date: Jun. 17, 2022

(87) PCT Pub. No.: WO2021/127337

PCT Pub. Date: Jun. 24, 2021

(65) Prior Publication Data

US 2023/0104936 A1 Apr. 6, 2023

Related U.S. Application Data

(60) Provisional application No. 62/950,768, filed on Dec. 19, 2019, provisional application No. 62/950,818, filed on Dec. 19, 2019, provisional application No. 63/119,888, filed on Dec. 1, 2020.

(51) Int. Cl.
*C07D 401/04* (2006.01)
*C07D 211/14* (2006.01)
*C07D 213/83* (2006.01)

(52) U.S. Cl.
CPC .......... *C07D 401/04* (2013.01); *C07D 211/14* (2013.01); *C07D 213/83* (2013.01)

(58) Field of Classification Search
CPC ... C07D 401/04; C07D 211/14; C07D 213/83
See application file for complete search history.

(56) References Cited

U.S. PATENT DOCUMENTS

| | | | |
|---|---|---|---|
| 6,403,607 | B1 | 6/2002 | Hidaka et al. |
| 2004/0259857 | A1 | 12/2004 | Deng et al. |
| 2005/0124613 | A1 | 6/2005 | Berger et al. |
| 2008/0119518 | A1 | 5/2008 | Suzuki et al. |
| 2008/0306044 | A1 | 12/2008 | Costanzo et al. |
| 2013/0079369 | A1 | 3/2013 | Hagiwara et al. |
| 2018/0062213 | A1 | 3/2018 | Matsuoka et al. |
| 2019/0248764 | A1 | 8/2019 | Liang |
| 2023/0416262 | A1 | 12/2023 | Maynard et al. |

FOREIGN PATENT DOCUMENTS

| | | | |
|---|---|---|---|
| CN | 109568321 | A | 4/2019 |
| EP | 1072587 | A1 | 1/2001 |
| EP | 3821947 | A1 | 5/2021 |
| JP | 2018-039757 | A | 3/2018 |
| WO | WO-98/03494 | A1 | 1/1998 |
| WO | WO-99/01435 | A1 | 1/1999 |
| WO | WO-2002/006232 | A1 | 1/2002 |
| WO | WO-2002/047679 | A2 | 6/2002 |
| WO | WO-2003/045393 | A1 | 6/2003 |
| WO | WO-2004/005253 | A1 | 1/2004 |
| WO | WO-2004/089905 | A1 | 10/2004 |
| WO | WO-2005/063293 | A1 | 7/2005 |
| WO | WO-2005/063745 | A2 | 7/2005 |
| WO | WO-2005/066126 | A1 | 7/2005 |
| WO | WO-2005/115146 | A1 | 12/2005 |
| WO | WO-2006/117075 | A1 | 11/2006 |
| WO | WO-2007/002114 | A1 | 1/2007 |
| WO | WO-2007/057775 | A1 | 5/2007 |
| WO | WO-2007/076070 | A2 | 7/2007 |
| WO | WO-2007/123516 | A1 | 11/2007 |
| WO | WO-2008/036755 | A1 | 3/2008 |
| WO | WO-2008/036759 | A1 | 3/2008 |
| WO | WO-2009/067202 | A1 | 5/2009 |
| WO | WO-2012/082568 | A1 | 6/2012 |
| WO | WO-2015/091315 | A1 | 6/2015 |
| WO | WO-2016/067043 | A1 | 5/2016 |
| WO | WO-2016/088903 | A1 | 6/2016 |
| WO | WO-2016/107603 | A1 | 7/2016 |
| WO | WO-2017/173544 | A1 | 10/2017 |
| WO | WO-2017/205464 | A1 | 11/2017 |
| WO | WO-2018/005713 | A1 | 1/2018 |
| WO | WO-2018/089433 | A1 | 5/2018 |
| WO | WO-2018/208630 | A1 | 11/2018 |
| WO | WO-2019/063996 | A1 | 4/2019 |

(Continued)

OTHER PUBLICATIONS

STN Registry entry for CAS RN 1347101-09-0; Accessed Mar. 21, 2025; STNext; Published Dec. 1, 2011.*
STN Registry entry for CAS RN 391907-44-1; Accessed Mar. 22, 2025; STNext; Published Feb. 13, 2002.*
STN Registry Entry for CAS RN 2109334-64-5; Entered STN Mar. 29, 1991; Accessed Oct. 3, 2025.*
STN Registry Entry for CAS RN 1114642-05-5; Entered STN Mar. 3, 2009; Accessed Oct. 3, 2025.*
CAS RN 1111011-76-7; Accessed via STNext on Dec. 10, 2025; Entry Date Feb. 24, 2009.*
CAS RN 1111162-93-6; Accessed via STNext on Dec. 10, 2025; Entry Date Feb. 24, 2009.*
Cao, Q. et al., The lysosomal Ca2+ release channel TRPML1 regulates lysosome size by activating calmodulin, J. Biol. Chem., 292(20):8424-8435 (2017).
Di Paola, S. et al., TRPML1: The Ca(2+) retaker of the lysosome, Cell Calcium, 69:112-121 (2018).

(Continued)

*Primary Examiner* — Alicia L Otton
(74) *Attorney, Agent, or Firm* — Choate, Hall & Stewart LLP; Michael A. Shinall; Lauren E. Markham

(57) ABSTRACT

The present invention provides compounds, pharmaceutically acceptable compositions thereof, and methods of using the same.

16 Claims, No Drawings

(56) References Cited

FOREIGN PATENT DOCUMENTS

| | | | |
|---|---|---|---|
| WO | WO-2019/097282 | A1 | 5/2019 |
| WO | WO-2020/022084 | A1 | 1/2020 |
| WO | WO-2020/067398 | A1 | 4/2020 |
| WO | WO-2020/104822 | A1 | 5/2020 |
| WO | WO-2021/041866 | A1 | 3/2021 |
| WO | WO-2021/094974 | A1 | 5/2021 |
| WO | WO-2021/127328 | A1 | 6/2021 |
| WO | WO-2021/127333 | A1 | 6/2021 |
| WO | WO-2021/127337 | A1 | 6/2021 |
| WO | WO-2022/032073 | A2 | 2/2022 |
| WO | WO-2022/032073 | A3 | 3/2022 |
| WO | WO-2022/076383 | A1 | 4/2022 |
| WO | WO-2023/055912 | A1 | 4/2023 |
| WO | WO-2023/055920 | A1 | 4/2023 |
| WO | WO-2024/092235 | A2 | 5/2024 |

OTHER PUBLICATIONS

Eskelinen, E. and Saftig, P., Authopagy: A lysosomal degradation pathway with a central role in health and disease, Biochimica et Biophysica Acta, 1793:664-673 (2009).
International Search Report for PCT/US20/65839 (TRPML Modulators, filed Dec. 18, 2020), received by ISA/US, 4 pages (Apr. 29, 2021).
International Search Report for PCT/US20/65845 (TRPML Modulators, filed Dec. 18, 2020), received by ISA/US, 4 pages (Apr. 23, 2021).
International Search Report for PCT/US20/65851 (TRPML Modulators, filed Dec. 18, 2020), received by ISA/US, 4 pages (Apr. 27, 2021).
Maiuri, M. and Kroemer, G., Therapeutic modulation of autophagy: which disease comes first?, Cell Death & Differentiation, 26:680-689 (2019).
Medina, D. et al., Lysosomal calcium signaling regulates autophacy via calcineurin and TFEB, Nat. Cell Biol., 17(3):288-299 (2015).
Nelson, M. and Shacka, J., Autophagy Modulation in Disease Therapy: Where To We Stand?, Curr. Pathobiol. Rep., 1:239-245 (2013).
Pastore, N. et al., Gene transfer of master autophagy regulator TFEB results in clearance of toxic protein and correction of hepatic disease in alpha-1-anti-trypsin deficiency, EMBO Mol Med., 5:397-412 (2013).
Pierzynowska, K. et al., Autophagy stimulation as a promising approach in treatment of neurodegenerative diseases, Metabolic Brain Disease, 33:989-1008 (2018).
Pubchem-SID: 150131526, AKOS013992171, 7 pages, deposit date: Jun. 2, 2019.
Pubchem-SID: 239336999, Curation Efforts Research and Development, 8 pages, deposit date: Feb. 13, 2013.
Pubchem-SID: 313559586, 1H-Pyrrole, 1-methyl-2-(1-methylethenyl)-, 6 pages, deposit date: Jun. 11, 2016.
Sciarretta, S. et al., The Role of Autophagy in the Heart, Annu. Rev. Physiol., 80:1-26 (2018).
Singer, M. et al., Inhibition of carbonic anhydrase isozymes with benzene sulfonamides incorporating thio, sulfinyl and sulfonyl glycoside moieties, Bioorg Med Chem Lett., 19(8):2273-2276 (2009).
Wang, W. et al., Up-regulation of lysosomal TRPML1 channels is essential for lysosomal adaptation to nutrient starvation, PNAS, E1373-E1381 (2015).
Written Opinion for PCT/US20/65839 (TRPML Modulators, filed Dec. 18, 2020), received by ISA/US, 7 pages (Apr. 29, 2021).
Written Opinion for PCT/US20/65845 (TRPML Modulators, filed Dec. 18, 2020), received by ISA/US, 5 pages (Apr. 23, 2021).
Written Opinion for PCT/US20/65851 (TRPML Modulators, filed Dec. 18, 2020), received by ISA/US, 6 pages (Apr. 27, 2021).
Yu, L. et al., Small-molecule activation of lysosomal TRP channels ameliorates Duchenne muscular dystrophy in mouse models, Sci. Adv., 6(6):1-13 (2020).
Baxter, I. and Cameron, D. W., Unusual Shielding Effects in Some 2-Phenylsulfonamido-N, N-dialkyl-anilinium Ions, Journal of the Chemical Society B, pp. 696-698, (1971).
Grimm, C. et al., Small Molecule Activators of TRPML3, Chemistry and Biology, 17(2):135-148 (2010).
International Search Report for PCT/US21/44911, 4 pages (Feb. 28, 2022).
Maben, Z. et al., Discovery of Selective Inhibitors of Endoplasmic Reticulum Aminopeptidase I, Journal of Medicinal Chemistry, 63(1):101-121 (2019).
PubChem-SID-320109121, retrieved from https://pubchem.ncbi.nlm.nlh.gov/substance/320109121, 7 pages (Jun. 3, 2019).
Ryan, S. J., et al., N-Aryl Atropizomerism Induces Facial Selectivity in Benzonitrile Oxide Cycloadditions with Exocyclic Methylene Benzosultams, Australian Journal of Chemistry, 66:874-881 (2013).
Written Opinion for PCT/US21/44911, 7 pages (Feb. 28, 2022).
Ye, Z. et al., Pyrrole- and Dihydropyrrole-Fused Neonicotinoids: Design, Synthesis, and Insecticidal Evaluation, J. Agric. Food Chem., 61:312-319 (2013).
Costanzo, M. et al., Potent, nonpeptide inhibitors of human mast cell tryptase. Synthesis and biological evaluation of novel spirocyclic piperidine amide derivatives, Bioorganic & Medicinal Chemistry Letters, 18:2114-2121 (2008).
Reddy, B. et al., $InCl_3$-catalyzed Prins bicyclization for the synthesis of spirotetrahydropyran derivatives, RSC Adv., 4:16739-16742 (2014).
Wang, Y. et al., Discovery of a Novel HIV-1 Integrase/p75 Interacting Inhibitor by Docking Screening, Biochemical Assay, and in Vitro Studies, J Chem Inf Model, 57(9):2336-2343 (2017).
Database Registry [Online], CAS Registry No. 1011060-68-6, 1 page (Mar. 31, 2008).
Database Registry [Online], CAS Registry No. 1011197-35-5, 1 page (Apr. 1, 2008).
Database Registry [Online], CAS Registry No. 2361885-48-3, 1 page (Jul. 28, 2019).
Database Registry [Online], CAS Registry No. 849058-39-5, 1 page (Apr. 22, 2005).
Database Registry [Online], CAS Registry No. 878611-38-2, 1 page (Mar. 30, 2006).

* cited by examiner

TRPML MODULATORS

CROSS-REFERENCE TO RELATED APPLICATIONS

The present application is the 371 national phase entry of PCT App. No. PCT/US20/65851, filed Dec. 18, 2020, which claims priority to U.S. Provisional Application No. 63/119,888, filed Dec. 1, 2020; U.S. Provisional Application No. 62/950,818, filed Dec. 19, 2019; and U.S. Provisional Application No. 62/950,768, filed Dec. 19, 2019, each of which is incorporated herein by reference in its entirety.

BACKGROUND

Transient Receptor Potential Mucolipin-1 (also known as TRPML1 or ML1) is a $Ca^{2+}$ channel in the lysosome that regulates certain aspects of lysosome trafficking, including autophagy. See Wang, et al., PNAS, E1373-E1381 (Mar. 2, 2015). In particular, TRPML1 is an inwardly rectifying current channel that transports cations from the lumen of the lysosome to the cytosol. See Di Paolda, et al., Cell Calcium 69:112-121 (2018). Release of $Ca^{2+}$ from the lysosome via TRPML1 modulates transcription factor EB activity. See Medina, et al., Nat. Cell. Biol., 17(3):288-299 (2015).

SUMMARY

It has recently been discovered that upregulation of autophagy is beneficial to patients suffering from a number of diseases and disorders. For example, it has been reported that inducing autophagy promotes clearance of hepatotoxic alpha-1-anti-trypsin (ATZ) in the liver. See Pastore, et al., EMBO Mol. Med. 5(3): 397-412 (March 2013). Moreover, autophagy was recently found to be useful in the treatment of neurodegenerative disorders, cancer, and heart disease. See Pierzynowska, et al., Metab. Brain Dis., 33(4); 989-1008 (2018) (discussing neurodegenerative disorders); Nelson & Shacka, Curr. Pathobiol. Rep., 1(4): 239-245 (2013) (discussing cancer); Sciaretta, et al., Annual Review of Physiology, 80:1-26 (2018) (discussing heart disease); Maiuri & Kroemer, Cell Death & Differentiation, 26: 680-689 (2019) (discussing therapeutic applications of autophagy, generally).

The present disclosure provides, among other things, technologies for regulating (e.g., up-regulating) autophagy. For example, in some embodiments, the present disclosure demonstrates effectiveness of certain approaches to TRPML1 modulation (e.g., TRPML1 agonism) in enhancing autophagy. Thus, among other things, the present disclosure demonstrates that targeting TRPML1 as described herein can enhance autophagy.

The present disclosure also provides certain technologies for use in medicine, and in particular for treating certain diseases, disorders or conditions and/or for identifying, characterizing, and/or manufacturing certain agents and/or compositions or that comprise or deliver them that are useful in treating such diseases, disorders or conditions.

In some embodiments, the present disclosure demonstrates that modulating (e.g., agonizing) TRPLM1 and/or otherwise enhancing autophagy is useful in the treatment of certain diseases, disorders or conditions.

It is, therefore, desirable to identify methods and modes of promoting autophagy. Given TRPML1's role in autophagy, described herein are TRPML1 modulators useful for promoting autophagy and/or treating certain diseases, disorders, or conditions.

In particular, the present application provides technologies useful for modulating TRPML1.

In some embodiments, the present application provides compounds having a structure as set forth in Formula I.

$$Z\text{-}L^1\text{-}Cy\text{-}A\text{-}L^2\text{-}V \qquad I$$

or a pharmaceutically acceptable salt thereof, wherein

A is $C_{6-12}$ aryl, 5- to 6-membered heteroaryl comprising 1 to 4 heteroatoms selected from N, O, and S, wherein A is substituted with 0, 1, 2, 3 or 4 $R^a$;

Cy is absent or a bivalent moiety selected from 4- to 12-membered monocyclic or polycyclic heterocyclyl comprising 1 to 4 heteroatoms selected from N, O, P, and S, 5- to 12-membered monocyclic or bicyclic heteroaryl comprising 1 to 4 heteroatoms selected from N, O, P, and S, $C_{1-6}$ aliphatic, $C_{3-12}$ cycloalkyl, or —$C_{0-6}$ alkylenyl-C(O)—NH—, wherein Cy is optionally substituted with one or more of $R^1$;

$L^1$ is absent, —$NR^3$—, —O—, —S—, —C(O)—$NR^3$—, —$NR^3$—C(O)—, —C(O)—C(O)—, or an optionally substituted group selected from $C_{1-6}$ alkylenyl, $C_{2-6}$ alkynylenyl, —$NR^3$—$C_{1-6}$ alkylenyl, —O—$C_{1-6}$ alkylenyl, —C(O)—$C_{0-6}$ alkylenyl, —$C_{0-6}$ alkylenyl-C(O)— and —$C_{0-6}$ alkylenyl-OC(O)—;

$L^2$ is —$(NR^3)_s$—S(O)—$C_{0-6}$ alkylenyl-, —$(NR^3)_s$—$S(O)_2$—$C_{0-6}$ alkylenyl-, —$(NR^3)_s$—S(O)($NR^3$)—, —$S(O)_2$—$NR^3$—, —$NR^3$—$C_{1-6}$ alkylenyl, —$NR^3$—$C_{1-6}$ haloalkylenyl, —$(NR^3)_s$—P(O)($R^3$)—, —$C_{1-6}$ alkylenyl-S(O)—, —$C_{1-6}$ alkylenyl-$S(O)_2$—, —C(O)—$(NR^3)_s$—, —$(NR^3)_s$—C(O)—, or an optionally substituted 4- to 12-membered monocyclic or bicyclic heterocyclyl comprising 1 to 4 heteroatoms selected from N, O, and S;

V is selected from $C_{1-6}$ aliphatic, $C_{6-12}$ aryl, 4- to 12-membered monocyclic or polycyclic heterocyclyl comprising 1 to 4 heteroatoms selected from N, O, and S, 5- to 12-membered monocyclic or bicyclic heteroaryl comprising 1 to 4 heteroatoms selected from N, O, and S, 5- to 12-membered monocyclic of bicyclic aryl, and $C_{3-12}$ monocyclic or polycyclic cycloalkyl, wherein V is substituted with $(R^6)_m$;

Z is $C_{1-6}$ aliphatic, 2- to 10-membered heteroaliphatic, $P(O)(R^3)_2$, —$C(O)C_{1-6}$ aliphatic, $C(O)N(R^3)_2$, $C_{6-12}$ aryl, $C_{3-12}$ monocyclic or polycyclic cycloalkyl, 4- to 16-membered monocyclic or polycyclic heterocyclyl comprising 1 to 4 heteroatoms selected from N, O, and S, or 5- to 12-membered monocyclic or bicyclic heteroaryl comprising 1 to 4 heteroatoms selected from N, O, and S, wherein Z is substituted with $(R^2)_q$;

each $R^a$ is independently halo, oxo, CN, optionally substituted $C_{1-6}$ aliphatic or O—$C_{1-6}$ aliphatic;

each $R^1$ is independently selected from halo, $N(R^3)_2$, OH, CN, $C(O)NHR^3$, and an optionally substituted group selected from $C_{1-6}$ aliphatic and $N(R^3)$—C(O)—$C_{1-6}$ alkyl;

each $R^2$ is independently selected from halo, oxo, CN, OH, C(O)O—$R^{2a}$, $C_{6-12}$ aryl, and an optionally substituted group selected from $C_{1-6}$ aliphatic, $C(O)C_{1-6}$ aliphatic, and O—$C_{1-6}$ aliphatic, where $R^{2a}$ is hydrogen or an optionally substitute group selected from 4- to 12-membered monocyclic or bicyclic heterocyclyl comprising 1 to 4 heteroatoms selected from N, O, and S, $C_{1-6}$ aliphatic, $C_{3-12}$ cycloalkyl;

each $R^3$ is independently selected from H and optionally substituted $C_{1-6}$ aliphatic;

each $R^5$ is independently selected from $C_{1-6}$ alkyl, —$N(R^3)_2$, —O—$C_{1-6}$ alkyl, C(O)—$C_{1-6}$ alkyl, P(O)

($C_{1-6}$ alkyl)$_2$, $C_{3-12}$ cycloalkyl, and 5- to 12-membered heterocyclyl comprising 1 to 4 heteroatoms selected from N, O, and S, wherein $R^5$ is optionally substituted with one or more substituents selected from halo, OH, and 2- to 12-membered heteroaliphatic;

each $R^6$ is halo, oxo, $SF_5$, S(O)—$R^5$, $S(O)_2$—$R^5$, S(O)(NH)—$R^5$, $S(O)_2$(NH)—$R^5$, —CN, —C(O)—$R^5$, —$C_{0-6}$ alkylenyl-C(O)O—$R^5$, —C(O)—NH($R^5$), —C(O)—N($R^5$)$_2$, —P(O)($R^5$)$_2$, —O—$R^5$, or an optionally substituted group selected from O—$C_{1-6}$ alkyl, S—$C_{1-6}$ alkyl, $C_{1-6}$ alkyl, $C_{6-12}$ aryl, 2- to 12-membered heteroaliphatic, $C_{3-12}$ cycloalkyl, —O—$C_{0-6}$ alkylenyl-$C_{3-12}$ cycloalkyl, and 4- to 7-membered monocyclic heterocyclyl comprising 1 to 4 heteroatoms selected from N, O, and S;

m is 0, 1, 2, 3, or 4;

q is 0, 1, 2, 3, or 4; and s is 0 or 1.

In some embodiments, the present disclosure provides a compound of Formula I':

I'

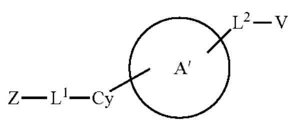

or a pharmaceutically acceptable salt thereof, wherein

A' is phenyl, 5- to 10-membered monocyclic or bicyclic heterocyclyl comprising 1 to 4 heteroatoms selected from N, O, P, and S, or 5- to 10-membered monocyclic or bicyclic heteroaryl comprising 1 to 4 heteroatoms selected from N, O, and S, optionally substituted with $R^a$;

Cy is absent, or a bivalent moiety selected from $C_{1-6}$ aliphatic, 4- to 14-membered monocyclic or polycyclic heterocyclyl comprising 1 to 4 heteroatoms selected from N, O, P, and S, 5- to 12-membered monocyclic or bicyclic heteroaryl comprising 1 to 4 heteroatoms selected from N, O, and S, $C_{6-12}$ aryl, or $C_{3-12}$ cycloalkyl, wherein Cy is optionally substituted with one or more of $R^1$;

$L^1$ is absent, —S—, —C(O)—$NR^3$—, —$NR^3$—C(O)—, or an optionally substituted bivalent moiety selected from $C_{1-6}$ alkylenyl, $C_{2-6}$ alkenylenyl, $C_{2-6}$ alkynylenyl, —$NR^3$—$C_{0-6}$ alkylenyl, —O—$C_{0-6}$ alkylenyl, —C(O)—$C_{0-6}$ alkylenyl, —$C_{1-6}$ alkylenyl-C(O)—, —C(O)O—$C_{0-6}$ alkylenyl, —$C_{1-6}$ alkylenyl-O—C(O)—, —$C_{3-6}$ cycloalkyl, and —$NR^3$—C(O)—$C_{0-6}$ alkylenyl-O—;

$L^2$ is —$(NR^3)_s$—S(O)—($NR^3$)—, —$(NR^3)_s$—$S(O)_2$—$NR^3$—, —$(NR^3)_s$—P(O)($R^3$)—, —C(O)—$(NR^3)_s$—, —$NR^3$—C(O)—, or an optionally substituted bivalent moiety selected from —$(NR^3)_s$—S(O)—$C_{0-6}$ alkylenyl-, —$(NR^3)_s$—$S(O)_2$—$C_{0-6}$ alkylenyl-, —$(NR^3)_s$—S(O)—$NR^3$—$C_{0-6}$ alkylenyl, —$(NR^3)_s$—$S(O)_2$—$NR^3$—$C_{0-6}$ alkylenyl, —$(NR^3)_s$—$S(O)_2$—$C_{3-6}$ cycloalkyl, —$NR^3$—$C_{0-6}$ alkylenyl, —$C_{1-6}$ alkylenyl-S(O)—$(NR^3)_s$—, —$C_{1-6}$ alkylenyl-$S(O)_2$—$(NR^3)_s$—, 2- to 6-membered heteroaliphatic, and 4- to 12-membered monocyclic or bicyclic heterocyclyl comprising 1 to 4 heteroatoms selected from N, O, and S;

V is selected from $C_{1-6}$ aliphatic, $C_{6-12}$ aryl, $C_{3-12}$ cycloaliphatic, 4- to 12-membered monocyclic or polycyclic heterocyclyl comprising 1 to 4 heteroatoms selected from N, O, and S, and 5- to 12-membered monocyclic or bicyclic heteroaryl comprising 1 to 4 heteroatoms selected from N, O, and S, wherein V is substituted with $(R^6)_m$;

Z is selected from P(O)($R^3$)$_2$, C(O)N($R^3$)$_2$, $C_{1-6}$ aliphatic, $C_{6-12}$ aryl, $C_{3-12}$ cycloaliphatic, 2- to 10-atom heteroaliphatic, 4- to 16-membered monocyclic or polycyclic heterocyclyl comprising 1 to 4 heteroatoms selected from N, O, and S, and 5- to 12-membered monocyclic or bicyclic heteroaryl comprising 1 to 4 heteroatoms selected from N, O, and S, wherein Z is substituted with $(R^2)_q$;

each $R^a$ is independently H, halo, —CN, oxo, or an optionally substituted group selected from $C_{1-6}$ aliphatic, $C_{3-6}$ cycloaliphatic, and O—$C_{1-6}$ aliphatic;

each $R^1$ is independently selected from halo, oxo, —N($R^3$)$_2$, —OH, —CN, —C(O)N($R^3$)$_2$, and an optionally substituted group selected from $C_{1-6}$ aliphatic and N($R^3$)—C(O)—$C_{1-6}$ aliphatic;

each $R^2$ is independently selected from halo, oxo, —CN, —OH, O—$R^{2a}$, —C(O)—$R^{2a}$, —C(O)O—$R^{2a}$, and an optionally group selected from $C_{1-6}$ aliphatic, $C_{6-12}$ aryl, and 5- to 12-membered monocyclic or bicyclic heteroaryl comprising 1 to 4 heteroatoms selected from N, O, and S;

each $R^{2a}$ is independently H or an optionally substituted group selected from $C_{1-6}$ aliphatic, $C_{3-12}$ cycloaliphatic, and 4- to 12-membered monocyclic or bicyclic heterocyclyl comprising 1 to 4 heteroatoms selected from N, O, and S;

each $R^3$ is independently selected from H and optionally substituted $C_{1-6}$ aliphatic;

each $R^5$ is —N($R^3$)$_2$ or an optionally substituted group selected from $C_{1-6}$ aliphatic, P(O)($C_{1-6}$ aliphatic)$_2$, $C_{3-12}$ cycloaliphatic, and 5- to 12-membered monocyclic or polycyclic heterocyclyl comprising 1 to 4 heteroatoms selected from N, O, and S;

each $R^6$ is independently selected from halo, oxo, —$SF_5$, —S(O)—$R^5$, $S(O)_2$—$R^5$, —S(O)(NH)—$R^5$, —$S(O)_2$—(NH)—$R^5$, —S(O)—N($R^5$)$_2$, —$S(O)_2$—N($R^5$)$_2$, —CN, —C(O)—NH($R^5$), —C(O)—N($R^5$)$_2$, —P(O)($R^5$)$_2$, —O—$R^5$, or an optionally substituted group selected from $C_{1-6}$ aliphatic, S—$C_{1-6}$ aliphatic, 2- to 12-membered heteroaliphatic, —$C_{0-6}$ alkylenyl-C(O)—$R^5$, —$C_{0-6}$ alkylenyl-C(O)O—$R^5$, $C_{6-12}$ aryl, $C_{3-12}$ cycloaliphatic, and 4- to 7-membered monocyclic heterocyclyl comprising 1 to 4 heteroatoms selected from N, O, and S;

m is 0, 1, 2, 3, or 4;

q is 0, 1, 2, 3, 4, 5, or 6; and each s is independently 0 or 1.

In some embodiments, the present disclosure provides a compound of Formula II':

II'

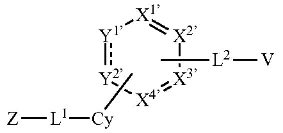

or a pharmaceutically acceptable salt thereof, wherein $X^{1'}$, $X^{2'}$, $X^{3'}$, and $X^{4'}$ are each independently selected from N, C, $CR^a$, wherein $X^{1'}$, $X^{2'}$, $X^{3'}$, and $X^{4'}$ are C when bound to Cy-$L^1$-Z or $L^2$-V, and are N or $CR^a$ when not bound to Cy-$L^1$-Z or $L^2$-V;

$Y^{1'}$ and $Y^{2'}$ are each $CR^a$ or $Y^{1'}$ and $Y^{2'}$ come together to form a fused optionally substituted fused heterocyclyl ring comprising 1 or 2 heteroatoms selected from N, O, and S, or an optionally substituted fused heteroaryl group comprising 1 or 2 heteroatoms selected from N, O, and S;

Cy is absent, $C_{1-6}$ aliphatic, 4- to 12-membered monocyclic or polycyclic heterocyclyl comprising 1 to 4 heteroatoms selected from N, O, P, and S, 5- to 12-membered monocyclic or bicyclic heteroaryl comprising 1 to 4 heteroatoms selected from N, O, and S, $C_{6-12}$ aryl, or $C_{3-12}$ cycloalkyl, wherein Cy is optionally substituted with one or more of $R^1$;

$L^1$ is absent, —S—, —C(O)—$NR^3$—, —$NR^3$—C(O)—, or an optionally substituted group selected from $C_{1-6}$ alkylenyl, $C_{2-6}$ alkynylenyl, —$NR^3$—$C_{0-6}$ alkylenyl, —O—$C_{0-6}$ alkylenyl, —C(O)—$C_{0-6}$ alkylenyl, —$C_{1-6}$ alkylenyl-C(O)—, —C(O)O—$C_{0-6}$ alkylenyl, —$C_{1-6}$ alkylenyl-O—C(O)—, and —$NR^3$—C(O)—$C_{0-6}$ alkylenyl-O—;

$L^2$ is —$(NR^3)_s$—S(O)—$(NR^3)$—, —$(NR^3)_s$—$S(O)_2$—$NR^3$—, —$(NR^3)_s$—P(O)$(R^3)$—, —C(O)—$(NR^3)_s$—, —$NR^3$—C(O)—, or an optionally substituted bivalent moiety selected from —$(NR^3)_s$—S(O)—$C_{0-6}$ alkylenyl-, —$(NR^3)_s$—$S(O)_2$—$C_{0-6}$ alkylenyl-, —$(NR^3)_s$—S(O)—$NR^3$—$C_{0-6}$ alkylenyl, —$(NR^3)_s$—$S(O)_2$—$NR^3$—$C_{0-6}$ alkylenyl, —$NR^3$—$C_{0-6}$ alkylenyl, —$C_{1-6}$ alkylenyl-S(O)—$(NR^3)_s$—, —$C_{1-6}$ alkylenyl-$S(O)_2$—$(NR^3)_s$—, and 4- to 12-membered monocyclic or bicyclic heterocyclyl comprising 1 to 4 heteroatoms selected from N, O, and S;

V is selected from $C_{1-6}$ aliphatic, $C_{6-12}$ aryl, $C_{3-12}$ cycloaliphatic, 4- to 12-membered monocyclic or polycyclic heterocyclyl comprising 1 to 4 heteroatoms selected from N, O, and S, and 5- to 12-membered monocyclic or bicyclic heteroaryl comprising 1 to 4 heteroatoms selected from N, O, and S, wherein V is substituted with $(R^6)_m$;

Z is selected from $P(O)(R^3)_2$, $C(O)N(R^3)_2$, $C_{1-6}$ aliphatic, $C_{6-12}$ aryl, $C_{3-12}$ cycloaliphatic, 2- to 10-atom heteroaliphatic, 4- to 16-membered monocyclic or polycyclic heterocyclyl comprising 1 to 4 heteroatoms selected from N, O, and S, and 5- to 12-membered monocyclic or bicyclic heteroaryl comprising 1 to 4 heteroatoms selected from N, O, and S, wherein Z is substituted with $(R^2)_q$;

each $R^a$ is independently H, halo, —CN, or an optionally substituted group selected from $C_{1-6}$ aliphatic, $C_{3-6}$ cycloaliphatic, and O—$C_{1-6}$ aliphatic;

each $R^1$ is independently selected from halo, —$N(R^3)_2$, —OH, —CN, —C(O)$N(R^3)_2$, and an optionally substituted group selected from $C_{1-6}$ aliphatic and $N(R^3)$—C(O)—$C_{1-6}$ aliphatic;

each $R^2$ is independently selected from halo, oxo, —CN, —OH, O—$R^{2a}$, —C(O)—$R^{2a}$, —C(O)O—$R^{2a}$, and an optionally group selected from $C_{1-6}$ aliphatic, $C_{6-12}$ aryl, and 5- to 12-membered monocyclic or bicyclic heteroaryl comprising 1 to 4 heteroatoms selected from N, O, and S;

each $R^{2a}$ is independently H or an optionally substituted group selected from $C_{1-6}$ aliphatic, $C_{3-12}$ cycloaliphatic, and 4- to 12-membered monocyclic or bicyclic heterocyclyl comprising 1 to 4 heteroatoms selected from N, O, and S;

each $R^3$ is independently selected from H and optionally substituted $C_{1-6}$ aliphatic;

each $R^5$ is —$N(R^3)_2$ or an optionally substituted group selected from $C_{1-6}$ aliphatic, $P(O)(C_{1-6}\text{ aliphatic})_2$, $C_{3-12}$ cycloaliphatic, and 5- to 12-membered monocyclic or polycyclic heterocyclyl comprising 1 to 4 heteroatoms selected from N, O, and S;

each $R^6$ is independently selected from halo, oxo, —$SF_5$, —S(O)—$R^5$, $S(O)_2$—$R^5$, —S(O)(NH)—$R^5$, —$S(O)_2$—(NH)—$R^5$, —S(O)—$N(R^5)_2$, —$S(O)_2$—$N(R^5)_2$, —CN, —C(O)—$NH(R^5)$, —C(O)—$N(R^5)_2$, —P(O)$(R^5)_2$, —O—$R^5$, or an optionally substituted group selected from $C_{1-6}$ aliphatic, S—$C_{1-6}$ aliphatic, 2- to 12-membered heteroaliphatic, —$C_{0-6}$ alkylenyl-C(O)—$R^5$, —$C_{0-6}$ alkylenyl-C(O)O—$R^5$, $C_{6-12}$ aryl, $C_{3-12}$ cycloaliphatic, and 4- to 7-membered monocyclic heterocyclyl comprising 1 to 4 heteroatoms selected from N, O, and S;

m is 0, 1, 2, 3, or 4;

q is 0, 1, 2, 3, 4, 5, or 6; and each s is independently 0 or 1.

Definitions

Agonist: As will be understood by those skilled in the art, the term "agonist" generally refers to an agent whose presence or level correlates with elevated level or activity of a target, as compared with that observed absent the agent (or with the agent at a different level). In some embodiments, an agonist is one whose presence or level correlates with a target level or activity that is comparable to or greater than a particular reference level or activity (e.g., that observed under appropriate reference conditions, such as presence of a known agonist, e.g., a positive control). In some embodiments, an agonist may be a direct agonist in that it exerts its influence directly on (e.g., interacts directly with) the target; in some embodiments, an agonist may be an indirect agonist in that it exerts its influence indirectly (e.g., by acting on, such as interacting with, a regulator of the target, or with some other component or entity.

Aliphatic: The term "aliphatic" refers to a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "cycloaliphatic"), that has a single point or more than one points of attachment to the rest of the molecule. Unless otherwise specified, aliphatic groups contain 1-12 aliphatic carbon atoms. In some embodiments, aliphatic groups contain 1-6 aliphatic carbon atoms (e.g., $C_{1-6}$). In some embodiments, aliphatic groups contain 1-5 aliphatic carbon atoms (e.g., $C_{1-5}$). In other embodiments, aliphatic groups contain 1-4 aliphatic carbon atoms (e.g., $C_{1-4}$). In still other embodiments, aliphatic groups contain 1-3 aliphatic carbon atoms (e.g., $C_{1-3}$), and in yet other embodiments, aliphatic groups contain 1-2 aliphatic carbon atoms (e.g., $C_{1-2}$). In some embodiments, "cycloaliphatic" refers to a monocyclic $C_{3-8}$ hydrocarbon or a bicyclic $C_{7-10}$ hydrocarbon that is completely saturated or that contains one or more units of unsaturation, but which is not aromatic, that has a single point or more than one points of attachment to the rest of the molecule. Suitable aliphatic groups include, but are not limited to, linear or branched, substituted or unsubstituted alkyl, alkylenyl, alkenyl, alkenylenyl, alkynyl, or alkynylenyl groups and hybrids thereof. A preferred aliphatic group is $C_{1-6}$ alkyl. In some embodiments, aliphatic is multivalent (i.e., has multiple points of attachment to the rest of the molecule). In some embodiments, aliphatic is bivalent (i.e., has two points of attachment to the rest of the molecule). An example bivalent aliphatic group can be referred to as "alkylenyl".

Alkyl: The term "alkyl", used alone or as part of a larger moiety, refers to a saturated, optionally substituted straight or branched chain or cyclic hydrocarbon group having (unless otherwise specified) 1-12, 1-10, 1-8, 1-6, 1-4, 1-3, or 1-2 carbon atoms (e.g., $C_{1-12}$, $C_{1-10}$, $C_{1-8}$, $C_{1-6}$, $C_{1-4}$, $C_{1-3}$, or $C_{1-2}$). Exemplary alkyl groups include methyl, ethyl, propyl (e.g., n-propyl, iso-propyl), butyl (e.g., n-butyl, sec-butyl, iso-butyl, tert-butyl), pentyl, hexyl, heptyl, $—CH_2—C(CH_3)_3$, $—CH_2—C(CH_3)_2—CH_2—CH_3$, $—C(CH_3)_2—CH_2—CH_3$, $—CH(CH_3)—C(CH_3)_3$. The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl. Exemplary polycyclic cycloalkyl rings include adamantyl,

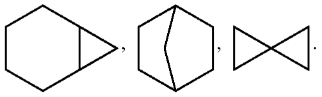

Alkylene: The term "alkylene" and "alkylenyl" are used interchangeably and refer to a bivalent alkyl group. In some embodiments, "alkylene" is a bivalent straight or branched alkyl group. In some embodiments, an "alkylene chain" is a polymethylene group, i.e., $—(CH_2)_n—$, wherein n is a positive integer, e.g., from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3- to 7-membered ring. The substituents can be on the same or different atoms. The term "haloalkylenyl" refers to an straight-chain or branched alkylenyl group substituted by one or more halogen atoms (e.g., one, two, three or four halo, such as fluoro, iodo, bromo, or chloro).

Alkenyl: The term "alkenyl", used alone or as part of a larger moiety, refers to an optionally substituted straight or branched chain or cyclic hydrocarbon group having at least one double bond and having (unless otherwise specified) 2-12, 2-10, 2-8, 2-6, 2-4, or 2-3 carbon atoms (e.g., $C_{2-12}$, $C_{2-10}$, $C_{2-8}$, $C_{2-6}$, $C_{2-4}$, or $C_{2-3}$). Exemplary alkenyl groups include ethenyl, propenyl, butenyl, pentenyl, hexenyl, and heptenyl. The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl, and cycloheptenyl.

Alkenylene: The term "alkenylene" and "alkenylenyl" are used interchangeably and refers to a bivalent alkenyl group. In some embodiments, "alkenylene" is a bivalent straight or branched alkenyl group.

Alkynyl: The term "alkynyl", used alone or as part of a larger moiety, refers to an optionally substituted straight or branched chain hydrocarbon group having at least one triple bond and having (unless otherwise specified) 2-12, 2-10, 2-8, 2-6, 2-4, or 2-3 carbon atoms (e.g., $C_{2-12}$, $C_{2-10}$, $C_{2-8}$, $C_{2-6}$, $C_{2-4}$, or $C_{2-3}$). Exemplary alkynyl groups include ethynyl, propynyl, butynyl, pentynyl, hexynyl, and heptynyl.

Alkynylene: The term "alkynylene" and "alkynylenyl" are used interchangeably and refers to a bivalent alkynyl group. In some embodiments, "alkynylene" is a bivalent straight or branched alkynyl group.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Antagonist: As will be understood by those skilled in the art, the term "antagonist" generally refers to an agent whose presence or level correlates with decreased level or activity of a target, as compared with that observed absent the agent (or with the agent at a different level). In some embodiments, an antagonist is one whose presence or level correlates with a target level or activity that is comparable to or less than a particular reference level or activity (e.g., that observed under appropriate reference conditions, such as presence of a known antagonist, e.g., a positive control). In some embodiments, an antagonist may be a direct antagonist in that it exerts its influence directly on (e.g., interacts directly with) the target; in some embodiments, an antagonist may be an indirect antagonist in that it exerts its influence indirectly (e.g., by acting on, such as interacting with, a regulator of the target, or with some other component or entity.

Aryl: The term "aryl" refers to monocyclic and bicyclic ring systems having a total of five to fourteen ring members (e.g., $C_{5-14}$), wherein at least one ring in the system is aromatic and wherein each ring in the system contains three to seven ring members. In some embodiments, an "aryl" group contains between six and twelve total ring members (e.g., $C_{6-12}$). The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Unless otherwise specified, "aryl" groups are hydrocarbons. In some embodiments, an "aryl" ring system is an aromatic ring (e.g., phenyl) that is fused to a non-aromatic ring (e.g., cycloalkyl). Examples of aryl rings include that are fused include

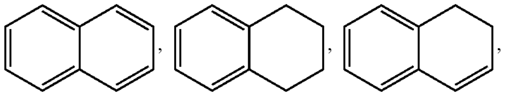

and

-continued

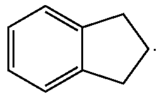

Associated: Two events or entities are "associated" with one another, as that term is used herein, if the presence, level and/or form of one is correlated with that of the other. For example, a particular entity (e.g., polypeptide, genetic signature, metabolite, microbe, etc) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biological sample: As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or bronchioalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example, nucleic acids or proteins extracted from a sample or obtained by subjecting a primary sample to techniques such as amplification or reverse transcription of mRNA, isolation and/or purification of certain components, etc.

Biomarker: The term "biomarker" is used herein, consistent with its use in the art, to refer to a to an entity (or form thereof) whose presence, or level, correlates with a particular biological event or state of interest, so that it is considered to be a "marker" of that event or state. To give but a few examples, in some embodiments, a biomarker may be or comprise a marker for a particular disease state, or for likelihood that a particular disease, disorder or condition may develop, occur, or reoccur. In some embodiments, a biomarker may be or comprise a marker for a particular disease or therapeutic outcome, or likelihood thereof. Thus, in some embodiments, a biomarker is predictive, in some embodiments, a biomarker is prognostic, in some embodiments, a biomarker is diagnostic, of the relevant biological event or state of interest.

Carrier: As used herein, the term "carrier" refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Combination therapy: As used herein, the term "combination therapy" refers to those situations in which a subject is simultaneously exposed to two or more therapeutic regimens (e.g., two or more therapeutic agents or modality(ies)). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Comparable: As used herein, the term "comparable" refers to two or more agents, entities, situations, sets of conditions, etc., that may not be identical to one another but that are sufficiently similar to permit comparison therebetween so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Composition: Those skilled in the art will appreciate that the term "composition" may be used to refer to a discrete physical entity that comprises one or more specified components. In general, unless otherwise specified, a composition may be of any form—e.g., gas, gel, liquid, solid, etc.

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen or therapeutic regimen: Those skilled in the art will appreciate that the terms "dosing regimen" and "therapeutic regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Engineered: In general, the term "engineered" refers to the aspect of having been manipulated by the hand of man. For example, in some embodiments, a small molecule may be considered to be engineered if its structure and/or production is designed and/or implemented by the hand of man. Analogously, in some embodiments, a polynucleotide may be considered to be "engineered" when two or more sequences, that are not linked together in that order in nature, are manipulated by the hand of man to be directly linked to one another in the engineered polynucleotide. For example, in some embodiments of the present invention, an engineered polynucleotide comprises a regulatory sequence that is found in nature in operative association with a first coding sequence but not in operative association with a second coding sequence, is linked by the hand of man so that it is operatively associated with the second coding sequence. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, expression products of an engineered polynucleotide, and/or progeny of an engineered polynucleotide or cell are typically still referred to as "engineered" even though the actual manipulation was performed on a prior entity.

Excipient: As used herein, the term "excipient" refers to a non-therapeutic agent that may be included in a pharmaceutical composition, for example, to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Heteroaliphatic: The term "heteroaliphatic" or "heteroaliphatic group", as used herein, denotes an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. The term "heteroatom" refers to nitrogen, oxygen, or sulfur, and includes any oxidized form of nitrogen or sulfur, and any quaternized form of a basic nitrogen. The term "nitrogen" also includes a substituted nitrogen. Unless otherwise specified, heteroaliphatic groups contain 1-10 carbon atoms wherein 1-3 carbon atoms are optionally and independently replaced with heteroatoms selected from oxygen, nitrogen, and sulfur. In some embodiments, heteroaliphatic groups contain 1-4 carbon atoms, wherein 1-2 carbon atoms are optionally and independently replaced with heteroatoms selected from oxygen, nitrogen, and sulfur. In yet other embodiments, heteroaliphatic groups contain 1-3 carbon atoms, wherein 1 carbon atom is optionally and independently replaced with a heteroatom selected from oxygen, nitrogen, and sulfur. Suitable heteroaliphatic groups include, but are not limited to, linear or branched, heteroalkyl, heteroalkenyl, and heteroalkynyl groups. For example, a 1- to 10 atom heteroaliphatic group includes the following exemplary groups: $-O-CH_3$, $-O-CH_2-CH_3$, $-O-CH_2-CH_2-CH_3$, $-CH_2-O-CH_3$, $-O-CH_2-CH_2-O-CH_2-CH_2-O-CH_3$, $-O-CH_2-CH_2-O-CH_2-CH_2-O-CH_2-CH_2-O-CH_3$, $-CH_2-O-CH_3$, $-CH_2-O-CH_2-CH_3$, $-CH_2-O-CH_2-CH_2-O-CH_3$, $-CH_2-O-CH_2-CH_2-O-CH_2-CH_2-O-CH_3$, $-CH_2-O-C(CH_3)_3$, $-C(CH_3)_2-O-CH_3$, $-C(CH_3)_2-CH_2-O-CH_3$, $-CH_2-CH_2-O-CH_2-CH_3$, $-CH_2-CH_2-CH_2-O-CH_3$, $-NH-C(CH_3)_3$, $-N(CH_2CH_3)_2$, $-S-C(CH_3)_3$ and the like.

Heteroaryl: The terms "heteroaryl" and "heteroar-", used alone or as part of a larger moiety, e.g., "heteroaralkyl", or "heteroaralkoxy", refer to monocyclic or bicyclic ring groups having 5 to 12 ring atoms (e.g., 5- to 6-membered monocyclic heteroaryl or 9- to 12-membered bicyclic heteroaryl); having 6, 10, or 14 π-electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolyl, indazolyl, indolizinyl, benzimidazolyl, purinyl, naphthyridinyl, pteridinyl, imidazo[1,2-a]pyrimidinyl, imidazo[1,2-a]pyridyl, imidazo[4,5-b]pyridyl, imidazo[4,5-c]pyridyl, pyrrolopyridyl, pyrazolopyridyl, pyrrolopyrazinyl, thienopyrimidinyl, triazolopyridyl, and benzoisoxazolyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring (i.e., a bicyclic heteroaryl ring having 1 to 3 heteroatoms). Nonlimiting examples include indolyl, isoindolyl, benzothienyl, benzofuranyl, dibenzofuranyl, indazolyl, benzimidazolyl, benzotriazolyl, benzothiazolyl, benzothiadiazolyl, benzoxazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, pyrido[2,3-b]-1,4-oxazin-3(4H)-one, benzoisoxazolyl,

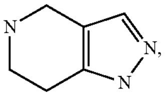 and 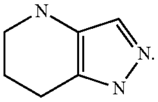

A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

Heteroatom: The term "heteroatom" as used herein refers to nitrogen, oxygen, or sulfur, and includes any oxidized form of nitrogen or sulfur, and any quaternized form of a basic nitrogen.

Heterocycle: As used herein, the terms "heterocycle", "heterocyclyl", "heterocyclic radical", and "heterocyclic ring" are used interchangeably and refer to a stable 3- to 8-membered monocyclic, a 7- to 12-membered bicyclic, or a 10- to 16-membered polycyclic heterocyclic moiety that is either saturated or partially unsaturated, and having, in addition to carbon atoms, one or more, such as one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $NR^+$ (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, azetidinyl, oxetanyl, tetrahydrofuranyl, tetrahydrothienyl, pyrrolidinyl, piperidinyl, decahydroquinolinyl, oxazolidinyl, piperazinyl, tetrahydropyranyl, dioxanyl, dioxolanyl, diazepinyl, oxazepinyl, thiazepinyl, morpholinyl, thiamorpholinyl, and

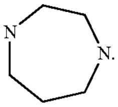

A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. A bicyclic heterocyclic ring also includes groups in which the heterocyclic ring is fused to one or more aryl rings. Exemplary bicyclic heterocyclic groups include indolinyl, isoindolinyl, benzodioxolyl, 1,3-dihydroisobenzofuranyl, 2,3-dihydrobenzofuranyl, tetrahydroquinolinyl,

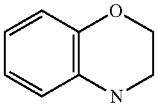, 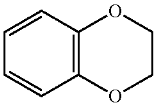, 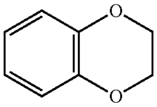,
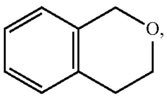 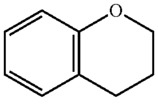,
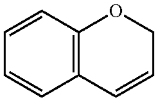, 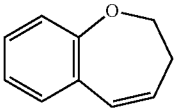,
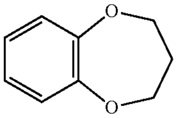, 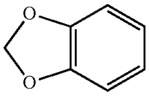,
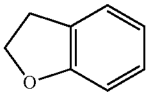, 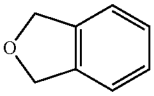, 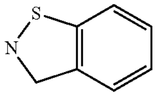,
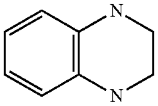, 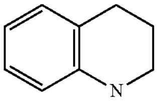, 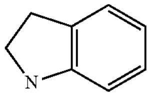,
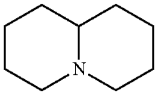, 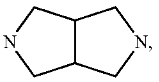 and
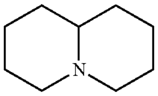.

A bicyclic heterocyclic ring can also be a spirocyclic ring system (e.g., 7- to 11-membered spirocyclic fused heterocyclic ring having, in addition to carbon atoms, one or more heteroatoms as defined above (e.g., one, two, three or four heteroatoms)). A bicyclic heterocyclic ring can also be a bridged ring system (e.g., 7- to 11-membered bridged heterocyclic ring having one, two, or three bridging atoms. Exemplary bridged ring systems include

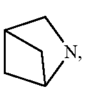 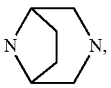 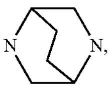 and 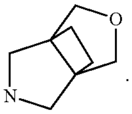.

Exemplary polycyclic heterocyclic ring systems that are spirocyclic include

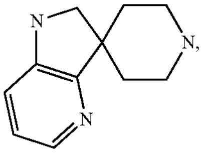 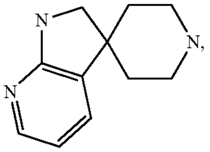

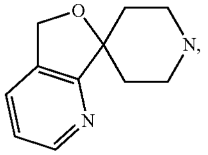 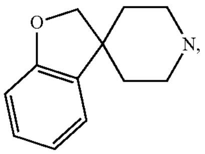

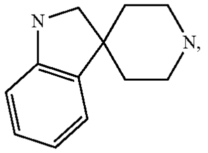 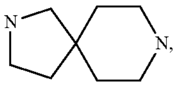

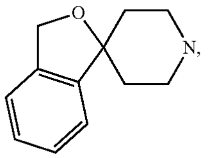 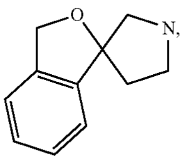

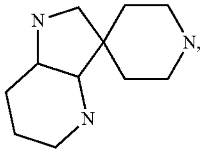 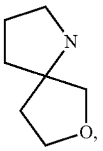

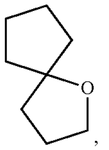 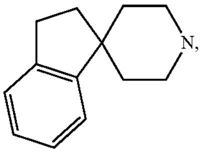

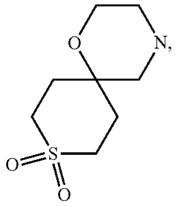 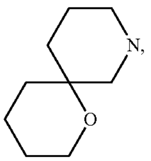

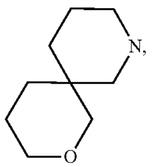 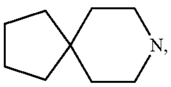

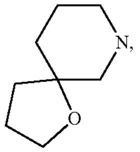 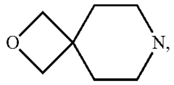

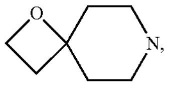 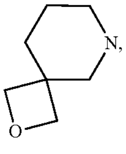 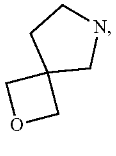

-continued

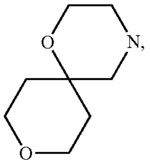 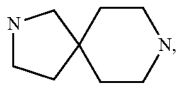

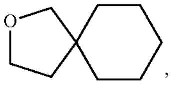 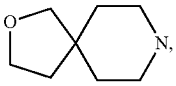

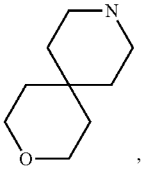 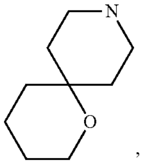

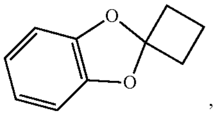 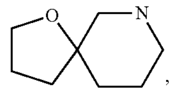

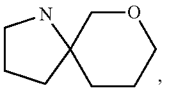 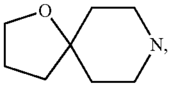

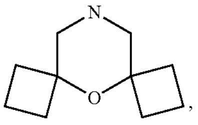 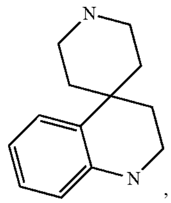

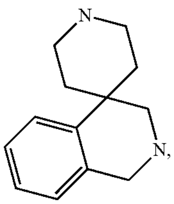 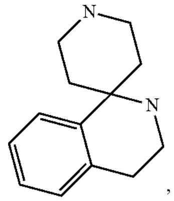

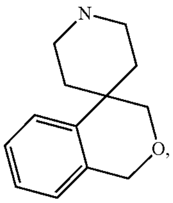 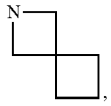

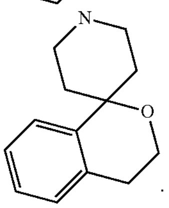

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection and infusion.

Partially unsaturated: As used herein, the term “partially unsaturated” refers to a ring moiety that includes at least one double or triple bond between ring atoms. The term “partially unsaturated” is intended to encompass rings having multiple sites of unsaturation, but is not intended to include aromatic (e.g., aryl or heteroaryl) moieties, as herein defined.

Patient or subject: As used herein, the term “patient” or “subject” refers to any organism to which a provided composition is or may be administered, e.g., for experimental, diagnostic, prophylactic, cosmetic, and/or therapeutic purposes. Typical patients or subjects include animals (e.g., mammals such as mice, rats, rabbits, non-human primates, and/or humans). In some embodiments, a patient is a human. In some embodiments, a patient or a subject is suffering from or susceptible to one or more disorders or conditions. In some embodiments, a patient or subject displays one or more symptoms of a disorder or condition. In some embodiments, a patient or subject has been diagnosed with one or more disorders or conditions. In some embodiments, a patient or a subject is receiving or has received certain therapy to diagnose and/or to treat a disease, disorder, or condition.

Pharmaceutical composition: As used herein, the term “pharmaceutical composition” refers to an active agent, formulated together with one or more pharmaceutically acceptable carriers. In some embodiments, the active agent is present in unit dose amount appropriate for administration in a therapeutic or dosing regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase “pharmaceutically acceptable” refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term “pharmaceutically acceptable carrier” means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be “acceptable” in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer’s solution; ethyl alcohol; pH buffered solutions; polyesters, polycarbonates and/or polyanhydrides; and other nontoxic compatible substances employed in pharmaceutical formulations.

Pharmaceutically acceptable salt: The term “pharmaceutically acceptable salt”, as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Polycyclic: As used herein, the term “polycyclic” refers to a saturated or unsaturated ring system having two or more rings (for example, heterocyclyl rings, heteroaryl rings, cycloalkyl rings, or aryl rings), having between 7 and 20 atoms, in which one or more carbon atoms are common to two adjacent rings. For example, in some embodiments, a polycyclic ring system refers to a saturated or unsaturated ring system having three or more rings (for example, heterocyclyl rings, heteroaryl rings, cycloalkyl rings, or aryl rings), having between 14 and 20 atoms, in which one or more carbon atoms are common to two adjacent rings. The rings in a polycyclic ring system may be fused (i.e., bicyclic or tricyclic), spirocyclic, or a combination thereof. Exemplary polyclic systems include adamantyl,

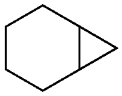, 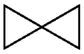, 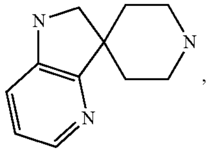,

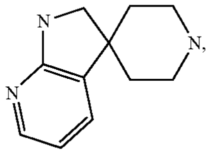 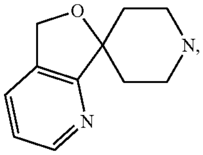

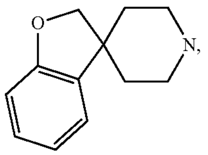 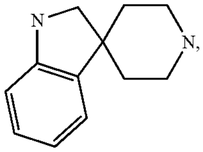

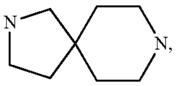 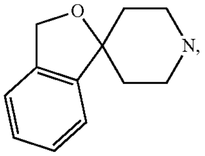

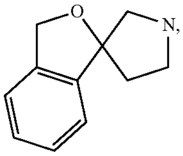 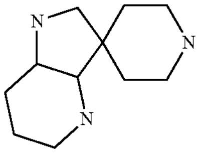' 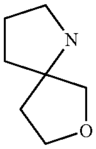,

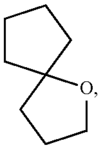 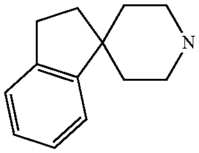, 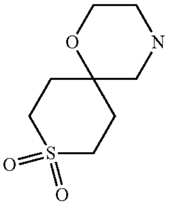,

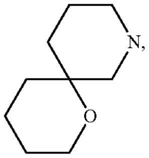 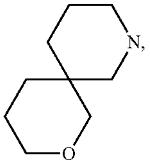 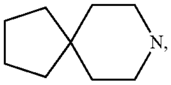

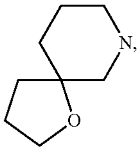 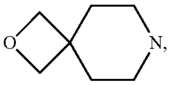 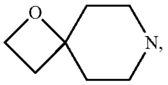

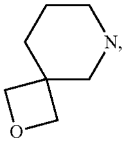 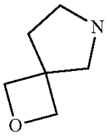, 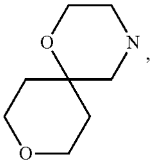,

-continued

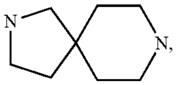 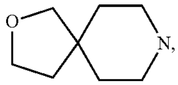 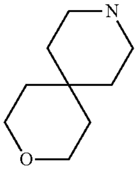,

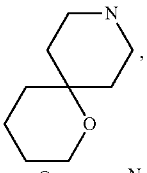, 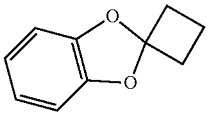,

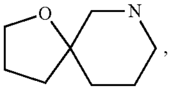, 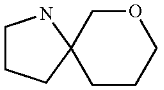,

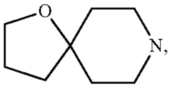 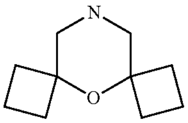,

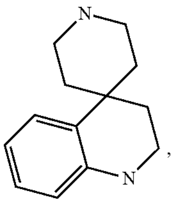, 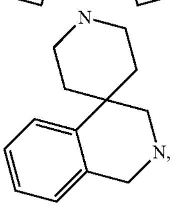

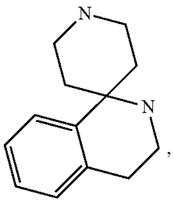, 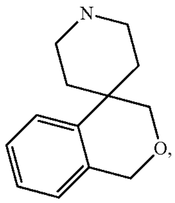

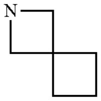, and 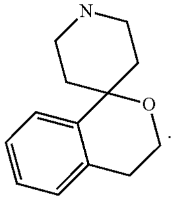.

Prevent or prevention: As used herein, the terms "prevent" or "prevention", when used in connection with the occurrence of a disease, disorder, and/or condition, refer to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Sample: As used herein, the term "sample" typically refers to an aliquot of material obtained or derived from a source of interest. In some embodiments, a source of interest is a biological or environmental source. In some embodiments, a source of interest may be or comprise a cell, tissue, or organism, such as a microbe, a plant, or an animal (e.g., a human). In some embodiments, a source of interest is or comprises biological tissue or fluid. In some embodiments, a source of interest may be or comprise a preparation generated in a production run. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample.

Specific: The term "specific", when used herein with reference to an agent having an activity, is understood by those skilled in the art to mean that the agent discriminates between potential target entities or states. For example, in some embodiments, an agent is said to bind "specifically" to its target if it binds preferentially with that target in the presence of one or more competing alternative targets. In many embodiments, specific interaction is dependent upon the presence of a particular structural feature of the target entity (e.g., an epitope, a cleft, a binding site). It is to be understood that specificity need not be absolute. In some embodiments, specificity may be evaluated relative to that of the binding agent for one or more other potential target entities (e.g., competitors). In some embodiments, specificity is evaluated relative to that of a reference specific binding agent. In some embodiments, specificity is evaluated relative to that of a reference non-specific binding agent. In some embodiments, the agent or entity does not detectably bind to the competing alternative target under conditions of binding to its target entity. In some embodiments, a binding agent binds with higher on-rate, lower off-rate, increased affinity, decreased dissociation, and/or increased stability to its target entity as compared with the competing alternative target(s).

Substituted or optionally substituted: As described herein, compounds of the invention may contain "optionally substituted" moieties. In general, the term "substituted," whether preceded by the term "optionally" or not, means that one or more hydrogens of the designated moiety are replaced with a suitable substituent. "Substituted" applies to one or more hydrogens that are either explicit or implicit from the structure (e.g., 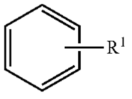

refers to at least

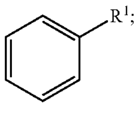; and 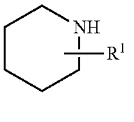

and refers to at least

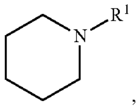, 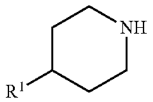 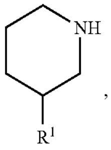, or

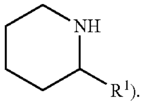).

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes provided herein. Groups described as being "substituted" preferably have between 1 and 4 substituents, more preferably 1 or 2 substituents. Groups described as being "optionally substituted" may be unsubstituted or be "substituted" as described above.

Suitable monovalent substituents on a substitutable carbon atom of an "optionally substituted" group are independently halogen; $—(CH_2)_{0-4}R°$; $—(CH_2)_{0-4}OR°$; $—O(CH_2)_{0-4}R°$, $—O—(CH_2)_{0-4}C(O)OR°$; $—(CH_2)_{0-4}CH(OR°)_2$; $—(CH_2)_{0-4}SR°$; $—(CH_2)_{0-4}Ph$, which may be substituted with R°; $—(CH_2)_{0-4}O(CH_2)_{0-1}Ph$ which may be substituted with R°; $—CH{=}CHPh$, which may be substituted with R°; $—(CH_2)_{0-4}O(CH_2)_{0-1}$-pyridyl which may be substituted with R°; $—NO_2$; —CN; $—N_3$; $—(CH_2)_{0-4}N(R°)_2$; $—(CH_2)_{0-4}N(R°)C(O)R°$; $—N(R°)C(S)R°$; $—(CH_2)_{0-4}N(R°)C(O)NR°_2$; $—N(R°)C(S)NR°_2$; $—(CH_2)_{0-4}N(R°)C(O)OR°$; $—N(R°)N(R°)C(O)R°$; $—N(R°)N(R°)C(O)NR°_2$; $—N(R°)N(R°)C(O)OR°$; $—(CH_2)_{0-4}C(O)R°$; C(S)R°; $—(CH_2)_{0-4}C(O)OR°$; $—(CH_2)_{0-4}C(O)SR°$; $—(CH_2)_{0-4}C(O)OSiR°_3$; $—(CH_2)_{0-4}OC(O)R°$; $—OC(O)(CH_2)_{0-4}SR°$; $—(CH_2)_{0-4}SC(O)R°$; $—(CH_2)_{0-4}C(O)NR°_2$; $—C(S)NR°_2$; —C(S)SR°; —SC(S)SR°, $—(CH_2)_{0-4}OC(O)NR°_2$; —C(O)N(OR°)R°; —C(O)C(O)R°; $—C(O)CH_2C(O)R°$; —C(NOR°)R°; $—(CH_2)_{0-4}SSR°$; $—(CH_2)_{0-4}S(O)_2R°$; $—(CH_2)_{0-4}S(O)_{2}0R°$; $—(CH_2)_{0-4}OS(O)_2R°$; $—S(O)_2NR°_2$; $—(CH_2)_{0-4}S(O)R°$; $—N(R°)S(O)_2NR°_2$; $—N(R°)S(O)_2R°$; —N(OR°)R°; $—C(NH)NR°_2$; $—P(O)_2R°$; $—P(O)R°_2$; $—OP(O)R°_2$; $—OP(O)(OR°)_2$; $SiR°_3$; $—(C_{1-4}$ straight or branched alkylene)O—$N(R°)_2$; or $—(C_{1-4}$ straight or branched alkylene)C(O)O—$N(R°)_2$, wherein each R° may be substituted as defined below and is independently hydrogen, $C_{1-6}$ aliphatic, $—CH_2Ph$, $—O(CH_2)_{0-1}$ Ph, $—CH_2$-(5- to 6-membered heteroaryl ring), or a 3- to 6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3- to 12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^•$, -(haloR$^•$), —$(CH_2)_{0-2}OH$, —$(CH_2)_{0-2}OR^•$, —$(CH_2)_{0-2}CH(OR^•)_2$, —O(haloR$^•$), —CN, —$N_3$, —$(CH_2)_{0-2}$ C(O)R$^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —SiR$^•$3, —OSiR$^•$3, —C(O)SR$^•$, —($C_{1-4}$ straight or branched alkylene)C(O)OR$^•$, or —SSR$^•$ wherein each R$^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 3- to 6-membered saturated, partially unsaturated, or aryl ring having 0-4 heteroatoms independently selected from nitrogen, oxygen, or sulfur. Suitable divalent substituents on a saturated carbon atom of R° include ═O and ═S. 100-541 Suitable divalent substituents on a saturated carbon atom of an "optionally substituted" group include the following: ═O ("oxo"), ═S, ═$NNR^*_2$, ═NNHC(O)R*, ═NNHC(O) OR*, ═$NNHS(O)_2R^*$, ═NR*, ═NOR*, —$O(C(R^*_2))_{2-3}O$—, or —$S(C(R^*_2))_{2-3}S$—, wherein each independent occurrence of R* is selected from hydrogen, $C_{1-6}$ aliphatic which may be substituted as defined below, or an unsubstituted 5- to 6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R$^•$ include halogen, —R$^•$, -(haloR$^•$), —OH, —OR$^•$, —O(haloR$^•$), —CN, —C(O)OH, —C(O)OR$^•$, —$NH_2$, —NHR$^•$, —$NR^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5- to 6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^†$, —$NR^†_2$, —$C(O)R^†$, —$C(O)OR^†$, —$C(O)C(O)R^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each $R^†$ is independently hydrogen, $C_{1-6}$ aliphatic which may be substituted as defined below, unsubstituted —OPh, or an unsubstituted 3- to 6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3- to 12-membered saturated, partially unsaturated, or aryl mono- or bicyclic ring having 0-4 heteroatoms independently selected from nitrogen, oxygen, or sulfur.

Suitable substituents on the aliphatic group of R are independently halogen, —R$^•$, -(haloR$^•$), —OH, —OR$^•$, —O(haloR$^•$), —CN, —C(O)OH, —C(O)OR$^•$, —$NH_2$, —NHR$^•$, —$NR^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 3- to 6-membered saturated, partially unsaturated, or aryl ring having 0-4 heteroatoms independently selected from nitrogen, oxygen, or sulfur.

Small molecule: As used herein, the term "small molecule" means a low molecular weight organic and/or inorganic compound. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer.

In some embodiments, a small molecule does not include a polymeric moiety. In some embodiments, a small molecule is not and/or does not comprise a protein or polypeptide (e.g., is not an oligopeptide or peptide). In some embodiments, a small molecule is not and/or does not comprise a polynucleotide (e.g., is not an oligonucleotide). In some embodiments, a small molecule is not and/or does not comprise a polysaccharide; for example, in some embodiments, a small molecule is not a glycoprotein, proteoglycan, glycolipid, etc.). In some embodiments, a small molecule is not a lipid.

In some embodiments, a small molecule is a modulating agent (e.g., is an inhibiting agent or an activating agent). In some embodiments, a small molecule is biologically active. In some embodiments, a small molecule is detectable (e.g., comprises at least one detectable moiety). In some embodiments, a small molecule is a therapeutic agent.

Those of ordinary skill in the art, reading the present disclosure, will appreciate that certain small molecule compounds described herein may be provided and/or utilized in any of a variety of forms such as, for example, crystal forms (e.g., polymorphs, solvates, etc), salt forms, protected forms, pro-drug forms, ester forms, isomeric forms (e.g., optical and/or structural isomers), isotopic forms, etc.

Those of ordinary skill in the art will appreciate that certain small molecule compounds have structures that can exist in one or more stereoisomeric forms. In some embodiments, such a small molecule may be utilized in accordance with the present disclosure in the form of an individual enantiomer, diastereomer or geometric isomer, or may be in the form of a mixture of stereoisomers; in some embodiments, such a small molecule may be utilized in accordance with the present disclosure in a racemic mixture form.

Those of skill in the art will appreciate that certain small molecule compounds have structures that can exist in one or more tautomeric forms. In some embodiments, such a small molecule may be utilized in accordance with the present disclosure in the form of an individual tautomer, or in a form that interconverts between tautomeric forms.

Those of skill in the art will appreciate that certain small molecule compounds have structures that permit isotopic substitution (e.g., $^2H$ or $^3H$ for H; $^{11}C$, $^{13}C$ or $^{14}C$ for $^{12}C$; $^{13}N$ or $^{15}N$ for $^{14}N$; $^{17}O$ or $^{18}O$ for 16O; $^{36}Cl$ for XXC; $^{18}F$ for XXF; 131I for XXXI; etc). In some embodiments, such a small molecule may be utilized in accordance with the present disclosure in one or more isotopically modified forms, or mixtures thereof.

In some embodiments, reference to a particular small molecule compound may relate to a specific form of that compound. In some embodiments, a particular small molecule compound may be provided and/or utilized in a salt form (e.g., in an acid-addition or base-addition salt form, depending on the compound); in some such embodiments, the salt form may be a pharmaceutically acceptable salt form.

In some embodiments, where a small molecule compound is one that exists or is found in nature, that compound may be provided and/or utilized in accordance in the present disclosure in a form different from that in which it exists or is found in nature. Those of ordinary skill in the art will appreciate that, in some embodiments, a preparation of a particular small molecule compound that contains an absolute or relative amount of the compound, or of a particular form thereof, that is different from the absolute or relative (with respect to another component of the preparation including, for example, another form of the compound) amount of the compound or form that is present in a reference preparation of interest (e.g., in a primary sample from a source of interest such as a biological or environmental source) is distinct from the compound as it exists in the reference preparation or source. Thus, in some embodiments, for example, a preparation of a single stereoisomer of a small molecule compound may be considered to be a different form of the compound than a racemic mixture of the compound; a particular salt of a small molecule compound may be considered to be a different form from another salt form of the compound; a preparation that contains only a form of the compound that contains one conformational isomer ((Z) or (E)) of a double bond may be considered to be a different form of the compound from one that contains the other conformational isomer ((E) or (Z)) of the double bond; a preparation in which one or more atoms is a different isotope than is present in a reference preparation may be considered to be a different form; etc.

Those skilled in the art will appreciate that a bond designated as ⎓ in a small molecule structure, as used herein, refers to a bond that, in some embodiments, is a single (e.g., saturated) bond, and in some embodiments, is a double (e.g., unsaturated) bond. For example, the following structure:

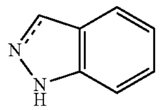

is intended to encompass both

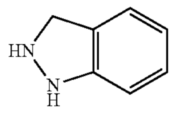 and 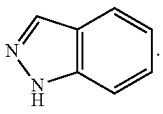.

Those skilled in the art will further appreciate that, in small molecule structures, the symbol ∿∿ , as used herein, refers to a point of attachment between two atoms.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Treat: As used herein, the terms "treat," "treatment," or "treating" refer to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example, for the purpose of decreasing the risk of developing pathology associated with the disease, disorder, and/or condition.

DETAILED DESCRIPTION OF CERTAIN EMBODIMENTS

TRPML1 and Autophagy

Autophagy is a mechanism of the cell that degrades cytoplasmic material and organelles. There are multiple types of autophagy: (1) macroautophagy (generally referred to as autophagy); (2) microautophagy; and (3) chaperone-mediateed autophagy. See Eskelinen & Saftig, Biochimica et Biophysica Acta-Mol. Cell Res., 1793(4):664-673 (2009). In macroautophagy, the autophagosome engulfs waste materials in the cytoplasm and fuses to the lysosome, where materials are delivered for degradation. The lysosome is as a subcellular organelle containing more than 50 soluble acid hydrolases useful for digesting cellular components. Fusion of the lysosome to the autophagosome is activated, in part, by release of ions through ion channels in the membrane of the lysome, including $Ca^{2+}$. See Cao, et al., J. Bio. Chem., 292(20) 8424-8435 (2017).

Transient Receptor Potential Mucolipin-1 (also known as TRPML1 or ML1) is a $Ca^{2+}$ channel in the lysosome that regulates autophagy. See Wang, et al., PNAS, E1373-E1381 (Mar. 2, 2015). In particular, TRPML1 is an inwardly rectifying current channel that transports cations from the lumen of the lysosome to the cytosol. See Di Paolda, et al., Cell Calcium 69:112-121 (2018). Release of $Ca^{2+}$ from the lysosome via TRPML1 modulates transcription factor EB activity via local calcineurin activation, which ultimately induces autophagy and lysosomal biogenesis. See Medina, et al., Nat. Cell. Biol., 17(3):288-299 (2015).

It has recently been discovered that upregulation of autophagy is beneficial to patients suffering from a number of diseases and disorders. For example, it has been reported that inducing autophagy promotes clearance of hepatotoxic alpha-1-anti-trypsin (ATZ) in the liver. See Pastore, et al., EMBO Mol. Med. 5(3): 397-412 (March 2013). Moreover, autophagy was recently found to be useful in the treatment of neurodegenerative disorders, cancer, and heart disease. See Pierzynowska, et al., Metab. Brain Dis., 33(4); 989-1008 (2018) (discussing neurodegenerative disorders); Nelson & Shacka, Curr. Pathobiol. Rep., 1(4): 239-245 (2013) (discussing cancer); Sciaretta, et al., Annual Review of Physiology, 80:1-26 (2018) (discussing heart disease); Maiuri & Kroemer, Cell Death & Differentiation, 26: 680-689 (2019) (discussing therapeutic applications of autophagy, generally). It is, therefore, desirable to identify methods and modes of promoting autophagy. Given TRPML1's role in autophagy, described herein are TRPML1 modulators useful for promoting autophagy and/or treating certain diseases, disorders, or conditions.

The present disclosure provides the insight that TRMPL1 may represent a particularly desirable target that, among other things, may permit modulation (e.g., enhancement) of autophagy in certain contexts.

TRPML1 Modulators

Structure

In some embodiments, the present disclosure provides and/or utilizes TRMPL1 modulators that are small molecule compounds having a chemical structure as indicated below in Formula I:

$Z\text{-}L^1\text{-}Cy\text{-}A\text{-}L^2\text{-}V$   I or a pharmaceutically acceptable salt thereof, wherein A is $C_{6-12}$ aryl, 5- to 6-membered heteroaryl comprising 1 to 4 heteroatoms selected from N, O, and S, wherein A is substituted with 0, 1, 2, 3 or 4 $R^a$;

Cy is absent or a bivalent moiety selected from 4- to 12-membered monocyclic or polycyclic heterocyclyl comprising 1 to 4 heteroatoms selected from N, O, P, and S, 5- to 12-membered monocyclic or bicyclic heteroaryl comprising 1 to 4 heteroatoms selected from N, O, P, and S, $C_{1-6}$ aliphatic, $C_{3-12}$ cycloalkyl, or —$C_{0-6}$ alkylenyl-C(O)—NH—, wherein Cy is optionally substituted with one or more of $R^1$;

$L^1$ is absent, —$NR^3$—, —O—, —S—, —C(O)—$NR^3$—, —$NR^3$—C(O)—, —C(O)—C(O)—, or an optionally substituted group selected from $C_{1-6}$ alkylenyl, $C_{2-6}$ alkynylenyl, —$NR^3$—$C_{1-6}$ alkylenyl, —O—$C_{1-6}$ alkylenyl, —C(O)—$C_{0-6}$ alkylenyl, —$C_{0-6}$ alkylenyl-C(O)— and —$C_{0-6}$ alkylenyl-OC(O)—;

$L^2$ is —$(NR^3)_s$—S(O)—$C_{0-6}$ alkylenyl-, —$(NR^3)_s$—$S(O)_2$—$C_{0-6}$ alkylenyl-, —$(NR^3)_s$—S(O)—$(NR^3)$—, —$S(O)_2$—$NR^3$—, —$NR^3$—$C_{1-6}$ alkylenyl, —$NR^3$—$C_{1-6}$ haloalkylenyl, —$(NR^3)_s$—P(O)($R^3$)—, —$C_{1-6}$ alkylenyl-S(O)—, —$C_{1-6}$ alkylenyl-$S(O)_2$—, —C(O)—$(NR^3)_s$—, —$(NR^3)_s$—C(O)—, or an optionally substituted 4- to 12-membered monocyclic or bicyclic heterocyclyl comprising 1 to 4 heteroatoms selected from N, O, and S;

V is selected from $C_{1-6}$ aliphatic, $C_{6-12}$ aryl, 4- to 12-membered monocyclic or polycyclic heterocyclyl comprising 1 to 4 heteroatoms selected from N, O, and S, 5- to 12-membered monocyclic or bicyclic heteroaryl comprising 1 to 4 heteroatoms selected from N, O, and S, 5- to 12-membered monocyclic of bicyclic aryl, and $C_{3-12}$ monocyclic or polycyclic cycloalkyl, wherein V is substituted with $(R^6)_m$;

Z is $C_{1-6}$ aliphatic, 2- to 10-membered heteroaliphatic, $P(O)(R^3)_2$, —$C(O)C_{1-6}$ aliphatic, —$C(O)N(R^3)_2$, $C_{6-12}$ aryl, $C_{3-12}$ monocyclic or polycyclic cycloalkyl, 4- to 16-membered monocyclic or polycyclic heterocyclyl comprising 1 to 4 heteroatoms selected from N, O, and S, or 5- to 12-membered monocyclic or bicyclic heteroaryl comprising 1 to 4 heteroatoms selected from N, O, and S, wherein Z is substituted with $(R^2)_q$;

each $R^a$ is independently hydrogen, halo, oxo, CN, or optionally substituted $C_{1-6}$ aliphatic or O—$C_{1-6}$ aliphatic;

each $R^1$ is independently selected from halo, $N(R^3)_2$, OH, CN, $C(O)NHR^3$, and an optionally substituted group selected from $C_{1-6}$ aliphatic and $N(R^3)$—C(O)—$C_{1-6}$ alkyl;

each $R^2$ is independently selected from halo, oxo, CN, OH, C(O)OH, C(O)O—$R^{2a}$, $C_{6-12}$ aryl, and an optionally substituted group selected from $C_{1-6}$ aliphatic, $C(O)C_{1-6}$ aliphatic, and O—$C_{1-6}$ aliphatic, where $R^{2a}$ is hydrogen or an optionally substitute group selected from 4- to 12-membered monocyclic or bicyclic heterocyclyl comprising 1 to 4 heteroatoms selected from N, O, and S, $C_{1-6}$ aliphatic, $C_{3-12}$ cycloalkyl;

each $R^3$ is independently selected from H and optionally substituted $C_{1-6}$ aliphatic;

each $R^5$ is independently selected from $C_{1-6}$ alkyl, —$N(R^3)_2$, —O—$C_{1-6}$ alkyl, C(O)—$C_{1-6}$ alkyl, $P(O)(C_{1-6}\text{ alkyl})_2$, $C_{3-12}$ cycloalkyl, and 5- to 12-membered heterocyclyl comprising 1 to 4 heteroatoms selected from N, O, and S, wherein $R^5$ is optionally substituted with one or more substituents selected from halo, OH, and 2- to 12-membered heteroaliphatic;

each $R^6$ is halo, oxo, $SF_5$, S(O)—$R^5$, $S(O)_2$—$R^5$, S(O)(NH)—$R^5$, $S(O)_2$(NH)—$R^5$, —CN, —C(O)—$R^5$, —$C_{0-6}$ alkylenyl-C(O)O—$R^5$, —C(O)—NH($R^5$), —C(O)—$N(R^5)_2$, —$P(O)(R^5)_2$, —O—$R^5$, or an optionally substituted group selected from O—$C_{1-6}$ alkyl, S—$C_{1-6}$ alkyl, $C_{1-6}$ alkyl, $C_{6-12}$ aryl, 2- to 12-membered heteroaliphatic, $C_{3-12}$ cycloalkyl, —O—$C_{0-6}$ alkylenyl-$C_{3-12}$ cycloalkyl, and 4- to 7-membered monocyclic heterocyclyl comprising 1 to 4 heteroatoms selected from N, O, and S;

m is 0, 1, 2, 3, or 4;

q is 0, 1, 2, 3, or 4; and s is 0 or 1.

In some embodiments, the present disclosure provides a compound of Formula I':

I'

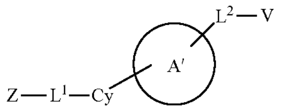

or a pharmaceutically acceptable salt thereof, wherein

A' is phenyl, 5- to 10-membered monocyclic or bicyclic heterocyclyl comprising 1 to 4 heteroatoms selected from N, O, P, and S, or 5- to 10-membered monocyclic or bicyclic heteroaryl comprising 1 to 4 heteroatoms selected from N, O, and S, optionally substituted with $R^a$;

Cy is absent, or a bivalent moiety selected from $C_{1-6}$ aliphatic, 4- to 14-membered monocyclic or polycyclic heterocyclyl comprising 1 to 4 heteroatoms selected from N, O, P, and S, 5- to 12-membered monocyclic or bicyclic heteroaryl comprising 1 to 4 heteroatoms selected from N, O, and S, $C_{6-12}$ aryl, and $C_{3-12}$ cycloalkyl, wherein Cy is optionally substituted with one or more of $R^1$;

$L^1$ is absent, —S—, —C(O)—$NR^3$—, —$NR^3$—C(O)—, or an optionally substituted bivalent moiety selected from $C_{1-6}$ alkylenyl, $C_{2-6}$ alkenylenyl, $C_{2-6}$ alkynylenyl, —$NR^3$—$C_{0-6}$ alkylenyl, —O—$C_{0-6}$ alkylenyl, —C(O)—$C_{0-6}$ alkylenyl, —$C_{1-6}$ alkylenyl-C(O)—, —C(O)O—$C_{0-6}$ alkylenyl, —$C_{1-6}$ alkylenyl-O—C(O)—, —$C_{3-6}$ cycloalkyl, and —$NR^3$—C(O)—$C_{0-6}$ alkylenyl-O—;

$L^2$ is —$(NR^3)_s$—S(O)—$(NR^3)$—, —$(NR^3)_s$—$S(O)_2$—$NR^3$—, —$(NR^3)_s$—$P(O)(R^3)$—, —C(O)—$(NR^3)_s$—, —$NR^3$—C(O)—, or an optionally substituted bivalent moiety selected from —$(NR^3)_s$—S(O)—$C_{0-6}$ alkylenyl-, —$(NR^3)_s$—$S(O)_2$—$C_{0-6}$ alkylenyl-, —$(NR^3)_s$—S(O)—$NR^3$—$C_{0-6}$ alkylenyl, —$(NR^3)_s$—$S(O)_2$—$NR^3$—$C_{0-6}$ alkylenyl, —$(NR^3)_s$—$S(O)_2$—$C_{3-6}$ cycloalkyl, —$NR^3$—$C_{0-6}$ alkylenyl, —$C_{1-6}$ alkylenyl-S(O)—$(NR^3)_s$—, —$C_{1-6}$ alkylenyl-$S(O)_2$—$(NR^3)_s$—, 2- to 6-membered heteroaliphatic, and 4- to 12-membered monocyclic or bicyclic heterocyclyl comprising 1 to 4 heteroatoms selected from N, O, and S;

V is selected from $C_{1-6}$ aliphatic, $C_{6-12}$ aryl, $C_{3-12}$ cycloaliphatic, 4- to 12-membered monocyclic or polycyclic heterocyclyl comprising 1 to 4 heteroatoms selected from N, O, and S, and 5- to 12-membered monocyclic or bicyclic heteroaryl comprising 1 to 4 heteroatoms selected from N, O, and S, wherein V is substituted with $(R^6)_m$;

Z is selected from $P(O)(R^3)_2$, $C(O)N(R^3)_2$, $C_{1-6}$ aliphatic, $C_{6-12}$ aryl, $C_{3-12}$ cycloaliphatic, 2- to 10-atom heteroaliphatic, 4- to 16-membered monocyclic or polycyclic heterocyclyl comprising 1 to 4 heteroatoms selected from N, O, and S, and 5- to 12-membered monocyclic or bicyclic heteroaryl comprising 1 to 4 heteroatoms selected from N, O, and S, wherein Z is substituted with $(R^2)_q$;

each $R^a$ is independently H, halo, —CN, oxo, or an optionally substituted group selected from $C_{1-6}$ aliphatic, $C_{3-6}$ cycloaliphatic, and O—$C_{1-6}$ aliphatic;

each $R^1$ is independently selected from halo, oxo, —$N(R^3)_2$, —OH, —CN, —$C(O)N(R^3)_2$, and an optionally substituted group selected from $C_{1-6}$ aliphatic and $N(R^3)$—C(O)—$C_{1-6}$ aliphatic;

each $R^2$ is independently selected from halo, oxo, —CN, —OH, O—$R^{2a}$, —C(O)—$R^{2a}$, —C(O)O—$R^{2a}$, and an optionally group selected from $C_{1-6}$ aliphatic, $C_{6-12}$ aryl, and 5- to 12-membered monocyclic or bicyclic heteroaryl comprising 1 to 4 heteroatoms selected from N, O, and S;

each $R^{2a}$ is independently H or an optionally substituted group selected from $C_{1-6}$ aliphatic, $C_{3-12}$ cycloaliphatic, and 4- to 12-membered monocyclic or bicyclic heterocyclyl comprising 1 to 4 heteroatoms selected from N, O, and S;

each $R^3$ is independently selected from H and optionally substituted $C_{1-6}$ aliphatic;

each $R^5$ is —$N(R^3)_2$ or an optionally substituted group selected from $C_{1-6}$ aliphatic, $P(O)(C_{1-6}\ aliphatic)_2$, $C_{3-12}$ cycloaliphatic, and 5- to 12-membered monocyclic or polycyclic heterocyclyl comprising 1 to 4 heteroatoms selected from N, O, and S;

each $R^6$ is independently selected from halo, oxo, —$SF_5$, —S(O)—$R^5$, $S(O)_2$—$R^5$, —S(O)(NH)—$R^5$, —$S(O)_2$—(NH)—$R^5$, —S(O)—$N(R^5)_2$, —$S(O)_2$—$N(R^5)_2$, —CN, —C(O)—$NH(R^5)$, —C(O)—$N(R^5)_2$, —$P(O)(R^5)_2$, —O—$R^5$, or an optionally substituted group selected from $C_{1-6}$ aliphatic, S—$C_{1-6}$ aliphatic, 2- to 12-membered heteroaliphatic, —$C_{0-6}$ alkylenyl-C(O)—$R^5$, —$C_{0-6}$ alkylenyl-C(O)O—$R^5$, $C_{6-12}$ aryl, $C_{3-12}$ cycloaliphatic, and 4- to 7-membered monocyclic heterocyclyl comprising 1 to 4 heteroatoms selected from N, O, and S;

m is 0, 1, 2, 3, or 4;

q is 0, 1, 2, 3, 4, 5, or 6; and each s is independently 0 or 1.

In some embodiments, the present disclosure provides and/or utilizes TRMPL1 modulators that are small molecule compounds having a chemical structure as indicated below in Formula II:

II

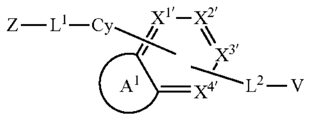

or a pharmaceutically acceptable salt thereof, wherein $X^{1'}$, $X^{2'}$, $X^{3'}$, and $X^{4'}$ are each independently selected from N, C, and $CR^a$, wherein $X^{1'}$, $X^{2'}$, $X^{3'}$, or $X^{4'}$ are C when bound to Cy-$L^1$-Z or $L^2$-V, and are N or $CR^a$ when not bound to Cy-$L^1$-Z or $L^2$-V;

A1 is absent, an optionally substituted fused heterocyclyl ring comprising 1 or 2 heteroatoms selected from N, O, and S, or an optionally substituted fused heteroaryl group comprising 1 or 2 heteroatoms selected from N, O, and S;

Cy is absent, 4- to 12-membered monocyclic or bicyclic heterocyclyl comprising 1 to 4 heteroatoms selected from N, O, and S, 5- to 12-membered monocyclic or bicyclic heteroaryl comprising 1 to 4 heteroatoms selected from N, O, and S, $C_{1-6}$ aliphatic, or $C_{3-12}$ cycloalkyl, wherein Cy is optionally substituted with one or more of $R^1$;

$L^1$ is absent, —$NR^3$—, —O—, —S—, $C_{1-6}$ alkylenyl, $C_{2-6}$ alkynylenyl, —$NR^3$—$C_{1-6}$ alkylenyl,—O—$C_{1-6}$ alkylenyl, —C(O)$C_{0-6}$ alkylenyl; —C(O)$NR^3$—, or —C(O)—C(O)—;

$L^2$ is —$(NR^3)_s$—S(O)—$C_{0-6}$ alkylenyl-, —$(NR^3)_s$—$S(O)_2$—$C_{0-6}$ alkylenyl-, —$(NR^3)_s$—S(O)$(NR^3)$—, —$S(O)_2$—$NR^3$—, —$NR^3$—$C_{1-6}$ haloalkylenyl, —$(NR^3)_s$—$P(O)(R^3)$—, —$C_{1-6}$ alkylenyl-S(O)—, —$C_{1-6}$ alkylenyl-$S(O)_2$—, —C(O)—$(NR^3)_s$—, —$(NR^3)_s$—C(O)—, or an optionally substituted 4- to 12-membered monocyclic or bicyclic heterocyclyl comprising 1 to 4 heteroatoms selected from N, O, and S;

V is selected from $C_{1-6}$ aliphatic, $C_{6-12}$ aryl, 4- to 12-membered monocyclic or bicyclic heterocyclyl comprising 1 to 4 heteroatoms selected from N, O, and S, 5- to 12-membered monocyclic or bicyclic heteroaryl comprising 1 to 4 heteroatoms selected from N, O, and S, 5- to 12-membered monocyclic of bicyclic aryl, and $C_{3-12}$ cycloalkyl, wherein V is substituted with $(R^6)_m$;

Z is $C_{1-6}$ aliphatic, 2- to 10-membered heteroaliphatic, $P(O)(R^3)_2$, —C(O)$C_{1-6}$ aliphatic, $C(O)N(R^3)_2$, $C_{6-12}$ aryl, $C_{3-12}$ cycloalkyl, 4- to 16-membered monocyclic or polycyclic heterocyclyl comprising 1 to 4 heteroatoms selected from N, O, and S, or 5- to 12-membered monocyclic or bicyclic heteroaryl comprising 1 to 4 heteroatoms selected from N, O, and S, wherein Z is substituted with $(R^2)_q$;

each $R^a$ is independently hydrogen, halo, oxo, or optionally substituted $C_{1-6}$ aliphatic;

each $R^1$ is independently selected from $N(R^3)_2$, OH, CN, $C(O)NHR^3$, and an optionally substituted group selected from $C_{1-6}$ aliphatic and $N(R^3)$—C(O)—$C_{1-6}$ alkyl;

each $R^2$ is independently selected from halo, —CN, C(O)OH, and an optionally substituted group selected from $C_{1-6}$ alkyl, C(O)$C_{1-6}$ aliphatic, and O—$C_{1-6}$ aliphatic;

each $R^3$ is independently selected from H and optionally substituted $C_{1-6}$ aliphatic;

each $R^5$ is independently selected from $C_{1-6}$ alkyl, —$N(R^3)_2$, —O—$C_{1-6}$ alkyl, C(O)—$C_{1-6}$ alkyl, P(O)($C_{1-6}$ alkyl)$_2$, $C_{3-12}$ cycloalkyl, and 5- to 12-membered heterocyclyl comprising 1 to 4 heteroatoms selected from N, O, and S, wherein $R^5$ is optionally substituted with one or more substituents selected from halo and OH;

each $R^6$ is halo, S(O)—$R^5$, $S(O)_2$—$R^5$, S(O)(NH)—$R^5$, —CN, —C(O)—$R^5$, —C(O)O—$R^5$, —C(O)—NH($R^5$), —C(O)—$N(R^5)_2$, —$P(O)(R^5)_2$, or an optionally substituted group selected from O—$C_{1-6}$ alkyl, $C_{1-6}$ alkyl, and $C_{6-12}$ aryl;

m is 0, 1, 2, 3, or 4;

q is 0, 1, 2, 3, or 4; and each s is independently 0 or 1.

In some embodiments the present disclosure provides a compound of Formula II':

II'

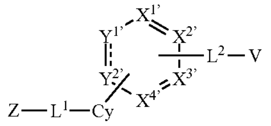

or a pharmaceutically acceptable salt thereof, wherein $X^{1'}$, $X^{2'}$, $X^{3'}$, and $X^{4'}$ are each independently selected from N, C, $CR^a$, wherein $X^{1'}$, $X^{2'}$, $X^{3'}$, and $X^{4'}$ are C when bound to Cy-$L^1$-Z or $L^2$-V, and are N or $CR^a$ when not bound to Cy-$L^1$-Z or $L^2$-V;

$Y^{1'}$ and $Y^{2'}$ are selected from each C, N, and $CR^a$, or one of $Y^{1'}$ or $Y^{2'}$ is absent and the other of $Y^{1'}$ or $Y^{2'}$ is selected from C, N, and $CR^a$;

Cy is absent, or a bivalent moiety selected from $C_{1-6}$ aliphatic, 4- to 12-membered monocyclic or polycyclic heterocyclyl comprising 1 to 4 heteroatoms selected from N, O, P, and S, 5- to 12-membered monocyclic or bicyclic heteroaryl comprising 1 to 4 heteroatoms selected from N, O, and S, and $C_{3-12}$ cycloalkyl, wherein Cy is optionally substituted with one or more of $R^1$;

$L^1$ is absent, —S—, —C(O)—$NR^3$—, —$NR^3$—C(O)—, —C(O)—C(O)—, or an optionally substituted bivalent group selected from $C_{1-6}$ alkylenyl, $C_{2-6}$ alkynylenyl, —$NR^3$—$C_{0-6}$ alkylenyl, —O—$C_{0-6}$ alkylenyl, —C(O)—$C_{0-6}$ alkylenyl, —$C_{1-6}$ alkylenyl-C(O)—, —C(O)O—$C_{0-6}$ alkylenyl, —$C_{1-6}$ alkylenyl-O—C(O)—, —$C_{3-6}$ cycloalkyl, and —$NR^3$—C(O)—$C_{0-6}$ alkylenyl-O—;

$L^2$ is —$(NR^3)_s$—S(O)—($NR^3$)—, —$(NR^3)_s$—$S(O)_2$—$NR^3$—, —$(NR^3)_s$—P(O)($R^3$)—, —C(O)—$(NR^3)_s$—, —$NR^3$—C(O)—, or an optionally substituted bivalent group selected from —$(NR^3)_s$—S(O)—$C_{0-6}$ alkylenyl-, —$(NR^3)_s$—$S(O)_2$—$C_{0-6}$ alkylenyl-,—$(NR^3)_s$—S(O)—$NR^3$—$C_{0-6}$ alkylenyl, —$(NR^3)_s$—$S(O)_2$—$NR^3$—$C_{0-6}$ alkylenyl, —$(NR^3)_s$—$S(O)_2$—$C_{3-6}$ cycloalkyl, —$NR^3$—$C_{0-6}$ alkylenyl, —$C_{1-6}$ alkylenyl-S(O)—$(NR^3)_s$—, —$C_{1-6}$ alkylenyl-$S(O)_2$—$(NR^3)_s$—, and 4- to 12-membered monocyclic or bicyclic heterocyclyl comprising 1 to 4 heteroatoms selected from N, O, and S;

V is selected from $C_{1-6}$ aliphatic, $C_{6-12}$ aryl, $C_{3-12}$ cycloaliphatic, 4- to 12-membered monocyclic or polycyclic heterocyclyl comprising 1 to 4 heteroatoms selected from N, O, and S, and 5- to 12-membered monocyclic or bicyclic heteroaryl comprising 1 to 4 heteroatoms selected from N, O, and S, wherein V is substituted with $(R^6)_m$;

Z is selected from $P(O)(R^3)_2$, $C(O)N(R^3)_2$, $C_{1-6}$ aliphatic, $C_{6-12}$ aryl, $C_{3-12}$ cycloaliphatic, 2- to 10-atom heteroaliphatic, 4- to 16-membered monocyclic or polycyclic heterocyclyl comprising 1 to 4 heteroatoms selected from N, O, and S, and 5- to 12-membered monocyclic or bicyclic heteroaryl comprising 1 to 4 heteroatoms selected from N, O, and S, wherein Z is substituted with $(R^2)_q$;

each $R^a$ is independently H, halo, —CN, oxo, or an optionally substituted group selected from $C_{1-6}$ aliphatic and O—$C_{1-6}$ aliphatic, or two $R^a$ together when on adjacent atoms form a fused optionally substituted fused heterocyclyl ring comprising 1 or 2 heteroatoms selected from N, O, and S, or a fused optionally substituted heteroaryl group comprising 1 or 2 heteroatoms selected from N, O, and S;

each $R^1$ is independently selected from halo, —$N(R^3)_2$, —OH, —CN, —C(O)$N(R^3)_2$, and an optionally substituted group selected from $C_{1-6}$ aliphatic and N($R^3$)—C(O)—$C_{1-6}$ aliphatic;

each $R^2$ is independently selected from halo, oxo, —CN, —OH, O—$R^{2a}$, —C(O)—$R^{2a}$, —C(O)O—$R^{2a}$, and an optionally group selected from $C_{1-6}$ aliphatic, $C_{6-12}$ aryl, and 5- to 12-membered monocyclic or bicyclic heteroaryl comprising 1 to 4 heteroatoms selected from N, O, and S;

each $R^{2a}$ is independently H or an optionally substituted group selected from $C_{1-6}$ aliphatic, $C_{3-12}$ cycloaliphatic, and 4- to 12-membered monocyclic or bicyclic heterocyclyl comprising 1 to 4 heteroatoms selected from N, O, and S;

each $R^3$ is independently selected from H and optionally substituted $C_{1-6}$ aliphatic;

each $R^5$ is —$N(R^3)_2$ or an optionally substituted group selected from $C_{1-6}$ aliphatic, P(O)($C_{1-6}$ aliphatic)$_2$, $C_{3-12}$ cycloaliphatic, and 5- to 12-membered monocyclic or polycyclic heterocyclyl comprising 1 to 4 heteroatoms selected from N, O, and S;

each $R^6$ is independently selected from halo, oxo, —$SF_5$, —S(O)—$R^5$, $S(O)_2$—$R^5$, —S(O)(NH)—$R^5$, —$S(O)_2$—(NH)—$R^5$, —S(O)—$N(R^5)_2$, —$S(O)_2$—$N(R^5)_2$, —CN, —C(O)—NH($R^5$), —C(O)—$N(R^5)_2$, —$P(O)(R^5)_2$, —O—$R^5$, or an optionally substituted group selected from $C_{1-6}$ aliphatic, S—$C_{1-6}$ aliphatic, 2- to 12-membered heteroaliphatic, —$C_{0-6}$ alkylenyl-C(O)—$R^5$, —$C_{0-6}$ alkylenyl-C(O)O—$R^5$, $C_{6-12}$ aryl, $C_{3-12}$ cycloaliphatic, and 4- to 7-membered monocyclic heterocyclyl comprising 1 to 4 heteroatoms selected from N, O, and S;

m is 0, 1, 2, 3, or 4;

q is 0, 1, 2, 3, 4, 5, or 6; and each s is independently 0 or 1.

Compounds of formula I, I', II, and/or II' are described with respect to the exemplary embodiments herein.

As defined generally above for compounds of formula I', A' is phenyl, 5- to 10-membered monocyclic or bicyclic heterocyclyl comprising 1 to 4 heteroatoms selected from N, O, P, and S, or 5- to 10-membered monocyclic or bicyclic heteroaryl comprising 1 to 4 heteroatoms selected from N, O, and S, optionally substituted with $R^a$.

In some embodiments, A' is phenyl.

In some embodiments, A' is 9-membered bicyclic heteroaryl comprising 1 to 4 heteroatoms selected from N, O, and S. In some embodiments, A' is indazolyl.

In some embodiments, A' is 5- to 6-membered monocyclic heteroaryl comprising 1 to 4 heteroatoms selected from N, O, and S. In some embodiments, A' is pyrazolyl, imidazolyl, triazolyl, thiadiazolyl, or isoxazolyl.

In some embodiments, A' is 9- or 10-membered bicyclic heterocyclyl comprising 1 to 4 heteroatoms selected from N, O, and S. In some embodiments, A' is isoindolinyl, tetrahydroquinoxalinyl, tetrahydropyrazolopyridinyl, tetrahydroquinoxalinyl, or dihydrobenzoimidazolonyl.

In some embodiments, A' is selected from Table A':

TABLE A'

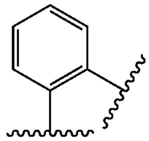,
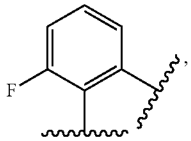,
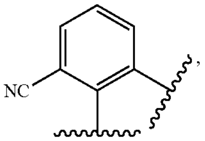,
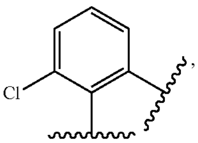,
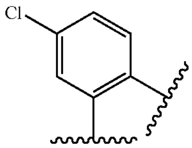,
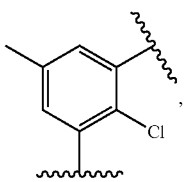,
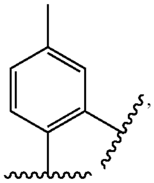,
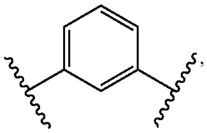,
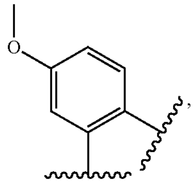,
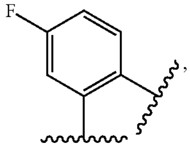,
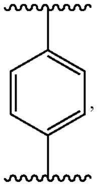,
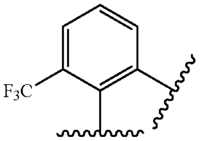,
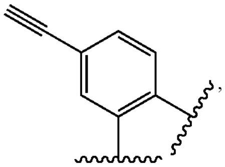,
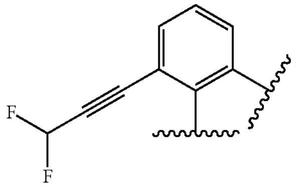,
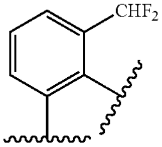, TABLE A'-continued

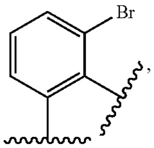,
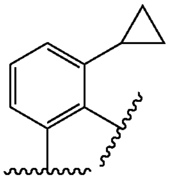,
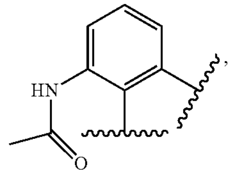,
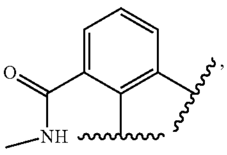,
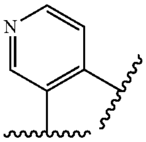,
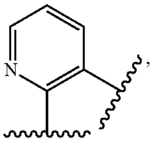,
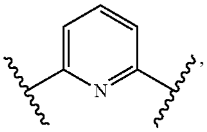,
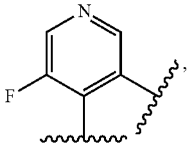,
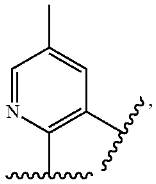,
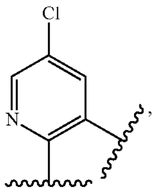,
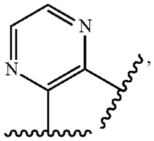,
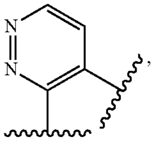,
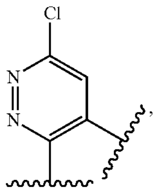,
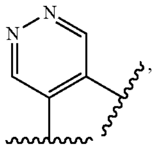,
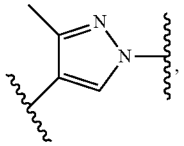,
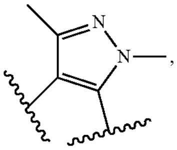,
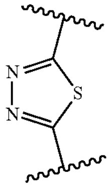,
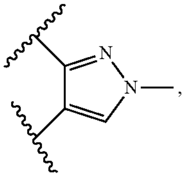,
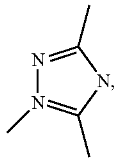,
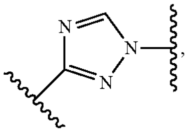,
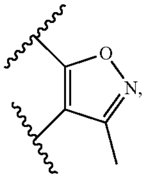,
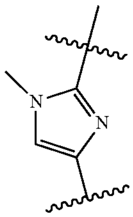,
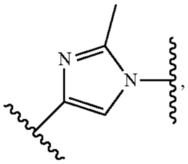,
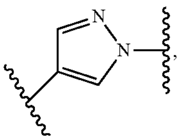, TABLE A'-continued

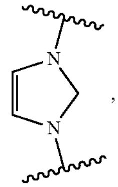, 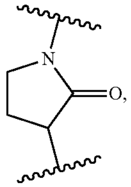 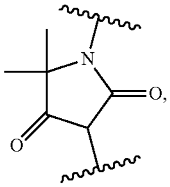

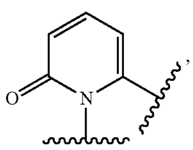 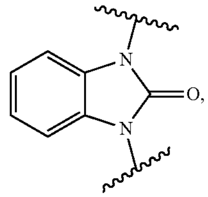

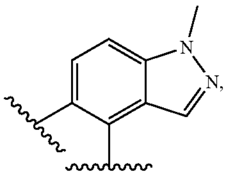 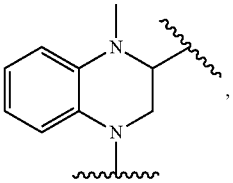

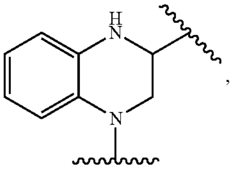 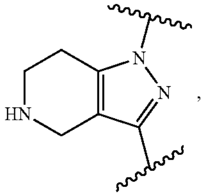

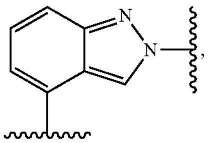 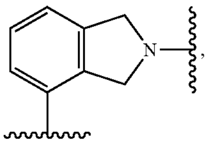

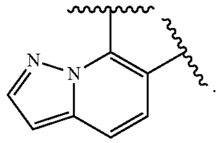 [SMILES: *c1ccc2ccnn2c1*]

In some embodiments, A' is

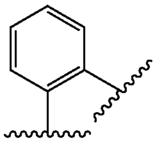 or 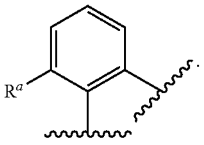

In some embodiments, A' is

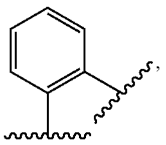 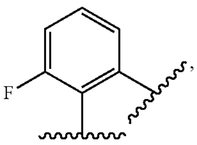 or

-continued

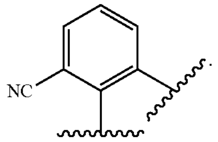

In some embodiments, A' is

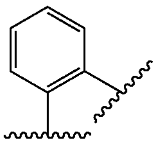 or 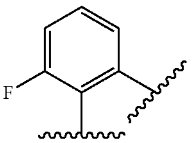

In some embodiments, A' is

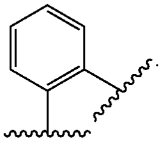 [SMILES: *c1ccccc1*]

As defined generally above for compounds of formula II and/or II', $X^{1'}$, $X^{2'}$, $X^{3'}$, and $X^{4'}$ are each independently selected from N, C, and $CR^a$, wherein $X^{1'}$, $X^{2'}$, $X^{3'}$, or $X^{4'}$ are C or N when bound to Cy-$L^1$-Z or $L^2$-V, as valency permits. That is, when any of $X^{1'}$, $X^{2'}$, $X^{3'}$, and $X^{4'}$ are bound to Cy-$L^1$-Z or $L^2$-V, a value for variables $X^{1'}$, $X^{2'}$, $X^{3'}$, or $X^{4'}$ is C-Cy-$L^1$-Z or C-$L^2$-V, and the remaining values for variables of $X^{1'}$, $X^{2'}$, $X^{3'}$, and $X^{4'}$ are independently selected from N and $CR^a$. It is understood that only one instance of Cy-$L^1$-Z and $L^2$-V will appear on a compound of formula II or II'.

In some embodiments, each of $X^{1'}$, $X^{2'}$, $X^{3'}$, and $X^{4'}$ are C or $CR^a$, where $X^{1'}$, $X^{2'}$, $X^{3'}$, or $X^{4'}$ are C when bound to Cy-$L^1$-Z or $L^2$-V, and the remaining variables are $CR^a$. In some embodiments, $X^{1'}$ is C-Cy-$L^1$-Z, $X^{2'}$ is C-$L^2$-V, and $X^{3'}$ and $X^{4'}$ are each $CR^a$. In some embodiments, $X^{2'}$ is C-Cy-$L^1$-Z, $X^{3'}$ is C-$L^2$-V, and $X^{1'}$ and $X^{4'}$ are each $CR^a$. In some embodiments, $X^{3'}$ is C-Cy-$L^1$-Z, $X^{4'}$ is C-$L^2$-V, and $X^{1'}$ and $X^{2'}$ are each $CR^a$. In some embodiments, $X^{4'}$ is C-Cy-$L^1$-Z, $X^{1'}$ is C-$L^2$-V, and $X^{2'}$ and $X^{3'}$ are each $CR^a$.

As defined generally above with respect to formula II', $Y^{1'}$ and $Y^{2'}$ are selected from each C, N, and $CR^a$, or one of $Y^{1'}$ or $Y^{2'}$ is absent and the other of $Y^{1'}$ or $Y^{2'}$ is selected from C, N, and $CR^a$. In some embodiments, each of $Y^{1'}$ and $Y^{2'}$ are $CR^a$. In some embodiments, when each of $Y^{1'}$ and $Y^{2'}$ are $CR^a$, two $R^a$ on can come together to form a ring, and formula II' may be represented by:

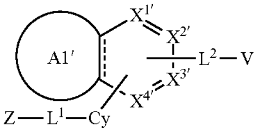

where A1' is a fused optionally substituted fused heterocyclyl ring comprising 1 or 2 heteroatoms selected from N, O, and S, or an optionally substituted fused heteroaryl group comprising 1 or 2 heteroatoms selected from N, O, and S.

As defined generally above, with respect to formula II, A1 is absent or an optionally substituted fused heterocyclyl ring comprising 1 or 2 heteroatoms selected from N, O, and S, or an optionally substituted fused heteroaryl group comprising 1 or 2 heteroatoms selected from N, O, and S. In some embodiments, A1 is absent, a compound of formula II is represented by:

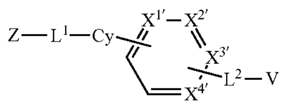

where Z, $L^1$, Cy, $X^{1'}$, $X^{1'}$, $X^{2'}$, $X^{3'}$, $X^{4'}$, L, and V are as defined in classes and subclasses herein.

In some embodiments, A1 is absent, and each $X^{1'}$, $X^{2'}$, $X^{3'}$, and $X^{4'}$ is C or $CR^a$, and wherein $X^{1'}$, $X^{2'}$, $X^{3'}$, or $X^{4'}$ are C when bound to Cy-$L^1$-Z or $L^2$-V, a compound of formula II is represented by:

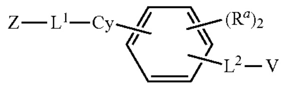

where Z, $L^1$, Cy, $R^a$, L, and V are as defined in classes and subclasses herein.

In some embodiments of formula II', each of $Y^{1'}$ and $Y^{2'}$ is $CR^a$, each of $X^{1'}$, $X^{2'}$, $X^{3'}$, and $X^{4'}$ is C or $CR^a$, wherein $X^{1'}$, $X^{2'}$, $X^{3'}$, or $X^{4'}$ are C when bound to Cy-$L^1$-Z or $L^2$-V, and a compound of formula II' is represented by:

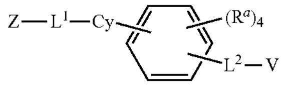

where Z, $L^1$, Cy, $R^a$, L, and V are as defined in classes and subclasses herein.

In some embodiments of formula II', each of $Y^{1'}$ and $Y^{2'}$ is $CR^a$, each of $X^{1'}$, $X^{2'}$, $X^{3'}$, and $X^{4'}$ is C or $CR^a$, wherein $X^{1'}$, $X^{2'}$, $X^{3'}$, or $X^{4'}$ are C when bound to Cy-$L^1$-Z or $L^2$-V, and a compound of formula II' is represented by:

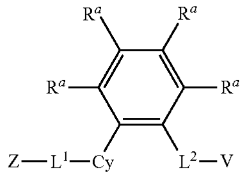

where Z, $L^1$, Cy, $R^a$, L, and V are as defined in classes and subclasses herein.

As defined generally above for compounds of formulae I, I', II, II', or any other formulae provided herein, each $R^a$ is independently H, halo, —CN, oxo, or an optionally substituted group selected from $C_{1-6}$ aliphatic and O—$C_{1-6}$ aliphatic, or two $R^a$ together when on adjacent atoms form a fused optionally substituted fused heterocyclyl ring comprising 1 or 2 heteroatoms selected from N, O, and S, or a fused optionally substituted heteroaryl group comprising 1 or 2 heteroatoms selected from N, O, and S.

In some embodiments, $R^a$ is hydrogen.

In some embodiments, $R^a$ is optionally substituted $C_{1-6}$ aliphatic. In some embodiments, $R^a$ is optionally substituted $C_{1-6}$ alkyl. In some embodiments, $R^a$ is optionally substituted $C_{1-3}$ alkyl. In some embodiments, $R^a$ is methyl.

In some embodiments, $R^a$ is optionally substituted O—$C_{1-6}$ alkyl. In some embodiments, $R^a$ is optionally substituted O—$C_{1-3}$ alkyl. In some embodiments, $R^a$ is $OCH_3$.

In some embodiments, $R^a$ is halo. In some embodiments, $R^a$ is bromo, chloro, fluoro, or iodo. In some embodiments, $R^a$ is bromo. In some embodiments, $R^a$ is chloro. In some embodiments, $R^a$ is fluoro. In some embodiments, $R^a$ is iodo.

In some embodiments, $R^a$ is CN.

In some embodiments, two $R^a$ together when on adjacent atoms form a fused optionally substituted fused heterocyclyl ring comprising 1 or 2 heteroatoms selected from N, O, and S, or a fused optionally substituted heteroaryl group comprising 1 or 2 heteroatoms selected from N, O, and S.

In some embodiments, a compound of formula I, I', II or II' is represented by:

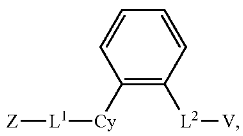,
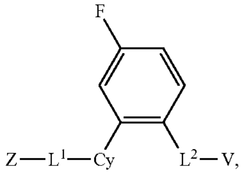,
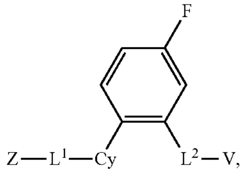,
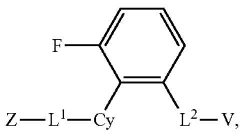,
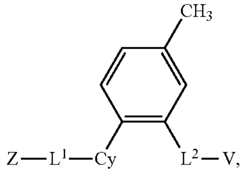,
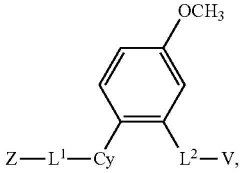,
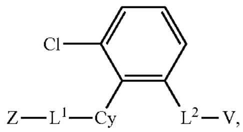,
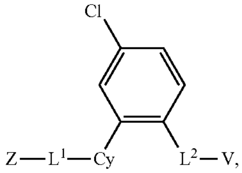,
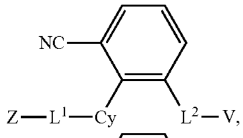, or
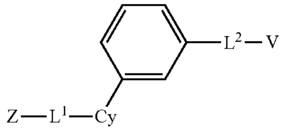

where Cy, $L^1$, $L^2$, Z, and V are described in classes and subclasses herein.

As defined generally above for compounds of formula I, I', II, II', or any other formulae provided herein, Cy is absent or a bivalent moiety selected from 4- to 12-membered monocyclic or bicyclic heterocyclyl comprising 1 to 4 heteroatoms selected from N, O, P, and S, 5- to 12-membered monocyclic or bicyclic heteroaryl comprising 1 to 4 heteroatoms selected from N, O, P, and S, $C_{1-6}$ aliphatic, or $C_{3-12}$ cycloalkyl, wherein Cy is optionally substituted with one or more $R^1$.

In some embodiments, Cy is absent, $C_{1-6}$ aliphatic, 4- to 12-membered monocyclic or polycyclic heterocyclyl comprising 1 to 4 heteroatoms selected from N, O, P, and S, 5- to 12-membered monocyclic or bicyclic heteroaryl comprising 1 to 4 heteroatoms selected from N, O, and S, or $C_{3-12}$ cycloaliphatic, wherein Cy is optionally substituted with one or more of $R^1$. It is understood that Cy is a bivalent moiety in any of formula I, I', II, II' or any other formulae provided herein. That is, reference to a particular Cy group is intended to refer to a bivalent variation of the referenced group.

In some embodiments, Cy is optionally substituted with one or more $R^1$, i.e., is substituted with 0, 1, 2, 3, or 4 $R^1$. In some embodiments, Cy is unsubstituted (i.e., is substituted with 0 $R^1$). In some embodiments, Cy is substituted with 1, 2, 3, or 4 $R^1$. In some embodiments, Cy is substituted with 1 $R^1$. In some embodiments, Cy is substituted with 2 $R^1$. In some embodiments, Cy is substituted with 3 $R^1$. In some embodiments, Cy is substituted with 4 $R^1$.

In some embodiments, Cy is absent.

In some embodiments, Cy is 4- to 12-membered monocyclic or polycyclic heterocyclyl comprising 1 to 4 heteroatoms selected from N, O, and S. In some embodiments, Cy is 4- to 7-membered monocyclic heterocyclyl comprising 1 to 3 heteroatoms selected from N, O, P, and S. In some embodiments, Cy is 4- to 7-membered monocyclic heterocyclyl comprising 1 heteroatom selected from N, O, P, and S. In some embodiments, Cy is 4-membered monocyclic heterocyclic comprising 1 heteroatom selected from N, O, P, and S. In some embodiments, Cy is 5-membered monocyclic heterocyclic comprising 1 to 2 heteroatoms selected from N, O, P, and S. In some embodiments, Cy is 6-membered monocyclic heterocyclic comprising 1 to 3 heteroatoms selected from N, O, P, and S. In some embodiments, Cy is 7-membered monocyclic heterocyclic comprising 1 to 3 heteroatoms selected from N, O, P, and S. In some embodiments, In some embodiments, Cy is azetidinyl, pyrrolidinyl, piperadinyl, piperazinyl, or azepanyl.

In some embodiments, Cy is azetidinyl, optionally substituted with one or more $R^1$.

In some embodiments, Cy is piperadinyl optionally substituted with one or more $R^1$. In some embodiments, Cy is unsubstituted piperadinyl. In some embodiments, Cy is piperadinyl substituted with one or more $R^1$.

In some embodiments, Cy is piperazinyl optionally substituted with one or more $R^1$. In some embodiments, Cy is unsubstituted piperazinyl. In some embodiments, Cy is piperazinyl substituted with one or more $R^1$.

In some embodiments, Cy is azepanyl optionally substituted with one or more $R^1$. In some embodiments, Cy is unsubstituted azepanyl. In some embodiments, Cy is azepanyl substituted with one or more $R^1$.

In some embodiments, Cy is

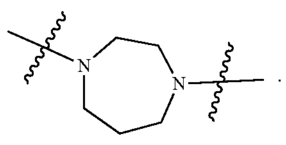 [SMILES: *N1CCCN(*)CC1]

optionally substituted with one or more $R^1$. In some embodiments, Cy is unsubstituted

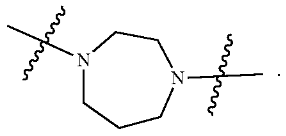 [SMILES: *N1CCCN(*)CC1]

In some embodiments, Cy is

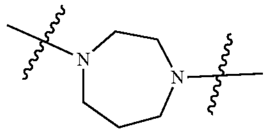 [SMILES: *N1CCCN(*)CC1]

substituted with one or more $R^1$.

In some embodiments, Cy is 7- to 12-membered polycyclic heterocyclyl comprising 1 to 4 heteroatoms selected from N, O, P, and S. In some embodiments, Cy is 10- to 12-membered polycyclic heterocyclyl comprising 1 to 4 heteroatoms selected from N, O, P, and S. In some embodiments, Cy is 10-membered polycyclic heterocyclyl comprising 1 to 4 heteroatoms selected from N, O, P, and S. In some embodiments, Cy is 11-membered polycyclic heterocyclyl comprising 1 to 4 heteroatoms selected from N, O, P, and S. In some embodiments, Cy is 12-membered polycyclic heterocyclyl comprising 1 to 4 heteroatoms selected from N, O, P, and S.

In some embodiments, Cy is

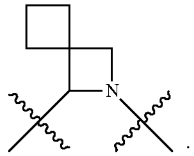 [SMILES: *C1N(*)CC12CCC2]

In some embodiments, Cy is

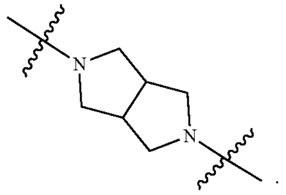 [SMILES: *N1CC2CN(*)CC2C1]

In some embodiments, Cy is

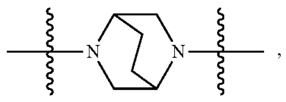 [SMILES: *N1CC2CCC1CN2*]
,

In some embodiments, Cy is

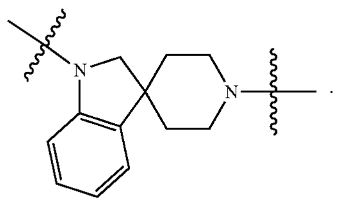 [SMILES: *N1CCC2(CC1)CN(*)c1ccccc12]

In some embodiments, Cy is 5- to 12-membered monocyclic or bicyclic heteroaryl comprising 1 to 4 heteroatoms selected from N, O, P, and S. In some embodiments, Cy is 5- or 6-membered monocyclic heteroaryl comprising 1 to 4 heteroatoms selected from N, O, and S. In some embodiments, Cy is 5-membered monocyclic heteroaryl comprising 1 to 4 heteroatoms selected from N, O, and S. In some embodiments, Cy is 6-membered monocyclic heteroaryl comprising 1 to 4 heteroatoms selected from N, O, and S.

In some embodiments, Cy is 7- to 12-membered bicyclic heteroaryl comprising 1 to 4 heteroatoms selected from N, O, P, and S. In some embodiments, Cy is 9- to 12-membered bicyclic heteroaryl comprising 1 to 4 heteroatoms selected from N, O, P, and S. In some embodiments, Cy is 9-membered bicyclic heteroaryl comprising 1 to 4 heteroatoms selected from N, O, P, and S. In some embodiments, Cy is 10-membered bicyclic heteroaryl comprising 1 to 4 heteroatoms selected from N, O, P, and S. In some embodiments, Cy is 11-membered bicyclic heteroaryl comprising 1 to 4 heteroatoms selected from N, O, P, and S. In some embodiments, Cy is 12-membered bicyclic heteroaryl comprising 1 to 4 heteroatoms selected from N, O, P, and S.

In some embodiments, Cy is $C_{1-6}$ aliphatic. In some embodiments, Cy is $C_{1-6}$ alkylenyl. In some embodiments, Cy is $C_{1-3}$ alkylenyl.

In some embodiments, Cy is $C_{3-12}$ cycloaliphatic. In some embodiments, Cy is $C_{3-12}$ cycloalkyl. In some embodiments, Cy is $C_{3-6}$ cycloalkyl. In some embodiments, Cy is cyclobutyl, cyclopentyl, or cyclohexyl. In some embodiments, Cy is cyclobutyl. In some embodiments, Cy is cyclopentyl. In some embodiments, Cy is cyclohexyl.

In some embodiments, Cy is absent or a bivalent moiety selected from 4- to 12-membered monocyclic or bicyclic heterocyclyl comprising 1 to 4 heteroatoms selected from N, O, P, and S, 5- to 12-membered monocyclic or bicyclic heteroaryl comprising 1 to 4 heteroatoms selected from N, O, P, and S, $C_{1-6}$ aliphatic, or $C_{3-12}$ cycloalkyl, wherein Cy is optionally substituted with one or more $R^1$, and wherein Cy is not piperazinyl. In some embodiments, Cy is 4- to 12-membered monocyclic or bicyclic heterocyclyl comprising 1 to 4 heteroatoms selected from N, O, P, and S, wherein Cy is not piperazinyl.

As defined generally above, each $R^1$ is independently selected from $N(R^3)_2$, OH, CN, $C(O)NHR^3$, and an optionally substituted group selected from $C_{1-6}$ aliphatic and $N(R^3)$—C(O)—$C_{1-6}$ alkyl.

As defined generally above for compounds of formulae I, I', II, II', or any other formulae provided herein, each $R^1$ is independently selected from halo, —$N(R^3)_2$, —OH, —CN, —$C(O)N(R^3)_2$, and an optionally substituted group selected from $C_{1-6}$ aliphatic and $N(R^3)$—C(O)—$C_{1-6}$ aliphatic.

In some embodiments, $R^1$ is halo. In some embodiments, $R^1$ is bromo, chloro, fluoro, or iodo. In some embodiments, $R^1$ is bromo. In some embodiments, $R^1$ is chloro. In some embodiments, $R^1$ is fluoro. In some embodiments, $R^1$ is iodo.

In some embodiments, $R^1$ is —$N(R^3)_2$. In some embodiments, $R^1$ is $NH_2$. In some embodiments, $R^1$ is $N(H)(C_{1-6}$ aliphatic). In some embodiments, $R^1$ is $N(H)(CH_3)$. In some embodiments, $R^1$ is $N(CH_3)_2$.

In some embodiments, $R^1$ is —OH. In some embodiments, $R^1$ is —CN.

In some embodiments, $R^1$ is —$C(O)N(R^3)_2$. In some embodiments, $R^1$ is —$C(O)NHR^3$. In some embodiments, $R^1$ is $C(O)N_{12}$.

In some embodiments, $R^1$ is optionally substituted $C_{1-6}$ aliphatic. In some embodiments, $R^1$ is optionally substituted $C_{1-6}$ alkyl. In some embodiments, $R^1$ is optionally substituted $C_{1-4}$ alkyl. In some embodiments, $R^1$ is optionally substituted methyl, ethyl, propyl, or butyl. In some embodiments, $R^1$ is methyl.

In some embodiments, $R^1$ is $N(R^3)$—C(O)—$C_{1-6}$ aliphatic. In some embodiments, $R^1$ is $N(R^3)$—C(O)—$C_{1-6}$ alkyl.

In some embodiments, a substituent on an optionally substituted carbon atom of an optionally substituted $R^1$ group is selected from: halo, OH, $NH_2$, and oxo.

In some embodiments, Cy is selected from Table Cy:

TABLE Cy

—$CH_2$—, —$CH_2$—C(O)—NH—,

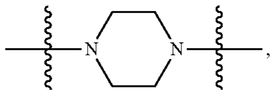, 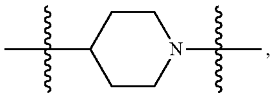,

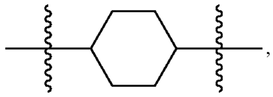, 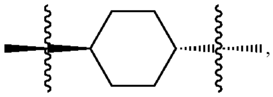,

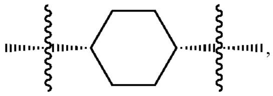, 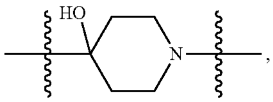,

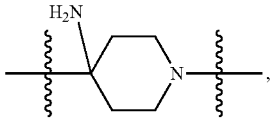, 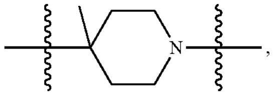,

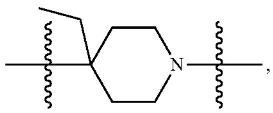, 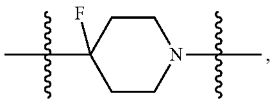,

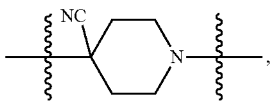, 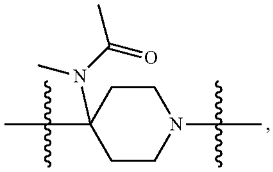,

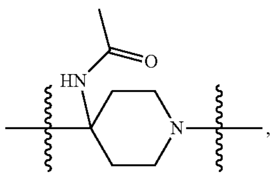, 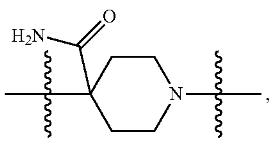,

TABLE Cy-continued
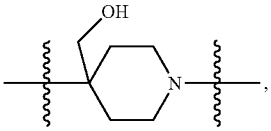, 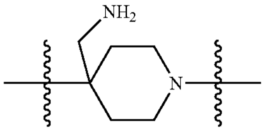,
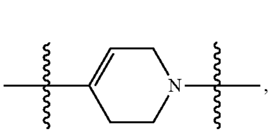, 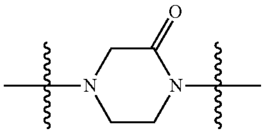,
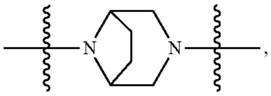, 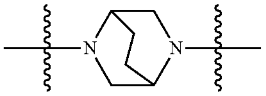,
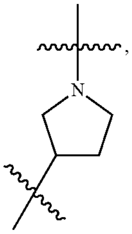, 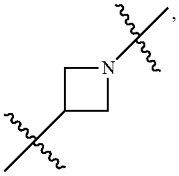, 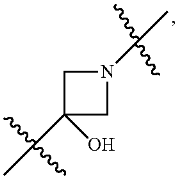,
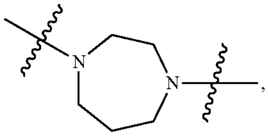, 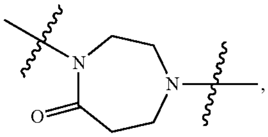,
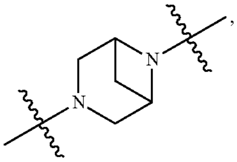, 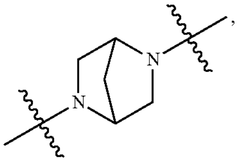,
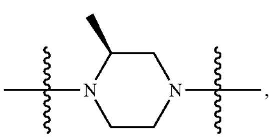, 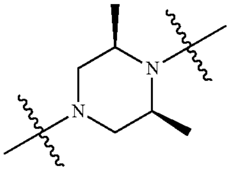,
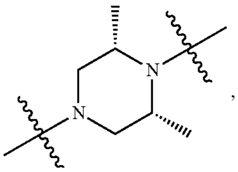, 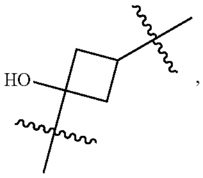,
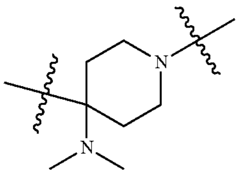, 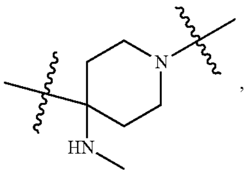,
TABLE Cy-continued
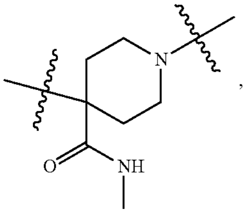, 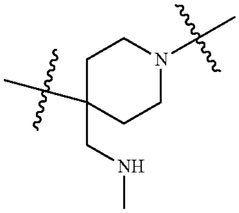,
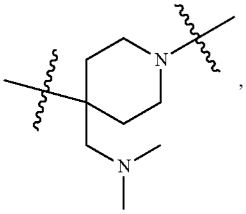, 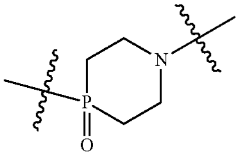,
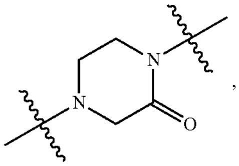, 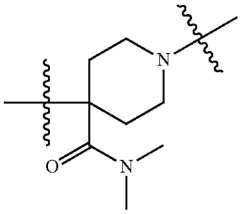,
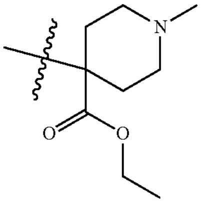, 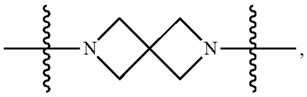,
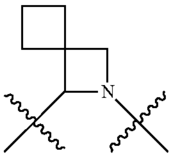, 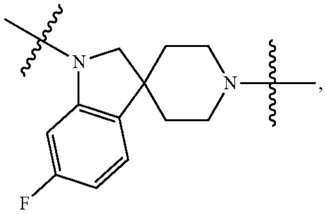,
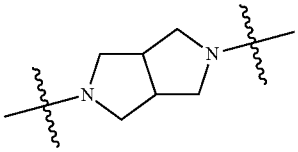,
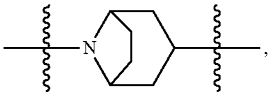, 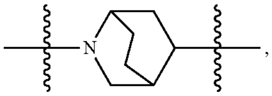,
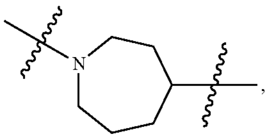, 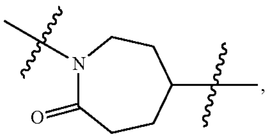, TABLE Cy-continued

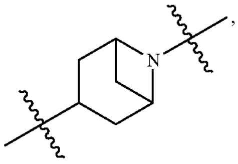,
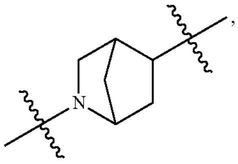,
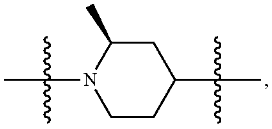,
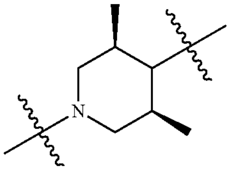,
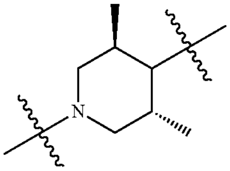,
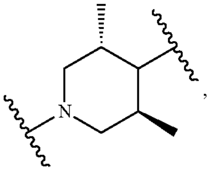,
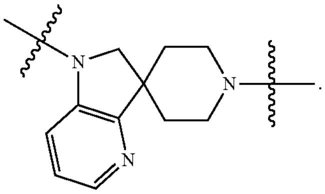 [SMILES: *N1CCC2(CC1)CN(*)c1cccnc12].

As defined generally above for compounds of formula I, I', II, II', or any other formulae provided herein, $L^1$ is absent, —$NR^3$—, —O—, —S—, $C_{1-6}$ alkylenyl, $C_{2-6}$ alkynylenyl, —$NR^3$—$C_{1-6}$ alkylenyl, —O—$C_{1-6}$ alkylenyl, —C(O)$C_{0-6}$ alkylenyl, —C(O)$NR^3$—, or —C(O)—C(O)—. It is understood that $L^1$ is a bivalent moiety in any of formula I, I', II, II' or any other formulae provided herein. That is, reference to a particular $L^1$ group is intended to refer to a bivalent variation of the referenced group.

In some embodiments, $L^1$ is absent, —S—, —C(O)—$NR^3$—, —$NR^3$—C(O)—, —C(O)—C(O)—, or an optionally substituted group selected from $C_{1-6}$ alkylenyl, $C_{2-6}$ alkynylenyl, —$NR^3$—$C_{0-6}$ alkylenyl, —O—$C_{0-6}$ alkylenyl, —C(O)—$C_{0-6}$ alkylenyl, —$C_{1-6}$ alkylenyl-C(O)—, —C(O)O—$C_{0-6}$ alkylenyl, —$C_{1-6}$ alkylenyl-O—C(O)—, —$C_{3-6}$ cycloalkyl, and —$NR^3$—C(O)—$C_{0-6}$ alkylenyl-O—.

In some embodiments, $L^1$ is absent.

In some embodiments, $L^1$ is —$NR^3$—. In some embodiments, $L^1$ is —N($C_{1-6}$ aliphatic)-. In some embodiments, $L^1$ is —N($CH_3$). In some embodiments, $L^1$ is —NH—.

In some embodiments, $L^1$ is —O—. In some embodiments, $L^1$ is —S—.

In some embodiments, $L^1$ is —C(O)—NR—. In some embodiments, $L^1$ is —C(O)—NH—. In some embodiments, $L^1$ is —C(O)—N($C_{1-6}$ aliphatic)-. In some embodiments, $L^1$ is —C(O)—N($CH_3$)—.

In some embodiments, $L^1$ is —$NR^3$—C(O)—. In some embodiments, $L^1$ is —N($C_{1-6}$ aliphatic)-C(O)—. In some embodiments, $L^1$ is —N($CH_3$)—C(O)—. In some embodiments, $L^1$ is —NH—C(O)—.

In some embodiments, $L^1$ is —C(O)—C(O)—.

In some embodiments, $L^1$ is optionally substituted $C_{1-6}$ alkylenyl. In some embodiments, $L^1$ is optionally substituted $C_{1-4}$ alkylenyl. In some embodiments, $L^1$ is $C_{1-6}$ alkylenyl. In some embodiments, $L^1$ is $C_{1-6}$ alkylenyl substituted with —$(CH_2)_{0-4}R°$; —$(CH_2)_{0-4}OR°$; —$O(CH_2)_{0-4}R°$. In some embodiments, $L^1$ is $C_{1-6}$ alkylenyl substituted with one or more R°, where R° is halo (e.g., fluoro, bromo, chloro, iodo). In some embodiments, $L^1$ is —$CH_2$—. In some embodiments, $L^1$ is —$(CH_2)_2$—. In some embodiments, $L^1$ is —$(CH_2)_3$—. In some embodiments, $L^1$ is —CH($CF_3$)—. In some embodiments, $L^1$ is —CH($CH_3$)—. In some embodiments, $L^1$ is —$CH_2$—CH($CH_3$)—. In some embodiments, $L^1$ is —C$(CH_3)_2$—.

In some embodiments, $L^1$ is optionally substituted $C_{2-6}$ alkynylenyl. In some embodiments, $L^1$ is

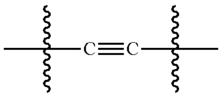.

In some embodiments, $L^1$ is optionally substituted —$NR^3$—$C_{1-6}$ alkylenyl. In some embodiments, $L^1$ is —$NR^3$—$C_{1-6}$ alkylenyl substituted with —$(CH_2)_{0-4}R°$; —$(CH_2)_{0-4}OR°$; —$O(CH_2)_{0-4}R°$. In some embodiments, $L^1$ is —$NR^3$—$C_{1-6}$ alkylenyl substituted with one or more R°, where R° is halo (e.g., fluoro, bromo, chloro, iodo). In some embodiments, $L^1$ is optionally substituted —O—$C_{1-6}$ alkylenyl. In some embodiments, $L^1$ is —O—$C_{1-6}$ alkylenyl substituted with —$(CH_2)_{0-4}R°$; —$(CH_2)_{0-4}OR°$; —$O(CH_2)_{0-4}R°$. In some embodiments, $L^1$ is -)—$C_{1-6}$ alkylenyl substituted with one or more R°, where R° is halo (e.g., fluoro, bromo, chloro, iodo). In some embodiments, $L^1$ is optionally substituted —O—$C_{1-3}$ alkylenyl. In some embodiments, $L^1$ is —O—$CH_2$—.

In some embodiments, $L^1$ is optionally substituted —C(O)$C_{0-6}$ alkylenyl. In some embodiments, $L^1$ is —C(O)—. In some embodiments, $L^1$ is —C(O)—$CH_2$—. In some embodiments, $L^1$ is —C(O)—C$(CH_3)_2$—. In some embodiments, $L^1$ is optionally substituted —$C_{0-6}$ alkylenyl-C(O)—. In some embodiments, $L^1$ is optionally substituted —$C_{1-3}$ alkylenyl-C(O)—. In some embodiments, $L^1$ is —$CH_2$—C(O)—. In some embodiments, $L^1$ is —CH($CH_3$)—C(O)—. In some embodiments, $L^1$ is —C$(CH_3)_2$—C(O)—. In some embodiments, $L^1$ is optionally substituted —$C_{0-6}$ alkylenyl-OC(O)—. In some embodiments, $L^1$ is optionally substituted —$C_{1-3}$ alkylenyl-OC(O)—. In some embodiments, $L^1$ is —OC(O)—. In some embodiments, $L^1$ is —$CH_2$—OC(O)—. In some embodiments, $L^1$ is —C$(CH_3)_2$—C(O)O—.

In some embodiments, $L^1$ is —C(O)NR—. In some embodiments, $L^1$ is —C(O)NH—. In some embodiments, $L^1$ is —C(O)N($C_{1-6}$ aliphatic)-. In some embodiments, $L^1$ is —C(O)N($CH_3$)—

In some embodiments, $L^1$ is —C(O)—C(O)—.

In some embodiments, $L^1$ is $C_{3-6}$ cycloalkyl. In some embodiment, $L^1$ is

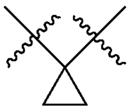 [SMILES: *C1(*)CC1]

As defined generally above formulae I, I', II, II', or any other formulae provided herein, Z is $C_{1-6}$ aliphatic, 2- to 10-membered heteroaliphatic, $P(O)(R^3)_2$, —C(O)$C_{1-6}$ aliphatic, $C(O)N(R^3)_2$, $C_{6-12}$ aryl, $C_{3-12}$ cycloalkyl, 4- to 16-membered monocyclic or polycyclic heterocyclyl comprising 1 to 4 heteroatoms selected from N, O, and S, or 5- to 12-membered monocyclic or bicyclic heteroaryl comprising 1 to 4 heteroatoms selected from N, O, and S, wherein Z is substituted with $(R^2)_q$.

In some embodiments, Z is selected from $P(O)(R^3)_2$, $C(O)N(R^3)_2$, $C_{1-6}$ aliphatic, $C_{6-12}$ aryl, $C_{3-12}$ cycloaliphatic, 2- to 10-atom heteroaliphatic, 4- to 16-membered monocyclic or polycyclic heterocyclyl comprising 1 to 4 heteroatoms selected from N, O, and S, and 5- to 12-membered monocyclic or bicyclic heteroaryl comprising 1 to 4 heteroatoms selected from N, O, and S, wherein Z is substituted with $(R^2)_q$.

In some embodiments, Z is substituted with $(R^2)_q$. As defined generally above, q is 0, 1, 2, 3, 4, 5, or 6. That is, in some embodiments, Z is substituted with 0, 1, 2, 3, 4, 5, or 6 $R^2$. In some embodiments, Z is unsubstituted (i.e., q is 0). In some embodiments, q is 1. In some embodiments, q is 2. In some embodiments, q is 3. In some embodiments, q is 4. In some embodiments, q is 5. In some embodiments, q is 6.

In some embodiments, Z is $P(O)(R^3)_2$. In some embodiments, Z is $P(O)(C_{1-6}$ aliphatic$)_2$. In some embodiments, Z is $P(O)(CH_3)_2$.

In some embodiments, Z is $—C(O)N(R^3)_2$. In some embodiments, Z is $—C(O)N(C_{1-6}$ aliphatic$)_2$. In some embodiments, Z is $—C(O)NH(C_{1-6}$ aliphatic). In some embodiments, Z is $—C(O)NHC(CH_3)_3$. In some embodiments, Z is $—C(O)N(CH_3)(C(CH_3)_3)$. In some embodiments, Z is $—C(O)N(CH_3)_2$.

In some embodiments, Z is $C_{1-6}$ aliphatic. In some embodiments, Z is $C_{1-6}$ alkyl. In some embodiments, Z is $C_{1-3}$ alkyl. In some embodiments, Z is methyl, ethyl, propyl (e.g., iso-propyl, n-propyl), butyl (e.g., n-butyl, iso-butyl, tert-butyl). In some embodiments, Z is methyl. In some embodiments, Z is ethyl. In some embodiments, Z is iso-propyl. In some embodiments, Z is tert-butyl. In some embodiments, Z is $—CH_2—C(CH_3)_2—CH_2—CH_3$. In some embodiments, Z is $—C(CH_3)_2—CH_2—CH_3$. In some embodiments, Z is methyl substituted with 1, 2 or 3 $R^2$. In some embodiments, Z is methyl substituted with 1, 2 or 3 halo. In some embodiments, Z is methyl substituted with 1, 2 or 3 fluoro. In some embodiments, Z is ethyl substituted with 1, 2, 3 or 4 $R^2$. In some embodiments, Z is ethyl substituted with 1, 2, 3 or 4 halo. In some embodiments, Z is ethyl substituted with 1, 2, 3 or 4 fluoro. In some embodiments, Z is iso-propyl substituted with 1, 2, 3 or 4 $R^2$.

In some embodiments, Z is $C_{6-12}$ aryl. In some embodiments, Z is phenyl. In some embodiments, Z is phenyl substituted with 0, 1, 2, 3, 4, 5, or 6 $R^2$. In some embodiments, Z is unsubstituted phenyl (i.e., Z is phenyl substituted with 0 $R^2$). In some embodiments, Z is phenyl substituted with 1, 2, 3, 4, or 5 $R^2$. In some embodiments, Z is phenyl substituted with 1 or 2 $R^2$. In some embodiments, Z is phenyl substituted with 1 $R^2$. In some embodiments, Z is phenyl substituted with $R^2$, and $R^2$ is selected from halo, $—C(O)—R^{2a}$, $—C(O)O—R^{2a}$, and 5- to 12-membered monocyclic or bicyclic heteroaryl comprising 1 to 4 heteroatoms selected from N, O, and S.

In some embodiments, Z is 2- to 10-membered heteroaliphatic. In some embodiments, Z is 2- to 5-membered heteroaliphatic. In some embodiments, Z is 2- to 5-membered heteroaliphatic substituted with 1, 2 or 3 $R^2$. In some embodiments, Z is $—O—CH_3$, $—O—CH_2—CH_3$, $—CH_2—O—CH_3$, $—O—CH_2—CH_2—O—CH_3$, $—O—CH_2—CH_2—O—CH_2—CH_2—O—CH_3$, $—O—C(CH_3)_3$, $—NH—C(CH_3)_3$, $—N(CH_2CH_3)_2$. In some embodiments, Z is $—O—CH_3$. In some embodiments, Z is $—CH_2—O—CH_3$. In some embodiments, Z is $—O—CH_2—CH_2—O—CH_2—CH_2—O—CH_3$. In some embodiments, Z is $—O—CH_2—CH_2—O—CH_3$. In some embodiments, Z is $—O—C(CH_3)_3$. In some embodiments, Z is $—O—CH_2—CH_3$. In some embodiments, Z is $—NH—C(CH_3)_3$. In some embodiments, Z is $—N(CH_2CH_3)_2$.

In some embodiments, Z is $C_{3-12}$ cycloalkyl (e.g., monocyclic or polycyclic cycloalkyl). In some embodiments, Z is $C_{3-6}$ monocyclic cycloalkyl. In some embodiments, Z is cyclopropyl. In some embodiments, Z is cyclobutyl. In some embodiments, Z is cyclopentyl. In some embodiments, Z is cyclohexyl. In some embodiments, Z is cyclopropyl substituted with 1, 2, 3 or 4 $R^2$. In some embodiments, Z is cyclobutyl substituted with 1, 2, 3, 4, 5, or 6 $R^2$. In some embodiments, Z is cyclopentyl substituted with 1, 2, 3, 4, 5, or 6 $R^2$. In some embodiments, Z is cyclohexyl substituted with 1, 2, 3, 4, 5, or 6 $R^2$.

In some embodiments, Z is $C_{5-12}$ polycyclic cycloalkyl. In some embodiments, Z is $C_{10-12}$ polycyclic cycloalkyl. In some embodiments, Z is adamantyl.

In some embodiments, Z is 4- to 16-membered monocyclic or polycyclic heterocyclyl comprising 1 to 4 heteroatoms selected from N, O, and S. In some embodiments, Z is 4- to 6-membered monocyclic heterocyclyl comprising 1 to 4 heteroatoms selected from N, O, and S. In some embodiments, Z is 4-membered monocyclic heterocyclyl comprising 1 heteroatom selected from N, O, and S. In some embodiments, Z is 5-membered monocyclic heterocyclyl comprising 1 to 2 heteroatoms selected from N, O, and S. In some embodiments, Z is 6-membered monocyclic heterocyclyl comprising 1 to 4 heteroatoms selected from N, O, and S. In some embodiments, Z is 4- to 6-membered monocyclic heterocyclyl comprising 1 to 4 heteroatoms selected from N, O, and S substituted with 0, 1, 2, 3, 4, 5, or 6 $R^2$.

In some embodiments, Z is 10- to 12-membered bicyclic heterocyclyl. In some embodiments, Z is 10- to 12-membered fused bicyclic heterocyclyl. In some embodiments, Z is 10- to 12-membered bridged bicyclic heterocyclyl. In some embodiments, Z is 10- to 12-membered bridged bicyclic heterocyclyl substituted with 0, 1, 2, 3, 4, 5, or 6 $R^2$.

In some embodiments, Z is 10- to 16-membered polycyclic heterocyclyl. In some embodiments, Z is 10-membered polycyclic heterocyclyl. In some embodiments, Z is 11-membered polycyclic heterocyclyl. In some embodiments, Z is 12-membered polycyclic heterocyclyl. In some embodiments, Z is 13-membered polycyclic heterocyclyl. In some embodiments, Z is 14-membered polycyclic heterocyclyl. In some embodiments, Z is 15-membered polycyclic heterocyclyl. In some embodiments, Z is 16-membered polycyclic heterocyclyl. In some embodiments, a polycyclic Z moiety is a spirocyclic and fused tricyclic moiety.

In some embodiments, Z is 9- to 12-membered spirocyclic heterocyclyl. In some embodiments, Z is 9-membered spirocyclic heterocyclyl. In some embodiments, Z is 10-membered spirocyclic heterocyclyl. In some embodiments, Z is 11-membered spirocyclic heterocyclyl. In some embodiments, Z is 12-membered spirocyclic heterocyclyl. In some embodiments, Z is 9- to 12-membered spirocyclic heterocyclyl substituted with 0, 1, 2, 3, 4, 5, or 6 $R^2$.

In some embodiments, Z is 5- to 12-membered monocyclic or bicyclic heteroaryl comprising 1 to 4 heteroatoms selected from N, O, and S. In some embodiments, Z is 5- to 6-membered monocyclic heteroaryl comprising 1 to 4 heteroatoms selected from N, O, and S. In some embodiments, Z is 5-membered monocyclic heteroaryl comprising 1 to 4 heteroatoms selected from N, O, and S. In some embodiments, Z is 6-membered monocyclic heteroaryl comprising 1 to 4 heteroatoms selected from N, O, and S.

In some embodiments, Z is 8- to 12-membered bicyclic heteroaryl comprising 1 to 4 heteroatoms selected from N, O, and S. In some embodiments, Z is 8-membered heteroaryl comprising 1 to 4 heteroatoms selected from N, O, and S. In some embodiments, Z is 9-membered heteroaryl comprising 1 to 4 heteroatoms selected from N, O, and S. In some embodiments, Z is 10-membered heteroaryl comprising 1 to 4 heteroatoms selected from N, O, and S. In some embodiments, Z is 11-membered heteroaryl comprising 1 to 4 heteroatoms selected from N, O, and S. In some embodiments, Z is 12-membered heteroaryl comprising 1 to 4 heteroatoms selected from N, O, and S.

As defined generally above for compounds of formulae I, I', II, II', or any other formulae provided herein, each $R^2$ is independently selected from halo, CN, C(O)OH, and an optionally substituted group selected from $C_{1-6}$ aliphatic, C(O)$C_{1-6}$ aliphatic, and O—$C_{1-6}$ aliphatic.

In some embodiments, each $R^2$ is independently selected from halo, oxo, —CN, —OH, 0-$R^{2a}$, —C(O)—$R^{2a}$, —C(O)O—$R^{2a}$, and an optionally group selected from $C_{1-6}$ aliphatic, $C_{6-12}$ aryl, and 5- to 12-membered monocyclic or bicyclic heteroaryl comprising 1 to 4 heteroatoms selected from N, O, and S.

In some embodiments, $R^2$ is halo. In some embodiments, $R^2$ is selected from fluoro, chloro, bromo, and iodo.

In some embodiments, $R^2$ is oxo.

In some embodiments, $R^2$ is —CN.

In some embodiments, $R^2$ is —OH.

In some embodiments, $R^2$ is C(O)—$R^{2a}$. In some embodiments, $R^2$ is optionally substituted C(O)—$C_{1-6}$ aliphatic. In some embodiments, $R^2$ is C(O)—$C_{1-6}$ aliphatic substituted with halogen; —$(CH_2)_{0-4}R°$; —$(CH_2)_{0-4}OR°$. In some embodiments, $R^2$ is C(O)—$C_{1-6}$ aliphatic substituted with halogen or 3- to 6-membered saturated, partially unsaturated, or aryl ring having 0-4 heteroatoms independently selected from nitrogen, oxygen, or sulfur.

In some embodiments, $R^2$ is C(O)O—$R^{2a}$. In some embodiments, $R^2$ is C(O)OH. In some embodiments, $R^2$ is optionally substituted C(O)O—$C_{1-6}$ aliphatic. In some embodiments, $R^2$ is C(O)O—$C_{1-6}$ aliphatic substituted with halogen; —$(CH_2)_{0-4}R°$; —$(CH_2)_{0-4}OR°$. In some embodiments, $R^2$ is C(O)O—$C_{1-6}$ aliphatic substituted with halogen or 3- to 6-membered saturated, partially unsaturated, or aryl ring having 0-4 heteroatoms independently selected from nitrogen, oxygen, or sulfur.

In some embodiments, $R^2$ is optionally substituted $C_{6-12}$ aryl. In some embodiments, $R^2$ is optionally substituted phenyl. In some embodiments, $R^2$ is phenyl substituted with substituted with halogen; —$(CH_2)_{0-4}R°$; —$(CH_2)_{0-4}OR°$.

In some embodiments, $R^2$ is an optionally substituted $C_{1-6}$ aliphatic. In some embodiments, $R^2$ is optionally substituted $C_{1-6}$ alkyl. In some embodiments, $R^2$ is optionally substituted $C_{1-4}$ alkyl. In some embodiments, $R^2$ is optionally substituted $C_{1-2}$ alkyl. In some embodiments, $R^2$ is methyl. In some embodiments, $R^2$ is ethyl. In some embodiments, $R^2$ is propyl (e.g., n-propyl, iso-propyl) In some embodiments, $R^2$ is butyl (e.g., n-butyl, isobutyl, tert-butyl, sec-butyl). In some embodiments, $R^2$ is $C_{1-6}$ aliphatic substituted with halogen; —$(CH_2)_{0-4}R°$; —$(CH_2)_{0-4}OR°$. In some embodiments, $R^2$ is $C_{1-6}$ aliphatic substituted with halogen or 3- to 6-membered saturated, partially unsaturated, or aryl ring having 0-4 heteroatoms independently selected from nitrogen, oxygen, or sulfur.

In some embodiments, $R^2$ is an optionally substituted O—$R^{2a}$. In some embodiments, $R^2$ is optionally substituted O—$C_{1-6}$ aliphatic. In some embodiments, $R^2$ is optionally substituted O—$C_{1-6}$ alkyl. In some embodiments, $R^2$ is optionally substituted O—$C_{1-4}$ alkyl. In some embodiments, $R^2$ is optionally substituted O—$C_{1-2}$ alkyl. In some embodiments, $R^2$ is O-methyl. In some embodiments, $R^2$ is O-ethyl. In some embodiments, $R^2$ is O-propyl (e.g., O-n-propyl, O-iso-propyl).

In some embodiments, $R^2$ is 5- to 12-membered monocyclic or bicyclic heteroaryl comprising 1 to 4 heteroatoms selected from N, O, and S. In some embodiments, $R^2$ is 5- to 6-membered monocyclic heteroaryl comprising 1 to 4 heteroatoms selected from N, O, and S. In some embodiments, $R^2$ is 5-membered bicyclic heteroaryl comprising 1 to 4 heteroatoms selected from N, O, and S. In some embodiments, $R^2$ is 6-membered bicyclic heteroaryl comprising 1 to 4 heteroatoms selected from N, O, and S.

In some embodiments, a substituent on an optionally substituted carbon atom of an optionally substituted $R^2$ group, as defined herein and above, is halo (e.g., bromo, chloro, fluoro, iodo).

As defined generally above for compounds of formulae I, I', II, II', or any other formulae provided herein, in some embodiments, each $R^{2a}$ is independently H or an optionally substituted group selected from $C_{1-6}$ aliphatic, $C_{3-12}$ cycloaliphatic, and 4- to 12-membered monocyclic or bicyclic heterocyclyl comprising 1 to 4 heteroatoms selected from N, O, and S. In some embodiments, $R^{2a}$ is H. In some embodiments, $R^{2a}$ is an optionally substituted $C_{1-6}$ aliphatic. In some embodiments, $R^{2a}$ is $C_{3-12}$ cycloaliphatic. In some embodiments, $R^{2a}$ is 4- to 12-membered monocyclic or bicyclic heterocyclyl comprising 1 to 4 heteroatoms selected from N, O, and S.

As defined generally above for compounds of formulae I, I', II, II', or any other formulae provided herein, each $R^3$ is independently selected from H and optionally substituted $C_{1-6}$ aliphatic. In some embodiments, $R^3$ is H. In some embodiments, $R^3$ is an optionally substituted $C_{1-6}$ aliphatic. In some embodiments, $R^3$ is optionally substituted $C_{1-6}$ alkyl. In some embodiments, $R^3$ is optionally substituted $C_{1-4}$ alkyl. In some embodiments, $R^3$ is optionally substituted $C_{1-2}$ alkyl. In some embodiments, $R^3$ is methyl. In some embodiments, $R^3$ is ethyl. In some embodiments, $R^3$ is tert-butyl.

In some embodiments, a substituent on an optionally substituted carbon atom of an optionally substituted $R^3$ group is halo (e.g., bromo, chloro, fluoro, iodo).

In some embodiments, Z is selected from Table Z:

TABLE Z halo (e.g., bromo, chloro, fluoro, iodo), —$CH_3$, —$CH_2$—$CH_3$, —$CH_2$—O—$CH_3$, —$CH(CH_3)$—$CH_2$—O—$CH_3$, —$CH_2$—O—$CH_2$—$CH_3$, —$CH_2$—$CH_2$—O—$CH_3$, —$CH_2$—$CH_2$—$CH_2$—O—$CH_3$, —$CH_2$—$CH_2$—O—$CH_2$—$CH_3$, —$CH_2$—O—$CH_2$—$CH_2$—O—$CH_3$, —$CH_2$—OH, —CH(OH)—$CH_3$, —$CH_2$—$CH_2$—OH, —$CH_2F$, —$CHF_2$, —$CF_3$, —$CH_2$—$CH_2F$, —$CH_2$—O—$C(CH_3)_3$, —$CH_2$—O—$CF_2$—$CH_2F$, —$C(CH_3)F_2$, —$CF_2$—$CHF_2$, —$CF_2$—$CH_3$, —$CF_2$—$CH_2$—O—$CH_3$, —$CH_2$—O—$CHF_2$, —$CH_2$—O—$CH_2$—$CHF_2$, —$CH_2$—O—$CF_3$, —O—$CH_3$, —O—$CH_2$—$CH_2$—O—$CH_2$—$CH_2$—O—$CH_3$, —O—$CH_2$—$CH_2$—O—$CH_3$, —O—$C(CH_3)_3$, —O—$CH_2$—$CH_3$, —O—$CHF_2$, —O—$CF_3$, —O—$CH_2$—$CHF_2$, —NH—$C(CH_3)_3$, —$N(CH_2CH_3)_2$,

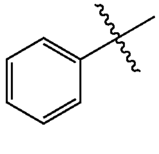
,
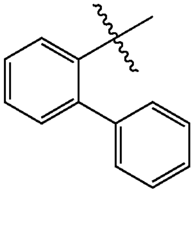
,
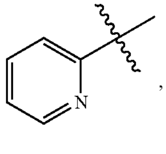
,

TABLE Z-continued
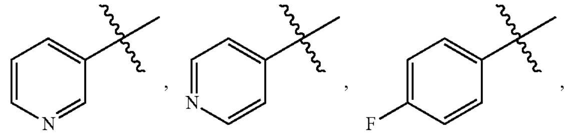 [SMILES: *c1cccnc1 ; *c1ccncc1 ; *c1ccc(F)cc1]
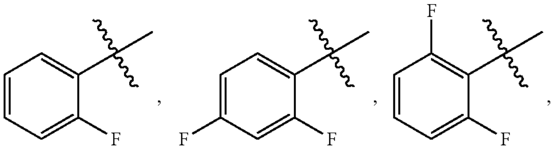 [SMILES: *c1ccccc1F ; *c1ccc(F)cc1F ; *c1c(F)cccc1F]
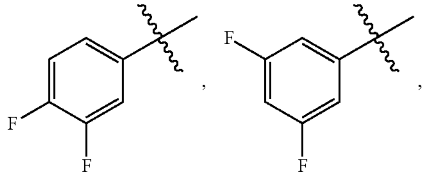 [SMILES: *c1ccc(F)c(F)c1 ; *c1cc(F)cc(F)c1]
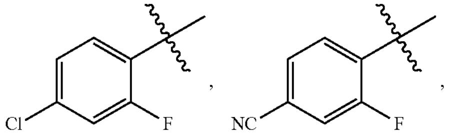 [SMILES: *c1ccc(Cl)cc1F ; *c1ccc(C#N)cc1F]
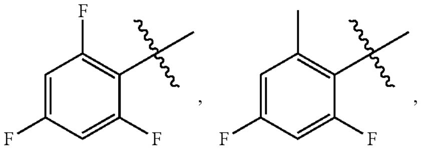
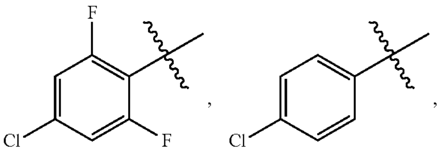 [SMILES: *c1c(F)cc(Cl)cc1F ; *c1ccc(Cl)cc1]
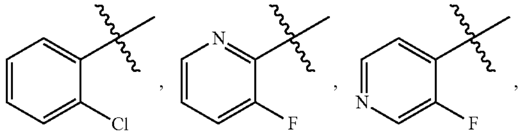 [SMILES: *c1ccccc1Cl ; *c1ncccc1F ; *c1ccncc1F]
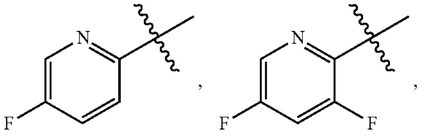 [SMILES: *c1ccc(F)cn1 ; *c1ncc(F)cc1F]
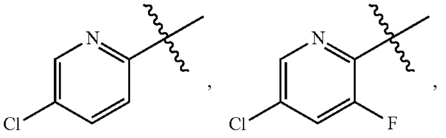 [SMILES: *c1ccc(Cl)cn1 ; *c1ncc(Cl)cc1F]
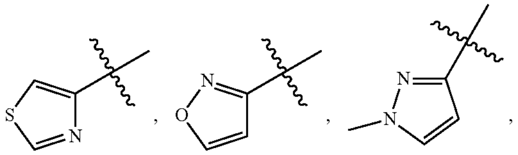
TABLE Z-continued
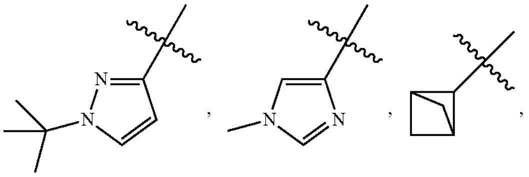
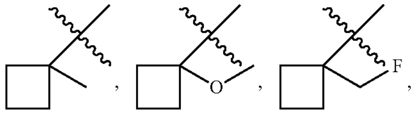
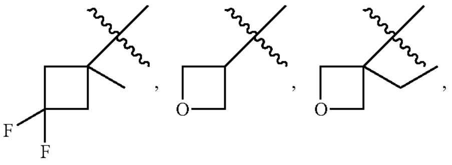
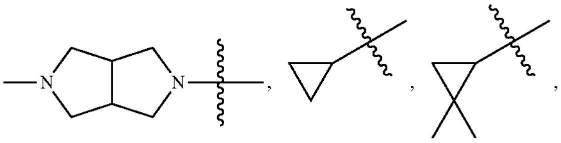
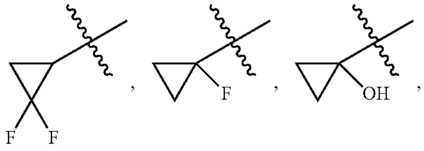 [SMILES: *C1CC1(F)F ; *C1(F)CC1 ; *C1(O)CC1]
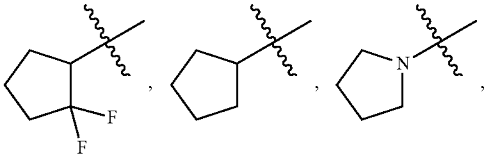 [SMILES: *C1CCCC1(F)F ; *C1CCCC1 ; *N1CCCC1]
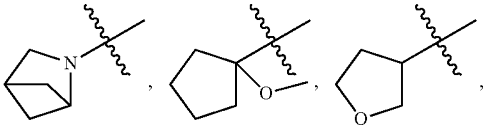
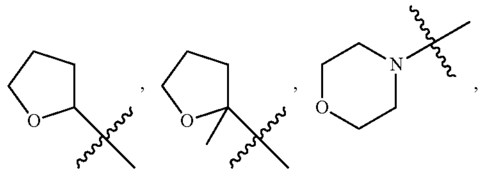
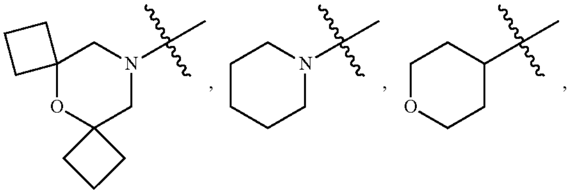 [SMILES: *N1CC2(CCC2)OC2(CCC2)C1 ; *N1CCCCC1 ; *C1CCOCC1]

TABLE Z-continued
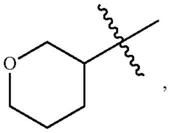, 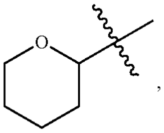, 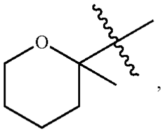,
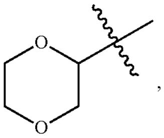, 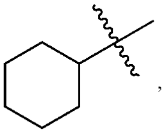, 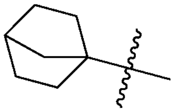,
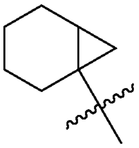, 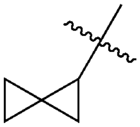, 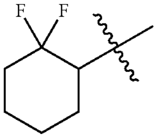,
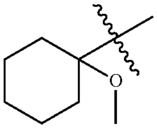, 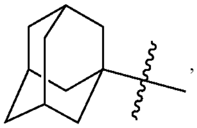,
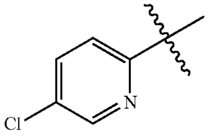, 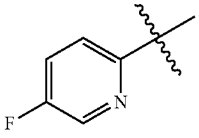,
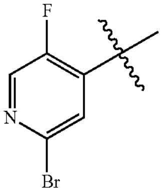, 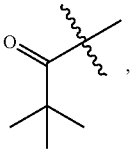, 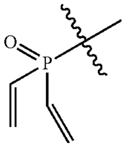,
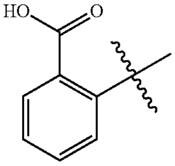, 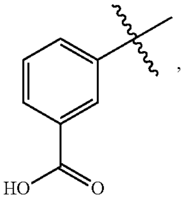,
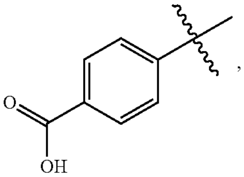, 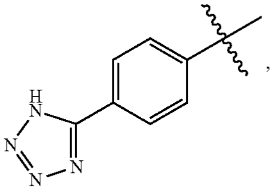,
TABLE Z-continued
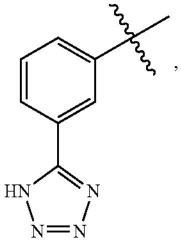, 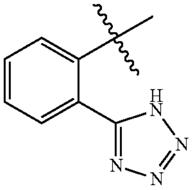, 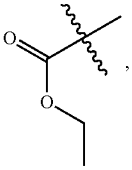,
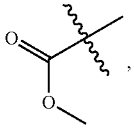, 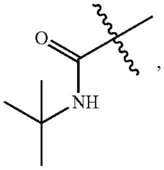, 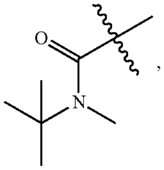,
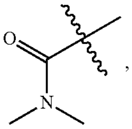, 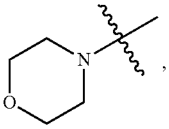, 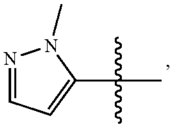,
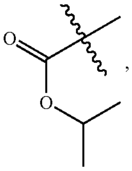, 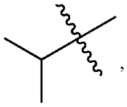, 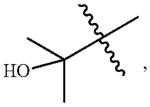, 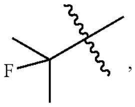,
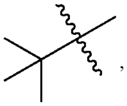, 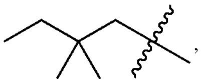, 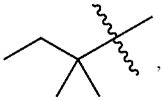,
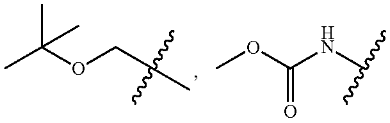,
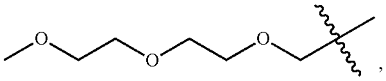 [SMILES: *COCCOCCOC],
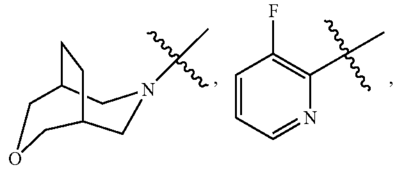 [SMILES: *N1CC2CCC(COC2)C1 ; *c1ncccc1F],
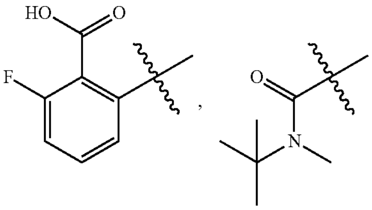, TABLE Z-continued
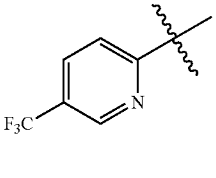
,
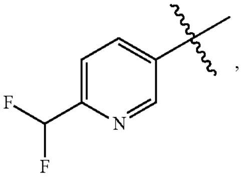
,
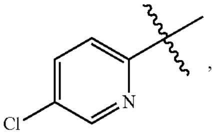
,
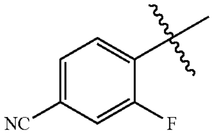
,
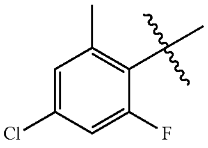
,
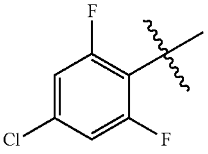
,
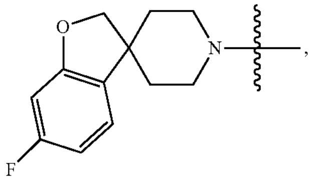 [SMILES: *N1CCC2(CC1)COc1cc(F)ccc12]
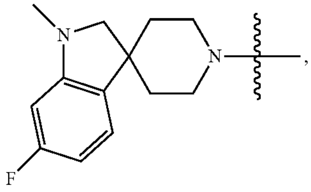 [SMILES: *N1CCC2(CC1)CN(C)c1cc(F)ccc12]
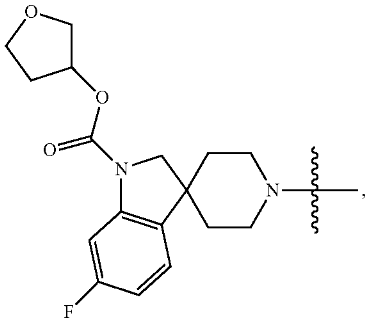 [SMILES: *N1CCC2(CC1)CN(C(=O)OC1CCOC1)c1cc(F)ccc12]
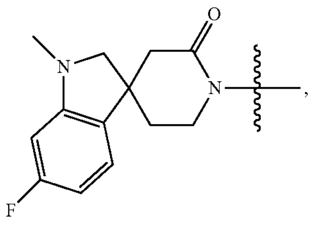 [SMILES: *N1CCC2(CC1=O)CN(C)c1cc(F)ccc12]
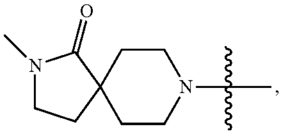 [SMILES: *N1CCC2(CC1)CCN(C)C2=O]
TABLE Z-continued
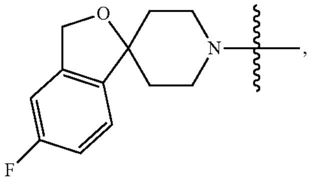 [SMILES: *N1CCC2(CC1)OCc1cc(F)ccc12]
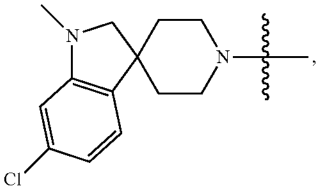 [SMILES: *N1CCC2(CC1)CN(C)c1cc(Cl)ccc12]
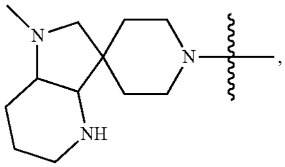 [SMILES: *N1CCC2(CC1)CN(C)C1CCCNC12]
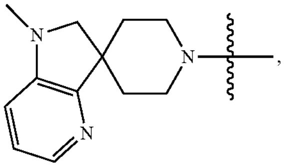
,
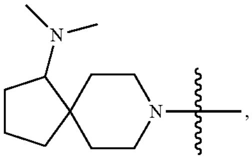
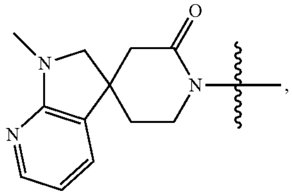 [SMILES: *N1CCC2(CC1=O)CN(C)c1ncccc12]
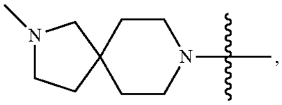
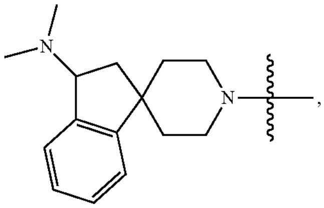 [SMILES: *N1CCC2(CC1)CC(N(C)C)c1ccccc12]
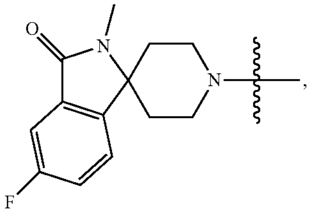 [SMILES: *N1CCC2(CC1)c1ccc(F)cc1C(=O)N2C]

TABLE Z-continued
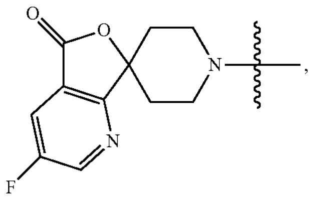 [SMILES: *N1CCC2(CC1)OC(=O)c1cc(F)cnc12],
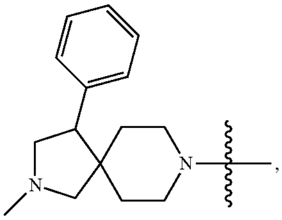 [SMILES: *N1CCC2(CC1)CN(C)CC2c1ccccc1],
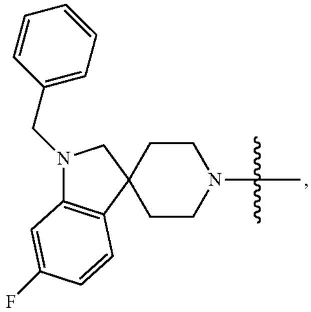 [SMILES: *N1CCC2(CC1)CN(Cc1ccccc1)c1cc(F)ccc12],
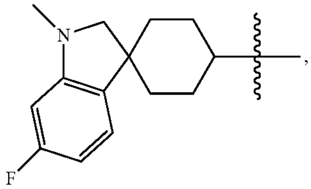 [SMILES: *C1CCC2(CC1)CN(C)c1cc(F)ccc12],
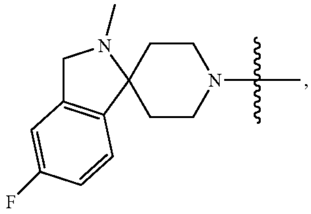 [SMILES: *N1CCC2(CC1)c1ccc(F)cc1CN2C],
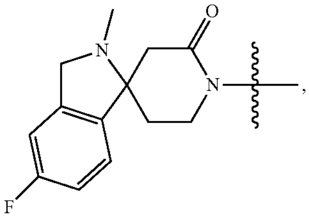, 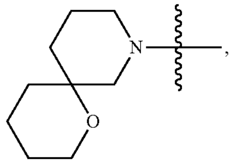,
TABLE Z-continued
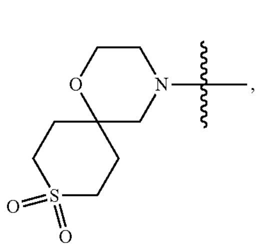, 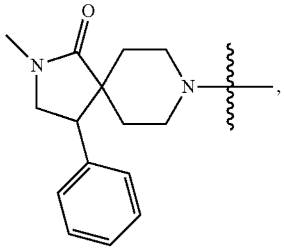,
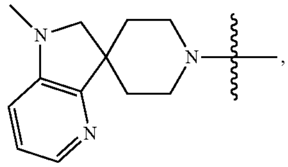 [SMILES: *N1CCC2(CC1)CN(C)c1cccnc12],
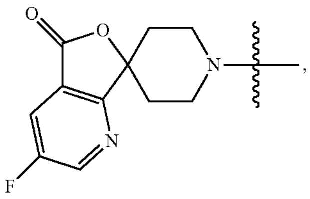, 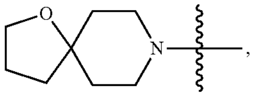,
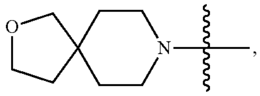, 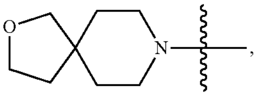,
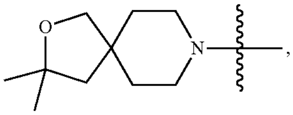 [SMILES: *N1CCC2(CC1)COC(C)(C)C2],
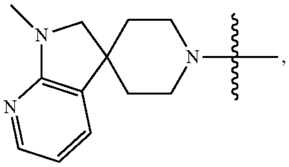, 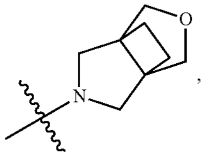,
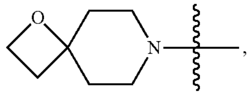, 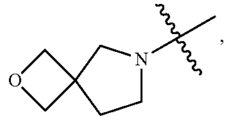,
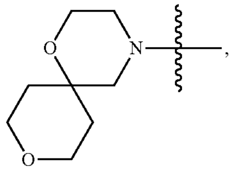, 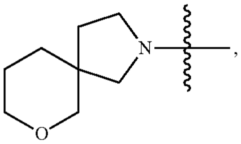,
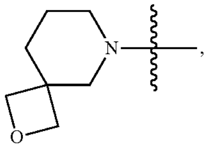, 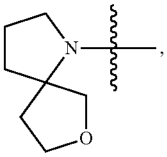, 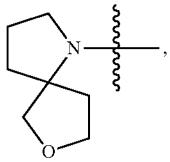, TABLE Z-continued
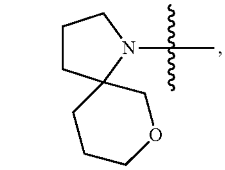
,
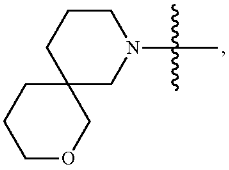
,
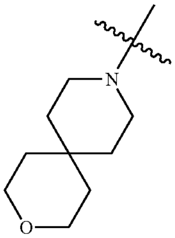
,
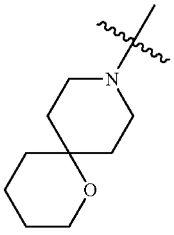
,
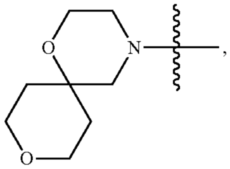
,
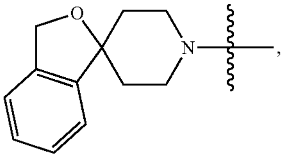
,
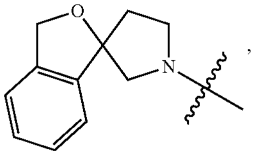
,
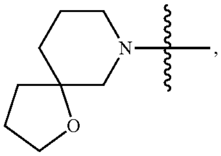
,
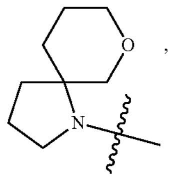
,
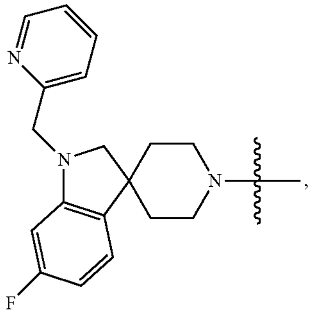
,
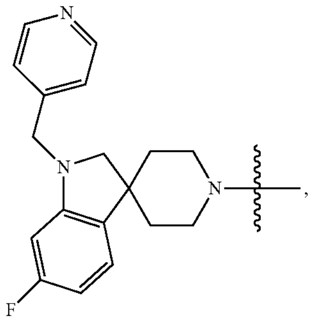 [SMILES: *N1CCC2(CC1)CN(Cc1ccncc1)c1cc(F)ccc12]
,
TABLE Z-continued
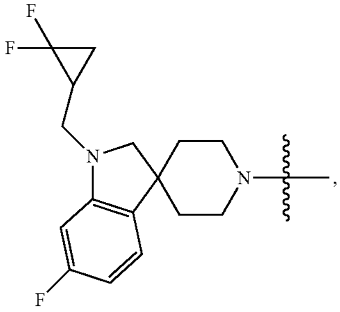 [SMILES: *N1CCC2(CC1)CN(CC1CC1(F)F)c1cc(F)ccc12]
,
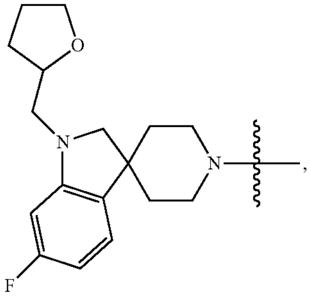 [SMILES: *N1CCC2(CC1)CN(CC1CCCO1)c1cc(F)ccc12]
,
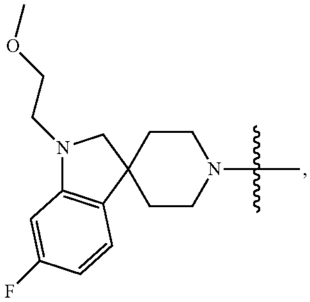 [SMILES: *N1CCC2(CC1)CN(CCOC)c1cc(F)ccc12]
,
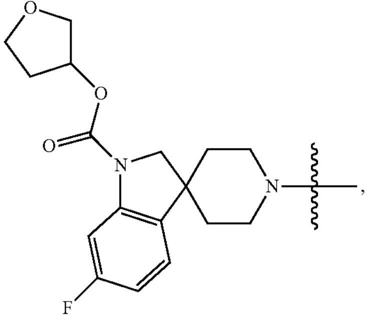 [SMILES: *N1CCC2(CC1)CN(C(=O)OC1CCOC1)c1cc(F)ccc12]
,
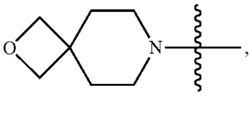
,
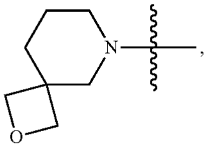
,
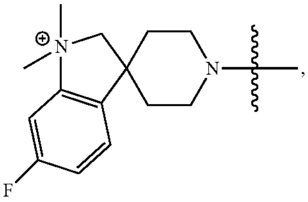 [SMILES: *N1CCC2(CC1)C[N+](C)(C)c1cc(F)ccc12]
, TABLE Z-continued
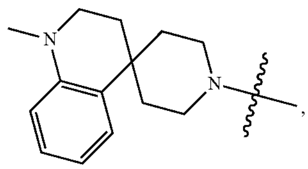 [SMILES: *N1CCC2(CC1)CCN(C)c1ccccc12]
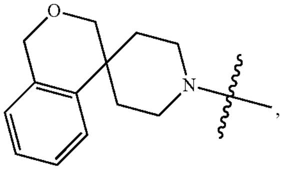 [SMILES: *N1CCC2(CC1)COCc1ccccc12]
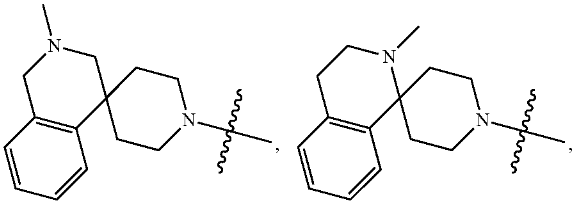 [SMILES: *N1CCC2(CC1)CN(C)Cc1ccccc12 ; *N1CCC2(CC1)c1ccccc1CCN2C]
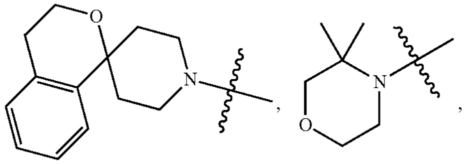
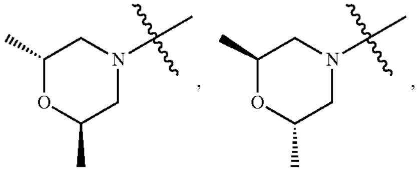
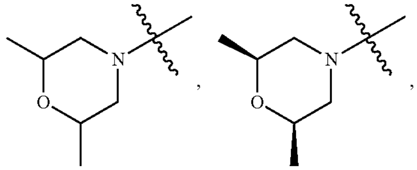
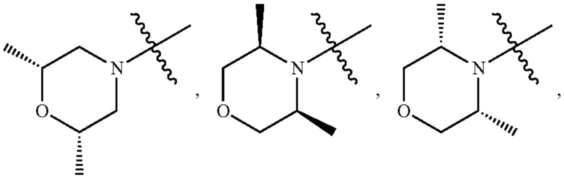
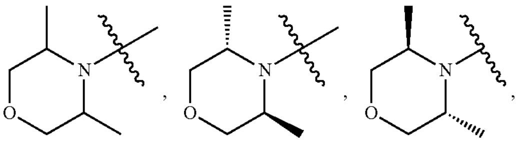
TABLE Z-continued
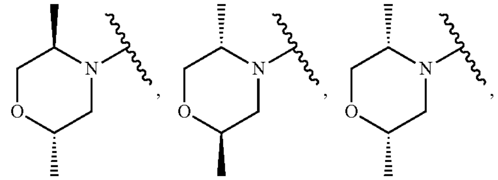
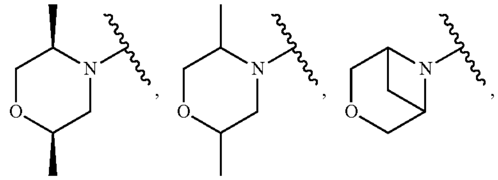
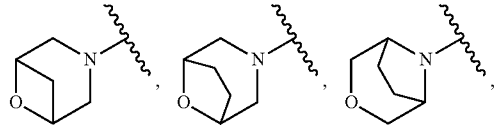 [SMILES: *N1CC2CC(C1)O2 ; *N1CC2CCC(C1)O2 ; *N1C2CCC1COC2]
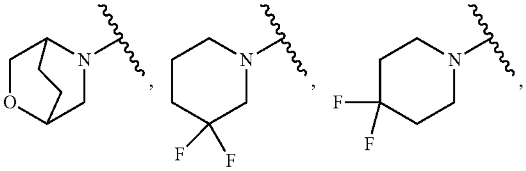
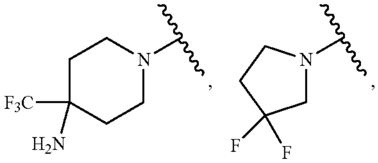 [SMILES: *N1CCC(N)(C(F)(F)F)CC1 ; *N1CCC(F)(F)C1]
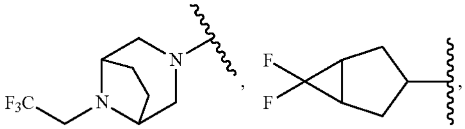
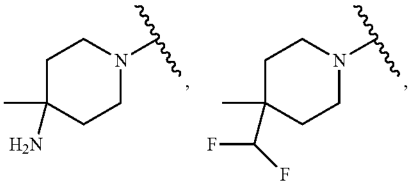
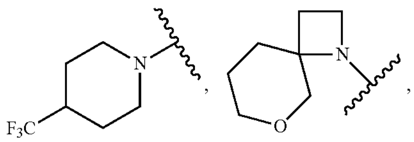 [SMILES: *N1CCC(C(F)(F)F)CC1 ; *N1CCC12CCCOC2]
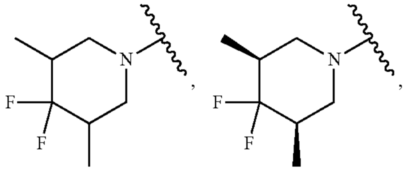

TABLE Z-continued

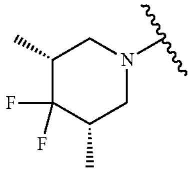, 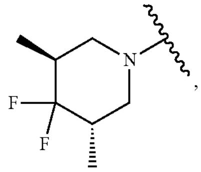,

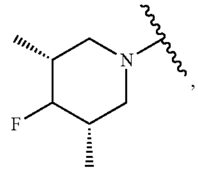, 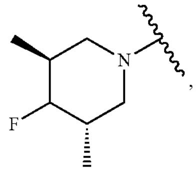,

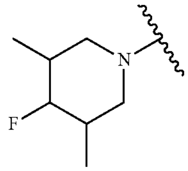, 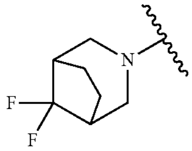,

As defined generally above for compounds of formulae I, I', II, II', or any other formulae provided herein, $L^2$ is absent, —$(NR^3)_s$—S(O)—$C_{0-6}$ alkylenyl-, —$(NR^3)_s$—$S(O)_2$—$C_{0-6}$ alkylenyl-, —$(NR^3)_s$—S(O)($NR^3$)—, —$S(O)_2$—$NR^3$—, —$NR^3$—$C_{1-6}$ haloalkylenyl, —$(NR^3)_s$—P(O)($R^3$)—, —$C_{1-6}$ alkylenyl-S(O)—, —$C_{1-6}$ alkylenyl-$S(O)_2$—, —C(O)—$(NR^3)_s$—, —$(NR^3)_s$—C(O)—, or an optionally substituted 4- to 12-membered monocyclic or bicyclic heterocyclyl comprising 1 to 4 heteroatoms selected from N, O, and S. It is understood that $L^2$ is a bivalent moiety in any of formula I, II, II' or any other formulae provided herein. That is, reference to a particular $L^2$ group is intended to refer to a bivalent variation of the referenced group.

In some embodiments, $L^2$ is —$(NR^3)_s$—S(O)—($NR^3$)—, —$(NR^3)_s$—$S(O)_2$—$NR^3$—, —$(NR^3)_s$—P(O)($R^3$)—, —C(O)—$(NR^3)_s$—, —$NR^3$—C(O)—, or an optionally substituted bivalent moiety selected from —$(NR^3)_s$—S(O)—$C_{0-6}$ alkylenyl-, —$(NR^3)_s$—$S(O)_2$—$C_{0-6}$ alkylenyl-,—$(NR^3)_s$—S(O)—$NR^3$—$C_{0-6}$ alkylenyl, —$(NR^3)_s$—$S(O)_2$—$NR^3$—$C_{0-6}$ alkylenyl, —$(NR^3)_s$—$S(O)_2$—$C_{3-6}$ cycloalkyl, —$NR^3$—$C_{0-6}$ alkylenyl, —$C_{1-6}$ alkylenyl-S(O)—$(NR^3)_s$—, —$C_{1-6}$ alkylenyl-$S(O)_2$—$(NR^3)_s$—, 2- to 6-membered heteroaliphatic, and 4- to 12-membered monocyclic or bicyclic heterocyclyl comprising 1 to 4 heteroatoms selected from N, O, and S.

In some embodiments, $L^2$ is absent.

In some embodiments, $L^2$ is —$(NR^3)_s$—S(O)—($NR^3$)—. In some embodiments, $L^2$ is S(O)—($NR^3$)—. In some embodiments, $L^2$ is S(O)—(NH)—. In some embodiments, $L^2$ is S(O)—N($C_{1-6}$ aliphatic)-. In some embodiments, $L^2$ is S(O)—N($CH_3$)—In some embodiments, $L^2$ is —($NR^3$)—S (O)—($NR^3$)—.

In some embodiments, $L^2$ is —$(NR^3)_s$—$S(O)_2$—$NR^3$—. In some embodiments, $L^2$ is $S(O)_2$—($NR^3$)—. In some embodiments, $L^2$ is $S(O)_2$—(NH)—. In some embodiments, $L^2$ is $S(O)_2$—N($C_{1-6}$ aliphatic)-. In some embodiments, $L^2$ is $S(O)_2$—N($CH_3$)—In some embodiments, $L^2$ is —($NR^3$)—$S(O)_2$—($NR^3$)—.

In some embodiments, $L^2$ is —$(NR^3)_s$—P(O)($R^3$)—. In some embodiments, $L^2$ is —P(O)($R^3$)—. In some embodiments, $L^2$ is —($NR^3$)—P(O)($R^3$)—. In some embodiments, $L^2$ is —P(O)($CH_3$)—. In some embodiments, $L^2$ is —NH—P(O)($CH_3$)—.

In some embodiments, $L^2$ is —C(O)—$(NR^3)_s$—. In some embodiments, $L^2$ is —C(O)—NH—. In some embodiments, $L^2$ is —C(O)—. In some embodiments, $L^2$ is —N($R^3$)—C (O)—.

In some embodiments, $L^2$ is —$NR^3$—C(O)—. In some embodiments, $L^2$ is —NH—C(O)—.

In some embodiments, $L^2$ is optionally substituted —$(NR^3)_s$—S(O)—$C_{0-6}$ alkylenyl. In some embodiments, $L^2$ is optionally substituted S(O)—$C_{0-6}$ alkylenyl. In some embodiments, $L^2$ is optionally substituted —$(NR^3)_s$—S (O)—$C_{1-6}$ alkylenyl. In some embodiments, $L^2$ is optionally substituted —S(O)—$C_{1-6}$ alkylenyl. In some embodiments, $L^2$ is —$(NR^3)_s$—S(O)—. In some embodiments, $L^2$ is —S(O)—. In some embodiments, $L^2$ is —$NR^3$—S(O)—. In some embodiments, $L^2$ is —NH—S(O)—. In some embodiments, $L^2$ is —N($CH_3$)—S(O)—.

In some embodiments, $L^2$ is —$(NR^3)_s$—$S(O)_2$— $C_{0-6}$ alkylenyl. In some embodiments, $L^2$ is optionally substituted $S(O)_2$—$C_{0-6}$ alkylenyl. In some embodiments, $L^2$ is optionally substituted —$(NR^3)_s$—$S(O)_2$—$C_{1-6}$ alkylenyl. In some embodiments, $L^2$ is optionally substituted —$S(O)_2$—$C_{1-6}$ alkylenyl. In some embodiments, $L^2$ is —$(NR^3)_s$—$S(O)_2$—. In some embodiments, $L^2$ is —$S(O)_2$—. In some embodiments, $L^2$ is —$NR^3$—$S(O)_2$—. In some embodiments, $L^2$ is —NH—$S(O)_2$—. In some embodiments, $L^2$ is —N($CH_3$)—$S(O)_2$—. In some embodiments, $L^2$ is —NH—$S(O)_2$—$CH_2$—. In some embodiments, $L^2$ is —NH—$S(O)_2$—$(CH_2)_3$—. In some embodiments, $L^2$ is —NH—$S(O)_2$—. In some embodiments, $L^2$ is —N($CH_3$)—$S(O)_2$—.

In some embodiments, $L^2$ is optionally substituted —$(NR^3)_s$—S(O)—$NR^3$—$C_{1-6}$ alkylenyl. In some embodiments, $L^2$ is optionally substituted S(O)—$NR^3$—$C_{1-6}$ alkylenyl. In some embodiments, $L^2$ is optionally substituted —$NR^3$—S(O)—$NR^3$—$C_{1-6}$ alkylenyl.

In some embodiments, $L^2$ is optionally substituted —$(NR^3)_s$—$S(O)_2$—$NR^3$—$C_{1-6}$ alkylenyl. In some embodiments, $L^2$ is optionally substituted $S(O)_2$—$NR^3$—$C_{1-6}$ alkylenyl. In some embodiments, $L^2$ is optionally substituted —$NR^3$—$S(O)_2$—$NR^3$—$C_{1-6}$ alkylenyl.

In some embodiments, $L^2$ is optionally substituted —$NR^3$—$C_{0-6}$ alkylenyl. In some embodiments, $L^2$ is —NR—. In some embodiments, $L^2$ is optionally substituted —$NR^3$—$C_{1-6}$ alkylenyl. In some embodiments, $L^2$ is —$NR^3$—$C_{1-6}$ alkylenyl substituted with halogen; —$(CH_2)_{0-4}R°$; and/or —$(CH_2)_{0-4}OR°$. In some embodiments, $L^2$ is optionally substituted —$NR^3$—$C_{1-3}$ alkylenyl. In some embodiments, $L^2$ is optionally substituted —$NR^3$—$C_2$ alkylenyl. In some embodiments, $L^2$ is optionally substituted —$NR^3$—$C_1$ alkylenyl. In some embodiments, $L^2$ is —$NR^3$—$CH_2$—. In some embodiments, $L^2$ is —NH—$CH_2$—. In some embodiments, $L^2$ is —N($CH_3$)—$CH_2$—. In some embodiments, $L^2$ is —$NR^3$—CH($CH_3$)—. In some embodiments, $L^2$ is —NH—CH($CH_3$)—. In some embodiments, $L^2$ is —N($CH_3$)—CH($CH_3$)—. In some embodiments, $L^2$ is —NH—CH($CF_3$)—.

In some embodiments, $L^2$ is —$NR^3$—$C_{1-6}$ haloalkylenyl.

In some embodiments, $L^2$ is optionally substituted —$C_{1-6}$ alkylenyl-S(O)—$(NR^3)_s$—. In some embodiments, $L^2$ is optionally substituted —$C_{1-6}$ alkylenyl-S(O)—. In some embodiments, $L^2$ is optionally substituted —$C_{1-6}$ alkylenyl-S(O)—($NR^3$)—. In some embodiments, $L^2$ is —$CH_2$—S (O)—.

In some embodiments, $L^2$ is optionally substituted —$C_{1-6}$ alkylenyl-$S(O)_2$—. In some embodiments, $L^2$ is optionally substituted —$C_{1-3}$ alkylenyl-$S(O)_2$—. In some embodiments, $L^2$ is optionally substituted —$C_1$ alkylenyl-$S(O)_2$—. In some embodiments, $L^2$ is —$CH_2$—$S(O)_2$. In some embodiments, $L^2$ is $—CH(CH_3)—S(O)_2—$. In some embodiments, $L^2$ is $—C(CH_3)_2—S(O)_2—$. In some embodiments, $L^2$ is:

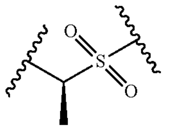

or

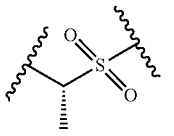

.

In some embodiments, $L^2$ is:

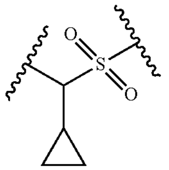

,

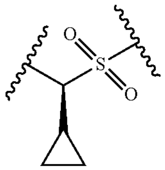

, or

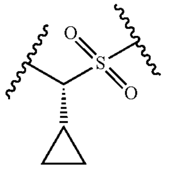

.

In some embodiments, $L^2$ is $—C(O)—(NR\,3)_s—$. In some embodiments, $L^2$ is $—C(O)—NH—$. In some embodiments, $L^2$ is $—C(O)—N(CH_3)—$.

In some embodiments, $L^2$ is $—(NR^3)_s—C(O)—$. In some embodiments, $L^2$ is $—(NR^3)—C(O)—$. In some embodiments, $L^2$ is $—NH—C(O)—$. In some embodiments, $L^2$ is $—N(C_{1-6}$ aliphatic)-C(O)—. In some embodiments, $L^2$ is $—N(CH_3)—C(O)—$. In some embodiments, $L^2$ is $—C(O)—$.

In some embodiments, $L^2$ is optionally substituted 4- to 12-membered monocyclic or bicyclic heterocyclyl comprising 1 to 4 heteroatoms selected from N, O, and S. In some embodiments, $L^2$ is optionally substituted 4- to 6-membered monocyclic heterocyclyl comprising 1 to 4 heteroatoms selected from N, O, and S. In some embodiments, $L^2$ is optionally substituted 4-membered monocyclic heterocyclyl comprising 1 heteroatom selected from N, O, and S. In some embodiments, $L^2$ is optionally substituted 5-membered monocyclic heterocyclyl comprising 1 to 4 heteroatoms selected from N, O, and S. In some embodiments, $L^2$ is optionally substituted 6-membered monocyclic heterocyclyl comprising 1 to 4 heteroatoms selected from N, O, and S.

In some embodiments, $L^2$ is optionally substituted 8- to 12-membered monocyclic or bicyclic heterocyclyl comprising 1 to 4 heteroatoms selected from N, O, and S. In some embodiments, $L^2$ is optionally substituted 8-membered monocyclic or bicyclic heterocyclyl comprising 1 to 4 heteroatoms selected from N, O, and S. In some embodiments, $L^2$ is optionally substituted 9-membered monocyclic or bicyclic heterocyclyl comprising 1 to 4 heteroatoms selected from N, O, and S. In some embodiments, $L^2$ is optionally substituted 10-membered monocyclic or bicyclic heterocyclyl comprising 1 to 4 heteroatoms selected from N, O, and S. In some embodiments, $L^2$ is optionally substituted 11-membered monocyclic or bicyclic heterocyclyl comprising 1 to 4 heteroatoms selected from N, O, and S. In some embodiments, $L^2$ is optionally substituted 12-membered monocyclic or bicyclic heterocyclyl comprising 1 to 4 heteroatoms selected from N, O, and S.

In some embodiments, $L^2$ is 2- to 6-membered heteroliphatic. In some embodiments, $L^2$ is $—CH(CH_3)—S—$.

In some embodiments, a substituent on an optionally substituted carbon atom of an optionally substituted $L^2$ group is halogen; $—(CH_2)_{0-4}R°$; $—(CH_2)_{0-4}OR°$. In some embodiments, a substituent on an optionally substituted carbon atom of an optionally substituted $L^2$ group is halogen or $C_{1-6}$ aliphatic.

As defined generally above for compounds of formulae I, I', II, II', or any other formulae provided herein, V is selected from $C_{1-6}$ aliphatic, $C_{6-12}$ aryl, 4- to 12-membered monocyclic or bicyclic heterocyclyl comprising 1 to 4 heteroatoms selected from N, O, and S, 5- to 12-membered monocyclic or bicyclic heteroaryl comprising 1 to 4 heteroatoms selected from N, O, and S, 5- to 12-membered monocyclic or bicyclic aryl, and $C_{3-12}$ cycloalkyl, wherein V is substituted with $(R^6)_m$.

In some embodiments, V is selected from $C_{1-6}$ aliphatic, $C_{6-12}$ aryl, $C_{3-12}$ cycloaliphatic, 4- to 12-membered monocyclic or polycyclic heterocyclyl comprising 1 to 4 heteroatoms selected from N, O, and S, and 5- to 12-membered monocyclic or bicyclic heteroaryl comprising 1 to 4 heteroatoms selected from N, O, and S, wherein V is substituted with $(R^6)_m$.

As defined generally above for each of formula I, II, and II', V is substituted with $(R^6)_m$. As defined generally above, m is 0, 1, 2, 3, or 4. That is, in some embodiments, V is substituted with 0, 1, 2, 3, or 4 $R^6$. In some embodiments, V is unsubstituted (i.e., m is 0). In some embodiments, m is 1. In some embodiments, m is 2. In some embodiments, m is 3. In some embodiments, m is 4.

In some embodiments, V is $C_{1-6}$ aliphatic. In some embodiments, V is $C_{1-6}$ alkyl. In some embodiments, V is selected from methyl, ethyl, propyl, butyl, propyl, and hexyl.

In some embodiments, V is $C_{6-12}$ aryl (e.g., monocyclic or bicyclic). In some embodiments, V is phenyl. In some embodiments, V is naphthalenyl.

In some embodiments, V is $C_{3-12}$ cycloaliphatic (e.g., monocyclic or polycyclic). In some embodiments, V is $C_{3-12}$ cycloalkyl (e.g., monocyclic or polycyclic). In some embodiments, V is $C_{3-6}$ monocyclic cycloalkyl. In some embodiments, V is cyclopropyl, cyclobutyl, cyclopentyl, or cyclohexyl. In some embodiments, V is cyclopropyl. In some embodiments, V is cyclobutyl. In some embodiments, V is cyclopentyl. In some embodiments, V is cyclohexyl. In some embodiments, V is $C_5$-$1_2$ polycyclic cycloalkyl. In some embodiments, V is adamantyl.

In some embodiments, V is 4- to 12-membered monocyclic or polycyclic heterocyclyl comprising 1 to 4 heteroatoms selected from N, O, and S. In some embodiments, V is 4- to 6-membered monocyclic heterocyclyl comprising 1 to 4 heteroatoms selected from N, O, and S. In some embodiments, V is 4-membered heterocyclic comprising 1 heteroatom selected from N, O, and S. In some embodiments, V is 5-membered heterocyclic comprising 1 to 4 heteroatom selected from N, O, and S. In some embodiments, V is 6-membered heterocyclic comprising 1 to 4 heteroatom selected from N, O, and S. In some embodiments, V is morpholinyl. In some embodiments, V is piperazinyl. In some embodiments, V is piperidinyl.

In some embodiments, V is 7- to 12-membered polycyclic heterocyclyl comprising 1 to 4 heteroatoms selected from N, O, and S. In some embodiments, V is 7-membered polycyclic heterocyclyl comprising 1 to 4 heteroatoms selected from N, O, and S. In some embodiments, V is 8-membered polycyclic heterocyclyl comprising 1 to 4 heteroatoms selected from N, O, and S. In some embodiments, V is 9-membered polycyclic heterocyclyl comprising 1 to 4 heteroatoms selected from N, O, and S. In some embodiments, V is 10-membered polycyclic heterocyclyl comprising 1 to 4 heteroatoms selected from N, O, and S. In some embodiments, V is 11-membered polycyclic heterocyclyl comprising 1 to 4 heteroatoms selected from N, O, and S. In some embodiments, V is 12-membered polycyclic heterocyclyl comprising 1 to 4 heteroatoms selected from N, O, and S.

In some embodiments, V is 5- to 12-membered monocyclic or bicyclic heteroaryl comprising 1 to 4 heteroatoms selected from N, O, and S. In some embodiments, V is 5- to 6-membered monocyclic heteroaryl comprising 1 to 4 heteroatoms selected from N, O, and S. In some embodiments, V is 5-membered monocyclic heteroaryl comprising 1 to 4 heteroatoms selected from N, O, and S. In some embodiments, V is thiophenyl. In some embodiments, V is pyrazolyl. In some embodiments, V is 6-membered monocyclic heteroaryl comprising 1 to 4 heteroatoms selected from N, O, and S. In some embodiments, V is pyridyl.

In some embodiments, V is 7- to 12-membered bicyclic heteroaryl comprising 1 to 4 heteroatoms selected from N, O, and S. In some embodiments, V is 7-membered bicyclic heteroaryl comprising 1 to 4 heteroatoms selected from N, O, and S. In some embodiments, V is 8-membered bicyclic heteroaryl comprising 1 to 4 heteroatoms selected from N, O, and S. In some embodiments, V is 9-membered bicyclic heteroaryl comprising 1 to 4 heteroatoms selected from N, O, and S. In some embodiments, V is 10-membered bicyclic heteroaryl comprising 1 to 4 heteroatoms selected from N, O, and S. In some embodiments, V is 11-membered bicyclic heteroaryl comprising 1 to 4 heteroatoms selected from N, O, and S. In some embodiments, V is 12-membered bicyclic heteroaryl comprising 1 to 4 heteroatoms selected from N, O, and S. In some embodiments, V is indolyl.

As defined generally above for compounds of formulae I, I', II, II', or any other formulae provided herein, each $R^6$ is independently selected from halo, S(O)—$R^5$, $S(O)_2$—$R^5$, S(O)(NH)—$R^5$, —CN, —C(O)—$R^5$, —C(O)O—$R^5$, —C(O)—NH($R^5$), —C(O)—N$(R^5)_2$, —P(O)$(R^5)_2$, or an optionally substituted group selected from O—$C_{1-6}$ alkyl, $C_{1-6}$ alkyl, and $C_{6-12}$ aryl.

In some embodiments, each $R^6$ is independently selected from halo, oxo, —$SF_5$, —S(O)—$R^5$, $S(O)_2$—$R^5$, —S(O)(NH)—$R^5$, —$S(O)_2$—(NH)—$R^5$, —S(O)—N$(R^5)_2$, —$S(O)_2$—N$(R^5)_2$, —CN, —C(O)—NH($R^5$), —C(O)—N$(R^5)_2$, —P(O)$(R^5)_2$, —O—$R^5$, or an optionally substituted group selected from $C_{1-6}$ aliphatic, S—$C_{1-6}$ aliphatic, 2- to 12-membered heteroaliphatic, —$C_{0-6}$ alkylenyl-C(O)—$R^5$, —$C_{0-6}$ alkylenyl-C(O)O—$R^5$, $C_{6-12}$ aryl, $C_{3-12}$ cycloaliphatic, and 4- to 7-membered monocyclic heterocyclyl comprising 1 to 4 heteroatoms selected from N, O, and S.

In some embodiments, $R^6$ is halo, S(O)—$R^5$, $S(O)_2$—$R^5$, or an optionally substituted $C_{1-6}$ aliphatic.

In some embodiments, $R^6$ is halo. In some embodiments, $R^6$ is chloro, fluoro, bromo, or iodo. In some embodiments, $R^6$ is fluoro. In some embodiments, $R^6$ is chloro. In some embodiments, $R^6$ is bromo. In some embodiments, $R^6$ is iodo.

In some embodiments, $R^6$ is oxo.

In some embodiments, $R^6$ is $SF_5$.

In some embodiments, $R^6$ is —S(O)—$R^5$. In some embodiments, $R^6$ is optionally substituted —S(O)—$C_{1-6}$ aliphatic. In some embodiments, $R^6$ is —S(O)—$CH_3$.

In some embodiments, $R^6$ is —$S(O)_2$—$R^5$. In some embodiments, $R^6$ is optionally substituted —$S(O)_2$—$C_{1-6}$ aliphatic. In some embodiments, $R^6$ is —$S(O)_2$—$CH_3$. In some embodiments, $R^6$ is —$S(O)_2$—$CH_2CH_3$. In some embodiments, $R^6$ is —$S(O)_2$—$CHF_2$. In some embodiments, $R^6$ is —$S(O)_2$—$CF_3$.

In some embodiment, $R^6$ is —S(O)—N$(R^5)_2$. In some embodiments, $R^6$ is optionally substituted —S(O)—N($C_{1-6}$ aliphatic)$_2$. In some embodiments, $R^6$ is —S(O)—N$(CH_3)_2$. In some embodiments, $R^6$ is —S(O)—NH($C_{1-6}$ aliphatic). In some embodiments, $R^6$ is —S(O)—NH—$CH_3$.

In some embodiment, $R^6$ is —$S(O)_2$—N$(R^5)_2$. In some embodiments, $R^6$ is optionally substituted —$S(O)_2$—N($C_{1-6}$ aliphatic)$_2$. In some embodiments, $R^6$ is —$S(O)_2$—N$(CH_3)_2$. In some embodiments, $R^6$ is —$S(O)_2$—NH($C_{1-6}$ aliphatic). In some embodiments, $R^6$ is —$S(O)_2$—NH—$CH_3$.

In some embodiments, $R^6$ is —CN.

In some embodiments, $R^6$ is optionally substituted —$C_{0-6}$ alkylenyl-C(O)—$R^5$. In some embodiments, $R^6$ is optionally substituted —$C_{1-6}$ alkylenyl-C(O)—$R^5$. In some embodiments, $R^6$ is —C(O)—$R^5$. In some embodiments, $R^6$ is —C(O)—$CH_3$. In some embodiments, $R^6$ is —C(O)—CH$(CH_3)_2$. In some embodiments, $R^6$ is —C(O)—$CF_3$. In some embodiments, $R^6$ is —C(O)-pyrolidinyl.

In some embodiments, $R^6$ is optionally substituted —$C_{0-6}$ alkylenyl-C(O)O—$R^5$. In some embodiments, $R^6$ is optionally substituted —C(O)O—$C_{1-6}$ aliphatic. In some embodiments, $R^6$ is —C(O)O—$CH_3$. In some embodiments, $R^6$ is —C(O)O—$CH_2CH_3$. In some embodiments, $R^6$ is —$C(CH_3)_2$—C(O)O—$CH_3$.

In some embodiments, $R^6$ is —C(O)—NH($R^5$). In some embodiments, $R^6$ is —C(O)—NH($CH_3$). In some embodiments, $R^6$ is —C(O)—NH-cyclopropyl.

In some embodiments, $R^6$ is —C(O)—N$(R^5)_2$. In some embodiments, $R^6$ is —C(O)—N$(CH_3)_2$.

In some embodiments, $R^6$ is —P(O)$(R^5)_2$. In some embodiments, $R^6$ is —P(O)$(CH_3)_2$.

In some embodiments, $R^6$ is —O—$R^5$. In some embodiments, $R^6$ is —O-cyclopentyl. In some embodiments, $R^6$ is optionally substituted O—$C_{1-6}$ aliphatic. In some embodiments, $R^6$ is optionally substituted O—$C_{1-6}$ alkyl. In some embodiments, $R^6$ is O—$CH_3$. In some embodiments, $R^6$ is O—$CH_2CH_3$. In some embodiments, $R^6$ is O—$CH_2$—$CH_2$—$CH_3$. In some embodiments, $R^6$ is O—$CF_3$. In some embodiments, $R^6$ is O—CH$(CH_3)_2$. In some embodiments, $R^6$ is —O—$CH_2$—$CF_3$. In some embodiments, $R^6$ is —O—$CHF_2$.

In some embodiments, $R^6$ is optionally substituted $C_{1-6}$ aliphatic. In some embodiments, $R^6$ is optionally substituted $C_{1-6}$ alkyl. In some embodiments, $R^6$ is optionally substituted $C_{1-4}$ alkyl. In some embodiments, $R^6$ is methyl. In some embodiments, $R^6$ is ethyl. In some embodiments, $R^6$ is propyl. In some embodiments, $R^6$ is iso-propyl. In some embodiments, $R^6$ is butyl. In some embodiments, $R^6$ is tert-butyl. In some embodiments, $R^6$ is pentyl. In some embodiments, $R^6$ is neo-pentyl. In some embodiments, $R^6$ is —$CH_2F$. In some embodiments, $R^6$ is —$CHF_2$. In some embodiments, $R^6$ is $CF_3$. In some embodiments, $R^6$ is —$CH_2$—$CF_3$. In some embodiments, $R^6$ is —$CF_2$—$CH_3$. In some embodiments, $R^6$ is —$CF_2$—$CF_3$. In some embodiments, $R^6$ is —$C(CH_3)_2$—$CF_3$. In some embodiments, $R^6$ is —$C(CH_3)_2$—CN.

In some embodiments, $R^6$ is optionally substituted S—$C_{1-6}$ aliphatic. In some embodiments, $R^6$ is S—$CH_3$.

In some embodiments, $R^6$ is optionally substituted 2- to 12-membered heteroaliphatic. In some embodiments, $R^6$ is —$C(CH_3)_2$—$OCH_3$. In some embodiments, $R^6$ is $-O-CH_2-CH_2-O-CH_2-CH_2-O-CH_2-CH_2-O-CH_3$. In some embodiments, $R^6$ is $-O-CH_2-CH_2-O-CH_2-CH_2-O-CH_3$. In some embodiments, $R^6$ is $-CF_2-CF_2-O-CH_3$.

In some embodiments, $R^6$ is optionally substituted $C_{6-12}$ aryl. In some embodiments, $R^6$ is phenyl.

In some embodiments, $R^6$ is optionally substituted $C_{3-12}$ cycloaliphatic. In some embodiments, $R^6$ is optionally substituted $C_{3-12}$ cycloalkyl. In some embodiments, $R^6$ is cyclopropyl. In some embodiments, $R^6$ is cyclobutyl. In some embodiments, $R^6$ is cyclopentyl. In some embodiments, $R^6$ is cyclohexyl.

In some embodiments, $R^6$ is 4- to 7-membered monocyclic heterocyclyl comprising 1 to 4 heteroatoms selected from N, O, and S. In some embodiments, $R^6$ is dioxolanyl.

In some embodiments, a substituent on an optionally substituted carbon atom of an optionally substituted $R^6$ is halo (e.g., bromo, chloro, fluoro, iodo), $-(CH_2)_{0-4}R°$; $-(CH_2)_{0-4}OR°$; $-O(CH_2)_{0-4}R°$, $-O-(CH_2)_{0-4}C(O)OR°$, OH, CN, or oxo, wherein R° is $C_{1-6}$ aliphatic.

As defined generally above for each of formula I, II, and II', each $R^5$ is independently selected from $C_{1-6}$ alkyl, $-N(R^3)_2$, $-O-C_{1-6}$ alkyl, $C(O)-C_{1-6}$ alkyl, $P(O)(C_{1-6}$ alkyl$)_2$, $C_{3-12}$ cycloalkyl, and 5- to 12-membered heterocyclyl comprising 1 to 4 heteroatoms selected from N, O, and S, wherein $R^5$ is optionally substituted with one or more substituents selected from halo, OH, and 2- to 12-membered heteroaliphatic.

In some embodiments, each $R^5$ is $-N(R^3)_2$ or an optionally substituted group selected from $C_{1-6}$ aliphatic, $P(O)(C_{1-6}$ aliphatic$)_2$, $C_{3-12}$ cycloaliphatic, and 5- to 12-membered heterocyclyl comprising 1 to 4 heteroatoms selected from N, O, and S.

In some embodiments, $R^5$ is $-N(R^3)_2$. In some embodiments, $R^5$ is optionally substituted $-N(C_{1-6}$ aliphatic$)_2$. In some embodiments, $R^5$ is optionally substituted $-NH(C_{1-6}$ aliphatic). In some embodiments, $R^5$ is $-NH_2$. In some embodiments, $R^5$ is $-NH(CH_3)$. In some embodiments, $R^5$ is $-N(CH_3)_2$.

In some embodiments, $R^5$ is optionally substituted $C_{1-6}$ aliphatic. In some embodiments, $R^5$ is optionally substituted $C_{1-6}$ alkyl. In some embodiments, $R^5$ is $C_{1-6}$ alkyl, wherein $R^5$ is optionally substituted with one or more substituents selected from halo, OH, and 2- to 12-membered heteroaliphatic.

In some embodiments, $R^5$ is optionally substituted $P(O)(C_{1-6}$ aliphatic$)_2$.

In some embodiments, $R^5$ is optionally substituted $C_{3-12}$ cycloaliphatic. In some embodiments, $R^5$ is cyclopentyl. In some embodiments, $R^5$ is $C_{3-12}$ cycloaliphatic, wherein $R^5$ is optionally substituted with one or more substituents selected from halo, OH, and 2- to 12-membered heteroaliphatic.

In some embodiments, $R^5$ is 5- to 12-membered heterocyclyl (e.g., monocyclic or polycyclic) comprising 1 to 4 heteroatoms selected from N, O, and S, wherein $R^5$ is optionally substituted with one or more substituents selected from halo and OH.

In some embodiments, V is selected from Table V:

TABLE V $-CH_2CH_2CH_3$,

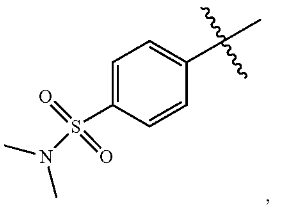

,

TABLE V-continued

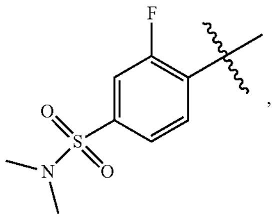

,

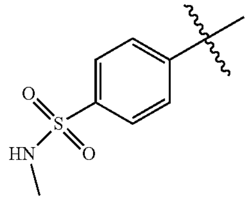

,

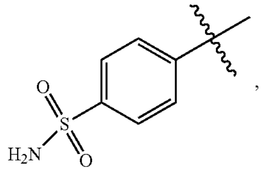 [SMILES: *c1ccc(S(N)(=O)=O)cc1]

,

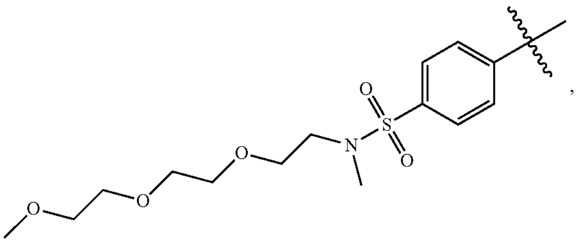 [SMILES: *c1ccc(S(=O)(=O)N(C)CCOCCOCCOC)cc1]

,

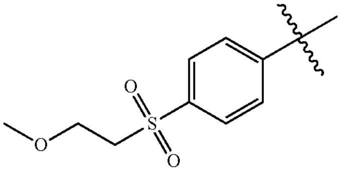

,

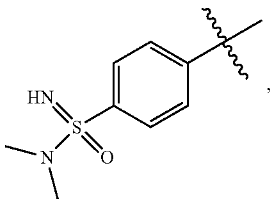

,

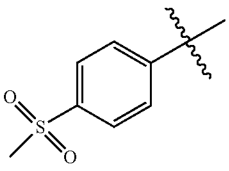

,

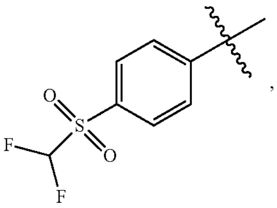

,

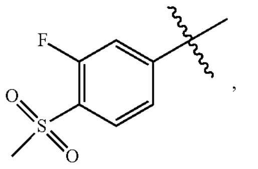

,

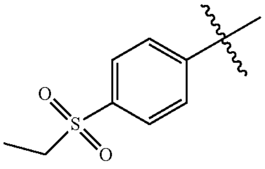

,

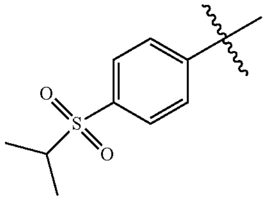

,

TABLE V-continued
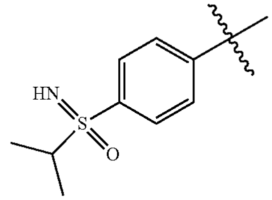,
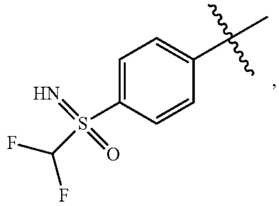,
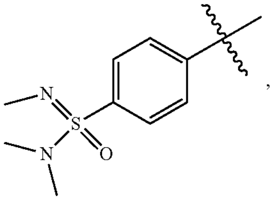 [SMILES: *c1ccc(S(=O)(=NC)N(C)C)cc1],
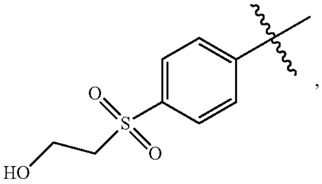 [SMILES: *c1ccc(S(=O)(=O)CCO)cc1],
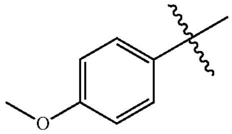,
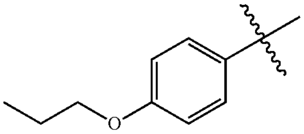,
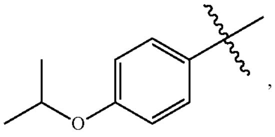,
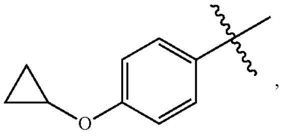,
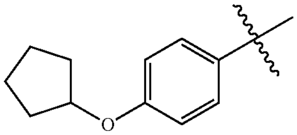,
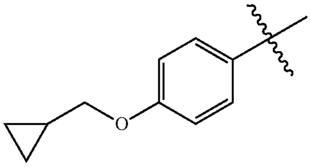,
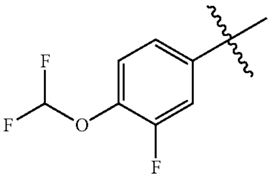,
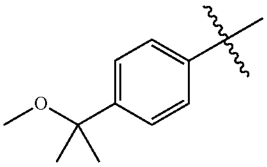,
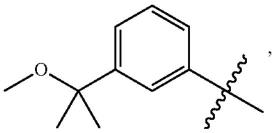 [SMILES: *c1cccc(C(C)(C)OC)c1],
TABLE V-continued
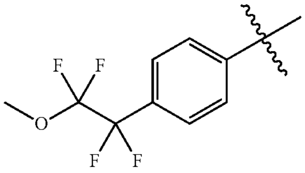,
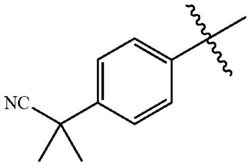,
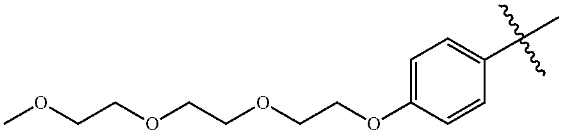,
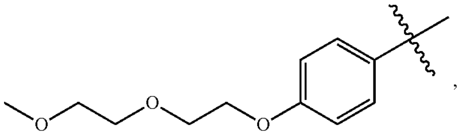 [SMILES: *c1ccc(OCCOCCOC)cc1],
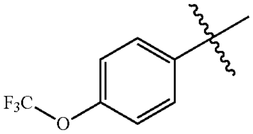,
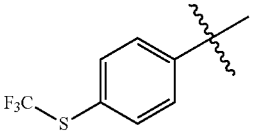,
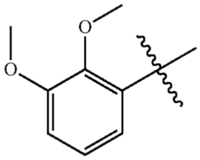,
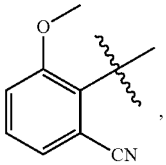,
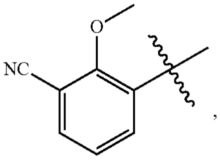,
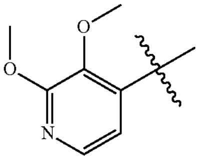,
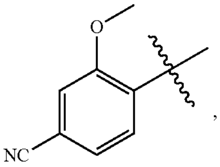,
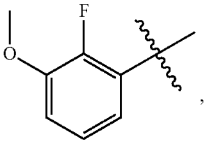,
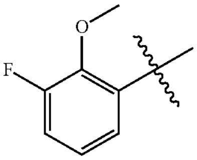,
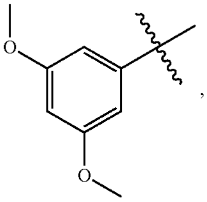,
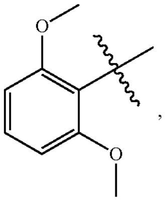,
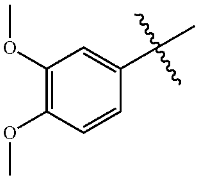, TABLE V-continued
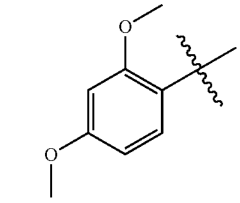, 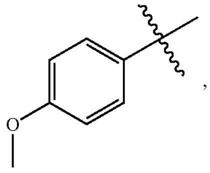,
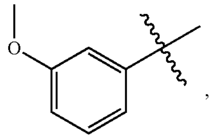, 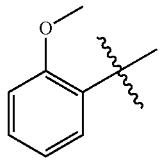,
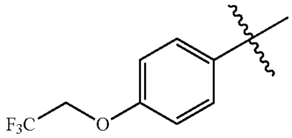,
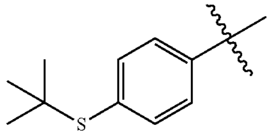, 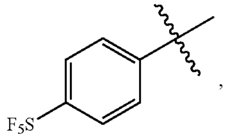,
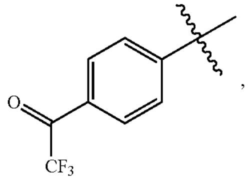, 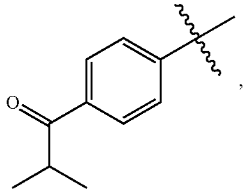,
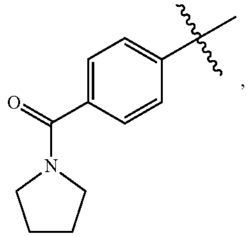, 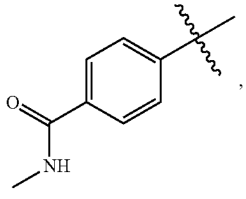,
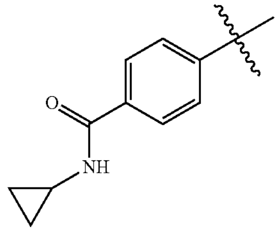, 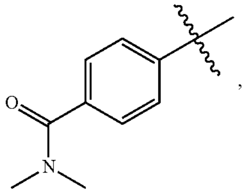,
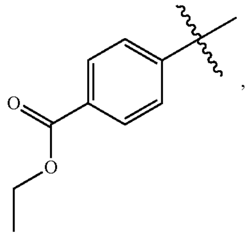, 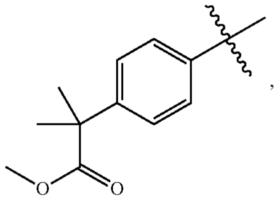,
TABLE V-continued
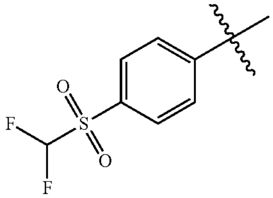, 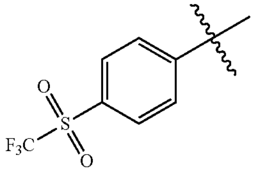,
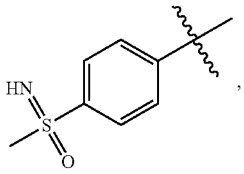, 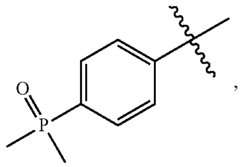,
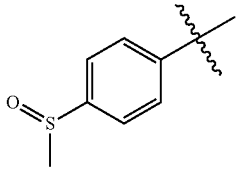, 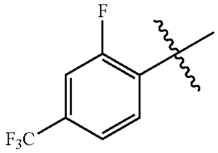,
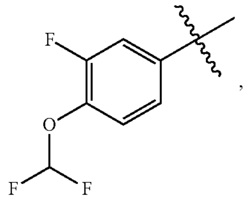, 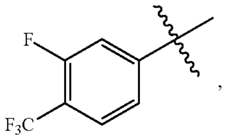,
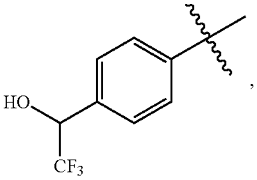, 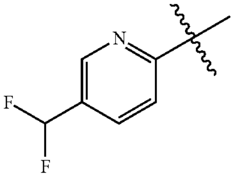,
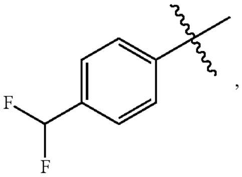, 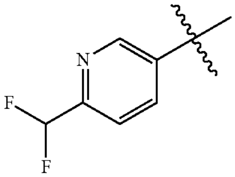,
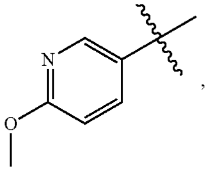, 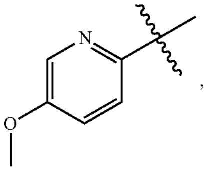,
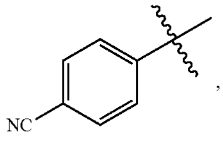, 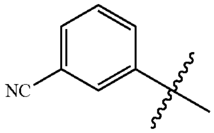, TABLE V-continued
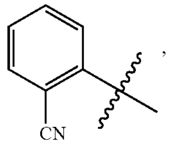 , 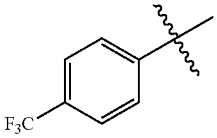 ,
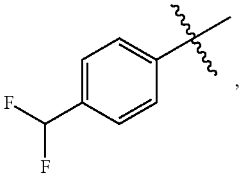 , 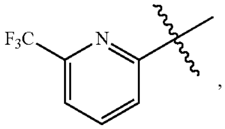 ,
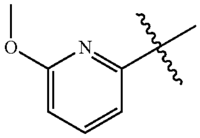 , 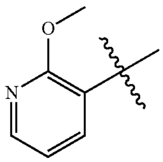 , 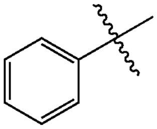 ,
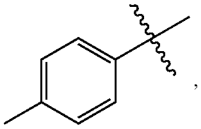 , 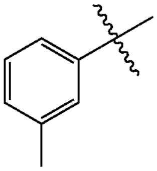 , 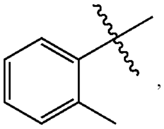 ,
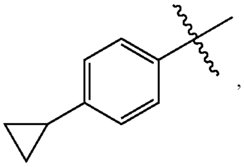 , 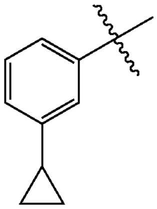 ,
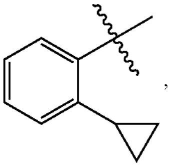 , 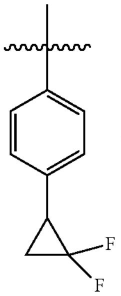 , 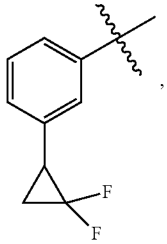 ,
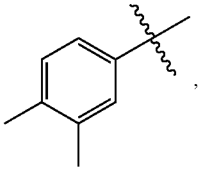 , 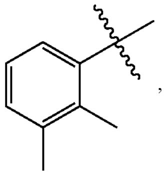 ,
TABLE V-continued
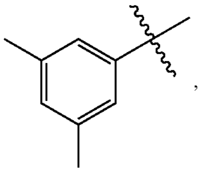 , 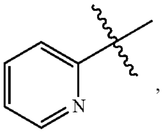 , 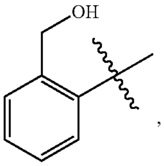 ,
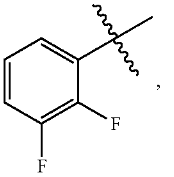 , 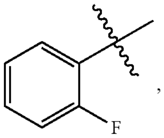 , 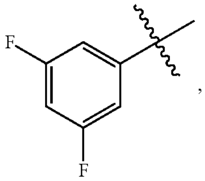 ,
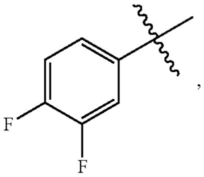 , 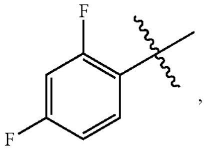 ,
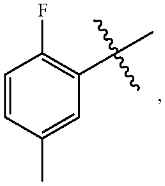 , 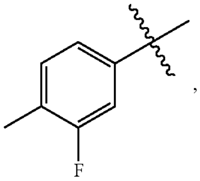 ,
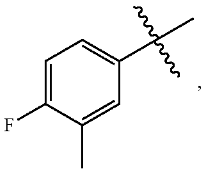 , 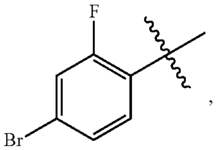 ,
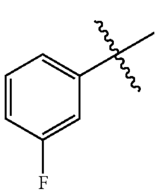 , 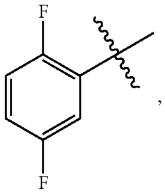 , 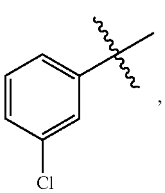 ,
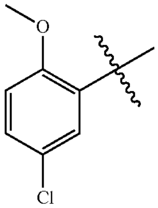 , 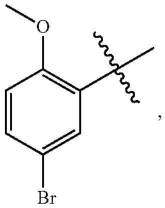 , 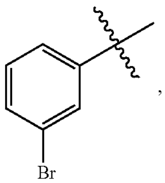 ,
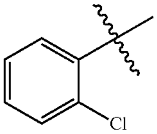 , 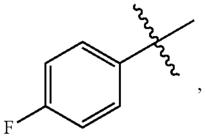 , TABLE V-continued
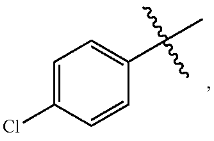, 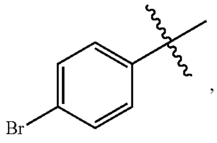,
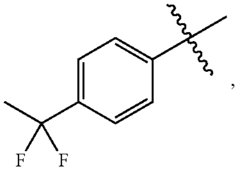, 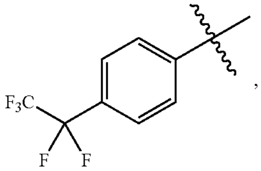,
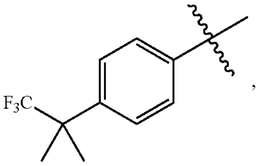, 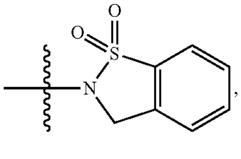,
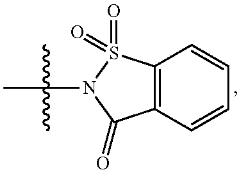, 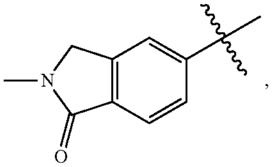,
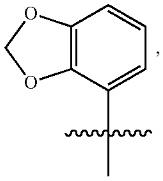, 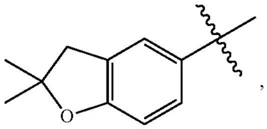,
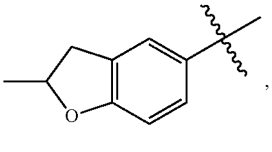, 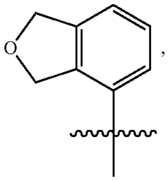,
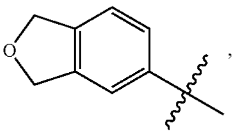, 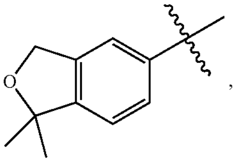,
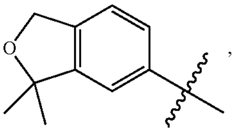, 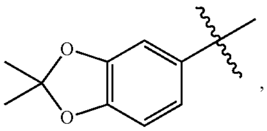,
TABLE V-continued
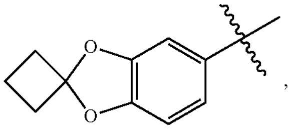, 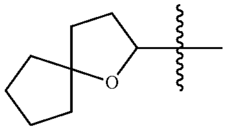,
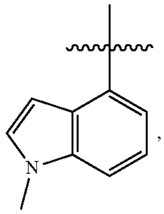, 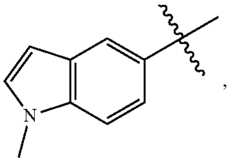,
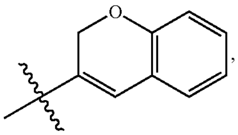, 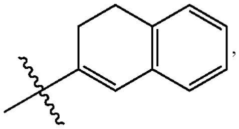,
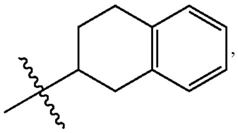, 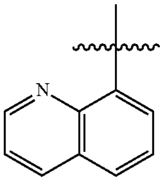,
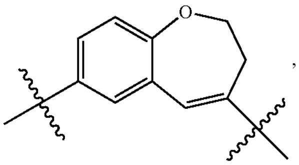, 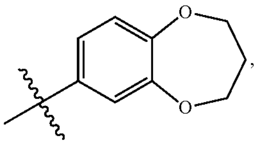,
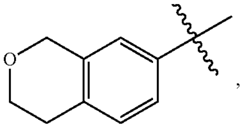, 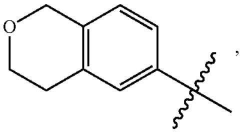,
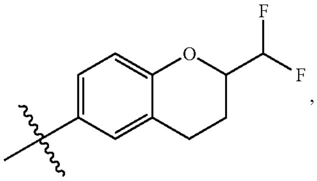, 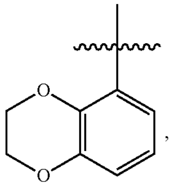,
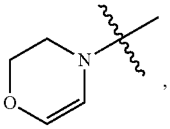, 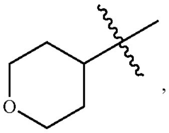, 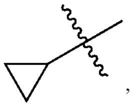, TABLE V-continued
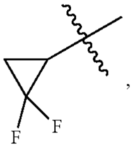, 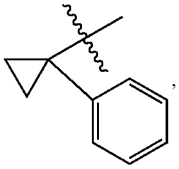, 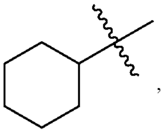,
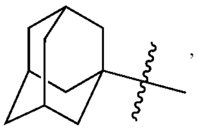, 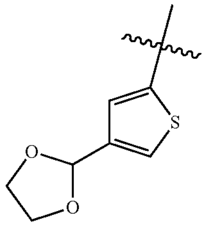, 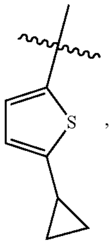,
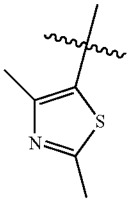, 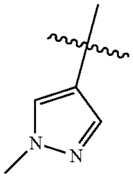, 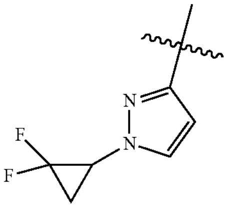,
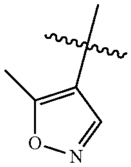, 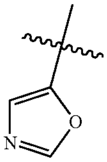, 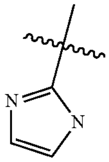, 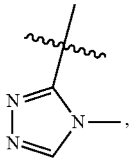,
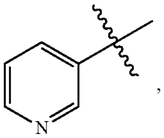, 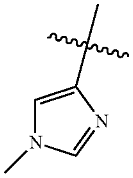, 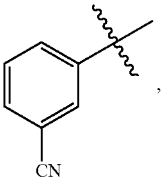,
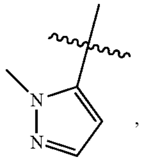, 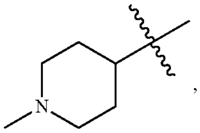, 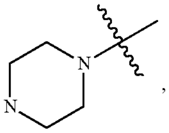,
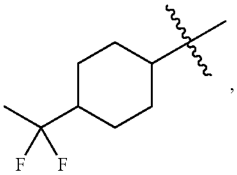, 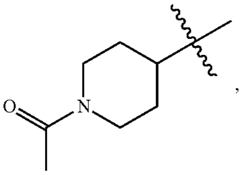,
TABLE V-continued
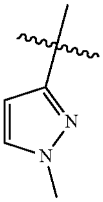, 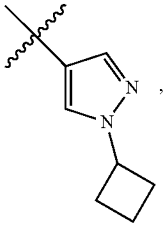, 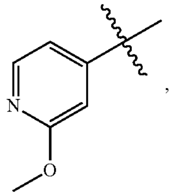,
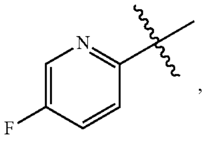, 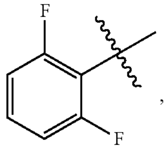, 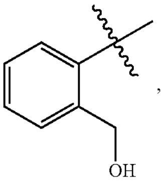,
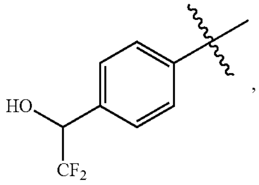, 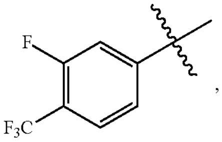,
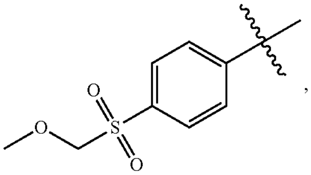 [SMILES: *c1ccc(S(=O)(=O)COC)cc1],
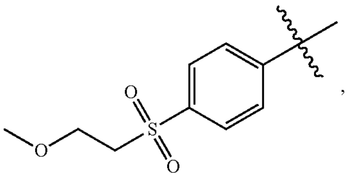, 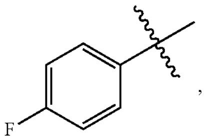,
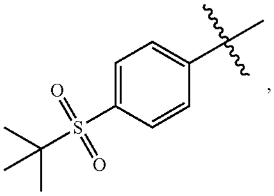 [SMILES: *c1ccc(S(=O)(=O)C(C)(C)C)cc1],
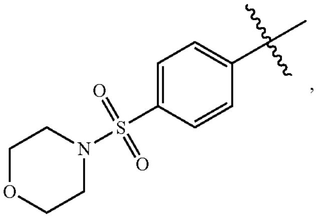 [SMILES: *c1ccc(S(=O)(=O)N2CCOCC2)cc1], TABLE V-continued
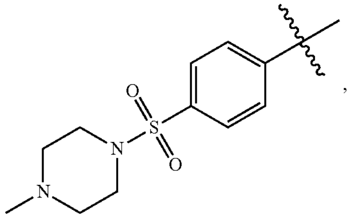 [SMILES: *c1ccc(S(=O)(=O)N2CCN(C)CC2)cc1],
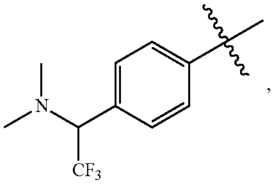, 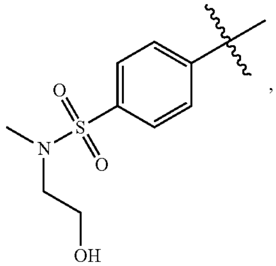,
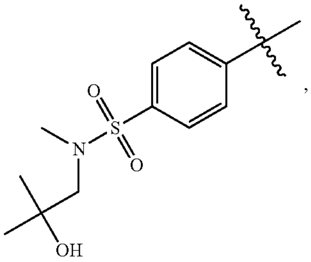, 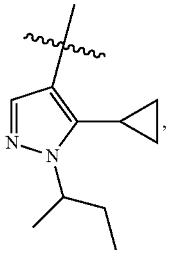,
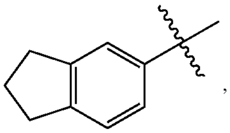, 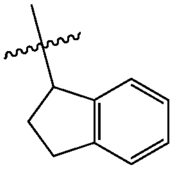,
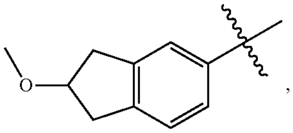, 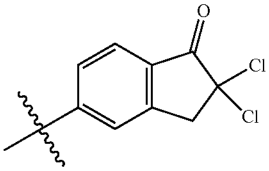,
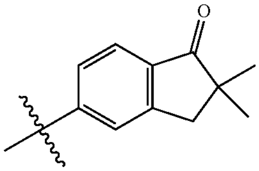, 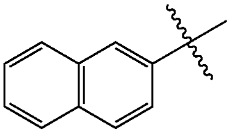,
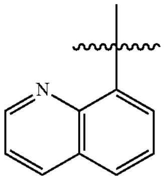, 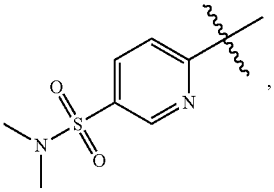,
TABLE V-continued
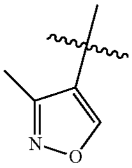, 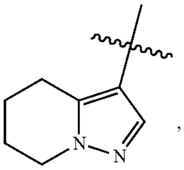,
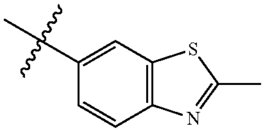, 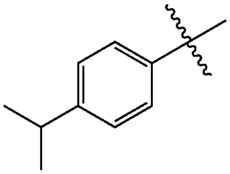,
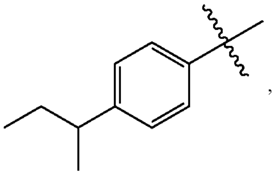, 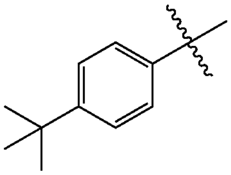,
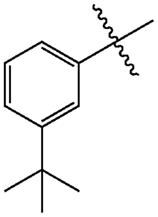, 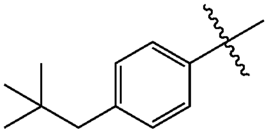,
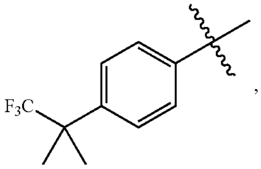 [SMILES: *c1ccc(C(C)(C)C(F)(F)F)cc1],
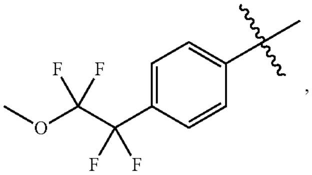 [SMILES: *c1ccc(C(F)(F)C(F)(F)OC)cc1],
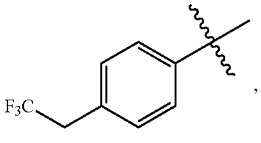, 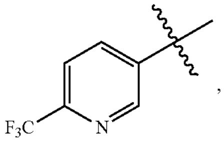,
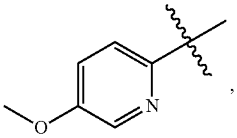, 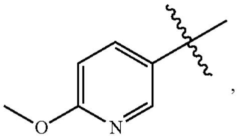, TABLE V-continued

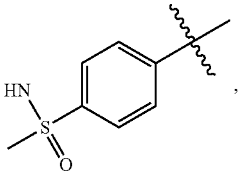, 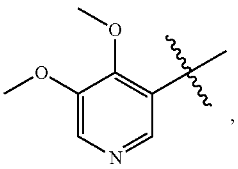,

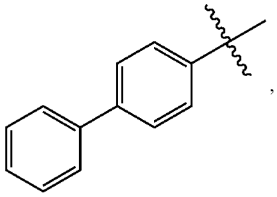, 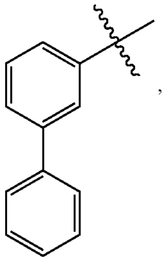,

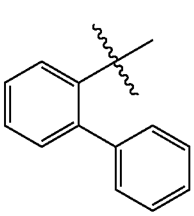, 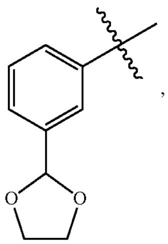, 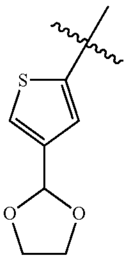,

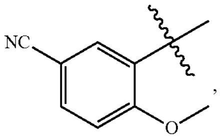, 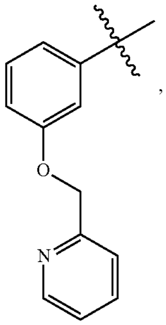, 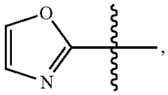,

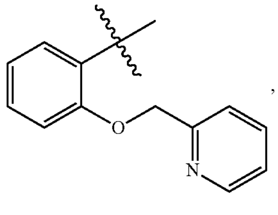, 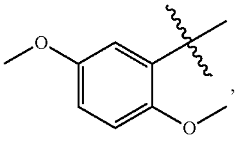,

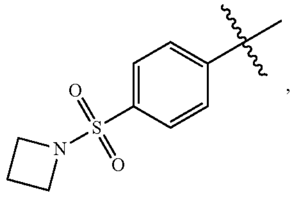 [SMILES: *c1ccc(S(=O)(=O)N2CCC2)cc1],

TABLE V-continued

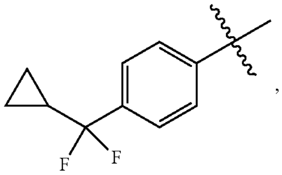, 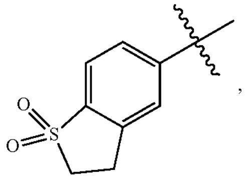,

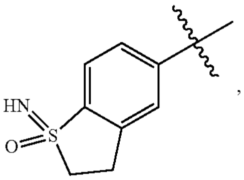, 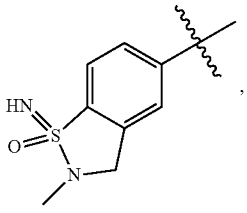,

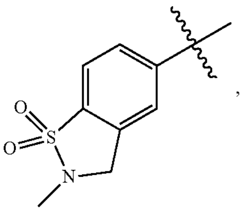, 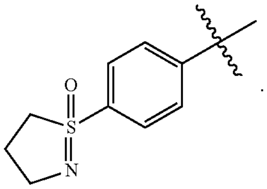.

In some embodiments, the present application provides a compound of formula IIa-1:

IIa-1

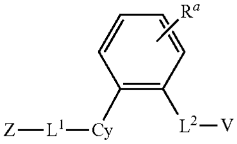

or a pharmaceutically acceptable salt thereof, wherein Z, $L^1$, Cy, $L^2$, V, and $R^a$ are defined in classes and subclasses provided herein.

In some embodiments, the present application provides a compound of formula IIa-2:

IIa-2

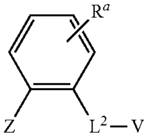

or a pharmaceutically acceptable salt thereof, wherein Z, $L^2$, V, and $R^a$ are defined in classes and subclasses provided herein.

In some embodiments, the present application provides a compound of formula IIa-3:

IIa-3

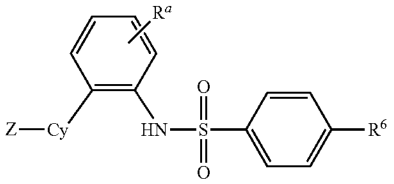

or a pharmaceutically acceptable salt thereof, wherein Z, Cy, $R^a$, and $R^6$ are defined in classes and subclasses provided herein.

In some embodiments, the present application provides a compound of formula IIa-4:

IIa-4

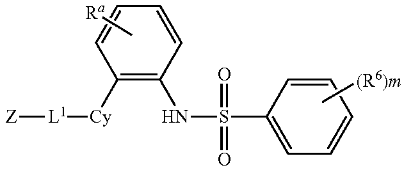

or a pharmaceutically acceptable salt thereof, wherein Z, $L^1$, Cy, $R^a$, and $R^6$ are defined in classes and subclasses provided herein.

In some embodiments, the present application provides a compound of formula IIb-1:

IIb-1

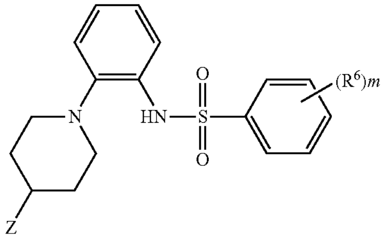

or a pharmaceutically acceptable salt thereof, wherein Z, $R^6$, and m are defined in classes and subclasses provided herein.

In some embodiments, the present application provides a compound of formula IIc:

IIc

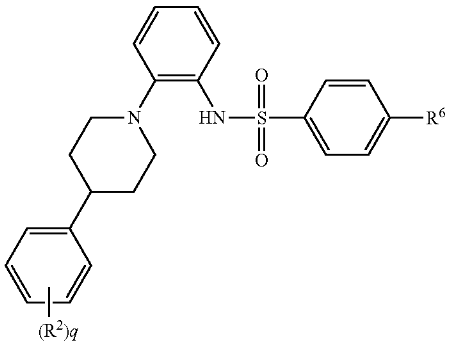

or a pharmaceutically acceptable salt thereof, wherein $R^2$, $R^6$, and q are defined in classes and subclasses provided herein.

In some embodiments, the present application provides a compound of formula IId:

IId

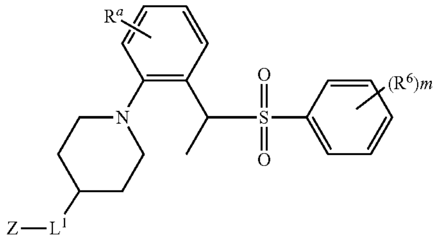

or a pharmaceutically acceptable salt thereof, wherein $R^a$, Z, $L^1$, $R^6$ and m are defined in classes and subclasses provided herein.

In some embodiments, the present application provides a compound of formula IId-1:

IId-1

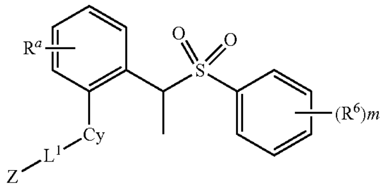

or a pharmaceutically acceptable salt thereof, wherein $R^a$, Z, $L^1$, Cy, $R^6$ and m are defined in classes and subclasses provided herein.

In some embodiments, the present application provides a compound of formula IId-2:

IId-2

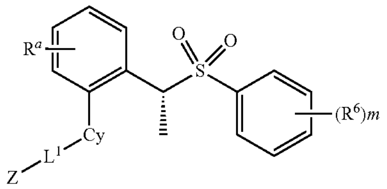

or a pharmaceutically acceptable salt thereof, wherein $R^a$, Z, $L^1$, Cy, $R^6$ and m are defined in classes and subclasses provided herein.

In some embodiments, the present application provides a compound of formula IId-3:

IId-3

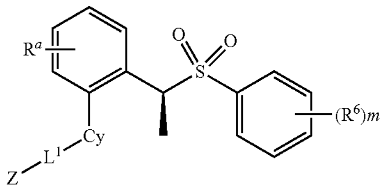

or a pharmaceutically acceptable salt thereof, wherein $R^a$, Z, $L^1$, Cy, $R^6$ and m are defined in classes and subclasses provided herein. It is to be understood that the above embodiments may be combined together, as if each and every combination were specifically and individually listed.

In some embodiments, the present application provides a compound of formula IIe:

IIe

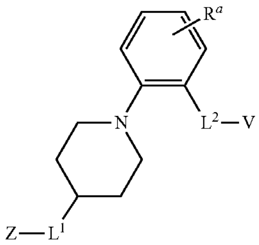

or a pharmaceutically acceptable salt thereof, wherein Z, $L^1$, $L^2$, V, and $R^a$ are defined in classes and subclasses provided herein.

In some embodiments, a compound of the present disclosure is selected from Table A:

TABLE A

| Structure | Compound No. |
|---|---|
| 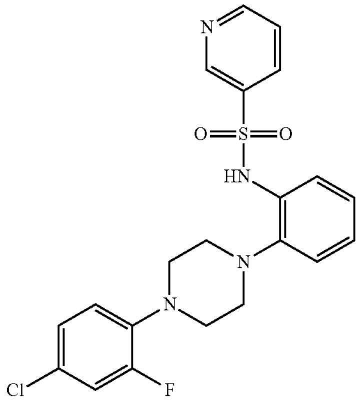 [SMILES: O=S(=O)(Nc1ccccc1N1CCN(c2ccc(Cl)cc2F)CC1)c1cccnc1] | A-1 |
| 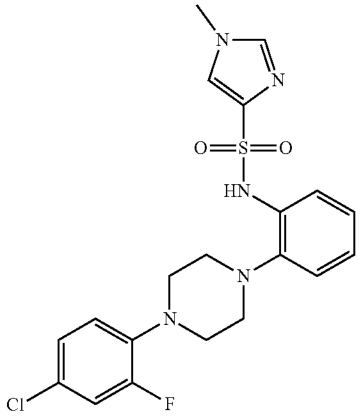 [SMILES: Cn1cnc(S(=O)(=O)Nc2ccccc2N2CCN(c3ccc(Cl)cc3F)CC2)c1] | A-2 |

TABLE A-continued
| Structure | Compound No. |
| --- | --- |
| 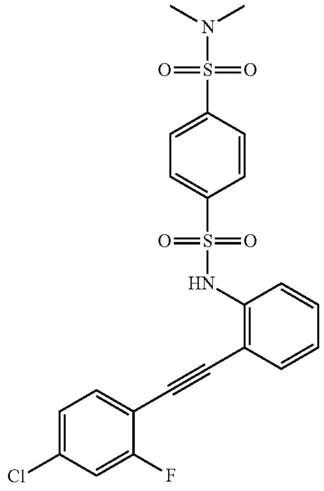 [SMILES: CN(C)S(=O)(=O)c1ccc(S(=O)(=O)Nc2ccccc2C#Cc2ccc(Cl)cc2F)cc1] | A-3 |
| 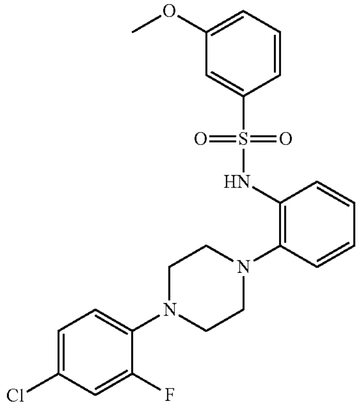 [SMILES: COc1cccc(S(=O)(=O)Nc2ccccc2N2CCN(c3ccc(Cl)cc3F)CC2)c1] | A-4 |
| 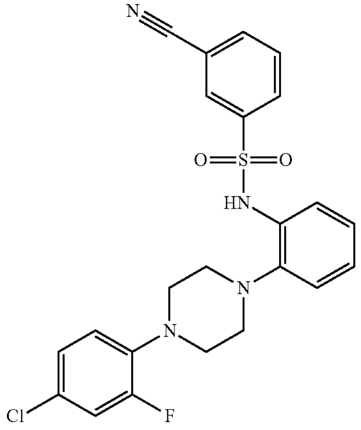 [SMILES: N#Cc1cccc(S(=O)(=O)Nc2ccccc2N2CCN(c3ccc(Cl)cc3F)CC2)c1] | A-5 |

TABLE A-continued
| Structure | Compound No. |
| --- | --- |
| 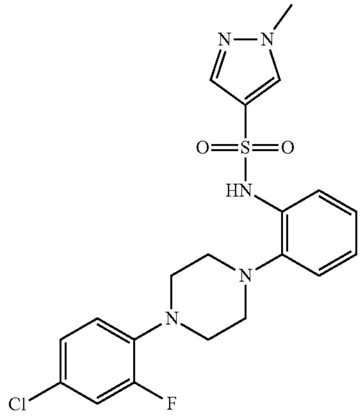 [SMILES: Cn1cc(S(=O)(=O)Nc2ccccc2N2CCN(c3ccc(Cl)cc3F)CC2)cn1] | A-6 |
| 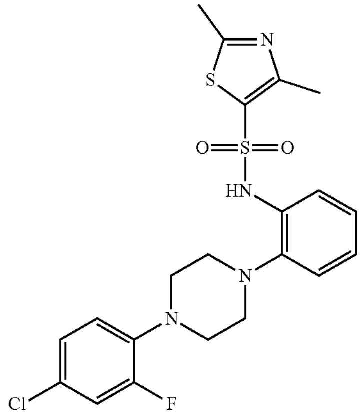 [SMILES: Cc1nc(C)c(S(=O)(=O)Nc2ccccc2N2CCN(c3ccc(Cl)cc3F)CC2)s1] | A-7 |
| 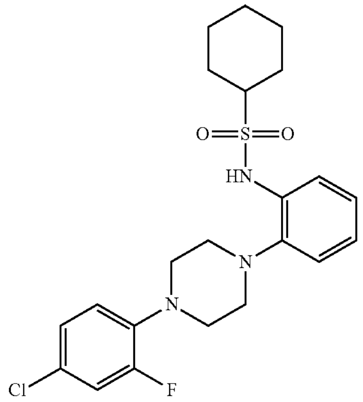 [SMILES: O=S(=O)(Nc1ccccc1N1CCN(c2ccc(Cl)cc2F)CC1)C1CCCCC1] | A-8 |
| 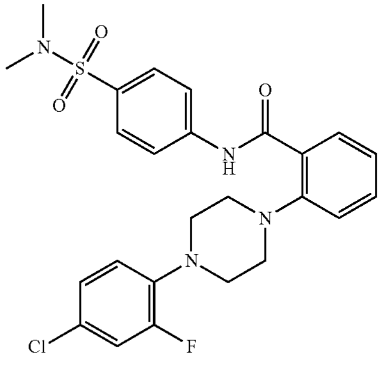 [SMILES: CN(C)S(=O)(=O)c1ccc(NC(=O)c2ccccc2N2CCN(c3ccc(Cl)cc3F)CC2)cc1] | A-9 |

TABLE A-continued
| Structure | Compound No. |
| --- | --- |
| 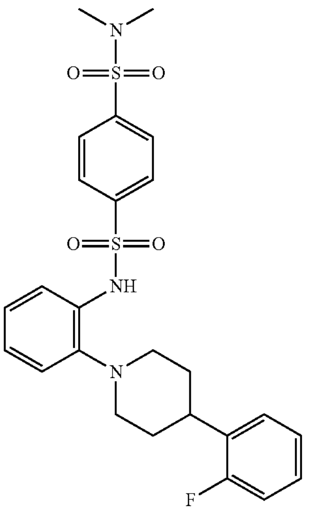 | A-10 |
| 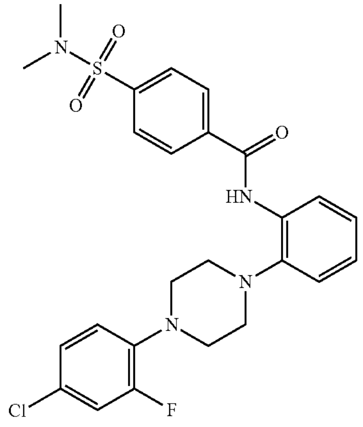 [SMILES: CN(C)S(=O)(=O)c1ccc(C(=O)Nc2ccccc2N2CCN(c3ccc(Cl)cc3F)CC2)cc1] | A-11 |
| 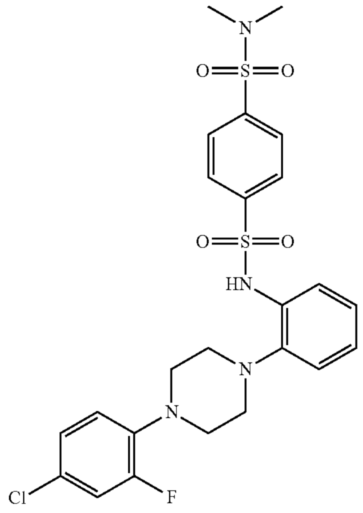 [SMILES: CN(C)S(=O)(=O)c1ccc(S(=O)(=O)Nc2ccccc2N2CCN(c3ccc(Cl)cc3F)CC2)cc1] | A-12 |

TABLE A-continued
| Structure | Compound No. |
| --- | --- |
| 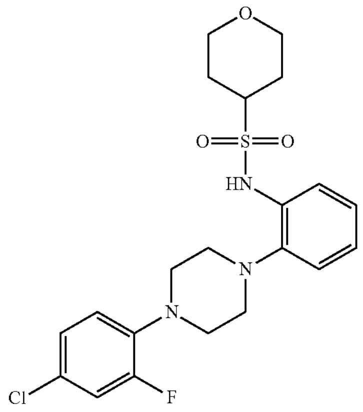 | A-14 |
| 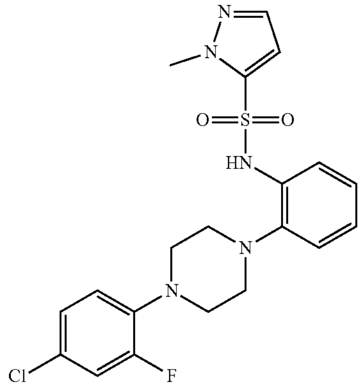 [SMILES: Cn1nccc1S(=O)(=O)Nc1ccccc1N1CCN(c2ccc(Cl)cc2F)CC1] | A-15 |
| 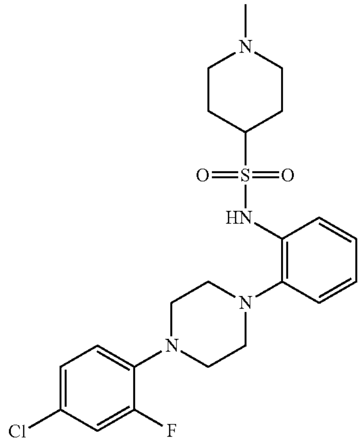 [SMILES: CN1CCC(S(=O)(=O)Nc2ccccc2N2CCN(c3ccc(Cl)cc3F)CC2)CC1] | A-16 |

TABLE A-continued
| Structure | Compound No. |
| --- | --- |
| 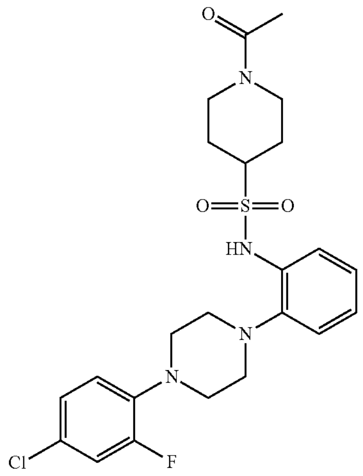 [SMILES: CC(=O)N1CCC(S(=O)(=O)Nc2ccccc2N2CCN(c3ccc(Cl)cc3F)CC2)CC1] | A-17 |
| 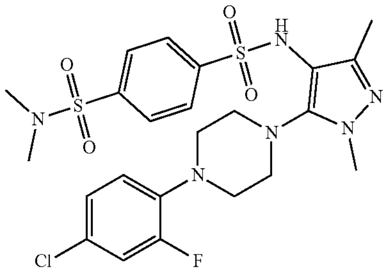 [SMILES: Cc1nn(C)c(N2CCN(c3ccc(Cl)cc3F)CC2)c1NS(=O)(=O)c1ccc(S(=O)(=O)N(C)C)cc1] | A-18 |
| 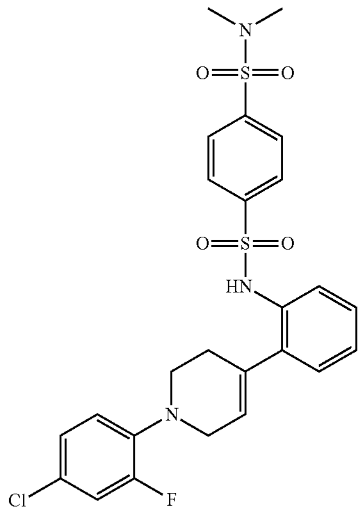 [SMILES: CN(C)S(=O)(=O)c1ccc(S(=O)(=O)Nc2ccccc2C2=CCN(c3ccc(Cl)cc3F)CC2)cc1] | A-19 |

TABLE A-continued
| Structure | Compound No. |
| --- | --- |
| 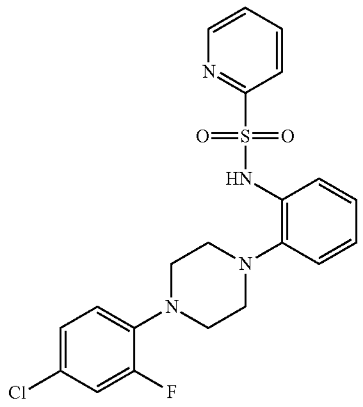 | A-20 |
| 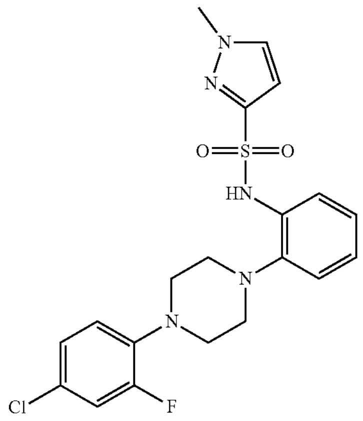 | A-21 |
| 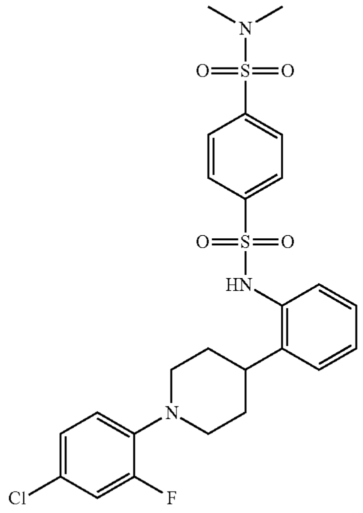 [SMILES: CN(C)S(=O)(=O)c1ccc(S(=O)(=O)Nc2ccccc2C2CCN(c3ccc(Cl)cc3F)CC2)cc1] | A-22 |

TABLE A-continued
| Structure | Compound No. |
| --- | --- |
| 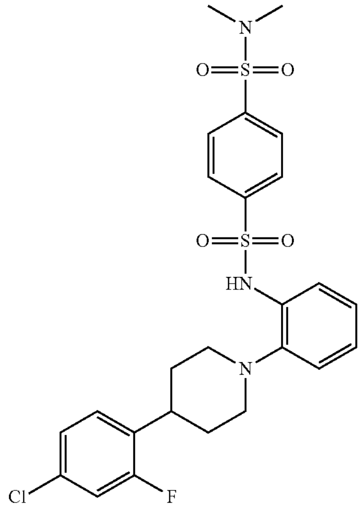 | A-23 |
| 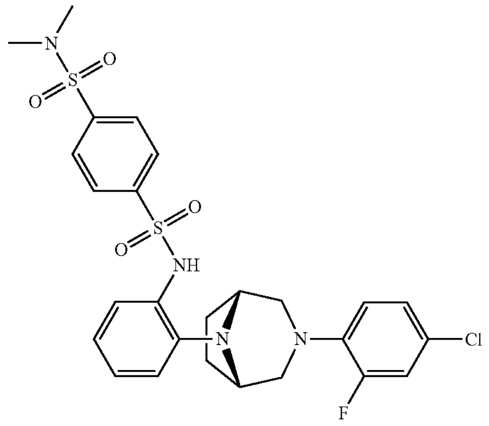 [SMILES: CN(C)S(=O)(=O)c1ccc(S(=O)(=O)Nc2ccccc2N2[C@@H]3CC[C@H]2CN(c2ccc(Cl)cc2F)C3)cc1] | A-25 |
| 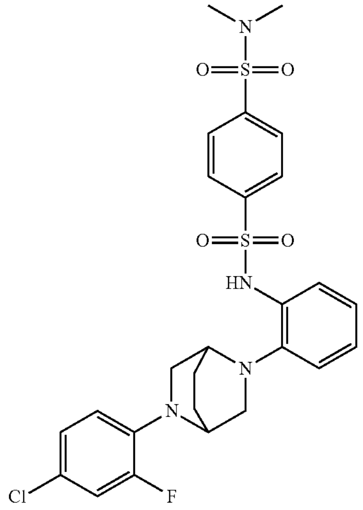 [SMILES: CN(C)S(=O)(=O)c1ccc(S(=O)(=O)Nc2ccccc2N2CC3CCC2CN3c2ccc(Cl)cc2F)cc1] | A-26 |

TABLE A-continued
| Structure | Compound No. |
|---|---|
| 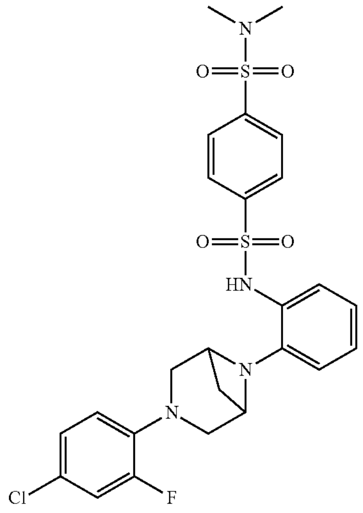 [SMILES: CN(C)S(=O)(=O)c1ccc(S(=O)(=O)Nc2ccccc2N2C3CC2CN(c2ccc(Cl)cc2F)C3)cc1] | A-27 |
| 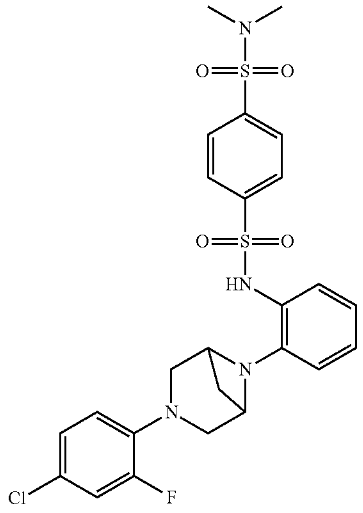 [SMILES: CN(C)S(=O)(=O)c1ccc(S(=O)(=O)Nc2ccccc2N2C3CC2CN(c2ccc(Cl)cc2F)C3)cc1] | A-28 |
| 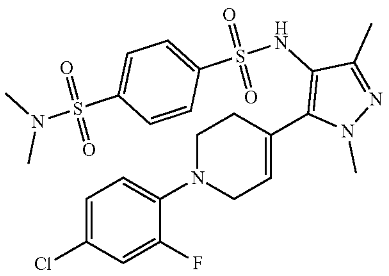 [SMILES: Cc1nn(C)c(C2=CCN(c3ccc(Cl)cc3F)CC2)c1NS(=O)(=O)c1ccc(S(=O)(=O)N(C)C)cc1] | A-29 |

TABLE A-continued
| Structure | Compound No. |
| --- | --- |
| 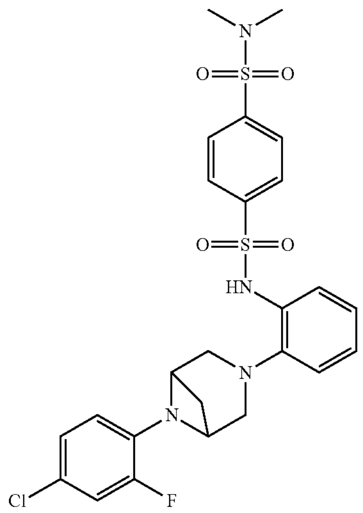 [SMILES: CN(C)S(=O)(=O)c1ccc(S(=O)(=O)Nc2ccccc2N2CC3CC(C2)N3c2ccc(Cl)cc2F)cc1] | A-30 |
| 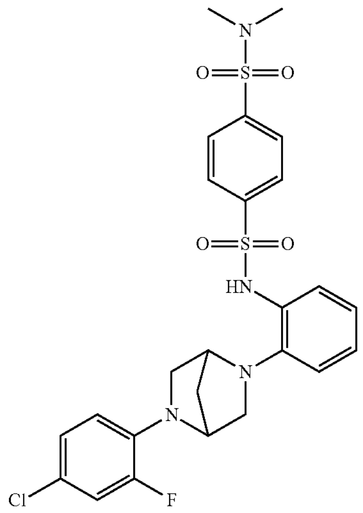 [SMILES: CN(C)S(=O)(=O)c1ccc(S(=O)(=O)Nc2ccccc2N2CC3CC2CN3c2ccc(Cl)cc2F)cc1] | A-31 |
| 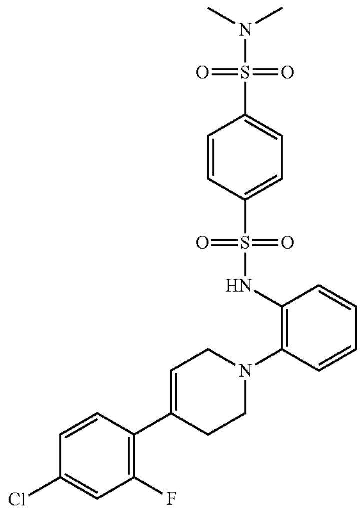 [SMILES: CN(C)S(=O)(=O)c1ccc(S(=O)(=O)Nc2ccccc2N2CC=C(c3ccc(Cl)cc3F)CC2)cc1] | A-32 |

TABLE A-continued
| Structure | Compound No. |
|---|---|
| 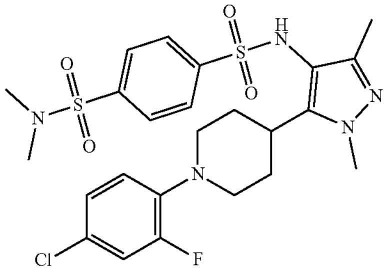 [SMILES: Cc1nn(C)c(C2CCN(c3ccc(Cl)cc3F)CC2)c1NS(=O)(=O)c1ccc(S(=O)(=O)N(C)C)cc1] | A-33 |
| 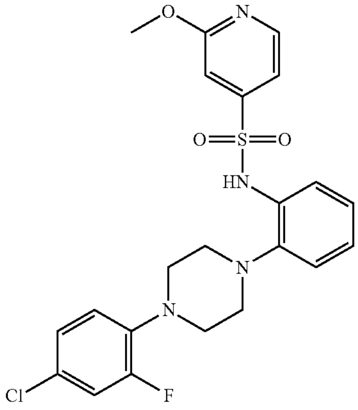 [SMILES: COc1cc(S(=O)(=O)Nc2ccccc2N2CCN(c3ccc(Cl)cc3F)CC2)ccn1] | A-34 |
| 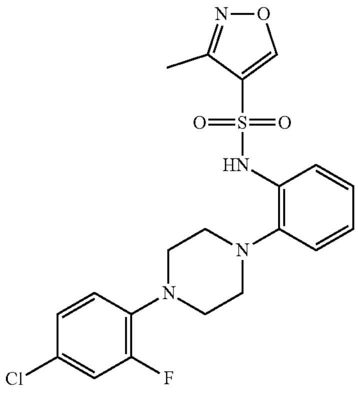 [SMILES: Cc1nocc1S(=O)(=O)Nc1ccccc1N1CCN(c2ccc(Cl)cc2F)CC1] | A-35 |
| 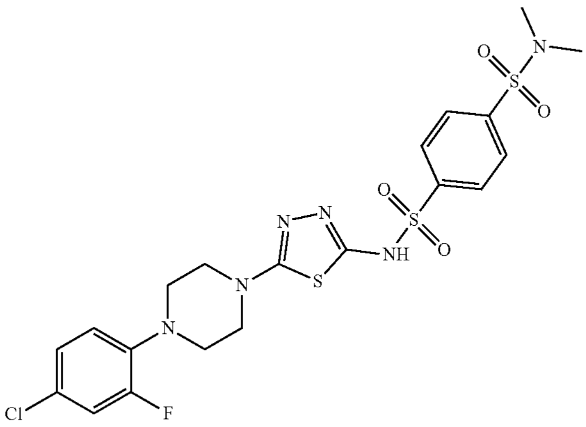 [SMILES: CN(C)S(=O)(=O)c1ccc(S(=O)(=O)Nc2nnc(N3CCN(c4ccc(Cl)cc4F)CC3)s2)cc1] | A-36 |

TABLE A-continued
| Structure | Compound No. |
|---|---|
| 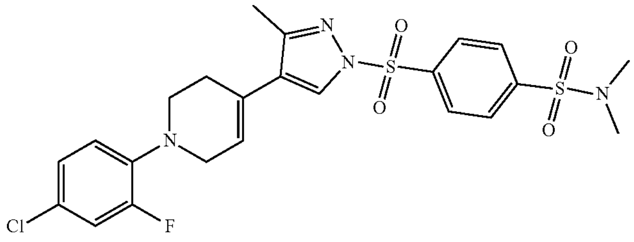 [SMILES: Cc1nn(S(=O)(=O)c2ccc(S(=O)(=O)N(C)C)cc2)cc1C1=CCN(c2ccc(Cl)cc2F)CC1] | A-37 |
| 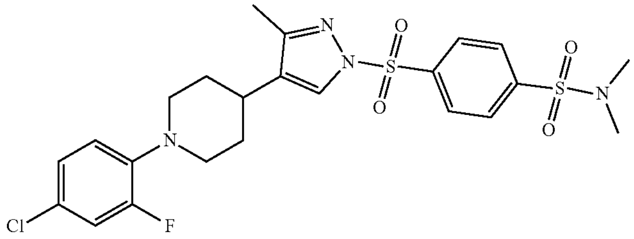 [SMILES: Cc1nn(S(=O)(=O)c2ccc(S(=O)(=O)N(C)C)cc2)cc1C1CCN(c2ccc(Cl)cc2F)CC1] | A-38 |
| 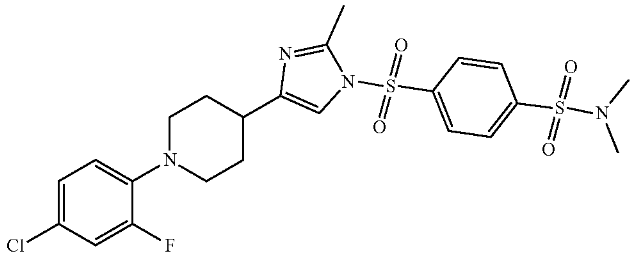 [SMILES: Cc1nc(C2CCN(c3ccc(Cl)cc3F)CC2)cn1S(=O)(=O)c1ccc(S(=O)(=O)N(C)C)cc1] | A-39 |
| 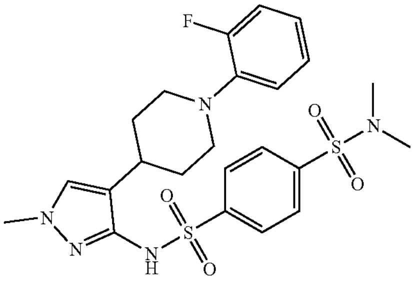 | A-40 |
| 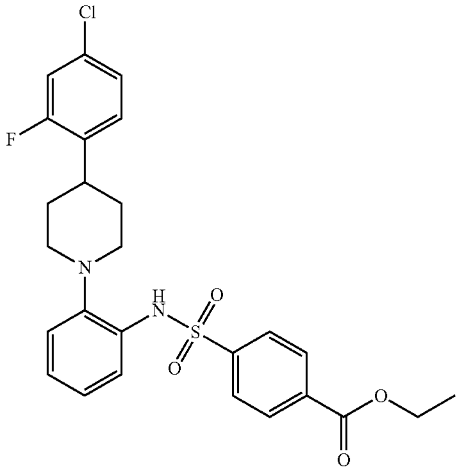 [SMILES: CCOC(=O)c1ccc(S(=O)(=O)Nc2ccccc2N2CCC(c3ccc(Cl)cc3F)CC2)cc1] | A-41 |

TABLE A-continued
| Structure | Compound No. |
|---|---|
| 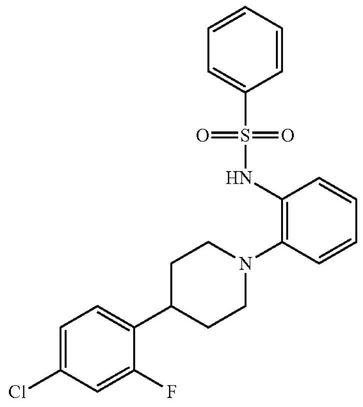 [SMILES: O=S(=O)(Nc1ccccc1N1CCC(c2ccc(Cl)cc2F)CC1)c1ccccc1] | A-42 |
| 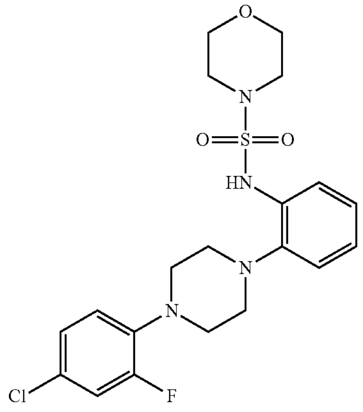 [SMILES: O=S(=O)(Nc1ccccc1N1CCN(c2ccc(Cl)cc2F)CC1)N1CCOCC1] | A-43 |
| 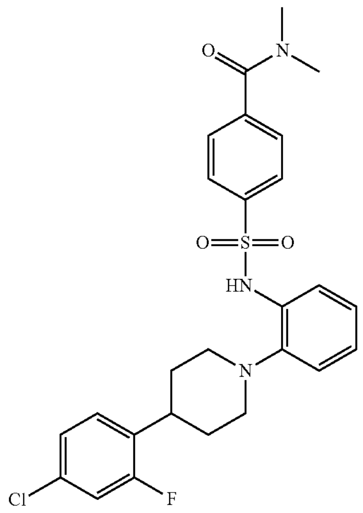 [SMILES: CN(C)C(=O)c1ccc(S(=O)(=O)Nc2ccccc2N2CCC(c3ccc(Cl)cc3F)CC2)cc1] | A-44 |

TABLE A-continued
| Structure | Compound No. |
| --- | --- |
| 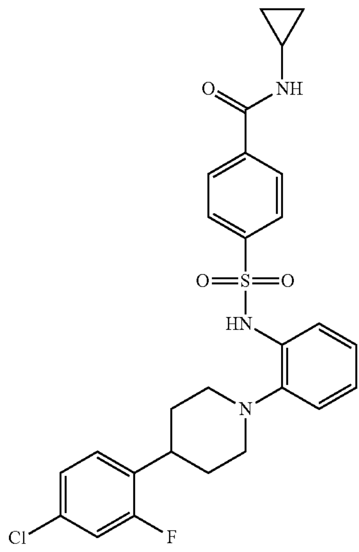 [SMILES: O=C(NC1CC1)c1ccc(S(=O)(=O)Nc2ccccc2N2CCC(c3ccc(Cl)cc3F)CC2)cc1] | A-45 |
| 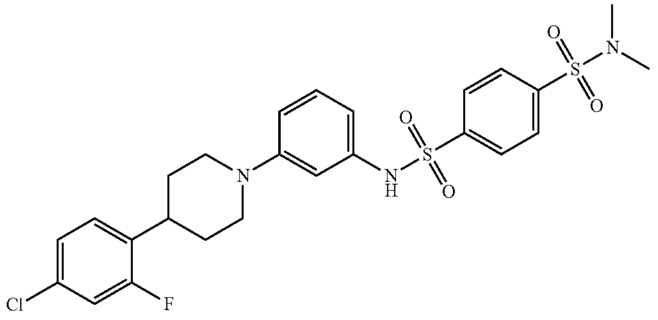 [SMILES: CN(C)S(=O)(=O)c1ccc(S(=O)(=O)Nc2cccc(N3CCC(c4ccc(Cl)cc4F)CC3)c2)cc1] | A-46 |
| 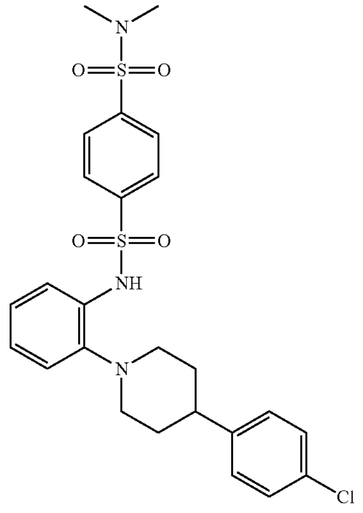 [SMILES: CN(C)S(=O)(=O)c1ccc(S(=O)(=O)Nc2ccccc2N2CCC(c3ccc(Cl)cc3)CC2)cc1] | A-47 |

TABLE A-continued
| Structure | Compound No. |
|---|---|
| 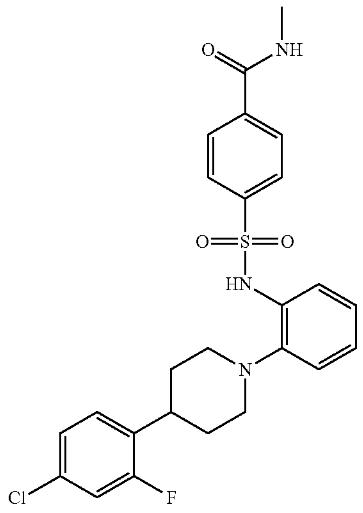 [SMILES: CNC(=O)c1ccc(S(=O)(=O)Nc2ccccc2N2CCC(c3ccc(Cl)cc3F)CC2)cc1] | A-48 |
| 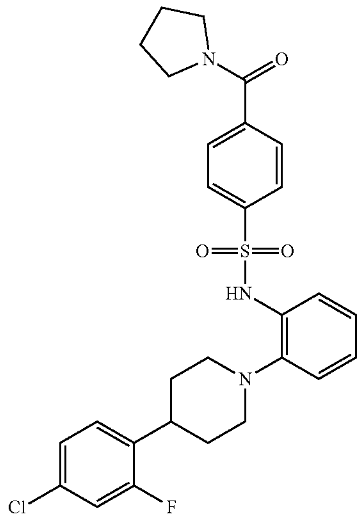 [SMILES: O=C(c1ccc(S(=O)(=O)Nc2ccccc2N2CCC(c3ccc(Cl)cc3F)CC2)cc1)N1CCCC1] | A-49 |
| 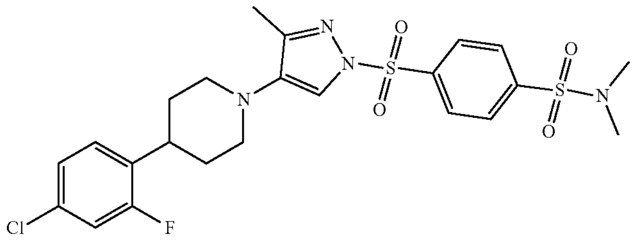 [SMILES: Cc1nn(S(=O)(=O)c2ccc(S(=O)(=O)N(C)C)cc2)cc1N1CCC(c2ccc(Cl)cc2F)CC1] | A-50 |

TABLE A-continued
| Structure | Compound No. |
| --- | --- |
| 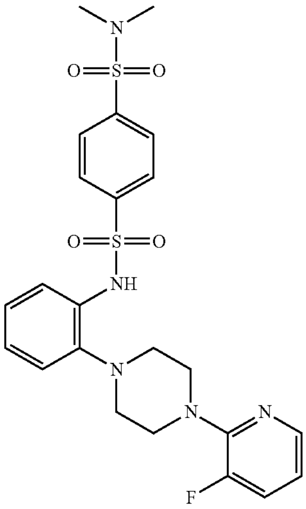 [SMILES: CN(C)S(=O)(=O)c1ccc(S(=O)(=O)Nc2ccccc2N2CCN(c3ncccc3F)CC2)cc1] | A-51 |
| 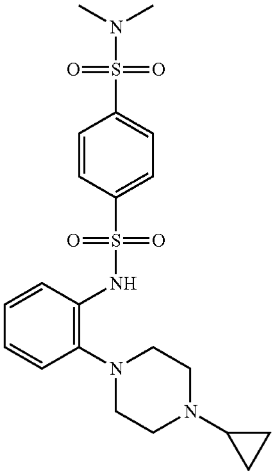 [SMILES: CN(C)S(=O)(=O)c1ccc(S(=O)(=O)Nc2ccccc2N2CCN(C3CC3)CC2)cc1] | A-52 |
| 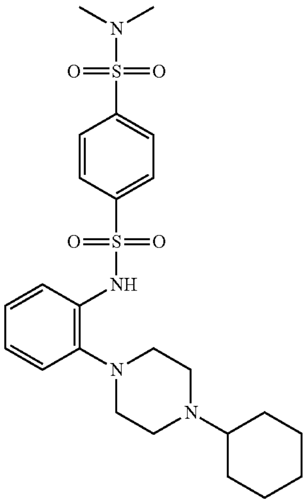 [SMILES: CN(C)S(=O)(=O)c1ccc(S(=O)(=O)Nc2ccccc2N2CCN(C3CCCCC3)CC2)cc1] | A-53 |

TABLE A-continued
| Structure | Compound No. |
|---|---|
| 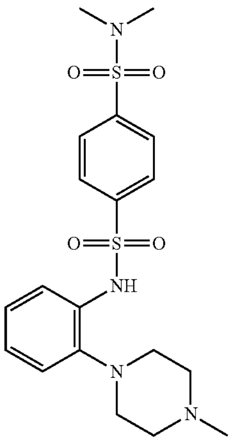 [SMILES: CN1CCN(c2ccccc2NS(=O)(=O)c2ccc(S(=O)(=O)N(C)C)cc2)CC1] | A-54 |
| 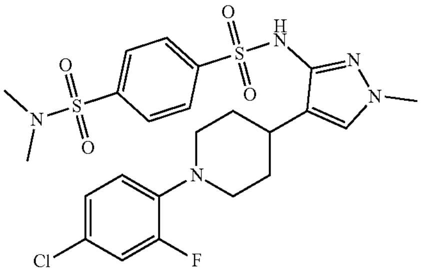 | A-55 |
| 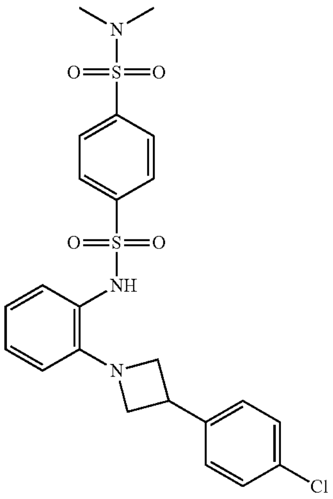 [SMILES: CN(C)S(=O)(=O)c1ccc(S(=O)(=O)Nc2ccccc2N2CC(c3ccc(Cl)cc3)C2)cc1] | A-56 |

TABLE A-continued
| Structure | Compound No. |
|---|---|
| 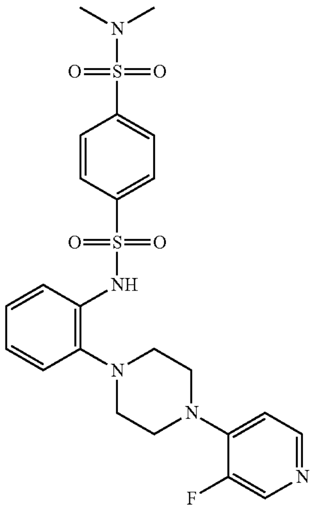 [SMILES: CN(C)S(=O)(=O)c1ccc(S(=O)(=O)Nc2ccccc2N2CCN(c3ccncc3F)CC2)cc1] | A-57 |
| 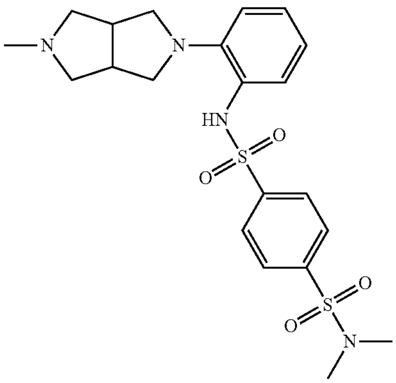 | A-58 |
| 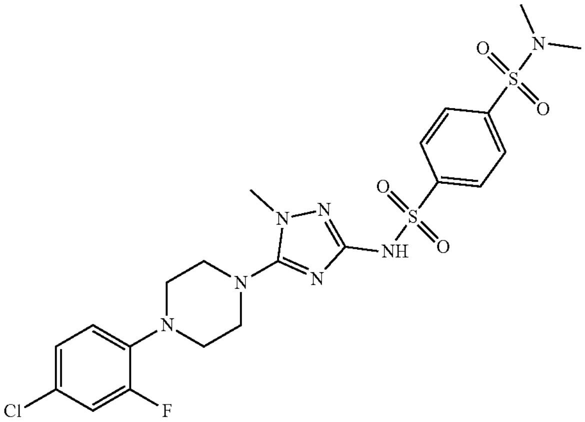 [SMILES: CN(C)S(=O)(=O)c1ccc(S(=O)(=O)Nc2nc(N3CCN(c4ccc(Cl)cc4F)CC3)n(C)n2)cc1] | A-59 |

TABLE A-continued
| Structure | Compound No. |
|---|---|
| 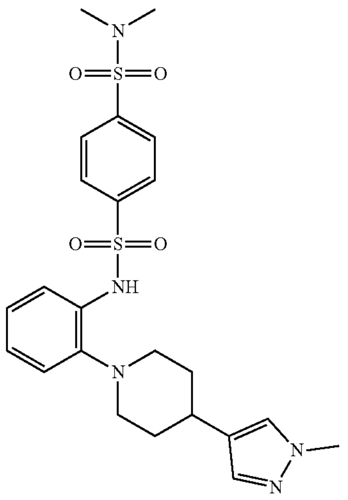 [SMILES: CN(C)S(=O)(=O)c1ccc(S(=O)(=O)Nc2ccccc2N2CCC(c3cnn(C)c3)CC2)cc1] | A-60 |
| 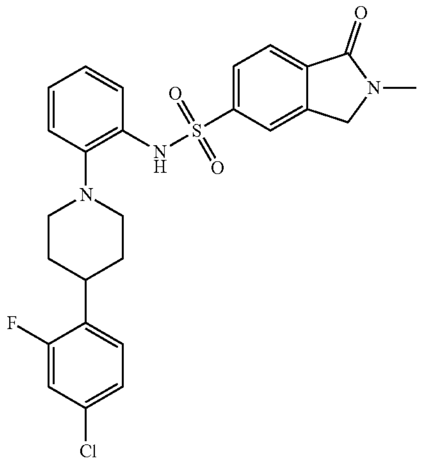 [SMILES: CN1Cc2cc(S(=O)(=O)Nc3ccccc3N3CCC(c4ccc(Cl)cc4F)CC3)ccc2C1=O] | A-61 |
| 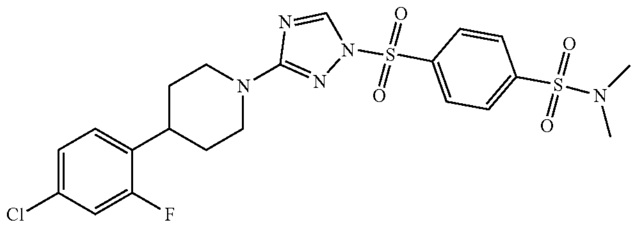 [SMILES: CN(C)S(=O)(=O)c1ccc(S(=O)(=O)n2cnc(N3CCC(c4ccc(Cl)cc4F)CC3)n2)cc1] | A-62 |

TABLE A-continued
| Structure | Compound No. |
|---|---|
| 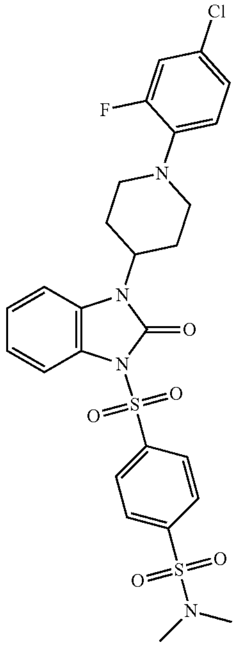 [SMILES: CN(C)S(=O)(=O)c1ccc(S(=O)(=O)n2c(=O)n(C3CCN(c4ccc(Cl)cc4F)CC3)c3ccccc32)cc1] | A-63 |
| 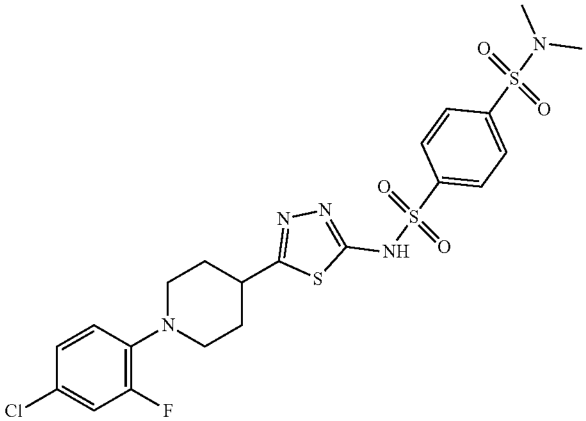 [SMILES: CN(C)S(=O)(=O)c1ccc(S(=O)(=O)Nc2nnc(C3CCN(c4ccc(Cl)cc4F)CC3)s2)cc1] | A-64 |
| 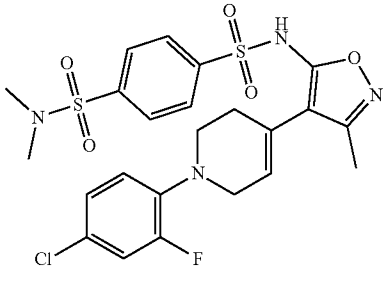 [SMILES: Cc1noc(NS(=O)(=O)c2ccc(S(=O)(=O)N(C)C)cc2)c1C1=CCN(c2ccc(Cl)cc2F)CC1] | A-65 |

TABLE A-continued
| Structure | Compound No. |
| --- | --- |
| 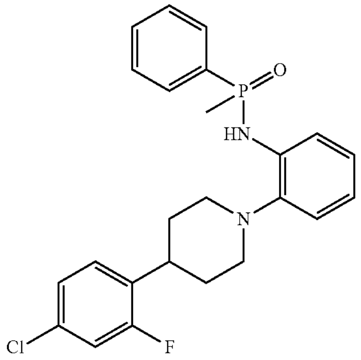 [SMILES: CP(=O)(Nc1ccccc1N1CCC(c2ccc(Cl)cc2F)CC1)c1ccccc1] | A-66 |
| 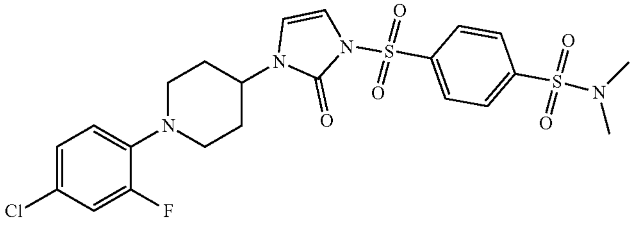 [SMILES: CN(C)S(=O)(=O)c1ccc(S(=O)(=O)n2ccn(C3CCN(c4ccc(Cl)cc4F)CC3)c2=O)cc1] | A-67 |
| 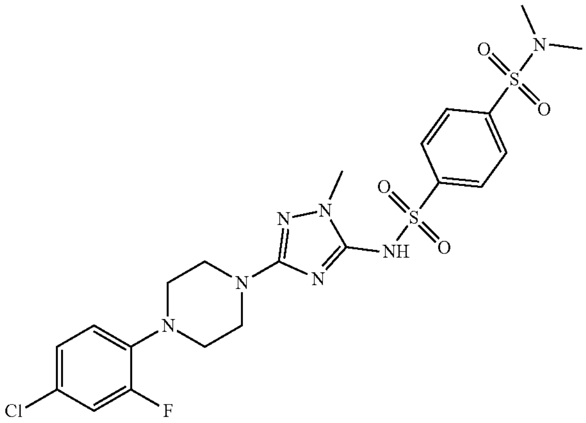 [SMILES: CN(C)S(=O)(=O)c1ccc(S(=O)(=O)Nc2nc(N3CCN(c4ccc(Cl)cc4F)CC3)nn2C)cc1] | A-68 |
| 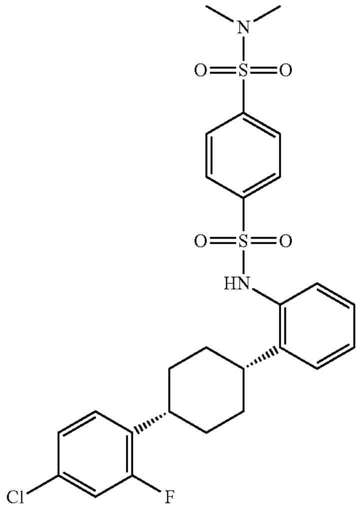 [SMILES: CN(C)S(=O)(=O)c1ccc(S(=O)(=O)Nc2ccccc2[C@H]2CC[C@@H](c3ccc(Cl)cc3F)CC2)cc1] | A-69 |

TABLE A-continued
| Structure | Compound No. |
| --- | --- |
| 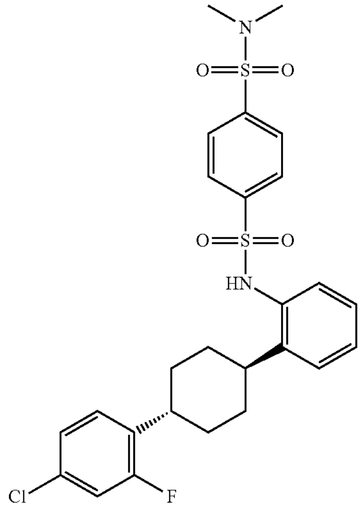 [SMILES: CN(C)S(=O)(=O)c1ccc(S(=O)(=O)Nc2ccccc2[C@H]2CC[C@H](c3ccc(Cl)cc3F)CC2)cc1] | A-70 |
| 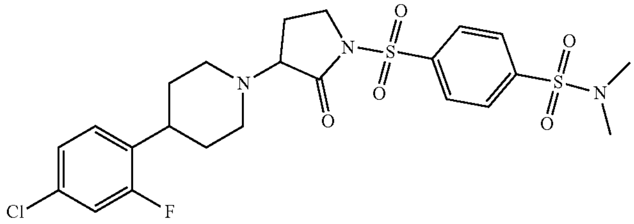 [SMILES: CN(C)S(=O)(=O)c1ccc(S(=O)(=O)N2CCC(N3CCC(c4ccc(Cl)cc4F)CC3)C2=O)cc1] | A-71 |
| 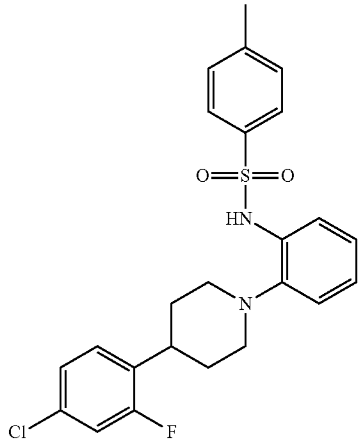 [SMILES: Cc1ccc(S(=O)(=O)Nc2ccccc2N2CCC(c3ccc(Cl)cc3F)CC2)cc1] | A-72 |

TABLE A-continued
| Structure | Compound No. |
|---|---|
| 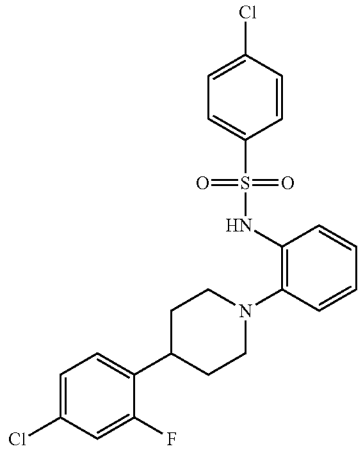 [SMILES: O=S(=O)(Nc1ccccc1N1CCC(c2ccc(Cl)cc2F)CC1)c1ccc(Cl)cc1] | A-73 |
| 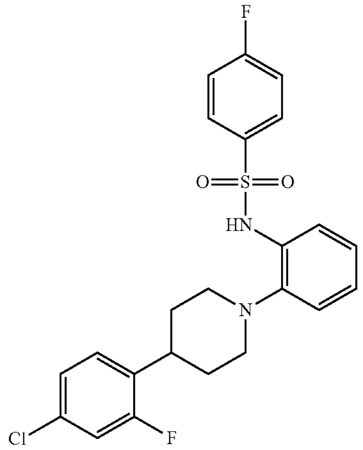 [SMILES: O=S(=O)(Nc1ccccc1N1CCC(c2ccc(Cl)cc2F)CC1)c1ccc(F)cc1] | A-74 |
| 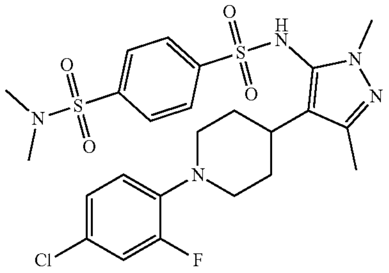 [SMILES: Cc1nn(C)c(NS(=O)(=O)c2ccc(S(=O)(=O)N(C)C)cc2)c1C1CCN(c2ccc(Cl)cc2F)CC1] | A-75 |
| 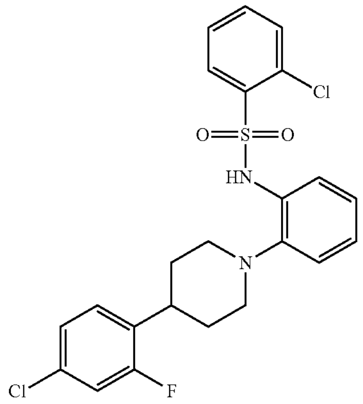 [SMILES: O=S(=O)(Nc1ccccc1N1CCC(c2ccc(Cl)cc2F)CC1)c1ccccc1Cl] | A-76 |

TABLE A-continued
| Structure | Compound No. |
|---|---|
| 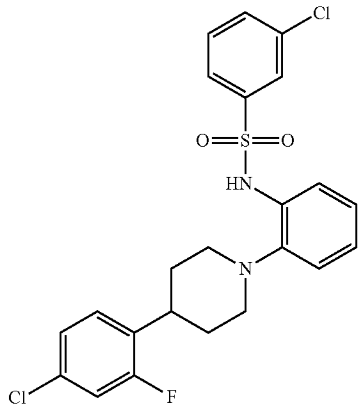 | A-77 |
| 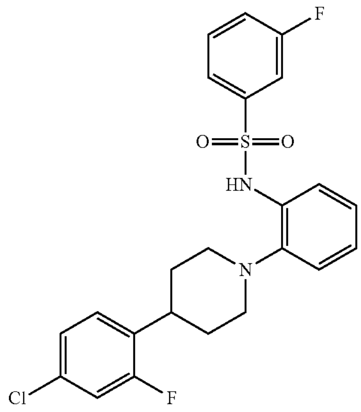 [SMILES: O=S(=O)(Nc1ccccc1N1CCC(c2ccc(Cl)cc2F)CC1)c1cccc(F)c1] | A-78 |
| 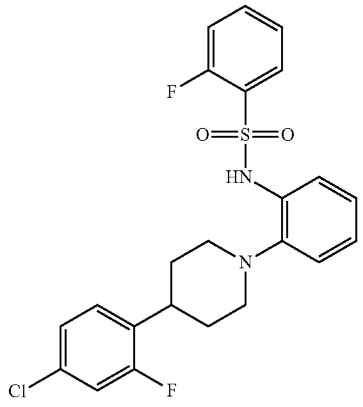 [SMILES: O=S(=O)(Nc1ccccc1N1CCC(c2ccc(Cl)cc2F)CC1)c1ccccc1F] | A-79 |

TABLE A-continued
| Structure | Compound No. |
| --- | --- |
| 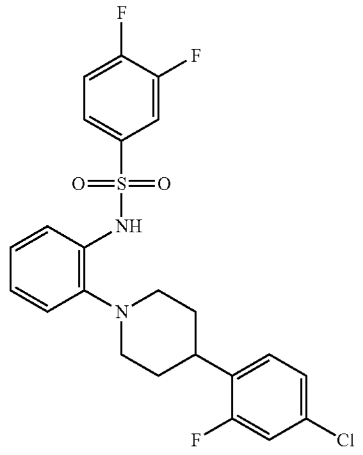 [SMILES: O=S(=O)(Nc1ccccc1N1CCC(c2ccc(Cl)cc2F)CC1)c1ccc(F)c(F)c1] | A-80 |
| 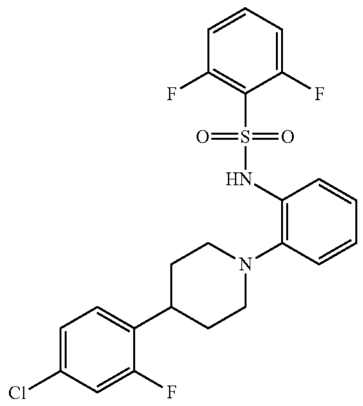 [SMILES: O=S(=O)(Nc1ccccc1N1CCC(c2ccc(Cl)cc2F)CC1)c1c(F)cccc1F] | A-81 |
| 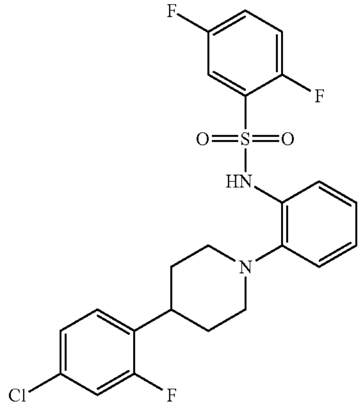 [SMILES: O=S(=O)(Nc1ccccc1N1CCC(c2ccc(Cl)cc2F)CC1)c1cc(F)ccc1F] | A-82 |

TABLE A-continued
| Structure | Compound No. |
| --- | --- |
| 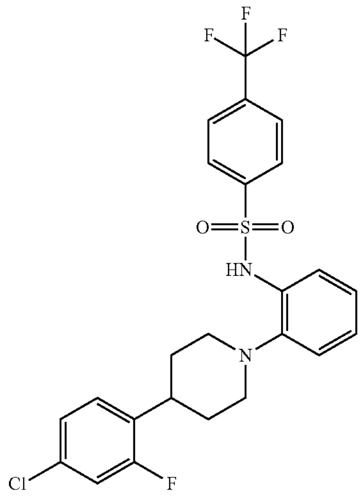 [SMILES: O=S(=O)(Nc1ccccc1N1CCC(c2ccc(Cl)cc2F)CC1)c1ccc(C(F)(F)F)cc1] | A-83 |
| 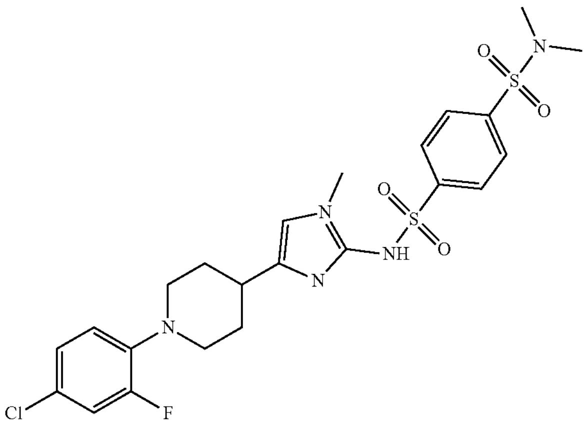 | A-84 |
| 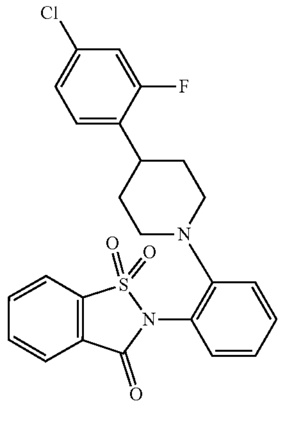 [SMILES: O=C1c2ccccc2S(=O)(=O)N1c1ccccc1N1CCC(c2ccc(Cl)cc2F)CC1] | A-85 |
| 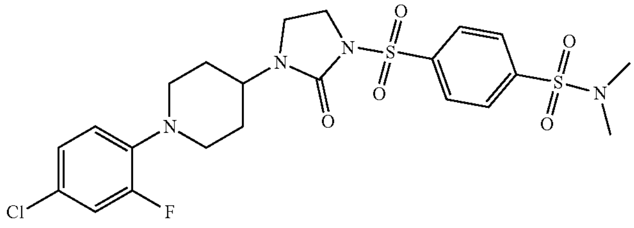 [SMILES: CN(C)S(=O)(=O)c1ccc(S(=O)(=O)N2CCN(C3CCN(c4ccc(Cl)cc4F)CC3)C2=O)cc1] | A-86 |

TABLE A-continued
| Structure | Compound No. |
| --- | --- |
| 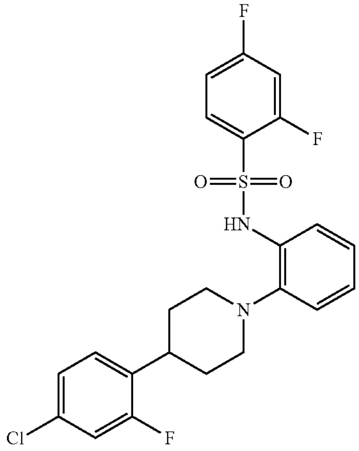 [SMILES: O=S(=O)(Nc1ccccc1N1CCC(c2ccc(Cl)cc2F)CC1)c1ccc(F)cc1F] | A-87 |
| 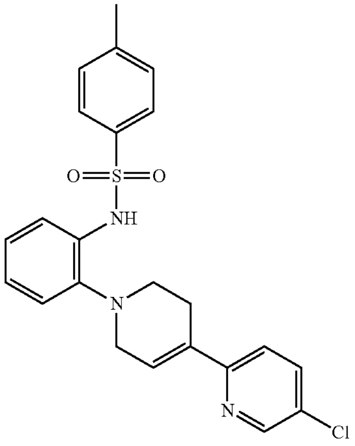 [SMILES: Cc1ccc(S(=O)(=O)Nc2ccccc2N2CC=C(c3ccc(Cl)cn3)CC2)cc1] | A-88 |
| 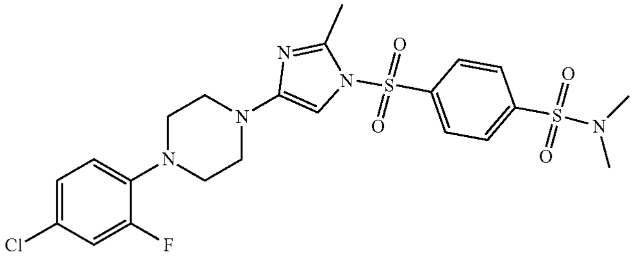 [SMILES: Cc1nc(N2CCN(c3ccc(Cl)cc3F)CC2)cn1S(=O)(=O)c1ccc(S(=O)(=O)N(C)C)cc1] | A-89 |
| 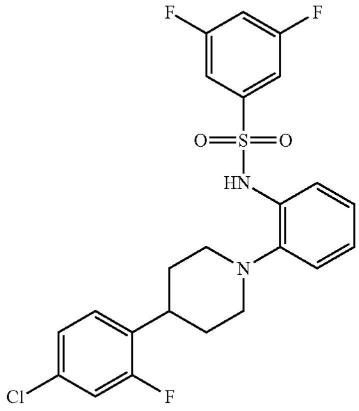 [SMILES: O=S(=O)(Nc1ccccc1N1CCC(c2ccc(Cl)cc2F)CC1)c1cc(F)cc(F)c1] | A-91 |

TABLE A-continued
| Structure | Compound No. |
|---|---|
| 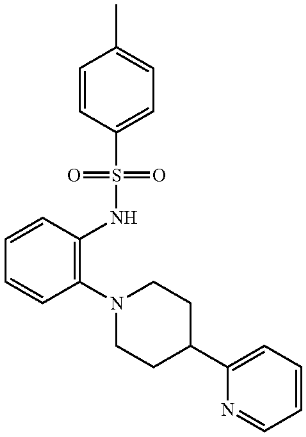 [SMILES: Cc1ccc(S(=O)(=O)Nc2ccccc2N2CCC(c3ccccn3)CC2)cc1] | A-92 |
| 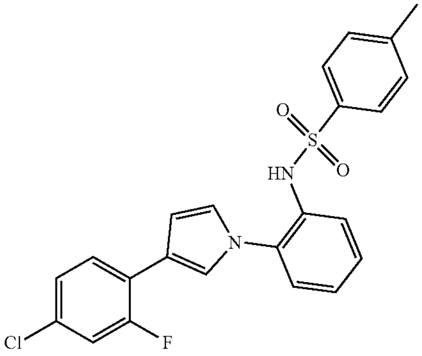 [SMILES: Cc1ccc(S(=O)(=O)Nc2ccccc2-n2ccc(-c3ccc(Cl)cc3F)c2)cc1] | A-93 |
| 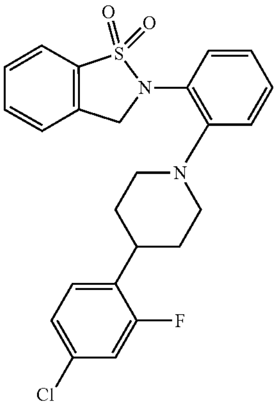 [SMILES: O=S1(=O)c2ccccc2CN1c1ccccc1N1CCC(c2ccc(Cl)cc2F)CC1] | A-94 |

TABLE A-continued
| Structure | Compound No. |
|---|---|
| 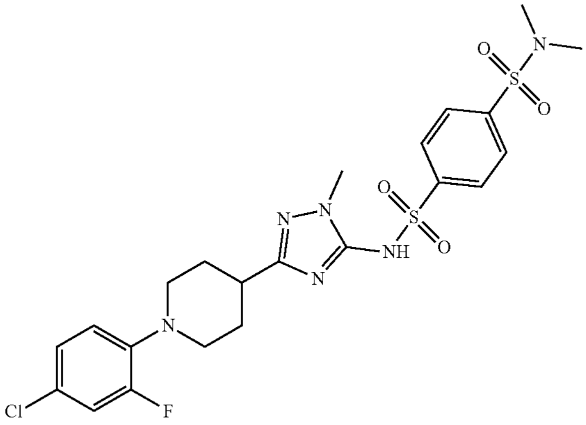 | A-95 |
| 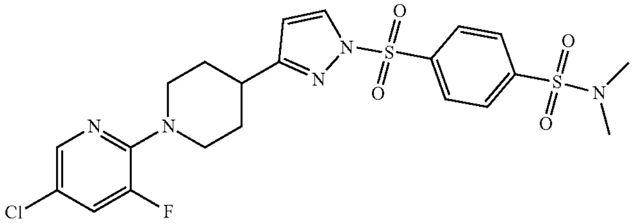 [SMILES: CN(C)S(=O)(=O)c1ccc(S(=O)(=O)n2ccc(C3CCN(c4ncc(Cl)cc4F)CC3)n2)cc1] | A-96 |
| 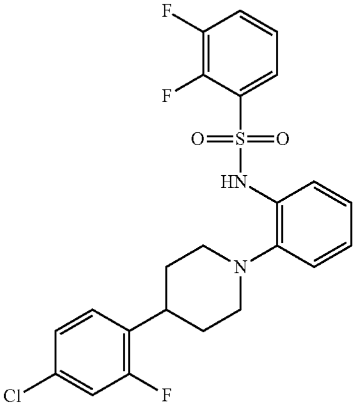 [SMILES: O=S(=O)(Nc1ccccc1N1CCC(c2ccc(Cl)cc2F)CC1)c1cccc(F)c1F] | A-97 |
| 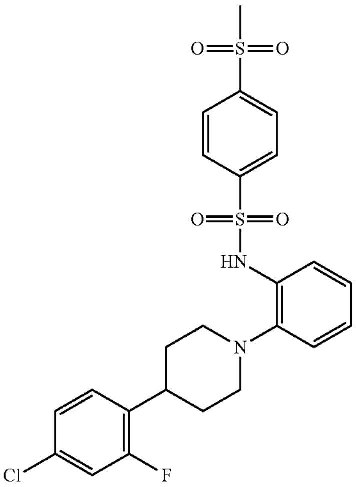 [SMILES: CS(=O)(=O)c1ccc(S(=O)(=O)Nc2ccccc2N2CCC(c3ccc(Cl)cc3F)CC2)cc1] | A-98 |

TABLE A-continued
| Structure | Compound No. |
| --- | --- |
| 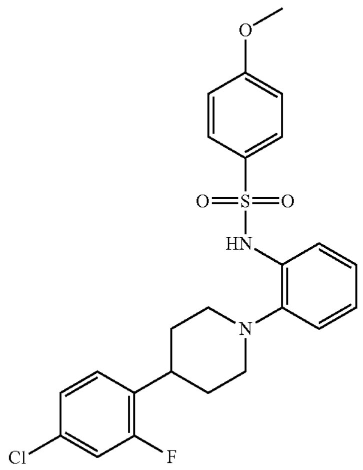 [SMILES: COc1ccc(S(=O)(=O)Nc2ccccc2N2CCC(c3ccc(Cl)cc3F)CC2)cc1] | A-99 |
| 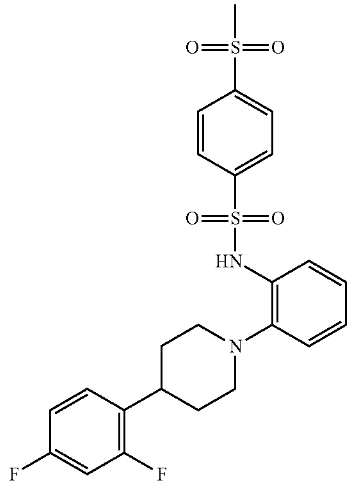 [SMILES: CS(=O)(=O)c1ccc(S(=O)(=O)Nc2ccccc2N2CCC(c3ccc(F)cc3F)CC2)cc1] | A-100 |
| 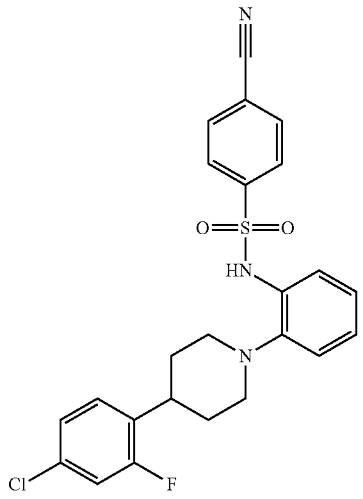 [SMILES: N#Cc1ccc(S(=O)(=O)Nc2ccccc2N2CCC(c3ccc(Cl)cc3F)CC2)cc1] | A-101 |

TABLE A-continued
| Structure | Compound No. |
|---|---|
| 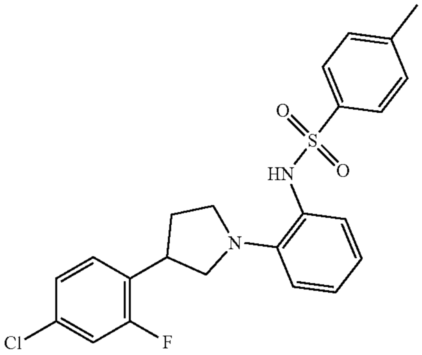 [SMILES: Cc1ccc(S(=O)(=O)Nc2ccccc2N2CCC(c3ccc(Cl)cc3F)C2)cc1] | A-102 |
| 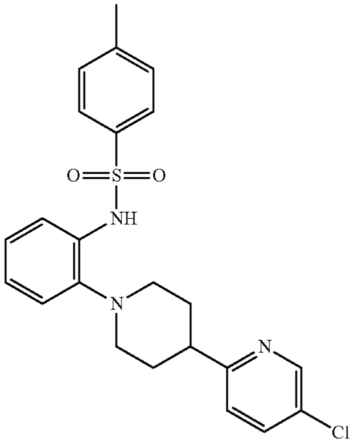 [SMILES: Cc1ccc(S(=O)(=O)Nc2ccccc2N2CCC(c3ccc(Cl)cn3)CC2)cc1] | A-103 |
| 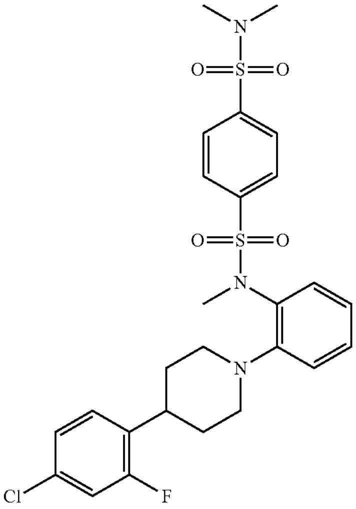 [SMILES: CN(C)S(=O)(=O)c1ccc(S(=O)(=O)N(C)c2ccccc2N2CCC(c3ccc(Cl)cc3F)CC2)cc1] | A-104 |
| 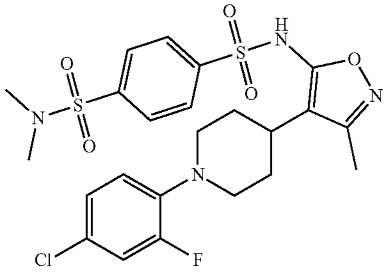 [SMILES: Cc1noc(NS(=O)(=O)c2ccc(S(=O)(=O)N(C)C)cc2)c1C1CCN(c2ccc(Cl)cc2F)CC1] | A-105 |

TABLE A-continued
| Structure | Compound No. |
| --- | --- |
| 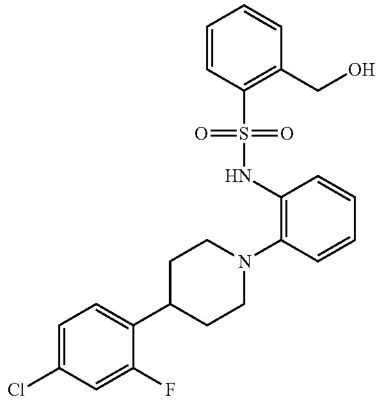 [SMILES: O=S(=O)(Nc1ccccc1N1CCC(c2ccc(Cl)cc2F)CC1)c1ccccc1CO] | A-106 |
| 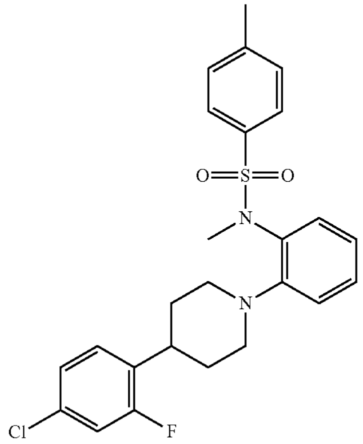 [SMILES: Cc1ccc(S(=O)(=O)N(C)c2ccccc2N2CCC(c3ccc(Cl)cc3F)CC2)cc1] | A-107 |
| 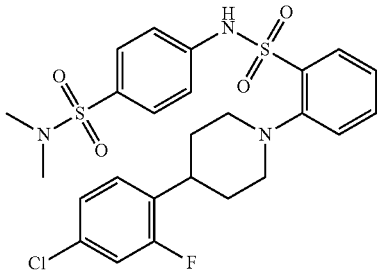 [SMILES: CN(C)S(=O)(=O)c1ccc(NS(=O)(=O)c2ccccc2N2CCC(c3ccc(Cl)cc3F)CC2)cc1] | A-108 |

TABLE A-continued
| Structure | Compound No. |
|---|---|
| 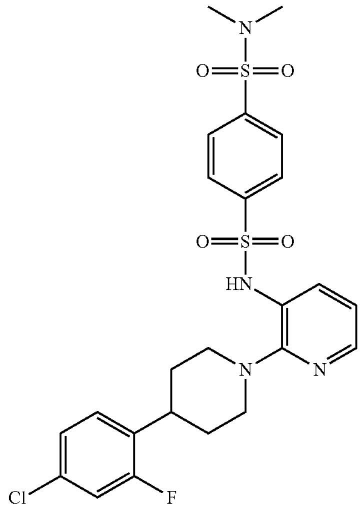 | A-109 |
| 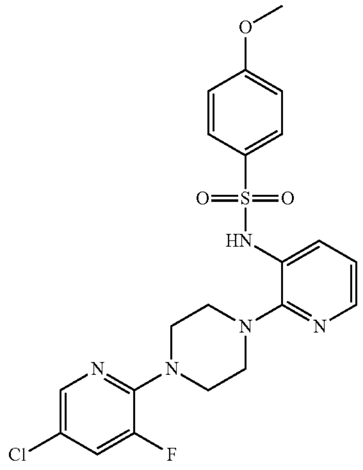 [SMILES: COc1ccc(S(=O)(=O)Nc2cccnc2N2CCN(c3ncc(Cl)cc3F)CC2)cc1] | A-110 |
| 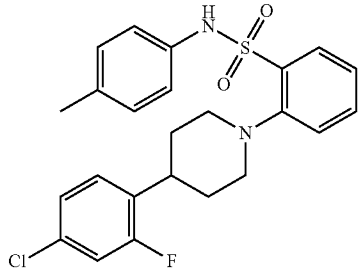 [SMILES: Cc1ccc(NS(=O)(=O)c2ccccc2N2CCC(c3ccc(Cl)cc3F)CC2)cc1] | A-111 |

TABLE A-continued
| Structure | Compound No. |
|---|---|
| 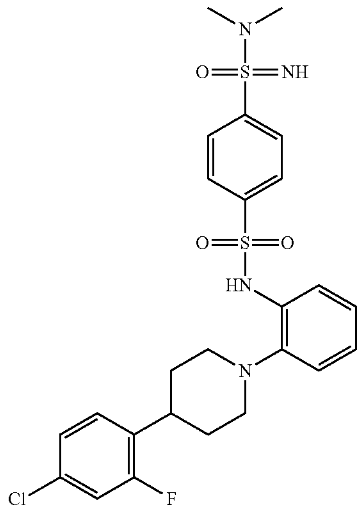 [SMILES: CN(C)S(=N)(=O)c1ccc(S(=O)(=O)Nc2ccccc2N2CCC(c3ccc(Cl)cc3F)CC2)cc1] | A-112 |
| 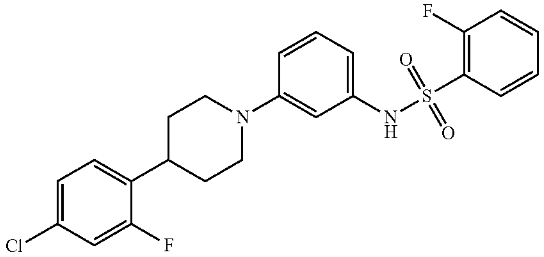 [SMILES: O=S(=O)(Nc1cccc(N2CCC(c3ccc(Cl)cc3F)CC2)c1)c1ccccc1F] | A-114 |
| 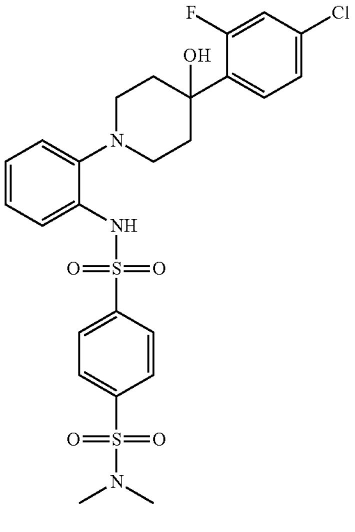 [SMILES: CN(C)S(=O)(=O)c1ccc(S(=O)(=O)Nc2ccccc2N2CCC(O)(c3ccc(Cl)cc3F)CC2)cc1] | A-115 |

TABLE A-continued
| Structure | Compound No. |
|---|---|
| 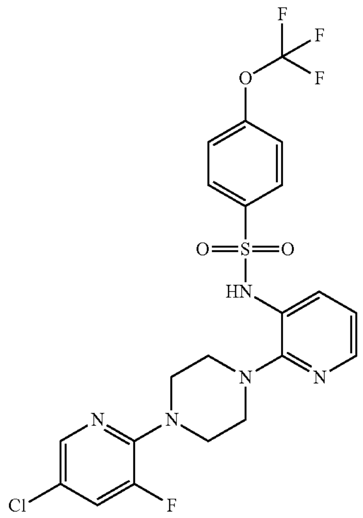 [SMILES: O=S(=O)(Nc1cccnc1N1CCN(c2ncc(Cl)cc2F)CC1)c1ccc(OC(F)(F)F)cc1] | A-116 |
| 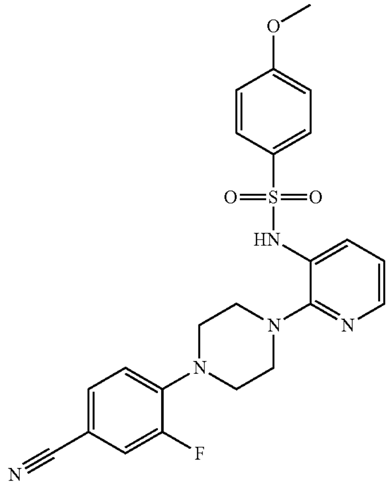 [SMILES: COc1ccc(S(=O)(=O)Nc2cccnc2N2CCN(c3ccc(C#N)cc3F)CC2)cc1] | A-117 |
| 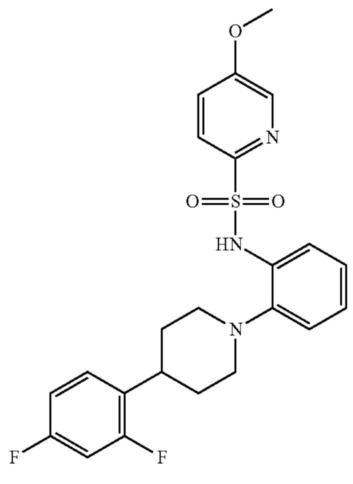 [SMILES: COc1ccc(S(=O)(=O)Nc2ccccc2N2CCC(c3ccc(F)cc3F)CC2)nc1] | A-118 |

TABLE A-continued
| Structure | Compound No. |
|---|---|
| 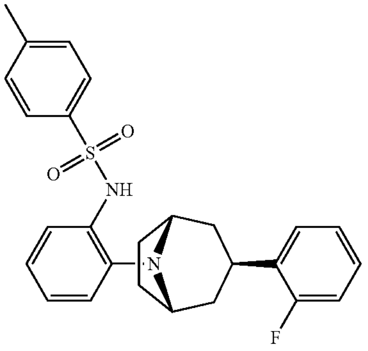 [SMILES: Cc1ccc(S(=O)(=O)Nc2ccccc2N2[C@@H]3CC[C@H]2C[C@H](c2ccccc2F)C3)cc1] | A-119 |
| 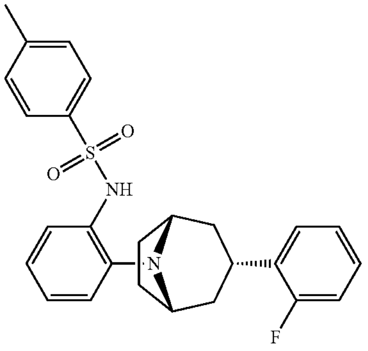 [SMILES: Cc1ccc(S(=O)(=O)Nc2ccccc2N2[C@@H]3CC[C@H]2C[C@@H](c2ccccc2F)C3)cc1] | A-120 |
| 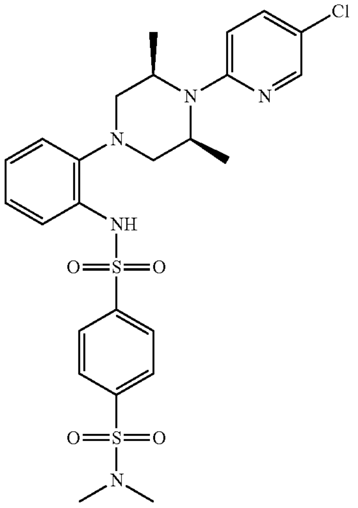 [SMILES: C[C@@H]1CN(c2ccccc2NS(=O)(=O)c2ccc(S(=O)(=O)N(C)C)cc2)C[C@H](C)N1c1ccc(Cl)cn1] | A-121 |
| 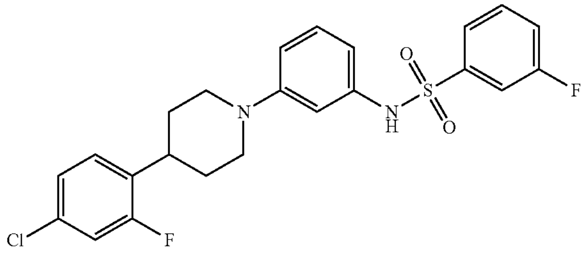 [SMILES: O=S(=O)(Nc1cccc(N2CCC(c3ccc(Cl)cc3F)CC2)c1)c1cccc(F)c1] | A-122 |

TABLE A-continued
| Structure | Compound No. |
| --- | --- |
| 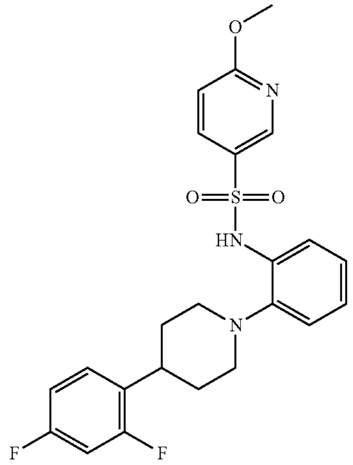 [SMILES: COc1ccc(S(=O)(=O)Nc2ccccc2N2CCC(c3ccc(F)cc3F)CC2)cn1] | A-123 |
| 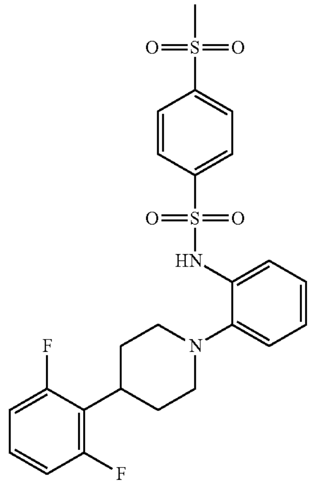 [SMILES: CS(=O)(=O)c1ccc(S(=O)(=O)Nc2ccccc2N2CCC(c3c(F)cccc3F)CC2)cc1] | A-124 |
| 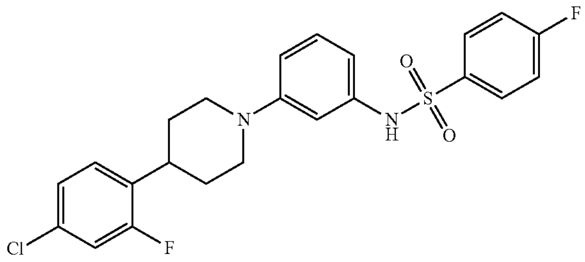 [SMILES: O=S(=O)(Nc1cccc(N2CCC(c3ccc(Cl)cc3F)CC2)c1)c1ccc(F)cc1] | A-128 |

TABLE A-continued
| Structure | Compound No. |
|---|---|
| 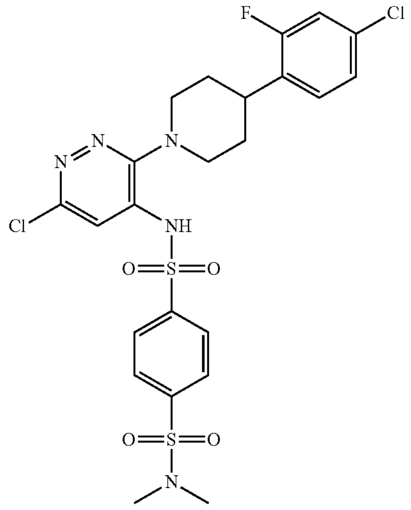 [SMILES: CN(C)S(=O)(=O)c1ccc(S(=O)(=O)Nc2cc(Cl)nnc2N2CCC(c3ccc(Cl)cc3F)CC2)cc1] | A-129 |
| 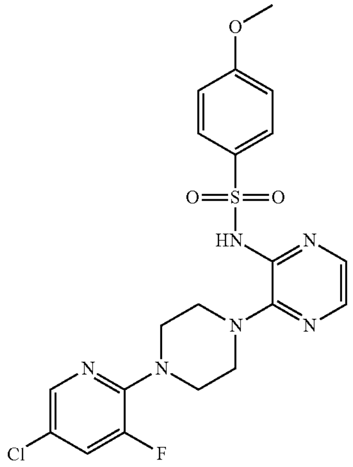 [SMILES: COc1ccc(S(=O)(=O)Nc2nccnc2N2CCN(c3ncc(Cl)cc3F)CC2)cc1] | A-130 |
| 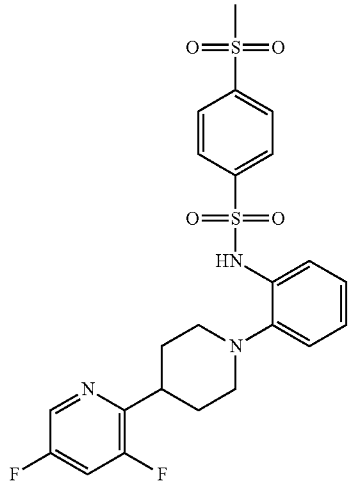 [SMILES: CS(=O)(=O)c1ccc(S(=O)(=O)Nc2ccccc2N2CCC(c3ncc(F)cc3F)CC2)cc1] | A-131 |

TABLE A-continued
| Structure | Compound No. |
|---|---|
| 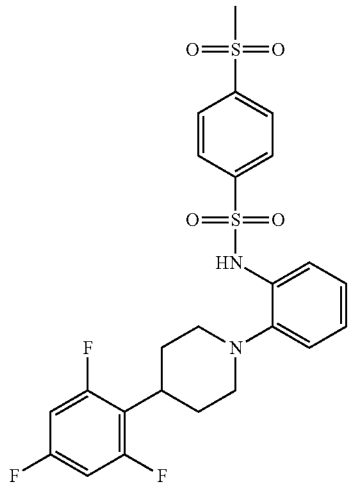 [SMILES: CS(=O)(=O)c1ccc(S(=O)(=O)Nc2ccccc2N2CCC(c3c(F)cc(F)cc3F)CC2)cc1] | A-132 |
| 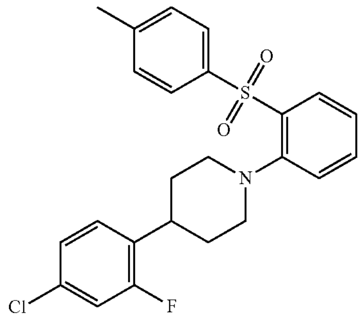 [SMILES: Cc1ccc(S(=O)(=O)c2ccccc2N2CCC(c3ccc(Cl)cc3F)CC2)cc1] | A-133 |
| 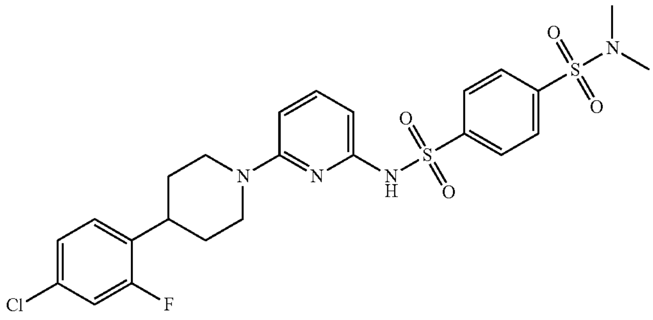 [SMILES: CN(C)S(=O)(=O)c1ccc(S(=O)(=O)Nc2cccc(N3CCC(c4ccc(Cl)cc4F)CC3)n2)cc1] | A-134 |
| 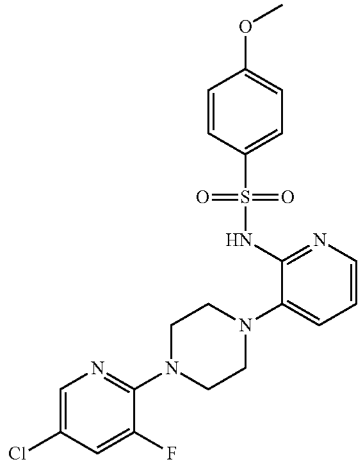 [SMILES: COc1ccc(S(=O)(=O)Nc2ncccc2N2CCN(c3ncc(Cl)cc3F)CC2)cc1] | A-135 |

TABLE A-continued
| Structure | Compound No. |
| --- | --- |
| 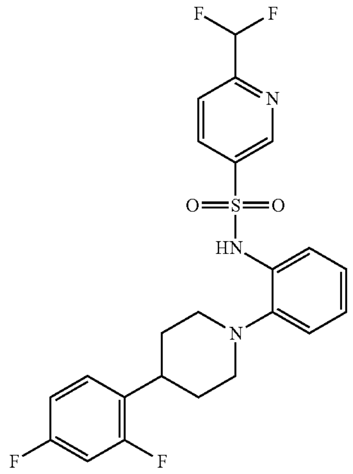 [SMILES: O=S(=O)(Nc1ccccc1N1CCC(c2ccc(F)cc2F)CC1)c1ccc(C(F)F)nc1] | A-136 |
| 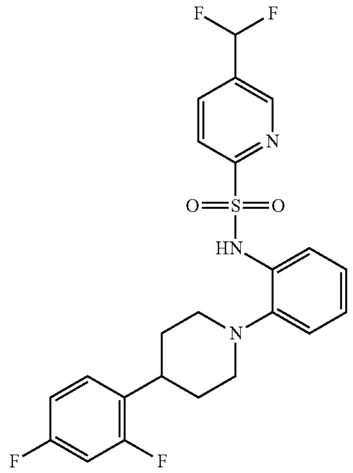 [SMILES: O=S(=O)(Nc1ccccc1N1CCC(c2ccc(F)cc2F)CC1)c1ccc(C(F)F)cn1] | A-137 |
| 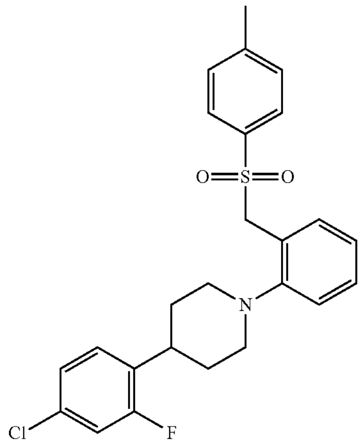 [SMILES: Cc1ccc(S(=O)(=O)Cc2ccccc2N2CCC(c3ccc(Cl)cc3F)CC2)cc1] | A-138 |

TABLE A-continued
| Structure | Compound No. |
|---|---|
| 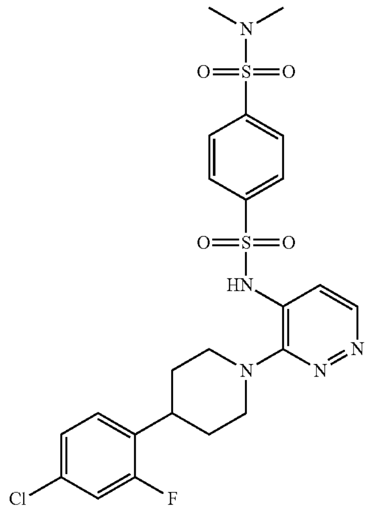 [SMILES: CN(C)S(=O)(=O)c1ccc(S(=O)(=O)Nc2ccnnc2N2CCC(c3ccc(Cl)cc3F)CC2)cc1] | A-139 |
| 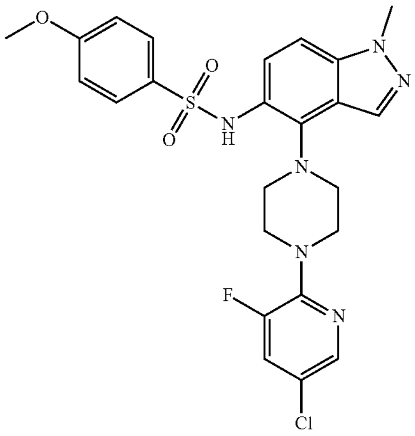 [SMILES: COc1ccc(S(=O)(=O)Nc2ccc3c(cnn3C)c2N2CCN(c3ncc(Cl)cc3F)CC2)cc1] | A-140 |
| 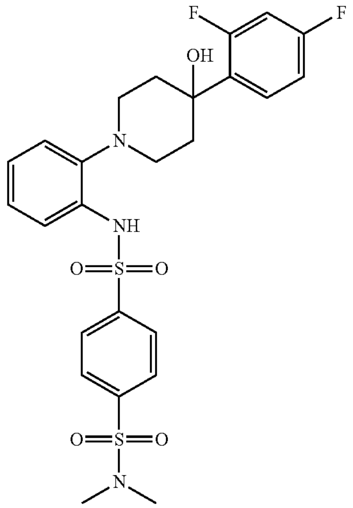 [SMILES: CN(C)S(=O)(=O)c1ccc(S(=O)(=O)Nc2ccccc2N2CCC(O)(c3ccc(F)cc3F)CC2)cc1] | A-141 |

TABLE A-continued
| Structure | Compound No. |
| --- | --- |
| 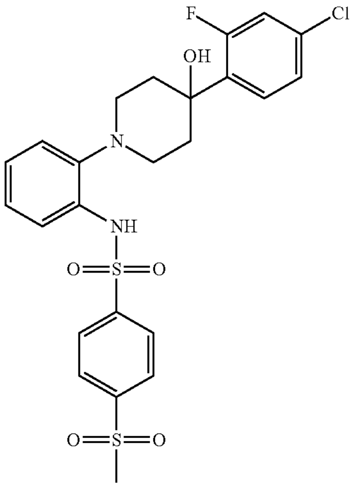 [SMILES: CS(=O)(=O)c1ccc(S(=O)(=O)Nc2ccccc2N2CCC(O)(c3ccc(Cl)cc3F)CC2)cc1] | A-142 |
| 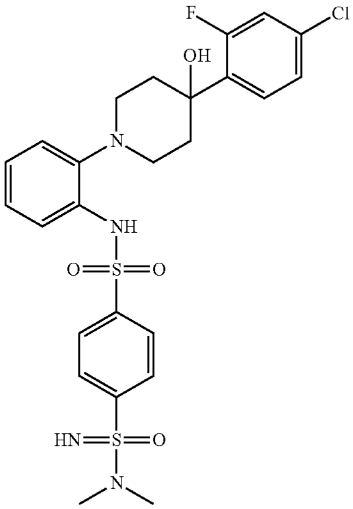 [SMILES: CN(C)S(=N)(=O)c1ccc(S(=O)(=O)Nc2ccccc2N2CCC(O)(c3ccc(Cl)cc3F)CC2)cc1] | A-143 |
| 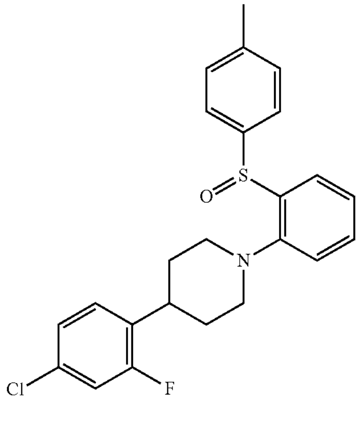 [SMILES: Cc1ccc(S(=O)c2ccccc2N2CCC(c3ccc(Cl)cc3F)CC2)cc1] | A-144 |

TABLE A-continued
| Structure | Compound No. |
|---|---|
| 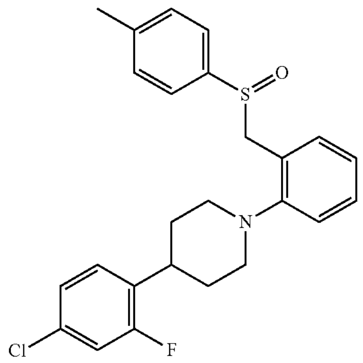 [SMILES: Cc1ccc(S(=O)Cc2ccccc2N2CCC(c3ccc(Cl)cc3F)CC2)cc1] | A-145 |
| 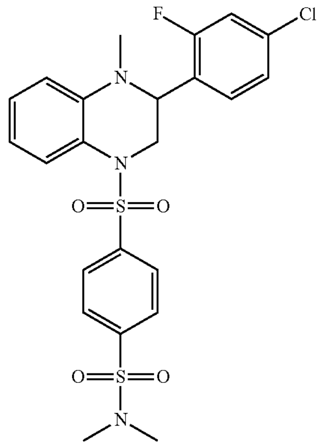 [SMILES: CN1c2ccccc2N(S(=O)(=O)c2ccc(S(=O)(=O)N(C)C)cc2)CC1c1ccc(Cl)cc1F] | A-146 |
| 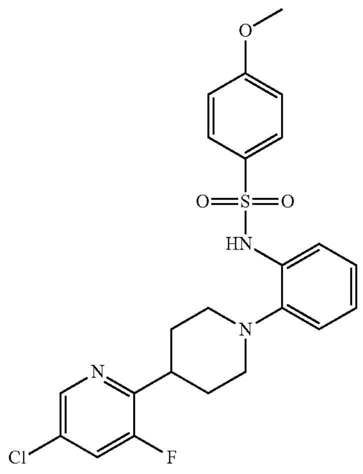 [SMILES: COc1ccc(S(=O)(=O)Nc2ccccc2N2CCC(c3ncc(Cl)cc3F)CC2)cc1] | A-147 |

TABLE A-continued
| Structure | Compound No. |
| --- | --- |
| 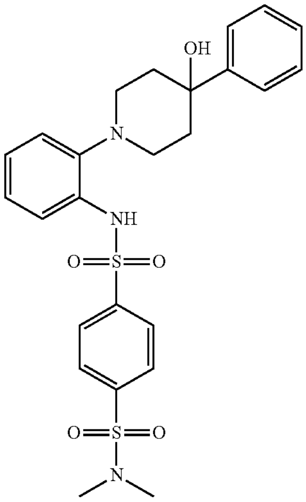 [SMILES: CN(C)S(=O)(=O)c1ccc(S(=O)(=O)Nc2ccccc2N2CCC(O)(c3ccccc3)CC2)cc1] | A-148 |
| 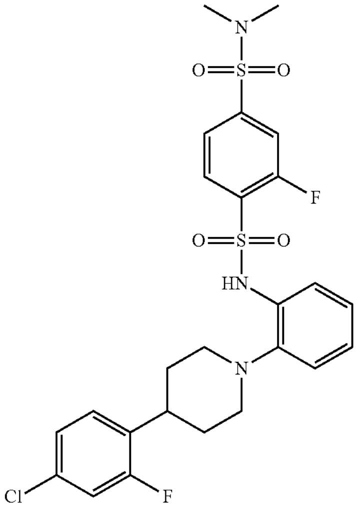 [SMILES: CN(C)S(=O)(=O)c1ccc(S(=O)(=O)Nc2ccccc2N2CCC(c3ccc(Cl)cc3F)CC2)c(F)c1] | A-149 |
| 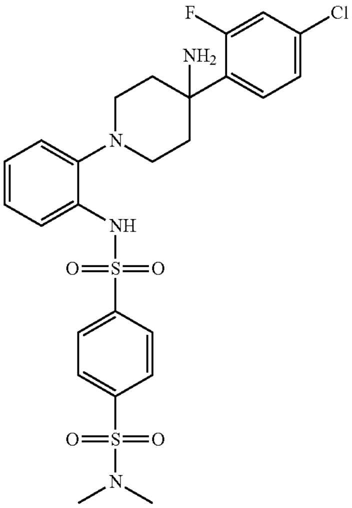 | A-150 |

TABLE A-continued
| Structure | Compound No. |
|---|---|
| 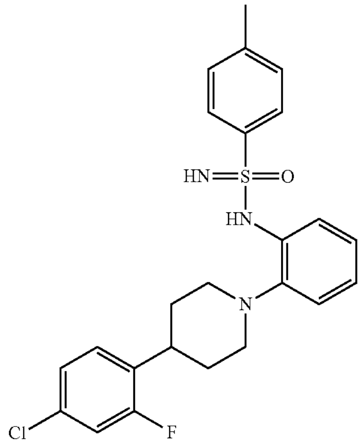 [SMILES: Cc1ccc(S(=N)(=O)Nc2ccccc2N2CCC(c3ccc(Cl)cc3F)CC2)cc1] | A-151 |
| 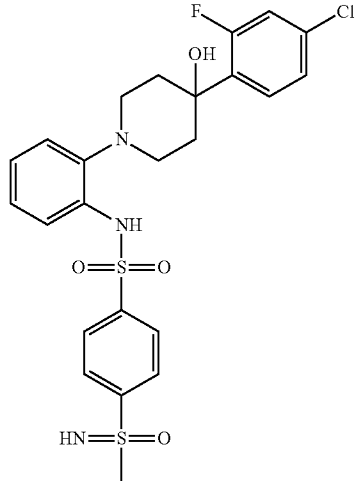 [SMILES: CS(=N)(=O)c1ccc(S(=O)(=O)Nc2ccccc2N2CCC(O)(c3ccc(Cl)cc3F)CC2)cc1] | A-152 |
| 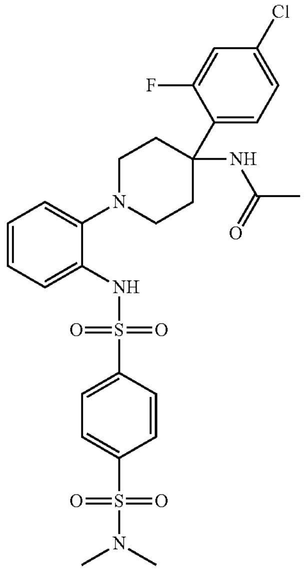 [SMILES: CC(=O)NC1(c2ccc(Cl)cc2F)CCN(c2ccccc2NS(=O)(=O)c2ccc(S(=O)(=O)N(C)C)cc2)CC1] | A-153 |

TABLE A-continued
| Structure | Compound No. |
| --- | --- |
| 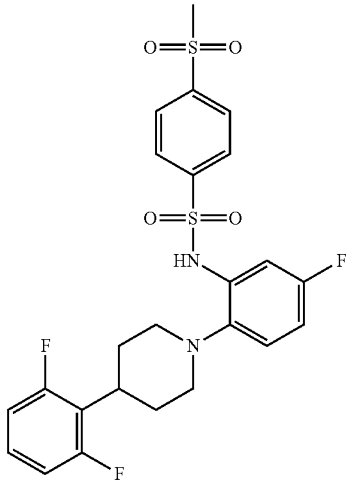 [SMILES: CS(=O)(=O)c1ccc(S(=O)(=O)Nc2cc(F)ccc2N2CCC(c3c(F)cccc3F)CC2)cc1] | A-154 |
| 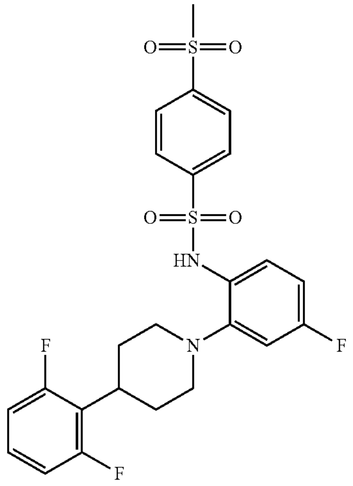 [SMILES: CS(=O)(=O)c1ccc(S(=O)(=O)Nc2ccc(F)cc2N2CCC(c3c(F)cccc3F)CC2)cc1] | A-155 |
| 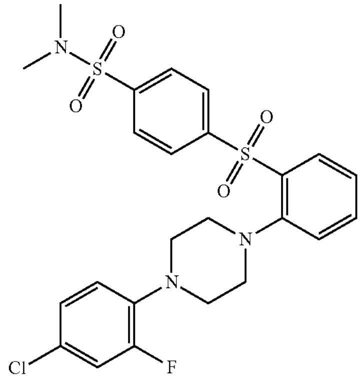 [SMILES: CN(C)S(=O)(=O)c1ccc(S(=O)(=O)c2ccccc2N2CCN(c3ccc(Cl)cc3F)CC2)cc1] | A-156 |

TABLE A-continued
| Structure | Compound No. |
| --- | --- |
| 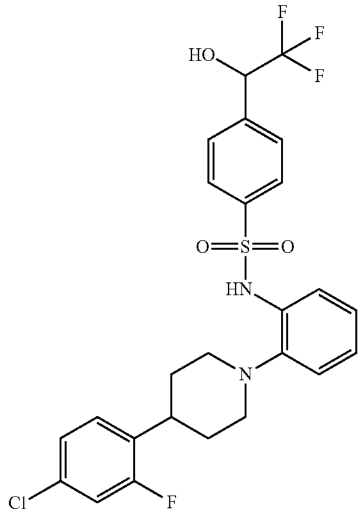 [SMILES: O=S(=O)(Nc1ccccc1N1CCC(c2ccc(Cl)cc2F)CC1)c1ccc(C(O)C(F)(F)F)cc1] | A-157 |
| 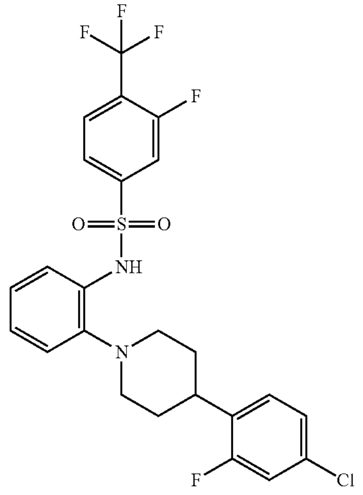 [SMILES: O=S(=O)(Nc1ccccc1N1CCC(c2ccc(Cl)cc2F)CC1)c1ccc(C(F)(F)F)c(F)c1] | A-158 |
| 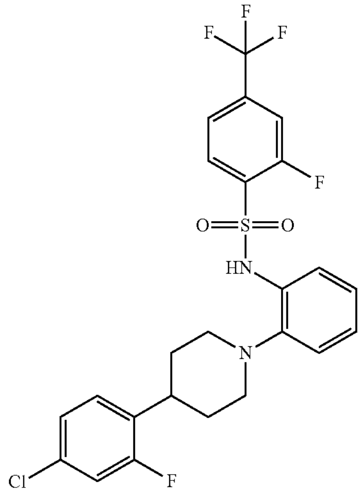 [SMILES: O=S(=O)(Nc1ccccc1N1CCC(c2ccc(Cl)cc2F)CC1)c1ccc(C(F)(F)F)cc1F] | A-159 |

TABLE A-continued
| Structure | Compound No. |
| --- | --- |
| 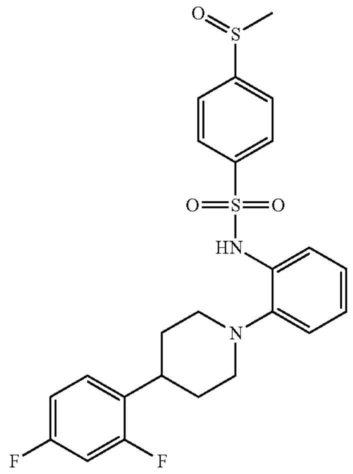 [SMILES: CS(=O)c1ccc(S(=O)(=O)Nc2ccccc2N2CCC(c3ccc(F)cc3F)CC2)cc1] | A-160 |
| 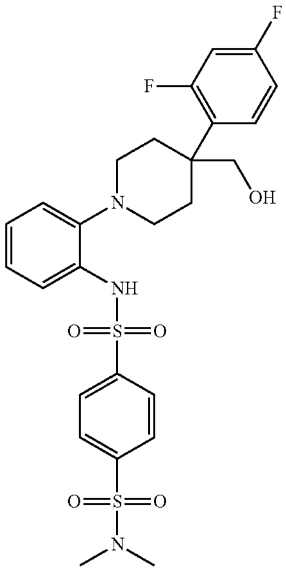 [SMILES: CN(C)S(=O)(=O)c1ccc(S(=O)(=O)Nc2ccccc2N2CCC(CO)(c3ccc(F)cc3F)CC2)cc1] | A-161 |
| 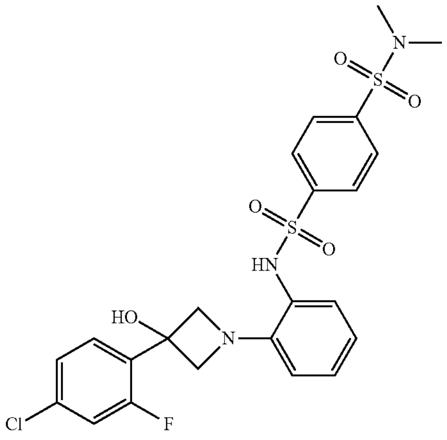 [SMILES: CN(C)S(=O)(=O)c1ccc(S(=O)(=O)Nc2ccccc2N2CC(O)(c3ccc(Cl)cc3F)C2)cc1] | A-162 |

TABLE A-continued
| Structure | Compound No. |
| --- | --- |
| 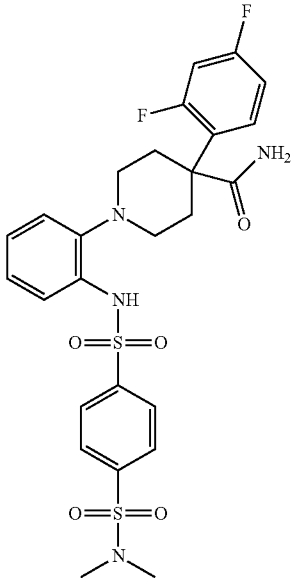 [SMILES: CN(C)S(=O)(=O)c1ccc(S(=O)(=O)Nc2ccccc2N2CCC(C(N)=O)(c3ccc(F)cc3F)CC2)cc1] | A-163 |
| 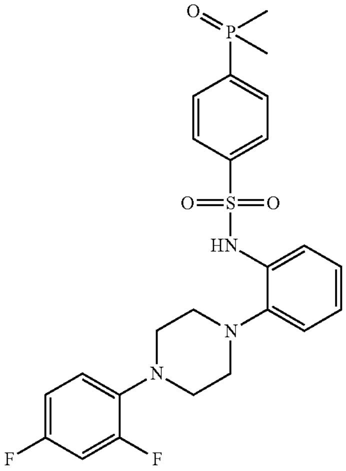 [SMILES: CP(C)(=O)c1ccc(S(=O)(=O)Nc2ccccc2N2CCN(c3ccc(F)cc3F)CC2)cc1] | A-165 |
| 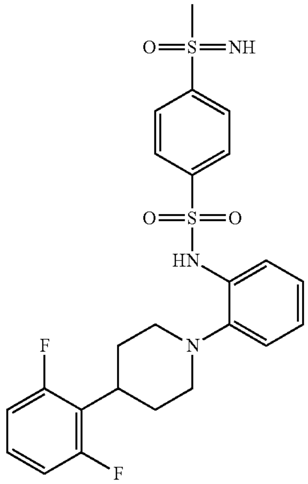 [SMILES: CS(=N)(=O)c1ccc(S(=O)(=O)Nc2ccccc2N2CCC(c3c(F)cccc3F)CC2)cc1] | A-166 |

TABLE A-continued
| Structure | Compound No. |
|---|---|
| 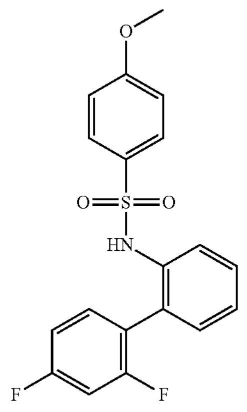 [SMILES: COc1ccc(S(=O)(=O)Nc2ccccc2-c2ccc(F)cc2F)cc1] | A-167 |
| 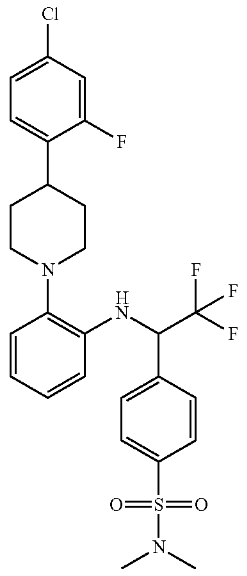 [SMILES: CN(C)S(=O)(=O)c1ccc(C(Nc2ccccc2N2CCC(c3ccc(Cl)cc3F)CC2)C(F)(F)F)cc1] | A-170 |
| 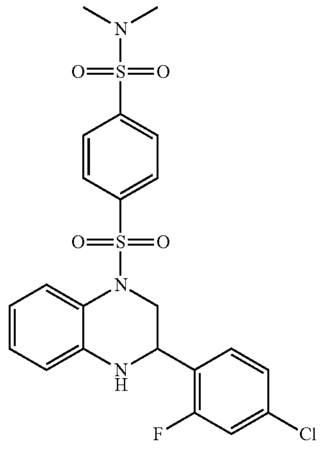 [SMILES: CN(C)S(=O)(=O)c1ccc(S(=O)(=O)N2CC(c3ccc(Cl)cc3F)Nc3ccccc32)cc1] | A-171 |

TABLE A-continued
| Structure | Compound No. |
| --- | --- |
| 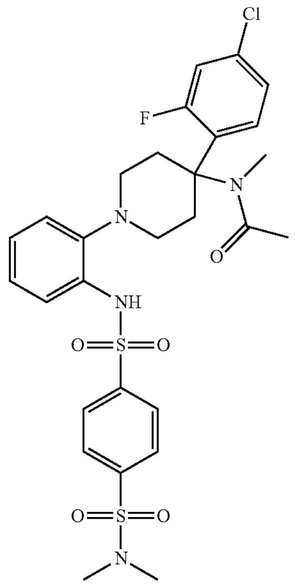 [SMILES: CC(=O)N(C)C1(c2ccc(Cl)cc2F)CCN(c2ccccc2NS(=O)(=O)c2ccc(S(=O)(=O)N(C)C)cc2)CC1] | A-172 |
| 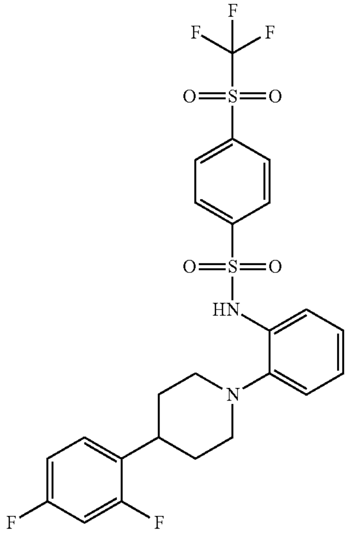 [SMILES: O=S(=O)(Nc1ccccc1N1CCC(c2ccc(F)cc2F)CC1)c1ccc(S(=O)(=O)C(F)(F)F)cc1] | A-173 |

TABLE A-continued
| Structure | Compound No. |
|---|---|
| 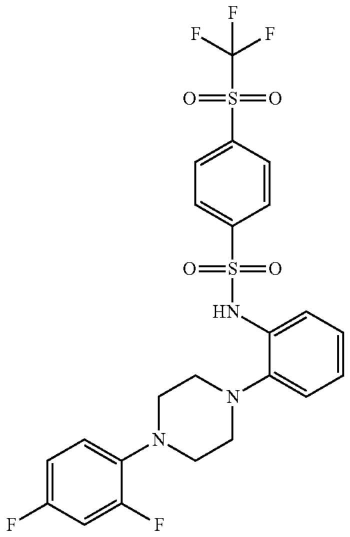 [SMILES: O=S(=O)(Nc1ccccc1N1CCN(c2ccc(F)cc2F)CC1)c1ccc(S(=O)(=O)C(F)(F)F)cc1] | A-174 |
| 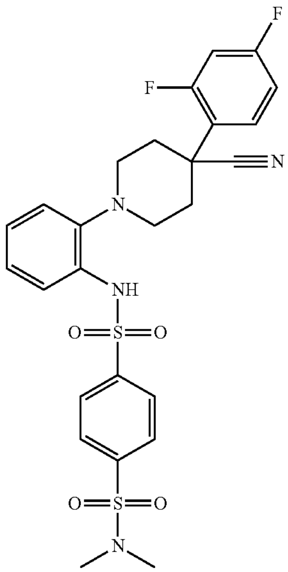 [SMILES: CN(C)S(=O)(=O)c1ccc(S(=O)(=O)Nc2ccccc2N2CCC(C#N)(c3ccc(F)cc3F)CC2)cc1] | A-175 |
| 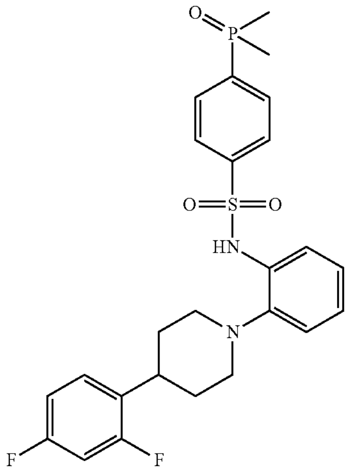 [SMILES: CP(C)(=O)c1ccc(S(=O)(=O)Nc2ccccc2N2CCC(c3ccc(F)cc3F)CC2)cc1] | A-176 |

TABLE A-continued
| Structure | Compound No. |
| --- | --- |
| 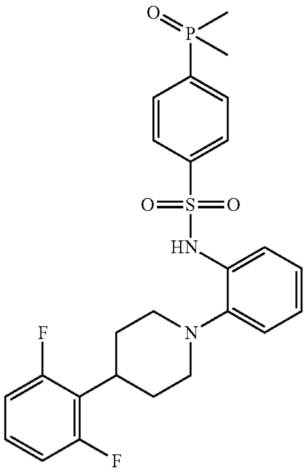 [SMILES: CP(C)(=O)c1ccc(S(=O)(=O)Nc2ccccc2N2CCC(c3c(F)cccc3F)CC2)cc1] | A-177 |
| 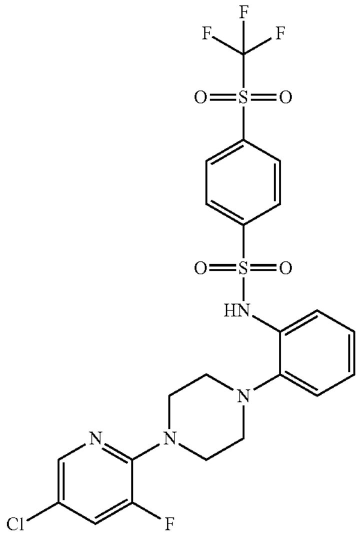 [SMILES: O=S(=O)(Nc1ccccc1N1CCN(c2ncc(Cl)cc2F)CC1)c1ccc(S(=O)(=O)C(F)(F)F)cc1] | A-178 |
| 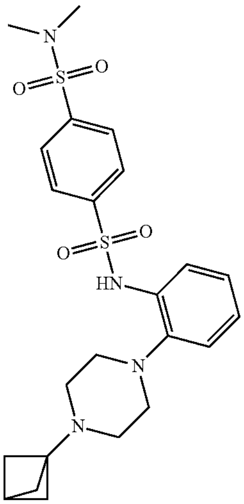 [SMILES: CN(C)S(=O)(=O)c1ccc(S(=O)(=O)Nc2ccccc2N2CCN(C34CC(C3)C4)CC2)cc1] | A-179 |

TABLE A-continued
| Structure | Compound No. |
|---|---|
| 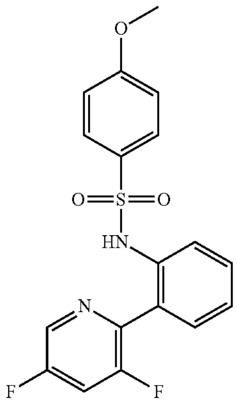 [SMILES: COc1ccc(S(=O)(=O)Nc2ccccc2-c2ncc(F)cc2F)cc1] | A-180 |
| 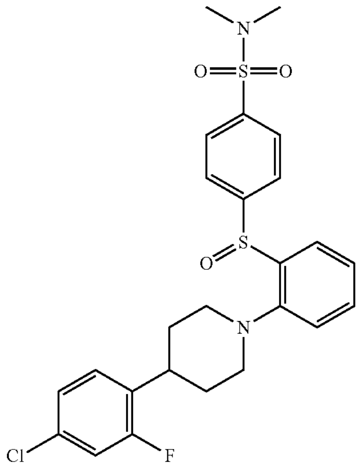 [SMILES: CN(C)S(=O)(=O)c1ccc(S(=O)c2ccccc2N2CCC(c3ccc(Cl)cc3F)CC2)cc1] | A-181 |
| 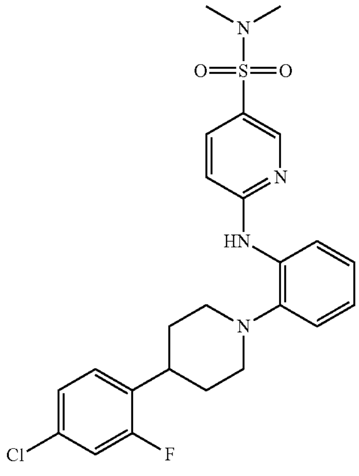 [SMILES: CN(C)S(=O)(=O)c1ccc(Nc2ccccc2N2CCC(c3ccc(Cl)cc3F)CC2)nc1] | A-182 |

TABLE A-continued
| Structure | Compound No. |
| --- | --- |
| 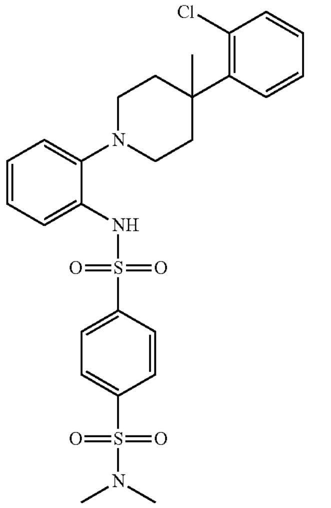 [SMILES: CN(C)S(=O)(=O)c1ccc(S(=O)(=O)Nc2ccccc2N2CCC(C)(c3ccccc3Cl)CC2)cc1] | A-183 |
| 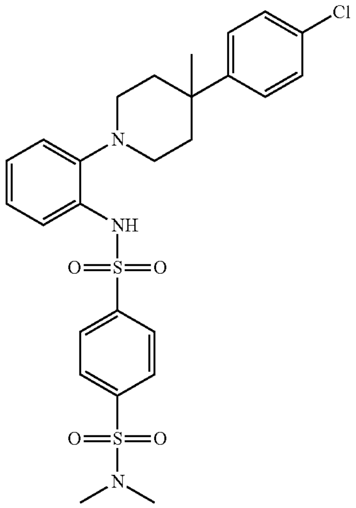 [SMILES: CN(C)S(=O)(=O)c1ccc(S(=O)(=O)Nc2ccccc2N2CCC(C)(c3ccc(Cl)cc3)CC2)cc1] | A-184 |
| 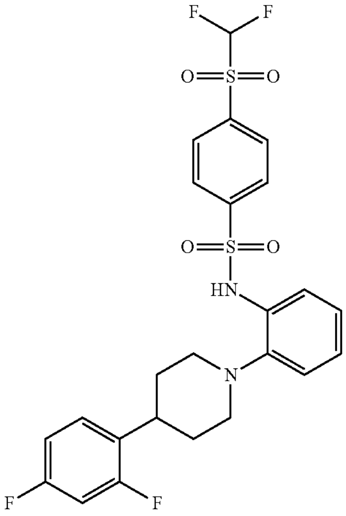 [SMILES: O=S(=O)(Nc1ccccc1N1CCC(c2ccc(F)cc2F)CC1)c1ccc(S(=O)(=O)C(F)F)cc1] | A-185 |

TABLE A-continued
| Structure | Compound No. |
|---|---|
| 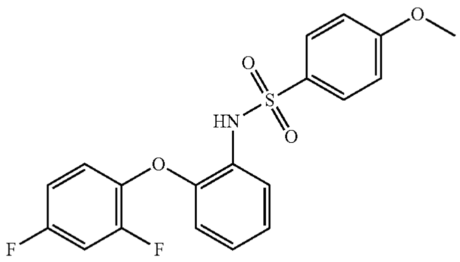 [SMILES: COc1ccc(S(=O)(=O)Nc2ccccc2Oc2ccc(F)cc2F)cc1] | A-186 |
| 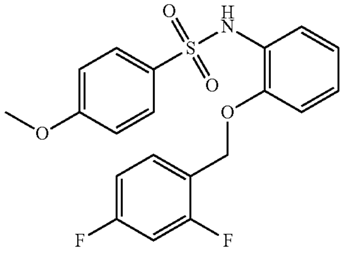 [SMILES: COc1ccc(S(=O)(=O)Nc2ccccc2OCc2ccc(F)cc2F)cc1] | A-187 |
| 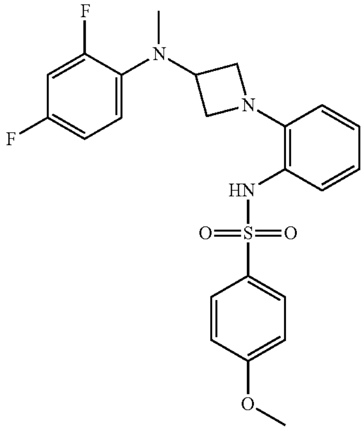 [SMILES: COc1ccc(S(=O)(=O)Nc2ccccc2N2CC(N(C)c3ccc(F)cc3F)C2)cc1] | A-188 |
| 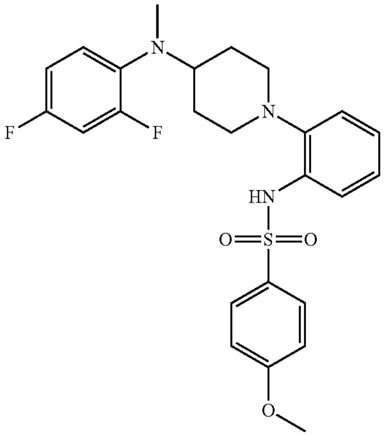 [SMILES: COc1ccc(S(=O)(=O)Nc2ccccc2N2CCC(N(C)c3ccc(F)cc3F)CC2)cc1] | A-189 |

TABLE A-continued
| Structure | Compound No. |
| --- | --- |
| 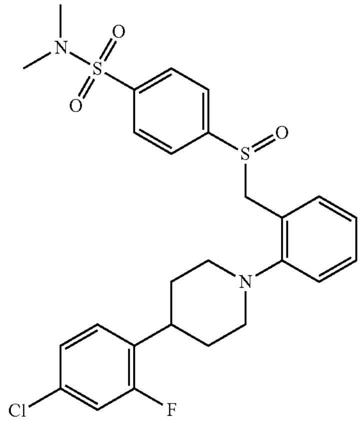 [SMILES: CN(C)S(=O)(=O)c1ccc(S(=O)Cc2ccccc2N2CCC(c3ccc(Cl)cc3F)CC2)cc1] | A-190 |
| 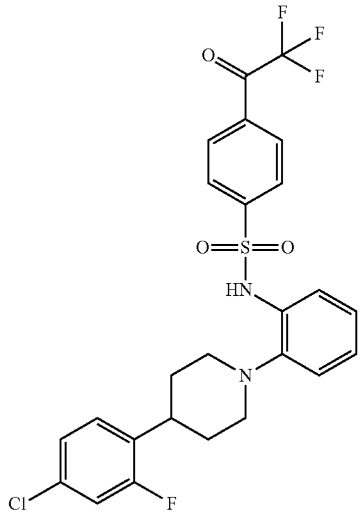 [SMILES: O=C(c1ccc(S(=O)(=O)Nc2ccccc2N2CCC(c3ccc(Cl)cc3F)CC2)cc1)C(F)(F)F] | A-191 |
| 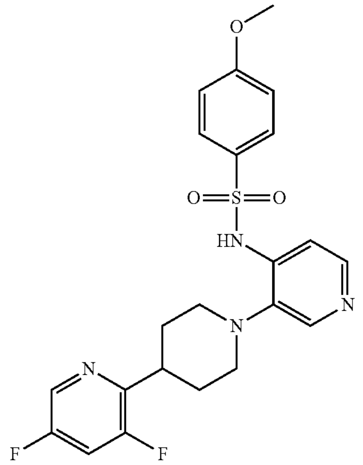 [SMILES: COc1ccc(S(=O)(=O)Nc2ccncc2N2CCC(c3ncc(F)cc3F)CC2)cc1] | A-192 |

TABLE A-continued
| Structure | Compound No. |
| --- | --- |
| 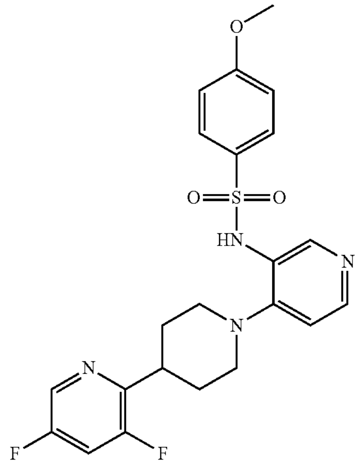 [SMILES: COc1ccc(S(=O)(=O)Nc2cnccc2N2CCC(c3ncc(F)cc3F)CC2)cc1] | A-193 |
| 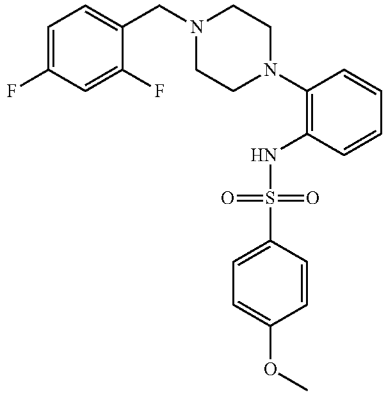 [SMILES: COc1ccc(S(=O)(=O)Nc2ccccc2N2CCN(Cc3ccc(F)cc3F)CC2)cc1] | A-194 |
| 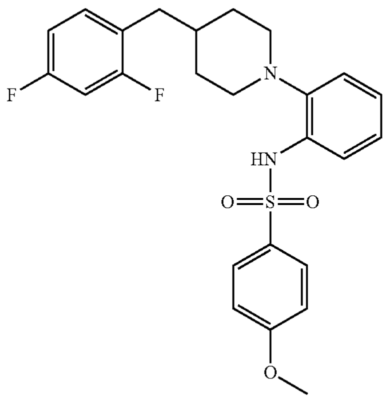 [SMILES: COc1ccc(S(=O)(=O)Nc2ccccc2N2CCC(Cc3ccc(F)cc3F)CC2)cc1] | A-195 |

TABLE A-continued
| Structure | Compound No. |
| --- | --- |
| 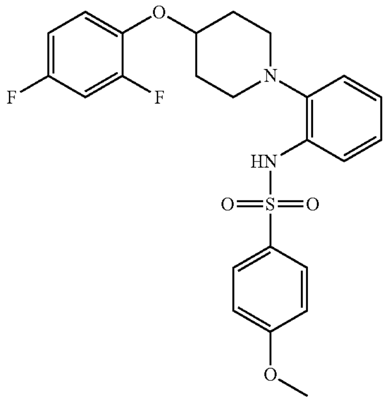 [SMILES: COc1ccc(S(=O)(=O)Nc2ccccc2N2CCC(Oc3ccc(F)cc3F)CC2)cc1] | A-196 |
| 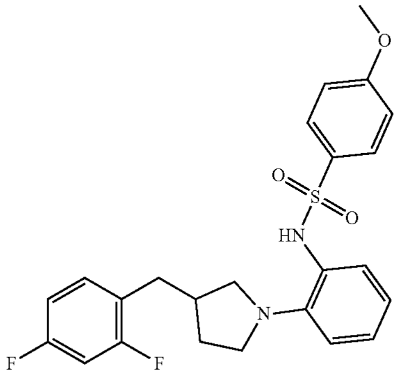 [SMILES: COc1ccc(S(=O)(=O)Nc2ccccc2N2CCC(Cc3ccc(F)cc3F)C2)cc1] | A-197 |
| 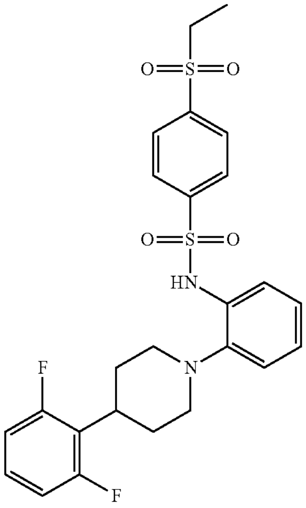 [SMILES: CCS(=O)(=O)c1ccc(S(=O)(=O)Nc2ccccc2N2CCC(c3c(F)cccc3F)CC2)cc1] | A-198 |
| 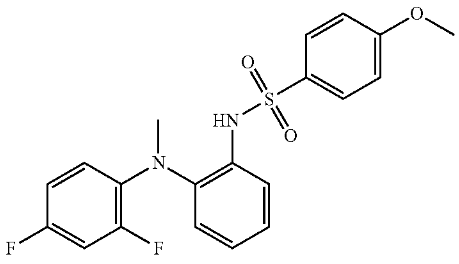 [SMILES: COc1ccc(S(=O)(=O)Nc2ccccc2N(C)c2ccc(F)cc2F)cc1] | A-199 |

TABLE A-continued
| Structure | Compound No. |
| --- | --- |
| 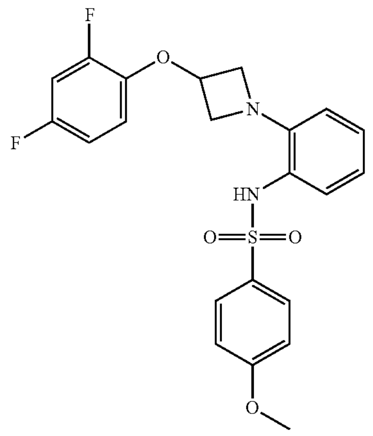 [SMILES: COc1ccc(S(=O)(=O)Nc2ccccc2N2CC(Oc3ccc(F)cc3F)C2)cc1] | A-200 |
| 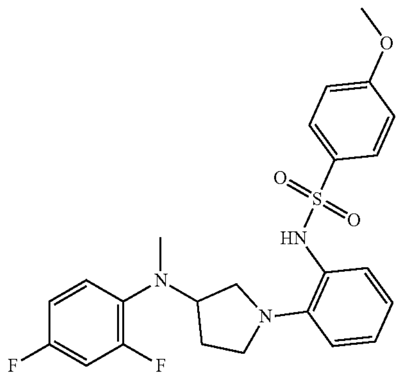 [SMILES: COc1ccc(S(=O)(=O)Nc2ccccc2N2CCC(N(C)c3ccc(F)cc3F)C2)cc1] | A-201 |
| 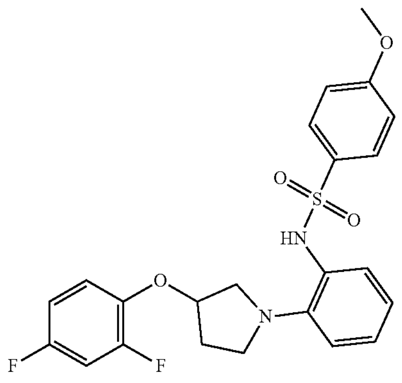 [SMILES: COc1ccc(S(=O)(=O)Nc2ccccc2N2CCC(Oc3ccc(F)cc3F)C2)cc1] | A-202 |

TABLE A-continued
| Structure | Compound No. |
|---|---|
| 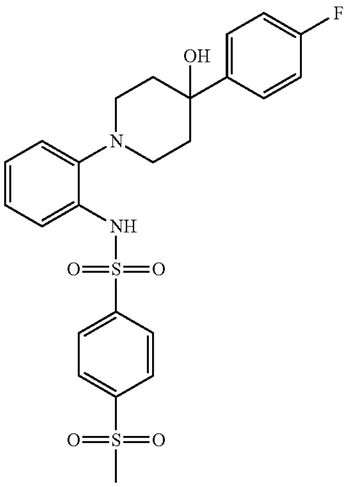 [SMILES: CS(=O)(=O)c1ccc(S(=O)(=O)Nc2ccccc2N2CCC(O)(c3ccc(F)cc3)CC2)cc1] | A-203 |
| 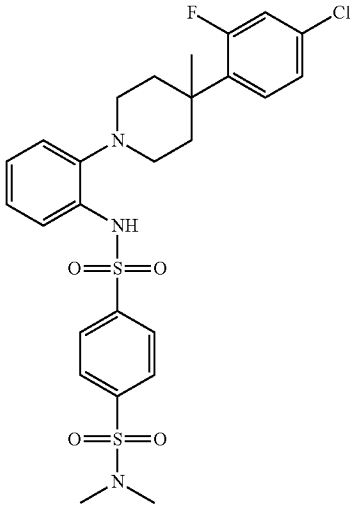 [SMILES: CN(C)S(=O)(=O)c1ccc(S(=O)(=O)Nc2ccccc2N2CCC(C)(c3ccc(Cl)cc3F)CC2)cc1] | A-204 |
| 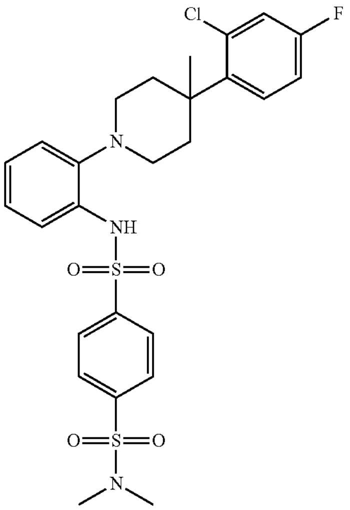 [SMILES: CN(C)S(=O)(=O)c1ccc(S(=O)(=O)Nc2ccccc2N2CCC(C)(c3ccc(F)cc3Cl)CC2)cc1] | A-205 |

TABLE A-continued
| Structure | Compound No. |
|---|---|
| 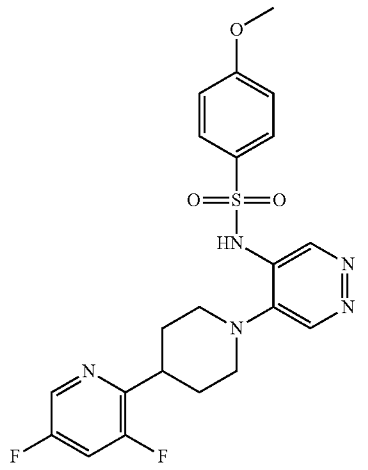 [SMILES: COc1ccc(S(=O)(=O)Nc2cnncc2N2CCC(c3ncc(F)cc3F)CC2)cc1] | A-206 |
| 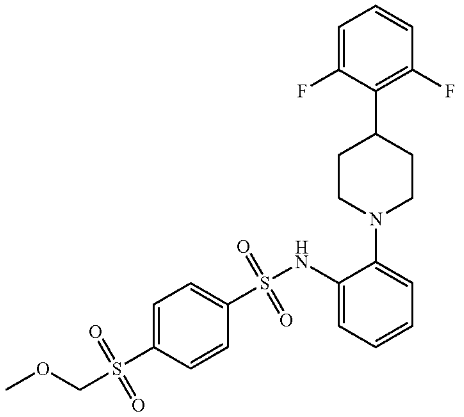 [SMILES: COCS(=O)(=O)c1ccc(S(=O)(=O)Nc2ccccc2N2CCC(c3c(F)cccc3F)CC2)cc1] | A-207 |
| 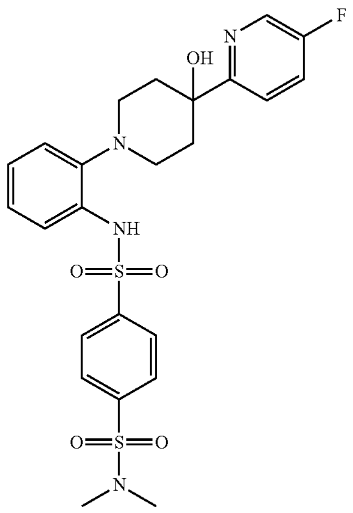 [SMILES: CN(C)S(=O)(=O)c1ccc(S(=O)(=O)Nc2ccccc2N2CCC(O)(c3ccc(F)cn3)CC2)cc1] | A-209 |

TABLE A-continued
| Structure | Compound No. |
| --- | --- |
| 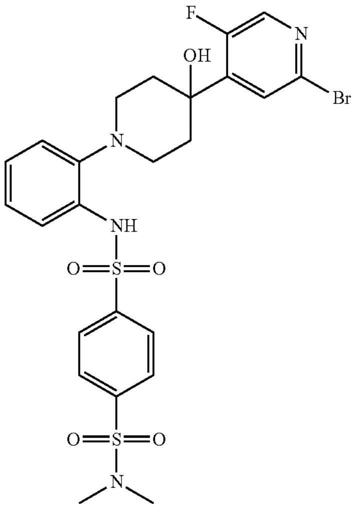 [SMILES: CN(C)S(=O)(=O)c1ccc(S(=O)(=O)Nc2ccccc2N2CCC(O)(c3cc(Br)ncc3F)CC2)cc1] | A-210 |
| 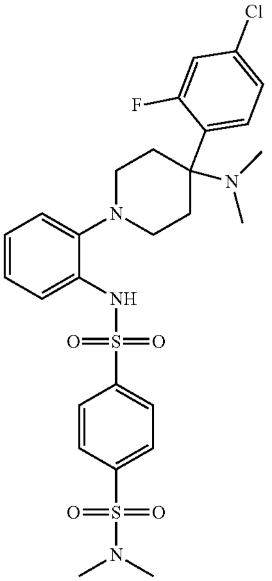 [SMILES: CN(C)C1(c2ccc(Cl)cc2F)CCN(c2ccccc2NS(=O)(=O)c2ccc(S(=O)(=O)N(C)C)cc2)CC1] | A-211 |

TABLE A-continued
| Structure | Compound No. |
| --- | --- |
| 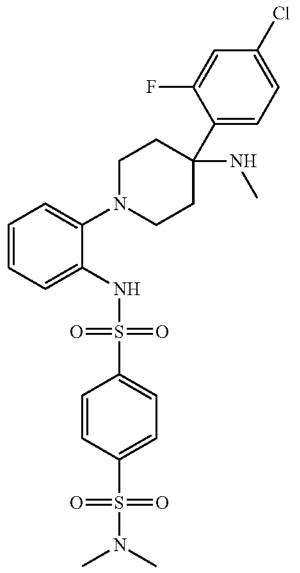 [SMILES: CNC1(c2ccc(Cl)cc2F)CCN(c2ccccc2NS(=O)(=O)c2ccc(S(=O)(=O)N(C)C)cc2)CC1] | A-212 |
| 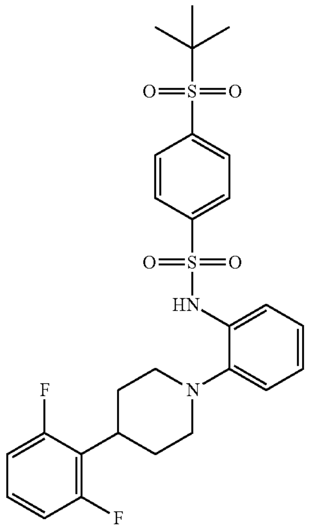 [SMILES: CC(C)(C)S(=O)(=O)c1ccc(S(=O)(=O)Nc2ccccc2N2CCC(c3c(F)cccc3F)CC2)cc1] | A-213 |
| 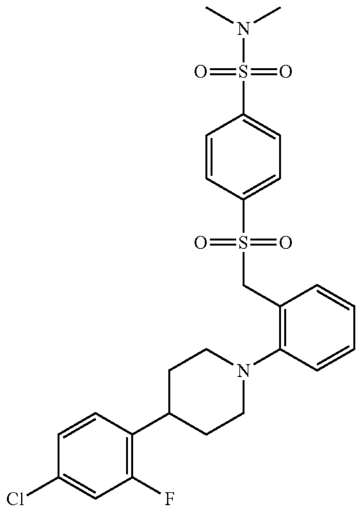 [SMILES: CN(C)S(=O)(=O)c1ccc(S(=O)(=O)Cc2ccccc2N2CCC(c3ccc(Cl)cc3F)CC2)cc1] | A-214 |

TABLE A-continued
| Structure | Compound No. |
| --- | --- |
| 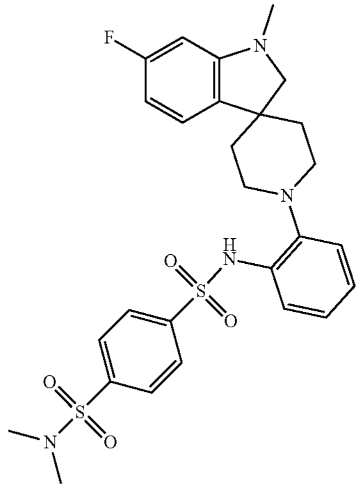 | A-215 |
| 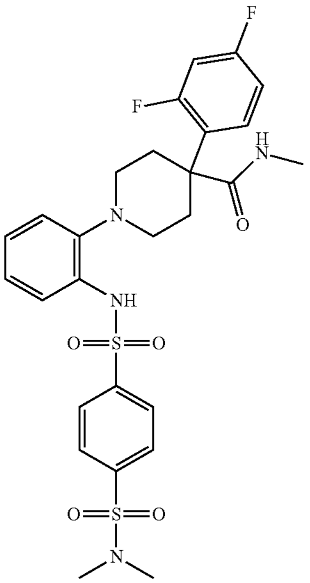 [SMILES: CNC(=O)C1(c2ccc(F)cc2F)CCN(c2ccccc2NS(=O)(=O)c2ccc(S(=O)(=O)N(C)C)cc2)CC1] | A-216 |

TABLE A-continued
| Structure | Compound No. |
| --- | --- |
| 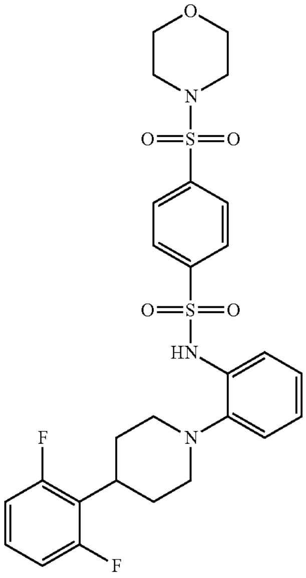 [SMILES: O=S(=O)(Nc1ccccc1N1CCC(c2c(F)cccc2F)CC1)c1ccc(S(=O)(=O)N2CCOCC2)cc1] | A-217 |
| 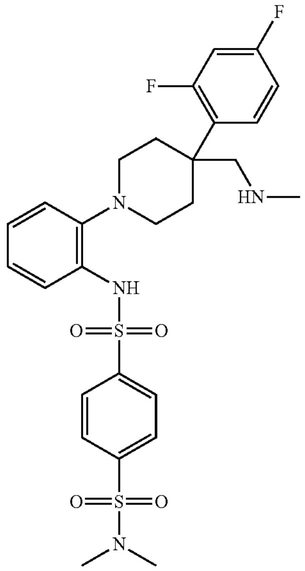 [SMILES: CNCC1(c2ccc(F)cc2F)CCN(c2ccccc2NS(=O)(=O)c2ccc(S(=O)(=O)N(C)C)cc2)CC1] | A-218 |
| 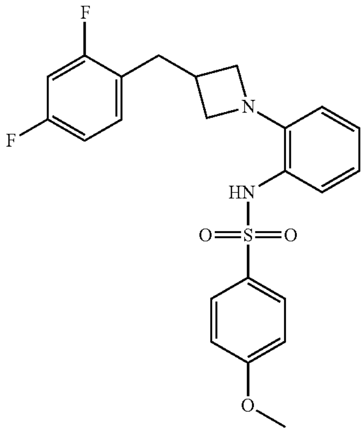 [SMILES: COc1ccc(S(=O)(=O)Nc2ccccc2N2CC(Cc3ccc(F)cc3F)C2)cc1] | A-219 |

TABLE A-continued
| Structure | Compound No. |
| --- | --- |
| 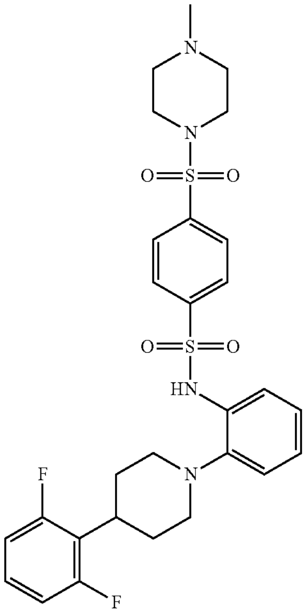 [SMILES: CN1CCN(S(=O)(=O)c2ccc(S(=O)(=O)Nc3ccccc3N3CCC(c4c(F)cccc4F)CC3)cc2)CC1] | A-220 |
| 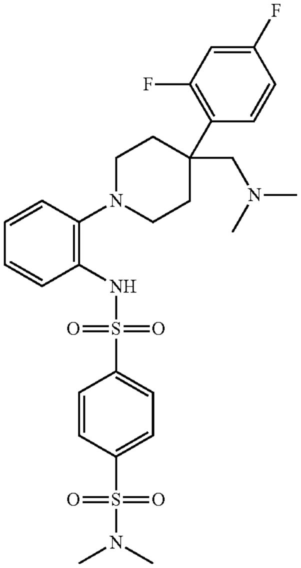 [SMILES: CN(C)CC1(c2ccc(F)cc2F)CCN(c2ccccc2NS(=O)(=O)c2ccc(S(=O)(=O)N(C)C)cc2)CC1] | A-221 |

TABLE A-continued
| Structure | Compound No. |
|---|---|
| 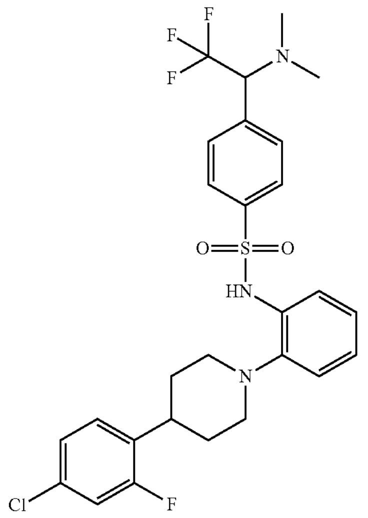 [SMILES: CN(C)C(c1ccc(S(=O)(=O)Nc2ccccc2N2CCC(c3ccc(Cl)cc3F)CC2)cc1)C(F)(F)F] | A-222 |
| 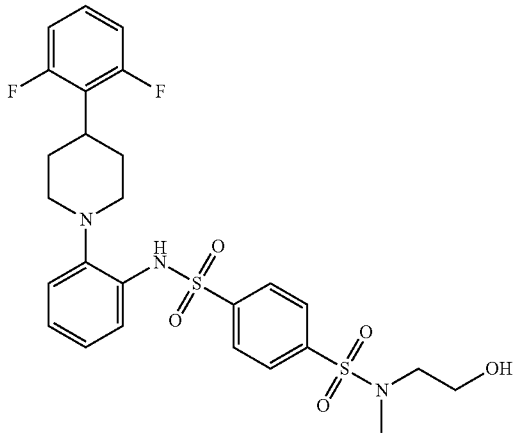 [SMILES: CN(CCO)S(=O)(=O)c1ccc(S(=O)(=O)Nc2ccccc2N2CCC(c3c(F)cccc3F)CC2)cc1] | A-223 |
| 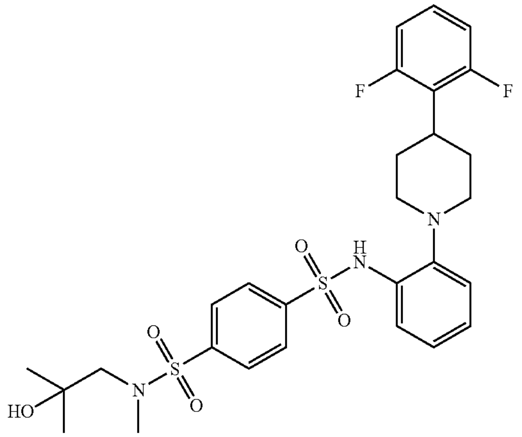 [SMILES: CN(CC(C)(C)O)S(=O)(=O)c1ccc(S(=O)(=O)Nc2ccccc2N2CCC(c3c(F)cccc3F)CC2)cc1] | A-224 |

TABLE A-continued
| Structure | Compound No. |
| --- | --- |
| 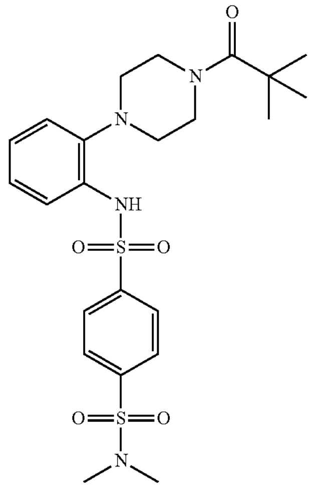 | A-225 |
| 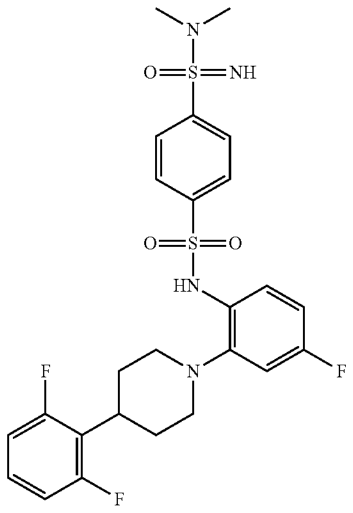 [SMILES: CN(C)S(=N)(=O)c1ccc(S(=O)(=O)Nc2ccc(F)cc2N2CCC(c3c(F)cccc3F)CC2)cc1] | A-226 |
| 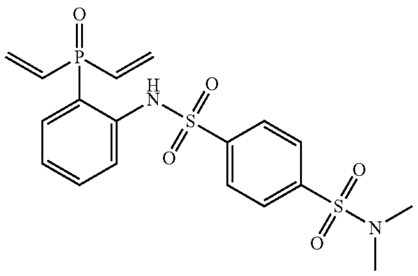 [SMILES: C=CP(=O)(C=C)c1ccccc1NS(=O)(=O)c1ccc(S(=O)(=O)N(C)C)cc1] | A-227 |

TABLE A-continued
| Structure | Compound No. |
| --- | --- |
| 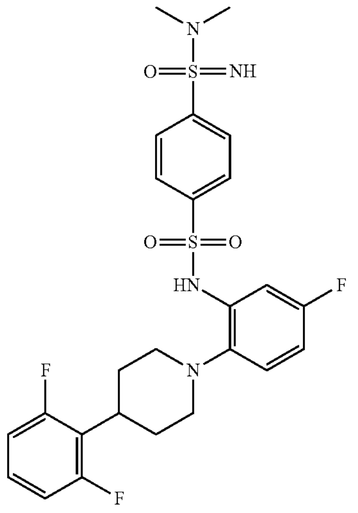 [SMILES: CN(C)S(=N)(=O)c1ccc(S(=O)(=O)Nc2cc(F)ccc2N2CCC(c3c(F)cccc3F)CC2)cc1] | A-228 |
| 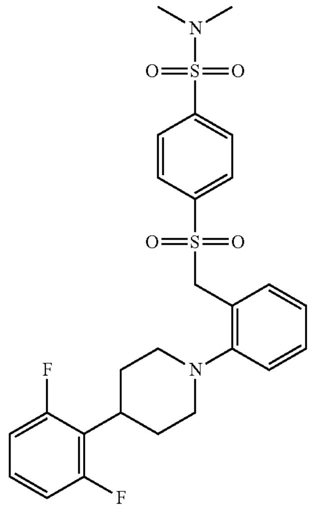 [SMILES: CN(C)S(=O)(=O)c1ccc(S(=O)(=O)Cc2ccccc2N2CCC(c3c(F)cccc3F)CC2)cc1] | A-229 |
| 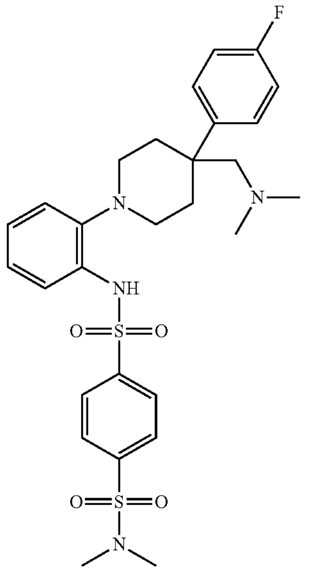 [SMILES: CN(C)CC1(c2ccc(F)cc2)CCN(c2ccccc2NS(=O)(=O)c2ccc(S(=O)(=O)N(C)C)cc2)CC1] | A-231 |

TABLE A-continued
| Structure | Compound No. |
|---|---|
| 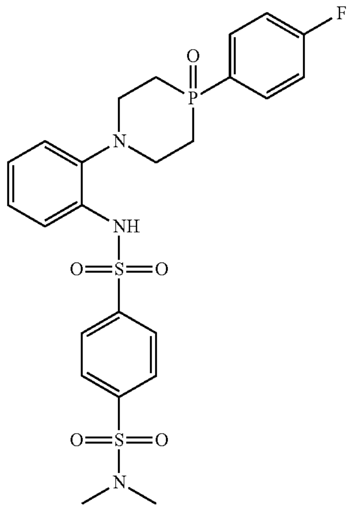 [SMILES: CN(C)S(=O)(=O)c1ccc(S(=O)(=O)Nc2ccccc2N2CCP(=O)(c3ccc(F)cc3)CC2)cc1] | A-232 |
| 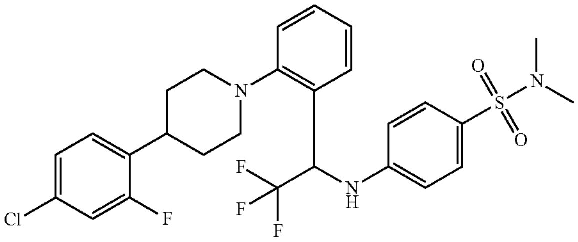 [SMILES: CN(C)S(=O)(=O)c1ccc(NC(c2ccccc2N2CCC(c3ccc(Cl)cc3F)CC2)C(F)(F)F)cc1] | A-241 |
| 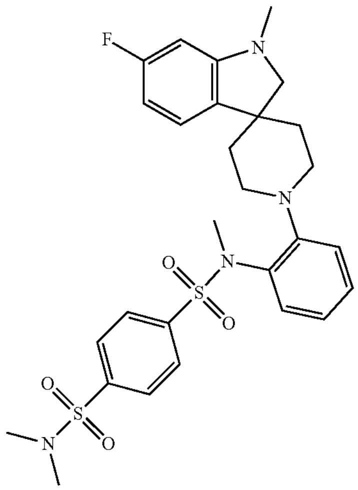 [SMILES: CN1CC2(CCN(c3ccccc3N(C)S(=O)(=O)c3ccc(S(=O)(=O)N(C)C)cc3)CC2)c2ccc(F)cc21] | A-243 |

TABLE A-continued
| Structure | Compound No. |
|---|---|
| 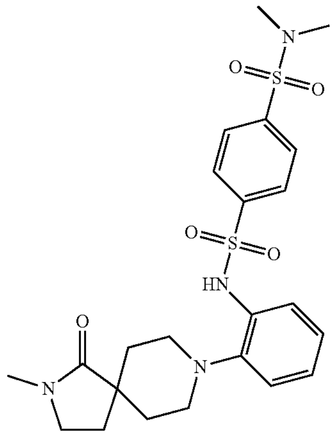 | A-244 |
| 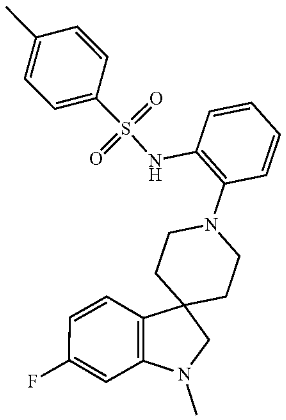 [SMILES: Cc1ccc(S(=O)(=O)Nc2ccccc2N2CCC3(CC2)CN(C)c2cc(F)ccc23)cc1] | A-245 |
| 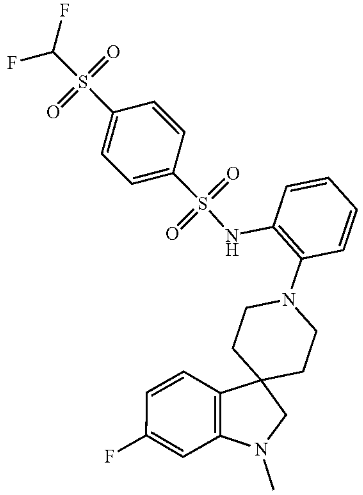 [SMILES: CN1CC2(CCN(c3ccccc3NS(=O)(=O)c3ccc(S(=O)(=O)C(F)F)cc3)CC2)c2ccc(F)cc21] | A-246 |

TABLE A-continued
| Structure | Compound No. |
|---|---|
| 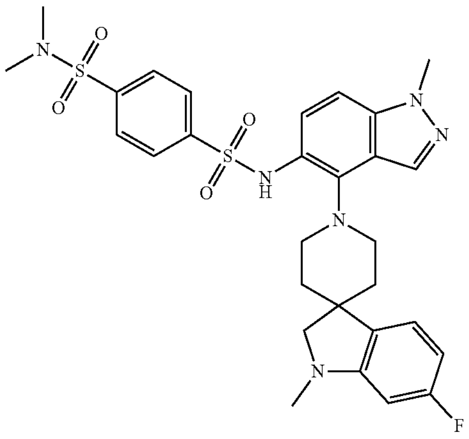 [SMILES: CN1CC2(CCN(c3c(NS(=O)(=O)c4ccc(S(=O)(=O)N(C)C)cc4)ccc4c3cnn4C)CC2)c2ccc(F)cc21] | A-247 |
| 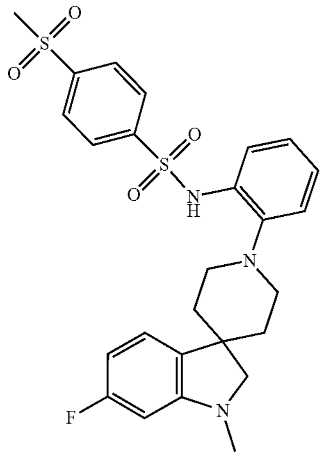 [SMILES: CN1CC2(CCN(c3ccccc3NS(=O)(=O)c3ccc(S(C)(=O)=O)cc3)CC2)c2ccc(F)cc21] | A-251 |
| 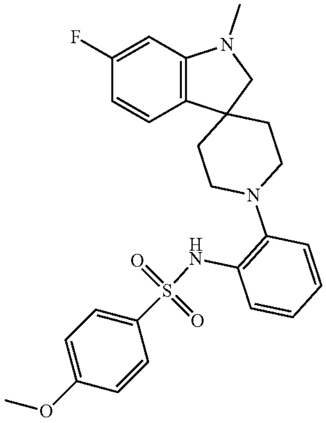 [SMILES: COc1ccc(S(=O)(=O)Nc2ccccc2N2CCC3(CC2)CN(C)c2cc(F)ccc23)cc1] | A-252 |

TABLE A-continued
| Structure | Compound No. |
| --- | --- |
| 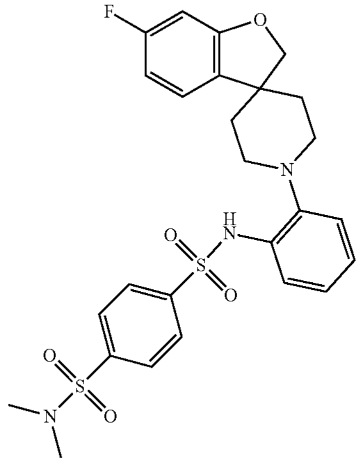 [SMILES: CN(C)S(=O)(=O)c1ccc(S(=O)(=O)Nc2ccccc2N2CCC3(CC2)COc2cc(F)ccc23)cc1] | A-253 |
| 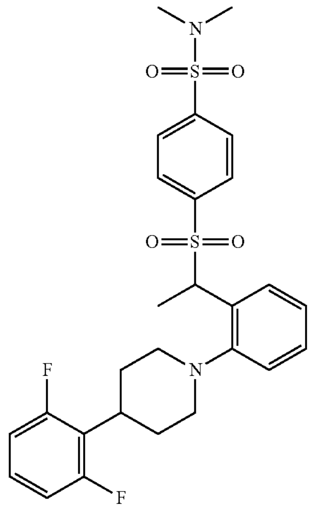 [SMILES: CC(c1ccccc1N1CCC(c2c(F)cccc2F)CC1)S(=O)(=O)c1ccc(S(=O)(=O)N(C)C)cc1] | A-254 |
| 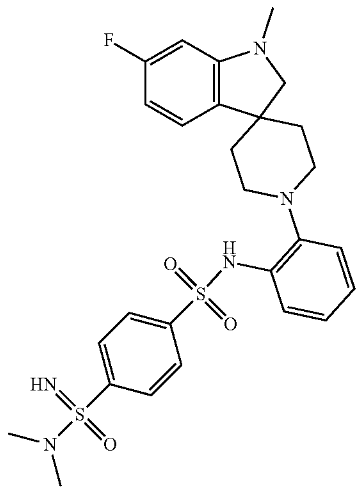 [SMILES: CN1CC2(CCN(c3ccccc3NS(=O)(=O)c3ccc(S(=N)(=O)N(C)C)cc3)CC2)c2ccc(F)cc21] | A-257 |

TABLE A-continued
| Structure | Compound No. |
|---|---|
| 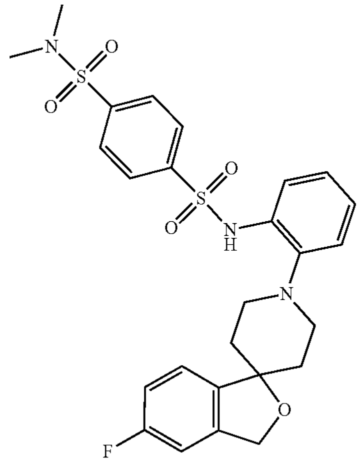 [SMILES: CN(C)S(=O)(=O)c1ccc(S(=O)(=O)Nc2ccccc2N2CCC3(CC2)OCc2cc(F)ccc23)cc1] | A-258 |
| 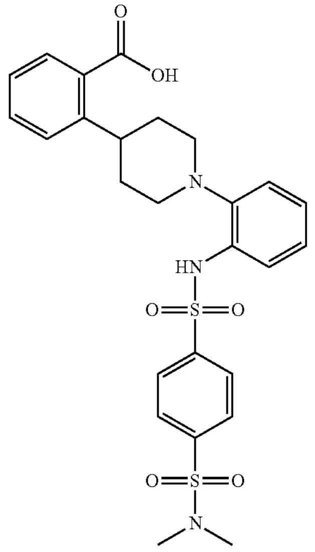 [SMILES: CN(C)S(=O)(=O)c1ccc(S(=O)(=O)Nc2ccccc2N2CCC(c3ccccc3C(=O)O)CC2)cc1] | A-259 |
| 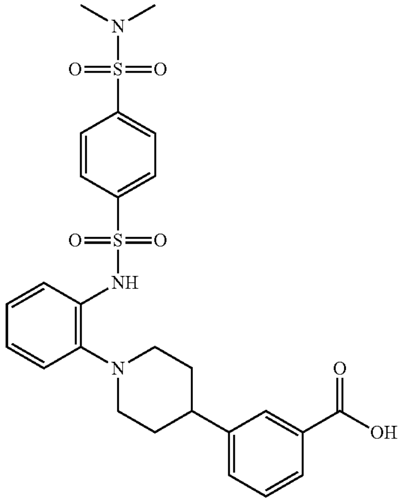 [SMILES: CN(C)S(=O)(=O)c1ccc(S(=O)(=O)Nc2ccccc2N2CCC(c3cccc(C(=O)O)c3)CC2)cc1] | A-266 |

TABLE A-continued
| Structure | Compound No. |
| --- | --- |
| 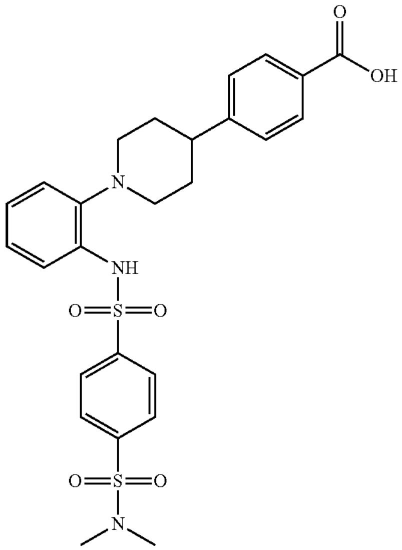 [SMILES: CN(C)S(=O)(=O)c1ccc(S(=O)(=O)Nc2ccccc2N2CCC(c3ccc(C(=O)O)cc3)CC2)cc1] | A-267 |
| 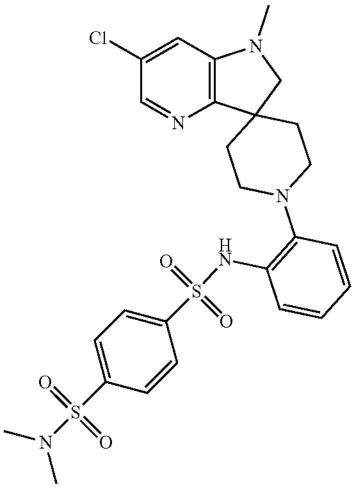 [SMILES: CN1CC2(CCN(c3ccccc3NS(=O)(=O)c3ccc(S(=O)(=O)N(C)C)cc3)CC2)c2ncc(Cl)cc21] | A-268 |
| 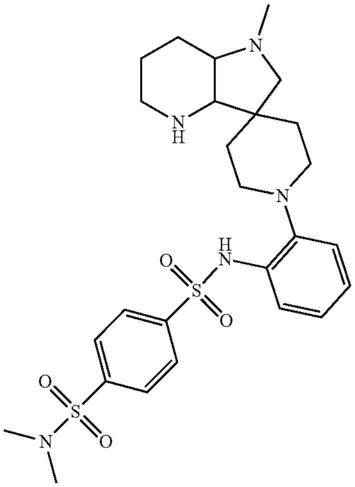 [SMILES: CN1CC2(CCN(c3ccccc3NS(=O)(=O)c3ccc(S(=O)(=O)N(C)C)cc3)CC2)C2NCCCC21] | A-269 |

TABLE A-continued
| Structure | Compound No. |
| --- | --- |
| 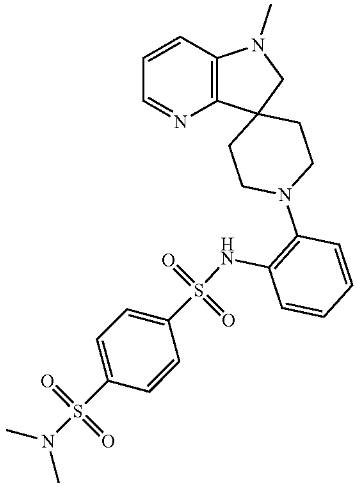 [SMILES: CN1CC2(CCN(c3ccccc3NS(=O)(=O)c3ccc(S(=O)(=O)N(C)C)cc3)CC2)c2ncccc21] | A-271 |
| 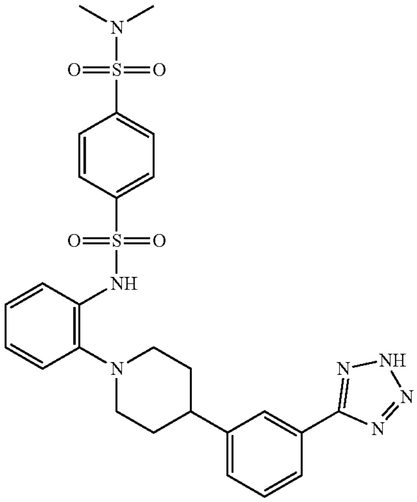 [SMILES: CN(C)S(=O)(=O)c1ccc(S(=O)(=O)Nc2ccccc2N2CCC(c3cccc(-c4nn[nH]n4)c3)CC2)cc1] | A-272 |
| 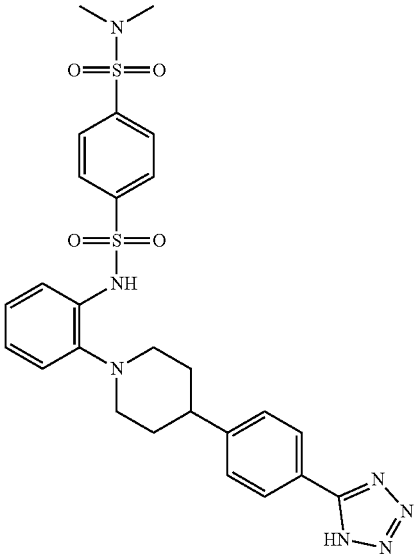 [SMILES: CN(C)S(=O)(=O)c1ccc(S(=O)(=O)Nc2ccccc2N2CCC(c3ccc(-c4nnn[nH]4)cc3)CC2)cc1] | A-273 |

TABLE A-continued
| Structure | Compound No. |
| --- | --- |
| 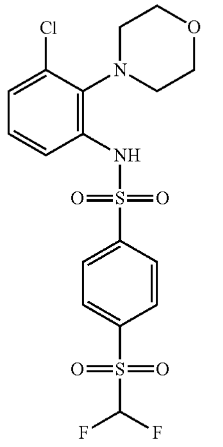 [SMILES: O=S(=O)(Nc1cccc(Cl)c1N1CCOCC1)c1ccc(S(=O)(=O)C(F)F)cc1] | A-274 |
| 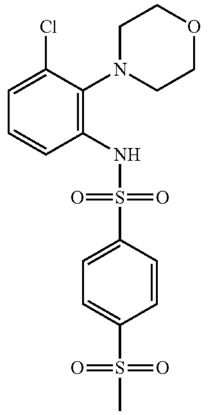 [SMILES: CS(=O)(=O)c1ccc(S(=O)(=O)Nc2cccc(Cl)c2N2CCOCC2)cc1] | A-275 |
| 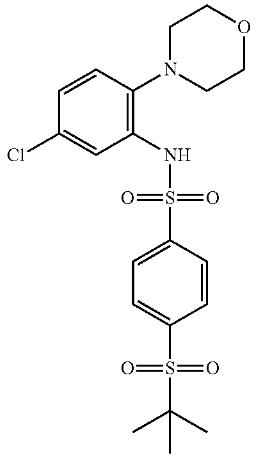 [SMILES: CC(C)(C)S(=O)(=O)c1ccc(S(=O)(=O)Nc2cc(Cl)ccc2N2CCOCC2)cc1] | A-276 |

TABLE A-continued
| Structure | Compound No. |
| --- | --- |
| 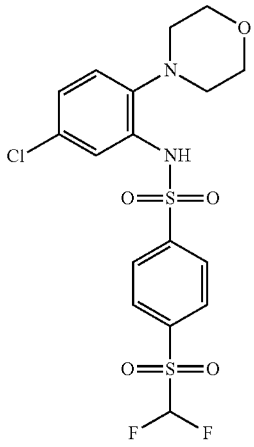 [SMILES: O=S(=O)(Nc1cc(Cl)ccc1N1CCOCC1)c1ccc(S(=O)(=O)C(F)F)cc1] | A-277 |
| 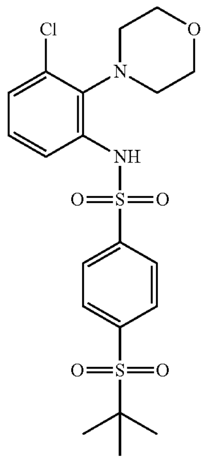 [SMILES: CC(C)(C)S(=O)(=O)c1ccc(S(=O)(=O)Nc2cccc(Cl)c2N2CCOCC2)cc1] | A-278 |
| 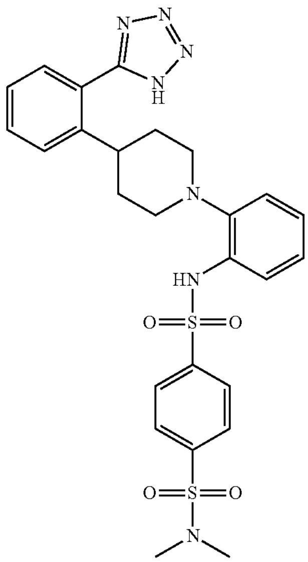 [SMILES: CN(C)S(=O)(=O)c1ccc(S(=O)(=O)Nc2ccccc2N2CCC(c3ccccc3-c3nnn[nH]3)CC2)cc1] | A-280 |

TABLE A-continued
| Structure | Compound No. |
| --- | --- |
| 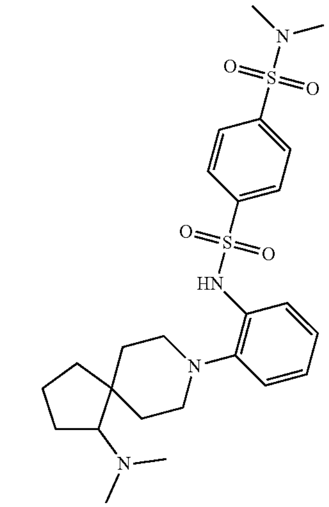 [SMILES: CN(C)C1CCCC12CCN(c1ccccc1NS(=O)(=O)c1ccc(S(=O)(=O)N(C)C)cc1)CC2] | A-281 |
| 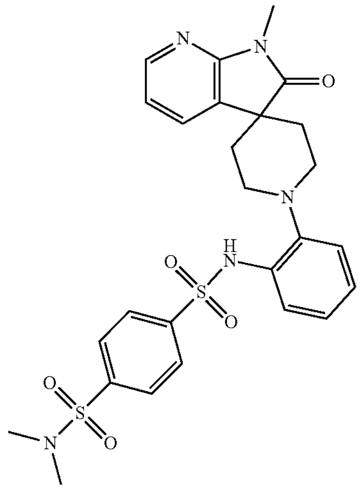 [SMILES: CN1C(=O)C2(CCN(c3ccccc3NS(=O)(=O)c3ccc(S(=O)(=O)N(C)C)cc3)CC2)c2cccnc21] | A-282 |
| 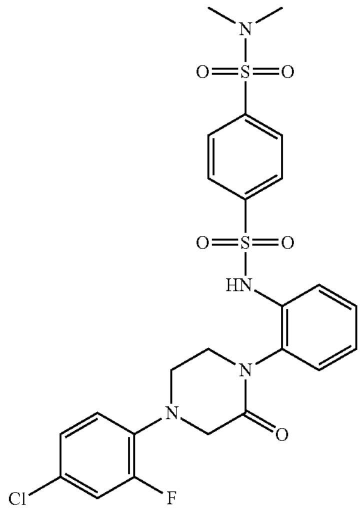 [SMILES: CN(C)S(=O)(=O)c1ccc(S(=O)(=O)Nc2ccccc2N2CCN(c3ccc(Cl)cc3F)CC2=O)cc1] | A-283 |

TABLE A-continued
| Structure | Compound No. |
| --- | --- |
| 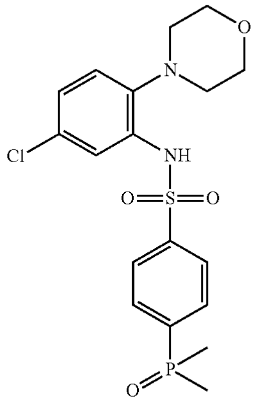 [SMILES: CP(C)(=O)c1ccc(S(=O)(=O)Nc2cc(Cl)ccc2N2CCOCC2)cc1] | A-284 |
| 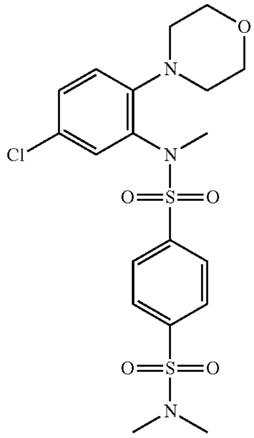 [SMILES: CN(C)S(=O)(=O)c1ccc(S(=O)(=O)N(C)c2cc(Cl)ccc2N2CCOCC2)cc1] | A-285 |
| 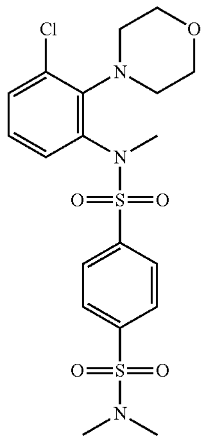 [SMILES: CN(C)S(=O)(=O)c1ccc(S(=O)(=O)N(C)c2cccc(Cl)c2N2CCOCC2)cc1] | A-286 |

TABLE A-continued
| Structure | Compound No. |
| --- | --- |
| 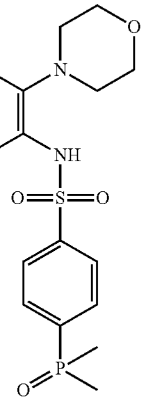 | A-287 |
| 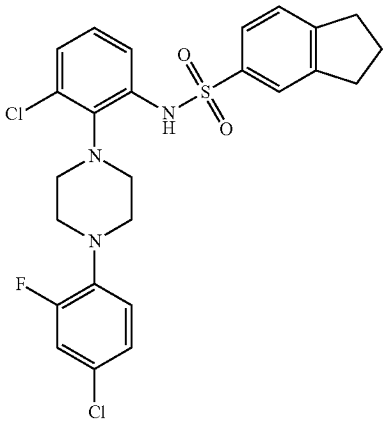 [SMILES: O=S(=O)(Nc1cccc(Cl)c1N1CCN(c2ccc(Cl)cc2F)CC1)c1ccc2c(c1)CCC2] | A-288 |
| 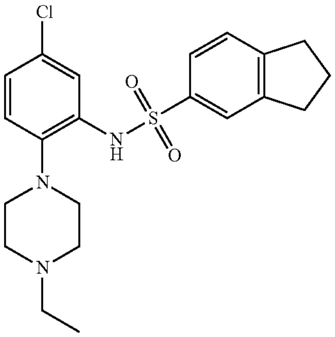 [SMILES: CCN1CCN(c2ccc(Cl)cc2NS(=O)(=O)c2ccc3c(c2)CCC3)CC1] | A-289 |
| 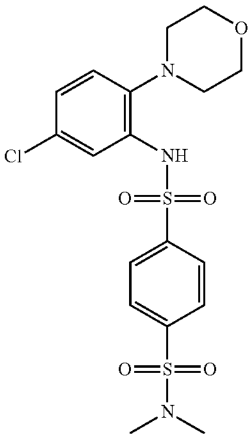 [SMILES: CN(C)S(=O)(=O)c1ccc(S(=O)(=O)Nc2cc(Cl)ccc2N2CCOCC2)cc1] | A-290 |

TABLE A-continued
| Structure | Compound No. |
| --- | --- |
| 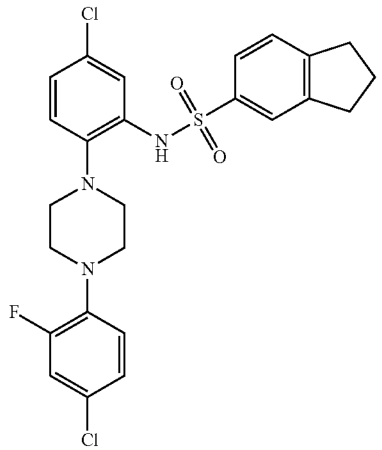 [SMILES: O=S(=O)(Nc1cc(Cl)ccc1N1CCN(c2ccc(Cl)cc2F)CC1)c1ccc2c(c1)CCC2] | A-291 |
| 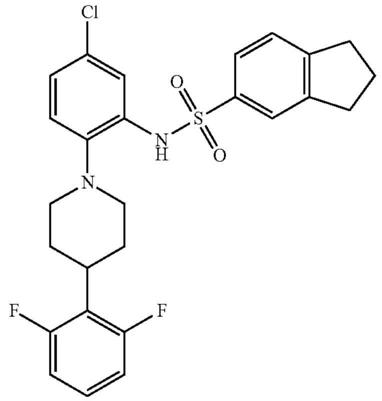 [SMILES: O=S(=O)(Nc1cc(Cl)ccc1N1CCC(c2c(F)cccc2F)CC1)c1ccc2c(c1)CCC2] | A-292 |
| 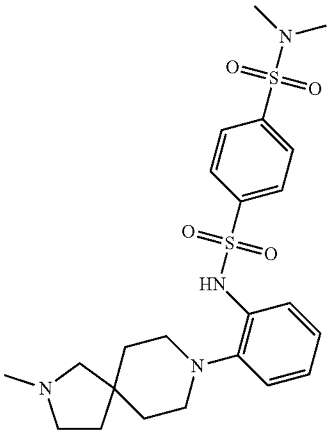 | A-293 |
| 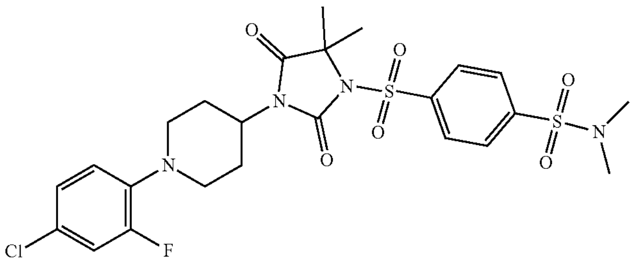 [SMILES: CN(C)S(=O)(=O)c1ccc(S(=O)(=O)N2C(=O)N(C3CCN(c4ccc(Cl)cc4F)CC3)C(=O)C2(C)C)cc1] | A-294 |

TABLE A-continued
| Structure | Compound No. |
|---|---|
| 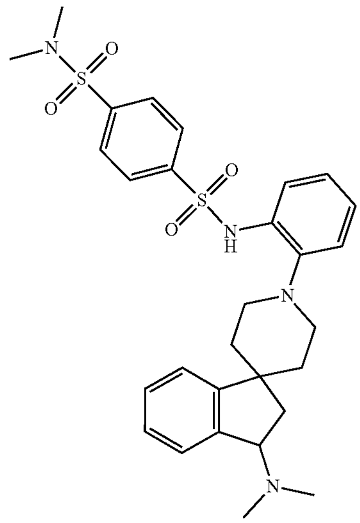 [SMILES: CN(C)C1CC2(CCN(c3ccccc3NS(=O)(=O)c3ccc(S(=O)(=O)N(C)C)cc3)CC2)c2ccccc21] | A-295 |
| 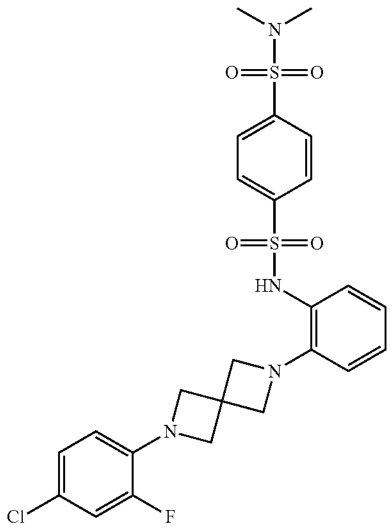 [SMILES: CN(C)S(=O)(=O)c1ccc(S(=O)(=O)Nc2ccccc2N2CC3(CN(c4ccc(Cl)cc4F)C3)C2)cc1] | A-296 |
| 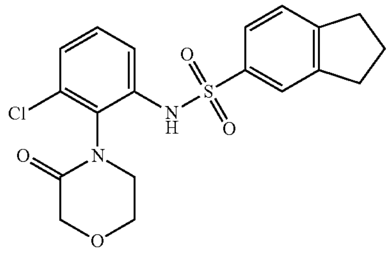 [SMILES: O=C1COCCN1c1c(Cl)cccc1NS(=O)(=O)c1ccc2c(c1)CCC2] | A-297 |

TABLE A-continued
| Structure | Compound No. |
|---|---|
| 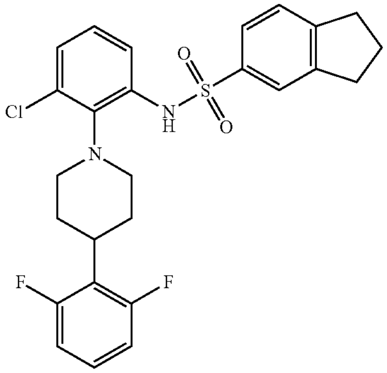 [SMILES: O=S(=O)(Nc1cccc(Cl)c1N1CCC(c2c(F)cccc2F)CC1)c1ccc2c(c1)CCC2] | A-298 |
| 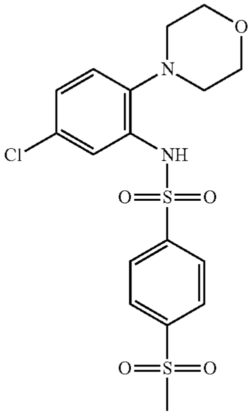 [SMILES: CS(=O)(=O)c1ccc(S(=O)(=O)Nc2cc(Cl)ccc2N2CCOCC2)cc1] | A-299 |
| 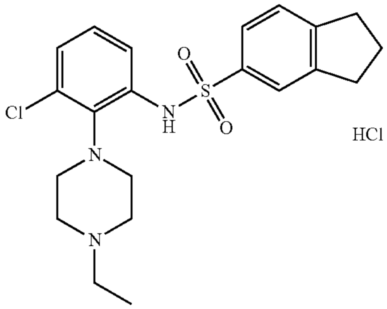 [SMILES: CCN1CCN(c2c(Cl)cccc2NS(=O)(=O)c2ccc3c(c2)CCC3)CC1 ; Cl] HCl | A-300 |
| 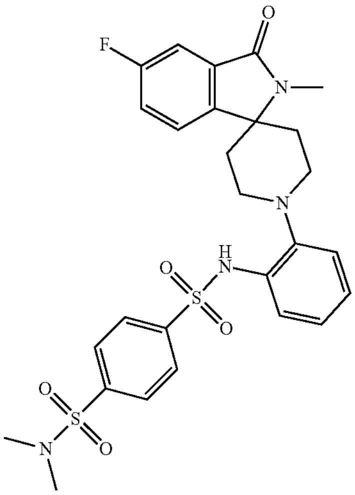 [SMILES: CN1C(=O)c2cc(F)ccc2C12CCN(c1ccccc1NS(=O)(=O)c1ccc(S(=O)(=O)N(C)C)cc1)CC2] | A-301 |

TABLE A-continued
| Structure | Compound No. |
| --- | --- |
| 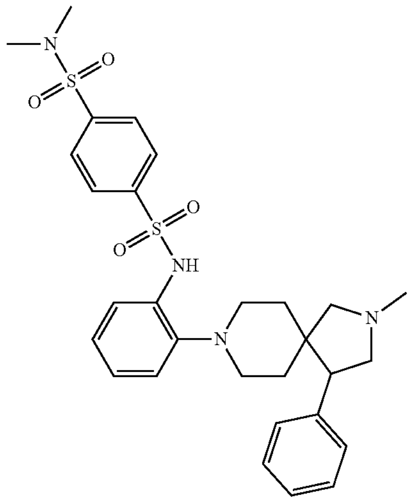 | A-302 |
| 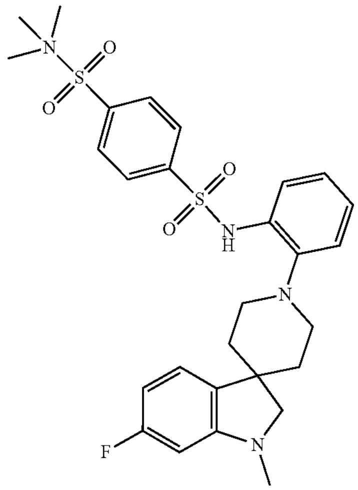 | A-303 |
| 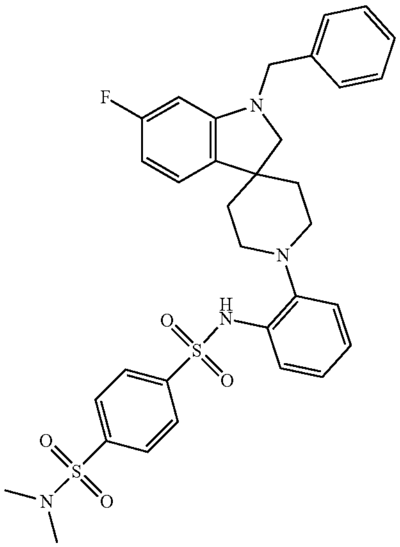 [SMILES: CN(C)S(=O)(=O)c1ccc(S(=O)(=O)Nc2ccccc2N2CCC3(CC2)CN(Cc2ccccc2)c2cc(F)ccc23)cc1] | A-304 |

TABLE A-continued
| Structure | Compound No. |
|---|---|
| 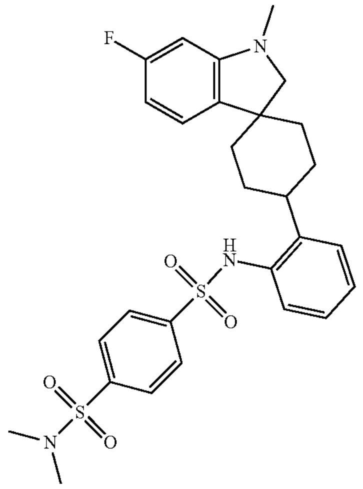 [SMILES: CN1CC2(CCC(c3ccccc3NS(=O)(=O)c3ccc(S(=O)(=O)N(C)C)cc3)CC2)c2ccc(F)cc21] | A-305 |
| 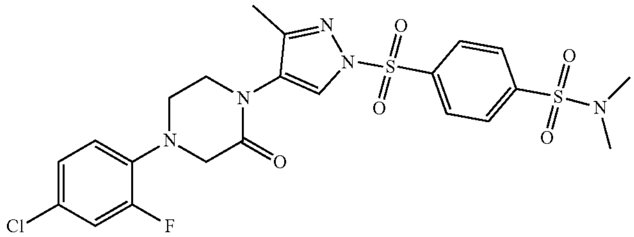 [SMILES: Cc1nn(S(=O)(=O)c2ccc(S(=O)(=O)N(C)C)cc2)cc1N1CCN(c2ccc(Cl)cc2F)CC1=O] | A-306 |
| 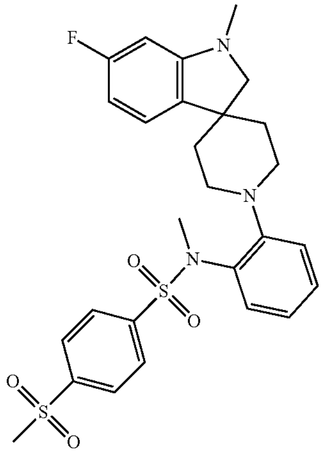 [SMILES: CN1CC2(CCN(c3ccccc3N(C)S(=O)(=O)c3ccc(S(C)(=O)=O)cc3)CC2)c2ccc(F)cc21] | A-307 |

TABLE A-continued
| Structure | Compound No. |
| --- | --- |
| 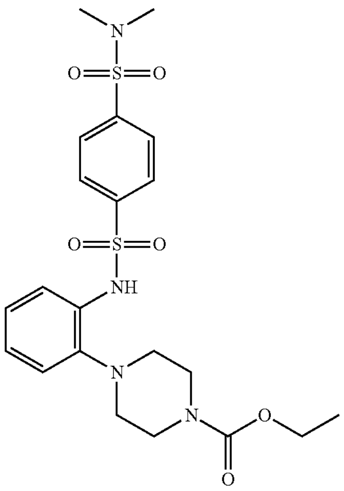 [SMILES: CCOC(=O)N1CCN(c2ccccc2NS(=O)(=O)c2ccc(S(=O)(=O)N(C)C)cc2)CC1] | A-308 |
| 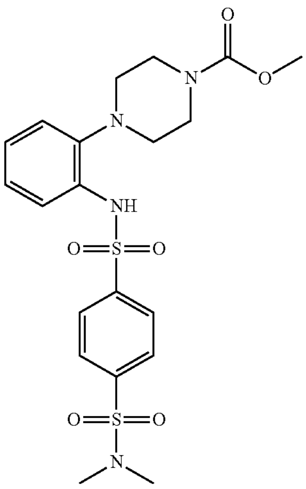 [SMILES: COC(=O)N1CCN(c2ccccc2NS(=O)(=O)c2ccc(S(=O)(=O)N(C)C)cc2)CC1] | A-309 |
| 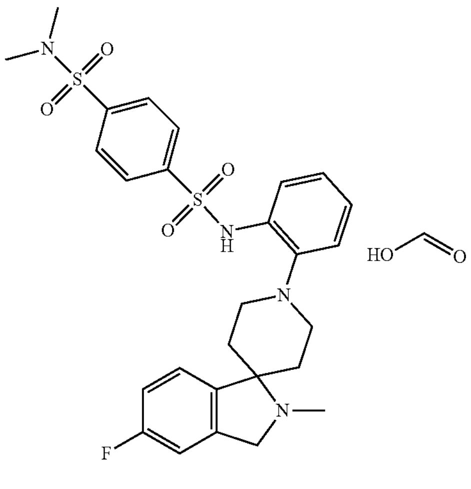 | A-310 |

TABLE A-continued
| Structure | Compound No. |
|---|---|
| 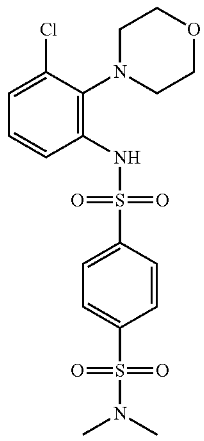 [SMILES: CN(C)S(=O)(=O)c1ccc(S(=O)(=O)Nc2cccc(Cl)c2N2CCOCC2)cc1] | A-311 |
| 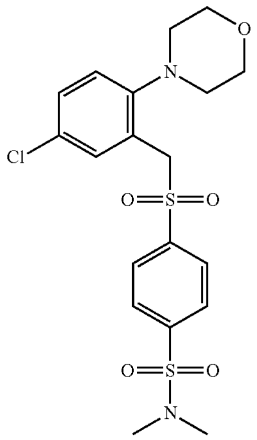 [SMILES: CN(C)S(=O)(=O)c1ccc(S(=O)(=O)Cc2cc(Cl)ccc2N2CCOCC2)cc1] | A-312 |
| 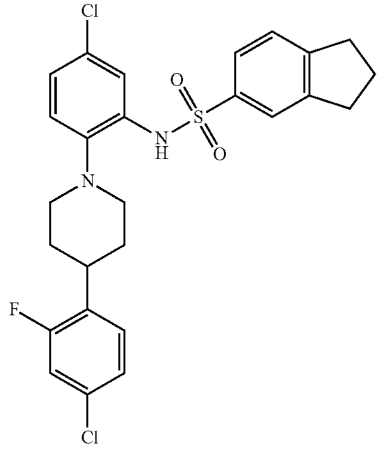 [SMILES: O=S(=O)(Nc1cc(Cl)ccc1N1CCC(c2ccc(Cl)cc2F)CC1)c1ccc2c(c1)CCC2] | A-313 |

TABLE A-continued
| Structure | Compound No. |
| --- | --- |
| 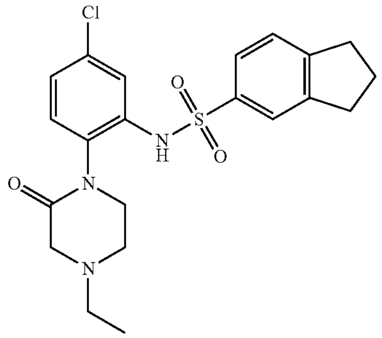 [SMILES: CCN1CCN(c2ccc(Cl)cc2NS(=O)(=O)c2ccc3c(c2)CCC3)C(=O)C1] | A-314 |
| 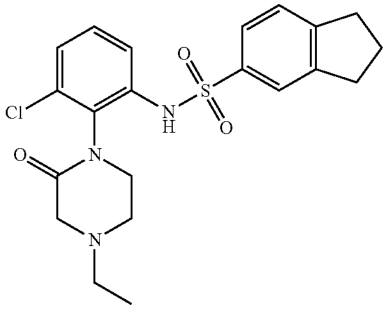 [SMILES: CCN1CCN(c2c(Cl)cccc2NS(=O)(=O)c2ccc3c(c2)CCC3)C(=O)C1] | A-315 |
| 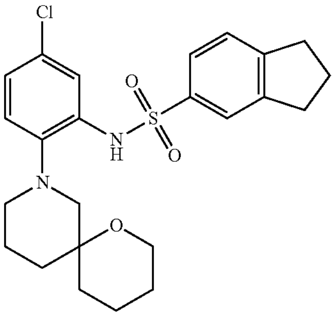 [SMILES: O=S(=O)(Nc1cc(Cl)ccc1N1CCCC2(CCCCO2)C1)c1ccc2c(c1)CCC2] | A-316 |
| 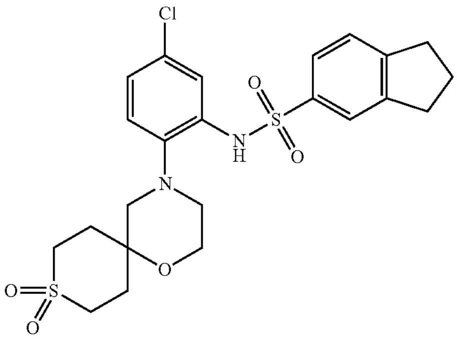 [SMILES: O=S1(=O)CCC2(CC1)CN(c1ccc(Cl)cc1NS(=O)(=O)c1ccc3c(c1)CCC3)CCO2] | A-317 |

TABLE A-continued
| Structure | Compound No. |
| --- | --- |
| 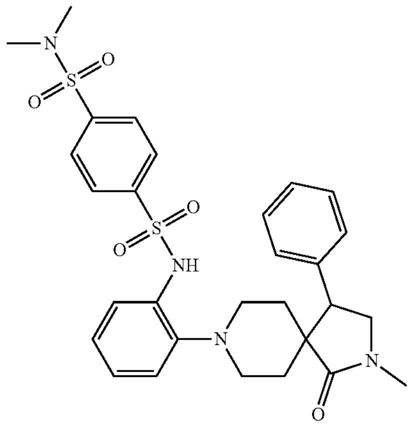 | A-318 |
| 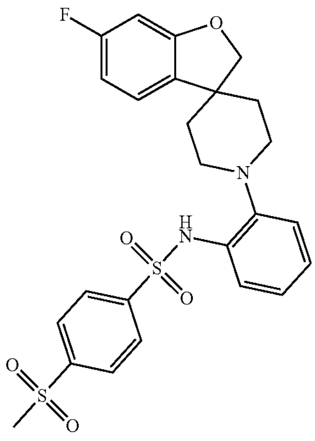 [SMILES: CS(=O)(=O)c1ccc(S(=O)(=O)Nc2ccccc2N2CCC3(CC2)COc2cc(F)ccc23)cc1] | A-319 |
| 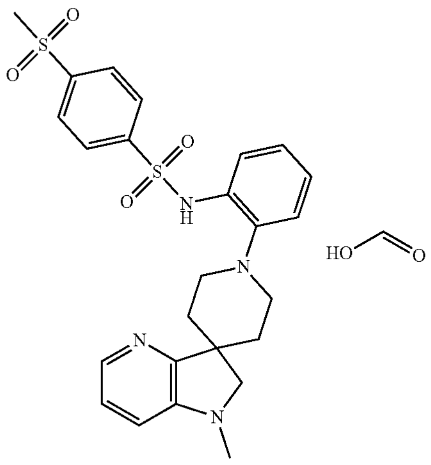 [SMILES: CN1CC2(CCN(c3ccccc3NS(=O)(=O)c3ccc(S(C)(=O)=O)cc3)CC2)c2ncccc21 ; O=CO] | A-320 |

TABLE A-continued
| Structure | Compound No. |
| --- | --- |
| 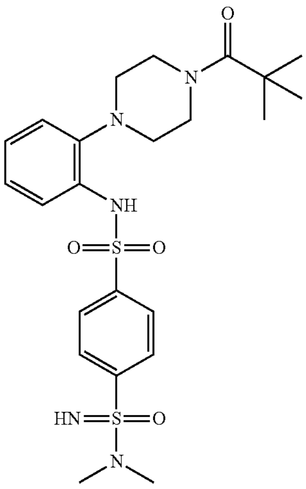 [SMILES: CN(C)S(=N)(=O)c1ccc(S(=O)(=O)Nc2ccccc2N2CCN(C(=O)C(C)(C)C)CC2)cc1] | A-321 |
| 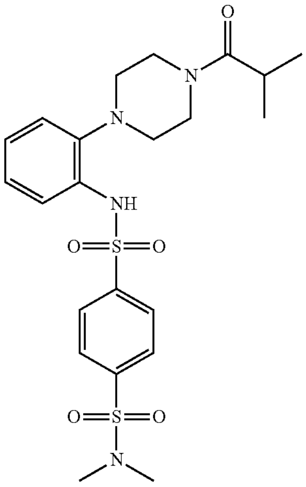 [SMILES: CC(C)C(=O)N1CCN(c2ccccc2NS(=O)(=O)c2ccc(S(=O)(=O)N(C)C)cc2)CC1] | A-322 |
| 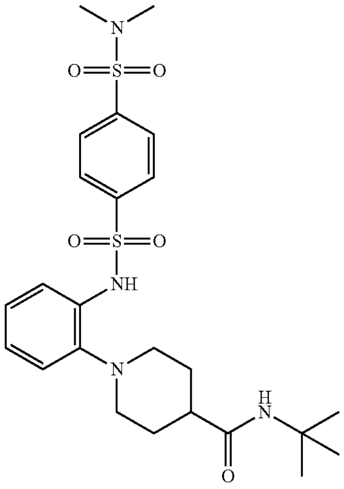 [SMILES: CN(C)S(=O)(=O)c1ccc(S(=O)(=O)Nc2ccccc2N2CCC(C(=O)NC(C)(C)C)CC2)cc1] | A-323 |

TABLE A-continued
| Structure | Compound No. |
|---|---|
| 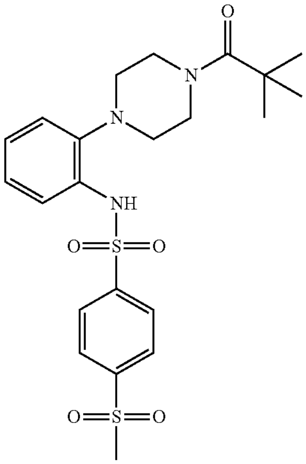 [SMILES: CC(C)(C)C(=O)N1CCN(c2ccccc2NS(=O)(=O)c2ccc(S(C)(=O)=O)cc2)CC1] | A-324 |
| 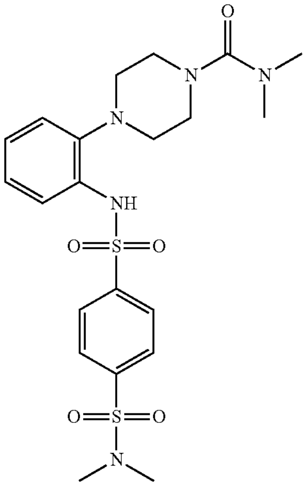 | A-325 |
| 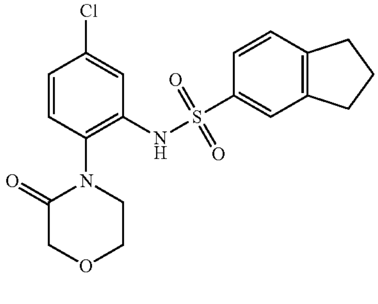 [SMILES: O=C1COCCN1c1ccc(Cl)cc1NS(=O)(=O)c1ccc2c(c1)CCC2] | A-326 |

TABLE A-continued
| Structure | Compound No. |
| --- | --- |
| 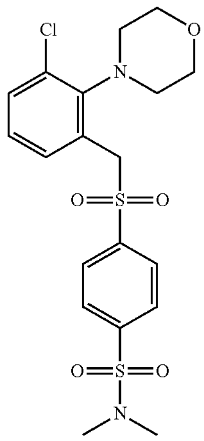 [SMILES: CN(C)S(=O)(=O)c1ccc(S(=O)(=O)Cc2cccc(Cl)c2N2CCOCC2)cc1] | A-327 |
| 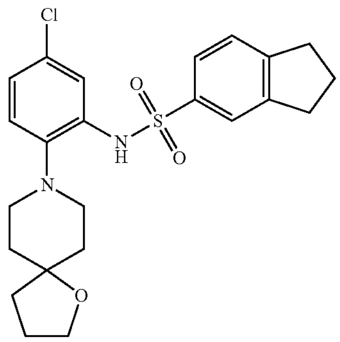 [SMILES: O=S(=O)(Nc1cc(Cl)ccc1N1CCC2(CCCO2)CC1)c1ccc2c(c1)CCC2] | A-328 |
| 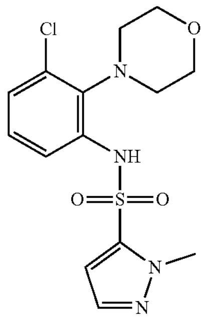 [SMILES: Cn1nccc1S(=O)(=O)Nc1cccc(Cl)c1N1CCOCC1] | A-329 |
| 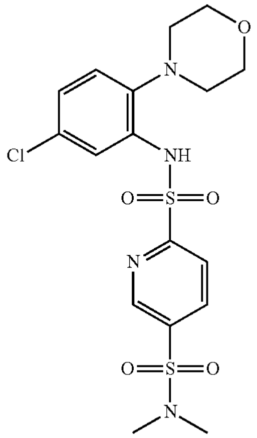 [SMILES: CN(C)S(=O)(=O)c1ccc(S(=O)(=O)Nc2cc(Cl)ccc2N2CCOCC2)nc1] | A-330 |

TABLE A-continued
| Structure | Compound No. |
|---|---|
| 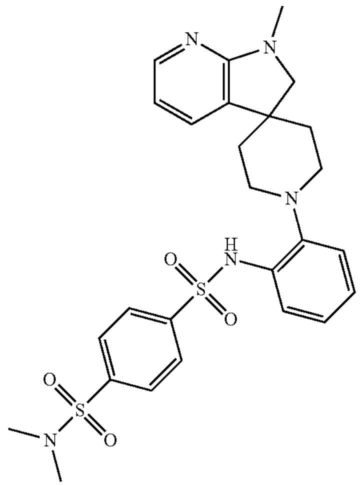 [SMILES: CN1CC2(CCN(c3ccccc3NS(=O)(=O)c3ccc(S(=O)(=O)N(C)C)cc3)CC2)c2cccnc21] | A-331 |
| 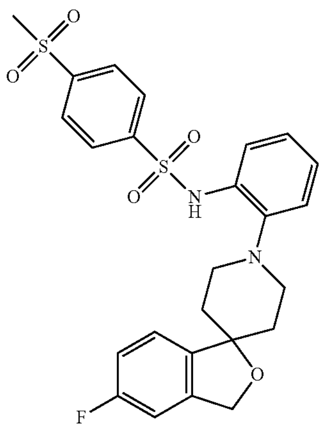 [SMILES: CS(=O)(=O)c1ccc(S(=O)(=O)Nc2ccccc2N2CCC3(CC2)OCc2cc(F)ccc23)cc1] | A-332 |
| 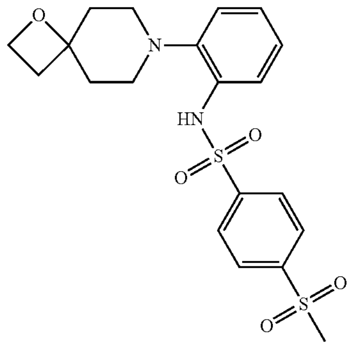 [SMILES: CS(=O)(=O)c1ccc(S(=O)(=O)Nc2ccccc2N2CCC3(CCO3)CC2)cc1] | A-333 |

TABLE A-continued
| Structure | Compound No. |
|---|---|
| 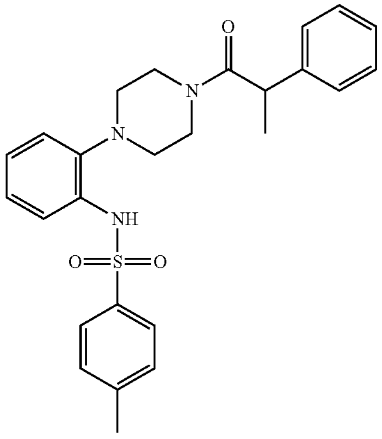 [SMILES: Cc1ccc(S(=O)(=O)Nc2ccccc2N2CCN(C(=O)C(C)c3ccccc3)CC2)cc1] | A-334 |
| 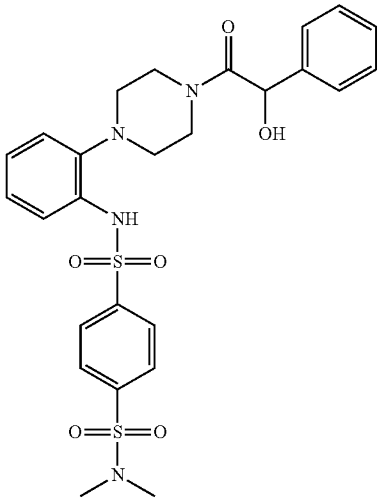 [SMILES: CN(C)S(=O)(=O)c1ccc(S(=O)(=O)Nc2ccccc2N2CCN(C(=O)C(O)c3ccccc3)CC2)cc1] | A-335 |
| 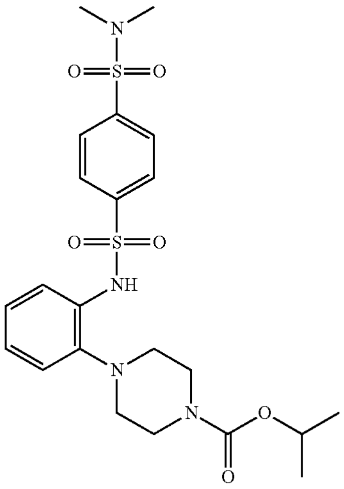 [SMILES: CC(C)OC(=O)N1CCN(c2ccccc2NS(=O)(=O)c2ccc(S(=O)(=O)N(C)C)cc2)CC1] | A-336 |

TABLE A-continued
| Structure | Compound No. |
|---|---|
| 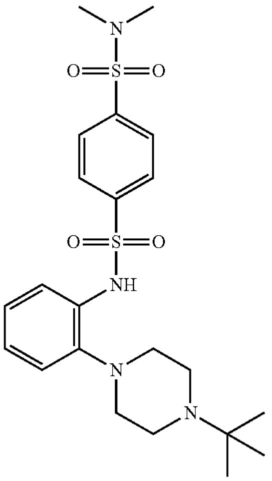 [SMILES: CN(C)S(=O)(=O)c1ccc(S(=O)(=O)Nc2ccccc2N2CCN(C(C)(C)C)CC2)cc1] | A-337 |
| 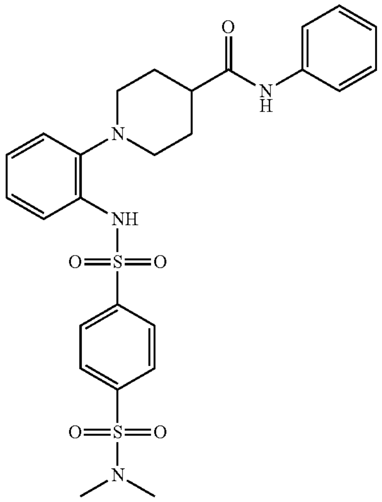 [SMILES: CN(C)S(=O)(=O)c1ccc(S(=O)(=O)Nc2ccccc2N2CCC(C(=O)Nc3ccccc3)CC2)cc1] | A-338 |
| 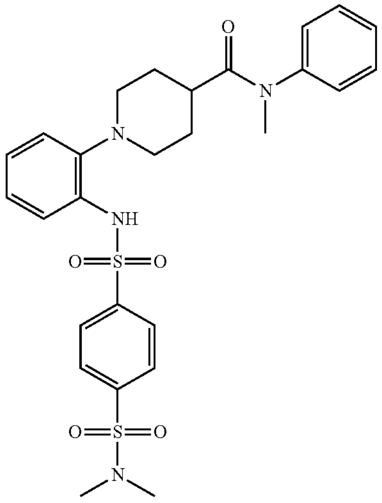 [SMILES: CN(C(=O)C1CCN(c2ccccc2NS(=O)(=O)c2ccc(S(=O)(=O)N(C)C)cc2)CC1)c1ccccc1] | A-339 |

TABLE A-continued
| Structure | Compound No. |
| --- | --- |
| 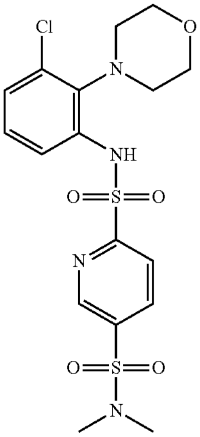 [SMILES: CN(C)S(=O)(=O)c1ccc(S(=O)(=O)Nc2cccc(Cl)c2N2CCOCC2)nc1] | A-340 |
| 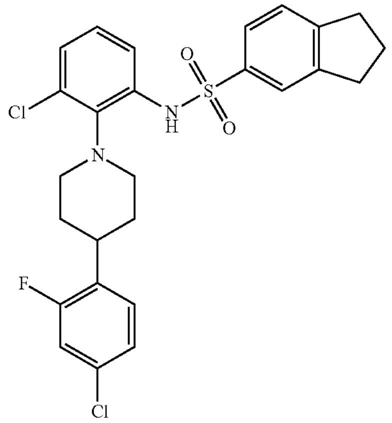 [SMILES: O=S(=O)(Nc1cccc(Cl)c1N1CCC(c2ccc(Cl)cc2F)CC1)c1ccc2c(c1)CCC2] | A-341 |
| 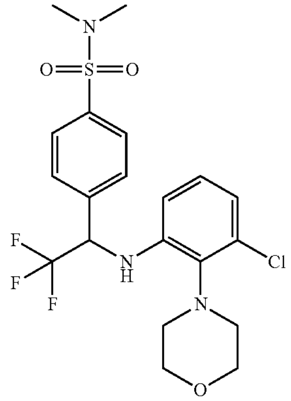 [SMILES: CN(C)S(=O)(=O)c1ccc(C(Nc2cccc(Cl)c2N2CCOCC2)C(F)(F)F)cc1] | A-342 |
| 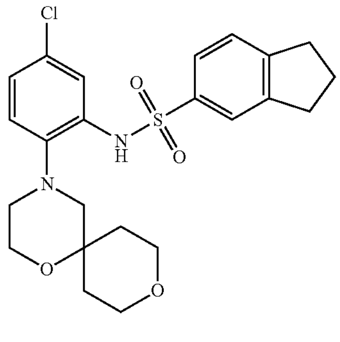 | A-343 |

TABLE A-continued
| Structure | Compound No. |
|---|---|
| 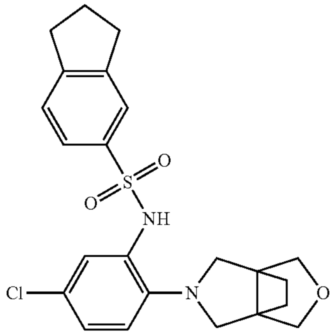 [SMILES: O=S(=O)(Nc1cc(Cl)ccc1N1CC23CCC2(COC3)C1)c1ccc2c(c1)CCC2] | A-344 |
| 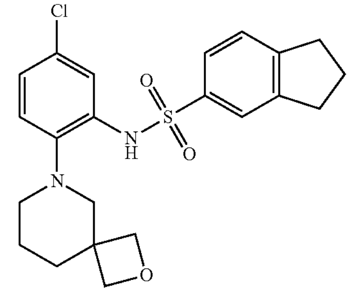 [SMILES: O=S(=O)(Nc1cc(Cl)ccc1N1CCCC2(COC2)C1)c1ccc2c(c1)CCC2] | A-345 |
| 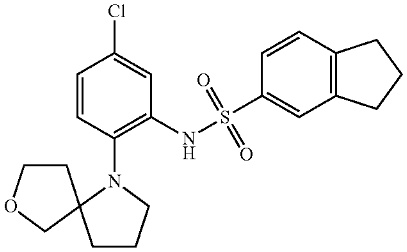 [SMILES: O=S(=O)(Nc1cc(Cl)ccc1N1CCCC12CCOC2)c1ccc2c(c1)CCC2] | A-346 |
| 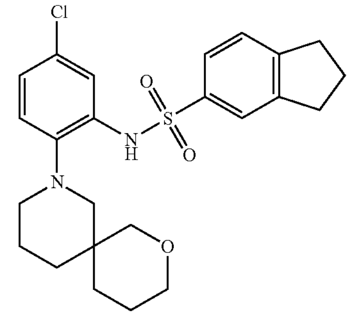 | A-347 |

TABLE A-continued
| Structure | Compound No. |
|---|---|
| 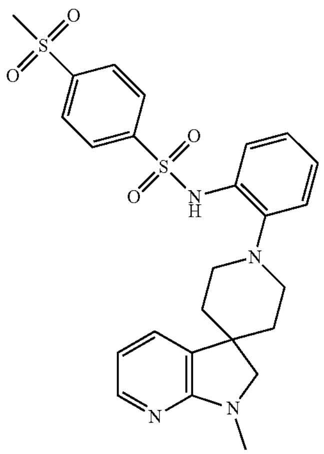 [SMILES: CN1CC2(CCN(c3ccccc3NS(=O)(=O)c3ccc(S(C)(=O)=O)cc3)CC2)c2cccnc21] | A-348 |
| 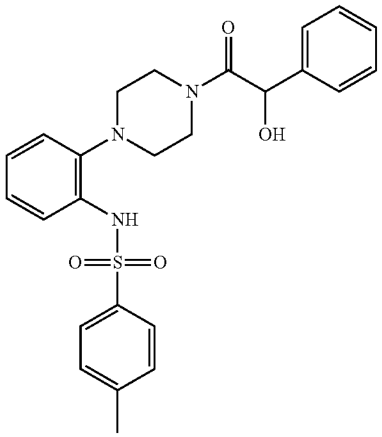 [SMILES: Cc1ccc(S(=O)(=O)Nc2ccccc2N2CCN(C(=O)C(O)c3ccccc3)CC2)cc1] | A-349 |
| 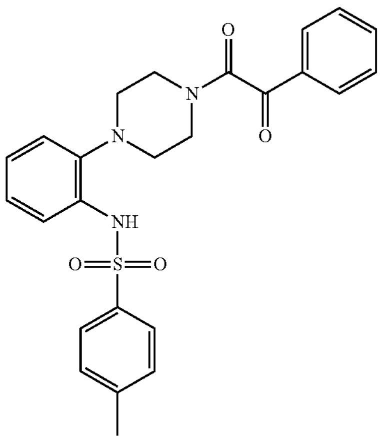 [SMILES: Cc1ccc(S(=O)(=O)Nc2ccccc2N2CCN(C(=O)C(=O)c3ccccc3)CC2)cc1] | A-350 |

TABLE A-continued
| Structure | Compound No. |
|---|---|
| 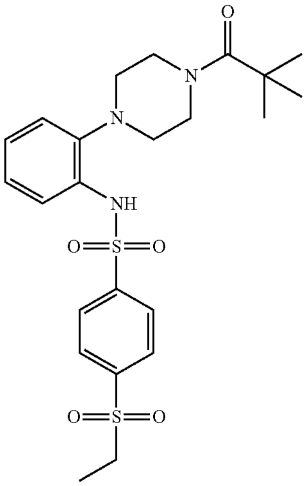 [SMILES: CCS(=O)(=O)c1ccc(S(=O)(=O)Nc2ccccc2N2CCN(C(=O)C(C)(C)C)CC2)cc1] | A-351 |
| 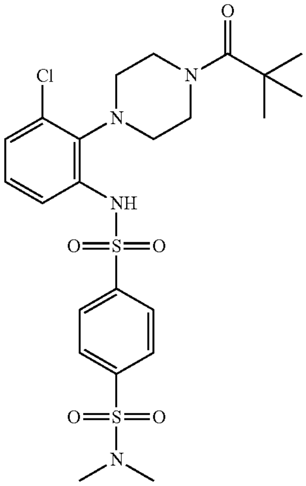 [SMILES: CN(C)S(=O)(=O)c1ccc(S(=O)(=O)Nc2cccc(Cl)c2N2CCN(C(=O)C(C)(C)C)CC2)cc1] | A-352 |
| 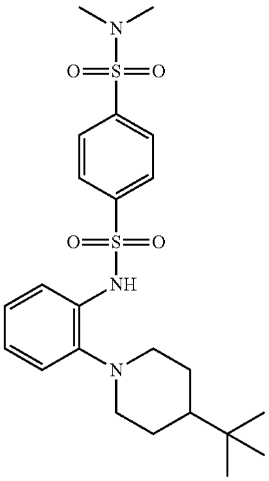 [SMILES: CN(C)S(=O)(=O)c1ccc(S(=O)(=O)Nc2ccccc2N2CCC(C(C)(C)C)CC2)cc1] | A-353 |

TABLE A-continued
| Structure | Compound No. |
| --- | --- |
| 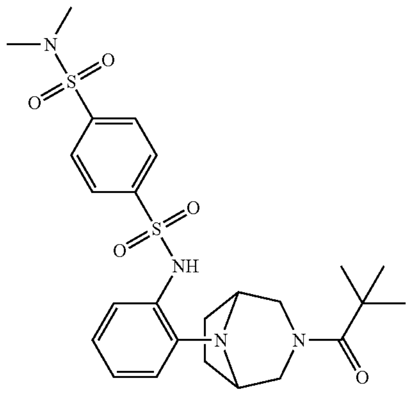 [SMILES: CN(C)S(=O)(=O)c1ccc(S(=O)(=O)Nc2ccccc2N2C3CCC2CN(C(=O)C(C)(C)C)C3)cc1] | A-354 |
| 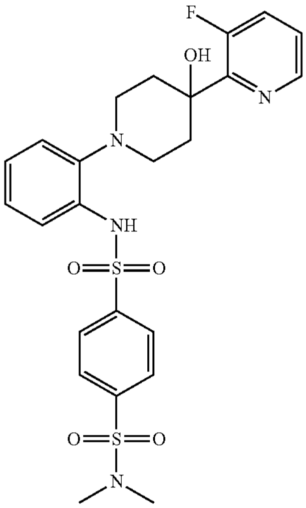 [SMILES: CN(C)S(=O)(=O)c1ccc(S(=O)(=O)Nc2ccccc2N2CCC(O)(c3ncccc3F)CC2)cc1] | A-355 |
| 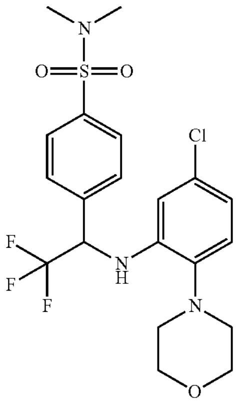 [SMILES: CN(C)S(=O)(=O)c1ccc(C(Nc2cc(Cl)ccc2N2CCOCC2)C(F)(F)F)cc1] | A-356 |

TABLE A-continued
| Structure | Compound No. |
|---|---|
| 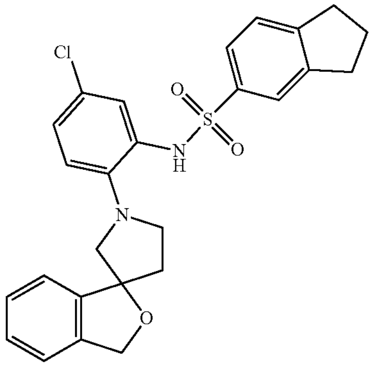 [SMILES: O=S(=O)(Nc1cc(Cl)ccc1N1CCC2(C1)OCc1ccccc12)c1ccc2c(c1)CCC2] | A-357 |
| 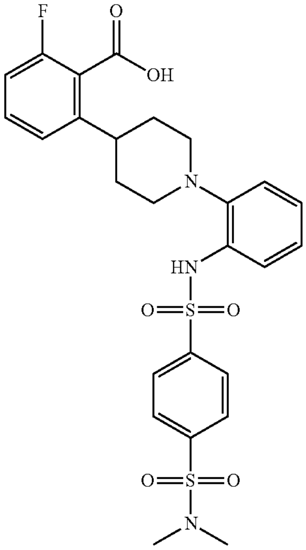 [SMILES: CN(C)S(=O)(=O)c1ccc(S(=O)(=O)Nc2ccccc2N2CCC(c3cccc(F)c3C(=O)O)CC2)cc1] | A-358 |
| 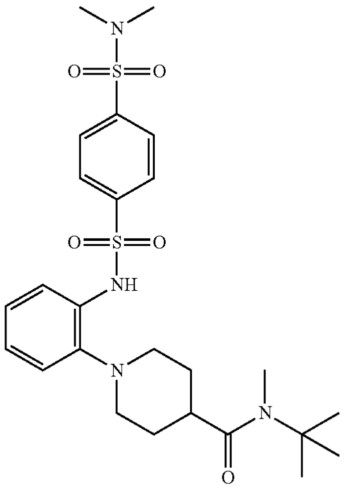 [SMILES: CN(C(=O)C1CCN(c2ccccc2NS(=O)(=O)c2ccc(S(=O)(=O)N(C)C)cc2)CC1)C(C)(C)C] | A-359 |

TABLE A-continued
| Structure | Compound No. |
|---|---|
| 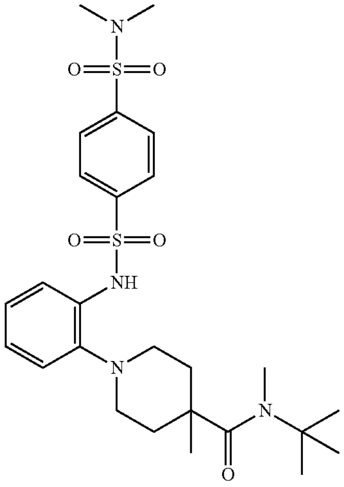 [SMILES: CN(C(=O)C1(C)CCN(c2ccccc2NS(=O)(=O)c2ccc(S(=O)(=O)N(C)C)cc2)CC1)C(C)(C)C] | A-360 |
| 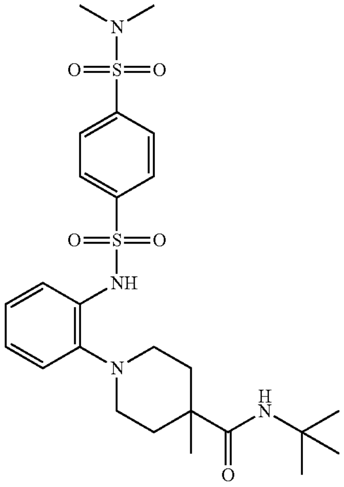 [SMILES: CN(C)S(=O)(=O)c1ccc(S(=O)(=O)Nc2ccccc2N2CCC(C)(C(=O)NC(C)(C)C)CC2)cc1] | A-361 |
| 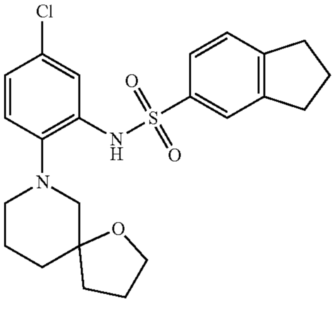 [SMILES: O=S(=O)(Nc1cc(Cl)ccc1N1CCCC2(CCCO2)C1)c1ccc2c(c1)CCC2] | A-362 |
| 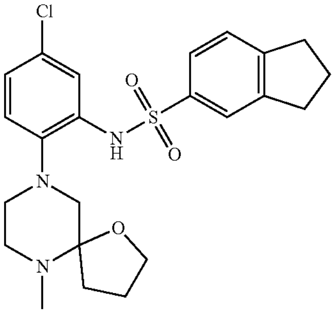 [SMILES: CN1CCN(c2ccc(Cl)cc2NS(=O)(=O)c2ccc3c(c2)CCC3)CC12CCCO2] | A-363 |

TABLE A-continued
| Structure | Compound No. |
|---|---|
| 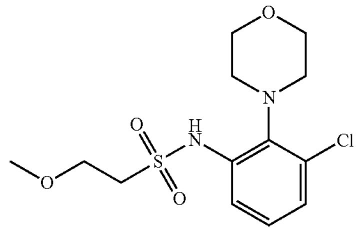 [SMILES: COCCS(=O)(=O)Nc1cccc(Cl)c1N1CCOCC1] | A-364 |
| 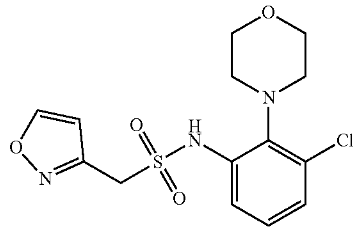 [SMILES: O=S(=O)(Cc1ccon1)Nc1cccc(Cl)c1N1CCOCC1] | A-365 |
| 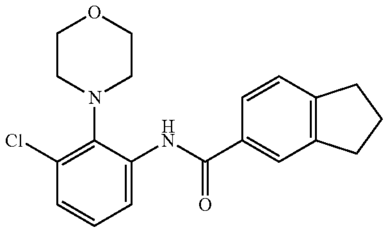 [SMILES: O=C(Nc1cccc(Cl)c1N1CCOCC1)c1ccc2c(c1)CCC2] | A-366 |
| 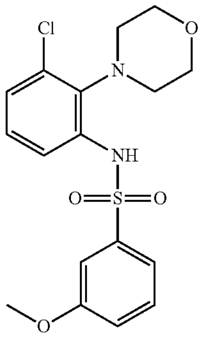 [SMILES: COc1cccc(S(=O)(=O)Nc2cccc(Cl)c2N2CCOCC2)c1] | A-367 |
| 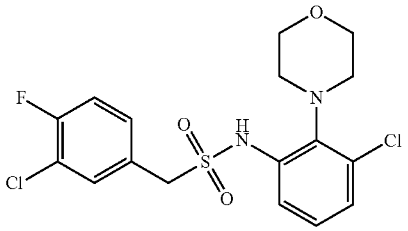 [SMILES: O=S(=O)(Cc1ccc(F)c(Cl)c1)Nc1cccc(Cl)c1N1CCOCC1] | A-368 |

TABLE A-continued
| Structure | Compound No. |
|---|---|
| 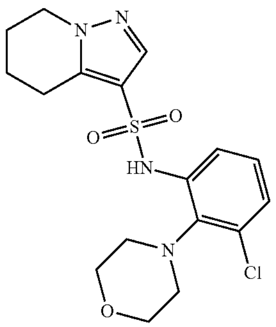 [SMILES: O=S(=O)(Nc1cccc(Cl)c1N1CCOCC1)c1cnn2c1CCCC2] | A-369 |
| 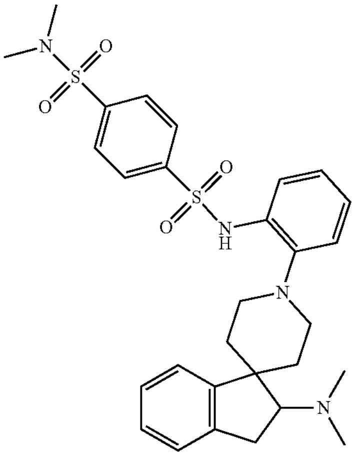 [SMILES: CN(C)C1Cc2ccccc2C12CCN(c1ccccc1NS(=O)(=O)c1ccc(S(=O)(=O)N(C)C)cc1)CC2] | A-370 |
| 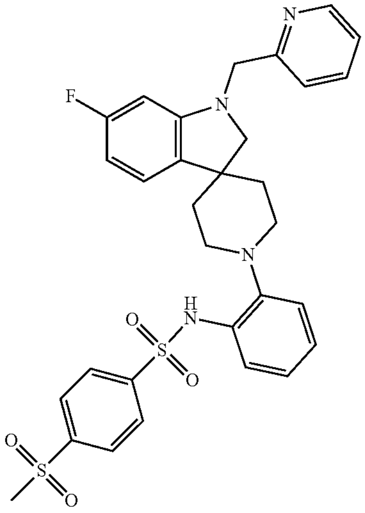 [SMILES: CS(=O)(=O)c1ccc(S(=O)(=O)Nc2ccccc2N2CCC3(CC2)CN(Cc2ccccn2)c2cc(F)ccc23)cc1] | A-371 |
| 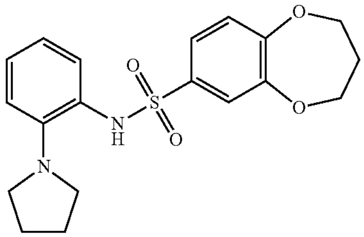 [SMILES: O=S(=O)(Nc1ccccc1N1CCCC1)c1ccc2c(c1)OCCCO2] | A-372 |

TABLE A-continued
| Structure | Compound No. |
| --- | --- |
| 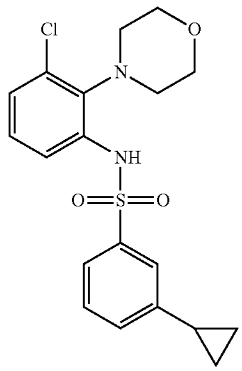 [SMILES: O=S(=O)(Nc1cccc(Cl)c1N1CCOCC1)c1cccc(C2CC2)c1] | A-390 |
| 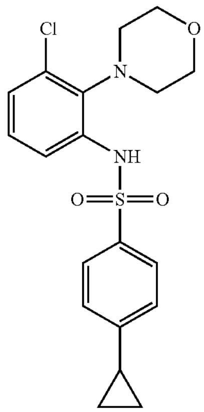 [SMILES: O=S(=O)(Nc1cccc(Cl)c1N1CCOCC1)c1ccc(C2CC2)cc1] | A-391 |
| 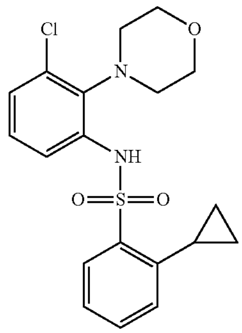 [SMILES: O=S(=O)(Nc1cccc(Cl)c1N1CCOCC1)c1ccccc1C1CC1] | A-392 |
| 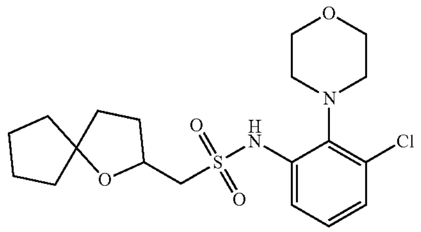 [SMILES: O=S(=O)(CC1CCC2(CCCC2)O1)Nc1cccc(Cl)c1N1CCOCC1] | A-393 |
| 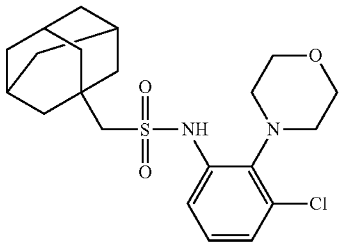 [SMILES: O=S(=O)(CC12CC3CC(CC(C3)C1)C2)Nc1cccc(Cl)c1N1CCOCC1] | A-394 |

TABLE A-continued
| Structure | Compound No. |
| --- | --- |
| 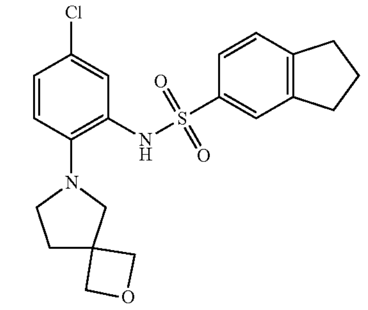 [SMILES: O=S(=O)(Nc1cc(Cl)ccc1N1CCC2(COC2)C1)c1ccc2c(c1)CCC2] | A-395 |
| 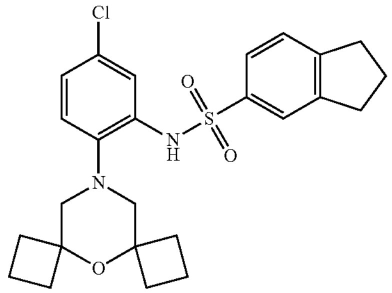 [SMILES: O=S(=O)(Nc1cc(Cl)ccc1N1CC2(CCC2)OC2(CCC2)C1)c1ccc2c(c1)CCC2] | A-396 |
| 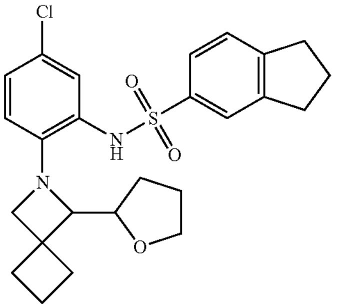 [SMILES: O=S(=O)(Nc1cc(Cl)ccc1N1CC2(CCC2)C1C1CCCO1)c1ccc2c(c1)CCC2] | A-397 |
| 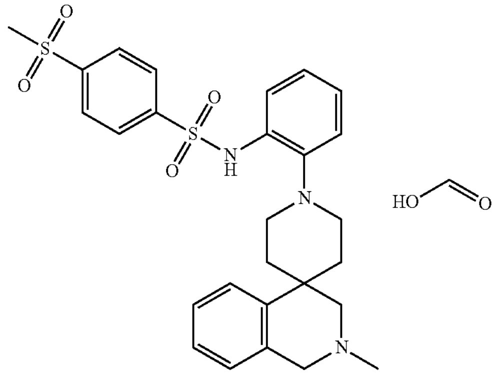 | A-398 |

TABLE A-continued
| Structure | Compound No. |
|---|---|
| 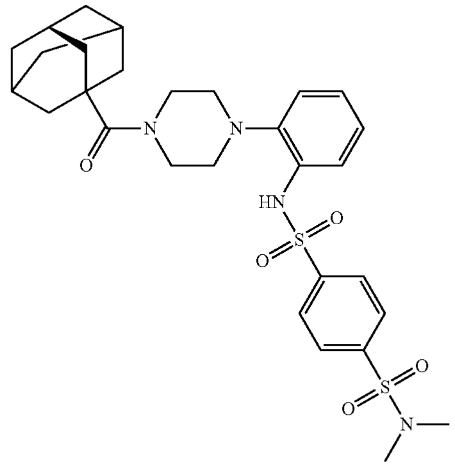 | A-399 |
| 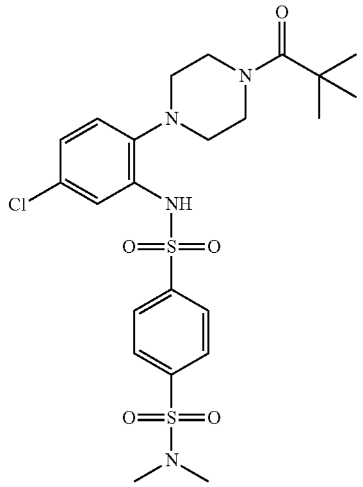 [SMILES: CN(C)S(=O)(=O)c1ccc(S(=O)(=O)Nc2cc(Cl)ccc2N2CCN(C(=O)C(C)(C)C)CC2)cc1] | A-400 |
| 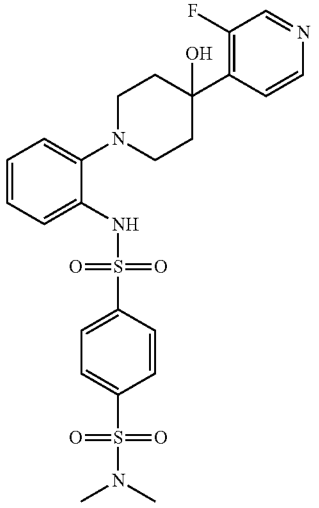 [SMILES: CN(C)S(=O)(=O)c1ccc(S(=O)(=O)Nc2ccccc2N2CCC(O)(c3ccncc3F)CC2)cc1] | A-401 |

TABLE A-continued
| Structure | Compound No. |
|---|---|
| 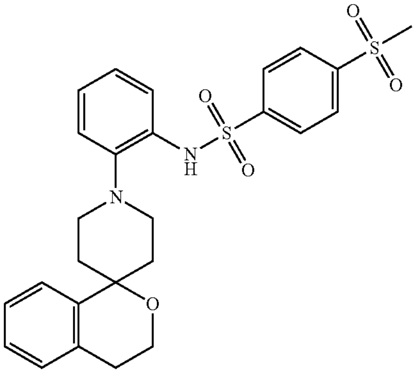 [SMILES: CS(=O)(=O)c1ccc(S(=O)(=O)Nc2ccccc2N2CCC3(CC2)OCCc2ccccc23)cc1] | A-402 |
| 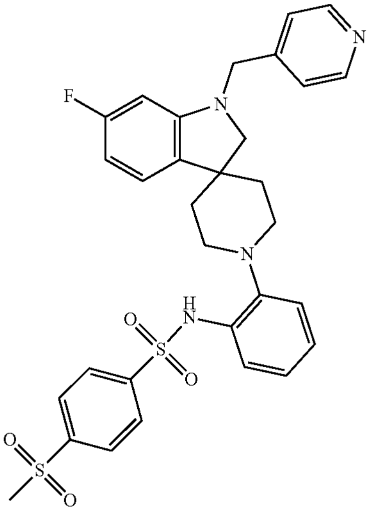 [SMILES: CS(=O)(=O)c1ccc(S(=O)(=O)Nc2ccccc2N2CCC3(CC2)CN(Cc2ccncc2)c2cc(F)ccc23)cc1] | A-403 |
| 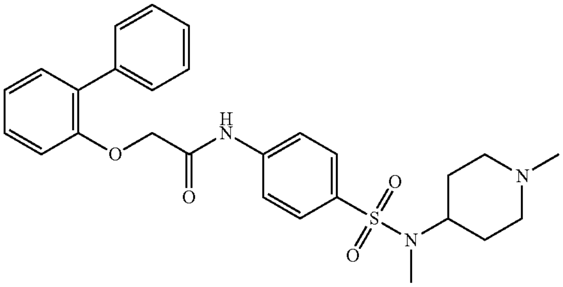 [SMILES: CN1CCC(N(C)S(=O)(=O)c2ccc(NC(=O)COc3ccccc3-c3ccccc3)cc2)CC1] | A-404 |
| 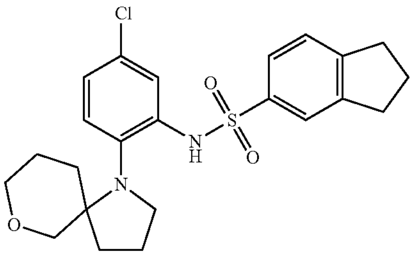 [SMILES: O=S(=O)(Nc1cc(Cl)ccc1N1CCCC12CCCOC2)c1ccc2c(c1)CCC2] | A-405 |

TABLE A-continued
| Structure | Compound No. |
|---|---|
| 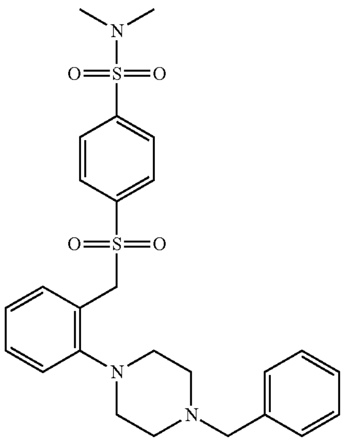 [SMILES: CN(C)S(=O)(=O)c1ccc(S(=O)(=O)Cc2ccccc2N2CCN(Cc3ccccc3)CC2)cc1] | A-406 |
| 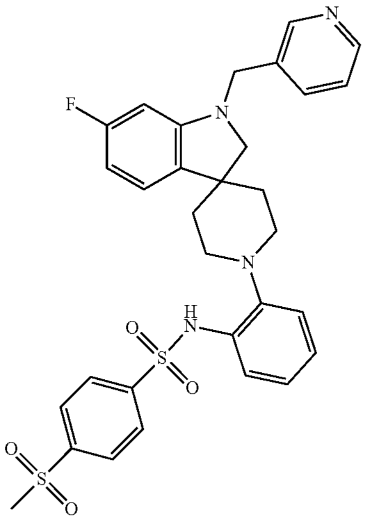 [SMILES: CS(=O)(=O)c1ccc(S(=O)(=O)Nc2ccccc2N2CCC3(CC2)CN(Cc2cccnc2)c2cc(F)ccc23)cc1] | A-407 |
| 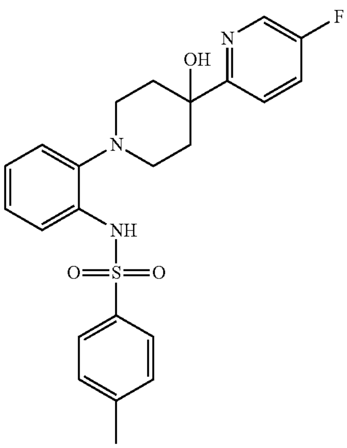 [SMILES: Cc1ccc(S(=O)(=O)Nc2ccccc2N2CCC(O)(c3ccc(F)cn3)CC2)cc1] | A-408 |

TABLE A-continued
| Structure | Compound No. |
| --- | --- |
| 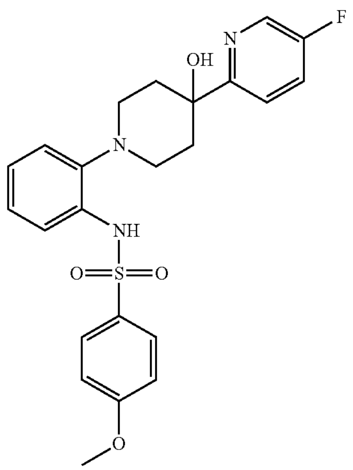 [SMILES: COc1ccc(S(=O)(=O)Nc2ccccc2N2CCC(O)(c3ccc(F)cn3)CC2)cc1] | A-409 |
| 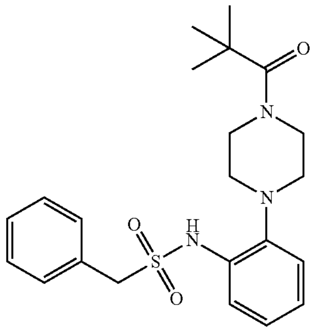 [SMILES: CC(C)(C)C(=O)N1CCN(c2ccccc2NS(=O)(=O)Cc2ccccc2)CC1] | A-410 |
| 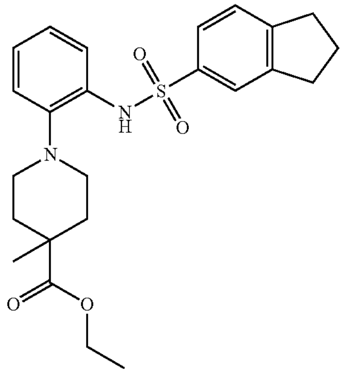 [SMILES: CCOC(=O)C1(C)CCN(c2ccccc2NS(=O)(=O)c2ccc3c(c2)CCC3)CC1] | A-411 |

TABLE A-continued
| Structure | Compound No. |
| --- | --- |
| 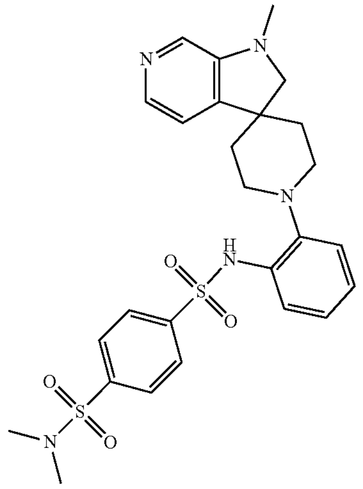 [SMILES: CN1CC2(CCN(c3ccccc3NS(=O)(=O)c3ccc(S(=O)(=O)N(C)C)cc3)CC2)c2ccncc21] | A-412 |
| 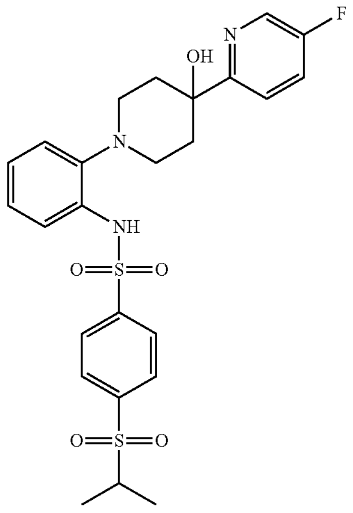 [SMILES: CC(C)S(=O)(=O)c1ccc(S(=O)(=O)Nc2ccccc2N2CCC(O)(c3ccc(F)cn3)CC2)cc1] | A-413 |
| 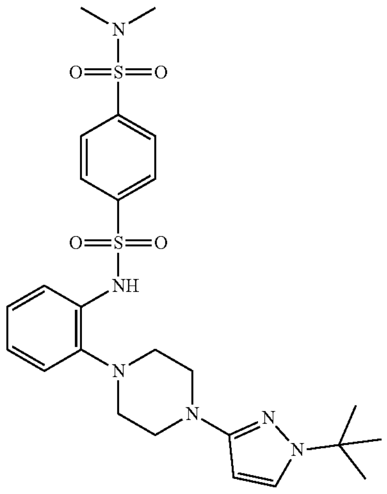 [SMILES: CN(C)S(=O)(=O)c1ccc(S(=O)(=O)Nc2ccccc2N2CCN(c3ccn(C(C)(C)C)n3)CC2)cc1] | A-414 |

TABLE A-continued
| Structure | Compound No. |
| --- | --- |
| 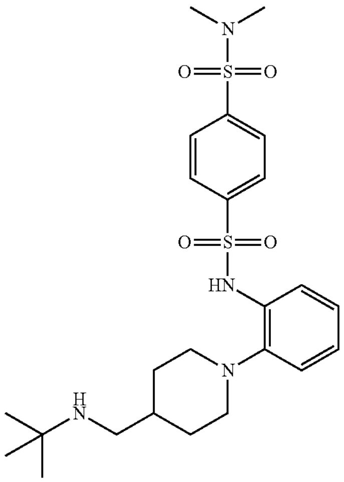 [SMILES: CN(C)S(=O)(=O)c1ccc(S(=O)(=O)Nc2ccccc2N2CCC(CNC(C)(C)C)CC2)cc1] | A-415 |
| 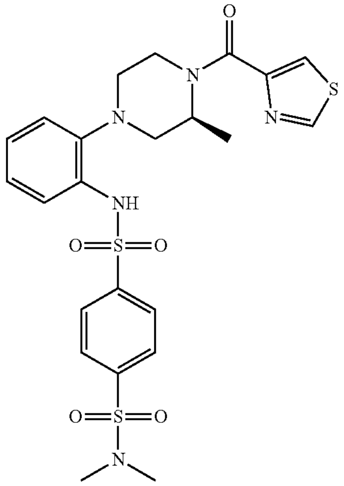 [SMILES: C[C@H]1CN(c2ccccc2NS(=O)(=O)c2ccc(S(=O)(=O)N(C)C)cc2)CCN1C(=O)c1cscn1] | A-416 |
| 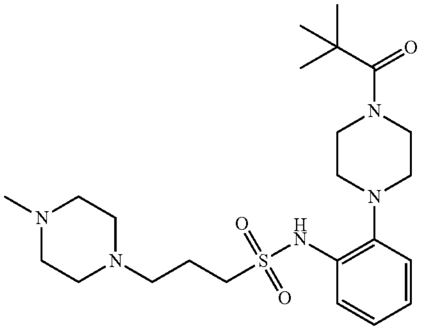 [SMILES: CN1CCN(CCCS(=O)(=O)Nc2ccccc2N2CCN(C(=O)C(C)(C)C)CC2)CC1] | A-417 |

TABLE A-continued
| Structure | Compound No. |
| --- | --- |
| 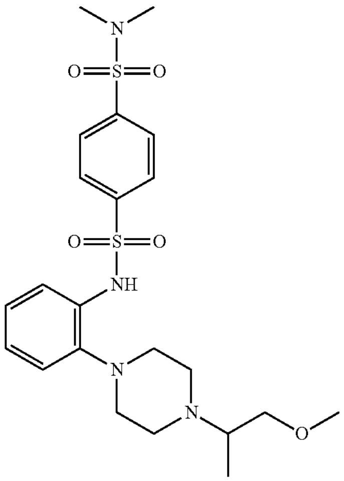 [SMILES: COCC(C)N1CCN(c2ccccc2NS(=O)(=O)c2ccc(S(=O)(=O)N(C)C)cc2)CC1] | A-418 |
| 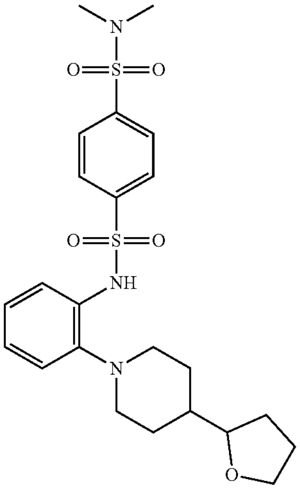 [SMILES: CN(C)S(=O)(=O)c1ccc(S(=O)(=O)Nc2ccccc2N2CCC(C3CCCO3)CC2)cc1] | A-419 |
| 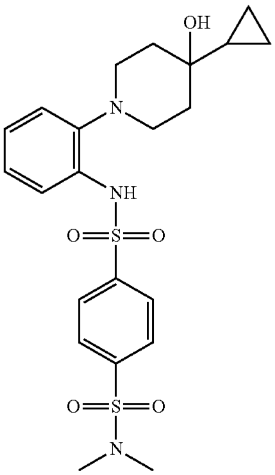 [SMILES: CN(C)S(=O)(=O)c1ccc(S(=O)(=O)Nc2ccccc2N2CCC(O)(C3CC3)CC2)cc1] | A-420 |

TABLE A-continued
| Structure | Compound No. |
| --- | --- |
| 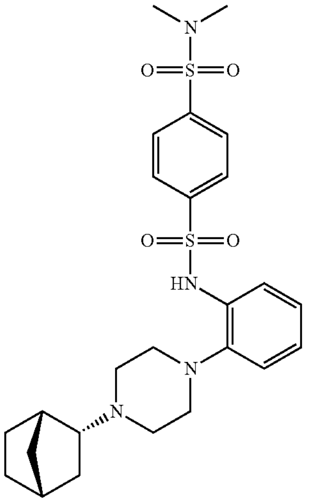 [SMILES: CN(C)S(=O)(=O)c1ccc(S(=O)(=O)Nc2ccccc2N2CCN([C@@H]3C[C@@H]4CC[C@H]3C4)CC2)cc1] | A-421 |
| 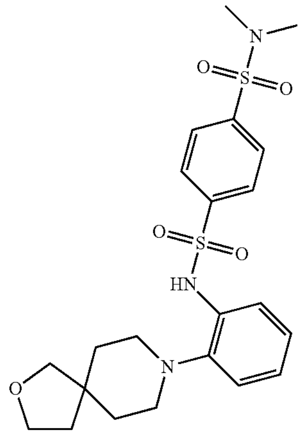 [SMILES: CN(C)S(=O)(=O)c1ccc(S(=O)(=O)Nc2ccccc2N2CCC3(CCOC3)CC2)cc1] | A-422 |
| 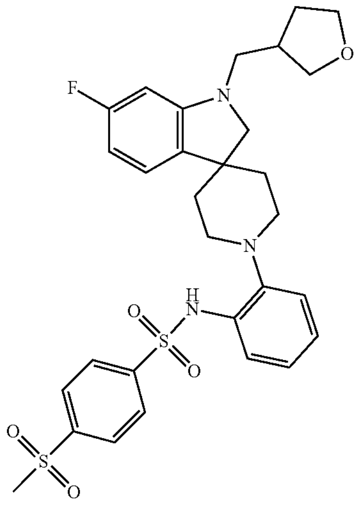 [SMILES: CS(=O)(=O)c1ccc(S(=O)(=O)Nc2ccccc2N2CCC3(CC2)CN(CC2CCOC2)c2cc(F)ccc23)cc1] | A-423 |

TABLE A-continued
| Structure | Compound No. |
| --- | --- |
| 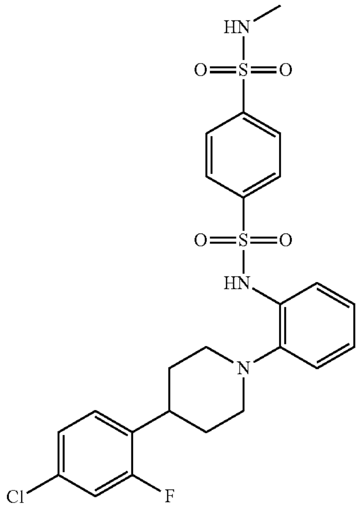 [SMILES: CNS(=O)(=O)c1ccc(S(=O)(=O)Nc2ccccc2N2CCC(c3ccc(Cl)cc3F)CC2)cc1] | A-424 |
| 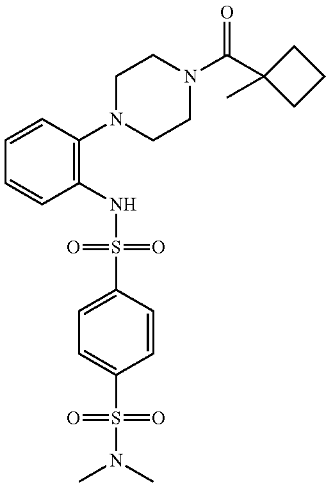 [SMILES: CN(C)S(=O)(=O)c1ccc(S(=O)(=O)Nc2ccccc2N2CCN(C(=O)C3(C)CCC3)CC2)cc1] | A-425 |
| 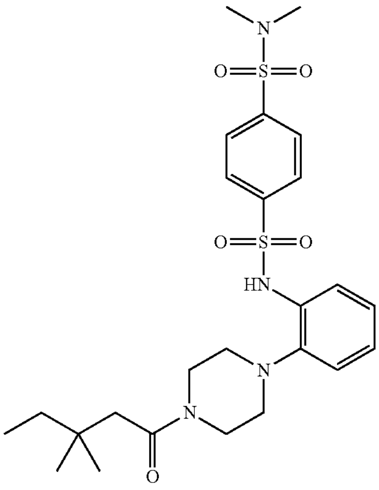 [SMILES: CCC(C)(C)CC(=O)N1CCN(c2ccccc2NS(=O)(=O)c2ccc(S(=O)(=O)N(C)C)cc2)CC1] | A-426 |

TABLE A-continued
| Structure | Compound No. |
|---|---|
| 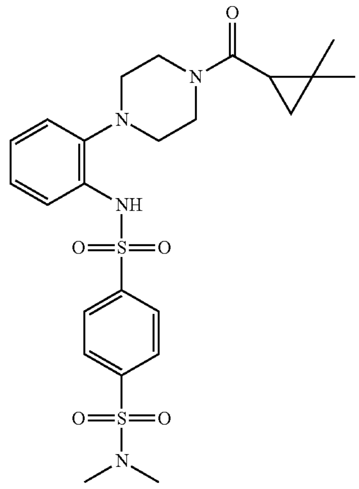 [SMILES: CN(C)S(=O)(=O)c1ccc(S(=O)(=O)Nc2ccccc2N2CCN(C(=O)C3CC3(C)C)CC2)cc1] | A-427 |
| 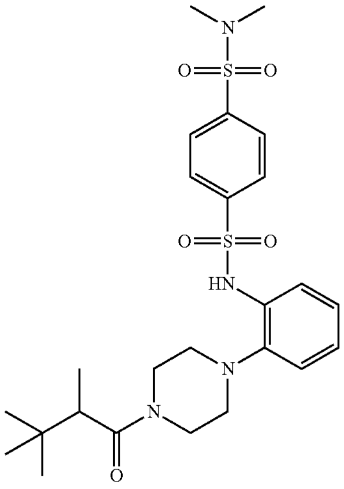 [SMILES: CC(C(=O)N1CCN(c2ccccc2NS(=O)(=O)c2ccc(S(=O)(=O)N(C)C)cc2)CC1)C(C)(C)C] | A-428 |
| 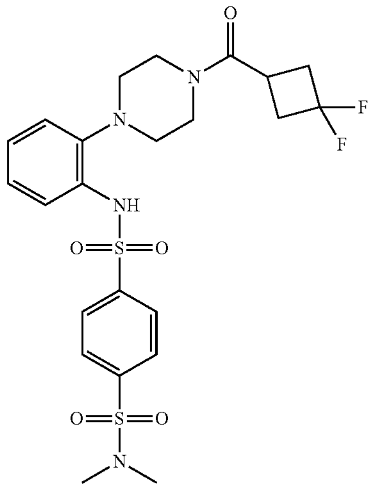 [SMILES: CN(C)S(=O)(=O)c1ccc(S(=O)(=O)Nc2ccccc2N2CCN(C(=O)C3CC(F)(F)C3)CC2)cc1] | A-429 |

TABLE A-continued
| Structure | Compound No. |
|---|---|
| 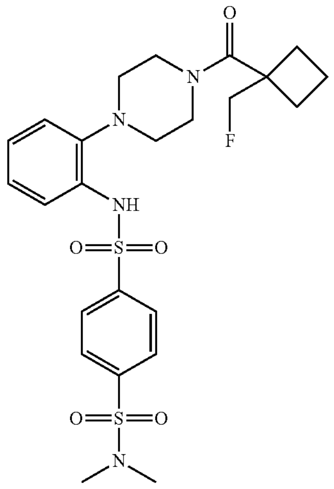 [SMILES: CN(C)S(=O)(=O)c1ccc(S(=O)(=O)Nc2ccccc2N2CCN(C(=O)C3(CF)CCC3)CC2)cc1] | A-430 |
| 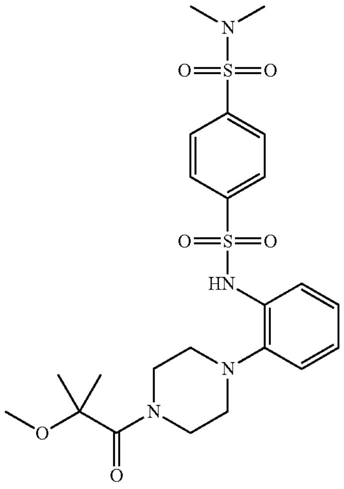 [SMILES: COC(C)(C)C(=O)N1CCN(c2ccccc2NS(=O)(=O)c2ccc(S(=O)(=O)N(C)C)cc2)CC1] | A-431 |
| 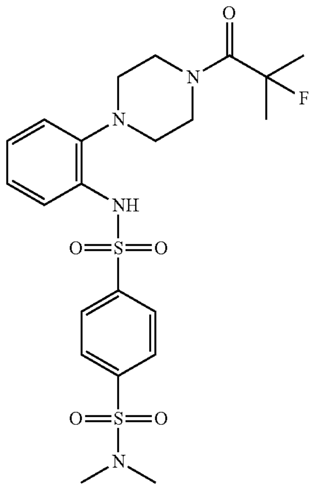 [SMILES: CN(C)S(=O)(=O)c1ccc(S(=O)(=O)Nc2ccccc2N2CCN(C(=O)C(C)(C)F)CC2)cc1] | A-432 |

TABLE A-continued
| Structure | Compound No. |
|---|---|
| 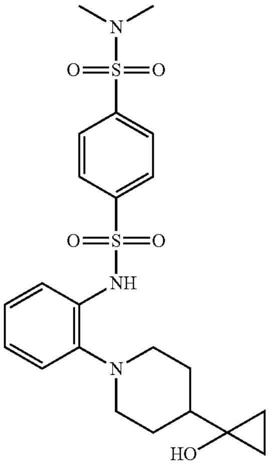 [SMILES: CN(C)S(=O)(=O)c1ccc(S(=O)(=O)Nc2ccccc2N2CCC(C3(O)CC3)CC2)cc1] | A-433 |
| 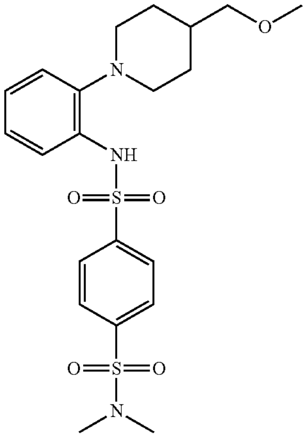 [SMILES: COCC1CCN(c2ccccc2NS(=O)(=O)c2ccc(S(=O)(=O)N(C)C)cc2)CC1] | A-434 |
| 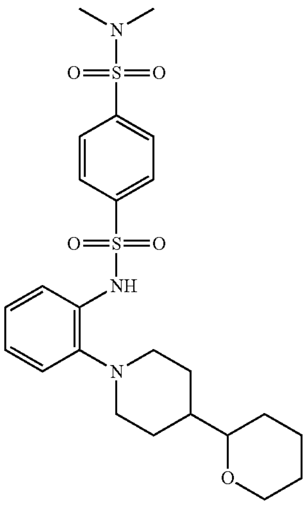 | A-435 |

TABLE A-continued
| Structure | Compound No. |
| --- | --- |
| 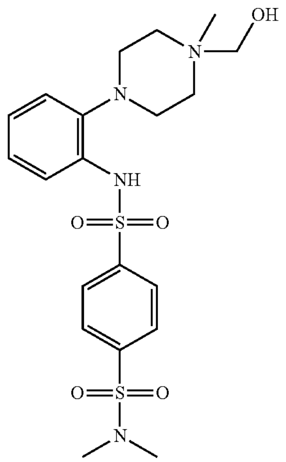 | A-436 |
| 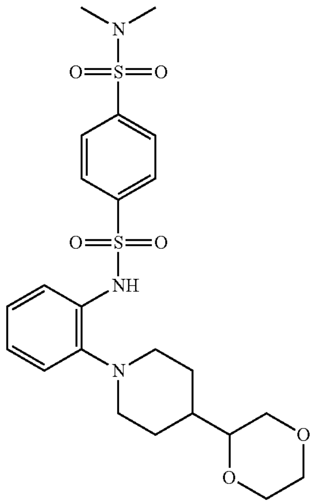 [SMILES: CN(C)S(=O)(=O)c1ccc(S(=O)(=O)Nc2ccccc2N2CCC(C3COCCO3)CC2)cc1] | A-437 |
| 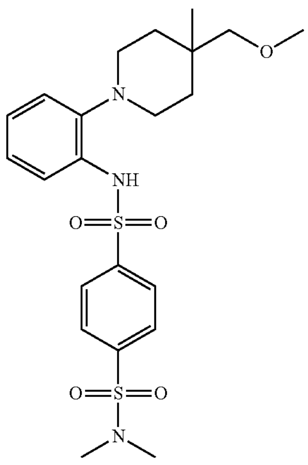 [SMILES: COCC1(C)CCN(c2ccccc2NS(=O)(=O)c2ccc(S(=O)(=O)N(C)C)cc2)CC1] | A-438 |

TABLE A-continued
| Structure | Compound No. |
|---|---|
| 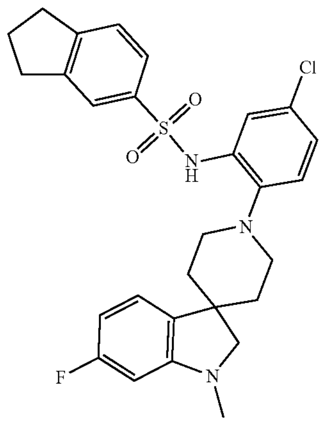 [SMILES: CN1CC2(CCN(c3ccc(Cl)cc3NS(=O)(=O)c3ccc4c(c3)CCC4)CC2)c2ccc(F)cc21] | A-439 |
| 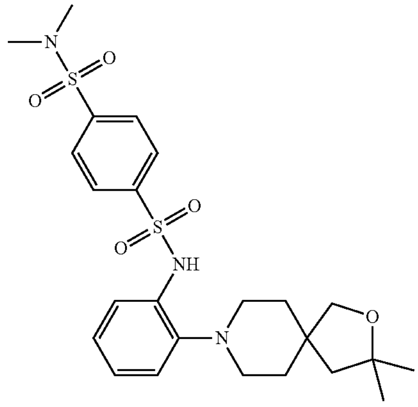 | A-440 |
| 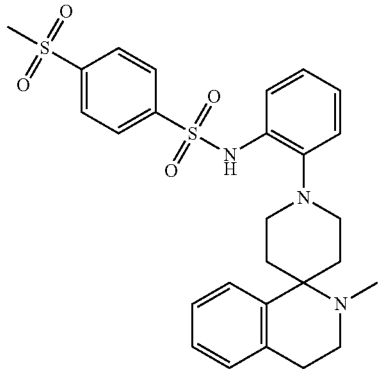 | A-441 |

TABLE A-continued
| Structure | Compound No. |
|---|---|
| 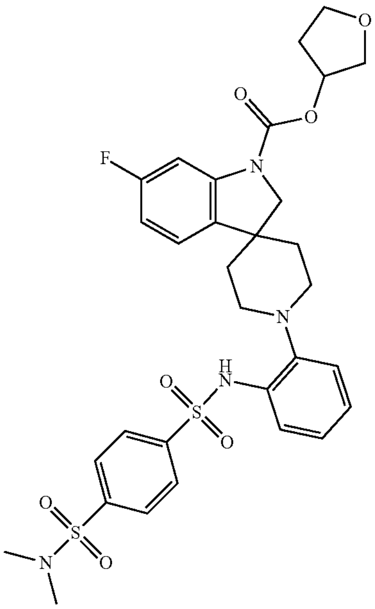 [SMILES: CN(C)S(=O)(=O)c1ccc(S(=O)(=O)Nc2ccccc2N2CCC3(CC2)CN(C(=O)OC2CCOC2)c2cc(F)ccc23)cc1] | A-442 |
| 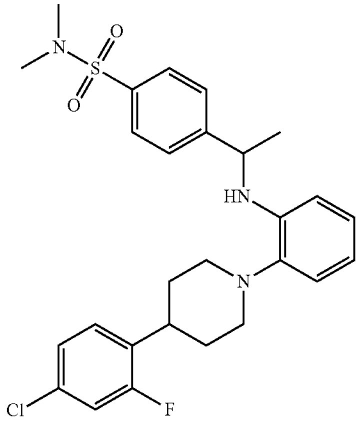 [SMILES: CC(Nc1ccccc1N1CCC(c2ccc(Cl)cc2F)CC1)c1ccc(S(=O)(=O)N(C)C)cc1] | A-443 |
| 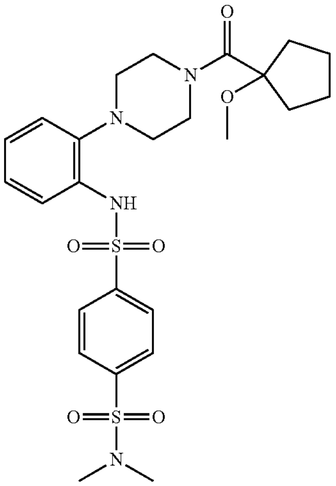 [SMILES: COC1(C(=O)N2CCN(c3ccccc3NS(=O)(=O)c3ccc(S(=O)(=O)N(C)C)cc3)CC2)CCCC1] | A-444 |

TABLE A-continued
| Structure | Compound No. |
| --- | --- |
| 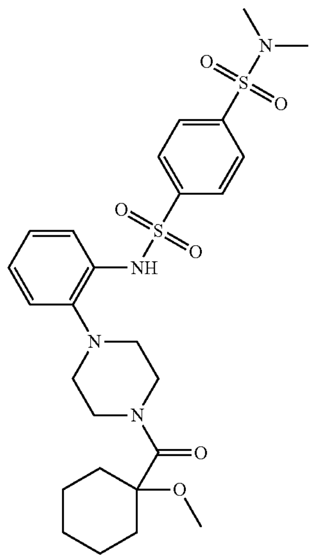 [SMILES: COC1(C(=O)N2CCN(c3ccccc3NS(=O)(=O)c3ccc(S(=O)(=O)N(C)C)cc3)CC2)CCCCC1] | A-445 |
| 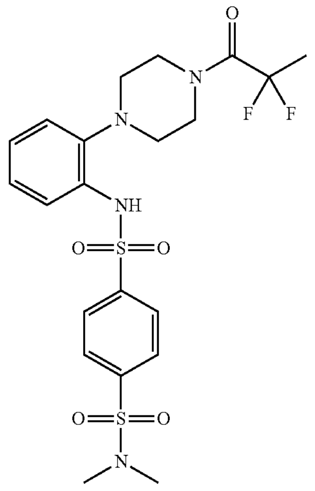 [SMILES: CN(C)S(=O)(=O)c1ccc(S(=O)(=O)Nc2ccccc2N2CCN(C(=O)C(C)(F)F)CC2)cc1] | A-446 |
| 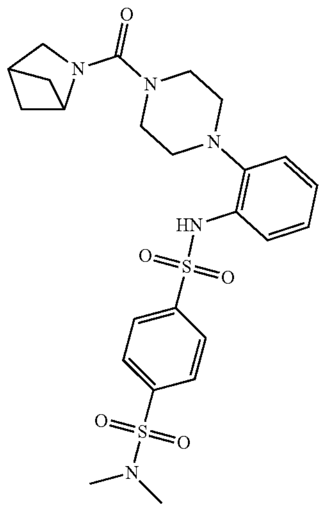 [SMILES: CN(C)S(=O)(=O)c1ccc(S(=O)(=O)Nc2ccccc2N2CCN(C(=O)N3CC4CC3C4)CC2)cc1] | A-447 |

TABLE A-continued
| Structure | Compound No. |
|---|---|
| 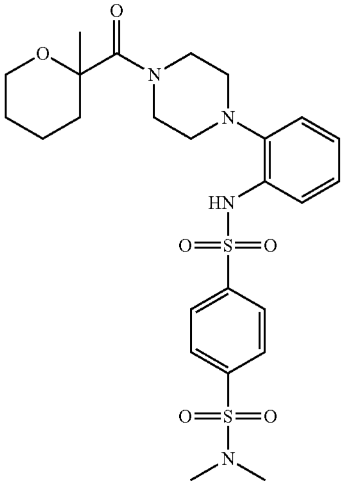 [SMILES: CN(C)S(=O)(=O)c1ccc(S(=O)(=O)Nc2ccccc2N2CCN(C(=O)C3(C)CCCCO3)CC2)cc1] | A-448 |
| 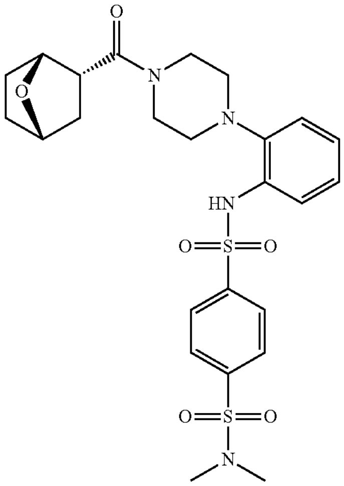 [SMILES: CN(C)S(=O)(=O)c1ccc(S(=O)(=O)Nc2ccccc2N2CCN(C(=O)[C@@H]3C[C@@H]4CC[C@H]3O4)CC2)cc1] | A-449 |
| 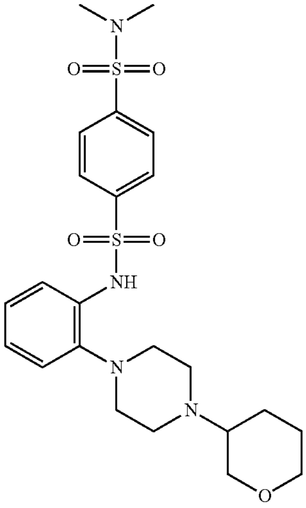 [SMILES: CN(C)S(=O)(=O)c1ccc(S(=O)(=O)Nc2ccccc2N2CCN(C3CCCOC3)CC2)cc1] | A-450 |

TABLE A-continued
| Structure | Compound No. |
| --- | --- |
| 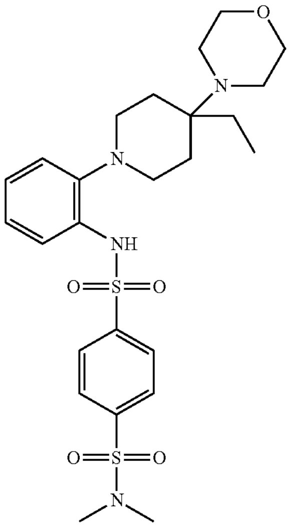 [SMILES: CCC1(N2CCOCC2)CCN(c2ccccc2NS(=O)(=O)c2ccc(S(=O)(=O)N(C)C)cc2)CC1] | A-451 |
| 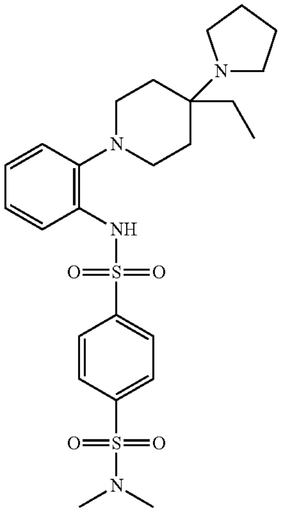 [SMILES: CCC1(N2CCCC2)CCN(c2ccccc2NS(=O)(=O)c2ccc(S(=O)(=O)N(C)C)cc2)CC1] | A-452 |
| 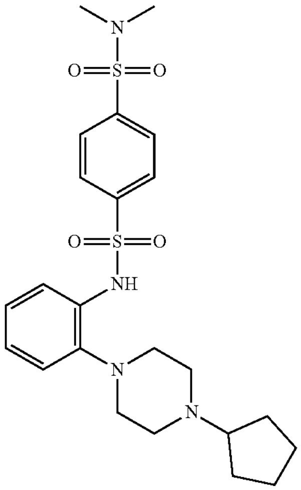 [SMILES: CN(C)S(=O)(=O)c1ccc(S(=O)(=O)Nc2ccccc2N2CCN(C3CCCC3)CC2)cc1] | A-453 |

TABLE A-continued
| Structure | Compound No. |
| --- | --- |
| 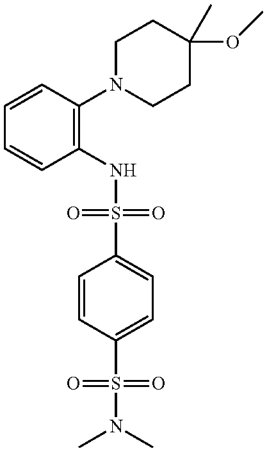 [SMILES: COC1(C)CCN(c2ccccc2NS(=O)(=O)c2ccc(S(=O)(=O)N(C)C)cc2)CC1] | A-454 |
| 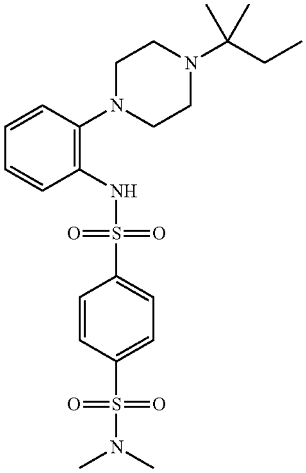 [SMILES: CCC(C)(C)N1CCN(c2ccccc2NS(=O)(=O)c2ccc(S(=O)(=O)N(C)C)cc2)CC1] | A-455 |
| 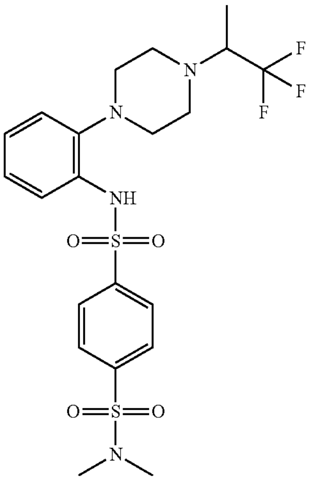 [SMILES: CC(N1CCN(c2ccccc2NS(=O)(=O)c2ccc(S(=O)(=O)N(C)C)cc2)CC1)C(F)(F)F] | A-456 |

TABLE A-continued
| Structure | Compound No. |
|---|---|
| 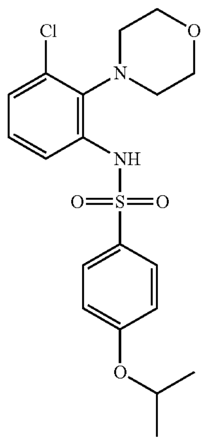 [SMILES: CC(C)Oc1ccc(S(=O)(=O)Nc2cccc(Cl)c2N2CCOCC2)cc1] | A-457 |
| 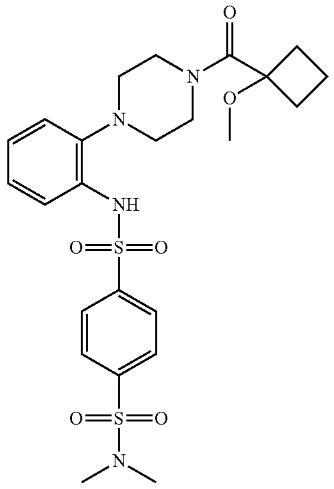 [SMILES: COC1(C(=O)N2CCN(c3ccccc3NS(=O)(=O)c3ccc(S(=O)(=O)N(C)C)cc3)CC2)CCC1] | A-458 |
| 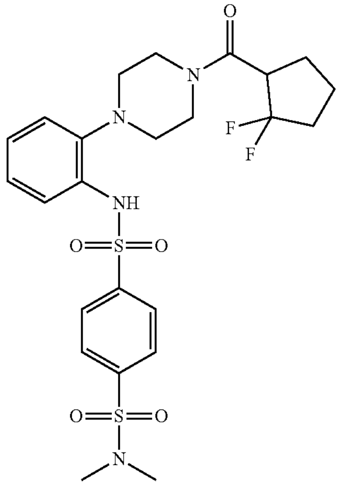 [SMILES: CN(C)S(=O)(=O)c1ccc(S(=O)(=O)Nc2ccccc2N2CCN(C(=O)C3CCCC3(F)F)CC2)cc1] | A-459 |

TABLE A-continued
| Structure | Compound No. |
| --- | --- |
| 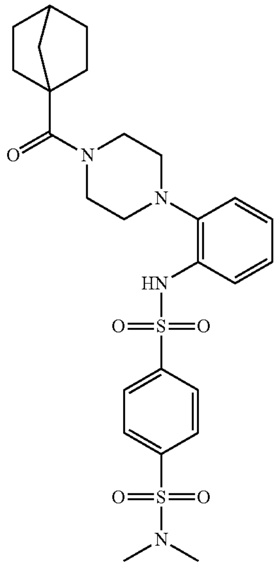 [SMILES: CN(C)S(=O)(=O)c1ccc(S(=O)(=O)Nc2ccccc2N2CCN(C(=O)C34CCC(CC3)C4)CC2)cc1] | A-460 |
| 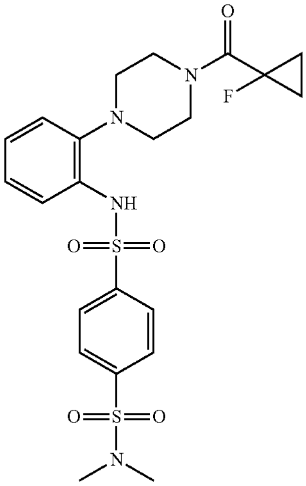 [SMILES: CN(C)S(=O)(=O)c1ccc(S(=O)(=O)Nc2ccccc2N2CCN(C(=O)C3(F)CC3)CC2)cc1] | A-461 |
| 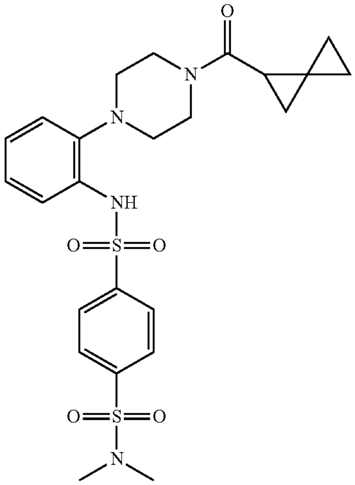 [SMILES: CN(C)S(=O)(=O)c1ccc(S(=O)(=O)Nc2ccccc2N2CCN(C(=O)C3CC34CC4)CC2)cc1] | A-462 |

TABLE A-continued
| Structure | Compound No. |
| --- | --- |
| 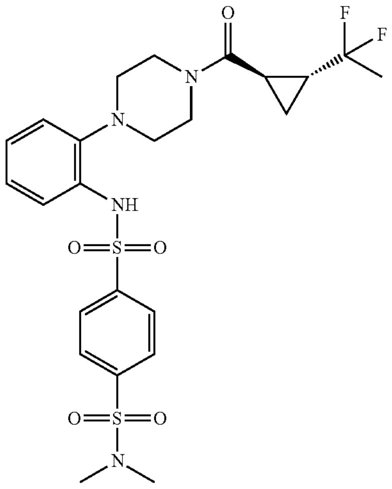 [SMILES: CN(C)S(=O)(=O)c1ccc(S(=O)(=O)Nc2ccccc2N2CCN(C(=O)[C@@H]3C[C@H]3C(C)(F)F)CC2)cc1] | A-463 |
| 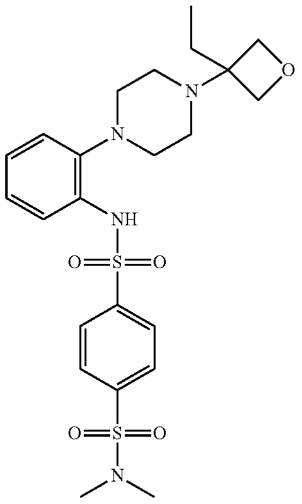 [SMILES: CCC1(N2CCN(c3ccccc3NS(=O)(=O)c3ccc(S(=O)(=O)N(C)C)cc3)CC2)COC1] | A-464 |
| 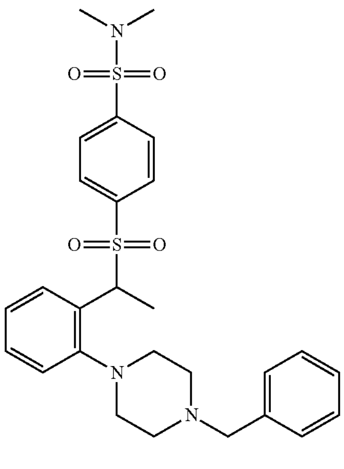 [SMILES: CC(c1ccccc1N1CCN(Cc2ccccc2)CC1)S(=O)(=O)c1ccc(S(=O)(=O)N(C)C)cc1] | A-465 |

TABLE A-continued
| Structure | Compound No. |
|---|---|
| 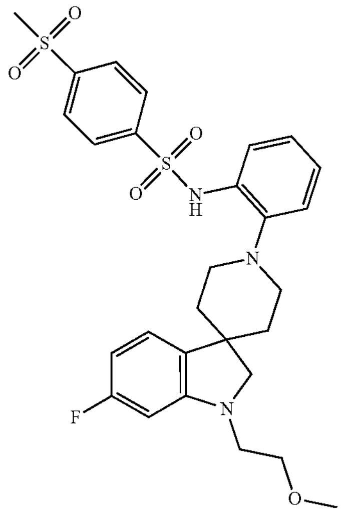 [SMILES: COCCN1CC2(CCN(c3ccccc3NS(=O)(=O)c3ccc(S(C)(=O)=O)cc3)CC2)c2ccc(F)cc21] | A-466 |
| 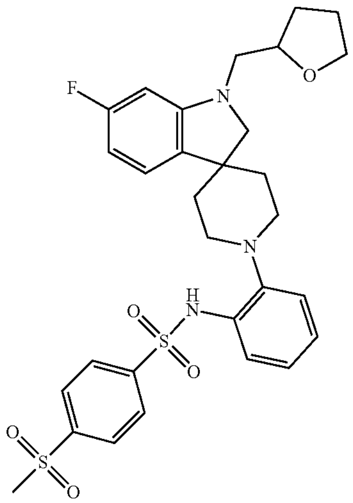 [SMILES: CS(=O)(=O)c1ccc(S(=O)(=O)Nc2ccccc2N2CCC3(CC2)CN(CC2CCCO2)c2cc(F)ccc23)cc1] | A-467 |
| 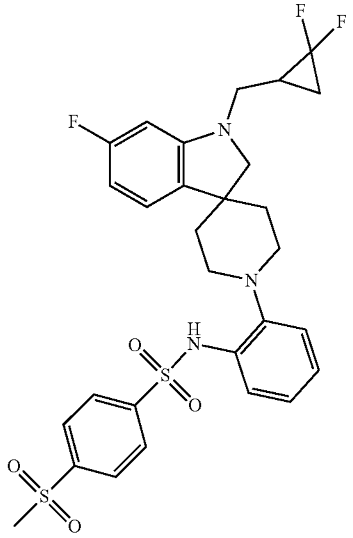 [SMILES: CS(=O)(=O)c1ccc(S(=O)(=O)Nc2ccccc2N2CCC3(CC2)CN(CC2CC2(F)F)c2cc(F)ccc23)cc1] | A-468 |

TABLE A-continued
| Structure | Compound No. |
| --- | --- |
| 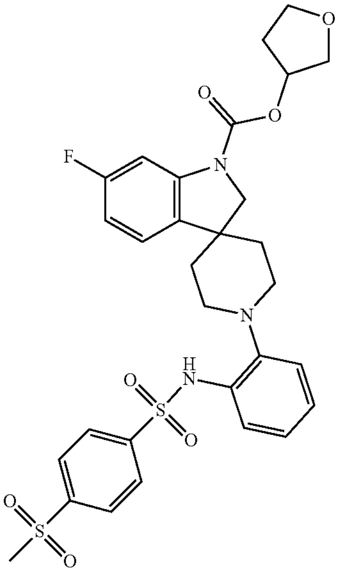 [SMILES: CS(=O)(=O)c1ccc(S(=O)(=O)Nc2ccccc2N2CCC3(CC2)CN(C(=O)OC2CCOC2)c2cc(F)ccc23)cc1] | A-469 |
| 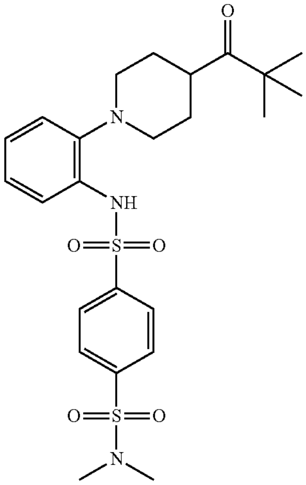 [SMILES: CN(C)S(=O)(=O)c1ccc(S(=O)(=O)Nc2ccccc2N2CCC(C(=O)C(C)(C)C)CC2)cc1] | A-470 |
| 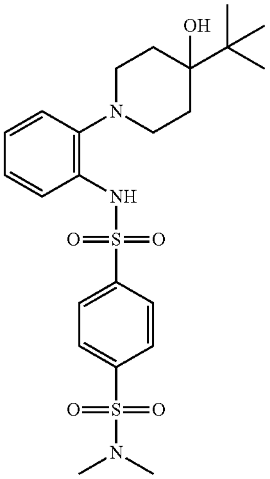 [SMILES: CN(C)S(=O)(=O)c1ccc(S(=O)(=O)Nc2ccccc2N2CCC(O)(C(C)(C)C)CC2)cc1] | A-471 |

TABLE A-continued
| Structure | Compound No. |
|---|---|
| 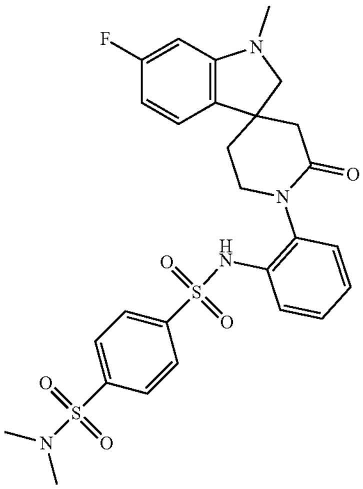 [SMILES: CN1CC2(CCN(c3ccccc3NS(=O)(=O)c3ccc(S(=O)(=O)N(C)C)cc3)C(=O)C2)c2ccc(F)cc21] | A-472 |
| 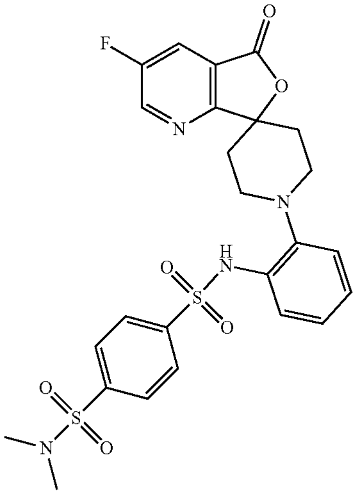 [SMILES: CN(C)S(=O)(=O)c1ccc(S(=O)(=O)Nc2ccccc2N2CCC3(CC2)OC(=O)c2cc(F)cnc23)cc1] | A-473 |
| 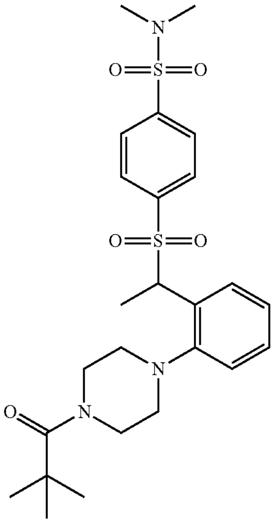 [SMILES: CC(c1ccccc1N1CCN(C(=O)C(C)(C)C)CC1)S(=O)(=O)c1ccc(S(=O)(=O)N(C)C)cc1] | A-474 |

TABLE A-continued
| Structure | Compound No. |
|---|---|
| 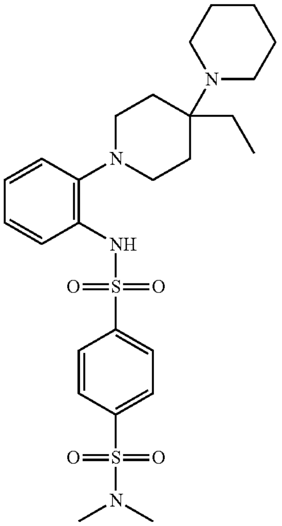 [SMILES: CCC1(N2CCCCC2)CCN(c2ccccc2NS(=O)(=O)c2ccc(S(=O)(=O)N(C)C)cc2)CC1] | A-475 |
| 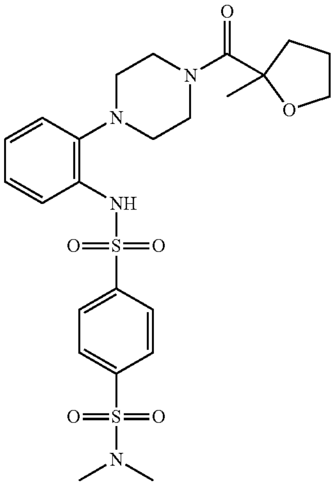 [SMILES: CN(C)S(=O)(=O)c1ccc(S(=O)(=O)Nc2ccccc2N2CCN(C(=O)C3(C)CCCO3)CC2)cc1] | A-476 |
| 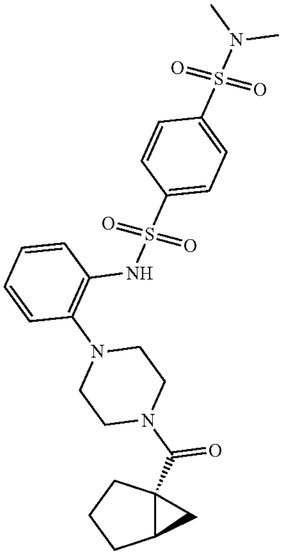 [SMILES: CN(C)S(=O)(=O)c1ccc(S(=O)(=O)Nc2ccccc2N2CCN(C(=O)[C@@]34CCC[C@@H]3C4)CC2)cc1] | A-477 |

TABLE A-continued
| Structure | Compound No. |
|---|---|
| 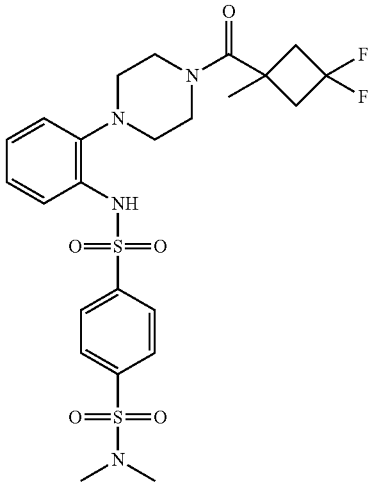 [SMILES: CN(C)S(=O)(=O)c1ccc(S(=O)(=O)Nc2ccccc2N2CCN(C(=O)C3(C)CC(F)(F)C3)CC2)cc1] | A-478 |
| 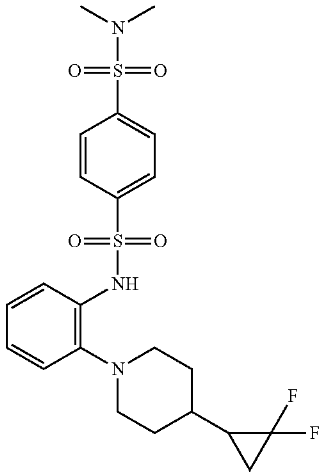 [SMILES: CN(C)S(=O)(=O)c1ccc(S(=O)(=O)Nc2ccccc2N2CCC(C3CC3(F)F)CC2)cc1] | A-479 |
| 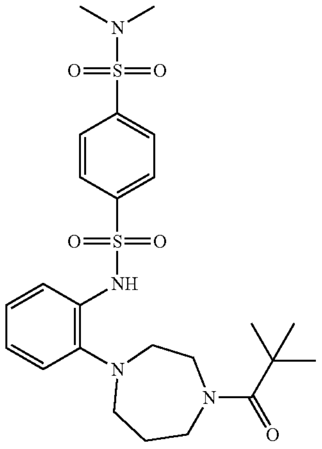 [SMILES: CN(C)S(=O)(=O)c1ccc(S(=O)(=O)Nc2ccccc2N2CCCN(C(=O)C(C)(C)C)CC2)cc1] | A-480 |

TABLE A-continued
| Structure | Compound No. |
|---|---|
| 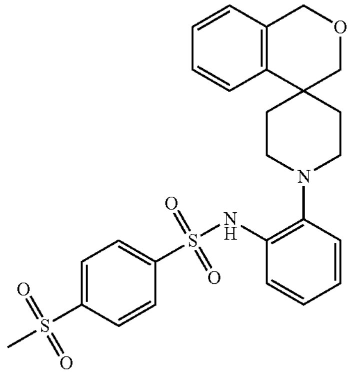 [SMILES: CS(=O)(=O)c1ccc(S(=O)(=O)Nc2ccccc2N2CCC3(CC2)COCc2ccccc23)cc1] | A-481 |
| 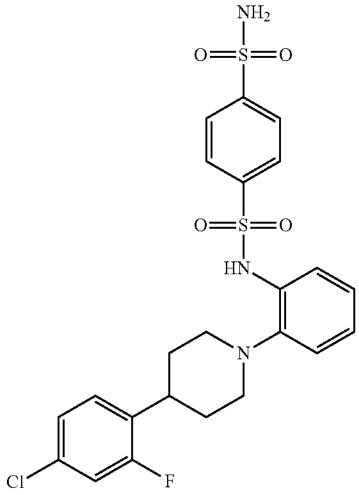 [SMILES: NS(=O)(=O)c1ccc(S(=O)(=O)Nc2ccccc2N2CCC(c3ccc(Cl)cc3F)CC2)cc1] | A-482 |
| 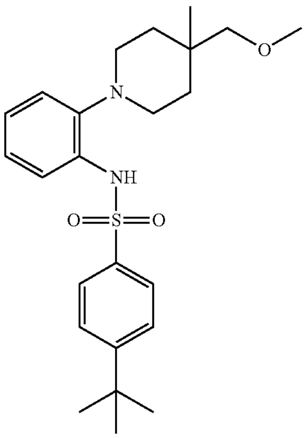 [SMILES: COCC1(C)CCN(c2ccccc2NS(=O)(=O)c2ccc(C(C)(C)C)cc2)CC1] | A-483 |

TABLE A-continued
| Structure | Compound No. |
| --- | --- |
| 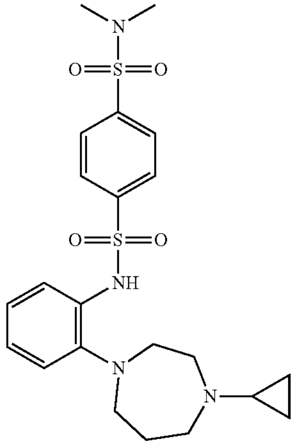 [SMILES: CN(C)S(=O)(=O)c1ccc(S(=O)(=O)Nc2ccccc2N2CCCN(C3CC3)CC2)cc1] | A-484 |
| 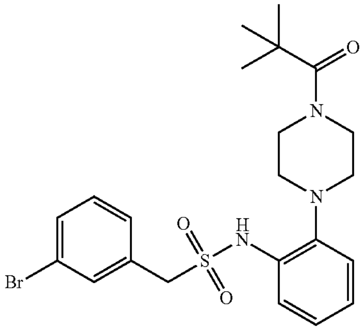 [SMILES: CC(C)(C)C(=O)N1CCN(c2ccccc2NS(=O)(=O)Cc2cccc(Br)c2)CC1] | A-485 |
| 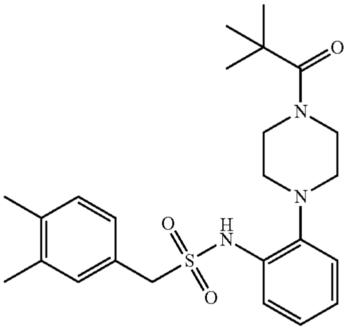 [SMILES: Cc1ccc(CS(=O)(=O)Nc2ccccc2N2CCN(C(=O)C(C)(C)C)CC2)cc1C] | A-486 |
| 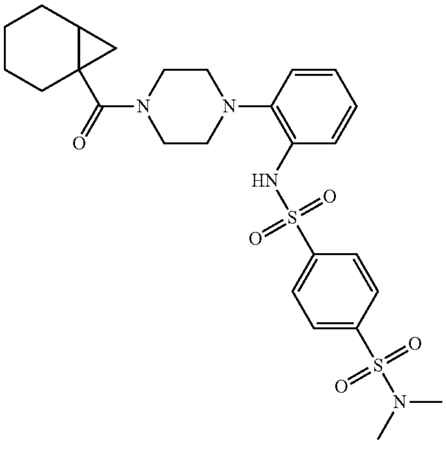 [SMILES: CN(C)S(=O)(=O)c1ccc(S(=O)(=O)Nc2ccccc2N2CCN(C(=O)C34CCCCC3C4)CC2)cc1] | A-487 |

TABLE A-continued
| Structure | Compound No. |
|---|---|
| 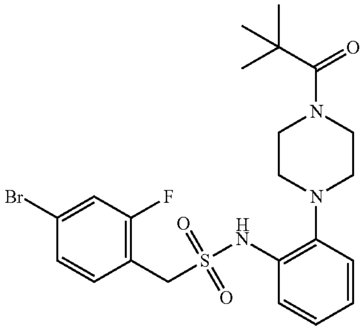 [SMILES: CC(C)(C)C(=O)N1CCN(c2ccccc2NS(=O)(=O)Cc2ccc(Br)cc2F)CC1] | A-488 |
| 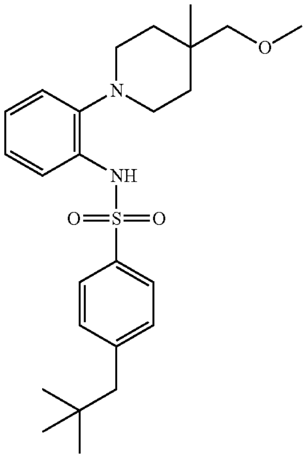 [SMILES: COCC1(C)CCN(c2ccccc2NS(=O)(=O)c2ccc(CC(C)(C)C)cc2)CC1] | A-489 |
| 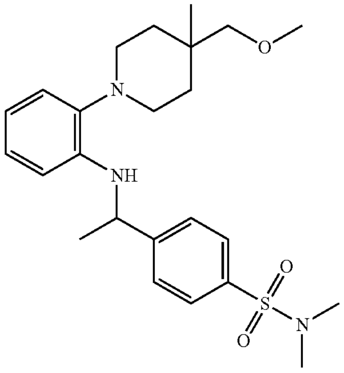 [SMILES: COCC1(C)CCN(c2ccccc2NC(C)c2ccc(S(=O)(=O)N(C)C)cc2)CC1] | A-490 |

TABLE A-continued
| Structure | Compound No. |
|---|---|
| 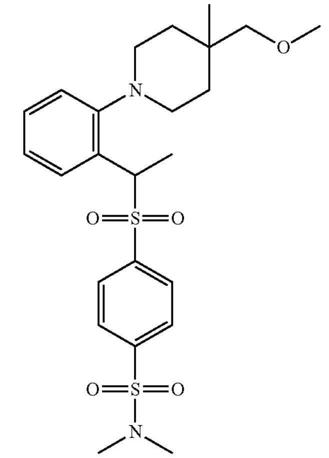 [SMILES: COCC1(C)CCN(c2ccccc2C(C)S(=O)(=O)c2ccc(S(=O)(=O)N(C)C)cc2)CC1] | A-491 |
| 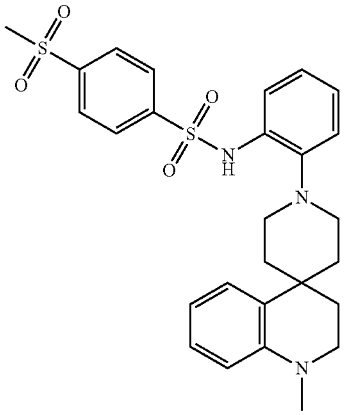 [SMILES: CN1CCC2(CCN(c3ccccc3NS(=O)(=O)c3ccc(S(C)(=O)=O)cc3)CC2)c2ccccc21] | A-492 |
| 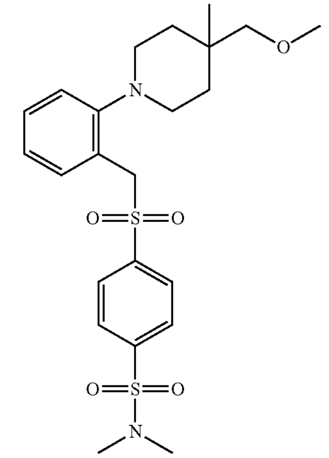 [SMILES: COCC1(C)CCN(c2ccccc2CS(=O)(=O)c2ccc(S(=O)(=O)N(C)C)cc2)CC1] | A-493 |

TABLE A-continued
| Structure | Compound No. |
| --- | --- |
| 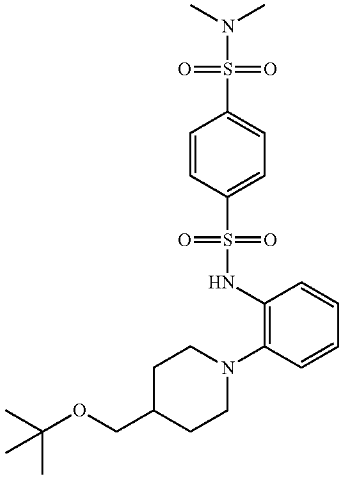 [SMILES: CN(C)S(=O)(=O)c1ccc(S(=O)(=O)Nc2ccccc2N2CCC(COC(C)(C)C)CC2)cc1] | A-494 |
| 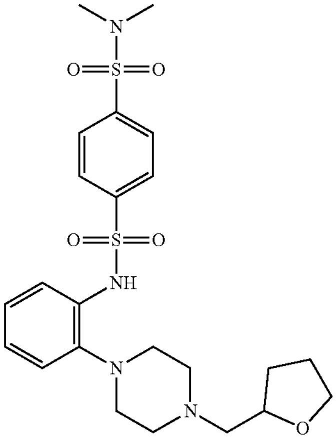 [SMILES: CN(C)S(=O)(=O)c1ccc(S(=O)(=O)Nc2ccccc2N2CCN(CC3CCCO3)CC2)cc1] | A-495 |
| 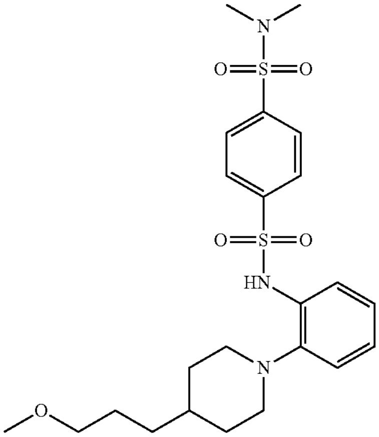 [SMILES: COCCCC1CCN(c2ccccc2NS(=O)(=O)c2ccc(S(=O)(=O)N(C)C)cc2)CC1] | A-496 |
| 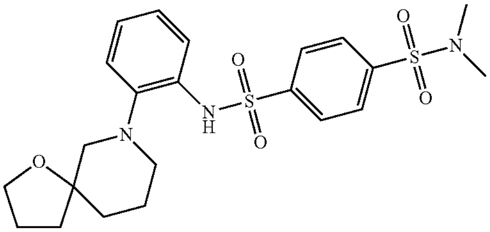 [SMILES: CN(C)S(=O)(=O)c1ccc(S(=O)(=O)Nc2ccccc2N2CCCC3(CCCO3)C2)cc1] | A-497 |

TABLE A-continued
| Structure | Compound No. |
|---|---|
| 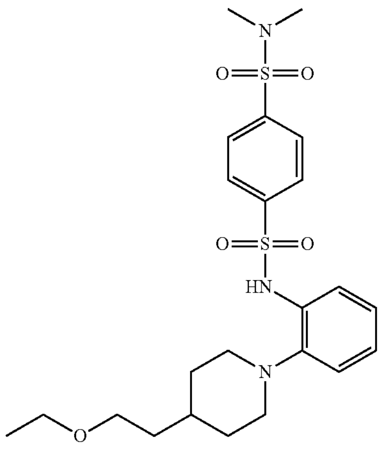 [SMILES: CCOCCC1CCN(c2ccccc2NS(=O)(=O)c2ccc(S(=O)(=O)N(C)C)cc2)CC1] | A-498 |
| 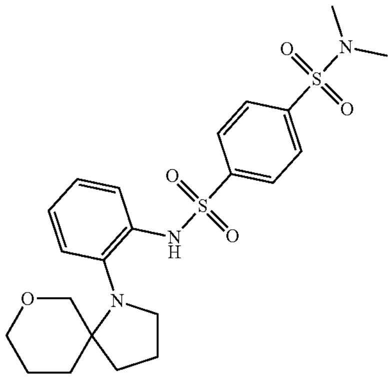 [SMILES: CN(C)S(=O)(=O)c1ccc(S(=O)(=O)Nc2ccccc2N2CCCC23CCCOC3)cc1] | A-499 |
| 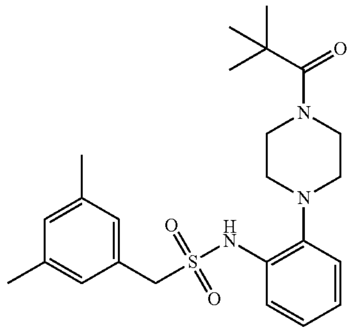 [SMILES: Cc1cc(C)cc(CS(=O)(=O)Nc2ccccc2N2CCN(C(=O)C(C)(C)C)CC2)c1] | A-500 |
| 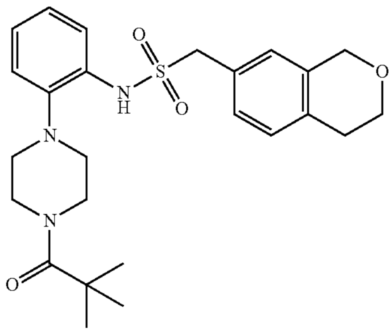 [SMILES: CC(C)(C)C(=O)N1CCN(c2ccccc2NS(=O)(=O)Cc2ccc3c(c2)COCC3)CC1] | A-501 |

TABLE A-continued
| Structure | Compound No. |
| --- | --- |
| 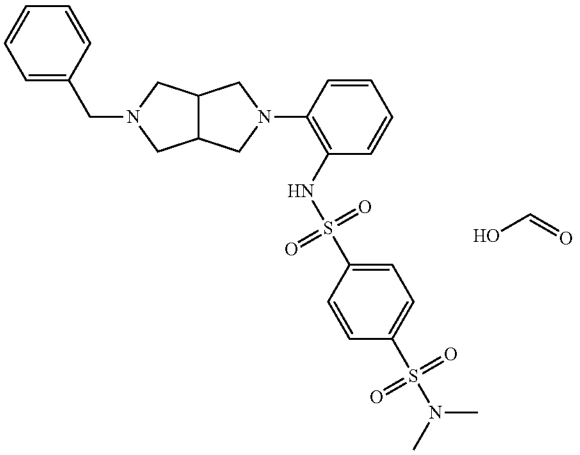 [SMILES: CN(C)S(=O)(=O)c1ccc(S(=O)(=O)Nc2ccccc2N2CC3CN(Cc4ccccc4)CC3C2)cc1 ; O=CO] | A-502 |
| 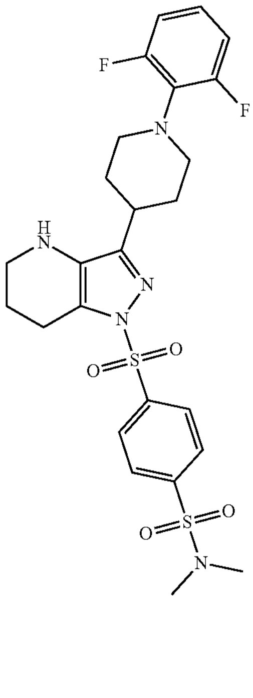 [SMILES: CN(C)S(=O)(=O)c1ccc(S(=O)(=O)n2nc(C3CCN(c4c(F)cccc4F)CC3)c3c2CCCN3)cc1] | A-503 |

TABLE A-continued
| Structure | Compound No. |
|---|---|
| 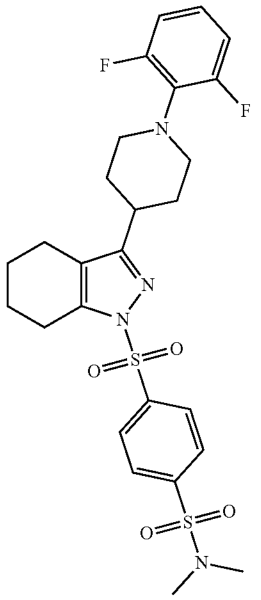 [SMILES: CN(C)S(=O)(=O)c1ccc(S(=O)(=O)n2nc(C3CCN(c4c(F)cccc4F)CC3)c3c2CCCC3)cc1] | A-504 |
| 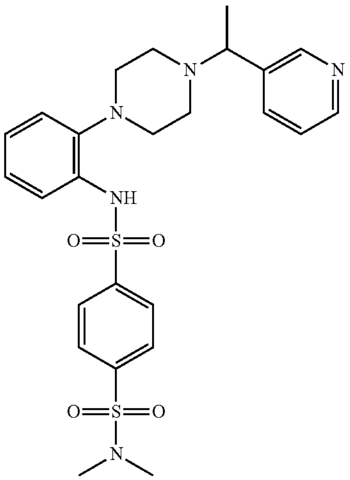 [SMILES: CC(c1cccnc1)N1CCN(c2ccccc2NS(=O)(=O)c2ccc(S(=O)(=O)N(C)C)cc2)CC1] | A-505 |
| 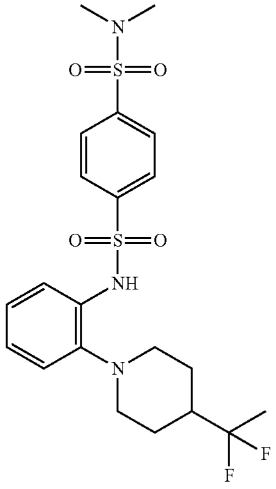 | A-506 |

TABLE A-continued
| Structure | Compound No. |
|---|---|
| 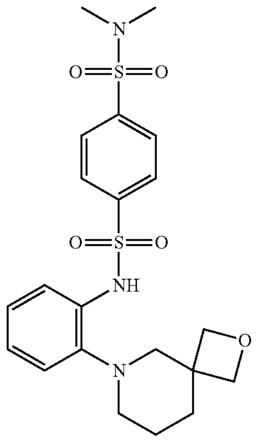 [SMILES: CN(C)S(=O)(=O)c1ccc(S(=O)(=O)Nc2ccccc2N2CCCC3(COC3)C2)cc1] | A-507 |
| 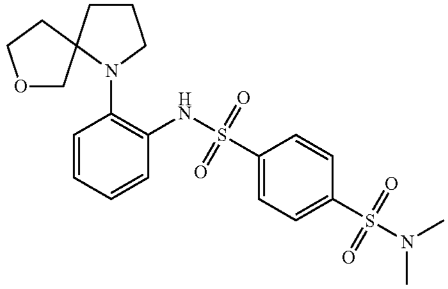 [SMILES: CN(C)S(=O)(=O)c1ccc(S(=O)(=O)Nc2ccccc2N2CCCC23CCOC3)cc1] | A-508 |
| 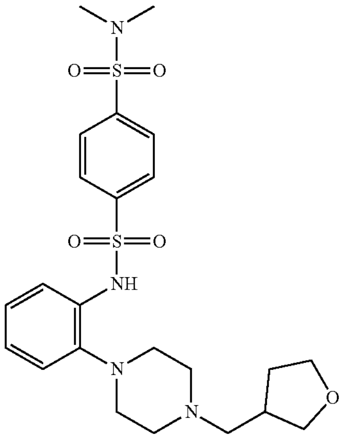 [SMILES: CN(C)S(=O)(=O)c1ccc(S(=O)(=O)Nc2ccccc2N2CCN(CC3CCOC3)CC2)cc1] | A-509 |
| 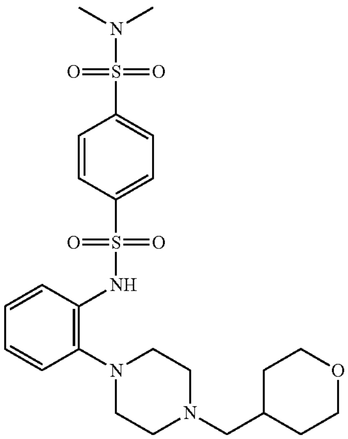 | A-510 |

TABLE A-continued
| Structure | Compound No. |
| --- | --- |
| 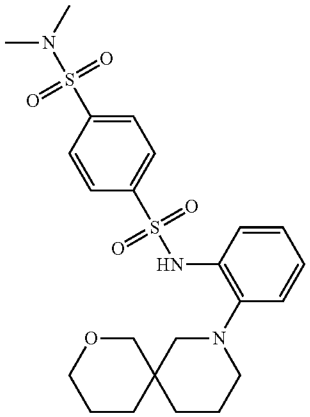 [SMILES: CN(C)S(=O)(=O)c1ccc(S(=O)(=O)Nc2ccccc2N2CCCC3(CCCOC3)C2)cc1] | A-511 |
| 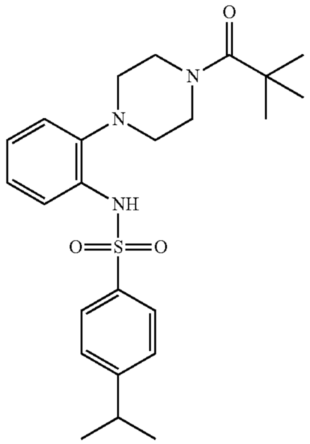 [SMILES: CC(C)c1ccc(S(=O)(=O)Nc2ccccc2N2CCN(C(=O)C(C)(C)C)CC2)cc1] | A-512 |
| 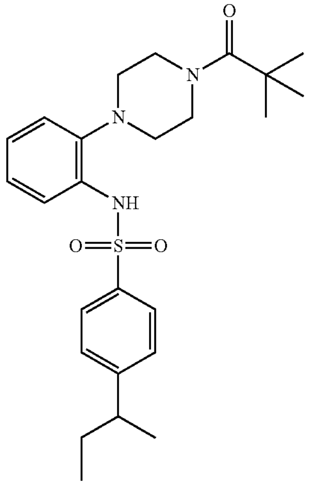 [SMILES: CCC(C)c1ccc(S(=O)(=O)Nc2ccccc2N2CCN(C(=O)C(C)(C)C)CC2)cc1] | A-513 |

TABLE A-continued
| Structure | Compound No. |
|---|---|
| 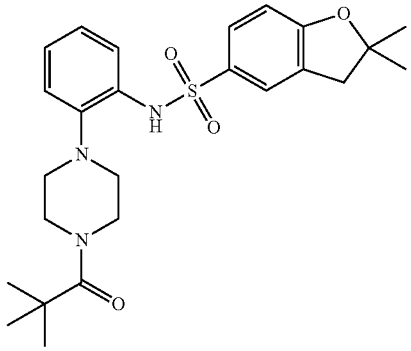 [SMILES: CC1(C)Cc2cc(S(=O)(=O)Nc3ccccc3N3CCN(C(=O)C(C)(C)C)CC3)ccc2O1] | A-514 |
| 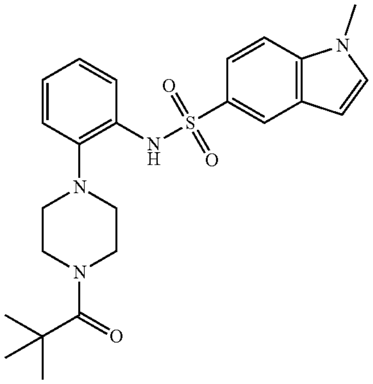 [SMILES: Cn1ccc2cc(S(=O)(=O)Nc3ccccc3N3CCN(C(=O)C(C)(C)C)CC3)ccc21] | A-515 |
| 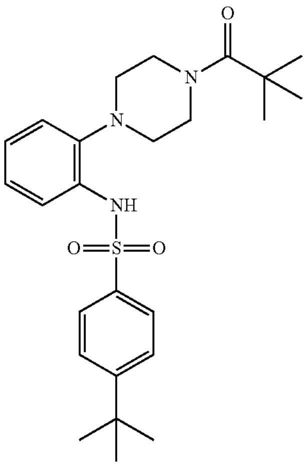 [SMILES: CC(C)(C)C(=O)N1CCN(c2ccccc2NS(=O)(=O)c2ccc(C(C)(C)C)cc2)CC1] | A-516 |

TABLE A-continued
| Structure | Compound No. |
| --- | --- |
| 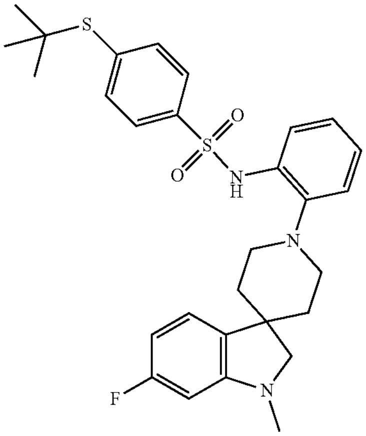 [SMILES: CN1CC2(CCN(c3ccccc3NS(=O)(=O)c3ccc(SC(C)(C)C)cc3)CC2)c2ccc(F)cc21] | A-517 |
| 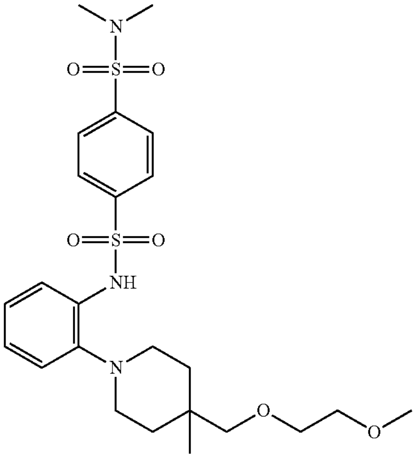 [SMILES: COCCOCC1(C)CCN(c2ccccc2NS(=O)(=O)c2ccc(S(=O)(=O)N(C)C)cc2)CC1] | A-518 |
| 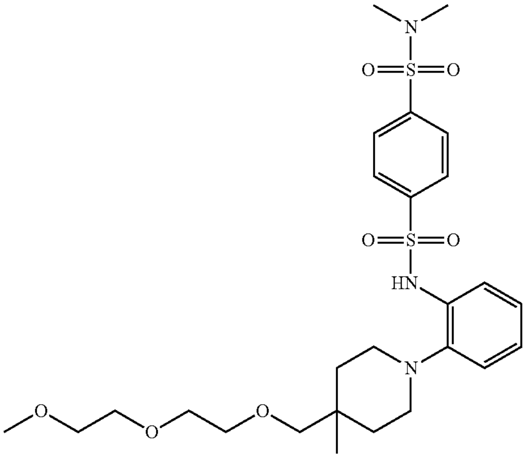 [SMILES: COCCOCCOCC1(C)CCN(c2ccccc2NS(=O)(=O)c2ccc(S(=O)(=O)N(C)C)cc2)CC1] | A-519 |

TABLE A-continued
| Structure | Compound No. |
|---|---|
| 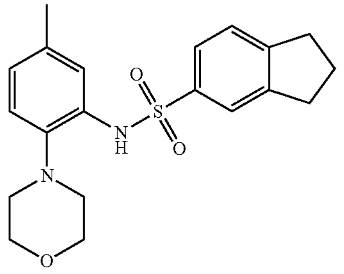 [SMILES: Cc1ccc(N2CCOCC2)c(NS(=O)(=O)c2ccc3c(c2)CCC3)c1] | A-520 |
| 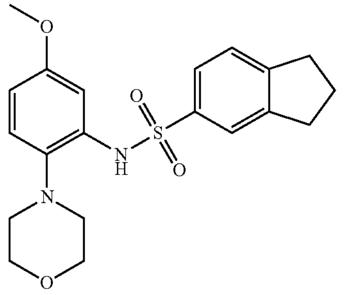 [SMILES: COc1ccc(N2CCOCC2)c(NS(=O)(=O)c2ccc3c(c2)CCC3)c1] | A-521 |
| 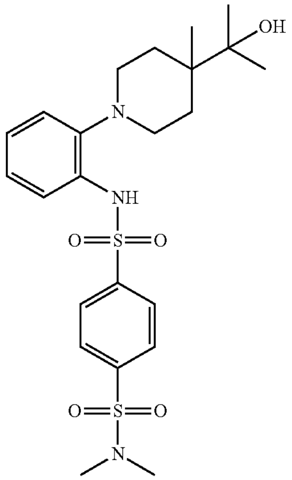 [SMILES: CN(C)S(=O)(=O)c1ccc(S(=O)(=O)Nc2ccccc2N2CCC(C)(C(C)(C)O)CC2)cc1] | A-522 |
| 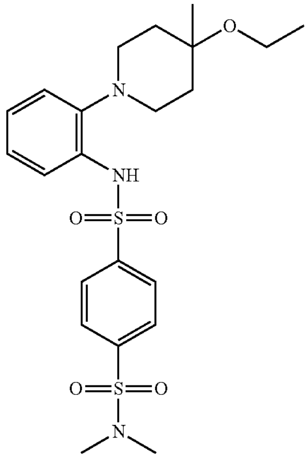 [SMILES: CCOC1(C)CCN(c2ccccc2NS(=O)(=O)c2ccc(S(=O)(=O)N(C)C)cc2)CC1] | A-523 |

TABLE A-continued
| Structure | Compound No. |
| --- | --- |
| 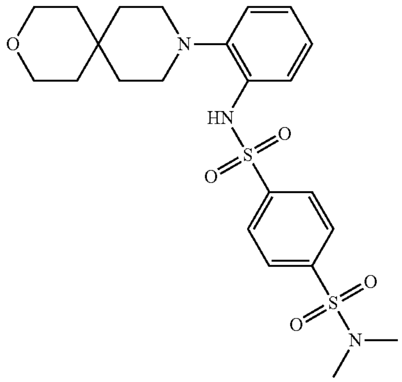 [SMILES: CN(C)S(=O)(=O)c1ccc(S(=O)(=O)Nc2ccccc2N2CCC3(CCOCC3)CC2)cc1] | A-524 |
| 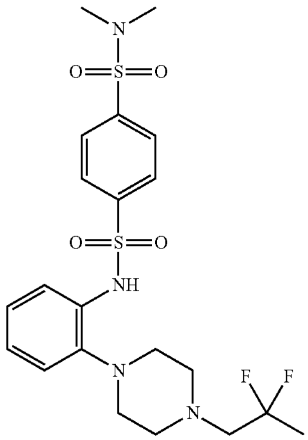 [SMILES: CN(C)S(=O)(=O)c1ccc(S(=O)(=O)Nc2ccccc2N2CCN(CC(C)(F)F)CC2)cc1] | A-525 |
| 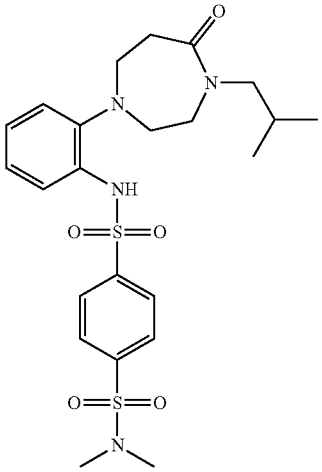 [SMILES: CC(C)CN1CCN(c2ccccc2NS(=O)(=O)c2ccc(S(=O)(=O)N(C)C)cc2)CCC1=O] | A-526 |

TABLE A-continued
| Structure | Compound No. |
|---|---|
| 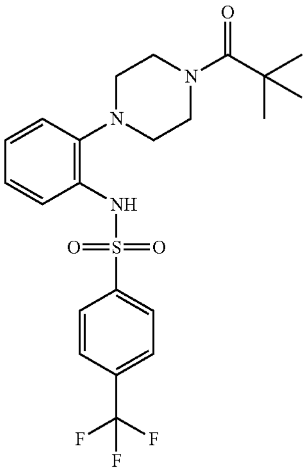 | A-527 |
| 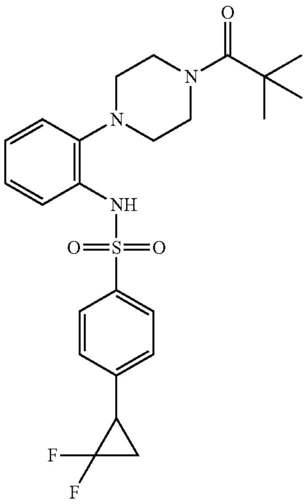 [SMILES: CC(C)(C)C(=O)N1CCN(c2ccccc2NS(=O)(=O)c2ccc(C3CC3(F)F)cc2)CC1] | A-528 |
| 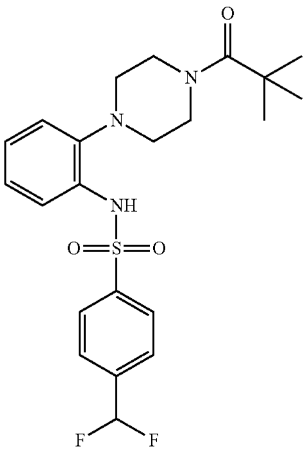 [SMILES: CC(C)(C)C(=O)N1CCN(c2ccccc2NS(=O)(=O)c2ccc(C(F)F)cc2)CC1] | A-529 |

TABLE A-continued
| Structure | Compound No. |
|---|---|
| 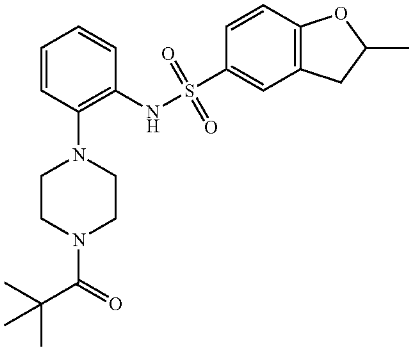 [SMILES: CC1Cc2cc(S(=O)(=O)Nc3ccccc3N3CCN(C(=O)C(C)(C)C)CC3)ccc2O1] | A-530 |
| 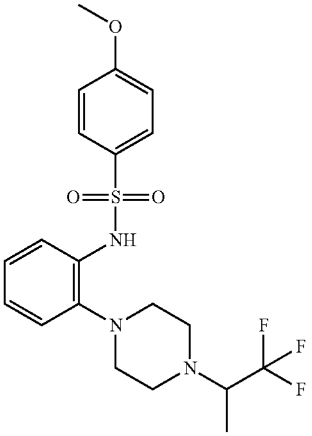 [SMILES: COc1ccc(S(=O)(=O)Nc2ccccc2N2CCN(C(C)C(F)(F)F)CC2)cc1] | A-531 |
| 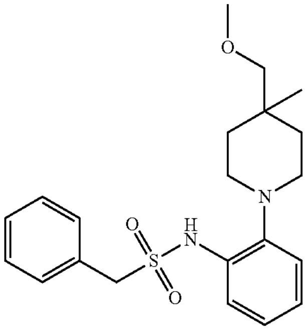 [SMILES: COCC1(C)CCN(c2ccccc2NS(=O)(=O)Cc2ccccc2)CC1] | A-532 |

TABLE A-continued
| Structure | Compound No. |
| --- | --- |
| 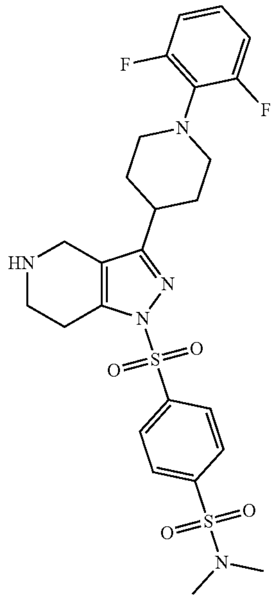 [SMILES: CN(C)S(=O)(=O)c1ccc(S(=O)(=O)n2nc(C3CCN(c4c(F)cccc4F)CC3)c3c2CCNC3)cc1] | A-533 |
| 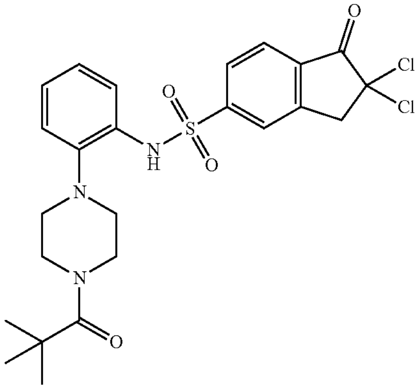 [SMILES: CC(C)(C)C(=O)N1CCN(c2ccccc2NS(=O)(=O)c2ccc3c(c2)CC(Cl)(Cl)C3=O)CC1] | A-534 |
| 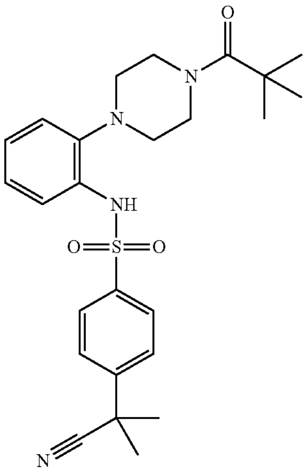 [SMILES: CC(C)(C)C(=O)N1CCN(c2ccccc2NS(=O)(=O)c2ccc(C(C)(C)C#N)cc2)CC1] | A-535 |

TABLE A-continued
| Structure | Compound No. |
|---|---|
| 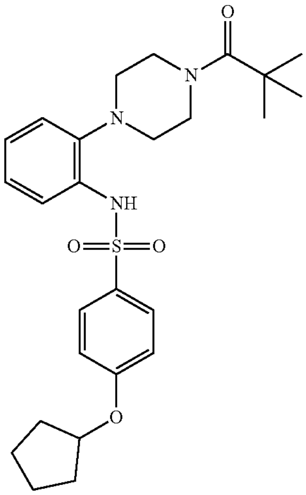 [SMILES: CC(C)(C)C(=O)N1CCN(c2ccccc2NS(=O)(=O)c2ccc(OC3CCCC3)cc2)CC1] | A-536 |
| 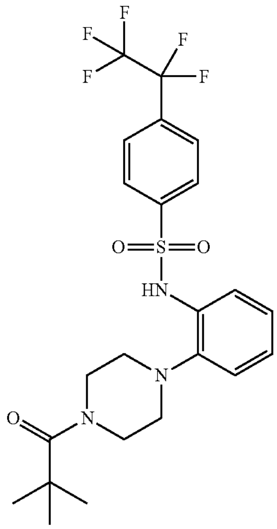 [SMILES: CC(C)(C)C(=O)N1CCN(c2ccccc2NS(=O)(=O)c2ccc(C(F)(F)C(F)(F)F)cc2)CC1] | A-537 |
| 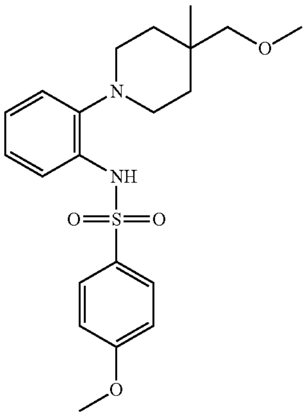 [SMILES: COCC1(C)CCN(c2ccccc2NS(=O)(=O)c2ccc(OC)cc2)CC1] | A-538 |

TABLE A-continued
| Structure | Compound No. |
|---|---|
| 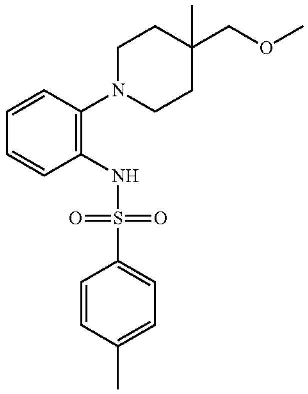 [SMILES: COCC1(C)CCN(c2ccccc2NS(=O)(=O)c2ccc(C)cc2)CC1] | A-539 |
| 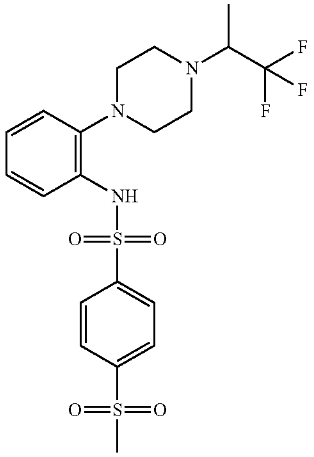 [SMILES: CC(N1CCN(c2ccccc2NS(=O)(=O)c2ccc(S(C)(=O)=O)cc2)CC1)C(F)(F)F] | A-540 |
| 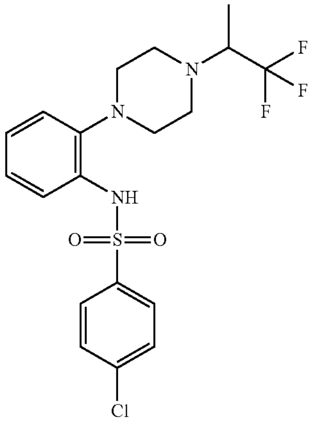 [SMILES: CC(N1CCN(c2ccccc2NS(=O)(=O)c2ccc(Cl)cc2)CC1)C(F)(F)F] | A-541 |
| 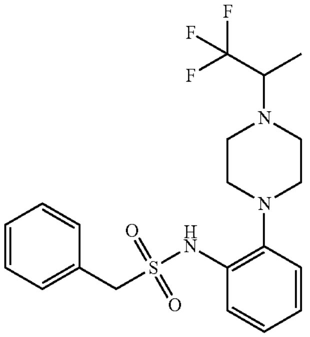 [SMILES: CC(N1CCN(c2ccccc2NS(=O)(=O)Cc2ccccc2)CC1)C(F)(F)F] | A-542 |

TABLE A-continued
| Structure | Compound No. |
|---|---|
| 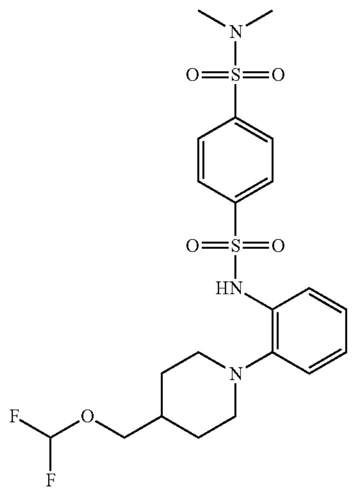 [SMILES: CN(C)S(=O)(=O)c1ccc(S(=O)(=O)Nc2ccccc2N2CCC(COC(F)F)CC2)cc1] | A-543 |
| 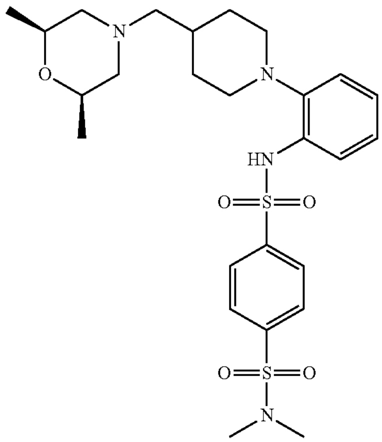 [SMILES: C[C@@H]1CN(CC2CCN(c3ccccc3NS(=O)(=O)c3ccc(S(=O)(=O)N(C)C)cc3)CC2)C[C@H](C)O1] | A-544 |
| 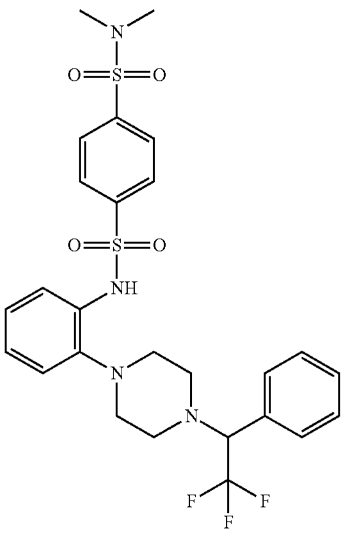 [SMILES: CN(C)S(=O)(=O)c1ccc(S(=O)(=O)Nc2ccccc2N2CCN(C(c3ccccc3)C(F)(F)F)CC2)cc1] | A-545 |

TABLE A-continued
| Structure | Compound No. |
|---|---|
| 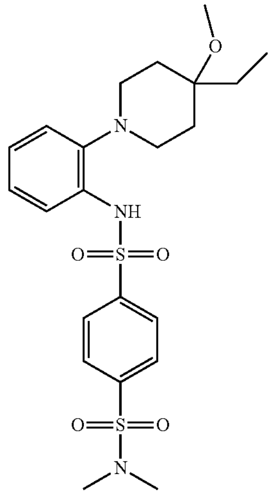 [SMILES: CCC1(OC)CCN(c2ccccc2NS(=O)(=O)c2ccc(S(=O)(=O)N(C)C)cc2)CC1] | A-546 |
| 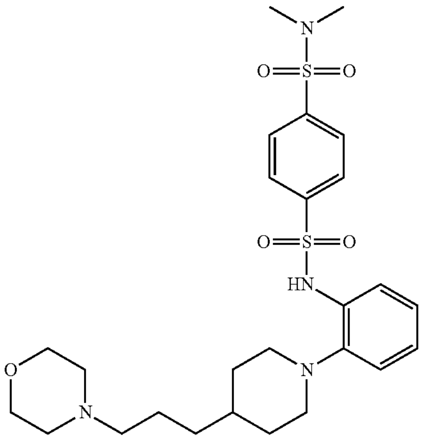 [SMILES: CN(C)S(=O)(=O)c1ccc(S(=O)(=O)Nc2ccccc2N2CCC(CCCN3CCOCC3)CC2)cc1] | A-547 |
| 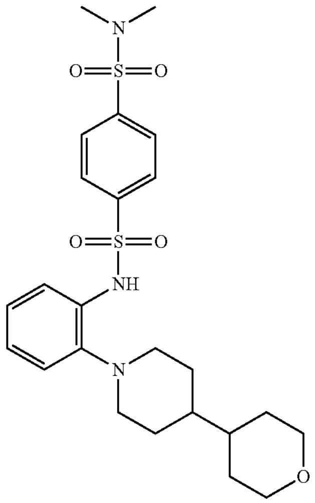 [SMILES: CN(C)S(=O)(=O)c1ccc(S(=O)(=O)Nc2ccccc2N2CCC(C3CCOCC3)CC2)cc1] | A-548 |

TABLE A-continued
| Structure | Compound No. |
|---|---|
| 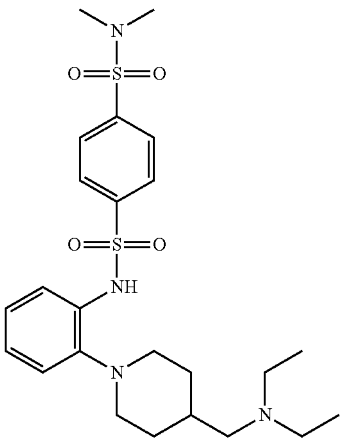 [SMILES: CCN(CC)CC1CCN(c2ccccc2NS(=O)(=O)c2ccc(S(=O)(=O)N(C)C)cc2)CC1] | A-549 |
| 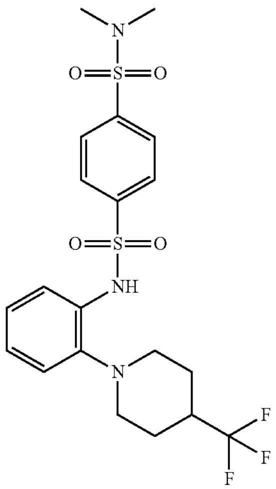 [SMILES: CN(C)S(=O)(=O)c1ccc(S(=O)(=O)Nc2ccccc2N2CCC(C(F)(F)F)CC2)cc1] | A-550 |
| 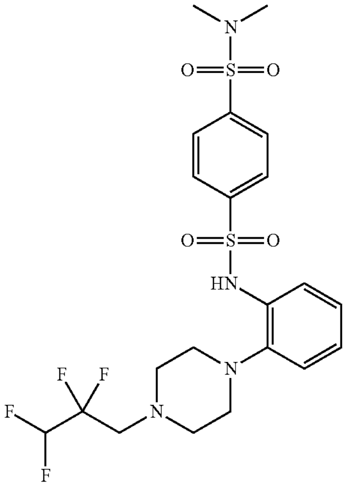 [SMILES: CN(C)S(=O)(=O)c1ccc(S(=O)(=O)Nc2ccccc2N2CCN(CC(F)(F)C(F)F)CC2)cc1] | A-551 |

TABLE A-continued
| Structure | Compound No. |
| --- | --- |
| 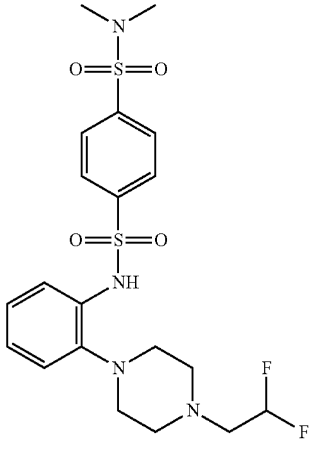 [SMILES: CN(C)S(=O)(=O)c1ccc(S(=O)(=O)Nc2ccccc2N2CCN(CC(F)F)CC2)cc1] | A-552 |
| 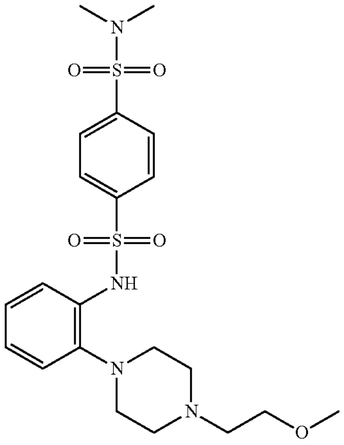 [SMILES: COCCN1CCN(c2ccccc2NS(=O)(=O)c2ccc(S(=O)(=O)N(C)C)cc2)CC1] | A-553 |
| 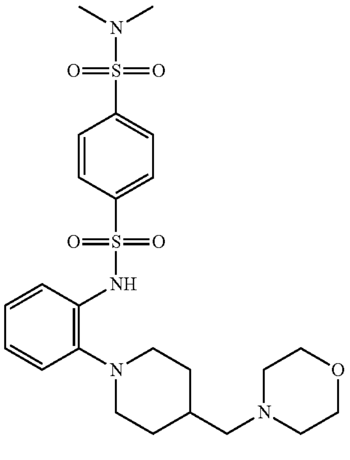 [SMILES: CN(C)S(=O)(=O)c1ccc(S(=O)(=O)Nc2ccccc2N2CCC(CN3CCOCC3)CC2)cc1] | A-554 |

TABLE A-continued
| Structure | Compound No. |
| --- | --- |
| 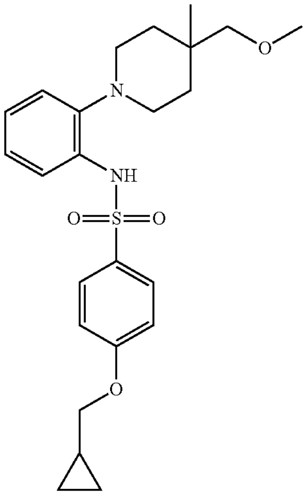 [SMILES: COCC1(C)CCN(c2ccccc2NS(=O)(=O)c2ccc(OCC3CC3)cc2)CC1] | A-555 |
| 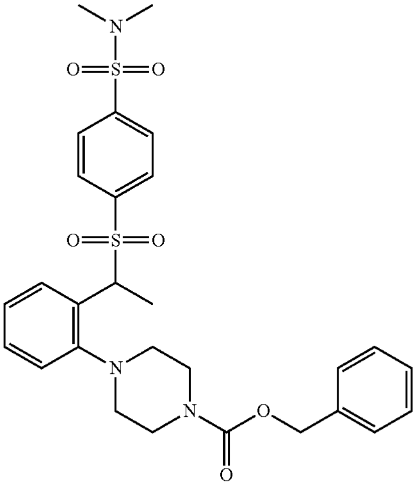 [SMILES: CC(c1ccccc1N1CCN(C(=O)OCc2ccccc2)CC1)S(=O)(=O)c1ccc(S(=O)(=O)N(C)C)cc1] | A-556 |
| 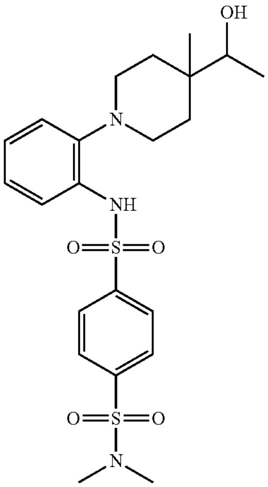 [SMILES: CC(O)C1(C)CCN(c2ccccc2NS(=O)(=O)c2ccc(S(=O)(=O)N(C)C)cc2)CC1] | A-557 |

TABLE A-continued
| Structure | Compound No. |
| --- | --- |
| 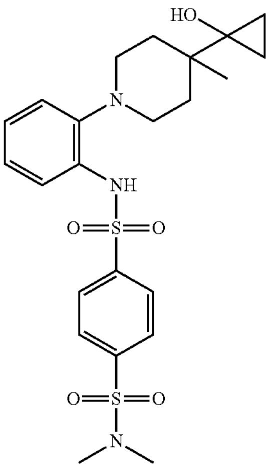 [SMILES: CN(C)S(=O)(=O)c1ccc(S(=O)(=O)Nc2ccccc2N2CCC(C)(C3(O)CC3)CC2)cc1] | A-558 |
| 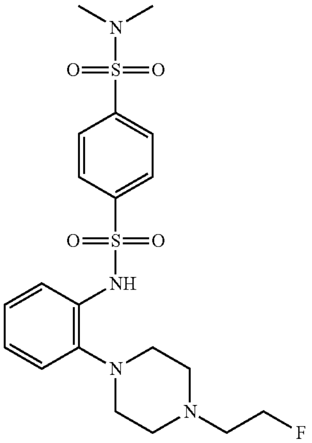 [SMILES: CN(C)S(=O)(=O)c1ccc(S(=O)(=O)Nc2ccccc2N2CCN(CCF)CC2)cc1] | A-559 |
| 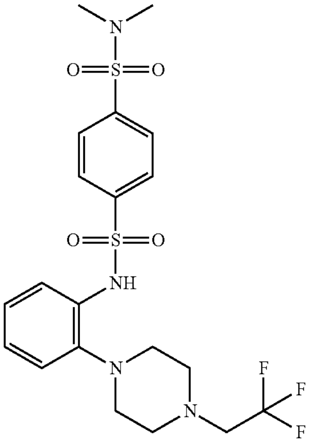 [SMILES: CN(C)S(=O)(=O)c1ccc(S(=O)(=O)Nc2ccccc2N2CCN(CC(F)(F)F)CC2)cc1] | A-560 |

TABLE A-continued
| Structure | Compound No. |
| --- | --- |
| 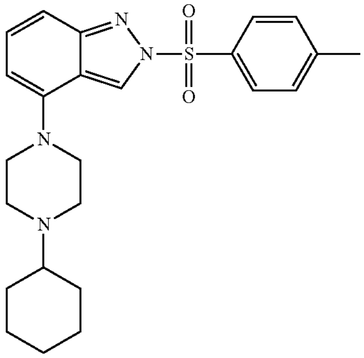 [SMILES: Cc1ccc(S(=O)(=O)n2cc3c(N4CCN(C5CCCCC5)CC4)cccc3n2)cc1] | A-561 |
| 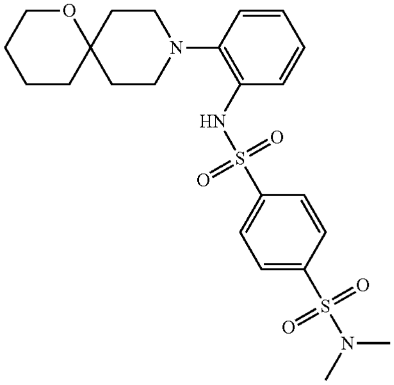 [SMILES: CN(C)S(=O)(=O)c1ccc(S(=O)(=O)Nc2ccccc2N2CCC3(CCCCO3)CC2)cc1] | A-562 |
| 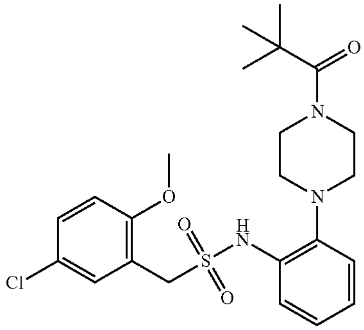 [SMILES: COc1ccc(Cl)cc1CS(=O)(=O)Nc1ccccc1N1CCN(C(=O)C(C)(C)C)CC1] | A-563 |
| 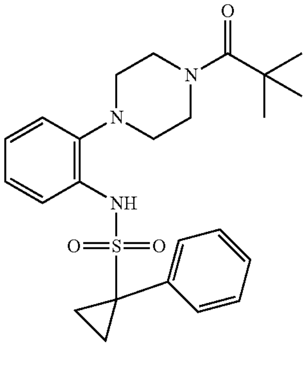 [SMILES: CC(C)(C)C(=O)N1CCN(c2ccccc2NS(=O)(=O)C2(c3ccccc3)CC2)CC1] | A-564 |

TABLE A-continued
| Structure | Compound No. |
| --- | --- |
| 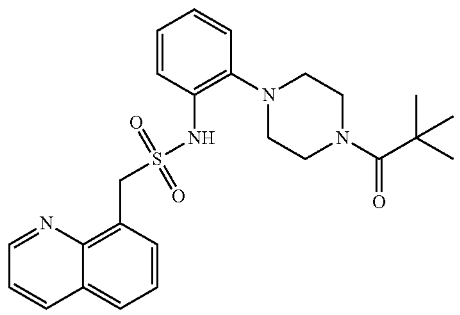 [SMILES: CC(C)(C)C(=O)N1CCN(c2ccccc2NS(=O)(=O)Cc2cccc3cccnc23)CC1] | A-565 |
| 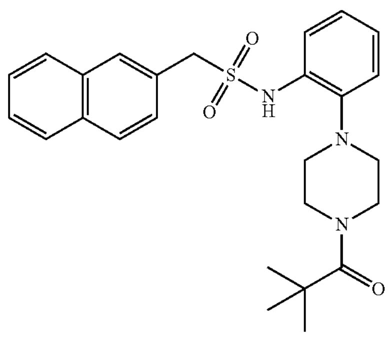 [SMILES: CC(C)(C)C(=O)N1CCN(c2ccccc2NS(=O)(=O)Cc2ccc3ccccc3c2)CC1] | A-566 |
| 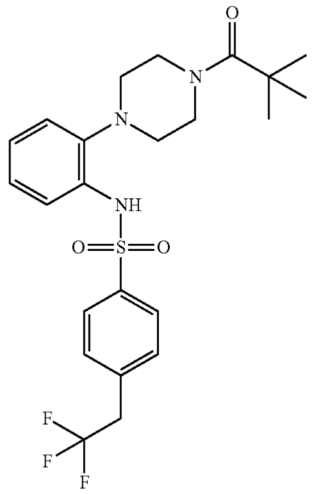 [SMILES: CC(C)(C)C(=O)N1CCN(c2ccccc2NS(=O)(=O)c2ccc(CC(F)(F)F)cc2)CC1] | A-567 |

TABLE A-continued
| Structure | Compound No. |
| --- | --- |
| 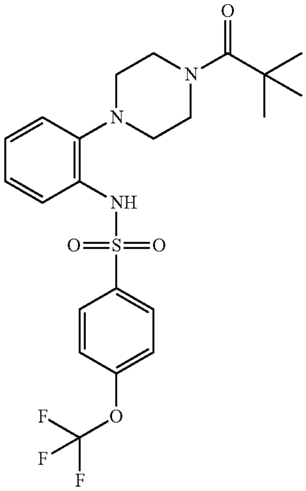 [SMILES: CC(C)(C)C(=O)N1CCN(c2ccccc2NS(=O)(=O)c2ccc(OC(F)(F)F)cc2)CC1] | A-568 |
| 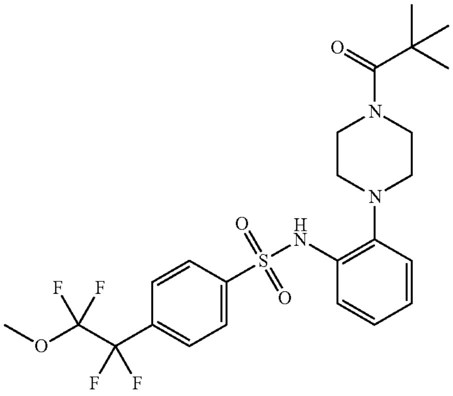 [SMILES: COC(F)(F)C(F)(F)c1ccc(S(=O)(=O)Nc2ccccc2N2CCN(C(=O)C(C)(C)C)CC2)cc1] | A-569 |
| 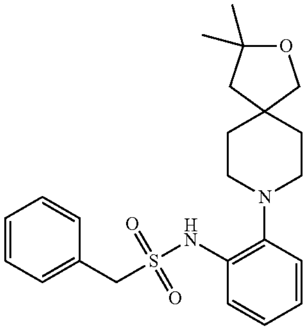 [SMILES: CC1(C)CC2(CCN(c3ccccc3NS(=O)(=O)Cc3ccccc3)CC2)CO1] | A-570 |
| 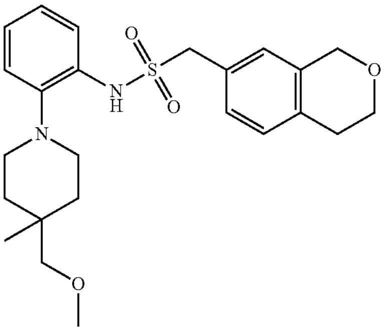 [SMILES: COCC1(C)CCN(c2ccccc2NS(=O)(=O)Cc2ccc3c(c2)COCC3)CC1] | A-571 |

TABLE A-continued
| Structure | Compound No. |
| --- | --- |
| 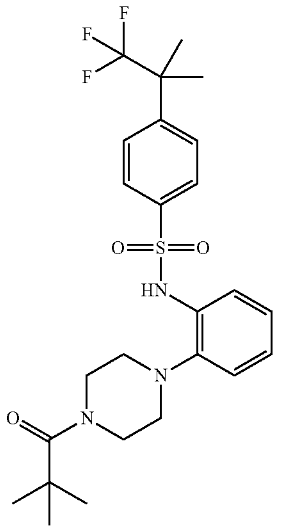 [SMILES: CC(C)(C)C(=O)N1CCN(c2ccccc2NS(=O)(=O)c2ccc(C(C)(C)C(F)(F)F)cc2)CC1] | A-572 |
| 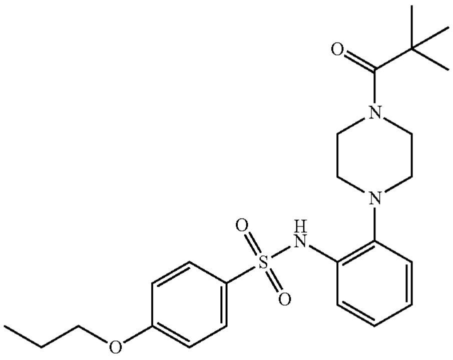 [SMILES: CCCOc1ccc(S(=O)(=O)Nc2ccccc2N2CCN(C(=O)C(C)(C)C)CC2)cc1] | A-573 |
| 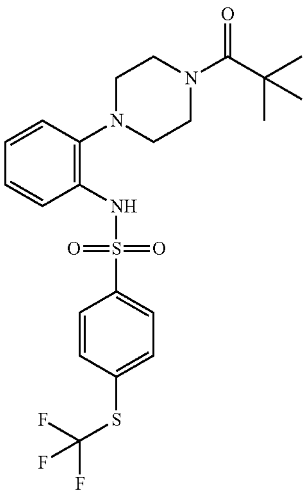 [SMILES: CC(C)(C)C(=O)N1CCN(c2ccccc2NS(=O)(=O)c2ccc(SC(F)(F)F)cc2)CC1] | A-574 |

TABLE A-continued
| Structure | Compound No. |
| --- | --- |
| 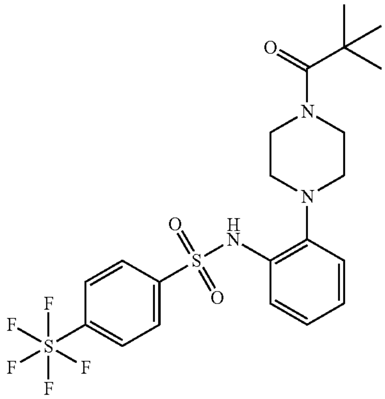 [SMILES: CC(C)(C)C(=O)N1CCN(c2ccccc2NS(=O)(=O)c2ccc(S(F)(F)(F)(F)F)cc2)CC1] | A-575 |
| 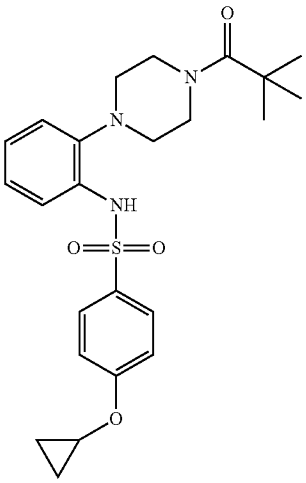 [SMILES: CC(C)(C)C(=O)N1CCN(c2ccccc2NS(=O)(=O)c2ccc(OC3CC3)cc2)CC1] | A-576 |
| 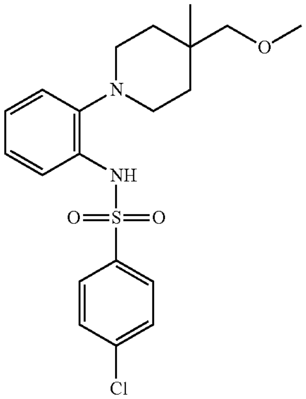 [SMILES: COCC1(C)CCN(c2ccccc2NS(=O)(=O)c2ccc(Cl)cc2)CC1] | A-577 |

TABLE A-continued
| Structure | Compound No. |
|---|---|
| 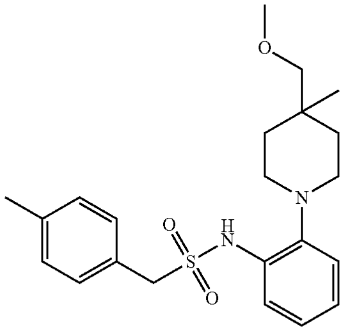 | A-578 |
| 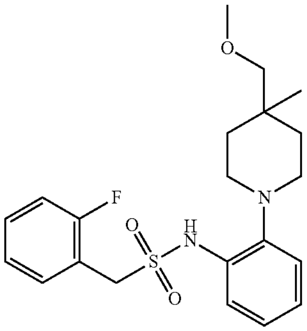 [SMILES: COCC1(C)CCN(c2ccccc2NS(=O)(=O)Cc2ccccc2F)CC1] | A-579 |
| 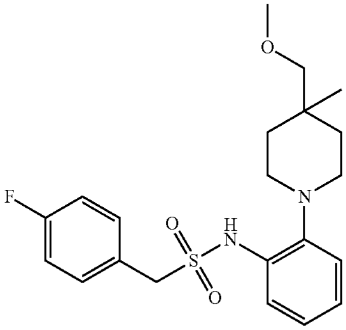 [SMILES: COCC1(C)CCN(c2ccccc2NS(=O)(=O)Cc2ccc(F)cc2)CC1] | A-580 |
| 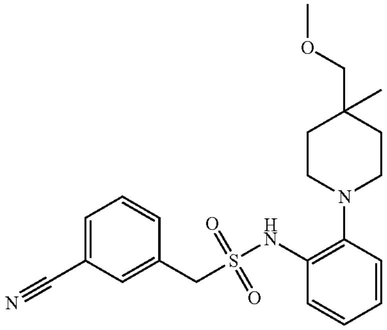 [SMILES: COCC1(C)CCN(c2ccccc2NS(=O)(=O)Cc2cccc(C#N)c2)CC1] | A-581 |

TABLE A-continued
| Structure | Compound No. |
|---|---|
| 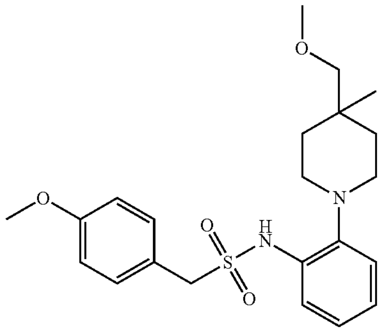 | A-582 |
| 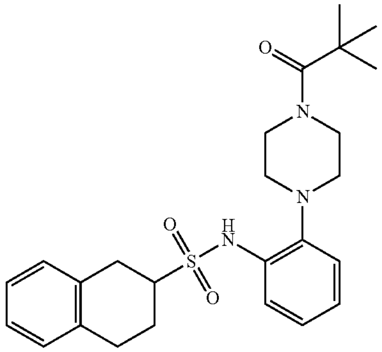 [SMILES: CC(C)(C)C(=O)N1CCN(c2ccccc2NS(=O)(=O)C2CCc3ccccc3C2)CC1] | A-583 |
| 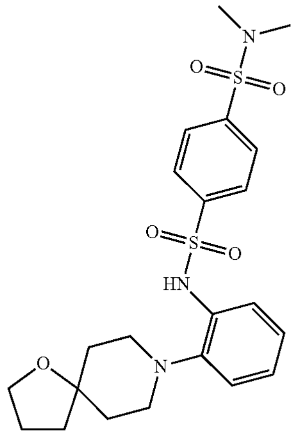 [SMILES: CN(C)S(=O)(=O)c1ccc(S(=O)(=O)Nc2ccccc2N2CCC3(CCCO3)CC2)cc1] | A-584 |
| 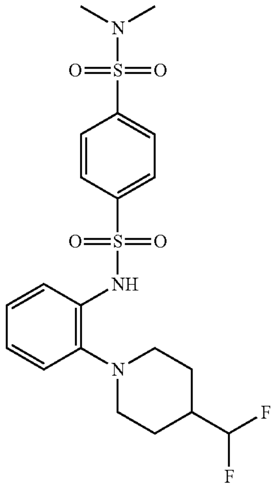 [SMILES: CN(C)S(=O)(=O)c1ccc(S(=O)(=O)Nc2ccccc2N2CCC(C(F)F)CC2)cc1] | A-585 |

TABLE A-continued
| Structure | Compound No. |
|---|---|
| 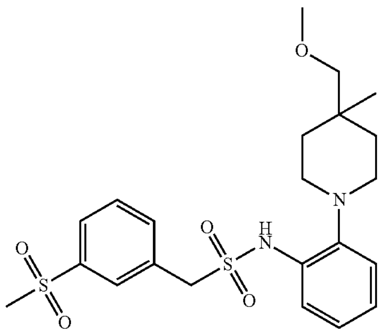 | A-586 |
| 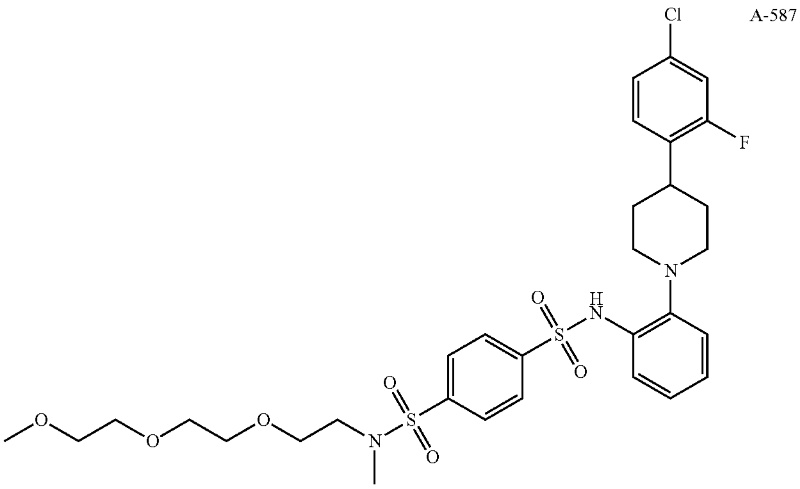 | A-587 |
| 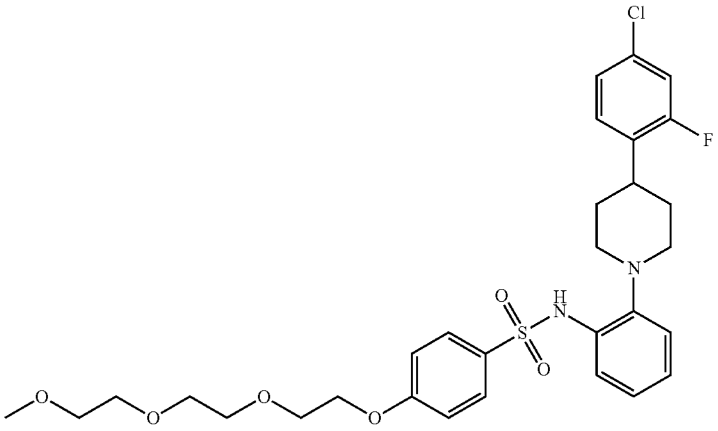 [SMILES: COCCOCCOCCOc1ccc(S(=O)(=O)Nc2ccccc2N2CCC(c3ccc(Cl)cc3F)CC2)cc1] | A-588 |

TABLE A-continued
| Structure | Compound No. |
| --- | --- |
| 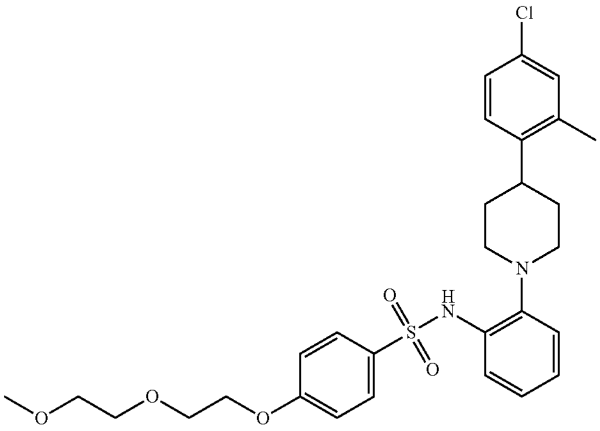 | A-589 |
| 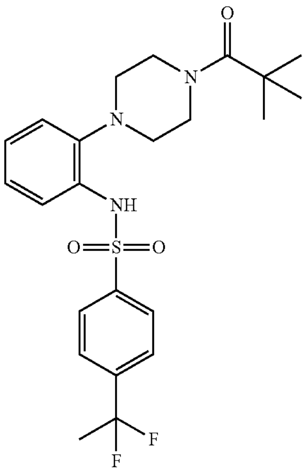 [SMILES: CC(C)(C)C(=O)N1CCN(c2ccccc2NS(=O)(=O)c2ccc(C(C)(F)F)cc2)CC1] | A-590 |
| 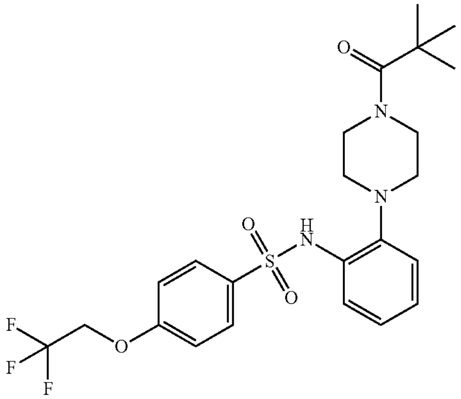 [SMILES: CC(C)(C)C(=O)N1CCN(c2ccccc2NS(=O)(=O)c2ccc(OCC(F)(F)F)cc2)CC1] | A-591 |

TABLE A-continued
| Structure | Compound No. |
| --- | --- |
| 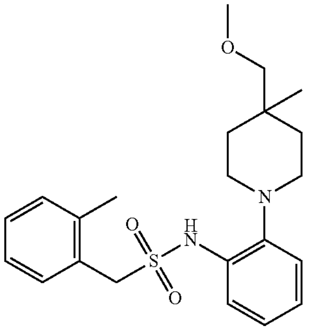 [SMILES: COCC1(C)CCN(c2ccccc2NS(=O)(=O)Cc2ccccc2C)CC1] | A-592 |
| 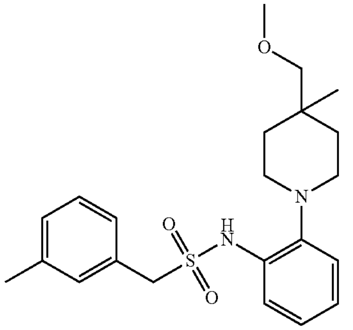 | A-593 |
| 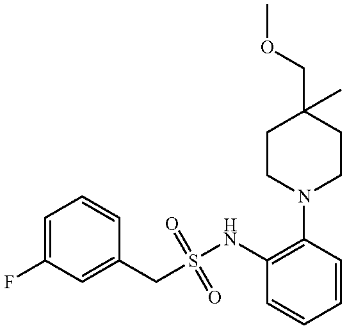 [SMILES: COCC1(C)CCN(c2ccccc2NS(=O)(=O)Cc2cccc(F)c2)CC1] | A-594 |
| 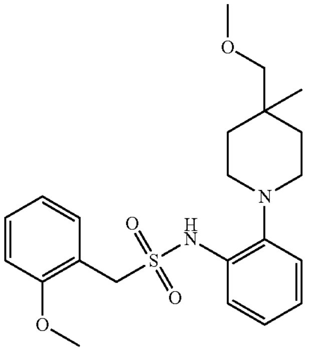 [SMILES: COCC1(C)CCN(c2ccccc2NS(=O)(=O)Cc2ccccc2OC)CC1] | A-595 |

TABLE A-continued
| Structure | Compound No. |
| --- | --- |
| 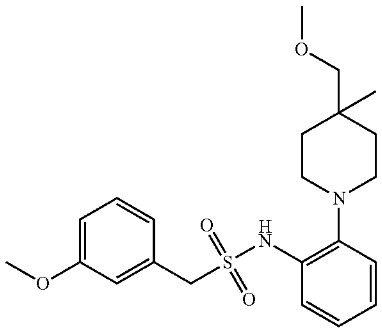 | A-596 |
| 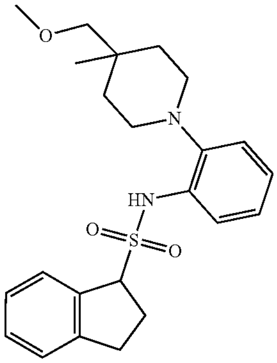 [SMILES: COCC1(C)CCN(c2ccccc2NS(=O)(=O)C2CCc3ccccc32)CC1] | A-597 |
| 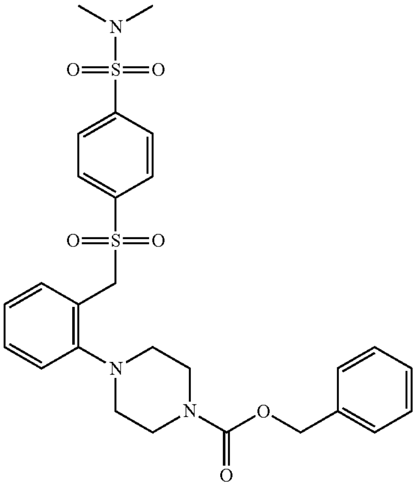 [SMILES: CN(C)S(=O)(=O)c1ccc(S(=O)(=O)Cc2ccccc2N2CCN(C(=O)OCc3ccccc3)CC2)cc1] | A-598 |

TABLE A-continued
| Structure | Compound No. |
| --- | --- |
| 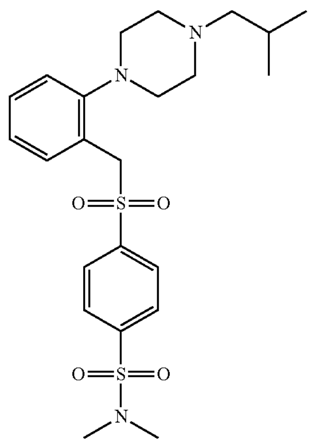 [SMILES: CC(C)CN1CCN(c2ccccc2CS(=O)(=O)c2ccc(S(=O)(=O)N(C)C)cc2)CC1] | A-599 |
| 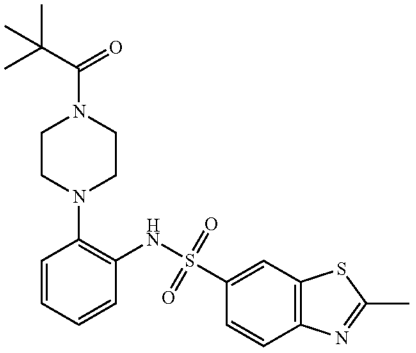 [SMILES: Cc1nc2ccc(S(=O)(=O)Nc3ccccc3N3CCN(C(=O)C(C)(C)C)CC3)cc2s1] | A-600 |
| 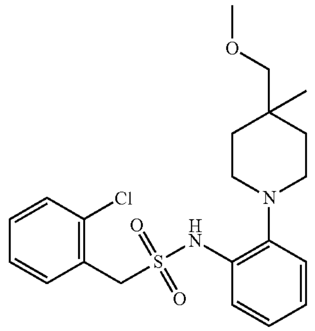 [SMILES: COCC1(C)CCN(c2ccccc2NS(=O)(=O)Cc2ccccc2Cl)CC1] | A-601 |
| 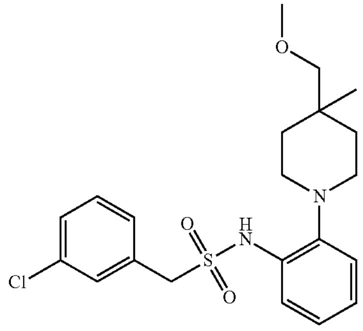 [SMILES: COCC1(C)CCN(c2ccccc2NS(=O)(=O)Cc2cccc(Cl)c2)CC1] | A-602 |

TABLE A-continued
| Structure | Compound No. |
|---|---|
| 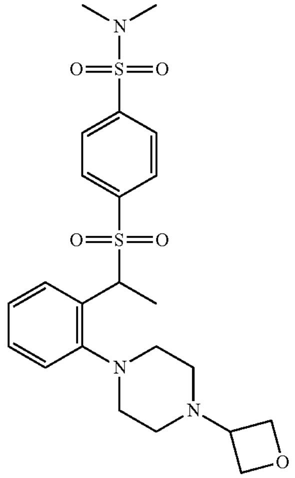 [SMILES: CC(c1ccccc1N1CCN(C2COC2)CC1)S(=O)(=O)c1ccc(S(=O)(=O)N(C)C)cc1] | A-603 |
| 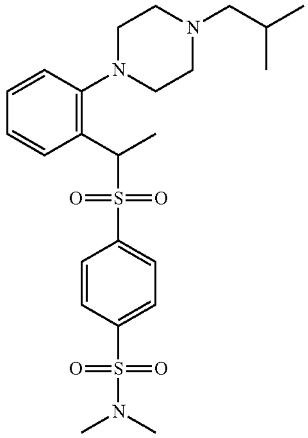 [SMILES: CC(C)CN1CCN(c2ccccc2C(C)S(=O)(=O)c2ccc(S(=O)(=O)N(C)C)cc2)CC1] | A-604 |
| 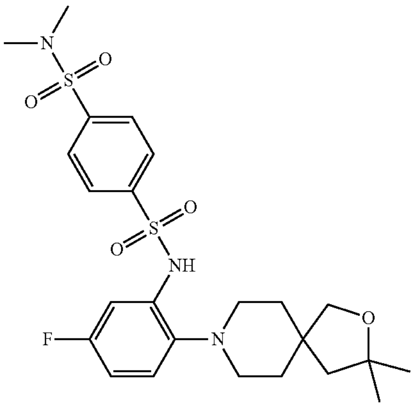 | A-605 |

TABLE A-continued
| Structure | Compound No. |
| --- | --- |
| 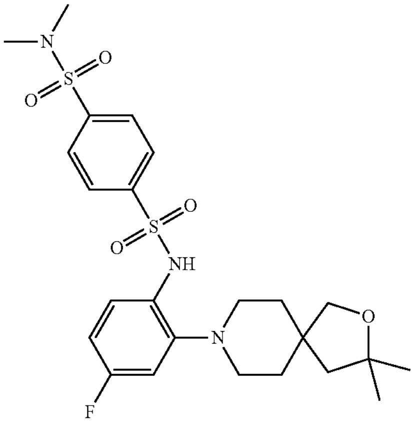 | A-606 |
| 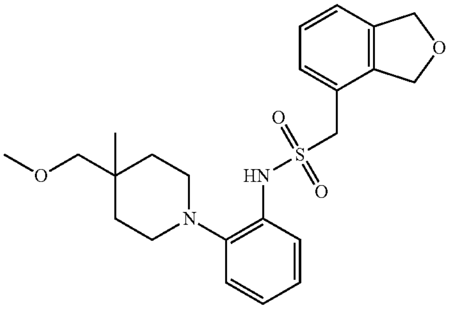 [SMILES: COCC1(C)CCN(c2ccccc2NS(=O)(=O)Cc2cccc3c2COC3)CC1] | A-607 |
| 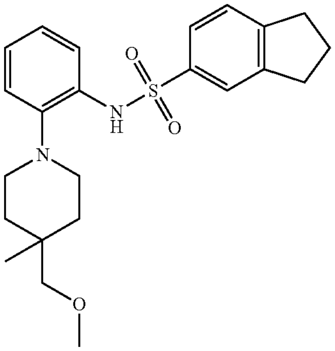 [SMILES: COCC1(C)CCN(c2ccccc2NS(=O)(=O)c2ccc3c(c2)CCC3)CC1] | A-608 |
| 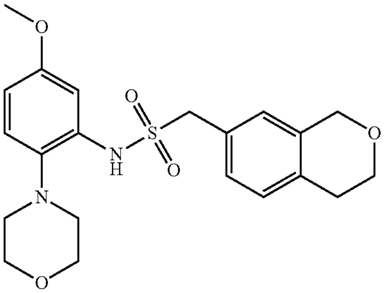 [SMILES: COc1ccc(N2CCOCC2)c(NS(=O)(=O)Cc2ccc3c(c2)COCC3)c1] | A-609 |

TABLE A-continued
| Structure | Compound No. |
|---|---|
| 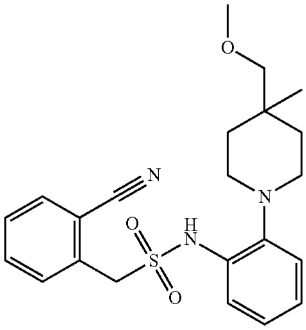 [SMILES: COCC1(C)CCN(c2ccccc2NS(=O)(=O)Cc2ccccc2C#N)CC1] | A-610 |
| 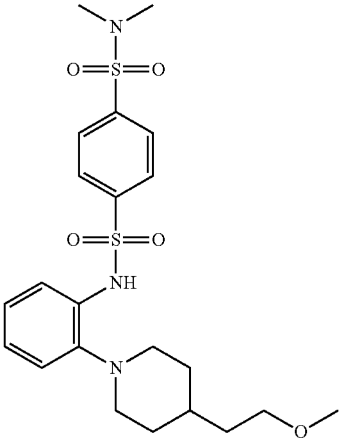 [SMILES: COCCC1CCN(c2ccccc2NS(=O)(=O)c2ccc(S(=O)(=O)N(C)C)cc2)CC1] | A-611 |
| 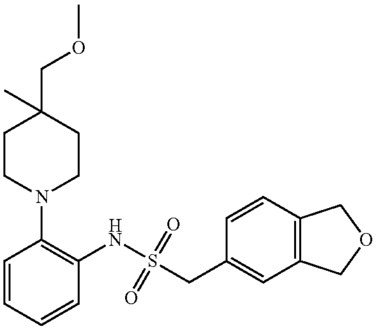 [SMILES: COCC1(C)CCN(c2ccccc2NS(=O)(=O)Cc2ccc3c(c2)COC3)CC1] | A-612 |
| 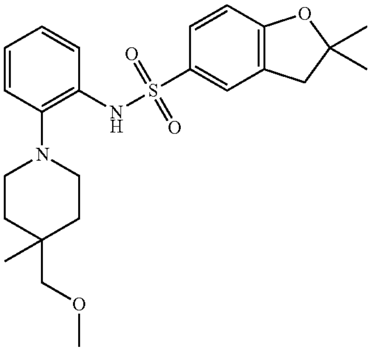 [SMILES: COCC1(C)CCN(c2ccccc2NS(=O)(=O)c2ccc3c(c2)CC(C)(C)O3)CC1] | A-613 |

TABLE A-continued
| Structure | Compound No. |
|---|---|
| 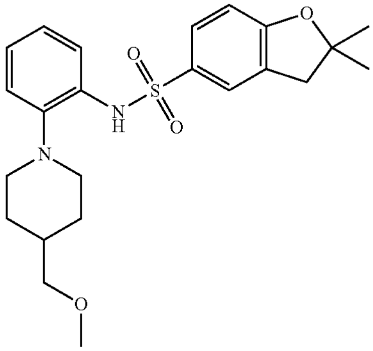 [SMILES: COCC1CCN(c2ccccc2NS(=O)(=O)c2ccc3c(c2)CC(C)(C)O3)CC1] | A-614 |
| 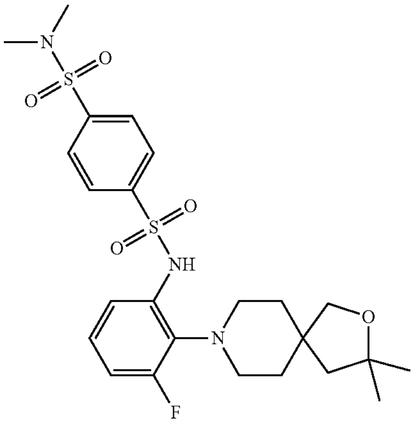 | A-615 |
| 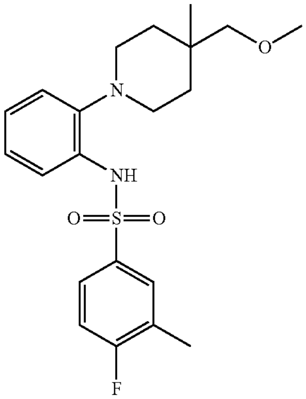 [SMILES: COCC1(C)CCN(c2ccccc2NS(=O)(=O)c2ccc(F)c(C)c2)CC1] | A-616 |
| 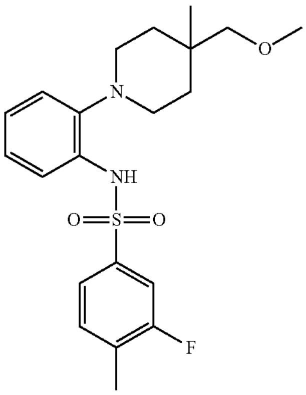 [SMILES: COCC1(C)CCN(c2ccccc2NS(=O)(=O)c2ccc(C)c(F)c2)CC1] | A-617 |

TABLE A-continued
| Structure | Compound No. |
|---|---|
| 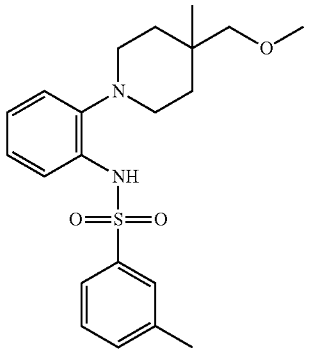 [SMILES: COCC1(C)CCN(c2ccccc2NS(=O)(=O)c2cccc(C)c2)CC1] | A-618 |
| 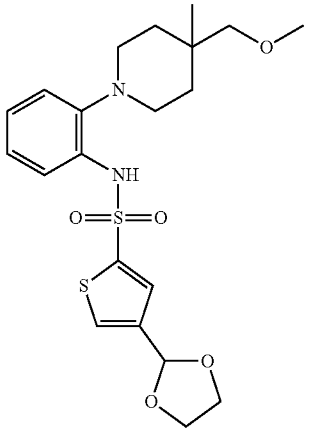 [SMILES: COCC1(C)CCN(c2ccccc2NS(=O)(=O)c2cc(C3OCCO3)cs2)CC1] | A-619 |
| 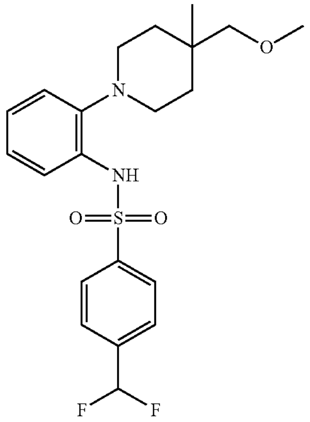 [SMILES: COCC1(C)CCN(c2ccccc2NS(=O)(=O)c2ccc(C(F)F)cc2)CC1] | A-620 |

TABLE A-continued
| Structure | Compound No. |
|---|---|
| 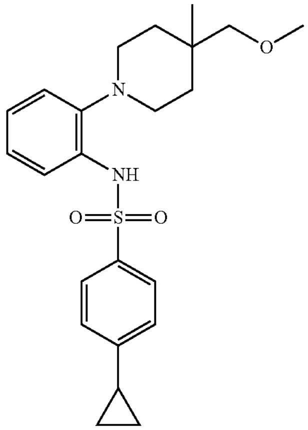 [SMILES: COCC1(C)CCN(c2ccccc2NS(=O)(=O)c2ccc(C3CC3)cc2)CC1] | A-621 |
| 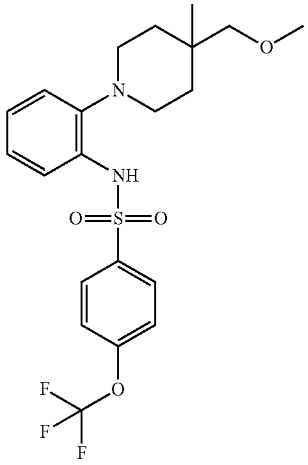 [SMILES: COCC1(C)CCN(c2ccccc2NS(=O)(=O)c2ccc(OC(F)(F)F)cc2)CC1] | A-622 |
| 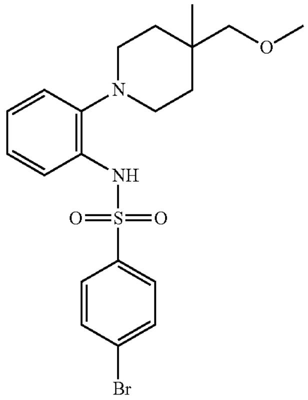 [SMILES: COCC1(C)CCN(c2ccccc2NS(=O)(=O)c2ccc(Br)cc2)CC1] | A-623 |

TABLE A-continued
| Structure | Compound No. |
| --- | --- |
| 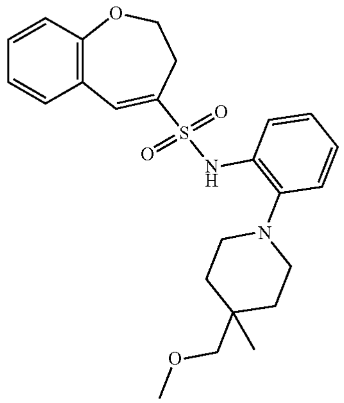 [SMILES: COCC1(C)CCN(c2ccccc2NS(=O)(=O)C2=Cc3ccccc3OCC2)CC1] | A-624 |
| 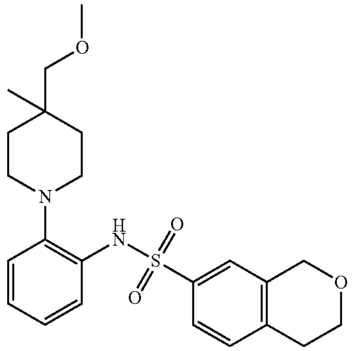 [SMILES: COCC1(C)CCN(c2ccccc2NS(=O)(=O)c2ccc3c(c2)COCC3)CC1] | A-625 |
| 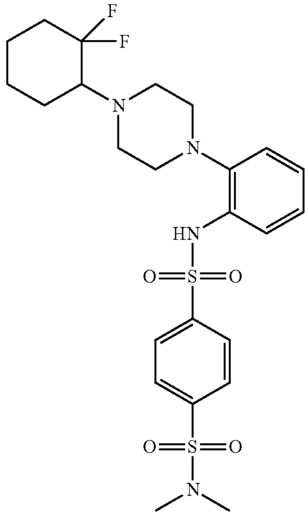 [SMILES: CN(C)S(=O)(=O)c1ccc(S(=O)(=O)Nc2ccccc2N2CCN(C3CCCCC3(F)F)CC2)cc1] | A-626 |
| 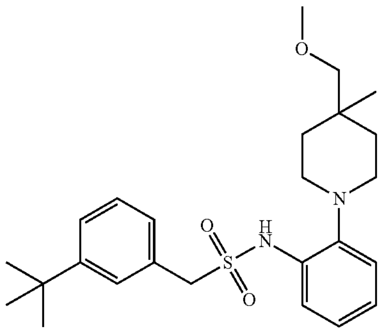 [SMILES: COCC1(C)CCN(c2ccccc2NS(=O)(=O)Cc2cccc(C(C)(C)C)c2)CC1] | A-627 |

TABLE A-continued
| Structure | Compound No. |
| --- | --- |
| 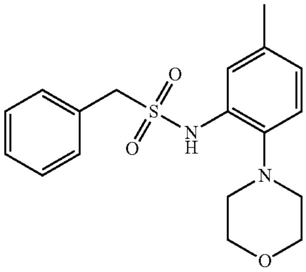 [SMILES: Cc1ccc(N2CCOCC2)c(NS(=O)(=O)Cc2ccccc2)c1] | A-628 |
| 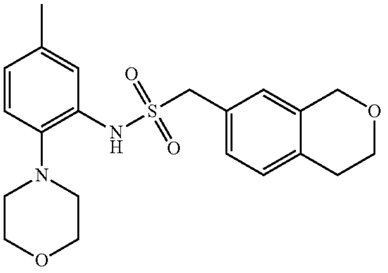 [SMILES: Cc1ccc(N2CCOCC2)c(NS(=O)(=O)Cc2ccc3c(c2)COCC3)c1] | A-629 |
| 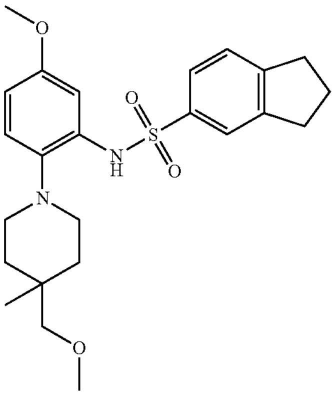 [SMILES: COCC1(C)CCN(c2ccc(OC)cc2NS(=O)(=O)c2ccc3c(c2)CCC3)CC1] | A-630 |
| 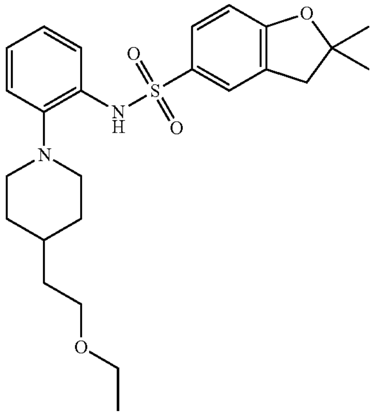 [SMILES: CCOCCC1CCN(c2ccccc2NS(=O)(=O)c2ccc3c(c2)CC(C)(C)O3)CC1] | A-631 |

TABLE A-continued
| Structure | Compound No. |
|---|---|
| 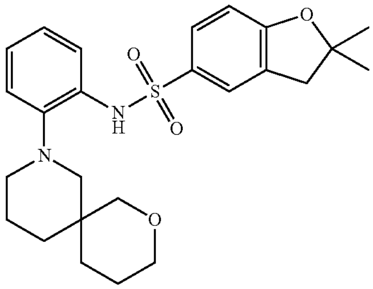 [SMILES: CC1(C)Cc2cc(S(=O)(=O)Nc3ccccc3N3CCCC4(CCCOC4)C3)ccc2O1] | A-632 |
| 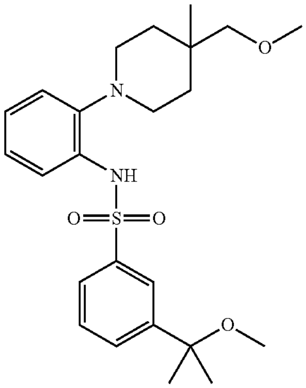 [SMILES: COCC1(C)CCN(c2ccccc2NS(=O)(=O)c2cccc(C(C)(C)OC)c2)CC1] | A-633 |
| 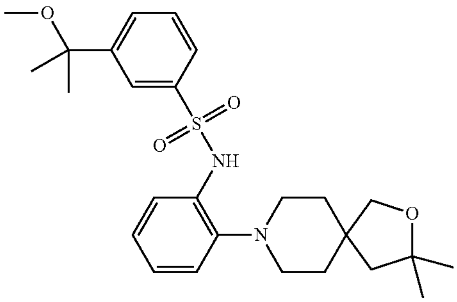 | A-634 |
| 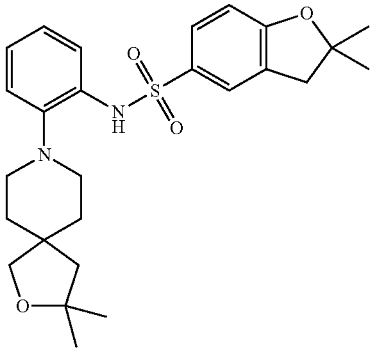 [SMILES: CC1(C)CC2(CCN(c3ccccc3NS(=O)(=O)c3ccc4c(c3)CC(C)(C)O4)CC2)CO1] | A-635 |

TABLE A-continued
| Structure | Compound No. |
| --- | --- |
| 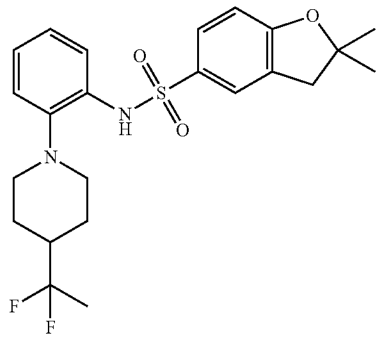 [SMILES: CC1(C)Cc2cc(S(=O)(=O)Nc3ccccc3N3CCC(C(C)(F)F)CC3)ccc2O1] | A-636 |
| 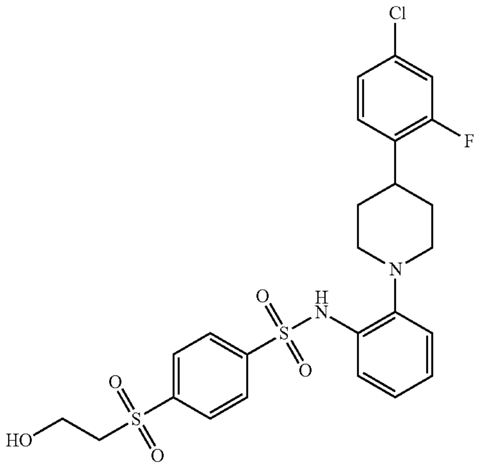 [SMILES: O=S(=O)(CCO)c1ccc(S(=O)(=O)Nc2ccccc2N2CCC(c3ccc(Cl)cc3F)CC2)cc1] | A-637 |
| 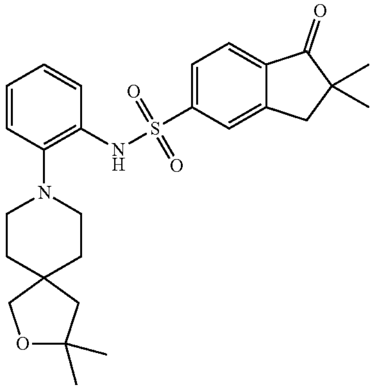 [SMILES: CC1(C)CC2(CCN(c3ccccc3NS(=O)(=O)c3ccc4c(c3)CC(C)(C)C4=O)CC2)CO1] | A-638 |
| 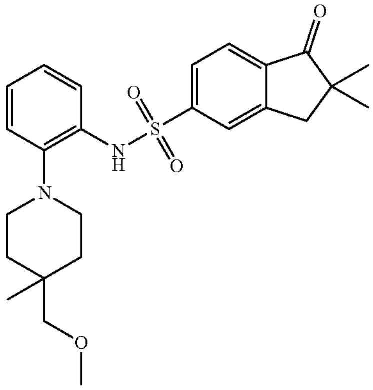 [SMILES: COCC1(C)CCN(c2ccccc2NS(=O)(=O)c2ccc3c(c2)CC(C)(C)C3=O)CC1] | A-639 |

TABLE A-continued
| Structure | Compound No. |
|---|---|
| 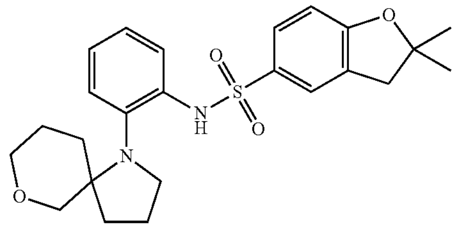 [SMILES: CC1(C)Cc2cc(S(=O)(=O)Nc3ccccc3N3CCCC34CCCOC4)ccc2O1] | A-640 |
| 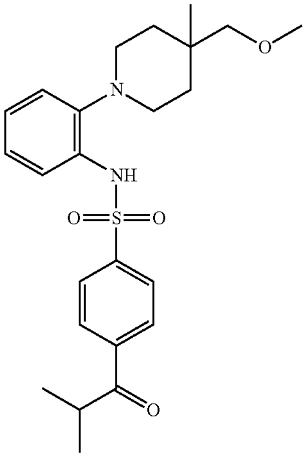 [SMILES: COCC1(C)CCN(c2ccccc2NS(=O)(=O)c2ccc(C(=O)C(C)C)cc2)CC1] | A-641 |
| 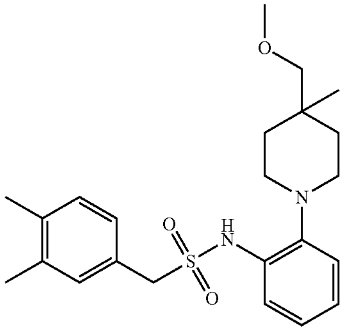 | A-642 |
| 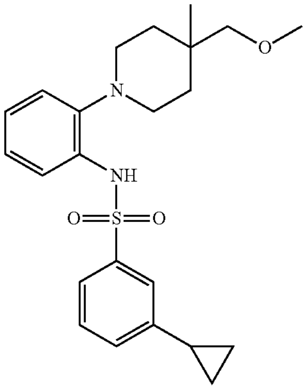 [SMILES: COCC1(C)CCN(c2ccccc2NS(=O)(=O)c2cccc(C3CC3)c2)CC1] | A-643 |

TABLE A-continued
| Structure | Compound No. |
|---|---|
| 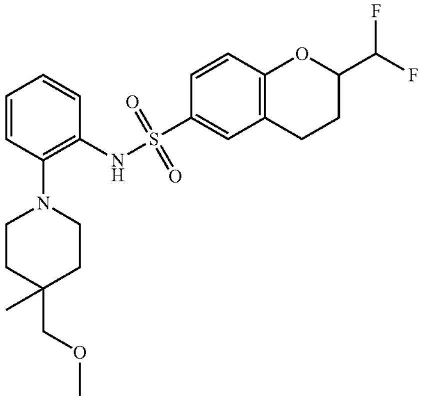 [SMILES: COCC1(C)CCN(c2ccccc2NS(=O)(=O)c2ccc3c(c2)CCC(C(F)F)O3)CC1] | A-644 |
| 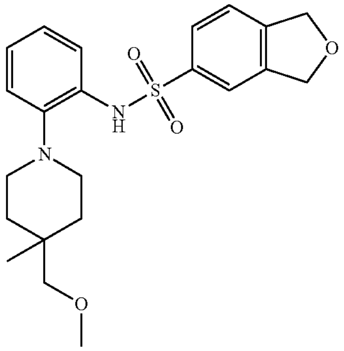 [SMILES: COCC1(C)CCN(c2ccccc2NS(=O)(=O)c2ccc3c(c2)COC3)CC1] | A-645 |
| 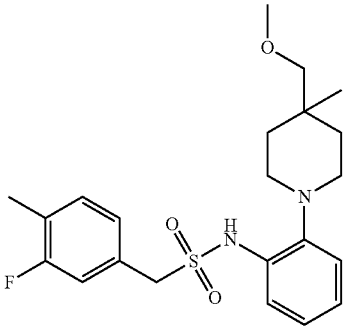 | A-646 |
| 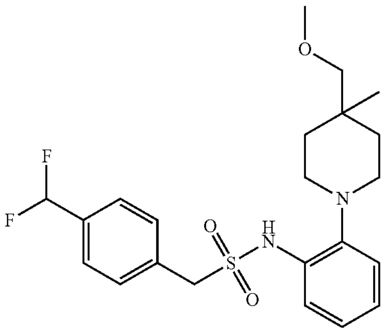 [SMILES: COCC1(C)CCN(c2ccccc2NS(=O)(=O)Cc2ccc(C(F)F)cc2)CC1] | A-647 |

TABLE A-continued
| Structure | Compound No. |
| --- | --- |
| 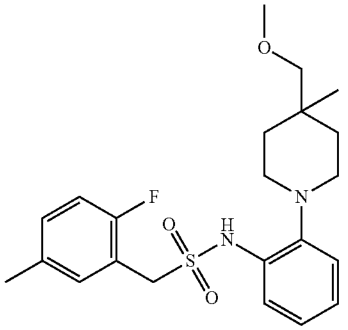 | A-648 |
| 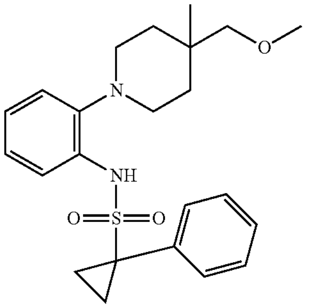 [SMILES: COCC1(C)CCN(c2ccccc2NS(=O)(=O)C2(c3ccccc3)CC2)CC1] | A-649 |
| 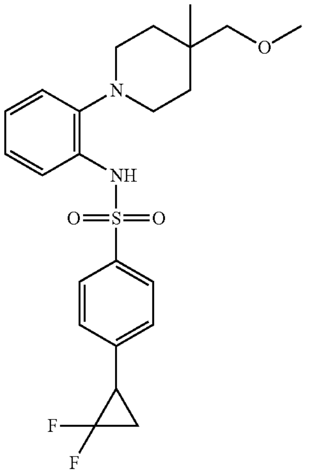 [SMILES: COCC1(C)CCN(c2ccccc2NS(=O)(=O)c2ccc(C3CC3(F)F)cc2)CC1] | A-650 |
| 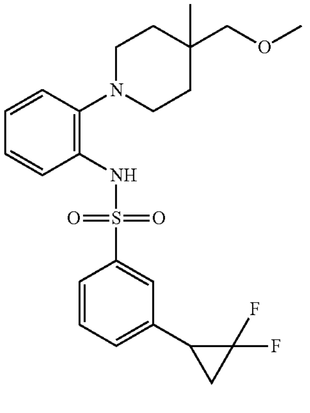 [SMILES: COCC1(C)CCN(c2ccccc2NS(=O)(=O)c2cccc(C3CC3(F)F)c2)CC1] | A-651 |

TABLE A-continued
| Structure | Compound No. |
|---|---|
| 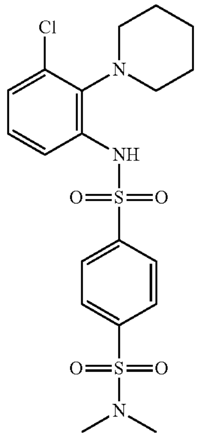 [SMILES: CN(C)S(=O)(=O)c1ccc(S(=O)(=O)Nc2cccc(Cl)c2N2CCCCC2)cc1] | A-652 |
| 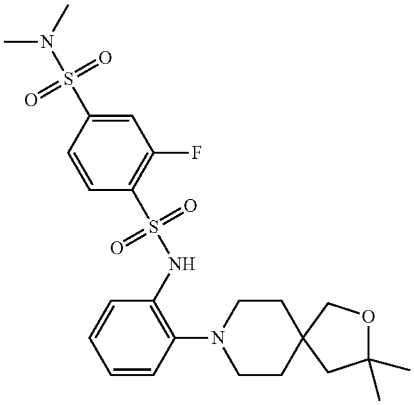 | A-653 |
| 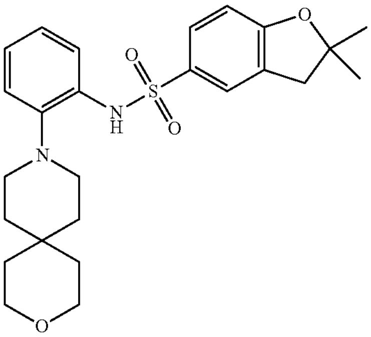 [SMILES: CC1(C)Cc2cc(S(=O)(=O)Nc3ccccc3N3CCC4(CCOCC4)CC3)ccc2O1] | A-654 |

TABLE A-continued
| Structure | Compound No. |
| --- | --- |
| 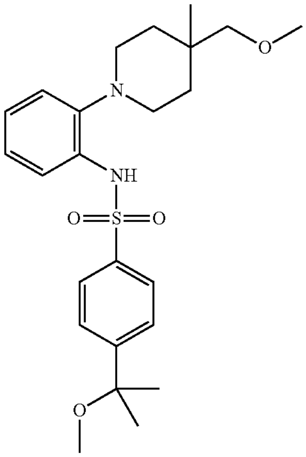 [SMILES: COCC1(C)CCN(c2ccccc2NS(=O)(=O)c2ccc(C(C)(C)OC)cc2)CC1] | A-655 |
| 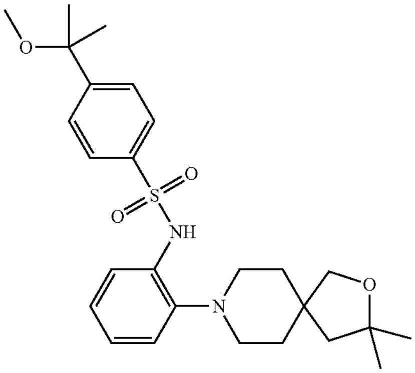 | A-656 |
| 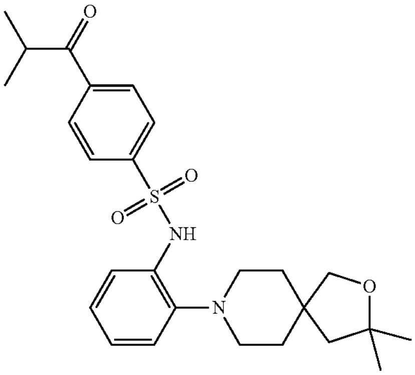 [SMILES: CC(C)C(=O)c1ccc(S(=O)(=O)Nc2ccccc2N2CCC3(CC2)COC(C)(C)C3)cc1] | A-657 |
| 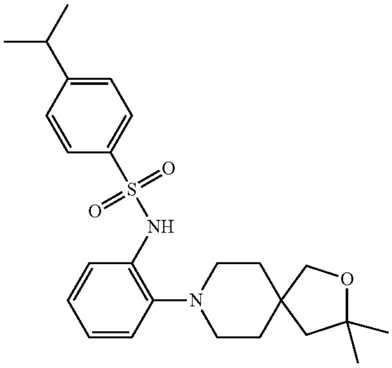 [SMILES: CC(C)c1ccc(S(=O)(=O)Nc2ccccc2N2CCC3(CC2)COC(C)(C)C3)cc1] | A-658 |

TABLE A-continued
| Structure | Compound No. |
|---|---|
| 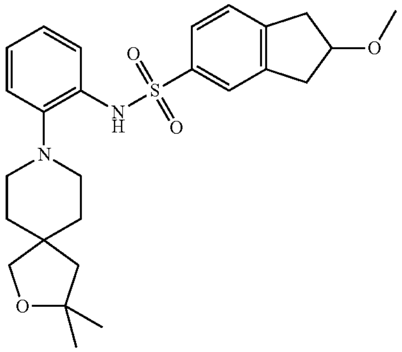 [SMILES: COC1Cc2ccc(S(=O)(=O)Nc3ccccc3N3CCC4(CC3)COC(C)(C)C4)cc2C1] | A-659 |
| 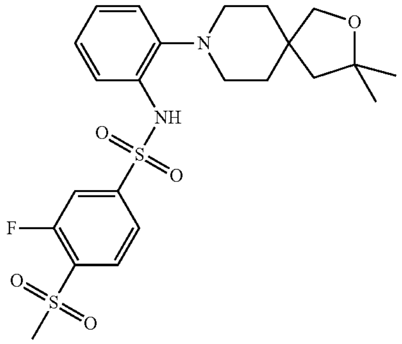 [SMILES: CC1(C)CC2(CCN(c3ccccc3NS(=O)(=O)c3ccc(S(C)(=O)=O)c(F)c3)CC2)CO1] | A-660 |
| 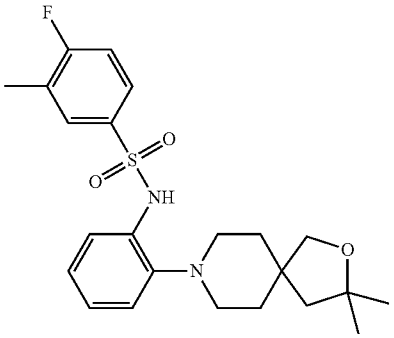 | A-661 |
| 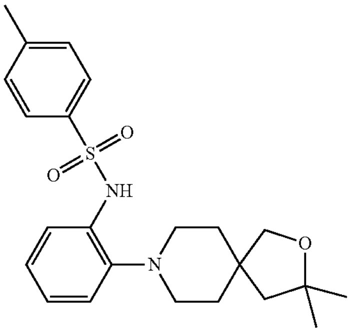 [SMILES: Cc1ccc(S(=O)(=O)Nc2ccccc2N2CCC3(CC2)COC(C)(C)C3)cc1] | A-662 |

TABLE A-continued
| Structure | Compound No. |
|---|---|
| 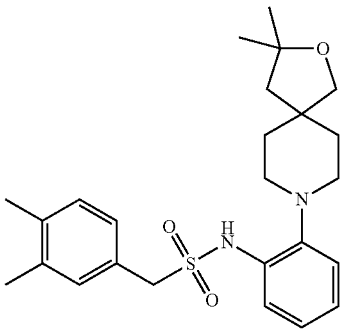 [SMILES: Cc1ccc(CS(=O)(=O)Nc2ccccc2N2CCC3(CC2)COC(C)(C)C3)cc1C] | A-663 |
| 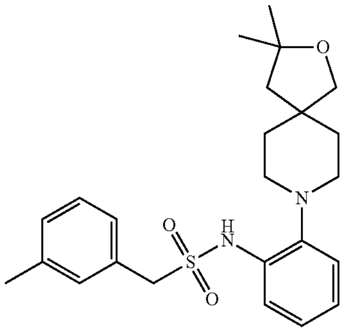 [SMILES: Cc1cccc(CS(=O)(=O)Nc2ccccc2N2CCC3(CC2)COC(C)(C)C3)c1] | A-664 |
| 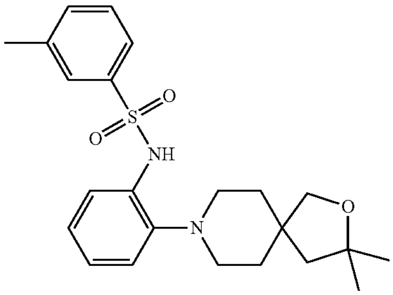 | A-665 |
| 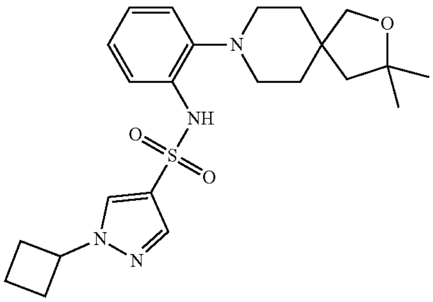 [SMILES: CC1(C)CC2(CCN(c3ccccc3NS(=O)(=O)c3cnn(C4CCC4)c3)CC2)CO1] | A-666 |

TABLE A-continued
| Structure | Compound No. |
|---|---|
| 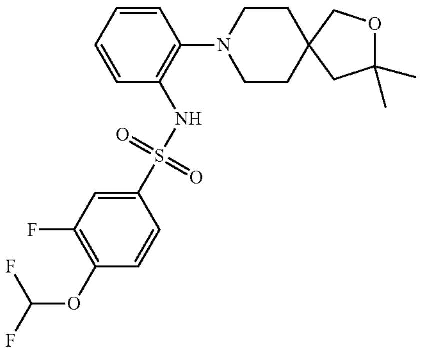 [SMILES: CC1(C)CC2(CCN(c3ccccc3NS(=O)(=O)c3ccc(OC(F)F)c(F)c3)CC2)CO1] | A-667 |
| 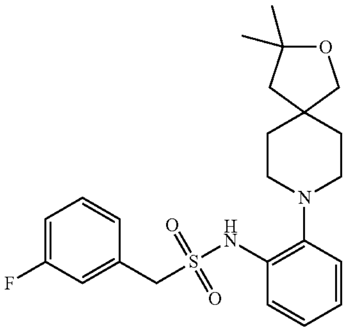 [SMILES: CC1(C)CC2(CCN(c3ccccc3NS(=O)(=O)Cc3cccc(F)c3)CC2)CO1] | A-668 |
| 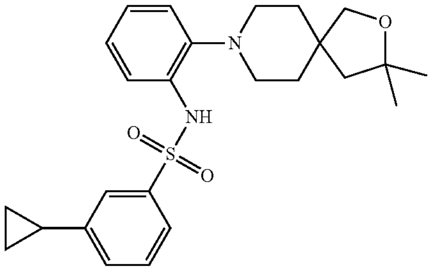 [SMILES: CC1(C)CC2(CCN(c3ccccc3NS(=O)(=O)c3cccc(C4CC4)c3)CC2)CO1] | A-669 |
| 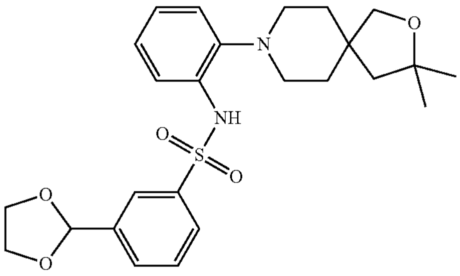 [SMILES: CC1(C)CC2(CCN(c3ccccc3NS(=O)(=O)c3cccc(C4OCCO4)c3)CC2)CO1] | A-670 |
| 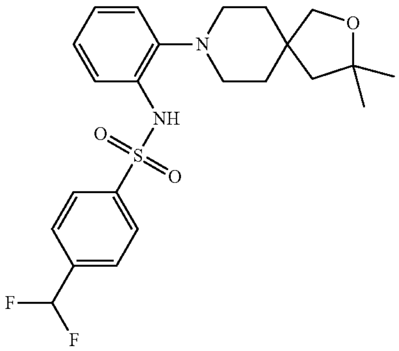 [SMILES: CC1(C)CC2(CCN(c3ccccc3NS(=O)(=O)c3ccc(C(F)F)cc3)CC2)CO1] | A-671 |

TABLE A-continued
| Structure | Compound No. |
|---|---|
| 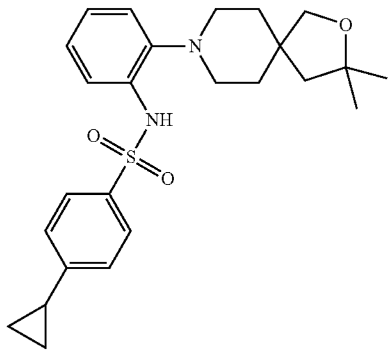 [SMILES: CC1(C)CC2(CCN(c3ccccc3NS(=O)(=O)c3ccc(C4CC4)cc3)CC2)CO1] | A-672 |
| 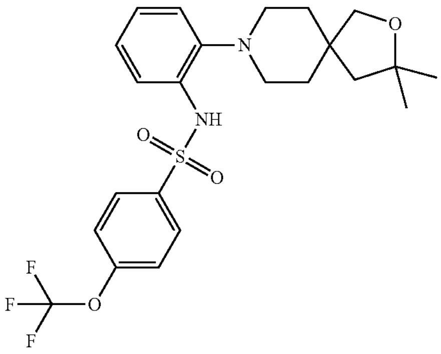 [SMILES: CC1(C)CC2(CCN(c3ccccc3NS(=O)(=O)c3ccc(OC(F)(F)F)cc3)CC2)CO1] | A-673 |
| 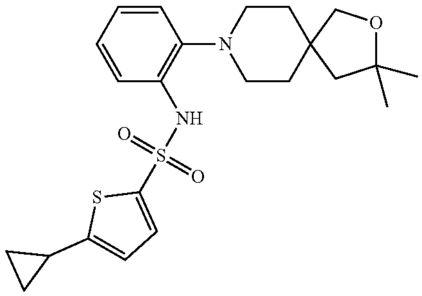 [SMILES: CC1(C)CC2(CCN(c3ccccc3NS(=O)(=O)c3ccc(C4CC4)s3)CC2)CO1] | A-674 |
| 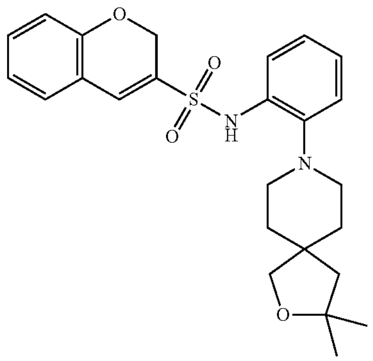 [SMILES: CC1(C)CC2(CCN(c3ccccc3NS(=O)(=O)C3=Cc4ccccc4OC3)CC2)CO1] | A-675 |

TABLE A-continued
| Structure | Compound No. |
| --- | --- |
| 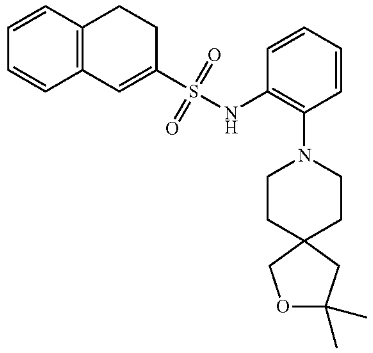 [SMILES: CC1(C)CC2(CCN(c3ccccc3NS(=O)(=O)C3=Cc4ccccc4CC3)CC2)CO1] | A-676 |
| 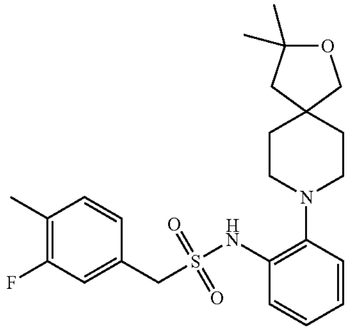 [SMILES: Cc1ccc(CS(=O)(=O)Nc2ccccc2N2CCC3(CC2)COC(C)(C)C3)cc1F] | A-677 |
| 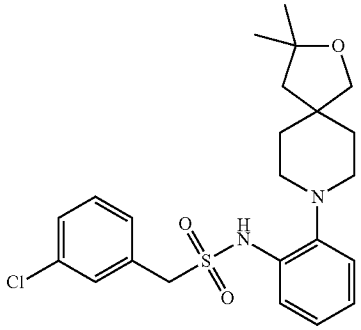 [SMILES: CC1(C)CC2(CCN(c3ccccc3NS(=O)(=O)Cc3cccc(Cl)c3)CC2)CO1] | A-678 |
| 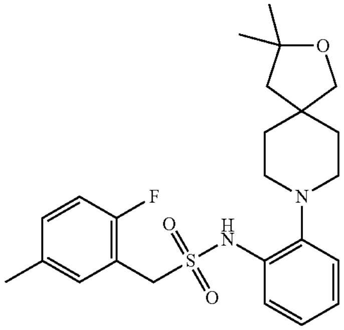 [SMILES: Cc1ccc(F)c(CS(=O)(=O)Nc2ccccc2N2CCC3(CC2)COC(C)(C)C3)c1] | A-679 |

TABLE A-continued
| Structure | Compound No. |
| --- | --- |
| 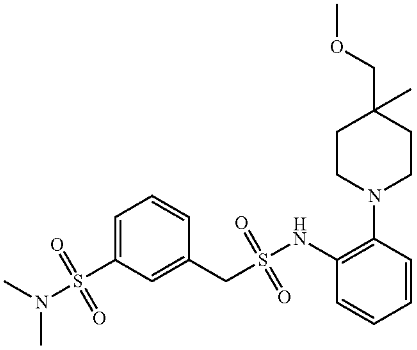 | A-680 |
| 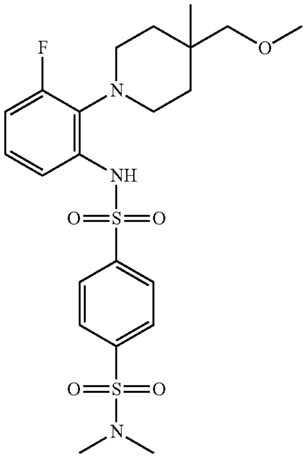 | A-681 |
| 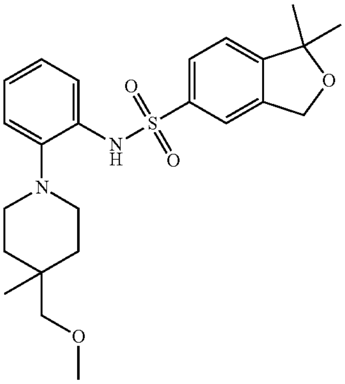 [SMILES: COCC1(C)CCN(c2ccccc2NS(=O)(=O)c2ccc3c(c2)COC3(C)C)CC1] | A-682 |
| 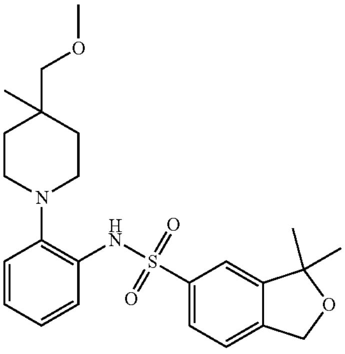 [SMILES: COCC1(C)CCN(c2ccccc2NS(=O)(=O)c2ccc3c(c2)C(C)(C)OC3)CC1] | A-683 |

TABLE A-continued
| Structure | Compound No. |
| --- | --- |
| 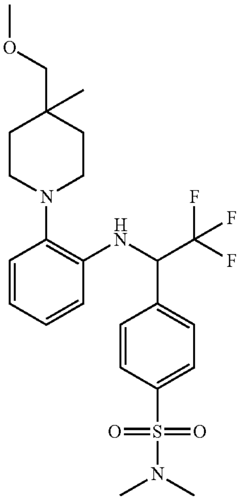 [SMILES: COCC1(C)CCN(c2ccccc2NC(c2ccc(S(=O)(=O)N(C)C)cc2)C(F)(F)F)CC1] | A-684 |
| 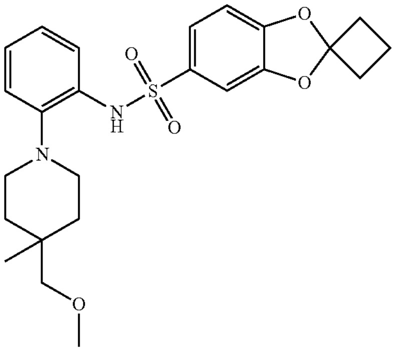 [SMILES: COCC1(C)CCN(c2ccccc2NS(=O)(=O)c2ccc3c(c2)OC2(CCC2)O3)CC1] | A-685 |
| 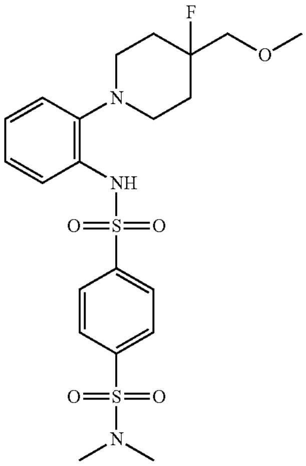 [SMILES: COCC1(F)CCN(c2ccccc2NS(=O)(=O)c2ccc(S(=O)(=O)N(C)C)cc2)CC1] | A-686 |
| 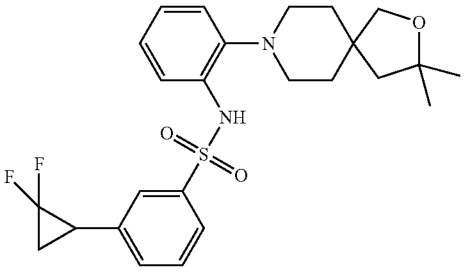 [SMILES: CC1(C)CC2(CCN(c3ccccc3NS(=O)(=O)c3cccc(C4CC4(F)F)c3)CC2)CO1] | A-687 |

TABLE A-continued
| Structure | Compound No. |
| --- | --- |
| 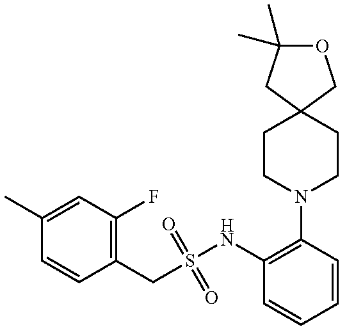 [SMILES: Cc1ccc(CS(=O)(=O)Nc2ccccc2N2CCC3(CC2)COC(C)(C)C3)c(F)c1] | A-688 |
| 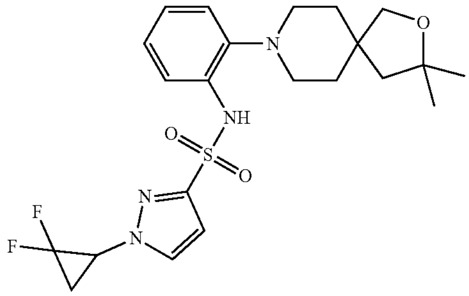 [SMILES: CC1(C)CC2(CCN(c3ccccc3NS(=O)(=O)c3ccn(C4CC4(F)F)n3)CC2)CO1] | A-689 |
| 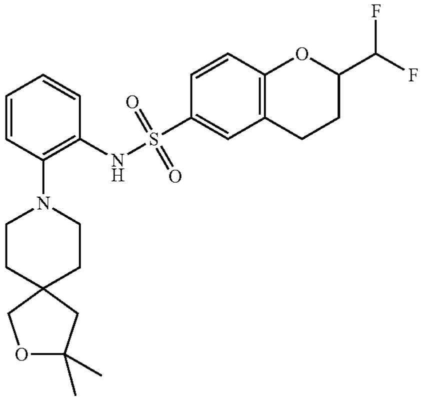 [SMILES: CC1(C)CC2(CCN(c3ccccc3NS(=O)(=O)c3ccc4c(c3)CCC(C(F)F)O4)CC2)CO1] | A-690 |
| 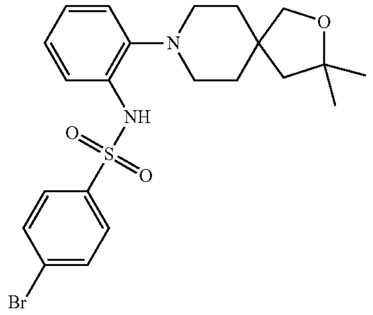 [SMILES: CC1(C)CC2(CCN(c3ccccc3NS(=O)(=O)c3ccc(Br)cc3)CC2)CO1] | A-691 |

TABLE A-continued
| Structure | Compound No. |
|---|---|
| 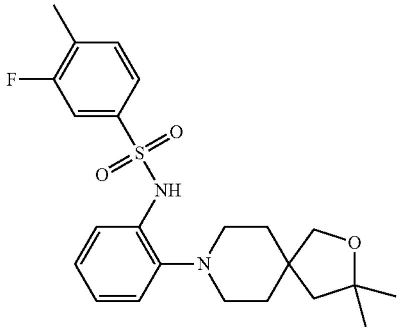 [SMILES: Cc1ccc(S(=O)(=O)Nc2ccccc2N2CCC3(CC2)COC(C)(C)C3)cc1F] | A-692 |
| 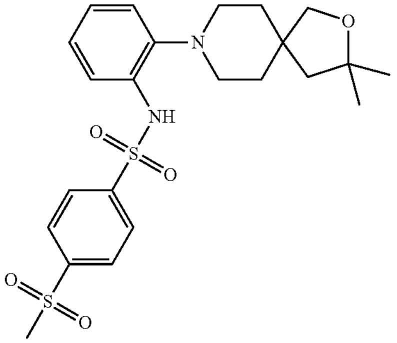 [SMILES: CC1(C)CC2(CCN(c3ccccc3NS(=O)(=O)c3ccc(S(C)(=O)=O)cc3)CC2)CO1] | A-693 |
| 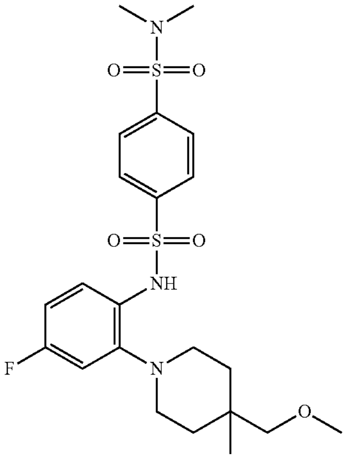 [SMILES: COCC1(C)CCN(c2cc(F)ccc2NS(=O)(=O)c2ccc(S(=O)(=O)N(C)C)cc2)CC1] | A-694 |
| 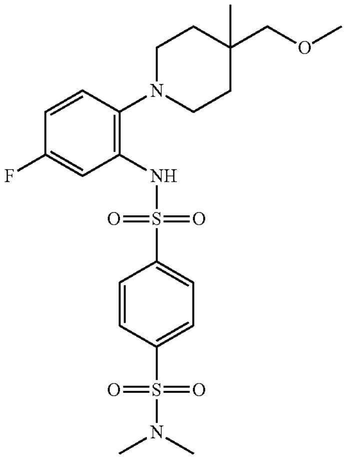 [SMILES: COCC1(C)CCN(c2ccc(F)cc2NS(=O)(=O)c2ccc(S(=O)(=O)N(C)C)cc2)CC1] | A-695 |

TABLE A-continued
| Structure | Compound No. |
| --- | --- |
| 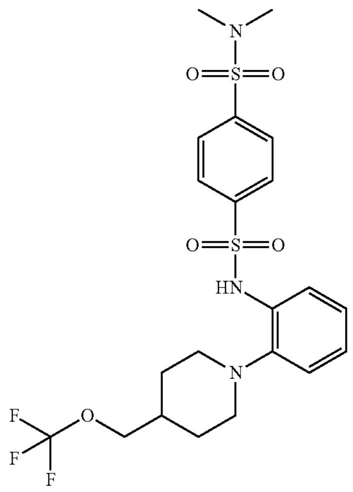 [SMILES: CN(C)S(=O)(=O)c1ccc(S(=O)(=O)Nc2ccccc2N2CCC(COC(F)(F)F)CC2)cc1] | A-696 |
| 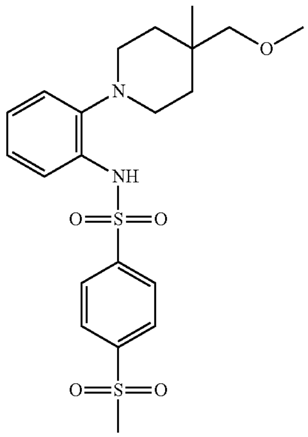 [SMILES: COCC1(C)CCN(c2ccccc2NS(=O)(=O)c2ccc(S(C)(=O)=O)cc2)CC1] | A-697 |
| 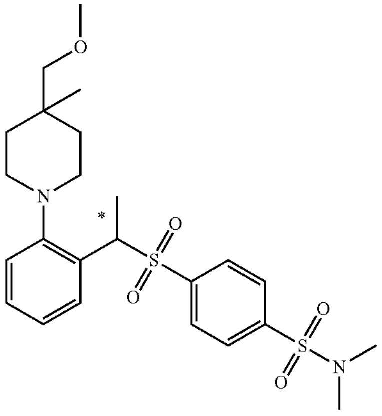<br>Eanantiomer 1 | A-698 |

TABLE A-continued
| Structure | Compound No. |
| --- | --- |
| 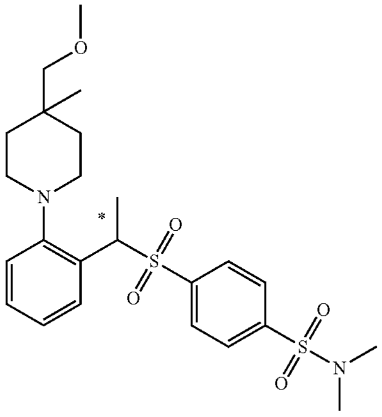 Eanantiomer 2 | A-699 |
| 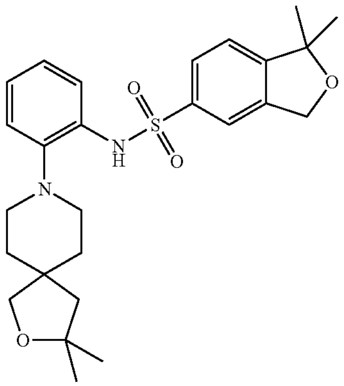 [SMILES: CC1(C)CC2(CCN(c3ccccc3NS(=O)(=O)c3ccc4c(c3)COC4(C)C)CC2)CO1] | A-700 |
| 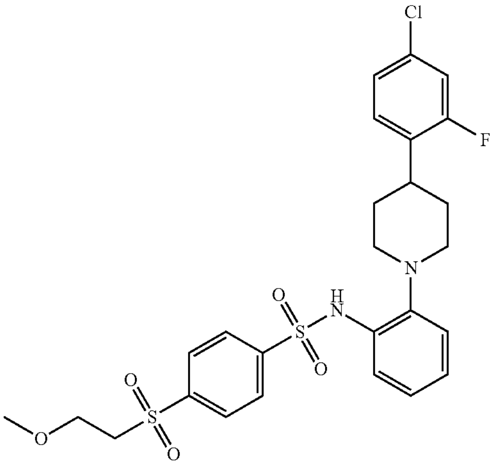 [SMILES: COCCS(=O)(=O)c1ccc(S(=O)(=O)Nc2ccccc2N2CCC(c3ccc(Cl)cc3F)CC2)cc1] | A-701 |

TABLE A-continued
| Structure | Compound No. |
|---|---|
| 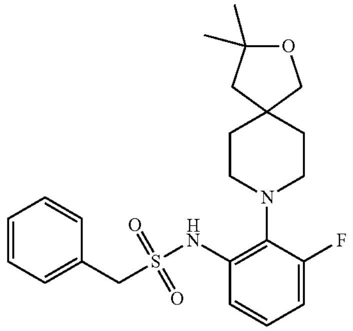 [SMILES: CC1(C)CC2(CCN(c3c(F)cccc3NS(=O)(=O)Cc3ccccc3)CC2)CO1] | A-702 |
| 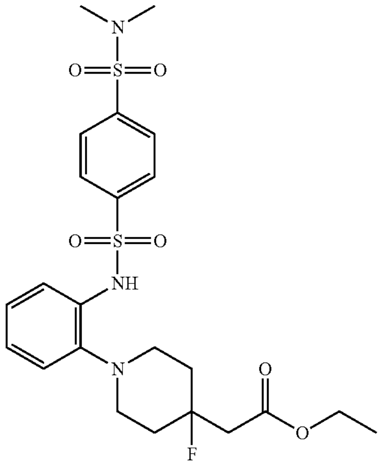 [SMILES: CCOC(=O)CC1(F)CCN(c2ccccc2NS(=O)(=O)c2ccc(S(=O)(=O)N(C)C)cc2)CC1] | A-703 |
| 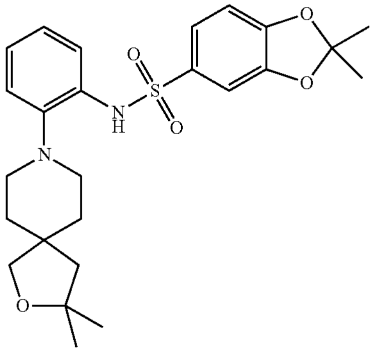 [SMILES: CC1(C)CC2(CCN(c3ccccc3NS(=O)(=O)c3ccc4c(c3)OC(C)(C)O4)CC2)CO1] | A-704 |
| 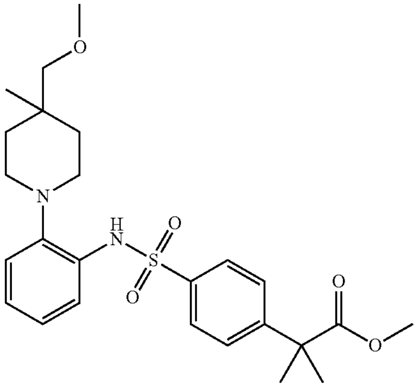 [SMILES: COCC1(C)CCN(c2ccccc2NS(=O)(=O)c2ccc(C(C)(C)C(=O)OC)cc2)CC1] | A-705 |

TABLE A-continued
| Structure | Compound No. |
|---|---|
| 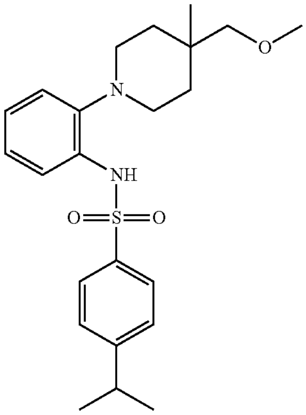 [SMILES: COCC1(C)CCN(c2ccccc2NS(=O)(=O)c2ccc(C(C)C)cc2)CC1] | A-706 |
| 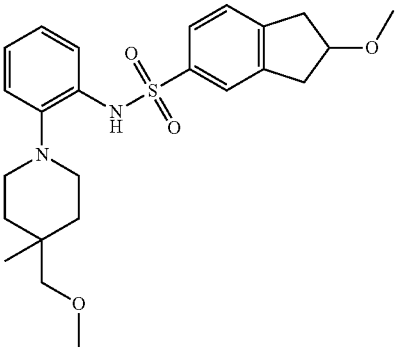 [SMILES: COCC1(C)CCN(c2ccccc2NS(=O)(=O)c2ccc3c(c2)CC(OC)C3)CC1] | A-707 |
| 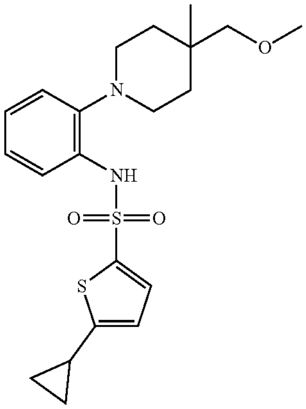 [SMILES: COCC1(C)CCN(c2ccccc2NS(=O)(=O)c2ccc(C3CC3)s2)CC1] | A-708 |
| 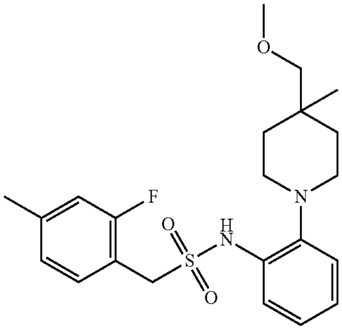 | A-709 |

TABLE A-continued
| Structure | Compound No. |
| --- | --- |
| 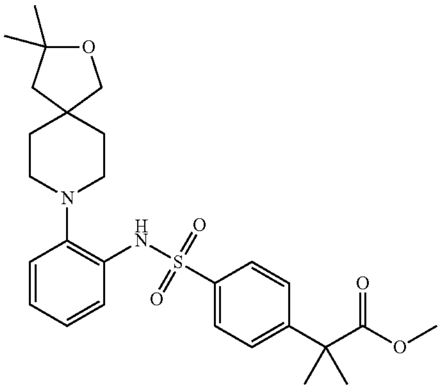 | A-710 |
| 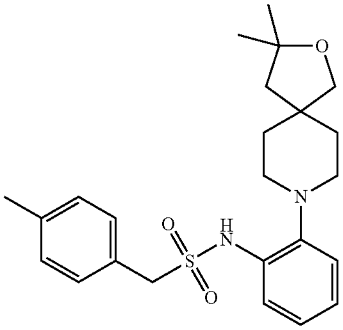 [SMILES: Cc1ccc(CS(=O)(=O)Nc2ccccc2N2CCC3(CC2)COC(C)(C)C3)cc1] | A-711 |
| 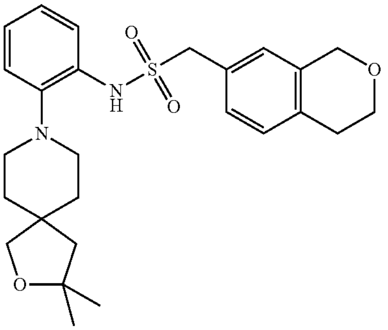 [SMILES: CC1(C)CC2(CCN(c3ccccc3NS(=O)(=O)Cc3ccc4c(c3)COCC4)CC2)CO1] | A-712 |
| 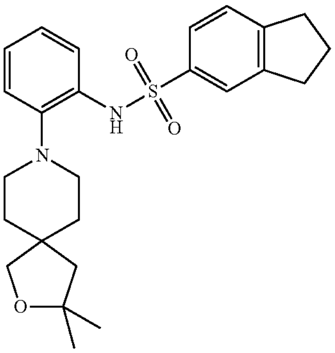 [SMILES: CC1(C)CC2(CCN(c3ccccc3NS(=O)(=O)c3ccc4c(c3)CCC4)CC2)CO1] | A-713 |

TABLE A-continued
| Structure | Compound No. |
|---|---|
| 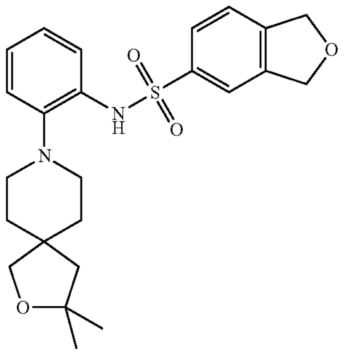 [SMILES: CC1(C)CC2(CCN(c3ccccc3NS(=O)(=O)c3ccc4c(c3)COC4)CC2)CO1] | A-714 |
| 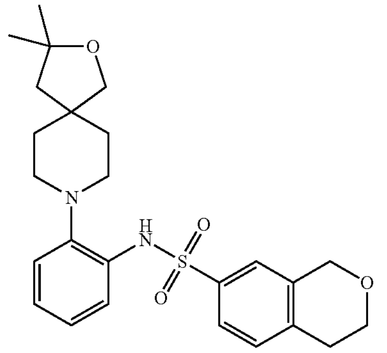 [SMILES: CC1(C)CC2(CCN(c3ccccc3NS(=O)(=O)c3ccc4c(c3)COCC4)CC2)CO1] | A-715 |
| 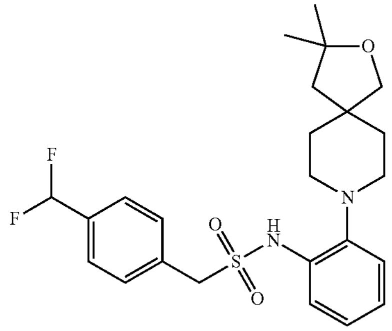 [SMILES: CC1(C)CC2(CCN(c3ccccc3NS(=O)(=O)Cc3ccc(C(F)F)cc3)CC2)CO1] | A-716 |
| 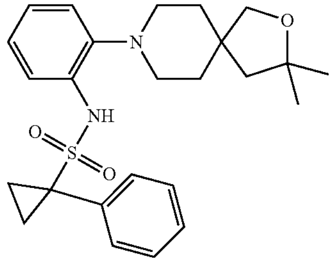 [SMILES: CC1(C)CC2(CCN(c3ccccc3NS(=O)(=O)C3(c4ccccc4)CC3)CC2)CO1] | A-717 |

TABLE A-continued
| Structure | Compound No. |
| --- | --- |
| 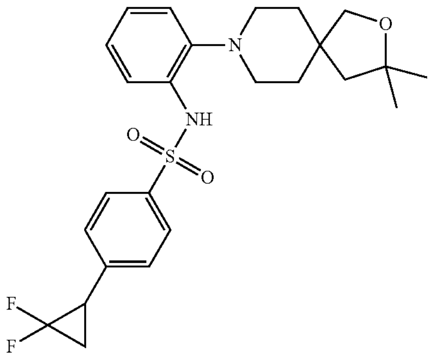 [SMILES: CC1(C)CC2(CCN(c3ccccc3NS(=O)(=O)c3ccc(C4CC4(F)F)cc3)CC2)CO1] | A-718 |
| 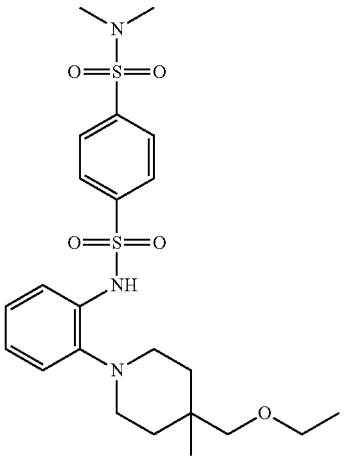 [SMILES: CCOCC1(C)CCN(c2ccccc2NS(=O)(=O)c2ccc(S(=O)(=O)N(C)C)cc2)CC1] | A-719 |
| 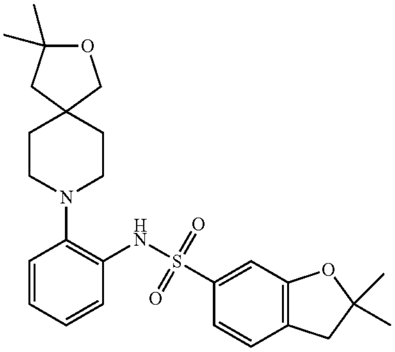 | A-720 |
| 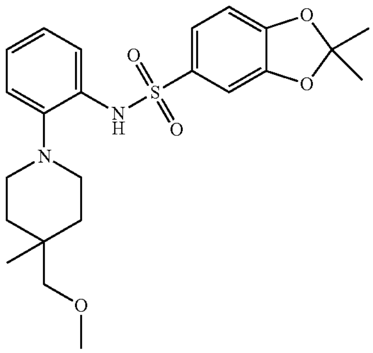 [SMILES: COCC1(C)CCN(c2ccccc2NS(=O)(=O)c2ccc3c(c2)OC(C)(C)O3)CC1] | A-721 |

TABLE A-continued
| Structure | Compound No. |
|---|---|
| 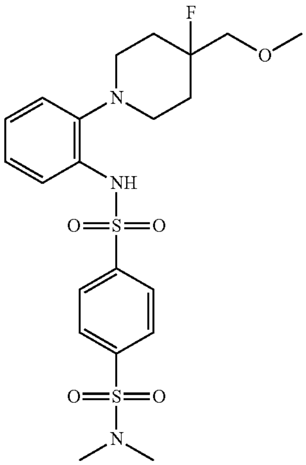 [SMILES: COCC1(F)CCN(c2ccccc2NS(=O)(=O)c2ccc(S(=O)(=O)N(C)C)cc2)CC1] | A-722 |
| 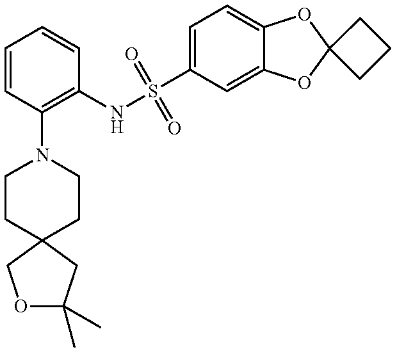 [SMILES: CC1(C)CC2(CCN(c3ccccc3NS(=O)(=O)c3ccc4c(c3)OC3(CCC3)O4)CC2)CO1] | A-723 |
| 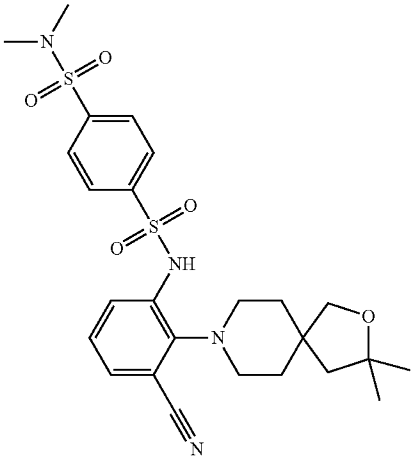 | A-724 |

TABLE A-continued
| Structure | Compound No. |
| --- | --- |
| 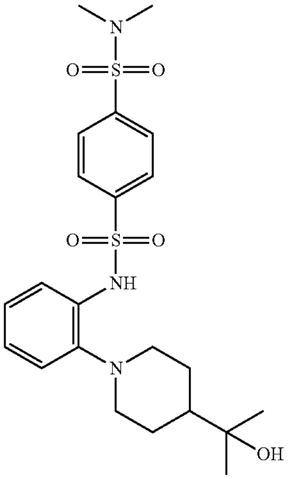 [SMILES: CN(C)S(=O)(=O)c1ccc(S(=O)(=O)Nc2ccccc2N2CCC(C(C)(C)O)CC2)cc1] | A-725 |
| 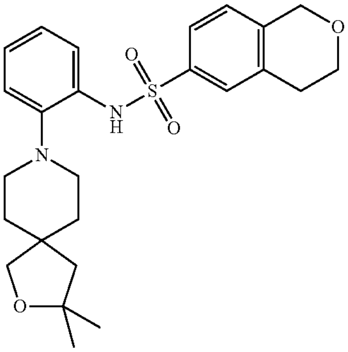 [SMILES: CC1(C)CC2(CCN(c3ccccc3NS(=O)(=O)c3ccc4c(c3)CCOC4)CC2)CO1] | A-726 |
| 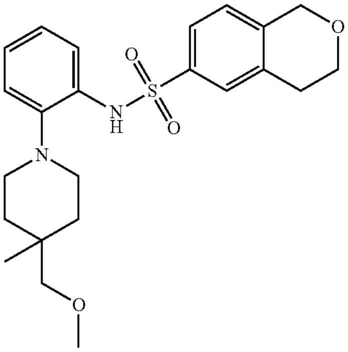 [SMILES: COCC1(C)CCN(c2ccccc2NS(=O)(=O)c2ccc3c(c2)CCOC3)CC1] | A-727 |
| 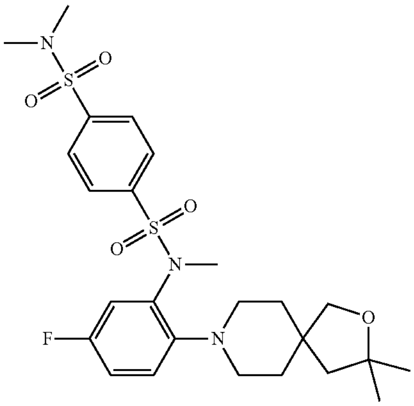 | A-728 |

TABLE A-continued
| Structure | Compound No. |
|---|---|
| 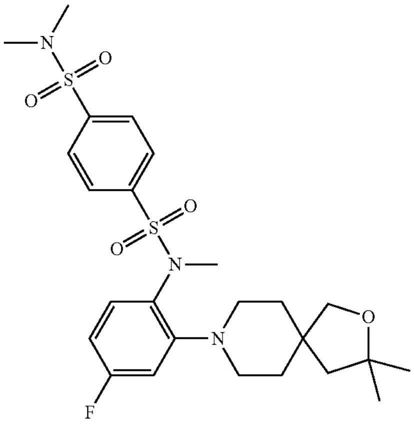 | A-729 |
| 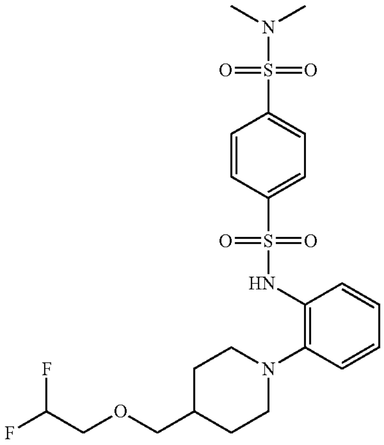 [SMILES: CN(C)S(=O)(=O)c1ccc(S(=O)(=O)Nc2ccccc2N2CCC(COCC(F)F)CC2)cc1] | A-730 |
| 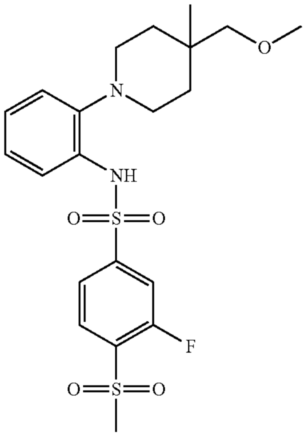 [SMILES: COCC1(C)CCN(c2ccccc2NS(=O)(=O)c2ccc(S(C)(=O)=O)c(F)c2)CC1] | A-731 |

TABLE A-continued
| Structure | Compound No. |
|---|---|
| 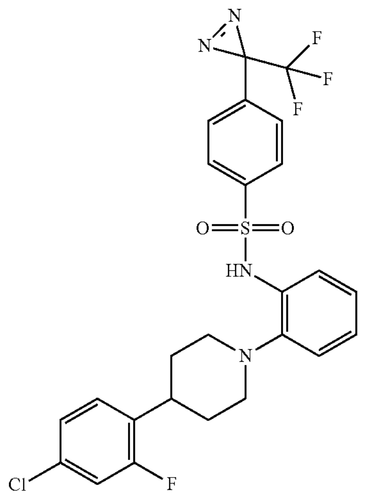 [SMILES: O=S(=O)(Nc1ccccc1N1CCC(c2ccc(Cl)cc2F)CC1)c1ccc(C2(C(F)(F)F)N=N2)cc1] | A-732 |
| 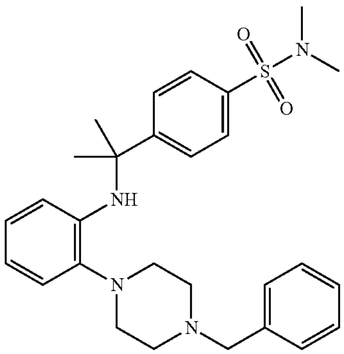 [SMILES: CN(C)S(=O)(=O)c1ccc(C(C)(C)Nc2ccccc2N2CCN(Cc3ccccc3)CC2)cc1] | A-733 |
| 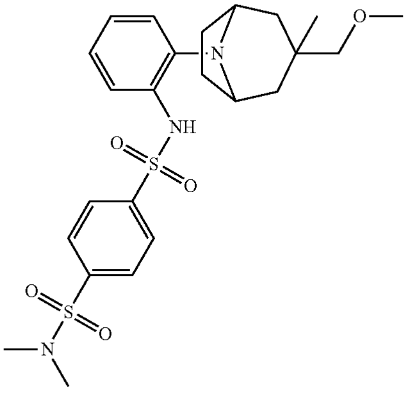 | A-734 |

TABLE A-continued
| Structure | Compound No. |
| --- | --- |
| 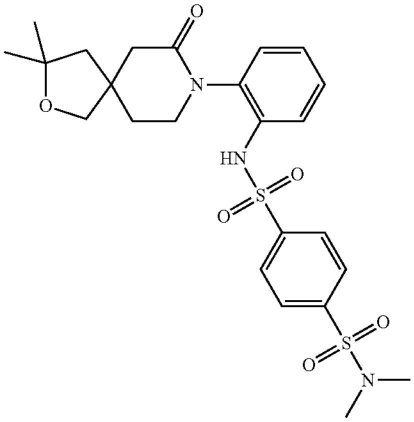 | A-735 |
| 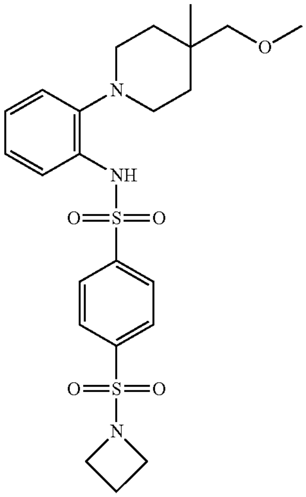 [SMILES: COCC1(C)CCN(c2ccccc2NS(=O)(=O)c2ccc(S(=O)(=O)N3CCC3)cc2)CC1] | A-736 |
| 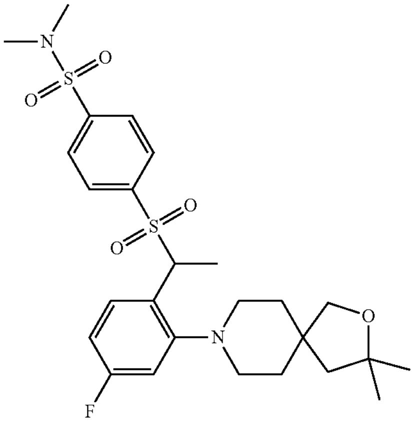 | A-737 |

TABLE A-continued
| Structure | Compound No. |
| --- | --- |
| 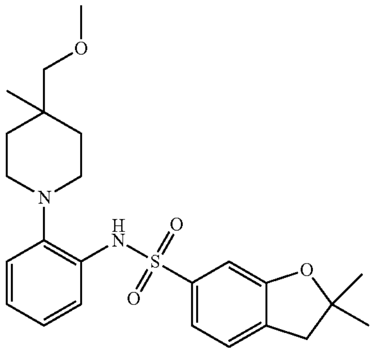 | A-738 |
| 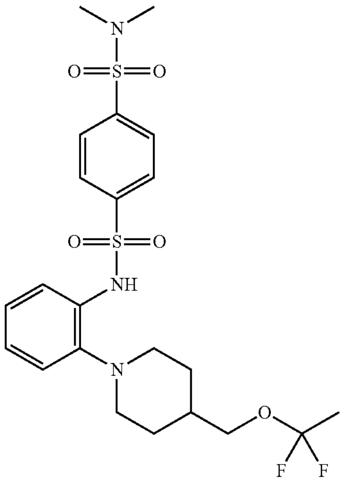 [SMILES: CN(C)S(=O)(=O)c1ccc(S(=O)(=O)Nc2ccccc2N2CCC(COC(C)(F)F)CC2)cc1] | A-739 |
| 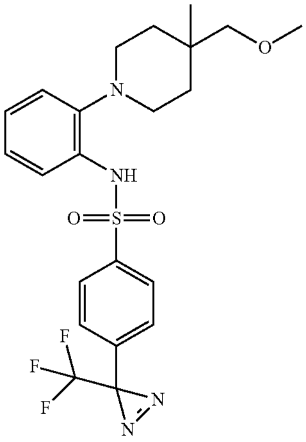 [SMILES: COCC1(C)CCN(c2ccccc2NS(=O)(=O)c2ccc(C3(C(F)(F)F)N=N3)cc2)CC1] | A-740 |

TABLE A-continued
| Structure | Compound No. |
| --- | --- |
| 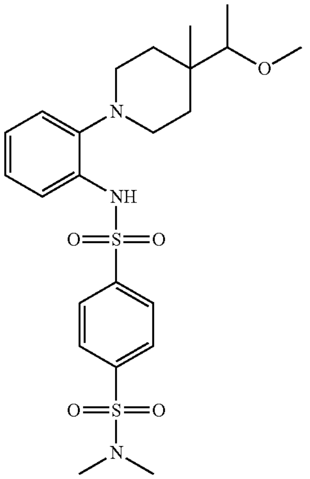 [SMILES: COC(C)C1(C)CCN(c2ccccc2NS(=O)(=O)c2ccc(S(=O)(=O)N(C)C)cc2)CC1] | A-741 |
| 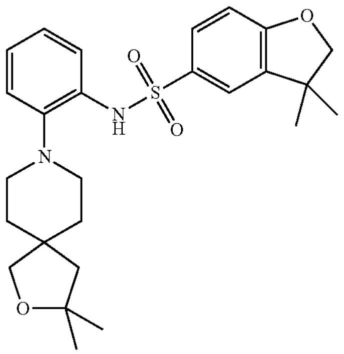 [SMILES: CC1(C)CC2(CCN(c3ccccc3NS(=O)(=O)c3ccc4c(c3)C(C)(C)CO4)CC2)CO1] | A-742 |
| 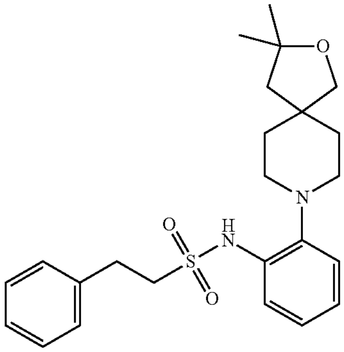 [SMILES: CC1(C)CC2(CCN(c3ccccc3NS(=O)(=O)CCc3ccccc3)CC2)CO1] | A-743 |
| 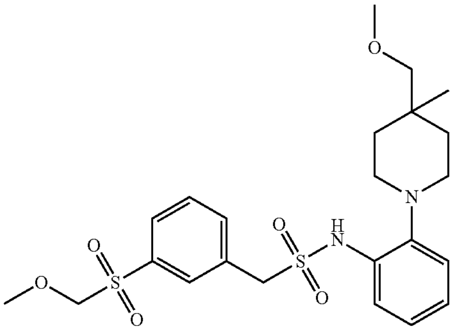 | A-744 |

TABLE A-continued
| Structure | Compound No. |
|---|---|
| 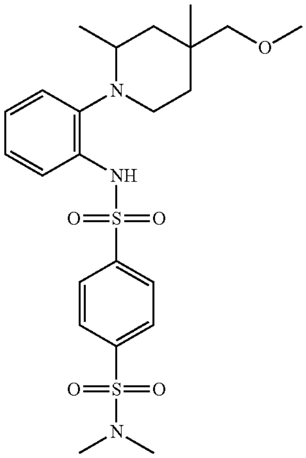 [SMILES: COCC1(C)CCN(c2ccccc2NS(=O)(=O)c2ccc(S(=O)(=O)N(C)C)cc2)C(C)C1] | A-745 |
| 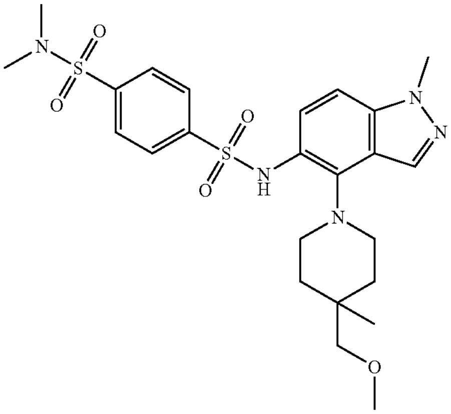 [SMILES: COCC1(C)CCN(c2c(NS(=O)(=O)c3ccc(S(=O)(=O)N(C)C)cc3)ccc3c2cnn3C)CC1] | A-746 |
| 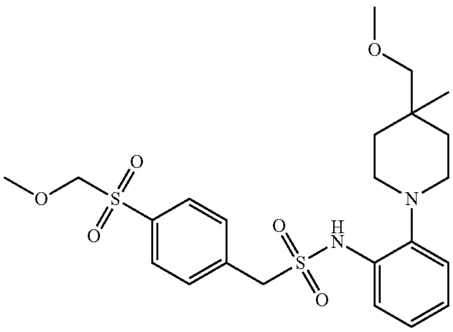 | A-747 |

TABLE A-continued
| Structure | Compound No. |
|---|---|
| 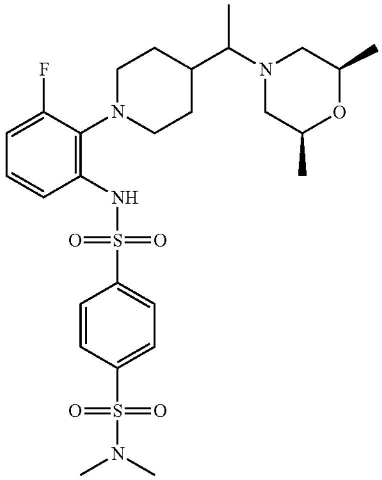 [SMILES: CC(C1CCN(c2c(F)cccc2NS(=O)(=O)c2ccc(S(=O)(=O)N(C)C)cc2)CC1)N1C[C@@H](C)O[C@@H](C)C1] | A-748 |
| 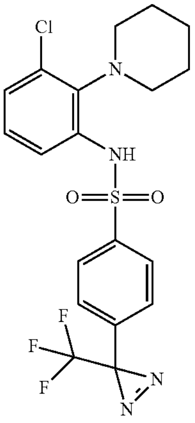 [SMILES: O=S(=O)(Nc1cccc(Cl)c1N1CCCCC1)c1ccc(C2(C(F)(F)F)N=N2)cc1] | A-749 |
| 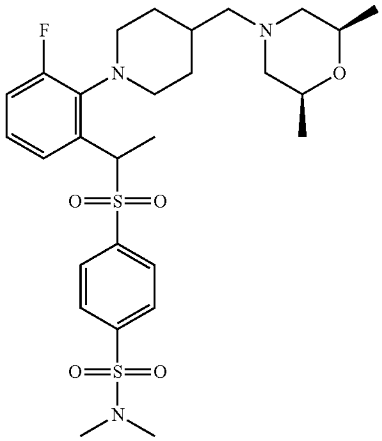 | A-750 |

TABLE A-continued
| Structure | Compound No. |
| --- | --- |
| 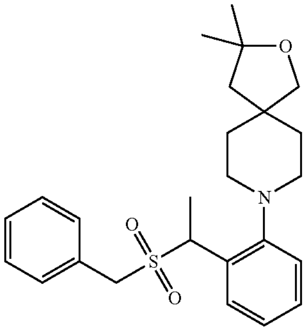 [SMILES: CC(c1ccccc1N1CCC2(CC1)COC(C)(C)C2)S(=O)(=O)Cc1ccccc1] | A-751 |
| 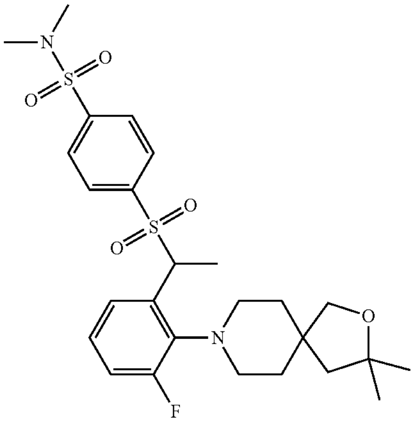 | A-752 |
| 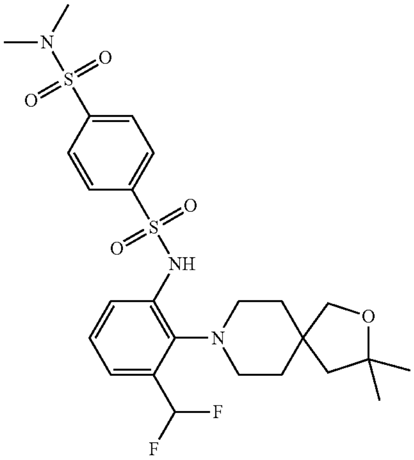 | A-753 |

TABLE A-continued
| Structure | Compound No. |
|---|---|
| 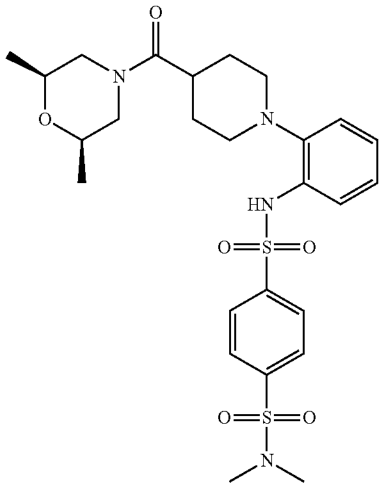 [SMILES: C[C@@H]1CN(C(=O)C2CCN(c3ccccc3NS(=O)(=O)c3ccc(S(=O)(=O)N(C)C)cc3)CC2)C[C@H](C)O1] | A-754 |
| 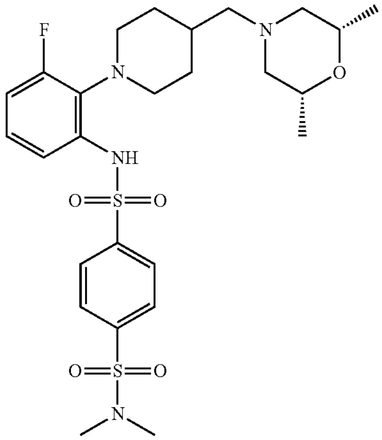 | A-755 |
| 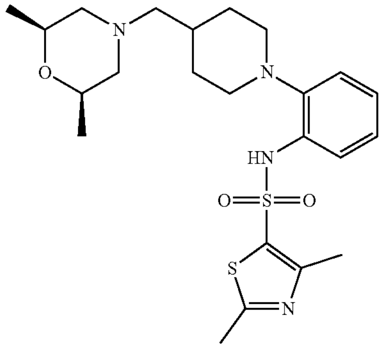 [SMILES: Cc1nc(C)c(S(=O)(=O)Nc2ccccc2N2CCC(CN3C[C@@H](C)O[C@@H](C)C3)CC2)s1] | A-756 |

TABLE A-continued
| Structure | Compound No. |
| --- | --- |
| 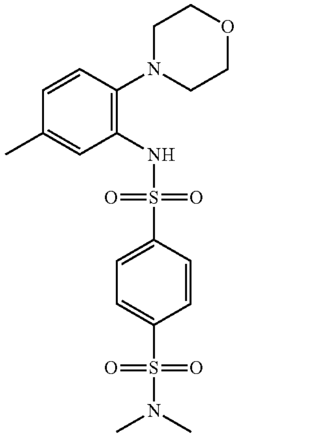 [SMILES: Cc1ccc(N2CCOCC2)c(NS(=O)(=O)c2ccc(S(=O)(=O)N(C)C)cc2)c1] | A-757 |
| 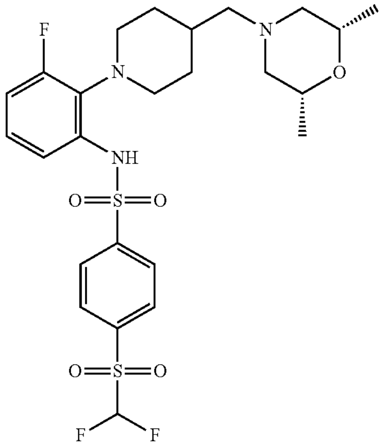 [SMILES: C[C@@H]1CN(CC2CCN(c3c(F)cccc3NS(=O)(=O)c3ccc(S(=O)(=O)C(F)F)cc3)CC2)C[C@H](C)O1] | A-758 |
| 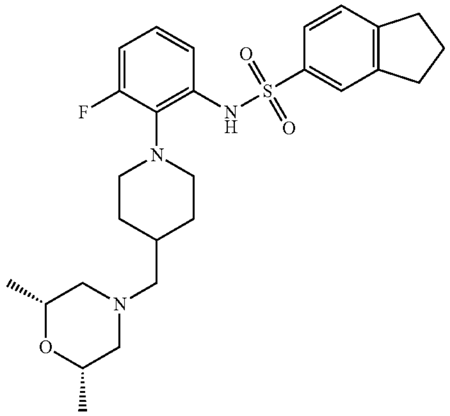 [SMILES: C[C@@H]1CN(CC2CCN(c3c(F)cccc3NS(=O)(=O)c3ccc4c(c3)CCC4)CC2)C[C@H](C)O1] | A-759 |
| 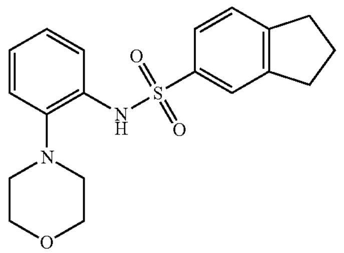 [SMILES: O=S(=O)(Nc1ccccc1N1CCOCC1)c1ccc2c(c1)CCC2] | A-760 |

TABLE A-continued
| Structure | Compound No. |
| --- | --- |
| 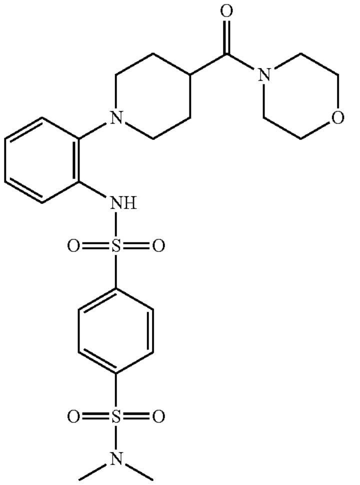 [SMILES: CN(C)S(=O)(=O)c1ccc(S(=O)(=O)Nc2ccccc2N2CCC(C(=O)N3CCOCC3)CC2)cc1] | A-761 |
| 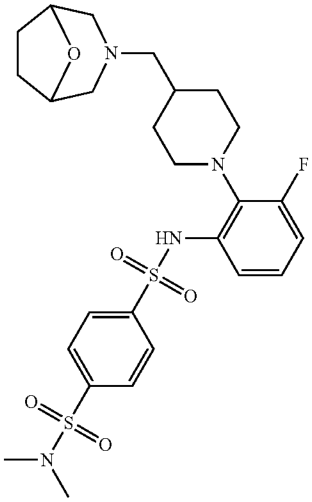 [SMILES: CN(C)S(=O)(=O)c1ccc(S(=O)(=O)Nc2cccc(F)c2N2CCC(CN3CC4CCC(C3)O4)CC2)cc1] | A-762 |
| 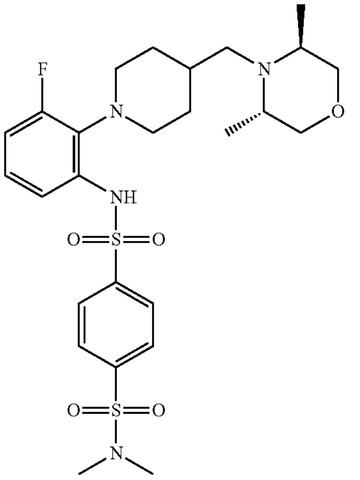 [SMILES: C[C@H]1COC[C@H](C)N1CC1CCN(c2c(F)cccc2NS(=O)(=O)c2ccc(S(=O)(=O)N(C)C)cc2)CC1] | A-763 |

TABLE A-continued
| Structure | Compound No. |
|---|---|
| 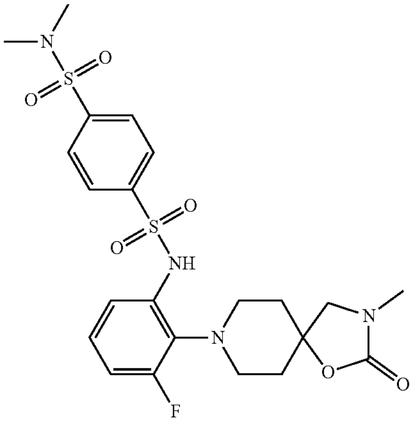 [SMILES: CN1CC2(CCN(c3c(F)cccc3NS(=O)(=O)c3ccc(S(=O)(=O)N(C)C)cc3)CC2)OC1=O] | A-764 |
| 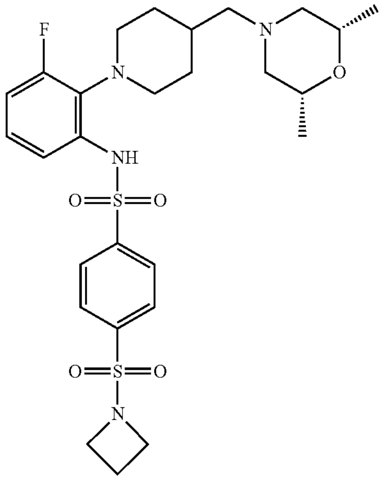 [SMILES: C[C@@H]1CN(CC2CCN(c3c(F)cccc3NS(=O)(=O)c3ccc(S(=O)(=O)N4CCC4)cc3)CC2)C[C@H](C)O1] | A-765 |
| 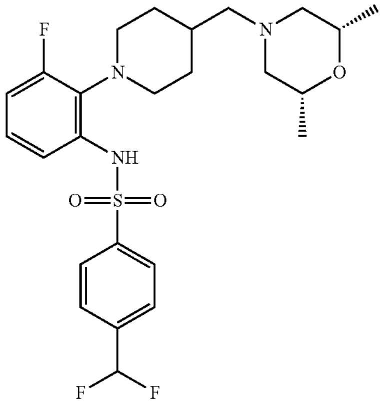 [SMILES: C[C@@H]1CN(CC2CCN(c3c(F)cccc3NS(=O)(=O)c3ccc(C(F)F)cc3)CC2)C[C@H](C)O1] | A-766 |
| 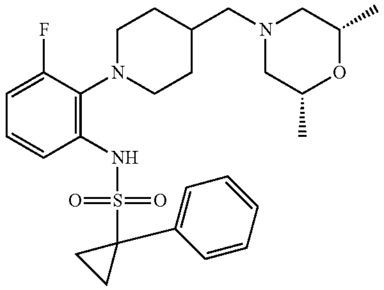 [SMILES: C[C@@H]1CN(CC2CCN(c3c(F)cccc3NS(=O)(=O)C3(c4ccccc4)CC3)CC2)C[C@H](C)O1] | A-767 |

TABLE A-continued
| Structure | Compound No. |
|---|---|
| 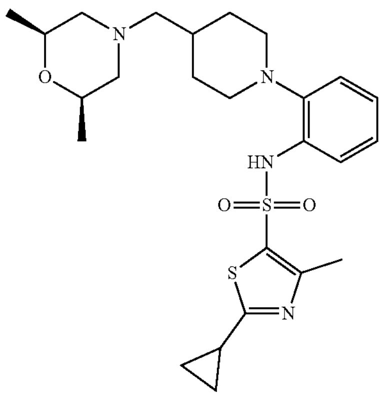 [SMILES: Cc1nc(C2CC2)sc1S(=O)(=O)Nc1ccccc1N1CCC(CN2C[C@@H](C)O[C@@H](C)C2)CC1] | A-768 |
| 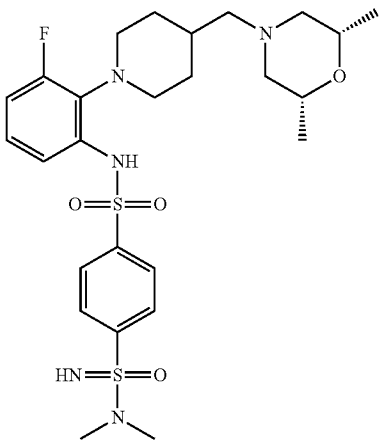 | A-769 |
| 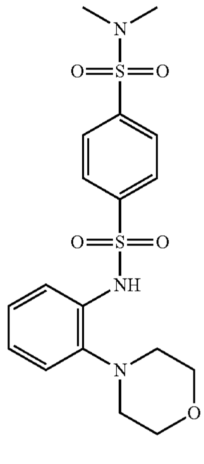 [SMILES: CN(C)S(=O)(=O)c1ccc(S(=O)(=O)Nc2ccccc2N2CCOCC2)cc1] | A-770 |

TABLE A-continued
| Structure | Compound No. |
|---|---|
| 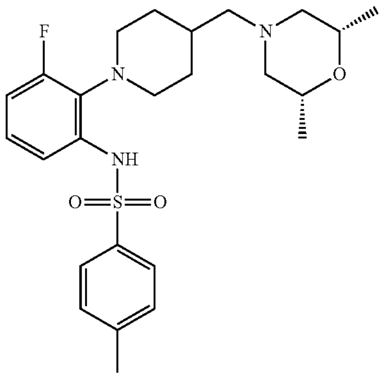 [SMILES: Cc1ccc(S(=O)(=O)Nc2cccc(F)c2N2CCC(CN3C[C@@H](C)O[C@@H](C)C3)CC2)cc1] | A-771 |
| 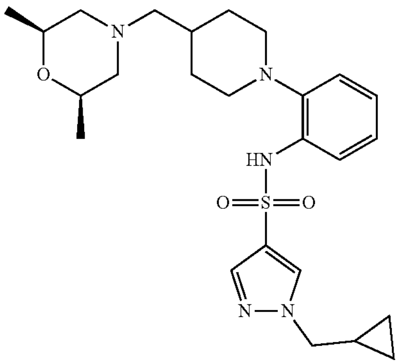 [SMILES: C[C@@H]1CN(CC2CCN(c3ccccc3NS(=O)(=O)c3cnn(CC4CC4)c3)CC2)C[C@H](C)O1] | A-772 |
| 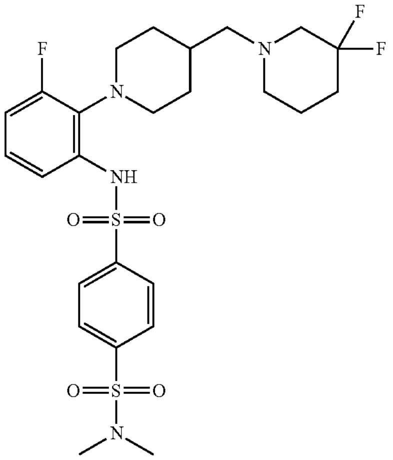 [SMILES: CN(C)S(=O)(=O)c1ccc(S(=O)(=O)Nc2cccc(F)c2N2CCC(CN3CCCC(F)(F)C3)CC2)cc1] | A-773 |

TABLE A-continued
| Structure | Compound No. |
|---|---|
| 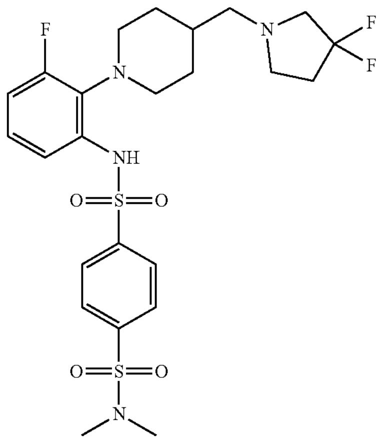 [SMILES: CN(C)S(=O)(=O)c1ccc(S(=O)(=O)Nc2cccc(F)c2N2CCC(CN3CCC(F)(F)C3)CC2)cc1] | A-774 |
| 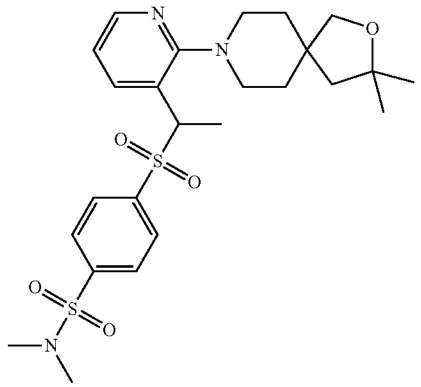 | A-775 |
| 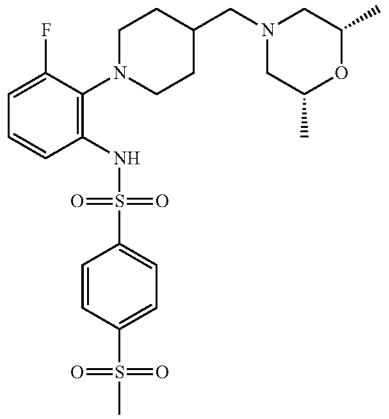 [SMILES: C[C@@H]1CN(CC2CCN(c3c(F)cccc3NS(=O)(=O)c3ccc(S(C)(=O)=O)cc3)CC2)C[C@H](C)O1] | A-776 |

TABLE A-continued
| Structure | Compound No. |
| --- | --- |
| 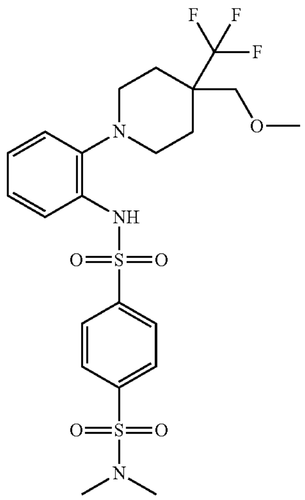 [SMILES: COCC1(C(F)(F)F)CCN(c2ccccc2NS(=O)(=O)c2ccc(S(=O)(=O)N(C)C)cc2)CC1] | A-777 |
| 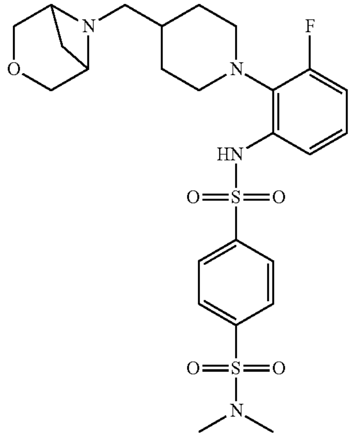 [SMILES: CN(C)S(=O)(=O)c1ccc(S(=O)(=O)Nc2cccc(F)c2N2CCC(CN3C4COCC3C4)CC2)cc1] | A-778 |
| 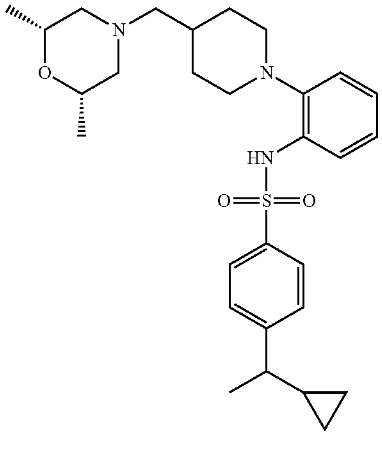 [SMILES: CC(c1ccc(S(=O)(=O)Nc2ccccc2N2CCC(CN3C[C@@H](C)O[C@@H](C)C3)CC2)cc1)C1CC1] | A-779 |

TABLE A-continued
| Structure | Compound No. |
|---|---|
| 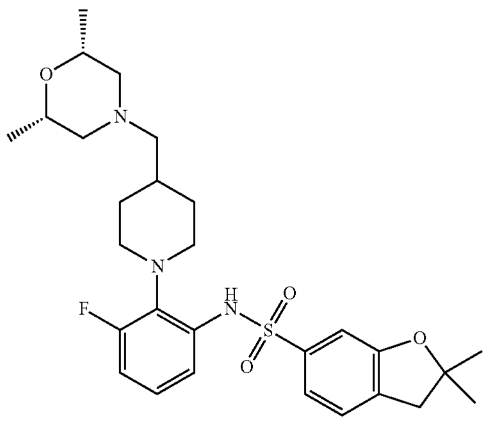 | A-780 |
| 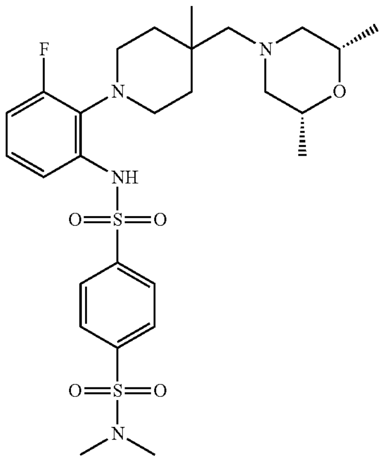 [SMILES: C[C@@H]1CN(CC2(C)CCN(c3c(F)cccc3NS(=O)(=O)c3ccc(S(=O)(=O)N(C)C)cc3)CC2)C[C@H](C)O1] | A-781 |
| 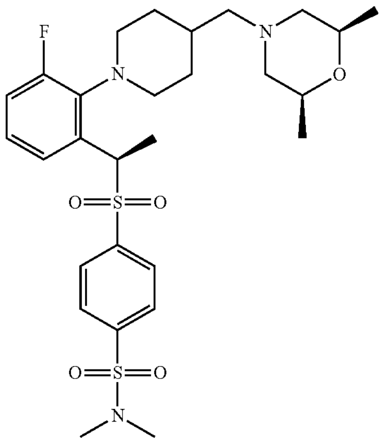 [SMILES: C[C@@H]1CN(CC2CCN(c3c(F)cccc3[C@@H](C)S(=O)(=O)c3ccc(S(=O)(=O)N(C)C)cc3)CC2)C[C@H](C)O1] | A-782 |

TABLE A-continued
| Structure | Compound No. |
| --- | --- |
| 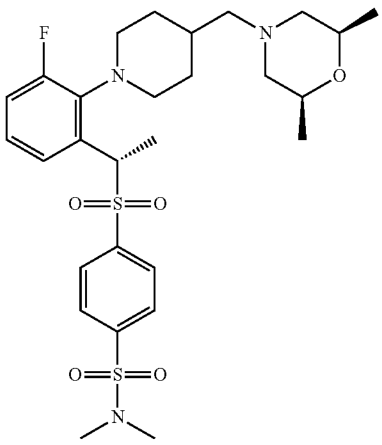 [SMILES: C[C@@H]1CN(CC2CCN(c3c(F)cccc3[C@H](C)S(=O)(=O)c3ccc(S(=O)(=O)N(C)C)cc3)CC2)C[C@H](C)O1] | A-783 |
| 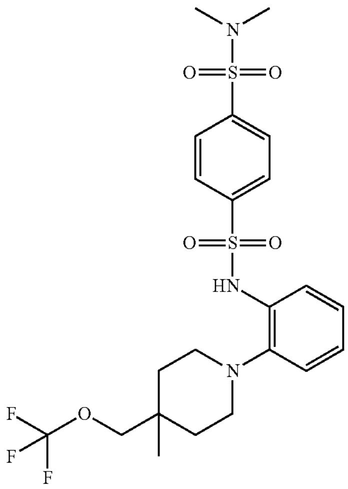 [SMILES: CN(C)S(=O)(=O)c1ccc(S(=O)(=O)Nc2ccccc2N2CCC(C)(COC(F)(F)F)CC2)cc1] | A-784 |
| 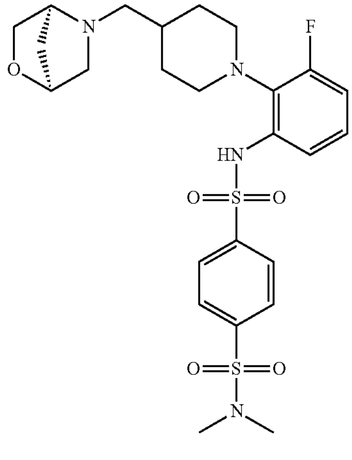 [SMILES: CN(C)S(=O)(=O)c1ccc(S(=O)(=O)Nc2cccc(F)c2N2CCC(CN3C[C@@H]4C[C@H]3CO4)CC2)cc1] | A-785 |

TABLE A-continued
| Structure | Compound No. |
| --- | --- |
| 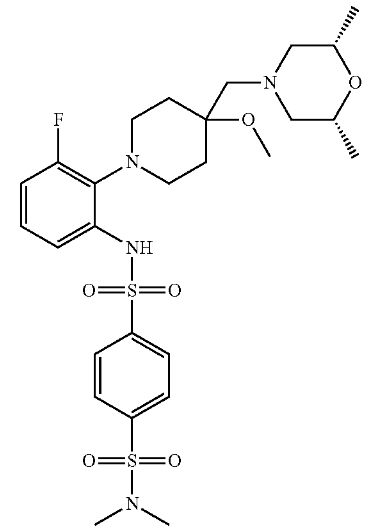 [SMILES: COC1(CN2C[C@@H](C)O[C@@H](C)C2)CCN(c2c(F)cccc2NS(=O)(=O)c2ccc(S(=O)(=O)N(C)C)cc2)CC1] | A-786 |
| 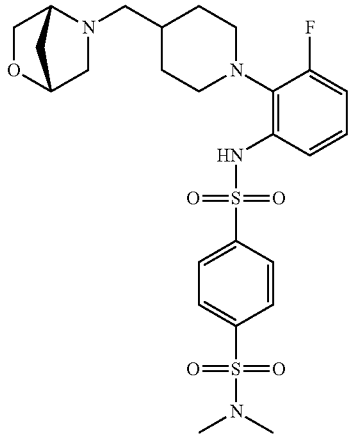 [SMILES: CN(C)S(=O)(=O)c1ccc(S(=O)(=O)Nc2cccc(F)c2N2CCC(CN3C[C@H]4C[C@@H]3CO4)CC2)cc1] | A-787 |
| 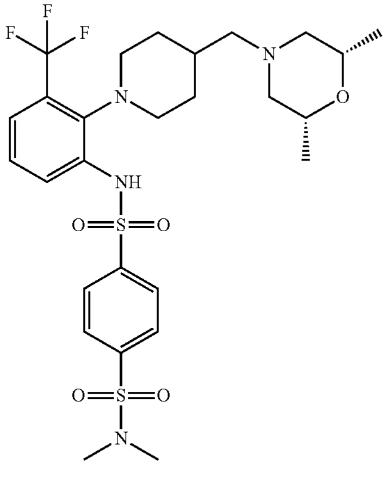 [SMILES: C[C@@H]1CN(CC2CCN(c3c(NS(=O)(=O)c4ccc(S(=O)(=O)N(C)C)cc4)cccc3C(F)(F)F)CC2)C[C@H](C)O1] | A-788 |

TABLE A-continued
| Structure | Compound No. |
|---|---|
| 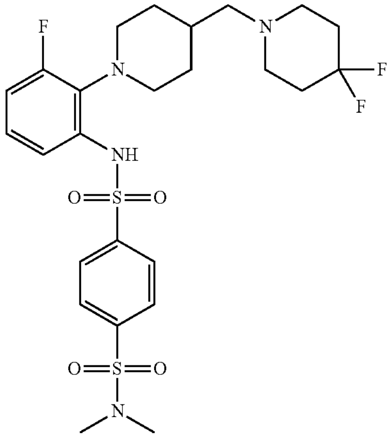 [SMILES: CN(C)S(=O)(=O)c1ccc(S(=O)(=O)Nc2cccc(F)c2N2CCC(CN3CCC(F)(F)CC3)CC2)cc1] | A-789 |
| 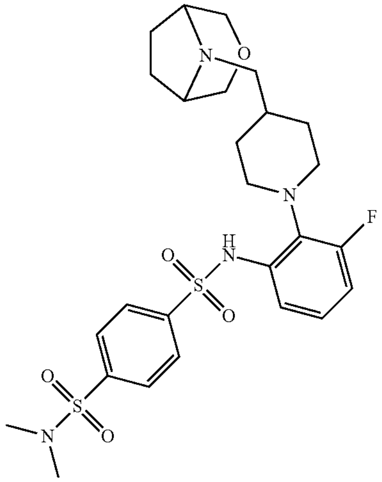 [SMILES: CN(C)S(=O)(=O)c1ccc(S(=O)(=O)Nc2cccc(F)c2N2CCC(CN3C4CCC3COC4)CC2)cc1] | A-790 |
| 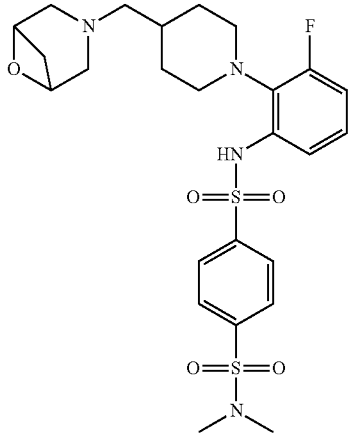 [SMILES: CN(C)S(=O)(=O)c1ccc(S(=O)(=O)Nc2cccc(F)c2N2CCC(CN3CC4CC(C3)O4)CC2)cc1] | A-791 |

TABLE A-continued
| Structure | Compound No. |
|---|---|
| 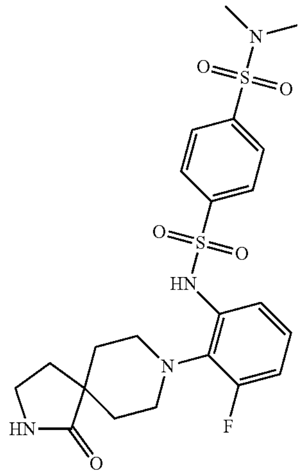 [SMILES: CN(C)S(=O)(=O)c1ccc(S(=O)(=O)Nc2cccc(F)c2N2CCC3(CCNC3=O)CC2)cc1] | A-792 |
| 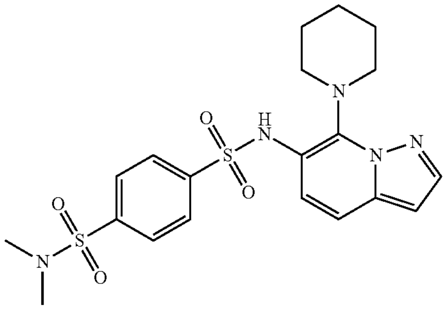 [SMILES: CN(C)S(=O)(=O)c1ccc(S(=O)(=O)Nc2ccc3ccnn3c2N2CCCCC2)cc1] | A-793 |
| 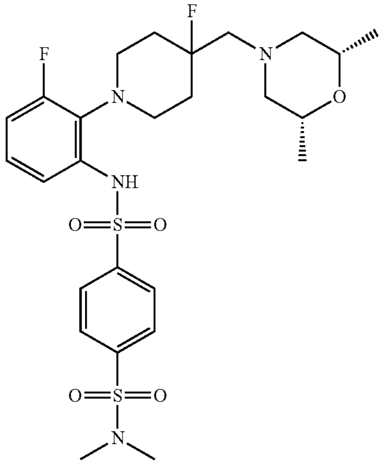 [SMILES: C[C@@H]1CN(CC2(F)CCN(c3c(F)cccc3NS(=O)(=O)c3ccc(S(=O)(=O)N(C)C)cc3)CC2)C[C@H](C)O1] | A-794 |

TABLE A-continued
| Structure | Compound No. |
| --- | --- |
| 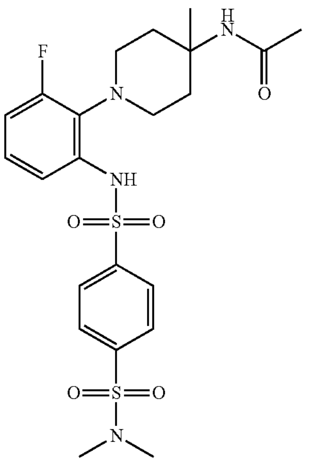 [SMILES: CC(=O)NC1(C)CCN(c2c(F)cccc2NS(=O)(=O)c2ccc(S(=O)(=O)N(C)C)cc2)CC1] | A-795 |
| 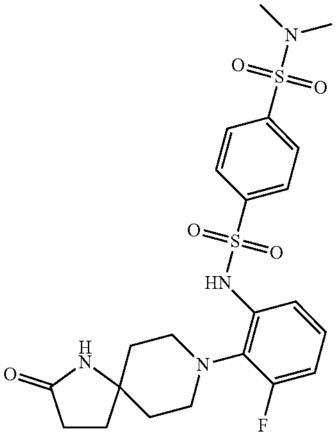 [SMILES: CN(C)S(=O)(=O)c1ccc(S(=O)(=O)Nc2cccc(F)c2N2CCC3(CCC(=O)N3)CC2)cc1] | A-796 |
| 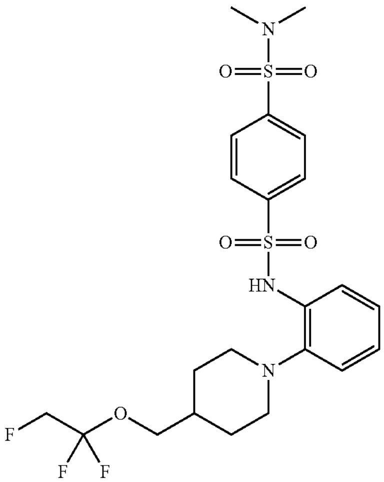 | A-797 |

TABLE A-continued
| Structure | Compound No. |
| --- | --- |
| 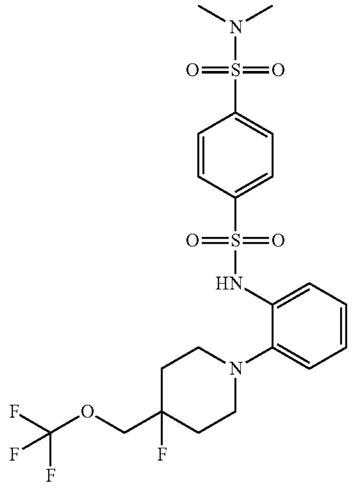 [SMILES: CN(C)S(=O)(=O)c1ccc(S(=O)(=O)Nc2ccccc2N2CCC(F)(COC(F)(F)F)CC2)cc1] | A-798 |
| 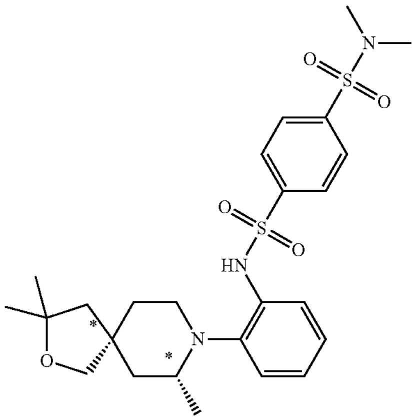<br>Cis isomer, racemic | A-799 |
| 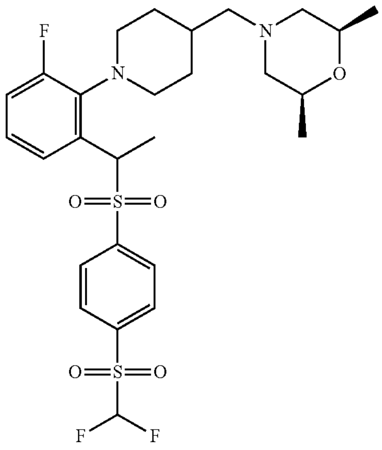 [SMILES: CC(c1cccc(F)c1N1CCC(CN2C[C@@H](C)O[C@@H](C)C2)CC1)S(=O)(=O)c1ccc(S(=O)(=O)C(F)F)cc1] | A-800 |

TABLE A-continued
| Structure | Compound No. |
|---|---|
| 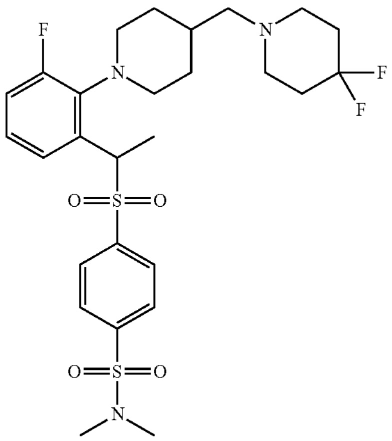 [SMILES: CC(c1cccc(F)c1N1CCC(CN2CCC(F)(F)CC2)CC1)S(=O)(=O)c1ccc(S(=O)(=O)N(C)C)cc1] | A-801 |
| 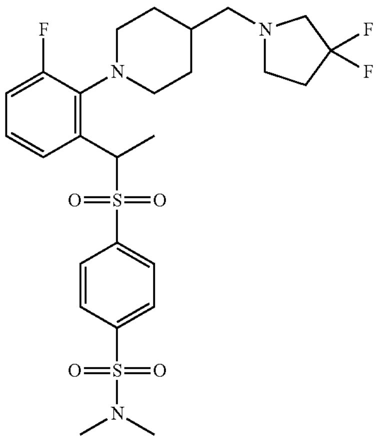 | A-802 |
| 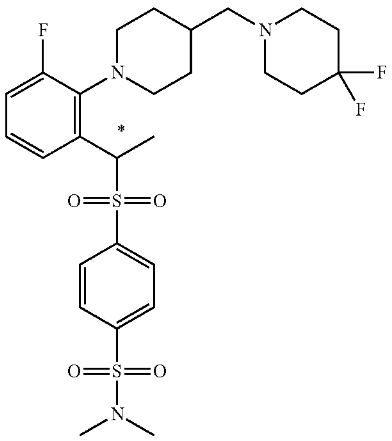 Enantiomer 1 | A-803 |

TABLE A-continued
| Structure | Compound No. |
|---|---|
| 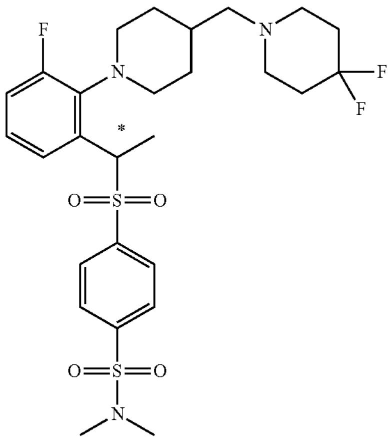 Enantiomer 2 | A-804 |
| 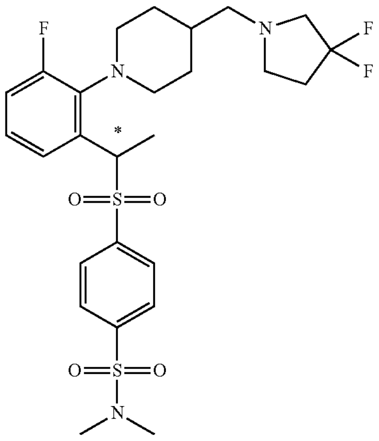 [SMILES: CC(c1cccc(F)c1N1CCC(CN2CCC(F)(F)C2)CC1)S(=O)(=O)c1ccc(S(=O)(=O)N(C)C)cc1] Enantiomer 1 | A-805 |
| 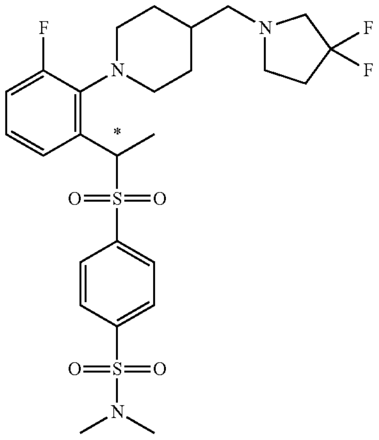 Enantiomer 2 | A-806 |

TABLE A-continued
| Structure | Compound No. |
|---|---|
| 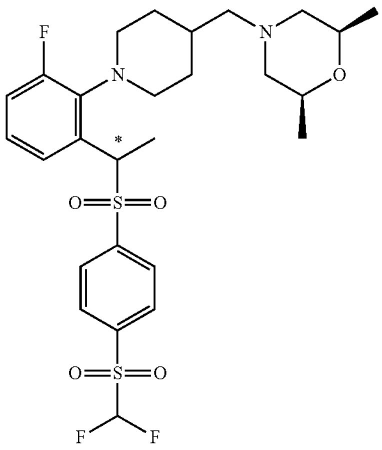 Enantiomer 1 | A-807 |
| 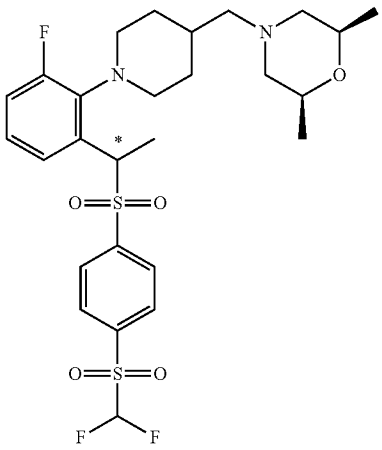 Enantiomer 2 | A-808 |
| 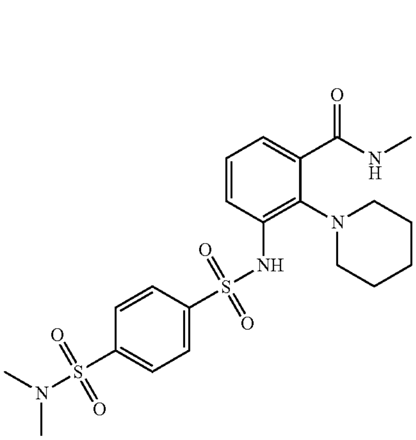 [SMILES: CNC(=O)c1cccc(NS(=O)(=O)c2ccc(S(=O)(=O)N(C)C)cc2)c1N1CCCCC1] | A-809 |

TABLE A-continued
| Structure | Compound No. |
|---|---|
| 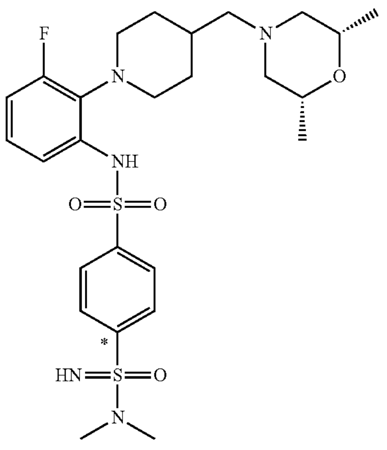 Enantiomer 1 | A-810 |
| 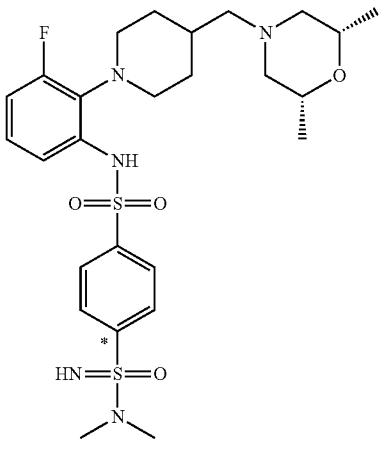 Enantiomer 2 | A-811 |
| 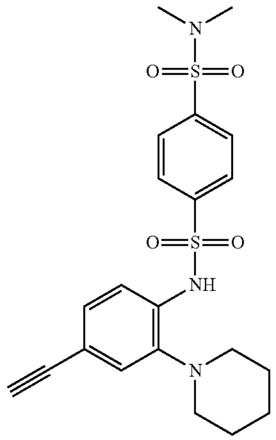 [SMILES: C#Cc1ccc(NS(=O)(=O)c2ccc(S(=O)(=O)N(C)C)cc2)c(N2CCCCC2)c1] | A-812 |

TABLE A-continued
| Structure | Compound No. |
|---|---|
| 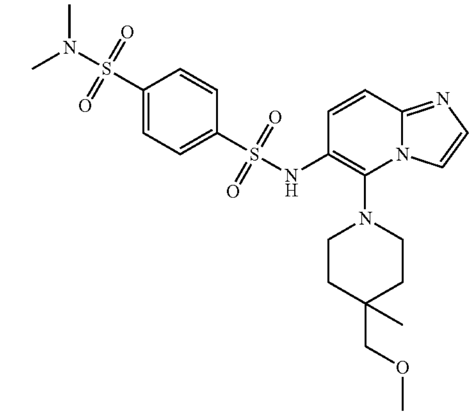 [SMILES: COCC1(C)CCN(c2c(NS(=O)(=O)c3ccc(S(=O)(=O)N(C)C)cc3)ccc3nccn23)CC1] | A-813 |
| 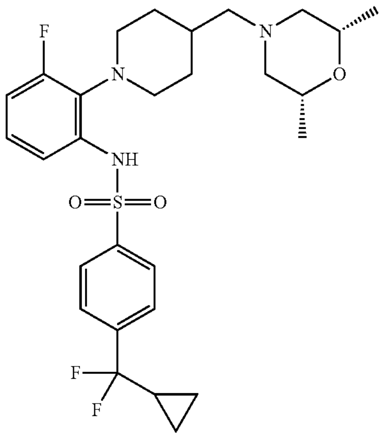 [SMILES: C[C@@H]1CN(CC2CCN(c3c(F)cccc3NS(=O)(=O)c3ccc(C(F)(F)C4CC4)cc3)CC2)C[C@H](C)O1] | A-814 |
| 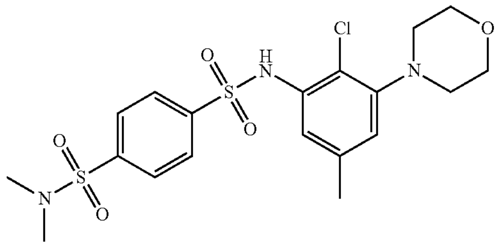 [SMILES: Cc1cc(NS(=O)(=O)c2ccc(S(=O)(=O)N(C)C)cc2)c(Cl)c(N2CCOCC2)c1] | A-815 |
| 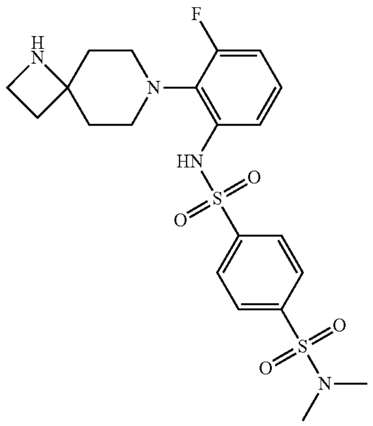 [SMILES: CN(C)S(=O)(=O)c1ccc(S(=O)(=O)Nc2cccc(F)c2N2CCC3(CCN3)CC2)cc1] | A-816 |

TABLE A-continued
| Structure | Compound No. |
|---|---|
| 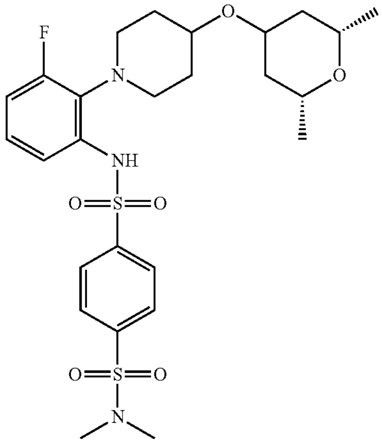 [SMILES: C[C@@H]1CC(OC2CCN(c3c(F)cccc3NS(=O)(=O)c3ccc(S(=O)(=O)N(C)C)cc3)CC2)C[C@H](C)O1] | A-817 |
| 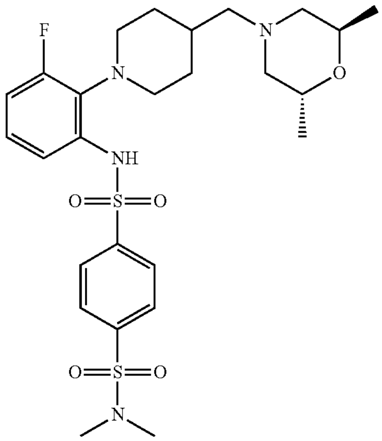 [SMILES: C[C@@H]1CN(CC2CCN(c3c(F)cccc3NS(=O)(=O)c3ccc(S(=O)(=O)N(C)C)cc3)CC2)C[C@@H](C)O1] | A-818 |
| 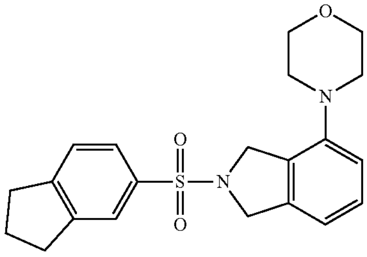 [SMILES: O=S(=O)(c1ccc2c(c1)CCC2)N1Cc2cccc(N3CCOCC3)c2C1] | A-819 |
| 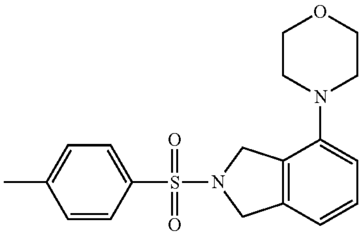 [SMILES: Cc1ccc(S(=O)(=O)N2Cc3cccc(N4CCOCC4)c3C2)cc1] | A-820 |

TABLE A-continued
| Structure | Compound No. |
|---|---|
| 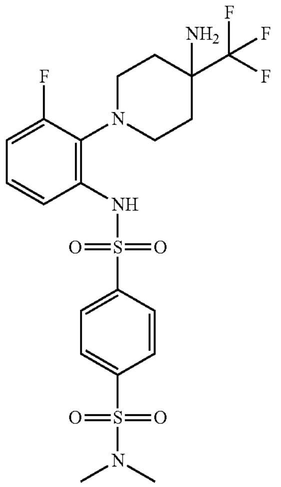 [SMILES: CN(C)S(=O)(=O)c1ccc(S(=O)(=O)Nc2cccc(F)c2N2CCC(N)(C(F)(F)F)CC2)cc1] | A-821 |
| 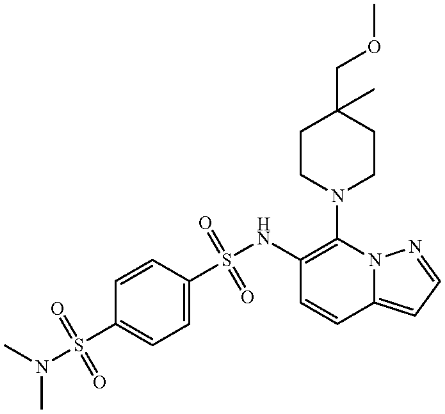 [SMILES: COCC1(C)CCN(c2c(NS(=O)(=O)c3ccc(S(=O)(=O)N(C)C)cc3)ccc3ccnn23)CC1] | A-822 |
| 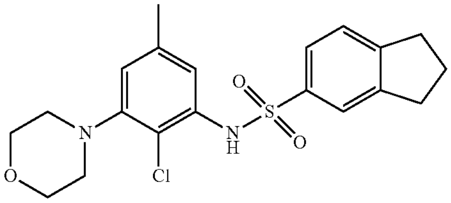 [SMILES: Cc1cc(NS(=O)(=O)c2ccc3c(c2)CCC3)c(Cl)c(N2CCOCC2)c1] | A-823 |
| 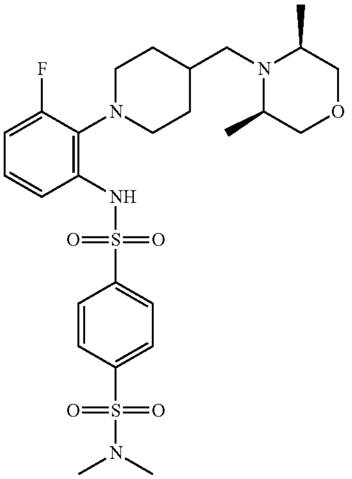 [SMILES: C[C@@H]1COC[C@H](C)N1CC1CCN(c2c(F)cccc2NS(=O)(=O)c2ccc(S(=O)(=O)N(C)C)cc2)CC1] | A-824 |

TABLE A-continued
| Structure | Compound No. |
| --- | --- |
| 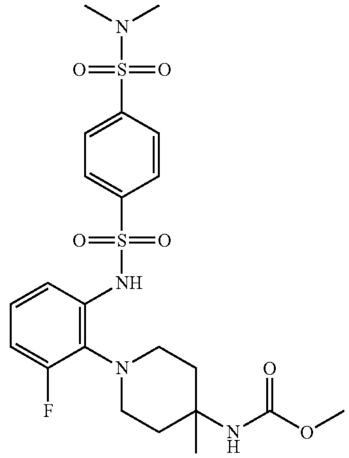 [SMILES: COC(=O)NC1(C)CCN(c2c(F)cccc2NS(=O)(=O)c2ccc(S(=O)(=O)N(C)C)cc2)CC1] | A-825 |
| 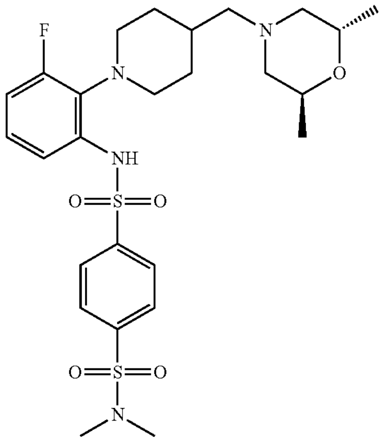 [SMILES: C[C@H]1CN(CC2CCN(c3c(F)cccc3NS(=O)(=O)c3ccc(S(=O)(=O)N(C)C)cc3)CC2)C[C@H](C)O1] | A-826 |
| 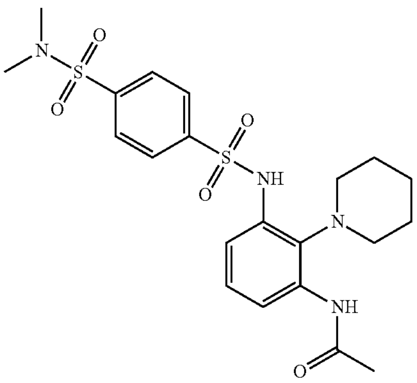 [SMILES: CC(=O)Nc1cccc(NS(=O)(=O)c2ccc(S(=O)(=O)N(C)C)cc2)c1N1CCCCC1] | A-827 |

TABLE A-continued
| Structure | Compound No. |
|---|---|
| 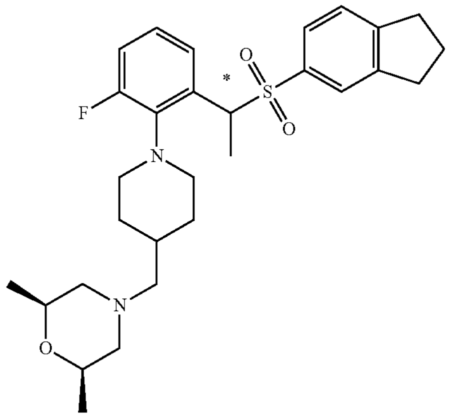 Enantiomer 1 | A-828 |
| 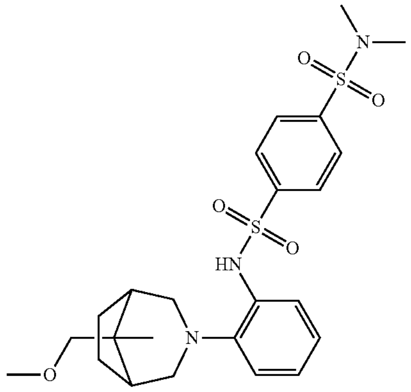 | A-829 |
| 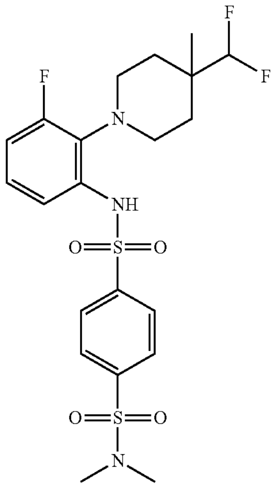 [SMILES: CN(C)S(=O)(=O)c1ccc(S(=O)(=O)Nc2cccc(F)c2N2CCC(C)(C(F)F)CC2)cc1] | A-830 |

TABLE A-continued
| Structure | Compound No. |
|---|---|
| 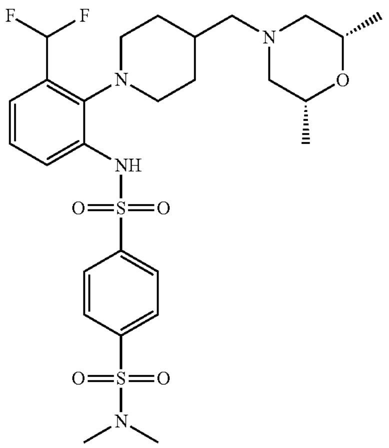 [SMILES: C[C@@H]1CN(CC2CCN(c3c(NS(=O)(=O)c4ccc(S(=O)(=O)N(C)C)cc4)cccc3C(F)F)CC2)C[C@H](C)O1] | A-831 |
| 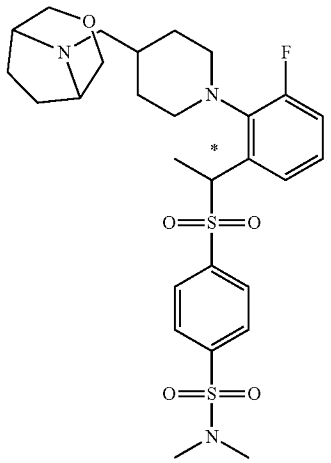<br>Enantiomer 1 | A-832 |
| 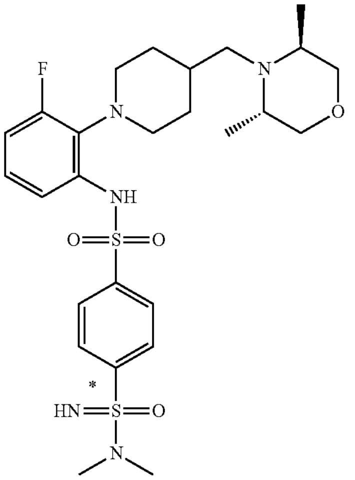<br>Diastereomer 1 | A-833 |

TABLE A-continued
| Structure | Compound No. |
|---|---|
| 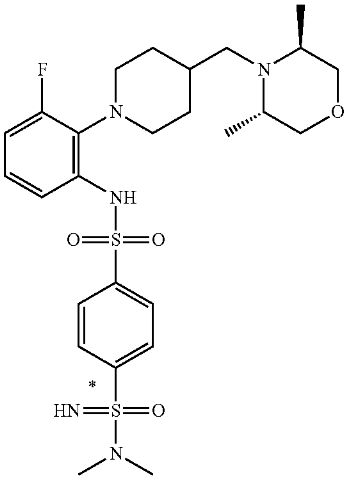 Diastereomer 1 | A-834 |
| 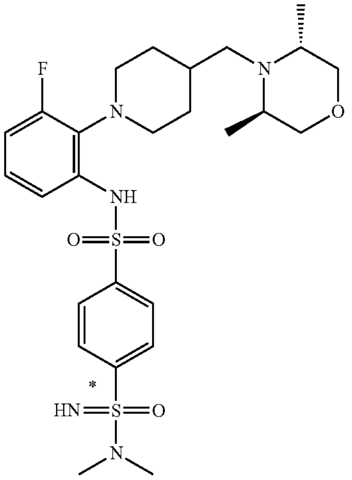 Diastereomer 3 | A-835 |
| 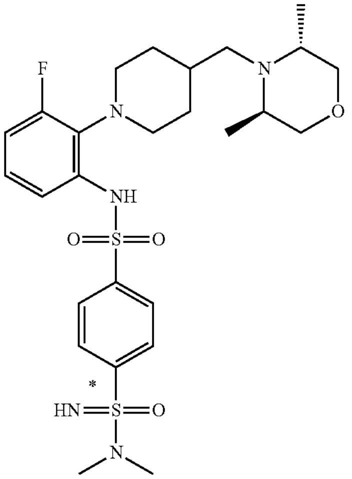 Diastereomer 4 | A-836 |

TABLE A-continued
| Structure | Compound No. |
| --- | --- |
| 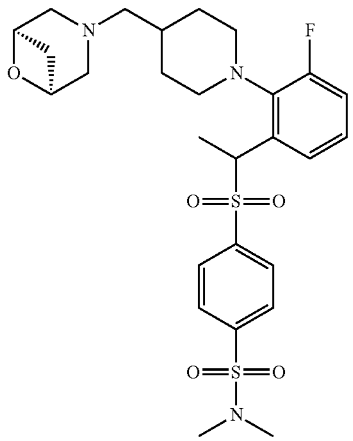 [SMILES: CC(c1cccc(F)c1N1CCC(CN2C[C@H]3C[C@@H](C2)O3)CC1)S(=O)(=O)c1ccc(S(=O)(=O)N(C)C)cc1] | A-837 |
| 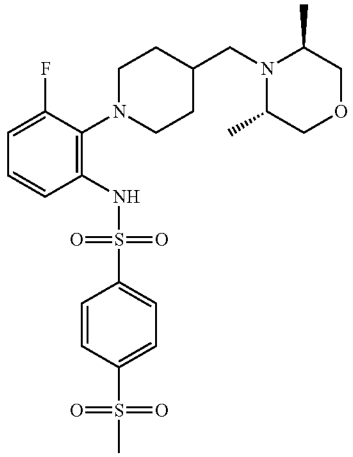 [SMILES: C[C@H]1COC[C@H](C)N1CC1CCN(c2c(F)cccc2NS(=O)(=O)c2ccc(S(C)(=O)=O)cc2)CC1] | A-838 |
| 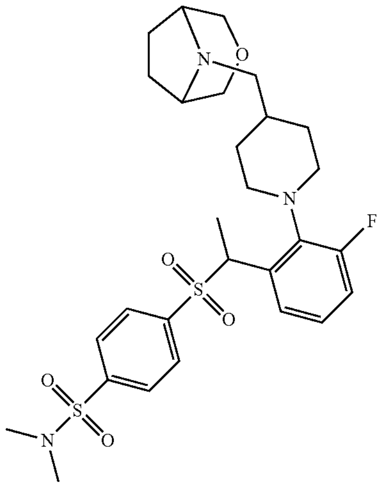 [SMILES: CC(c1cccc(F)c1N1CCC(CN2C3CCC2COC3)CC1)S(=O)(=O)c1ccc(S(=O)(=O)N(C)C)cc1] | A-839 |

TABLE A-continued
| Structure | Compound No. |
| --- | --- |
| 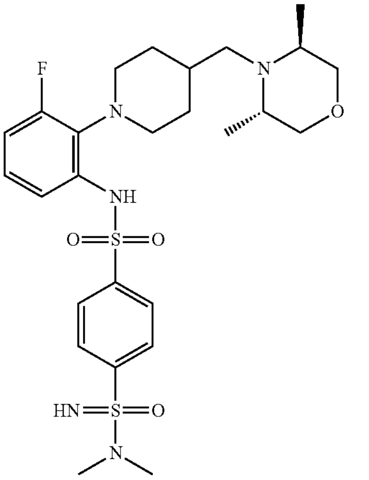 [SMILES: C[C@H]1COC[C@H](C)N1CC1CCN(c2c(F)cccc2NS(=O)(=O)c2ccc(S(=N)(=O)N(C)C)cc2)CC1] | A-840 |
| 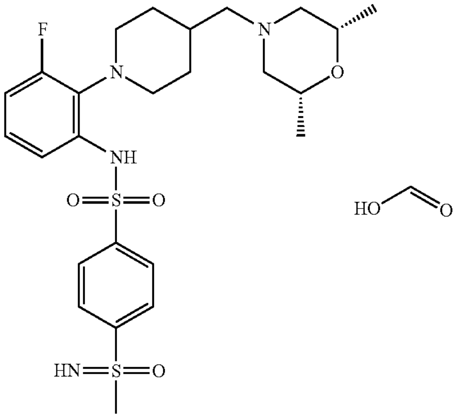 [SMILES: C[C@@H]1CN(CC2CCN(c3c(F)cccc3NS(=O)(=O)c3ccc(S(C)(=N)=O)cc3)CC2)C[C@H](C)O1 ; O=CO] | A-841 |
| 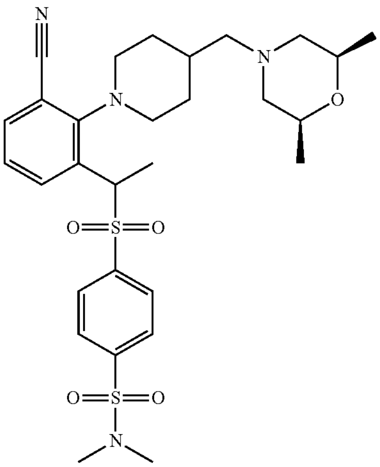 [SMILES: CC(c1cccc(C#N)c1N1CCC(CN2C[C@@H](C)O[C@@H](C)C2)CC1)S(=O)(=O)c1ccc(S(=O)(=O)N(C)C)cc1] | A-842 |

TABLE A-continued
| Structure | Compound No. |
| --- | --- |
| 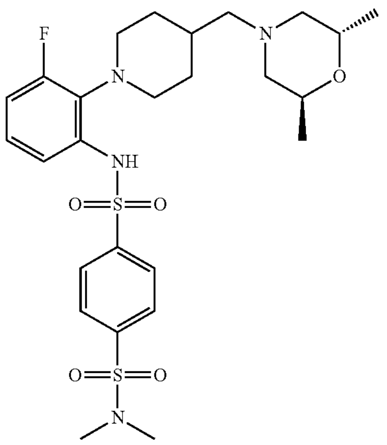 Trans, racemic | A-843 |
| 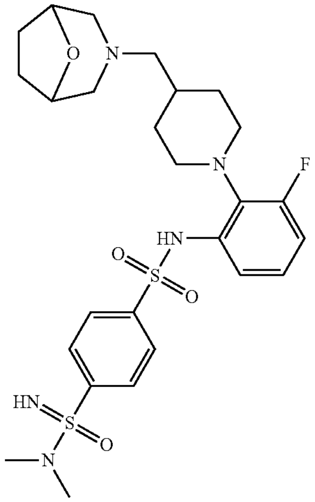 [SMILES: CN(C)S(=N)(=O)c1ccc(S(=O)(=O)Nc2cccc(F)c2N2CCC(CN3CC4CCC(C3)O4)CC2)cc1] | A-844 |
| 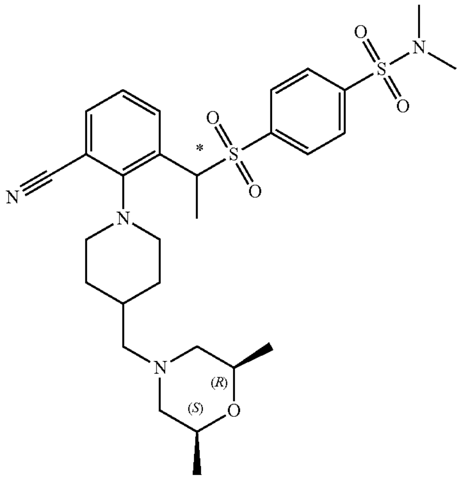 Enantiomer 2 | A-845 |

TABLE A-continued
| Structure | Compound No. |
|---|---|
| 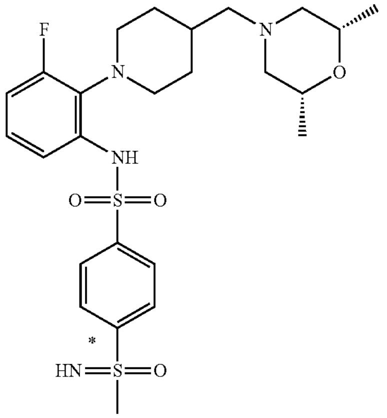 Enantiomer 1 | A-846 |
| 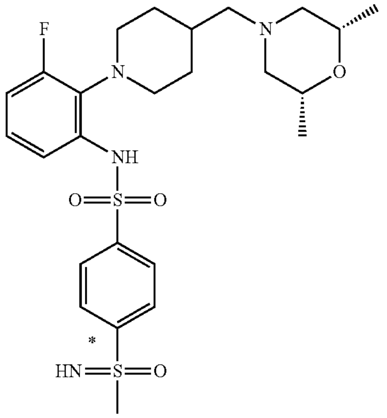 Enantiomer 2 | A-847 |
| 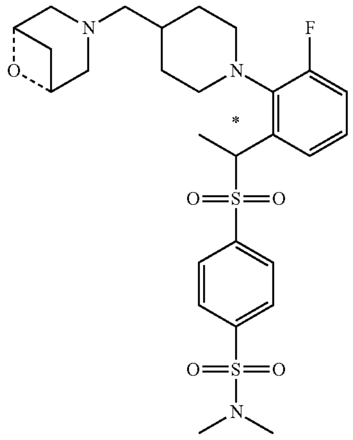 Enantiomer 1 | A-848 |

TABLE A-continued
| Structure | Compound No. |
| --- | --- |
| 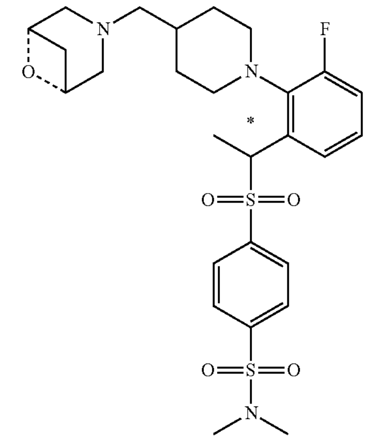 Enantiomer 1 | A-849 |
| 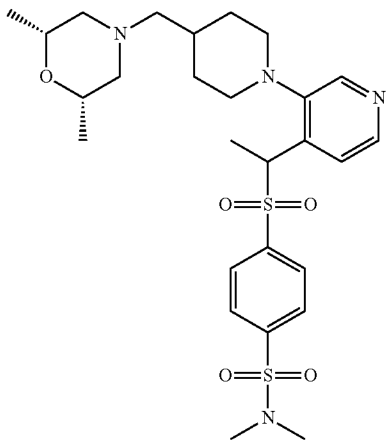 [SMILES: CC(c1ccncc1N1CCC(CN2C[C@@H](C)O[C@@H](C)C2)CC1)S(=O)(=O)c1ccc(S(=O)(=O)N(C)C)cc1] | A-850 |
| 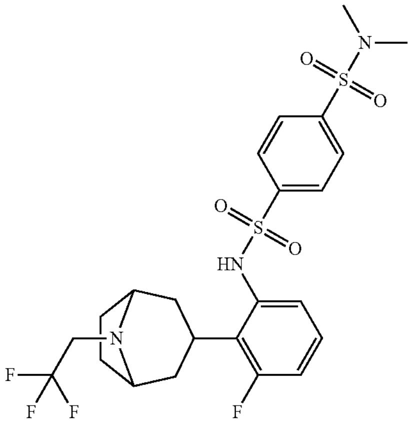 [SMILES: CN(C)S(=O)(=O)c1ccc(S(=O)(=O)Nc2cccc(F)c2C2CC3CCC(C2)N3CC(F)(F)F)cc1] | A-851 |

TABLE A-continued
| Structure | Compound No. |
|---|---|
| 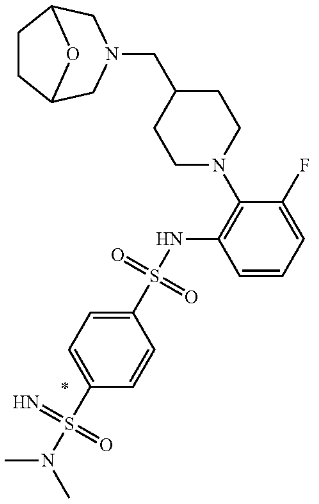<br>Enantiomer 1 | A-852 |
| 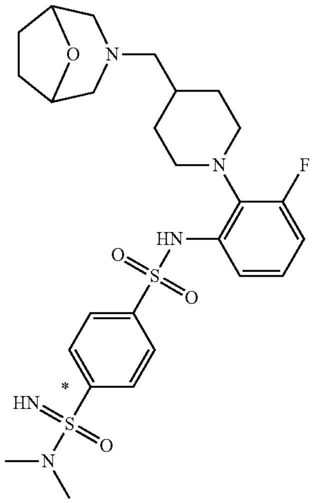<br>Enantiomer 2 | A-853 |
| 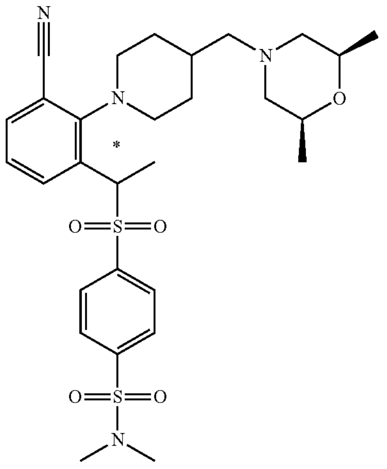<br>Enantiomer 1 | A-854 |

TABLE A-continued
| Structure | Compound No. |
| --- | --- |
| 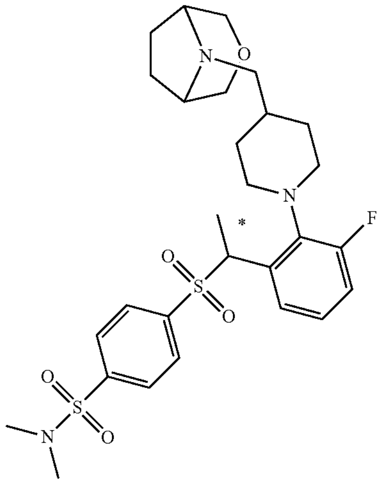<br>Enantiomer 2 | A-855 |
| 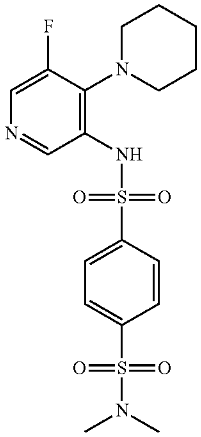 [SMILES: CN(C)S(=O)(=O)c1ccc(S(=O)(=O)Nc2cncc(F)c2N2CCCCC2)cc1] | A-856 |
| 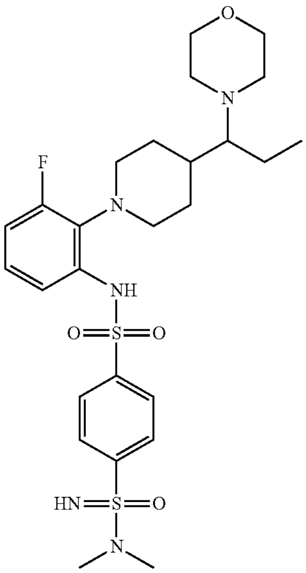 [SMILES: CCC(C1CCN(c2c(F)cccc2NS(=O)(=O)c2ccc(S(=N)(=O)N(C)C)cc2)CC1)N1CCOCC1] | A-857 |

TABLE A-continued
| Structure | Compound No. |
|---|---|
| 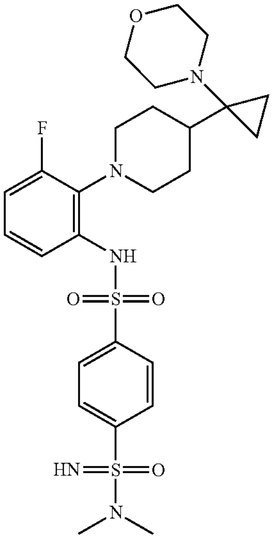 [SMILES: CN(C)S(=N)(=O)c1ccc(S(=O)(=O)Nc2cccc(F)c2N2CCC(C3(N4CCOCC4)CC3)CC2)cc1] | A-858 |
| 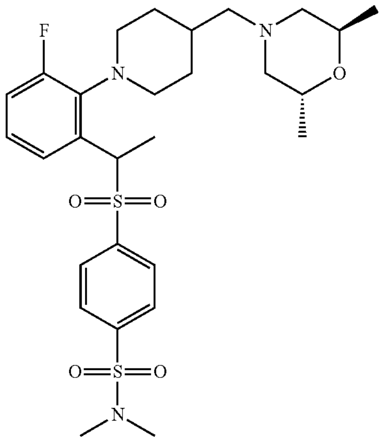 [SMILES: CC(c1cccc(F)c1N1CCC(CN2C[C@@H](C)O[C@H](C)C2)CC1)S(=O)(=O)c1ccc(S(=O)(=O)N(C)C)cc1] | A-859 |
| 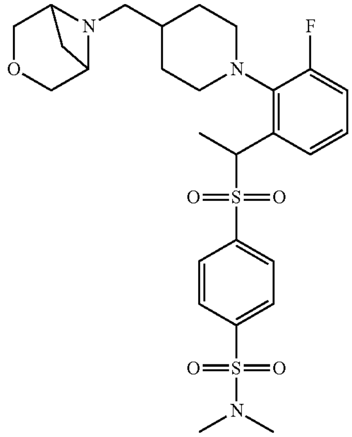 [SMILES: CC(c1cccc(F)c1N1CCC(CN2C3COCC2C3)CC1)S(=O)(=O)c1ccc(S(=O)(=O)N(C)C)cc1] | A-860 |

TABLE A-continued
| Structure | Compound No. |
| --- | --- |
| 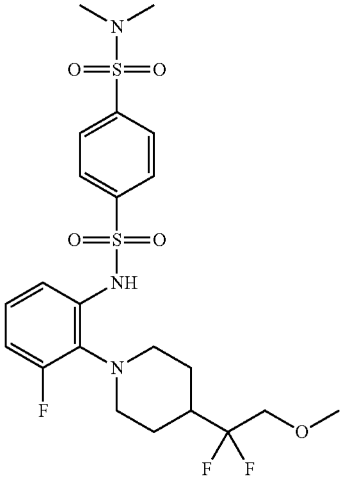 [SMILES: COCC(F)(F)C1CCN(c2c(F)cccc2NS(=O)(=O)c2ccc(S(=O)(=O)N(C)C)cc2)CC1] | A-861 |
| 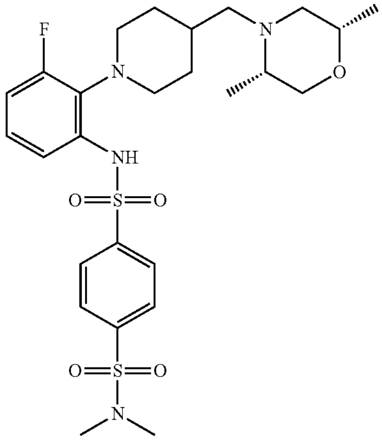 [SMILES: C[C@H]1CN(CC2CCN(c3c(F)cccc3NS(=O)(=O)c3ccc(S(=O)(=O)N(C)C)cc3)CC2)[C@@H](C)CO1] | A-862 |
| 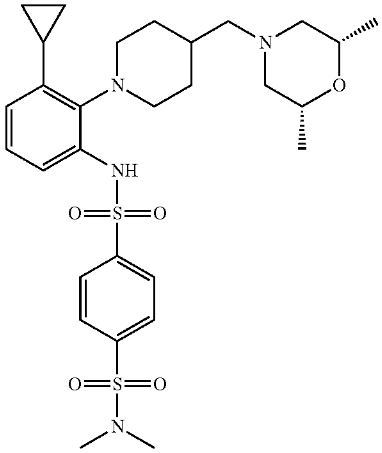 [SMILES: C[C@@H]1CN(CC2CCN(c3c(NS(=O)(=O)c4ccc(S(=O)(=O)N(C)C)cc4)cccc3C3CC3)CC2)C[C@H](C)O1] | A-863 |

TABLE A-continued
| Structure | Compound No. |
|---|---|
| 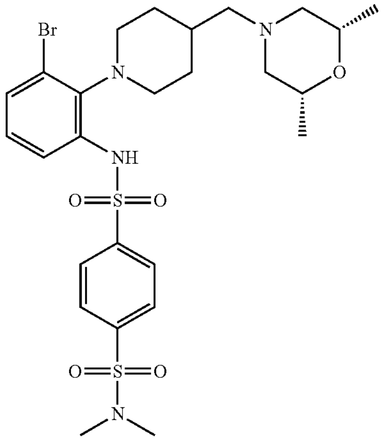 [SMILES: C[C@@H]1CN(CC2CCN(c3c(Br)cccc3NS(=O)(=O)c3ccc(S(=O)(=O)N(C)C)cc3)CC2)C[C@H](C)O1] | A-864 |
| 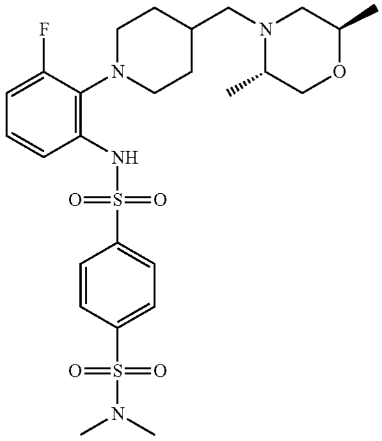 [SMILES: C[C@@H]1CN(CC2CCN(c3c(F)cccc3NS(=O)(=O)c3ccc(S(=O)(=O)N(C)C)cc3)CC2)[C@@H](C)CO1] | A-865 |
| 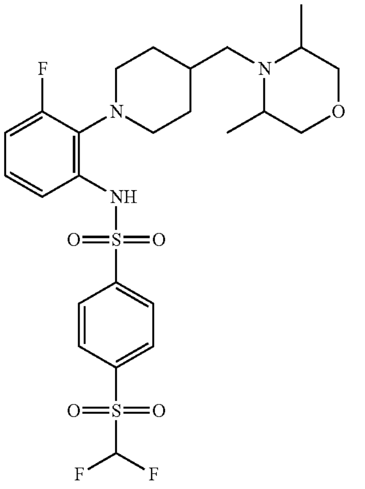 [SMILES: CC1COCC(C)N1CC1CCN(c2c(F)cccc2NS(=O)(=O)c2ccc(S(=O)(=O)C(F)F)cc2)CC1] | A-866 |

TABLE A-continued
| Structure | Compound No. |
|---|---|
| 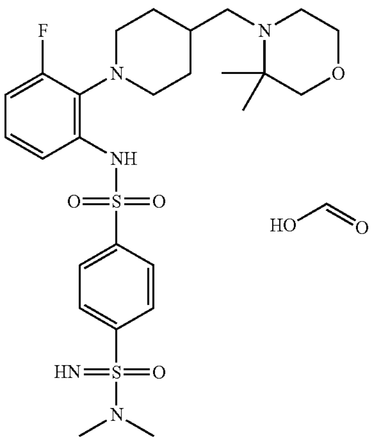 [SMILES: CN(C)S(=N)(=O)c1ccc(S(=O)(=O)Nc2cccc(F)c2N2CCC(CN3CCOCC3(C)C)CC2)cc1 ; O=CO] | A-867 |
| 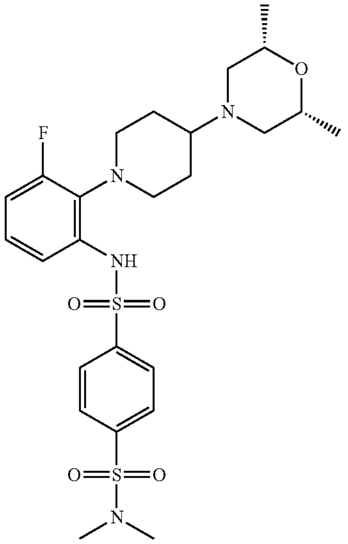 [SMILES: C[C@@H]1CN(C2CCN(c3c(F)cccc3NS(=O)(=O)c3ccc(S(=O)(=O)N(C)C)cc3)CC2)C[C@H](C)O1] | A-868 |
| 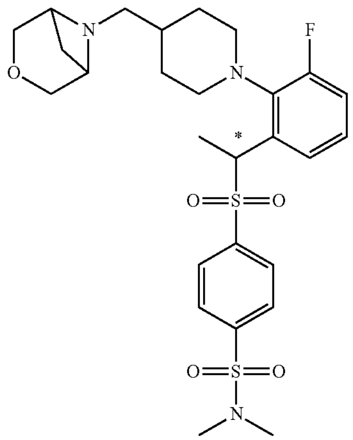 Enantiomer 1 | A-869 |

TABLE A-continued
| Structure | Compound No. |
|---|---|
| 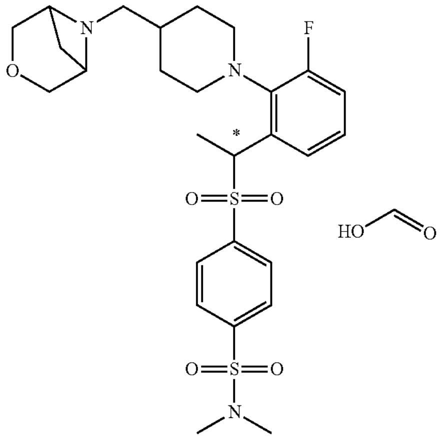 Enantiomer 2 | A-870 |
| 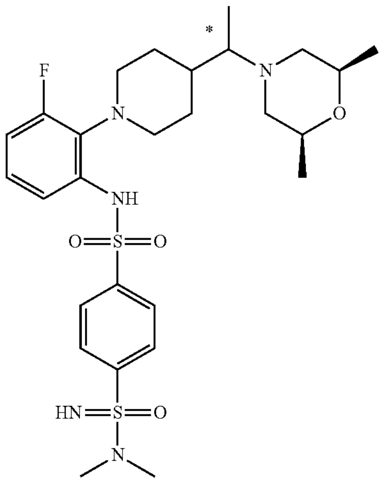 Isomer 1 | A-871 |
| 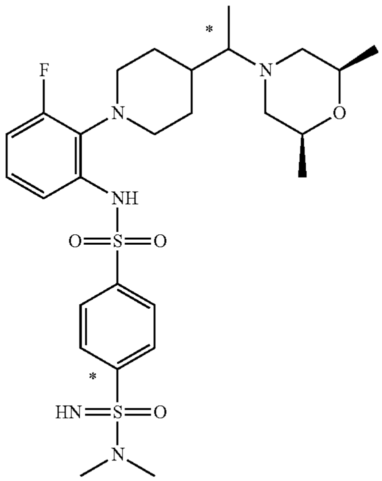 Diastereomer 1 | A-871A |

TABLE A-continued
| Structure | Compound No. |
| --- | --- |
| 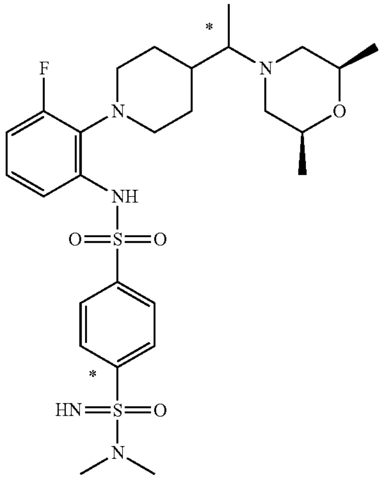 Diastereomer 2 | A-871B |
| 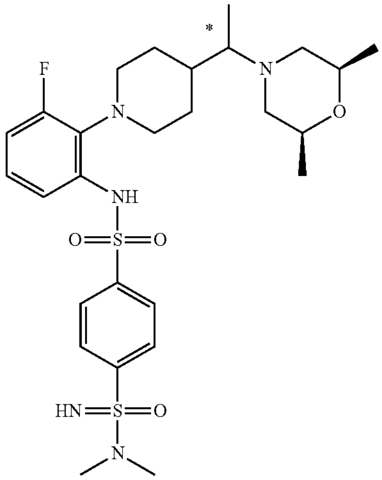 Isomer 2 | A-872 |
| 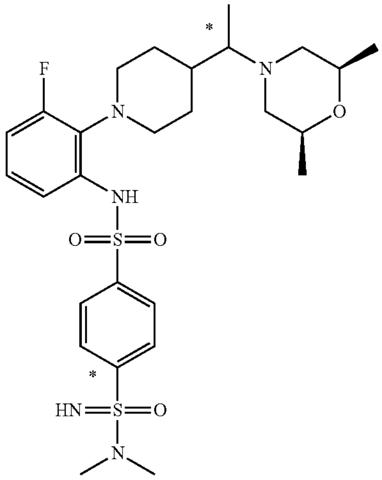 Diastereomer 3 | A-872A |

TABLE A-continued
| Structure | Compound No. |
| --- | --- |
| 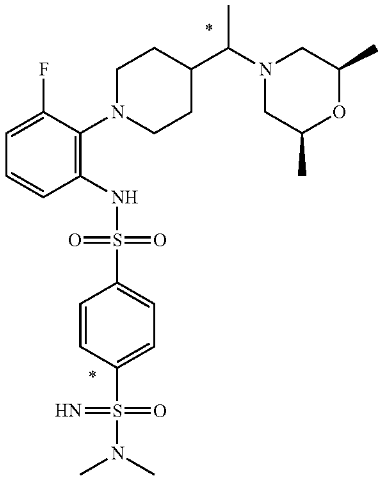 Diastereomer 4 | A-872B |
| 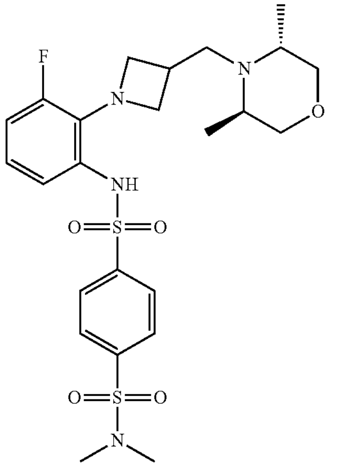 Trans, racemic | A-873 |
| 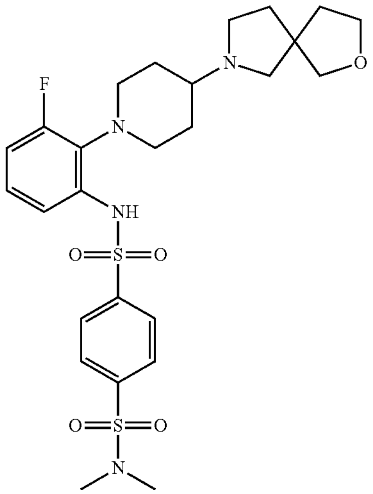 [SMILES: CN(C)S(=O)(=O)c1ccc(S(=O)(=O)Nc2cccc(F)c2N2CCC(N3CCC4(CCOC4)C3)CC2)cc1] | A-874 |

TABLE A-continued
| Structure | Compound No. |
|---|---|
| 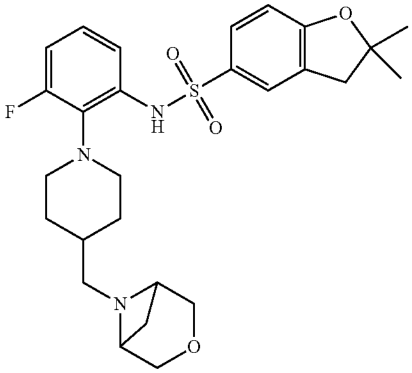 [SMILES: CC1(C)Cc2cc(S(=O)(=O)Nc3cccc(F)c3N3CCC(CN4C5COCC4C5)CC3)ccc2O1] | A-875 |
| 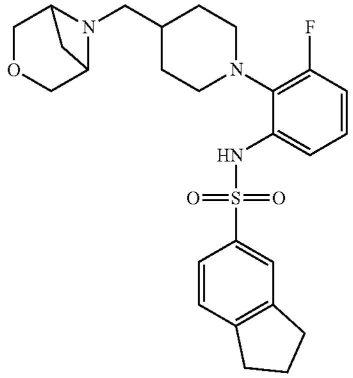 [SMILES: O=S(=O)(Nc1cccc(F)c1N1CCC(CN2C3COCC2C3)CC1)c1ccc2c(c1)CCC2] | A-876 |
| 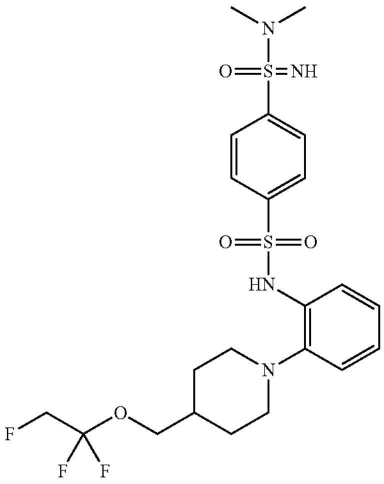 [SMILES: CN(C)S(=N)(=O)c1ccc(S(=O)(=O)Nc2ccccc2N2CCC(COC(F)(F)CF)CC2)cc1] | A-877 |

TABLE A-continued
| Structure | Compound No. |
|---|---|
| 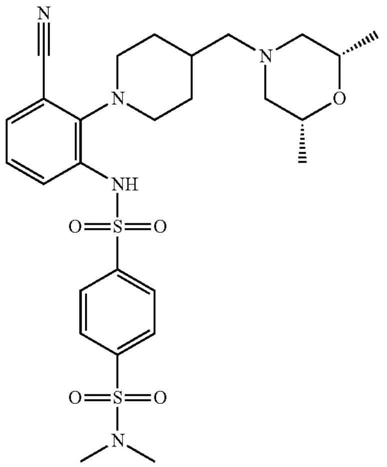 [SMILES: C[C@@H]1CN(CC2CCN(c3c(C#N)cccc3NS(=O)(=O)c3ccc(S(=O)(=O)N(C)C)cc3)CC2)C[C@H](C)O1] | A-878 |
| 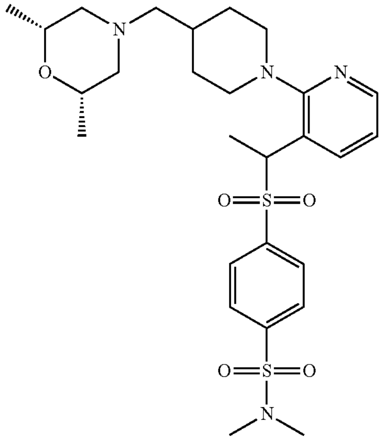 [SMILES: CC(c1cccnc1N1CCC(CN2C[C@@H](C)O[C@@H](C)C2)CC1)S(=O)(=O)c1ccc(S(=O)(=O)N(C)C)cc1] | A-879 |
| 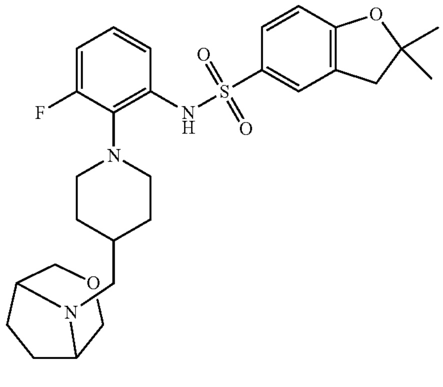 [SMILES: CC1(C)Cc2cc(S(=O)(=O)Nc3cccc(F)c3N3CCC(CN4C5CCC4COC5)CC3)ccc2O1] | A-880 |

TABLE A-continued
| Structure | Compound No. |
| --- | --- |
| 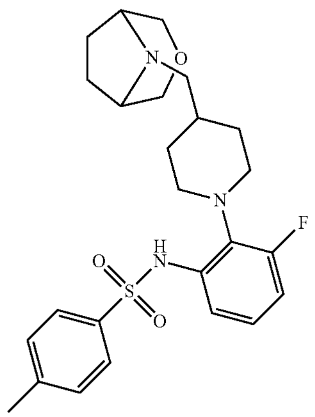 [SMILES: Cc1ccc(S(=O)(=O)Nc2cccc(F)c2N2CCC(CN3C4CCC3COC4)CC2)cc1] | A-881 |
| 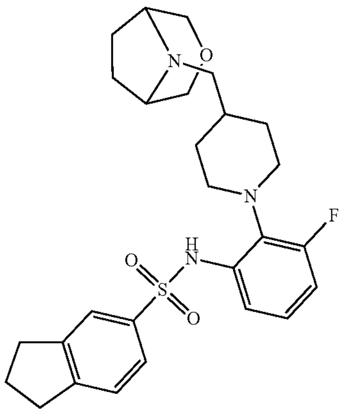 [SMILES: O=S(=O)(Nc1cccc(F)c1N1CCC(CN2C3CCC2COC3)CC1)c1ccc2c(c1)CCC2] | A-882 |
| 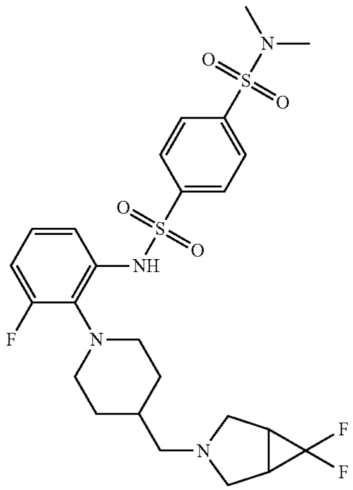 [SMILES: CN(C)S(=O)(=O)c1ccc(S(=O)(=O)Nc2cccc(F)c2N2CCC(CN3CC4C(C3)C4(F)F)CC2)cc1] | A-883 |

TABLE A-continued
| Structure | Compound No. |
|---|---|
| 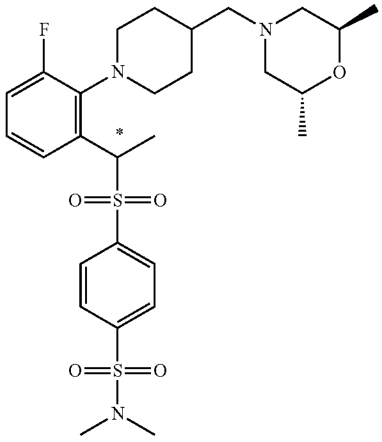<br>Diastereomer 4 | A-885 |
| 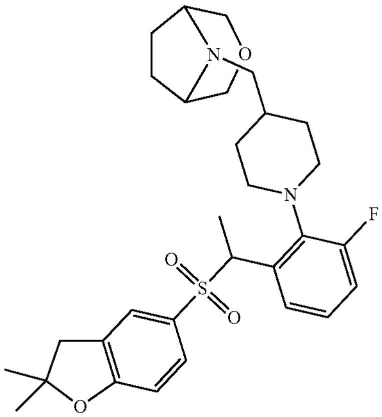 [SMILES: CC(c1cccc(F)c1N1CCC(CN2C3CCC2COC3)CC1)S(=O)(=O)c1ccc2c(c1)CC(C)(C)O2] | A-886 |
| 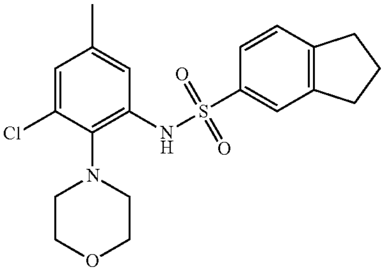 [SMILES: Cc1cc(Cl)c(N2CCOCC2)c(NS(=O)(=O)c2ccc3c(c2)CCC3)c1] | A-887 |
| 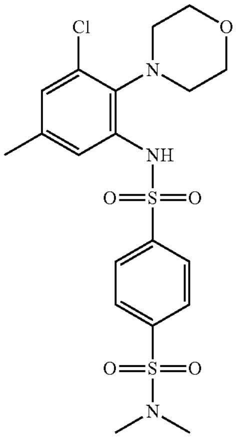 [SMILES: Cc1cc(Cl)c(N2CCOCC2)c(NS(=O)(=O)c2ccc(S(=O)(=O)N(C)C)cc2)c1] | A-888 |

TABLE A-continued
| Structure | Compound No. |
|---|---|
| 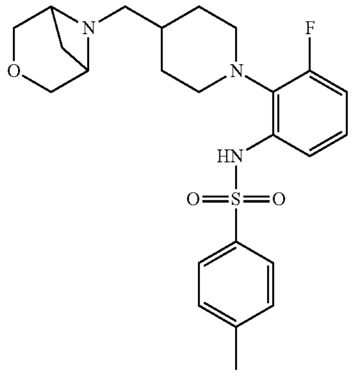 [SMILES: Cc1ccc(S(=O)(=O)Nc2cccc(F)c2N2CCC(CN3C4COCC3C4)CC2)cc1] | A-889 |
| 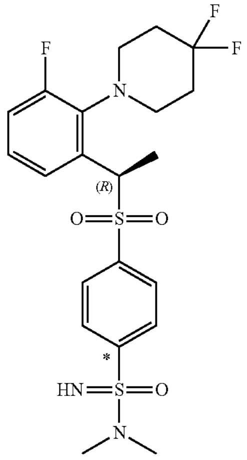 Diastereomer 1 | A-890 |
| 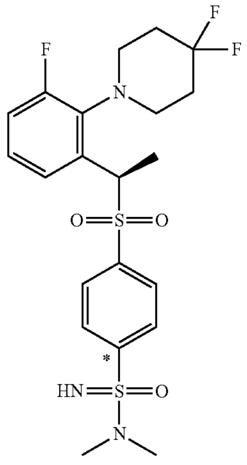 Diastereomer 2 | A-891 |

TABLE A-continued
| Structure | Compound No. |
|---|---|
| 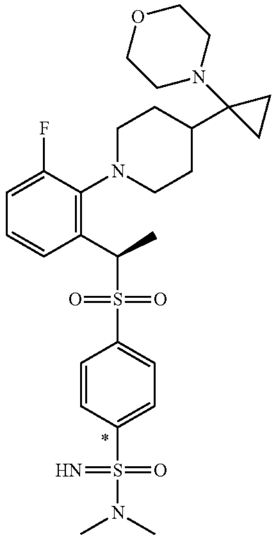 Diastereomer 1 | A-892 |
| 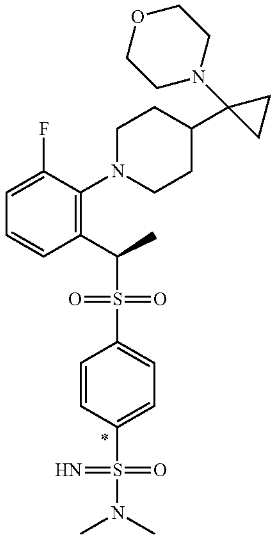 Diastereomer 2 | A-893 |
| 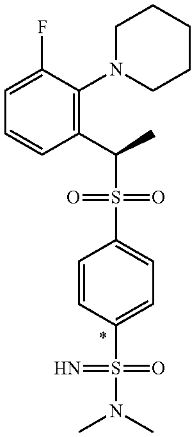 Diastereomer 1 | A-894 |

TABLE A-continued
| Structure | Compound No. |
|---|---|
| 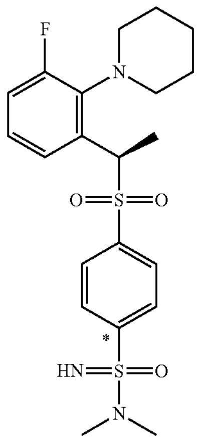<br>Diastereomer 2 | A-895 |
| 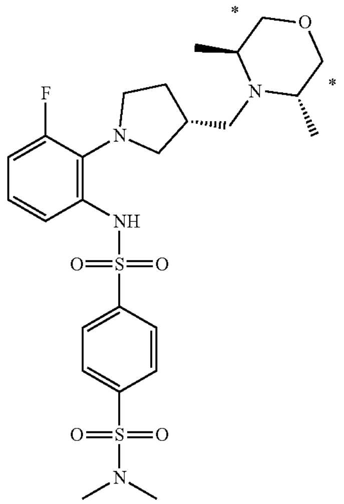<br>trans, diastereomer 1 | A-896 |
| 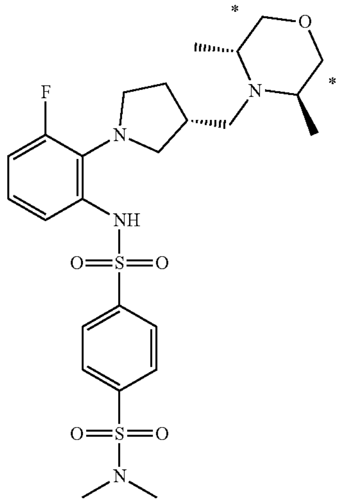<br>trans, diastereomer 2 | A-897 |

TABLE A-continued
| Structure | Compound No. |
|---|---|
| 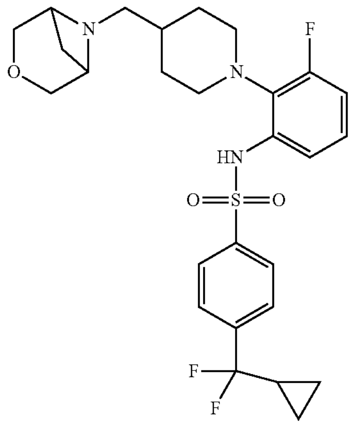 [SMILES: O=S(=O)(Nc1cccc(F)c1N1CCC(CN2C3COCC2C3)CC1)c1ccc(C(F)(F)C2CC2)cc1] | A-898 |
| 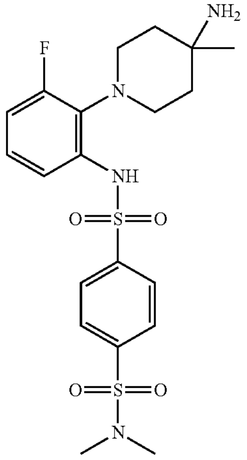 [SMILES: CN(C)S(=O)(=O)c1ccc(S(=O)(=O)Nc2cccc(F)c2N2CCC(C)(N)CC2)cc1] | A-899 |
| 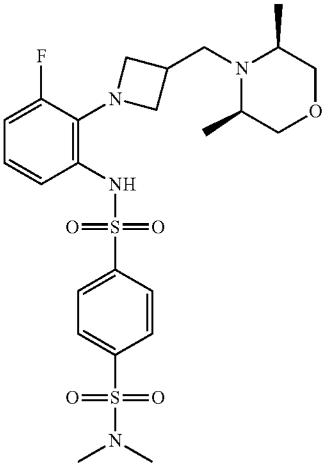 [SMILES: C[C@@H]1COC[C@H](C)N1CC1CN(c2c(F)cccc2NS(=O)(=O)c2ccc(S(=O)(=O)N(C)C)cc2)C1] | A-900 |

TABLE A-continued
| Structure | Compound No. |
| --- | --- |
| 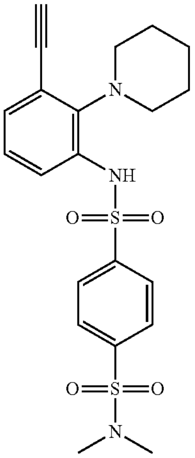 [SMILES: C#Cc1cccc(NS(=O)(=O)c2ccc(S(=O)(=O)N(C)C)cc2)c1N1CCCCC1] | A-901 |
| 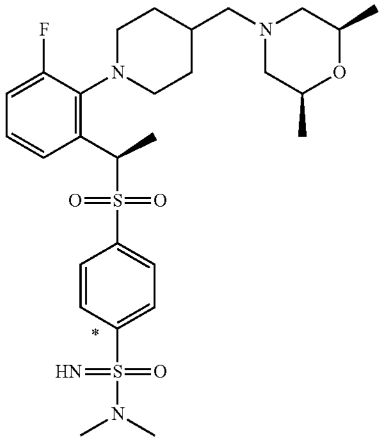<br>Diastereomer 3 | A-902 |
| 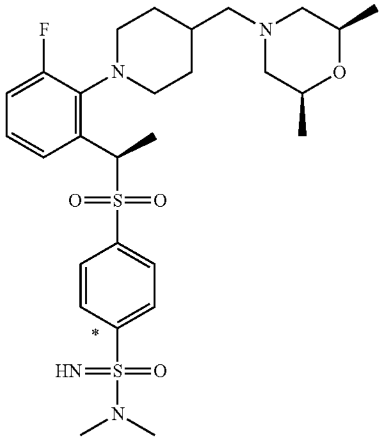<br>Diastereomer 4 | A-903 |

TABLE A-continued
| Structure | Compound No. |
| --- | --- |
| 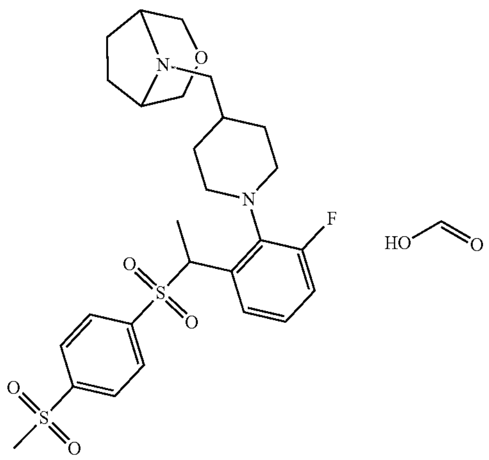 [SMILES: CC(c1cccc(F)c1N1CCC(CCN2C3CCC2COC3)CC1)S(=O)(=O)c1ccc(S(C)(=O)=O)cc1 ; O=CO] | A-904 |
| 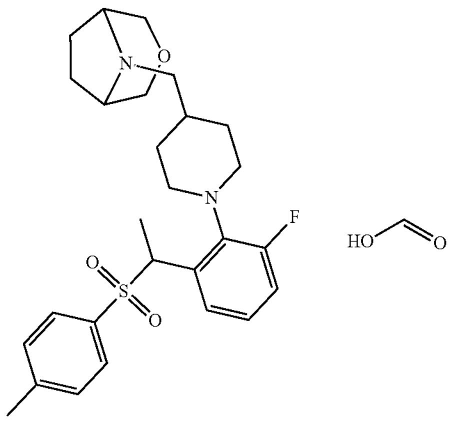 [SMILES: Cc1ccc(S(=O)(=O)C(C)c2cccc(F)c2N2CCC(CCN3C4CCC3COC4)CC2)cc1 ; O=CO] | A-905 |
| 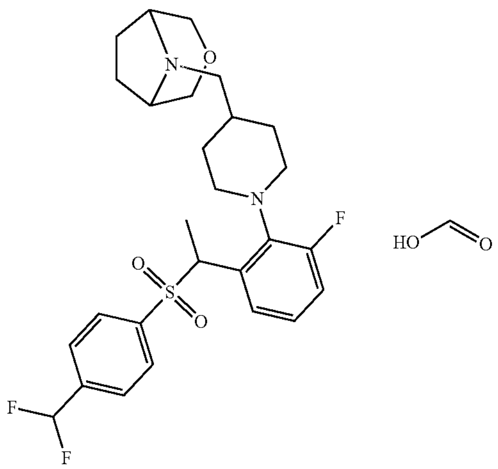 [SMILES: CC(c1cccc(F)c1N1CCC(CCN2C3CCC2COC3)CC1)S(=O)(=O)c1ccc(C(F)F)cc1 ; O=CO] | A-906 |

TABLE A-continued
| Structure | Compound No. |
|---|---|
| 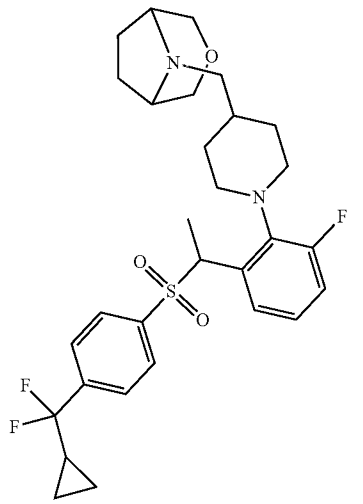 [SMILES: CC(c1cccc(F)c1N1CCC(CCN2C3CCC2COC3)CC1)S(=O)(=O)c1ccc(C(F)(F)C2CC2)cc1] | A-907 |
| 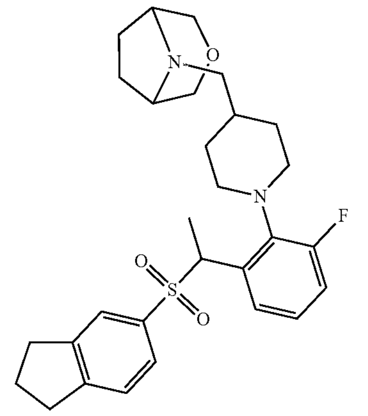 [SMILES: CC(c1cccc(F)c1N1CCC(CCN2C3CCC2COC3)CC1)S(=O)(=O)c1ccc2c(c1)CCC2] | A-908 |
| 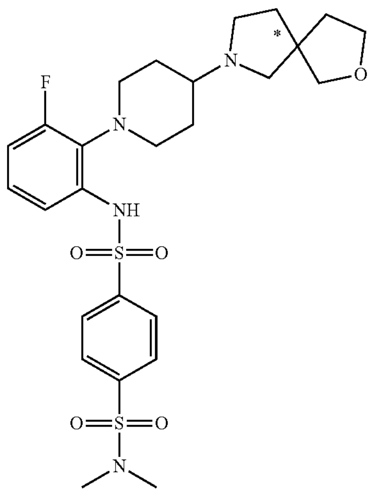 Enantiomer 1 | A-909 |

TABLE A-continued
| Structure | Compound No. |
|---|---|
| 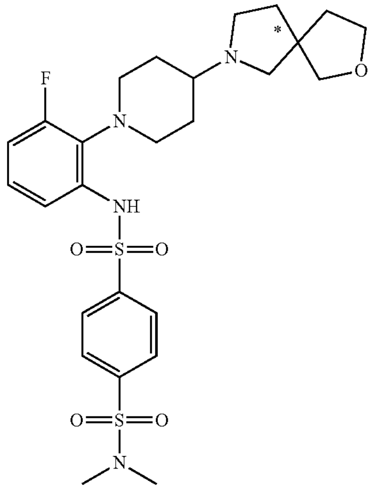 Enantiomer 2 | A-910 |
| 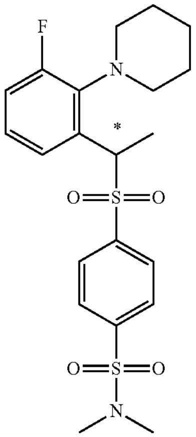 Enantiomer 1 | A-911 |
| 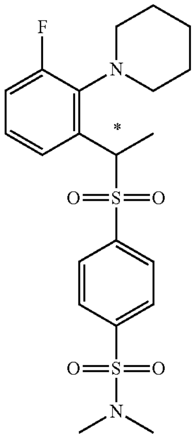 Enantiomer 2 | A-912 |

TABLE A-continued
| Structure | Compound No. |
| --- | --- |
| 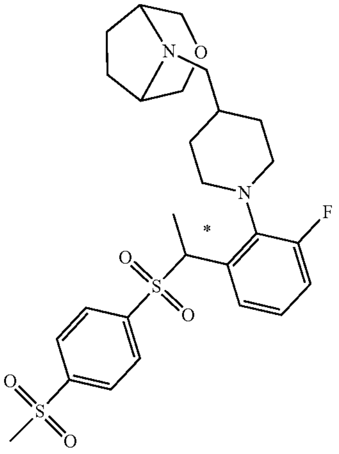 Enantiomer 1 | A-913 |
| 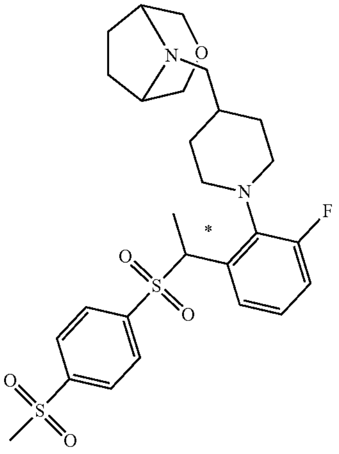 Enantiomer 2 | A-914 |
| 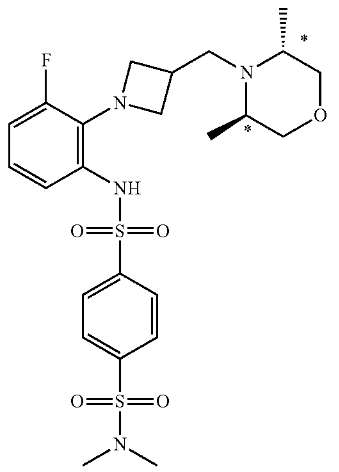 trans, diastereomer 1 | A-915 |

TABLE A-continued
| Structure | Compound No. |
| --- | --- |
| 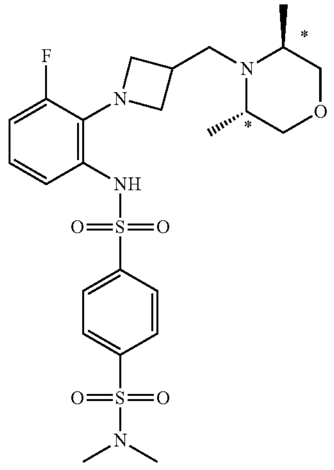 trans, diastereomer 2 | A-916 |
| 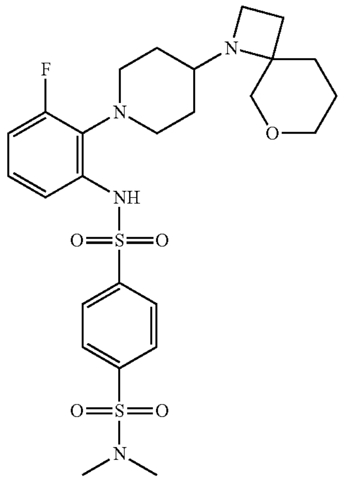 [SMILES: CN(C)S(=O)(=O)c1ccc(S(=O)(=O)Nc2cccc(F)c2N2CCC(N3CCC34CCCOC4)CC2)cc1] | A-917 |
| 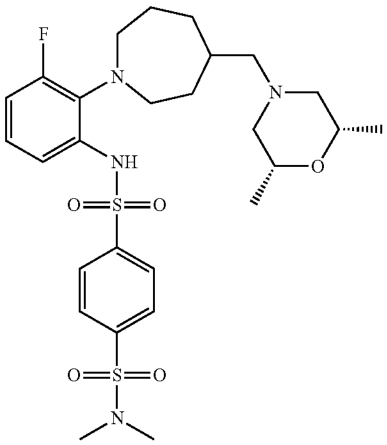 [SMILES: C[C@@H]1CN(CC2CCCN(c3c(F)cccc3NS(=O)(=O)c3ccc(S(=O)(=O)N(C)C)cc3)CC2)C[C@H](C)O1] | A-918 |

TABLE A-continued
| Structure | Compound No. |
|---|---|
| 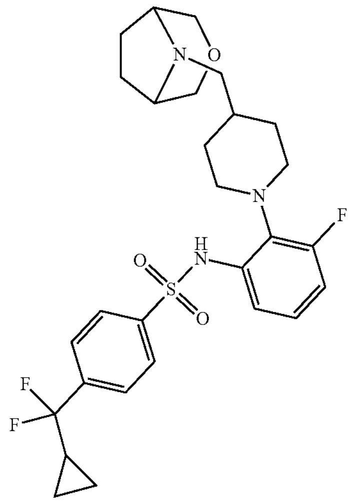 [SMILES: O=S(=O)(Nc1cccc(F)c1N1CCC(CN2C3CCC2COC3)CC1)c1ccc(C(F)(F)C2CC2)cc1] | A-919 |
| 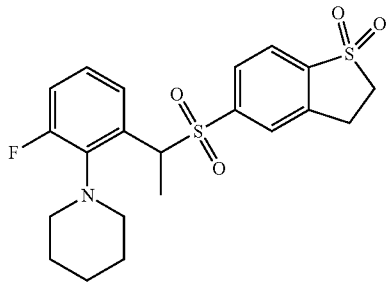 [SMILES: CC(c1cccc(F)c1N1CCCCC1)S(=O)(=O)c1ccc2c(c1)CCS2(=O)=O] | A-920 |
| 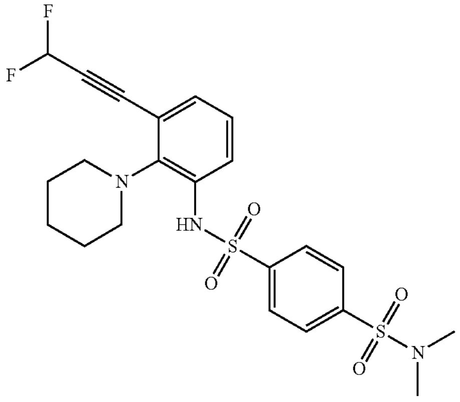 [SMILES: CN(C)S(=O)(=O)c1ccc(S(=O)(=O)Nc2cccc(C#CC(F)F)c2N2CCCCC2)cc1] | A-921 |

TABLE A-continued
| Structure | Compound No. |
|---|---|
| 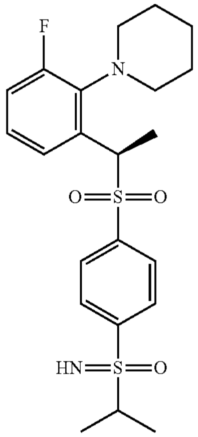 [SMILES: CC(C)S(=N)(=O)c1ccc(S(=O)(=O)[C@H](C)c2cccc(F)c2N2CCCCC2)cc1] | A-922 |
| 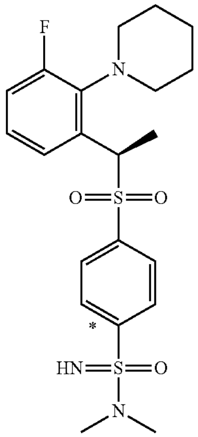<br>Diastereomer 3 | A-923 |
| 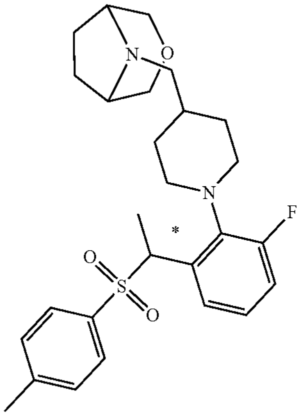<br>Enantiomer 1 | A-924 |

TABLE A-continued
| Structure | Compound No. |
| --- | --- |
| 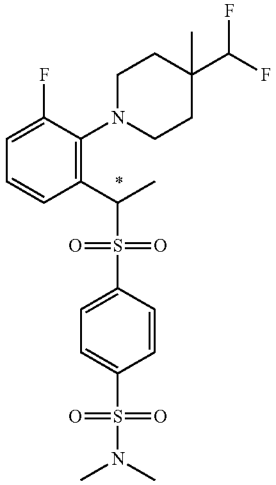 Enantiomer 1 | A-925 |
| 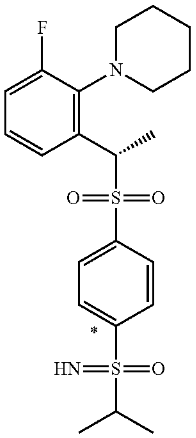 diastereomer 1 | A-926 |
| 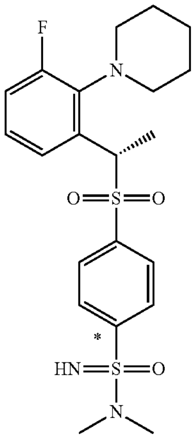 diastereomer 2 | A-927 |

TABLE A-continued
| Structure | Compound No. |
|---|---|
| 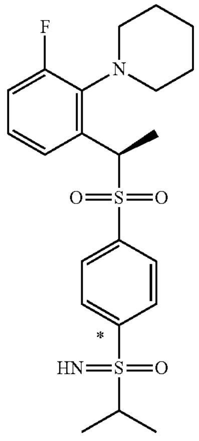 diastereomer 4 | A-928 |
| 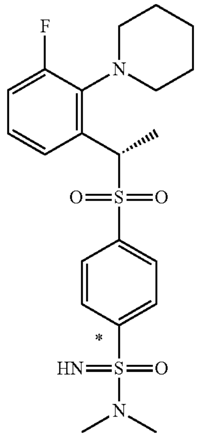 diastereomer 1 | A-929 |
| 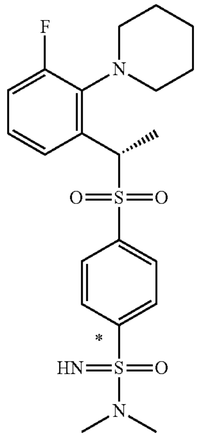 diastereomer 2 | A-930 |

TABLE A-continued
| Structure | Compound No. |
|---|---|
| 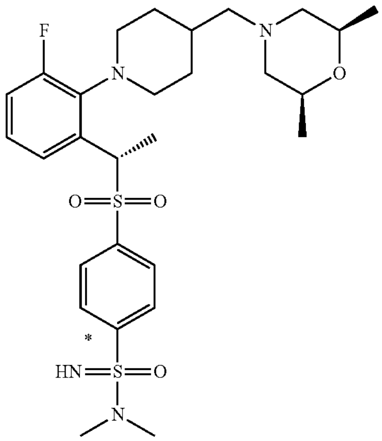 diastereomer 1 | A-931 |
| 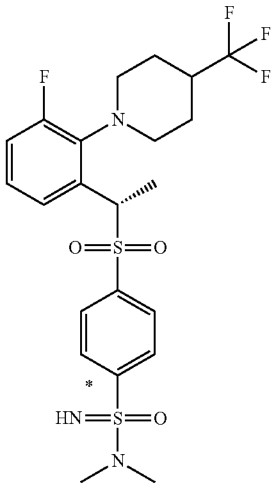 diastereomer 1 | A-932 |
| 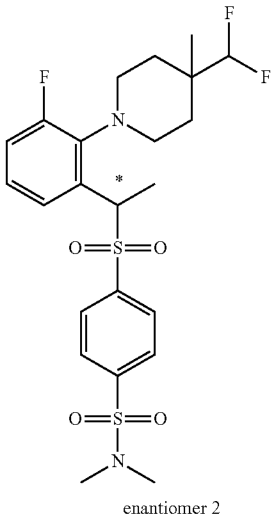 enantiomer 2 | A-933 |

TABLE A-continued
| Structure | Compound No. |
| --- | --- |
| 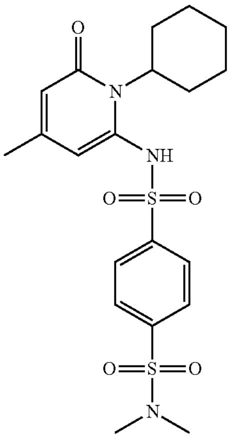 [SMILES: Cc1cc(NS(=O)(=O)c2ccc(S(=O)(=O)N(C)C)cc2)n(C2CCCCC2)c(=O)c1] | A-934 |
| 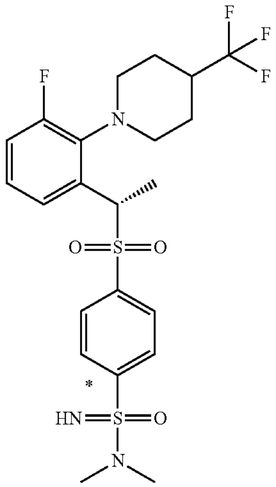<br>diastereomer 2 | A-935 |
| 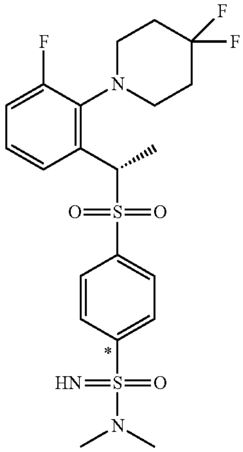<br>Diastereomer 2 | A-936 |

TABLE A-continued
| Structure | Compound No. |
|---|---|
| 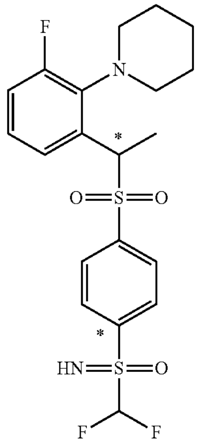<br>Diastereomer 1 | A-937 |
| 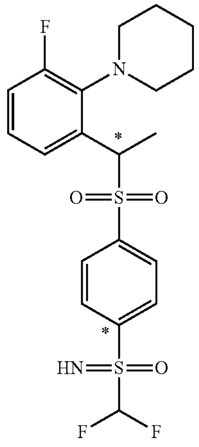<br>Diastereomer 2 | A-938 |
| 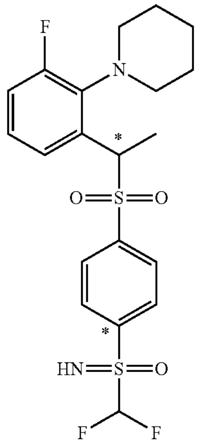<br>Diastereomer 3 | A-939 |

TABLE A-continued
| Structure | Compound No. |
|---|---|
| 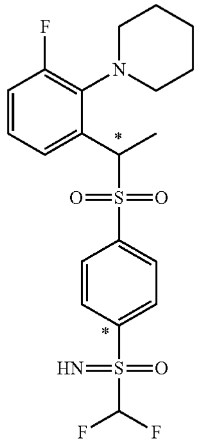 Diastereomer 4 | A-940 |
| 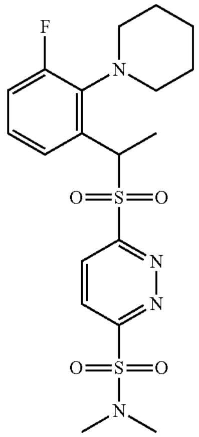 [SMILES: CC(c1cccc(F)c1N1CCCCC1)S(=O)(=O)c1ccc(S(=O)(=O)N(C)C)nn1] | A-941 |
| 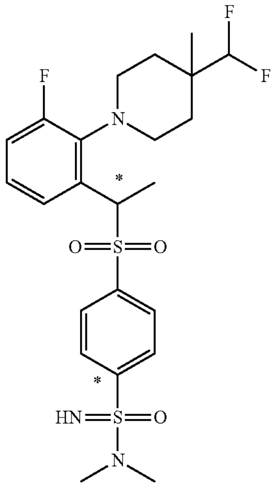 Diastereomer 1 | A-942 |

TABLE A-continued
| Structure | Compound No. |
| --- | --- |
| 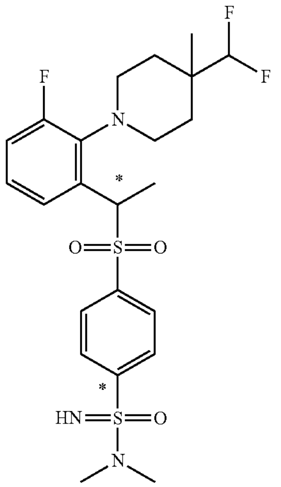<br>Diastereomer 2 | A-943 |
| 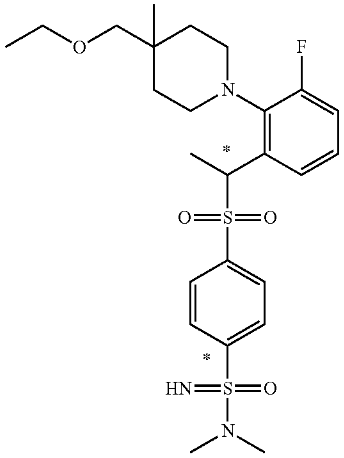<br>Diastereomer 1 | A-944 |
| 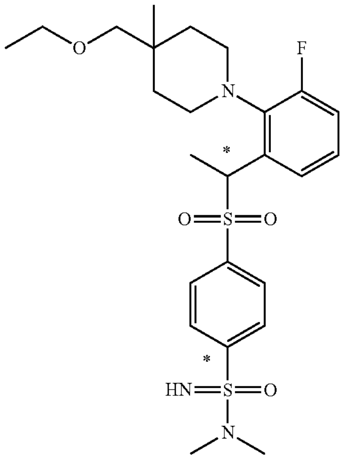<br>Diastereomer 2 | A-945 |

TABLE A-continued
| Structure | Compound No. |
|---|---|
| 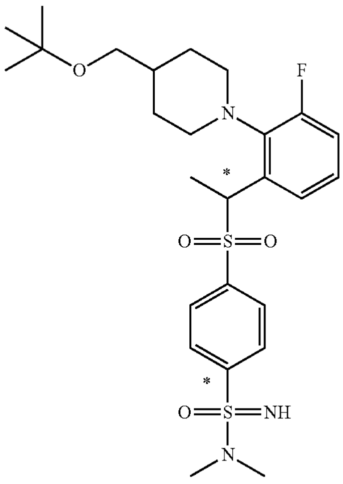 Diastereomer 1 | A-946 |
| 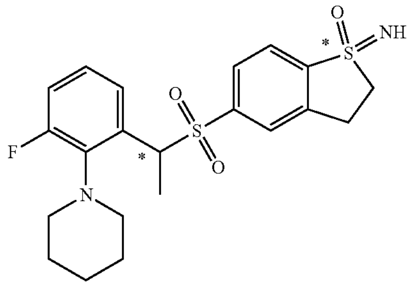 Diastereomer 1 | A-947 |
| 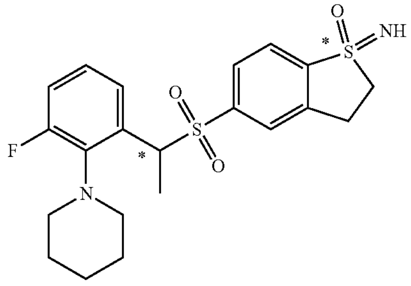 Diastereomer 2 | A-948 |

TABLE A-continued
| Structure | Compound No. |
| --- | --- |
| 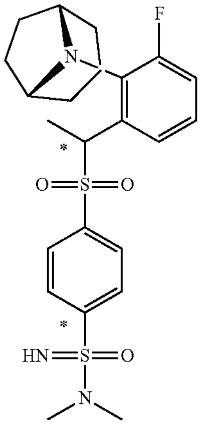 Diastereomer 1 | A-949 |
| 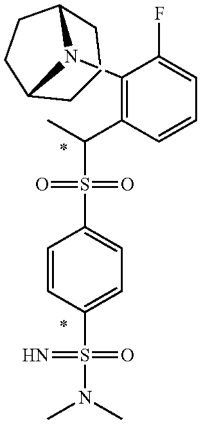 Diastereomer 2 | A-950 |
| 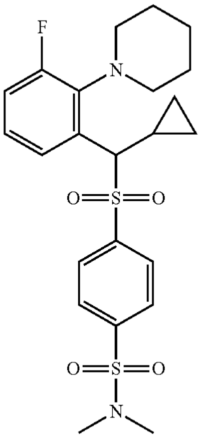 [SMILES: CN(C)S(=O)(=O)c1ccc(S(=O)(=O)C(c2cccc(F)c2N2CCCCC2)C2CC2)cc1] | A-951 |

TABLE A-continued
| Structure | Compound No. |
|---|---|
| 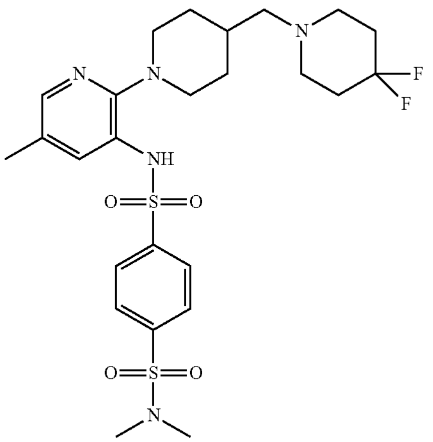 [SMILES: Cc1cnc(N2CCC(CN3CCC(F)(F)CC3)CC2)c(NS(=O)(=O)c2ccc(S(=O)(=O)N(C)C)cc2)c1] | A-952 |
| 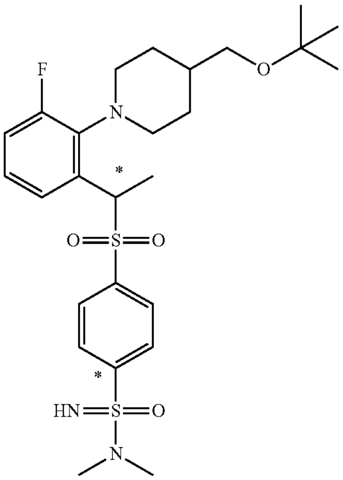 Diastereomer 2 | A-953 |
| 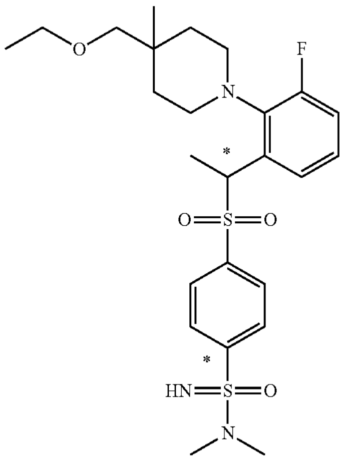 Diastereomer 3 | A-954 |

TABLE A-continued
| Structure | Compound No. |
|---|---|
| 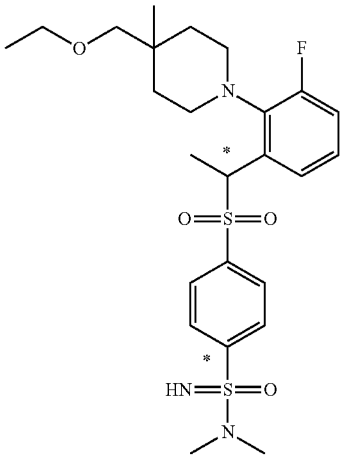 Diastereomer 4 | A-955 |
| 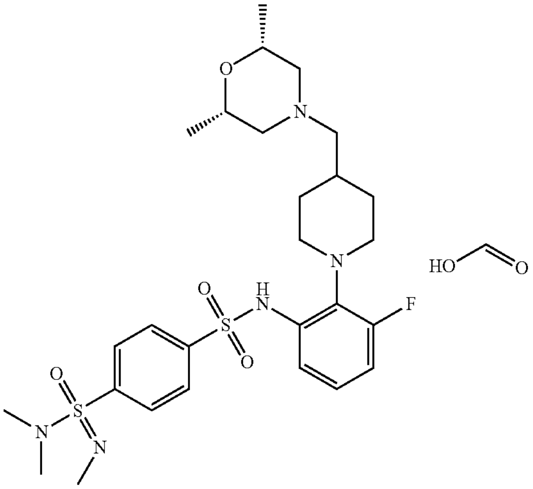 | A-956 |
| 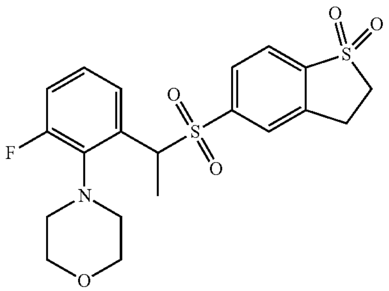 [SMILES: CC(c1cccc(F)c1N1CCOCC1)S(=O)(=O)c1ccc2c(c1)CCS2(=O)=O] | A-957 |

TABLE A-continued
| Structure | Compound No. |
|---|---|
| 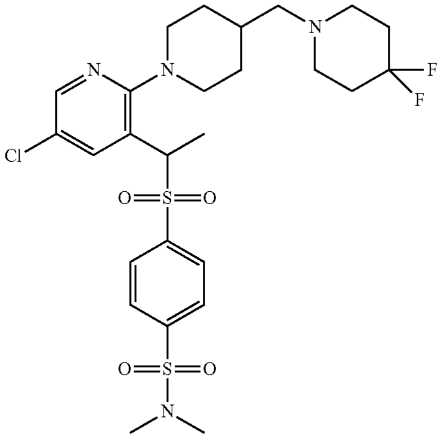 [SMILES: CC(c1cc(Cl)cnc1N1CCC(CN2CCC(F)(F)CC2)CC1)S(=O)(=O)c1ccc(S(=O)(=O)N(C)C)cc1] | A-958 |
| 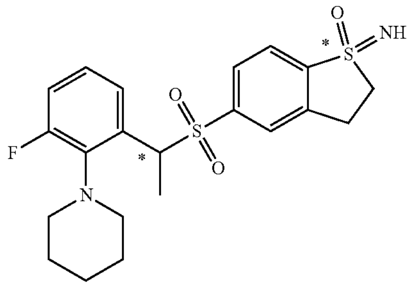<br>Diastereomer 3 | A-959 |
| 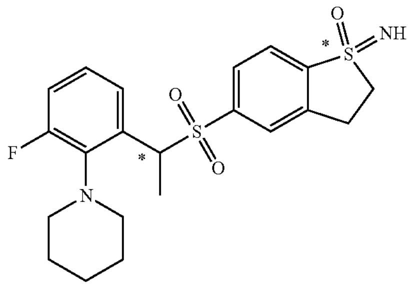<br>Diastereomer 4 | A-960 |
| 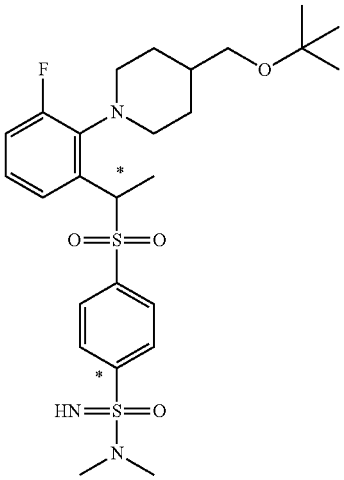<br>Diastereomer 4 | A-961 |

TABLE A-continued
| Structure | Compound No. |
|---|---|
| 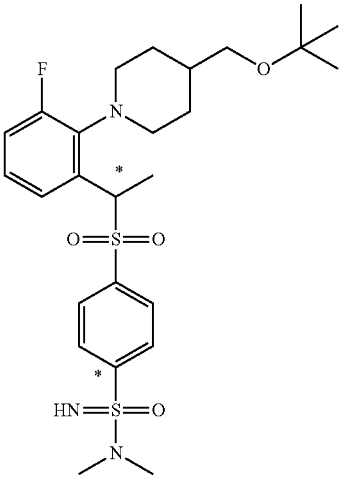 Diastereomer 3 | A-962 |
| 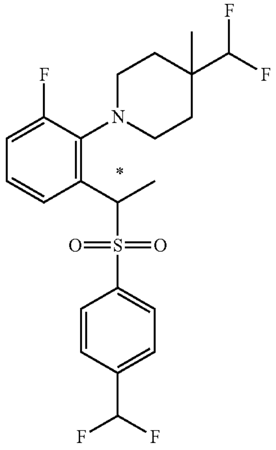 Enantiomer 1 | A-963 |
| 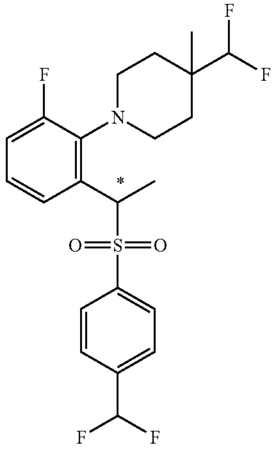 Enantiomer 2 | A-964 |

TABLE A-continued
| Structure | Compound No. |
|---|---|
| 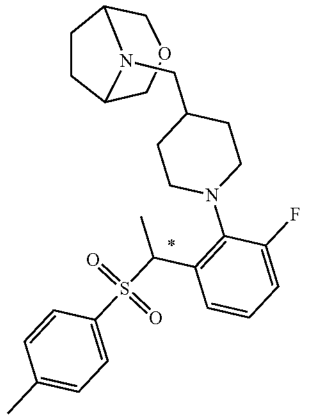 Enantiomer 2 | A-965 |
| 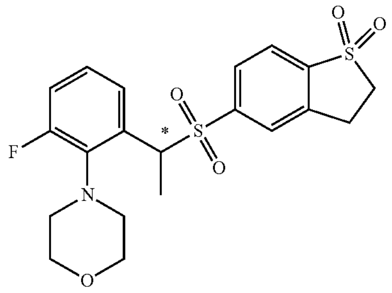 Enantiomer 1 | A-966 |
| 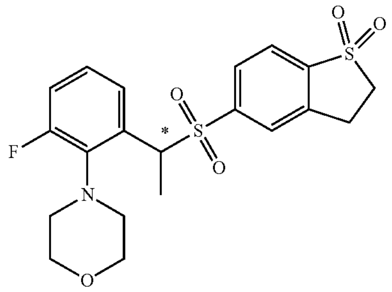 Enantiomer 2 | A-967 |
| 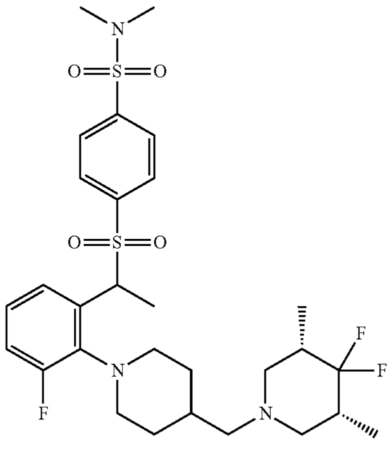 [SMILES: CC(c1cccc(F)c1N1CCC(CN2C[C@@H](C)C(F)(F)[C@@H](C)C2)CC1)S(=O)(=O)c1ccc(S(=O)(=O)N(C)C)cc1] | A-970 |

TABLE A-continued
| Structure | Compound No. |
| --- | --- |
| 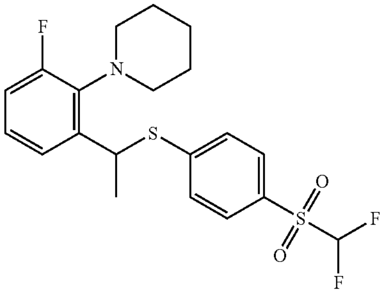 [SMILES: CC(Sc1ccc(S(=O)(=O)C(F)F)cc1)c1cccc(F)c1N1CCCCC1] | A-971 |
| 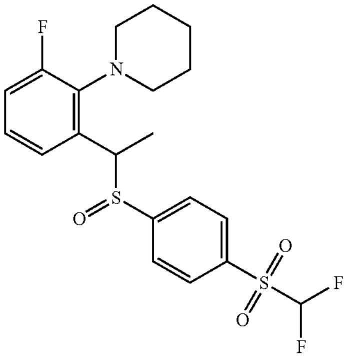 [SMILES: CC(c1cccc(F)c1N1CCCCC1)S(=O)c1ccc(S(=O)(=O)C(F)F)cc1] | A-972 |
| 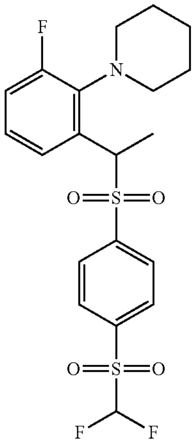 [SMILES: CC(c1cccc(F)c1N1CCCCC1)S(=O)(=O)c1ccc(S(=O)(=O)C(F)F)cc1] | A-973 |

TABLE A-continued
| Structure | Compound No. |
|---|---|
| 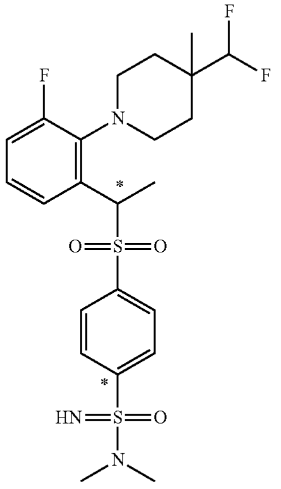 Diastereomer 3 | A-974 |
| 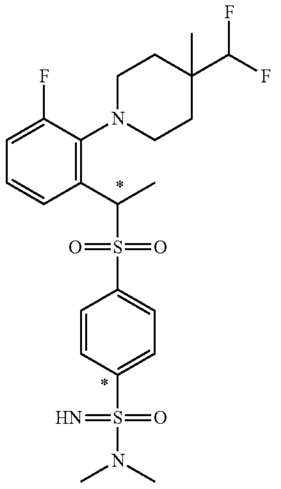 Diastereomer 4 | A-975 |
| 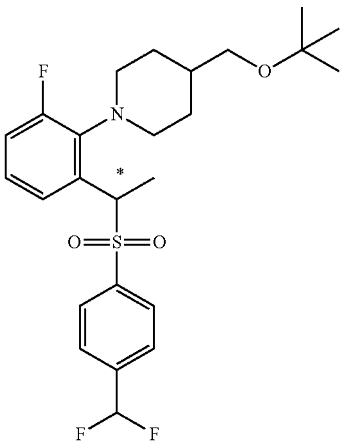 Enantiomer 1 | A-976 |

TABLE A-continued
| Structure | Compound No. |
|---|---|
| 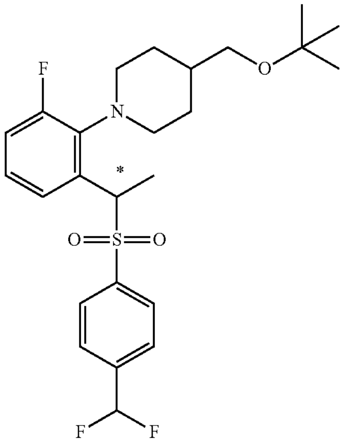 Enantiomer 2 | A-977 |
| 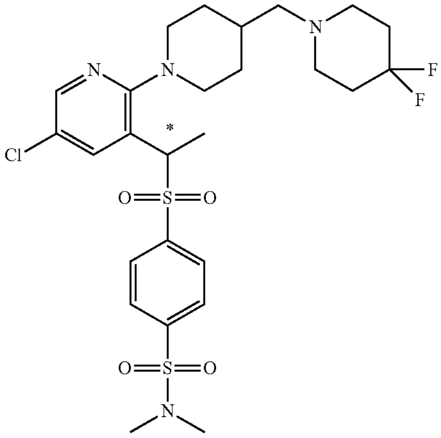 Enantiomer 1 | A-978 |
| 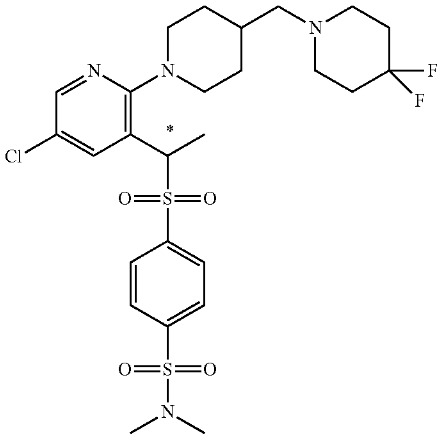 Enantiomer 2 | A-979 |

TABLE A-continued
| Structure | Compound No. |
| --- | --- |
| 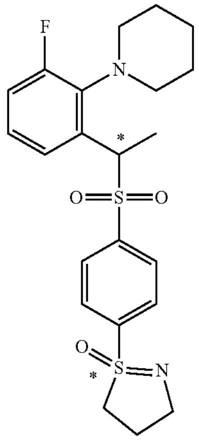<br>Diastereomer 2 | A-980 |
| 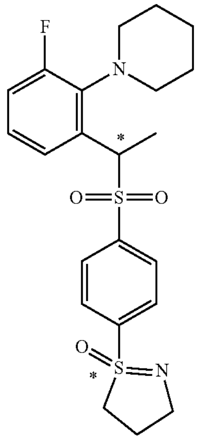<br>Diastereomer 1 | A-981 |
| 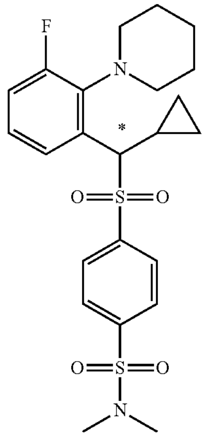<br>Enantiomer 1 | A-982 |

TABLE A-continued
| Structure | Compound No. |
|---|---|
| 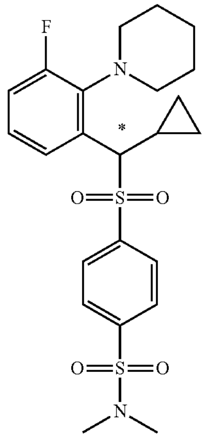 Enantiomer 2 | A-983 |
| 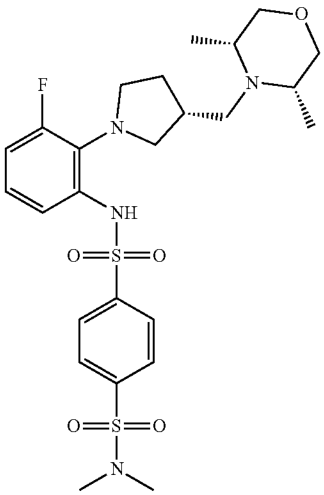 [SMILES: C[C@@H]1COC[C@H](C)N1C[C@H]1CCN(c2c(F)cccc2NS(=O)(=O)c2ccc(S(=O)(=O)N(C)C)cc2)C1] | A-984 |
| 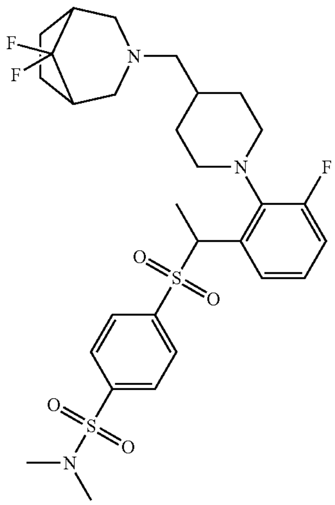 [SMILES: CC(c1cccc(F)c1N1CCC(CN2CC3CCC(C2)C3(F)F)CC1)S(=O)(=O)c1ccc(S(=O)(=O)N(C)C)cc1] | A-985 |

TABLE A-continued
| Structure | Compound No. |
| --- | --- |
| 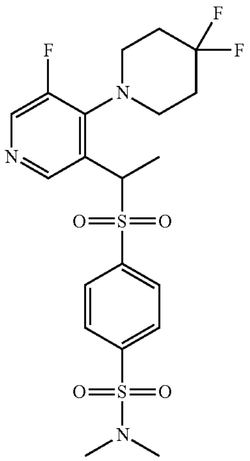 [SMILES: CC(c1cncc(F)c1N1CCC(F)(F)CC1)S(=O)(=O)c1ccc(S(=O)(=O)N(C)C)cc1] | A-986 |
| 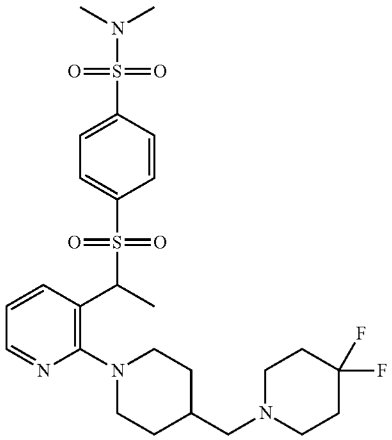 [SMILES: CC(c1cccnc1N1CCC(CN2CCC(F)(F)CC2)CC1)S(=O)(=O)c1ccc(S(=O)(=O)N(C)C)cc1] | A-987 |
| 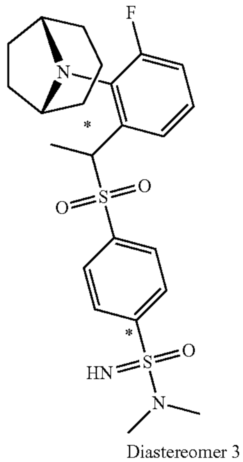 [SMILES: CC(c1cccc(F)c1N1[C@@H]2CCC[C@H]1CC2)S(=O)(=O)c1ccc(S(=N)(=O)N(C)C)cc1] Diastereomer 3 | A-988 |

TABLE A-continued
| Structure | Compound No. |
|---|---|
| 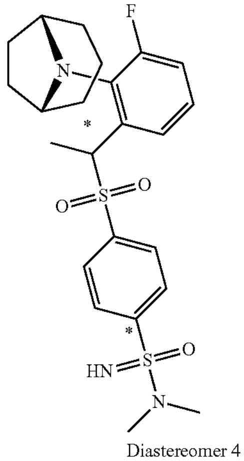 [SMILES: CC(c1cccc(F)c1N1[C@@H]2CCC[C@H]1CC2)S(=O)(=O)c1ccc(S(=N)(=O)N(C)C)cc1]<br>Diastereomer 4 | A-989 |
| 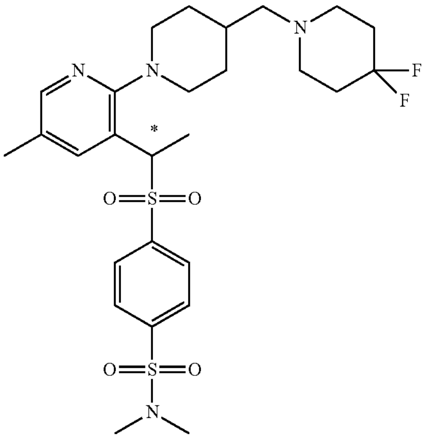<br>Enantiomer 1 | A-990 |
| 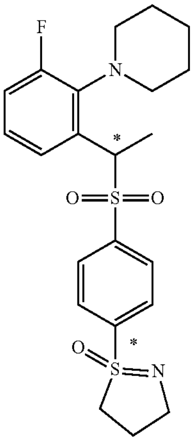<br>diastereomer 3 | A-991 |

TABLE A-continued
| Structure | Compound No. |
| --- | --- |
| 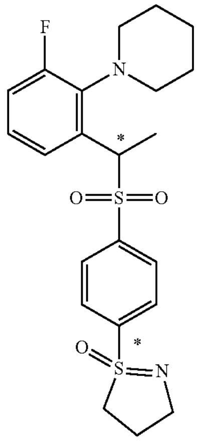<br>diastereomer 4 | A-992 |
| 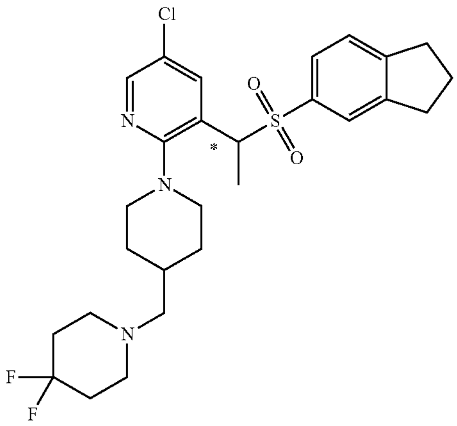<br>Enantiomer 1 | A-993 |
| 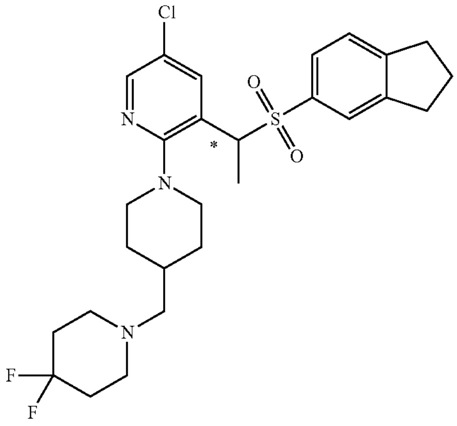<br>Enantiomer 2 | A-994 |

TABLE A-continued
| Structure | Compound No. |
|---|---|
| 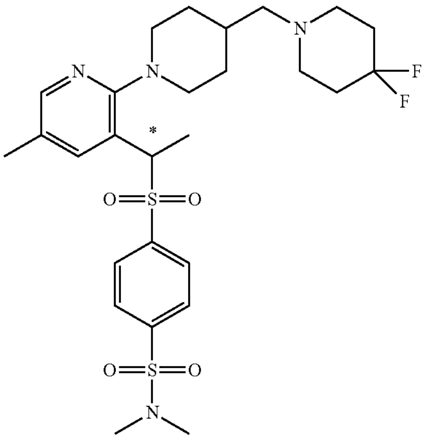 Enantiomer 2 | A-995 |
| 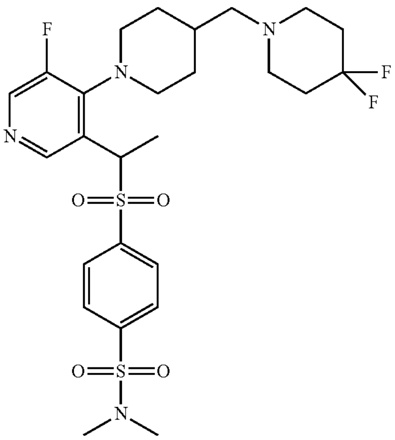 [SMILES: CC(c1cncc(F)c1N1CCC(CN2CCC(F)(F)CC2)CC1)S(=O)(=O)c1ccc(S(=O)(=O)N(C)C)cc1] | A-996 |
| 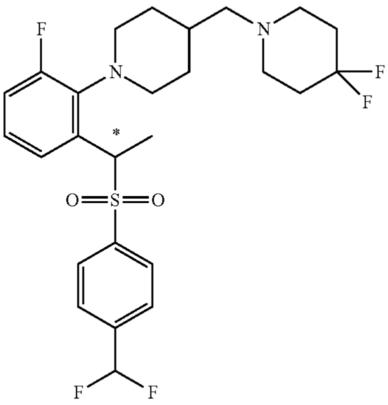 Enantiomer 1 | A-997 |

TABLE A-continued
| Structure | Compound No. |
|---|---|
| 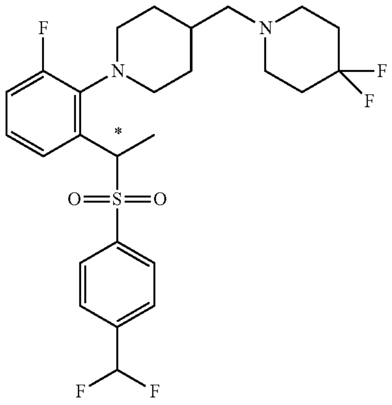 Enantiomer 2 | A-998 |
| 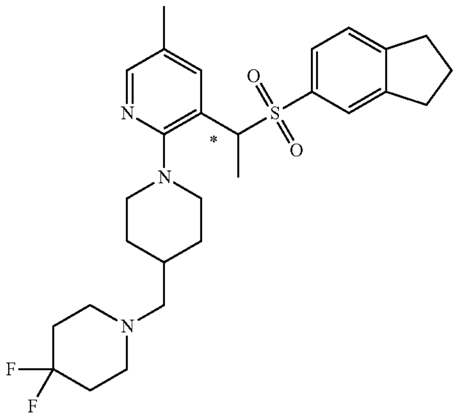 Enantiomer 1 | A-999 |
| 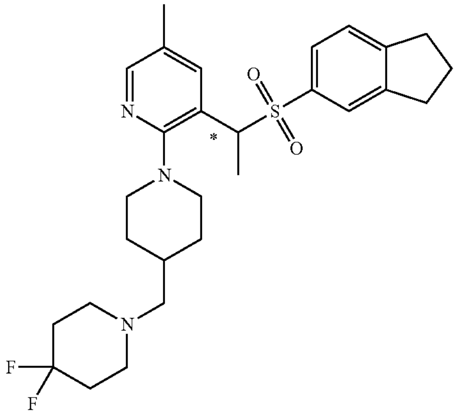 Enantiomer 2 | A-1000 |

TABLE A-continued

| Structure | Compound No. |
|---|---|
| 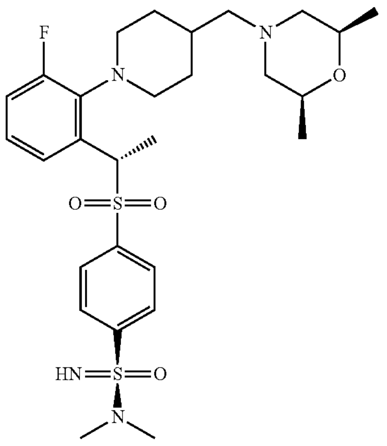 [SMILES: C[C@@H]1CN(CC2CCN(c3c(F)cccc3[C@H](C)S(=O)(=O)c3ccc([S@@](=N)(=O)N(C)C)cc3)CC2)C[C@H](C)O1] | A-1001 |
| 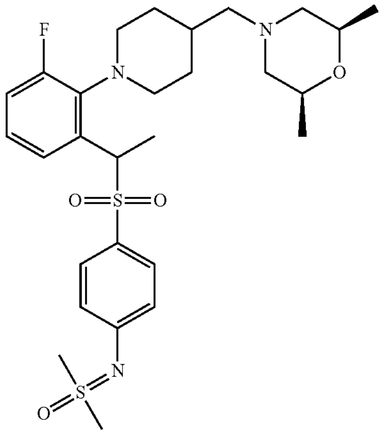 [SMILES: CC(c1cccc(F)c1N1CCC(CN2C[C@@H](C)O[C@@H](C)C2)CC1)S(=O)(=O)c1ccc(N=S(C)(C)=O)cc1] | A-1002 |

In some embodiments, a compound of the present disclosure is selected from Table B:

TABLE B

| Compound No. | Compound Name |
|---|---|
| A-1 | N-{2-[4-(4-chloro-2-fluorophenyl)piperazin-1-yl]phenyl}pyridine-3-sulfonamide |
| A-2 | N-{2-[4-(4-chloro-2-fluorophenyl)piperazin-1-yl]phenyl}-1-methyl-1H-imidazole-4-sulfonamide |
| A-3 | N4-{2-[2-(4-chloro-2-fluorophenyl)ethynyl]phenyl}-N1,N1-dimethylbenzene-1,4-disulfonamide |
| A-4 | N-{2-[4-(4-chloro-2-fluorophenyl)piperazin-1-yl]phenyl}-3-methoxybenzene-1-sulfonamide |
| A-5 | N-{2-[4-(4-chloro-2-fluorophenyl)piperazin-1-yl]phenyl}-3-cyanobenzene-1-sulfonamide |
| A-6 | N-{2-[4-(4-chloro-2-fluorophenyl)piperazin-1-yl]phenyl}-1-methyl-1H-pyrazole-4-sulfonamide |
| A-7 | N-{2-[4-(4-chloro-2-fluorophenyl)piperazin-1-yl]phenyl}-2,4-dimethyl-1,3-thiazole-5-sulfonamide |
| A-8 | N-{2-[4-(4-chloro-2-fluorophenyl)piperazin-1-yl]phenyl}cyclohexanesulfonamide |
| A-9 | 2-[4-(4-chloro-2-fluorophenyl)piperazin-1-yl]-N-[4-(dimethylsulfamoyl)phenyl]benzamide |
| A-10 | N4-{2-[4-(2-fluorophenyl)piperidin-1-yl]phenyl}-N1,N1-dimethylbenzene-1,4-disulfonamide |
| A-11 | N-{2-[4-(4-chloro-2-fluorophenyl)piperazin-1-yl]phenyl}-4-(dimethylsulfamoyl)benzamide |

TABLE B-continued

| Compound No. | Compound Name |
|---|---|
| A-12 | N4-{2-[4-(4-chloro-2-fluorophenyl)piperazin-1-yl]phenyl}-N1,N1-dimethylbenzene-1,4-disulfonamide |
| A-14 | N-{2-[4-(4-chloro-2-fluorophenyl)piperazin-1-yl]phenyl}oxane-4-sulfonamide |
| A-15 | N-{2-[4-(4-chloro-2-fluorophenyl)piperazin-1-yl]phenyl}-1-methyl-1H-pyrazole-5-sulfonamide |
| A-16 | N-{2-[4-(4-chloro-2-fluorophenyl)piperazin-1-yl]phenyl}-1-methylpiperidine-4-sulfonamide |
| A-17 | 1-acetyl-N-{2-[4-(4-chloro-2-fluorophenyl)piperazin-1-yl]phenyl}piperidine-4-sulfonamide |
| A-18 | N4-{5-[4-(4-chloro-2-fluorophenyl)piperazin-1-yl]-1,3-dimethyl-1H-pyrazol-4-yl}-N1,N1-dimethylbenzene-1,4-disulfonamide |
| A-19 | N4-{2-[1-(4-chloro-2-fluorophenyl)-1,2,3,6-tetrahydropyridin-4-yl]phenyl}-N1,N1-dimethylbenzene-1,4-disulfonamide |
| A-20 | N-{2-[4-(4-chloro-2-fluorophenyl)piperazin-1-yl]phenyl}pyridine-2-sulfonamide |
| A-21 | N-{2-[4-(4-chloro-2-fluorophenyl)piperazin-1-yl]phenyl}-1-methyl-1H-pyrazole-3-sulfonamide |
| A-22 | N4-{2-[1-(4-chloro-2-fluorophenyl)piperidin-4-yl]phenyl}-N1,N1-dimethylbenzene-1,4-disulfonamide |
| A-23 | N4-{2-[4-(4-chloro-2-fluorophenyl)piperidin-1-yl]phenyl}-N1,N1-dimethylbenzene-1,4-disulfonamide |
| A-25 | N4-{2-[(1R,5S)-3-(4-chloro-2-fluorophenyl)-3,8-diazabicyclo[3.2.1]octan-8-yl]phenyl}-N1,N1-dimethylbenzene-1,4-disulfonamide |
| A-26 | N4-{2-[5-(4-chloro-2-fluorophenyl)-2,5-diazabicyclo[2.2.2]octan-2-yl]phenyl}-N1,N1-dimethylbenzene-1,4-disulfonamide |
| A-27 | N4-{2-[3-(4-chloro-2-fluorophenyl)-3,6-diazabicyclo[3.1.1]heptan-6-yl]phenyl}-N1,N1-dimethylbenzene-1,4-disulfonamide |
| A-28 | N4-{2-[3-(4-chloro-2-fluorophenyl)-3,6-diazabicyclo[3.1.1]heptan-6-yl]phenyl}-N1,N1-dimethylbenzene-1,4-disulfonamide |
| A-29 | N4-{5-[1-(4-chloro-2-fluorophenyl)-1,2,3,6-tetrahydropyridin-4-yl]-1,3-dimethyl-1H-pyrazol-4-yl}-N1,N1-dimethylbenzene-1,4-disulfonamide |
| A-30 | N4-{2-[6-(4-chloro-2-fluorophenyl)-3,6-diazabicyclo[3.1.1]heptan-3-yl]phenyl}-N1,N1-dimethylbenzene-1,4-disulfonamide |
| A-31 | N4-{2-[5-(4-chloro-2-fluorophenyl)-2,5-diazabicyclo[2.2.1]heptan-2-yl]phenyl}-N1,N1-dimethylbenzene-1,4-disulfonamide |
| A-32 | N4-{2-[4-(4-chloro-2-fluorophenyl)-1,2,3,6-tetrahydropyridin-1-yl]phenyl}-N1,N1-dimethylbenzene-1,4-disulfonamide |
| A-33 | N4-{5-[1-(4-chloro-2-fluorophenyl)piperidin-4-yl]-1,3-dimethyl-1H-pyrazol-4-yl}-N1,N1-dimethylbenzene-1,4-disulfonamide |
| A-34 | N-{2-[4-(4-chloro-2-fluorophenyl)piperazin-1-yl]phenyl}-2-methoxypyridine-4-sulfonamide |
| A-35 | N-{2-[4-(4-chloro-2-fluorophenyl)piperazin-1-yl]phenyl}-3-methyl-1,2-oxazole-4-sulfonamide |
| A-36 | N4-{5-[4-(4-chloro-2-fluorophenyl)piperazin-1-yl]-1,3,4-thiadiazol-2-yl}-N1,N1-dimethylbenzene-1,4-disulfonamide |
| A-37 | 4-({4-[1-(4-chloro-2-fluorophenyl)-1,2,3,6-tetrahydropyridin-4-yl]-3-methyl-1H-pyrazol-1-yl}sulfonyl)-N,N-dimethylbenzene-1-sulfonamide |
| A-38 | 4-({4-[1-(4-chloro-2-fluorophenyl)piperidin-4-yl]-3-methyl-1H-pyrazol-1-yl}sulfonyl)-N,N-dimethylbenzene-1-sulfonamide |
| A-39 | 4-({4-[1-(4-chloro-2-fluorophenyl)piperidin-4-yl]-2-methyl-1H-imidazol-1-yl}sulfonyl)-N,N-dimethylbenzene-1-sulfonamide |
| A-40 | N4-{4-[1-(2-fluorophenyl)piperidin-4-yl]-1-methyl-1H-pyrazol-3-yl}-N1,N1-dimethylbenzene-1,4-disulfonamide |
| A-41 | ethyl 4-({2-[4-(4-chloro-2-fluorophenyl)piperidin-1-yl]phenyl}sulfamoyl)benzoate |
| A-42 | N-{2-[4-(4-chloro-2-fluorophenyl)piperidin-1-yl]phenyl}benzenesulfonamide |
| A-43 | N-{2-[4-(4-chloro-2-fluorophenyl)piperazin-1-yl]phenyl}morpholine-4-sulfonamide |
| A-44 | 4-({2-[4-(4-chloro-2-fluorophenyl)piperidin-1-yl]phenyl}sulfamoyl)-N,N-dimethylbenzamide |
| A-45 | 4-({2-[4-(4-chloro-2-fluorophenyl)piperidin-1-yl]phenyl}sulfamoyl)-N-cyclopropylbenzamide |
| A-46 | N4-{3-[4-(4-chloro-2-fluorophenyl)piperidin-1-yl]phenyl}-N1,N1-dimethylbenzene-1,4-disulfonamide |
| A-47 | N4-{2-[4-(4-chlorophenyl)piperidin-1-yl]phenyl}-N1,N1-dimethylbenzene-1,4-disulfonamide |
| A-48 | 4-({2-[4-(4-chloro-2-fluorophenyl)piperidin-1-yl]phenyl}sulfamoyl)-N-methylbenzamide |
| A-49 | N-{2-[4-(4-chloro-2-fluorophenyl)piperidin-1-yl]phenyl}-4-(pyrrolidine-1-carbonyl)benzene-1-sulfonamide |
| A-50 | 4-({4-[4-(4-chloro-2-fluorophenyl)piperidin-1-yl]-3-methyl-1H-pyrazol-1-yl}sulfonyl)-N,N-dimethylbenzene-1-sulfonamide |
| A-51 | N4-{2-[4-(3-fluoropyridin-2-yl)piperazin-1-yl]phenyl}-N1,N1-dimethylbenzene-1,4-disulfonamide |
| A-52 | N4-[2-(4-cyclopropylpiperazin-1-yl)phenyl]-N1,N1-dimethylbenzene-1,4-disulfonamide |

TABLE B-continued

| Compound No. | Compound Name |
|---|---|
| A-53 | N4-[2-(4-cyclohexylpiperazin-1-yl)phenyl]-N1,N1-dimethylbenzene-1,4-disulfonamide |
| A-54 | N1,N1-dimethyl-N4-[2-(4-methylpiperazin-1-yl)phenyl]benzene-1,4-disulfonamide |
| A-55 | N4-{4-[1-(4-chloro-2-fluorophenyl)piperidin-4-yl]-1-methyl-1H-pyrazol-3-yl}-N1,N1-dimethylbenzene-1,4-disulfonamide |
| A-56 | N4-{2-[3-(4-chlorophenyl)azetidin-1-yl]phenyl}-N1,N1-dimethylbenzene-1,4-disulfonamide |
| A-57 | N4-{2-[4-(3-fluoropyridin-4-yl)piperazin-1-yl]phenyl}-N1,N1-dimethylbenzene-1,4-disulfonamide |
| A-58 | N1,N1-dimethyl-N4-(2-{5-methyl-octahydropyrrolo[3,4-c]pyrrol-2-yl}phenyl)benzene-1,4-disulfonamide |
| A-59 | N4-{5-[4-(4-chloro-2-fluorophenyl)piperazin-1-yl]-1-methyl-1H-1,2,4-triazol-3-yl}-N1,N1-dimethylbenzene-1,4-disulfonamide |
| A-60 | N1,N1-dimethyl-N4-{2-[4-(1-methyl-1H-pyrazol-4-yl)piperidin-1-yl]phenyl}benzene-1,4-disulfonamide |
| A-61 | N-{2-[4-(4-chloro-2-fluorophenyl)piperidin-1-yl]phenyl}-2-methyl-1-oxo-2,3-dihydro-1H-isoindole-5-sulfonamide |
| A-62 | 4-({3-[4-(4-chloro-2-fluorophenyl)piperidin-1-yl]-1H-1,2,4-triazol-1-yl}sulfonyl)-N,N-dimethylbenzene-1-sulfonamide |
| A-63 | 4-({3-[1-(4-chloro-2-fluorophenyl)piperidin-4-yl]-2-oxo-2,3-dihydro-1H-1,3-benzodiazol-1-yl}sulfonyl)-N,N-dimethylbenzene-1-sulfonamide |
| A-64 | N4-{5-[1-(4-chloro-2-fluorophenyl)piperidin-4-yl]-1,3,4-thiadiazol-2-yl}-N1,N1-dimethylbenzene-1,4-disulfonamide |
| A-65 | N4-{4-[1-(4-chloro-2-fluorophenyl)-1,2,3,6-tetrahydropyridin-4-yl]-3-methyl-1,2-oxazol-5-yl}-N1,N1-dimethylbenzene-1,4-disulfonamide |
| A-66 | 4-(4-chloro-2-fluorophenyl)-1-(2-{[methyl(phenyl)phosphoryl]amino}phenyl)piperidine |
| A-67 | 4-({3-[1-(4-chloro-2-fluorophenyl)piperidin-4-yl]-2-oxo-2,3-dihydro-1H-imidazol-1-yl}sulfonyl)-N,N-dimethylbenzene-1-sulfonamide |
| A-68 | N4-{3-[4-(4-chloro-2-fluorophenyl)piperazin-1-yl]-1-methyl-1H-1,2,4-triazol-5-yl}-N1,N1-dimethylbenzene-1,4-disulfonamide |
| A-69 | N1,N1-dimethyl-N4-{2-[(1s,4s)-4-(4-chloro-2-fluorophenyl)cyclohexyl]phenyl}benzene-1,4-disulfonamide |
| A-70 | N1,N1-dimethyl-N4-{2-[(1r,4r)-4-(4-chloro-2-fluorophenyl)cyclohexyl]phenyl}benzene-1,4-disulfonamide |
| A-71 | 4-({3-[4-(4-chloro-2-fluorophenyl)piperidin-1-yl]-2-oxopyrrolidin-1-yl}sulfonyl)-N,N-dimethylbenzene-1-sulfonamide |
| A-72 | N-{2-[4-(4-chloro-2-fluorophenyl)piperidin-1-yl]phenyl}-4-methylbenzene-1-sulfonamide |
| A-73 | 4-chloro-N-{2-[4-(4-chloro-2-fluorophenyl)piperidin-1-yl]phenyl}benzene-1-sulfonamide |
| A-74 | N-{2-[4-(4-chloro-2-fluorophenyl)piperidin-1-yl]phenyl}-4-fluorobenzene-1-sulfonamide |
| A-75 | N4-{4-[1-(4-chloro-2-fluorophenyl)piperidin-4-yl]-1,3-dimethyl-1H-pyrazol-5-yl}-N1,N1-dimethylbenzene-1,4-disulfonamide |
| A-76 | 2-chloro-N-{2-[4-(4-chloro-2-fluorophenyl)piperidin-1-yl]phenyl}benzene-1-sulfonamide |
| A-77 | 3-chloro-N-{2-[4-(4-chloro-2-fluorophenyl)piperidin-1-yl]phenyl}benzene-1-sulfonamide |
| A-78 | N-{2-[4-(4-chloro-2-fluorophenyl)piperidin-1-yl]phenyl}-3-fluorobenzene-1-sulfonamide |
| A-79 | N-{2-[4-(4-chloro-2-fluorophenyl)piperidin-1-yl]phenyl}-2-fluorobenzene-1-sulfonamide |
| A-80 | N-{2-[4-(4-chloro-2-fluorophenyl)piperidin-1-yl]phenyl}-3,4-difluorobenzene-1-sulfonamide |
| A-81 | N-{2-[4-(4-chloro-2-fluorophenyl)piperidin-1-yl]phenyl}-2,6-difluorobenzene-1-sulfonamide |
| A-82 | N-{2-[4-(4-chloro-2-fluorophenyl)piperidin-1-yl]phenyl}-2,5-difluorobenzene-1-sulfonamide |
| A-83 | N-{2-[4-(4-chloro-2-fluorophenyl)piperidin-1-yl]phenyl}-4-(trifluoromethyl)benzene-1-sulfonamide |
| A-84 | N4-{4-[1-(4-chloro-2-fluorophenyl)piperidin-4-yl]-1-methyl-1H-imidazol-2-yl}-N1,N1-dimethylbenzene-1,4-disulfonamide |
| A-85 | 2-{2-[4-(4-chloro-2-fluorophenyl)piperidin-1-yl]phenyl}-2,3-dihydro-1$\lambda^6$,2-benzothiazole-1,1,3-trione |
| A-86 | 4-({3-[1-(4-chloro-2-fluorophenyl)piperidin-4-yl]-2-oxoimidazolidin-1-yl}sulfonyl)-N,N-dimethylbenzene-1-sulfonamide |
| A-87 | N-{2-[4-(4-chloro-2-fluorophenyl)piperidin-1-yl]phenyl}-2,4-difluorobenzene-1-sulfonamide |
| A-88 | N-(2-{5-chloro-1',2',3',6'-tetrahydro-[2,4'-bipyridin]-1'-yl}phenyl)-4-methylbenzene-1-sulfonamide |
| A-89 | 4-({4-[4-(4-chloro-2-fluorophenyl)-2-oxopiperazin-1-yl]-2-methyl-1H-imidazol-1-yl}sulfonyl)-N,N-dimethylbenzene-1-sulfonamide |
| A-91 | N-{2-[4-(4-chloro-2-fluorophenyl)piperidin-1-yl]phenyl}-3,5-difluorobenzene-1-sulfonamide |
| A-92 | 4-methyl-N-{2-[4-(pyridin-2-yl)piperidin-1-yl]phenyl}benzene-1-sulfonamide |

TABLE B-continued

| Compound No. | Compound Name |
|---|---|
| A-93 | N-{2-[3-(4-chloro-2-fluorophenyl)-1H-pyrrol-1-yl]phenyl}-4-methylbenzene-1-sulfonamide |
| A-94 | 2-{2-[4-(4-chloro-2-fluorophenyl)piperidin-1-yl]phenyl}-2,3-dihydro-1$\lambda^6$,2-benzothiazole-1,1-dione |
| A-95 | N4-{3-[1-(4-chloro-2-fluorophenyl)piperidin-4-yl]-1-methyl-1H-1,2,4-triazol-5-yl}-N1,N1-dimethylbenzene-1,4-disulfonamide |
| A-96 | 4-({3-[1-(5-chloro-3-fluoropyridin-2-yl)piperidin-4-yl]-1H-pyrazol-1-yl}sulfonyl)-N,N-dimethylbenzene-1-sulfonamide |
| A-97 | N-{2-[4-(4-chloro-2-fluorophenyl)piperidin-1-yl]phenyl}-2,3-difluorobenzene-1-sulfonamide |
| A-98 | N-{2-[4-(4-chloro-2-fluorophenyl)piperidin-1-yl]phenyl}-4-methanesulfonylbenzene-1-sulfonamide |
| A-99 | N-{2-[4-(4-chloro-2-fluorophenyl)piperidin-1-yl]phenyl}-4-methoxybenzene-1-sulfonamide |
| A-100 | N-{2-[4-(2,4-difluorophenyl)piperidin-1-yl]phenyl}-4-methanesulfonylbenzene-1-sulfonamide |
| A-101 | N-{2-[4-(4-chloro-2-fluorophenyl)piperidin-1-yl]phenyl}-4-cyanobenzene-1-sulfonamide |
| A-102 | N-{2-[3-(4-chloro-2-fluorophenyl)pyrrolidin-1-yl]phenyl}-4-methylbenzene-1-sulfonamide |
| A-103 | N-{2-[4-(5-chloropyridin-2-yl)piperidin-1-yl]phenyl}-4-methylbenzene-1-sulfonamide |
| A-104 | N1-{2-[4-(4-chloro-2-fluorophenyl)piperidin-1-yl]phenyl}-N1,N4,N4-trimethylbenzene-1,4-disulfonamide |
| A-105 | N4-{4-[1-(4-chloro-2-fluorophenyl)piperidin-4-yl]-3-methyl-1,2-oxazol-5-yl}-N1,N1-dimethylbenzene-1,4-disulfonamide |
| A-106 | N-{2-[4-(4-chloro-2-fluorophenyl)piperidin-1-yl]phenyl}-2-(hydroxymethyl)benzene-1-sulfonamide |
| A-107 | N-{2-[4-(4-chloro-2-fluorophenyl)piperidin-1-yl]phenyl}-N,4-dimethylbenzene-1-sulfonamide |
| A-108 | 2-[4-(4-chloro-2-fluorophenyl)piperidin-1-yl]-N-[4-(dimethylsulfamoyl)phenyl]benzene-1-sulfonamide |
| A-109 | N4-{2-[4-(4-chloro-2-fluorophenyl)piperidin-1-yl]pyridin-3-yl}-N1,N1-dimethylbenzene-1,4-disulfonamide |
| A-110 | N-{2-[4-(5-chloro-3-fluoropyridin-2-yl)piperazin-1-yl]pyridin-3-yl}-4-methoxybenzene-1-sulfonamide |
| A-111 | 2-[4-(4-chloro-2-fluorophenyl)piperidin-1-yl]-N-(4-methylphenyl)benzene-1-sulfonamide |
| A-112 | 4-({2-[4-(4-chloro-2-fluorophenyl)piperidin-1-yl]phenyl}sulfamoyl)-N,N-dimethylbenzene-1-sulfonoimidamide |
| A-114 | N-{3-[4-(4-chloro-2-fluorophenyl)piperidin-1-yl]phenyl}-2-fluorobenzene-1-sulfonamide |
| A-115 | N4-{2-[4-(4-chloro-2-fluorophenyl)-4-hydroxypiperidin-1-yl]phenyl}-N1,N1-dimethylbenzene-1,4-disulfonamide |
| A-116 | N-{2-[4-(5-chloro-3-fluoropyridin-2-yl)piperazin-1-yl]pyridin-3-yl}-4-(trifluoromethoxy)benzene-1-sulfonamide |
| A-117 | N-{2-[4-(4-cyano-2-fluorophenyl)piperazin-1-yl]pyridin-3-yl}-4-methoxybenzene-1-sulfonamide |
| A-118 | N-{2-[4-(2,4-difluorophenyl)piperidin-1-yl]phenyl}-5-methoxypyridine-2-sulfonamide |
| A-119 | N-{2-[(1R,3S,5S)-3-(2-fluorophenyl)-8-azabicyclo[3.2.1]octan-8-yl]phenyl}-4-methylbenzene-1-sulfonamide |
| A-120 | N-{2-[(1R,3R,5S)-3-(2-fluorophenyl)-8-azabicyclo[3.2.1]octan-8-yl]phenyl}-4-methylbenzene-1-sulfonamide |
| A-121 | N4-{2-[(3R,5S)-4-(5-chloropyridin-2-yl)-3,5-dimethylpiperazin-1-yl]phenyl}-N1,N1-dimethylbenzene-1,4-disulfonamide |
| A-122 | N-{3-[4-(4-chloro-2-fluorophenyl)piperidin-1-yl]phenyl}-3-fluorobenzene-1-sulfonamide |
| A-123 | N-{2-[4-(2,4-difluorophenyl)piperidin-1-yl]phenyl}-6-methoxypyridine-3-sulfonamide |
| A-124 | N-{2-[4-(2,6-difluorophenyl)piperidin-1-yl]phenyl}-4-methanesulfonylbenzene-1-sulfonamide |
| A-128 | N-{3-[4-(4-chloro-2-fluorophenyl)piperidin-1-yl]phenyl}-4-fluorobenzene-1-sulfonamide |
| A-129 | N4-{6-chloro-3-[4-(4-chloro-2-fluorophenyl)piperidin-1-yl]pyridazin-4-yl}-N1,N1-dimethylbenzene-1,4-disulfonamide |
| A-130 | N-{3-[4-(5-chloro-3-fluoropyridin-2-yl)piperazin-1-yl]pyrazin-2-yl}-4-methoxybenzene-1-sulfonamide |
| A-131 | N-{2-[4-(3,5-difluoropyridin-2-yl)piperidin-1-yl]phenyl}-4-methanesulfonylbenzene-1-sulfonamide |
| A-132 | 4-methanesulfonyl-N-{2-[4-(2,4,6-trifluorophenyl)piperidin-1-yl]phenyl}benzene-1-sulfonamide |
| A-133 | 4-(4-chloro-2-fluorophenyl)-1-[2-(4-methylbenzenesulfonyl)phenyl]piperidine |
| A-134 | N4-{6-[4-(4-chloro-2-fluorophenyl)piperidin-1-yl]pyridin-2-yl}-N1,N1-dimethylbenzene-1,4-disulfonamide |
| A-135 | N-{3-[4-(5-chloro-3-fluoropyridin-2-yl)piperazin-1-yl]pyridin-2-yl}-4-methoxybenzene-1-sulfonamide |

TABLE B-continued

| Compound No. | Compound Name |
|---|---|
| A-136 | 6-(difluoromethyl)-N-{2-[4-(2,4-difluorophenyl)piperidin-1-yl]phenyl}pyridine-3-sulfonamide |
| A-137 | 5-(difluoromethyl)-N-{2-[4-(2,4-difluorophenyl)piperidin-1-yl]phenyl}pyridine-2-sulfonamide |
| A-138 | 4-(4-chloro-2-fluorophenyl)-1-{2-[(4-methylbenzenesulfonyl)methyl]phenyl}piperidine |
| A-139 | N4-{3-[4-(4-chloro-2-fluorophenyl)piperidin-1-yl]pyridazin-4-yl}-N1,N1-dimethylbenzene-1,4-disulfonamide |
| A-140 | N-{4-[4-(5-chloro-3-fluoropyridin-2-yl)piperazin-1-yl]-1-methyl-1H-indazol-5-yl}-4-methoxybenzene-1-sulfonamide |
| A-141 | N4-{2-[4-(2,4-difluorophenyl)-4-hydroxypiperidin-1-yl]phenyl}-N1,N1-dimethylbenzene-1,4-disulfonamide |
| A-142 | N-{2-[4-(4-chloro-2-fluorophenyl)-4-hydroxypiperidin-1-yl]phenyl}-4-methanesulfonylbenzene-1-sulfonamide |
| A-143 | 4-({2-[4-(4-chloro-2-fluorophenyl)-4-hydroxypiperidin-1-yl]phenyl}sulfamoyl)-N,N-dimethylbenzene-1-sulfonoimidamide |
| A-144 | 4-(4-chloro-2-fluorophenyl)-1-[2-(4-methylbenzenesulfinyl)phenyl]piperidine |
| A-145 | 4-(4-chloro-2-fluorophenyl)-1-{2-[(4-methylbenzenesulfinyl)methyl]phenyl}piperidine |
| A-146 | 4-{[3-(4-chloro-2-fluorophenyl)-4-methyl-1,2,3,4-tetrahydroquinoxalin-1-yl]sulfonyl}-N,N-dimethylbenzene-1-sulfonamide |
| A-147 | N-{2-[4-(5-chloro-3-fluoropyridin-2-yl)piperidin-1-yl]phenyl}-4-methoxybenzene-1-sulfonamide |
| A-148 | N4-[2-(4-hydroxy-4-phenylpiperidin-1-yl)phenyl]-N1,N1-dimethylbenzene-1,4-disulfonamide |
| A-149 | N4-{2-[4-(4-chloro-2-fluorophenyl)piperidin-1-yl]phenyl}-3-fluoro-N1,N1-dimethylbenzene-1,4-disulfonamide |
| A-150 | N4-{2-[4-amino-4-(4-chloro-2-fluorophenyl)piperidin-1-yl]phenyl}-N1,N1-dimethylbenzene-1,4-disulfonamide |
| A-151 | N-{2-[4-(4-chloro-2-fluorophenyl)piperidin-1-yl]phenyl}-4-methylbenzene-1-sulfonoimidamide |
| A-152 | N-{2-[4-(4-chloro-2-fluorophenyl)-4-hydroxypiperidin-1-yl]phenyl}-4-[iimino(methyl)oxo-$\lambda^6$-sulfanyl]benzene-1-sulfonamide |
| A-153 | N-[4-(4-chloro-2-fluorophenyl)-1-{2-[4-(dimethylsulfamoyl)benzenesulfonamido]phenyl}piperidin-4-yl]acetamide |
| A-154 | N-{2-[4-(2,6-difluorophenyl)piperidin-1-yl]-5-fluorophenyl}-4-methanesulfonylbenzene-1-sulfonamide |
| A-155 | N-{2-[4-(2,6-difluorophenyl)piperidin-1-yl]-4-fluorophenyl}-4-methanesulfonylbenzene-1-sulfonamide |
| A-156 | 4-{2-[4-(4-chloro-2-fluorophenyl)piperidin-1-yl]benzenesulfonyl}-N,N-dimethylbenzene-1-sulfonamide |
| A-157 | N-{2-[4-(4-chloro-2-fluorophenyl)piperidin-1-yl]phenyl}-4-(2,2,2-trifluoro-1-hydroxyethyl)benzene-1-sulfonamide |
| A-158 | N-{2-[4-(4-chloro-2-fluorophenyl)piperidin-1-yl]phenyl}-3-fluoro-4-(trifluoromethyl)benzene-1-sulfonamide |
| A-159 | N-{2-[4-(4-chloro-2-fluorophenyl)piperidin-1-yl]phenyl}-2-fluoro-4-(trifluoromethyl)benzene-1-sulfonamide |
| A-160 | N-{2-[4-(2,4-difluorophenyl)piperidin-1-yl]phenyl}-4-methanesulfinylbenzene-1-sulfonamide |
| A-161 | N4-{2-[4-(2,4-difluorophenyl)-4-(hydroxymethyl)piperidin-1-yl]phenyl}-N1,N1-dimethylbenzene-1,4-disulfonamide |
| A-162 | N4-{2-[3-(4-chloro-2-fluorophenyl)-3-hydroxyazetidin-1-yl]phenyl}-N1,N1-dimethylbenzene-1,4-disulfonamide |
| A-163 | 4-(2,4-difluorophenyl)-1-{2-[4-(dimethylsulfamoyl)benzenesulfonamido]phenyl}piperidine-4-carboxamide |
| A-165 | N-{2-[4-(2,4-difluorophenyl)piperazin-1-yl]phenyl}-4-(dimethylphosphoryl)benzene-1-sulfonamide |
| A-166 | N-{2-[4-(2,6-difluorophenyl)piperidin-1-yl]phenyl}-4-[imino(methyl)oxo-$\lambda^6$-sulfanyl]benzene-1-sulfonamide |
| A-167 | N-{2',4'-difluoro-[1,1'-biphenyl]-2-yl}-4-methoxybenzene-1-sulfonamide |
| A-170 | 4-[1-({2-[4-(4-chloro-2-fluorophenyl)piperidin-1-yl]phenyl}amino)-2,2,2-trifluoroethyl]-N,N-dimethylbenzene-1-sulfonamide |
| A-171 | 4-{[3-(4-chloro-2-fluorophenyl)-1,2,3,4-tetrahydroquinoxalin-1-yl]sulfonyl}-N,N-dimethylbenzene-1-sulfonamide |
| A-172 | N-[4-(4-chloro-2-fluorophenyl)-1-{2-[4-(dimethylsulfamoyl)benzenesulfonamido]phenyl}piperidin-4-yl]-N-methylacetamide |
| A-173 | N-{2-[4-(2,4-difluorophenyl)piperidin-1-yl]phenyl}-4-trifluoromethanesulfonylbenzene-1-sulfonamide |
| A-174 | N-{2-[4-(2,4-difluorophenyl)piperazin-1-yl]phenyl}-4-trifluoromethanesulfonylbenzene-1-sulfonamide |
| A-175 | N4-{2-[4-cyano-4-(2,4-difluorophenyl)piperidin-1-yl]phenyl}-N1,N1-dimethylbenzene-1,4-disulfonamide |
| A-176 | N-{2-[4-(2,4-difluorophenyl)piperidin-1-yl]phenyl}-4-(dimethylphosphoryl)benzene-1-sulfonamide |
| A-177 | N-{2-[4-(2,6-difluorophenyl)piperidin-1-yl]phenyl}-4-(dimethylphosphoryl)benzene-1-sulfonamide |

TABLE B-continued

| Compound No. | Compound Name |
|---|---|
| A-178 | N-{2-[4-(5-chloro-3-fluoropyridin-2-yl)piperazin-1-yl]phenyl}-4-trifluoromethanesulfonylbenzene-1-sulfonamide |
| A-179 | N4-[2-(4-{bicyclo[1.1.1]pentan-1-yl}piperazin-1-yl)phenyl]-N1,N1-dimethylbenzene-1,4-disulfonamide |
| A-180 | N-[2-(3,5-difluoropyridin-2-yl)phenyl]-4-methoxybenzene-1-sulfonamide |
| A-181 | 4-{2-[4-(4-chloro-2-fluorophenyl)piperidin-1-yl]benzenesulfinyl}-N,N-dimethylbenzene-1-sulfonamide |
| A-182 | N2-{2-[4-(4-chloro-2-fluorophenyl)piperidin-1-yl]phenyl}-N5,N5-dimethylpyridine-2,5-disulfonamide |
| A-183 | N4-{2-[4-(2-chlorophenyl)-4-methylpiperidin-1-yl]phenyl}-N1,N1-dimethylbenzene-1,4-disulfonamide |
| A-184 | N4-{2-[4-(4-chlorophenyl)-4-methylpiperidin-1-yl]phenyl}-N1,N1-dimethylbenzene-1,4-disulfonamide |
| A-185 | 4-difluoromethanesulfonyl-N-{2-[4-(2,4-difluorophenyl)piperidin-1-yl]phenyl}benzene-1-sulfonamide |
| A-186 | N-[2-(2,4-difluorophenoxy)phenyl]-4-methoxybenzene-1-sulfonamide |
| A-187 | N-{2-[(2,4-difluorophenyl)methoxy]phenyl}-4-methoxybenzene-1-sulfonamide |
| A-188 | N-(2-{3-[(2,4-difluorophenyl)(methyl)amino]azetidin-1-yl}phenyl)-4-methoxybenzene-1-sulfonamide |
| A-189 | N-(2-{4-[(2,4-difluorophenyl)(methyl)amino]piperidin-1-yl}phenyl)-4-methoxybenzene-1-sulfonamide |
| A-190 | 4-({2-[4-(4-chloro-2-fluorophenyl)piperidin-1-yl]phenyl}methanesulfinyl)-N,N-dimethylbenzene-1-sulfonamide |
| A-191 | N-{2-[4-(4-chloro-2-fluorophenyl)piperidin-1-yl]phenyl}-4-(2,2,2-trifluoroacetyl)benzene-1-sulfonamide |
| A-192 | N-{3-[4-(3,5-difluoropyridin-2-yl)piperidin-1-yl]pyridin-4-yl}-4-methoxybenzene-1-sulfonamide |
| A-193 | N-{4-[4-(3,5-difluoropyridin-2-yl)piperidin-1-yl]pyridin-3-yl}-4-methoxybenzene-1-sulfonamide |
| A-194 | N-(2-{4-[(2,4-difluorophenyl)methyl]piperazin-1-yl}phenyl)-4-methoxybenzene-1-sulfonamide |
| A-195 | N-(2-{4-[(2,4-difluorophenyl)methyl]piperidin-1-yl}phenyl)-4-methoxybenzene-1-sulfonamide |
| A-196 | N-{2-[4-(2,4-difluorophenoxy)piperidin-1-yl]phenyl}-4-methoxybenzene-1-sulfonamide |
| A-197 | N-(2-{3-[(2,4-difluorophenyl)methyl]pyrrolidin-1-yl}phenyl)-4-methoxybenzene-1-sulfonamide |
| A-198 | N-{2-[4-(2,6-difluorophenyl)piperidin-1-yl]phenyl}-4-(ethanesulfonyl)benzene-1-sulfonamide |
| A-199 | N-{2-[(2,4-difluorophenyl)(methyl)amino]phenyl}-4-methoxybenzene-1-sulfonamide |
| A-200 | N-{2-[3-(2,4-difluorophenoxy)azetidin-1-yl]phenyl}-4-methoxybenzene-1-sulfonamide |
| A-201 | N-(2-{3-[(2,4-difluorophenyl)(methyl)amino]pyrrolidin-1-yl}phenyl)-4-methoxybenzene-1-sulfonamide |
| A-202 | N-{2-[3-(2,4-difluorophenoxy)pyrrolidin-1-yl]phenyl}-4-methoxybenzene-1-sulfonamide |
| A-203 | N-{2-[4-(4-fluorophenyl)-4-hydroxypiperidin-1-yl]phenyl}-4-methanesulfonylbenzene-1-sulfonamide |
| A-204 | N4-{2-[4-(4-chloro-2-fluorophenyl)-4-methylpiperidin-1-yl]phenyl}-N1,N1-dimethylbenzene-1,4-disulfonamide |
| A-205 | N4-{2-[4-(2-chloro-4-fluorophenyl)-4-methylpiperidin-1-yl]phenyl}-N1,N1-dimethylbenzene-1,4-disulfonamide |
| A-206 | N-{5-[4-(3,5-difluoropyridin-2-yl)piperidin-1-yl]pyridazin-4-yl}-4-methoxybenzene-1-sulfonamide |
| A-207 | N-{2-[4-(2,6-difluorophenyl)piperidin-1-yl]phenyl}-4-methoxymethanesulfonylbenzene-1-sulfonamide |
| A-209 | N4-{2-[4-(5-fluoropyridin-2-yl)-4-hydroxypiperidin-1-yl]phenyl}-N1,N1-dimethylbenzene-1,4-disulfonamide |
| A-210 | N4-{2-[4-(2-bromo-5-fluoropyridin-4-yl)-4-hydroxypiperidin-1-yl]phenyl}-N1,N1-dimethylbenzene-1,4-disulfonamide |
| A-211 | N4-{2-[4-(4-chloro-2-fluorophenyl)-4-(dimethylamino)piperidin-1-yl]phenyl}-N1,N1-dimethylbenzene-1,4-disulfonamide |
| A-212 | N4-{2-[4-(4-chloro-2-fluorophenyl)-4-(methylamino)piperidin-1-yl]phenyl}-N1,N1-dimethylbenzene-1,4-disulfonamide |
| A-213 | N-{2-[4-(2,6-difluorophenyl)piperidin-1-yl]phenyl}-4-(2-methylpropane-2-sulfonyl)benzene-1-sulfonamide |
| A-214 | 4-({2-[4-(4-chloro-2-fluorophenyl)piperidin-1-yl]phenyl}methanesulfonyl)-N,N-dimethylbenzene-1-sulfonamide |
| A-215 | N4-(2-{6-fluoro-1-methyl-1,2-dihydrospiro[indole-3,4'-piperidin]-1'-yl}phenyl)-N1,N1-dimethylbenzene-1,4-disulfonamide |
| A-216 | 4-(2,4-difluorophenyl)-1-{2-[4-(dimethylsulfamoyl)benzenesulfonamido]phenyl}-N-methylpiperidine-4-carboxamide |
| A-217 | N-{2-[4-(2,6-difluorophenyl)piperidin-1-yl]phenyl}-4-(morpholine-4-sulfonyl)benzene-1-sulfonamide |

TABLE B-continued

| Compound No. | Compound Name |
|---|---|
| A-218 | N4-{2-[4-(2,4-difluorophenyl)-4-[(methylamino)methyl]piperidin-1-yl]phenyl}-N1,N1-dimethylbenzene-1,4-disulfonamide |
| A-219 | N-(2-{3-[(2,4-difluorophenyl)methyl]azetidin-1-yl}phenyl)-4-methoxybenzene-1-sulfonamide |
| A-220 | N-{2-[4-(2,6-difluorophenyl)piperidin-1-yl]phenyl}-4-[(4-methylpiperazin-1-yl)sulfonyl]benzene-1-sulfonamide |
| A-221 | N4-{2-[4-(2,4-difluorophenyl)-4-[(dimethylamino)methyl]piperidin-1-yl]phenyl}-N1,N1-dimethylbenzene-1,4-disulfonamide |
| A-222 | N-{2-[4-(4-chloro-2-fluorophenyl)piperidin-1-yl]phenyl}-4-[1-(dimethylamino)-2,2,2-trifluoroethyl]benzene-1-sulfonamide |
| A-223 | N4-{2-[4-(2,6-difluorophenyl)piperidin-1-yl]phenyl}-N1-(2-hydroxyethyl)-N1-methylbenzene-1,4-disulfonamide |
| A-224 | N4-{2-[4-(2,6-difluorophenyl)piperidin-1-yl]phenyl}-N1-(2-hydroxy-2-methylpropyl)-N1-methylbenzene-1,4-disulfonamide |
| A-225 | N4-{2-[4-(2,2-dimethylpropanoyl)piperazin-1-yl]phenyl}-N1,N1-dimethylbenzene-1,4-disulfonamide |
| A-226 | 4-({2-[4-(2,6-difluorophenyl)piperidin-1-yl]-4-fluorophenyl}sulfamoyl)-N,N-dimethylbenzene-1-sulfonoimidamide |
| A-227 | N4-[2-(diethenylphosphoryl)phenyl]-N1,N1-dimethylbenzene-1,4-disulfonamide |
| A-228 | 4-({2-[4-(2,6-difluorophenyl)piperidin-1-yl]-5-fluorophenyl}sulfamoyl)-N,N-dimethylbenzene-1-sulfonoimidamide |
| A-229 | 4-({2-[4-(2,6-difluorophenyl)piperidin-1-yl]phenyl}methanesulfonyl)-N,N-dimethylbenzene-1-sulfonamide |
| A-231 | N4-(2-{4-[(dimethylamino)methyl]-4-(4-fluorophenyl)piperidin-1-yl}phenyl)-N1,N1-dimethylbenzene-1,4-disulfonamide |
| A-232 | N4-{2-[4-(4-fluorophenyl)-4-oxo-1,4$\lambda^5$-azaphosphinan-1-yl]phenyl}-N1,N1-dimethylbenzene-1,4-disulfonamide |
| A-241 | 4-[(1-{2-[4-(4-chloro-2-fluorophenyl)piperidin-1-yl]phenyl}-2,2,2-trifluoroethyl)amino]-N,N-dimethylbenzene-1-sulfonamide |
| A-243 | N1-(2-{6-fluoro-1-methyl-1,2-dihydrospiro[indole-3,4'-piperidin]-1'-yl}phenyl)-N1,N4,N4-trimethylbenzene-1,4-disulfonamide |
| A-244 | N1,N1-dimethyl-N4-(2-{2-methyl-1-oxo-2,8-diazaspiro[4.5]decan-8-yl}phenyl)benzene-1,4-disulfonamide |
| A-245 | N-(2-{6-fluoro-1-methyl-1,2-dihydrospiro[indole-3,4'-piperidin]-1'-yl}phenyl)-4-methylbenzene-1-sulfonamide |
| A-246 | 4-difluoromethanesulfonyl-N-(2-{6-fluoro-1-methyl-1,2-dihydrospiro[indole-3,4'-piperidin]-1'-yl}phenyl)benzene-1-sulfonamide |
| A-247 | N4-(4-{6-fluoro-1-methyl-1,2-dihydrospiro[indole-3,4'-piperidin]-1'-yl}-1-methyl-1H-indazol-5-yl)-N1,N1-dimethylbenzene-1,4-disulfonamide |
| A-251 | N-(2-{6-fluoro-1-methyl-1,2-dihydrospiro[indole-3,4'-piperidin]-1'-yl}phenyl)-4-methanesulfonylbenzene-1-sulfonamide |
| A-252 | N-(2-{6-fluoro-1-methyl-1,2-dihydrospiro[indole-3,4'-piperidin]-1'-yl}phenyl)-4-methoxybenzene-1-sulfonamide |
| A-253 | N4-(2-{6-fluoro-2H-spiro[1-benzofuran-3,4'-piperidin]-1'-yl}phenyl)-N1,N1-dimethylbenzene-1,4-disulfonamide |
| A-254 | 4-(1-{2-[4-(2,6-difluorophenyl)piperidin-1-yl]phenyl}ethanesulfonyl)-N,N-dimethylbenzene-1-sulfonamide |
| A-257 | 4-[(2-{6-fluoro-1-methyl-1,2-dihydrospiro[indole-3,4'-piperidin]-1'-yl}phenyl)sulfamoyl]-N,N-dimethylbenzene-1-sulfonoimidamide |
| A-258 | N4-(2-{5-fluoro-3H-spiro[2-benzofuran-1,4'-piperidin]-1'-yl}phenyl)-N1,N1-dimethylbenzene-1,4-disulfonamide |
| A-259 | 2-(1-{2-[4-(dimethylsulfamoyl)benzenesulfonamido]phenyl}piperidin-4-yl)benzoic acid |
| A-266 | 3-(1-{2-[4-(dimethylsulfamoyl)benzenesulfonamido]phenyl}piperidin-4-yl)benzoic acid |
| A-267 | 4-(1-{2-[4-(dimethylsulfamoyl)benzenesulfonamido]phenyl}piperidin-4-yl)benzoic acid |
| A-268 | N4-(2-{6'-chloro-1'-methyl-1',2'-dihydrospiro[piperidine-4,3'-pyrrolo[3,2-b]pyridin]-1-yl}phenyl)-N1,N1-dimethylbenzene-1,4-disulfonamide |
| A-269 | N1,N1-dimethyl-N4-(2-{1'-methyl-octahydrospiro[piperidine-4,3'-pyrrolo[3,2-b]pyridin]-1-yl}phenyl)benzene-1,4-disulfonamide |
| A-271 | N1,N1-dimethyl-N4-(2-{1'-methyl-1',2'-dihydrospiro[piperidine-4,3'-pyrrolo(3,2-b]pyridin]-1-yl}phenyl)benzene-1,4-disulfonamide |
| A-272 | N1,N1-dimethyl-N4-(2-{4-[3-(2H-1,2,3,4-tetrazol-5-yl)phenyl]piperidin-1-yl}phenyl)benzene-1,4-disulfonamide |
| A-273 | N1,N1-dimethyl-N4-(2-{4-[4-(1H-1,2,3,4-tetrazol-5-yl)phenyl]piperidin-1-yl}phenyl)benzene-1,4-disulfonamide |
| A-274 | N-[3-chloro-2-(morpholin-4-yl)phenyl]-4-difluoromethanesulfonylbenzene-1-sulfonamide |
| A-275 | N-[3-chloro-2-(morpholin-4-yl)phenyl]-4-methanesulfonylbenzene-1-sulfonamide |
| A-276 | N-[5-chloro-2-(morpholin-4-yl)phenyl]-4-(2-methylpropane-2-sulfonyl)benzene-1-sulfonamide |
| A-277 | N-[5-chloro-2-(morpholin-4-yl)phenyl]-4-difluoromethanesulfonylbenzene-1-sulfonamide |
| A-278 | N-[3-chloro-2-(morpholin-4-yl)phenyl]-4-(2-methylpropane-2-sulfonyl)benzene-1-sulfonamide |

TABLE B-continued

| Compound No. | Compound Name |
|---|---|
| A-280 | N1,N1-dimethyl-N4-(2-{4-[2-(1H-1,2,3,4-tetrazol-5-yl)phenyl]piperidin-1-yl}phenyl)benzene-1,4-disulfonamide |
| A-281 | N4-{2-[1-(dimethylamino)-8-azaspiro[4.5]decan-8-yl]phenyl}-N1,N1-dimethylbenzene-1,4-disulfonamide |
| A-282 | N1,N1-dimethyl-N4-(2-{1'-methyl-2'-oxo-1',2'-dihydrospiro[piperidine-4,3'-pyrrolo[2,3-b]pyridin]-1-yl}phenyl)benzene-1,4-disulfonamide |
| A-283 | N4-{2-[4-(4-chloro-2-fluorophenyl)-2-oxopiperazin-1-yl]phenyl}-N1,N1-dimethylbenzene-1,4-disulfonamide |
| A-284 | N-[5-chloro-2-(morpholin-4-yl)phenyl]-4-(dimethylphosphoryl)benzene-1-sulfonamide |
| A-285 | N1-[5-chloro-2-(morpholin-4-yl)phenyl]-N1,N4,N4-trimethylbenzene-1,4-disulfonamide |
| A-286 | N1-[3-chloro-2-(morpholin-4-yl)phenyl]-N1,N4,N4-trimethylbenzene-1,4-disulfonamide |
| A-287 | N-[3-chloro-2-(morpholin-4-yl)phenyl]-4-(dimethylphosphoryl)benzene-1-sulfonamide |
| A-288 | N-{3-chloro-2-[4-(4-chloro-2-fluorophenyl)piperazin-1-yl]phenyl}-2,3-dihydro-1H-indene-5-sulfonamide |
| A-289 | N-[5-chloro-2-(4-ethylpiperazin-1-yl)phenyl]-2,3-dihydro-1H-indene-5-sulfonamide |
| A-290 | N4-[5-chloro-2-(morpholin-4-yl)phenyl]-N1,N1-dimethylbenzene-1,4-disulfonamide |
| A-291 | N-{5-chloro-2-[4-(4-chloro-2-fluorophenyl)piperazin-1-yl]phenyl}-2,3-dihydro-1H-indene-5-sulfonamide |
| A-292 | N-{5-chloro-2-[4-(2,6-difluorophenyl)piperidin-1-yl]phenyl}-2,3-dihydro-1H-indene-5-sulfonamide |
| A-293 | N1,N1-dimethyl-N4-(2-{2-methyl-2,8-diazaspiro[4.5]decan-8-yl}phenyl)benzene-1,4-disulfonamide |
| A-294 | 4-({3-[1-(4-chloro-2-fluorophenyl)piperidin-4-yl]-5,5-dimethyl-2,4-dioxoimidazolidin-1-yl}sulfonyl)-N,N-dimethylbenzene-1-sulfonamide |
| A-295 | N4-{2-[3-(dimethylamino)-2,3-dihydrospiro[indene-1,4'-piperidin]-1'-yl]phenyl}-N1,N1-dimethylbenzene-1,4-disulfonamide |
| A-296 | N4-{2-[6-(4-chloro-2-fluorophenyl)-2,6-diazaspiro[3.3]heptan-2-yl]phenyl}-N1,N1-dimethylbenzene-1,4-disulfonamide |
| A-297 | N-[3-chloro-2-(3-oxomorpholin-4-yl)phenyl]-2,3-dihydro-1H-indene-5-sulfonamide |
| A-298 | N-{3-chloro-2-[4-(2,6-difluorophenyl)piperidin-1-yl]phenyl}-2,3-dihydro-1H-indene-5-sulfonamide |
| A-299 | N-[5-chloro-2-(morpholin-4-yl)phenyl]-4-methanesulfonylbenzene-1-sulfonamide |
| A-300 | N-[3-chloro-2-(4-ethylpiperazin-1-yl)phenyl]-2,3-dihydro-1H-indene-5-sulfonamide hydrochloride |
| A-301 | N4-(2-{5-fluoro-2-methyl-3-oxo-2,3-dihydrospiro[isoindole-1,4'-piperidin]-1'-yl}phenyl)-N1,N1-dimethylbenzene-1,4-disulfonamide |
| A-302 | N1,N1-dimethyl-N4-(2-{2-methyl-4-phenyl-2,8-diazaspiro[4.5]decan-8-yl}phenyl)benzene-1,4-disulfonamide |
| A-303 | N-(2-{6-fluoro-1-methyl-1,2-dihydrospiro[indole-3,4'-piperidin]-1'-yl}phenyl)-4-(2-methylpropane-2-sulfonyl)benzene-1-sulfonamide |
| A-304 | N4-(2-{1-benzyl-6-fluoro-1,2-dihydrospiro[indole-3,4'-piperidin]-1'-yl}phenyl)-N1,N1-dimethylbenzene-1,4-disulfonamide |
| A-305 | N4-(2-{6'-fluoro-1'-methyl-1',2'-dihydrospiro[cyclohexane-1,3'-indol]-4-yl}phenyl)-N1,N1-dimethylbenzene-1,4-disulfonamide |
| A-306 | 4-({4-[4-(4-chloro-2-fluorophenyl)-2-oxopiperazin-1-yl]-3-methyl-1H-pyrazol-1-yl}sulfonyl)-N,N-dimethylbenzene-1-sulfonamide |
| A-307 | N-(2-{6-fluoro-1-methyl-1,2-dihydrospiro[indole-3,4'-piperidin]-1'-yl}phenyl)-4-methanesulfonyl-N-methylbenzene-1-sulfonamide |
| A-308 | ethyl 4-{2-[4-(dimethylsulfamoyl)benzenesulfonamido]phenyl}piperazine-1-carboxylate |
| A-309 | methyl 4-{2-[4-(dimethylsulfamoyl)benzenesulfonamido]phenyl}piperazine-1-carboxylate |
| A-310 | N4-(2-{5-fluoro-2-methyl-2,3-dihydrospiro[isoindole-1,4'-piperidin]-1'-yl}phenyl)-N1,N1-dimethylbenzene-1,4-disulfonamide; formic acid |
| A-311 | N4-[3-chloro-2-(morpholin-4-yl)phenyl]-N1,N1-dimethylbenzene-1,4-disulfonamide |
| A-312 | 4-{[5-chloro-2-(morpholin-4-yl)phenyl]methanesulfonyl}-N,N-dimethylbenzene-1-sulfonamide |
| A-313 | N-{5-chloro-2-[4-(4-chloro-2-fluorophenyl)piperidin-1-yl]phenyl}-2,3-dihydro-1H-indene-5-sulfonamide |
| A-314 | N-[5-chloro-2-(4-ethyl-2-oxopiperazin-1-yl)phenyl]-2,3-dihydro-1H-indene-5-sulfonamide |
| A-315 | N-[3-chloro-2-(4-ethyl-2-oxopiperazin-1-yl)phenyl]-2,3-dihydro-1H-indene-5-sulfonamide |
| A-316 | N-(5-chloro-2-{1-oxa-8-azaspiro[5.5]undecan-8-yl}phenyl)-2,3-dihydro-1H-indene-5-sulfonamide |
| A-317 | N-(5-chloro-2-{9,9-dioxo-1-oxa-9$\lambda^6$-thia-4-azaspiro[5.5]undecan-4-yl}phenyl)-2,3-dihydro-1H-indene-5-sulfonamide |
| A-318 | N1,N1-dimethyl-N4-(2-{2-methyl-1-oxo-4-phenyl-2,8-diazaspiro[4.5]decan-8-yl}phenyl)benzene-1,4-disulfonamide |

TABLE B-continued

| Compound No. | Compound Name |
|---|---|
| A-319 | N-(2-{6-fluoro-2H-spiro[1-benzofuran-3,4'-piperidin]-1'-yl}phenyl)-4-methanesulfonylbenzene-1-sulfonamide |
| A-320 | 4-methanesulfonyl-N-(2-{1'-methyl-1',2'-dihydrospiro[piperidine-4,3'-pyrrolo[3,2-b]pyridin]-1-yl}phenyl)benzene-1-sulfonamide; formic acid |
| A-321 | 4-({2-[4-(2,2-dimethylpropanoyl)piperazin-1-yl]phenyl}sulfamoyl)-N,N-dimethylbenzene-1-sulfonoimidamide |
| A-322 | N1,N1-dimethyl-N4-{2-[4-(2-methylpropanoyl)piperazin-1-yl]phenyl}benzene-1,4-disulfonamide |
| A-323 | N-tert-butyl-1-{2-[4-(dimethylsulfamoyl)benzenesulfonamido]phenyl}piperidine-4-carboxamide |
| A-324 | N-{2-[4-(2,2-dimethylpropanoyl)piperazin-1-yl]phenyl}-4-methanesulfonylbenzene-1-sulfonamide |
| A-325 | 4-{2-[4-(dimethylsulfamoyl)benzenesulfonamido]phenyl}-N,N-dimethylpiperazine-1-carboxamide |
| A-326 | N-[5-chloro-2-(3-oxomorpholin-4-yl)phenyl]-2,3-dihydro-1H-indene-5-sulfonamide |
| A-327 | 4-{[3-chloro-2-(morpholin-4-yl)phenyl]methanesulfonyl}-N,N-dimethylbenzene-1-sulfonamide |
| A-328 | N-(5-chloro-2-{1-oxa-8-azaspiro[4.5]decan-8-yl}phenyl)-2,3-dihydro-1H-indene-5-sulfonamide |
| A-329 | N-[3-chloro-2-(morpholin-4-yl)phenyl]-1-methyl-1H-pyrazole-5-sulfonamide |
| A-330 | N2-[5-chloro-2-(morpholin-4-yl)phenyl]-N5,N5-dimethylpyridine-2,5-disulfonamide |
| A-331 | N1,N1-dimethyl-N4-(2-{1'-methyl-1',2'-dihydrospiro[piperidine-4,3'-pyrrolo[2,3-b]pyridin]-1-yl}phenyl)benzene-1,4-disulfonamide |
| A-332 | N-(2-{5-fluoro-3H-spiro[2-benzofuran-1,4'-piperidin]-1'-yl}phenyl)-4-methanesulfonylbenzene-1-sulfonamide |
| A-333 | 4-methanesulfonyl-N-(2-{1-oxa-7-azaspiro[3.5]nonan-7-yl}phenyl)benzene-1-sulfonamide |
| A-334 | 4-methyl-N-{2-[4-(2-phenylpropanoyl)piperazin-1-yl]phenyl}benzene-1-sulfonamide |
| A-335 | N4-{2-[4-(2-hydroxy-2-phenylacetyl)piperazin-1-yl]phenyl}-N1,N1-dimethylbenzene-1,4-disulfonamide |
| A-336 | propan-2-yl 4-{2-[4-(dimethylsulfamoyl)benzenesulfonamido]phenyl}piperazine-1-carboxylate |
| A-337 | N4-[2-(4-tert-butylpiperazin-1-yl)phenyl]-N1,N1-dimethylbenzene-1,4-disulfonamide |
| A-338 | 1-{2-[4-(dimethylsulfamoyl)benzenesulfonamido]phenyl}-N-phenylpiperidine-4-carboxamide |
| A-339 | 1-{2-[4-(dimethylsulfamoyl)benzenesulfonamido]phenyl}-N-methyl-N-phenylpiperidine-4-carboxamide |
| A-340 | N2-[3-chloro-2-(morpholin-4-yl)phenyl]-N5,N5-dimethylpyridine-2,5-disulfonamide |
| A-341 | N-{3-chloro-2-[4-(4-chloro-2-fluorophenyl)piperidin-1-yl]phenyl}-2,3-dihydro-1H-indene-5-sulfonamide |
| A-342 | 4-(1-{[3-chloro-2-(morpholin-4-yl)phenyl]amino}-2,2,2-trifluoroethyl)-N,N-dimethylbenzene-1-sulfonamide |
| A-343 | N-(5-chloro-2-{1,9-dioxa-4-azaspiro[5.5]undecan-4-yl}phenyl)-2,3-dihydro-1H-indene-5-sulfonamide |
| A-344 | N-(5-chloro-2-{3-oxa-7-azatricyclo[3.3.2.0$^{1,5}$]decan-7-yl}phenyl)-2,3-dihydro-1H-indene-5-sulfonamide |
| A-345 | N-(5-chloro-2-{2-oxa-6-azaspiro[3.5]nonan-6-yl}phenyl)-2,3-dihydro-1H-indene-5-sulfonamide |
| A-346 | N-(5-chloro-2-{7-oxa-1-azaspiro[4.4]nonan-1-yl}phenyl)-2,3-dihydro-1H-indene-5-sulfonamide |
| A-347 | N-(5-chloro-2-{2-oxa-8-azaspiro[5.5]undecan-8-yl}phenyl)-2,3-dihydro-1H-indene-5-sulfonamide |
| A-348 | 4-methanesulfonyl-N-(2-{1'-methyl-1',2'-dihydrospiro[piperidine-4,3'-pyrrolo[2,3-b]pyridin]-1-yl}phenyl)benzene-1-sulfonamide |
| A-349 | N-{2-[4-(2-hydroxy-2-phenylacetyl)piperazin-1-yl]phenyl}-4-methylbenzene-1-sulfonamide |
| A-350 | 4-methyl-N-{2-[4-(2-oxo-2-phenylacetyl)piperazin-1-yl]phenyl}benzene-1-sulfonamide |
| A-351 | N-{2-[4-(2,2-dimethylpropanoyl)piperazin-1-yl]phenyl}-4-(ethanesulfonyl)benzene-1-sulfonamide |
| A-352 | N4-{3-chloro-2-[4-(2,2-dimethylpropanoyl)piperazin-1-yl]phenyl}-N1,N1-dimethylbenzene-1,4-disulfonamide |
| A-353 | N4-[2-(4-tert-butylpiperidin-1-yl)phenyl]-N1,N1-dimethylbenzene-1,4-disulfonamide |
| A-354 | N4-{2-[3-(2,2-dimethylpropanoyl)-3,8-diazabicyclo[3.2.1]octan-8-yl]phenyl}-N1,N1-dimethylbenzene-1,4-disulfonamide |
| A-355 | N4-{2-[4-(3-fluoropyridin-2-yl)-4-hydroxypiperidin-1-yl]phenyl}-N1,N1-dimethylbenzene-1,4-disulfonamide |
| A-356 | 4-(1-{[5-chloro-2-(morpholin-4-yl)phenyl]amino}-2,2,2-trifluoroethyl)-N,N-dimethylbenzene-1-sulfonamide |
| A-357 | N-(5-chloro-2-{3H-spiro[2-benzofuran-1,3'-pyrrolidin]-1'-yl}phenyl)-2,3-dihydro-1H-indene-5-sulfonamide |

TABLE B-continued

| Compound No. | Compound Name |
|---|---|
| A-358 | 2-(1-{2-[4-(dimethylsulfamoyl)benzenesulfonamido]phenyl}piperidin-4-yl)-6-fluorobenzoic acid |
| A-359 | N-tert-butyl-1-{2-[4-(dimethylsulfamoyl)benzenesulfonamido]phenyl}-N-methylpiperidine-4-carboxamide |
| A-360 | N-tert-butyl-1-{2-[4-(dimethylsulfamoyl)benzenesulfonamido]phenyl}-N,4-dimethylpiperidine-4-carboxamide |
| A-361 | N-tert-butyl-1-{2-[4-(dimethylsulfamoyl)benzenesulfonamido]phenyl}-4-methylpiperidine-4-carboxamide |
| A-362 | N-(5-chloro-2-{1-oxa-7-azaspiro[4.5]decan-7-yl}phenyl)-2,3-dihydro-1H-indene-5-sulfonamide |
| A-363 | N-(5-chloro-2-{6-methyl-2-oxa-6,9-diazaspiro[4.5]decan-9-yl}phenyl)-2,3-dihydro-1H-indene-5-sulfonamide |
| A-364 | N-[3-chloro-2-(morpholin-4-yl)phenyl]-2-methoxyethane-1-sulfonamide |
| A-365 | N-[3-chloro-2-(morpholin-4-yl)phenyl]-1-(1,2-oxazol-3-yl)methanesulfonamide |
| A-366 | N-[3-chloro-2-(morpholin-4-yl)phenyl]-2,3-dihydro-1H-indene-5-carboxamide |
| A-367 | N-[3-chloro-2-(morpholin-4-yl)phenyl]-3-methoxybenzene-1-sulfonamide |
| A-368 | N-[3-chloro-2-(morpholin-4-yl)phenyl]-1-(3-chloro-4-fluorophenyl)methanesulfonamide |
| A-369 | N-[3-chloro-2-(morpholin-4-yl)phenyl]-4H,5H,6H,7H-pyrazolo[1,5-a]pyridine-3-sulfonamide |
| A-370 | N4-{2-[2-(dimethylamino)-2,3-dihydrospiro[indene-1,4'-piperidin]-1'-yl]phenyl}-N1,N1-dimethylbenzene-1,4-disulfonamide |
| A-371 | N-(2-{6-fluoro-1-[(pyridin-2-yl)methyl]-1,2-dihydrospiro[indole-3,4'-piperidin]-1'-yl}phenyl)-4-methanesulfonylbenzene-1-sulfonamide |
| A-372 | N-[2-(pyrrolidin-1-yl)phenyl]-3,4-dihydro-2H-1,5-benzodioxepine-7-sulfonamide |
| A-390 | N-[3-chloro-2-(morpholin-4-yl)phenyl]-3-cyclopropylbenzene-1-sulfonamide |
| A-391 | N-[3-chloro-2-(morpholin-4-yl)phenyl]-4-cyclopropylbenzene-1-sulfonamide |
| A-392 | N-[3-chloro-2-(morpholin-4-yl)phenyl]-2-cyclopropylbenzene-1-sulfonamide |
| A-393 | N-[3-chloro-2-(morpholin-4-yl)phenyl]-1-{1-oxaspiro[4.4]nonan-2-yl}methanesulfonamide |
| A-394 | 1-(adamantan-1-yl)-N-[3-chloro-2-(morpholin-4-yl)phenyl]methanesulfonamide |
| A-395 | N-(5-chloro-2-{2-oxa-6-azaspiro[3.4]octan-6-yl}phenyl)-2,3-dihydro-1H-indene-5-sulfonamide |
| A-396 | N-(5-chloro-2-{5-oxa-11-azadispiro[3.1.$3^6$.$3^4$]dodecan-11-yl}phenyl)-2,3-dihydro-1H-indene-5-sulfonamide |
| A-397 | N-{5-chloro-2-[1-(oxolan-2-yl)-2-azaspiro[3.3]heptan-2-yl]phenyl}-2,3-dihydro-1H-indene-5-sulfonamide |
| A-398 | 4-methanesulfonyl-N-(2-{2-methyl-2,3-dihydro-1H-spiro[isoquinoline-4,4'-piperidin]-1'-yl}phenyl)benzene-1-sulfonamide; formic acid |
| A-399 | N4-{2-[4-(adamantane-1-carbonyl)piperazin-1-yl]phenyl}-N1,N1-dimethylbenzene-1,4-disulfonamide |
| A-400 | N4-{5-chloro-2-[4-(2,2-dimethylpropanoyl)piperazin-1-yl]phenyl}-N1,N1-dimethylbenzene-1,4-disulfonamide |
| A-401 | N4-{2-[4-(3-fluoropyridin-4-yl)-4-hydroxypiperidin-1-yl]phenyl}-N1,N1-dimethylbenzene-1,4-disulfonamide |
| A-402 | N-(2-{3,4-dihydrospiro[2-benzopyran-1,4'-piperidin]-1'-yl}phenyl)-4-methanesulfonylbenzene-1-sulfonamide |
| A-403 | N-(2-{6-fluoro-1-[(pyridin-4-yl)methyl]-1,2-dihydrospiro[indole-3,4'-piperidin]-1'-yl}phenyl)-4-methanesulfonylbenzene-1-sulfonamide |
| A-404 | 2-{[1,1'-biphenyl]-2-yloxy}-N-{4-[methyl(1-methylpiperidin-4-yl)sulfamoyl]phenyl}acetamide |
| A-405 | N-(5-chloro-2-{7-oxa-1-azaspiro[4.5]decan-1-yl}phenyl)-2,3-dihydro-1H-indene-5-sulfonamide |
| A-406 | 4-{[2-(4-benzylpiperazin-1-yl)phenyl]methanesulfonyl}-N,N-dimethylbenzene-1-sulfonamide |
| A-407 | N-(2-{6-fluoro-1-[(pyridin-3-yl)methyl]-1,2-dihydrospiro[indole-3,4'-piperidin]-1'-yl}phenyl)-4-methanesulfonylbenzene-1-sulfonamide |
| A-408 | N-{2-[4-(5-fluoropyridin-2-yl)-4-hydroxypiperidin-1-yl]phenyl}-4-methylbenzene-1-sulfonamide |
| A-409 | N-{2-[4-(5-fluoropyridin-2-yl)-4-hydroxypiperidin-1-yl]phenyl}-4-methoxybenzene-1-sulfonamide |
| A-410 | N-{2-[4-(2,2-dimethylpropanoyl)piperazin-1-yl]phenyl}-1-phenylmethanesulfonamide |
| A-411 | ethyl 1-[2-(2,3-dihydro-1H-indene-5-sulfonamido)phenyl]-4-methylpiperidine-4-carboxylate |
| A-412 | N1,N1-dimethyl-N4-(2-{1'-methyl-1',2'-dihydrospiro[piperidine-4,3'-pyrrolo[2,3-c]pyridin]-1-yl}phenyl)benzene-1,4-disulfonamide |
| A-413 | N-{2-[4-(5-fluoropyridin-2-yl)-4-hydroxypiperidin-1-yl]phenyl(-4-(propane-2-sulfonyl)benzene-1-sulfonamide |
| A-414 | N4-{2-[4-(1-tert-butyl-1H-pyrazol-3-yl)piperazin-1-yl]phenyl}-N1,N1-dimethylbenzene-1,4-disulfonamide |

TABLE B-continued

| Compound No. | Compound Name |
|---|---|
| A-415 | N4-(2-{4-[(tert-butylamino)methyl]piperidin-1-yl}phenyl)-N1,N1-dimethylbenzene-1,4-disulfonamide |
| A-416 | N1,N1-dimethyl-N4-{2-[(3S)-3-methyl-4-(1,3-thiazole-4-carbonyl)piperazin-1-yl]phenyl}benzene-1,4-disulfonamide |
| A-417 | N-{2-[4-(2,2-dimethylpropanoyl)piperazin-1-yl]phenyl}-3-(4-methylpiperazin-1-yl)propane-1-sulfonamide |
| A-418 | N4-{2-[4-(1-methoxypropan-2-yl)piperazin-1-yl]phenyl}-N1,N1-dimethylbenzene-1,4-disulfonamide |
| A-419 | N1,N1-dimethyl-N4-{2-[4-(oxolan-2-yl)piperidin-1-yl]phenyl}benzene-1,4-disulfonamide |
| A-420 | N4-[2-(4-cyclopropyl-4-hydroxypiperidin-1-yl)phenyl]-N1,N1-dimethylbenzene-1,4-disulfonamide |
| A-421 | rac-N4-(2-{4-[(1R,2S,4S)-bicyclo[2.2.1]heptan-2-yl]piperazin-1-yl}phenyl)-N1,N1-dimethylbenzene-1,4-disulfonamide |
| A-422 | N1,N1-dimethyl-N4-(2-{2-oxa-8-azaspiro[4.5]decan-8-yl}phenyl)benzene-1,4-disulfonamide |
| A-423 | N-(2-{6-fluoro-1-[(oxolan-3-yl)methyl]-1,2-dihydrospiro[indole-3,4'-piperidin]-1'-yl}phenyl)-4-methanesulfonylbenzene-1-sulfonamide |
| A-424 | N1-{2-[4-(4-chloro-2-fluorophenyl)piperidin-1-yl]phenyl}-N4-methylbenzene-1,4-disulfonamide |
| A-425 | N1,N1-dimethyl-N4-{2-[4-(1-methylcyclobutanecarbonyl)piperazin-1-yl]phenyl}benzene-1,4-disulfonamide |
| A-426 | N4-{2-[4-(3,3-dimethylpentanoyl)piperazin-1-yl]phenyl}-N1,N1-dimethylbenzene-1,4-disulfonamide |
| A-427 | N4-{2-[4-(2,2-dimethylcyclopropanecarbonyl)piperazin-1-yl]phenyl}-N1,N1-dimethylbenzene-1,4-disulfonamide |
| A-428 | N1,N1-dimethyl-N4-{2-[4-(2,3,3-trimethylbutanoyl)piperazin-1-yl]phenyl}benzene-1,4-disulfonamide |
| A-429 | N4-{2-[4-(3,3-difluorocyclobutanecarbonyl)piperazin-1-yl]phenyl}-N1,N1-dimethylbenzene-1,4-disulfonamide |
| A-430 | N4-(2-{4-[1-(fluoromethyl)cyclobutanecarbonyl]piperazin-1-yl}phenyl)-N1,N1-dimethylbenzene-1,4-disulfonamide |
| A-431 | N4-{2-[4-(2-methoxy-2-methylpropanoyl)piperazin-1-yl]phenyl}-N1,N1-dimethylbenzene-1,4-disulfonamide |
| A-432 | N4-{2-[4-(2-fluoro-2-methylpropanoyl)piperazin-1-yl]phenyl}-N1,N1-dimethylbenzene-1,4-disulfonamide |
| A-433 | N4-{2-[4-(1-hydroxycyclopropyl)piperidin-1-yl]phenyl}-N1,N1-dimethylbenzene-1,4-disulfonamide |
| A-434 | N4-{2-[4-(methoxymethyl)piperidin-1-yl]phenyl}-N1,N1-dimethylbenzene-1,4-disulfonamide |
| A-435 | N1,N1-dimethyl-N4-{2-[4-(oxan-2-yl)piperidin-1-yl]phenyl}benzene-1,4-disulfonamide |
| A-436 | N4-{2-[4-(hydroxymethyl)-4-methylpiperidin-1-yl]phenyl}-N1,N1-dimethylbenzene-1,4-disulfonamide |
| A-437 | N4-{2-[4-(1,4-dioxan-2-yl)piperidin-1-yl]phenyl}-N1,N1-dimethylbenzene-1,4-disulfonamide |
| A-438 | N4-{2-[4-(methoxymethyl)-4-methylpiperidin-1-yl]phenyl}-N1,N1-dimethylbenzene-1,4-disulfonamide |
| A-439 | N-(5-chloro-2-{6-fluoro-1-methyl-1,2-dihydrospiro[indole-3,4'-piperidin]-1'-yl}phenyl)-2,3-dihydro-1H-indene-5-sulfonamide |
| A-440 | N4-(2-{3,3-dimethyl-2-oxa-8-azaspiro[4.5]decan-8-yl}phenyl)-N1,N1-dimethylbenzene-1,4-disulfonamide |
| A-441 | 4-methanesulfonyl-N-(2-{2-methyl-3,4-dihydro-2H-spiro[isoquinoline-1,4'-piperidin]-1'-yl}phenyl)benzene-1-sulfonamide |
| A-442 | oxolan-3-yl 1'-{2-[4-(dimethylsulfamoyl)benzenesulfonamido]phenyl}-6-fluoro-1,2-dihydrospiro[indole-3,4'-piperidine]-1-carboxylate |
| A-443 | 4-[1-({2-[4-(4-chloro-2-fluorophenyl)piperidin-1-yl]phenyl}amino)ethyl]-N,N-dimethylbenzene-1-sulfonamide |
| A-444 | N4-{2-[4-(1-methoxycyclopentanecarbonyl)piperazin-1-yl]phenyl}-N1,N1-dimethylbenzene-1,4-disulfonamide |
| A-445 | N4-{2-[4-(1-methoxycyclohexanecarbonyl)piperazin-1-yl]phenyl}-N1,N1-dimethylbenzene-1,4-disulfonamide |
| A-446 | N4-{2-[4-(2,2-difluoropropanoyl)piperazin-1-yl]phenyl}-N1,N1-dimethylbenzene-1,4-disulfonamide |
| A-447 | N4-[2-(4-{2-azabicyclo[2.1.1]hexane-2-carbonyl(piperazin-1-yl)phenyl]-N1,N1-dimethylbenzene-1,4-disulfonamide |
| A-448 | N1,N1-dimethyl-N4-{2-[4-(2-methyloxane-2-carbonyl)piperazin-1-yl]phenyl}benzene-1,4-disulfonamide |
| A-449 | rac-N1,N1-dimethyl-N4-(2-{4-[(1R,2R,4S)-7-oxabicyclo[2.2.1]heptane-2-carbonyl]piperazin-1-yl}phenyl)benzene-1,4-disulfonamide |
| A-450 | N1,N1-dimethyl-N4-{2-[4-(oxan-3-yl)piperazin-1-yl]phenyl}benzene-1,4-disulfonamide |
| A-451 | N4-{2-[4-ethyl-4-(morpholin-4-yl)piperidin-1-yl]phenyl}-N1,N1-dimethylbenzene-1,4-disulfonamide |
| A-452 | N4-{2-[4-ethyl-4-(pyrrolidin-1-yl)piperidin-1-yl]phenyl}-N1,N1-dimethylbenzene-1,4-disulfonamide |
| A-453 | N4-[2-(4-cyclopentylpiperazin-1-yl)phenyl]-N1,N1-dimethylbenzene-1,4-disulfonamide |

TABLE B-continued

| Compound No. | Compound Name |
|---|---|
| A-454 | N4-[2-(4-methoxy-4-methylpiperidin-1-yl)phenyl]-N1,N1-dimethylbenzene-1,4-disulfonamide |
| A-455 | N1,N1-dimethyl-N4-{2-[4-(2-methylbutan-2-yl)piperazin-1-yl]phenyl}benzene-1,4-disulfonamide |
| A-456 | N1,N1-dimethyl-N4-{2-[4-(1,1,1-trifluoropropan-2-yl)piperazin-1-yl]phenyl}benzene-1,4-disulfonamide |
| A-457 | N-[3-chloro-2-(morpholin-4-yl)phenyl]-4-(propan-2-yloxy)benzene-1-sulfonamide |
| A-458 | N4-{2-[4-(1-methoxycyclobutanecarbonyl)piperazin-1-yl]phenyl}-N1,N1-dimethylbenzene-1,4-disulfonamide |
| A-459 | N4-{2-[4-(2,2-difluorocyclopentanecarbonyl)piperazin-1-yl]phenyl}-N1,N1-dimethylbenzene-1,4-disulfonamide |
| A-460 | N4-[2-(4-{bicyclo[2.2.1]heptane-1-carbonyl}piperazin-1-yl)phenyl]-N1,N1-dimethylbenzene-1,4-disulfonamide |
| A-461 | N4-{2-[4-(1-fluorocyclopropanecarbonyl)piperazin-1-yl]phenyl}-N1,N1-dimethylbenzene-1,4-disulfonamide |
| A-462 | N1,N1-dimethyl-N4-[2-(4-{spiro[2.2]pentane-1-carbonyl}piperazin-1-yl)phenyl]benzene-1,4-disulfonamide |
| A-463 | rac-N4-(2-{4-[(1R,2R)-2-(1,1-difluoroethyl)cyclopropanecarbonyl]piperazin-1-yl}phenyl)-N1,N1-dimethylbenzene-1,4-disulfonamide |
| A-464 | N4-{2-[4-(3-ethyloxetan-3-yl)piperazin-1-yl]phenyl}-N1,N1-dimethylbenzene-1,4-disulfonamide |
| A-465 | 4-{1-[2-(4-benzylpiperazin-1-yl)phenyl]ethanesulfonyl}-N,N-dimethylbenzene-1-sulfonamide |
| A-466 | N-{2-[6-fluoro-1-(2-methoxyethyl)-1,2-dihydrospiro[indole-3,4'-piperidin]-1'-yl]phenyl}-4-methanesulfonylbenzene-1-sulfonamide |
| A-467 | N-(2-{6-fluoro-1-[(oxolan-2-yl)methyl]-1,2-dihydrospiro[indole-3,4'-piperidin]-1'-yl}phenyl)-4-methanesulfonylbenzene-1-sulfonamide |
| A-468 | N-(2-{1-[(2,2-difluorocyclopropyl)methyl]-6-fluoro-1,2-dihydrospiro[indole-3,4'-piperidin]-1'-yl}phenyl)-4-methanesulfonylbenzene-1-sulfonamide |
| A-469 | oxolan-3-yl 6-fluoro-1'-[2-(4-methanesulfonylbenzenesulfonamido)phenyl]-1,2-dihydrospiro[indole-3,4'-piperidine]-1-carboxylate |
| A-470 | N4-{2-[4-(2,2-dimethylpropanoyl)piperidin-1-yl]phenyl}-N1,N1-dimethylbenzene-1,4-disulfonamide |
| A-471 | N4-[2-(4-tert-butyl-4-hydroxypiperidin-1-yl)phenyl]-N1,N1-dimethylbenzene-1,4-disulfonamide |
| A-472 | N4-(2-{6-fluoro-1-methyl-2'-oxo-1,2-dihydrospiro[indole-3,4'-piperidin]-1'-yl}phenyl)-N1,N1-dimethylbenzene-1,4-disulfonamide |
| A-473 | N4-(2-{3-fluoro-5-oxo-5H-spiro[furo[3,4-b]pyridine-7,4'-piperidin]-1'-yl}phenyl)-N1,N1-dimethylbenzene-1,4-disulfonamide |
| A-474 | 4-(1-{2-[4-(2,2-dimethylpropanoyl)piperazin-1-yl]phenyl}ethanesulfonyl)-N,N-dimethylbenzene-1-sulfonamide |
| A-475 | N4-(2-{4'-ethyl-[1,4'-bipiperidin]-1'-yl}phenyl)-N1,N1-dimethylbenzene-1,4-disulfonamide |
| A-476 | N1,N1-dimethyl-N4-{2-[4-(2-methyloxolane-2-carbonyl)piperazin-1-yl]phenyl}benzene-1,4-disulfonamide |
| A-477 | rac-N4-(2-{4-[(1R,5R)-bicyclo[3.1.0]hexane-1-carbonyl]piperazin-1-yl}phenyl)-N1,N1-dimethylbenzene-1,4-disulfonamide |
| A-478 | N4-{2-[4-(3,3-difluoro-1-methylcyclobutanecarbonyl)piperazin-1-yl]phenyl}-N1,N1-dimethylbenzene-1,4-disulfonamide |
| A-479 | N4-{2-[4-(2,2-difluorocyclopropyl)piperidin-1-yl]phenyl}-N1,N1-dimethylbenzene-1,4-disulfonamide |
| A-480 | N4-{2-[4-(2,2-dimethylpropanoyl)-1,4-diazepan-1-yl]phenyl}-N1,N1-dimethylbenzene-1,4-disulfonamide |
| A-481 | N-(2-{1,3-dihydrospiro[2-benzopyran-4,4'-piperidin]-1'-yl}phenyl)-4-methanesulfonylbenzene-1-sulfonamide |
| A-482 | N1-{2-[4-(4-chloro-2-fluorophenyl)piperidin-1-yl]phenyl}benzene-1,4-disulfonamide |
| A-483 | 4-tert-butyl-N-{2-[4-(methoxymethyl)-4-methylpiperidin-1-yl]phenyl}benzene-1-sulfonamide |
| A-484 | N4-[2-(4-cyclopropyl-1,4-diazepan-1-yl)phenyl]-N1,N1-dimethylbenzene-1,4-disulfonamide |
| A-485 | 1-(3-bromophenyl)-N-{2-[4-(2,2-dimethylpropanoyl)piperazin-1-yl]phenyl}methanesulfonamide |
| A-486 | 1-(3,4-dimethylphenyl)-N-{2-[4-(2,2-dimethylpropanoyl)piperazin-1-yl]phenyl}methanesulfonamide |
| A-487 | N4-[2-(4-{bicyclo[4.1.0]heptane-1-carbonyl}piperazin-1-yl)phenyl]-N1,N1-dimethylbenzene-1,4-disulfonamide |
| A-488 | 1-(4-bromo-2-fluorophenyl)-N-{2-[4-(2,2-dimethylpropanoyl)piperazin-1-yl]phenyl}methanesulfonamide |
| A-489 | 4-(2,2-dimethylpropyl)-N-{2-[4-(methoxymethyl)-4-methylpiperidin-1-yl]phenyl}benzene-1-sulfonamide |
| A-490 | 4-[1-({2-[4-(methoxymethyl)-4-methylpiperidin-1-yl]phenyl}amino)ethyl]-N,N-dimethylbenzene-1-sulfonamide |
| A-491 | 4-(1-{2-[4-(methoxymethyl)-4-methylpiperidin-1-yl]phenyl}ethanesulfonyl)-N,N-dimethylbenzene-1-sulfonamide |

TABLE B-continued

| Compound No. | Compound Name |
|---|---|
| A-492 | 4-methanesulfonyl-N-(2-{1'-methyl-2',3'-dihydro-1'H-spiro[piperidine-4,4'-quinolin]-1-yl}phenyl)benzene-1-sulfonamide |
| A-493 | 4-({2-[4-(methoxymethyl)-4-methylpiperidin-1-yl]phenyl}methanesulfonyl)-N,N-dimethylbenzene-1-sulfonamide |
| A-494 | N4-(2-{4-[(tert-butoxy)methyl]piperidin-1-yl}phenyl)-N1,N1-dimethylbenzene-1,4-disulfonamide |
| A-495 | N1,N1-dimethyl-N4-(2-{4-[(oxolan-2-yl)methyl]piperazin-1-yl}phenyl)benzene-1,4-disulfonamide |
| A-496 | N4-{2-[4-(3-methoxypropyl)piperidin-1-yl]phenyl}-N1,N1-dimethylbenzene-1,4-disulfonamide |
| A-497 | N1,N1-dimethyl-N4-(2-{1-oxa-7-azaspiro[4.5]decan-7-yl}phenyl)benzene-1,4-disulfonamide |
| A-498 | N4-{2-[4-(2-ethoxyethyl)piperidin-1-yl]phenyl}-N1,N1-dimethylbenzene-1,4-disulfonamide |
| A-499 | N1,N1-dimethyl-N4-(2-{7-oxa-1-azaspiro[4.5]decan-1-yl}phenyl)benzene-1,4-disulfonamide |
| A-500 | 1-(3,5-dimethylphenyl)-N-{2-[4-(2,2-dimethylpropanoyl)piperazin-1-yl]phenyl}methanesulfonamide |
| A-501 | 1-(3,4-dihydro-1H-2-benzopyran-7-yl)-N-{2-[4-(2,2-dimethylpropanoyl)piperazin-1-yl]phenyl}methanesulfonamide |
| A-502 | N4-(2-{5-benzyl-octahydropyrrolo[3,4-c]pyrrol-2-yl}phenyl)-N1,N1-dimethylbenzene-1,4-disulfonamide; formic acid |
| A-503 | 4-({3-[1-(2,6-difluorophenyl)piperidin-4-yl]-1H,4H,5H,6H,7H-pyrazolo[4,3-b]pyridin-1-yl}sulfonyl)-N,N-dimethylbenzene-1-sulfonamide |
| A-504 | 4-({3-[1-(2,6-difluorophenyl)piperidin-4-yl]-4,5,6,7-tetrahydro-1H-indazol-1-yl}sulfonyl)-N,N-dimethylbenzene-1-sulfonamide |
| A-505 | N1,N1-dimethyl-N4-(2-{4-[1-(pyridin-3-yl)ethyl]piperazin-1-yl}phenyl)benzene-1,4-disulfonamide |
| A-506 | N4-{2-[4-(1,1-difluoroethyl)piperidin-1-yl]phenyl}-N1,N1-dimethylbenzene-1,4-disulfonamide |
| A-507 | N1,N1-dimethyl-N4-(2-{2-oxa-6-azaspiro[3.5]nonan-6-yl}phenyl)benzene-1,4-disulfonamide |
| A-508 | N1,N1-dimethyl-N4-(2-{7-oxa-1-azaspiro[4.4]nonan-1-yl}phenyl)benzene-1,4-disulfonamide |
| A-509 | N1,N1-dimethyl-N4-(2-{4-[(oxolan-3-yl)methyl]piperazin-1-yl}phenyl)benzene-1,4-disulfonamide |
| A-510 | N1,N1-dimethyl-N4-(2-{4-[(oxan-4-yl)methyl]piperazin-1-yl}phenyl)benzene-1,4-disulfonamide |
| A-511 | N1,N1-dimethyl-N4-(2-{2-oxa-8-azaspiro[5.5]undecan-8-yl}phenyl)benzene-1,4-disulfonamide |
| A-512 | N-{2-[4-(2,2-dimethylpropanoyl)piperazin-1-yl]phenyl}-4-(propan-2-yl)benzene-1-sulfonamide |
| A-513 | 4-(butan-2-yl)-N-{2-[4-(2,2-dimethylpropanoyl)piperazin-1-yl]phenyl}benzene-1-sulfonamide |
| A-514 | N-{2-[4-(2,2-dimethylpropanoyl)piperazin-1-yl]phenyl}-2,2-dimethyl-2,3-dihydro-1-benzofuran-5-sulfonamide |
| A-515 | N-{2-[4-(2,2-dimethylpropanoyl)piperazin-1-yl]phenyl}-1-methyl-1H-indole-5-sulfonamide |
| A-516 | 4-tert-butyl-N-{2-[4-(2,2-dimethylpropanoyl)piperazin-1-yl]phenyl}benzene-1-sulfonamide |
| A-517 | 4-(tert-butylsulfanyl)-N-(2-{6-fluoro-1-methyl-1,2-dihydrospiro[indole-3,4'-piperidin]-1'-yl}phenyl)benzene-1-sulfonamide |
| A-518 | N4-(2-{4-[(2-methoxyethoxy)methyl]-4-methylpiperidin-1-yl}phenyl)-N1,N1-dimethylbenzene-1,4-disulfonamide |
| A-519 | N4-[2-(4-{[2-(2-methoxyethoxy)ethoxy]methyl}-4-methylpiperidin-1-yl)phenyl]-N1,N1-dimethylbenzene-1,4-disulfonamide |
| A-520 | N-[5-methyl-2-(morpholin-4-yl)phenyl]-2,3-dihydro-1H-indene-5-sulfonamide |
| A-521 | N-[5-methoxy-2-(morpholin-4-yl)phenyl]-2,3-dihydro-1H-indene-5-sulfonamide |
| A-522 | N4-{2-[4-(2-hydroxypropan-2-yl)-4-methylpiperidin-1-yl]phenyl}-N1,N1-dimethylbenzene-1,4-disulfonamide |
| A-523 | N4-[2-(4-ethoxy-4-methylpiperidin-1-yl)phenyl]-N1,N1-dimethylbenzene-1,4-disulfonamide |
| A-524 | N1,N1-dimethyl-N4-(2-{3-oxa-9-azaspiro[5.5]undecan-9-yl}phenyl)benzene-1,4-disulfonamide |
| A-525 | N4-{2-[4-(2,2-difluoropropyl)piperazin-1-yl]phenyl}-N1,N1-dimethylbenzene-1,4-disulfonamide |
| A-526 | N1,N1-dimethyl-N4-{2-[4-(2-methylpropyl)-5-oxo-1,4-diazepan-1-yl]phenyl}benzene-1,4-disulfonamide |
| A-527 | N-{2-[4-(2,2-dimethylpropanoyl)piperazin-1-yl]phenyl}-4-(trifluoromethyl)benzene-1-sulfonamide |
| A-528 | 4-(2,2-difluorocyclopropyl)-N-{2-[4-(2,2-dimethylpropanoyl)piperazin-1-yl]phenyl}benzene-1-sulfonamide |
| A-529 | 4-(difluoromethyl)-N-{2-[4-(2,2-dimethylpropanoyl)piperazin-1-yl]phenyl}benzene-1-sulfonamide |
| A-530 | N-{2-[4-(2,2-dimethylpropanoyl)piperazin-1-yl]phenyl}-2-methyl-2,3-dihydro-1-benzofuran-5-sulfonamide |

TABLE B-continued

| Compound No. | Compound Name |
|---|---|
| A-531 | 4-methoxy-N-{2-[4-(1,1,1-trifluoropropan-2-yl)piperazin-1-yl]phenyl}benzene-1-sulfonamide |
| A-532 | N-{2-[4-(methoxymethyl)-4-methylpiperidin-1-yl]phenyl}-1-phenylmethanesulfonamide |
| A-533 | 4-({3-[1-(2,6-difluorophenyl)piperidin-4-yl]-1H,4H,5H,6H,7H-pyrazolo[4,3-c]pyridin-1-yl}sulfonyl)-N,N-dimethylbenzene-1-sulfonamide |
| A-534 | 2,2-dichloro-N-{2-[4-(2,2-dimethylpropanoyl)piperazin-1-yl]phenyl}-1-oxo-2,3-dihydro-1H-indene-5-sulfonamide |
| A-535 | 4-(1-cyano-1-methylethyl)-N-{2-[4-(2,2-dimethylpropanoyl)piperazin-1-yl]phenyl}benzene-1-sulfonamide |
| A-536 | 4-(cyclopentyloxy)-N-{2-[4-(2,2-dimethylpropanoyl)piperazin-1-yl]phenyl}benzene-1-sulfonamide |
| A-537 | N-{2-[4-(2,2-dimethylpropanoyl)piperazin-1-yl]phenyl}-4-(1,1,2,2,2-pentafluoroethyl)benzene-1-sulfonamide |
| A-538 | 4-methoxy-N-{2-[4-(methoxymethyl)-4-methylpiperidin-1-yl]phenyl}benzene-1-sulfonamide |
| A-539 | N-{2-[4-(methoxymethyl)-4-methylpiperidin-1-yl]phenyl}-4-methylbenzene-1-sulfonamide |
| A-540 | 4-methanesulfonyl-N-{2-[4-(1,1,1-trifluoropropan-2-yl)piperazin-1-yl]phenyl}benzene-1-sulfonamide |
| A-541 | 4-chloro-N-{2-[4-(1,1,1-trifluoropropan-2-yl)piperazin-1-yl]phenyl}benzene-1-sulfonamide |
| A-542 | 1-phenyl-N-{2-[4-(1,1,1-trifluoropropan-2-yl)piperazin-1-yl]phenyl}methanesulfonamide |
| A-543 | N4-(2-{4-[(difluoromethoxy)methyl]piperidin-1-yl}phenyl)-N1,N1-dimethylbenzene-1,4-disulfonamide |
| A-544 | N4-[2-(4-{[(2R,6S)-2,6-dimethylmorpholin-4-yl]methyl}piperidin-1-yl)phenyl]-N1,N1-dimethylbenzene-1,4-disulfonamide |
| A-545 | N1,N1-dimethyl-N4-{2-[4-(2,2,2-trifluoro-1-phenylethyl)piperazin-1-yl]phenyl}benzene-1,4-disulfonamide |
| A-546 | N4-[2-(4-ethyl-4-methoxypiperidin-1-yl)phenyl]-N1,N1-dimethylbenzene-1,4-disulfonamide |
| A-547 | N1,N1-dimethyl-N4-(2-{4-[3-(morpholin-4-yl)propyl]piperidin-1-yl}phenyl)benzene-1,4-disulfonamide |
| A-548 | N1,N1-dimethyl-N4-{2-[4-(oxan-4-yl)piperidin-1-yl]phenyl}benzene-1,4-disulfonamide |
| A-549 | N4-(2-{4-[(diethylamino)methyl]piperidin-1-yl}phenyl)-N1,N1-dimethylbenzene-1,4-disulfonamide |
| A-550 | N1,N1-dimethyl-N4-{2-[4-(trifluoromethyl)piperidin-1-yl]phenyl}benzene-1,4-disulfonamide |
| A-551 | N1,N1-dimethyl-N4-{2-[4-(2,2,3,3-tetrafluoropropyl)piperazin-1-yl]phenyl}benzene-1,4-disulfonamide |
| A-552 | N4-{2-[4-(2,2-difluoroethyl)piperazin-1-yl]phenyl}-N1,N1-dimethylbenzene-1,4-disulfonamide |
| A-553 | N4-{2-[4-(2-methoxyethyl)piperazin-1-yl]phenyl}-N1,N1-dimethylbenzene-1,4-disulfonamide |
| A-554 | N1,N1-dimethyl-N4-(2-{4-[(morpholin-4-yl)methyl]piperidin-1-yl}phenyl)benzene-1,4-disulfonamide |
| A-555 | 4-(cyclopropylmethoxy)-N-{2-[4-(methoxymethyl)-4-methylpiperidin-1-yl]phenyl}benzene-1-sulfonamide |
| A-556 | benzyl 4-(2-{1-[4-(dimethylsulfamoyl)benzenesulfonyl]ethyl}phenyl)piperazine-1-carboxylate |
| A-557 | N4-{2-[4-(1-hydroxyethyl)-4-methylpiperidin-1-yl]phenyl}-N1,N1-dimethylbenzene-1,4-disulfonamide |
| A-558 | N4-{2-[4-(1-hydroxycyclopropyl)-4-methylpiperidin-1-yl]phenyl}-N1,N1-dimethylbenzene-1,4-disulfonamide |
| A-559 | N4-{2-[4-(2-fluoroethyl)piperazin-1-yl]phenyl}-N1,N1-dimethylbenzene-1,4-disulfonamide |
| A-560 | N1,N1-dimethyl-N4-{2-[4-(2,2,2-trifluoroethyl)piperazin-1-yl]phenyl}benzene-1,4-disulfonamide |
| A-562 | N1,N1-dimethyl-N4-(2-{1-oxa-9-azaspiro[5.5]undecan-9-yl}phenyl)benzene-1,4-disulfonamide |
| A-563 | 1-(5-chloro-2-methoxyphenyl)-N-{2-[4-(2,2-dimethylpropanoyl)piperazin-1-yl]phenyl}methanesulfonamide |
| A-564 | N-{2-[4-(2,2-dimethylpropanoyl)piperazin-1-yl]phenyl}-1-phenylcyclopropane-1-sulfonamide |
| A-565 | N-{2-[4-(2,2-dimethylpropanoyl)piperazin-1-yl]phenyl}-1-(quinolin-8-yl)methanesulfonamide |
| A-566 | N-{2-[4-(2,2-dimethylpropanoyl)piperazin-1-yl]phenyl}-1-(naphthalen-2-yl)methanesulfonamide |
| A-567 | N-{2-[4-(2,2-dimethylpropanoyl)piperazin-1-yl]phenyl}-4-(2,2,2-trifluoroethyl)benzene-1-sulfonamide |
| A-568 | N-{2-[4-(2,2-dimethylpropanoyl)piperazin-1-yl]phenyl}-4-(trifluoromethoxy)benzene-1-sulfonamide |
| A-569 | N-{2-[4-(2,2-dimethylpropanoyl)piperazin-1-yl]phenyl}-4-(1,1,2,2-tetrafluoro-2-methoxyethyl)benzene-1-sulfonamide |
| A-570 | N-(2-{3,3-dimethyl-2-oxa-8-azaspiro[4.5]decan-8-yl}phenyl)-1-phenylmethanesulfonamide |

TABLE B-continued

| Compound No. | Compound Name |
|---|---|
| A-571 | 1-(3,4-dihydro-1H-2-benzopyran-7-yl)-N-{2-[4-(methoxymethyl)-4-methylpiperidin-1-yl]phenyl}methanesulfonamide |
| A-572 | N-{2-[4-(2,2-dimethylpropanoyl)piperazin-1-yl]phenyl}-4-(1,1,1-trifluoro-2-methylpropan-2-yl)benzene-1-sulfonamide |
| A-573 | N-{2-[4-(2,2-dimethylpropanoyl)piperazin-1-yl]phenyl}-4-propoxybenzene-1-sulfonamide |
| A-574 | N-{2-[4-(2,2-dimethylpropanoyl)piperazin-1-yl]phenyl}-4-[(trifluoromethyl)sulfanyl]benzene-1-sulfonamide |
| A-575 | N-{2-[4-(2,2-dimethylpropanoyl)piperazin-1-yl]phenyl}-4-(pentafluoro-$\lambda^6$-sulfanyl)benzene-1-sulfonamide |
| A-576 | 4-cyclopropoxy-N-{2-[4-(2,2-dimethylpropanoyl)piperazin-1-yl]phenyl}benzene-1-sulfonamide |
| A-577 | 4-chloro-N-{2-[4-(methoxymethyl)-4-methylpiperidin-1-yl]phenyl}benzene-1-sulfonamide |
| A-578 | N-{2-[4-(methoxymethyl)-4-methylpiperidin-1-yl]phenyl}-1-(4-methylphenyl)methanesulfonamide |
| A-579 | 1-(2-fluorophenyl)-N-{2-[4-(methoxymethyl)-4-methylpiperidin-1-yl]phenyl}methanesulfonamide |
| A-580 | 1-(4-fluorophenyl)-N-{2-[4-(methoxymethyl)-4-methylpiperidin-1-yl]phenyl}methanesulfonamide |
| A-581 | 1-(3-cyanophenyl)-N-{2-[4-(methoxymethyl)-4-methylpiperidin-1-yl]phenyl}methanesulfonamide |
| A-582 | N-{2-[4-(methoxymethyl)-4-methylpiperidin-1-yl]phenyl}-1-(4-methoxyphenyl)methanesulfonamide |
| A-583 | N-{2-[4-(2,2-dimethylpropanoyl)piperazin-1-yl]phenyl}-1,2,3,4-tetrahydronaphthalene-2-sulfonamide |
| A-584 | N1,N1-dimethyl-N4-(2-{1-oxa-8-azaspiro[4.5]decan-8-yl}phenyl)benzene-1,4-disulfonamide |
| A-585 | N4-{2-[4-(difluoromethyl)piperidin-1-yl]phenyl}-N1,N1-dimethylbenzene-1,4-disulfonamide |
| A-586 | l-(3-methanesulfonylphenyl)-N-{2-[4-(methoxymethyl)-4-methylpiperidin-1-yl]phenyl}methanesulfonamide |
| A-587 | N4-{2-[4-(4-chloro-2-fluorophenyl)piperidin-1-yl]phenyl}-N1-{2-[2-(2-methoxyethoxy)ethoxylethyl}-N1-methylbenzene-1,4-disulfonamide |
| A-588 | N-{2-[4-(4-chloro-2-fluorophenyl)piperidin-1-yl]phenyl}-4-{2-[2-(2-methoxyethoxy)ethoxy]ethoxy}benzene-1-sulfonamide |
| A-589 | N-{2-[4-(4-chloro-2-fluorophenyl)piperidin-1-yl]phenyl}-4-[2-(2-methoxyethoxy)ethoxy]benzene-1-sulfonamide |
| A-590 | 4-(1,1-difluoroethyl)-N-{2-[4-(2,2-dimethylpropanoyl)piperazin-1-yl]phenyl}benzene-1-sulfonamide |
| A-591 | N-{2-[4-(2,2-dimethylpropanoyl)piperazin-1-yl]phenyl}-4-(2,2,2-trifluoroethoxy)benzene-1-sulfonamide |
| A-592 | N-{2-[4-(methoxymethyl)-4-methylpiperidin-1-yl]phenyl}-1-(2-methylphenyl)methanesulfonamide |
| A-593 | N-{2-[4-(methoxymethyl)-4-methylpiperidin-1-yl]phenyl}-1-(3-methylphenyl)methanesulfonamide |
| A-594 | 1-(3-fluorophenyl)-N-{2-[4-(methoxymethyl)-4-methylpiperidin-1-yl]phenyl}methanesulfonamide |
| A-595 | N-{2-[4-(methoxymethyl)-4-methylpiperidin-1-yl]phenyl}-1-(2-methoxyphenyl)methanesulfonamide |
| A-596 | N-{2-[4-(methoxymethyl)-4-methylpiperidin-1-yl]phenyl}-1-(3-methoxyphenyl)methanesulfonamide |
| A-597 | N-{2-[4-(methoxymethyl)-4-methylpiperidin-1-yl]phenyl}-2,3-dihydro-1H-indene-1-sulfonamide |
| A-598 | benzyl 4-(2-{[4-(dimethylsulfamoyl)benzenesulfonyl]methyl}phenyl)piperazine-1-carboxylate |
| A-599 | N,N-dimethyl-4-({2-[4-(2-methylpropyl)piperazin-1-yl]phenyl}methanesulfonyl)benzene-1-sulfonamide |
| A-600 | N-{2-[4-(2,2-dimethylpropanoyl)piperazin-1-yl]phenyl}-2-methyl-1,3-benzothiazole-6-sulfonamide |
| A-601 | 1-(2-chlorophenyl)-N-{2-[4-(methoxymethyl)-4-methylpiperidin-1-yl]phenyl}methanesulfonamide |
| A-602 | 1-(3-chlorophenyl)-N-{2-[4-(methoxymethyl)-4-methylpiperidin-1-yl]phenyl}methanesulfonamide |
| A-603 | N,N-dimethyl-4-(1-{2-[4-(oxetan-3-yl)piperazin-1-yl]phenyl}ethanesulfonyl)benzene-1-sulfonamide |
| A-604 | N,N-dimethyl-4-(1-{2-[4-(2-methylpropyl)piperazin-1-yl]phenyl}ethanesulfonyl)benzene-1-sulfonamide |
| A-605 | N4-(2-{3,3-dimethyl-2-oxa-8-azaspiro[4.5]decan-8-yl}-5-fluorophenyl)-N1,N1-dimethylbenzene-1,4-disulfonamide |
| A-606 | N4-(2-{3,3-dimethyl-2-oxa-8-azaspiro[4.5]decan-8-yl}-4-fluorophenyl)-N1,N1-dimethylbenzene-1,4-disulfonamide |
| A-607 | 1-(1,3-dihydro-2-benzofuran-4-yl)-N-{2-[4-(methoxymethyl)-4-methylpiperidin-1-yl]phenyl}methanesulfonamide |
| A-608 | N-{2-[4-(methoxymethyl)-4-methylpiperidin-1-yl]phenyl}-2,3-dihydro-1H-indene-5-sulfonamide |

TABLE B-continued

| Compound No. | Compound Name |
|---|---|
| A-609 | 1-(3,4-dihydro-1H-2-benzopyran-7-yl)-N-[5-methoxy-2-(morpholin-4-yl)phenyl]methanesulfonamide |
| A-610 | 1-(2-cyanophenyl)-N-{2-[4-(methoxymethyl)-4-methylpiperidin-1-yl]phenyl}methanesulfonamide |
| A-611 | N4-{2-[4-(2-methoxyethyl)piperidin-1-yl]phenyl}-N1,N1-dimethylbenzene-1,4-disulfonamide |
| A-612 | 1-(1,3-dihydro-2-benzofuran-5-yl)-N-{2-[4-(methoxymethyl)-4-methylpiperidin-1-yl]phenyl}methanesulfonamide |
| A-613 | N-{2-[4-(methoxymethyl)-4-methylpiperidin-1-yl]phenyl}-2,2-dimethyl-2,3-dihydro-1-benzofuran-5-sulfonamide |
| A-614 | N-{2-[4-(methoxymethyl)piperidin-1-yl]phenyl}-2,2-dimethyl-2,3-dihydro-1-benzofuran-5-sulfonamide |
| A-615 | N4-(2-{3,3-dimethyl-2-oxa-8-azaspiro[4.5]decan-8-yl(-3-fluorophenyl)-N1,N1-dimethylbenzene-1,4-disulfonamide |
| A-616 | 4-fluoro-N-{2-[4-(methoxymethyl)-4-methylpiperidin-1-yl]phenyl}-3-methylbenzene-1-sulfonamide |
| A-617 | 3-fluoro-N-{2-[4-(methoxymethyl)-4-methylpiperidin-1-yl]phenyl}-4-methylbenzene-1-sulfonamide |
| A-618 | N-{2-[4-(methoxymethyl)-4-methylpiperidin-1-yl]phenyl}-3-methylbenzene-1-sulfonamide |
| A-619 | 4-(1,3-dioxolan-2-yl)-N-{2-[4-(methoxymethyl)-4-methylpiperidin-1-yl]phenyl}thiophene-2-sulfonamide |
| A-620 | 4-(difluoromethyl)-N-{2-[4-(methoxymethyl)-4-methylpiperidin-1-yl]phenyl}benzene-1-sulfonamide |
| A-621 | 4-cyclopropyl-N-{2-[4-(methoxymethyl)-4-methylpiperidin-1-yl]phenyl}benzene-1-sulfonamide |
| A-622 | N-{2-[4-(methoxymethyl)-4-methylpiperidin-1-yl]phenyl}-4-(trifluoromethoxy)benzene-1-sulfonamide |
| A-623 | 4-bromo-N-{2-[4-(methoxymethyl)-4-methylpiperidin-1-yl]phenyl}benzene-1-sulfonamide |
| A-624 | N-{2-[4-(methoxymethyl)-4-methylpiperidin-1-yl]phenyl}-2,3-dihydro-1-benzoxepine-4-sulfonamide |
| A-625 | N-{2-[4-(methoxymethyl)-4-methylpiperidin-1-yl]phenyl}-3,4-dihydro-1H-2-benzopyran-7-sulfonamide |
| A-626 | N4-{2-[4-(2,2-difluorocyclohexyl)piperazin-1-yl]phenyl}-N1,N1-dimethylbenzene-1,4-disulfonamide |
| A-627 | 1-(3-tert-butylphenyl)-N-{2-[4-(methoxymethyl)-4-methylpiperidin-1-yl]phenyl}methanesulfonamide |
| A-628 | N-[5-methyl-2-(morpholin-4-yl)phenyl]-1-phenylmethanesulfonamide |
| A-629 | 1-(3,4-dihydro-1H-2-benzopyran-7-yl)-N-[5-methyl-2-(morpholin-4-yl)phenyl]methanesulfonamide |
| A-630 | N-{5-methoxy-2-[4-(methoxymethyl)-4-methylpiperidin-1-yl]phenyl}-2,3-dihydro-1H-indene-5-sulfonamide |
| A-631 | N-{2-[4-(2-ethoxyethyl)piperidin-1-yl]phenyl}-2,2-dimethyl-2,3-dihydro-1-benzofuran-5-sulfonamide |
| A-632 | 2,2-dimethyl-N-(2-{2-oxa-8-azaspiro[5.5]undecan-8-yl}phenyl)-2,3-dihydro-1-benzofuran-5-sulfonamide |
| A-633 | N-{2-[4-(methoxymethyl)-4-methylpiperidin-1-yl]phenyl}-3-(2-methoxypropan-2-yl)benzene-1-sulfonamide |
| A-634 | N-(2-{3,3-dimethyl-2-oxa-8-azaspiro[4.5]decan-8-yl}phenyl)-3-(2-methoxypropan-2-yl)benzene-1-sulfonamide |
| A-635 | N-(2-{3,3-dimethyl-2-oxa-8-azaspiro[4.5]decan-8-yl}phenyl)-2,2-dimethyl-2,3-dihydro-1-benzofuran-5-sulfonamide |
| A-636 | N-{2-[4-(1,1-difluoroethyl)piperidin-1-yl]phenyl}-2,2-dimethyl-2,3-dihydro-1-benzofuran-5-sulfonamide |
| A-637 | N-{2-[4-(4-chloro-2-fluorophenyl)piperidin-1-yl]phenyl}-4-(2-hydroxyethanesulfonyl)benzene-1-sulfonamide |
| A-638 | N-(2-{3,3-dimethyl-2-oxa-8-azaspiro[4.5]decan-8-yl}phenyl)-2,2-dimethyl-1-oxo-2,3-dihydro-1H-indene-5-sulfonamide |
| A-639 | N-{2-[4-(methoxymethyl)-4-methylpiperidin-1-yl]phenyl}-2,2-dimethyl-1-oxo-2,3-dihydro-1H-indene-5-sulfonamide |
| A-640 | 2,2-dimethyl-N-(2-{7-oxa-1-azaspiro[4.5]decan-1-yl}phenyl)-2,3-dihydro-1-benzofuran-5-sulfonamide |
| A-641 | N-{2-[4-(methoxymethyl)-4-methylpiperidin-1-yl]phenyl}-4-(2-methylpropanoyl)benzene-1-sulfonamide |
| A-642 | 1-(3,4-dimethylphenyl)-N-{2-[4-(methoxymethyl)-4-methylpiperidin-1-yl]phenyl}methanesulfonamide |
| A-643 | 3-cyclopropyl-N-{2-[4-(methoxymethyl)-4-methylpiperidin-1-yl]phenyl}benzene-1-sulfonamide |
| A-644 | 2-(difluoromethyl)-N-{2-[4-(methoxymethyl)-4-methylpiperidin-1-yl]phenyl}-3,4-dihydro-2H-1-benzopyran-6-sulfonamide |
| A-645 | N-{2-[4-(methoxymethyl)-4-methylpiperidin-1-yl]phenyl}-1,3-dihydro-2-benzofuran-5-sulfonamide |
| A-646 | 1-(3-fluoro-4-methylphenyl)-N-{2-[4-(methoxymethyl)-4-methylpiperidin-1-yl]phenyl}methanesulfonamide |
| A-647 | 1-[4-(difluoromethyl)phenyl]-N-{2-[4-(methoxymethyl)-4-methylpiperidin-1-yl]phenyl}methanesulfonamide |

TABLE B-continued

| Compound No. | Compound Name |
|---|---|
| A-648 | 1-(2-fluoro-5-methylphenyl)-N-{2-[4-(methoxymethyl)-4-methylpiperidin-1-yl]phenyl}methanesulfonamide |
| A-649 | N-{2-[4-(methoxymethyl)-4-methylpiperidin-1-yl]phenyl}-1-phenylcyclopropane-1-sulfonamide |
| A-650 | 4-(2,2-difluorocyclopropyl)-N-{2-[4-(methoxymethyl)-4-methylpiperidin-1-yl]phenyl}benzene-1-sulfonamide |
| A-651 | 3-(2,2-difluorocyclopropyl)-N-{2-[4-(methoxymethyl)-4-methylpiperidin-1-yl]phenyl}benzene-1-sulfonamide |
| A-652 | N4-[3-chloro-2-(piperidin-1-yl)phenyl]-N1,N1-dimethylbenzene-1,4-disulfonamide |
| A-653 | N4-(2-{3,3-dimethyl-2-oxa-8-azaspiro[4.5]decan-8-yl}phenyl)-3-fluoro-N1,N1-dimethylbenzene-1,4-disulfonamide |
| A-654 | 2,2-dimethyl-N-(2-{3-oxa-9-azaspiro[5.5]undecan-9-yl}phenyl)-2,3-dihydro-1-benzofuran-5-sulfonamide |
| A-655 | N-{2-[4-(methoxymethyl)-4-methylpiperidin-1-yl]phenyl}-4-(2-methoxypropan-2-yl)benzene-1-sulfonamide |
| A-656 | N-(2-{3,3-dimethyl-2-oxa-8-azaspiro[4.5]decan-8-yl}phenyl)-4-(2-methoxypropan-2-yl)benzene-1-sulfonamide |
| A-657 | N-(2-{3,3-dimethyl-2-oxa-8-azaspiro[4.5]decan-8-yl}phenyl)-4-(2-methylpropanoyl)benzene-1-sulfonamide |
| A-658 | N-(2-{3,3-dimethyl-2-oxa-8-azaspiro[4.5]decan-8-yl}phenyl)-4-(propan-2-yl)benzene-1-sulfonamide |
| A-659 | N-(2-{3,3-dimethyl-2-oxa-8-azaspiro[4.5]decan-8-yl]phenyl)-2-methoxy-2,3-dihydro-1H-indene-5-sulfonamide |
| A-660 | N-(2-{3,3-dimethyl-2-oxa-8-azaspiro[4.5]decan-8-yl}phenyl)-3-fluoro-4-methanesulfonylbenzene-1-sulfonamide |
| A-661 | N-(2-{3,3-dimethyl-2-oxa-8-azaspiro[4.5]decan-8-yl}phenyl)-4-fluoro-3-methylbenzene-1-sulfonamide |
| A-662 | N-(2-{3,3-dimethyl-2-oxa-8-azaspiro[4.5]decan-8-yl}phenyl)-4-methylbenzene-1-sulfonamide |
| A-663 | N-(2-{3,3-dimethyl-2-oxa-8-azaspiro[4.5]decan-8-yl}phenyl)-1-(3,4-dimethylphenyl)methanesulfonamide |
| A-664 | N-(2-{3,3-dimethyl-2-oxa-8-azaspiro[4.5]decan-8-yl}phenyl)-1-(3-methylphenyl)methanesulfonamide |
| A-665 | N-(2-{3,3-dimethyl-2-oxa-8-azaspiro[4.5]decan-8-yl}phenyl)-3-methylbenzene-1-sulfonamide |
| A-666 | 1-cyclobutyl-N-(2-{3,3-dimethyl-2-oxa-8-azaspiro[4.5]decan-8-yl}phenyl)-1H-pyrazole-4-sulfonamide |
| A-667 | 4-(difluoromethoxy)-N-(2-{3,3-dimethyl-2-oxa-8-azaspiro[4.5]decan-8-yl}phenyl)-3-fluorobenzene-1-sulfonamide |
| A-668 | N-(2-{3,3-dimethyl-2-oxa-8-azaspiro[4.5]decan-8-yl}phenyl)-1-(3-fluorophenyl)methanesulfonamide |
| A-669 | 3-cyclopropyl-N-(2-{3,3-dimethyl-2-oxa-8-azaspiro[4.5]decan-8-yl}phenyl)benzene-1-sulfonamide |
| A-670 | N-(2-{3,3-dimethyl-2-oxa-8-azaspiro[4.5]decan-8-yl}phenyl)-3-(1,3-dioxolan-2-yl)benzene-1-sulfonamide |
| A-671 | 4-(difluoromethyl)-N-(2-{3,3-dimethyl-2-oxa-8-azaspiro[4.5]decan-8-yl}phenyl)benzene-1-sulfonamide |
| A-672 | 4-cyclopropyl-N-(2-{3,3-dimethyl-2-oxa-8-azaspiro[4.5]decan-8-yl}phenyl)benzene-1-sulfonamide |
| A-673 | N-(2-{3,3-dimethyl-2-oxa-8-azaspiro[4.5]decan-8-yl}phenyl)-4-(trifluoromethoxy)benzene-1-sulfonamide |
| A-674 | 5-cyclopropyl-N-(2-{3,3-dimethyl-2-oxa-8-azaspiro[4.5]decan-8-yl}phenyl)thiophene-2-sulfonamide |
| A-675 | N-(2-{3,3-dimethyl-2-oxa-8-azaspiro[4.5]decan-8-yl}phenyl)-2H-chromene-3-sulfonamide |
| A-676 | N-(2-{3,3-dimethyl-2-oxa-8-azaspiro[4.5]decan-8-yl}phenyl)-3,4-dihydronaphthalene-2-sulfonamide |
| A-677 | N-(2-{3,3-dimethyl-2-oxa-8-azaspiro[4.5]decan-8-yl}phenyl)-1-(3-fluoro-4-methylphenyl)methanesulfonamide |
| A-678 | 1-(3-chlorophenyl)-N-(2-{3,3-dimethyl-2-oxa-8-azaspiro[4.5]decan-8-yl}phenyl)methanesulfonamide |
| A-679 | N-(2-{3,3-dimethyl-2-oxa-8-azaspiro[4.5]decan-8-yl}phenyl)-1-(2-fluoro-5-methylphenyl)methanesulfonamide |
| A-680 | 3-[({2-[4-(methoxymethyl)-4-methylpiperidin-1-yl]phenyl}sulfamoyl)methyl]-N,N-dimethylbenzene-1-sulfonamide |
| A-681 | N4-{3-fluoro-2-[4-(methoxymethyl)-4-methylpiperidin-1-yl]phenyl}-N1,N1-dimethylbenzene-1,4-disulfonamide |
| A-682 | N-{2-[4-(methoxymethyl)-4-methylpiperidin-1-yl]phenyl}-1,1-dimethyl-1,3-dihydro-2-benzofuran-5-sulfonamide |
| A-683 | N-{2-[4-(methoxymethyl)-4-methylpiperidin-1-yl]phenyl}-3,3-dimethyl-1,3-dihydro-2-benzofuran-5-sulfonamide |
| A-684 | N,N-dimethyl-4-[2,2,2-trifluoro-1-({2-[4-(methoxymethyl)-4-methylpiperidin-1-yl]phenyl}amino)ethyl]benzene-1-sulfonamide |
| A-685 | N-{2-[4-(methoxymethyl)-4-methylpiperidin-1-yl]phenyl}spiro[1,3-benzodioxole-2,1'-cyclobutane]-6-sulfonamide |
| A-686 | N4-[2-[4-fluoro-4-(methoxymethyl)piperidin-1-yl]phenyl}-N1,N1-dimethylbenzene-1,4-disulfonamide |

TABLE B-continued

| Compound No. | Compound Name |
|---|---|
| A-687 | 3-(2,2-difluorocyclopropyl)-N-(2-{3,3-dimethyl-2-oxa-8-azaspiro[4.5]decan-8-yl}phenyl)benzene-1-sulfonamide |
| A-688 | N-(2-{3,3-dimethyl-2-oxa-8-azaspiro[4.5]decan-8-yl}phenyl)-1-(2-fluoro-4-methylphenyl)methanesulfonamide |
| A-689 | 1-(2,2-difluorocyclopropyl)-N-(2-{3,3-dimethyl-2-oxa-8-azaspiro[4.5]decan-8-yl}phenyl)-1H-pyrazole-3-sulfonamide |
| A-690 | 2-(difluoromethyl)-N-(2-{3,3-dimethyl-2-oxa-8-azaspiro[4.5]decan-8-yl}phenyl)-3,4-dihydro-2H-1-benzopyran-6-sulfonamide |
| A-691 | 4-bromo-N-(2-{3,3-dimethyl-2-oxa-8-azaspiro[4.5]decan-8-yl}phenyl)benzene-1-sulfonamide |
| A-692 | N-(2-{3,3-dimethyl-2-oxa-8-azaspiro[4.5]decan-8-yl}phenyl)-3-fluoro-4-methylbenzene-1-sulfonamide |
| A-693 | N-(2-{3,3-dimethyl-2-oxa-8-azaspiro[4.5]decan-8-yl}phenyl)-4-methanesulfonylbenzene-1-sulfonamide |
| A-694 | N4-{4-fluoro-2-[4-(methoxymethyl)-4-methylpiperidin-1-yl]phenyl}-N1,N1-dimethylbenzene-1,4-disulfonamide |
| A-695 | N4-{5-fluoro-2-[4-(methoxymethyl)-4-methylpiperidin-1-yl]phenyl}-N1,N1-dimethylbenzene-1,4-disulfonamide |
| A-696 | N1,N1-dimethyl-N4-(2-{4-[(trifluoromethoxy)methyl]piperidin-1-yl}phenyl)benzene-1,4-disulfonamide |
| A-697 | 4-methanesulfonyl-N-{2-[4-(methoxymethyl)-4-methylpiperidin-1-yl]phenyl}benzene-1-sulfonamide |
| A-698 | 4-((1-(2-(4-(methoxymethyl)-4-methylpiperidin-1-yl)phenyl)ethyl)sulfonyl)-N,N-dimethylbenzenesulfonamide, enantiomer 1 |
| A-699 | 4-((1-(2-(4-(methoxymethyl)-4-methylpiperidin-1-yl)phenyl)ethyl)sulfonyl)-N,N-dimethylbenzenesulfonamide, enantiomer 2 |
| A-700 | N-(2-{3,3-dimethyl-2-oxa-8-azaspiro[4.5]decan-8-yl}phenyl)-1,1-dimethyl-1,3-dihydro-2-benzofuran-5-sulfonamide |
| A-701 | N-{2-[4-(4-chloro-2-fluorophenyl)piperidin-1-yl]phenyl}-4-(2-methoxyethanesulfonyl)benzene-1-sulfonamide |
| A-702 | N-(2-{3,3-dimethyl-2-oxa-8-azaspiro[4.5]decan-8-yl}-3-fluorophenyl)-1-phenylmethanesulfonamide |
| A-703 | ethyl 2-(1-{2-[4-(dimethylsulfamoyl)benzenesulfonamido]phenyl}-4-fluoropiperidin-4-yl)acetate |
| A-704 | N-(2-{3,3-dimethyl-2-oxa-8-azaspiro[4.5]decan-8-yl}phenyl)-2,2-dimethyl-2H-1,3-benzodioxole-5-sulfonamide |
| A-705 | methyl 2-[4-({2-[4-(methoxymethyl)-4-methylpiperidin-1-yl]phenyl}sulfamoyl)phenyl]-2-methylpropanoate |
| A-706 | N-{2-[4-(methoxymethyl)-4-methylpiperidin-1-yl]phenyl}-4-(propan-2-yl)benzene-1-sulfonamide |
| A-707 | 2-methoxy-N-{2-[4-(methoxymethyl)-4-methylpiperidin-1-yl]phenyl}-2,3-dihydro-1H-indene-5-sulfonamide |
| A-708 | 5-cyclopropyl-N-{2-[4-(methoxymethyl)-4-methylpiperidin-1-yl]phenyl}thiophene-2-sulfonamide |
| A-709 | 1-(2-fluoro-4-methylphenyl)-N-{2-[4-(methoxymethyl)-4-methylpiperidin-1-yl]phenyl}methanesulfonamide |
| A-710 | methyl 2-{4-[(2-{3,3-dimethyl-2-oxa-8-azaspiro[4.5]decan-8-yl}phenyl)sulfamoyl]phenyl}-2-methylpropanoate |
| A-711 | N-(2-{3,3-dimethyl-2-oxa-8-azaspiro[4.5]decan-8-yl}phenyl)-1-(4-methylphenyl)methanesulfonamide |
| A-712 | 1-(3,4-dihydro-1H-2-benzopyran-7-yl)-N-(2-{3,3-dimethyl-2-oxa-8-azaspiro[4.5]decan-8-yl}phenyl)methanesulfonamide |
| A-713 | N-(2-{3,3-dimethyl-2-oxa-8-azaspiro[4.5]decan-8-yl}phenyl)-2,3-dihydro-1H-indene-5-sulfonamide |
| A-714 | N-(2-{3,3-dimethyl-2-oxa-8-azaspiro[4.5]decan-8-yl}phenyl)-1,3-dihydro-2-benzofuran-5-sulfonamide |
| A-715 | N-(2-{3,3-dimethyl-2-oxa-8-azaspiro[4.5]decan-8-yl}phenyl)-3,4-dihydro-1H-2-benzopyran-7-sulfonamide |
| A-716 | 1-[4-(difluoromethyl)phenyl]-N-(2-{3,3-dimethyl-2-oxa-8-azaspiro[4.5]decan-8-yl}phenyl)methanesulfonamide |
| A-717 | N-(2-{3,3-dimethyl-2-oxa-8-azaspiro[4.5]decan-8-yl}phenyl)-1-phenylcyclopropane-1-sulfonamide |
| A-718 | 4-(2,2-difluorocyclopropyl)-N-(2-{3,3-dimethyl-2-oxa-8-azaspiro[4.5]decan-8-yl}phenyl)benzene-1-sulfonamide |
| A-719 | N4-{2-[4-(ethoxymethyl)-4-methylpiperidin-1-yl]phenyl}-N1,N1-dimethylbenzene-1,4-disulfonamide |
| A-720 | N-(2-{3,3-dimethyl-2-oxa-8-azaspiro[4.5]decan-8-yl}phenyl)-2,2-dimethyl-2,3-dihydro-1-benzofuran-6-sulfonamide |
| A-721 | N-{2-[4-(methoxymethyl)-4-methylpiperidin-1-yl]phenyl}-2,2-dimethyl-2H-1,3-benzodioxole-5-sulfonamide |
| A-722 | N4-{2-[4-fluoro-4-(2-hydroxyethyl)piperidin-1-yl]phenyl}-N1,N1-dimethylbenzene-1,4-disulfonamide |
| A-723 | N-(2-{3,3-dimethyl-2-oxa-8-azaspiro[4.5]decan-8-yl}phenyl)spiro[1,3-benzodioxole-2,1'-cyclobutane]-6-sulfonamide |
| A-724 | N4-(3-cyano-2-{3,3-dimethyl-2-oxa-8-azaspiro[4.5]decan-8-yl}phenyl)-N1,N1-dimethylbenzene-1,4-disulfonamide |
| A-725 | N4-{2-[4-(2-hydroxypropan-2-yl)piperidin-1-yl]phenyl}-N1,N1-dimethylbenzene-1,4-disulfonamide |

TABLE B-continued

| Compound No. | Compound Name |
| --- | --- |
| A-726 | N-(2-{3,3-dimethyl-2-oxa-8-azaspiro[4.5]decan-8-yl}phenyl)-3,4-dihydro-1H-2-benzopyran-6-sulfonamide |
| A-727 | N-{2-[4-(methoxymethyl)-4-methylpiperidin-1-yl]phenyl}-3,4-dihydro-1H-2-benzopyran-6-sulfonamide |
| A-728 | N1-(2-{3,3-dimethyl-2-oxa-8-azaspiro[4.5]decan-8-yl}-5-fluorophenyl)-N1,N4,N4-trimethylbenzene-1,4-disulfonamide |
| A-729 | N1-(2-{3,3-dimethyl-2-oxa-8-azaspiro[4.5]decan-8-yl}-4-fluorophenyl)-N1,N4,N4-trimethylbenzene-1,4-disulfonamide |
| A-730 | N4-(2-{4-[(2,2-difluoroethoxy)methyl]piperidin-1-yl}phenyl)-N1,N1-dimethylbenzene-1,4-disulfonamide |
| A-731 | 3-fluoro-4-methanesulfonyl-N-{2-[4-(methoxymethyl)-4-methylpiperidin-1-yl]phenyl}benzene-1-sulfonamide |
| A-732 | N-{2-[4-(4-chloro-2-fluorophenyl)piperidin-1-yl]phenyl}-4-[3-(trifluoromethyl)-3H-diazirin-3-yl]benzene-1-sulfonamide |
| A-733 | 4-(2-{[2-(4-benzylpiperazin-1-yl)phenyl]amino}propan-2-yl)-N,N-dimethylbenzene-1-sulfonamide |
| A-734 | N4-{2-[3-(methoxymethyl)-3-methyl-8-azabicyclo[3.2.1]octan-8-yl]phenyl}-N1,N1-dimethylbenzene-1,4-disulfonamide |
| A-735 | N4-(2-{3,3-dimethyl-7-oxo-2-oxa-8-azaspiro[4.5]decan-8-yl}phenyl)-N1,N1-dimethylbenzene-1,4-disulfonamide |
| A-736 | 4-(azetidine-1-sulfonyl)-N-{2-[4-(methoxymethyl)-4-methylpiperidin-1-yl]phenyl}benzene-1-sulfonamide |
| A-737 | 4-[1-(2-{3,3-dimethyl-2-oxa-8-azaspiro[4.5]decan-8-yl}-4-fluorophenyl)ethanesulfonyl]-N,N-dimethylbenzene-1-sulfonamide |
| A-738 | N-{2-[4-(methoxymethyl)-4-methylpiperidin-1-yl]phenyl}-2,2-dimethyl-2,3-dihydro-1-benzofuran-6-sulfonamide |
| A-739 | N4-(2-{4-[(1,1-difluoroethoxy)methyl]piperidin-1-yl}phenyl)-N1,N1-dimethylbenzene-1,4-disulfonamide |
| A-740 | N-{2-[4-(methoxymethyl)-4-methylpiperidin-1-yl]phenyl}-4-[3-(trifluoromethyl)-3H-diazirin-3-yl]benzene-1-sulfonamide |
| A-741 | N4-{2-[4-(1-methoxyethyl)-4-methylpiperidin-1-yl]phenyl}-N1,N1-dimethylbenzene-1,4-disulfonamide |
| A-742 | N-(2-{3,3-dimethyl-2-oxa-8-azaspiro[4.5]decan-8-yl}phenyl)-3,3-dimethyl-2,3-dihydro-1-benzofuran-5-sulfonamide |
| A-743 | N-(2-{3,3-dimethyl-2-oxa-8-azaspiro[4.5]decan-8-yl}phenyl)-2-phenylethane-1-sulfonamide |
| A-744 | 1-(3-methoxymethanesulfonylphenyl)-N-{2-[4-(methoxymethyl)-4-methylpiperidin-1-yl]phenyl}methanesulfonamide |
| A-745 | N4-{2-[4-(methoxymethyl)-2,4-dimethylpiperidin-1-yl]phenyl}-N1,N1-dimethylbenzene-1,4-disulfonamide |
| A-746 | N4-{4-[4-(methoxymethyl)-4-methylpiperidin-1-yl]-1-methyl-1H-indazol-5-yl}-N1,N1-dimethylbenzene-1,4-disulfonamide |
| A-747 | 1-(4-methoxymethanesulfonylphenyl)-N-{2-[4-(methoxymethyl)-4-methylpiperidin-1-yl]phenyl}methanesulfonamide |
| A-748 | N4-[2-(4-{1-[(2R,6S)-2,6-dimethylmorpholin-4-yl]ethyl}piperidin-1-yl)-3-fluorophenyl]-N1,N1-dimethylbenzene-1,4-disulfonamide |
| A-749 | N-[3-chloro-2-(piperidin-1-yl)phenyl]-4-[3-(trifluoromethyl)-3H-diazirin-3-yl]benzene-1-sulfonamide |
| A-750 | 4-{1-[2-(4-{[(2R,6S)-2,6-dimethylmorpholin-4-yl]methyl}piperidin-1-yl)-3-fluorophenyl]ethanesulfonyl}-N,N-dimethylbenzene-1-sulfonamide |
| A-751 | 3,3-dimethyl-8-[2-(1-phenylmethanesulfonylethyl)phenyl]-2-oxa-8-azaspiro[4.5]decane |
| A-752 | 4-[1-(2-{3,3-dimethyl-2-oxa-8-azaspiro[4.5]decan-8-yl}-3-fluorophenyl)ethanesulfonyl]-N,N-dimethylbenzene-1-sulfonamide |
| A-753 | N4-[3-(difluoromethyl)-2-{3,3-dimethyl-2-oxa-8-azaspiro[4.5]decan-8-yl}phenyl]-N1,N1-dimethylbenzene-1,4-disulfonamide |
| A-754 | N4-(2-{4-[(2R,6S)-2,6-dimethylmorpholine-4-carbonyl]piperidin-1-yl}phenyl)-N1,N1-dimethylbenzene-1,4-disulfonamide |
| A-755 | N4-[2-(4-{[(2R,6S)-2,6-dimethylmorpholin-4-yl]methyl}piperidin-1-yl)-3-fluorophenyl]-N1,N1-dimethylbenzene-1,4-disulfonamide |
| A-756 | N-[2-(4-{[(2R,6S)-2,6-dimethylmorpholin-4-yl]methyl}piperidin-1-yl)phenyl]-2,4-dimethyl-1,3-thiazole-5-sulfonamide |
| A-757 | N1,N1-dimethyl-N4-[5-methyl-2-(morpholin-4-yl)phenyl]benzene-1,4-disulfonamide |
| A-758 | 4-difluoromethanesulfonyl-N-[2-(4-{[(2R,6S)-2,6-dimethylmorpholin-4-yl]methyl}piperidin-1-yl)-3-fluorophenyl]benzene-1-sulfonamide |
| A-759 | N-[2-(4-{[(2R,6S)-2,6-dimethylmorpholin-4-yl]methyl}piperidin-1-yl)-3-fluorophenyl]-2,3-dihydro-1H-indene-5-sulfonamide |
| A-760 | N-[2-(morpholin-4-yl)phenyl]-2,3-dihydro-1H-indene-5-sulfonamide |
| A-761 | N1,N1-dimethyl-N4-{2-[4-(morpholine-4-carbonyl)piperidin-1-yl]phenyl}benzene-1,4-disulfonamide |
| A-762 | N4-{3-fluoro-2-[4-({8-oxa-3-azabicyclo[3.2.1]octan-3-yl}methyl)piperidin-1-yl]phenyl}-N1,N1-dimethylbenzene-1,4-disulfonamide |
| A-763 | rac-N4-[2-(4-{[(3R,5R)-3,5-dimethylmorpholin-4-yl]methyl}piperidin-1-yl)-3-fluorophenyl]-N1,N1-dimethylbenzene-1,4-disulfonamide |
| A-764 | N4-(3-fluoro-2-{3-methyl-2-oxo-1-oxa-3,8-diazaspiro[4.5]decan-8-yl}phenyl)-N1,N1-dimethylbenzene-1,4-disulfonamide |

TABLE B-continued

| Compound No. | Compound Name |
|---|---|
| A-765 | 4-(azetidine-1-sulfonyl)-N-[2-(4-{[(2R,6S)-2,6-dimethylmorpholin-4-yl]methyl}piperidin-1-yl)-3-fluorophenyl]benzene-1-sulfonamide |
| A-766 | 4-(difluoromethyl)-N-[2-(4-{[(2R,6S)-2,6-dimethylmorpholin-4-yl]methyl}piperidin-1-yl)-3-fluorophenyl]benzene-1-sulfonamide |
| A-767 | N-[2-(4-{[(2R,6S)-2,6-dimethylmorpholin-4-yl]methyl}piperidin-1-yl)-3-fluorophenyl]-1-phenylcyclopropane-1-sulfonamide |
| A-768 | 2-cyclopropyl-N-[2-(4-{[(2R,6S)-2,6-dimethylmorpholin-4-yl]methyl}piperidin-1-yl)phenyl]-4-methyl-1,3-thiazole-5-sulfonamide |
| A-769 | 4-{[2-(4-{[(2R,6S)-2,6-dimethylmorpholin-4-yl]methyl}piperidin-1-yl)-3-fluorophenyl]sulfamoyl}-N,N-dimethylbenzene-1-sulfonoimidamide |
| A-770 | N1,N1-dimethyl-N4-[2-(morpholin-4-yl)phenyl]benzene-1,4-disulfonamide |
| A-771 | N-[2-(4-{[(2R,6S)-2,6-dimethylmorpholin-4-yl]methyl}piperidin-1-yl)-3-fluorophenyl]-4-methylbenzene-1-sulfonamide |
| A-772 | 1-(cyclopropylmethyl)-N-[2-(4-{[(2R,6S)-2,6-dimethylmorpholin-4-yl]methyl}piperidin-1-yl)phenyl]-1H-pyrazole-4-sulfonamide |
| A-773 | N4-(2-{4-[(3,3-difluoropiperidin-1-yl)methyl]piperidin-1-yl}-3-fluorophenyl)-N1,N1-dimethylbenzene-1,4-disulfonamide |
| A-774 | N4-(2-{4-[(3,3-difluoropyrrolidin-1-yl)methyl]piperidin-1-yl}-3-fluorophenyl)-N1,N1-dimethylbenzene-1,4-disulfonamide |
| A-775 | 4-[1-(2-{3,3-dimethyl-2-oxa-8-azaspiro[4.5]decan-8-yl}pyridin-3-yl)ethanesulfonyl]-N,N-dimethylbenzene-1-sulfonamide |
| A-776 | N-[2-(4-{[(2R,6S)-2,6-dimethylmorpholin-4-yl]methyl}piperidin-1-yl)-3-fluorophenyl]-4-methanesulfonylbenzene-1-sulfonamide |
| A-777 | N4-{2-[4-(methoxymethyl)-4-(trifluoromethyl)piperidin-1-yl]phenyl}-N1,N1-dimethylbenzene-1,4-disulfonamide |
| A-778 | N4-{3-fluoro-2-[4-({3-oxa-6-azabicyclo[3.1.1]heptan-6-yl}methyl)piperidin-1-yl]phenyl}-N1,N1-dimethylbenzene-1,4-disulfonamide |
| A-779 | 4-(1-cyclopropylethyl)-N-[2-(4-{[(2R,6S)-2,6-dimethylmorpholin-4-yl]methyl}piperidin-1-yl)phenyl]benzene-1-sulfonamide |
| A-780 | N-[2-(4-{[(2R,6S)-2,6-dimethylmorpholin-4-yl]methyl}piperidin-1-yl)-3-fluorophenyl]-2,2-dimethyl-2,3-dihydro-1-benzofuran-6-sulfonamide |
| A-781 | N4-[2-(4-{[(2R,6S)-2,6-dimethylmorpholin-4-yl]methyl}-4-methylpiperidin-1-yl)-3-fluorophenyl]-N1,N1-dimethylbenzene-1,4-disulfonamide |
| A-782 | 4-[(1R)-1-[2-(4-{[(2R,6S)-2,6-dimethylmorpholin-4-yl]methyl}piperidin-1-yl)-3-fluorophenyl]ethanesulfonyl]-N,N-dimethylbenzene-1-sulfonamide |
| A-783 | 4-[(1S)-1-[2-(4-{[(2R,6S)-2,6-dimethylmorpholin-4-yl]methyl}piperidin-1-yl)-3-fluorophenyl]ethanesulfonyl]-N,N-dimethylbenzene-1-sulfonamide |
| A-784 | N1,N1-dimethyl-N4-(2-{4-methyl-4-[(trifluoromethoxy)methyl]piperidin-1-yl}phenyl)benzene-1,4-disulfonamide |
| A-785 | N4-[3-fluoro-2-(4-{[(1S,4S)-2-oxa-5-azabicyclo[2.2.1]heptan-5-yl]methyl}piperidin-1-yl)phenyl]-N1,N1-dimethylbenzene-1,4-disulfonamide |
| A-786 | N4-[2-(4-{[(2R,6S)-2,6-dimethylmorpholin-4-yl]methyl}-4-methoxypiperidin-1-yl)-3-fluorophenyl]-N1,N1-dimethylbenzene-1,4-disulfonamide |
| A-787 | N4-[3-fluoro-2-(4-{[(1R,4R)-2-oxa-5-azabicyclo[2.2.1]heptan-5-yl]methyl}piperidin-1-yl)phenyl]-N1,N1-dimethylbenzene-1,4-disulfonamide |
| A-788 | N4-[2-(4-{[(2R,6S)-2,6-dimethylmorpholin-4-yl]methyl}piperidin-1-yl)-3-(trifluoromethyl)phenyl]-N1,N1-dimethylbenzene-1,4-disulfonamide |
| A-789 | N4-(2-{4-[(4,4-difluoropiperidin-1-yl)methyl]piperidin-1-yl}-3-fluorophenyl)-N1,N1-dimethylbenzene-1,4-disulfonamide |
| A-790 | N4-{3-fluoro-2-[4-({3-oxa-8-azabicyclo[3.2.1]octan-8-yl}methyl)piperidin-1-yl]phenyl}-N1,N1-dimethylbenzene-1,4-disulfonamide |
| A-791 | N4-{3-fluoro-2-[4-({6-oxa-3-azabicyclo[3.1.1]heptan-3-yl}methyl)piperidin-1-yl]phenyl}-N1,N1-dimethylbenzene-1,4-disulfonamide |
| A-792 | N4-(3-fluoro-2-{1-oxo-2,8-diazaspiro[4.5]decan-8-yl}phenyl)-N1,N1-dimethylbenzene-1,4-disulfonamide |
| A-793 | N1,N1-dimethyl-N4-[7-(piperidin-1-yl)pyrazolo[1,5-a]pyridin-6-yl]benzene-1,4-disulfonamide |
| A-794 | N4-[2-(4-{[(2R,6S)-2,6-dimethylmorpholin-4-yl]methyl}-4-fluoropiperidin-1-yl)-3-fluorophenyl]-N1,N1-dimethylbenzene-1,4-disulfonamide |
| A-795 | N-(1-{2-[4-(dimethylsulfamoyl)benzenesulfonamido]-6-fluorophenyl}-4-methylpiperidin-4-yl)acetamide |
| A-796 | N4-(3-fluoro-2-{2-oxo-1,8-diazaspiro[4.5]decan-8-yl}phenyl)-N1,N1-dimethylbenzene-1,4-disulfonamide |
| A-797 | N1,N1-dimethyl-N4-(2-{4-[(1,1,2-trifluoroethoxy)methyl]piperidin-1-yl}phenyl)benzene-1,4-disulfonamide |
| A-798 | N4-(2-{4-fluoro-4-[(trifluoromethoxy)methyl]piperidin-1-yl}phenyl)-N1,N1-dimethylbenzene-1,4-disulfonamide |
| A-799 | N1,N1-dimethyl-N4-(2-((5R,7R)-3,3,7-trimethyl-2-oxa-8-azaspiro[4.5]decan-8-yl)phenyl)benzene-1,4-disulfonamide, cis, racemic |
| A-800 | (2R,6S)-4-[(1-{2-[1-(4-difluoromethanesulfonylbenzenesulfonyl)ethyl]-6-fluorophenyl}piperidin-4-yl)methyl]-2,6-dimethylmorpholine |

TABLE B-continued

| Compound No. | Compound Name |
|---|---|
| A-801 | 4-[1-(2-{4-[(4,4-difluoropiperidin-1-yl)methyl]piperidin-1-yl}-3-fluorophenyl)ethanesulfonyl]-N,N-dimethylbenzene-1-sulfonamide |
| A-802 | 4-[1-(2-{4-[(3,3-difluoropyrrolidin-1-yl)methyl]piperidin-1-yl}-3-fluorophenyl)ethanesulfonyl]-N,N-dimethylbenzene-1-sulfonamide |
| A-803 | 4-((1-(2-(4-((4,4-difluoropiperidin-1-yl)methyl)piperidin-1-yl)-3-fluorophenyl)ethyl)sulfonyl)-N,N-dimethylbenzenesulfonamide; enantiomer 1 |
| A-804 | 4-((1-(2-(4-((4,4-difluoropiperidin-1-yl)methyl)piperidin-1-yl)-3-fluorophenyl)ethyl)sulfonyl)-N,N-dimethylbenzenesulfonamide; enantiomer 2 |
| A-805 | 4-((1-(2-(4-((3,3-difluoropyrrolidin-1-yl)methyl)piperidin-1-yl)-3-fluorophenyl)ethyl)sulfonyl)-N,N-dimethylbenzenesulfonamide; enantiomer 1 |
| A-806 | 4-((1-(2-(4-((3,3-difluoropyrrolidin-1-yl)methyl)piperidin-1-yl)-3-fluorophenyl)ethyl)sulfonyl)-N,N-dimethylbenzenesulfonamide; enantiomer 2 |
| A-807 | 4-((1-(2-(1-((4-((difluoromethyl)sulfonyl)phenyl)sulfonyl)ethyl)-6-fluorophenyl)piperidin-4-yl)methyl)-2,6-dimethylmorpholine; enantiomer 1 |
| A-808 | 4-((1-(2-(1-((4-((difluoromethyl)sulfonyl)phenyl)sulfonyl)ethyl)-6-fluorophenyl)piperidin-4-yl)methyl)-2,6-dimethylmorpholine; enantiomer 2 |
| A-809 | 3-[4-(dimethylsulfamoyl)benzenesulfonamido]-N-methyl-2-(piperidin-1-yl)benzamide |
| A-810 | 4-{[2-(4-{[(2R,6S)-2,6-dimethylmorpholin-4-yl]methyl}piperidin-1-yl)-3-fluorophenyl]sulfamoyl}-N,N-dimethylbenzene-1-sulfonoimidamide; enantiomer 1 |
| A-811 | 4-{[2-(4-{[(2R,6S)-2,6-dimethylmorpholin-4-yl]methyl}piperidin-1-yl)-3-fluorophenyl]sulfamoyl}-N,N-dimethylbenzene-1-sulfonoimidamide; enantiomer 2 |
| A-812 | N4-[4-ethynyl-2-(piperidin-1-yl)phenyl]-N1,N1-dimethylbenzene-1,4-disulfonamide |
| A-813 | N4-{5-[4-(methoxymethyl)-4-methylpiperidin-1-yl]imidazo[1,2-a]pyridin-6-yl}-N1,N1-dimethylbenzene-1,4-disulfonamide |
| A-814 | 4-(cyclopropyldifluoromethyl)-N-[2-(4-{[(2R,6S)-2,6-dimethylmorpholin-4-yl]methyl}piperidin-1-yl)-3-fluorophenyl]benzene-1-sulfonamide |
| A-815 | N4-[2-chloro-5-methyl-3-(morpholin-4-yl)phenyl]-N1,N1-dimethylbenzene-1,4-disulfonamide |
| A-816 | N4-(2-{1,7-diazaspiro[3.5]nonan-7-yl}-3-fluorophenyl)-N1,N1-dimethylbenzene-1,4-disulfonamide |
| A-817 | N4-[2-(4-{[(2R,6S)-2,6-dimethyloxan-4-yl]oxy}piperidin-1-yl)-3-fluorophenyl]-N1,N1-dimethylbenzene-1,4-disulfonamide |
| A-818 | N4-[2-(4-{[(2R,6R)-2,6-dimethylmorpholin-4-yl]methyl}piperidin-1-yl)-3-fluorophenyl]-N1,N1-dimethylbenzene-1,4-disulfonamide |
| A-819 | 2-(2,3-dihydro-1H-indene-5-sulfonyl)-4-(morpholin-4-yl)-2,3-dihydro-1H-isoindole |
| A-820 | 2-(4-methylbenzenesulfonyl)-4-(morpholin-4-yl)-2,3-dihydro-1H-isoindole |
| A-821 | N4-{2-[4-amino-4-(trifluoromethyl)piperidin-1-yl]-3-fluorophenyl}-N1,N1-dimethylbenzene-1,4-disulfonamide |
| A-822 | N4-{7-[4-(methoxymethyl)-4-methylpiperidin-1-yl]pyrazolo[1,5-a]pyridin-6-yl}-N1,N1-dimethylbenzene-1,4-disulfonamide |
| A-823 | N-[2-chloro-5-methyl-3-(morpholin-4-yl)phenyl]-2,3-dihydro-1H-indene-5-sulfonamide |
| A-824 | N4-[2-(4-{[(3R,5S)-3,5-dimethylmorpholin-4-yl]methyl}piperidin-1-yl)-3-fluorophenyl]-N1,N1-dimethylbenzene-1,4-disulfonamide |
| A-825 | methyl N-(1-{2-[4-(dimethylsulfamoyl)benzenesulfonamido]-6-fluorophenyl}-4-methylpiperidin-4-yl)carbamate |
| A-826 | N4-[2-(4-{[(2S,6S)-2,6-dimethylmorpholin-4-yl]methyl}piperidin-1-yl)-3-fluorophenyl]-N1,N1-dimethylbenzene-1,4-disulfonamide |
| A-827 | N-{3-[4-(dimethylsulfamoyl)benzenesulfonamido]-2-(piperidin-1-yl)phenyl}acetamide |
| A-828 | (2S,6R)-4-((1-(2-(1-((2,3-dihydro-1H-inden-5-yl)sulfonyl)ethyl)-6-fluorophenyl)piperidin-4-yl)methyl)-2,6-dimethylmorpholine; enantiomer 1 |
| A-829 | N4-{2-[8-(methoxymethyl)-8-methyl-3-azabicyclo[3.2.1]octan-3-yl]phenyl}-N1,N1-dimethylbenzene-1,4-disulfonamide |
| A-830 | N4-{2-[4-(difluoromethyl)-4-methylpiperidin-1-yl]-3-fluorophenyl}-N1,N1-dimethylbenzene-1,4-disulfonamide |
| A-831 | N4-[3-(difluoromethyl)-2-(4-{[(2R,6S)-2,6-dimethylmorpholin-4-yl]methyl}piperidin-1-yl)phenyl]-N1,N1-dimethylbenzene-1,4-disulfonamide |
| A-832 | 4-((1-(2-(4-((3-oxa-8-azabicyclo[3.2.1]octan-8-yl)methyl)piperidin-1-yl)-3-fluorophenyl)ethyl)sulfonyl)-N,N-dimethylbenzenesulfonamide; enantiomer 1 |
| A-833 | N-(2-(4-((3,5-dimethylmorpholino)methyl)piperidin-1-yl)-3-fluorophenyl)-4-(N,N-dimethylsulfamidimidoyl)benzenesulfonamide; diastereomer 1 |
| A-834 | N-(2-(4-((3,5-dimethylmorpholino)methyl)piperidin-1-yl)-3-fluorophenyl)-4-(N,N-dimethylsulfamidimidoyl)benzenesulfonamide; diastereomer 2 |
| A-835 | N-(2-(4-((3,5-dimethylmorpholino)methyl)piperidin-1-yl)-3-fluorophenyl)-4-(N,N-dimethylsulfamidimidoyl)benzenesulfonamide; diastereomer 3 |
| A-836 | N-(2-(4-((3,5-dimethylmorpholino)methyl)piperidin-1-yl)-3-fluorophenyl)-4-(N,N-dimethylsulfamidimidoyl)benzenesulfonamide; diastereomer 4 |
| A-837 | 4-{1-[3-fluoro-2-(4-{[(1R,5S)-6-oxa-3-azabicyclo[3.1.1]heptan-3-yl]methyl}piperidin-1-yl)phenyl]ethanesulfonyl}-N,N-dimethylbenzene-1-sulfonamide |
| A-838 | N-[2-(4-{[(3S,5S)-3,5-dimethylmorpholin-4-yl]methyl}piperidin-1-yl)-3-fluorophenyl]-4-methanesulfonylbenzene-1-sulfonamide |

TABLE B-continued

| Compound No. | Compound Name |
|---|---|
| A-839 | 4-(1-{3-fluoro-2-[4-({3-oxa-8-azabicyclo[3.2.1]octan-8-yl}methyl)piperidin-1-yl]phenyl}ethanesulfonyl)-N,N-dimethylbenzene-1-sulfonamide |
| A-840 | 4-{[2-(4-{[(3S,5S)-3,5-dimethylmorpholin-4-yl]methyl}piperidin-1-yl)-3-fluorophenyl]sulfamoyl}-N,N-dimethylbenzene-1-sulfonoimidamide |
| A-841 | N-(2-(4-(((2R,6S)-2,6-dimethylmorpholino)methyl)piperidin-1-yl)-3-fluorophenyl)-4-(S-methylsulfonimidoyl)benzenesulfonamide; formic acid |
| A-842 | 4-{1-[3-cyano-2-(4-{[(2R,6S)-2,6-dimethylmorpholin-4-yl]methyl}piperidin-1-yl)phenyl]ethanesulfonyl}-N,N-dimethylbenzene-1-sulfonamide |
| A-843 | N1-(2-(4-((2,6-dimethylmorpholino)methyl)piperidin-1-yl)-3-fluorophenyl)-N4,N4-dimethylbenzene-1,4-disulfonamide, trans |
| A-844 | 4-({3-fluoro-2-[4-({8-oxa-3-azabicyclo[3.2.1]octan-3-yl}methyl)piperidin-1-yl]phenyl}sulfamoyl)-N,N-dimethylbenzene-1-sulfonoimidamide |
| A-845 | 4-[1-[3-cyano-2-(4-{[(2R,6S)-2,6-dimethylmorpholin-4-yl]methyl}piperidin-1-yl)phenyl]ethanesulfonyl]-N,N-dimethylbenzene-1-sulfonamide; enantiomer 2 |
| A-846 | N-(2-(4-(((2R,6S)-2,6-dimethylmorpholino)methyl)piperidin-1-yl)-3-fluorophenyl)-4-(S-methylsulfonimidoyl)benzenesulfonamide; enantiomer 1 |
| A-847 | N-(2-(4-(((2R,6S)-2,6-dimethylmorpholino)methyl)piperidin-1-yl)-3-fluorophenyl)-4-(S-methylsulfonimidoyl)benzenesulfonamide; enantiomer 2 |
| A-848 | 4-[1-[3-fluoro-2-(4-{[(1R,5S)-6-oxa-3-azabicyclo[3.1.1]heptan-3-yl]methyl}piperidin-1-yl)phenyl]ethanesulfonyl]-N,N-dimethylbenzene-1-sulfonamide; enantiomer 1 |
| A-849 | 4-[1-[3-fluoro-2-(4-{[(1R,5S)-6-oxa-3-azabicyclo[3.1.1]heptan-3-yl]methyl}piperidin-1-yl)phenyl]ethanesulfonyl]-N,N-dimethylbenzene-1-sulfonamide; enantiomer 2 |
| A-850 | 4-{1-[3-(4-{[(2R,6S)-2,6-dimethylmorpholin-4-yl]methyl}piperidin-1-yl)pyridin-4-yl]ethanesulfonyl}-N,N-dimethylbenzene-1-sulfonamide |
| A-851 | N4-{3-fluoro-2-[8-(2,2,2-trifluoroethyl)-3,8-diazabicyclo[3.2.1]octan-3-yl]phenyl}-N1,N1-dimethylbenzene-1,4-disulfonamide |
| A-852 | N-(2-(4-((8-oxa-3-azabicyclo[3.2.1]octan-3-yl)methyl)piperidin-1-yl)-3-fluorophenyl)-4-(N,N-dimethylsulfamidimidoyl)benzenesulfonamide; enantiomer 1 |
| A-853 | N-(2-(4-((8-oxa-3-azabicyclo[3.2.1]octan-3-yl)methyl)piperidin-1-yl)-3-fluorophenyl)-4-(N,N-dimethylsulfamidimidoyl)benzenesulfonamide; enantiomer 2 |
| A-854 | 4-((-1-(3-cyano-2-(4-(((2S,6R)-2,6-dimethylmorpholino)methyl)piperidin-1-yl)phenyl)ethyl)sulfonyl)-N,N-dimethylbenzenesulfonamide; enantiomer 1 |
| A-855 | 4-((1-(2-(4-((3-oxa-8-azabicyclo[3.2.1]octan-8-yl)methyl)piperidin-1-yl)-3-fluorophenyl)ethyl)sulfonyl)-N,N-dimethylbenzenesulfonamide; enantiomer 2 |
| A-856 | N4-[5-fluoro-4-(piperidin-1-yl)pyridin-3-yl]-N1,N1-dimethylbenzene-1,4-disulfonamide |
| A-857 | 4-[(3-fluoro-2-{4-[1-(morpholin-4-yl)propyl]piperidin-1-yl}phenyl)sulfamoyl]-N,N-dimethylbenzene-1-sulfonoimidamide |
| A-858 | 4-[(3-fluoro-2-{4-[1-(morpholin-4-yl)cyclopropyl]piperidin-1-yl}phenyl)sulfamoyl]-N,N-dimethylbenzene-1-sulfonoimidamide |
| A-859 | 4-{1-[2-(4-{[(2R,6R)-2,6-dimethylmorpholin-4-yl]methyl}piperidin-1-yl)-3-fluorophenyl]ethanesulfonyl}-N,N-dimethylbenzene-1-sulfonamide |
| A-860 | 4-(1-{3-fluoro-2-[4-({3-oxa-6-azabicyclo[3.1.1]heptan-6-yl}methyl)piperidin-1-yl]phenyl}ethanesulfonyl)-N,N-dimethylbenzene-1-sulfonamide |
| A-861 | N4-{2-[4-(1,1-difluoro-2-methoxyethyl)piperidin-1-yl]-3-fluorophenyl}-N1,N1-dimethylbenzene-1,4-disulfonamide |
| A-862 | N4-[2-(4-{[(2S,5S)-2,5-dimethylmorpholin-4-yl]methyl}piperidin-1-yl)-3-fluorophenyl]-N1,N1-dimethylbenzene-1,4-disulfonamide |
| A-863 | N4-[3-cyclopropyl-2-(4-{[(2R,6S)-2,6-dimethylmorpholin-4-yl]methyl}piperidin-1-yl)phenyl]-N1,N1-dimethylbenzene-1,4-disulfonamide |
| A-864 | N4-[3-bromo-2-(4-{[(2R,6S)-2,6-dimethylmorpholin-4-yl]methyl}piperidin-1-yl)phenyl]-N1,N1-dimethylbenzene-1,4-disulfonamide |
| A-865 | N4-[2-(4-{[(2R,5S)-2,5-dimethylmorpholin-4-yl]methyl}piperidin-1-yl)-3-fluorophenyl]-N1,N1-dimethylbenzene-1,4-disulfonamide |
| A-866 | 4-difluoromethanesulfonyl-N-(2-{4-[(3,5-dimethylmorpholin-4-yl)methyl]piperidin-1-yl}-3-fluorophenyl)benzene-1-sulfonamide |
| A-867 | 4-[(2-{4-[(3,3-dimethylmorpholin-4-yl)methyl]piperidin-1-yl}-3-fluorophenyl)sulfamoyl]-N,N-dimethylbenzene-1-sulfonoimidamide; formic acid |
| A-868 | N4-(2-{4-[(2R,6S)-2,6-dimethylmorpholin-4-yl]piperidin-1-yl}-3-fluorophenyl)-N1,N1-dimethylbenzene-1,4-disulfonamide |
| A-869 | rel-4-[(1R)-1-{3-fluoro-2-[4-({3-oxa-6-azabicyclo[3.1.1]heptan-6-yl}methyl)piperidin-1-yl]phenyl}ethanesulfonyl]-N,N-dimethylbenzene-1-sulfonamide; formic acid |
| A-870 | 4-((1-(2-(4-((3-oxa-6-azabicyclo[3.1.1]heptan-6-yl)methyl)piperidin-1-yl)-3-fluorophenyl)ethyl)sulfonyl)-N,N-dimethylbenzenesulfonamideformate; enantiomer 2 |

TABLE B-continued

| Compound No. | Compound Name |
|---|---|
| A-871 | N-(2-(4-(1-((2S,6R)-2,6-dimethylmorpholino)ethyl)piperidin-1-yl)-3-fluorophenyl)-4-(N,N-dimethylsulfamidimidoyl)benzenesulfonamide; isomer 1 |
| A-871A | N-(2-(4-(1-((2S,6R)-2,6-dimethylmorpholino)ethyl)piperidin-1-yl)-3-fluorophenyl)-4-(N,N-dimethylsulfamidimidoyl)benzenesulfonamide; diastereomer 1 |
| A-871B | N-(2-(4-(1-((2S,6R)-2,6-dimethylmorpholino)ethyl)piperidin-1-yl)-3-fluorophenyl)-4-(N,N-dimethylsulfamidimidoyl)benzenesulfonamide; diastereomer 2 |
| A-872 | N-(2-(4-(1-((2S,6R)-2,6-dimethylmorpholino)ethyl)piperidin-1-yl)-3-fluorophenyl)-4-(N,N-dimethylsulfamidimidoyl)benzenesulfonamide; isomer 2 |
| A-872A | N-(2-(4-(1-((2S,6R)-2,6-dimethylmorpholino)ethyl)piperidin-1-yl)-3-fluorophenyl)-4-(N,N-dimethylsulfamidimidoyl)benzenesulfonamide; diastereomer 3 |
| A-872B | N-(2-(4-(1-((2S,6R)-2,6-dimethylmorpholino)ethyl)piperidin-1-yl)-3-fluorophenyl)-4-(N,N-dimethylsulfamidimidoyl)benzenesulfonamide; diastereomer 4 |
| A-873 | N1-(2-(3-((3,5-dimethylmorpholino)methyl)azetidin-1-yl)-3-fluorophenyl)-N4,N4-dimethylbenzene-1,4-disulfonamide |
| A-874 | N4-[3-fluoro-2-(4-{2-oxa-7-azaspiro[4.4]nonan-7-yl}piperidin-1-yl)phenyl]-N1,N1-dimethylbenzene-1,4-disulfonamide |
| A-875 | N-{3-fluoro-2-[4-({3-oxa-6-azabicyclo[3.1.1]heptan-6-yl}methyl)piperidin-1-yl]phenyl}-2,2-dimethyl-2,3-dihydro-1-benzofuran-5-sulfonamide |
| A-876 | N-{3-fluoro-2-[4-({3-oxa-6-azabicyclo[3.1.1]heptan-6-yl}methyl)piperidin-1-yl]phenyl}-2,3-dihydro-1H-indene-5-sulfonamide |
| A-877 | N,N-dimethyl-4-[(2-{4-[(1,1,2-trifluoroethoxy)methyl]piperidin-1-yl}phenyl)sulfamoyl]benzene-1-sulfonoimidamide |
| A-878 | N4-[3-cyano-2-(4-{[(2R,6S)-2,6-dimethylmorpholin-4-yl]methyl}piperidin-1-yl)phenyl]-N1,N1-dimethylbenzene-1,4-disulfonamide |
| A-879 | 4-{1-[2-(4-{[(2R,6S)-2,6-dimethylmorpholin-4-yl]methyl}piperidin-1-yl)pyridin-3-yl]ethanesulfonyl}-N,N-dimethylbenzene-1-sulfonamide |
| A-880 | N-{3-fluoro-2-[4-({3-oxa-8-azabicyclo[3.2.1]octan-8-yl}methyl)piperidin-1-yl]phenyl}-2,2-dimethyl-2,3-dihydro-1-benzofuran-5-sulfonamide |
| A-881 | N-{3-fluoro-2-[4-({3-oxa-8-azabicyclo[3.2.1]octan-8-yl}methyl)piperidin-1-yl]phenyl}-4-methylbenzene-1-sulfonamide |
| A-882 | N-{3-fluoro-2-[4-({3-oxa-8-azabicyclo[3.2.1]octan-8-yl}methyl)piperidin-1-yl]phenyl}-2,3-dihydro-1H-indene-5-sulfonamide |
| A-883 | N4-{2-[4-({6,6-difluoro-3-azabicyclo[3.1.0]hexan-3-yl}methyl)piperidin-1-yl]-3-fluorophenyl}-N1,N1-dimethylbenzene-1,4-disulfonamide |
| A-884 | 4-(((R)-1-(2-(4,4-difluoropiperidin-1-yl)-3-fluorophenyl)ethyl)sulfonyl)-N,N-dimethylbenzenesulfonimidamide |
| A-885 | 4-[1-[2-(4-{[2,6-dimethylmorpholin-4-yl]methyl}piperidin-1-yl)-3-fluorophenyl]ethanesulfonyl]-N,N-dimethylbenzene-1-sulfonamide; diastereomer 4 |
| A-886 | 8-{[1-(2-{1-[(2,2-dimethyl-2,3-dihydro-1-benzofuran-5-yl)sulfonyl]ethyl}-6-fluorophenyl)piperidin-4-yl]methyl}-3-oxa-8-azabicyclo[3.2.1]octane |
| A-887 | N-[3-chloro-5-methyl-2-(morpholin-4-yl)phenyl]-2,3-dihydro-1H-indene-5-sulfonamide |
| A-888 | N4-[3-chloro-5-methyl-2-(morpholin-4-yl)phenyl]-N1,N1-dimethylbenzene-1,4-disulfonamide |
| A-889 | N-{3-fluoro-2-[4-({3-oxa-6-azabicyclo[3.1.1]heptan-6-yl}methyl)piperidin-1-yl]phenyl}-4-methylbenzene-1-sulfonamide |
| A-890 | 4-[(1R)-1-[2-(4,4-difluoropiperidin-1-yl)-3-fluorophenyl]ethanesulfonyl]-N,N-dimethylbenzene-1-sulfonoimidamide; diastereomer 1 |
| A-891 | 4-[(1R)-1-[2-(4,4-difluoropiperidin-1-yl)-3-fluorophenyl]ethanesulfonyl]-N,N-dimethylbenzene-1-sulfonoimidamide; diastereomer 2 |
| A-892 | 4-[(1R)-1-(3-fluoro-2-{4-[1-(morpholin-4-yl)cyclopropyl]piperidin-1-yl}phenyl)ethanesulfonyl]-N,N-dimethylbenzene-1-sulfonoimidamide; diastereomer 1 |
| A-893 | 4-[(1R)-1-(3-fluoro-2-{4-[1-(morpholin-4-yl)cyclopropyl]piperidin-1-yl}phenyl)ethanesulfonyl]-N,N-dimethylbenzene-1-sulfonoimidamide; diastereomer 2 |
| A-894 | 4-[(1R)-1-[3-fluoro-2-(piperidin-1-yl)phenyl]ethanesulfonyl]-N,N-dimethylbenzene-1-sulfonoimidamide; diastereomer 1 |
| A-895 | 4-[(1R)-1-[3-fluoro-2-(piperidin-1-yl)phenyl]ethanesulfonyl]-N,N-dimethylbenzene-1-sulfonoimidamide; diastereomer 2 |
| A-896 | N4-{2-[(3R)-3-{[3,5-dimethylmorpholin-4-yl]methyl}pyrrolidin-1-yl]-3-fluorophenyl}-N1,N1-dimethylbenzene-1,4-disulfonamide; diastereomer 1 |
| A-897 | N4-{2-[(3R)-3-{[3,5-dimethylmorpholin-4-yl]methyl}pyrrolidin-1-yl]-3-fluorophenyl}-N1,N1-dimethylbenzene-1,4-disulfonamide; diastereomer 2 |
| A-898 | 4-(cyclopropyldifluoromethyl)-N-{3-fluoro-2-[4-({3-oxa-6-azabicyclo[3.1.1]heptan-6-yl}methyl)piperidin-1-yl]phenyl}benzene-1-sulfonamide |
| A-899 | N4-[2-(4-amino-4-methylpiperidin-1-yl)-3-fluorophenyl]-N1,N1-dimethylbenzene-1,4-disulfonamide |
| A-900 | N4-[2-(3-{[(3R,5S)-3,5-dimethylmorpholin-4-yl]methyl}azetidin-1-yl)-3-fluorophenyl]-N1,N1-dimethylbenzene-1,4-disulfonamide |

TABLE B-continued

| Compound No. | Compound Name |
|---|---|
| A-901 | N4-[3-ethynyl-2-(piperidin-1-yl)phenyl]-N1,N1-dimethylbenzene-1,4-disulfonamide |
| A-902 | 4-[(1R)-1-[2-(4-{[(2R,6S)-2,6-dimethylmorpholin-4-yl]methyl}piperidin-1-yl)-3-fluorophenyl]ethanesulfonyl]-N,N-dimethylbenzene-1-sulfonoimidamide; diastereomer 3 |
| A-903 | 4-[(1R)-1-[2-(4-{[(2R,6S)-2,6-dimethylmorpholin-4-yl]methyl}piperidin-1-yl)-3-fluorophenyl]ethanesulfonyl]-N,N-dimethylbenzene-1-sulfonoimidamide; diastereomer 4 |
| A-904 | 8-[(1-{2-fluoro-6-[1-(4-methanesulfonylbenzenesulfonyl)ethyl]phenyl}piperidin-4-yl)methyl]-3-oxa-8-azabicyclo[3.2.1]octane; formic acid |
| A-905 | 8-[(1-{2-fluoro-6-[1-(4-methylbenzenesulfonyl)ethyl]phenyl}piperidin-4-yl)methyl]-3-oxa-8-azabicyclo[3.2.1]octane; formic acid |
| A-906 | 8-{[1-(2-{1-[4-(difluoromethyl)benzenesulfonyl]ethyl}-6-fluorophenyl)piperidin-4-yl]methyl}-3-oxa-8-azabicyclo[3.2.1]octane; formic acid |
| A-907 | 8-{[1-(2-{1-[4-(cyclopropyldifluoromethyl)benzenesulfonyl]ethyl}-6-fluorophenyl)piperidin-4-yl]methyl}-3-oxa-8-azabicyclo[3.2.1]octane |
| A-908 | 8-[(1-{2-[1-(2,3-dihydro-1H-indene-5-sulfonyl)ethyl]-6-fluorophenyl}piperidin-4-yl)methyl]-3-oxa-8-azabicyclo[3.2.1]octane |
| A-909 | N1-(2-(4-(2-oxa-7-azaspiro[4.4]nonan-7-yl)piperidin-1-yl)-3-fluorophenyl)-N4,N4-dimethylbenzene-1,4-disulfonamide; enantiomer 1 |
| A-910 | N1-(2-(4-(2-oxa-7-azaspiro[4.4]nonan-7-yl)piperidin-1-yl)-3-fluorophenyl)-N4,N4-dimethylbenzene-1,4-disulfonamide; enantiomer 2 |
| A-911 | 4-((1-(3-fluoro-2-(piperidin-1-yl)phenyl)ethyl)sulfonyl)-N,N-dimethylbenzenesulfonamide; enantiomer 1 |
| A-912 | 4-((1-(3-fluoro-2-(piperidin-1-yl)phenyl)ethyl)sulfonyl)-N,N-dimethylbenzenesulfonamide; enantiomer 2 |
| A-913 | 8-((1-(2-fluoro-6-(1-((4-(methylsulfonyl)phenyl)sulfonyl)ethyl)phenyl)piperidin-4-yl)methyl)-3-oxa-8-azabicyclo[3.2.1]octane; enantiomer 1 |
| A-914 | 8-((1-(2-fluoro-6-(1-((4-(methylsulfonyl)phenyl)sulfonyl)ethyl)phenyl)piperidin-4-yl)methyl)-3-oxa-8-azabicyclo[3.2.1]octane; enantiomer 2 |
| A-915 | rel-N4-[2-(3-{[(3R,5R)-3,5-dimethylmorpholin-4-yl]methyl}azetidin-1-yl)-3-fluorophenyl]-N1,N1-dimethylbenzene-1,4-disulfonamide; diastereomer 1 |
| A-916 | rel-N4-[2-(3-{[(3R,5R)-3,5-dimethylmorpholin-4-yl]methyl}azetidin-1-yl)-3-fluorophenyl]-N1,N1-dimethylbenzene-1,4-disulfonamide; diastereomer 2 |
| A-917 | N4-[3-fluoro-2-(4-{6-oxa-1-azaspiro[3.5]nonan-1-yl}piperidin-1-yl)phenyl]-N1,N1-dimethylbenzene-1,4-disulfonamide |
| A-918 | N4-[2-(4-{[(2R,6S)-2,6-dimethylmorpholin-4-yl]methyl}azepan-1-yl)-3-fluorophenyl]-N1,N1-dimethylbenzene-1,4-disulfonamide |
| A-919 | 4-(cyclopropyldifluoromethyl)-N-{3-fluoro-2-[4-({3-oxa-8-azabicyclo[3.2.1]octan-8-yl}methyl)piperidin-1-yl]phenyl}benzene-1-sulfonamide |
| A-920 | 5-{1-[3-fluoro-2-(piperidin-1-yl)phenyl]ethanesulfonyl}-2,3-dihydro-1$\lambda^6$-benzothiophene-1,1-dione |
| A-921 | N4-[3-(3,3-difluoroprop-1-yn-1-yl)-2-(piperidin-1-yl)phenyl]-N1,N1-dimethylbenzene-1,4-disulfonamide |
| A-922 | (4-(((R)-1-(3-fluoro-2-(piperidin-1-yl)phenyl)ethyl)sulfonyl)phenyl)(imino)(isopropyl)-$\lambda^6$-sulfanone |
| A-923 | (4-(((R)-1-(3-fluoro-2-(piperidin-1-yl)phenyl)ethyl)sulfonyl)phenyl)(imino)(isopropyl)-$\lambda^6$-sulfanone; diastereomer 3 |
| A-924 | 8-((1-(2-fluoro-6-(1-tosylethyl)phenyl)piperidin-4-yl)methyl)-3-oxa-8-azabicyclo[3.2.1]octane; enantiomer 1 |
| A-925 | 4-((1-(2-(4-(difluoromethyl)-4-methylpiperidin-1-yl)-3-fluorophenyl)ethyl)sulfonyl)-N,N-dimethylbenzenesulfonamide, enantiomer 1 |
| A-926 | 4-(((S)-1-(3-fluoro-2-(piperidin-1-yl)phenyl)ethyl)sulfonyl)-N,N-dimethylbenzenesulfonimidamide; diastereomer 1 |
| A-927 | 4-(((S)-1-(3-fluoro-2-(piperidin-1-yl)phenyl)ethyl)sulfonyl)-N,N-dimethylbenzenesulfonimidamide; diastereomer 2 |
| A-928 | 4-(((R)-1-(3-fluoro-2-(piperidin-1-yl)phenyl)ethyl)sulfonyl)-N,N-dimethylbenzenesulfonimidamide; diastereomer 2 |
| A-929 | 4-(((R)-1-(3-fluoro-2-(piperidin-1-yl)phenyl)ethyl)sulfonyl)-N,N-dimethylbenzenesulfonimidamide; diastereomer 1 |
| A-930 | 4-[(1S)-1-[3-fluoro-2-(piperidin-1-yl)phenyl]ethanesulfonyl]-N,N-dimethylbenzene-1-sulfonoimidamide; diastereomer 2 |
| A-931 | 4-[(1S)-1-[2-(4-{[(2R,6S)-2,6-dimethylmorpholin-4yl]methyl}piperidin-1-yl)-3-fluorophenyl]ethanesulfonyl]-N,N-dimethylbenzene-1-sulfonoimidamide; diastereomer 1 |
| A-932 | 4-[(1S)-1-{3-fluoro-2-[4-(trifluoromethyl)piperidin-1-yl]phenyl}ethanesulfonyl]-N,N-dimethylbenzene-1-sulfonoimidamide; diastereomer 1 |
| A-933 | 4-((1-(2-(4-(difluoromethyl)-4-methylpiperidin-1-yl)-3-fluorophenyl)ethyl)sulfonyl)-N,N-dimethylbenzenesulfonamide; enantiomer 2 |

TABLE B-continued

| Compound No. | Compound Name |
| --- | --- |
| A-934 | N4-(1-cyclohexyl-4-methyl-6-oxo-1,6-dihydropyridin-2-yl)-N1,N1-dimethylbenzene-1,4-disulfonamide |
| A-935 | 4-(((S)-1-(3-fluoro-2-(4-(trifluoromethyl)piperidin-1-yl)phenyl)ethyl)sulfonyl)-N,N-dimethylbenzenesulfonimidamide; diastereomer 2 |
| A-936 | 4-[(1S)-1-[2-(4,4-difluoropiperidin-1-yl)-3-fluorophenyl]ethanesulfonyl]-N,N-dimethylbenzene-1-sulfonoimidamide; diastereomer 2 |
| A-937 | (difluoromethyl)(4-((1-(3-fluoro-2-(piperidin-1-yl)phenyl)ethyl)sulfonyl)phenyl)(imino)-l6-sulfanone; diastereomer 1 |
| A-938 | (difluoromethyl)(4-((1-(3-fluoro-2-(piperidin-1-yl)phenyl)ethyl)sulfonyl)phenyl)(imino)-l6-sulfanone; diastereomer 2 |
| A-939 | (difluoromethyl)(4-((1-(3-fluoro-2-(piperidin-1-yl)phenyl)ethyl)sulfonyl)phenyl)(imino)-l6-sulfanone; diastereomer 3 |
| A-940 | (difluoromethyl)(4-((1-(3-fluoro-2-(piperidin-1-yl)phenyl)ethyl)sulfonyl)phenyl)(imino)-l6-sulfanone; diastereomer 4 |
| A-941 | 6-{1-[3-fluoro-2-(piperidin-1-yl)phenyl]ethanesulfonyl}-N,N-dimethylpyridazine-3-sulfonamide |
| A-942 | 4-((1-(2-(4-(difluoromethyl)-4-methylpiperidin-1-yl)-3-fluorophenyl)ethyl)sulfonyl)-N,N-dimethylbenzenesulfonimidamide; diastereomer 1 |
| A-943 | 4-((1-(2-(4-(difluoromethyl)-4-methylpiperidin-1-yl)-3-fluorophenyl)ethyl)sulfonyl)-N,N-dimethylbenzenesulfonimidamide; diastereomer 2 |
| A-944 | 4-((1-(2-(4-(ethoxymethyl)-4-methylpiperidin-1-yl)-3-fluorophenyl)ethyl)sulfonyl)-N,N-dimethylbenzenesulfonimidamide; diastereomer 1 |
| A-945 | 4-((1-(2-(4-(ethoxymethyl)-4-methylpiperidin-1-yl)-3-fluorophenyl)ethyl)sulfonyl)-N,N-dimethylbenzenesulfonimidamide; diastereomer 2 |
| A-946 | 4-((1-(2-(4-(tert-butoxymethyl)piperidin-1-yl)-3-fluorophenyl)ethyl)sulfonyl)-N,N-dimethylbenzenesulfonimidamide; diastereomer 1 |
| A-947 | 5-((1-(3-fluoro-2-(piperidin-1-yl)phenyl)ethyl)sulfonyl)-1-imino-2,3-dihydro-1H-1l4-benzo[b]thiophene 1-oxide; diastereomer 1 |
| A-948 | 5-((1-(3-fluoro-2-(piperidin-1-yl)phenyl)ethyl)sulfonyl)-1-imino-2,3-dihydro-1H-1l4-benzo[b]thiophene 1-oxide; diastereomer 2 |
| A-949 | 4-((1-(2-(8-azabicyclo[3.2.1]octan-8-yl)-3-fluorophenyl)ethyl)sulfonyl)-N,N-dimethylbenzenesulfonimidamide; diastereomer 1 |
| A-950 | 4-((1-(2-(8-azabicyclo[3.2.1]octan-8-yl)-3-fluorophenyl)ethyl)sulfonyl)-N,N-dimethylbenzenesulfonimidamide; diastereomer 2 |
| A-951 | 4-{cyclopropyl[3-fluoro-2-(piperidin-1-yl)phenyl]methanesulfonyl}-N,N-dimethylbenzene-1-sulfonamide |
| A-952 | N4-(2-{4-[(4,4-difluoropiperidin-1-yl)methyl]piperidin-1-yl}-5-methylpyridin-3-yl)-N1,N1-dimethylbenzene-1,4-disulfonamide |
| A-953 | 4-((1-(2-(4-(tert-butoxymethyl)piperidin-1-yl)-3-fluorophenyl)ethyl)sulfonyl)-N,N-dimethylbenzenesulfonimidamide; diastereomer 2 |
| A-954 | 4-((1-(2-(4-(ethoxymethyl)-4-methylpiperidin-1-yl)-3-fluorophenyl)ethyl)sulfonyl)-N,N-dimethylbenzenesulfonimidamide; diastereomer 3 |
| A-955 | 4-((1-(2-(4-(ethoxymethyl)-4-methylpiperidin-1-yl)-3-fluorophenyl)ethyl)sulfonyl)-N,N-dimethylbenzenesulfonimidamide; diastereomer 4 |
| A-956 | 4-{[2-(4-{[(2R,6S)-2,6-dimethylmorpholin-4-yl]methyl}piperidin-1-yl)-3-fluorophenyl]sulfamoyl}-N,N,N-trimethylbenzene-1-sulfonoimidamide; formic acid |
| A-957 | 5-{1-[3-fluoro-2-(morpholin-4-yl)phenyl]ethanesulfonyl}-2,3-dihydro-1$\lambda^6$-benzothiophene-1,1-dione |
| A-958 | 4-[1-(5-chloro-2-{4-[(4,4-difluoropiperidin-1-yl)methyl]piperidin-1-yl}pyridin-3-yl)ethanesulfonyl]-N,N-dimethylbenzene-1-sulfonamide |
| A-959 | 5-(((S)-1-(3-fluoro-2-(piperidin-1-yl)phenyl)ethyl)sulfonyl)-1-imino-2,3-dihydro-1H-1$\lambda^4$-benzo[b]thiophene 1-oxide; diastereomer 3 |
| A-960 | 5-(((S)-1-(3-fluoro-2-(piperidin-1-yl)phenyl)ethyl)sulfonyl)-1-imino-2,3-dihydro-1H-1$\lambda^4$-benzo[b]thiophene 1-oxide; diastereomer 4 |
| A-961 | 4-((1-(2-(4-(tert-butoxymethyl)piperidin-1-yl)-3-fluorophenyl)ethyl)sulfonyl)-N,N-dimethylbenzenesulfonimidamide; diastereomer 4 |
| A-962 | 4-((1-(2-(4-(tert-butoxymethyl)piperidin-1-yl)-3-fluorophenyl)ethyl)sulfonyl)-N,N-dimethylbenzenesulfonimidamide; diastereomer 3 |
| A-963 | 4-(difluoromethyl)-1-(2-(1-((4-(difluoromethyl)phenyl)sulfonyl)ethyl)-6-fluorophenyl)-4-methylpiperidine; enantiomer 1 |
| A-964 | 4-(difluoromethyl)-1-(2-(1-((4-(difluoromethyl)phenyl)sulfonyl)ethyl)-6-fluorophenyl)-4-methylpiperidine; enantiomer 2 |
| A-965 | 8-((1-(2-fluoro-6-(1-tosylethyl)phenyl)piperidin-4-yl)methyl)-3-oxa-8-azabicyclo[3.2.1]octane; enantiomer 2 |
| A-966 | 5-((1-(3-fluoro-2-morpholinophenyl)ethyl)sulfonyl)-2,3-dihydrobenzo[b]thiophene 1,1-dioxide; enantiomer 1 |

TABLE B-continued

| Compound No. | Compound Name |
|---|---|
| A-967 | 5-((1-(3-fluoro-2-morpholinophenyl)ethyl)sulfonyl)-2,3-dihydrobenzo[b]thiophene 1,1-dioxide; enantiomer 2 |
| A-968 | 4-({3-[(3R,5S)-4,4-difluoro-3,5-dimethylpiperidin-1-yl]-1H-indazol-1-yl}sulfonyl)-N,N-dimethylbenzene-1-sulfonamide |
| A-969 | 4-({3-[(3R,5S)-4-fluoro-3,5-dimethylpiperidin-1-yl]-1H-indazol-1-yl}sulfonyl)-N,N-dimethylbenzene-1-sulfonamide |
| A-970 | 4-{1-[2-(4-{[(3R,5S)-4,4-difluoro-3,5-dimethylpiperidin-1-yl]methyl}piperidin-1-yl)-3-fluorophenyl]ethanesulfonyl}-N,N-dimethylbenzene-1-sulfonamide |
| A-971 | 1-(2-{1-[(4-difluoromethanesulfonylphenyl)sulfanyl]ethyl}-6-fluorophenyl)piperidine |
| A-972 | 1-{2-[1-(4-difluoromethanesulfonylbenzenesulfinyl)ethyl]-6-fluorophenyl}piperidine |
| A-973 | 1-{2-[1-(4-difluoromethanesulfonylbenzenesulfonyl)ethyl]-6-fluorophenyl}piperidine |
| A-974 | 4-((1-(2-(4-(difluoromethyl)-4-methylpiperidin-1-yl)-3-fluorophenyl)ethyl)sulfonyl)-N,N-dimethylbenzenesulfonimidamide; diastereomer 3 |
| A-975 | 4-((1-(2-(4-(difluoromethyl)-4-methylpiperidin-1-yl)-3-fluorophenyl)ethyl)sulfonyl)-N,N-dimethylbenzenesulfonimidamide; diastereomer 4 |
| A-976 | 4-(tert-butoxymethyl)-1-(2-(1-((4-(difluoromethyl)phenyl)sulfonyl)ethyl)-6-fluorophenyl)piperidine; enantiomer 1 |
| A-977 | 4-(tert-butoxymethyl)-1-(2-(1-((4-(difluoromethyl)phenyl)sulfonyl)ethyl)-6-fluorophenyl)piperidine; enantiomer 2 |
| A-978 | 4-((1-(5-chloro-2-(4-((4,4-difluoropiperidin-1-yl)methyl)piperidin-1-yl)pyridin-3-yl)ethyl)sulfonyl)-N,N-dimethylbenzenesulfonamide; enantiomer 1 |
| A-979 | 4-((1-(5-chloro-2-(4-((4,4-difluoropiperidin-1-yl)methyl)piperidin-1-yl)pyridin-3-yl)ethyl)sulfonyl)-N,N-dimethylbenzenesulfonamide; enantiomer 2 |
| A-980 | 1-(4-((1-(3-fluoro-2-(piperidin-1-yl)phenyl)ethyl)sulfonyl)phenyl)-4,5-dihydro-3H-isothiazole 1-oxide;; diastereomer 2 |
| A-981 | 1-(4-((1-(3-fluoro-2-(piperidin-1-yl)phenyl)ethyl)sulfonyl)phenyl)-4,5-dihydro-3H-isothiazole 1-oxide;; diastereomer 1 |
| A-982 | 4-((cyclopropyl(3-fluoro-2-(piperidin-1-yl)phenyl)methyl)sulfonyl)-N,N-dimethylbenzenesulfonamide; enantiomer 1 |
| A-983 | 4-((cyclopropyl(3-fluoro-2-(piperidin-1-yl)phenyl)methyl)sulfonyl)-N,N-dimethylbenzenesulfonamide; enantiomer 2 |
| A-984 | N4-{2-[(3R)-3-{[(3R,5S)-3,5-dimethylmorpholin-4-yl]methyl(pyrrolidin-1-yl]-3-fluorophenyl}-N1,N1-dimethylbenzene-1,4-disulfonamide |
| A-985 | 4-(1-{2-[4-({8,8-difluoro-3-azabicyclo[3.2.1]octan-3-yl}methyl)piperidin-1-yl]-3-fluorophenyl}ethanesulfonyl)-N,N-dimethylbenzene-1-sulfonamide |
| A-986 | 4-{1-[4-(4,4-difluoropiperidin-1-yl)-5-fluoropyridin-3-yl]ethanesulfonyl}-N,N-dimethylbenzene-1-sulfonamide |
| A-987 | 4-[1-(2-{4-[(4,4-difluoropiperidin-1-yl)methyl]piperidin-1-yl}pyridin-3-yl)ethanesulfonyl]-N,N-dimethylbenzene-1-sulfonamide |
| A-988 | 4-((1-(2-(8-azabicyclo[3.2.1]octan-8-yl)-3-fluorophenyl)ethyl)sulfonyl)-N,N-dimethylbenzenesulfonimidamide; diastereomer 3 |
| A-989 | 4-((1-(2-(8-azabicyclo[3.2.1]octan-8-yl)-3-fluorophenyl)ethyl)sulfonyl)-N,N-dimethylbenzenesulfonimidamide; diastereomer 4 |
| A-990 | 4-((1-(2-(4-((4,4-difluoropiperidin-1-yl)methyl)piperidin-1-yl)-5-methylpyridin-3-yl)ethyl)sulfonyl)-N,N-dimethylbenzenesulfonamide;; enantiomer 1 |
| A-991 | 1-(4-((1-(3-fluoro-2-(piperidin-1-yl)phenyl)ethyl)sulfonyl)phenyl)-4,5-dihydro-3H-isothiazole 1-oxide; diastereomer 3 |
| A-992 | 1-(4-((1-(3-fluoro-2-(piperidin-1-yl)phenyl)ethyl)sulfonyl)phenyl)-4,5-dihydro-3H-isothiazole 1-oxide; diastereomer 4 |
| A-993 | 5-chloro-2-(4-((4,4-difluoropiperidin-1-yl)methyl)piperidin-1-yl)-3-(1-((2,3-dihydro-1H-inden-5-yl)sulfonyl)ethyl)pyridine; enantiomer 1 |
| A-994 | 5-chloro-2-(4-((4,4-difluoropiperidin-1-yl)methyl)piperidin-1-yl)-3-(1-((2,3-dihydro-1H-inden-5-yl)sulfonyl)ethyl)pyridine;; enantiomer 2 |
| A-995 | 4-((1-(2-(4-((4,4-difluoropiperidin-1-yl)methyl)piperidin-1-yl)-5-methylpyridin-3-yl)ethyl)sulfonyl)-N,N-dimethylbenzenesulfonamide; enantiomer 2 |
| A-996 | 4-[1-(4-{4-[(4,4-difluoropiperidin-1-yl)methyl]piperidin-1-yl}-5-fluoropyridin-3-yl)ethanesulfonyl]-N,N-dimethylbenzene-1-sulfonamide |
| A-997 | 1-((1-(2-(1-((4-(difluoromethyl)phenyl)sulfonyl)ethyl)-6-fluorophenyl)piperidin-4-yl)methyl)-4,4-difluoropiperidine; enantiomer 1 |
| A-998 | 1-((1-(2-(1-((4-(difluoromethyl)phenyl)sulfonyl)ethyl)-6-fluorophenyl)piperidin-4-yl)methyl)-4,4-difluoropiperidine; enantiomer 2 |
| A-999 | 2-(4-((4,4-difluoropiperidin-1-yl)methyl)piperidin-1-yl)-3-(1-((2,3-dihydro-1H-inden-5-yl)sulfonyl)ethyl)-5-methylpyridine; enantiomer 1 |
| A-1000 | 2-(4-((4,4-difluoropiperidin-1-yl)methyl)piperidin-1-yl)-3-(1-((2,3-dihydro-1H-inden-5-yl)sulfonyl)ethyl)-5-methylpyridine; enantiomer 2 |
| A-1001 | 4-[(1S)-1-[2-(4-{[(2R,6S)-2,6-dimethylmorpholin-4-yl]methyl}piperidin-1-yl)-3-fluorophenyl]ethanesulfonyl]-N,N-dimethylbenzene-1-sulfonoimidamide; diastereomer 2 |

TABLE B-continued

| Compound No. | Compound Name |
|---|---|
| A-1002 | [(4-{1-[2-(4-{[(2R,6S)-2,6-dimethylmorpholin-4-yl]methyl}piperidin-1-yl)-3-fluorophenyl]ethanesulfonyl}phenyl)imino]dimethyl-$\lambda^6$-sulfanone |

Characteristics

Among other things, in some embodiments, the present disclosure describes one or more characteristics of certain TRPML1 modulators provided by and/or useful in the practice of the present disclosure.

In some embodiments, the present disclosure provides technologies for assessing one or more relevant characteristics and/or for identifying, selecting, prioritizing, and/or characterizing one or more useful TRPML1 modulators.

In some embodiments, the present disclosure provides certain biological and/or chemical assays (e.g., that facilitate and/or permit assessment of one or more feature(s) of TRMPL1 expression and/or activity, and/or of impact of TRPML1 modulator(s) on such expression and/or activity. Alternatively or additionally, the present disclosure provides technologies for identifying and/or characterizing one or more aspects of biological pathway(s) (e.g., autophagy pathway(s)) involving TRMPL1, and thus permits identification and/or characterization of additional useful targets within such pathway(s) and/or of modulator(s) that impact such pathway(s) (whether or not targeting TRPML1 itself).

Compositions

In some embodiments, the present disclosure provides and/or utilizes a composition that comprises and/or delivers a compound as described herein (e.g., together with one or more other components).

In some embodiments, the present disclosure provides compositions that comprise and/or deliver compounds reported herein (e.g., compounds of Formula I-IIc), or an intermediate, degradant, or an active metabolite thereof, e.g., when contacted with or otherwise administered to a system or environment e.g., which system or environment may include TRPML1 activity; in some embodiments, administration of such a composition to the system or environment achieves the regulation of autophagy and lysosomal biogenesis as described herein.

In some embodiments, a provided composition as described herein may be a pharmaceutical composition in that it comprises an active agent (e.g., a compound of Formula I-IIc or an active metabolite thereof) and one or more pharmaceutically acceptable excipients (e.g., one or more pharmaceutically acceptable adjuvants, carriers, excipients, and/or vehicles); in some such embodiments, a provided pharmaceutical composition comprises and/or delivers a compound described herein (e.g., a compound of Formula I-IIc), or an active metabolite thereof to a relevant system or environment (e.g., to a subject in need thereof) as described herein.

In some embodiments, a provided composition (e.g., a pharmaceutical composition) includes a compound (e.g., as described herein) in a salt form such as a pharmaceutically acceptable salt form.

Is some embodiments, a provided composition (e.g., a pharmaceutical composition) may be formulated for administration to a subject (e.g., a human) according to a particular route (e.g., orally, parenterally, by inhalation or nasal spray, topically (e.g., as by powders, ointments, or drops), rectally, buccally, intravaginally, intraperitoneally, intracisternally or via an implanted reservoir, etc).

In some embodiments, a provided composition (e.g., a pharmaceutical composition) comprises or delivers an amount of a compound as described herein (or an active metabolite thereof) that is effective to measurably modulate TRPML1 activity, and/or to induce autophagy and/or lysosomal biogenesis in a biological sample or in a subject, when administered in accordance with a therapeutic regimen.

In certain embodiments, a provided compound or composition is formulated for administration to a patient in need of such composition. In some embodiments, a compound or composition as described herein may be administered in a dose amount and/or by a route of administration effective for treating or lessening the severity of a disease or disorder described herein.

In some embodiments, a composition (e.g., a pharmaceutical composition) as described herein may be formulated in unit form (e.g., which may offer ease of administration and/or uniformity of dosage).

Those skilled in the art will appreciate that effective dose amounts may vary from subject to subject, for example depending on a variety of factors, including the disorder being treated and the severity of the disorder; the activity of the specific compound employed; the specific composition employed and its route of administration; the species, age, body weight, sex and diet of the patient; the general condition of the subject; the time of administration; the rate of excretion of the specific compound employed; the duration of the treatment; drugs used in combination or coincidental with the specific compound employed, and the like.

In some embodiments, an appropriate dosage level may be within a range of about 0.01 mg/kg to about 50 mg/kg, of subject body weight per day, one or more times a day, to obtain the desired therapeutic effect.

Applications and Uses

The present application provides a variety of uses and applications for compounds and/or compositions as described herein, for example in light of their activities and/or characteristics as described herein. In some embodiments, such uses may include therapeutic and/or diagnostic uses. Alternatively, in some embodiments such uses may include research, production, and/or other technological uses.

Among other things, in some embodiments, the present disclosure provides technologies for modulating TRPML1 activity. In some embodiments, the present application relates to a method of modulating TRPML1 activity in a subject comprising administering to the subject a provided compound, or a composition as described herein.

Diseases, Disorders, and Conditions

The present disclosure demonstrates that compounds and/or compositions as described herein may be useful in medicine (e.g., in the treatment of one or more diseases, disorders, or conditions).

Among other things, as described herein, the present disclosure provides an insight that targeting (e.g., agonizing) TRPML1 may be a particularly effective strategy for modulating (e.g., enhancing) autophagy and/or lysosomal biogenesis.

In some embodiments, a disease, disorder or condition that may be treated as described herein may be or comprise a disease, disorder or condition associated with TRPML1 deficiency. Furthermore, in some embodiments, the present disclosure identifies that TRMPL1 deficiency is associated with particular diseases, disorders or conditions, some or all of which may be treated in accordance with the present disclosure.

In some embodiments, treatment provided herein involves administration of a TRMPL1 modulator as described herein in an amount effective to modulate TRMPL1 activity in a lysosome and/or increase autophagy.

In some embodiments, a disease, disorder, or condition amenable to treatment as described herein is or comprises a liver disease, a neurodegenerative disorder, cancer, or a heart disease.

In some embodiments, a disease, disorder, or condition amenable to treatment as described herein is or comprises a lysosomal storage disease, such as Niemann-Pick C (NPC) disease, Gaucher disease, and Pompe disease.

In some embodiments, a disease, disorder, or condition amenable to treatment as described herein is an age-related common neurodegenerative disease, such as Alzheimer's Disease, Parkinson's Disease, and Huntington's Disease.

In some embodiments, a disease, disorder, or condition amenable to treatment as described herein is a type IV Mucolipidosis (ML4) neurodegenerative lysosomal storage disease caused by mutations in TRPML1.

In some embodiments, a disease, disorder, or condition amenable to treatment as described herein is related to reactive oxygen species or oxidative stress.

In some embodiments, a disease, disorder, or condition is a muscular disease, a liver disease, a metabolic disease, an atherosclerotic disease, an inflammatory bowel disease, an atherosclerotic disease, a neurodegenerative disease, an oncological disease, or an infectious disease.

In some embodiments, a disease, disorder, or condition is a muscular disease. In some embodiments, a muscular disease is a muscular dystrophy. In some embodiments, a muscular dystrophy is Duchenne muscular dystrophy.

In some embodiments, a disease, disorder, or condition is a liver disease. In some embodiments, a disease, disorder, or condition is a metabolic disease. In some embodiments, a disease, disorder, or condition is an atherosclerotic disease. In some embodiments, a disease, disorder, or condition is an inflammatory bowel disease. In some embodiments, a disease, disorder, or condition is an atherosclerotic disease. In some embodiments, a disease, disorder, or condition is a neurodegenerative disease. In some embodiments, a disease, disorder, or condition is an oncological disease. In some embodiments, a disease, disorder, or condition is an infectious disease.

In some embodiments, an infectious disease is an infection of *Helicobacter pylori* or *Mycobacterium tuberculosis*. In some embodiments, an infectious disease is an infection of *Helicobacter pylori*. In some embodiments, an infectious disease is an infection of *Mycobacterium tuberculosis*. In some embodiments, the infectious disease is tuberculosis.

In some embodiments, the present application relates to use of a compound and/or composition described herein for use in the manufacture of a medicament e.g., for modulation of TRPML1 activity.

In some embodiments, the present application relates to use of a compound and/or composition described herein for use in the manufacture of a medicament for treating a disease, disorder or condition, e.g., through modulation of TRPML1 activity; in some embodiments, the disease, disorder, or condition is a liver disease, a neurodegenerative disorder, cancer, or a heart disease.

Exemplary Embodiments

The following numbered embodiments, while non-limiting, are exemplary of certain aspects of the disclosure:

1. A compound of Formula II:

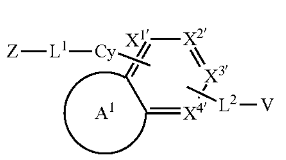

II or a pharmaceutically acceptable salt thereof, wherein $X^{1'}$, $X^{2'}$, $X^{3'}$, and $X^{4'}$ are each independently selected from N, C, and $CR^{a'}$, wherein $X^{1'}$, $X^{2'}$, $X^{3'}$, and $X^{4'}$ are C when bound to Cy-$L^1$-Z or $L^2$-V; A1 is absent, an optionally substituted fused heterocyclyl ring comprising 1 or 2 heteroatoms selected from N, O, and S, or an optionally substituted fused heteroaryl group comprising 1 or 2 heteroatoms selected from N, O, and S Cy is absent, 4- to 12-membered monocyclic or bicyclic heterocyclyl comprising 1 to 4 heteroatoms selected from N, O, P, and S, 5- to 12-membered monocyclic or bicyclic heteroaryl comprising 1 to 4 heteroatoms selected from N, O, and S, $C_{1-6}$ aliphatic, or $C_{3-12}$ cycloalkyl, wherein Cy is optionally substituted with one or more of $R^1$;

$L^1$ is absent, —$NR^3$—, —O—, —S—, $C_{1-6}$ alkylenyl, $C_{2-6}$ alkynylenyl, —$NR^3$—$C_{1-6}$ alkylenyl,—O—$C_{1-6}$ alkylenyl, —C(O)$C_{0-6}$ alkylenyl; —C(O)$NR^3$—, —C(O)—C(O)—;

$L^2$ is —$(NR^3)_s$—S(O)—$C_{0-6}$ alkylenyl-, —$(NR^3)_s$—$S(O)_2$—$C_{0-6}$ alkylenyl-, —$(NR^3)_s$—S(O)($NR^3$)—, —$S(O)_2$—$NR^3$—, —$NR^3$—$C_{1-6}$ haloalkylenyl, —$(NR^3)_s$—P(O)($R^3$)—, —$C_{1-6}$ alkylenyl-S(O)—, —$C_{1-6}$ alkylenyl-$S(O)_2$—, —C(O)—$(NR^3)_s$—, —$(NR^3)_s$—C(O)—, or an optionally substituted 4- to 12-membered monocyclic or bicyclic heterocyclyl comprising 1 to 4 heteroatoms selected from N, O, and S;

V is selected from $C_{1-6}$ aliphatic, $C_{6-12}$ aryl, 4- to 12-membered monocyclic or bicyclic heterocyclyl comprising 1 to 4 heteroatoms selected from N, O, and S, 5- to 12-membered monocyclic or bicyclic heteroaryl comprising 1 to 4 heteroatoms selected from N, O, and S, 5- to 12-membered monocyclic of bicyclic aryl, and $C_{3-12}$ cycloalkyl, wherein V is substituted with $(R^6)_m$;

Z is $C_{1-6}$ aliphatic, 2- to 10-atom heteroaliphatic, P(O)$(R^3)_2$, —C(O)$C_{1-6}$ aliphatic, C(O)N$(R^3)_2$, $C_{6-12}$ aryl, $C_{3-12}$ cycloalkyl, 4- to 16-membered monocyclic or polycyclic heterocyclyl comprising 1 to 4 heteroatoms selected from N, O, and S, or 5- to 12-membered monocyclic or bicyclic heteroaryl comprising 1 to 4 heteroatoms selected from N, O, and S, wherein Z is substituted with $(R^2)_q$;

each $R^a$ is independently halo, oxo, or optionally substituted $C_{1-6}$ aliphatic;

each $R^1$ is independently selected from N$(R^3)_2$, OH, CN, C(O)NH$R^3$, and an optionally substituted group selected from $C_{1-6}$ aliphatic and N($R^3$)—C(O)—$C_{1-6}$ alkyl;

each $R^2$ is independently selected from halo, —CN, C(O)OH, and an optionally substituted group selected from $C_{1-6}$ alkyl, C(O)$C_{1-6}$ aliphatic, and O—$C_{1-6}$ aliphatic;

each $R^3$ is independently selected from H and optionally substituted $C_{1-6}$ aliphatic;

each $R^5$ is independently selected from $C_{1-6}$ alkyl, —N($C_{1-6}$ alkyl)$_2$, —O—$C_{1-6}$ alkyl, C(O)—$C_{1-6}$ alkyl, P(O)($C_{1-6}$ alkyl)$_2$, $C_{3-12}$ cycloalkyl, and 5- to 12-membered heterocyclyl comprising 1 to 4 heteroatoms selected from N, O, and S, wherein $R^5$ is optionally substituted with one or more substituents selected from halo and OH;

each $R^6$ is halo, S(O)—$R^5$, S(O)$_2$—$R^5$, S(O)(NH)—$R^5$, —CN, —C(O)—$R^5$, —C(O)O—$R^5$, —C(O)—NH($R^5$), —C(O)—N($R^5$)$_2$, —P(O)($R^5$)$_2$, or an optionally substituted group selected from O—$C_{1-6}$ alkyl, $C_{1-6}$ alkyl, and $C_{6-12}$ aryl;

m is 0, 1, 2, 3, or 4;

q is 0, 1, 2, 3, or 4; and s is 0 or 1.

2. The compound embodiment 1, wherein Cy is absent or 4- to 12-membered monocyclic or bicyclic heterocyclyl comprising 1 to 4 heteroatoms selected from N, O, and S.

3. The compound of any one of the preceding embodiments, wherein Cy is absent.

4. The compound of any one of the preceding embodiments, wherein Cy is 4- to 12-membered monocyclic or bicyclic heterocyclyl comprising 1 to 4 heteroatoms selected from N, O, and S.

5. The compound of any one of the preceding embodiments, wherein Cy is 4- to 6-membered monocyclic heterocyclic comprising 1 to 3 heteroatoms selected from N, O, and S.

6. The compound of any one of the preceding embodiments, wherein Cy is piperadinyl or piperazinyl.

7. The compound of any one of the preceding embodiments, wherein Cy is selected from Table Cy.

8. The compound of any one of the preceding embodiments, wherein $L^1$ is absent, —$NR^3$—, or $C_{1-6}$ alkylenyl.

9. The compound of any one of the preceding embodiments, wherein $L^1$ is absent.

10. The compound of any one of the preceding embodiments, wherein $L^1$ is —NR—.

11. The compound of any one of the preceding embodiments, wherein $L^2$ is absent, —$(NR^3)_s$—S(O)—$C_{0-6}$ alkylenyl, or —$(NR^3)_s$—S(O)$_2$—$C_{0-6}$ alkylenyl.

12. The compound of any one of the preceding embodiments, wherein $L^2$ is absent, —$(NR^3)_s$—S(O)—, or —$(NR^3)_s$—S(O)$_2$—.

13. The compound of any one of the preceding embodiments, wherein $L^2$ is absent or —$(NR^3)_s$—S(O)$_2$—.

14. The compound of any one of the preceding embodiments, wherein $L^2$ is —$NR^3$—S(O)$_2$—.

15. The compound of any one of the preceding embodiments, wherein $L^2$ is —NH—S(O)$_2$—.

16. The compound of any one of the preceding embodiments, wherein Z is $C_{6-12}$ aryl, 2- to 10-atom heteroaliphatic, 4- to 12-membered monocyclic or polycyclic heterocyclyl comprising 1 to 4 heteroatoms selected from N, O, and S, or 5- to 12-membered monocyclic or bicyclic heteroaryl comprising 1 to 4 heteroatoms selected from N, O, and S, wherein Z is substituted with $(R^2)_q$.

17. The compound of any one of the preceding embodiments, wherein Z is $C_{6-12}$ aryl or 4- to 12-membered monocyclic or polycyclic heterocyclyl comprising 1 to 4 heteroatoms selected from N, O, and S.

18. The compound of any one of the preceding embodiments, wherein Z is $C_{6-12}$ aryl.

19. The compound of any one of the preceding embodiments, wherein Z is $C_{6-12}$ aryl substituted with 1, 2, 3, or 4 $R^2$.

20. The compound of any one of the preceding embodiments, wherein $R^2$ is halo.

21. The compound of any one of the preceding embodiments, wherein Z is selected from Table Z.

22. The compound of any one of the preceding embodiments, wherein V is $C_{6-12}$ aryl or 4- to 12-membered monocyclic or bicyclic heterocyclyl comprising 1 to 4 heteroatoms selected from N, O, and S.

23. The compound of any one of the preceding embodiments, wherein V is $C_{6-12}$ aryl.

24. The compound of any one of the preceding embodiments, wherein V is $C_{6-12}$ aryl substituted with 1, 2, 3, or 4 $R^6$.

25. The compound of any one of the preceding embodiments, wherein $R^6$ is halo, S(O)—$R^5$, S(O)$_2$—$R^5$, S(O)(NH)—$R^5$, or an optionally substituted O—$C_{1-6}$ alkyl.

26. The compound of any one of the preceding embodiments, wherein $R^6$ is S(O)—$R^5$, S(O)$_2$—$R^5$, or an optionally substituted $C_{1-6}$ alkyl.

27. The compound of any one of the preceding embodiments, wherein $R^6$ is halo.

28. The compound of any one of the preceding embodiments, wherein $R^6$ is fluoro or chloro.

29. The compound of any one of the preceding embodiments, wherein $R^6$ is S(O)$_2$—$R^5$.

30. The compound of any one of the preceding embodiments, wherein $R^6$ is —S(O)$_2$—$C_{1-6}$ alkyl.

31. The compound of any one of the preceding embodiments, wherein $R^6$ is —S(O)$_2$—$CH_3$.

32. The compound of any one of the preceding embodiments, wherein $R^6$ is —S(O)$_2$—N($C_{1-6}$ alkyl)$_2$.

33. The compound of any one of the preceding embodiments, wherein $R^6$ is —S(O)$_2$—N($CH_3$)$_2$.

34. The compound of any one of the preceding embodiments, wherein V is selected from Table V.

36. The compound of any one of the preceding embodiments, wherein the compound is of formula IIa-1:

IIa-1

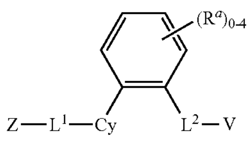

or a pharmaceutically acceptable salt thereof.

37. The compound of any one of the preceding embodiments, wherein the compound is of formula IIa-2:

IIa

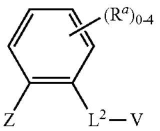

or a pharmaceutically acceptable salt thereof.

38. The compound of any one of the preceding embodiments, wherein the compound is of formula IIb-1:

IIb-1

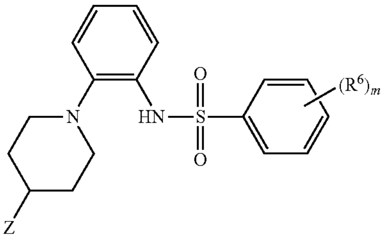

or a pharmaceutically acceptable salt thereof.

39. The compound of any one of the preceding embodiments, wherein the compound is of formula IIc:

IIc

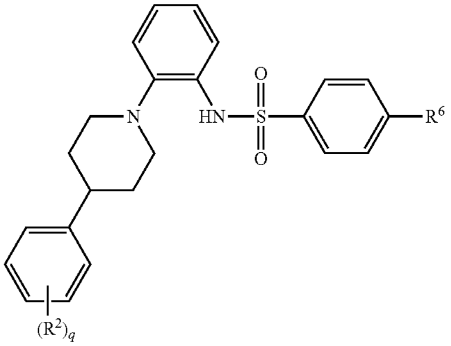

or a pharmaceutically acceptable salt thereof.

40. A compound selected from Table A.

41. A compound selected from Table B.

42. A pharmaceutical composition comprising a compound of any one of the preceding embodiments and a pharmaceutically acceptable carrier, adjuvant, or vehicle.

43. A method of modulating TRPML1 comprising administering to a subject a compound of any one of the preceding embodiments.

44. A method of treating a disease, disorder, or condition in a subject comprising administering a compound of any one of the preceding embodiments.

45. The method of embodiment 44, wherein the disease, disorder, or condition is a lysosomal storage disorder.

46. The method of embodiment 45, wherein the lysosomal storage disorder is selected from Niemann-Pick C disease, Gaucher disease, and Pompe disease.

47. The method of embodiment 45, wherein the disease, disorder, or condition is age-related common neurodegenerative disease.

48. The method of embodiment 47, wherein the disease, disorder, or condition is selected from Alzheimer's Disease, Parkinson's Disease, and Huntington's Disease.

49. The method of embodiment 45, wherein the disease, disorder, or condition is a type IV Mucolipidosis (ML4) neurodegenerative lysosomal storage disease caused by mutations in TRPML1.

EXEMPLIFICATION

The present teachings include descriptions provided in the Examples that are not intended to limit the scope of any claim. Unless specifically presented in the past tense, inclusion in the Examples is not intended to imply that the experiments were actually performed. The following non-limiting examples are provided to further illustrate the present teachings. Those of skill in the art, in light of the present application, will appreciate that many changes can be made in the specific embodiments that are provided herein and still obtain a like or similar result without departing from the spirit and scope of the present teachings Table of Abbreviatons

| | |
|---|---|
| ACN | Acetonitrile |
| $B_2pin_2$ | Bis(pinacolato)diboron |
| $BH_3$•DMS | Borane dimethylsulfide |
| BINAP | (2,2'-bis(diphenylphosphino)-1,1'-binaphthyl) |
| Boc | tert-Butyloxycarbonyl |
| CMBP | Cyanomethyltributylphosphorane |
| Davephos | 2-Dicyclohexylphosphino-2'-(N,N-dimethylamino)biphenyl |
| DBU | 1,8-Diazabicyclo[5.4.0]undec-7-ene |
| DCE | Dichloroethane |
| DCM | Dichloromethane |
| DEAD | Diethyl azodicarboxylate |
| DIPEA | N,N-Diisopropylethylamine |
| DMA | Dimethylacetamide |
| DMAP | 4-dimethylaminopyridine |
| DMF | N,N-Dimethylformamide |
| DMSO | Dimethylsulfoxide |
| eq | Equivalent |
| EtOAc | Ethyl acetate |
| h | Hour or hours |
| HATU | 1-[Bis(dimethylamino)methylene]-1H-1,2,3-triazolo[4,5-b]pyridinium 3-oxide hexafluorophosphate |
| HPLC | High pressure liquid chromatography |
| IPA | Isopropyl alcohol |
| Jones reagent | Chromium trioxide in diluted sulfuric acid |
| LAH | Lithium aluminum hydride |
| Lawesson's Reagent | 2,4-Bis(4-methoxyphenyl)-1,3,2,4-dithiadiphosphetane-2,4-disulfide |
| LCMS | Liquid chromatography mass spectrometry |
| LDA | Lithium diisopropylamine |
| LiHMDS | Lithium bis(trimethylsilyl)amide |
| mCPBA | m-chloroperbenzoic acid |
| MHz | Megahertz |
| MS | Mass spectrometry |
| MsCl | Mesylchlroide |
| MW | Microwave |
| NaHMDS | Sodium bis(trimethylsilyl)amide |
| NaOtBu | Sodium tert-butoxide |
| NBS | N-bromosuccinimide |
| n-BuLi | n-butyl lithium |
| NMR | Nuclear Magnetic Resonance |
| ON | Overnight |
| $Pd_2(dba)_3$ | Tris(dibenzylideneacetone)dipalladium(0) |
| $PdCl_2(dppf)$ | [1,1'-bis(diphenylphosphino)ferrocene] palladium(II) dichloride |
| PTSA | p-Toluenesulfonic acid |
| Py | Pyridine |
| PyBOP | benzotriazol-1-yl-oxytripyrrolidinophosphonium hexafluorophosphate |

-continued

Table of Abbreviatons

| | |
|---|---|
| RT | Room temperature |
| RuPhos | 2-Dicyclohexylphosphino-2',6'-diisopropoxybiphenyl |
| STAB | Sodium triacetoxyborohydride |
| TBA•$HSO_4$ | Tetrabutylammonium hydrogensulfate |
| TBAI | Tetrabutylammonium iodide |
| TEA | Triethylamine |
| TFA | Trifluoroacetic acid |
| THF | Tetrahydrofuran |
| TLC | Thin layer chromatography |
| TMS | Trimethylsilyl |
| TsCl | Tosylchloride |
| Xantphos | 4,5-Bis(diphenylphosphino)-9,9-dimethylxanthene |
| X-phos | 2-Dicyclohexylphosphino-2',4',6'-triisopropylbiphenyl |

Synthetic Examples

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

A. Certain Synthetic Intermediates

Scheme 1:
Procedure of synthesis of 1-(2,3-dimethoxyphenyl)ethan-1-one

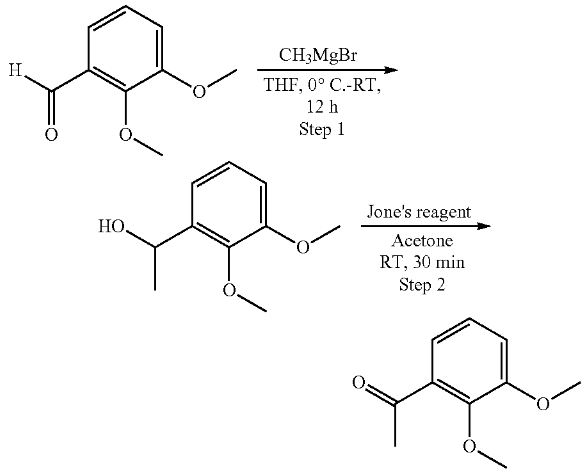

Step-1: Synthesis of 1-(2,3-dimethoxyphenyl)ethan-1-ol

To a stirred solution of 2,3-dimethoxybenzaldehyde (1 g, 6.01 mmol, 1 eq) in THF (20 mL) was added dropwise a 3 M solution of methyl magnesium bromide in diethyl ether (3 ml, 9.03 mmol, 1.5 eq) at 0° C. The reaction mixture was stirred at room temperature for overnight. The progress of the reaction was monitored by TLC. After completion, the reaction mixture was diluted with water and extracted with ethyl acetate. The organic layers were washed with water, brine, dried over anhydrous sodium sulfate and evaporated under reduced pressure. The crude product was purified by silica gel column chromatography to afford the titled compound 1-(2,3-dimethoxyphenyl)ethan-1-ol (0.7 g, 64%). LCMS: 183.09 $[M+H]^+$.

Step-2: Synthesis of 1-(2,3-dimethoxyphenyl)ethan-1-one

To a stirred mixture of 1-(2,3-dimethoxyphenyl)ethan-1-ol (0.8 g, 4.39 mmol, 1 eq) in acetone (20 ml), was added 2 M Jones reagent in aq. $H_2SO_4$ (6.6 ml, 13.18 mmol, 3 eq) at room temperature. The reaction mixture was stirred at room temperature for 30 min. The progress of the reaction was monitored by TLC. After completion of the reaction, the reaction mixture was quenched with isopropanol and concentrated under reduced pressure. The crude product was purified by column chromatography to afford the desired product 1-(2,3-dimethoxyphenyl)ethan-1-one (0.6 g, 76%). LCMS: 181.08 $[M+1]^+$.

Procedure for synthesis of 1-methyl-1H-indole-4-carbaldehyde

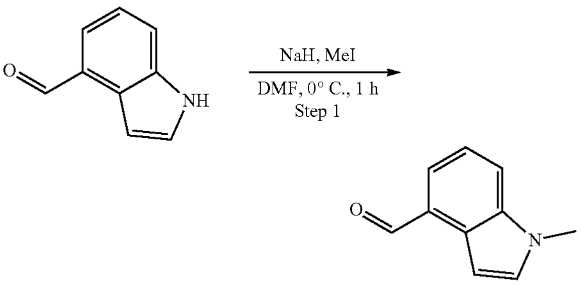

Step-1: Synthesis of 1-methyl-1H-indole-4-carbaldehyde

To a stirred solution of 1H-indole-4-carbaldehyde (1 g, 6.8 mmol, 1 eq) in DMF (10 mL) was added NaH (0.130 g, 7.4 mmol, 1.1 eq) at 0° C. under the nitrogen atmosphere followed by addition of methyl iodide (1.06 g, 7.5 mmol, 1.1 eq). The reaction mixture was stirred at 0° C. for 1 hour. The progress of the reaction was monitored by TLC. After completion, the reaction mixture was quenched with water and extracted with ethyl acetate. The organic layers were washed with water, brine, dried over anhydrous sodium sulfate and evaporated under reduced pressure. The crude product was purified by column chromatography to afford the titled compound 1-methyl-1H-indole-4-carbaldehyde (0.90 g, 82.56%). LCMS: 160.07 $[M+H]^+$.

Scheme 2

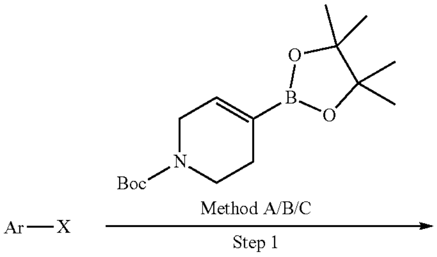

-continued

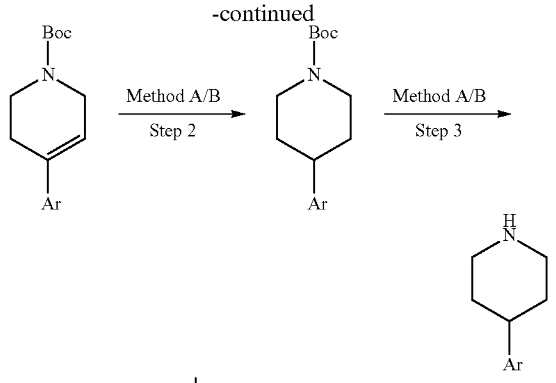

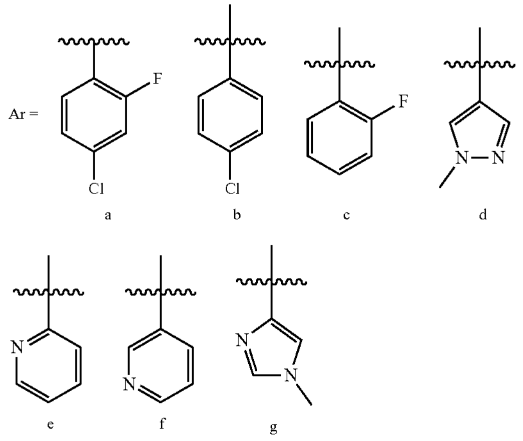

Step-1: General procedure for synthesis of 1-Boc-4-aryl-3,6-dihydropyridine Derivatives Method A (Ar=a/c/f): A pyrex tube was charged with respective aryl halides (1.1 eq), tert-butyl 4-(4,4,5,5-tetramethyl-1,3,2-dioxaborolan-2-yl)-3,6-dihydropyridine-1(2H)-carboxylate (1 eq), 2 M $Na_2CO_3$ solution (3 eq) in a mixture of 1.4 dioxane:$H_2O$ (4:1, 10 vol) and the reaction mixture was purged with argon for 15 min. Tetrakis(triphenylphosphine)palladium(0) (0.1 eq) was added to then reaction under an argon atmosphere and purged the reaction mixture with argon for 15 min. The tube was then fitted with a screw cap and the reaction was stirred at 90° C. for 3 h. The progress of the reaction was monitored by TLC. After completion of the reaction, the reaction mixture cooled to room temperature, filtered through a pad of Celite and the Celite pad was washed with ethyl acetate. The filtrate was diluted with water and extracted ethyl acetate. The combine organic layers were washed with water and brine, dried over anhydrous $Na_2SO_4$, filtered and concentrated under reduced pressure. The crude product was purified by column chromatography on silica gel to afford respective 1-Boc-4-aryl-3,6-dihydropyridine derivative.

Method B (Ar=b/e/g): A pyrex tube was charged with respective aryl halide (1.1 eq), tert-butyl 4-(4,4,5,5-tetramethyl-1,3,2-dioxaborolan-2-yl)-3,6-dihydropyridine-1(2H)-carboxylate (1 eq), potassium carbonate (2 eq) in a mixture of DMF:$H_2O$ (5:1, 10 vol) and the reaction mixture was purged with argon for 10 min. [1,1'-Bis(diphenylphosphino)ferrocene]dichloropalladium(II) (0.1 eq) was then added to the reaction under an argon atmosphere and purged the reaction mixture with argon for 5 min. The tube was then fitted with a screw cap and the reaction was stirred at 80° C. for 16 h. The progress of the reaction was monitored by TLC. After completion of reaction, the reaction mixture was cooled to room temperature, filtered through a pad of Celite and the Celite pad was washed with ethyl acetate. The filtrate was diluted with water and extracted ethyl acetate. The combine organic layers were washed with water and brine, dried over anhydrous $Na_2SO_4$, filtered and concentrated under reduced pressure. The crude product was purified by column chromatography on silica gel to afford respective 1-Boc-4-aryl-3,6-dihydropyridine derivative.

Method C (Ar=d): A pyrex tube was charged with respective aryl halide (1.1 eq), tert-butyl 4-(4,4,5,5-tetramethyl-1,3,2-dioxaborolan-2-yl)-3,6-dihydropyridine-1(2H)-carboxylate (1 eq), cesium carbonate (2 eq) in a mixture of 1.4 dioxane:$H_2O$ (4:1, 10 vol) and the reaction mixture was purged with argon for 10 min. Dichlorobis(triphenylphosphine)palladium(II) (0.1 eq) was then added to the reaction under an argon atmosphere and purged the reaction mixture with argon for 15 min. The tube was then fitted with a screw cap and the reaction was stirred at 80° C. for 12 h. The progress of the reaction was monitored by TLC. After completion of the reaction, the reaction mixture cooled to room temperature, filtered through a pad of Celite and the Celite pad was washed with ethyl acetate. The filtrate was diluted with water and extracted ethyl acetate. The combine organic layers were washed with water and brine, dried over anhydrous $Na_2SO_4$, filtered and concentrated under reduced pressure. The crude product was purified by column chromatography on silica gel to afford respective 1-Boc-4-aryl-3,6-dihydropyridine derivative.

Step-2: General Procedure for Synthesis of 1-Boc-4-arylpiperidine Derivatives

Method A (Ar=a/b): A solution of respective 1-Boc-4-aryl-3,6-dihydropyridine (1 eq) in ethyl acetate was purged with nitrogen for 10 min. Platinum (IV) oxide (10% w/w) was added to the reaction under a nitrogen atmosphere at room temperature. The reaction mixture was purged with hydrogen for 2-3 minutes and stirred at room temperature for 3 h under an atmosphere of hydrogen (100 Psi pressure). The progress of the reaction was monitored by TLC. After completion of the reaction, the reaction mixture was filtered through a pad of Celite and the Celite pad was washed with ethyl acetate. The filtrate was concentrated under reduced pressure to dryness to afford respective 1-Boc-4-arylpiperidine derivative. The crude product was used in the next step without further purification.

Method B (Ar=c/d/e/f/g): A solution of respective 1-Boc-4-aryl-3,6-dihydropyridine (1 eq) in methanol was purged with nitrogen for 10 min. 10-20% Palladium on carbon (10% w/w) was added to the reaction under nitrogen atmosphere at room temperature. The reaction mixture was purged with hydrogen for 2-3 minutes and stirred at room temperature for 12 h under an atmosphere of hydrogen under balloon pressure. The progress of the reaction was monitored by TLC. After completion of reaction, the reaction mixture was filtered through a pad of Celite and the Celite pad was washed with methanol. The filtrate was concentrated under reduced pressure to dryness to afford respective 1-Boc-4-arylpiperidine derivative. The crude product was used in the next step without further purification.

Step-3: General Procedure for Synthesis of 4-arylpiperidine Derivatives

Method A (Ar=a/c/e/f/g): To stirred solution of respective 1-Boc-4-arylpiperidine (1 eq) in DCM (5 vol), a 50% solution of trifluoroacetic acid solution in DCM (5 vol) was added dropwise at 0° C. The reaction mixture was warmed to room temperature and stirred for 2 to 16 h. The progress of the reaction was monitored by TLC. After completion of the reaction, the reaction mixture was quenched with saturated aqueous $NaHCO_3$ solution and extracted with DCM. The combined organic layers were washed with water and brine, dried over anhydrous $Na_2SO_4$, filtered and concentrated under reduced pressure to dryness to afford the respective 4-arylpiperidine derivative. The crude product was used in the next step without further purification.

Method B (Ar=b/d): To a stirred solution of respective 1-Boc-4-arylpiperidine (1 eq) in 1,4-dioxane (10 vol), a 4 M solution of HCl in 1,4-dioxane (5 vol) was added at 5 to 10° C. The reaction mixture was warmed to room temperature and stirred for 4 to 16 h. The progress of the reaction was monitored by TLC. After completion of the reaction, the reaction mixture was concentrated under reduced pressure, the residue was dissolve in saturated aqueous $NaHCO_3$ solution and extracted with DCM. The combined organic layers were washed with water and brine, dried over anhydrous $Na_2SO_4$, filtered and concentrated under reduced pressure to dryness to afford the respective 4-arylpiperidine derivative. The crude product was used in the next step without further purification.

| Ar = | Structure | MS |
|---|---|---|
| a | 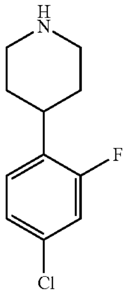 | 214.07 $[M + H]^+$ |
| b | 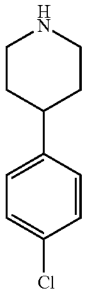 | 196.08 $[M + H]^+$ |
| c | 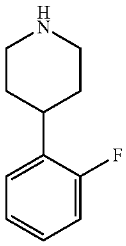 | 180.10 $[M + H]^+$ |

-continued

| Ar = | Structure | MS |
|---|---|---|
| d | 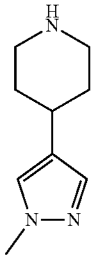 | 166.13 $[M + H]^+$ |
| e | 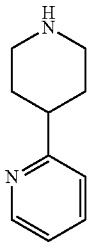 [SMILES: c1ccc(C2CCNCC2)nc1] | NA |
| f | 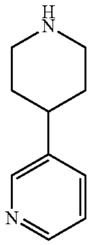 [SMILES: c1cncc(C2CCNCC2)c1] | 163.12 $[M + H]^+$ |
| g | 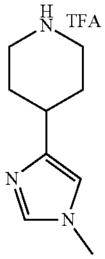 TFA | 166.13 $[M + H]^+$ |

Synthesis of 3-(piperidin-4-yl)isoxazole

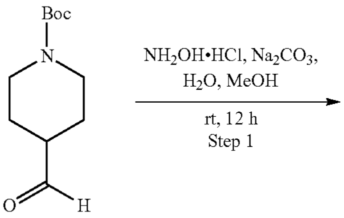

-continued

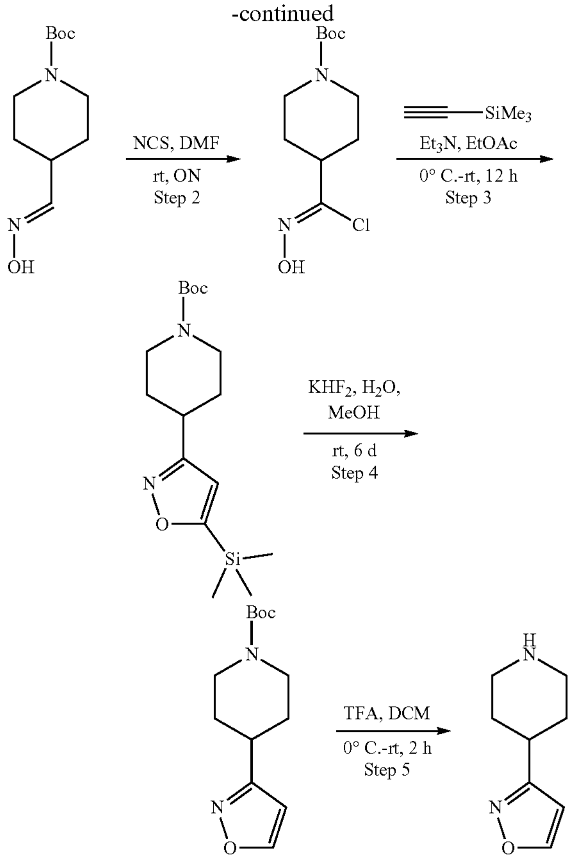

Step-1: Synthesis of tert-butyl (E)-4-((hydroxyimino)methyl)piperidine-1-carboxylate To a stirred solution of tert-butyl 4-formylpiperidine-1-carboxylate (1 g, 4.6 mmol, 1 eq) in water (10 mL) in methanol (10 mL), hydroxyl amine hydrochloride (390 mg, 5.6 mmol, 1.2 eq) followed by $Na_2CO_3$ (248 mg, 2.3 mmol, 0.5 eq) were added. The reaction mixture was stirred at room temperature for 12 h. The progress of the reaction was monitored by TLC. After completion of the reaction, the reaction mixture was diluted with water and extracted with ethyl acetate. The combined organic layers were washed with water and brine, dried over anhydrous $Na_2SO_4$, filtered and concentrated under reduced pressure to dryness to afford the titled compound tert-butyl (E)-4-((hydroxyimino)methyl)piperidine-1-carboxylate (The reaction was repeated on 1 g scale) (1.9 g, crude, combined yields from 1 gx2 batches). This compound was used in the next step without further purification. LCMS: 229.15 $[M+H]^+$.

Step-2: Synthesis of tert-butyl (Z)-4-(chloro(hydroxyimino)methyl)piperidine-1-carboxylate To a stirred solution of tert-butyl (E)-4-((hydroxyimino)methyl)piperidine-1-carboxylate (1 g, 4.4 mmol, 1 eq) in DMF (3 mL), N-chlorosuccinimide (0.59 g, 4.4 mmol, 1 eq) was added. The reaction mixture was stirred at room temperature for overnight. The progress of the reaction was monitored by TLC. After completion of the reaction, the reaction mixture was diluted with water, the resulting solid was filtered out and dried under reduced pressure to afford the titled compound tert-butyl (Z)-4-(chloro(hydroxyimino)methyl)piperidine-1-carboxylate (1 g, Crude). This compound was used in the next step without further purification. LCMS: 263.11 $[M+H]^+$.

Step-3: Synthesis of tert-butyl 4-(5-(trimethylsilyl)isoxazol-3-yl)piperidine-1-carboxylate To a stirred solution of tert-butyl (Z)-4-(chloro(hydroxyimino)methyl)piperidine-1-carboxylate (1.7 g, 6.4 mmol, 1 eq) in ethyl acetate (100 mL), ethynyltrimethylsilane (3.14 g, 32 mmol, 5 eq) followed by triethyl amine (1.24 g, 9.6 mmol, 1.5 eq) were added at 0° C. The reaction mixture was warmed to room temperature and stirred for 12 h. The progress of the reaction was monitored by TLC. After completion of the reaction, the reaction mixture was filtered and the filtrate was concentrated under reduced pressure. The crude product was purified by column chromatography on silica gel to afford the titled compound tert-butyl 4-(5-(trimethylsilyl)isoxazol-3-yl)piperidine-1-carboxylate (2 g, 96%). LCMS: 325.19 $[M+H]^+$.

Step-4: Synthesis of tert-butyl 4-(isoxazol-3-yl)piperidine-1-carboxylate

To a stirred solution of tert-butyl 4-(5-(trimethylsilyl)isoxazol-3-yl)piperidine-1-carboxylate (1.4 g, 4.3 mmol, 1 eq) in a mixture of water (1 mL) and methanol (10 mL), potassium bifluoride (33 mg, 0.43 mmol, 0.1 eq) was added. The reaction mixture was stirred at room temperature for 6 days. The progress of the reaction was monitored by TLC. After completion of the reaction, the reaction mixture was concentrated under reduced pressure and the residue was dissolved in ethyl acetate. The organic layer was washed with water and brine, dried over anhydrous $Na_2SO_4$ and concentrated under reduced pressure to afford the titled compound tert-butyl 4-(isoxazol-3-yl)piperidine-1-carboxylate (1 g, crude). This compound was used in the next step without further purification. LCMS: 253.15 $[M+H]^+$.

Step-5: Synthesis of 3-(piperidin-4-yl)isoxazole

To a stirred solution of tert-butyl 4-(isoxazol-3-yl)piperidine-1-carboxylate (1 g, 4 mmol, 1 eq) in DCM (20 mL), trifluoroacetic acid (10 mL) was added dropwise at 0° C. The reaction mixture was warmed to room temperature and stirred for 2 h. The progress of the reaction was monitored by TLC. After completion of the reaction, the reaction mixture was concentrated under reduced pressure to dryness to afford the titled compound 3-(piperidin-4-yl)isoxazole (1 g. crude). This compound was used in the next step without further purification. LCMS: 153.09 $[M+H]^+$.

Synthesis of 3-formyl-2-methoxybenzonitrile

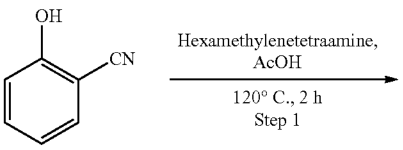

-continued

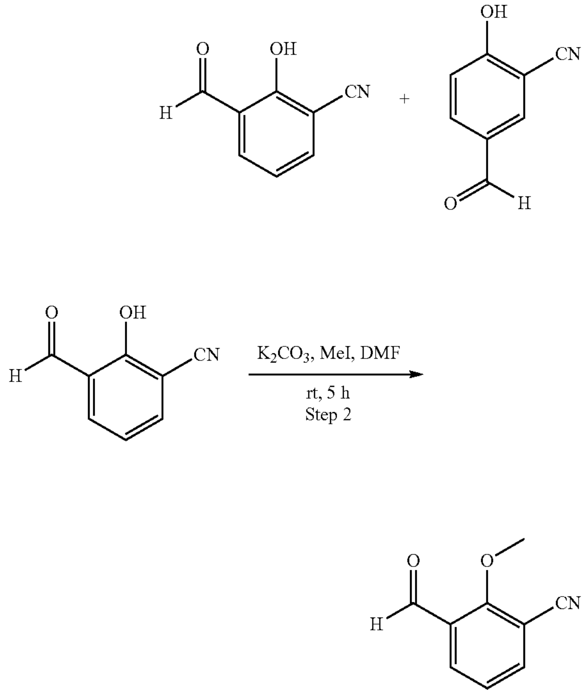

Step 1: Synthesis of 3-formyl-2-hydroxybenzonitrile

To a stirred solution of 2-hydroxybenzonitrile (1 g, 8.39 mmol, 1 eq) in acetic acid (10 mL), hexamethylenetetramine (1.8 g, 12.59 mmol, 1.5 eq) was added. The reaction was stirred at 120° C. for 2 h. The progress of the reaction was monitored by TLC. After completion of the reaction, the reaction mixture was cooled to room temperature and concentrated under reduced pressure. The residue was dissolved in ethyl acetate and washed with water. The organic layer was dried over anhydrous $Na_2SO_4$, filtered and concentrated under reduced pressure. The crude product was purified by column chromatography on silica gel to afford the titled compound 3-formyl-2-hydroxybenzonitrile (105 mg, 8.5%) and 5-formyl-2-hydroxybenzonitrile (330 mg, 27%). LCMS: No ionization.

Step 2: Synthesis of 3-formyl-2-methoxybenzonitrile

To a stirred solution of 3-formyl-2-hydroxybenzonitrile (100 mg, 0.68 mmol, 1 eq) in DMF (2 mL), potassium carbonate (188 mg, 1.36 mmol, 2 eq) followed by iodomethane (145 mg, 1.02 mmol, 1.5 eq) were added. The reaction was stirred at room temperature for 5 h. The progress of the reaction was monitored by TLC. After completion of the reaction, water was added to the reaction mixture and extracted with ethyl acetate. The combined organic layers were dried over anhydrous $Na_2SO_4$, filtered and concentrated under reduced pressure to dryness to afford the titled compound 3-formyl-2-methoxybenzonitrile (100 mg, crude). This compound was used in the next step without further purification. LCMS: No ionization.

Synthesis of (pyridin-2-ylmethoxy)benzaldehyde Derivatives

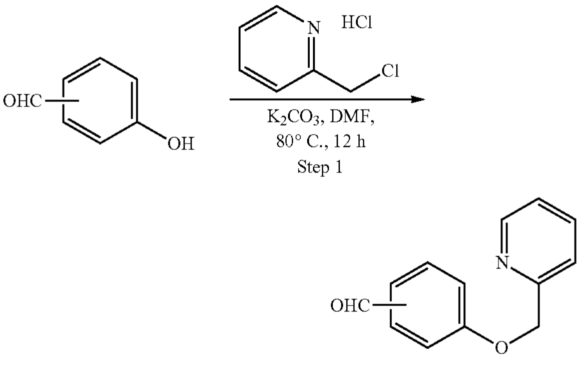

General Procedure for Synthesis of (pyridin-2-ylmethoxy)benzaldehyde Derivatives To a stirred solution of respective hydroxybenzaldehyde (1 eq) in DMF (10 vol), potassium carbonate (3 eq) followed by 2-(chloromethyl)pyridine hydrochloride (1.1 eq) were added. The reaction was stirred at 80° C. for 12 h. The progress of the reaction was monitored by TLC. After completion of the reaction, the reaction was cooled to room temperature; ice-cold water was added and extracted with ethyl acetate. The combined organic layers were dried over anhydrous $Na_2SO_4$, filtered and concentrated under reduced pressure. The crude product was purified by column chromatography on silica gel to afford the respective (pyridin-2-ylmethoxy)benzaldehyde derivative.

| Aldehyde | Structure | MS |
|---|---|---|
| a | 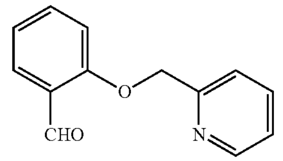 [SMILES: O=Cc1ccccc1OCc1ccccn1] | 214.10 $[M + H]^+$ |
| b | 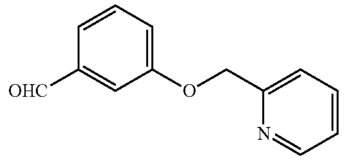 [SMILES: O=Cc1cccc(OCc2ccccn2)c1] | 214.10 $[M + H]^+$ |
| c | 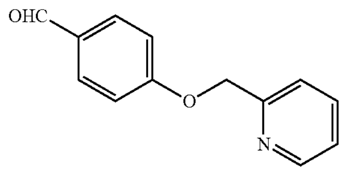 [SMILES: O=Cc1ccc(OCc2ccccn2)cc1] | 214.10 $[M + H]^+$ |

Synthesis of [1,1'-biphenyl]-4-carbaldehyde

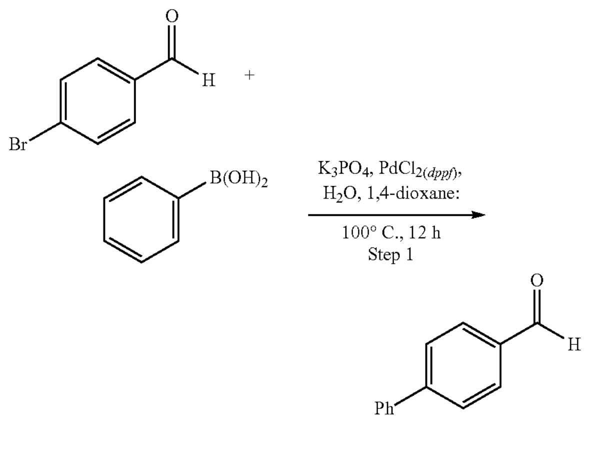

A pyrex tube was charged with a solution of 4-bromobenzaldehyde (1.86 g, 10.06 mmol, 1.2 eq), phenylboronic acid (1 g, 8.38 mmol, 1 eq) and $K_3PO_4$ (4.44 g, 20.9 mmol, 2.5 eq) in water (3 mL) and 1,4-dioxane (6 mL). The tube was sealed with a septum and the reaction mixture was purged with argon via an argon balloon for 15 min. $PdCl_2$(dppf) (183 mg, 0.25 mmol, 0.03 eq) was then added to the reaction under an argon atmosphere and the purging with argon was continued for 5 min. The tube was then sealed with a screw cap and the reaction was heated at 100° C. for 12 h. The progress of the reaction was monitored by TLC. After completion of the reaction, the reaction was cooled to room temperature and the reaction mixture was filtered through a pad of Celite and the Celite pad was washed with ethyl acetate. The filtrate was diluted with ethyl acetate and washed with water and brine. The organic layer was dried over anhydrous $Na_2SO_4$, filtered and concentrated under reduced pressure to dryness to afford the titled compound [1,1'-biphenyl]-4-carbaldehyde (500 mg, crude). This compound was used in the next without further purification. LCMS: No ionization.

Synthesis of 3,4-dimethoxypicolinaldehyde

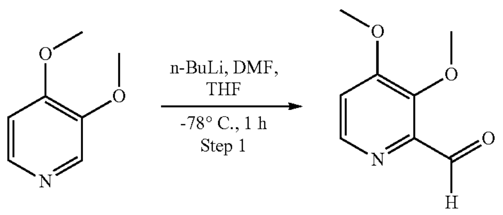

To a stirred solution of 3,4-dimethoxypyridine (250 mg, 1.79 mmol, 1 eq) in THE (5 mL), 1.6 M solution of n-BuLi in hexane (1.2 mL, 1.97 mmol, 1.1 eq) was added dropwise at −78° C. under an argon atmosphere. The reaction was stirred at the same temperature for 30 min. DMF (0.31 mL, 3.95 mmol, 2.2 eq) was then added to the reaction at −78° C. under an argon atmosphere. The reaction was stirred at the same temperature for 30 min under an argon atmosphere. The progress of the reaction was monitored by TLC. After completion of the reaction, the reaction was quenched with saturated aqueous $NH_4Cl$ solution and extracted with ethyl acetate. The combined organic layers were dried over anhydrous $Na_2SO_4$, filtered and concentrated under reduced pressure. The crude product was purified by column chromatography on silica gel to afford the titled compound 3,4-dimethoxypicolinaldehyde (62 mg, 20.6%). LCMS: 168.10 $[M+H]^+$.

Synthesis of 4,5-dimethoxynicotinaldehyde

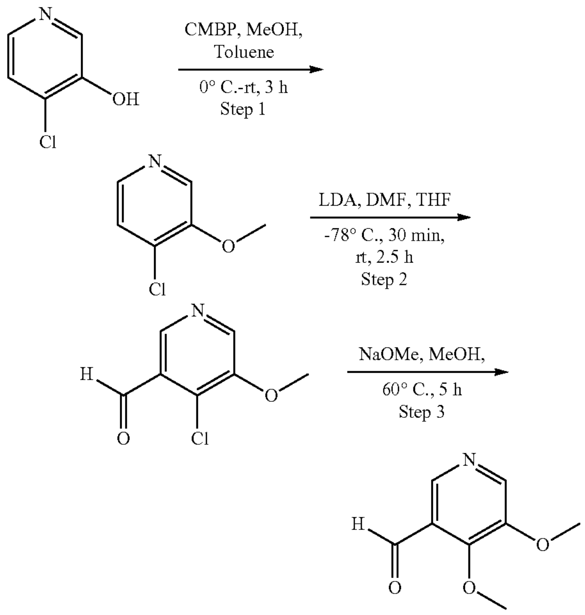

Step-1: Synthesis of 4-chloro-3-methoxypyridine

To a stirred solution of 4-chloropyridin-3-ol (1 g, 7.71 mmol, 1 eq) in toluene (10 mL), a solution of cyanomethyltributylphosphorane (CMBP) 1 M in toluene (23.1 mL, 23.1 mmol, 3 eq) followed by methanol (0.93 mL, 23.1 mmol, 3 eq) were added at 0° C. The reaction was warmed to room temperature and stirred for 3 h. The progress of the reaction was monitored by TLC. After completion of the reaction, the reaction mixture was diluted with water and extracted with ethyl acetate. The combined organic layers were washed with brine, dried over anhydrous $Na_2SO_4$, filtered and concentrated under reduced pressure. The crude product was purified by column chromatography on silica gel to afford the titled compound 4-chloro-3-methoxypyridine (280 mg, 25.45%). LCMS: 144.00 $[M+H]^+$.

Step-2: Synthesis of 4-chloro-5-methoxynicotinaldehyde

A stirred solution of 4-chloro-3-methoxypyridine (180 mg, 1.25 mmol, 1 eq) in THE (5 mL) was cooled to −78° C. and to which a 2 M solution of LDA in THE (1.25 mL, 2.51 mmol, 2 eq) was added. The reaction was stirred at the same temperature for 30 min. N,N-Dimethylformamide (0.19 mL, 2.51 mmol, 2 eq) was then added to the reaction at −78° C. The reaction was gradually warmed to room temperature and stirred for 2.5 h. The progress of the reaction was monitored by TLC. After completion of the reaction, the reaction mixture was cooled to 0° C., quenched with saturated aqueous $NH_4Cl$ solution and extracted with ethyl acetate. The combined organic layers were washed with brine, dried over anhydrous $Na_2SO_4$, filtered and concentrated under reduced pressure to dryness to afford the titled compound 4-chloro-5-methoxynicotinaldehyde (210 mg, crude). This compound was used in the next step without further purification. LCMS: 172.00 $[M+H]^+$.

Step-3: Synthesis of 4,5-dimethoxynicotinaldehyde

To a stirred solution 4-chloro-5-methoxynicotinaldehyde (200 mg, 1.16 mmol, 1 eq) in methanol (5 mL), sodium methoxide (126 mg, 2.33 mmol, 2 eq) was added and the reaction was stirred at 60° C. for 5 h. The progress of the reaction was monitored by TLC. After completion of the reaction, the reaction mixture was cooled to room temperature, diluted with water and extracted with ethyl acetate. The combined organic layers were washed with brine, dried over anhydrous $Na_2SO_4$, filtered and concentrated under reduced pressure to dryness. The crude product was purified by column chromatography on silica gel to afford the titled compound 4,5-dimethoxynicotinaldehyde (83 mg, 43%). LCMS: 168.10 $[M+H]^+$.

Synthesis of 2,3-dimethoxyisonicotinaldehyde

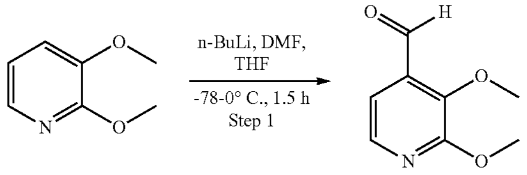

To a stirred solution of 2,3-dimethoxypyridine (1 g, 7.18 mmol, 1 eq) in THF, 2.5 M solution of n-BuLi in hexane (6.33 mL, 15.7 mmol, 2.2 eq) was added dropwise at −78° C. under an argon atmosphere. The reaction was warmed to 0° C. and stirred for 1 h. DMF (2.4 mL, 31.4 mmol, 4.38 eq) was then added dropwise to the reaction at −78° C. under an argon atmosphere. The reaction was warmed to 0° C. and stirred for 30 min under an argon atmosphere. The progress of the reaction was monitored by TLC. After completion of the reaction, the reaction was quenched with saturated aqueous $NH_4Cl$ solution and extracted with ethyl acetate. The combined organic layers were dried over anhydrous $Na_2SO_4$, filtered and concentrated under reduced pressure. The crude product was purified by column chromatography on silica gel to afford the titled compound 2,3-dimethoxyisonicotinaldehyde (250 mg, 20.83%). LCMS: 168.00 $[M+H]^+$.

Synthesis of 4-(4-chlorophenyl)piperidine

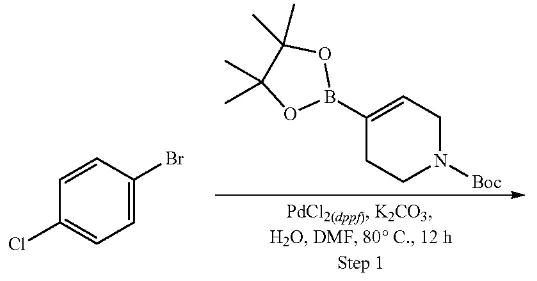

-continued

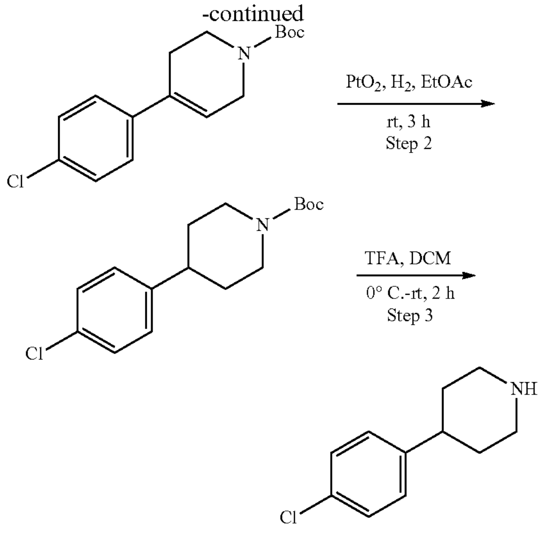

Step-1: Synthesis of tert-butyl 4-(4-chlorophenyl)-3,6-dihydropyridine-1(2H)-carboxylate A pyrex tube was charged with a solution of 1-bromo-4-chlorobenzene (2 g, 10.44 mmol, 1 eq), tert-butyl 4-(4,4,5,5-tetramethyl-1,3,2-dioxaborolan-2-yl)-3,6-dihydropyridine-1(2H)-carboxylate (3.87 g, 12.53 mmol, 1.2 eq) and potassium carbonate (2.8 g, 20.6 mmol, 2.5 eq) in a mixture of water (4 mL) and DMF (20 mL). The tube was sealed with a septum and the reaction mixture was purged with argon via an argon balloon for 15 min. [1,1'-Bis(diphenylphosphino)ferrocene]palladium(II) dichloride (752 mg, 1.04 mmol, 0.1 eq) was then added to the reaction under an argon atmosphere and the purging with argon was continued for 5 min. The tube was then sealed with a screw cap and the reaction was heated at 80° C. for 12 h. The progress of the reaction was monitored by TLC. After completion of the reaction, the reaction was cooled to room temperature and the reaction mixture was filtered through a pad of Celite and the Celite pad was washed with ethyl acetate. The filtrate was diluted with ethyl acetate and washed with water and brine. The organic layer was dried over anhydrous $Na_2SO_4$, filtered and concentrated under reduced pressure. The crude product was purified by column chromatography on silica gel to afford the titled compound tert-butyl 4-(4-chlorophenyl)-3,6-dihydropyridine-1(2H)-carboxylate (1.5 g, 49%). LCMS: 294.10 $[M+H]^+$.

Step-2: Synthesis of tert-butyl 4-(4-chlorophenyl)piperidine-1-carboxylate

To a stirred solution of tert-butyl 4-(4-chlorophenyl)-3,6-dihydropyridine-1(2H)-carboxylate (1 g, 3.4 mmol, 1 eq) in ethyl acetate (20 mL), the reaction mixture was purged with nitrogen for 5 min and platinum (IV) oxide (150 mg, 15% w/w) was added under an atmosphere of nitrogen. The reaction mixture was then purged with hydrogen for 2 min and stirred at room temperature for 3 h under an atmosphere of hydrogen via hydrogen balloon. The progress of the reaction was monitored by TLC. After completion of the reaction, the reaction mixture was filtered through a pad of Celite and the Celite pad was washed with ethyl acetate. The filtrate was concentrated under reduced pressure to dryness to afford the titled compound tert-butyl 4-(4-chlorophenyl)

piperidine-1-carboxylate (900 mg, crude). This compound was used in the next step without further purification. LCMS: 296.10 $[M+H]^+$.

Step-3: Synthesis of 4-(4-chlorophenyl)piperidine

To a stirred solution of tert-butyl 4-(4-chlorophenyl) piperidine-1-carboxylate (990 mg, 3.35 mmol, 1 eq) in DCM (5 mL), trifluoroacetic acid (5 mL) was added dropwise at 0° C. The reaction was warmed to room temperature and stirred for 2 h. The progress of the reaction was monitored by TLC. After completion of the reaction, the reaction mixture was concentrated under reduced pressure. The residue was dissolved in saturated aqueous $NaHCO_3$ solution and extracted with DCM. The combined organic layers were dried over anhydrous $Na_2SO_4$, filtered and concentrated under reduced pressure. The crude product was purified by column chromatography on silica gel to afford the titled compound 4-(4-chlorophenyl)piperidine (600 g, 91.6%). LCMS: 196.10 $[M+H]^+$.

Synthesis of tert-butyl 3-(((methylsulfonyl)oxy) methyl)pyrrolidine-1-carboxylate

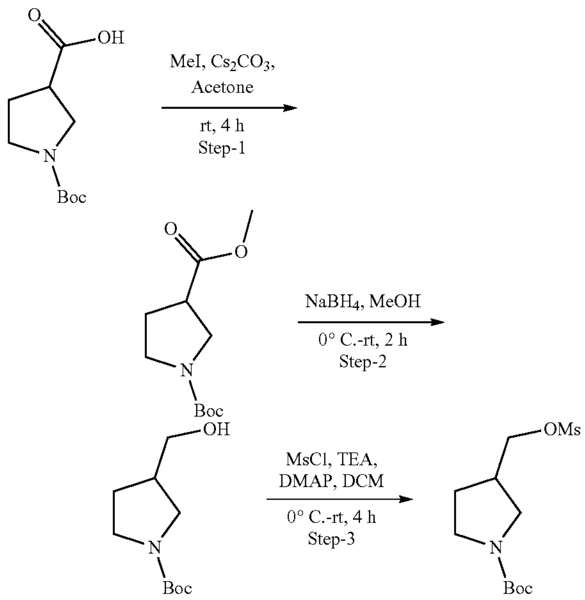

Step-1: Procedure for Synthesis of 1-(tert-butyl) 3-methyl pyrrolidine-1,3-dicarboxylate To a stirred solution of 1-(tert-butoxycarbonyl)pyrrolidine-3-carboxylic acid (5 g, 23.23 mmol, 1 eq) in acetone (20 mL), cesium carbonate (15.14 g, 46.46 mmol, 2 eq) followed by iodomethane (4.9 g, 34.85 mmol, 1.5 eq) were added. The reaction was stirred at room temperature for 4 h. The progress of the reaction was monitored by TLC. After completion of the reaction, the reaction mixture was concentrated under reduced pressure. The residue was dissolve in water and extracted with ethyl acetate. The combined organic layers were dried over anhydrous $Na_2SO_4$, filtered and concentrated under reduced pressure to dryness to afford the titled compound 1-(tert-butyl) 3-methyl pyrrolidine-1,3-dicarboxylate (3 g, crude). This compound was used in the next step without further purification. LCMS: 230.15 $[M+H]^+$.

Step-2: Procedure for Synthesis of tert-butyl 3-(hydroxymethyl)pyrrolidine-1-carboxylate To a stirred solution of 1-(tert-butyl) 3-methyl pyrrolidine-1,3-dicarboxylate (3 g, 13.33 mmol, 1 eq) in methanol (10 mL), sodium borohydride (1.5 g, 39.99 mmol, 3 eq) was added in portions at 0° C. The reaction was warmed to room temperature and stirred for 2 h. The progress of the reaction was monitored by TLC. After completion of the reaction, the reaction was quenched with water and extracted with ethyl acetate. The combined organic layers were dried over anhydrous $Na_2SO_4$, filtered and concentrated under reduced pressure. The crude product was purified by column chromatography on silica gel to afford the titled compound tert-butyl 3-(hydroxymethyl)pyrrolidine-1-carboxylate (1 g, 50%). LCMS: 202.15 $[M+H]^+$.

Step-3: Procedure for Synthesis of tert-butyl 3-(((methylsulfonyl)oxy)methyl)pyrrolidine-1-carboxylate To a stirred solution of tert-butyl 3-(hydroxymethyl) pyrrolidine-1-carboxylate (500 mg, 2.53 mmol, 1 eq), triethyl amine (0.71 mL, 5.07 mmol, 2 eq) and DMAP (31 mg, 0.025 mmol, 0.01 eq) in DCM (5 mL), methanesulfonyl chloride (0.24 mL, 3.04 mmol, 1.2 eq) was added dropwise at 0° C. The reaction was warmed to room temperature and stirred for 4 h. The progress of the reaction was monitored by TLC. After completion of the reaction, the reaction was quenched with water and extracted with ethyl acetate. The combined organic layers were dried over anhydrous $Na_2SO_4$, filtered and concentrated under reduced pressure to dryness to afford the titled compound tert-butyl 3-(((methylsulfonyl)oxy)methyl)pyrrolidine-1-carboxylate (600 mg, crude). This compound was used in the next step without further purification.

B. SYNTHETIC EXAMPLES

Example 1: Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention can be synthesized by following the steps outlined in General Schemes 1, 2, 3, and 4, which comprise different sequences of assembling intermediates III, IV, V, VI VII, and VIII. Starting materials are either commercially available or made by known procedures in the reported literature or as illustrated.

General Scheme 1

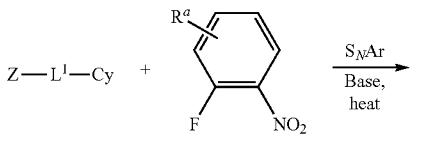

III IVa

-continued
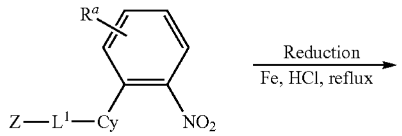
Va
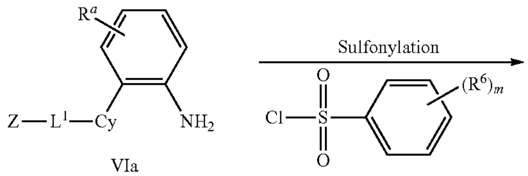
VIa
VIIa
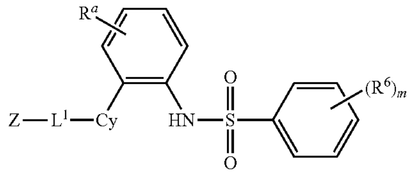
IIa-4
wherein Cy, $L^1$, $R^a$, $R^6$ and Z are as defined herein.
General Scheme 2
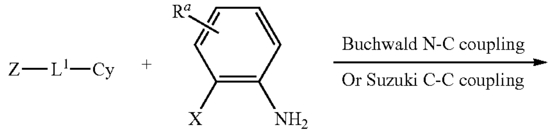
III
IVb
X =Br, I
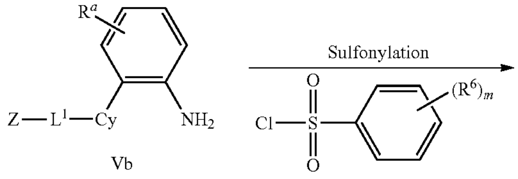
Vb
VIIa
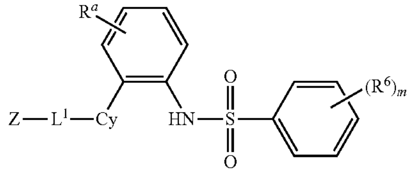
IIa-4
wherein Cy, $L^1$, $R^a$, $R^6$ and Z are as defined herein.
General Scheme 4
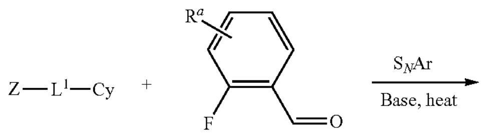
III
IVc
-continued
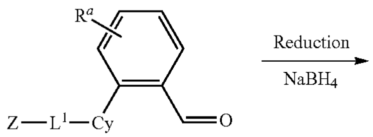
Vc
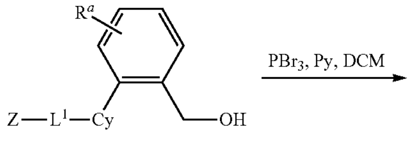
VIc
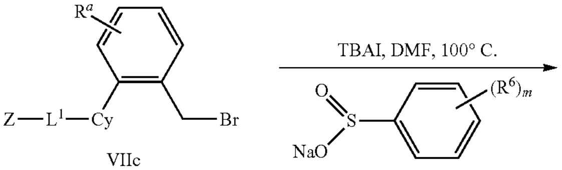
VIIc
VIII
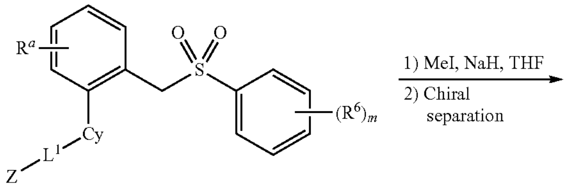
IId'
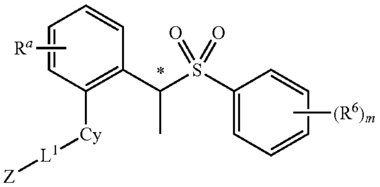
IId-2/IId-3
wherein Cy, Lt, $R^a$, $R^6$ and Z are as defined herein.
General Scheme 3
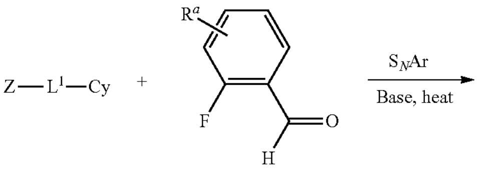
III
IVc
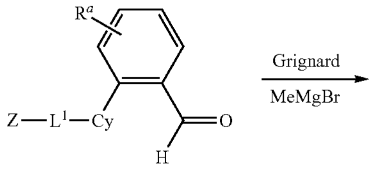
Vc -continued

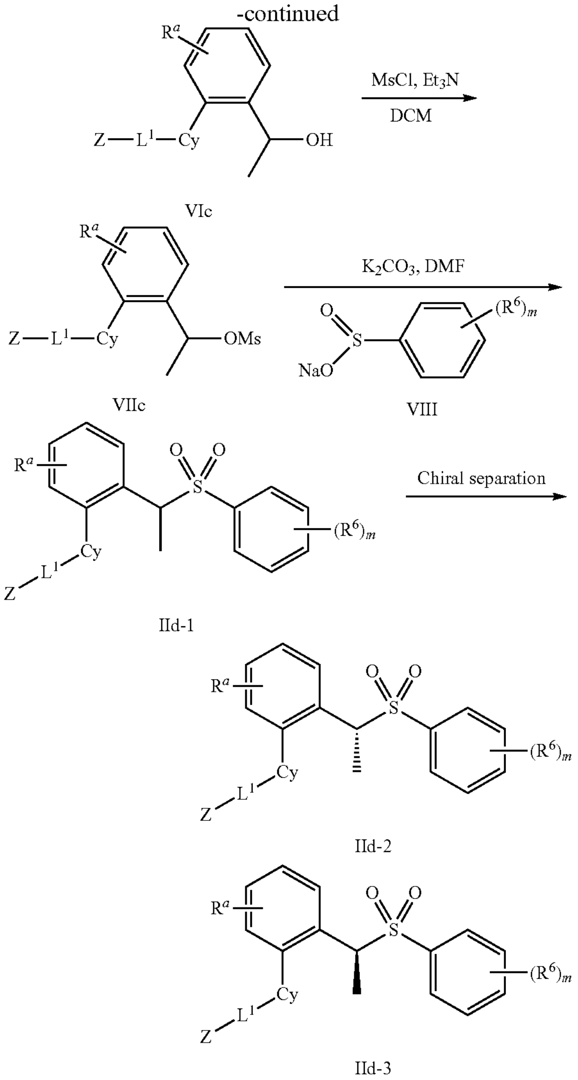

wherein Cy, $L^1$, $R^a$, $R^6$ and Z are as defined herein.

The general way of preparing target molecules IIa and IIc by using intermediates III, IV, V, VI, VII and VIII is outlined in General Scheme 1-4. Displacement of aryl halides (IV) with intermediates amine (III) under standard nucleophilic substitution conditions using base such as N,N-diisopropylethylamine, and/or potassium carbonate, cesium carbonate in solvent DMSO or DMF gives intermediate Va or Vc. Buchwald N—C coupling or Suzuki C—C coupling of aryl halides (IV) with 2° amine or boronic acid (III), in presence of palladium catalyst under elevated temperature also yield intermediate (Vb). Following multiple step chemical transformation from intermediate V to VII leads the formation of the final compounds of Formulae I, I', II, and/or II', as provided herein. A mixture of enantiomers, diastereomers, cis/trans isomers resulted from the process can be separated into their single components by chiral salt technique, chromatography using normal phase, reverse phase or chiral column, depending on the nature of the separation.

It should be understood that in the description and formulae shown above, the various groups Cy, $L^1$, $R^a$, $R^6$ and Z and other variables are as defined above, except where otherwise indicated. Furthermore, for synthetic purposes, the compounds of General Schemes 1-4 are mere representative with elected radicals to illustrate the general synthetic methodology of the compound of Formulae I, I', II, and/or II', as provided herein.

Example A1: Synthesis of N1-(2-(6'-fluoro-1'-methylspiro[cyclohexane-1,3'-indolin]-4-yl)phenyl)-N4, N4-dimethylbenzene-1,4-disulfonamide (A-305)

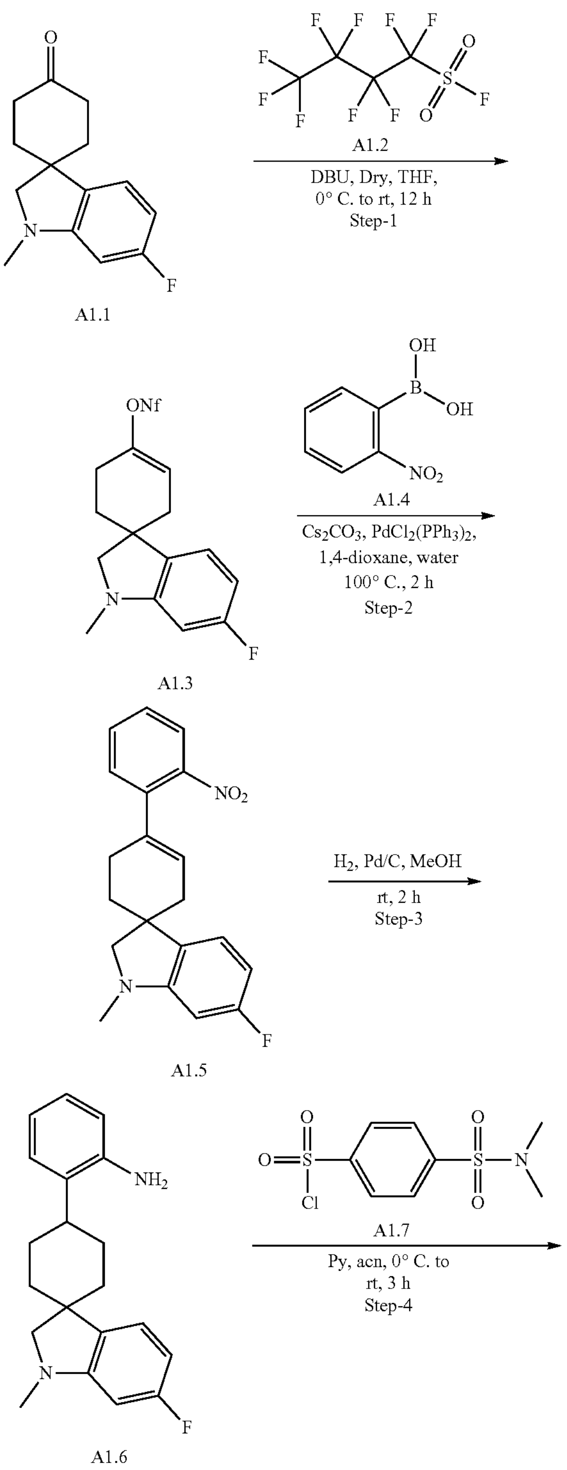

-continued

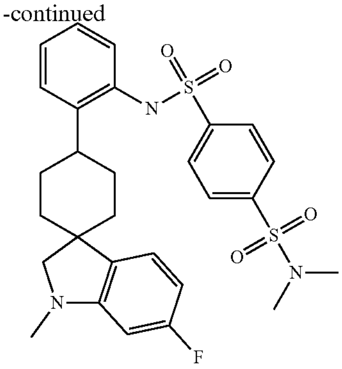

A305

Step-1: Procedure for Synthesis of 6'-fluoro-1'-methylspiro[cyclohexane-1,3'-indolin]-3-en-4-yl 1,1,2,2,3,3,4,4,4-nonafluorobutane-1-sulfonate (A1.3)

To a stirred solution of 6'-fluoro-1'-methylspiro[cyclohexane-1,3'-indolin]-4-one (A1.1) (720 mg 3 mmol, 1 eq) in THF (dry) (10 mL) was added DBU (1.17 mL, 7.7 mmol, 2.5 eq) at 0° C. and the reaction mixture was stirred at the same temperature for 10 min. 1,1,2,2,3,3,4,4,4-nonafluorobutane-1-sulfonyl fluoride (A1.2) (1.39 g, 4.6 mmol, 1.5 eq) was then added to the reaction mixture at 0° C. The reaction mixture was warmed to room temperature and stirred for 12 h. The progress of the reaction was monitored by TLC. After completion of the reaction, the reaction mixture was diluted with ethyl acetate and washed with water. The organic layer was dried over anhydrous $Na_2SO_4$, filtered and concentrated under reduced pressure. The crude product was purified by column chromatography on silica gel to afford the titled compound 6'-fluoro-1'-methylspiro[cyclohexane-1,3'-indolin]-3-en-4-yl 1,1,2,2,3,3,4,4,4-nonafluorobutane-1-sulfonate A1.3 (800 mg, 50.3%). LCMS: 516.10 $[M+H]^+$.

Step-2: Procedure for Synthesis of 2-(6'-fluoro-1'-methylspiro[cyclohexane-1,3'-indolin]-3-en-4-yl) nitrobenzene (A1.5)

A pyres tube was charged with a solution of 6'-fluoro-1'-methylspiro[cyclohexane-1,3'-indolin]-3-en-4-yl 1,1,2,2,3,3,4,4,4-nonafluorobutane-1-sulfonate (A1.3) (800 mg, 1.5 mmol, 1 eq), (2-Nitrophenyl)boronic acid (A1.4) (280 mg, 1.7 mmol, 1.1 eq) and cesium carbonate (1 g, 3.1 mmol, 2 eq) in a mixture of water (4 mL) and 1,4-dioxane (16 mL). The tube was sealed with a septum and the reaction mixture was purged with argon for 10 min. Bis(triphenylphosphine) palladium(II) dichloride (54 mg, 0.07 mmol, 0.05 eq) was then added to the reaction mixture under an argon atmosphere. The tube was then fitted with a screw cap and the reaction mixture was heated at 100° C. for 2 h. The progress of the reaction was monitored by TLC. After completion of the reaction, the reaction mixture was cooled to room temperature and filtered through a pad of Celite and the Celite pad was washed with ethyl acetate. The filtrate diluted with water and extracted with ethyl acetate. The combined organic layer was dried over anhydrous $Na_2SO_4$, filtered and concentrated under reduced pressure. The crude product was purified by column chromatography on silica gel to afford the titled compound 2-(6'-fluoro-1'-methylspiro[cyclohexane-1,3'-indolin]-3-en-4-yl)nitrobenzene (A1.5) (450 mg, 86.5%). LCMS: 339.15 $[M+H]^+$.

Step-3: Procedure for Synthesis of 2-(6'-fluoro-1'-methylspiro[cyclohexane-1,3'-indolin]-4-yl)aniline (A1.6)

An autoclave was charged with a solution of 2-(6'-fluoro-1'-methylspiro[cyclohexane-1,3'-indolin]-3-en-4-yl)nitrobenzene (A1.5) (450 mg, 1.3 mmol, 1 eq) in methanol (10 mL) was purged with nitrogen for 5 min. 10% Palladium on carbon (135 mg, 30% w/w) was added to the reaction mixture under nitrogen atmosphere. The reaction mixture was purged with hydrogen and stirred at room temperature for 2 h under hydrogen atmosphere (60 psi pressure). The progress of the reaction was monitored by TLC. After completion of the reaction, the reaction mixture was filtered through a pad of Celite and the Celite pad was washed with ethyl acetate. The filtrate was concentrated under reduced pressure to dryness. The crude product was purified by column chromatography on silica gel to afford the titled compound 2-(6'-fluoro-1'-methylspiro[cyclohexane-1,3'-indolin]-4-yl)aniline (A1.6) (200 mg, 47.8). LCMS: 313.20 $[M+H]^+$.

Step-4: Procedure for Synthesis of N-(2-(6'-fluoro-1'-methylspiro[cyclohexane-1,3'-indolin]-4-yl)phenyl)-N4,N4-dimethylbenzene-1,4-disulfonamide (A-305)

To a stirred solution of 2-(6'-fluoro-1'-methylspiro[cyclohexane-1,3'-indolin]-4-yl)aniline (A1.6) (200 mg, 0.6 mmol, 1 eq) in acetonitrile (4 mL) was added pyridine (0.1 mL, 1.2 mmol, 2 eq) at 0° C. and the reaction mixture was stirred at the same temperature for 10 min. Compound A1.7 (200 mg, 0.7 mmol, 1.1 eq) was then added to the reaction mixture at 0° C. The reaction mixture was warmed to room temperature and stirred for 3 h. The progress of the reaction was monitored by TLC. After completion of the reaction, the reaction mixture was diluted with ethyl acetate and washed with water. The organic layer was dried over anhydrous $Na_2SO_4$, filtered and concentrated under reduced pressure. The crude product was purified by column chromatography on silica gel to afford the titled compound N1-(2-(6'-fluoro-1'-methylspiro[cyclohexane-1,3'-indolin]-4-yl)phenyl)-N4,N4-dimethylbenzene-1,4-disulfonamide (A-305). Yield: 60 mg, 17.14%; Appearance: Off white solid; $^1H$ NMR (400 MHz, DMSO-$d_6$) δ 10.04 (s, 1H), 7.93 (d, J=8.0 Hz, 2H), 7.87 (d, J=8.0 Hz, 2H), 7.42-7.14 (m, 2H), 7.27 (t, J=8.0 Hz, 1H), 7.16 (t, J=6.8 Hz, 1H), 7.04 (d, J=8.0 Hz, 1H), 6.38-6.31 (m, 2H), 3.04 (s, 2H), 2.74-2.65 (m, 1H), 2.68 (s, 3H), 2.62 (s, 6H), 1.73-1.55 (m, 4H), 1.44-1.33 (m, 2H), 1.12 (d, J=12.0 Hz, 2H); HPLC purity: 99.52%; LCMS Calculated for $C_{28}H_{32}FN_3O_4S_2$: 557.18; Observed: 558.40 $[M+H]^+$.

Example A2: Synthesis of 4-((4-(1-(4-chloro-2-fluorophenyl)piperidin-4-yl)-2-methyl-1H-imidazol-1-yl)sulfonyl)-N,N-dimethylbenzenesulfonamide (A-39)
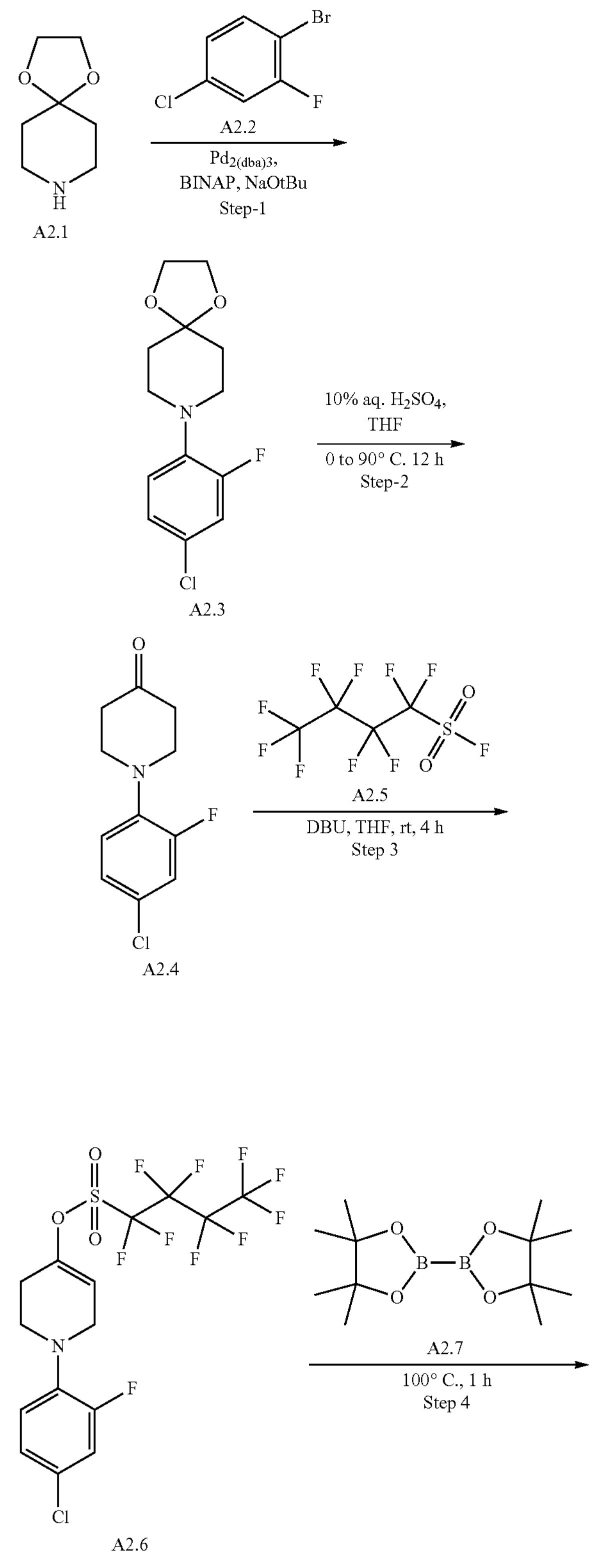
A2.1
A2.2
A2.3
A2.4
A2.5
A2.6
A2.7
-continued
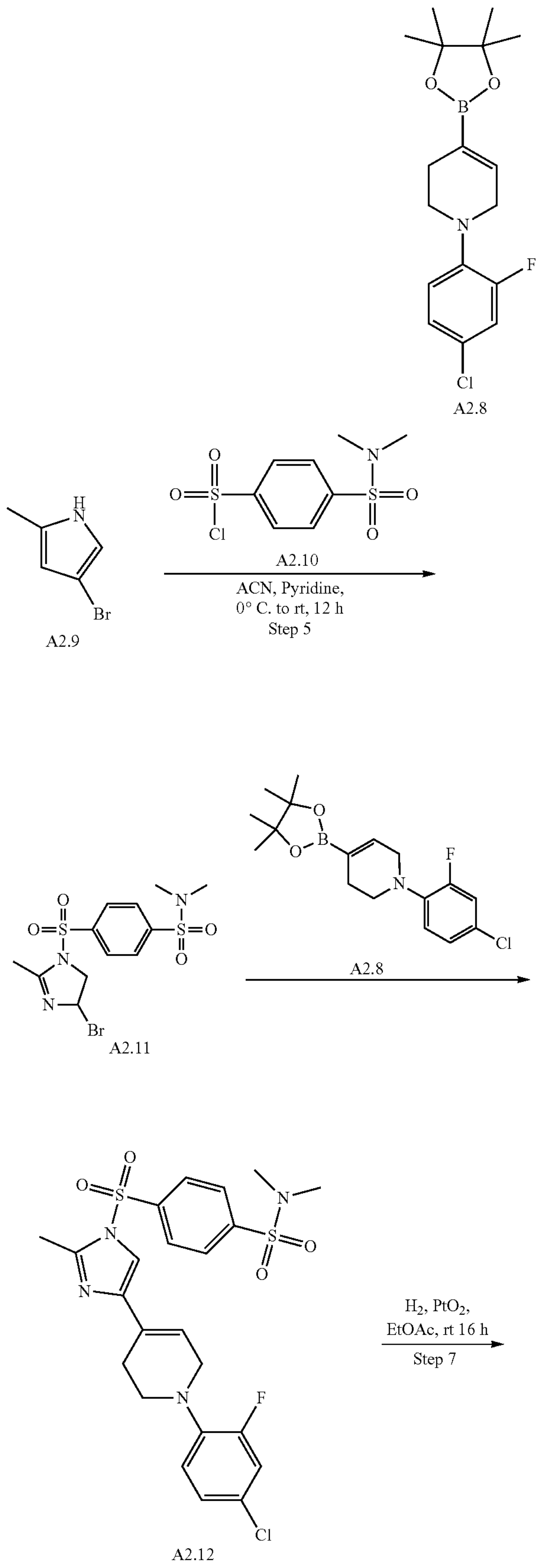
A2.8
A2.9
A2.10
A2.11
A2.8
A2.12

-continued

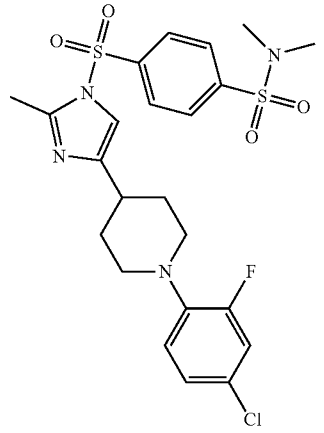

A-39

Step-1: Procedure for Synthesis of 8-(4-chloro-2-fluorophenyl)-1,4-dioxa-8-azaspiro[4.5]decane (A2.3)

To a stirred mixture of 1,4-dioxa-8-azaspiro[4.5]decane (A2.1) (26 g, 124 mmol, 1 eq) and 1-bromo-4-chloro-2-fluorobenzene 2.2 (18 g, 130 mmol, 1.05 eq) in 1,4-dioxane (250 mL) was added NaOtBu (23 g, 248 mmol, 2 eq) (0.1 eq), purged reaction mixture with argon for 20 min followed by the addition of Tris(dibenzylideneacetone)dipalladium(0) (3.4 g, 3.7 mmol, 0.03 eq) and BINAP (4.62 g, 7.4 mmol, 0.06 eq). The reaction mixture was stirred at 80° C. for 2 h. The progress of the reaction was monitored by TLC. After completion of the reaction, the reaction mixture was cooled to room temperature, filtered through a pad of Celite, the Celite pad was washed with ethyl acetate and the filtrate was evaporated to dryness under reduced pressure. The crude was purified by column chromatography on silica gel to afford 8-(4-chloro-2-fluorophenyl)-1,4-dioxa-8-azaspiro[4.5]decane (A2.3) (20 g, 60%). LCMS: 272.08 $[M+H]^+$.

Step-2: Procedure for Synthesis of 1-(4-chloro-2-fluorophenyl)piperidin-4-one (A2.4)

To a stirred solution of 8-(4-chloro-2-fluorophenyl)-1,4-dioxa-8-azaspiro[4.5]decane (A2.3) (20 g) in THE (70 mL), 10% $H_2SO_4$ (300 mL) was added at 0° C. The resulting reaction mixture was stirred at 90° C. for 12 h. The progress of the reaction was monitored by TLC. After completion, the reaction mixture was quenched with saturated aqueous solution of sodium bicarbonate and extracted with ethyl acetate. The combined organic layers were washed with water and brine, dried over anhydrous sodium sulfate and evaporated under reduced pressure. The crude product was purified by column chromatography on silica gel to afford 1-(4-chloro-2-fluorophenyl)piperidin-4-one (A2.4) (15 g, 89%). LCMS: 228.05 $[M+H]^+$.

Step-3: Procedure for Synthesis of 1-(4-chloro-2-fluorophenyl)-1,2,3,6-tetrahydropyridin-4-yl 1,1,2,2,3,3,4,4,4-nonafluorobutane-1-sulfonate (A2.6)

To a stirred mixture of 1-(4-chloro-2-fluorophenyl)piperidin-4-one (A2.4) (5 g, 22.05 mmol, 1 eq) and 1,1,2,2,3,3,4,4,4-nonafluorobutane-1-sulfonyl fluoride (A2.5) (4.5 mL, 26.46 mmol, 1.2 eq) in THE (50 mL) DBU (3.9 mL, 26.46 mmol, 1.2 eq) was added and stirred at room temperature for 4 h. The progress of the reaction was monitored by TLC. After completion of the reaction, the reaction mixture was concentrated under reduced pressure. The crude product was purified by column chromatography on silica gel to afford 1-(4-chloro-2-fluorophenyl)-1,2,3,6-tetrahydropyridin-4-yl 1,1,2,2,3,3,4,4,4-nonafluorobutane-1-sulfonate (A2.6) (9 g, 80%). LCMS: 509.99 $[M+H]^+$.

Step-4: Procedure for Synthesis of 1-(4-chloro-2-fluorophenyl)-4-(4,4,5,5-tetramethyl-1,3,2-dioxaborolan-2-yl)-1,2,3,6-tetrahydropyridine (A2.8)

To a mixture of 1-(4-chloro-2-fluorophenyl)-1,2,3,6-tetrahydropyridin-4-yl 1,1,2,2,3,3,4,4,4-nonafluorobutane-1-sulfonate (A2.6) (9 g, 17.68 mmol, 1 eq) and bispinacolato diboron (A2.7) (4.47 g, 17.68 mmol, 1 eq) in 1,4-dioxane (70 mL), purged the reaction mixture with argon for 10 min followed by the addition of dppf (0.29 g, 0.053 mmol, 3 eq) and [1,1'-Bis(diphenylphosphino)ferrocene]-dichloropalladium(II) (0.39 g, 0.53 mmol, 0.03 eq) and stirred at 100° C. for 1 h. The progress of the reaction was monitored by TLC. After completion of the reaction, the reaction mixture was cooled to room temperature, diluted ethyl acetate and water. The organic layer was washed with water and brine, dried over anhydrous sodium sulfate and evaporated under reduced pressure. The crude product was purified by column chromatography on silica gel to afford 1-(4-chloro-2-fluorophenyl)-4-(4,4,5,5-tetramethyl-1,3,2-dioxaborolan-2-yl)-1,2,3,6-tetrahydropyridine (A2.8). Yield: 4.5 g, 76%; Appearance: Pale yellow solid; $^1H$ NMR (400 MHz, $CdCl_3$) δ 7.09-6.93 (m, 2H), 6.88 (t, J=9.1 Hz, 1H), 6.59 (dq, J=4.5, 2.2 Hz, 1H), 3.68 (q, J=2.9 Hz, 2H), 3.18 (q, J=6.4, 6.0 Hz, 2H), 2.40 (m, J=6.8, 3.5, 2.9 Hz, 2H), 1.28 (d, J=5.1 Hz, 12H); LCMS Calculated for $C_{17}H_{22}BClFNO_2$: 337.14; Observed: 338.14 $[M+H]^+$.

Step-5: General Procedure for Synthesis of 4-((4-bromo-2-methyl-1H-imidazol-1-yl)sulfonyl)-N,N-dimethylbenzenesulfonamide (A2.11)

To a stirred solution of 4-bromo-2-methyl-1H-imidazole (A2.9) (0.5 g, 3.11 mmol, 1 eq) in acetonitrile (20 mL) was added pyridine (0.5 g, 6.21 mmol, 2 eq) at 0° C. followed by addition of 4-(N,N-dimethylsulfamoyl)benzenesulfonyl chloride (A2.10) (0.97 g, 3.42 mmol, 1.1 eq) at 0° C. The reaction mixture was stirred at room temperature for 12 h. The progress of the reaction was monitored by TLC. After completion of the reaction, the precipitated solid was filtered, washed with acetonitrile. The reaction mixture was quenched with water and extracted with ethyl acetate. The combined organic layers were washed with water and brine, dried over anhydrous $Na_2SO_4$, filtered and concentrated under reduced pressure. The crude was purified by column chromatography followed by prep HPLC to afford 4-((4-bromo-2-methyl-1H-imidazol-1-yl)sulfonyl)-N,N-dimethylbenzenesulfonamide (A2.11) (1 g, 79.3%). LCMS: 407.96 $[M+H]^+$.

Step-6: General Procedure for Synthesis of 4-((4-(1-(4-chloro-2-fluorophenyl)-1,2,3,6-tetrahydropyridin-4-yl)-2-methyl-1H-imidazol-1-yl)sulfonyl)-N,N-dimethylbenzenesulfonamide (A2.12)

To a stirred solution of 4-((4-bromo-2-methyl-1H-imidazol-1-yl)sulfonyl)-N,N-dimethylbenzenesulfonamide (A2.11) (0.25 g, 0.61 mmol, 1 eq) and 1-(4-chloro-2-fluorophenyl)-4-(4,4,5,5-tetramethyl-1,3,2-dioxaborolan-2-yl)-1,2,3,6-tetrahydropyridine (A2.8) (0.27 g, 0.80 mmol, 1.3 eq) in 1,4-dioxane and water (10:2 mL) was added $Cs_2CO_3$ (0.4 g, 1.23 mmol, 2 eq) and $PdCl_2(PPh_3)_2$ (0.043 g, 0.061 mmol, 0.1 eq) at room temperature. The reaction mixture was stirred at 65° C. for 7 h; the reaction progress was monitored by TLC. After completion, the reaction mixture was cooled to room temperature, diluted with water and extracted with ethyl acetate. The combined organic layers were washed with water, dried over $Na_2SO_4$ and concentrated. The crude residue was purified by column chromatography on silica gel to afford compound 4-((4-(1-(4-chloro-2-fluorophenyl)-1,2,3,6-tetrahydropyridin-4-yl)-2-methyl-1H-imidazol-1-yl)sulfonyl)-N,N-dimethylbenzenesulfonamide (A2.12) (0.24 g, 71.1%). LCMS: 539.09 $[M+H]^+$.

Step-7: General Procedure for Synthesis of 4-((4-(1-(4-chloro-2-fluorophenyl)piperidin-4-yl)-2-methyl-1H-imidazol-1-yl)sulfonyl)-N,N-dimethylbenzenesulfonamide (A2.13)

To a stirred solution of 4-((4-(1-(4-chloro-2-fluorophenyl)-1,2,3,6-tetrahydropyridin-4-yl)-2-methyl-1H-imidazol-1-yl)sulfonyl)-N,N-dimethylbenzenesulfonamide (A2.12) (0.23 g, 0.43 mmol, 1 eq) in ethyl acetate (25 mL) was added $PtO_2$ (0.12 g) at room temperature. The reaction mixture was stirred under hydrogen gas pressure (75 psi) at room temperature for 16 h. The progress of the reaction was monitored by TLC. After completion, the reaction mixture was filtered through a pad of Celite, the Celite pad was washed with ethyl acetate and the filtrate was evaporated under reduced pressure. The crude product was purified by column chromatography on silica gel to afford 4-((4-(1-(4-chloro-2-fluorophenyl)piperidin-4-yl)-2-methyl-1H-imidazol-1-yl)sulfonyl)-N,N-dimethylbenzenesulfonamide (A-39). Yield: 10 mg, 4.33%; Appearance: Off-white solid; $^1H$ NMR (400 MHz, DMSO-$d_6$) δ 8.28 (d, J=8.2 Hz, 2H), 8.04 (d, J=8.2 Hz, 2H), 7.50 (s, 1H), 7.31 (dd, J=12.4, 2.5 Hz, 1H), 7.17 (dd, J=8.7, 2.5 Hz, 1H), 7.06 (t, J=9.1 Hz, 1H), 3.39-3.33 (m, 2H), 2.78-2.68 (m, 8H), 2.61 (m, 1H), 2.47 (m, 3H), 2.00-1.92 (m, 2H), 1.68 (tt, J=12.0, 6.1 Hz, 2H); HPLC purity: >99%; LCMS Calculated for $C_{23}H_{26}ClFN_4O_4S_2$: 540.11; Observed: 541.30 $[M+H]^+$.

The following examples were prepared using standard chemical manipulations and procedures similar to those used for the preparation of the previous example.

| Compound No. | Structure | Analytical data |
| --- | --- | --- |
| A-37 | 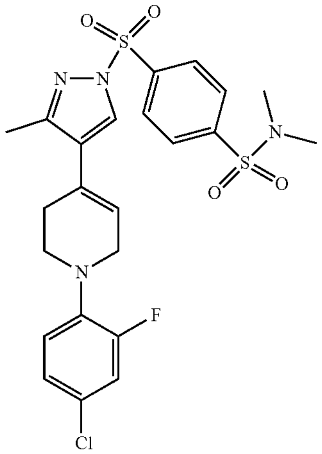 | Yield: 0.46 mg, 58.97%; Appearance: Off-white solid; $^1H$ NMR (400 MHz, DMSO-$d_6$) δ 8.46 (s, 1H), 8.19 (d, J = 7.6 Hz, 2H), 8.02 – 8.0 (m, 2H), 7.35 – 7.32 (m, 1H), 7.17 (m, 1H), 7.08 (t, J = 9.6 Hz, 1H), 6.08 (m, 1H), 3.69 (m, 2H), 3.25 (m, 4H), 2.65 (s, 6H), 2.29 (s, 3H); HPLC purity: 97.41%; LCMS Calculated for $C_{23}H_{24}ClFN_4O_4S_2$: 538.09; Observed: 539.1 $[M + H]^+$. |
| A-38 | 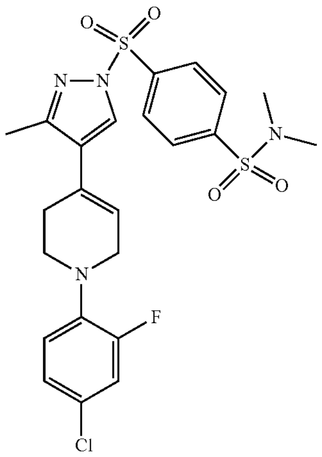 | Yield: 0.04 g, 25%; Appearance: White solid; $^1H$ NMR (400 MHz, DMSO-$d_6$) δ 8.28 (s, IH), 8.24 – 8.14 (m, 2H), 8.05 – 7.97 (m, 2H), 7.32 (dd, J = 12.4, 2.4 Hz, 1H), 7.17 (ddd, J = 8.7, 2.4, 1.0 Hz, 1H), 7.07 (t, J = 9.1 Hz, 1H), 3.37 (d, J = 12.3 Hz, 2H), 2.74 (t, J = 11.6 Hz, 2H), 2.66 (s, 6H), 2.60 – 2.47 (m, 1H), 2.19 (s, 3H), 1.87 (d, J = 12.3 Hz, 2H), 1.74 – 1.64 (m, 2H); HPLC purity: 98.86%; LCMS Calculated for $C_{23}H_{26}ClFN_4O_4S_2$: 540.11; Observed: 541.30 $[M + H]^+$. |

-continued

| Compound No. | Structure | Analytical data |
|---|---|---|
| A-84 | 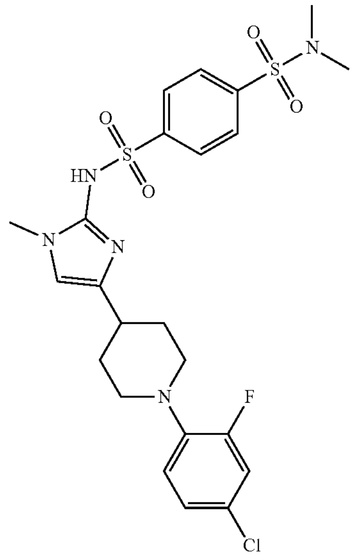 | Yield: 0.01 g, 6.66%; Appearance: Off-white solid; $^1$H NMR (400 MHz, DMSO-$d_6$) δ 11.39 (s, 1H), 8.07 - 8.05 (m, 2H), 7.86 - 7.84 (m, 2H), 7.33 (m, 1H), 7.17 (d, J = 8 Hz, 1H), 7.08 (t, J = 9.2 Hz, 1H), 6.71 (s, 1H), 3.38 - 3.35 (m, 2H), 3.25 (s, 3H), 2.73 - 2.68 (m, 3H), 2.64 (s, 6H), 1.99 - 1.96 (m, 2H), 1.62 - 1.53 (m, 2H); HPLC purity: >99%; LCMS Calculated for $C_{23}H_{27}ClFN_5O_4S_2$: 555.12; Observed: 556.10 [M + H]$^+$. |

Example A3: Synthesis of N1-(5-(1-(4-chloro-2-fluorophenyl)piperidin-4-yl)-1,3-dimethyl-1H-pyrazol-4-yl)-N4,N4-dimethylbenzene-1,4-disulfonamide (A-33) and N1-(5-(1-(4-chloro-2-fluorophenyl)-1,2,3,6-tetrahydropyridin-4-yl)-1,3-dimethyl-1H-pyrazol-4-yl)-N4,N4-dimethylbenzene-1,4-disulfonamide (A-29)

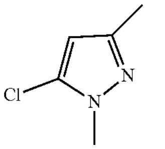

A3.1

$KNO_3$, $H_2SO_4$,
0° C. 1 h
Step 1

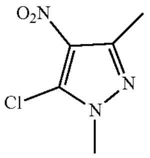

A3.2

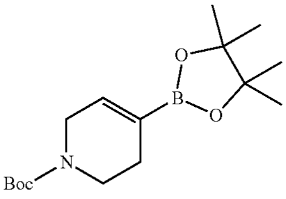

A2.3

2M $Na_2CO_3$, $Pd(PPh_3)_4$
1,4-Dioxane,
100° C., 4 h
Step-2

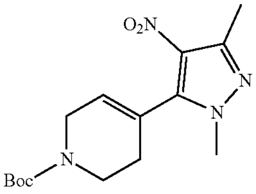

A3.4

TFA,DCM
12 h, 0° C. to RT
Step 3

-continued

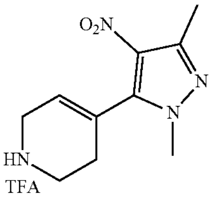

TFA

A3.5

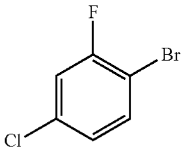

A3.6

$Pd_{2(dba)3}$, Davephos
$Cs_2CO_3$, 1,4-dioxane
90° C., 1 h
Step-4

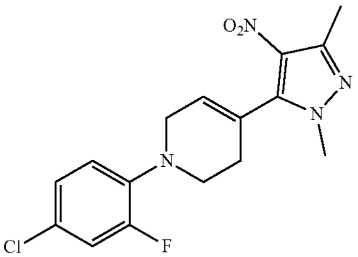

A3.7

Fe, $NH_4Cl$,
EtOH,
$H_2O$, 90° C.,
3 h
Step-5

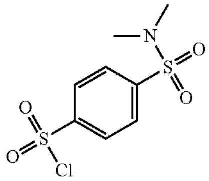

A3.9

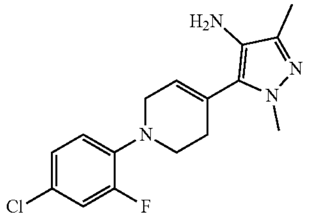

A3.8

-continued

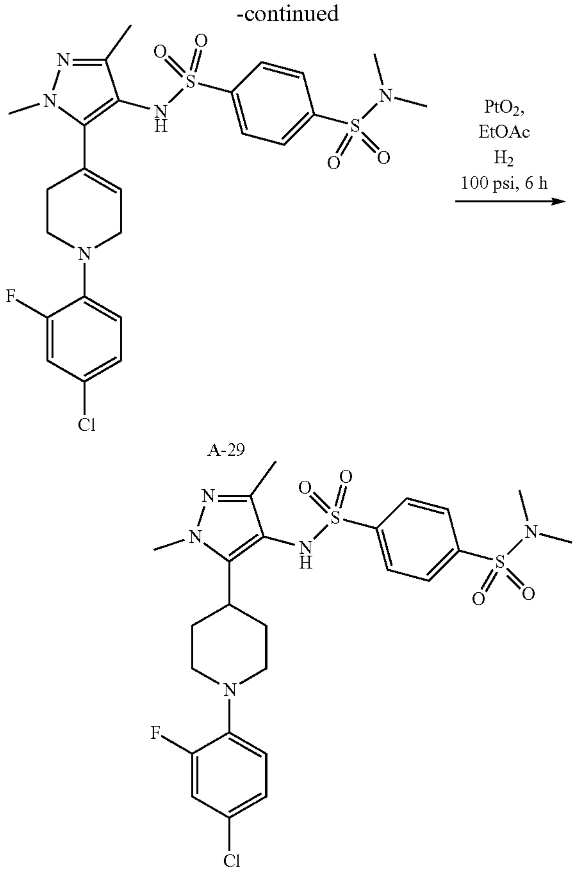

A-29

A-33

Step-1: Synthesis of 5-chloro-1,3-dimethyl-4-nitro-1H-pyrazole (A3.2)

To a stirred solution of 5-chloro-1,3-dimethyl-1H-pyrazole (A3.1) (3.85 g, 29.6 mmol, 1 eq) in $H_2SO_4$ (15 mL) was added portion wise $KNO_3$ (3.59 g, 35.5 mmol, 1.2 eq) at 0° C. The reaction mixture was stirred at 0° C. for 1 h. The progress of the reaction was monitored by TLC. After completion of the reaction, the reaction mixture poured into ice water. The obtained solid separated, dissolved in DCM and washed with water. The combined organic layers were washed with brine, dried over anhydrous sodium sulfate and concentrated under reduced pressure to afford the desired product 5-chloro-1,3-dimethyl-4-nitro-1H-pyrazole (A3.2) (3.8 g, 73%). LCMS: 176.01 $[M+H]^+$.

Step-2: Synthesis of tert-butyl 4-(1,3-dimethyl-4-nitro-1H-pyrazol-5-yl)-3,6-dihydropyridine-1(2H)-carboxylate (A3.4)

To a stirred solution of 5-chloro-1,3-dimethyl-4-nitro-1H-pyrazole (A3.2) (2 g, 11 mmol, 1 eq) and tert-butyl 4-(4,4,5,5-tetramethyl-1,3,2-dioxaborolan-2-yl)-3,6-dihydropyridine-1(2H)-carboxylate (A3.3) (3.88 g, 12.5 mmol, 1.1 eq) in 1,4-dioxane (50 mL) was added 2 M $Na_2CO_3$ (3.29 g, 34.2 mmol, 3 eq) purged reaction mixture with argon for 15 min followed by the addition of Tetrakis(triphenylphosphine) palladium(0) (1.32 g, 1.14 mmol, 0.1 eq) and stirred at 100° C. for 4 h. The progress of the reaction was monitored by TLC. After completion of the reaction, the reaction mixture was filtered through Celite and evaporated to dryness. The residue was dissolved in ethyl acetate, washed with water, brine, dried over anhydrous sodium sulfate and evaporated under reduced pressure. The crude product was purified by column chromatography to afford the desired product tert-butyl 4-(1,3-dimethyl-4-nitro-1H-pyrazol-5-yl)-3,6-dihydropyridine-1(2H)-carboxylate (A3.4) (3.5 g, 94%). LCMS: 323.16 $[M+H]^+$.

Step-3: Synthesis of 4-(1,3-dimethyl-4-nitro-1H-pyrazol-5-yl)-1,2,3,6-tetrahydropyridine, TFA Salt (A3.5)

To a stirred solution of tert-butyl 4-(1,3-dimethyl-4-nitro-1H-pyrazol-5-yl)-3,6-dihydropyridine-1(2H)-carboxylate (A3.4) (3.5 g, 10.8 mmol, 1 eq) in DCM (40 mL) was added dropwise TFA (20 mL) at 0° C. The reaction mixture was stirred at room temperature for 12 h; the reaction progress was monitored by TLC. After completion, the reaction mixture was concentrated under reduced pressure. The crude was triturated with diethyl ether, obtained precipitate was filtered and concentrated to provide the desired compound 4-(1,3-dimethyl-4-nitro-1H-pyrazol-5-yl)-1,2,3,6-tetrahydropyridine, TFA salt (A3.5) (2 g, 82%).

Step-4: Synthesis of 1-(4-chloro-2-fluorophenyl)-4-(1,3-dimethyl-4-nitro-1H-pyrazol-5-yl)-1,2,3,6-tetrahydropyridine (A3.7)

To a stirred mixture of 4-(1,3-dimethyl-4-nitro-1H-pyrazol-5-yl)-1,2,3,6-tetrahydropyridine, TFA salt. (A3.5) (2 g, 5.9 mmol, 1 eq), 1-bromo-4-chloro-2-fluorobenzene (A3.6) (1.37 g, 6.5 mmol, 1.1 eq) in 1.4 dioxane (100 mL) was added followed by $Cs_2CO_3$ (3.88 g, 11.9 mmol, 2 eq) purged the reaction mixture with argon followed by addition of Davephos (0.47 gm 11.9 mmol, 0.2 eq) and $Pd_2(dba)_3$ (0.54 g, 0.59 mmol, 0.1 eq). The reaction mixture was stirred at 90° C. for 1 h. The progress of the reaction was monitored by TLC. After completion of the reaction, the reaction mixture was filtered through celite and the filtrate was concentrated under reduced pressure. The crude product was purified by column chromatography to afford the desired product 1-(4-chloro-2-fluorophenyl)-4-(1,3-dimethyl-4-nitro-1H-pyrazol-5-yl)-1,2,3,6-tetrahydropyridine (A3.7) (1.5 g, 63.5%). LCMS: m/z 351.09 $[M+H]^+$.

Step-5: Synthesis of 5-(1-(4-chloro-2-fluorophenyl)-1,2,3,6-tetrahydropyridin-4-yl)-1,3-dimethyl-1H-pyrazol-4-amine (A3.8)

To a stirred solution of 1-(4-chloro-2-fluorophenyl)-4-(1,3-dimethyl-4-nitro-1H-pyrazol-5-yl)-1,2,3,6-tetrahydropyridine (A3.7) (0.6 g, 1.7 mmol, 1 eq) in mixture of ethanol (20 mL) and water (6 mL) was added ammonium chloride (0.45 g, 8.5 mmol, 5 eq) followed by addition of Fe powder (0.47 g, 8.57 mmol, 5 eq) at room temperature. The resulting reaction mixture was refluxed at 90° C. for 3 h. The progress of the reaction was monitored by TLC. After completion of the reaction, the reaction mixture was filtered through Celite and the filtrate was evaporated to dryness. The crude was diluted with water and extracted with ethyl acetate, washed with water, brine, dried over anhydrous sodium sulfate and evaporated under reduced pressure. The crude product was purified by column chromatography to afford the desired product 5-(1-(4-chloro-2-fluorophenyl)-1,2,3,6-tetrahydropyridin-4-yl)-1,3-dimethyl-1H-pyrazol-4-amine A3.8 (500 mg, 90%). 321.12: $[M+H]^+$.

Step-6: Synthesis of N1-(5-(1-(4-chloro-2-fluorophenyl)-1,2,3,6-tetrahydropyridin-4-yl)-1,3-dimethyl-1H-pyrazol-4-yl)-N4,N4-dimethylbenzene-1,4-disulfonamide (A-29)

To a stirred solution of 5-(1-(4-chloro-2-fluorophenyl)-1,2,3,6-tetrahydropyridin-4-yl)-1,3-dimethyl-1H-pyrazol-4-amine (A3.8) (100 mg, 0.31 mmol, 1 eq) and 4-(N,N-dimethylsulfamoyl)benzenesulfonyl chloride (A3.9) (0.11 gm 0.37 mmol, 1.2 eq) in acetonitrile (3 mL) was added pyridine (0.075 mL, 0.93 mmol, 3 eq) at room temperature. The reaction mixture was stirred at room temperature for 12 h. The progress of the reaction was monitored by TLC. After completion, the reaction mixture was concentrated under reduced pressure. The crude was purified by prep HPLC to afford the titled compound N1-(5-(1-(4-chloro-2-fluorophenyl)-1,2,3,6-tetrahydropyridin-4-yl)-1,3-dimethyl-1H-pyrazol-4-yl)-N4,N4-dimethylbenzene-1,4-disulfonamide (A-29). Yield: 35 mg, 19%; Appearance: Off-white solid; $^1$H NMR (400 MHz, DMSO-$d_6$) δ 9.49 (bs, 1H), 7.93-7.83 (m, 4H), 7.31 (dd, J=12.6, 2.5 Hz, 1H), 7.15 (ddd, J=8.6, 2.6, 1.2 Hz, 1H), 7.02 (t, J=9.1 Hz, 1H), 5.65 (m, 1H), 3.53 (d, J=14.3 Hz, 5H), 2.98 (t, J=5.5 Hz, 2H), 2.58 (s, 6H), 2.17 (d, J=4.0 Hz, 2H), 1.71 (s, 3H); HPLC purity: 98.3%; LCMS Calculated for $C_{24}H_{27}ClFN_5O_4S_2$: 567.12; Observed: 568.35 [M+H]$^+$.

Step-7: Synthesis of N1-(5-(1-(4-chloro-2-fluorophenyl)piperidin-4-yl)-1,3-dimethyl-1H-pyrazol-4-yl)-N4,N4-dimethylbenzene-1,4-disulfonamide (A-33)

To a stirred solution of N1-(5-(1-(4-chloro-2-fluorophenyl)-1,2,3,6-tetrahydropyridin-4-yl)-1,3-dimethyl-1H-pyrazol-4-yl)-N4,N4-dimethylbenzene-1,4-disulfonamide (A-29) (0.20 g, 0.35 mmol, 1 eq) in ethyl acetate (10 mL) was added $PtO_2$ (0.10 g) under nitrogen atmosphere. The reaction mixture was stirred at 100 psi hydrogen gas pressure at room temperature for 6 h. The progress of the reaction was monitored by TLC. After completion, the reaction mixture was filtered through a pad of Celite and the Celite pad was washed with ethyl acetate. The filtrate was evaporated under reduced pressure. The crude was purified by column chromatography followed by prep HPLC to afford the titled compound N1-(5-(1-(4-chloro-2-fluorophenyl)piperidin-4-yl)-1,3-dimethyl-1H-pyrazol-4-yl)-N4,N4-dimethylbenzene-1,4-disulfonamide (A-33). Yield: 50 mg, 25%; Appearance: Off-white solid; $^1$H NMR (400 MHz, DMSO-$d_6$) δ 9.51 (s, 1H), 7.96 (m, 4H), 7.38-7.29 (m, 1H), 7.23-7.15 (m, 1H), 7.06 (t, J=9.0 Hz, 1H), 3.71 (s, 3H), 3.33 (m, 2H), 2.64-2.50 (m, 9H), 2.11-1.96 (m, 2H), 1.48 (d, J=32.2 Hz, 5H); HPLC purity: 96.85%; LCMS Calculated for $C_{24}H_{29}ClFN_5O_4S_2$:569.13; Observed: 570.1 [M+H]$^+$.

Example A4: Synthesis of N1-(4-(1-(4-chloro-2-fluorophenyl)piperidin-4-yl)-1,3-dimethyl-1H-pyrazol-5-yl)-N4,N4-dimethylbenzene-1,4-disulfonamide (A-75)

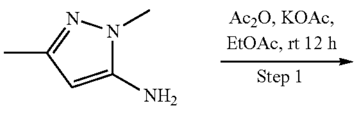

A4.1

-continued

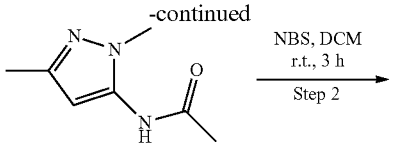

A4.2

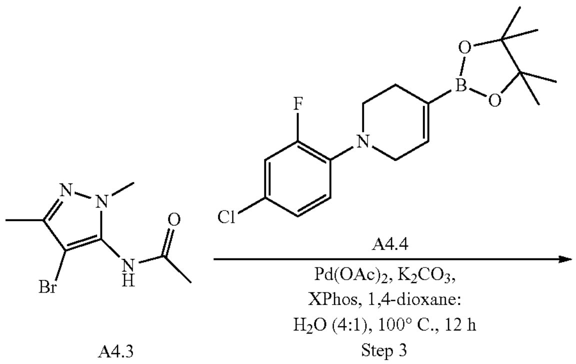

A4.3

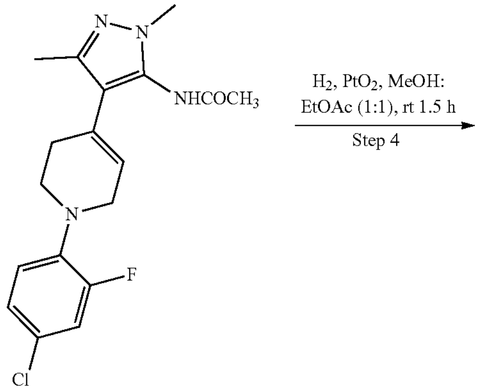

A4.5

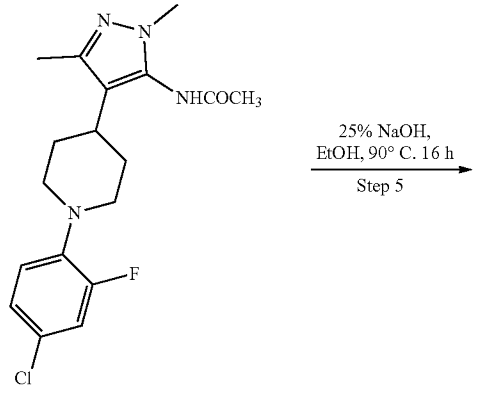

A4.6

-continued

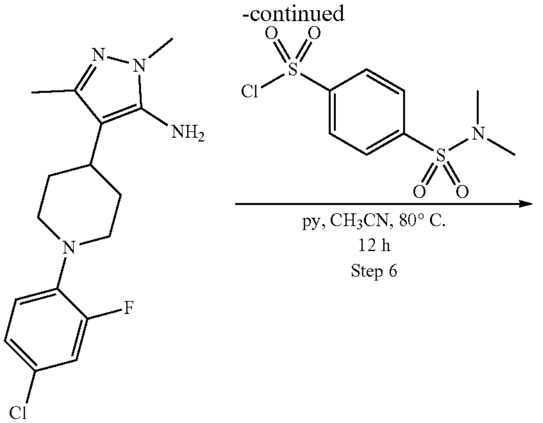

A4.6

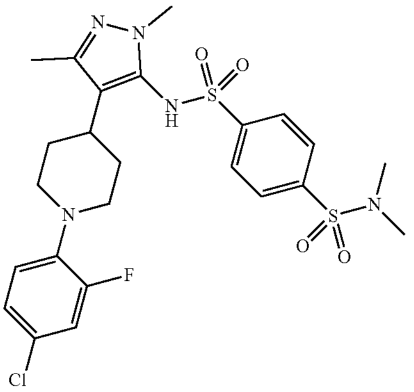

A-75

Step-1: Synthesis of N-(1,3-dimethyl-1H-pyrazol-5-yl)acetamide (A4.2)

To a stirred solution of 1,3-dimethyl-1H-pyrazol-5-amine (A4.1) (3 g, 27 mmol, 1 eq) in ethyl acetate (30 mL) was added potassium acetate (2.91 g, 29.70 mmol, 1.1 eq) and acetic anhydride (3.03 g, 29.7 mmol, 1.1 eq) at 0° C. The reaction mixture was stirred at room temperature for 12 h. The progress of reaction was monitored by TLC. After completion of the reaction, the reaction mixture was diluted with water and extracted with ethyl acetate, washed with brine, dried over anhydrous sodium sulfate and evaporated under reduced pressure. The crude product was purified by column chromatography to afford the desired product N-(1,3-dimethyl-1H-pyrazol-5-yl)acetamide A4.2 (4 g, 96.8%). LCMS: 154.09 [M+H]$^+$.

Step-2: Synthesis of N-(4-bromo-1,3-dimethyl-1H-pyrazol-5-yl)acetamide (A4.3)

To a stirred solution of N-(1,3-dimethyl-1H-pyrazol-5-yl) acetamide (A4.2) (4 g, 26.14 mmol, 1 eq) in DCM (40 mL) was added NBS (5.58 g, 31.37 mmol, 1.2 eq) at 0° C. The reaction mixture was stirred at room temperature for 3 h. The progress of reaction was monitored by TLC. After completion, the reaction mixture was diluted with DCM and washed with sodium thiosulphate solution. The organic layer was separated, washed with brine, dried over anhydrous $Na_2SO_4$, filtered and concentrated under reduced pressure to provide titled compound N-(4-bromo-1,3-dimethyl-1H-pyrazol-5-yl)acetamide (A4.3) (5.5 g, crude). The crude was used as such for next step without purification. LCMS: 232 [M+H]$^+$.

Step-3: Synthesis of N-(4-(1-(4-chloro-2-fluorophenyl)-1,2,3,6-tetrahydropyridin-4-yl)-1,3-dimethyl-1H-pyrazol-5-yl)acetamide (A4.5)

To a stirred solution of N-(4-bromo-1,3-dimethyl-1H-pyrazol-5-yl)acetamide (A4.3) (1.5 g, 6.46 mmol, 1 eq) and 1-(4-chloro-2-fluorophenyl)-4-(4,4,5,5-tetramethyl-1,3,2-dioxaborolan-2-yl)-1,2,3,6-tetrahydropyridine (A4.4) (4.3 g, 12.93 mmol, 2 eq) in 1.4 dioxane:$H_2O$ (4:1, 30 mL) was added $K_2CO_3$ (1.78 g, 10.29 mmol, 2 eq) at room temperature. reaction mixture was purged with argon for 10 min followed by addition of X-phos (0.061 g, 0.12 mmol, 0.02 eq) and $Pd(OAC)_2$ (0.1 g, 0.45 mmol, 0.07 eq) The reaction mixture was stirred at 100° C. for 12 h; the reaction progress was monitored by TLC. After completion, the reaction mixture was partitioned between water and ethyl acetate. The organic layers were separated, washed with water dried over $Na_2SO_4$ and concentrated. The crude residue was purified by column chromatography to provide the desired compound N-(4-(1-(4-chloro-2-fluorophenyl)-1,2,3,6-tetrahydropyridin-4-yl)-1,3-dimethyl-1H-pyrazol-5-yl)acetamide (A4.5) (1 g, 42.7%). LCMS: 363.13 [M+H]$^+$.

Step-4: Synthesis of N-(4-(1-(4-chloro-2-fluorophenyl)piperidin-4-yl)-1,3-dimethyl-1H-pyrazol-5-yl) acetamide (A4.6)

To a stirred solution of N-(4-(1-(4-chloro-2-fluorophenyl)-1,2,3,6-tetrahydropyridin-4-yl)-1,3-dimethyl-1H-pyrazol-5-yl)acetamide (A4.5) (1 g, 2.75 mmol, 1 eq) in MeOH: ethyl acetate (1:1, 20 mL) was added and $PtO_2$ (0.2 g) at room temperature. the reaction mixture was stirred at 50 Psi hydrogen gas pressure at room temperature for 1.5 h. The progress of the reaction was monitored by TLC. After completion, the reaction mixture was filtered through a pad of Celite, the filtrate was evaporated under reduced pressure. The crude was purified by column chromatography followed by prep HPLC to afford titled compound N-(4-(1-(4-chloro-2-fluorophenyl)piperidin-4-yl)-1,3-dimethyl-1H-pyrazol-5-yl)acetamide (A4.6) (0.7 g, 71%). LCMS: 365.15 [M+H]$^+$.

Step-5: Synthesis of 4-(1-(4-chloro-2-fluorophenyl) piperidin-4-yl)-1,3-dimethyl-1H-pyrazol-5-amine (A4.7)

A solution of N-(4-(1-(4-chloro-2-fluorophenyl)piperidin-4-yl)-1,3-dimethyl-1H-pyrazol-5-yl)acetamide (A4.6) (0.71 g, 1.94 mmol, 1 eq) in a mixture of ethanol and a solution of sodium hydroxide (50% aq) (1:1, 14 mL) was stirred at 90° C. for 16 h. The progress of the reaction was monitored by TLC. After completion of the reaction, reaction mixture was concentrated under reduced pressure. The crude was diluted with water and extracted with DCM. The combined organic extracts were washed with water, brine, dried over anhydrous $Na_2SO_4$, filtered and concentrated under reduced pressure. The crude was purified by column chromatography to afford titled compound 4-(1-(4-chloro-2-fluorophenyl)piperidin-4-yl)-1,3-dimethyl-1H-pyrazol-5-amine (A4.7) (0.45 g, 72.5%). LCMS: 323.14 [M+H]$^+$.

Step-6: Synthesis of N1-(4-(1-(4-chloro-2-fluorophenyl)piperidin-4-yl)-1,3-dimethyl-1H-pyrazol-5-yl)-N4,N4-dimethylbenzene-1,4-disulfonamide (A-75)

To a stirred solution of 4-(1-(4-chloro-2-fluorophenyl) piperidin-4-yl)-1,3-dimethyl-1H-pyrazol-5-amine (A4.7)

(0.45 g, 1.39 mmol, 1 eq) in ACN (10 mL) was added pyridine (0.22 mL, 2.78 mmol, 2 eq) at 0° C., stirred the reaction mixture for 10 min at same temperature followed by addition of 4-(N,N-dimethylsulfamoyl)benzenesulfonyl chloride (A4.8) (0.44 g, 1.53 mmol, 1.1 eq) at 0° C. The reaction mixture was stirred at 80° C. for 12 h. The progress of the reaction was monitored by TLC. After completion of the reaction, reaction mixture was quenched with water and extracted with ethyl acetate. The combined organic extracts were washed with water, brine, dried over anhydrous $Na_2SO_4$, filtered and concentrated under reduced pressure. The crude was purified by prep HPLC to afford titled compound N1-(4-(1-(4-chloro-2-fluorophenyl)piperidin-4-yl)-1,3-dimethyl-1H-pyrazol-5-yl)-N4,N4-dimethylbenzene-1,4-disulfonamide (A-75). Yield: 20 mg, 2.5%; Appearance: Off-white solid; $^1H$ NMR (400 MHz, DMSO-$d_6$) δ 10.48 (s, 1H), 8.02 (d, J=1.3 Hz, 4H), 7.29 (dd, J=12.3, 2.5 Hz, 1H), 7.19-7.11 (m, 1H), 6.98 (t, J=9.1 Hz, 1H), 3.52 (s, 3H), 3.18 (d, J=11.4 Hz, 2H), 2.66 (s, 6H), 2.22 (t, J=12.0 Hz, 2H), 2.10 (s, 3H), 1.81 (ddd, J=15.4, 7.8, 3.3 Hz, 1H), 1.72-1.64 (m, 2H), 1.08 (s, 2H); HPLC purity: 98.14%; LCMS Calculated for $C_{24}H_{29}ClFN_5O_4S_2$: 569.13; Observed: 570.20 $[M+H]^+$.

Example A5: Synthetic Scheme for Synthesis of N1-(4-(1-(4-chloro-2-fluorophenyl)piperidin-4-yl)-1-methyl-1H-pyrazol-3-yl)-N4,N4-dimethylbenzene-1,4-disulfonamide (A-55)

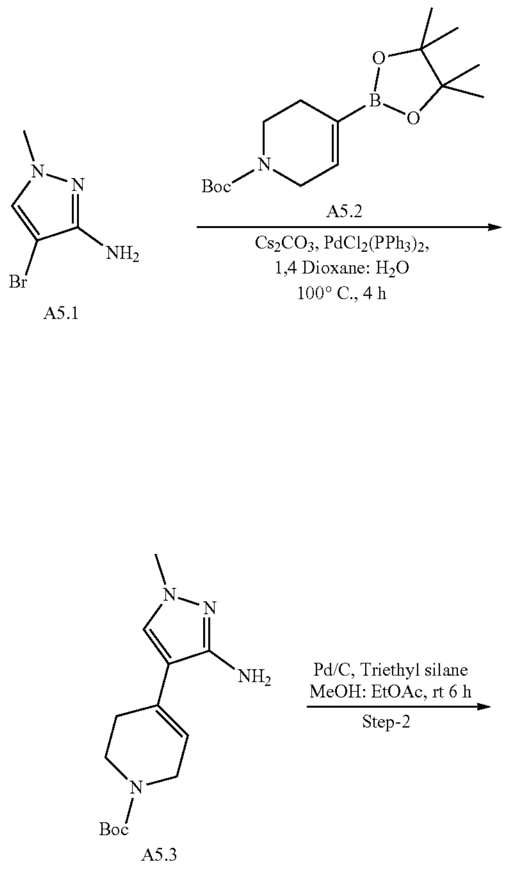

-continued

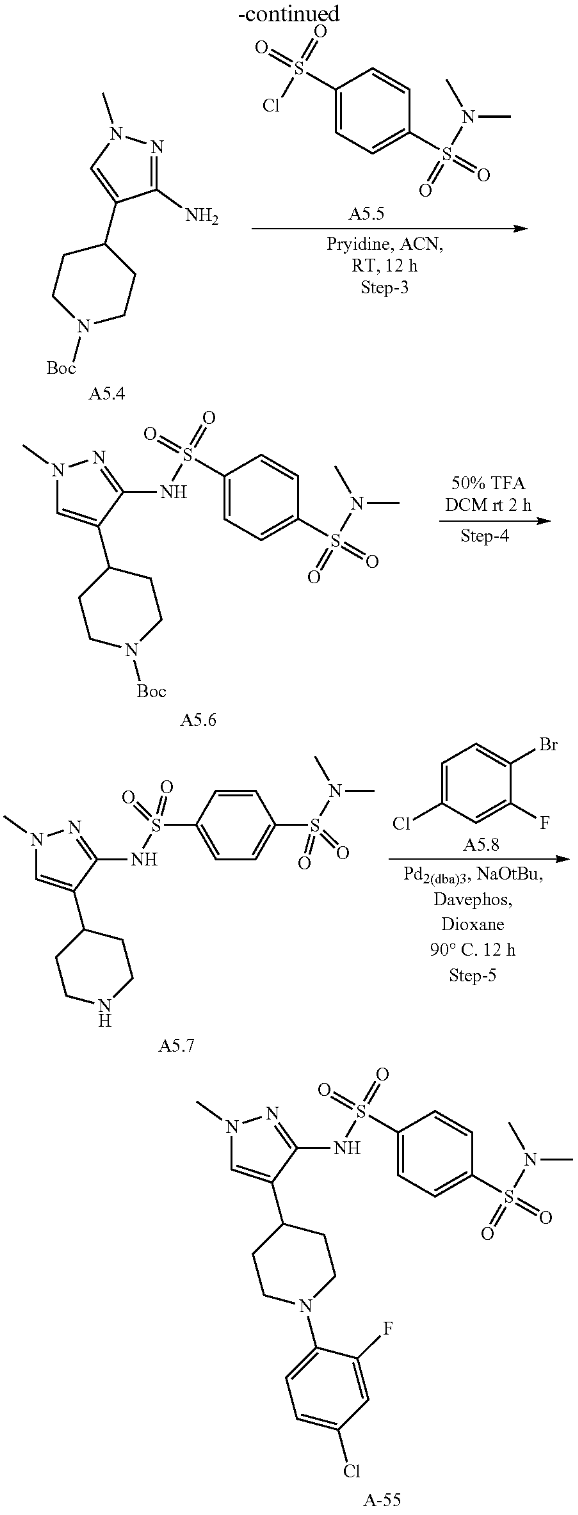

Step-1: Synthesis of tert-butyl 4-(3-amino-1-methyl-1H-pyrazol-4-yl)-3,6-dihydropyridine-1(2H)-carboxylate (A5.3)

To a mixture of 4-bromo-1-methyl-1H-pyrazol-3-amine (A5.1) (1.5 g, 8.5 mmol, 1 eq) and tert-butyl 4-(4,4,5,5-tetramethyl-1,3,2-dioxaborolan-2-yl)-3,6-dihydropyridine-1(2H)-carboxylate (A5.2) (3.42 g, 11 mmol, 1.3 eq) in 1,4- dioxane:$H_2O$ mixture (4:1, 20 mL), $Cs_2CO_3$ (5.55 g, 17.03 mmol, 2 eq) was added at room temperature, purged reaction mixture with argon for 10 min followed by the addition of dichlorobis(triphenylphosphine)palladium(II) $PdCl_2(PPh_3)_2$ (0.41 g, 0.59 mmol, 0.07 eq) and stirred at 100° C. for 4 h. The progress of the reaction was monitored by TLC. After completion of the reaction, the reaction mixture was quenched with water and extracted with ethyl acetate, washed with water, brine, dried over anhydrous sodium sulfate and evaporated under reduced pressure. The crude product was purified by column chromatography to afford the desired product tert-butyl 4-(3-amino-1-methyl-1H-pyrazol-4-yl)-3,6-dihydropyridine-1(2H)-carboxylate (A5.3) (1.8 g, 75.9%). LCMS: 279.17 $[M+H]^+$.

Step-2: Synthesis of tert-butyl 4-(3-amino-1-methyl-1H-pyrazol-4-yl)piperidine-1-carboxylate (A5.4)

To a stirred solution of 4-(3-amino-1-methyl-1H-pyrazol-4-yl)-3,6-dihydropyridine-1(2H)-carboxylate (A5.3) (1.8 g, 6.4 mmol, 1 eq) in a mixture of methanol and ethyl acetate (1:1, 36 mL) was added triethylsilane (16 mL, 97.12 mmol, 15 eq) and Pd/C (0.36 g) at 0° C. The reaction mixture was stirred under hydrogen atmosphere (balloon pressure) at room temperature for 6 h. The progress of the reaction was monitored by TLC. After completion, the reaction mixture was filtered through a pad of Celite, the filtrate was evaporated under reduced pressure. The crude product was purified by column chromatography to afford the desired compound tert-butyl 4-(3-amino-1-methyl-1H-pyrazol-4-yl) piperidine-1-carboxylate (A5.4) (1.3 g, 71.8%). LCMS: 281.19 $[M+H]^+$.

Step-3: Synthesis of tert-butyl 4-(3-((4-(N,N-dimethylsulfamoyl)phenyl)sulfonamido)-1-methyl-1H-pyrazol-4-yl)piperidine-1-carboxylate (A5.6)

To a stirred solution of tert-butyl 4-(3-amino-1-methyl-1H-pyrazol-4-yl)piperidine-1-carboxylate (A5.4) (1.3 g, 4.63 mmol, 1 eq) in acetonitrile (25 mL) was added pyridine (0.73 mL, 9.27 mmol, 2 eq) at 0° C., stirred the reaction mixture for 5 min at same temperature followed by portion wise addition of 4-(N,N-dimethylsulfamoyl)benzenesulfonyl chloride A5.5 (1.44 g, 5.10 mmol, 1.1 eq). The reaction mixture was stirred at room temperature for 12 h. The progress of the reaction was monitored by TLC. After completion of the reaction, reaction mixture was diluted with water and extracted with ethyl acetate, washed with water, brine, dried over anhydrous sodium sulfate and evaporated under reduced pressure. The crude product was purified by column chromatography to afford the desired compound tert-butyl 4-(3-((4-(N,N-dimethylsulfamoyl)phenyl)sulfonamido)-1-methyl-1H-pyrazol-4-yl)piperidine-1-carboxylate (A5.6) (1.5 g, 61.4%). LCMS: 528.19 $[M+H]^+$.

Step-4: Synthesis of N1,N1-dimethyl-N4-(1-methyl-4-(piperidin-4-yl)-1H-pyrazol-3-yl)benzene-1,4-disulfonamide (A5.7)

To a stirred solution of tert-butyl 4-(3-((4-(N,N-dimethylsulfamoyl)phenyl)sulfonamido)-1-methyl-1H-pyrazol-4-yl)piperidine-1-carboxylate (A5.6) (1.5 g, 2.8 mmol, 1 eq) in DCM (7.5 mL, 5 Vol) was added TFA (7.5 mL, 5 Vol) at 0° C. The reaction mixture was stirred at room temperature for 2 h; the reaction progress was monitored by TLC. After completion, the reaction mixture was evaporated to dryness and crude salt was neutralized by using saturated solution of sodium bicarbonate to attain a pH of about 7 and extracted with DCM. The organic layers were separated, washed with water dried over $Na_2SO_4$ and concentrated under reduced pressure to provide the desired compound N1,N1-dimethyl-N4-(1-methyl-4-(piperidin-4-yl)-1H-pyrazol-3-yl)benzene-1,4-disulfonamide (A5.7) (0.5 g, crude). The crude was used as such next step without purification. LCMS: 428.13 $[M+H]^+$.

Step-5: Synthesis of N1-(4-(1-(4-chloro-2-fluorophenyl)piperidin-4-yl)-1-methyl-1H-pyrazol-3-yl)-N4,N4-dimethylbenzene-1,4-disulfonamide (A-55)

To a stirred solution of N1,N1-dimethyl-N4-(1-methyl-4-(piperidin-4-yl)-1H-pyrazol-3-yl)benzene-1,4-disulfonamide (A5.7) (0.12 g, 0.57 mmol, 1 eq) and 1-bromo-4-chloro-2-fluorobenzene (A5.8) (0.27 g, 0.63 mmol, 1.1 eq) in 1,4-dioxane (5 mL) was added NaOtBu (0.11 g, 1.14 mmol, 2 eq) at room temperature, reaction mixture was purged with argon for 10 min followed by addition of Davephos (13.45 mg, 0.03 mmol, 0.06 eq) and $Pd_2(dba)_3$ (15.66 mg, 0.02 mmol, 0.03 eq). The reaction mixture was stirred at 90° C. for 12 h; the reaction progress was monitored by TLC. After completion, the reaction mixture was diluted with water and extracted with ethyl acetate. The organic layers were separated, washed with water dried over $Na_2SO_4$ and concentrated. The crude residue was purified by silica gel column chromatography to provide the desired compound N1-(4-(1-(4-chloro-2-fluorophenyl)piperidin-4-yl)-1-methyl-1H-pyrazol-3-yl)-N4,N4-dimethylbenzene-1,4-disulfonamide (A-55). Yield: 0.018 mg, 5.1%; Appearance: Off-white solid; 1H NMR (400 MHz, DMSO-$d_6$) δ 10.04 (s, 1H), 8.06-7.92 (m, 4H), 7.52 (s, 1H), 7.31 (dd, J=12.5, 2.5 Hz, 1H), 7.22-7.14 (m, 1H), 7.06 (t, J=9.1 Hz, 1H), 3.62 (s, 3H), 3.30 (m, 2H), 2.65-2.57 (m, 8H), 2.38 (m, 1H), 1.73 (d, J=10.8 Hz, 2H), 1.55 (qd, J=12.2, 3.7 Hz, 2H); HPLC purity: >99%; LCMS Calculated for $C_{23}H_{27}ClFN_5O_4S_2$: 555.12; Observed: 556.1 $[M+H]^+$.

Example A6: Synthesis of N1-(2-(6-(4-chloro-2-fluorophenyl)-2,6-diazaspiro[3.3]heptan-2-yl)phenyl)-N4,N4-dimethylbenzene-1,4-disulfonamide (A-296)

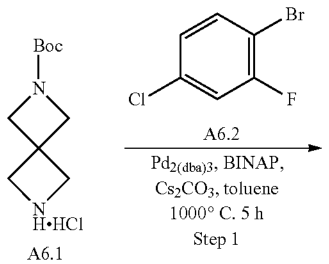

A6.1

-continued

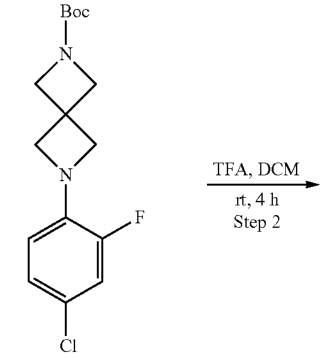

A6.3

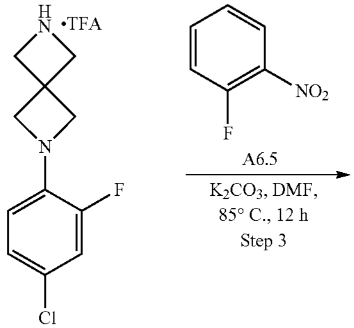

A6.4

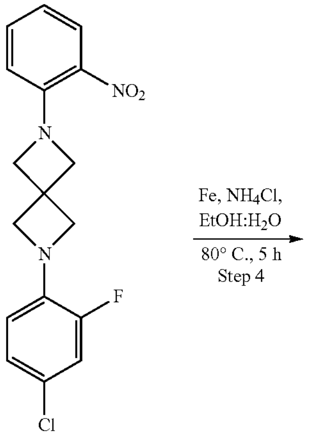

A6.6

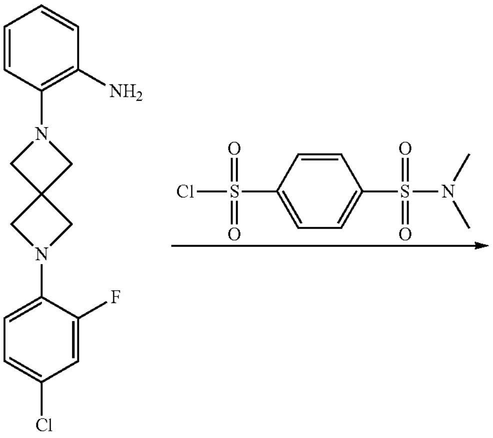

A6.7

-continued

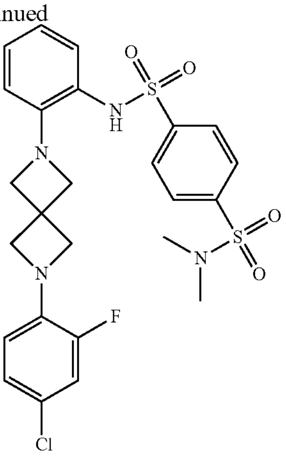

A-296

Step-1: Synthesis of tert-butyl 6-(4-chloro-2-fluorophenyl)-2,6-diazaspiro[3.3]heptane-2-carboxylate (A6.3)

A pyrex tube was charged with a solution of tert-butyl 2,6-diazaspiro[3.3]heptane-2-carboxylate hydrochloride (A6.1) (850 mg, 3.62 mmol, 1 eq), 1-bromo-4-chloro-2-fluorobenzene (A6.2) (833 mg, 3.98 mmol, 1.1 eq) and cesium carbonate (2.36 g, 7.23 mmol, 2 eq) in toluene (15 mL). The tube was sealed with a septum and the reaction mixture was purged with argon for 15 min. Tris(dibenzylideneacetone)dipalladium(0) (99 mg, 0.108 mmol, 0.3 eq) and BINAP (157 gm 0.253 mmol, 0.07 eq) were added to the reaction mixture under an argon atmosphere. The tube was then fitted with a screw cap and the reaction mixture was heated at 100° C. for 5 h. The progress of the reaction was monitored by TLC. After completion of the reaction, the reaction mixture was cooled to room temperature, filtered through a pad of Celite and the Celite pad was washed with ethyl acetate. The filtrate was concentrated under reduced pressure to dryness. The crude product was purified by column chromatography on silica gel to afford the titled compound tert-butyl 6-(4-chloro-2-fluorophenyl)-2,6-diazaspiro[3.3]heptane-2-carboxylate (A6.3) (1 g, 84.74%). LCMS: 327.10 $[M+H]^+$.

Step-2: Synthesis of 2-(4-chloro-2-fluorophenyl)-2,6-diazaspiro[3.3]heptane TFA Salt (A6.4)

To a stirred solution of tert-butyl 6-(4-chloro-2-fluorophenyl)-2,6-diazaspiro[3.3]heptane-2-carboxylate (A6.3) (1 g, 3.07 mmol, 1 eq) in DCM (20 mL) was added trifluoroacetic acid (1.75 mL, 12.27 mmol, 4 eq) at room temperature and the reaction mixture was stirred at the same temperature for 4 h. The progress of the reaction was monitored by TLC. After completion of the reaction, the reaction mixture was concentrated to dryness under reduced pressure. The residue was further co-evaporated with DCM to dryness under reduced pressure to afford the titled compound 2-(4-chloro-2-fluorophenyl)-2,6-diazaspiro[3.3]heptane (A6.4) (1.1 g, crude) as TFA salt. This compound was used in the next step without further purification. LCMS: 227.10 $[M+H]^+$.

Step-3: Synthesis of 2-(4-chloro-2-fluorophenyl)-6-(2-nitrophenyl)-2,6-diazaspiro[3.3]heptane (A6.6)

To a stirred solution of 2-(4-chloro-2-fluorophenyl)-2,6-diazaspiro[3.3]heptane TFA salt (A6.4) (1.1 g, 3.41 mmol, 1 eq) in DMF (20 mL) was added potassium carbonate and 1-fluoro-2-nitrobenzene (A6.5) (0.528 g, 3.75 mmol, 1.1 eq). The reaction mixture was heated at 85° C. for 12 h. The progress of the reaction was monitored by TLC. After completion of the reaction, the reaction mixture was cooled to room temperature, diluted with ice-cold water and extracted with ethyl acetate. The combined organic layers were washed with ice-cold water and brine, dried over anhydrous $Na_2SO_4$, filtered and concentrated reduced pressure to dryness to afford the titled compound 2-(4-chloro-2-fluorophenyl)-6-(2-nitrophenyl)-2,6-diazaspiro[3.3]heptane (A6.6) (0.71 g, crude). This compound was used in the next step without further purification. LCMS: 348.10 $[M+H]^+$.

Step-4: Synthesis of 2-(6-(4-chloro-2-fluorophenyl)-2,6-diazaspiro[3.3]heptan-2-yl)aniline (A6.7)

To a stirred solution of 2-(4-chloro-2-fluorophenyl)-6-(2-nitrophenyl)-2,6-diazaspiro[3.3]heptane (A6.6) (600 mg, 1.73 mmol, 1 eq) in a mixture of water (2 mL) and ethanol (10 mL) was added iron powder (386 mg, 6.92 mmol, 4 eq) and ammonium chloride (370 mg, 6.92 mmol, 4 eq). The reaction mixture was heated at 80° C. for 5 h. The progress of the reaction was monitored by TLC. After completion of the reaction, the reaction mixture was cooled to room temperature, filtered through a pad of Celite and the Celite pad was washed with ethyl acetate. The filtrate was concentrated under reduced pressure to dryness. The crude product was purified by column chromatography on silica gel to afford the titled compound 2-(6-(4-chloro-2-fluorophenyl)-2,6-diazaspiro[3.3]heptan-2-yl)aniline (A6.7) (310 mg, 56.56%). LCMS: 318.10 $[M+H]^+$.

Step-5: Synthesis of N-(2-(6-(4-chloro-2-fluorophenyl)-2,6-diazaspiro[3.3]heptan-2-yl)phenyl)-N4,N4-dimethylbenzene-1,4-disulfonamide (A6.9)

To a stirred solution of 2-(6-(4-chloro-2-fluorophenyl)-2,6-diazaspiro[3.3]heptan-2-yl)aniline (A6.7) (200 mg, 0.631 mmol, 1 eq) in acetonitrile (5 mL) was added pyridine (0.1 mL, 1.26 mmol, 2 eq) and followed by 4-(N,N-dimethylsulfamoyl)benzenesulfonyl chloride A6.8 (196 mg, 0.694 mmol, 1.1 eq) at room temperature and the reaction mixture was stirred for 12 h. The progress of the reaction was monitored by TLC. After completion of the reaction, the reaction mixture was diluted with 1N aqueous HCl solution and extracted with ethyl acetate. The combined organic layers were dried over anhydrous $Na_2SO_4$, filtered and concentrated under reduced pressure. The crude product was purified by column chromatography on silica gel. The compound was further triturated with diethyl ether, the solids were filtered out and dried under reduced pressure to afford the titled compound N1-(2-(6-(4-chloro-2-fluorophenyl)-2,6-diazaspiro[3.3]heptan-2-yl)phenyl)-N4,N4-dimethylbenzene-1,4-disulfonamide (A-296). Yield: 30 mg, 8.42%; Appearance: White solid; $^1H$ NMR (400 MHz, DMSO-$d_6$) δ 9.58 (s, 1H), 7.95 (s, 4H), 7.24 (d, J=12.4 Hz, 1H), 7.12-7.03 (m, 2H), 6.58 (t, J=9.2 Hz, 1H), 6.52 (t, J=7.6 Hz, 1H), 6.48-6.38 (m, 2H), 4.03 (d, J=6.8 Hz, 8H), 2.65 (s, 6H); HPLC purity: 99.53%; LCMS calculated for $C_{25}H_{26}ClFN_4O_4S_2$: 564.11; Observed: 565.15 $[M+H]^+$.

Example A7: Synthesis of N1-(4-(1-(2-fluorophenyl)piperidin-4-yl)-1-methyl-1H-pyrazol-3-yl)-N4,N4-dimethylbenzene-1,4-disulfonamide (A-40)

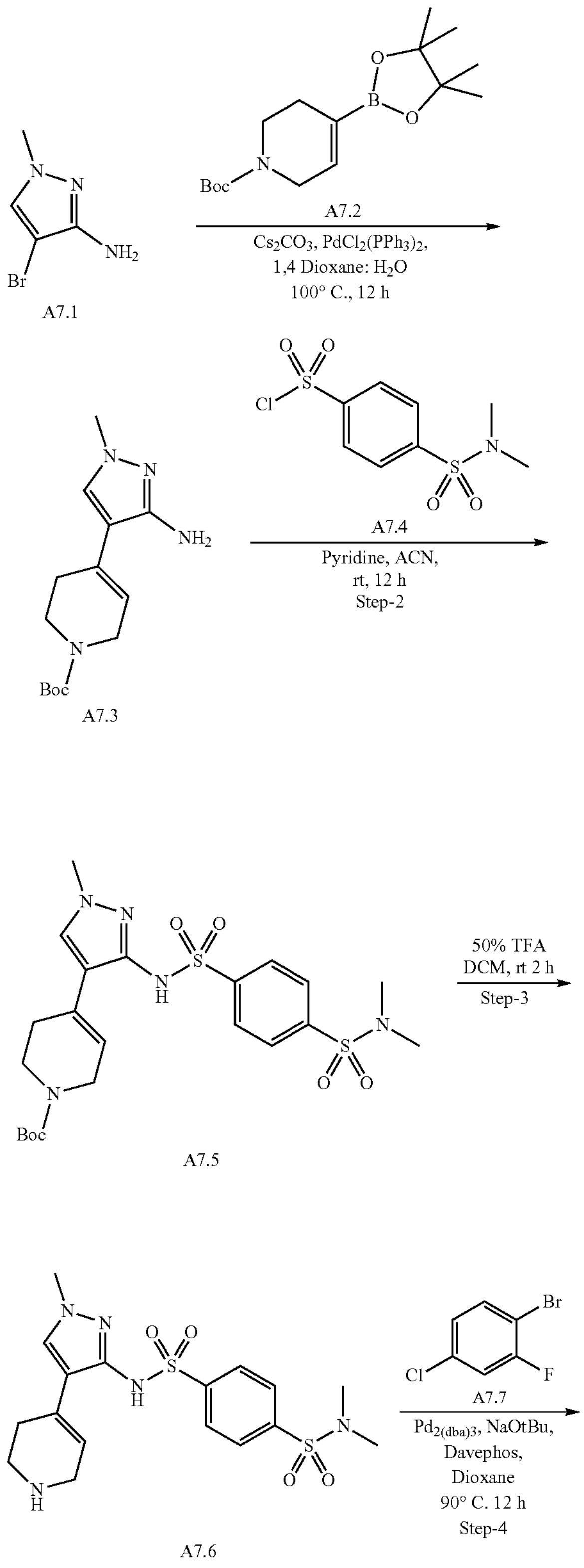

-continued

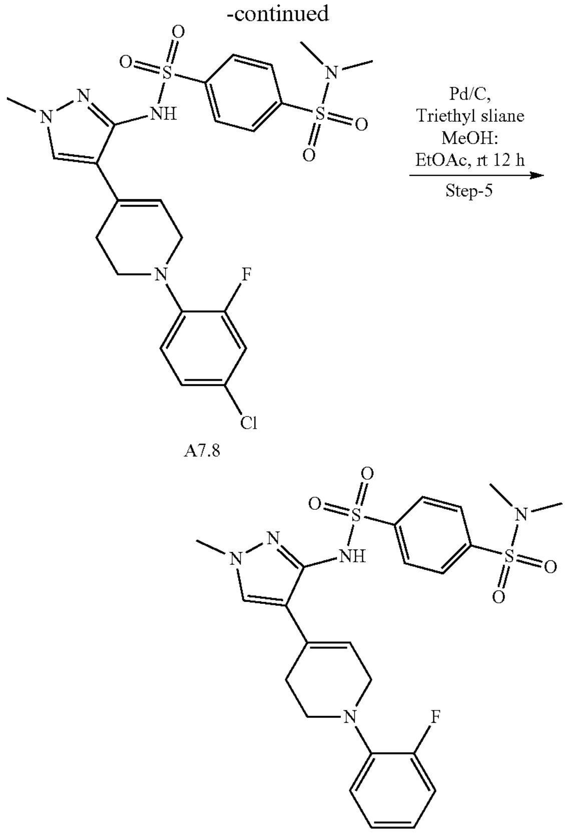

A7.8

A-40

Step-1: Synthesis of tert-butyl 4-(3-amino-1-methyl-1H-pyrazol-4-yl)-3,6-dihydropyridine-1(2H)-carboxylate (A7.3)

To a mixture of 4-bromo-1-methyl-1H-pyrazol-3-amine (A7.1) (1.5 g, 8.5 mmol, 1 eq) and tert-butyl 4-(4,4,5,5-tetramethyl-1,3,2-dioxaborolan-2-yl)-3,6-dihydropyridine-1(2H)-carboxylate (A7.2) (3.42 g, 11 mmol, 1.3 eq) in 1,4-dioxane:$H_2O$ mixture (4:1, 20 mL), $Cs_2CO_3$ (5.55 g, 17.03 mmol, 2 eq) was added at room temperature, purged reaction mixture with argon for 10 min followed by the addition of Dichlorobis(triphenylphosphine)palladium(II) $PdCl_2(PPh_3)_2$ (0.41 g, 0.59 mmol, 0.07 eq) and stirred at 100° C. for 12 h. The progress of the reaction was monitored by TLC. After completion of the reaction, the reaction mixture was quenched with water and extracted with ethyl acetate, washed with water, brine, dried over anhydrous sodium sulfate and evaporated under reduced pressure. The crude product was purified by column chromatography to afford the desired product tert-butyl 4-(3-amino-1-methyl-1H-pyrazol-4-yl)-3,6-dihydropyridine-1(2H)-carboxylate (A7.3) (1.5 g, 63.5%). LCMS: 279.17 $[M+H]^+$.

Step-2: Synthesis of tert-butyl 4-(3-((4-(N,N-dimethylsulfamoyl)phenyl)sulfonamido)-1-methyl-1H-pyrazol-4-yl)-3,6-dihydropyridine-1(2H)-carboxylate (A7.5)

To a stirred solution of tert-butyl 4-(3-amino-1-methyl-1H-pyrazol-4-yl)-3,6-dihydropyridine-1(2H)-carboxylate (A7.3) (1.5 g, 5.39 mmol, 1 eq) in acetonitrile (20 mL) was added pyridine (0.9 mL, 10.79 2 eq) at 0° C., stirred the reaction mixture for 5 min at same temperature followed by portion wise addition of 4-(N,N-dimethylsulfamoyl)benzenesulfonyl chloride (A7.4) (1.68 g, 5.93 mmol, 1.1 eq). The reaction mixture was stirred at room temperature for 12 h. The progress of the reaction was monitored by TLC. After completion of the reaction, reaction mixture was concentrated under reduced pressure. The crude was purified by column chromatography to afford titled compound tert-butyl 4-(3-((4-(N,N-dimethylsulfamoyl)phenyl)sulfonamido)-1-methyl-1H-pyrazol-4-yl)-3,6-dihydropyridine-1(2H)-carboxylate (A7.5) (1.85 g, 65.3%). LCMS: 526.17 $[M+H]^+$.

Step-3: Synthesis of N1,N1-dimethyl-N4-(1-methyl-4-(1,2,3,6-tetrahydropyridin-4-yl)-1H-pyrazol-3-yl)benzene-1,4-disulfonamide (A7.6)

To a stirred solution of tert-butyl 4-(3-((4-(N,N-dimethylsulfamoyl)phenyl)sulfonamido)-1-methyl-1H-pyrazol-4-yl)-3,6-dihydropyridine-1(2H)-carboxylate (A7.5) (1.85 g, 3.5 mmol, 1 eq) in DCM (9.25 mL, 5 Vol) was added TFA (9.25 mL, 5 Vol) at 0° C. The reaction mixture was stirred at room temperature for 2 h; the reaction progress was monitored by TLC. After completion, the reaction mixture was evaporated to dryness and saturated solution of sodium bicarbonate was added to reaction mixture up to pH of about 8, obtained solid was filtered and concentrated under reduced pressure provide the desired N1,N1-dimethyl-N4-(1-methyl-4-(1,2,3,6-tetrahydropyridin-4-yl)-1H-pyrazol-3-yl)benzene-1,4-disulfonamide (A7.6) (0.8 g, crude). The crude was used as such next step without purification. LCMS: 426.12 $[M+H]^+$.

Step-4: Synthesis of N1-(4-(1-(4-chloro-2-fluorophenyl)-1,2,3,6-tetrahydropyridin-4-yl)-1-methyl-1H-pyrazol-3-yl)-N4,N4-dimethylbenzene-1,4-disulfonamide (A7.8)

To a stirred solution of N1,N1-dimethyl-N4-(1-methyl-4-(1,2,3,6-tetrahydropyridin-4-yl)-1H-pyrazol-3-yl)benzene-1,4-disulfonamide A7.6 (0.32 g, 1.5 mmol, 1 eq) and 1-bromo-4-chloro-2-fluorobenzene (A7.7) (0.71 g, 1.68 mmol, 1.1 eq) in 1,4-dioxane (20 mL) was added NaOtBu (0.29 g, 3 mmol, 2 eq) at room temperature, reaction mixture was purged with argon for 15 min followed by addition of Davephos (3 mg, 0.09 mmol, 0.06 eq) and $Pd_2(dba)_3$ (42 mg, 0.46 mmol, 0.03 eq). The reaction mixture was stirred at 90° C. for 12 h; the reaction progress was monitored by TLC. After completion, the reaction mixture was diluted with water and extracted with ethyl acetate. The organic layers were separated, washed with water dried over $Na_2SO_4$ and concentrated. The crude residue was purified by silica gel column chromatography to provide the desired compound N1-(4-(1-(4-chloro-2-fluorophenyl)-1,2,3,6-tetrahydropyridin-4-yl)-1-methyl-1H-pyrazol-3-yl)-N4,N4-dimethylbenzene-1,4-disulfonamide (A7.8) (0.33 g, 35.8%). LCMS: 554.10 $[M+H]^+$.

Step-5: Synthesis of N-(4-(1-(2-fluorophenyl)piperidin-4-yl)-1-methyl-1H-pyrazol-3-yl)-N4,N4-dimethylbenzene-1,4-disulfonamide (A7.9)

To a stirred solution of N1-(4-(1-(4-chloro-2-fluorophenyl)-1,2,3,6-tetrahydropyridin-4-yl)-1-methyl-1H-pyrazol-3-yl)-N4,N4-dimethylbenzene-1,4-disulfonamide (A7.8) (0.3 g, 0.54 mmol, 1 eq) in methanol:ethyl acetate (1:1, 9 mL) was added triethylsilane (0.94 mL, 8.12 mmol, 15 eq) and Pd/C (0.06 g) at 0° C. The reaction mixture was stirred under hydrogen atmosphere (balloon pressure) at room temperature for 12 h. The progress of the reaction was monitored by TLC. After completion, the reaction mixture was filtered through a pad of Celite, the filtrate was evaporated under reduced pressure. The crude was diluted with water and extracted with ethyl acetate, washed with water, brine, dried over anhydrous sodium sulfate and evaporated under reduced pressure. The crude product was purified by column chromatography to afford the desired N1-(4-(1-(2-fluorophenyl)piperidin-4-yl)-1-methyl-1H-pyrazol-3-yl)-N4,N4-dimethylbenzene-1,4-disulfonamide (A-40). Yield: 0.015 g, 5.3%; Appearance: Off-white solid; $^1$H NMR (400 MHz, DMSO-$d_6$) δ 10.04 (s, 1H), 8.06-7.93 (m, 4H), 7.53 (s, 1H), 7.17-7.01 (m, 3H), 7.01-6.91 (m, 1H), 3.64 (s, 3H), 3.35 (s, 2H), 2.65 (s, 6H), 2.62-2.56 (m, 2H), 2.39-2.33 (m, 1H), 1.77-1.68 (m, 2H), 1.61-1.52 (m, 2H); HPLC purity: 97.08%; LCMS Calculated for $C_{23}H_{28}FN_5O_4S_2$: 521.16; Observed: 522.40 $[M+H]^+$.

Example A8: Synthesis of N1-(4-(1-(4-chloro-2-fluorophenyl)-1,2,3,6-tetrahydropyridin-4-yl)-3-methylisoxazol-5-yl)-N4,N4-dimethylbenzene-1,4-disulfonamide (A-65)

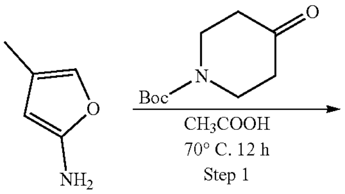

A8.1

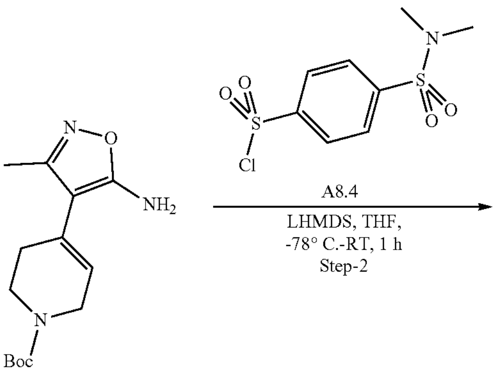

A8.3

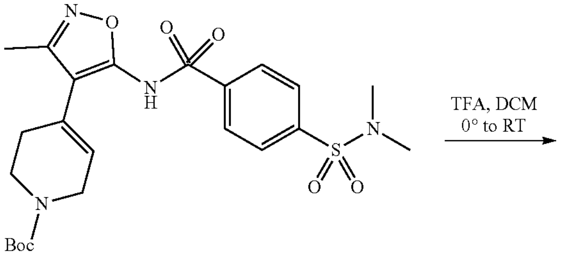

A8.5

-continued

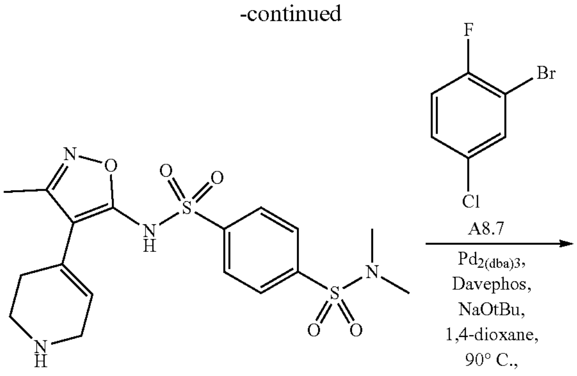

A8.6

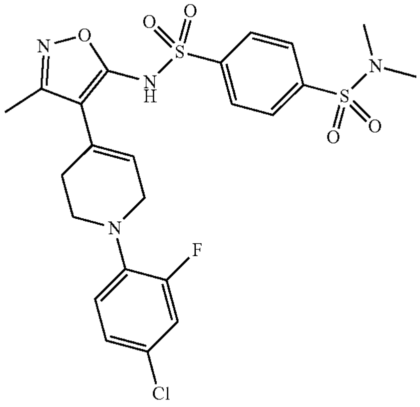

A-65

Step-1: Synthesis of tert-butyl 4-(5-amino-3-methylisoxazol-4-yl)-3,6-dihydropyridine-1(2H)-carboxylate (A8.3)

To a stirred solution of 3-methylisoxazol-5-amine A8.1 (1 g, 10 mmol, 1 eq) in acetic acid (15 mL) was added tert-butyl 4-oxopiperidine-1-carboxylate (A8.2) (3.04 g, 15 mmol, 1.5 eq). The reaction mixture was stirred at 70° C. for 12 h. The progress of reaction was monitored by TLC. After completion of the reaction, the reaction mixture was concentrated; crude was basified with 10% NaOH solution and extracted with ethyl acetate. The combined organic extracted were dried over anhydrous sodium sulfate and evaporated under reduced pressure. The crude product was purified by column chromatography to afford the desired product tert-butyl 4-(5-amino-3-methylisoxazol-4-yl)-3,6-dihydropyridine-1(2H)-carboxylate (A8.3) (2 g, 70%). LCMS: 280.16 $[M+H]^+$.

Step-2: Synthesis of tert-butyl 4-(5-((4-(N,N-dimethylsulfamoyl)phenyl)sulfonamido)-3-methylisoxazol-4-yl)-3,6-dihydropyridine-1(2H)-carboxylate (A8.5)

To a mixture of tert-butyl 4-(5-amino-3-methylisoxazol-4-yl)-3,6-dihydropyridine-1(2H)-carboxylate (A8.3) (2 g, 7.16 mmol, 1 eq) and 4-(N,N-dimethylsulfamoyl)benzenesulfonyl chloride (A8.4) (2.44 g, 8.6 mmol, 1.2 eq) in dry THE (15 mL) was added LiHMDS (11 mL, 10.7 mmol, 1.5 eq) at −78° C., stirred reaction mixture for 15 min at same temperature then again stirred at room temperature for 1 h. The progress of the reaction was monitored by TLC. After completion of the reaction, the reaction mixture was quenched with 1N HCl and extracted with ethyl acetate. The organic layer was dried over anhydrous sodium sulfate and evaporated under reduced pressure. The crude product was triturated with diethyl ether and concentrated under reduced pressure to afford the desired product tert-butyl 4-(5-((4-(N,N-dimethylsulfamoyl)phenyl)sulfonamido)-3-methylisoxazol-4-yl)-3,6-dihydropyridine-1(2H)-carboxylate (A8.5) (3 g, 79%). LCMS: 527.16 $[M+H]^+$.

Step-3: Synthesis of N,N-dimethyl-N4-(3-methyl-4-(1,2,3,6-tetrahydropyridin-4-yl)isoxazol-5-yl)benzene-1,4-disulfonamide, TFA Salt (A8.6)

To a stirred solution of tert-butyl 4-(5-((4-(N,N-dimethylsulfamoyl)phenyl)sulfonamido)-3-methylisoxazol-4-yl)-3,6-dihydropyridine-1(2H)-carboxylate (A8.5) (2 g, 3.8 mmol, 1 eq) in DCM (50 mL) was added dropwise TFA (20 mL) at 0° C. The reaction mixture was stirred at room temperature for 2 h. The reaction progress was monitored by TLC. After completion, the reaction mixture was concentrated, crude was triturated with diethyl ether dried under reduced pressure to provide the desired compound N1,N1-dimethyl-N4-(3-methyl-4-(1,2,3,6-tetrahydropyridin-4-yl)isoxazol-5-yl)benzene-1,4-disulfonamide, TFA salt (A8.6) (2 g, crude). The crude was used as such next step without purification. LCMS: 427.10 $[M+H]^+$.

Step-4: Synthesis of N1-(4-(1-(4-chloro-2-fluorophenyl)-1,2,3,6-tetrahydropyridin-4-yl)-3-methylisoxazol-5-yl)-N4,N4-dimethylbenzene-1,4-disulfonamide (A8.8)

To a mixture of N1,N1-dimethyl-N4-(3-methyl-4-(1,2,3,6-tetrahydropyridin-4-yl)isoxazol-5-yl)benzene-1,4-disulfonamide, TFA salt (A8.6) (2 g, 3.6 mmol, 1 eq) and 2-bromo-4-chloro-1-fluorobenzene (A8.7) (0.92 g, 4.4 mmol, 1.2 eq) in 1,4-dioxane (50 mL) was added NaOtBu (1.41 g, 14.7 mmol, 4 eq) purged reaction mixture with nitrogen followed by addition of Davephos (84 mg, 2.16 mmol, 0.06 eq) and $Pd_2(dba)_3$ (98 mg, 0.11 mmol, 0.03 eq). The reaction mixture was stirred at 90° C. for 12 h. The progress of the reaction was monitored by TLC. After completion of the reaction, the reaction mixture was filtered through a pad of Celite and the Celite pad was washed with ethyl acetate. The filtrate was concentrated under reduced pressure. The crude product was triturated with hexane and concentrated under reduced pressure. The crude product was purified by prep HPLC to afford the desired product N1-(4-(1-(4-chloro-2-fluorophenyl)-1,2,3,6-tetrahydropyridin-4-yl)-3-methylisoxazol-5-yl)-N4,N4-dimethylbenzene-1,4-disulfonamide (A-65). Yield: 30 mg, 2%; Appearance: Orange solid; $^1H$ NMR (400 MHz, DMSO-$d_6$) δ 8.08-7.92 (m, 4H), 7.33 (dt, J=11.4, 3.2 Hz, 1H), 7.17 (dd, J=8.8, 2.5 Hz, 1H), 7.05 (t, J=9.1 Hz, 1H), 5.83-5.69 (m, 1H), 3.59 (q, J=3.6 Hz, 2H), 3.11 (t, J=5.5 Hz, 2H), 2.63 (s, 6H), 2.89 (m, 2H), 2.16 (s, 3H), 1 exchangeable proton not observed due to moisture in the solvent; HPLC purity: 95.85%; LCMS Calculated for $C_{23}H_{24}ClFN_4O_5S_2$: 554.09; Observed: 555.0 $[M+H]^+$.

Example A9: Synthesis of N1-(5-(1-(4-chloro-2-fluorophenyl)piperidin-4-yl)-1,3,4-thiadiazol-2-yl)-N4,N4-dimethylbenzene-1,4-disulfonamide (A-64)

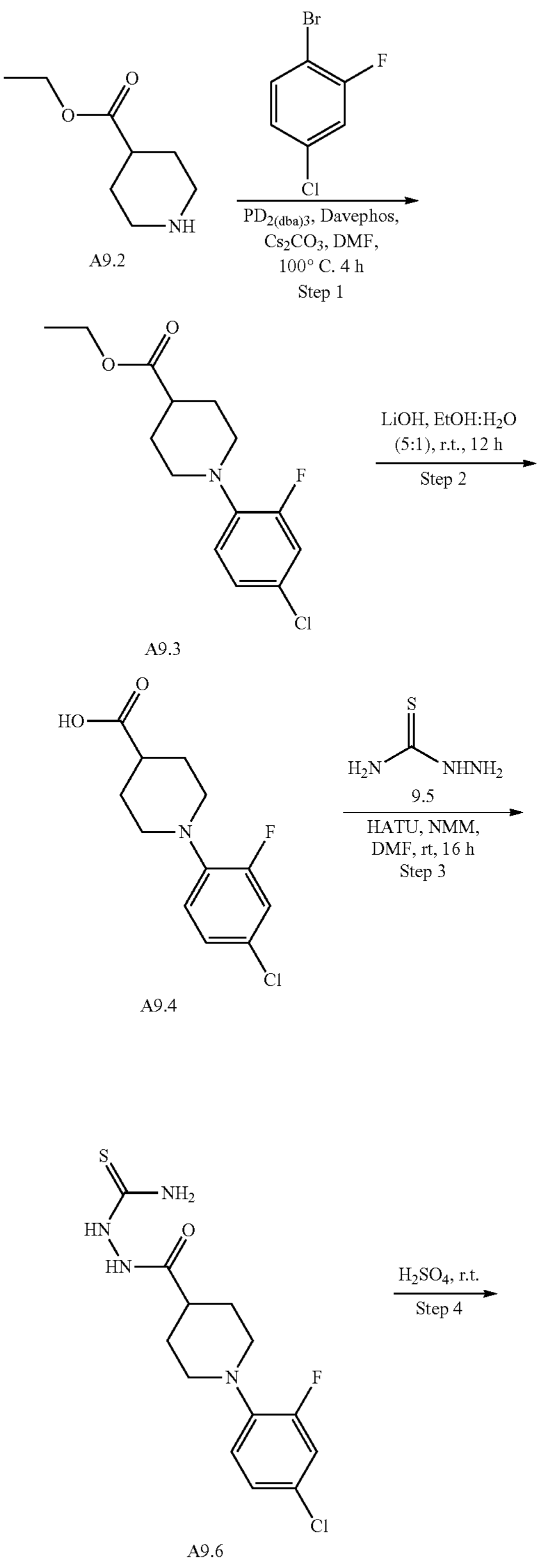

A9.2

A9.3

A9.4

A9.6

-continued

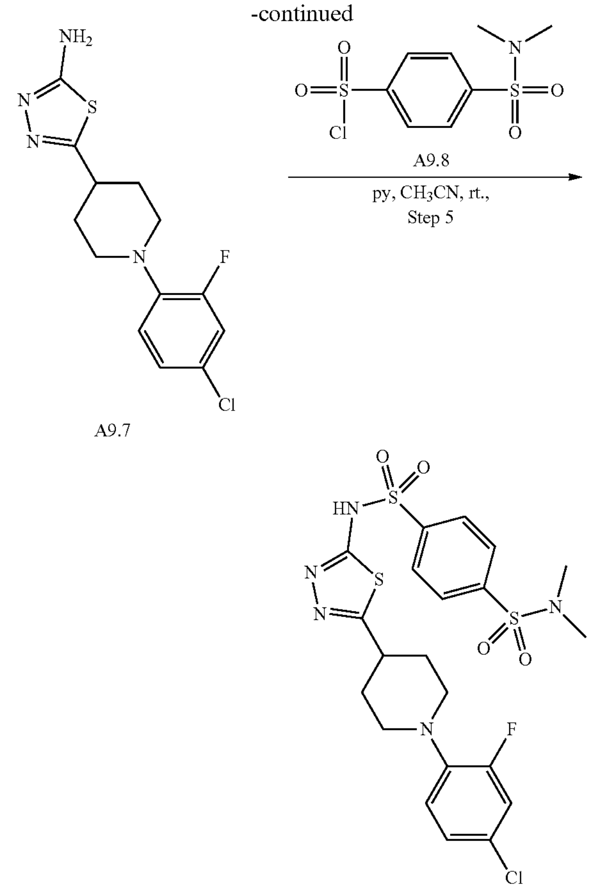

A9.7

A9.8

A-64

Step-1: Synthesis of ethyl 1-(4-chloro-2-fluorophenyl)piperidine-4-carboxylate (A9.3)

To a stirred solution of 1-bromo-4-chloro-2-fluorobenzene (A9.1) (1 g, 4.7 mmol, 1 eq) and ethyl piperidine-4-carboxylate (A9.2) (1.1 g, 7.1 mmol, 1.5 eq) in DMF (20 mL) was added $Cs_2CO_3$ (3 g, 9.4 mmol, 2 eq) reaction mixture was purged with argon for 15 min followed by addition of Davephos (110 mg, 0.28 mmol, 0.06 eq) and $Pd_2(dba)_3$ (430 mg, 0.47 mmol, 0.1 eq). The reaction mixture was stirred at 100° C. for 4 h; the reaction progress was monitored by TLC. After completion, the reaction mixture was diluted with water and extracted with ethyl acetate. The organic layers were separated, washed with water dried over $Na_2SO_4$ and concentrated. The crude residue was purified by silica gel column chromatography to provide the desired ethyl 1-(4-chloro-2-fluorophenyl)piperidine-4-carboxylate (A9.3) (500 mg, 38%). LCMS: 286.09 $[M+H]^+$.

Step-2: Synthesis of 1-(4-chloro-2-fluorophenyl)piperidine-4-carboxylic Acid (A9.4)

To stirred solution of ethyl 1-(4-chloro-2-fluorophenyl)piperidine-4-carboxylate (A9.3) (0.5 g, 2.78 mmol, 1 eq) in ethanol:Water (5:1, 12 mL) was added LiOH (83 mg, 3.5 mmol, 2 eq) at room temperature. The mixture was stirred at room temperature for 12 h. The progress of the reaction was monitored by TLC. After completion of reaction, the reaction mixture was concentrated and the residue was acidified with dil. HCl and extracted with DCM. The combined organic extracts were washed with water, brine, dried over anhydrous $Na_2SO_4$, filtered and concentrated under reduced pressure to afford titled compound 1-(4-chloro-2-fluorophenyl)piperidine-4-carboxylic acid (A9.4) (400 mg, crude). The crude was used as such next step without purification. LCMS: 258.06 $[M+H]^+$.

Step-3: Synthesis of 2-(1-(4-chloro-2-fluorophenyl)piperidine-4-carbonyl)hydrazine-1-carbothioamide (A9.6)

To a stirred solution of 1-(4-chloro-2-fluorophenyl)piperidine-4-carboxylic acid (A9.4) (400 mg, 1.5 mmol, 1 eq) in DMF (10 mL) was added HATU (855 mg, 2.2 mmol, 1.5 eq) and NMM (454 mg, 4.5 mmol, 3 eq) at room temperature, stirred the reaction mixture for 10 min followed by addition of hydrazinecarbothioamide (A9.5) (170 mg, 1.86 mmol, 1.2 eq). The reaction mixture was stirred at room temperature for 16 h. The reaction progress of reaction was monitored by TLC. After completion, the reaction mixture was diluted with water then methanol was added, filtered the solid formed and filtrate was concentrated under reduced pressure to afford the titled 2-(1-(4-chloro-2-fluorophenyl)piperidine-4-carbonyl)hydrazine-1-carbothioamide (A9.6) (450 mg, 87%). LCMS: 331.07 $[M+H]^+$.

Step-4: Synthesis of 5-(1-(4-chloro-2-fluorophenyl)piperidin-4-yl)-1,3,4-thiadiazol-2-amine (A9.7)

Stirred the solution of 2-(1-(4-chloro-2-fluorophenyl)piperidine-4-carbonyl)hydrazine-1-carbothioamide (A9.6) (450 mg, 1.3 mmol, 1 eq) in $H_2SO_4$ (15 mL) at room temperature for overnight. The progress of the reaction was monitored by TLC. After completion of the reaction, the reaction mixture was quenched with ice water then ammonia solution and methanol were added, filtered the reaction mixture, filtrated was concentrated under reduced pressure to afford the desired product 5-(1-(4-chloro-2-fluorophenyl)piperidin-4-yl)-1,3,4-thiadiazol-2-amine (A9.7) (400 mg, crude). The crude was used as such next step without purification. LCMS: 313.06 $[M+H]^+$.

Step-5: Synthesis of N1-(5-(1-(4-chloro-2-fluorophenyl)piperidin-4-yl)-1,3,4-thiadiazol-2-yl)-N4,N4-dimethylbenzene-1,4-disulfonamide (A-64)

To a stirred solution of 5-(1-(4-chloro-2-fluorophenyl)piperidin-4-yl)-1,3,4-thiadiazol-2-amine (A9.7) (400 mg, 1.2 mmol, 1 eq) in acetonitrile (20 mL) was added pyridine (0.21 mL, 2.4 mmol, 2 eq) at 0° C., stirred the reaction mixture for 15 min followed addition of 4-(N,N-dimethylsulfamoyl)benzenesulfonyl chloride (A9.8) (407 g, 1.4 mmol, 1.2 eq). The reaction mixture was stirred at room temperature for overnight. The progress of the reaction was monitored by TLC. After completion of the reaction, reaction mixture was diluted with water and extracted with ethyl acetate. The combined organic extracts were washed with water, brine, dried over anhydrous $Na_2SO_4$, filtered and concentrated under reduced pressure. The crude was purified by column chromatography to afford titled compound N1-(5-(1-(4-chloro-2-fluorophenyl)piperidin-4-yl)-1,3,4-thiadiazol-2-yl)-N4,N4-dimethylbenzene-1,4-disulfonamide (A-64). Yield: 60 mg, 8%; Appearance: Off-white solid; $^1H$ NMR (400 MHz, DMSO-$d_6$) δ 14.27 (s, 1H), 8.08-8.00 (m, 2H), 7.96-7.88 (m, 2H), 7.32 (dd, J=12.4, 2.5 Hz, 1H), 7.17 (ddd, J=8.8, 2.4, 1.0 Hz, 1H), 7.07 (t, J=9.1 Hz, 1H), 3.39-3.32 (m, 2H), 3.13-3.06 (m, 1H), 2.83-2.6 (m, 2H), 2.64 (s, 6H), 2.13-2.04 (m, 2H), 1.88-1.73 (m, 2H); HPLC purity: 96.07%; LCMS Calculated for $C_{21}H_{23}ClFN_5O_4S_3$: 559.06; Observed: 559.9 $[M+H]^+$.
Example A10: Synthesis of N1-(3-(1-(4-chloro-2-fluorophenyl)piperidin-4-yl)-1-methyl-1H-1,2,4-triazol-5-yl)-N4,N4-dimethylbenzene-1,4-disulfonamide (A-95)
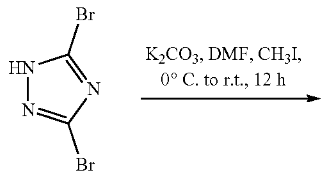
A10.1
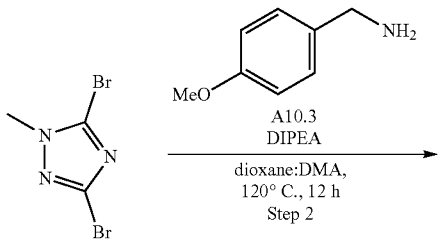
A10.2
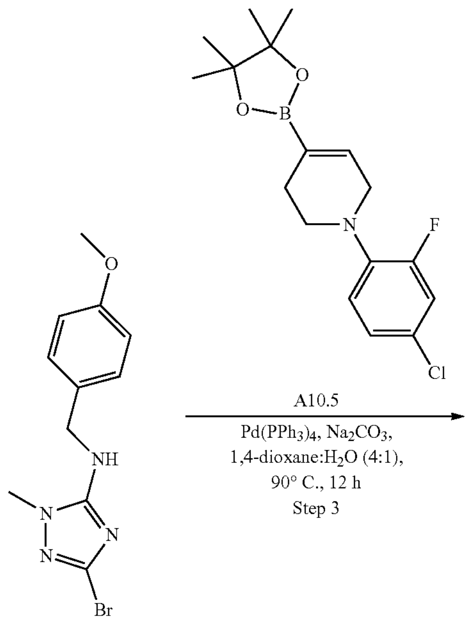
A10.4
-continued
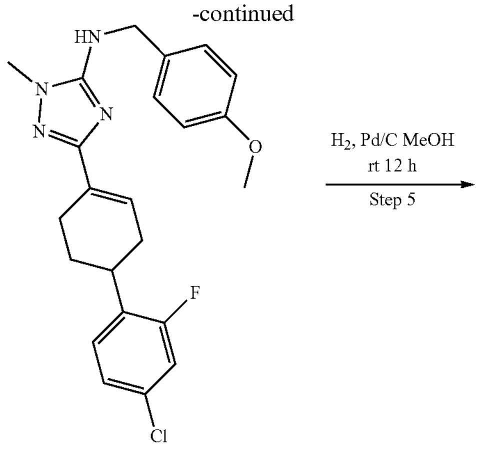
A10.6
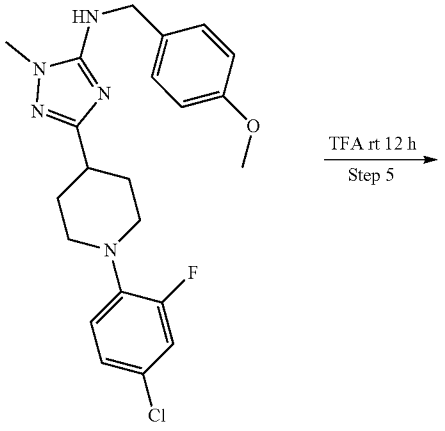
A10.7
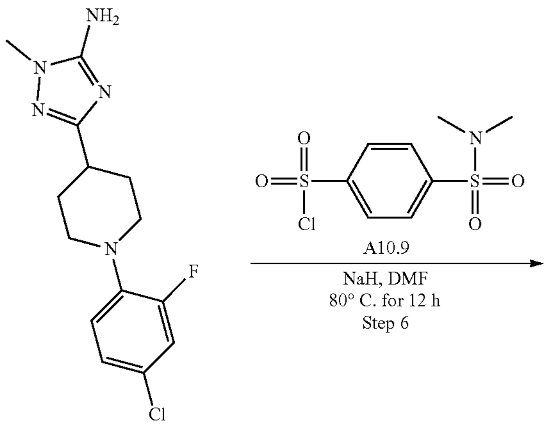
A10.8

-continued

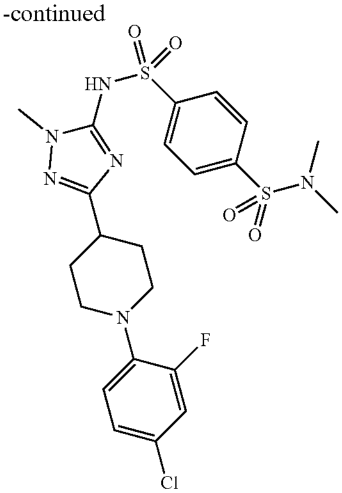

A-95

Step-1: Synthesis of 3,5-dibromo-1-methyl-1H-1,2,4-triazole (A10.2)

To a stirred solution of compound (A10.1) (5 g, 22 mmol, 1 eq) in DMF (25 mL) was added $K_2CO_3$ (4.56 g, 33 mmol, 1.5 eq) at 0° C. followed by addition of methyl iodide (1.64 g, 26.4 mmol, 1.2 eq) at room temperature. The reaction mixture was stirred at room temperature for 12 h. The reaction progress was monitored by TLC. After completion, the reaction mixture was quenched with water and extracted with ethyl acetate. The organic layer was separated, washed with water, dried over $Na_2SO_4$ and concentrated. The crude was purified by column chromatography to provide the desired compound 3,5-dibromo-1-methyl-1H-1,2,4-triazole (A10.2). The reaction was repeated on 5 g scale & combined yield details are (9 g, 85.87%). LCMS: 239.87 $[M+H]^+$.

Step-2: Synthesis of 3-bromo-N-(4-methoxybenzyl)-1-methyl-1H-1,2,4-triazol-5-amine (A10.4)

To a stirred solution of 3,5-dibromo-1-methyl-1H-1,2,4-triazole (A10.2) (4 g, 16.8 mmol, 1 eq) in 1,4-dioxane (30 mL) were added DIPEA (5.8 g, 33.6 mmol, 2 eq) and DMA (15 mL) at room temperature followed by addition of (4-methoxyphenyl)methanamine A10.3 (9.2 g, 67.2 mmol, 4 eq). The reaction mixture was stirred at 120° C. for 12 h. The reaction progress was monitored by TLC. After completion, the reaction mixture was partitioned between water and ethyl acetate. The organic layer was separated, washed with water, dried over $Na_2SO_4$ and concentrated. The crude was purified by silica gel column chromatography to provide the desired compound 3-bromo-N-(4-methoxybenzyl)-1-methyl-1H-1,2,4-triazol-5-amine (A10.4) (2.6 g, 53%). LCMS: 297.03 $[M+H]^+$.

Step-3: Synthesis of 3-(1-(4-chloro-2-fluorophenyl)-1,2,3,6-tetrahydropyridin-4-yl)-N-(4-methoxybenzyl)-1-methyl-1H-1,2,4-triazol-5-amine (A10.6)

To a mixture of 3-bromo-N-(4-methoxybenzyl)-1-methyl-1H-1,2,4-triazol-5-amine (A10.4) (1 g, 3.37 mmol, 1 eq), 1-(4-chloro-2-fluorophenyl)-4-(4,4,5,5-tetramethyl-1,3,2-dioxaborolan-2-yl)-1,2,3,6-tetrahydropyridine (A10.5) (1.25 g, 3.71 mmol, 1.1 eq) and $Na_2CO_3$ (0.71 g, 6.75 mmol, 2 eq) in a mixture of 1,4-dioxane and water (4:1, 10 mL) was purged with argon for 15 min followed by the addition of Tetrakis(triphenylphosphine)palladium(0) (0.27 g, 2.36 mmol, 0.07 eq). The reaction mixture was stirred at 90° C. for 12 h. The progress of the reaction was monitored by TLC. After completion of the reaction, the reaction mixture was diluted with water and extracted with ethyl acetate, washed with water, brine, dried over anhydrous sodium sulfate and evaporated under reduced pressure. The crude product was purified by column chromatography to afford the desired product 3-(1-(4-chloro-2-fluorophenyl)-1,2,3,6-tetrahydropyridin-4-yl)-N-(4-methoxybenzyl)-1-methyl-1H-1,2,4-triazol-5-amine (A10.6) (1 g, 69.4%). LCMS: 428.16 $[M+H]^+$.

Step-4: Synthesis of 3-(1-(4-chloro-2-fluorophenyl)piperidin-4-yl)-N-(4-methoxybenzyl)-1-methyl-1H-1,2,4-triazol-5-amine (A10.7)

To a stirred solution of 3-(1-(4-chloro-2-fluorophenyl)-1,2,3,6-tetrahydropyridin-4-yl)-N-(4-methoxybenzyl)-1-methyl-1H-1,2,4-triazol-5-amine (A10.6) (1 g, 2.34 mmol, 1 eq) in methanol (20 mL), Pd/C (0.2 g) was added. The reaction mixture was stirred at room temperature for 12 h under hydrogen balloon pressure. The progress of reaction was monitored by TLC. After completion of reaction, the reaction mixture was filtered through Celite, filtrate was concentrated under reduced pressure. The crude product was purified by column chromatography to afford the desired product 3-(1-(4-chloro-2-fluorophenyl)piperidin-4-yl)-N-(4-methoxybenzyl)-1-methyl-1H-1,2,4-triazol-5-amine (A10.7) (0.5 g, 50%). LCMS: 430.17 $[M+H]^+$.

Step-5: Synthesis of 3-(1-(4-chloro-2-fluorophenyl)piperidin-4-yl)-1-methyl-1H-1,2,4-triazol-5-amine (A10.8)

3-(1-(4-chloro-2-fluorophenyl)piperidin-4-yl)-N-(4-methoxybenzyl)-1-methyl-1H-1,2,4-triazol-5-amine (A10.7) (0.5 g, 1.16 mmol, 1 eq) was taken in TFA (2.5 mL) at 0° C. then stirred it room temperature for 12 h. The reaction progress was monitored by TLC. After completion, the reaction mixture was quenched with ice cold $NaHCO_3$ solution and extracted with ethyl acetate. The organic layer was separated, washed with water, dried over $Na_2SO_4$ and concentrated. The crude was washed with water and pentane to provide the desired compound 3-(1-(4-chloro-2-fluorophenyl)piperidin-4-yl)-1-methyl-1H-1,2,4-triazol-5-amine (A10.8) (0.3 g, 82.87%). LCMS: 310.12 $[M+H]^+$.

Step-6: Synthesis of N1-(3-(1-(4-chloro-2-fluorophenyl)piperidin-4-yl)-1-methyl-1H-1,2,4-triazol-5-yl)-N4,N4-dimethylbenzene-1,4-disulfonamide (A-95)

To a stirred solution of 3-(1-(4-chloro-2-fluorophenyl)piperidin-4-yl)-1-methyl-1H-1,2,4-triazol-5-amine (A10.8) (0.3 g, 0.97 mmol, 1 eq) in DMF (15 mL) was added NaH (0.14 g, 5.8 mmol, 6 eq) at 0° C., stirred the reaction mixture at room temperature for 15 min followed by addition of 4-(N,N-dimethylsulfamoyl)benzenesulfonyl chloride (A10.9) (0.41 g, 1.45 mmol, 1.5 eq). The reaction mixture was stirred at 80° C. for 12 h. The reaction progress was monitored by TLC. After completion, the reaction mixture was quenched with water and extracted with ethyl acetate. The organic layer was separated, washed with water, dried over $Na_2SO_4$ and concentrated. The crude was purified by column chromatography followed by prep HPLC to provide the desired compound N1-(3-(1-(4-chloro-2-fluorophenyl)piperidin-4-yl)-1-methyl-1H-1,2,4-triazol-5-yl)-N4,N4-dimethylbenzene-1,4-disulfonamide (A-95). Yield: 0.07 g, 13.2%; Appearance: White solid; $^1$H NMR (400 MHz, DMSO-$d_6$) δ 12.78 (s, 1H), 8.08 (d, J=8.1 Hz, 2H), 7.88 (d, J=8.1 Hz, 2H), 7.32 (dd, J=12.2, 2.4 Hz, 1H), 7.21-7.13 (m, 1H), 7.08 (t, J=9.1 Hz, 1H), 3.45 (s, 3H), 3.38 (d, J=12.2 Hz, 2H), 2.91-2.89 (m, 1H), 2.80-2.69 (m, 2H), 2.64 (s, 6H), 2.10-1.97 (m, 2H), 1.81-1.73 (m, 2H); HPLC purity: >99%; LCMS Calculated for $C_{22}H_{26}ClFN_6O_4S_2$:556.11; Observed: 557.10 [M+H]$^+$.

Example A11: Synthesis of 4-((3-(1-(5-chloro-3-fluoropyridin-2-yl)piperidin-4-yl)-1H-pyrazol-1-yl)sulfonyl)-N,N-dimethylbenzenesulfonamide (A-96)

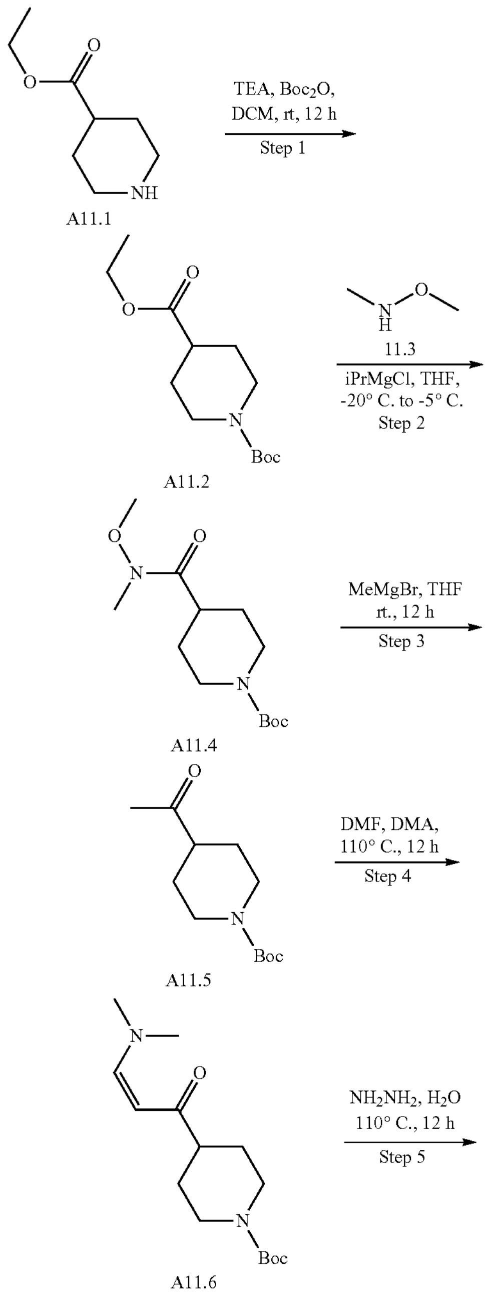

-continued

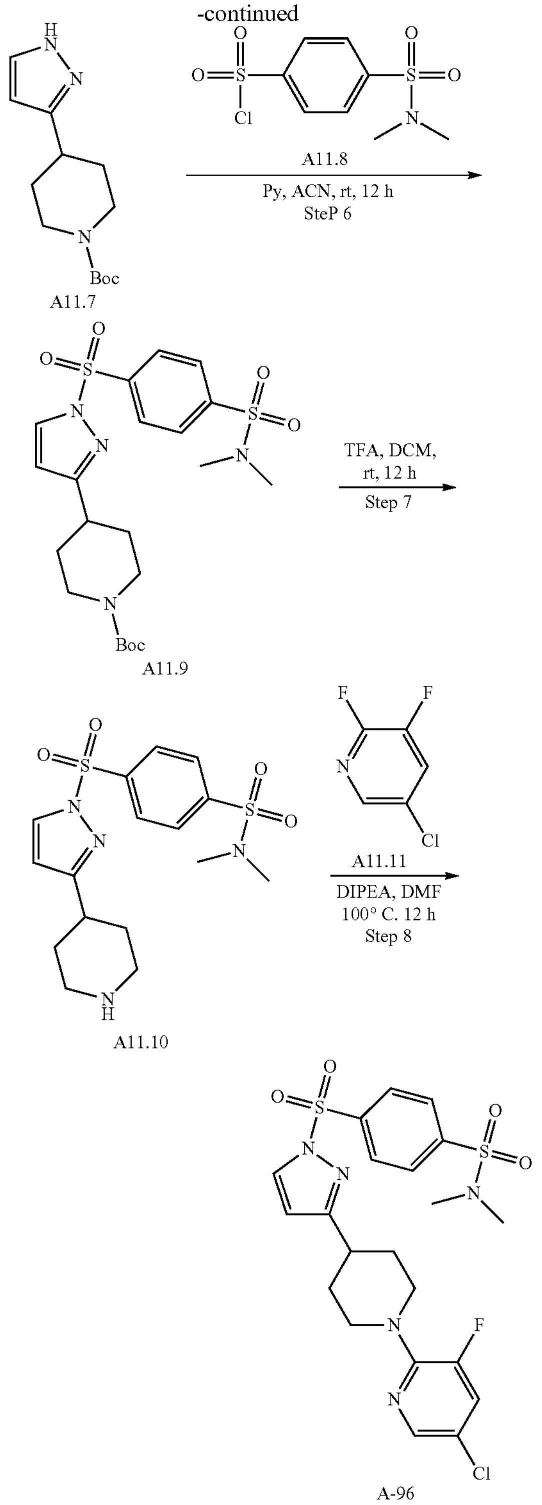

Step-1: Synthesis of 1-(tert-butyl) 4-ethyl piperidine-1,4-dicarboxylate A11.2

To a stirred solution of ethyl piperidine-4-carboxylate (A11.1) (10 g, 63.61 mmol, 1 eq) and boc anhydride (13.4 mL, 95.41 mmol, 1.5 eq) in DCM (300 mL) was added drop wise TEA (13.4 mL, 95.41 mmol, 1.5 eq). The reaction mixture was stirred at room temperature for 12 h. The progress of the reaction was monitored by TLC. After completion of the reaction, the reaction mixture was concentrated under reduced pressure. The crude product was purified by column chromatography to afford the desired product 1-(tert-butyl) 4-ethyl piperidine-1,4-dicarboxylate A11.2 (8 g, 48.89%). LCMS: 358.16 $[M+H]^+$.

Step-2: Synthesis of tert-butyl 4-(methoxy(methyl) carbamoyl)piperidine-1-carboxylate (A11.4)

To a stirred solution of 1-(tert-butyl) 4-ethyl piperidine-1,4-dicarboxylate (A11.2) (3 g, 11.66 mmol, 1 eq) and N,O-dimethylhydroxylamine (A11.3) (1.3 g, 13.99 mmol, 1.2 eq) in THE (100 mL) was added drop wise isopropyl magnesium chloride (11.66 mL, 23.32 mmol, 2 eq) at −20° C. The reaction mixture was stirred at −5° C. for 1 h. The progress of the reaction was monitored by TLC. After completion of the reaction, the reaction mixture was diluted with water and extracted with ethyl acetate. The organic layer was separated washed with water, brine, dried over anhydrous sodium sulfate and evaporated under reduced pressure. The crude product was purified by column chromatography to afford the desired product tert-butyl 4-(methoxy(methyl)carbamoyl)piperidine-1-carboxylate (A11.4) (2.1 g, 66.12%). LCMS: 273.17 $[M+H]^+$.

Step-3: Synthesis of tert-butyl 4-acetylpiperidine-1-carboxylate (A11.5)

To a stirred solution of tert-butyl 4-(methoxy(methyl) carbamoyl)piperidine-1-carboxylate (A11.4) (2 g, 10.64 mmol, 1 eq) in THE (40 mL) was added methyl magnesium chloride (10.29 mL, 30.87 mmol, 2.9 eq). The reaction mixture was stirred at room temperature for 12 h. The progress of the reaction was monitored by TLC. After completion of the reaction, the reaction mixture was quenched with $NH_4Cl$ and extracted with ethyl acetate. The organic layer was separated washed with water and brine, dried over anhydrous sodium sulfate and evaporated under reduced pressure. The crude product was purified by column chromatography to afford the desired product tert-butyl 4-acetylpiperidine-1-carboxylate (A11.5) (1.3 g, 89.82%). LCMS: 228.15 $[M+H]^+$.

Step-4: Synthesis of tert-butyl (Z)-4-(3-(dimethylamino)acryloyl)piperidine-1-carboxylate (A11.6)

A solution of tert-butyl 4-acetylpiperidine-1-carboxylate (A11.5) (2 g, 8.80 mmol, 1 eq) in DMF.DMA (6.3 g, 53.79 mmol, 6 eq) was stirred at 110° C. for 12 h. The reaction progress was monitored by TLC. After completion, the reaction mixture was diluted with water and ethyl acetate. The organic layer was separated, washed with water and 1% HCl, dried over $Na_2SO_4$ and concentrated to provide the desired tert-butyl (Z)-4-(3-(dimethylamino)acryloyl)piperidine-1-carboxylate (A11.6) (2 g Crude). The crude was used as such next step without further purification LCMS: 283.19 $[M+H]^+$.

Step-5: Synthesis of tert-butyl 4-(1H-pyrazol-3-yl) piperidine-1-carboxylate (A11.7)

To a stirred solution of tert-butyl (Z)-4-(3-(dimethylamino)acryloyl)piperidine-1-carboxylate (A11.6) (2 g, 7.80 mmol, 1 eq) in hydrazine hydrate (30 mL). The reaction mixture was stirred at 110° C. for 12 h. The progress of the reaction was monitored by TLC. After completion of the reaction, the reaction mixture was quenched with water and extracted with ethyl acetate. The organic layer was separated washed with water, brine, dried over anhydrous sodium sulfate and evaporated under reduced pressure. The crude product was purified by column chromatography to afford the desired tert-butyl 4-(1H-pyrazol-3-yl)piperidine-1-carboxylate (A11.7). LCMS: 252.16 $[M+H]^+$.

Step-6: Synthesis of tert-butyl 4-(1-((4-(N,N-dimethylsulfamoyl)phenyl)sulfonyl)-1H-pyrazol-3-yl) piperidine-1-carboxylate (A11.9)

To a stirred solution of tert-butyl 4-(1H-pyrazol-3-yl) piperidine-1-carboxylate A11.7 (0.45 g, 1.77 mmol, 1 eq) & 4-(N,N-dimethylsulfamoyl)benzenesulfonyl chloride (A11.8) (0.61 g, 2.15 mmol, 1.2 eq) in ACN (8 mL) was added pyridine (0.42 mL, 5.31 mmol, 3 eq) at 0° C. followed by addition of compound 11.8 (0.21 g, 0.75 mmol, 1.1 eq). The reaction mixture was stirred at room temperature for 12 h. The progress of the reaction was monitored by TLC. After completion of the reaction, the reaction mixture was quenched with water and extracted with ethyl acetate. The organic layer was separated washed with water, brine, dried over anhydrous sodium sulfate and evaporated under reduced pressure. The crude product was purified by column chromatography to afford the desired product tert-butyl 4-(1-((4-(N,N-dimethylsulfamoyl)phenyl)sulfonyl)-1H-pyrazol-3-yl)piperidine-1-carboxylate (A11.9). LCMS: 499.16 $[M+H]^+$.

Step-7: Synthesis of N,N-dimethyl-4-((3-(piperidin-4-yl)-1H-pyrazol-1-yl)sulfonyl)benzenesulfonamide (A11.10)

To a stirred solution of tert-butyl 4-(1-((4-(N,N-dimethylsulfamoyl)phenyl)sulfonyl)-1H-pyrazol-3-yl)piperidine-1-carboxylate (A11.9) (0.3 g, 0.60 mmol, 1 eq) in DCM (5 mL), 50% TFA (2 mL) was added dropwise at 0° C. and the reaction mixture was stirred at room temperature for 12 h. The progress of the reaction was monitored by TLC. After completion, the reaction mixture was concentrated under reduced pressure. The crude product was triturated with ether & concentrated to afford the titled compound N,N-dimethyl-4-((3-(piperidin-4-yl)-1H-pyrazol-1-yl)sulfonyl) benzenesulfonamide (A11.10) (0.26 g, Crude). The crude was used as such next step without purification. LCMS: 399.11 $[M+H]^+$.

Step-8: Synthesis of 4-((3-(1-(5-chloro-3-fluoropyridin-2-yl)piperidin-4-yl)-1H-pyrazol-1-yl)sulfonyl)-N,N-dimethylbenzenesulfonamide (A-96)

To a stirred solution of N,N-dimethyl-4-((3-(piperidin-4-yl)-1H-pyrazol-1-yl)sulfonyl)benzenesulfonamide (A11.10) (0.07 g, 0.18 mmol, 1 eq) and 5-chloro-2,3-difluoropyridine (A11.11) (39 mg, 0.26 mmol, 1.5 eq) in DMF (3 mL) was added DIPEA (0.15 mL, 0.88 mmol, 5 eq) at room temperature. The reaction mixture was stirred at 100° C. for 12 h. The reaction progress was monitored by TLC. After completion, the reaction mixture was diluted with water and ethyl acetate. The organic layer was separated, washed with water and 1% HCl, dried over $Na_2SO_4$ and concentrated. The crude was purified by silica gel column chromatography followed by prep HPLC to provide the desired compound 4-((3-(1-(5-chloro-3-fluoropyridin-2-yl)piperidin-4-yl)-1H-pyrazol-1-yl)sulfonyl)-N,N-dimethylbenzenesulfonamide (A-96). Yield: 2 mg, 9%; Appearance: White solid; $^1H$ NMR (400 MHz, DMSO-$d_6$) δ 8.44 (d, J=2.9 Hz, 1H), 8.18 (d, J=8.2 Hz, 2H), 8.13-7.98 (m, 3H), 7.80 (d, J=13.0 Hz, 1H), 6.65 (d, J=2.7 Hz, 1H), 3.92 (d, J=13.4 Hz, 2H), 2.64 (s, 6H), 2.94 (dt, J=32.4, 12.3 Hz, 3H), 1.93-1.84 (m, 2H), 1.72-1.60 (m, 2H); HPLC purity: 98.54%; LCMS Calculated for $C_{21}H_{23}ClFN_5O_4S_2$: 527.09; Observed: 528.0 $[M+H]^+$.

Example A12: Synthesis of 4-((3-(1-(4-chloro-2-fluorophenyl)piperidin-4-yl)-2-oxoimidazolidin-1-yl)sulfonyl)-N,N-dimethylbenzenesulfonamide)(A-86)

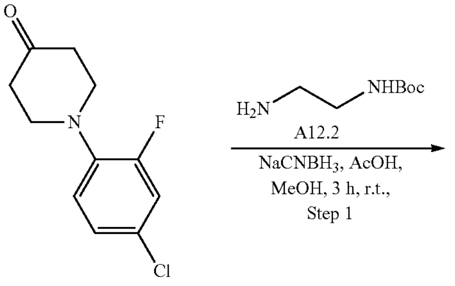

A12.1

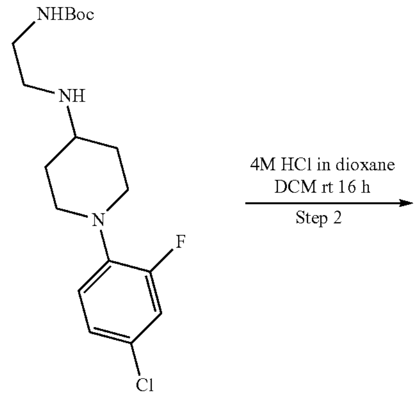

A12.3

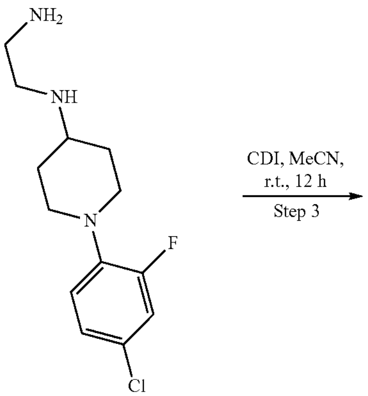

A12.4

-continued

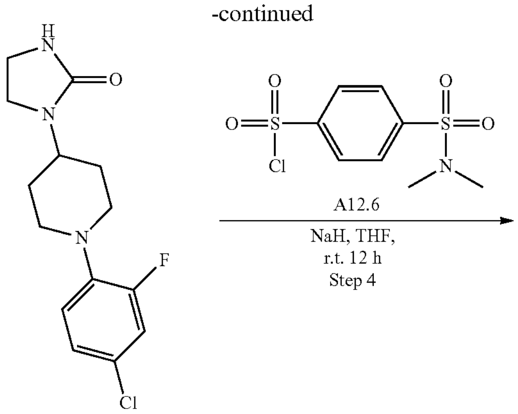

A12.5

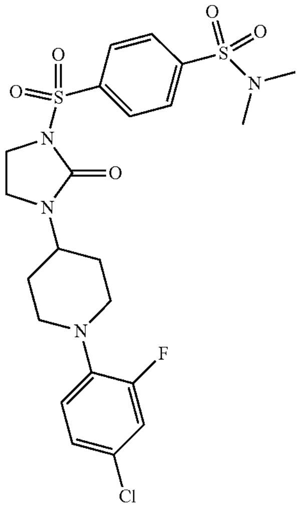

A-86

Step-1: Synthesis of tert-butyl (2-((1-(4-chloro-2-fluorophenyl)piperidin-4-yl)amino)ethyl)carbamate (A12.3)

To a stirred solution of 1-(4-chloro-2-fluorophenyl)piperidin-4-one (A12.1) (3.5 g, 11.32 mmol, 1 eq) and tert-butyl (2-aminoethyl)carbamate (A12.2) (1.81 g, 11.32 mmol, 1 eq) in methanol (50 mL) was added acetic acid (3.23 mL, 56.61 mmol, 5 eq) at room temperature, reaction mixture was stirred at room temperature for 3.5 h followed by addition of sodium cyanoborohydride (2.13 g, 33.96 mmol, 3 eq). The reaction mixture was stirred at room temperature for 3 h. The progress of the reaction was monitored by TLC. After completion of the reaction, the reaction mixture was concentrated under reduce pressure, crude was diluted with saturated solution of sodium bicarbonate and DCM. The organic layers were washed with water, brine, dried over anhydrous sodium sulfate and evaporated under reduced pressure. The crude product was purified by column chromatography to afford the titled compound tert-butyl (2-((1-(4-chloro-2-fluorophenyl)piperidin-4-yl)amino)ethyl)carbamate (A12.3) (3.5 g, 83.3%). LCMS: 372.18 $[M+H]^+$.

Step-2: Synthesis of N1-(1-(4-chloro-2-fluorophenyl)piperidin-4-yl)ethane-1,2-diamine (A12.4)

To a stirred solution of tert-butyl (2-((1-(4-chloro-2-fluorophenyl)piperidin-4-yl)amino)ethyl)carbamate (A12.3)

(3.5 g, 9.41 mmol, 1 eq) in DCM (35 mL) was added HCl in 1,4-dioxane (35 mL) at 0° C. The reaction mixture was stirred at room temperature for 16 h. The reaction progress was monitored by TLC. After completion of reaction, the reaction mixture was concentrated, and the resulting residue was washed with ether and dried under vacuum to give desired compound N1-(1-(4-chloro-2-fluorophenyl)piperidin-4-yl)ethane-1,2-diamine (A12.4) (2.4 g, 94.11%). LCMS: 272.13 $[M+H]^+$.

Step-3: Synthesis of 1-(1-(4-chloro-2-fluorophenyl) piperidin-4-yl)imidazolidin-2-one (A12.5)

To a stirred solution of N1-(1-(4-chloro-2-fluorophenyl) piperidin-4-yl)ethane-1,2-diamine (A12.4) (2.4 g, 8.83 mmol, 1 eq) in ACN (25 mL) was added CDI (1.57 g, 9.71 mmol, 1.1 eq) at room temperature. The reaction mixture was stirred at room temperature for 12 h. The progress of the reaction was monitored by TLC. After completion of the reaction, the reaction mixture was diluted with saturated solution of sodium bicarbonate and DCM. The organic layers were washed with water, brine, dried over anhydrous sodium sulfate and evaporated under reduced pressure. The crude product was purified by column chromatography to afford the titled compound 1-(1-(4-chloro-2-fluorophenyl) piperidin-4-yl)imidazolidin-2-one (A12.5) (1.3 g, 49.42%). LCMS: 298.10 $[M+H]^+$.

Step-4: Synthesis of 4-((3-(1-(4-chloro-2-fluorophenyl)piperidin-4-yl)-2-oxoimidazolidin-1-yl)sulfonyl)-N,N-dimethylbenzenesulfonamide (A-86)

To a stirred solution of 1-(1-(4-chloro-2-fluorophenyl) piperidin-4-yl)imidazolidin-2-one (A12.5) (0.4 g, 1.34 mmol, 1 eq) in THE (8 mL) was added NaH (0.06 g, 2.68 mmol, 2 eq) at 0° C., stirred the reaction mixture for 5 min at same temperature followed by addition of 4-(N,N-dimethylsulfamoyl)benzenesulfonyl chloride (A12.6) (0.41 g, 1.47 mmol, 1.1 eq). The reaction mixture was stirred at room temperature for 12 h. The progress of the reaction was monitored by TLC. After completion of the reaction, the reaction mixture was diluted with water and extracted with ethyl acetate. The organic layers were washed with water, brine, dried over anhydrous sodium sulfate and evaporated under reduced pressure. The crude product was purified by prep HPLC to afford the titled compound 4-((3-(1-(4-chloro-2-fluorophenyl)piperidin-4-yl)-2-oxoimidazolidin-1-yl) sulfonyl)-N,N-dimethylbenzenesulfonamide (A-86). Yield: 30 mg, 8%; Appearance: White solid; $^1H$ NMR (400 MHz, DMSO-$d_6$) δ 8.19 (d, J=8.1 Hz, 2H), 8.01 (d, J=8.1 Hz, 2H), 7.30 (d, J=12.4 Hz, 1H), 7.16-7.14 (m, 1H), 7.06-7.03 (m, 1H), 3.86 (t, J=7.6 Hz, 2H), 3.62 (m, 1H), 3.50-3.41 (m, 2H), 2.67 (s, 9H), 1.74 (q, J=11.7 Hz, 2H), 1.62 (t, J=7.8 Hz, 3H); HPLC purity: 98.25%; LCMS Calculated for $C_{22}H_{26}ClFN_4O_5S_2$: 544.10; Observed: 545.10 $[M+H]^+$.

Example A13: Synthesis of 4-((3-(1-(4-chloro-2-fluorophenyl)piperidin-4-yl)-2-oxo-2,3-dihydro-1H-imidazol-1-yl)sulfonyl)-N,N-dimethylbenzenesulfonamide (A-67)

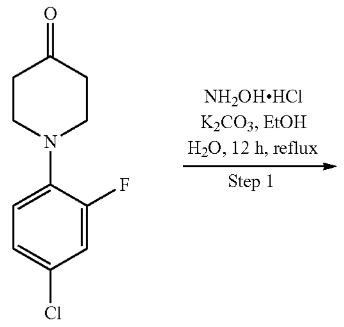

A13.1

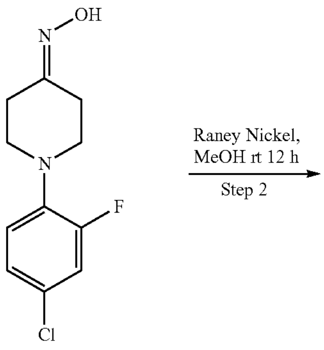

A13.2

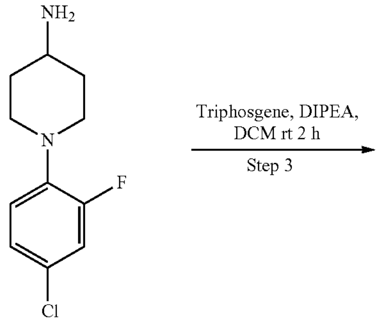

A13.3

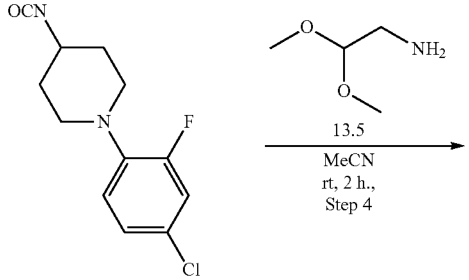

A13.4

-continued

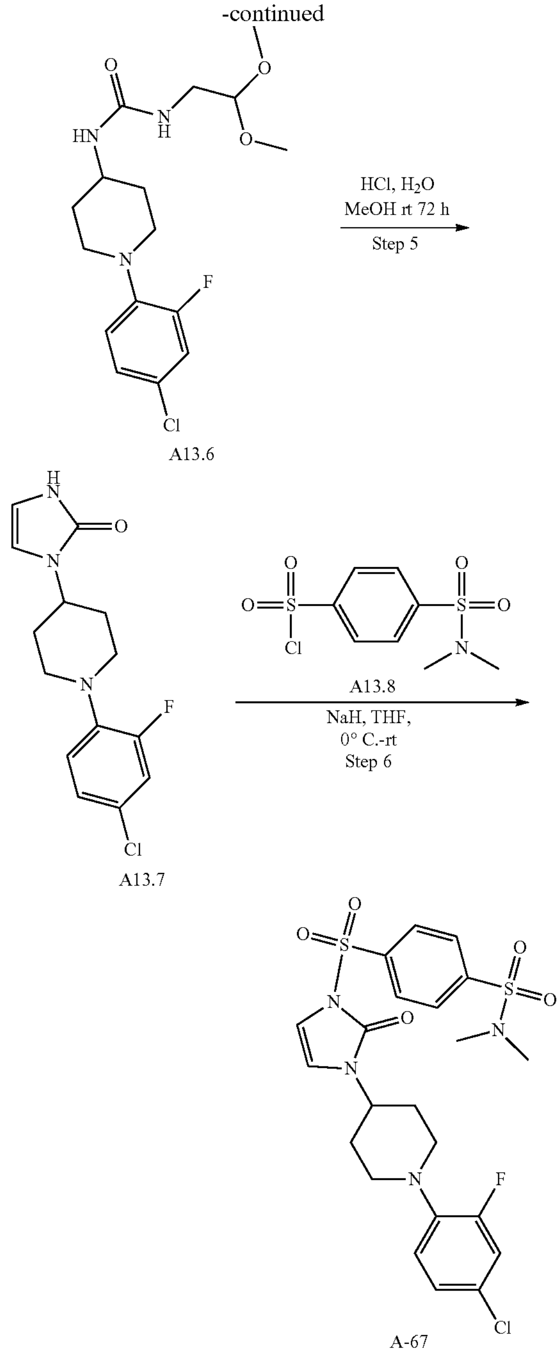

A13.6

A13.7

A-67

A13.7

Step-1: Synthesis of 1-(4-chloro-2-fluorophenyl) piperidin-4-one Oxime (A13.2)

To a stirred solution of 1-(4-chloro-2-fluorophenyl)piperidin-4-one (A13.1) (3.5 g, 15.42 mmol, 1 eq) in ethanol (35 mL) and water (35 mL) was added hydroxyl amine hydrochloride (1.6 g, 23.12 mmol, 1.5 eq). The reaction mixture was refluxed for 12 h. The progress of the reaction was monitored by TLC. After completion of the reaction, the reaction mixture was poured in ice water; obtained solid was filtered & concentrated under reduced pressure to afford the desired product 1-(4-chloro-2-fluorophenyl)piperidin-4-one oxime (A13.2) (3.6 g, Crude). LCMS: 243.06 $[M+H]^+$.

Step-2: Synthesis of 1-(4-chloro-2-fluorophenyl) piperidin-4-amine (A13.3)

To a stirred solution of 1-(4-chloro-2-fluorophenyl)piperidin-4-one oxime (A13.2) (3.5 g, 14.52 mmol, 1 eq) in methanol (40 mL) was added Raney Nickel (1.8 g, 50%) at room temperature, stirred the reaction mixture at room temperature for 12 h under hydrogen gas balloon pressure. The progress of the reaction was monitored by TLC. After completion of the reaction, the reaction mixture was filtered through Celite and evaporated under reduced pressure. The crude product was purified by silica gel column chromatography to afford the titled compound 1-(4-chloro-2-fluorophenyl)piperidin-4-amine (A13.3) (2.1 g, 63.44%). LCMS: 229.08 $[M+H]^+$.

Step-3: Synthesis of 1-(4-chloro-2-fluorophenyl)-4-isocyanatopiperidine (A13.4)

To a stirred solution of triphosgene (1.56 g, 5.26 mmol, 1 eq) in DCM (20 mL) was added 1-(4-chloro-2-fluorophenyl) piperidin-4-amine (A13.3) (1.2 g, 5.26 mmol, 1 eq) and DIPEA (3.6 mL, 21.05 mmol, 4 eq) at 0° C. The reaction mixture was stirred at room temperature for 2 h. The progress of the reaction was monitored by TLC. After completion of the reaction, the reaction mixture was diluted with water and DCM. The organic layers were washed with brine, dried over anhydrous sodium sulfate and evaporated under reduced pressure to afford the desired product 1-(4-chloro-2-fluorophenyl)-4-isocyanatopiperidine (A13.4) (1.3 g, 97.77%). LCMS: 255.06 $[M+H]^+$.

Step-4: Synthesis of 1-(1-(4-chloro-2-fluorophenyl) piperidin-4-yl)-3-(2,2-dimethoxyethyl)urea (A13.6)

To a stirred solution of 1-(4-chloro-2-fluorophenyl)-4-isocyanatopiperidine (A13.4) (1.3 g, 5.12 mmol, 1 eq) in acetonitrile (10 mL) was added 2,2-dimethoxyethan-1-amine (A13.5) (0.81 g, 7.67 mmol, 1.5 eq) at room temperature. The reaction mixture was stirred at room temperature for 2 h. The progress of the reaction was monitored by TLC. After completion of the reaction, the resultant precipitate was filtered out and dried under reduced pressure to afford the desired product 1-(1-(4-chloro-2-fluorophenyl) piperidin-4-yl)-3-(2,2-dimethoxyethyl)urea (A13.6) (1.5 g, 88.96%). LCMS: 360.14 $[M+H]^+$.

Step-5: Synthesis of 1-(1-(4-chloro-2-fluorophenyl) piperidin-4-yl)-1,3-dihydro-2H-imidazol-2-one (A13.7)

To a stirred solution of 1-(1-(4-chloro-2-fluorophenyl) piperidin-4-yl)-3-(2,2-dimethoxyethyl)urea (A13.6) (1.5 g, 4.18 mmol, 1 eq) in methanol (15 mL) and water (15 mL) was added 1 M HCl (15 mL). The reaction mixture was stirred at room temperature for 72 h. The progress of the reaction was monitored by TLC. After completion of the reaction, the reaction mixture was concentrated under reduced pressure and extracted with ethyl acetate. The organic layers were washed with water, brine, dried over anhydrous sodium sulfate and evaporated under reduced pressure. The crude product was purified by silica gel column chromatography to afford the titled compound 1-(1-

(4-chloro-2-fluorophenyl)piperidin-4-yl)-1,3-dihydro-2H-imidazol-2-one (A13.7) (1.1 g, 89%). LCMS: 296.09 [M+H]$^+$.

Step-6: Synthesis of 4-((3-(1-(4-chloro-2-fluorophenyl)piperidin-4-yl)-2-oxo-2,3-dihydro-1H-imidazol-1-yl)sulfonyl)-N,N-dimethylbenzenesulfonamide (A-67)

To a stirred solution of 1-(1-(4-chloro-2-fluorophenyl) piperidin-4-yl)-1,3-dihydro-2H-imidazol-2-one (A13.7) (0.3 g, 1.02 mmol, 1 eq) in THE (6 mL) was added NaH (41 mg 31.02 mmol, 1 eq) at 0° C., stirred reaction mixture at same temperature for 5 min followed by addition of 4-(N, N-dimethylsulfamoyl)benzenesulfonyl chloride (A13.8) (0.29 g, 1.02 mmol, 1 eq). The reaction mixture was stirred at room temperature for 30 min. The progress of the reaction was monitored by TLC. After completion of the reaction, the reaction mixture was poured in ice cold water; obtained precipitate was filtered and dried under reduced pressure. The crude product was purified by column chromatography followed by prep HPLC to afford the desired product 4-((3-(1-(4-chloro-2-fluorophenyl)piperidin-4-yl)-2-oxo-2,3-dihydro-1H-imidazol-1-yl)sulfonyl)-N,N-dimethylbenzenesulfonamide (A-67). Yield: 30 mg, 5.44%; Appearance: White solid; $^1$H NMR (400 MHz, DMSO-d$_6$) δ 8.28-8.21 (m, 2H), 8.09-8.02 (m, 2H), 7.31 (dd, J=12.8 Hz, 12.4 Hz, 1H), 7-7.15 (m, 1H), 7.21-6.98 (m, 3H), 3.90-3.84 (m, 1H), 3.38-3.35 (m, 2H), 2.75 (t, J=12 Hz, 2H), 2.67 (s, 6H), 1.93-1.85 (m, 2H), 1.76-1.74 (m, 2H); HPLC purity: 98.23%; LCMS Calculated for $C_{22}H_{24}ClFN_4O_5S_2$: 542.09; Observed: 543.10 [M+H]$^+$.

Example A14: Synthesis of N1-(2-(1-(4-chloro-2-fluorophenyl)-1,2,3,6-tetrahydropyridin-4-yl)phenyl)-N4,N4-dimethylbenzene-1,4-disulfonamide (A-19) and N1-(2-(1-(4-chloro-2-fluorophenyl)piperidin-4-yl)phenyl)-N4,N4-dimethylbenzene-1,4-disulfonamide (A-22)

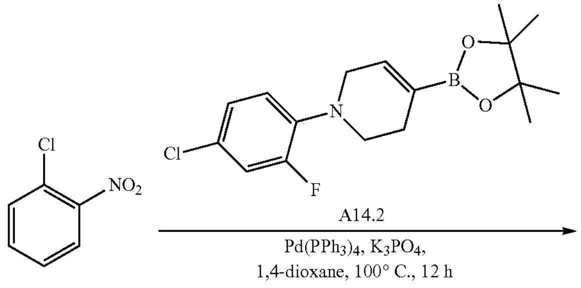

A14.1

-continued

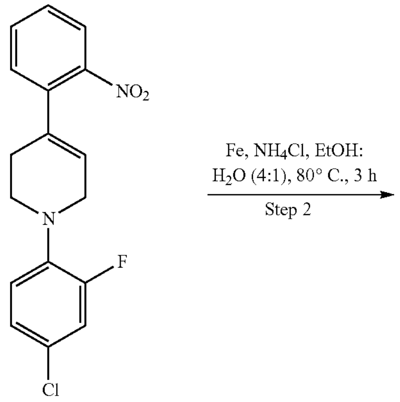

A14.3

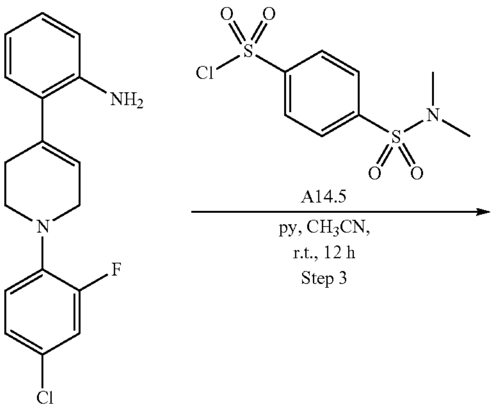

A14.4

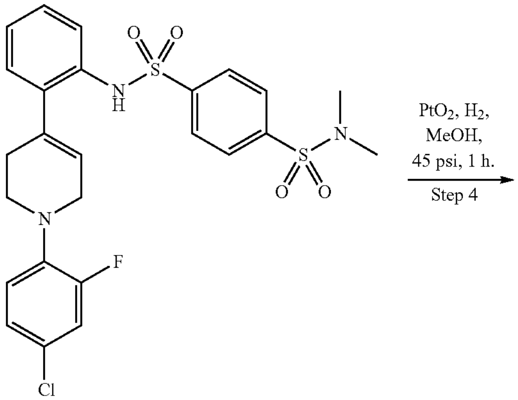

A-19

-continued

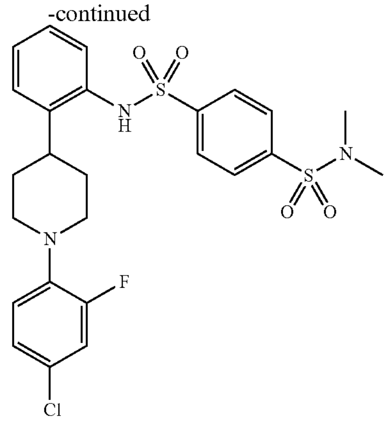

A-22

Step-1: Synthesis of 1-(4-chloro-2-fluorophenyl)-4-(2-nitrophenyl)-1,2,3,6-tetrahydropyridine (A14.3)

To a stirred solution of 1-chloro-2-nitrobenzene (A14.1) (0.2 g, 1.2 mmol, 1 eq) and 1-(4-chloro-2-fluorophenyl)-4-(4,4,5,5-tetramethyl-1,3,2-dioxaborolan-2-yl)-1,2,3,6-tetrahydropyridine (A14.2) (0.47 g, 1.4 mmol, 1.1 eq) in a mixture of 1,4-dioxane and water (4:1), $K_3PO_4$ (0.81 g, 3.7 mmol, 3 eq) was added and purged with argon for 30 min followed by the addition of Tetrakis(triphenylphosphine) palladium(0) (0.15 g, 0.1 mmol, 0.1 eq) and stirred at 100° C. for overnight. The progress of the reaction was monitored by TLC. After completion of the reaction, the reaction mixture was filtered through Celite and evaporated under reduced pressure. The crude product was purified by column chromatography to afford the desired product 1-(4-chloro-2-fluorophenyl)-4-(2-nitrophenyl)-1,2,3,6-tetrahydropyridine (A14.3) (0.3 g, 71%). LCMS: 333.07 $[M+H]^+$.

Step-2: Synthesis of 2-(1-(4-chloro-2-fluorophenyl)-1,2,3,6-tetrahydropyridin-4-yl)aniline (A14.4)

To a stirred solution of 1-(4-chloro-2-fluorophenyl)-4-(2-nitrophenyl)-1,2,3,6-tetrahydropyridine (A14.3) (0.3 g, 1.5 mmol, 1 eq) in mixture of ethanol (3 mL) and water (1.2 mL) were added iron powder (0.24 g, 7.5 mmol, 5 eq) and ammonium chloride (0.24 g, 7.5 mmol, 5 eq) at room temperature. The resulting reaction mixture was heated at 80° C. for 3 h. The progress of the reaction was monitored by TLC. After completion of the reaction, the reaction mixture was filtered through a pad of Celite and the filtrate was evaporated. The crude reaction mixture was diluted with water and extracted with ethyl acetate. The combined organic layers were washed with water, brine, dried over anhydrous sodium sulfate and evaporated under reduced pressure. The crude product was purified by silica gel column chromatography to afford the titled compound 2-(1-(4-chloro-2-fluorophenyl)-1,2,3,6-tetrahydropyridin-4-yl) aniline (A14.4) (0.2 g, 44%). LCMS: 303.10 $[M+H]^+$.

Step-3: Synthesis of Synthesis of N1-(2-(1-(4-chloro-2-fluorophenyl)-1,2,3,6-tetrahydropyridin-4-yl)phenyl)-N4,N4-dimethylbenzene-1,4-disulfonamide (A-19)

To a stirred solution of 2-(1-(4-chloro-2-fluorophenyl)-1,2,3,6-tetrahydropyridin-4-yl)aniline (A14.4) (0.1 g, 0.33 mmol, 1 eq) in acetonitrile (1 mL) was added pyridine (0.08 mL, 0.99 mmol, 3 eq) at 0° C. followed by addition of 4-(N,N-dimethylsulfamoyl)benzenesulfonyl chloride (A14.5) (0.11 g, 0.397 mmol, 1.2 eq). The reaction mixture was stirred at room temperature for overnight; the reaction progress was monitored by TLC. After completion, the reaction mixture was concentrated under reduced pressure. The crude residue was purified by column chromatography to afford the desired product N1-(2-(1-(4-chloro-2-fluorophenyl)-1,2,3,6-tetrahydropyridin-4-yl)phenyl)-N4,N4-dimethylbenzene-1,4-disulfonamide (A-19). Yield: 15 mg, 8%; Appearance: Off-white solid; $^1H$ NMR (400 MHz, DMSO-$d_6$) δ 9.83 (s, 1H), 7.92 (s, 4H), 7.36 (dd, J=12.8 Hz, 2.8 Hz, 1H), 7.23-7.17 (m, 4H), 7.10 (t, J=9.2 Hz, 1H), 7.05-7.02 (m, 1H), 5.47 (m, 1H), 3.59 (m, 2H), 3.16 (t, J=5.6 Hz, 2H), 2.62 (s, 6H), 2.23 (m, 2H): HPLC purity: >99%; LCMS Calculated for $C_{25}H_{25}ClFN_3O_4S_2$: 549.10; Observed: 550.15 $[M+H]^+$.

Step-4: Synthesis of N1-(2-(1-(4-chloro-2-fluorophenyl)piperidin-4-yl)phenyl)-N4,N4-dimethylbenzene-1,4-disulfonamide (A-22)

To the stirred solution of N1-(2-(1-(4-chloro-2-fluorophenyl)-1,2,3,6-tetrahydropyridin-4-yl)phenyl)-N4,N4-dimethylbenzene-1,4-disulfonamide (A-19) (0.12 g, 2.1 mmol, 1 eq) in methanol (6 mL) was added $PtO_2$ (24 mg). The reaction mixture was hydrogenated at 45 psi for 1 h at room temperature. The progress of the reaction was monitored by TLC. After completion of the reaction, the reaction mixture was filtered through a pad of Celite, the Celite pad was washed with methanol and the filtrate was concentrated under reduced pressure. The crude product was purified by column chromatography to afford the titled compound N1-(2-(1-(4-chloro-2-fluorophenyl)piperidin-4-yl)phenyl)-N4,N4-dimethylbenzene-1,4-disulfonamide (A-22). Yield: 43 mg, 35.83%; Appearance: Off-white solid; $^1H$ NMR (400 MHz, DMSO-$d_6$) δ 10.11 (s, 1H), 7.96 (d, J=8.4 Hz, 2H), 7.88 (d, J=7.6 Hz, 2H), 7.34-7.30 (m, 2H), 7.26-7.15 (m, 3H), 7.06 (t, J=9.2 Hz, 2H), 3.29-3.26 (m, 2H), 2.64 (m, 8H), 1.65-1.57 (m, 2H), 1.23-1.20 (m, 2H), (1 is proton merged with solvent peak): HPLC purity: 99.31%; LCMS Calculated for $C_{25}H_{27}ClFN_3O_4S_2$: 551.11; Observed: 552.1 $[M+H]^+$.

Example A15: Synthesis of N1-(2-(4-(4-chloro-2-fluorophenyl)cyclohexyl)phenyl)-N4,N4-dimethylbenzene-1,4-disulfonamide (A-69/Isomer-I) and (A-70/Isomer-II)

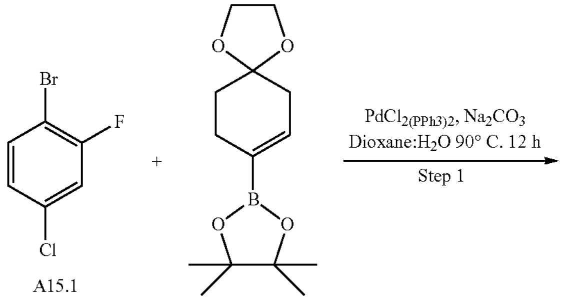

A15.1

A15.2

-continued
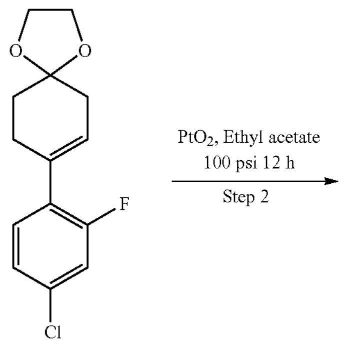
A15.3
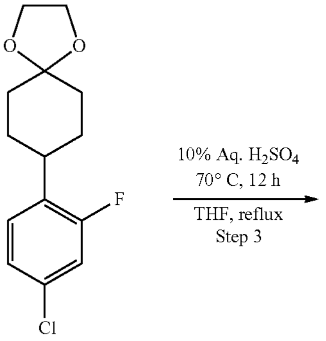
A15.4
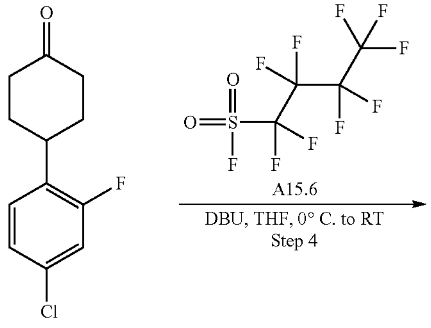
A15.4
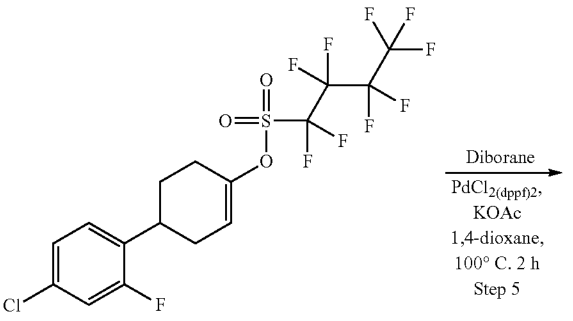
A15.7
-continued
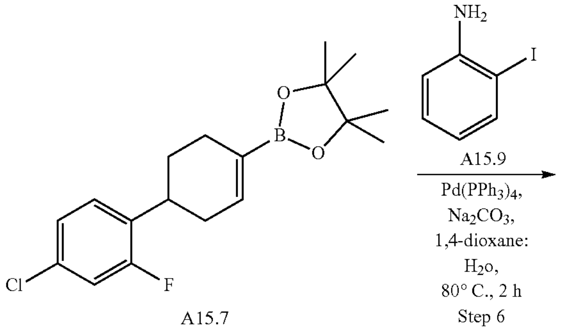
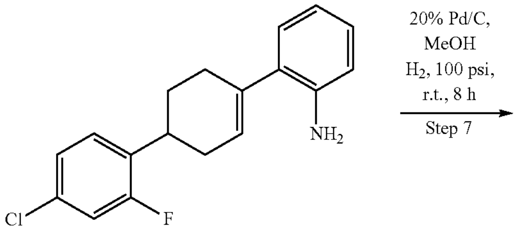
A15.10
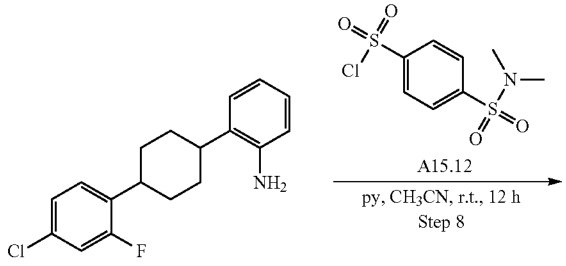
A15.11
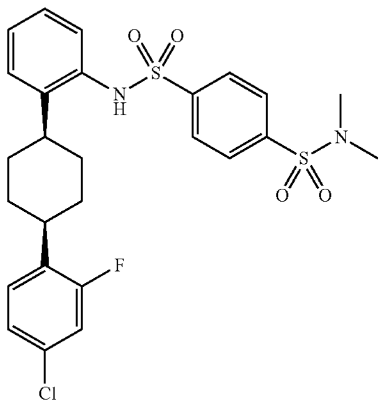
+
A-69 (Isomer-I)

-continued

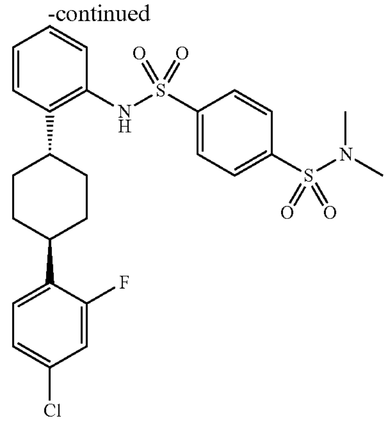

A-70 (Isomer-I)

Step-1: Synthesis of 8-(4-chloro-2-fluorophenyl)-1,4-dioxaspiro[4.5]dec-7-ene A15.3

To a mixture of 1-bromo-4-chloro-2-fluorobenzene A15.1 (3 g, 14.3 mmol, 1 eq) and 4,4,5,5-tetramethyl-2-(1,4-dioxaspiro[4.5]dec-7-en-8-yl)-1,3,2-dioxaborolane (A15.2) (4.48 g, 15.7 mmol, 1.1 eq) in a mixture of 1,4-dioxane and water (4:1, 50 mL), $Na_2CO_3$ (3 g, 28.7 mmol, 2 eq) was added and purged with argon for 30 min followed by the addition of Tetrakis(triphenylphosphine)palladium(0) (1 g, 1.43 mmol, 0.1 eq) and stirred at 90° C. for 12 h. The progress of the reaction was monitored by TLC. After completion of the reaction, the reaction mixture was quenched with water and extracted with ethyl acetate, washed with water, brine, dried over anhydrous sodium sulfate and evaporated under reduced pressure. The crude product was purified by column chromatography to afford the desired product 8-(4-chloro-2-fluorophenyl)-1,4-dioxaspiro[4.5]dec-7-ene (A15.3) (3.3 g, 85.93%). LCMS: 269.07 $[M+H]^+$.

Step-2: Synthesis of 8-(4-chloro-2-fluorophenyl)-1,4-dioxaspiro[4.5]decane (A15.4)

The solution of 8-(4-chloro-2-fluorophenyl)-1,4-dioxaspiro[4.5]dec-7-ene A15.3 (3.3 g, 12.3 mmol, 1 eq) in ethyl acetate (50 mL) was added $PtO_2$ (1.65 g), the reaction mixture was hydrogenated at 100 psi for 12 h. The progress of the reaction was monitored by TLC. After completion of the reaction, the reaction mixture was concentrated under reduced pressure. The crude product was purified by column chromatography to afford the desired product 8-(4-chloro-2-fluorophenyl)-1,4-dioxaspiro[4.5]decane (A15.4) (1.1 g, 33.13%). LCMS: 271.08 $[M+H]^+$.

Step-3: Synthesis of 4-(4-chloro-2-fluorophenyl)cyclohexan-1-one (A15.5)

To a stirred solution of 8-(4-chloro-2-fluorophenyl)-1,4-dioxaspiro[4.5]decane A15.4 (1.1 g, 4.07 mmol, 1 eq) in THE (20 mL) was added 10% aqueous $H_2SO_4$ (16.5 ml). The reaction mixture was stirred at 70° C. for 12 h. The reaction progress was monitored by TLC. After completion of the reaction, the reaction mixture was quenched with saturated aqueous $NaHCO_3$ at 0° C. and extracted with ethyl acetate. The combined organic layers were washed with water and brine, dried over anhydrous sodium sulfate and evaporated under reduced pressure. The crude product was purified by column chromatography to afford the desired product 4-(4-chloro-2-fluorophenyl)cyclohexan-1-one (A15.5) (0.8 g, 86.95%). LCMS: 227.06 $[M+H]^+$.

Step-4: Synthesis of 4'-chloro-2'-fluoro-1,2,3,6-tetrahydro-[,1'-biphenyl]-4-yl 1,1,2,2,3,3,4,4,4-nonafluorobutane-1-sulfonate (A15.7)

To a stirred solution of 4-(4-chloro-2-fluorophenyl)cyclohexan-1-one (A15.5) (0.8 g, 3.53 mmol, 1 eq) in THE (10 mL) were added DBU (0.64 g, 4.24 mmol, 1.2 eq) and 1,1,2,2,3,3,4,4,4-nonafluorobutane-1-sulfonyl fluoride (A15.6) (1.28 g, 4.24 mmol, 1.2 eq) at 0° C. The reaction mixture was stirred at room temperature for 3 h. The reaction progress was monitored by TLC. After completion of the reaction, the reaction mixture was quenched with water and ethyl acetate. The organic layer was separated, washed with water, brine, dried over anhydrous sodium sulfate and evaporated under reduced pressure. The crude product was purified by column chromatography to afford the desired product 4'-chloro-2'-fluoro-1,2,3,6-tetrahydro-[1,1'-biphenyl]-4-yl 1,1,2,2,3,3,4,4,4-nonafluorobutane-1-sulfonate (A15.7) (1.4 g, 78.21%). LCMS: 509.00 $[M+H]^+$.

Step-5: Synthesis of 2-(4'-chloro-2'-fluoro-1,2,3,6-tetrahydro-[,1'-biphenyl]-4-yl)-4,4,5,5-tetramethyl-1,3,2-dioxaborolane (A15.8)

To a stirred solution of 4'-chloro-2'-fluoro-1,2,3,6-tetrahydro-[1,1'-biphenyl]-4-yl 1,1,2,2,3,3,4,4,4-nonafluorobutane-1-sulfonate (A15.7) (0.7 g, 1.37 mmol, 1 eq) in 1,4-dioxane (20 mL) were added 4,4,4',4',5,5,5',5'-octamethyl-2,2'-bi(1,3,2-dioxaborolane) (0.35 g, 1.37 mmol, 1 eq), KOAc (0.4 g, 4.11 mmol, 3 eq) reaction mixture was purged with argon for 30 min followed by addition of $PdCl_2$(dppf) (0.03 g, 0.04 mmol, 0.03 eq). The reaction mixture was stirred at 100° C. for 2 h. The reaction progress was monitored by TLC. After completion of the reaction, the reaction mixture was quenched with water and ethyl acetate. The organic layer was separated washed with water, brine, dried over anhydrous sodium sulfate and evaporated under reduced pressure. Same reaction was repeated on 0.7 g. The crude product was combined and purified by column chromatography to afford the desired product 2-(4'-chloro-2'-fluoro-1,2,3,6-tetrahydro-[1,1'-biphenyl]-4-yl)-4,4,5,5-tetramethyl-1,3,2-dioxaborolane (A15.8) (0.6 g, 63%). LCMS: 337.15 $[M+H]^+$.

Step-6: Synthesis of 4"-chloro-2"-fluoro-2',3',4',5'-tetrahydro-[,1':4',1"-terphenyl]-2-amine (A15.10)

To a mixture of 2-(4'-chloro-2'-fluoro-1,2,3,6-tetrahydro-[1,1'-biphenyl]-4-yl)-4,4,5,5-tetramethyl-1,3,2-dioxaborolane (A15.8) (0.3 g, 1.36 mmol, 1 eq) and 2-iodoaniline (A15.9) (0.5 g, 1.50 mmol, 1.1 eq) in a mixture of 1,4-dioxane and water (4:1, 20 mL), $Na_2CO_3$ (0.29 g, 2.7 mmol, 2 eq) was added and purged with argon for 30 min followed by the addition of Tetrakis(triphenylphosphine)palladium(0) (0.1 g, 0.09 mmol, 0.07 eq) and stirred at 90° C. for 12 h. The progress of the reaction was monitored by TLC. After completion of the reaction, the reaction mixture was quenched with water and ethyl acetate. The organic layer was separated, washed with water, brine, dried over anhydrous sodium sulfate and evaporated under reduced pressure. The crude product was purified by column chromatography to afford the desired product 4"-chloro-2"-fluoro- 2',3',4',5'-tetrahydro-[1,1':4',1"-terphenyl]-2-amine (A15.10) (0.35 g, 85%). LCMS: 302.10 $[M+H]^+$.

Step-7: Synthesis of 2-(4-(4-chloro-2-fluorophenyl) cyclohexyl)aniline (A15.11)

To a stirred solution of 4"-chloro-2"-fluoro-2',3',4',5'-tetrahydro-[1,1':4',1"-terphenyl]-2-amine (A15.10) (0.3 g, 0.99 mmol, 1 eq) in methanol (30 mL) was added Pd/C (0.15 g). The reaction mixture was stirred under hydrogen at 100 psi pressure at room temperature for 8 h. The progress of reaction was monitored by TLC. After completion of reaction, the reaction mixture was filtered through a pad of Celite and the Celite pad was washed with methanol. The filtrate was concentrated under reduced pressure to obtained crude residue. The crude product was purified by column chromatography to afford the titled compound 2-(4-(4-chloro-2-fluorophenyl)cyclohexyl)aniline (A15.11) (0.14 mg, 46.51%).

Step-8: Synthesis of N1-(2-(4-(4-chloro-2-fluorophenyl)cyclohexyl)phenyl)-N4,N4-dimethylbenzene-1,4-disulfonamide (A-69 Isomer-I) and (A-70 Isomer-II)

To a stirred solution of 2-(4-(4-chloro-2-fluorophenyl) cyclohexyl)aniline (A15.11) (0.14 g, 0.46 mmol, 1 eq) in MeCN (10 mL) was added pyridine (0.1 g, 0.92 mmol, 2 eq) at 0° C., and stirred for 10 min followed by addition of 4-(N,N-dimethylsulfamoyl)benzenesulfonyl chloride (A15.12) (0.16 g, 0.55 mmol, 1.2 eq). The reaction mixture was stirred at room temperature for 12 h; the reaction progress was monitored by TLC. After completion, reaction mixture was quenched with water and extracted with ethyl acetate. The organic layer was separated, washed with brine, dried over anhydrous sodium sulfate and evaporated under reduced pressure. The crude product was purified preparative HPLC to afford N1-(2-(4-(4-chloro-2-fluorophenyl)cyclohexyl)phenyl)-N4,N4-dimethylbenzene-1,4-disulfonamide (A-70/Isomer-I) and (A-70/Isomer-II), which were confirmed by NOE.

A-69 (Isomer-I): Yield: 25 mg, 5.56%; Appearance: White solid; $^1H$ NMR (400 MHz, DMSO-$d_6$) δ 10.06 (s, 1H), 7.95 (d, J=8.4 Hz, 2H), 7.88 (d, J=8.8 Hz, 2H), 7.55-7.51 (m, 1H), 7.34 (dd, J=11.2 Hz, 10.8 Hz, 1H), 7.25 (dd, J=8.4 Hz, 8.4 Hz, 1H), 7.22-7.11 (m, 3H), 7.03-7.01 (m, 1H), 3.18 (m, 1H), 2.82-2.73 (m, 1H), 2.64 (m, 6H), 1.91-1.88 (m, 2H), 1.71-1.65 (m, 2H), 1.43-1.36 (m, 2H), 1.17-1.14 (m, 2H); HPLC purity: >99%; LCMS Calculated for $C_{26}H_{28}ClFN_2O_4S_2$: 550.12; Observed: 551.15 $[M+H]^+$.

A-70 (Isomer-II): Yield: 25 mg, 5.56%; Appearance: White solid; $^1H$ NMR (400 MHz, DMSO-$d_6$) δ 10.06 (s, 1H), 7.95 (d, J=8 Hz, 2H), 7.89 (d, J=8 Hz, 2H), 7.39-7.34 (m, 2H), 7.31-7.21 (m, 3H), 7.16-7.12 (m, 1H), 7.06-7.04 (m, 1H), 2.84-2.79 (s, 1H), 2.67-2.64 (m, 1H), 2.62 (s, 6H), 1.71-1.68 (m, 2H), 1.47-1.34 (m, 4H), 1.29-1.24 (m, 2H); HPLC purity: 98.15%; LCMS Calculated for $C_{26}H_{28}ClFN_2O_4S_2$: 550.12; Observed: 551.15 $[M+H]^+$.

Example A16: Synthesis of N1-(2-((4-chloro-2-fluorophenyl)ethynyl)phenyl)-N4,N4-dimethylbenzene-1,4-disulfonamide (A-3)

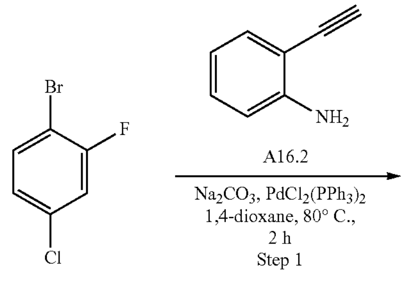

A16.1

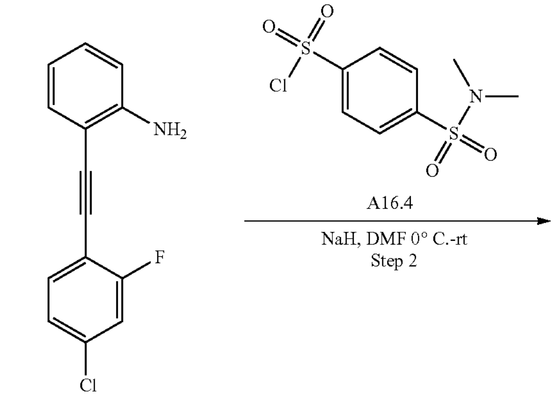

A16.3

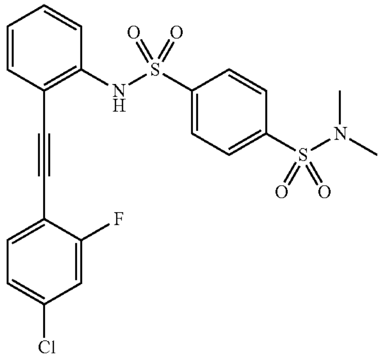

A-3

Step-1: Synthesis of 2-((4-chloro-2-fluorophenyl) ethynyl)aniline (A16.3)

To a stirred solution of 1-bromo-4-chloro-2-fluorobenzene A16.1 (0.1 g, 0.48 mmol, 1 eq) and 2-ethynylaniline (A16.2) (0.056 g, 0.48 mmol, 1 eq) in DMF (4 mL) was added DIPEA (0.17 mL, 0.96 mmol, 2 eq). The reaction mixture was purged with argon for 15 min followed by the addition of copper iodide (0.036 g, 0.19 mmol, 0.4 eq) and Bis(triphenylphosphine)palladium chloride (0.07 g, 0.095 mmol, 0.2 eq) stirred at 80° C. for 2 h. The progress of the reaction was monitored by TLC. After completion of the reaction, the reaction mixture was filtered through a pad of Celite, the Celite pad was washed with ethyl acetate. The filtrate was evaporated to dryness. The residue was dissolved in ethyl acetate, washed with water and brine, dried over anhydrous sodium sulfate and evaporated under reduced pressure. The crude product was purified by flash column chromatography to afford the desired product 2-((4-chloro-2-fluorophenyl)ethynyl)aniline (A16.3) (50 mg, 42%). LCMS: 246.04 [M+H]$^+$.

Step-2: Synthesis of N1-(2-((4-chloro-2-fluorophenyl)ethynyl)phenyl)-N4,N4-dimethylbenzene-1,4-disulfonamide (A-3)

To a stirred solution of 2-((4-chloro-2-fluorophenyl)ethynyl)aniline (A16.3) (500 mg, 0.2 mmol, 1 eq) in DMF (6 mL) was added a 60% suspension of sodium hydride in mineral oil (122 mg, 3.06 mmol, 1.5 eq) at 0° C. and reaction mixture was stirred for 10 min followed by addition of 4-(N,N-dimethylsulfamoyl)benzenesulfonyl chloride (A16.4) (579 mg, 2 mmol, 1 eq). The reaction mixture was stirred at room temperature for 2 h; the reaction progress was monitored by TLC. After completion of the reaction, the reaction mixture diluted with water and ethyl acetate. The organic layer was separated, washed with water and brine, dried over $Na_2SO_4$ and evaporated to provide crude residue which was purified by column chromatography followed by prep HPLC to afford the desired product N1-(2-((4-chloro-2-fluorophenyl)ethynyl)phenyl)-N4,N4-dimethylbenzene-1,4-disulfonamide (A-3). Yield: 25 mg, 3%; Appearance: Off-white solid; 1H NMR (400 MHz, DMSO-$d_6$) δ 7.92-7.91 (m, 2H), 7.78-7.71 (m, 3H), 7.44-7.37 (m, 3H), 7.24-7.11 (m, 4H), 2.67 (s, 6H); HPLC purity: >99%; LCMS Calculated for $C_{22}H_{18}ClFN_2O_4S_2$:492.04; Observed: 494.75 [M+2]$^+$.

Example A17: Synthesis of 4-((3-(4-(4-chloro-2-fluorophenyl)piperidin-1-yl)-1H-1,2,4-triazol-1-yl)sulfonyl)-N,N-dimethylbenzenesulfonamide (A-62)

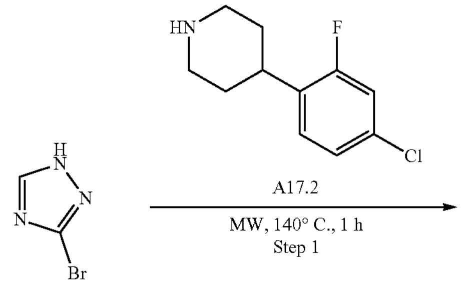

A17.1

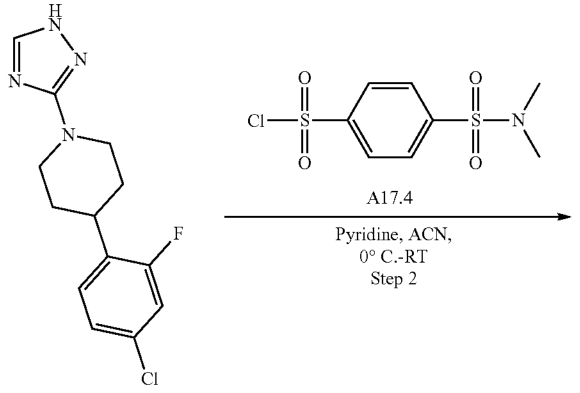

A17.3

-continued

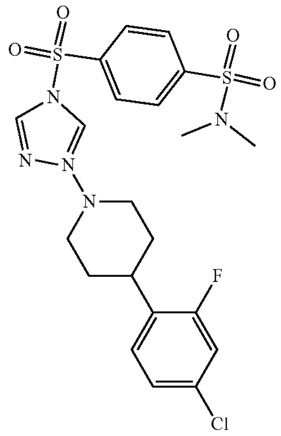

A-62

Step-1: Synthesis of 4-(4-chloro-2-fluorophenyl)-1-(1H-1,2,4-triazol-3-yl)piperidine (A17.3)

A solution of 3-bromo-1H-1,2,4-triazole (A17.1) (400 mg, 2.7 mmol, 1 eq) and 4-(4-chloro-2-fluorophenyl)piperidine (A17.2) (1.15 g, 5.4 mmol, 2 eq) was stirred at 140° C. in microwave for 1 h. The progress of the reaction was monitored by TLC. After completion of the reaction, the reaction mixture was washed with ether & pentane to afford the desired product 4-(4-chloro-2-fluorophenyl)-1-(1H-1,2,4-triazol-3-yl)piperidine (A17.3) (400 mg, Crude). The crude was used as such next step without purification. LCMS: 281.09 [M+H]$^+$.

Step-2: Synthesis of 4-((3-(4-(4-chloro-2-fluorophenyl)piperidin-1-yl)-1H-1,2,4-triazol-1-yl)sulfonyl)-N,N-dimethylbenzenesulfonamide (A-62)

To a stirred solution of 4-(4-chloro-2-fluorophenyl)-1-(1H-1,2,4-triazol-3-yl)piperidine (A17.3) (400 mg, 0.4 mmol, 1 eq) in ACN (8 mL) was added pyridine (0.023 mL, 0.29 mmol, 2 eq) at 0° C. followed by addition of 4-(N,N-dimethylsulfamoyl)benzenesulfonyl chloride (A17.4) (445 mg, 0.16 mmol, 1.1 eq). The reaction mixture was stirred at room temperature for 16 h. The progress of the reaction was monitored by TLC. After completion of the reaction, the reaction mixture was concentrated under reduced pressure. The crude was diluted with water and extracted with ethyl acetate. The organic layer was separated washed with water, brine, dried over anhydrous sodium sulfate and evaporated under reduced pressure. The crude product was purified by column chromatography to afford the desired product 4-((3-(4-(4-chloro-2-fluorophenyl)piperidin-1-yl)-1H-1,2,4-triazol-1-yl)sulfonyl)-N,N-dimethylbenzenesulfonamide (A-62). Yield: 30 mg, 4%; Appearance: White solid; $^1H$ NMR (400 MHz, DMSO-$d_6$) δ 9.11 (s, 1H), 8.30-8.22 (m, 2H), 8.09-7.97 (m, 2H), 7.40-7.26 (m, 2H), 7.22 (dd, J=8.4, 2.2 Hz, 1H), 4.08-4.00 (m, 2H), 2.96 (ddd, J=15.3, 10.0, 2.9 Hz, 3H), 2.67 (s, 6H), 1.73 (dd, J=12.8, 3.4 Hz, 2H), 1.60 (qd, J=12.5, 4.1 Hz, 2H); HPLC purity: 95.33%; LCMS Calculated for $C_{21}H_{23}ClFN_5O_4S_2$: 527.09; Observed: 528.05 [M+H]$^+$.

Example A18: Synthesis of 4-((4-(4-(4-chloro-2-fluorophenyl)piperidin-1-yl)-3-methyl-1H-pyrazol-1-yl)sulfonyl)-N,N-dimethylbenzenesulfonamide (A-50)

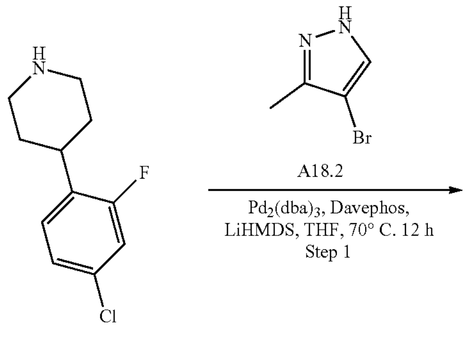

A18.1

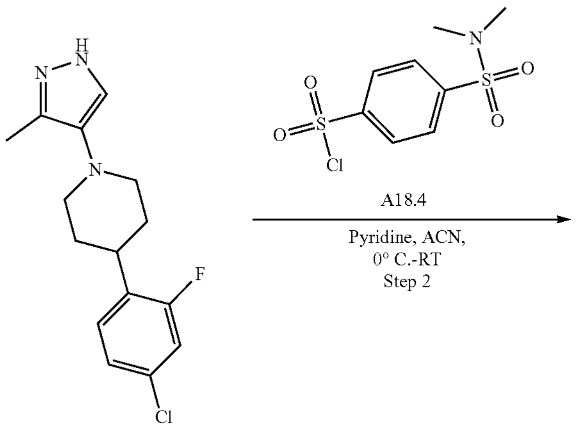

A18.3

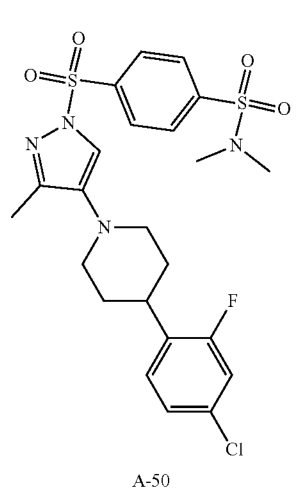

A-50

Step-1: Synthesis of 4-(4-chloro-2-fluorophenyl)-1-(3-methyl-1H-pyrazol-4-yl)piperidine (A18.3)

A solution of 4-(4-chloro-2-fluorophenyl)piperidine (A18.1) (0.1 g, 6.2 mmol, 1 eq) and 4-bromo-3-methyl-1H-pyrazole (A18.2) (0.15 g, 0.68 mmol, 1.1 eq) in THF (10 mL) was purged with argon for 10 min followed by the addition Tris(dibenzylideneacetone)dipalladium(0) (0.06 g, 0.06 mmol, 0.1 eq), Davephos (0.06 g, 0.15 mmol, 0.25 eq) at room temperature, cooled the reaction mixture at 0° C. then dropwise 1 M in THE LiHMDS (1.5 mL, 1.49 mmol, 2.4 eq) was added. The reaction mixture was stirred at 70° C. for 12 h. The progress of the reaction was monitored by TLC. After completion of the reaction, the reaction mixture was quenched with ammonium chloride solution and extracted with ethyl acetate. The organic layer was separated washed with water, brine, dried over anhydrous sodium sulfate and evaporated under reduced pressure. The crude product was purified by column chromatography to afford the desired product 4-(4-chloro-2-fluorophenyl)-1-(3-methyl-1H-pyrazol-4-yl)piperidine (A18.3). Four more batches were repeated on same scale and the combined yield details are (0.4 g, 44.44%), LCMS: 294.11 $[M+1]^+$.

Step-2: Synthesis of 4-((4-(4-(4-chloro-2-fluorophenyl)piperidin-1-yl)-3-methyl-1H-pyrazol-1-yl)sulfonyl)-N,N-dimethylbenzenesulfonamide (A-50)

To a stirred solution of 4-(4-chloro-2-fluorophenyl)-1-(3-methyl-1H-pyrazol-4-yl)piperidine (A18.3) (0.2 g, 6.8 mmol, 1 eq) in ACN (10 mL) was added pyridine (0.1 g, 1.36 mmol, 2 eq) at 0° C. followed by addition of 4-(N,N-dimethylsulfamoyl)benzenesulfonyl chloride (A18.4) (0.21 g, 0.75 mmol, 1.1 eq). The reaction mixture was stirred at room temperature for 12 h. The progress of the reaction was monitored by TLC. After completion of the reaction, the reaction mixture was quenched with water and extracted with ethyl acetate. The organic layer was separated washed with water, brine, dried over anhydrous sodium sulfate and evaporated under reduced pressure. The crude product was purified by column chromatography followed by prep HPLC to afford the desired product 4-((4-(4-(4-chloro-2-fluorophenyl)piperidin-1-yl)-3-methyl-1H-pyrazol-1-yl)sulfonyl)-N,N-dimethylbenzenesulfonamide (A-50). Yield: 0.05 g, 13.58%; Appearance: White solid; $^1H$ NMR (400 MHz, DMSO-$d_6$) δ 8.15-8.07 (m, 2H), 7.99-7.89 (m, 3H), 7.41-7.30 (m, 2H), 7.22 (dd, J=8.3, 2.1 Hz, 1H), 3.25 (dd, J=12.5, 3.3 Hz, 2H), 2.85 (tt, J=10.9, 4.8 Hz, 1H), 2.62 (s, 8H), 2.12 (s, 3H), 1.75 (ddt, J=12.5, 8.9, 4.5 Hz, 4H); HPLC purity: 97.52%; LCMS Calculated for $C_{23}H_{26}ClFN_4O_4S_2$: 540.11; Observed: 541.05 $[M+H]^+$.

Example A19: Synthesis of 4-((3-(4-(4-chloro-2-fluorophenyl)piperidin-1-yl)-2-oxopyrrolidin-1-yl)sulfonyl)-N,N-dimethylbenzenesulfonamide (A-71)

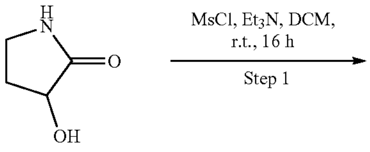

A19.1

-continued

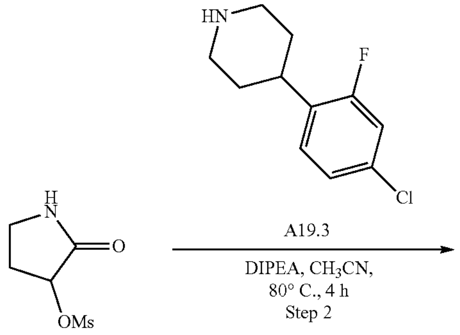

A19.2

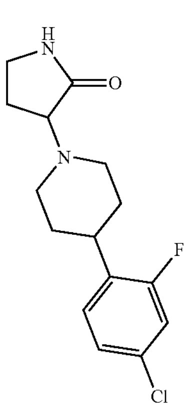

A19.4

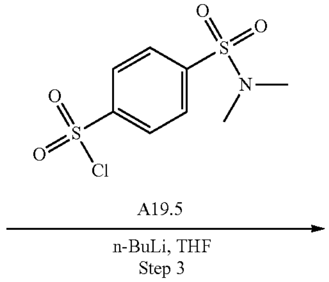

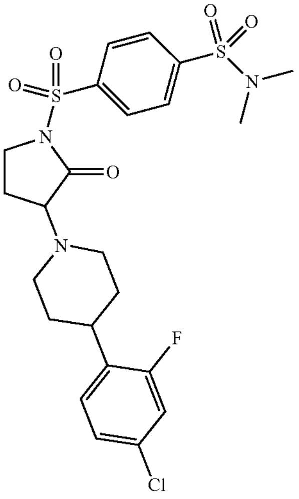

A-71

Step-1: Synthesis of 2-oxopyrrolidin-3-yl Methanesulfonate A19.2

To a stirred solution of 3-hydroxypyrrolidin-2-one (A19.1) (4.66 g, 46.09 mmol, 1 eq) in DCM (80 mL) was added triethyl amine (13 mL, 92.18 mmol, 2 eq) and dropwise methane sulphonyl chloride (1.5 mL, 14.84 mmol, 1.5 eq) at 0° C. The reaction mixture was stirred at room temperature for 16 h. The progress of the reaction was monitored by TLC. After completion of the reaction, the reaction mixture was diluted with water and extracted with DCM. The organic layer was separated washed with water, brine, dried over anhydrous sodium sulfate and evaporated under reduced pressure. The crude product was purified by column chromatography to afford the desired product 2-oxopyrrolidin-3-yl methanesulfonate (A19.2) (6.5 g, 79.2%). LCMS: 180.03 [M+H]+.

Step-2: Synthesis of 3-(4-(4-chloro-2-fluorophenyl) piperidin-1-yl)pyrrolidin-2-one (A19.4)

To a stirred solution of 4-(4-chloro-2-fluorophenyl)piperidine (A19.3) (0.2 g, 0.61 mmol, 1 eq) in ACN (10 mL) was added DIPEA (0.7 mL, 3.67 mmol, 6 eq) and 2-oxopyrrolidin-3-yl methanesulfonate (A19.2) (0.12 g, 0.67 mmol, 1.1 eq) at room temperature. The reaction mixture was stirred at 80° C. for 4 h. The reaction progress was monitored by TLC. After completion, the reaction mixture was diluted with water and ethyl acetate. The organic layer was separated, washed with water, brine, dried over $Na_2SO_4$ and concentrated. The crude was purified by silica gel column chromatography to provide the desired compound 3-(4-(4-chloro-2-fluorophenyl)piperidin-1-yl)pyrrolidin-2-one (A19.4) (15 mg, 8.2%). LCMS: 297.11 $[M+H]^+$.

Step-3: Synthesis of 4-((3-(4-(4-chloro-2-fluorophenyl)piperidin-1-yl)-2-oxopyrrolidin-1-yl)sulfonyl)-N,N-dimethylbenzenesulfonamide (A-71)

To a stirred solution of 3-(4-(4-chloro-2-fluorophenyl) piperidin-1-yl)pyrrolidin-2-one (A19.4) (1 g, 3.38 mmol, 1 eq) in dry THF (20 mL) was added dropwise 2 M solution of n-BuLi (0.3 mL, 0.74 mmol, 1.1 eq) in hexane at −78° C., stirred the reaction mixture. at same temperature for 1 h followed by drop wise addition of solution of 4-(N,N-dimethylsulfamoyl)benzenesulfonyl chloride (A19.5) (0.29 g, 1.01 mmol, 1.5 eq) in THF. The reaction mixture was stirred at room temperature for 30 min. The progress of the reaction was monitored by TLC. After completion of the reaction, the reaction mixture was quenched at −78° C. with saturated solution of ammonium chloride; reaction mixture was diluted with water and extracted with ethyl acetate. The organic layer was separated washed with water, brine, dried over anhydrous sodium sulfate and evaporated under reduced pressure. The crude product was purified by column chromatography followed by prep HPLC to afford the desired product 4-((3-(4-(4-chloro-2-fluorophenyl)piperidin-1-yl)-2-oxopyrrolidin-1-yl)sulfonyl)-N,N-dimethylbenzenesulfonamide (A-71). Yield: 100 mg, 27.32%; Appearance: Off-white solid; 1H NMR (400 MHz, DMSO-$d_6$) δ 8.22 (d, J=8 Hz, 2H), 8.01 (d, J=8.4 Hz, 2H), 7.34-7.31 (m, 2H), 7.22-7.20 (m, 1H), 4.00-3.92 (m, 1H), 3.77-3.65 (m, 2H), 2.99-2.83 (m, 1H), 2.72-2.62 (m, 9H), 2.29-2.01' (m, 3H), 1.60-1.54 (m, 4H); HPLC purity: 97.62%; LCMS Calculated for $C_{23}H_{27}ClFN_3O_5S_2$: 543.11; Observed: 544.05 $[M+H]^+$.

Example A20: Synthesis of 2-(4-chloro-2-fluorophenyl)-4-(4-methoxybenzyl)-2H-benzo[b][1,4]oxazin-3(4H)-one (A-371)

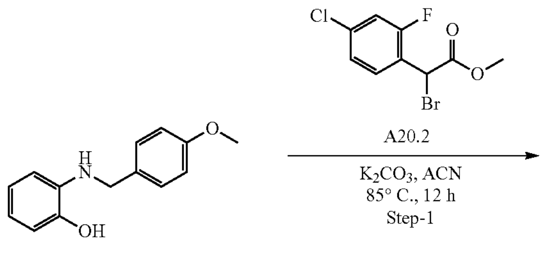

A20.1

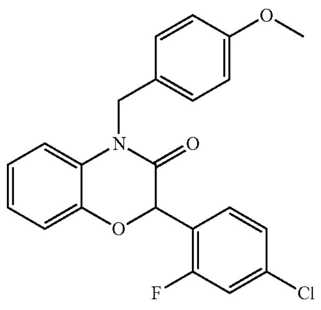

A-371

Step-1: Synthesis of 2-(4-chloro-2-fluorophenyl)-4-(4-methoxybenzyl)-2H-benzo[b][1,4]oxazin-3(4H)-one (A-371)

To a stirred solution of 2-((4-methoxybenzyl)amino)phenol (A20.1) (0.3 g, 1.31 mmol, 1 eq) and methyl 2-bromo-2-(4-chloro-2-fluorophenyl)acetate (A20.2) (0.43 g, 1.57 mmol, 1.2 eq) in ACN (10 mL) was added $K_2CO_3$ (542 mg, 3.93 mmol, 3 eq) at room temperature. The reaction mixture was stirred at 80° C. for 12 h. The reaction progress was monitored by TLC. After completion of reaction, the reaction mixture was concentrated; crude was diluted with water and extracted with ethyl acetate. The combined organic extracts were washed with water, brine, dried over anhydrous $Na_2SO_4$, filtered and concentrated under reduced pressure. The crude was purified by column chromatography to afford titled compound 2-(4-chloro-2-fluorophenyl)-4-(4-methoxybenzyl)-2H-benzo[b][1,4]oxazin-3(4H)-one (A-371). Yield: 100 mg, 19%; Appearance: White solid; $^1H$ NMR (400 MHz, DMSO-$d_6$) δ 7.63-7.49 (m, 2H), 7.37 (dd, J=8.3, 2.0 Hz, 1H), 7.29-7.21 (m, 2H), 7.22-7.12 (m, 1H), 7.01 (ddt, J=9.9, 6.8, 3.9 Hz, 3H), 6.94-6.85 (m, 2H), 6.09 (d, J=1.5 Hz, 1H), 5.23-5.09 (m, 2H), 3.71 (d, J=1.6 Hz, 3H); HPLC purity: 95.41%; LCMS Calculated for $C_{22}H_{17}ClFNO_3$: 397.09; Observed: 398.00 $[M+H]^+$.

Example A21: Synthesis of 2-(4-(4-chloro-2-fluorophenyl)piperidin-1-yl)-N-(p-tolyl)benzenesulfonamide (A-111)

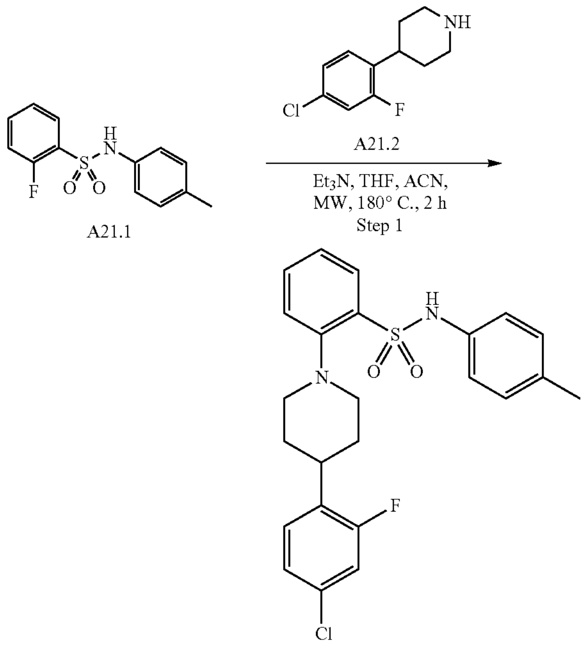

A-111

Step-1: Synthesis of 2-(4-(4-chloro-2-fluorophenyl)piperidin-1-yl)-N-(p-tolyl)benzenesulfonamide (A-111)

To a stirred solution of 2-fluoro-N-(p-tolyl)benzenesulfonamide (A21.1) (400 mg, 1.51 mmol, 1 eq) and 4-(4-chloro-2-fluorophenyl)piperidine A21.2 (385 mg, 1.81 mmol, 1.2 eq) in THF (5 mL) and acetonitrile (5 mL), triethyl amine (0.630 mL, 4.52 mmol, 3 eq) was added in a microwave tube. The tube was sealed with a septum and the reaction was heated at 180° C. for 2 h in a microwave reactor. The progress of the reaction was monitored by TLC. After completion of the reaction, the reaction mixture was cooled to room temperature and quenched with water, and the product was extracted with ethyl acetate. The combined organic layers were dried over anhydrous $Na_2SO_4$, filtered and concentrated under reduced pressure to dryness. The crude product was purified by reverse phase preparative HPLC to afford the titled compound 2-(4-(4-chloro-2-fluorophenyl)piperidin-1-yl)-N-(p-tolyl)benzenesulfonamide (A-111). Yield: 92 mg, 13%; Appearance: white solid; $^1H$ NMR (400 MHz, DMSO-$d_6$) δ 9.41 (s, 1H), 7.88 (d, J=8.0 Hz, 1H), 7.70 (t, J=8.0 Hz, 1H), 7.60-7.53 (m, 1H), 7.51-7.45 (m, 1H), 7.40-7.30 (m, 2H), 7.26 (t, J=7.6 Hz, 1H), 7.00-6.90 (m, 4H), 3.11-3.01 (m, 2H), 3.00-2.90 (m, 1H), 2.84 (t, J=10.8 Hz, 2H), 2.25-2.10 (m, 2H), 2.12 (s, 3H), 1.72 (d, J=11.6 Hz, 2H); HPLC purity: 99.53%; LCMS Calculated for $C_{24}H_{24}ClFN_2O_2S$: 458.12; Observed: 459.05 $[M+H]^+$.

Example A22: Synthesis of 4-((2-(4-(4-chloro-2-fluorophenyl)piperidin-1-yl)phenyl)sulfonamido)-N,N-dimethylbenzenesulfonamide (A-108)

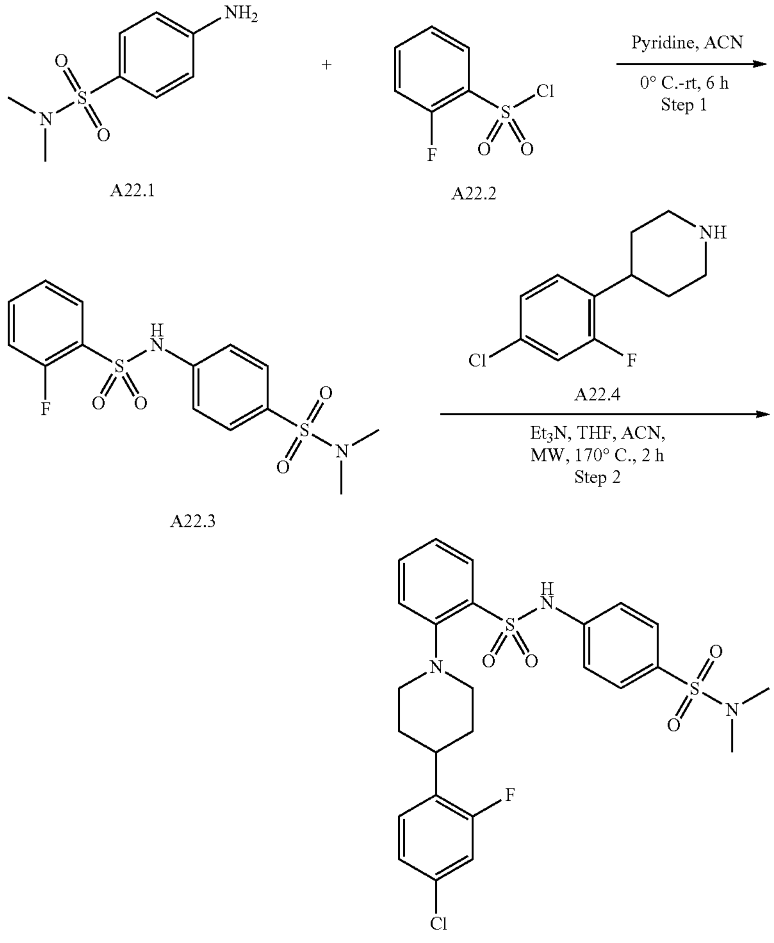

A22.1 A22.2 A22.3 A22.4

A-108

Step-1: Synthesis of 4-((2-fluorophenyl)sulfonamido)-N,N-dimethylbenzenesulfonamide (A22.3)

To a stirred solution of 4-amino-N,N-dimethylbenzenesulfonamide (A22.1) (500 mg, 2.57 mmol, 1 eq) and 2-fluorobenzenesulfonyl chloride (A22.2) (514 mg, 2.57 mmol) in acetonitrile (5 mL), pyridine (609 mg, 7.71 mmol, 3 eq) was added at 0° C. The reaction was warmed to room temperature and stirred for 6 h. The progress of the reaction was monitored by TLC. After completion of the reaction, the reaction mixture was quenched with water, and the product was extracted with ethyl acetate. The combined organic layers were dried over anhydrous $Na_2SO_4$, filtered and concentrated under reduced pressure to dryness. The crude product was purified by column chromatography on silica gel to afford the titled compound 4-((2-fluorophenyl)sulfonamido)-N,N-dimethylbenzenesulfonamide (A22.3) (600 mg, 65.2%). LCMS: 359.10 $[M+H]^+$.

Step-2: Synthesis of 4-((2-(4-(4-chloro-2-fluorophenyl)piperidin-1-yl)phenyl)sulfonamido)-N,N-dimethylbenzenesulfonamide)(A-108)

To a stirred solution of 4-((2-fluorophenyl)sulfonamido)-N,N-dimethylbenzenesulfonamide (A22.3) (300 mg, 0.837 mmol, 1 eq) and 4-(4-chloro-2-fluorophenyl)piperidine (A22.4) (215 mg, 1 mmol, 1.2 eq) in THF (5 mL) and acetonitrile (5 mL), triethyl amine (0.350 mL, 2.51 mmol, 3 eq) was added in a microwave tube. The tube was sealed with a septum and the reaction was heated at 170° C. for 2 h in a microwave reactor. The progress of the reaction was monitored by TLC. After completion of the reaction, the reaction mixture was cooled to room temperature and quenched with water, and the product was extracted with ethyl acetate. The combined organic layers were dried over anhydrous $Na_2SO_4$, filtered and concentrated under reduced pressure. The crude product was purified by reverse phase preparative HPLC to afford the titled compound 4-((2-(4-(4-chloro-2-fluorophenyl)piperidin-1-yl)phenyl)sulfonamido)-N,N-dimethylbenzenesulfonamide (A-108). Yield: 96 mg, 20.8%; Appearance: white solid; $^1H$ NMR (400 MHz, DMSO-$d_6$) δ 10.39 (s, 1H), 8.02 (d, J=8.0 Hz, 1H), 7.68-7.60 (m, 2H), 7.58-7.49 (m, 3H), 7.41-7.32 (m, 3H), 7.23 (d, J=8.4 Hz, 2H), 3.00-2.90 (m, 3H), 2.88-2.80 (m, 2H), 2.48 (s, 6H), 2.20-2.06 (m, 2H), 1.71 (d, J=11.2 Hz, 2H); HPLC purity: 97.01%; LCMS Calculated for $C_{25}H_{27}ClFN_3O_4S_2$: 551.11; Observed: 552.10 $[M+H]^+$.

Example A23: Synthesis of 4-((2-(4-(4-chloro-2-fluorophenyl)piperidin-1-yl)benzyl)sulfonyl)-N,N-dimethylbenzenesulfonamide (A-214)

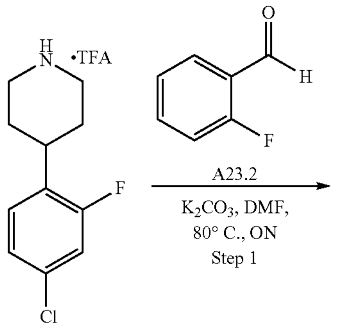

A23.1

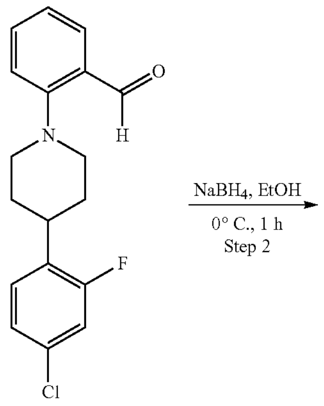

A23.3

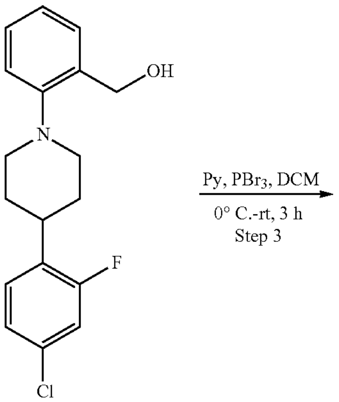

A23.4

-continued

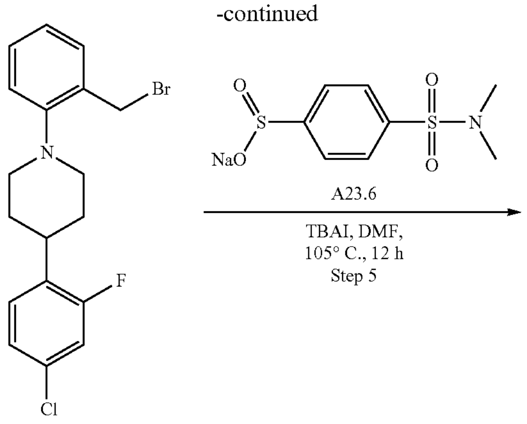

A23.5

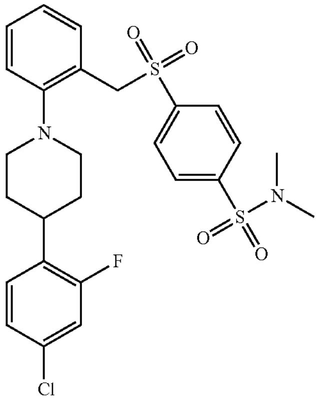

A-214

Synthesis of A23.6:

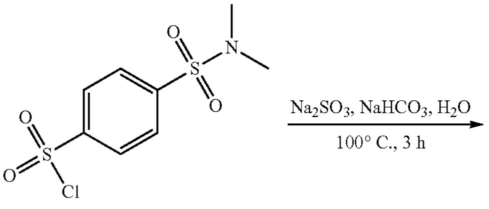

A23.7

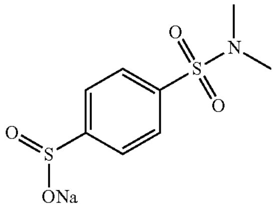

A23.6

Step-1: Synthesis of 2-(4-(4-chloro-2-fluorophenyl)piperidin-1-yl)benzaldehyde A23.3

To a stirred solution of 4-(4-chloro-2-fluorophenyl)piperidine TFA salt A23.1 (2 g, 6.1 mmol, 1 eq) and 2-fluorobenzaldehyde (A23.2) (910 mg, 7.32 mmol, 1.2 eq) in DMF (15 mL), potassium carbonate (2.53 g, 18.3 mmol, 3 eq) was added in one lot. The reaction was heated at 80° C. for overnight. The progress of the reaction was monitored by TLC. After completion of the reaction, the reaction mixture was cooled to room temperature and diluted with cold water (50 mL) and extracted with ethyl acetate. The combined organic layers were dried over anhydrous $Na_2SO_4$, filtered and concentrated under reduced pressure. The crude product was purified by flash column chromatography on silica gel to afford the titled compound 2-(4-(4-chloro-2-fluorophenyl)piperidin-1-yl)benzaldehyde (A23.3) (1.6 g, 82.5%). LCMS: 318.10 $[M+H]^+$.

Step-2: Synthesis of (2-(4-(4-chloro-2-fluorophenyl) piperidin-1-yl)phenyl)methanol (A23.4)

A stirred solution of 2-(4-(4-chloro-2-fluorophenyl)piperidin-1-yl)benzaldehyde (A23.3) (1.6 g, 5.03 mmol, 1 eq) in ethanol (30 mL) and THE (20 mL) at 0° C. was added sodium borohydride (290 mg, 7.55 mmol, 1.5 eq). The reaction was stirred at the same temperature for 1 h. The progress of the reaction was monitored by TLC. After completion of the reaction as indicated by TLC, the reaction mixture was quenched with saturated aqueous $NH_4Cl$ solution (25 mL). The product was extracted with DCM. The combined organic layers were dried over anhydrous $Na_2SO_4$, filtered and concentrated under reduced pressure. The residue was purified by trituration with n-hexane and the solids were filtered out, and dried under reduced pressure to afford the titled compound (2-(4-(4-chloro-2-fluorophenyl)piperidin-1-yl)phenyl)methanol (A23.4) (1.5 g, 93.2%) as a white solid. This compound was used in the next step without further purification. LCMS: 320.11 $[M+H]^+$.

Step-3: Synthesis of 1-(2-(bromomethyl)phenyl)-4-(4-chloro-2-fluorophenyl)piperidine (A23.5)

To a stirred solution of (2-(4-(4-chloro-2-fluorophenyl) piperidin-1-yl)phenyl)methanol (A23.4) (500 mg, 1.56 mmol, 1 eq) in DCM (10 mL), pyridine (0.24 mL, 3.13 mmol, 2 eq) was added at 0° C. and the reaction was stirred for 10 min. $PBr_3$ (0.22 mL, 2.34 mmol, 1.5 eq) was then added dropwise to the reaction at 0° C. The reaction was warmed to room temperature and stirred for 3 h. The progress of the reaction was monitored by TLC. After completion of the reaction, the reaction was quenched slowly with saturated aqueous $NaHCO_3$ solution and the product was extracted with DCM. The combined organic layers were dried over anhydrous $Na_2SO_4$, filtered and concentrated under reduced pressure to dryness to afford the titled compound 1-(2-(bromomethyl)phenyl)-4-(4-chloro-2-fluorophenyl)piperidine (A23.5) (400 mg, crude). This compound was used in the next step without further purification. LCMS: 382.10 $[M+H]^+$.

Step-4: Synthesis of Sodium 4-(N,N-dimethylsulfamoyl)benzenesulfinate (A23.6)

To a stirred solution of 4-(N,N-dimethylsulfamoyl)benzenesulfonyl chloride (A23.7) (1.5 g, 5.2 mmol, 1 eq) in water (15 mL), $Na_2SO_3$ (1.33 g, 10.57 mmol, 2 eq) followed by $NaHCO_3$ (0.82 g, 10.57 mmol, 2 eq) were added at room temperature. The reaction was heated at 100-110° C. for 3 h. The progress of the reaction was monitored by TLC. After completion of the reaction, the reaction mixture was concentrated to dryness under reduced pressure. The residue was dissolved in ethanol, filtered and the filtrate was concentrated to dryness under reduced pressure to afford the titled compound sodium 4-(N,N-dimethylsulfamoyl)benzenesulfinate (A23.6) (0.8 g, crude). This compound was used in the next step without further purification. LCMS: 250.00 $[M+H]^+$ (Observed mass for corresponding acid).

Step-5: Synthesis of 4-((2-(4-(4-chloro-2-fluorophenyl)piperidin-1-yl)benzyl)sulfonyl)-N,N-dimethylbenzenesulfonamide (A-214)

To a stirred solution of 1-(2-(bromomethyl)phenyl)-4-(4-chloro-2-fluorophenyl)piperidine (A23.5) (400 mg, 1.04 mmol, 1 eq) in DMF (10 mL), sodium 4-(N,N-dimethylsulfamoyl)benzenesulfinate A23.6 (390 mg, 1.36 mmol, 1.3 eq) followed by tetra-n-butylammonium bromide (38 mg, 0.10 mmol, 0.1 eq) were added at room temperature. The reaction was heated at 105° C. for 12 h. The progress of the reaction was monitored by TLC. After completion of the reaction, the reaction mixture was cooled to room temperature, diluted with ethyl acetate, and washed with ice-cold water. The combined organic layers were dried over anhydrous $Na_2SO_4$, filtered and concentrated under reduced pressure. The crude product was purified by column chromatography followed by reverse phase preparative HPLC to afford the titled compound 4-((2-(4-(4-chloro-2-fluorophenyl)piperidin-1-yl)benzyl)sulfonyl)-N,N-dimethylbenzenesulfonamide (A-214). Yield: 30 mg, 5.2%; Appearance: White solid; $^1H$ NMR (400 MHz, $CDCl_3$) δ; 7.80-7.10 (m, 4H), 7.57 (d, J=7.2 Hz, 1H), 2.37-7.31 (m, 1H), 7.21-7.14 (m, 3H), 7.08 (d, J=10.4 Hz, 1H), 7.02 (d, J=7.6 Hz, 1H), 4.66 (s, 2H), 2.88-2.74 (m, 1H), 2.71 (s, 6H), 2.70-2.60 (m, 2H), 2.50-2.42 (m, 2H), 1.83-1.75 (m, 2H), 1.69-1.55 (m, 2H); HPLC purity: 97.95%; LCMS calculated for $C_{26}H_{28}ClFN_2O_4S_2$: 550.12; Observed: 551.15 $[M+H]^+$.

Example A24: Synthesis of 4-((2-(4-(2,6-difluorophenyl)piperidin-1-yl)benzyl)sulfonyl)-N,N-dimethylbenzenesulfonamide (A-229)

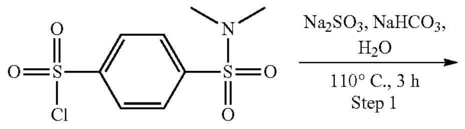

A24.1

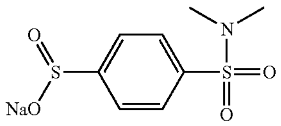

A24.2

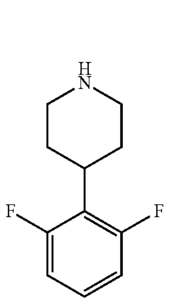

A24.3

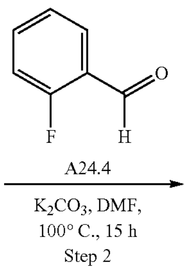

-continued

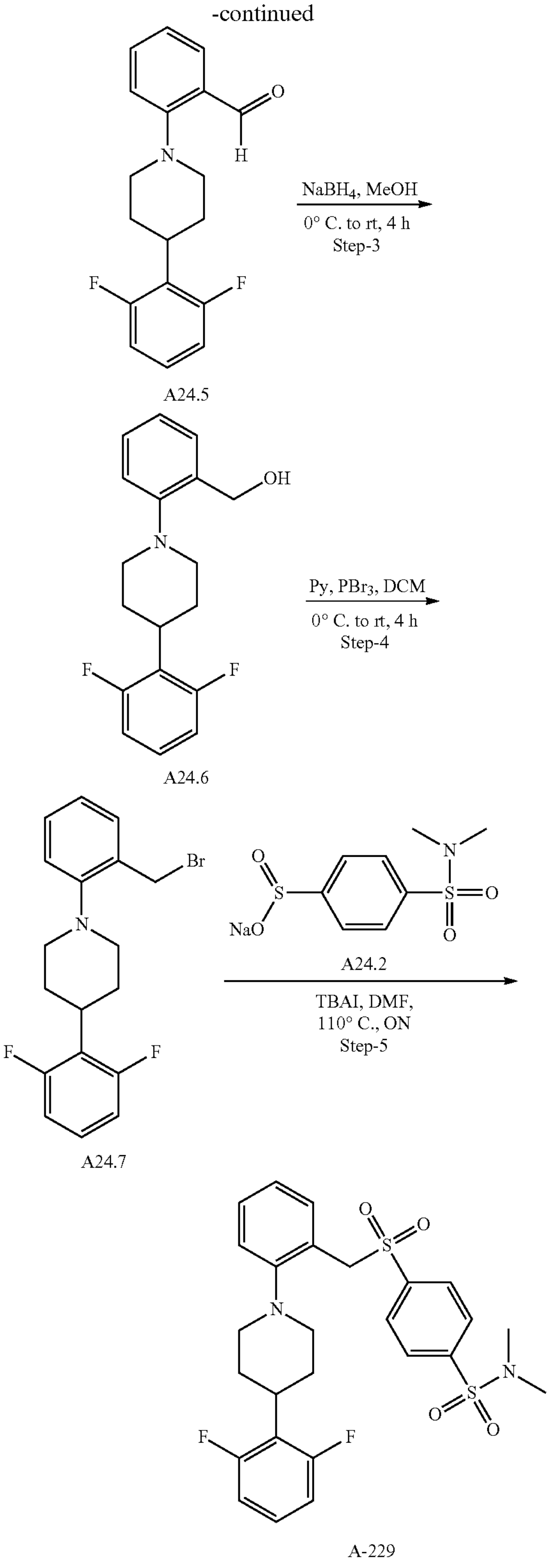

Step-1: Synthesis of Sodium 4-(N,N-dimethylsulfamoyl)benzenesulfinate (A24.2)

To a stirred solution of 4-(N,N-dimethylsulfamoyl)benzenesulfonyl chloride (A24.1) (1.5 g, 5.28 mmol, 1 eq) in water (15 mL), sodium sulfite (1.33 g, 10.57 mmol, 2 eq) and sodium bicarbonate (0.88 g, 10.57 mmol, 2 eq) were added at room temperature. The reaction mixture was stirred at 110° C. for 3 h. The progress of the reaction was monitored by TLC. After completion of the reaction, the reaction mixture was cooled to room temperature and concentrated under reduced pressure. The residue was dissolved in ethanol and filtered. The filtrate was concentrated under reduced pressure to dryness to afford the titled compound sodium 4-(N,N-dimethylsulfamoyl)benzenesulfinate (A24.2) (0.8 g, crude). LCMS: No ionization.

Step-2: Synthesis of 2-(4-(2,6-difluorophenyl)piperidin-1-yl)benzaldehyde (A24.5)

To a stirred solution of 4-(2,6-difluorophenyl)piperidine (A24.3) (2 g, 10.14 mmol, 1 eq) in DMF (20 mL), potassium carbonate (3.51 g, 25.38 mmol, 2.5 eq) and 2-fluorobenzaldehyde (A24.4) (1.5 g, 12.17 mmol, 1.2 eq) were added at room temperature. The reaction mixture was stirred at 100° C. for 12 h. The progress of the reaction was monitored by TLC. After completion of the reaction, the reaction mixture was cooled to room temperature, diluted with ethyl acetate and washed with ice-cold water. The organic layer was dried over anhydrous $Na_2SO_4$, filtered and concentrated under reduced pressure to dryness to afford the titled compound 2-(4-(2,6-difluorophenyl)piperidin-1-yl)benzaldehyde (A24.5) (2.9 g, crude). LCMS: 302.15 $[M+H]^+$.

Step-3: Synthesis of (2-(4-(2,6-difluorophenyl)piperidin-1-yl)phenyl)methanol (A24.6)

To a stirred solution of 2-(4-(2,6-difluorophenyl)piperidin-1-yl)benzaldehyde (A24.5) (2.9 g, 9.6 mmol, 1 eq) in methanol (3 mL), sodium borohydride (1.06 g, 28 mmol, 2.9 eq) was added in portions at 0° C. The reaction mixture was warmed to room temperature and stirred for 4 h. The progress of the reaction was monitored by TLC. After completion of the reaction, the reaction mixture was quenched with ice-cold water and extracted with ethyl acetate. The combined organic layers were dried over anhydrous $Na_2SO_4$, filtered and concentrated under reduced pressure. The crude product was purified by column chromatography on silica gel to afford the titled compound (2-(4-(2,6-difluorophenyl)piperidin-1-yl)phenyl)methanol (A24.6 (0.7 g, 24%). LCMS: 304.15 $[M+H]^+$.

Step-4: Synthesis of 1-(2-(bromomethyl)phenyl)-4-(2,6-difluorophenyl)piperidine (A24.7)

To a stirred solution of (2-(4-(2,6-difluorophenyl)piperidin-1-yl)phenyl)methanol (A24.6) (700 mg, 2.3 mmol, 1 eq) in DCM (15 mL), pyridine (0.36 mL, 4.6 mmol, 2 eq) was added at 0° C. and the reaction mixture was stirred at the same temperature for 10 min. Phosphorus tribromide (0.32 mL, 3.4 mmol, 1.5 eq) was then added dropwise to the reaction mixture at 0° C. The reaction mixture was warmed to room temperature and stirred for 4 h. The progress of the reaction was monitored by TLC. After completion of the reaction, the reaction mixture was dilute with DCM and washed with saturated aqueous $NaHCO_3$ solution. The organic layer was dried over anhydrous $Na_2SO_4$, filtered and concentrated under reduced pressure to dryness to afford the titled compound 1-(2-(bromomethyl)phenyl)-4-(2,6-difluorophenyl)piperidine (A24.7) (410 mg, crude). This compound was used in the next step without further purification. LCMS: 366.10 $[M+H]^+$.

Step-5: Synthesis of 4-((2-(4-(2,6-difluorophenyl) piperidin-1-yl)benzyl)sulfonyl)-N,N-dimethylbenzenesulfonamide (A-229)

To a stirred solution of 1-(2-(bromomethyl)phenyl)-4-(2,6-difluorophenyl)piperidine (A24.7) (300 mg, 0.82 mmol, 1 eq) and sodium 4-(N,N-dimethylsulfamoyl)benzenesulfinate (A24.2) (300 mg, 1.05 mmol, 1.3 eq) in DMF (6 mL), tetra-butylammonium bromide (30 mg, 0.08 mmol, 0.1 eq) was added at room temperature. The reaction mixture was stirred at 110° C. for overnight. The progress of the reaction was monitored by TLC. After completion of the reaction, the reaction mixture was cooled to room temperature, diluted with ethyl acetate and washed with ice-cold water. The organic layer was dried over anhydrous $Na_2SO_4$, filtered and concentrated under reduced pressure to dryness. The crude product was purified by reverse phase preparative HPLC to afford the titled compound 4-((2-(4-(2,6-difluorophenyl)piperidin-1-yl)benzyl)sulfonyl)-N,N-dimethylbenzenesulfonamide (A-229). Yield: 50 mg, 11.6%; Appearance: White solid; 1H NMR (400 MHz, DMSO-$d_6$) δ 7.88 (d, J=8.4 Hz, 2H), 7.74 (d, J=8.0 Hz, 2H), 7.46 (d, J=7.6 Hz, 1H), 7.38-7.29 (m, 2H), 7.20-7.14 (m, 1H), 7.13-7.05 (m, 3H), 4.79 (s, 2H), 3.00-2.90 (m, 1H), 2.61 (s, 6H), 1.98-1.85 (m, 2H), 1.61 (d, J=11.2 Hz, 2H), (4H merged with the solvent peak); HPLC purity: 99.71%; LCMS calculated for C26H28F2N2O4S2: 534.15; Observed: 535.15 $[M+H]^+$.

Example A25: Synthesis of 4-((1-(2-(4-(2,6-difluorophenyl)piperidin-1-yl)phenyl)ethyl)sulfonyl)-N,N-dimethylbenzenesulfonamide (A-254)

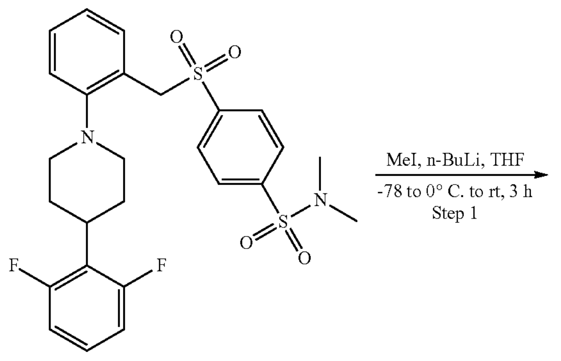

A-229

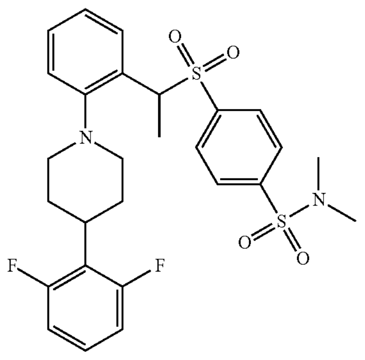

A-254

Step-1: Synthesis of 4-((1-(2-(4-(2,6-difluorophenyl)piperidin-1-yl)phenyl)ethyl)sulfonyl)-N,N-dimethylbenzenesulfonamide (A-254)

To a stirred solution of 4-((2-(4-(2,6-difluorophenyl)piperidin-1-yl)benzyl)sulfonyl)-N,N-dimethylbenzenesulfonamide (A-229) (300 mg, 0.561 mmol, 1 eq) in THE (6 mL), a 2.5 M solution of n-butyl lithium in hexanes (0.26 mL, 0.673 mmol, 1.2 eq) was added dropwise at −78° C. and the reaction mixture was stirred at the same temperature for 15 min and slowly allowed to attain 0° C. and methyl iodide (0.04 mL, 0.673 mmol, 1.2 eq) was added and stirred at room temperature for 3 h. The progress of the reaction was monitored by TLC. After completion of the reaction, the reaction mixture was cooled to 0° C., quenched with saturated aqueous $NH_4Cl$ solution and extracted with ethyl acetate. The combined organic layers were washed with brine, dried over anhydrous $Na_2SO_4$, filtered and concentrated under reduced pressure. The crude product was purified by reverse phase preparative HPLC to afford the titled compound 4-((1-(2-(4-(2,6-difluorophenyl)piperidin-1-yl) phenyl)ethyl)sulfonyl)-N,N-dimethylbenzenesulfonamide (A-254). Yield: 70 mg, 23.3%; Appearance: White solid; $^1H$ NMR (400 MHz, DMSO-$d_6$) δ 7.81 (d, J=8.0 Hz, 2H), 7.63 (d, J=8.8 Hz, 2H), 7.59 (dd, J=1.2, 8.0 Hz, 1H), 7.38-7.29 (m, 2H), 7.23 (t, J=6.8 Hz, 1H), 7.14-7.06 (m, 2H), 7.00 (d, J=8.0 Hz, 1H), 5.14 (q, J=7.2 Hz, 1H), 3.01-2.92 (m, 1H), 2.81-2.70 (m, 2H), 2.59 (s, 6H), 2.50-2.40 (m, 1H), 2.20-2.07 (m, 1H), 1.91-1.79 (m, 2H), 1.76 (d, J=6.8 Hz, 3H), 1.69 (d, J=12.8 Hz, 1H), 1.59 (d, J=11.6 Hz, 1H); HPLC purity: 99.89%; LCMS calculated for $C_{27}H_{30}F2N_2O_4S_2$: 548.16; Observed: 549.25 $[M+H]^+$.

Example A26: Synthesis of 4-(4-chloro-2-fluorophenyl)-1-(2-(tosylmethyl)phenyl)piperidine (A-138); 4-(4-chloro-2-fluorophenyl)-1-(2-((p-tolylsulfinyl)methyl)phenyl)piperidine (A-145)

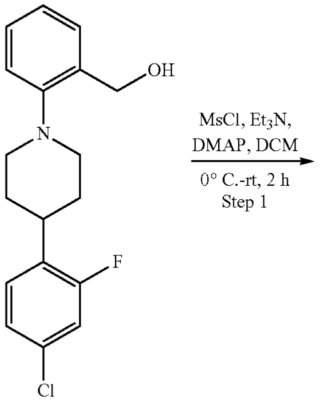

A26.1

-continued

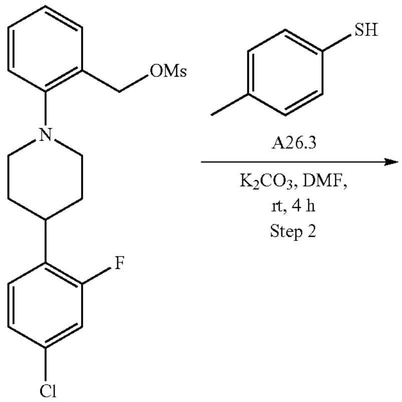

A26.2

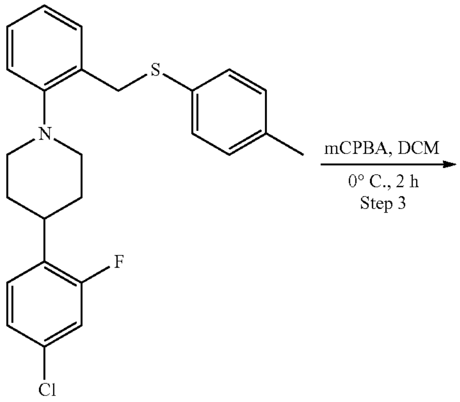

A26.4

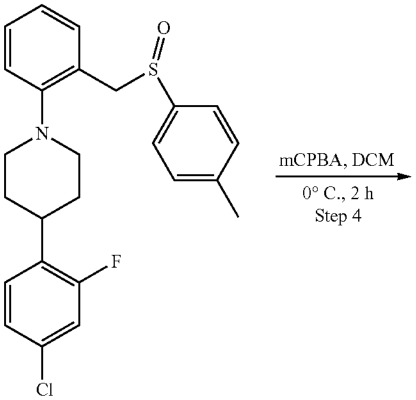

A-154

-continued

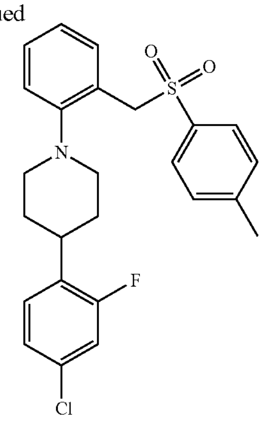

A-138

Step-1: Synthesis of 2-(4-(4-chloro-2-fluorophenyl) piperidin-1-yl)benzyl Methanesulfonate (A26.2)

A solution of (2-(4-(4-chloro-2-fluorophenyl)piperidin-1-yl)phenyl)methanol A26.1 (0.5 g, 1.56 mmol, 1 eq), triethyl amine (0.44 mL, 3.13 mmol, 2 eq) and DMAP (25 mg, catalytic) in DCM (20 mL) were cooled to 0° C. and treated with methanesulfonyl chloride (0.182 mL, 2.35 mmol, 1.5 eq) dropwise. The reaction was warmed to room temperature and stirred for 2 h. The progress of the reaction was monitored by TLC. After completion of the reaction, the reaction was quenched with water (25 mL) and the product was extracted with DCM. The combined organic layers were dried over anhydrous $Na_2SO_4$, filtered and concentrated under reduced pressure to dryness to afford the titled compound 2-(4-(4-chloro-2-fluorophenyl)piperidin-1-yl)benzyl methanesulfonate (A26.2) (600 mg, crude). This compound was used in the next step without further purification. LCMS: No ionization.

Step-2: Synthesis of 4-(4-chloro-2-fluorophenyl)-1-(2-((p-tolylthio)methyl)phenyl)piperidine (A26.4)

To a stirred solution of 2-(4-(4-chloro-2-fluorophenyl) piperidin-1-yl)benzyl methanesulfonate (A26.2) (600 mg, 1.51 mmol, 1 eq) and 4-methylbenzenethiol A26.3 (206 mg, 1.66 mmol, 1.1 eq) in DMF (5 mL), potassium carbonate (625 mg, 4.52 mmol, 3 eq) was added. The reaction was stirred at room temperature for 4 h. The progress of the reaction was monitored by TLC. After completion of the reaction, the reaction was quenched with water (25 mL) and the product was extracted with ethyl acetate. The combined organic layers were dried over anhydrous $Na_2SO_4$, filtered and concentrated under reduced pressure to dryness. The crude product was purified by flash column chromatography on silica gel to afford the titled compound 4-(4-chloro-2-fluorophenyl)-1-(2-((p-tolylthio)methyl)phenyl)piperidine (A26.4) (400 mg, 62.3%) as a white solid. LCMS: 426.14 $[M+H]^+$.

Step-3: Synthesis of 4-(4-chloro-2-fluorophenyl)-1-(2-((p-tolylsulfinyl)methyl)phenyl)piperidine (A-145)

To a stirred solution of 4-(4-chloro-2-fluorophenyl)-1-(2-((p-tolylthio)methyl)phenyl)piperidine (A26.4) (300 mg, 0.704 mmol, 1 eq) in DCM (10 mL), m-chloroperoxybenzoic acid (65%) (190 mg, 0.704, 1 eq) was added at 0° C. The reaction was stirred at the same temperature for 2 h. The progress of the reaction was monitored by TLC. After completion of the reaction, the reaction was quenched with saturated aqueous $NaHCO_3$ solution (10 mL) and stirred for 15 min. the product was extracted with DCM. The combined organic layers were dried over anhydrous $Na_2SO_4$, filtered and concentrated under reduced pressure to dryness. The crude product was purified by flash column chromatography on silica gel to afford the titled compound 4-(4-chloro-2-fluorophenyl)-1-(2-((p-tolylsulfinyl)methyl)phenyl)piperidine (A-145). Yield: 200 mg, 64.3%; Appearance: White solid; $^1$H NMR (400 MHz, DMSO-$d_6$) δ 7.47-7.24 (m, 9H), 7.17-7.12 (m, 1H), 7.10-7.04 (m, 1H), 4.19 (s, 2H), 2.90-2.80 (m, 2H), 2.80-2.64 (m, 3H), 2.33 (s, 3H), 1.80-1.68 (m, 4H); HPLC purity: 99.16%; LCMS calculated for $C_{25}$H25ClFNOS: 441.13; Observed: 442.05 $[M+H]^+$.

Step-4: Synthesis of 4-(4-chloro-2-fluorophenyl)-1-(2-(tosylmethyl)phenyl)piperidine (A-138)

To a stirred solution of 4-(4-chloro-2-fluorophenyl)-1-(2-((p-tolylsulfinyl)methyl)phenyl)piperidine (A-145) (175 mg, 0.396 mmol, 1 eq) in DCM (5 mL), m-chloroperoxybenzoic acid (65%) (105 mg, 0.396, 1 eq) was added at 0° C. The reaction was stirred at the same temperature for 2 h. The progress of the reaction was monitored by TLC. After completion of the reaction, the reaction was quenched with saturated aqueous $NaHCO_3$ solution (10 mL) and stirred for 15 min and extracted with DCM. The combined organic layers were dried over anhydrous $Na_2SO_4$, filtered and concentrated under reduced pressure to dryness. The crude product was purified by reverse phase preparative HPLC to afford the titled compound 4-(4-chloro-2-fluorophenyl)-1-(2-(tosylmethyl)phenyl)piperidine (A-138). Yield: 22 mg, 12%; Appearance: Off white solid; $^1$H NMR (400 MHz, DMSO-$d_6$) δ 7.49-7.42 (m, 4H), 7.38 (d, J=10.8 Hz, 1H), 7.34-7.28 (m, 4H), 7.17-7.08 (m, 2H), 4.66 (s, 2H), 2.84-2.73 (m, 1H), 2.62-2.55 (m, 2H), 2.50-2.40 (m, 2H), 2.33 (s, 3H), 1.69-1.55 (m, 4H); HPLC purity: 99.34%; LCMS calculated for $C_{25}H_{25}ClFNO_2S$: 457.13; Observed: 458.05 $[M+H]^+$.

Example A27: Synthesis of 4-((2-(4-(4-chloro-2-fluorophenyl)piperidin-1-yl)benzyl)sulfinyl)-N,N-dimethylbenzenesulfonamide (A-190)

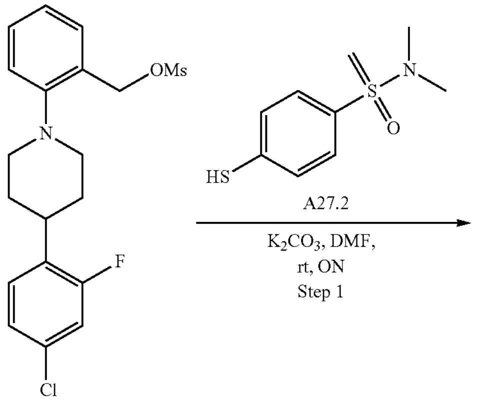

A27.1

-continued

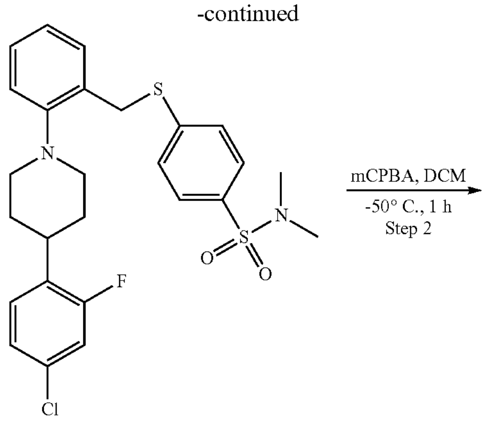

A27.3

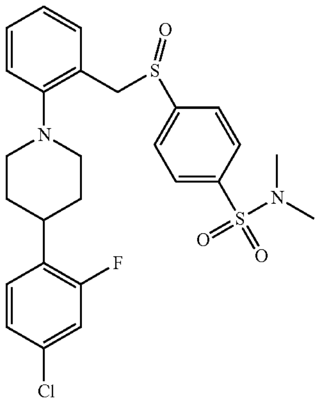

A27.3

Step-1: Synthesis of 4-((2-(4-(4-chloro-2-fluorophenyl)piperidin-1-yl)benzyl)thio)-N,N-dimethylbenzenesulfonamide (A27.3)

To a stirred solution of 2-(4-(4-chloro-2-fluorophenyl)piperidin-1-yl)benzyl methanesulfonate (A27.1) (720 mg, 1.81 mmol, 1 eq) and 4-mercapto-N,N-dimethylbenzenesulfonamide (A27.2) (432 mg, 1.99 mmol, 1.1 eq) in DMF (10 mL), potassium carbonate (750 mg, 5.43 mmol, 3 eq) was added. The reaction mixture was stirred at room temperature for overnight. The progress of the reaction was monitored by TLC. After completion of the reaction, the reaction mixture was quenched with water and the product was extracted with ethyl acetate. The combined organic layers were dried over anhydrous $Na_2SO_4$, filtered and concentrated under reduced pressure. The crude product was purified by column chromatography on silica gel to afford the titled compound 4-((2-(4-(4-chloro-2-fluorophenyl)piperidin-1-yl)benzyl)thio)-N,N-dimethylbenzenesulfonamide (A27.3) (300 mg, 32%). LCMS: 519.13 $[M+H]^+$.

Step-2: Synthesis of 4-((2-(4-(4-chloro-2-fluorophenyl)piperidin-1-yl)benzyl)sulfinyl)-N,N-dimethylbenzenesulfonamide (A-190)

To a stirred solution of 4-((2-(4-(4-chloro-2-fluorophenyl)piperidin-1-yl)benzyl)thio)-N,N-dimethylbenzenesulfonamide (A27.3) (300 mg, 0.578 mmol, 1 eq) in DCM (15 mL), m-chloroperbenzoic acid (65%) (153 mg, 0.578 mmol, 1 eq) was added at −50° C. The reaction was stirred at the same temperature for 1 h. The progress of the reaction was monitored by TLC. After completion of the reaction, the reaction was quenched with saturated aqueous $NaHCO_3$ solution and stirred for 15 min and the product was extracted with DCM. The combined organic layers were dried over anhydrous $Na_2SO_4$, filtered and concentrated under reduced pressure to dryness. The crude product was purified by column chromatography on silica gel followed by reverse phase preparative HPLC to afford the titled compound 4-((2-(4-(4-chloro-2-fluorophenyl)piperidin-1-yl)benzyl)sulfinyl)-N,N-dimethylbenzenesulfonamide (A-190). Yield: 20 mg, 6%; Appearance: Off white solid; $^1$H NMR (400 MHz, DMSO-$d_6$) δ 7.79 (d, J=7.2 Hz, 2H), 7.62 (d, J=7.2 Hz, 2H), 7.51-7.46 (m, 1H), 7.41-7.36 (m, 1H), 7.32-7.24 (m, 3H), 7.10-7.04 (m, 2H), 4.42 (d, J=12.4 Hz, 1H), 4.27 (d, J=12.4 Hz, 1H), 2.90-2.80 (m, 1H), 2.75-2.65 (m, 4H), 2.59 (s, 6H), 1.81-1.66 (m, 4H); HPLC purity: 98.10%; LCMS Calculated for $C_{26}H_{28}ClFN_2O_3S_2$: 534.12; Observed: 535.10 [M+H]$^+$.

Example A28: Synthesis of 4-(4-chloro-2-fluorophenyl)-1-(2-tolylphenyl)piperidine (A-133) and 4-(4-chloro-2-fluorophenyl)-1-(2-(p-tolylsulfinyl)phenyl)piperidine (A-144)

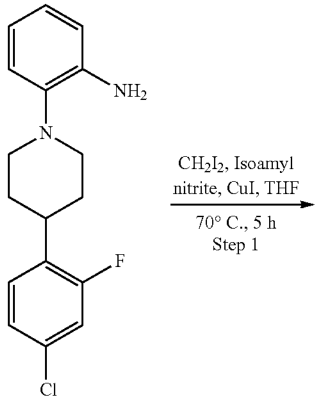

A28.1

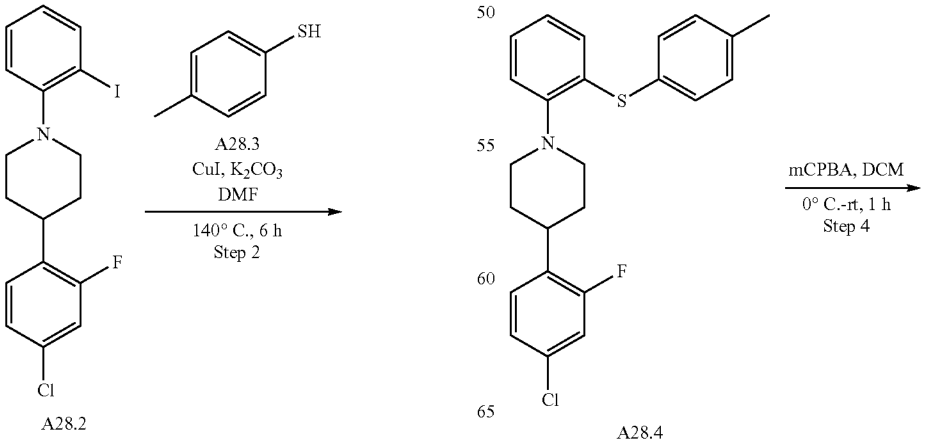

A28.2

A28.4

-continued

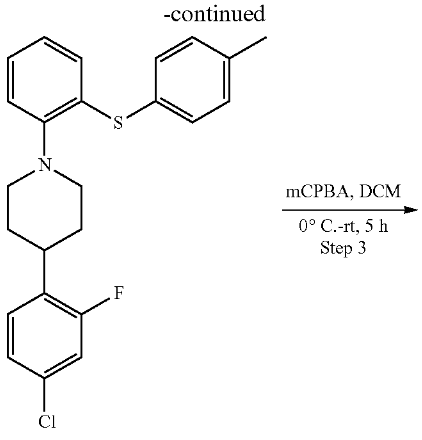

A28.4

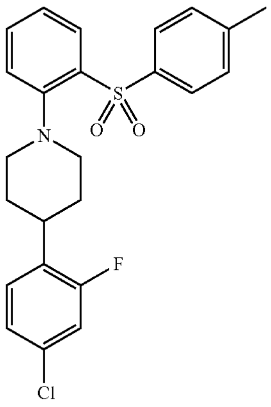

A-133

-continued

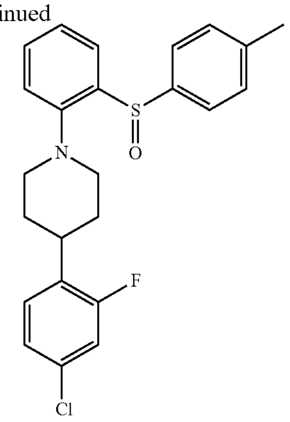

A-144

Step-1: Synthesis of 4-(4-chloro-2-fluorophenyl)-1-(2-iodophenyl)piperidine (A28.2)

To a stirred solution of 2-(4-(4-chloro-2-fluorophenyl) piperidin-1-yl)aniline (A28.1) (1.4 g, 4.59 mmol, 1 eq) in THF (20 mL), copper iodide (875 mg, 4.59 mmol, 1 eq), diiodomethane (1.85 mL, 23 mmol, 5 eq) and isoamyl nitrite (1.6 g, 13.8 mmol, 3 eq) were added at room temperature. The reaction was heated at 70° C. for 5 h. The progress of the reaction was monitored by TLC. After completion of the reaction, the reaction mixture was cooled to room temperature and diluted with water. The product was extracted with ethyl acetate. The combined organic layers were dried over anhydrous $Na_2SO_4$, filtered and concentrated under reduced pressure. The crude product was purified by column chromatography on silica gel to afford the titled compound 4-(4-chloro-2-fluorophenyl)-1-(2-iodophenyl)piperidine (A28.2) (900 mg, 47.1%). LCMS: 416.00 $[M+H]^+$.

Step-2: Synthesis of 4-(4-chloro-2-fluorophenyl)-1-(2-(p-tolylthio)phenyl)piperidine (A28.4)

To a stirred solution of 4-(4-chloro-2-fluorophenyl)-1-(2-iodophenyl)piperidine (A28.2) (900 mg, 2.17 mmol, 1 eq) and 4-methylbenzenethiol (A28.3) (283 mg, 2.27 mmol, 1.05 eq) in DMF (20 mL), potassium carbonate (598 mg, 4.33 mmol, 2 eq) and copper iodide (21 mg, 0.108 mmol, 0.05 eq) were added and heated at 140° C. for 6 h. The progress of the reaction was monitored by TLC. After completion of the reaction, the reaction mixture was cooled to room temperature, diluted with water and extracted with ethyl acetate. The combined organic layers were dried over anhydrous $Na_2SO_4$, filtered and concentrated under reduced pressure. The crude product was purified by column chromatography on silica gel to afford the titled compound 4-(4-chloro-2-fluorophenyl)-1-(2-(p-tolylthio)phenyl)piperidine (A28.4) (400 mg, 44.8%). LCMS: 412.10 $[M+H]^+$.

Step-3: Synthesis of 4-(4-chloro-2-fluorophenyl)-1-(2-tolylphenyl)piperidine (A-133)

To a stirred solution of 4-(4-chloro-2-fluorophenyl)-1-(2-(p-tolylthio)phenyl)piperidine (A28.4) (380 mg, 0.922 mmol, 1 eq) in DCM (8 mL), m-chloroperbenzoic acid (65%) (490 mg, 1.84 mmol, 2 eq) was added at 0° C. The reaction was warmed to room temperature and stirred for 5 h. The progress of the reaction was monitored by TLC. After completion of the reaction, the reaction was quenched with saturated aqueous $NaHCO_3$ solution (10 mL) and stirred for 15 min. the product was extracted with DCM. The combined organic layers were dried over anhydrous $Na_2SO_4$, filtered and concentrated under reduced pressure to dryness. The crude product was purified by column chromatography on silica gel followed by reverse phase preparative HPLC to afford the titled compound 4-(4-chloro-2-fluorophenyl)-1-(2-tolylphenyl)piperidine (A-133). Yield: 13 mg, 3.17%; Appearance: Off white solid; $^1H$ NMR (400 MHz, DMSO-$d_6$) δ 8.16 (d, J=7.2 Hz, 1H), 7.76-7.70 (m, 3H), 7.53-7.44 (m, 2H), 7.42-7.32 (m, 5H), 2.88-2.71 (m, 5H), 2.36 (s, 3H), 1.62-1.52 (m, 4H); HPLC purity: 96.85%; LCMS Calculated for $C_{24}H_{23}ClFNO_2S$: 443.11; Observed: 444.05 $[M+H]^+$.

Step-4: Synthesis of 4-(4-chloro-2-fluorophenyl)-1-(2-(p-tolylsulfinyl)phenyl)piperidine (A-144)

To a stirred solution of 4-(4-chloro-2-fluorophenyl)-1-(2-(p-tolylthio)phenyl)piperidine (A28.4) (500 mg, 1.21 mmol, 1 eq) in DCM (10 mL), m-chloroperbenzoic acid (65%) (322 mg, 1.84 mmol, 1 eq) was added at 0° C. The reaction was warmed to room temperature and stirred for 1 h. The progress of the reaction was monitored by TLC. After completion of the reaction, the reaction was quenched with saturated aqueous $NaHCO_3$ solution (10 mL) and stirred for 15 min. the product was extracted with DCM. The combined organic layers were dried over anhydrous $Na_2SO_4$, filtered and concentrated under reduced pressure to dryness. The crude product was purified by column chromatography on silica gel to afford the titled compound 4-(4-chloro-2-fluorophenyl)-1-(2-(p-tolylsulfinyl)phenyl)piperidine (A-144). Yield: 180 mg, 34.7%; Appearance: white solid; $^1H$ NMR (400 MHz, DMSO-$d_6$) δ 7.85 (d, J=7.2 Hz, 1H), 7.59 (d, J=8.0 Hz, 2H), 7.52-7.42 (m, 2H), 7.41-7.35 (m, 2H), 7.34-7.25 (m, 4H), 3.42 (d, J=11.2 Hz, 1H), 3.00-2.83 (m, 2H), 2.74 (t, J=11.2 Hz, 1H), 2.43 (d, J=11.2 Hz, 1H), 2.30 (s, 3H), 2.02-1.90 (m, 1H), 1.85-1.78 (m, 1H), 1.70-1.51 (m, 2H); HPLC purity: 95.11%; LCMS Calculated for $C_{24}H_{23}ClFNOS$: 427.12; Observed: 428.05 $[M+H]^+$.

Example A29: Synthesis of 4-((2-(4-(4-chloro-2-fluorophenyl)piperidin-1-yl)phenyl)sulfonyl)-N,N-dimethylbenzenesulfonamide (A-156)

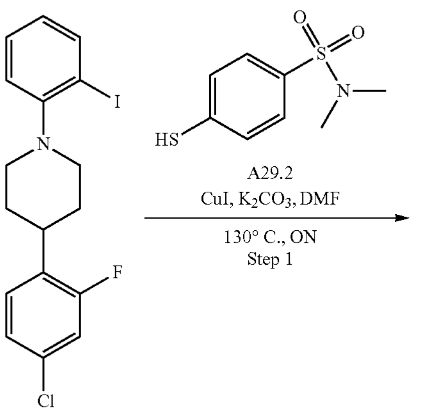

A29.1

-continued

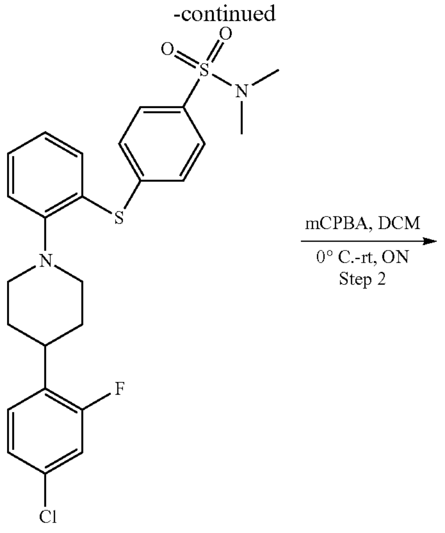

A29.3

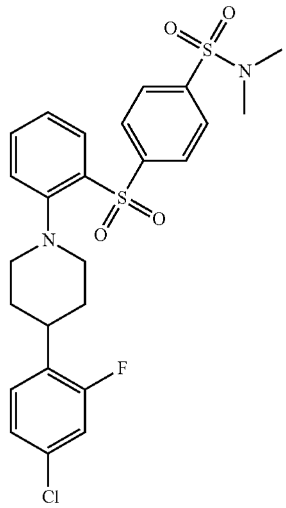

A-156

Step-1: Synthesis of 4-((2-(4-(4-chloro-2-fluorophenyl)piperidin-1-yl)phenyl)thio)-N,N-dimethylbenzenesulfonamide (A29.3)

To a stirred solution of 4-(4-chloro-2-fluorophenyl)-1-(2-iodophenyl)piperidine (A29.1) (400 mg, 0.962 mmol, 1 eq) and compound (A29.2) (219 mg, 1.01 mmol, 1.05 eq) in DMF (10 mL), potassium carbonate (264 mg, 1.92 mmol, 2 eq) and copper iodide (9 mg, 0.05 mmol, 0.05 eq) were added and heated at 130° C. for overnight. The progress of the reaction was monitored by TLC. After completion of the reaction, the reaction mixture was cooled to room temperature, diluted with water and extracted with ethyl acetate. The combined organic layers were dried over anhydrous $Na_2SO_4$, filtered and concentrated under reduced pressure. The crude product was purified by column chromatography on silica gel to afford the titled compound 4-((2-(4-(4-chloro-2-fluorophenyl)piperidin-1-yl)phenyl)thio)-N,N-dimethylbenzenesulfonamide (A29.3) (480 mg, 98.8%). LCMS: 505.10 $[M+H]^+$.

Step-2: Synthesis of 4-((2-(4-(4-chloro-2-fluorophenyl)piperidin-1-yl)phenyl)sulfonyl)-N,N-dimethylbenzenesulfonamide (A-156)

To a stirred solution of 4-((2-(4-(4-chloro-2-fluorophenyl)piperidin-1-yl)phenyl)thio)-N,N-dimethylbenzenesulfonamide (A29.3) (200 mg, 0.396 mmol, 1 eq) in DCM (15 mL), m-chloroperbenzoic acid (65%) (105 mg, 0.396 mmol) was added at 0° C. The reaction mixture was warmed to room temperature and stirred for overnight. The progress of the reaction was monitored by TLC. After completion of the reaction, the reaction was quenched with saturated aqueous $NaHCO_3$ solution (10 mL) and stirred for 15 min, and extracted with ethyl acetate. The combined organic layers were dried over anhydrous $Na_2SO_4$, filtered and concentrated under reduced pressure. The crude product was purified by reverse phase preparative HPLC to afford the titled compound, 4-((2-(4-(4-chloro-2-fluorophenyl)piperidin-1-yl)phenyl)sulfonyl)-N,N-dimethylbenzenesulfonamide (A-156). Yield: 20 mg; 9.4%: Appearance: White solid; $^1H$ NMR (400 MHz, DMSO-$d_6$) δ 8.21 (d, J=8.0 Hz, 1H), 8.04 (d, J=8.4 Hz, 2H), 7.96 (d, J=8.4 Hz, 2H), 7.40-7.79 (m, 1H), 7.62-7.53 (m, 2H), 7.39-7.32 (m, 2H), 7.31-27 (m, 1H), 2.84-2.65 (m, 5H), 2.52 (s, 6H), 1.52 (d, J=11.6 Hz, 2H), 1.34-1.22 (m, 2H); HPLC purity: 97.55%; LCMS calculated for $C_{25}H_{26}ClFN_2O_4S_2$: 536.10; Observed: 537.05 $[M+H]^+$.

Example A30: Synthesis of 4-((2-(4-(4-chloro-2-fluorophenyl)piperidin-1-yl)phenyl)sulfinyl)-N,N-dimethylbenzenesulfonamide (A-181)

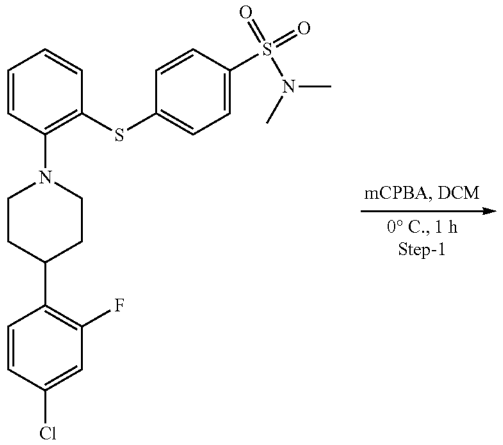

A30.1

-continued

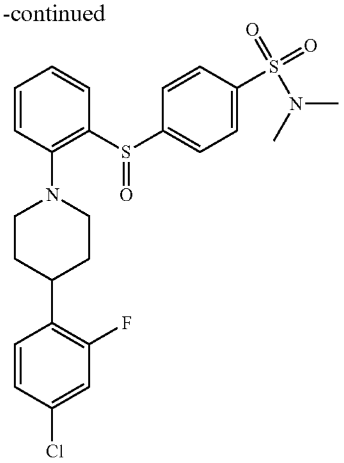

A-181

Step-1: Synthesis of 4-((2-(4-(4-chloro-2-fluorophenyl)piperidin-1-yl)phenyl)sulfinyl)-N,N-dimethylbenzenesulfonamide (A-181)

To a stirred solution of 4-((2-(4-(4-chloro-2-fluorophenyl)piperidin-1-yl)phenyl)thio)-N,N-dimethylbenzenesulfonamide (A30.1) (200 mg, 0.39 mmol, 1 eq) in DCM (10 mL), m-chloroperbenzoic acid (65%) (105 mg, 0.39 mmol, 1 eq) was added at 0° C. and the reaction was stirred at the same temperature for 1 h. The progress of the reaction was monitored by TLC. After completion of the reaction, the reaction mixture was quenched with saturated aqueous $NaHCO_3$ solution and stirred for 15 min, and the product was extracted with DCM. The combined organic layers were dried over anhydrous $Na_2SO_4$, filtered and concentrated under reduced pressure to dryness. The crude product was purified by reverse phase preparative HPLC to afford the titled compound 4-((2-(4-(4-chloro-2-fluorophenyl)piperidin-1-yl)phenyl)sulfinyl)-N,N-dimethylbenzenesulfonamide (A-181). Yield: 21 mg, 8%; Appearance: off white solid; $^1H$ NMR (400 MHz, DMSO-$d_6$) δ 7.97 (d, J=8.4 Hz, 2H), 7.89 (d, J=8.4 Hz, 2H), 7.86 (d, J=8.0 Hz, 1H), 7.58-7.34 (m, 5H), 7.30 (d, J=8.4 Hz, 1H), 3.42 (d, J=11.6 Hz, 1H), 3.04-2.96 (m, 1H), 2.95-2.85 (m, 1H), 2.79-2.71 (m, 1H), 2.57 (s, 6H), 2.46 (m, 1H), 1.99-1.86 (m, 1H), 1.85-1.78 (m, 1H), 1.71-1.64 (m, 1H), 1.62-1.50 (m, 1H); HPLC purity: 99.17%; LCMS Calculated for $C_{25}H_{26}ClFN_2O_3S_2$: 520.11; Observed: 521.05 $[M+H]^+$.

Example A31: Synthesis of 4-((1-(2-(4-(4-chloro-2-fluorophenyl)piperidin-1-yl)phenyl)-2,2,2-trifluoroethyl)amino)-N,N-dimethylbenzenesulfonamide (A-241)

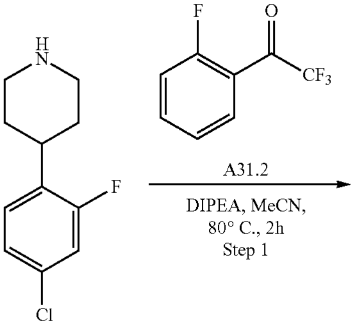

A33.1

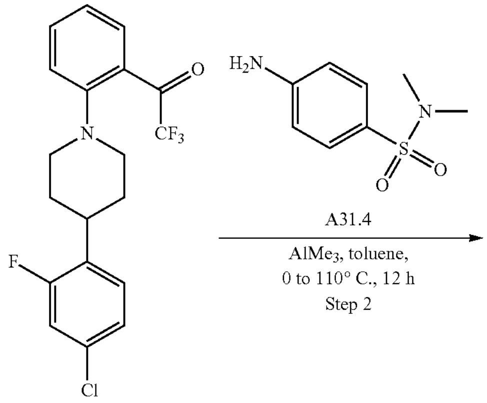

A31.3

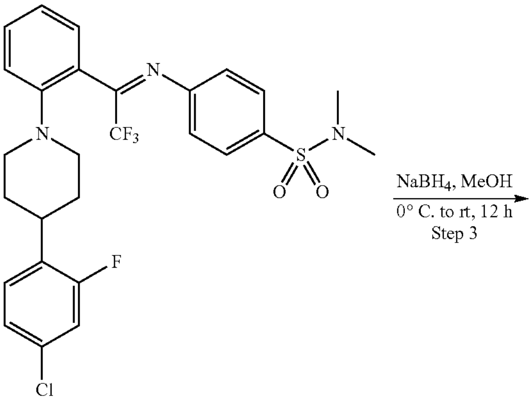

A31.5

-continued

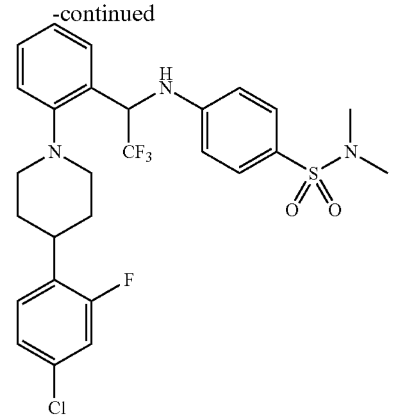

A-241

Step-1: Synthesis of 1-(2-(4-(4-chloro-2-fluorophenyl)piperidin-1-yl)phenyl)-2,2,2-trifluoroethan-1-one (A31.3)

To a stirred solution of 4-(4-chloro-2-fluorophenyl)piperidine (A31.1) (500 mg, 2.35 mmol, 1 eq) and 2,2,2-trifluoro-1-(2-fluorophenyl)ethan-1-one (A31.2) (540 mg, 2.81 mmol, 1.2 eq) in acetonitrile (5 mL), DIPEA (1.02 mL, 5.86 mmol, 2.5 eq) was added at room temperature. The reaction mixture was stirred at 80° C. for 2 h. The progress of the reaction was monitored by TLC. After completion of the reaction, the reaction mixture was cooled to room temperature, diluted with water and extracted with ethyl acetate. The combined organic layers were washed with water, dried over anhydrous $Na_2SO_4$, filtered and concentrated under reduced pressure. The crude product was purified by column chromatography on silica gel to afford the titled compound 1-(2-(4-(4-chloro-2-fluorophenyl)piperidin-1-yl)phenyl)-2,2,2-trifluoroethan-1-one (A31.3) (105 mg, 11.6%). LCMS: 403.90 $[M+H_3O]^+$.

Step-2: Synthesis of (Z)-4-((1-(2-(4-(4-chloro-2-fluorophenyl)piperidin-1-yl)phenyl)-2,2,2-trifluoroethylidene)amino)-N,N-dimethylbenzenesulfonamide (A31.5)

To a stirred solution of 1-(2-(4-(4-chloro-2-fluorophenyl)piperidin-1-yl)phenyl)-2,2,2-trifluoroethan-1-one (A31.3) (100 mg, 0.259 mmol, 1 eq) and 4-amino-N,N-dimethylbenzenesulfonamide (A31.4) (52 mg, 0.259 mmol, 1 eq) in toluene (3 mL), a 2 M solution of trimethyl aluminium in toluene (0.65 mL, 1.3 mmol, 5 eq) was added dropwise at 0° C. The reaction mixture was warmed to room temperature over a period of 10 min and heated at 110° C. for 12 h. The progress of the reaction was monitored by TLC. After completion of the reaction, the reaction mixture was cooled to room temperature, quenched with saturated aqueous $NaHCO_3$ solution and extracted with ethyl acetate. The combined organic layers were washed with water, dried over anhydrous $Na_2SO_4$, filtered and concentrated under reduced pressure. The crude product was purified by column chromatography on silica gel to afford the titled (Z)-4-((1-(2-(4-(4-chloro-2-fluorophenyl)piperidin-1-yl)phenyl)-2,2,2-trifluoroethylidene)amino)-N,N-dimethylbenzenesulfonamide (A31.5) (55 mg, 37.36%). LCMS: 568.15 $[M+H]^+$.

Step-3: Synthesis of 4-((1-(2-(4-(4-chloro-2-fluorophenyl)piperidin-1-yl)phenyl)-2,2,2-trifluoroethyl)amino)-N,N-dimethylbenzenesulfonamide (A-241)

To a stirred solution of (Z)-4-((1-(2-(4-(4-chloro-2-fluorophenyl)piperidin-1-yl)phenyl)-2,2,2-trifluoroethylidene)amino)-N,N-dimethylbenzenesulfonamide (A31.5) (55 mg, 0.095 mmol, 1 eq) in methanol (5 mL), sodium borohydride (18 mg, 0.48 mmol, 5 eq) was added at 0° C. The reaction mixture was warmed to room temperature and stirred for 12 h. The progress of the reaction was monitored by TLC. After completion of the reaction, the reaction mixture was quenched with water and extracted with ethyl acetate. The combined organic layers were dried over anhydrous $Na_2SO_4$, filtered and concentrated under reduced pressure. The crude product was purified by column chromatography on silica gel followed by reverse phase preparative HPLC to afford the titled compound 4-((1-(2-(4-(4-chloro-2-fluorophenyl)piperidin-1-yl)phenyl)-2,2,2-trifluoroethyl)amino)-N,N-dimethylbenzenesulfonamide (A-241). Yield: 20 mg, 36.36%; Appearance: Off white solid; $^1H$ NMR (400 MHz, $CDCl_3$) δ 7.59 (d, J=8.8 Hz, 2H), 7.52 (d, J=8.0 Hz, 1H), 7.46-7.37 (m, 2H), 7.26-7.21 (m, 1H), 7.20-7.16 (m, 1H), 7.10 (dd, J=2.0, 10.0 Hz, 1H), 6.85 (d, J=9.2 Hz, 2H), 6.00-5.92 (m, 1H), 5.20 (bs, 1H), 3.16-3.10 (m, 1H), 3.03-2.90 (m, 4H), 2.65 (s, 6H), 2.02-1.80 (m, 4H), (1H merged with the solvent peak); HPLC purity: 99.77%; LCMS calculated for $C27H28ClF_4N_3O_2S$: 569.15; Observed: 570.25 $[M+H]^+$.

Example A32: Synthesis of 4-((4-(4-(4-chloro-2-fluorophenyl)-2-oxopiperazin-1-yl)-2-methyl-1H-imidazol-1-yl)sulfonyl)-N,N-dimethylbenzenesulfonamide (A-89)

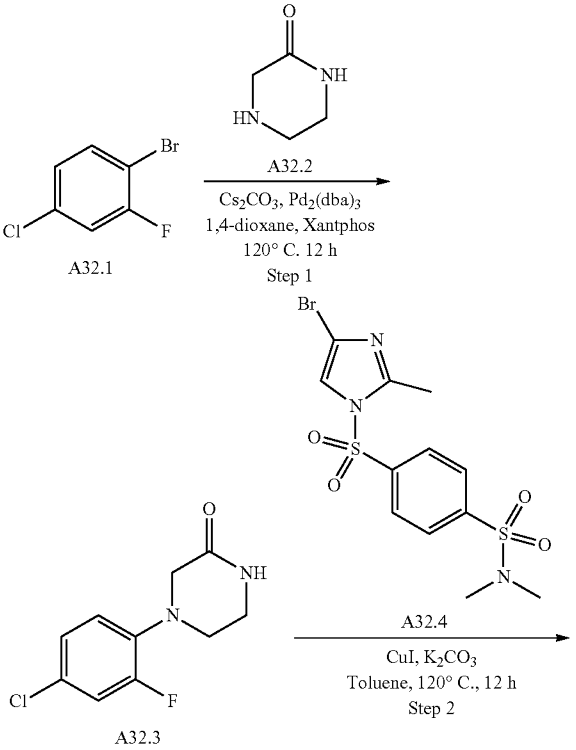

-continued

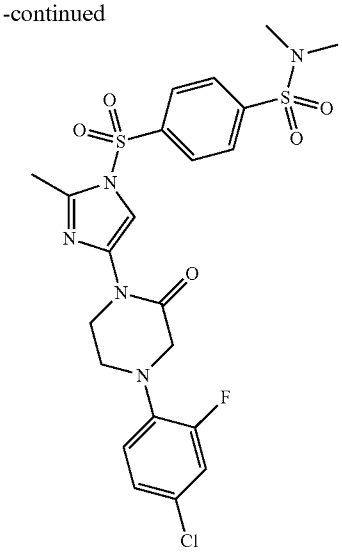

A-89

Step-1: Procedure for Synthesis of 4-(4-chloro-2-fluorophenyl)piperazin-2-one (A32.3)

To a stirred solution of 1-bromo-4-chloro-2-fluorobenzene (A32.1) (2 g, 9.67 mmol, 1 eq) and piperazin-2-one (A32.2) (1.06 g, 10.63 mmol, 1.1 eq) in 1,4-dioxane (30 mL) was added $Cs_2CO_3$ (9.45 g, 29.01 mmol, 3 eq), reaction mixture was purged with argon for 15 min followed by addition of $Pd_2(dba)_3$ (531 mg, 0.58 mmol, 0.03 eq) and xantphos (335 mg, 0.58 mmol, 0.06 eq). The reaction mixture was stirred at 120° C. for 12 h; the reaction progress was monitored by TLC. After completion, the reaction mixture was partitioned between water and ethyl acetate. The organic layers were separated, washed with water dried over $Na_2SO_4$ and concentrated to provide 4-(4-chloro-2-fluorophenyl)piperazin-2-one (A32.3) (0.54 g, crude). The crude was used as such next step without purification. LCMS: 229.05 $[M+H]^+$.

Step-2: Procedure for Synthesis of 4-((4-(4-(4-chloro-2-fluorophenyl)-2-oxopiperazin-1-yl)-2-methyl-1H-imidazol-1-yl)sulfonyl)-N,N-dimethylbenzenesulfonamide (A-89)

To a stirred solution of 4-(4-chloro-2-fluorophenyl)piperazin-2-one (A32.3) (0.2 g, 0.88 mmol, 1 eq) and 4-((4-bromo-2-methyl-1H-imidazol-1-yl)sulfonyl)-N,N-dimethylbenzenesulfonamide (A32.4) (0.43 g, 1.06 mmol, 1.2 eq) in toluene (5 mL) was added $K_2CO_3$ (0.33 g, 1.76 mmol, 2 eq), purged reaction mixture with argon for 15 min followed by addition of (1R,2R)-(−)-N,N-Dimethylcyclohexane-1,2-diamine (0.05 g, 0.35 mmol, 0.4 eq) and Copper iodide (0.033 g, 1.76 mol, 0.2 eq) at room temperature. The reaction mixture was stirred at 120° C. for 12 h. The reaction progress was monitored by TLC. After completion, the reaction mixture was quenched with water and extracted with ethyl acetate. The organic layer was separated, washed with water, dried over $Na_2SO_4$ and concentrated. The crude was purified by prep HPLC to provide 4-((4-(4-(4-chloro-2-fluorophenyl)-2-oxopiperazin-1-yl)-2-methyl-1H-imidazol-1-yl)sulfonyl)-N,N-dimethylbenzenesulfonamide (A-89). Yield: 0.140 g, 29%; Appearance: Yellow solid; $^1H$ NMR (400 MHz, DMSO-$d_6$) δ 8.31-8.29 (m, 2H), 8.05-8.03 (m, 2H), 7.90 (s, 1H), 7.41-7.38 (m, 1H), 7.22-7.2 (m, 1H), 7.09 (t, J=9.2 Hz, 1H), 3.90 (m, 4H), 3.46 (m, 2H), 2.67 (s, 6H), 2.52 (m, 3H); HPLC purity: 97.11%; LCMS Calculated for $C_{22}H_{23}ClFN_5O_5S_2$: 555.08; Observed: 556 $[M+H]^+$.

Example A33: Synthesis of N1-(3-(4-(4-chloro-2-fluorophenyl)piperazin-1-yl)-1-methyl-1H-1,2,4-triazol-5-yl)-N4,N4-dimethylbenzene-1,4-disulfonamide (A-68) and N1-(5-(4-(4-chloro-2-fluorophenyl)piperazin-1-yl)-1-methyl-1H-1,2,4-triazol-3-yl)-N4,N4-dimethylbenzene-1,4-disulfonamide (A-59)

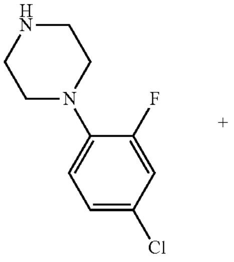

A33.1

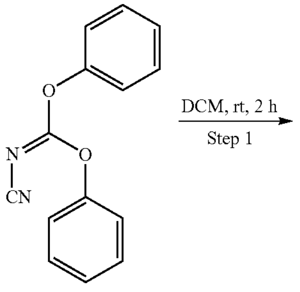

A33.2

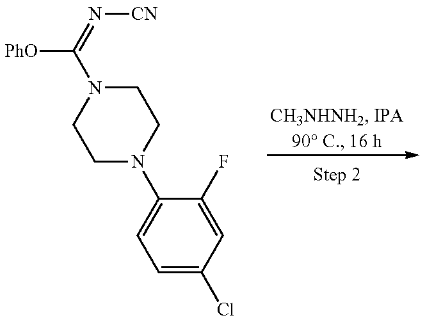

A33.3

-continued

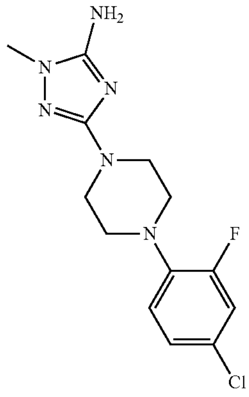

A33.4

+

-continued

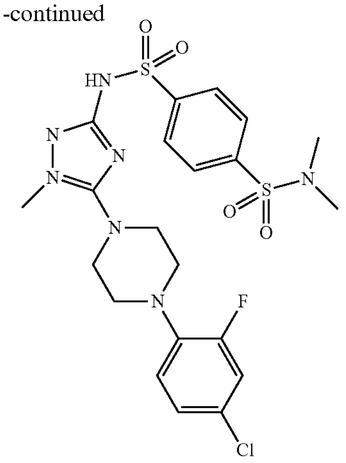

A-59

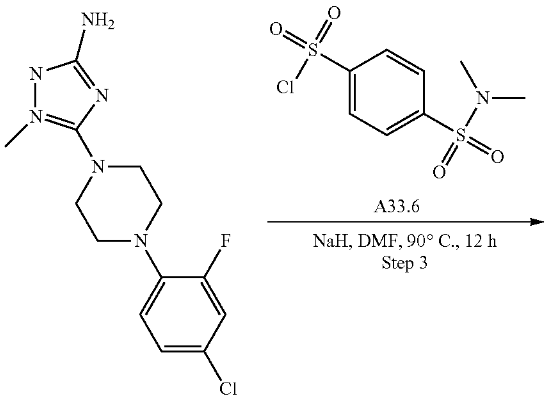

A33.5

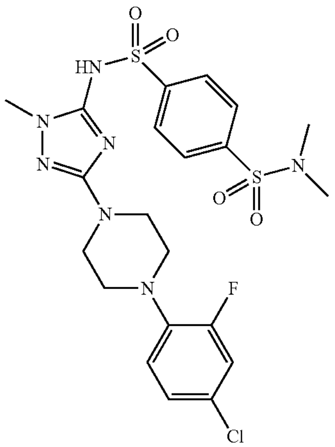

+

A-68

Step-1: Procedure for Synthesis of Phenyl (E)-4-(4-chloro-2-fluorophenyl)-N-cyanopiperazine-1-carbimidate (A33.3)

To a stirred solution of 1-(4-chloro-2-fluorophenyl)piperazine (A33.1) (1 g, 4.6 mmol, 1 eq) in DCM (20 mL) was added diphenyl cyanocarbonimidate (A33.2) (1.1 g, 4.6 mmol, 1 eq). The reaction mixture was stirred at room temperature for 2 h. The progress of the reaction was monitored by TLC. After completion of the reaction, reaction mixture was concentrated under reduced pressure. The crude was purified by column chromatography to afford phenyl (E)-4-(4-chloro-2-fluorophenyl)-N-cyanopiperazine-1-carbimidate (A33.3) (0.7 g, 41.91%). LCMS: 359.10 $[M+H]^+$.

Step-2: Procedure for Synthesis of 3-(4-(4-chloro-2-fluorophenyl)piperazin-1-yl)-1-methyl-1H-1,2,4-triazol-5-amine (A33.4) and 5-(4-(4-chloro-2-fluorophenyl)piperazin-1-yl)-1-methyl-1H-1,2,4-triazol-3-amine (A33.5)

To a stirred solution of (E)-4-(4-chloro-2-fluorophenyl)-N-cyanopiperazine-1-carbimidate (A33.3) (0.5 g, 1.39 mmol, 1 eq) in IPA (30 mL) was added methyl hydrazine (0.13 g, 2.79 mmol, 2 eq) at room temperature. The reaction mixture was stirred at 90° C. for 16 h. The progress of the reaction was monitored by TLC. After completion of the reaction, reaction mixture was concentrated under reduced pressure. The crude was diluted with water and extracted with ethyl acetate. The combined organic extracts were washed with water, brine, dried over anhydrous $Na_2SO_4$, filtered and concentrated under reduced pressure to afford mixture of regioisomers 3-(4-(4-chloro-2-fluorophenyl)piperazin-1-yl)-1-methyl-1H-1,2,4-triazol-5-amine (A33.4) and 5-(4-(4-chloro-2-fluorophenyl)piperazin-1-yl)-1-methyl-1H-1,2,4-triazol-3-amine (A33.5) (0.3 g, crude). The crude was used as such next step without purification. LCMS: 311.11 $[M+H]^+$.

Step-3: Procedure for Synthesis of N-(3-(4-(4-chloro-2-fluorophenyl)piperazin-1-yl)-1-methyl-1H-1,2,4-triazol-5-yl)-N4,N4-dimethylbenzene-1,4-disulfonamide (A-68) and NJ-(5-(4-(4-chloro-2-fluorophenyl)piperazin-1-yl)-1-methyl-1H-1,2,4-triazol-3-yl)-N4,N4-dimethylbenzene-1,4-disulfonamide (A-59)

To a stirred solution of mixture of regioisomers 3-(4-(4-chloro-2-fluorophenyl)piperazin-1-yl)-1-methyl-1H-1,2,4-triazol-5-amine (A33.4) and 5-(4-(4-chloro-2-fluorophenyl)piperazin-1-yl)-1-methyl-1H-1,2,4-triazol-3-amine (A33.5) (0.25 g, 0.8 mmol, 1 eq) in DMF (5 mL) was added NaH (0.12 g, 4.8 mmol, 6 eq) at 0° C., stirred the reaction mixture at room temperature for 10 min followed by addition of 4-(N,N-dimethylsulfamoyl)benzenesulfonyl chloride (A33.6) (0.34 g, 1.2 mmol, 1.5 eq). The reaction mixture was stirred at 90° C. for 12 h. The reaction progress was monitored by TLC. After completion, the reaction mixture was quenched with water and extracted with ethyl acetate. The organic layer was separated, washed with water, dried over $Na_2SO_4$ and concentrated. The crude was purified by column chromatography followed by prep HPLC to provide the N1-(3-(4-(4-chloro-2-fluorophenyl)piperazin-1-yl)-1-methyl-1H-1,2,4-triazol-5-yl)-N4,N4-dimethylbenzene-1,4-disulfonamide (A-68) and N1-(5-(4-(4-chloro-2-fluorophenyl)piperazin-1-yl)-1-methyl-1H-1,2,4-triazol-3-yl)-N4,N4-dimethylbenzene-1,4-disulfonamide (A-59) as separate product. A-68: Yield: 0.03 g, 6.68%; Appearance: Off-white solid; $^1$H NMR (400 MHz, DMSO-$d_6$) δ 12.23 (s, 1H), 8.05 (d, J=8.1 Hz, 2H), 7.87 (d, J=8.2 Hz, 2H), 7.35 (dd, J=12.5, 2.4 Hz, 1H), 7.18 (dd, J=8.7, 2.3 Hz, 1H), 7.08 (t, J=9.0 Hz, 1H), 3.37 (d, J=7.8 Hz, 7H), 3.09-3.02 (m, 4H), 2.62 (s, 6H); HPLC purity: 98.75%; LCMS Calculated for $C_{21}H_{25}ClFN_7O_4S_2$: 557.11; Observed: 558.0 $[M+H]^+$. A-59: Yield: 0.035 g, 6.5%; Appearance: white solid; $^1$H NMR (400 MHz, DMSO-$d_6$) δ 11.16 (s, 1H), 8.19-8.11 (m, 2H), 8.00-7.92 (m, 2H), 7.36 (dd, J=12.5, 2.4 Hz, 1H), 7.20 (ddd, J=8.5, 2.4, 1.1 Hz, 1H), 7.07 (t, J=9.1 Hz, 1H), 3.54 (s, 3H), 3.20 (dd, J=6.6, 3.2 Hz, 4H), 3.12-3.04 (m, 4H), 2.63 (s, 6H); HPLC purity: 98.04%; LCMS Calculated for $C_{21}H_{25}ClFN_7O_4S_2$: 557.11; Observed: 558.0 $[M+H]^+$.

Example A34: Synthesis of N1-(5-(4-(4-chloro-2-fluorophenyl)piperazin-1-yl)-1,3-dimethyl-1H-pyrazol-4-yl)-N4,N4-dimethylbenzene-1,4-disulfonamide (A-18)

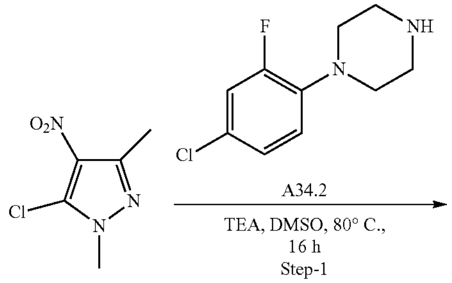

A34.1

-continued

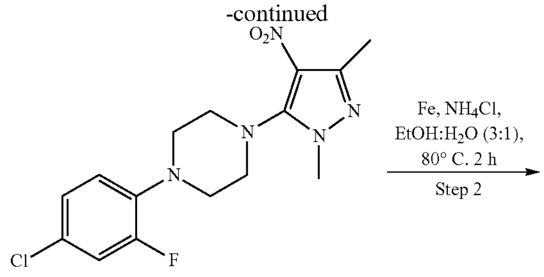

A34.3

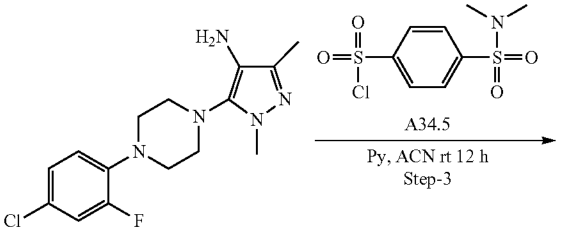

A34.4

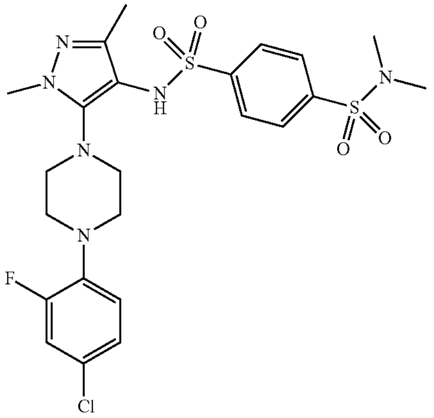

A-18

Step-1: Procedure for Synthesis of 1-(4-chloro-2-fluorophenyl)-4-(1,3-dimethyl-4-nitro-1H-pyrazol-5-yl)piperazine (A34.3)

To a stirred solution of 5-chloro-1,3-dimethyl-4-nitro-1H-pyrazole (A34.1) (1 g, 5.7 mmol, 1 eq) and 1-(4-chloro-2-fluorophenyl)piperazine (A34.2) (1.3 g, 6.2 mmol, 1.1 eq) in DMSO (10 mL) was added TEA (3 mL, 22.8 mmol, 4 eq) at room temperature. The reaction mixture was stirred at 80° C. for 16 h. The progress of reaction was monitored by TLC. After completion, the reaction mixture was diluted with water and extracted with ethyl acetate. The combined organic extracts were washed with water, brine, dried over anhydrous $Na_2SO_4$, filtered and concentrated under reduced pressure to afford 1-(4-chloro-2-fluorophenyl)-4-(1,3-dimethyl-4-nitro-1H-pyrazol-5-yl)piperazine (A34.3) (0.9 g, crude). The crude was used as such next step without purification. LCMS: 354.11 $[M+H]^+$.

Step-2: Procedure for Synthesis of 5-(4-(4-chloro-2-fluorophenyl)piperazin-1-yl)-1,3-dimethyl-1H-pyrazol-4-amine (A34.4)

To a stirred solution of 1-(4-chloro-2-fluorophenyl)-4-(1,3-dimethyl-4-nitro-1H-pyrazol-5-yl)piperazine (A34.3) (0.9 g, 2.5 mmol, 1 eq) in mixture of ethanol (12 mL) and water (4 mL) was added Fe powder (0.71 g, 12.7 mmol, 5 eq) and ammonium chloride (0.67 g, 12.7 mmol, 5 eq) at room temperature. The resulting reaction mixture was stirred at 80° C. for 2 h. The progress of the reaction was monitored by TLC. After completion of the reaction, the reaction mixture was filtered through celite and evaporated to dryness to afford 5-(4-(4-chloro-2-fluorophenyl)piperazin-1-yl)-1,3-dimethyl-1H-pyrazol-4-amine (A34.4) (0.7 g, crude). The crude was used as such next step without purification. LCMS: 324.13 $[M+H]^+$.

Step-3: Procedure for Synthesis of N1-(5-(4-(4-chloro-2-fluorophenyl)piperazin-1-yl)-1,3-dimethyl-1H-pyrazol-4-yl)-N4,N4-dimethylbenzene-1,4-disulfonamide (A-18)

To a stirred solution of 5-(4-(4-chloro-2-fluorophenyl) piperazin-1-yl)-1,3-dimethyl-1H-pyrazol-4-amine (A34.4) (0.1 g, 0.31 mmol, 1 eq) and 4-(N,N-dimethylsulfamoyl) benzenesulfonyl chloride (A34.5) (96 mg, 0.34 mmol, 1.1 eq) in ACN (5 mL) was added pyridine (0.08 mL, 0.93 mmol, 3 eq) at room temperature. The reaction mixture was stirred at room temperature for 12 h. The progress of the reaction was monitored by TLC. After completion of the reaction, reaction mixture was diluted with water and extracted with ethyl acetate. The combined organic extracts were washed with water, brine, dried over anhydrous $Na_2SO_4$, filtered and concentrated under reduced pressure. The crude was purified by prep HPLC to afford N1-(5-(4-(4-chloro-2-fluorophenyl)piperazin-1-yl)-1,3-dimethyl-1H-pyrazol-4-yl)-N4,N4-dimethylbenzene-1,4-disulfonamide (A-18). Yield: 60 mg, 34%; Appearance: White solid; $^1H$ NMR (400 MHz, DMSO-$d_6$) δ 9.44 (s, 1H), 7.95 (q, J=8.5 Hz, 4H), 7.37 (dd, J=12.5, 2.4 Hz, 1H), 7.23-7.2 (m, 1H), 7.09 (t, J=9.1 Hz, 1H), 3.53 (s, 3H), 3.23 (m, 4H), H), 3.08 (m, 4H), 2.61 (s, 6H), 1.24 (s, 3H); HPLC purity: >99%; LCMS Calculated for $C_{23}H_{28}ClFN_6O_4S_2$: 570.13; Observed: 571.30 $[M+H]^+$.

Example A35: Synthesis of 2-(4-(4-chloro-2-fluorophenyl)piperazin-1-yl)-N-(4-(N,N-dimethylsulfamoyl)phenyl)benzamide (A-9)

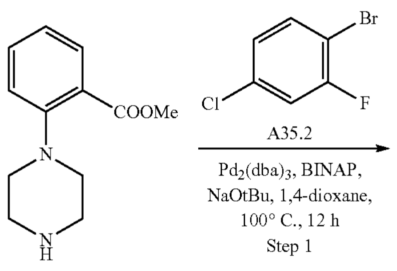

A35.1

-continued

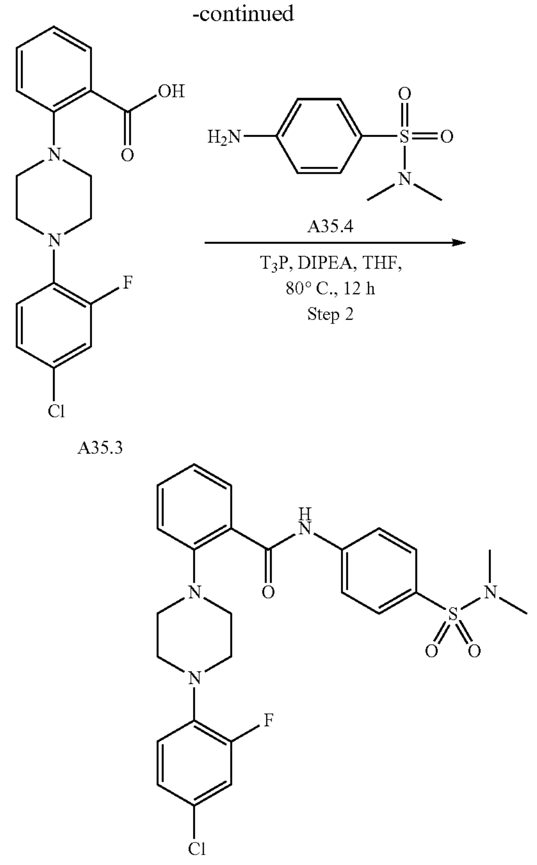

A-9

Step-1: Procedure for synthesis of 2-(4-(4-chloro-2-fluorophenyl)piperazin-1-yl)benzoic Acid (A35.3)

To a stirred solution of methyl 2-(piperazin-1-yl)benzoate (A35.1) (3.1 g, 14.09 mmol, 1 eq) and 1-bromo-4-chloro-2-fluorobenzene (A35.2) (4.4 g, 21.14 mmol, 1.5 eq) in 1,4-dioxane (40 mL) was added sodium tert-butoxide (4.7 g. 49.32 mmol, 3.5 eq). The reaction mixture was purged with argon for 20 min followed by addition of and BINAP (1.75 g, 2.81 mmol, 0.2 eq) and $Pd_2(dba)_3$ (1.28 g, 1.41 mmol, 0.1 eq). The reaction mixture was stirred at 100° C. for 12 h. The reaction progress was monitored by TLC. After completion, the reaction mixture was poured in water and extracted with ethyl acetate. The organic layers were washed with water, brine, dried over anhydrous sodium sulfate and evaporated under reduced pressure. The crude product was purified by column chromatography to afford the pure compound 2-(4-(4-chloro-2-fluorophenyl)piperazin-1-yl)benzoic acid (A35.3) (2.2 g, 44.89%). LCMS: 335.09 $[M+H]^+$.

Step-2: Procedure for Synthesis of 2-(4-(4-chloro-2-fluorophenyl)piperazin-1-yl)-N-(4-(N,N-dimethylsulfamoyl)phenyl)benzamide (A-9)

To a stirred solution of 2-(4-(4-chloro-2-fluorophenyl) piperazin-1-yl)benzoic acid (A35.3) (0.4 g, 1.19 mmol, 1 eq) and 4-amino-N,N-dimethylbenzenesulfonamide (A35.4) (0.29 g, 1.44 mmol, 1.2 eq) in THF (3 mL) was added $T_3P$ (1.13 g, 3.57 mmol, 3 eq) and DIPEA (0.6 mL, 3.57 mmol, 3 eq) at room temperature. The reaction mixture was stirred at 80° C. for 12 h. The progress of the reaction was monitored by TLC. After completion, the reaction mixture was poured in water and extracted with ethyl acetate. The organic layers were washed with water, brine, dried over anhydrous sodium sulfate and evaporated under reduced pressure. The crude product was purified by prep HPLC to afford the titled compound 2-(4-(4-chloro-2-fluorophenyl)piperazin-1-yl)-N-(4-(N,N-dimethylsulfamoyl)phenyl)benzamide (A-9). Yield: 0.03 g, 4.55%; Appearance: White solid; $^1$H NMR (400 MHz, DMSO-$d_6$) δ 11.46 (s, 1H), 8.01 (d, J=8.8 Hz, 2H), 7.73 (m, 3H), 7.57-7.53 (m, 1H), 7.38-7.32 (m, 2H), 7.24 (t, J=7.2 Hz, 1H), 7.17 (dd, J=8.4 Hz, 8.8 Hz, 1H), 7.01 (t, J=8.8 Hz, 1H)), 3.15-3.13 (m, 8H), 2.58 (s, 6H); HPLC purity: >99%; LCMS Calculated for $C_{25}H_{26}ClFN_4O_3S$: 516.14; Observed: 517.30 [M+H]$^+$.

Example A36: Synthesis of N-(2-(3,5-difluoropyridin-2-yl)phenyl)-4-methoxybenzenesulfonamide (A-180)

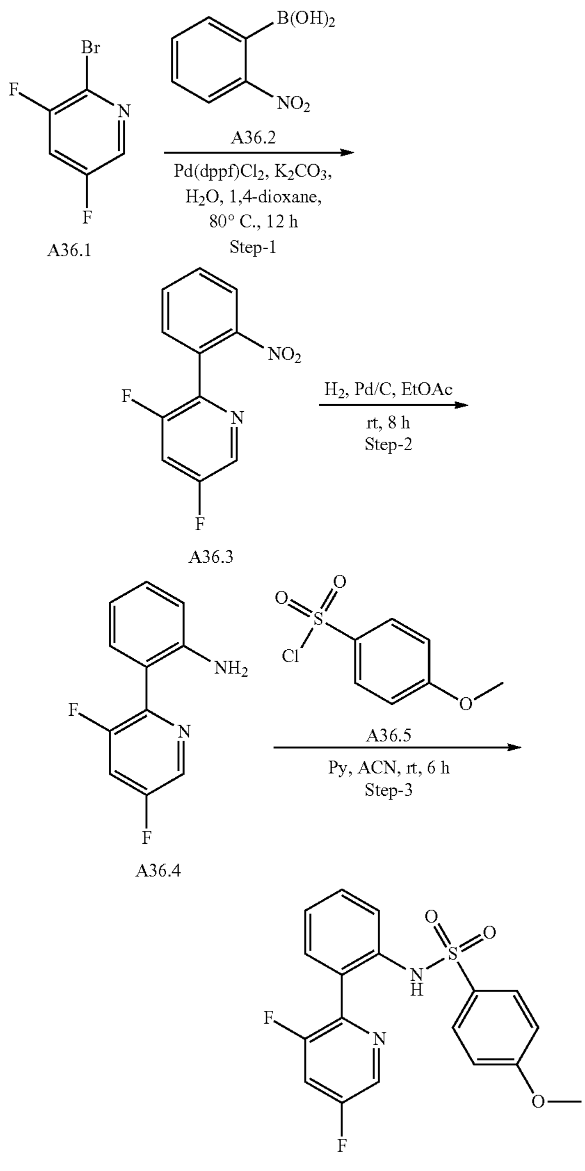

A36.1
A36.2
A36.3
A36.4
A36.5
A-180

Step-1: Synthesis of 3,5-difluoro-2-(2-nitrophenyl)pyridine (A36.3)

A pyrex tube was charged with 2-bromo-3,5-difluoropyridine A41.1 (1 g, 5.1 mmol, 1 eq), (2-nitrophenyl)boronic acid (A36.2) (1.03 g, 6.1 mmol, 1.2 eq) and potassium carbonate (1.62 g, 11.7 mmol, 2.3 eq) in a mixture of 1,4-dioxane (40 mL) and water (10 mL). The tube was sealed with a septum and the reaction mixture was purged with argon for 30 min. [1,1'-Bis(diphenylphosphino)ferrocene]palladium(II) dichloride (0.26 g, 0.35 mmol, 0.07 eq) was then added to the reaction mixture under an argon atmosphere and the reaction mixture was purged with argon for 5 min. The tube was then fitted with a screw cap and the reaction mixture was stirred at 80° C. for 12 h. The progress of the reaction was monitored by TLC. After completion of the reaction, the reaction mixture was cooled to room temperature, filtered through a pad of Celite and the Celite pad was washed with ethyl acetate. The filtrate was diluted with water and extracted with ethyl acetate. The combined organic layers were washed with water and brine, dried over anhydrous $Na_2SO_4$, filtered and concentrated under reduced pressure. The crude product was purified by column chromatography on silica gel to afford the titled compound 3,5-difluoro-2-(2-nitrophenyl)pyridine (A36.3) (0.36 g, 20%). LCMS: 237.04 [M+H]$^+$.

Step-2: Synthesis of 2-(3,5-difluoropyridin-2-yl)aniline (A36.4)

A stirred solution of 3,5-difluoro-2-(2-nitrophenyl)pyridine (A36.3) (0.36 g, 4.9 mmol, 1 eq) in ethyl acetate (3 mL) was purged with nitrogen for 5 min. 10% Palladium on carbon (0.036 g, 10% w/w) was added to the reaction mixture under a nitrogen atmosphere. The reaction mixture was stirred under a hydrogen atmosphere via a hydrogen balloon at room temperature for 8 h. The progress of the reaction was monitored by TLC. After completion of the reaction, the reaction mixture was filtered through a pad of Celite and the Celite pad was washed with methanol. The filtrate was concentrated under reduced pressure to dryness. The crude product was purified by column chromatography on silica gel to afford the titled compound 2-(3,5-difluoropyridin-2-yl)aniline (A36.4) (0.22 g, 88%). LCMS: 207.07 [M+H]$^+$.

Step-3: Synthesis of N-(2-(3,5-difluoropyridin-2-yl)phenyl)-4-methoxybenzenesulfonamide (A-180)

To a stirred solution of 2-(3,5-difluoropyridin-2-yl)aniline (A36.4) (220 mg, 1.06 mmol, 1 eq) in acetonitrile (3 mL), pyridine (0.213 mL, 2.66 mmol, 2.5 eq) was added at room temperature and stirred for 5 min. 4-methoxybenzenesulfonyl chloride (A36.5) (262 mg, 1.28 mmol, 1.2 eq) was then added to the reaction mixture. The reaction mixture was stirred at room temperature for 6 h. The progress of the reaction was monitored by TLC. After completion of the reaction, the reaction mixture was diluted with water and extracted with ethyl acetate. The combined organic layers were washed with water and brine, dried over anhydrous $Na_2SO_4$, filtered and concentrated under reduced pressure. The crude product was purified by column chromatography on silica gel to afford the titled compound N-(2-(3,5-difluoropyridin-2-yl)phenyl)-4-methoxybenzenesulfonamide (A-180). Yield: 48 mg, 13%; Appearance: White sticky solid; $^1$H NMR (400 MHz, DMSO-$d_6$) δ 9.58 (s, 1H), 8.57 (d, J=2.4 Hz, 1H), 8.02-7.91 (m, 1H), 7.46-7.23 (m, 6H), 6.96-6.87 (m, 2H), 3.79 (s, 3H); HPLC purity: >99%; LCMS Calculated for $C_{18}H_{14}F_2N_2O_3S$: 376.07; Observed: 377.00 $[M+H]^+$.

Example A37: Synthesis of N1-(2-(divinylphosphoryl)phenyl)-N4,N4-dimethylbenzene-1,4-disulfonamide (A-227)

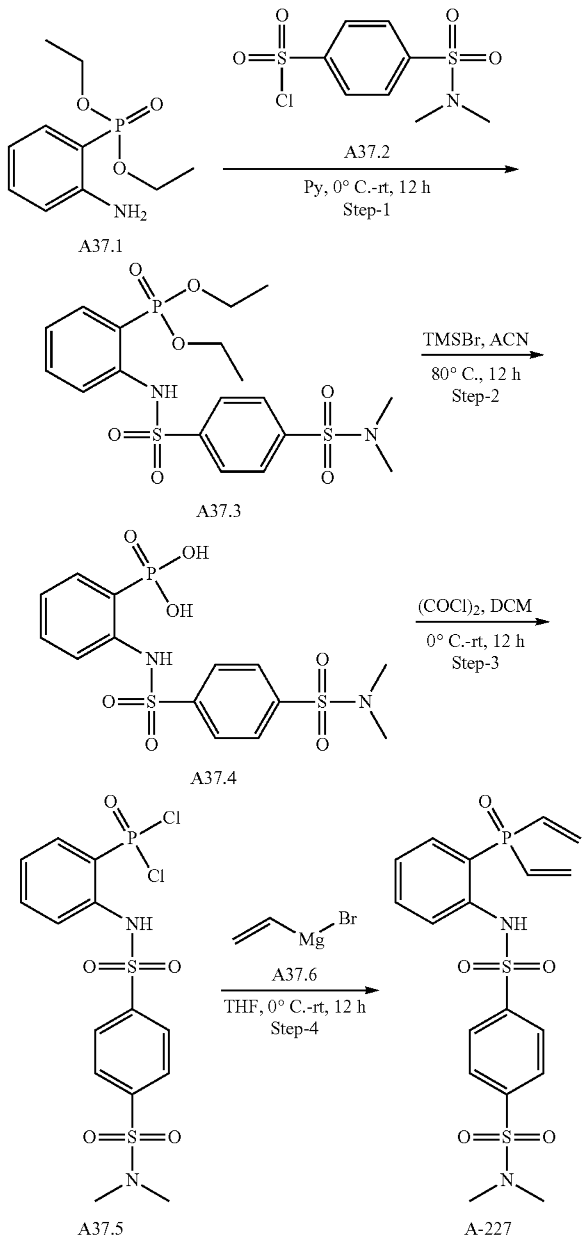

Step-1: Synthesis of Diethyl (2-((4-(N,N-dimethylsulfamoyl)phenyl)sulfonamido)phenyl)phosphonate (A37.3)

To a stirred solution of diethyl (2-aminophenyl)phosphonate (A37.1) (4 g, 17.4 mmol, 1 eq) in acetonitrile (40 mL), pyridine (2.75 mL, 34.9 mmol, 2 eq) was added at 0° C. and stirred the reaction mixture for 10 min. 4-(N,N-Dimethylsulfamoyl)benzenesulfonyl chloride A37.2 (5.44 g, 19.1 mmol, 1.1 eq) was then added to the reaction mixture at 0° C. The reaction mixture was warmed to room temperature and stirred for 12 h. The progress of the reaction was monitored by TLC. After completion of the reaction, the reaction mixture was diluted with water and extracted with ethyl acetate. The combined organic layers were washed with water and brine, dried over anhydrous $Na_2SO_4$, filtered and concentrated under reduced pressure. The crude product was purified by column chromatography on silica gel to afford the titled compound diethyl (2-((4-(N,N-dimethylsulfamoyl)phenyl)sulfonamido)phenyl)phosphonate (A37.3) (7 g, 84%). LCMS: 477.08 $[M+H]^+$.

Step-2: Synthesis of (2-((4-(N,N-dimethylsulfamoyl)phenyl)sulfonamido)phenyl)phosphonic Acid (A37.4)

To a stirred solution of diethyl (2-((4-(N,N-dimethylsulfamoyl)phenyl)sulfonamido)phenyl)phosphonate A37.3 (2 g, 4.19 mmol, 1 eq) in acetonitrile (20 mL), trimethylsilyl bromide (4 mL) was added at room temperature. The reaction mixture was stirred at 80° C. for 12 h. The progress of the reaction was monitored by TLC. After completion of the reaction, the reaction mixture was concentrated under reduced pressure, the residue was triturated with n-pentane, the solids were filtered out and dried under reduced pressure to afford the titled compound (2-((4-(N,N-dimethylsulfamoyl)phenyl)sulfonamido)phenyl)phosphonic acid (A37.4) (1.5 g, crude). This compound was used in the next step without further purification. LCMS: 421.02 $[M+H]^+$.

Step-3: Synthesis of (2-((4-(N,N-dimethylsulfamoyl)phenyl)sulfonamido)phenyl)phosphonic dichloride (A37.5)

To a stirred solution of (2-((4-(N,N-dimethylsulfamoyl)phenyl)sulfonamido)phenyl)phosphonic acid (A37.4) (1.5 g, 3.57 mmol, 1 eq) in DCM (15 mL), DMF (2-3 drop) followed by oxalyl chloride (1.15 g, 8.92 mmol, 2.5 eq) were added at 0° C. under a nitrogen atmosphere. The reaction mixture was warmed to room temperature and stirred for 12 h. The progress of the reaction was monitored by TLC. After completion of the reaction, the reaction mixture was concentrated under reduced pressure to dryness to afford the titled compound (2-((4-(N,N-dimethylsulfamoyl)phenyl)sulfonamido)phenyl)phosphonic dichloride (A37.5) (1.6 g, crude). This compound was used in the next step without further purification. LCMS: No ionization.

Step-4: Synthesis of N1-(2-(divinylphosphoryl)phenyl)-N4,N4-dimethylbenzene-1,4-disulfonamide (A-227)

To a stirred solution of (2-((4-(N,N-dimethylsulfamoyl)phenyl)sulfonamido)phenyl)phosphonic dichloride (A37.5) (1.6 g, 3.51 mmol, 1 eq) in THF (20 mL), a 2 M solution of vinyl magnesium bromide in THF A37.6 (5.26 mL, 10.52 mmol, 3 eq) was added dropwise at 0° C. The resulting reaction mixture was warmed to room temperature and stirred for 12 h. The progress of the reaction was monitored by TLC. After completion of the reaction, the reaction mixture was quenched with saturated aqueous ammonium chloride solution and extracted with ethyl acetate. The combined organic layers were washed with water and brine, dried over anhydrous $Na_2SO_4$, filtered and concentrated under reduced pressure. The crude product was purified by reverse phase preparative HPLC to afford the titled compound N1-(2-(divinylphosphoryl)phenyl)-N4,N4-dimethylbenzene-1,4-disulfonamide (A-227). Yield: 240 mg, 19%; Appearance: Brown solid; $^{1}H$ NMR (400 MHz, DMSO-$d_6$) δ 11.50 (s, 1H), 8.03-7.94 (m, 2H), 7.89 (d, J=8.4 Hz, 2H), 7.57-7.43 (m, 3H), 7.22 (t, J=6.8 Hz, 1H), 6.63 (ddd, J=26.6, 18.5, 12.7 Hz, 2H), 6.25 (dd, J=12.4, 1.8 Hz, 1H), 6.18-5.98 (m, 3H), 2.60 (s, 6H); HPLC purity: 96.77%; LCMS Calculated for $C_{18}H_{21}N_2O_5PS_2$: 440.06; Observed: 441.00 $[M+H]^+$.

Example A38: Synthesis of N-(2',4'-difluoro-[1,1'-biphenyl]-2-yl)-4-methoxybenzenesulfonamide (A-167)

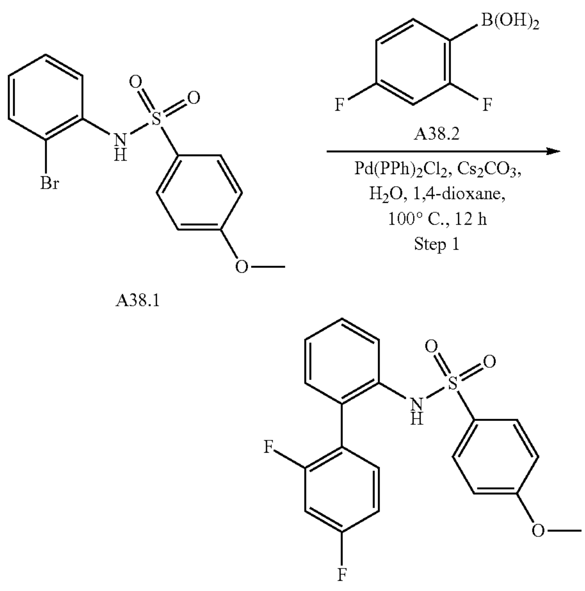

A38.1

A-167

Step-1: Synthesis of N-(2',4'-difluoro-[1,1'-biphenyl]-2-yl)-4-methoxybenzenesulfonamide, (A-167)

A pyrex tube was charged with N-(2-bromophenyl)-4-methoxybenzenesulfonamide (A38.1) (0.4 g, 1.17 mmol, 1 eq), (2,4-difluorophenyl)boronic acid A38.2 (0.22 g, 1.41 mmol, 1.2 eq) and cesium carbonate (0.76 g, 2.34 mmol, 2 eq) in a mixture of 1,4-dioxane (16 mL) and water (4 mL). The tube was sealed with a septum and the reaction mixture was purged with nitrogen for 30 min. Bis(triphenylphosphine)palladium(II) dichloride (0.06 g, 0.08 mmol, 0.07 eq) was then added to the reaction mixture under the atmosphere of nitrogen at room temperature. The tube was then sealed with screw cap and the reaction mixture was stirred at 100° C. for 12 h. The progress of the reaction was monitored by TLC. After completion of the reaction, the reaction mixture was filtered through a pad of Celite and the Celite pad was washed with ethyl acetate. The filtrate was diluted with brine and extracted with ethyl acetate. The combined organic layers were washed with water and brine, dried over anhydrous $Na_2SO_4$, filtered and concentrated under reduced pressure. The crude product was purified by column chromatography on silica gel to afford title compound N-(2',4'-difluoro-[1,1'-biphenyl]-2-yl)-4-methoxybenzenesulfonamide (A-167). Yield: 0.025 g, 11%; Appearance: White solid; $^{1}H$ NMR (400 MHz, DMSO-$d_6$) δ 9.40 (s, 1H), 7.56-7.45 (m, 2H), 7.36-6.95 (m, 9H), 3.85-3.80 (m, 3H); HPLC purity: 97.13%; LCMS Calculated for $C_{19}H_{15}F_2NO_3S$: 375.07; Observed: 375.95 $[M+H]^+$.

Example A39: Synthesis of N-(2-(2,4-difluorophenoxy)phenyl)-4-methoxybenzenesulfonamide (A-186)

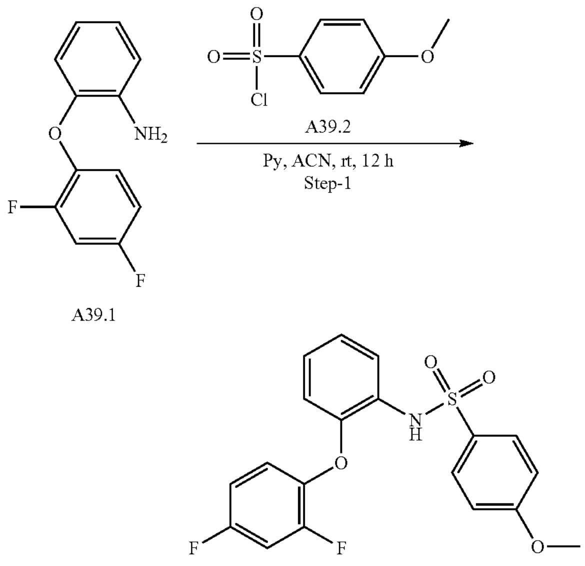

A39.1

A-186

Step-1: Synthesis of N-(2-(2,4-difluorophenoxy)phenyl)-4-methoxybenzenesulfonamide (A-186)

To a stirred solution of 2-(2,4-difluorophenoxy)aniline (A39.1) (0.2 g, 0.9 mmol, 1 eq) in acetonitrile (5 mL), pyridine (0.18 mL, 2.2 mmol, 2.5 eq) was added at room temperature and the reaction mixture was stirred at the same temperature for 5 min. 4-Methoxybenzenesulfonyl chloride A39.2 (0.22 g, 1.08 mmol, 1.2 eq) was then added to the reaction mixture. The reaction mixture was stirred at room temperature for 4 h. The progress of the reaction was monitored by TLC. After completion of the reaction, reaction mixture was diluted with water and extracted with ethyl acetate. The combined organic layers were washed with water and brine, dried over anhydrous $Na_2SO_4$, filtered and concentrated under reduced pressure. The crude product was purified by column chromatography on silica gel to afford the titled compound N-(2-(2,4-difluorophenoxy)phenyl)-4-methoxybenzenesulfonamide (A-186). Yield: 0.12 g, 34%; Appearance: White solid; $^{1}H$ NMR (400 MHz, DMSO-$d_6$) δ 9.87 (s, 1H), 7.72-7.63 (m, 2H), 7.47-7.30 (m, 2H), 7.12-6.94 (m, 5H), 6.75-6.59 (m, 2H), 3.79 (d, J=1.0 Hz, 3H); HPLC purity: 98.28%; LCMS Calculated for $C_{19}H_{15}F_2NO_4S$: 391.07; Observed: 391.95 $[M+H]^+$.

Example A40: Synthesis of N-(2-((2,4-difluorobenzyl)oxy)phenyl)-4-methoxybenzenesulfonamide (A-187)

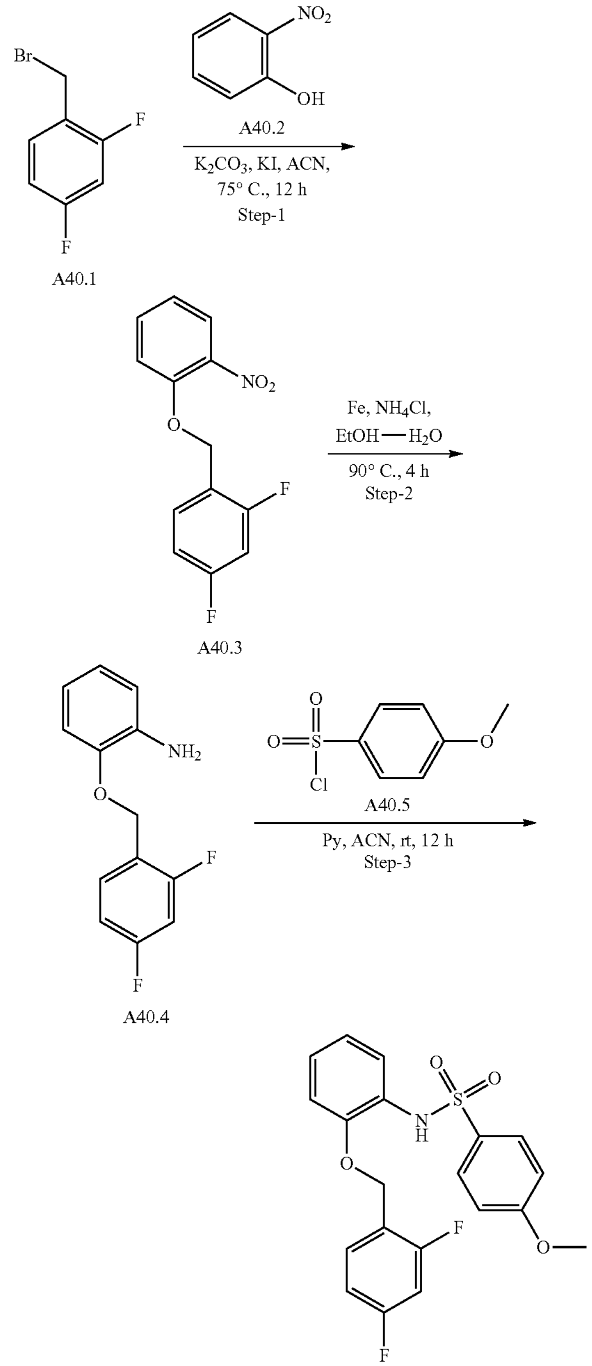

A-187

Step-1: Synthesis of 2,4-difluoro-1-((2-nitrophenoxy)methyl)benzene (A40.3)

To a stirred solution of 1-(bromomethyl)-2,4-difluorobenzene (A40.1) (1 g, 4.83 mmol, 1 eq) in acetonitrile (20 mL), potassium carbonate (1.3 g, 9.66 mmol, 2 eq), 2-nitrophenol (A40.2) (739 mg, 5.31 mmol, 1.1 eq) and potassium iodide (80 mg, 0.48 mmol, 0.1 eq) were added at room temperature. The reaction mixture was stirred at 75° C. for 12 h. The progress of the reaction was monitored by TLC. After completion of the reaction, the reaction mixture was cooled to room temperature, diluted with water and extracted with ethyl acetate. The combined organic layers were washed with water and brine, dried over anhydrous $Na_2SO_4$, filtered and concentrated under reduced pressure. The crude product was purified by column chromatography on silica gel to afford the titled compound 2,4-difluoro-1-((2-nitrophenoxy)methyl)benzene A40.3 (1 g, 78.12%). LCMS: 266.06 $[M+H]^+$.

Step-2: Synthesis of 2-((2,4-difluorobenzyl)oxy)aniline (A40.4)

To a stirred solution of 2,4-difluoro-1-((2-nitrophenoxy)methyl)benzene (A40.3) (1 g, 3.77 mmol, 1 eq) in a mixture of ethanol (14 mL) and water (3 mL), iron powder (1.05 g, 18.87 mmol, 5 eq) and ammonium chloride (1 g, 18.87 mmol, 5 eq) were added at room temperature. The resulting reaction mixture was stirred at 90° C. for 4 h. The progress of the reaction was monitored by TLC. After completion of the reaction, the reaction mixture was cooled to room temperature, filtered through a pad of Celite and the Celite pad was washed with ethanol. The filtrated was concentrated under reduced pressure to dryness. The crude product was purified by column chromatography on silica gel to afford the titled compound 2-((2,4-difluorobenzyl)oxy)aniline (A40.4) (680 mg, 76.74%). LCMS: 236.08 $[M+H]^+$.

Step-3: Synthesis of N-(2-((2,4-difluorobenzyl)oxy)phenyl)-4-methoxybenzenesulfonamide (A40.6)

To a stirred solution of 2-((2,4-difluorobenzyl)oxy)aniline (A40.4) (200 mg, 0.85 mmol, 1 eq) in acetonitrile (10 mL), pyridine (171 mL, 2.13 mmol, 2.5 eq) and 4-methoxybenzenesulfonyl chloride (A40.5) (211 mg, 1.02 mmol, 1.2 eq) were added at room temperature and the reaction mixture was stirred at the same temperature for 4 h. The progress of the reaction was monitored by TLC. After completion of the reaction, 1N aqueous HCl solution was added and extracted with ethyl acetate. The combined organic layers were washed with water and brine, dried over anhydrous $Na_2SO_4$, filtered and concentrated under reduced pressure. The crude product was purified by column chromatography on silica gel to afford the titled compound N-(2-((2,4-difluorobenzyl)oxy)phenyl)-4-methoxybenzenesulfonamide (A-187). Yield: 180 mg, 52.32%; Appearance: White solid; $^1H$ NMR (400 MHz, DMSO-$d_6$) δ 9.34 (s, 1H), 7.58-7.44 (m, 3H), 7.33-7.22 (m, 2H), 7.16-7.05 (m, 2H), 7.01 (dd, J=8.3, 1.5 Hz, 1H), 6.95-6.84 (m, 3H), 4.87 (s, 2H), 3.75 (d, J=1.4 Hz, 3H); HPLC purity: >99%; LCMS Calculated for $C_{20}H_{17}F_2NO_4S$: 405.08; Observed: 405.90 $[M+H]^+$.

Example A41

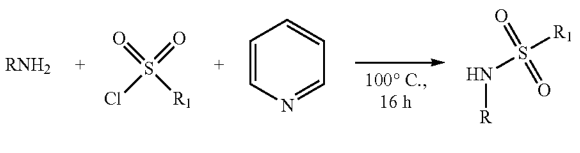

General Procedure for Synthesis of Aminobenzyl Series Compounds—Method A

Sulfonyl chloride (1.1 eq) was added to the vial containing aniline (1 eq) in dry pyridine (1 mL). The reaction mixture was heated at 100° C. with stirring for 16 h. After cooling to the room temperature the mixture was evaporated. The residue was dissolved in DMSO (2 mL), filtered from non-soluble impurities if there were any. The resulting filtrate was subjected to HPLC purification (deionized water/HPLC-grade methanol (acetonitrile)).

The following examples were prepared using method A:

| Compound No. | Structure | Analytical data |
|---|---|---|
| A-390 | 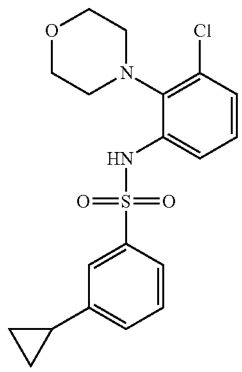 [SMILES: O=S(=O)(Nc1cccc(Cl)c1N1CCOCC1)c1cccc(C2CC2)c1] | Yield: 106.4 mg, 50.7%; Appearance: Light-brown solid; $^1$H NMR (400 MHz, DMSO-d$_6$) δ 9.00 (s, 1H), 7.47-7.29 (m, 5H), 7.24-7.15 (m, 2H), 3.69-3.55 (m, 4H), 3.31-3.20 (m, 2H), 2.13-1.89 (m, 3H), 1.06-0.91 (m, 2H), 0.65-0.50 (m, 2H); HPLC purity: 100%; LCMS Calculated for $C_{19}H_{21}ClN_2O_3S$: 392.90; Observed: 392.12 [M − H]$^-$. |
| A-392 | 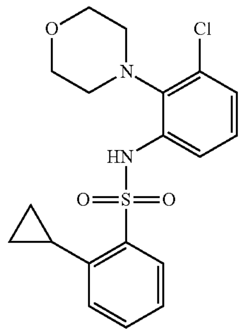 [SMILES: O=S(=O)(Nc1cccc(Cl)c1N1CCOCC1)c1ccccc1C1CC1] | Yield: 80.4 mg, 38.3%; Appearance: Brown solid; $^1$H NMR (500 MHz, DMSO-d$_6$) δ 9.17 (s, 1H), 7.88 (dd, J = 8.0, 1.4 Hz, 1H), 7.51 (t, J = 7.5 Hz, 1H), 7.31 (t, J = 7.8 Hz, 1H), 7.19-7.06 (m, 3H), 7.03 (d, J = 7.9 Hz, 1H), 3.67 (s, 4H), 3.48-3.35 (m, 2H), 3.32-3.19 (m, 2H), 2.73-2.59 (m, 1H), 0.97 (dt, J = 8.5, 3.2 Hz, 2H), 0.82-0.70 (m, 2H); HPLC purity: 100%; LCMS Calculated for $C_{19}H_{21}ClN_2O_3S$: 392.90; Observed: 392.12 [M − H]$^-$. |
| A-393 | 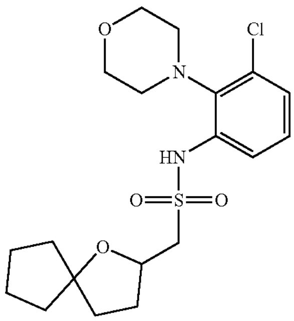 [SMILES: O=S(=O)(CC1CCC2(CCCC2)O1)Nc1cccc(Cl)c1N1CCOCC1] | Yield: 70.3 mg, 33.6%; Appearance: Light-brown solid; $^1$H NMR (400 MHz, DMSO-d$_6$) δ 8.62 (s, 1H), 7.40 (dd, J = 8.0, 1.6 Hz, 1H), 7.21 (t, J = 8.1 Hz, 1H), 7.15 (dd, J = 8.1, 1.6 Hz, 1H), 4.26 (p, J = 6.2 Hz, 1H), 3.87-3.74 (m, 2H), 3.74-3.61 (m, 2H), 3.56-3.42 (m, 4H), 2.84-2.61 (m, 2H), 2.18-2.05 (m, 1H), 1.81-1.67 (m, 3H), 1.56-1.39 (m, 8H); HPLC purity: 98.05%; LCMS Calculated for $C_{19}H_{27}ClN_2O_4S$: 414.95; Observed: 414.17 [M − H]$^-$. |
| A-394 | 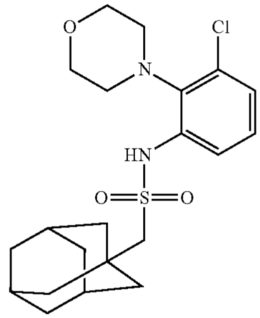 [SMILES: O=S(=O)(CC12CC3CC(CC(C3)C1)C2)Nc1cccc(Cl)c1N1CCOCC1] | Yield: 9.9 mg, 4.72%; Appearance: Beige solid; $^1$H NMR (500 MHz, Chloroform-d$_6$) δ 8.40 (s, 1H), 7.45 (dd, J = 8.2, 1.4 Hz, 1H), 7.15 (t, J = 8.1 Hz, 1H), 7.02 (dd, J = 8.1, 1.4 Hz, 1H), 3.98 (dd, J = 11.2, 2.9 Hz, 2H), 3.89-3.79 (m, 2H), 3.71 (td, J = 11.4, 2.4 Hz, 2H), 2.94 (s, 2H), 2.57 (d, J = 11.7 Hz, 2H), 2.01 (s, 3H), 1.85-1.79 (m, 5H), 1.77-1.61 (m, 8H); HPLC purity: 98.96%; LCMS Calculated for $C_{21}H_{29}ClN_2O_3S$: 424.98; Observed: 424.2 [M − H]$^-$. |

-continued

| Compound No. | Structure | Analytical data |
|---|---|---|
| A-410 | 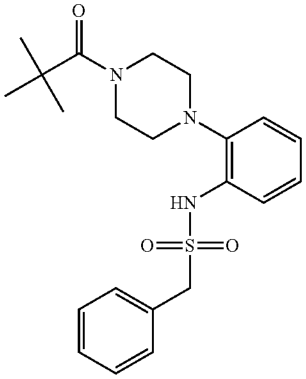 [SMILES: CC(C)(C)C(=O)N1CCN(c2ccccc2NS(=O)(=O)Cc2ccccc2)CC1] | Yield: 62.8 mg, 40.0%; Appearance: Pink solid; $^1H$ NMR (400 MHz, DMSO-$d_6$) δ 8.35 (s, 1H), 7.40-7.32 (m, 3H), 7.34-7.27 (m, 3H), 7.30-7.20 (m, 2H), 7.13-7.05 (m, 2H), 4.62 (s, 2H), 3.65 (t, J = 4.7 Hz, 4H), 2.72 (t, J = 4.5 Hz, 4H), 1.21 (s, 9H); HPLC purity: 95.72%; LCMS Calculated for $C_{22}H_{29}N_3O_3S$: 415.55; Observed: 415.23 $[M - H]^-$. |
| A-563 | 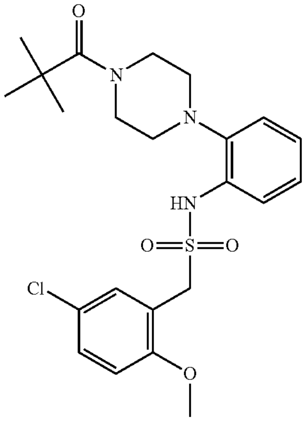 [SMILES: COc1ccc(Cl)cc1CS(=O)(=O)Nc1ccccc1N1CCN(C(=O)C(C)(C)C)CC1] | Yield: 11.9 mg, 32.8%; Appearance: Beige solid; $^1H$ NMR (600 MHz, DMSO-$d_6$) δ 8.44 (s, 1H), 7.36 (dd, J = 8.8, 2.5 Hz, 1H), 7.32 (d, J = 2.5 Hz, 1H), 7.29 (dd, J = 7.6, 1.9 Hz, 1H), 7.20 (dd, J = 7.6, 2.0 Hz, 1H), 7.12-7.03 (m, 2H), 7.00 (d, J = 8.9 Hz, 1H), 4.60 (s, 2H), 3.64 (t, J = 4.8 Hz, 4H), 3.57 (s, 3H), 2.70 (t, J = 4.8 Hz, 4H), 1.19 (s, 9H); HPLC purity: 100%; LCMS Calculated for $C_{23}H_{30}ClN_3O_4S$: 480.02; Observed: 479.2 $[M - H]^-$. |
| A-485 | 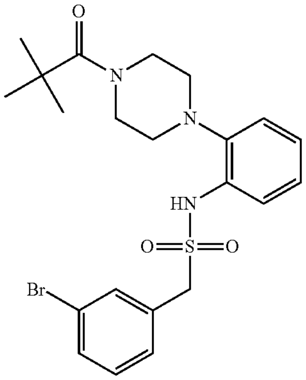 [SMILES: CC(C)(C)C(=O)N1CCN(c2ccccc2NS(=O)(=O)Cc2cccc(Br)c2)CC1] | Yield: 59.5 mg, 20.9%; Appearance: Light brown solid; $^1H$ NMR (400 MHz, DMSO-$d_6$) δ 8.45 (s, 1H), 7.58-7.53 (m, 1H), 7.50 (s, 1H), 7.32 (d, J = 3.9 Hz, 2H), 7.30-7.19 (m, 2H), 7.12-7.04 (m, 2H), 4.65 (s, 2H), 3.65 (s, 4H), 2.72 (t, J = 4.7 Hz, 4H), 1.19 (s, 9H); HPLC purity: 99.64%; LCMS Calculated for $C_{22}H_{28}BrN_3O_3S$: 494.45; Observed: 493.45 $[M - H]^-$. |
| A-500 | 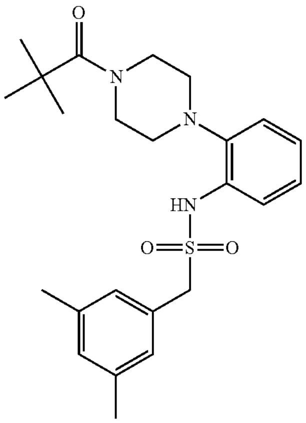 [SMILES: Cc1cc(C)cc(CS(=O)(=O)Nc2ccccc2N2CCN(C(=O)C(C)(C)C)CC2)c1] | Yield: 36.2 mg, 32.8%; Appearance: Yellow solid; $^1H$ NMR (400 MHz, DMSO-$d_6$) δ 8.35 (s, 1H), 7.32 (d, J = 5.9 Hz, 1H), 7.23 (d, J = 5.3 Hz, 1H), 7.13-7.06 (m, 2H), 6.98 (s, 1H), 6.90 (s, 2H), 4.53 (s, 2H), 3.65 (t, J = 5.2 Hz, 4H), 2.69 (t, J = 4.9 Hz, 4H), 2.22 (s, 6H), 1.21 (s, 9H); HPLC purity: 100%; LCMS Calculated for $C_{24}H_{33}N_3O_3S$: 443.61; Observed: 443.27 $[M - H]^-$. |

-continued

| Compound No. | Structure | Analytical data |
|---|---|---|
| A-564 | 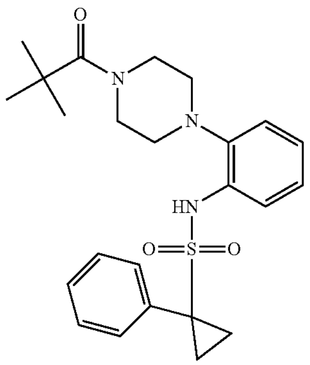 [SMILES: CC(C)(C)C(=O)N1CCN(c2ccccc2NS(=O)(=O)C2(c3ccccc3)CC2)CC1] | Yield: 16.5 mg, 10.6%; Appearance: Beige solid; $^1$H NMR (600 MHz, DMSO-$d_6$) δ 7.99 (s, 1H), 7.38-7.28 (m, 5H), 7.17 (dd, J = 7.6, 1.9 Hz, 1H), 7.06-6.95 (m, 3H), 3.51 (s, 4H), 2.60 (t, J = 4.9 Hz, 4H), 1.73-1.67 (m, 2H), 1.31 (q, J = 5.0 Hz, 2H), 1.17 (s, 9H); HPLC purity: 99.37%; LCMS Calculated for $C_{24}H_{33}N_3O_3S$: 441.59; Observed: 441.25 $[M-H]^-$. |
| A-501 | 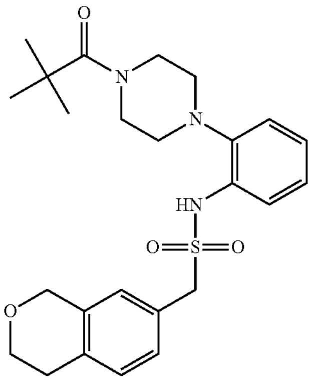 [SMILES: CC(C)(C)C(=O)N1CCN(c2ccccc2NS(=O)(=O)Cc2ccc3c(c2)COCC3)CC1] | Yield: 41.3 mg, 26.3%; Appearance: Yellow solid; $^1$H NMR (400 MHz, DMSO-$d_6$) δ 8.33 (s, 1H), 7.31 (d, J = 5.9 Hz, 1H), 7.23 (d, J = 5.9 Hz, 1H), 7.14-7.06 (m, 4H), 6.95 (s, 1H), 4.58 (d, J = 13.9 Hz, 4H), 3.89-3.81 (m, 2H), 3.63 (t, J = 5.1 Hz, 4H), 2.76 (s, 2H), 2.69 (t, J = 3.8 Hz, 4H), 1.21 (s, 9H); HPLC purity: 95.53%; LCMS Calculated for $C_{25}H_{33}N_3O_4S$: 471.62; Observed: 471.26 $[M-H]^-$. |
| A-486 | 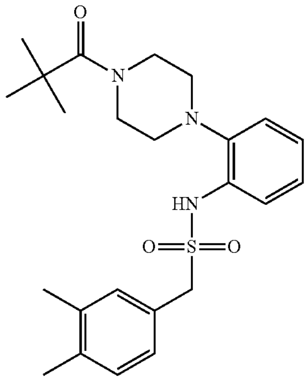 [SMILES: Cc1ccc(CS(=O)(=O)Nc2ccccc2N2CCN(C(=O)C(C)(C)C)CC2)cc1C] | Yield: 48.5 mg, 30.8%; Appearance: Yellow solid; $^1$H NMR (400 MHz, DMSO-$d_6$) δ 8.03 (s, 1H), 7.38 (d, J = 7.9 Hz, 1H), 7.19-7.00 (m, 4H), 6.99 (s, 1H), 6.92 (d, J = 8.1 Hz, 1H), 4.39 (s, 2H), 3.62 (s, 4H), 2.69 (t, J = 4.9 Hz, 4H), 2.25 (s, 3H), 2.21 (s, 3H), 1.24 (s, 9H); HPLC purity: 96.53%; LCMS Calculated for $C_{24}H_{33}N_3O_3S$: 443.61; Observed: 443.27 $[M-H]^-$. |
| A-488 | 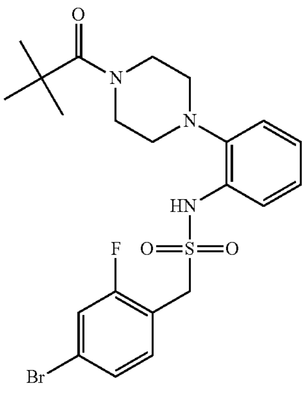 [SMILES: CC(C)(C)C(=O)N1CCN(c2ccccc2NS(=O)(=O)Cc2ccc(Br)cc2F)CC1] | Yield: 34.3 mg, 20.9%; Appearance: Light brown solid; $^1$H NMR (400 MHz, DMSO-$d_6$) δ 8.62 (s, 1H), 7.59 (dd, J = 9.3, 2.2 Hz, 1H), 7.50-7.42 (m, 1H), 7.42-7.30 (m, 1H), 7.30-7.19 (m, 2H), 7.13-7.03 (m, 2H), 4.66-4.61 (m, 2H), 3.66 (s, 4H), 2.75 (d, J = 5.1 Hz, 4H), 1.20 (s, 9H); HPLC purity: 96.83%; LCMS Calculated for $C_{22}H_{27}BrFN_3O_3S$: 512.44; Observed: 512.13 $[M-H]^-$. |

-continued

| Compound No. | Structure | Analytical data |
|---|---|---|
| A-512 | 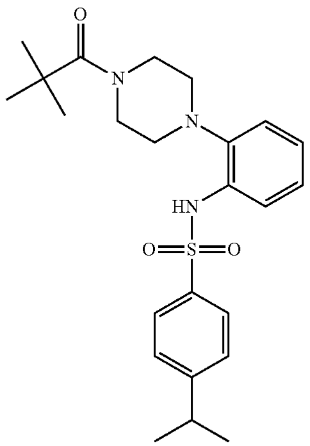 [SMILES: CC(C)c1ccc(S(=O)(=O)Nc2ccccc2N2CCN(C(=O)C(C)(C)C)CC2)cc1] | Yield: 69.6 mg, 44.3%; Appearance: Light-brown solid; $^1$H NMR (400 MHz, DMSO-$d_6$) δ 8.71 (s, 1H), 7.65 (d, J = 8.0 Hz, 2H), 7.43 (d, J = 7.6 Hz, 1H), 7.32 (d, J = 8.0 Hz, 2H), 7.12-7.00 (m, 3H), 3.56 (t, J = 4.9 Hz, 4H), 2.95 (p, J = 6.9 Hz, 1H), 2.35 (t, J = 4.8 Hz, 4H), 1.23 (d, J = 6.8 Hz, 6H), 1.21 (s, 9H); HPLC purity: 96.81%; LCMS Calculated for $C_{24}H_{33}N_3O_3S$: 443.61; Observed: 444.1 $[M+H]^-$. |
| A-513 | 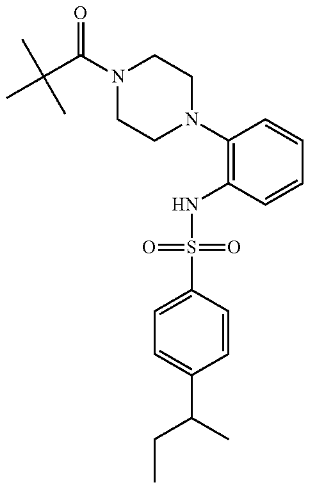 [SMILES: CCC(C)c1ccc(S(=O)(=O)Nc2ccccc2N2CCN(C(=O)C(C)(C)C)CC2)cc1] | Yield: 73.9 mg, 47.1%; Appearance: Pink solid; $^1$H NMR (400 MHz, DMSO-$d_6$) δ 8.70 (s, 1H), 7.64 (d, J = 8.5 Hz, 2H), 7.45 (d, J = 7.8 Hz, 1H), 7.27 (d, J = 8.5 Hz, 2H), 7.11-7.00 (m, 3H), 3.56 (s, 4H), 2.65 (q, J = 7.2 Hz, 1H), 2.33 (t, J = 4.4 Hz, 4H), 1.62-1.52 (m, 2H), 1.21 (d, J = 2.7 Hz, 12H), 0.77 (t, J = 7.4 Hz, 3H); HPLC purity: 96.93%; LCMS Calculated for $C_{25}H_{35}N_3O_3S$: 457.63; Observed: 457.29 $[M-H]^-$. |
| A-514 | 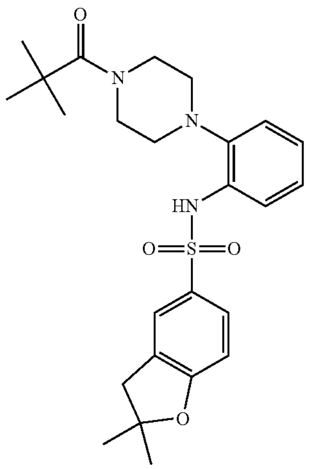 [SMILES: CC1(C)Cc2cc(S(=O)(=O)Nc3ccccc3N3CCN(C(=O)C(C)(C)C)CC3)ccc2O1] | Yield: 16.2 mg, 11.5%; Appearance: Yellow solid; $^1$H NMR (500 MHz, DMSO-$d_6$) δ 8.79 (s, 1H), 7.64 (s, 1H), 7.48 (dd, J = 8.4, 2.0 Hz, 1H), 7.38 (dd, J = 7.7, 1.8 Hz, 1H), 7.15 (d, J = 7.4 Hz, 1H), 7.13-7.03 (m, 3H), 6.79 (d, J = 8.4 Hz, 1H), 3.61 (t, J = 4.8 Hz, 4H), 3.01 (s, 2H), 2.43 (t, J = 4.9 Hz, 4H), 1.40 (s, 6H), 1.20 (s, 9H); HPLC purity: 99.13%; LCMS Calculated for $C_{25}H_{33}N_3O_4S$: 471.62; Observed: 471.26 $[M-H]^-$. |

-continued

| Compound No. | Structure | Analytical data |
| --- | --- | --- |
| A-527 | 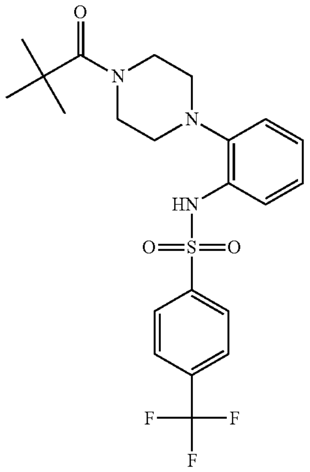 [SMILES: CC(C)(C)C(=O)N1CCN(c2ccccc2NS(=O)(=O)c2ccc(C(F)(F)F)cc2)CC1] | Yield: 28.0 mg, 17.8%; Appearance: Yellow solid; $^1$H NMR (400 MHz, DMSO-$d_6$) δ 9.21 (s, 1H), 7.99 (d, J = 8.1 Hz, 2H), 7.83 (d, J = 8.1 Hz, 2H), 7.34 (d, J = 6.6 Hz, 1H), 7.06 (s, 3H), 3.57 (t, J = 4.5 Hz, 4H), 2.47 (t, J = 4.7 Hz, 4H), 1.22 (s, 9H); HPLC purity: 97.38%; LCMS Calculated for $C_{22}H_{26}F_3N_3O_3S$: 469.52; Observed: 469.2 $[M - H]^-$. |
| A-515 | 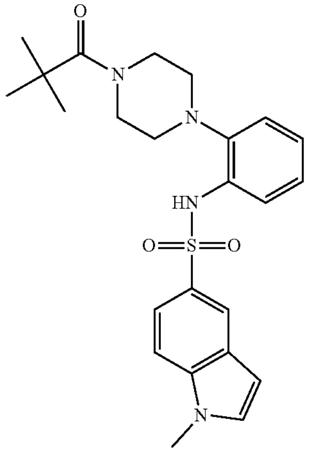 [SMILES: Cn1ccc2cc(S(=O)(=O)Nc3ccccc3N3CCN(C(=O)C(C)(C)C)CC3)ccc21] | Yield: 34.9 mg, 22.2%; Appearance: Pink solid; $^1$H NMR (400 MHz, DMSO-$d_6$) δ 8.48 (s, 1H), 8.07 (s, 1H), 7.52 (d, J = 8.8 Hz, 1H), 7.45 (d, J = 8.3 Hz, 2H), 7.36 (d, J = 3.3 Hz, 1H), 7.09-6.91 (m, 3H), 6.53 (d, J = 3.3 Hz, 1H), 3.84 (s, 3H), 3.59 (s, 4H), 2.37 (t, J = 4.9 Hz, 4H), 1.20 (s, 9H); HPLC purity: 100%; LCMS Calculated for $C_{24}H_{30}N_4O_3S$: 454.59; Observed: 454.24 $[M - H]^-$. |
| A-528 | 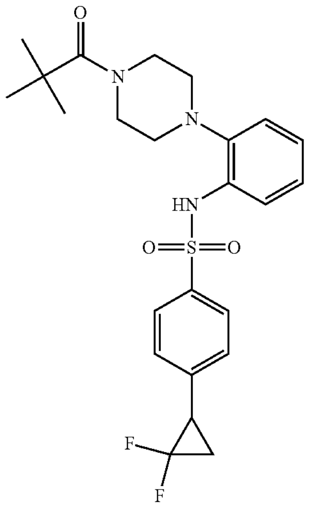 [SMILES: CC(C)(C)C(=O)N1CCN(c2ccccc2NS(=O)(=O)c2ccc(C3CC3(F)F)cc2)CC1] | Yield: 31.6 mg, 20.1%; Appearance: Beige solid; $^1$H NMR (600 MHz, DMSO-$d_6$) δ 9.04 (s, 1H), 7.67 (d, J = 8.1 Hz, 2H), 7.43 (d, J = 8.0 Hz, 2H), 7.34 (dd, J = 7.4, 2.1 Hz, 1H), 7.14-7.03 (m, 3H), 3.51 (t, J = 4.7 Hz, 4H), 3.08 (q, J = 10.1 Hz, 1H), 2.31 (t, J = 5.2 Hz, 4H), 2.01 (q, J = 9.9 Hz, 2H), 1.16 (s, 9H); HPLC purity: 100%; LCMS Calculated for $C_{24}H_{29}F_2N_3O_3S$: 477.57; Observed: 477.23 $[M - H]^-$. |

-continued

| Compound No. | Structure | Analytical data |
|---|---|---|
| A-516 | 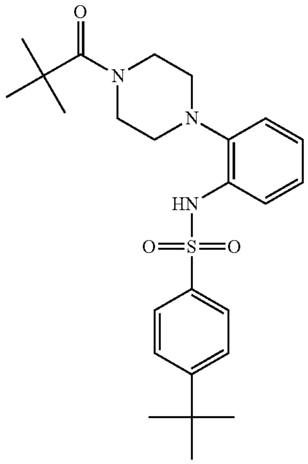 [SMILES: CC(C)(C)C(=O)N1CCN(c2ccccc2NS(=O)(=O)c2ccc(C(C)(C)C)cc2)CC1] | Yield: 48.5 mg, 30.8%; Appearance: Beige solid; $^1$H NMR (400 MHz, DMSO-$d_6$) δ 8.72 (s, 1H), 7.68-7.56 (m, 2H), 7.48-7.41 (m, 3H), 7.11-7.01 (m, 3H), 3.55 (s, 4H), 2.32 (t, J = 4.8 Hz, 4H), 1.30 (s, 9H), 1.20 (s, 9H); HPLC purity: 98.57%; LCMS Calculated for $C_{25}H_{35}N_3O_3S$: 457.63; Observed: 457.29 $[M - H]^-$. |
| A-529 | 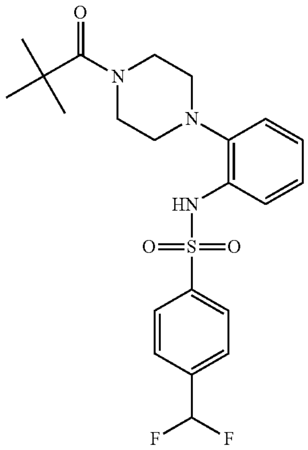 [SMILES: CC(C)(C)C(=O)N1CCN(c2ccccc2NS(=O)(=O)c2ccc(C(F)F)cc2)CC1] | Yield: 50.1 mg, 31.8%; Appearance: Beige solid; $^1$H NMR (400 MHz, DMSO-$d_6$) δ 9.20 (s, 1H), 8.04-7.97 (m, 2H), 7.92 (d, J = 8.2 Hz, 2H), 7.48-7.41 (m, 1H), 7.11-6.71 (m, 4H), 3.55 (s, 4H), 2.32 (t, J = 4.8 Hz, 4H), 1.24 (s, 9H); HPLC purity: 100%; LCMS Calculated for $C_{22}H_{27}F_2N_3O_3S$: 451.53; Observed: 451.21 $[M - H]^-$. |
| A-534 | 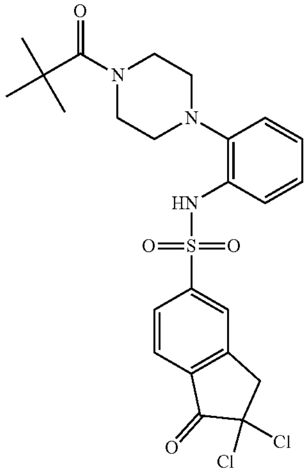 [SMILES: CC(C)(C)C(=O)N1CCN(c2ccccc2NS(=O)(=O)c2ccc3c(c2)CC(Cl)(Cl)C3=O)CC1] | Yield: 15.1 mg, 9.59%; Appearance: Violet solid; $^1$H NMR (600 MHz, DMSO-$d_6$) δ 9.53 (s, 1H), 8.05 (d, J = 8.1 Hz, 1H), 7.99 (s, 1H), 7.87 (dd, J = 8.1, 1.6 Hz, 1H), 7.31-7.26 (m, 1H), 7.15-7.10 (m, 2H), 7.11-7.05 (m, 1H), 4.16 (s, 2H), 3.47 (t, J = 4.9 Hz, 4H), 2.44 (t, J = 4.7 Hz, 4H), 1.14 (s, 9H); HPLC purity: 100%; LCMS Calculated for $C_{24}H_{27}Cl_2N_3O_4S$: 524.46; Observed: 524.14 $[M - H]^-$. |

-continued

| Compound No. | Structure | Analytical data |
|---|---|---|
| A-535 | 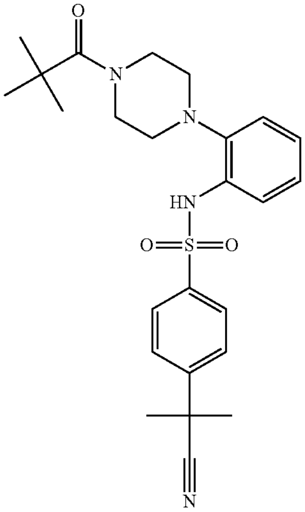 [SMILES: CC(C)(C)C(=O)N1CCN(c2ccccc2NS(=O)(=O)c2ccc(C(C)(C)C#N)cc2)CC1] | Yield: 26.3 mg, 16.7%; Appearance: White solid; $^{1}H$ NMR (600 MHz, DMSO-$d_6$) δ 9.15 (s, 1H), 7.77 (d, J = 8.6 Hz, 2H), 7.69 (d, J = 8.6 Hz, 2H), 7.37-7.31 (m, 1H), 7.14-7.05 (m, 3H), 3.50 (t, J = 4.6 Hz, 4H), 2.33 (t, J = 4.8 Hz, 4H), 1.65 (s, 6H), 1.16 (s, 9H); HPLC purity: 100%; LCMS Calculated for $C_{25}H_{32}N_4O_3S$: 468.62; Observed: 468.26 $[M - H]^-$. |
| A-572 | 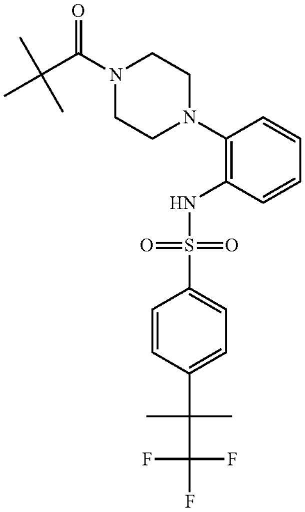 [SMILES: CC(C)(C)C(=O)N1CCN(c2ccccc2NS(=O)(=O)c2ccc(C(C)(C)C(F)(F)F)cc2)CC1] | Yield: 16.3 mg, 10.3%; Appearance: Beige solid; $^{1}H$ NMR (600 MHz, DMSO-$d_6$) δ 9.10 (s, 1H), 7.70 (s, 4H), 7.40 (d, J = 6.8 Hz, 1H), 7.15-7.06 (m, 3H), 3.49-3.44 (m, 4H), 2.23 (t, J = 4.8 Hz, 4H), 1.51 (s, 6H), 1.14 (s, 9H); HPLC purity: 100%; LCMS Calculated for $C_{25}H_{32}F_3N_3O_3S$: 511.6; Observed: 511.26 $[M - H]^-$. |
| A-536 | 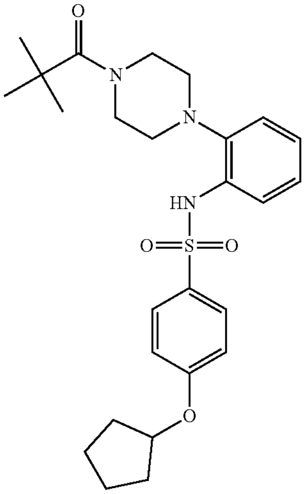 [SMILES: CC(C)(C)C(=O)N1CCN(c2ccccc2NS(=O)(=O)c2ccc(OC3CCCC3)cc2)CC1] | Yield: 19.5 mg, 12.4%; Appearance: Yellow Solid; $^{1}H$ NMR (600 MHz, DMSO-$d_6$) δ 8.84 (s, 1H), 7.66-7.60 (m, 2H), 7.35 (dd, J = 7.8, 1.8 Hz, 1H), 7.12 (dd, J = 7.4, 2.0 Hz, 1H), 7.10-7.02 (m, 2H), 7.02-6.95 (m, 2H), 4.87-4.81 (m, 1H), 3.56 (t, J = 4.7 Hz, 4H), 2.38 (t, J = 4.9 Hz, 4H), 1.92-1.85 (m, 2H), 1.66-1.59 (m, 4H), 1.59-1.52 (m, 2H), 1.16 (s, 9H); HPLC purity: 100%; LCMS Calculated for $C_{26}H_{35}N_6O_4S$: 485.64; Observed: 485.28 $[M - H]^-$. |

-continued

| Compound No. | Structure | Analytical data |
|---|---|---|
| A-530 | 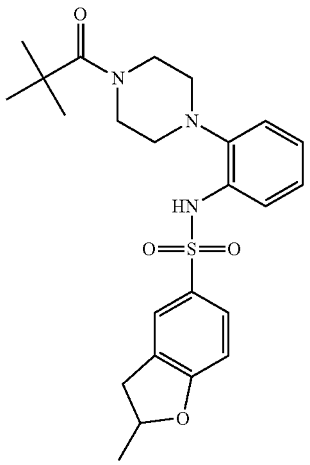 [SMILES: CC1Cc2cc(S(=O)(=O)Nc3ccccc3N3CCN(C(=O)C(C)(C)C)CC3)ccc2O1] | Yield: 65.9 mg, 42.0%; Appearance: Pink solid; $^1$H NMR (400 MHz, DMSO-$d_6$) δ 8.55 (s, 1H), 7.62 (s, 1H), 7.50 (d, J = 8.5 Hz, 1H), 7.40 (d, J = 7.7 Hz, 1H), 7.10-6.98 (m, 3H), 6.71 (d, J = 8.4 Hz, 1H), 5.00 (dd, J = 14.2, 6.6 Hz, 1H), 3.66 (s, 4H), 3.42-3.31 (m, 1H), 2.81 (dd, J = 16.2, 7.4 Hz, lH), 2.50(s, 7H), 1.43 (d, J = 6.1 Hz, 3H), 1.23 (s, 9H); HPLC purity: 97.23%; LCMS Calculated for $C_{24}H_{31}N_3O_4S$: 457.59; Observed: 457.24 [M − H]$^-$. |
| A-590 | 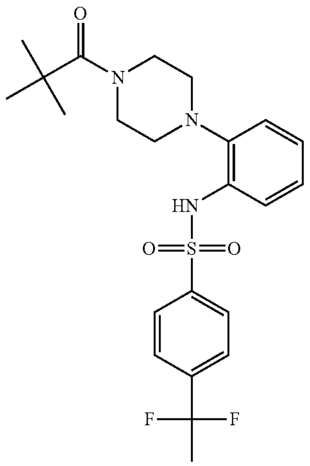 [SMILES: CC(C)(C)C(=O)N1CCN(c2ccccc2NS(=O)(=O)c2ccc(C(C)(F)F)cc2)CC1] | Yield: 32.0 mg, 20.4%; Appearance: Yellow solid; $^1$H NMR (600 MHz, DMSO-$d_6$) δ 9.26 (s, 1H), 7.84 (d, J = 8.2 Hz, 2H), 7.73 (d, J = 8.2 Hz, 2H), 7.34-7.28 (m, 1H), 7.12-7.06 (m, 3H), 3.49 (t, J = 4.8 Hz, 4H), 2.36 (t, J = 4.8 Hz, 4H), 1.93 (t, J = 19.0 Hz, 4H), 1.15 (s, 9H).; HPLC purity: 100%; LCMS Calculated for $C_{23}H_{29}F_2N_3O_3S$: 465.56; Observed: 465.23 [M − H]$^-$. |
| A-591 | 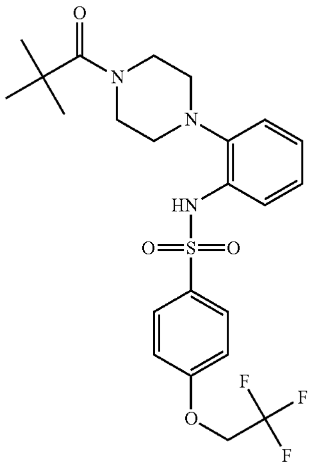 [SMILES: CC(C)(C)C(=O)N1CCN(c2ccccc2NS(=O)(=O)c2ccc(OCC(F)(F)F)cc2)CC1] | Yield: 4.3 mg, 2.73%; Appearance: Beige solid; $^1$H NMR (600 MHz, DMSO-$d_6$) δ 8.98 (s, 2H), 7.76-7.70 (m, 2H), 7.30 (d, J = 8.6 Hz, 1H), 7.18 (d, J = 9.0 Hz, 2H), 7.11 (d, J = 7.3 Hz, 1H), 7.06-7.01 (m, 2H), 4.83 (q, J = 8.8 Hz, 2H), 3.59 (t, J = 4.6 Hz, 4H), 2.45-2.41 (m, 4H), 1.17 (s, 9H); HPLC purity: 95.24%; LCMS Calculated for $C_{23}H_{28}F_3N_3O_4S$: 499.55; Observed: 499.21 [M − H]$^-$. |

-continued

| Compound No. | Structure | Analytical data |
|---|---|---|
| A-573 | 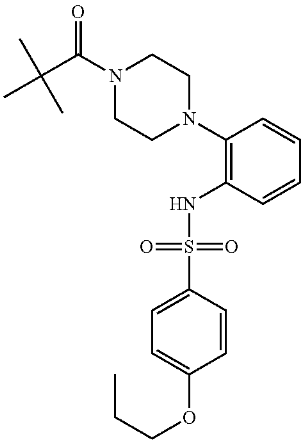 [SMILES: CCCOc1ccc(S(=O)(=O)Nc2ccccc2N2CCN(C(=O)C(C)(C)C)CC2)cc1] | Yield: 14.5 mg, 9.19%; Appearance: Beige solid; $^{1}H$ NMR (400 MHz, DMSO-$d_6$) δ 8.89 (s, 1H), 7.69 (d, J = 8.7 Hz, 2H), 7.35 (dd, J = 7.0, 2.4 Hz, 1H), 7.18-7.11 (m, 1H), 7.14-7.02 (m, 4H), 3.97 (t, J = 6.4 Hz, 2H), 3.62 (s, 4H), 2.44 (t, J = 4.8 Hz, 4H), 1.76-1.66 (m, 2H), 1.20 (s, 9H), 1.01-0.90 (m, 3H); HPLC purity: 100%; LCMS Calculated for $C_{24}H_{33}N_3O_4S$: 459.61; Observed: 459.26 $[M-H]^-$. |
| A-574 | 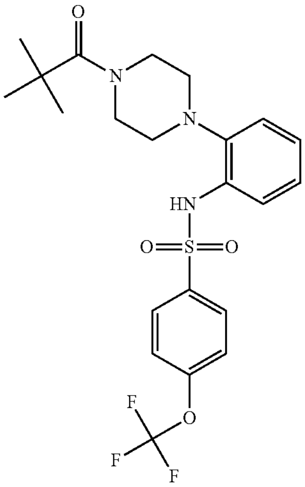 | Yield: 21.4 mg, 13.6%; Appearance: Beige solid; $^{1}H$ NMR (400 MHz, DMSO-$d_6$) δ 9.38 (s, 1H), 7.94-7.81 (m, 4H), 7.41-7.34 (m, 1H), 7.19-7.09 (m, 3H), 3.53 (s, 4H), 2.35 (s, 4H), 1.18 (s, 9H); HPLC purity: 100%; LCMS Calculated for $C_{22}H_{26}F_3N_3O_3S_2$: 501.58; Observed: 501.17 $[M-H]^-$. |
| A-567 | 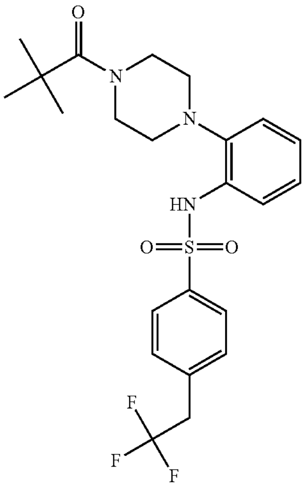 [SMILES: CC(C)(C)C(=O)N1CCN(c2ccccc2NS(=O)(=O)c2ccc(CC(F)(F)F)cc2)CC1] | Yield: 37.6 mg, 23.9%; Appearance: Light brown solid; $^{1}H$ NMR (600 MHz, DMSO-$d_6$) δ 9.06 (s, 1H), 7.71 (d, J = 8.5 Hz, 2H), 7.50 (d, J = 7.9 Hz, 2H), 7.37 (d, J = 7.5 Hz, 1H), 7.14-7.04 (m, 3H), 3.73 (q, J = 11.4 Hz, 2H), 3.50 (s, 4H), 2.28 (s, 4H), 1.15 (s, 9H); HPLC purity: 100%; LCMS Calculated for $C_{23}H_{28}F_3N_3O_3S$: 483.55; Observed: 483.22 $[M-H]^-$. |

-continued

| Compound No. | Structure | Analytical data |
|---|---|---|
| A-568 | 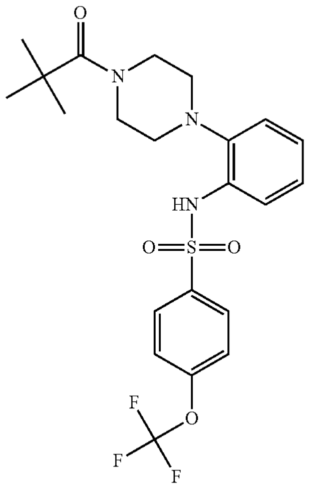 [SMILES: CC(C)(C)C(=O)N1CCN(c2ccccc2NS(=O)(=O)c2ccc(OC(F)(F)F)cc2)CC1] | Yield: 38.4 mg, 24.4%; Appearance: Light brown solid; $^1$H NMR (400 MHz, DMSO-$d_6$) δ 9.06 (s, 1H), 7.93-7.84 (m, 2H), 7.40 (d, J = 8.4 Hz, 3H), 7.07 (d, J = 3.0 Hz, 3H), 3.59 (s, 4H), 2.44 (t, J = 4.9 Hz, 4H), 1.22 (s, 9H); HPLC purity: 100%; LCMS Calculated for $C_{22}H_{26}F_3N_3O_4S$: 485.52; Observed: 485.19 $[M-H]^-$. |
| A-575 | 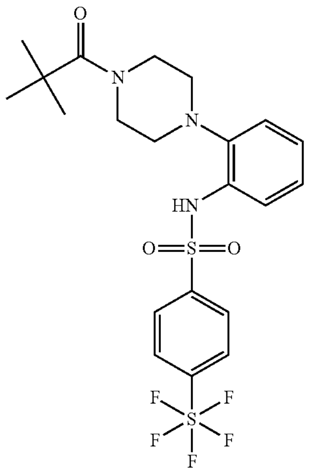 [SMILES: CC(C)(C)C(=O)N1CCN(c2ccccc2NS(=O)(=O)c2ccc(S(F)(F)(F)(F)F)cc2)CC1] | Yield: 21.4 mg, 13.6%; Appearance: Yellow solid; $^1$H NMR (400 MHz, DMSO-$d_6$) δ 9.31 (s, 1H), 8.02-7.92 (m, 4H), 7.35 (d, J = 8.7 Hz, 1H), 7.13-7.03 (m, 3H), 3.54 (t, J = 5.3 Hz, 4H), 2.44 (t, J = 4.8 Hz, 4H), 1.21 (s, 9H); HPLC purity: 100%; LCMS Calculated for $C_{21}H_{26}F_5N_3O_3S_2$: 527.57; Observed: 527.17 $[M-H]^-$. |
| A-537 | 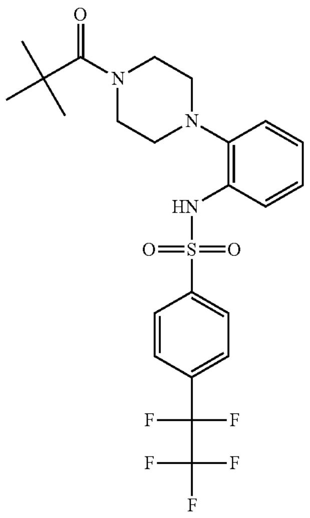 [SMILES: CC(C)(C)C(=O)N1CCN(c2ccccc2NS(=O)(=O)c2ccc(C(F)(F)C(F)(F)F)cc2)CC1] | Yield: 39.8 mg, 25.3%; Appearance: Brown solid; $^1$H NMR (400 MHz, DMSO-$d_6$) δ 9.49 (s, 1H), 8.00-7.90 (m, 4H), 7.41-7.33 (m, 1H), 7.18-7.09 (m, 3H), 3.47 (d, J = 6.1 Hz, 4H), 2.34 (t, J = 4.7 Hz, 4H), 1.17 (s, 9H); HPLC purity: 96.14%; LCMS Calculated for $C_{23}H_{26}F_5N_3O_3S$: 519.53; Observed: 519.2 $[M-H]^-$. |

-continued

| Compound No. | Structure | Analytical data |
|---|---|---|
| A-569 | 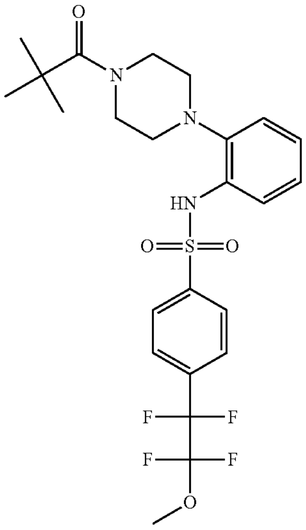 [SMILES: COC(F)(F)C(F)(F)c1ccc(S(=O)(=O)Nc2ccccc2N2CCN(C(=O)C(C)(C)C)CC2)cc1] | Yield: 16.0 mg, 10.2%; Appearamce: Light brown solid; $^1$H NMR (600 MHz, DMSO-$d_6$) δ 9.35 (s, 1H), 7.86 (d, J = 8.3 Hz, 2H), 7.76 (d, J = 8.3 Hz, 2H), 7.38-7.33 (m, 1H), 7.15-7.08 (m, 3H), 3.61 (s, 3H), 3.48-3.41 (m, 4H), 2.28 (t, J = 4.9 Hz, 4H), 1.15 (s, 9H); HPLC purity: 96%; LCMS Calculated for $C_{24}H_{29}F_4N_3O_4S$: 531.57; Observed: 531.22 $[M - H]^-$. |
| A-576 | 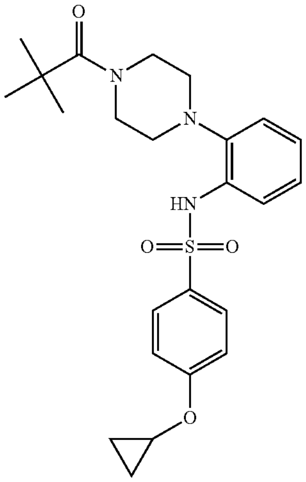 [SMILES: CC(C)(C)C(=O)N1CCN(c2ccccc2NS(=O)(=O)c2ccc(OC3CC3)cc2)CC1] | Yield: 39.2 mg, 24.9%; Appearance: Light brown solid; $^1$H NMR (400 MHz, DMSO-$d_6$) δ 8.91 (s, 1H), 7.72 (d, J = 8.6 Hz, 2H), 7.36 (dd, J = 12, 2.4 Hz, 1H), 7.26-7.03 (m, 5H), 4.00-3.87 (m, 1H), 3.71-3.57 (m, 4H), 2.47-2.39 (m, 4H), 1.20 (s, 9H), 0.85-0.76 (m, 2H), 0.69-0.62 (m, 2H); HPLC purity: 100%; LCMS Calculated for $C_{24}H_{31}N_3O_4S$: 457.59; Observed: 457.24 $[M - H]^-$. |
| A-538 | 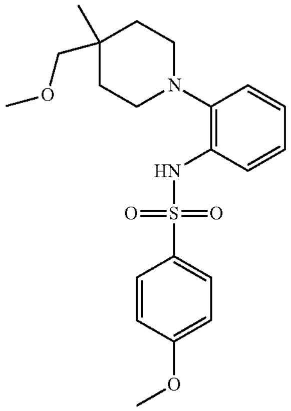 [SMILES: COCC1(C)CCN(c2ccccc2NS(=O)(=O)c2ccc(OC)cc2)CC1] | Yield: 23.9 mg, 15.7%; Appearance: Yellow solid; $^1$H NMR (600 MHz, DMSO-$d_6$) δ 8.48 (s, 1H), 7.69 (d, J = 8.8 Hz, 2H), 7.32-7.26 (m, 1H), 7.21-7.15 (m, 1H), 7.05-6.98 (m, 4H), 3.76 (s, 3H), 3.26 (s, 3H), 3.12 (s, 2H), 2.51-2.47 (m, 21H), 2.44-2.37 (m, 2H), 1.60-1.53 (m, 2H), 1.33-1.26 (m, 2H), 0.92 (s, 3H); HPLC purity: 100%; LCMS Calculated for $C_{21}H_{28}N_2O_4S$: 404.53; Observed: 404.21 $[M - H]^-$. |

-continued

| Compound No. | Structure | Analytical data |
|---|---|---|
| A-539 | 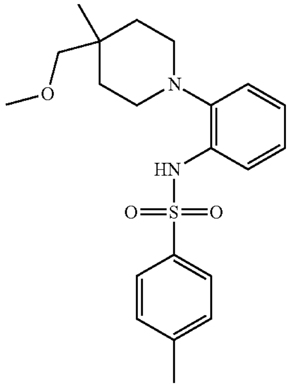 [SMILES: COCC1(C)CCN(c2ccccc2NS(=O)(=O)c2ccc(C)cc2)CC1] | Yield: 47.8 mg, 32.6%; Appearance: Blue solid; $^1H$ NMR (600 MHz, DMSO-$d_6$) δ 8.56 (s, 1H), 7.64 (d, J = 8.2 Hz, 2H), 7.33-7.24 (m, 3H), 7.21-7.15 (m, 1H), 7.04-6.97 (m, 2H), 3.26 (s, 3H), 3.11 (s, 2H), 2.52-2.48 (m, 3H), 2.43-2.36 (m, 2H), 2.30 (s, 3H), 1.60-1.52 (m, 2H), 1.29 (dt, J = 13.4, 3.9 Hz, 2H), 0.92 (s, 3H); HPLC purity: 100%; LCMS Calculated for $C_{21}H_{28}N_2O_3S$: 388.53; Observed: 388.22 $[M - H]^-$. |
| A-577 | 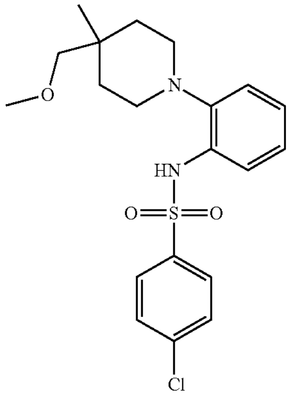 [SMILES: COCC1(C)CCN(c2ccccc2NS(=O)(=O)c2ccc(Cl)cc2)CC1] | Yield: 10.2 mg, 6.97%; Appearance: Beige solid; $^1H$ NMR (600 MHz, DMSO-$d_6$) δ 8.86 (s, 1H), 7.76 (d, J = 8.5 Hz, 2H), 7.60 (d, J = 8.4 Hz, 2H), 7.22 (d, J = 8.0 Hz, 1H), 7.17 (d, J = 7.9 Hz, 1H), 7.06 (t, J = 7.6 Hz, 1H), 7.04-6.97 (m, 1H), 3.26 (s, 3H), 3.10 (s, 2H), 2.56-2.50 (m, 2H), 2.44 (d, J = 6.3 Hz, 2H), 1.55-1.47 (m, 2H), 1.29-1.22 (m, 2H), 0.91 (s, 3H); HPLC purity: 100%; LCMS Calculated for $C_{20}H_{25}ClN_2O_3S$: 408.94; Observed: 408.16 $[M - H]^-$. |
| A-532 | 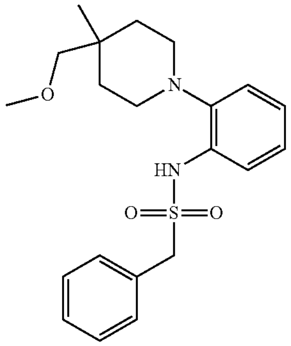 [SMILES: COCC1(C)CCN(c2ccccc2NS(=O)(=O)Cc2ccccc2)CC1] | Yield: 26.7 mg, 16.0%; Appearance: Yellow oil; $^1H$ NMR (600 MHz, DMSO-$d_6$) δ 7.96 (s, 1H), 7.36-7.29 (m, 3H), 7.29-7.25 (m, 1H), 7.25-7.18 (m, 3H), 7.08-7.01 (m, 2H), 4.60 (s, 2H), 3.24 (s, 3H), 3.09 (s, 2H), 2.72-2.61 (m, 4H), 1.56-1.48 (m, 2H), 1.32-1.25 (m, 2H), 0.93 (s, 3H); HPLC purity: 100%; LCMS Calculated for $C_{21}H_{28}N_2O_3S$: 388.53; Observed: 388.53 $[M - H]^-$. |
| A-540 | 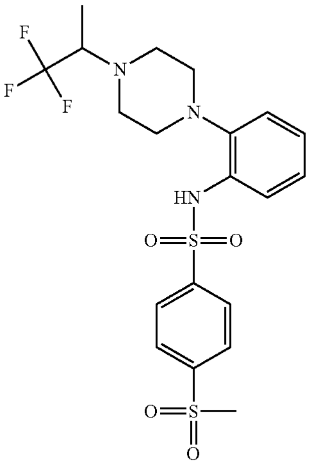 [SMILES: CC(N1CCN(c2ccccc2NS(=O)(=O)c2ccc(S(C)(=O)=O)cc2)CC1)C(F)(F)F] | Yield: 21.7 mg, 16.0%; Appearance: Yellow oil; $^1H$ NMR (400 MHz, DMSO-$d_6$) δ 9.32 (s, 1H), 8.11 (d, J = 8.4 Hz, 2H), 8.02 (d, J = 8.4 Hz, 2H), 7.21 (d, J = 7.8 Hz, 1H), 7.19-7.09 (m, 2H), 7.10-7.01 (m, 1H), 3.52-3.42 (m, 1H), 3.27 (s, 3H), 2.70-2.61 (m, 4H), 2.62-2.53 (m, 6H), 1.19 (d, J = 7.0 Hz, 3H); HPLC purity: 100%; LCMS Calculated for $C_{20}H_{24}F_3N_3O_4S_2$: 491.54; Observed: 491.14 $[M - H]^-$. |

-continued

| Compound No. | Structure | Analytical data |
|---|---|---|
| A-531 | 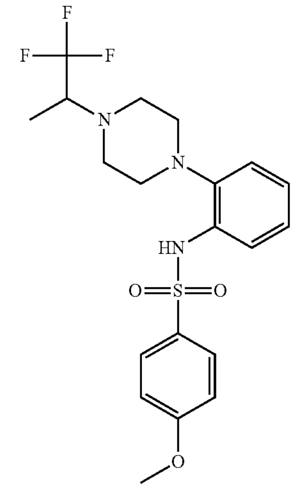 [SMILES: COc1ccc(S(=O)(=O)Nc2ccccc2N2CCN(C(C)C(F)(F)F)CC2)cc1] | Yield: 13.8 mg, 9.56%; Appearance: Brown solid; $^1$H NMR (400 MHz, DMSO-$d_6$) δ 8.64 (s, 1H), 7.69 (d, J = 8.8 Hz, 2H), 7.29-7.22 (m, 1H), 7.17-7.10 (m, 1H), 7.07-6.97 (m, 4H), 3.77 (s, 3H), 3.53-3.42 (m, 1H), 2.78-2.64 (m, 4H), 2.52 (d, J = 4.6 Hz, 4H), 1.18 (d, J = 7.1 Hz, 3H); HPLC purity: 100%; LCMS Calculated for $C_{20}H_{24}F_3N_3O_3S$: 443.49; Observed: 443.18 $[M - H]^-$. |
| A-541 | 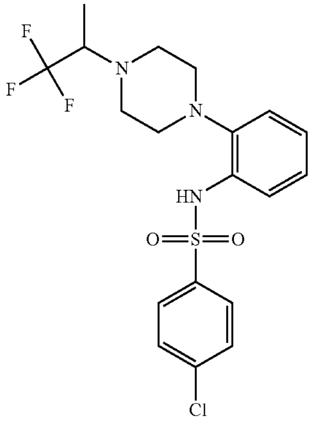 [SMILES: CC(N1CCN(c2ccccc2NS(=O)(=O)c2ccc(Cl)cc2)CC1)C(F)(F)F] | Yield: 69.7 mg, 47.2%; Appearance: Pink solid; $^1$H NMR (600 MHz, DMSO-$d_6$) δ 9.03 (s, 1H), 7.75 (d, J = 8.6 Hz, 2H), 7.60 (d, J = 8.6 Hz, 2H), 7.19 (dd, J = 8.0, 1.5 Hz, 1H), 7.12 (dd, J = 8.0, 1.6 Hz, 1H), 7.08 (td, J = 7.6, 1.6 Hz, 1H), 7.02 (td, J = 7.6, 1.6 Hz, 1H), 3.51-3.39 (m, 1H), 2.71-2.59 (m, 4H), 2.58-2.52 (m, 4H), 1.17 (d, J = 7.0 Hz, 3H); HPLC purity: 100%; LCMS Calculated for $C_{19}H_{21}ClF_3N_3O_2S$: 447.9; Observed: 447.13 $[M - H]^-$. |
| A-542 | 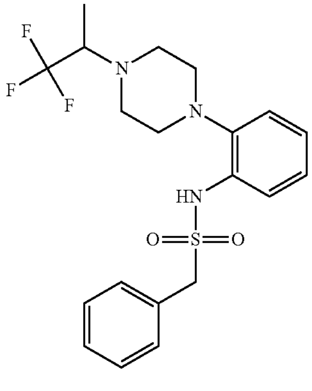 [SMILES: CC(N1CCN(c2ccccc2NS(=O)(=O)Cc2ccccc2)CC1)C(F)(F)F] | Yield: 24.9 mg, 15.8%; Appearance: Brown solid; $^1$H NMR (400 MHz, DMSO-$d_6$) δ 7.90 (s, 1H), 7.35-7.21 (m, 6H), 7.17 (d, J = 7.6 Hz, 1H), 7.11-6.99 (m, 2H), 4.49 (s, 2H), 3.38-3.25 (m, 1H), 2.83-2.69 (m, 8H), 1.24 (d, J = 7.0 Hz, 3H); HPLC purity: 100%; LCMS Calculated for $C_{20}H_{24}F_3N_3O_2S$: 427.49; Observed: 427.19 $[M - H]^-$. |

-continued

| Compound No. | Structure | Analytical data |
|---|---|---|
| A-592 | 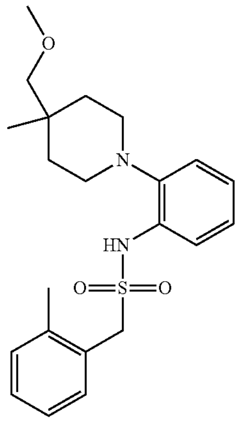 [SMILES: COCC1(C)CCN(c2ccccc2NS(=O)(=O)Cc2ccccc2C)CC1] | Yield: 67.8 mg, 43.8%; Appearance: Green oil; $^1$H NMR (600 MHz, DMSO-$d_6$) δ 8.09 (s, 1H), 7.28 (dd, J = 7.4, 2.1 Hz, 1H), 7.25-7.10 (m, 5H), 7.09-7.00 (m, 2H), 4.60 (s, 2H), 3.24 (s, 3H), 3.10 (s, 2H), 2.76-2.65 (m, 4H), 2.26 (s, 3H), 1.60-1.53 (m, 2H), 1.35-1.28 (m, 2H), 0.94 (s, 3H); HPLC purity: 100%; LCMS Calculated for $C_{22}H_{30}N_2O_3S$: 402.55; Observed: 402.24 $[M - H]^-$. |
| A-593 | 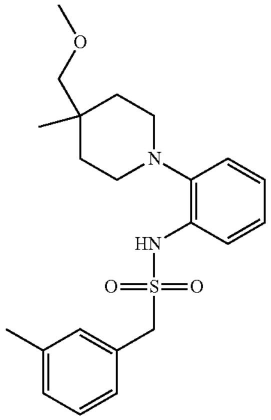 [SMILES: COCC1(C)CCN(c2ccccc2NS(=O)(=O)Cc2cccc(C)c2)CC1] | Yield: 40.6 mg, 25.8%; Appearance: Olive solid; $^1$H NMR (600 MHz, DMSO-$d_6$) δ 7.96 (s, 1H), 7.31-7.22 (m, 2H), 7.20 (t, J = 7.5 Hz, 1H), 7.13 (d, J = 7.7 Hz, 1H), 7.09-7.03 (m, 2H), 7.03-6.98 (m, 2H), 4.56 (s, 2H), 3.24 (s, 3H), 3.09 (s, 2H), 2.73-2.59 (m, 4H), 2.22 (s, 3H), 1.55-1.48 (m, 2H), 1.32-1.25 (m, 2H), 0.93 (s, 3H).; HPLC purity: 100%; LCMS Calculated for $C_{22}H_{30}N_2O_3S$: 402.55; Observed: 402.24 $[M - H]^-$. |
| A-578 | 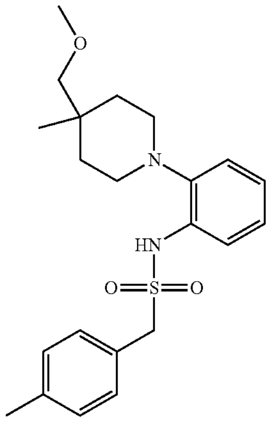 [SMILES: COCC1(C)CCN(c2ccccc2NS(=O)(=O)Cc2ccc(C)cc2)CC1] | Yield: 65.9 mg, 43.4%; Appearance: Beige solid; $^1$H NMR (500 MHz, DMSO-$d_6$) δ 7.73 (s, 1H), 7.35 (d, J = 7.8 Hz, 1H), 7.20 (d, J = 7.6 Hz, 1H), 7.11-6.99 (m, 6H), 4.40 (s, 2H), 3.30 (s, 3H), 3.11 (s, 2H), 2.81-2.60 (m, 4H), 2.33 (s, 3H), 1.57-1.48 (m, 2H), 1.37-1.28 (m, 2H), 0.97 (s, 3H); HPLC purity: 100%; LCMS Calculated for $C_{22}H_{30}N_2O_3S$: 402.55; Observed: 402.24 $[M - H]^-$. |

-continued

| Compound No. | Structure | Analytical data |
|---|---|---|
| A-579 | 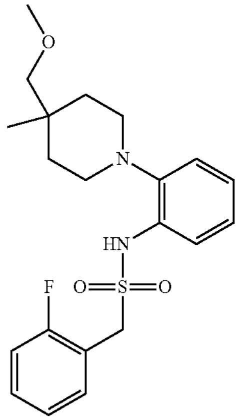 [SMILES: COCC1(C)CCN(c2ccccc2NS(=O)(=O)Cc2ccccc2F)CC1] | Yield: 47.6 mg, 30.3%; Appearance: Beige solid; $^1$H NMR (500 MHz, DMSO-$d_6$) δ 8.03 (s, 1H), 7.41-7.33 (m, 2H), 7.32-7.26 (m, 1H), 7.24 (s, 1H), 7.16 (t, J = 7.5 Hz, 1H), 7.09 (t, J = 9.3 Hz, 1H), 7.06-7.00 (m, 2H), 4.55 (s, 2H), 3.31 (s, 3H), 3.14 (s, 2H), 2.77 (s, 4H), 1.63 (s, 2H), 1.40 (d, J = 13.1 Hz, 2H), 1.00 (s, 3H); HPLC purity: 100%; LCMS Calculated for $C_{21}H_{27}FN_2O_3S$: 406.52; Observed: 406.21 $[M - H]^-$. |
| A-594 | 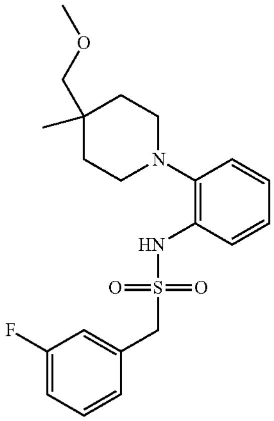 [SMILES: COCC1(C)CCN(c2ccccc2NS(=O)(=O)Cc2cccc(F)c2)CC1] | Yield: 56.6 mg, 36.0%; Appearance: Light brown solid; $^1$H NMR (600 MHz, DMSO-$d_6$) δ 8.04 (s, 1H), 7.37 (td, J = 8.0, 6.1 Hz, 1H), 7.32-7.25 (m, 1H), 7.23-7.20 (m, 1H), 7.18 (td, J = 8.7, 2.7 Hz, 1H), 7.09 (d, J = 7.9 Hz, 1H), 7.09-7.01 (m, 3H), 4.66 (s, 2H), 3.24 (s, 3H), 3.10 (s, 2H), 2.73-2.62 (m, 4H), 1.58-1.50 (m, 2H), 1.33-1.26 (m, 2H), 0.93 (s, 3H); HPLC purity: 95.73%; LCMS Calculated for $C_{21}H_{27}FN_2O_3S$: 406.52; Observed: 406.21 $[M - H]^-$. |
| A-580 | 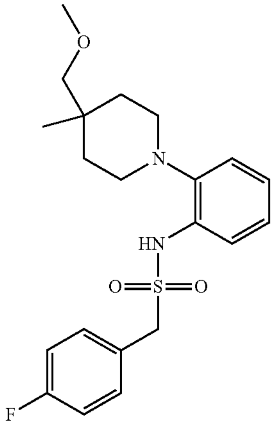 [SMILES: COCC1(C)CCN(c2ccccc2NS(=O)(=O)Cc2ccc(F)cc2)CC1] | Yield: 62.6 mg, 39.8%; Appearance: Brown oil; $^1$H NMR (400 MHz, DMSO-$d_6$) δ 7.82 (s, 1H), 7.33-7.17 (m, 4H), 7.10-6.99 (m, 4H), 4.49 (s, 2H), 3.31 (s, 3H), 2.79-2.65 (m, 4H), 1.64-1.53 (m, 2H), 1.36 (d, J = 13.6 Hz, 2H), 0.99 (s, 3H); HPLC purity: 95.73%; LCMS Calculated for $C_{21}H_{27}FN_2O_3S$: 406.52; Observed: 406.21 $[M - H]^-$. |

-continued

| Compound No. | Structure | Analytical data |
|---|---|---|
| A-601 | 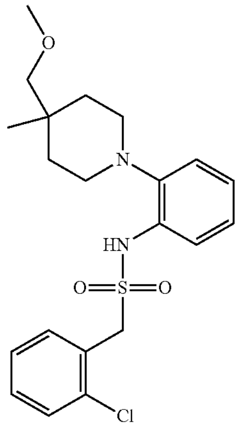 [SMILES: COCC1(C)CCN(c2ccccc2NS(=O)(=O)Cc2ccccc2Cl)CC1] | Yield: 4.8 mg, 2.78%; Appearance: Yellow oil; $^{1}H$ NMR (600 MHz, DMSO-$d_6$) δ 8.26 (s, 1H), 7.48-7.41 (m, 2H), 7.40-7.31 (m, 2H), 7.29 (dd, J = 7.7, 1.8 Hz, 1H),7.22 (dd, J = 7.8, 1.9 Hz, 1H), 7.10-7.01 (m, 2H), 4.75 (s, 2H), 3.24 (s, 3H), 3.11 (s, 2H), 2.77-2.67 (m, 4H), 1.62-1.54 (m, 2H), 1.36-1.29 (m, 2H), 0.94 (s, 3H); HPLC purity: 100%; LCMS Calculated for $C_{21}H_{27}ClN_2O_3S$: 422.97; Observed: 422.18 $[M - H]^-$. |
| A-602 | 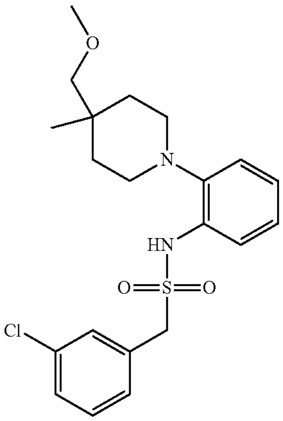 [SMILES: COCC1(C)CCN(c2ccccc2NS(=O)(=O)Cc2cccc(Cl)c2)CC1] | Yield: 33.0 mg, 19.0%; Appearance: Yellow oil; $^{1}H$ NMR (400 MHz, DMSO-$d_6$) δ 7.91 (s, 1H), 7.37-7.26 (m, 4H), 7.24-7.16 (m, 3H), 7.05 (t, J = 5.8 Hz, 2H), 4.52 (s, 2H), 3.30 (s, 3H), 3.12 (s, 2H), 2.76-2.69 (m, 4H), 1.65-1.53 (m, 2H), 1.36 (d, J = 13.0 Hz, 2H), 0.99 (s, 3H); HPLC purity: 95.33%; LCMS Calculated for $C_{21}H_{27}ClN_2O_3S$: 422.97; Observed: 422.18 $[M - H]^-$. |
| A-610 | 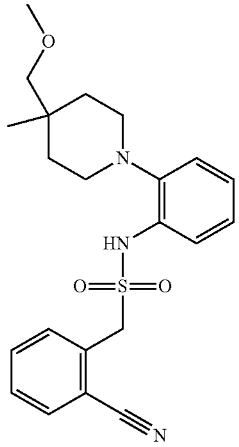 [SMILES: COCC1(C)CCN(c2ccccc2NS(=O)(=O)Cc2ccccc2C#N)CC1] | Yield: 14.9 mg, 9.46%; Appearance: Beige solid; $^{1}H$ NMR (600 MHz, DMSO-$d_6$) δ 8.46 (s, 1H), 7.87 (d, J = 7.7 Hz, 1H), 7.70 (t, J = 7.7 Hz, 1H), 7.59-7.52 (m, 2H), 7.28 (d, J = 7.9 Hz, 1H), 7.20 (d, J = 8.1 Hz, 1H), 7.09 (t, J = 7.6 Hz, 1H), 7.02 (t, J = 7.6 Hz, 1H), 4.78 (s, 2H), 3.25 (s, 3H), 3.12 (s, 2H), 2.76 (t, J = 5.6 Hz, 4H), 1.66-1.58 (m, 2H), 1.39-1.32 (m, 2H), 0.95 (s, 3H); HPLC purity: 100%; LCMS Calculated for $C_{22}H_{27}N_3O_3S$: 413.54; Observed: 413.21 $[M - H]^-$. |

-continued

| Compound No. | Structure | Analytical data |
|---|---|---|
| A-581 | 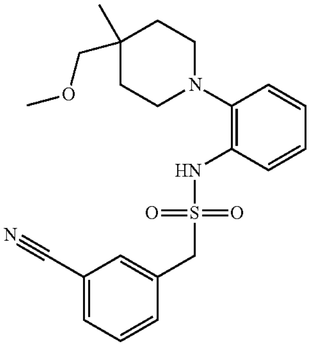 [SMILES: COCC1(C)CCN(c2ccccc2NS(=O)(=O)Cc2cccc(C#N)c2)CC1] | Yield: 37.3 mg, 23.7%; Appearance: Yellow solid; $^1$H NMR (400 MHz, DMSO-$d_6$) δ 7.98 (s, 1H), 7.71 (d, J = 7.6 Hz, 1H), 7.65-7.58 (m, 2H), 7.53 (t, J = 8.0 Hz, 1H), 7.35-7.26 (m, 1H), 7.23 (dd, J = 6.0, 3.5 Hz, 1H), 7.10-7.01 (m, 2H), 4.62 (s, 2H), 3.31 (s, 3H), 3.14(s, 2H), 2.82-2.69 (m, 4H), 1.69-1.57 (m, 2H), 1.39 (d, J = 12.8 Hz, 2H), 1.00 (s, 3H); HPLC purity: 100%; LCMS Calculated for $C_{22}H_{27}N_3O_3S$: 413.54; Observed: 413.21 [M − H]$^-$. |
| A-596 | 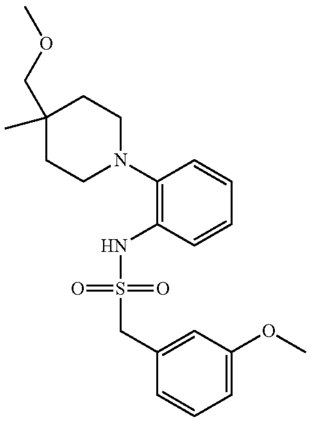 | Yield: 38.4 mg, 24.4%; Appearance: Beige solid; $^1$H NMR (600 MHz, DMSO-$d_6$) δ 7.95 (s, 1H), 7.31-7.20 (m, 3H), 7.09-7.01 (m, 2H), 6.90 (dd, J = 8.3, 2.7 Hz, 1H), 6.80 (dt, J = 7.6, 1.2 Hz, 1H), 6.74 (dd, J = 2.6, 1.5 Hz, 1H), 4.58 (s, 2H), 3.65 (s, 3H), 3.24 (s, 3H), 3.09 (s, 2H), 2.71-2.58 (m, 4H), 1.54-1.46 (m, 2H), 1.31-1.24 (m, 2H), 0.92 (s, 3H); HPLC purity: 100%; LCMS Calculated for $C_{22}H_{30}N_2O_4S$: 418.55; Observed: 418.23 [M − H]$^-$. |
| A-705 | 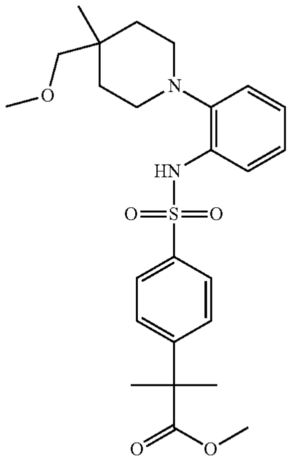 [SMILES: COCC1(C)CCN(c2ccccc2NS(=O)(=O)c2ccc(C(C)(C)C(=O)OC)cc2)CC1] | Yield: 8.3 mg, 5.08%; Appearance: Beige solid; $^1$H NMR (600 MHz, DMSO-$d_6$) δ 8.62 (s, 1H), 7.67 (d, J = 8.3 Hz, 2H), 7.43 (d, J = 8.3 Hz, 2H), 7.34-7.30 (m, 1H), 7.20-7.15 (m, 1H), 7.07-7.02 (m, 2H), 3.53 (s, 3H), 3.25 (s, 3H), 3.09 (s, 2H), 2.41 (t, J = 9.8 Hz, 3H), 2.32-2.27 (m, 2H), 1.53-1.45 (m, 3H), 1.44 (s, 6H), 1.26-1.20 (m, 2H), 0.90 (s, 3H); HPLC purity: 100%; LCMS Calculated for $C_{25}H_{34}N_2O_5S$: 474.62; Observed: 474.26 [M − H]$^-$. |

-continued

| Compound No. | Structure | Analytical data |
|---|---|---|
| A-641 | 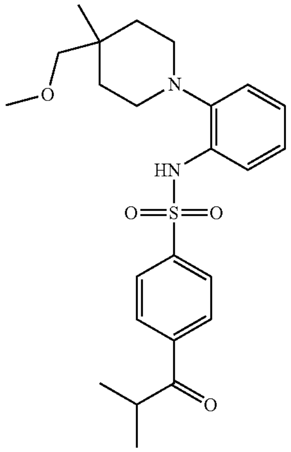 [SMILES: COCC1(C)CCN(c2ccccc2NS(=O)(=O)c2ccc(C(=O)C(C)C)cc2)CC1] | Yield: 49.1 mg, 30.4%; Appearance: Beige solid; $^1$H NMR (600 MHz, DMSO-$d_6$) δ 8.96 (s, 1H), 8.05 (d, J = 8.0 Hz, 2H), 7.87 (d, J = 8.0 Hz, 2H), 7.25 (d, J = 7.9 Hz, 1H), 7.16 (d, J = 7.9 Hz, 1H), 7.06 (t, J = 7.6 Hz, 1H), 7.01 (t, J = 7.7 Hz, 1H), 3.60 (p, J = 6.9 Hz, 1H), 3.24 (s, 3H), 3.07 (s, 2H), 2.53-2.49 (m, 2H), 2.45-2.38 (m, 2H), 1.52-1.44 (m, 2H), 1.22 (d, J = 13.0 Hz, 2H), 1.05 (d, J = 6.8 Hz, 6H), 0.89 (s, 3H); HPLC purity: 98.66%; LCMS Calculated for $C_{24}Hz_{32}NO_4S$: 444.59; Observed: 444.25 [M − H]$^-$. |
| A-706 | 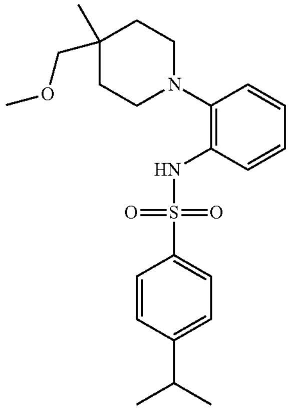 [SMILES: COCC1(C)CCN(c2ccccc2NS(=O)(=O)c2ccc(C(C)C)cc2)CC1] | Yield: 15.4 mg, 9.29%; Appearance: White solid; $^1$H NMR (600 MHz, DMSO-$d_6$) δ 8.54 (s, 1H), 7.64 (d, J = 8.2 Hz, 2H), 7.37 (d, J = 8.5 Hz, 2H), 7.35-7.28 (m, 1H), 7.20-7.15 (m, 1H), 7.07-7.00 (m, 2H), 3.25 (s, 4H), 3.10 (s, 2H), 2.94-2.86 (m, 1H), 2.45-2.40 (m, 2H), 2.36-2.29 (m, 2H), 1.55-1.47 (m, 2H), 1.28-1.21 (m, 2H), 1.13 (d, J = 6.9 Hz, 6H), 0.90 (s, 3H); HPLC purity: 100%; LCMS Calculated for $C_{23}H_{32}N_2O_3S$: 416.58; Observed: 416.26 [M − H]$^-$. |
| A-707 | 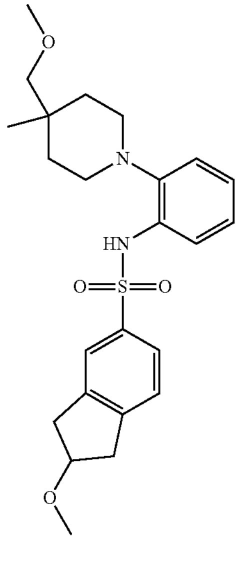 [SMILES: COCC1(C)CCN(c2ccccc2NS(=O)(=O)c2ccc3c(c2)CC(OC)C3)CC1] | Yield: 19.2 mg, 11.3%; Appearance: Colorless oil; $^1$H NMR (600 MHz, DMSO-$d_6$) δ 8.55 (s, 1H), 7.64 (s, 1H), 7.49 (d, J = 7.8 Hz, 1H), 7.33-7.25 (m, 2H), 7.18 (dd, J = 5.9, 3.6 Hz, 1H), 7.04-6.99 (m, 2H), 4.19-4.12 (m, 1H), 3.26 (s, 3H), 3.18 (s, 3H), 3.11 (s, 2H), 3.11-3.02 (m, 3H), 2.91-2.83 (m, 2H), 2.53-2.49 (m, 2H), 2.43-2.35 (m, 3H), 1.59-1.52 (m, 2H), 1.32-1.25 (m, 2H), 0.92 (s, 3H); HPLC purity: 100%; LCMS Calculated for $C_{24}H_{32}N_2O_4S$: 444.59; Observed: 444.25 [M − H]$^-$. |

-continued

| Compound No. | Structure | Analytical data |
|---|---|---|
| A-616 | 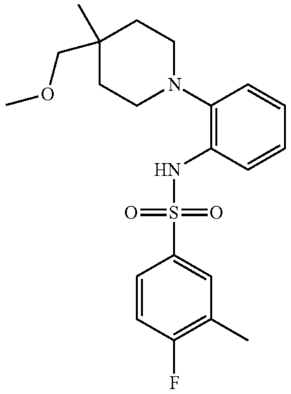 [SMILES: COCC1(C)CCN(c2ccccc2NS(=O)(=O)c2ccc(F)c(C)c2)CC1] | Yield: 66.9 mg, 41.7%; Appearance: Beige solid; $^{1}H$ NMR (400 MHz, DMSO-$d_6$) δ 8.38 (s, 1H), 7.72 (d, J = 6.6 Hz, 1H), 7.66-7.57 (m, 1H), 7.40-7.32 (m, 1H), 7.18-7.08 (m, 2H), 7.07-6.96 (m, 2H), 3.32 (s, 3H), 3.14 (s, 2H), 2.61-2.50 (m, 3H), 2.49-2.39 (m, 2H), 2.28 (s, 3H), 1.70-1.58 (m, 2H), 1.42-1.31 (m, 2H), 0.98 (s, 3H); HPLC purity: 100%; LCMS Calculated for $C_{21}H_{27}FN_2O_3S$: 406.52; Observed: 406.21 $[M-H]^-$. |
| A-642 | 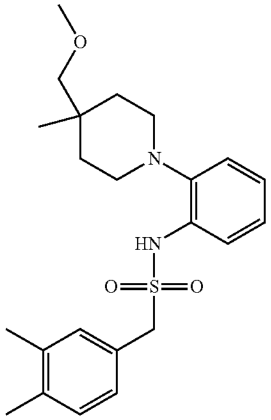 [SMILES: COCC1(C)CCN(c2ccccc2NS(=O)(=O)Cc2ccc(C)c(C)c2)CC1] | Yield: 47.1 mg, 28.1%; Appearance: Light brown solid; $^{1}H$ NMR (400 MHz, DMSO-$d_6$) δ 7.74 (s, 1H), 7.38 (dd, J = 7.9, 1.7 Hz, 1H), 7.20 (dd, J = 7.7, 1.8 Hz, 1H), 7.12-6.99 (m, 3H), 6.92 (s, 1H), 6.87 (d, J = 7.8 Hz, 1H), 4.37 (s, 2H), 3.30 (s, 3H), 3.11 (s, 2H), 2.74-2.57 (m, 4H), 2.21 (d, J = 15.0 Hz, 6H), 1.58-1.46 (m, 2H), 1.37-1.26 (m, 2H), 0.98 (s, 3H); HPLC purity: 100%; LCMS Calculated for $C_{23}H_{32}N_2O_3S$: 416.58; Observed: 416.26 $[M-H]^-$. |
| A-617 | 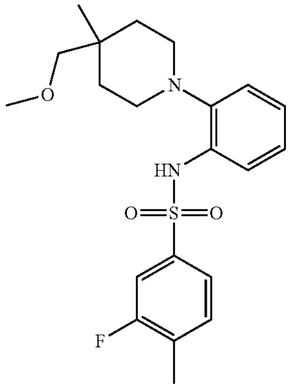 [SMILES: COCC1(C)CCN(c2ccccc2NS(=O)(=O)c2ccc(C)c(F)c2)CC1] | Yield: 62.0 mg, 39.7%; Appearance: Light brown solid; $^{1}H$ NMR (400 MHz, DMSO-$d_6$) δ 8.50 (s, 1H), 7.53-7.43 (m, 2H), 7.40-7.30 (m, 2H), 7.13 (dd, J = 6.1, 3.4 Hz, 1H), 7.06-6.97 (m, 2H), 3.32 (s, 3H), 3.14 (s, 2H), 2.63-2.51 (m, 2H), 2.51-2.42 (m, 2H), 2.30 (s, 3H), 1.69-1.58 (m, 2H), 1.42-1.31 (m, 2H), 0.98 (s, 3H); HPLC purity: 100%; LCMS Calculated for $C_{21}H_{27}FN_2O_3S$: 406.52; Observed: 406.21 $[M-H]^-$. |
| A-618 | 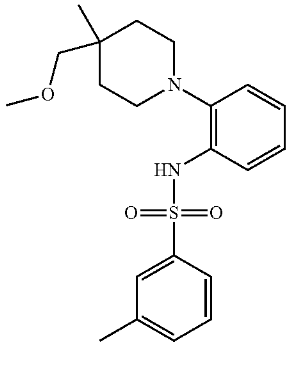 [SMILES: COCC1(C)CCN(c2ccccc2NS(=O)(=O)c2cccc(C)c2)CC1] | Yield: 73.8 mg, 45.8%; Appearance: Grey solid; $^{1}H$ NMR (400 MHz, DMSO-$d_6$) δ 8.28 (s, 1H), 7.59 (s, 1H), 7.56-7.49 (m, 1H), 7.40 (d, J = 7.6 Hz, 1H), 7.39-7.28 (m, 2H), 7.12 (d, J = 7.3 Hz, 1H), 7.07-6.95 (m, 2H), 3.32 (s, 3H), 3.14 (s, 2H), 2.54 (s, 2H), 2.40 (s, 2H), 2.37 (s, 3H), 1.62 (t, J = 11.4 Hz, 2H), 1.35 (d, J = 13.0 Hz, 2H), 0.98 (s, 3H); HPLC purity: 100%; LCMS Calculated for $C_{21}H_{28}N_2O_3S$: 388.53; Observed: 388.22 $[M-H]^-$. |

-continued

| Compound No. | Structure | Analytical data |
|---|---|---|
| A-619 | 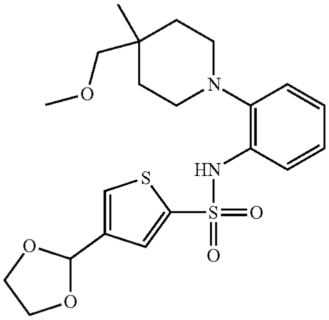 [SMILES: COCC1(C)CCN(c2ccccc2NS(=O)(=O)c2cc(C3OCCO3)cs2)CC1] | Yield: 59.0 mg, 37.0%; Appearance: Light brown solid; $^1$H NMR (400 MHz, DMSO-$d_6$) δ 8.50 (s, 1H), 7.74 (s, 1H), 7.50-7.41 (m, 2H), 7.21-7.14 (m, 1H), 7.12-7.01 (m, 2H), 5.71 (s, 1H), 4.00-3.88 (m, 4H), 3.32 (s, 3H), 3.14 (s, 2H), 2.62-2.52 (m, 3H), 2.49-2.42 (m, 3H), 1.63 (t, J = 10.7 Hz, 2H), 1.37 (d, J = 13.1 Hz, 2H), 0.98 (s, 3H); HPLC purity: 97.62%; LCMS Calculated for $C_{21}H_{28}N_2O_5S_2$: 452.58; Observed: 452.17 $[M - H]^-$. |
| A-643 | 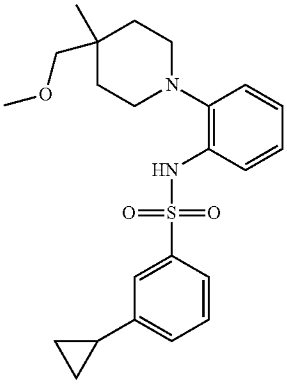 [SMILES: COCC1(C)CCN(c2ccccc2NS(=O)(=O)c2cccc(C3CC3)c2)CC1] | Yield: 65.4 mg, 40.8%; Appearance: Light brown oil; $^1$H NMR (600 MHz, DMSO-$d_6$) δ 8.57 (s, 1H), 7.49-7.43 (m, 1H), 7.40-7.33 (m, 2H), 7.33-7.26 (m, 2H), 7.22-7.15 (m, 1H), 7.10-7.00 (m, 2H), 3.25 (s, 3H), 3.10 (s, 2H), 2.46-2.40 (m, 2H), 2.36-2.29 (m, 2H), 1.94 (tt, J = 8.3, 5.1 Hz, 1H), 1.56-1.49 (m, 2H), 1.29-1.22 (m, 2H), 0.98-0.90 (m, 2H), 0.91 (s, 3H), 0.61-0.54 (m, 2H); HPLC purity: 100%; LCMS Calculated for $C_{23}H_{30}N_2O_3S$: 414.56; Observed: 414.24 $[M - H]^-$. |
| A-620 | 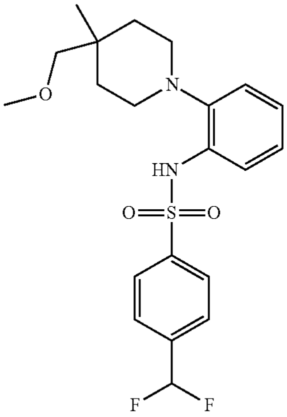 [SMILES: COCC1(C)CCN(c2ccccc2NS(=O)(=O)c2ccc(C(F)F)cc2)CC1] | Yield: 60.1 mg, 36.5%; Appearance: Beige solid; $^1$H NMR (400 MHz, DMSO-$d_6$) δ 8.58 (s, 1H), 7.90 (d, J = 8.0 Hz, 2H), 7.67 (d, J = 8.0 Hz, 2H), 7.39-7.31 (m, 1H), 7.12-6.78 (m, 4H), 3.32 (s, 3H), 3.13 (s, 2H), 2.54 (t, J = 9.3 Hz, 2H), 2.49-2.38 (m, 2H), 1.61 (tt, J = 9.6, 3.9 Hz, 2H), 1.34 (d, J = 12.4 Hz, 2H), 0.97 (s, 3H); HPLC purity: 100%; LCMS Calculated for $C_{21}H_{26}F_2N_2O_3S$: 424.51; Observed: 424.2 $[M - H]^-$. |
| A-621 | 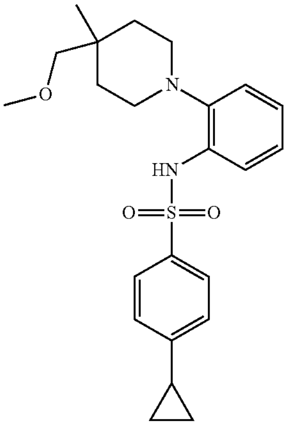 [SMILES: COCC1(C)CCN(c2ccccc2NS(=O)(=O)c2ccc(C3CC3)cc2)CC1] | Yield: 95.2 mg, 58.7%; Appearance: Pink solid; $^1$H NMR (400 MHz, DMSO-$d_6$) δ 8.22 (s, 1H), 7.61 (d, J = 8.1 Hz, 2H), 7.38 (dd, J = 7.2, 2.1 Hz, 1H), 7.11 (d, J = 7.8 Hz, 3H), 7.06-6.94 (m, 2H), 3.32 (s, 3H), 3.14 (s, 2H), 2.54 (d, J = 10.6 Hz, 2H), 2.45-2.35 (m, 2H), 1.93 (tt, J = 8.7, 4.9 Hz, 1H), 1.67-1.56 (m, 2H), 1.35 (d, J = 13.2 Hz, 2H), 1.08-0.99 (m, 2H), 0.98 (s, 3H), 0.77-0.68 (m, 2H); HPLC purity: 100%; LCMS Calculated for $C_{23}H_{30}N_2O_3S$: 414.56; Observed: 414.24 $[M - H]^-$. |

-continued

| Compound No. | Structure | Analytical data |
| --- | --- | --- |
| A-622 | 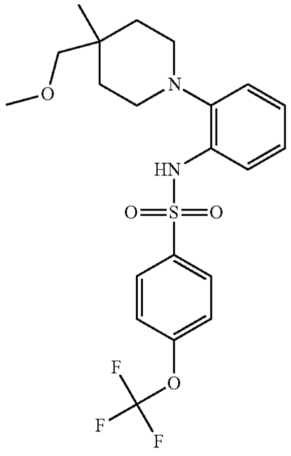 [SMILES: COCC1(C)CCN(c2ccccc2NS(=O)(=O)c2ccc(OC(F)(F)F)cc2)CC1] | Yield: 80.4 mg, 51.5%; Appearance: yellow solid; $^1$H NMR (400 MHz, DMSO-$d_6$) δ 8.59 (s, 1H), 7.89 (d, J = 8.7 Hz, 2H), 7.37 (d, J = 9.1 Hz, 3H), 7.16-7.08 (m, 1H), 7.08-6.98 (m, 2H), 3.32 (s, 3H), 3.12 (s, 2H), 2.54 (d, J = 8.8 Hz, 2H), 2.47-2.36 (m, 2H), 1.66-1.54 (m, 2H), 1.38-1.27 (m, 2H), 0.96 (s, 3H); HPLC purity: 100%; LCMS Calculated for $C_{21}H_{25}F_3N_2O_4S$: 458.5; Observed: 458.18 $[M - H]^-$. |
| A-623 | 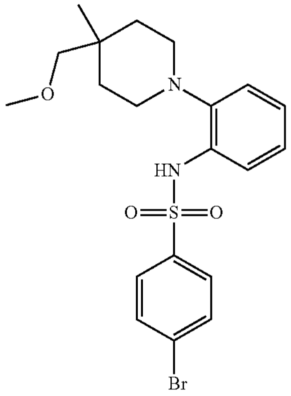 [SMILES: COCC1(C)CCN(c2ccccc2NS(=O)(=O)c2ccc(Br)cc2)CC1] | Yield: 53.2 mg, 33.8%; Appearance: Pink solid; $^1$H NMR (400 MHz, DMSO-$d_6$) δ 8.55 (s, 1H), 7.71 (d, J = 8.6 Hz, 2H), 7.64 (d, J = 8.7 Hz, 2H), 7.37-7.28 (m, 1H), 7.16-7.08 (m, 1H), 7.07-6.96 (m, 2H), 3.32 (s, 3H), 3.14 (s, 2H), 2.63-2.51 (m, 2H), 2.51-2.39 (m, 2H), 1.68-1.57 (m, 2H), 1.36 (t, J = 9.0 Hz, 2H), 0.98 (s, 3H); HPLC purity: 100%; LCMS Calculated for $C_{20}H_{25}BrN_2O_3S$: 453.4; Observed: 453.11 $[M - H]^-$. |
| A-708 | 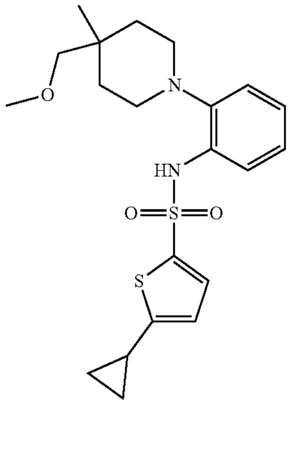 [SMILES: COCC1(C)CCN(c2ccccc2NS(=O)(=O)c2ccc(C3CC3)s2)CC1] | Yield: 20.5 mg, 12.5%; Appearance: Beige solid; $^1$H NMR (600 MHz, DMSO-$d_6$) δ 8.65 (s, 1H), 7.37-7.32 (m, 1H), 7.30 (d, J = 3.9 Hz, 1H), 7.26-7.21 (m, 1H), 7.11-7.03 (m, 2H), 6.77 (d, J = 3.9 Hz, 1H), 3.26 (s, 3H), 3.11 (s, 2H), 2.58-2.52 (m, 2H), 2.46-2.39 (m, 4H), 2.13 (tt, J = 8.6, 5.0 Hz, 1H), 1.60-1.53 (m, 2H), 1.33-1.26 (m, 2H), 1.08-0.99 (m, 2H), 0.93 (s, 3H), 0.69-0.61 (m, 2H); HPLC purity: 100%; LCMS Calculated for $C_{21}H_{28}N_2O_3S_2$: 420.59; Observed: 420.19 $[M - H]^-$. |

-continued

| Compound No. | Structure | Analytical data |
|---|---|---|
| A-644 | 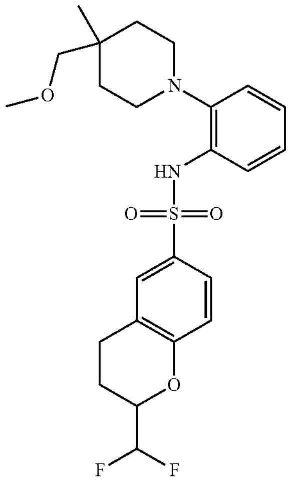 [SMILES: COCC1(C)CCN(c2ccccc2NS(=O)(=O)c2ccc3c(c2)CCC(C(F)F)O3)CC1] | Yield: 43.3 mg, 27.0%; Appearance: Beige solid; $^1H$ NMR (600 MHz, DMSO-$d_6$) δ 8.48 (s, 1H), 7.58 (s, 1H), 7.44 (d, J = 8.7 Hz, 1H), 7.32-7.26 (m, 1H), 7.23-7.16 (m, 1H), 7.05-6.99 (m, 2H), 6.90 (d, J = 8.6 Hz, 1H), 6.21 (t, J = 52.8 Hz, 1H), 4.43 (q, J = 11.0 Hz, 1H), 3.26 (s, 3H), 3.12 (s, 2H), 2.86-2.74 (m, 2H), 2.56-2.46 (m, 2H), 2.42 (td, J = 12.2, 11.6, 5.7 Hz, 2H), 2.10-2.03 (m, 1H), 1.77-1.67 (m, 1H), 1.60-1.53 (m, 2H), 1.33-1.27 (m, 2H), 0.93 (s, 3H); HPLC purity: 100%; LCMS Calculated for $C_{24}H_{30}F_2N_2O_4S$: 480.57; Observed: 480.23 $[M-H]^-$. |
| A-645 | 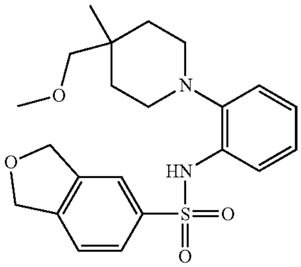 [SMILES: COCC1(C)CCN(c2ccccc2NS(=O)(=O)c2ccc3c(c2)COC3)CC1] | Yield: 40.7 mg, 25.3%; Appearance: Brown solid; $^1H$ NMR (600 MHz, DMSO-$d_6$) δ 8.68 (s, 1H), 7.76 (s, 1H), 7.65 (d, J = 7.6 Hz, 1H), 7.43 (d, J = 8.0 Hz, 1H), 7.26 (dd, J = 7.5, 2.0 Hz, 1H), 7.18 (dd, J = 7.3, 2.0 Hz, 1H), 7.06-6.98 (m, 2H), 4.97 (d, J = 5.0 Hz, 4H), 3.26 (s, 3H), 3.11 (s, 2H), 2.50 (d, J = 8.2 Hz, 2H), 2.45-2.38 (m, 2H), 1.58-1.50 (m, 2H), 1.31-1.24 (m, 2H), 0.92 (s, 3H); HPLC purity: 100%; LCMS Calculated for $C_{22}H_{28}N_2O_4S$: 416.54; Observed: 416.21 $[M-H]^-$. |
| A-625 | 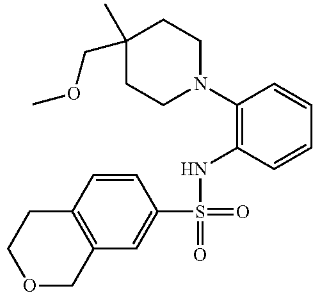 [SMILES: COCC1(C)CCN(c2ccccc2NS(=O)(=O)c2ccc3c(c2)COCC3)CC1] | Yield: 11.4 mg, 6.83%; Appearance: White solid; $^1H$ NMR (600 MHz, DMSO-$d_6$) δ 8.59 (s, 1H), 7.50 (s, 2H), 7.28-7.22 (m, 2H), 7.21-7.15 (m, 1H), 7.06-6.98 (m, 2H), 4.65 (s, 2H), 3.85-3.78 (m, 2H), 3.26 (s, 3H), 3.11 (s, 2H), 2.78 (t, J = 5.9 Hz, 2H), 2.50 (s, 2H), 2.41 (dd, J = 11.2, 5.3 Hz, 2H), 1.59-1.49 (m, 2H), 1.32-1.25 (m, 2H), 0.92 (d, J = 1.8 Hz, 3H); HPLC purity: 100%; LCMS Calculated for $C_{23}H_{30}N_2O_4S$: 430.56; Observed: 430.23 $[M-H]^-$. |
| A-624 | 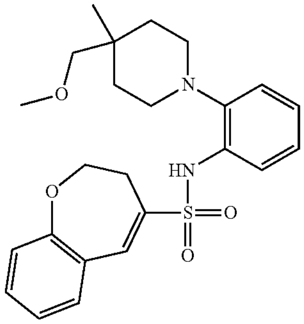 [SMILES: COCC1(C)CCN(c2ccccc2NS(=O)(=O)C2=Cc3ccccc3OCC2)CC1] | Yield: 51.7 mg, 30.6%; Appearance: Violet solid; $^1H$ NMR (400 MHz, DMSO-$d_6$) δ 8.20 (s, 1H), 7.43-7.14 (m, 6H), 7.07-6.96 (m, 3H), 6.91 (d, J = 8.1 Hz, 1H), 4.18 (s, 2H), 3.32 (s, 3H), 3.16 (s, 2H), 2.91 (d, J = 5.2 Hz, 2H), 2.76 (d, J = 6.5 Hz, 4H), 1.78-1.64 (m, 2H), 1.45 (d, J = 12.9 Hz, 2H), 1.01 (s, 3H); HPLC purity: 100%; LCMS Calculated for $C_{24}H_{30}N_2O_4S$: 442.57; Observed: 442.23 $[M-H]^-$. |

-continued

| Compound No. | Structure | Analytical data |
| --- | --- | --- |
| A-646 | 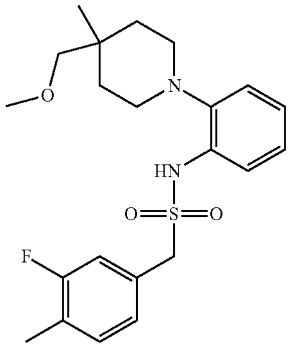 [SMILES: COCC1(C)CCN(c2ccccc2NS(=O)(=O)Cc2ccc(C)c(F)c2)CC1] | Yield: 38.8 mg, 23.8%; Appearance: Brown oil; $^1$H NMR (600 MHz, DMSO-$d_6$) δ 8.19 (s, 1H), 7.54-7.42 (m, 3H), 7.32-7.24 (m, 2H), 7.19 (d, J = 9.0 Hz, 2H), 4.83 (s, 2H), 3.47 (s, 3H), 3.32 (s, 2H), 2.95-2.82 (m, 4H), 2.41 (s, 3H), 1.79-1.69 (m, 2H), 1.55-1.47 (m, 2H), 1.15 (s, 3H); HPLC purity: 98.79%; LCMS Calculated for $C_{22}H_{29}FN_2O_3S$: 420.54; Observed: 420.23 [M − H]$^-$. |
| A-709 | 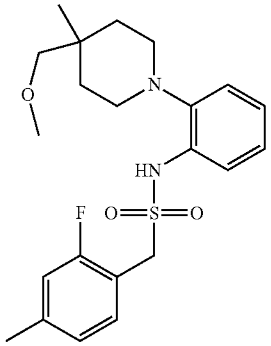 [SMILES: COCC1(C)CCN(c2ccccc2NS(=O)(=O)Cc2ccc(C)cc2F)CC1] | Yield: 17.5 mg, 11.2%; Appearance: Beige oil; $^1$H NMR (600 MHz, DMSO-$d_6$) δ 8.13 (s, 1H), 7.27 (dd, J = 6.9, 2.3 Hz, 1H), 7.25-7.19 (m, 2H), 7.09-6.97 (m, 4H), 4.57 (s, 2H), 3.24 (s, 3H), 3.10 (s, 2H), 2.76-2.65 (m, 4H), 2.28 (s, 3H), 1.59-1.52 (m, 2H), 1.34-1.27 (m, 2H), 0.94 (s, 3H); HPLC purity: 100%; LCMS Calculated for $C_{22}H_{29}FN_2O_3S$: 420.54; Observed: 420.23 [M − H]$^-$. |
| A-647 | 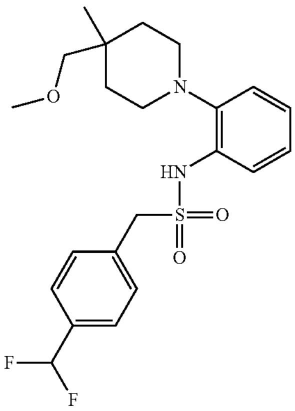 [SMILES: COCC1(C)CCN(c2ccccc2NS(=O)(=O)Cc2ccc(C(F)F)cc2)CC1] | Yield: 6.2 mg, 3.97%; Appearance: Orange oil; $^1$H NMR (600 MHz, DMSO-$d_6$) δ 8.03 (s, 1H), 7.52 (d, J = 7.8 Hz, 2H), 7.38 (d, J = 7.9 Hz, 2H), 7.27 (dd, J = 6.8, 2.4 Hz, 1H), 7.25-7.19 (m, 1H), 7.10-6.90 (m, 3H), 4.70 (s, 2H), 3.24 (s, 3H), 3.09 (s, 2H), 2.72-2.60 (m, 4H), 1.55-1.48 (m, 2H), 1.31-1.24 (m, 2H), 0.92 (s, 3H); HPLC purity: 98.99%; LCMS Calculated for $C_{22}H_{28}F_2N_2O_3S$: 438.53; Observed: 438.22 [M − H]$^-$. |
| A-648 | 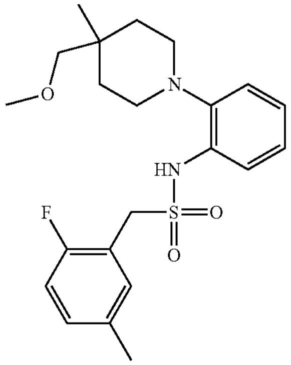 [SMILES: COCC1(C)CCN(c2ccccc2NS(=O)(=O)Cc2cc(C)ccc2F)CC1] | Yield: 71.1 mg, 44.4%; Appearance: Yellow oil; $^1$H NMR (500 MHz, DMSO-$d_6$) δ 8.45 (s, 1H), 7.52 (dd, J = 6.9, 2.3 Hz, 1H), 7.47 (dd, J = 7.0, 2.6 Hz, 1H), 7.45-7.35 (m, 2H), 7.34-7.24 (m, 3H), 4.83 (s, 2H), 3.48 (s, 3H), 3.35 (s, 2H), 3.01-2.89 (m, 4H), 2.45 (s, 3H), 1.86-1.77 (m, 2H), 1.60-1.52 (m, 2H), 1.18 (s, 3H); HPLC purity: 100%; LCMS Calculated for $C_{22}H_{29}FN_2O_3S$: 420.54; Observed: 420.23 [M − H]$^-$. |

-continued

| Compound No. | Structure | Analytical data |
|---|---|---|
| A-649 | 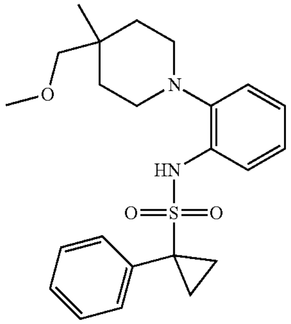 [SMILES: COCC1(C)CCN(c2ccccc2NS(=O)(=O)C2(c3ccccc3)CC2)CC1] | Yield: 14.0 mg, 8.47%; Appearance: Brown oil; $^1$H NMR (600 MHz, DMSO-$d_6$) δ 7.72 (s, 1H), 7.33-7.24 (m, 6H), 7.12-7.06 (m, 1H), 7.00 (tt, J = 7.4, 5.5 Hz, 2H), 3.23 (s, 3H), 3.06 (s, 2H), 2.65-2.57 (m, 2H), 2.57-2.51 (m, 2H), 1.72-1.64 (m, 2H), 1.42-1.35 (m, 2H), 1.32-1.25 (m, 2H), 1.24-1.17 (m, 2H), 0.90 (d, J = 1.4 Hz, 3H); HPLC purity: 100%; LCMS Calculated for $C_{23}H_{30}N_2O_3S$: 414.56; Observed: 414.24 $[M-H]^-$. |
| A-650 | 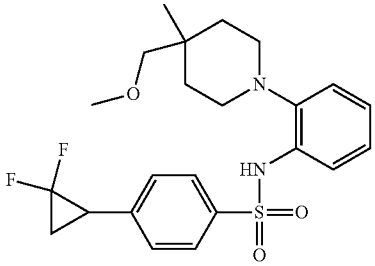 [SMILES: COCC1(C)CCN(c2ccccc2NS(=O)(=O)c2ccc(C3CC3(F)F)cc2)CC1] | Yield: 79.8 mg, 50.8%; Appearance: Grey solid; $^1$H NMR (400 MHz, DMSO-$d_6$) δ 8.34 (s, 1H), 7.72 (dd, J = 8.4, 2.0 Hz, 2H), 7.42-7.32 (m, 3H), 7.15-7.08 (m, 1H), 7.07-6.96 (m, 2H), 3.32 (s, 3H), 3.13 (s, 2H), 2.98-2.87 (m, 1H), 2.49 (d, J = 1.5 Hz, 2H), 2.38 (q, J = 9.4 Hz, 2H), 2.02-1.79 (m, 2H), 1.66-1.55 (m, 2H), 1.34 (d, J = 13.1 Hz, 2H), 0.97 (s, 3H); HPLC purity: 100%; LCMS Calculated for $C_{23}H_{28}F_2N_2O_3S$: 450,54; Observed: 450.22 $[M-H]^-$. |
| A-651 | 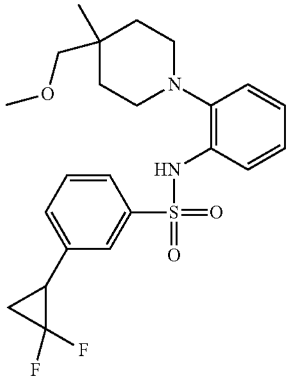 [SMILES: COCC1(C)CCN(c2ccccc2NS(=O)(=O)c2cccc(C3CC3(F)F)c2)CC1] | Yield: 13.9 mg, 8.85%; Appearance: Light brown oil; $^1$H NMR (600 MHz, DMSO-$d_6$) δ 8.67 (s, 1H), 7.67-7.61 (m, 2H), 7.48 (d, J = 7.0 Hz, 2H), 7.28 (dd, J = 7.4, 2.2 Hz, 1H), 7.18 (dd, J = 7.4, 2.1 Hz, 1H), 7.07-6.98 (m, 2H), 3.25 (s, 3H), 3.10 (s, 2H), 3.09-3.04 (m, 1H), 2.46-2.40 (m, 2H), 2.39-2.30 (m, 2H), 2.04-1.95 (m, 1H), 1.92-1.83 (m, 1H), 1.57-1.49 (m, 2H), 1.29-1.23 (m, 2H), 0.91 (s, 3H); HPLC purity: 100%; LCMS Calculated for $C_{23}H_{28}F_2N_2O_3S$: 450.54; Observed: 450.22 $[M-H]^-$. |
| A-710 | 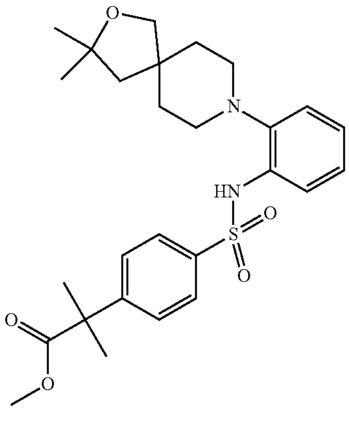 [SMILES: COC(=O)C(C)(C)c1ccc(S(=O)(=O)Nc2ccccc2N2CCC3(CC2)COC(C)(C)C3)cc1] | Yield: 56.0 mg, 35.7%; Appearance: Grey solid; $^1$H NMR (600 MHz, DMSO-$d_6$) δ 8.69 (s, 1H), 7.68 (d, J = 8.3 Hz, 2H), 7.43 (d, J = 8.3 Hz, 2H), 7.33 (dt, J = 7.6, 3.8 Hz, 1H), 7.12 (dt, J = 7.6, 3.8 Hz, 1H), 7.05 (dd, J = 6.0, 3.5 Hz, 2H), 3.54 (s, 3H), 3.52 (s, 2H), 2.29 (d, J = 5.7 Hz, 4H), 1.57 (s, 2H), 1.52 (tq, J = 13.1, 7.6, 6.4 Hz, 4H), 1.44 (s, 6H), 1.16 (s, 6H). HPLC purity: 100%; LCMS Calculated for $C_{27}H_{36}N_2O_5S$: 500.23; Observed: 499.2 $[M-H]^-$. |

-continued

| Compound No. | Structure | Analytical data |
|---|---|---|
| A-657 | 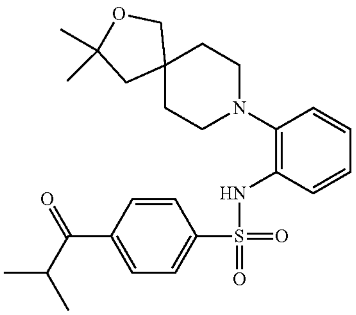 [SMILES: CC(C)C(=O)c1ccc(S(=O)(=O)Nc2ccccc2N2CCC3(CC2)COC(C)(C)C3)cc1] | Yield: 29.0 mg, 16.7%; Appearance: Yellow solid; $^1$H NMR (400 MHz, DMSO-$d_6$) δ 8.68 (s, 1H), 8.06-7.98 (m, 2H), 7.94-7.83 (m, 2H), 7.41-7.31 (m, 1H), 7.07 (dd, J = 6.0, 3.5 Hz, 1H), 7.02 (dp, J = 7.3, 3.5 Hz, 2H), 3.66-3.50 (m, 3H), 2.45 (t, J = 5.6 Hz, 4H), 1.63 (d, J = 5.4 Hz, 6H), 1.21 (d, J = 2.5 Hz, 6H), 1.14 (dd, J = 6.8, 2.5 Hz, 6H). HPLC purity: 100%; LCMS Calculated for $C_{26}H_{34}N_2O_4S$: 470.63; Observed: 469.4 [M − H]$^-$. |
| A-658 | 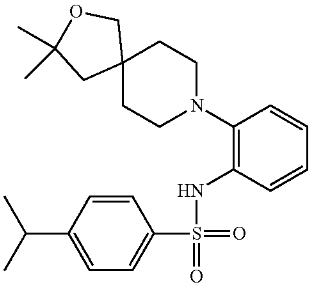 [SMILES: CC(C)c1ccc(S(=O)(=O)Nc2ccccc2N2CCC3(CC2)COC(C)(C)C3)cc1] | Yield: 71.7 mg, 41.5%; Appearance: Grey solid; $^1$H NMR (400 MHz, DMSO-$d_6$) δ 8.28 (s, 1H), 7.71-7.60 (m, 2H), 7.42 (dt, J = 7.7, 1.8 Hz, 1H), 7.35-7.25 (m, 2H), 7.14-6.92 (m, 3H), 3.57 (d, J = 1.6 Hz, 2H), 2.94 (p, J = 6.8 Hz, 1H), 2.38 (d, J = 5.6 Hz, 4H), 1.62 (q, J = 4.1 Hz, 6H), 1.23 (d, J = 1.6 Hz, 3H), 1.21 (d, J = 1.6 Hz, 9H). HPLC purity: 97.02%; LCMS Calculated for $C_{25}H_{34}N_2O_3S$: 442.62; Observed: 441.2 [M − H]$^-$. |
| A-659 | 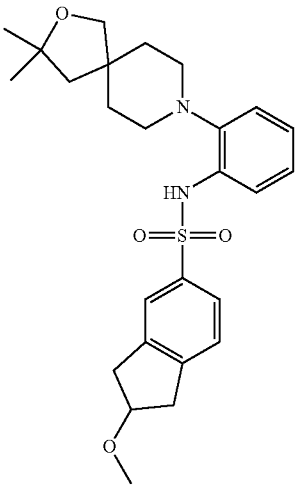 [SMILES: COC1Cc2ccc(S(=O)(=O)Nc3ccccc3N3CCC4(CC3)COC(C)(C)C4)cc2C1] | Yield: 19.2 mg, 11.3%; Appearance: Colorless oil; $^1$H NMR (400 MHz, DMSO-$d_6$) δ 8.27 (s, 1H), 7.64 (s, 1H), 7.50 (d, J = 7.9 Hz, 1H), 7.41 (dt, J = 7.8, 1.5 Hz, 1H), 7.26 (d, J = 7.9 Hz, 1H), 7.12-7.04 (m, 1H), 7.04-6.95 (m, 2H), 4.20 (dt, J = 6.6, 3.2 Hz, 1H), 3.58 (s, 2H), 3.20 (s, 3H), 3.11 (dd, J = 16.9, 6.2 Hz, 2H), 2.93 (d, J = 16.6 Hz, 2H), 2.43 (d, J = 7.8 Hz, 4H), 1.65 (d, J = 6.8 Hz, 6H), 1.22 (d, J = 1.3 Hz, 6H). HPLC purity: 100%; LCMS Calculated for $C_{26}H_{34}N_2O_4S$: 470.63; Observed: 469.2 [M − H]$^-$. |
| A-693 | 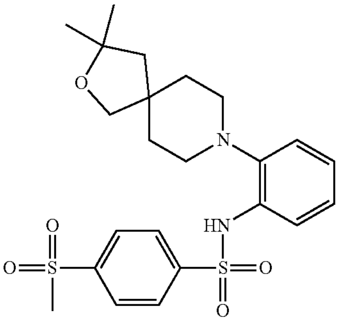 [SMILES: CC1(C)CC2(CCN(c3ccccc3NS(=O)(=O)c3ccc(S(C)(=O)=O)cc3)CC2)CO1] | Yield: 75.9 mg, 43.9%; Appearance: Pink solid; $^1$H NMR (600 MHz, DMSO-$d_6$) δ 9.19 (s, 1H), 8.14-8.03 (m, 2H), 8.04-7.90 (m, 2H), 7.22 (dd, J = 8.0, 1.5 Hz, 1H),7.11 (dd, J = 8.0, 1.7 Hz, 1H), 7.08 (td, J = 7.6, 1.5 Hz, 1H), 7.01 (td, J = 7.6, 1.7 Hz, 1H), 3.52 (s, 2H), 3.24 (s, 3H), 2.46-2.42 (m, 4H), 1.57 (s, 2H), 1.50 (h, J = 7.9 Hz, 4H), 1.16 (s, 6H). HPLC purity: 95.40%; LCMS Calculated for $C_{23}H_{30}N_2O_5S_2$: 478.62; Observed: 477.1 [M − H]$^-$. |

-continued

| Compound No. | Structure | Analytical data |
|---|---|---|
| A-660 | 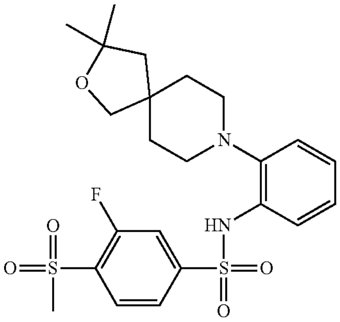 [SMILES: CC1(C)CC2(CCN(c3ccccc3NS(=O)(=O)c3ccc(S(C)(=O)=O)c(F)c3)CC2)CO1] | Yield: 26.9 mg, 15.5%; Appearance: Pink solid; $^1H$ NMR (400 MHz, DMSO-$d_6$) δ 9.14 (s, 1H), 8.02 (t, J = 7.4 Hz, 1H), 7.87 (d, J = 9.2 Hz, 1H), 7.82 (d, J = 8.1 Hz, 1H), 7.28 (d, J = 7.8 Hz, 1H), 7.16-7.06 (m, 2H), 7.06-6.93 (m, 1H), 3.57 (s, 2H), 3.28 (s, 3H), 2.55 (t, J = 5.5 Hz, 4H), 1.63 (d, J = 6.1 Hz, 6H), 1.22 (s, 6H). HPLC purity: 100%; LCMS Calculated for $C_{23}H_{29}FN_2O_5S_2$: 496.61; Observed: 495.2 $[M - H]^-$. |
| A-661 | 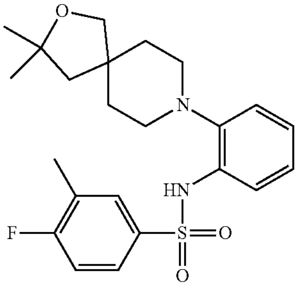 [SMILES: Cc1cc(S(=O)(=O)Nc2ccccc2N2CCC3(CC2)COC(C)(C)C3)ccc1F] | Yield: 70.8 mg, 40.9% ; Appearance: Grey solid; $^1H$ NMR (400 MHz, DMSO-$d_6$) δ 8.43 (s, 1H), 7.73 (dd, J = 7.0, 2.4 Hz, 1H), 7.62 (ddd, J = 7.5, 4.7, 2.3 Hz, 1H), 7.42-7.35 (m, 1H), 7.19-7.10 (m, 1H), 7.08 (dt, J = 7.7, 1.8 Hz, 1H), 7.05-6.95 (m, 2H), 3.59 (s, 2H), 2.47 (t, J = 5.5 Hz, 4H), 2.29 (d, J = 2.0 Hz, 3H), 1.69 (dd, J = 13.3, 7.5 Hz, 3H), 1.64 (d, J = 1.6 Hz, 3H), 1.22 (d, J = 1.6 Hz, 6H). HPLC purity: 100%; LCMS Calculated for $C_{23}H_{29}FN_2O_3S$: 432.55; Observed: 431.2 $[M - H]^-$. |
| A-711 | 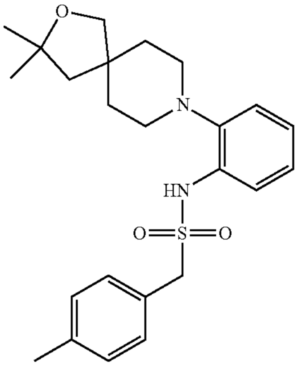 [SMILES: Cc1ccc(CS(=O)(=O)Nc2ccccc2N2CCC3(CC2)COC(C)(C)C3)cc1] | Yield: 44.2 mg, 28.1%; Appearance: Grey solid; $^1H$ NMR (600 MHz, DMSO-$d_6$) δ 7.94 (s, 1H), 7.26 (dd, J = 7.5, 2.0 Hz, 1H), 7.24-7.17 (m, 1H), 7.12 (d, J = 7.9 Hz, 2H), 7.08 (d, J = 8.0 Hz, 2H), 7.07-6.99 (m, 2H), 4.54 (s, 2H), 3.54 (s, 2H), 2.61 (t, J = 5.5 Hz, 4H), 2.26 (s, 3H), 1.60 (s, 2H), 1.54 (q, J = 5.9 Hz, 4H), 1.17 (s, 6H). HPLC purity: 100%; LCMS Calculated for $C_{24}H_{32}N_2O_3S$: 428.59; Observed: 427.2 $[M - H]^-$. |
| A-662 | 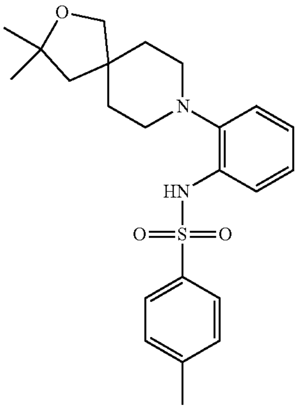 [SMILES: Cc1ccc(S(=O)(=O)Nc2ccccc2N2CCC3(CC2)COC(C)(C)C3)cc1] | Yield: 38.1 mg, 22.0%; Appearance: Beige solid; $^1H$ NMR (400 MHz, DMSO-$d_6$) δ 8.30 (s, 1H), 7.75-7.57 (m, 2H), 7.39 (dt, J = 7.6, 1.9 Hz, 1H), 7.26 (d, J = 7.8 Hz, 2H), 7.16-7.04 (m, 1H), 7.00 (tt, J = 92, 6.3 Hz, 2H), 3.58 (d, J = 1.7 Hz, 2H), 2.44 (t, J = 5.0 Hz, 4H), 2.38 (s, 3H), 1.82-1.50 (m, 6H), 1.22 (d, J = 1.7 Hz, 6H). HPLC purity: 100%; LCMS Calculated for $C_{23}H_{30}N_2O_3S$: 414.56; Observed: 413.2 $[M - H]^-$. |

-continued

| Compound No. | Structure | Analytical data |
|---|---|---|
| A-663 | 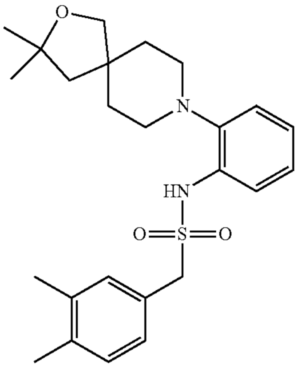 [SMILES: Cc1ccc(CS(=O)(=O)Nc2ccccc2N2CCC3(CC2)COC(C)(C)C3)cc1C] | Yield: 36.9 mg, 21.3%; Appearance: Light brown solid; $^{1}H$ NMR (400 MHz, DMSO-$d_6$) δ 7.77 (s, 1H), 7.38 (dd, J = 8.0, 1.6 Hz, 1H), 7.16 (dd, J = 7.7, 1.7 Hz, 1H), 7.08 (td, J = 7.7, 1.7 Hz, 1H), 7.05-6.99 (m, 2H), 6.91 (d, J = 1.9 Hz, 1H), 6.87 (dd, J = 7.7, 1.8 Hz, 1H), 4.37 (s, 2H), 3.57 (s, 2H), 2.63 (t, J = 5.5 Hz, 4H), 2.21 (d, J = 15.9 Hz, 6H), 1.63 (s, 3H), 1.59 (q, J = 5.5 Hz, 3H), 1.22 (d, J = 2.0 Hz, 6H). HPLC purity: 100%; LCMS Calculated for $C_{25}H_{34}N_2O_3S$: 442.62; Observed: 441.1 $[M - H]^-$. |
| A-692 | 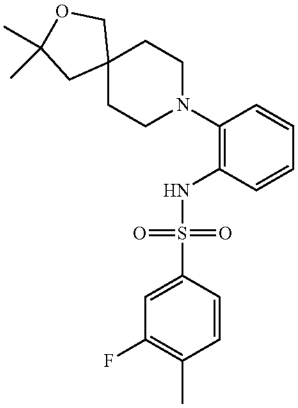 [SMILES: Cc1ccc(S(=O)(=O)Nc2ccccc2N2CCC3(CC2)COC(C)(C)C3)cc1F] | Yield: 52.5 mg, 30.3%; Appearance: Grey solid; $^{1}H$ NMR (600 MHz, DMSO-$d_6$) δ 8.86 (s, 1H), 7.54 (dd, J = 9.3, 1.8 Hz, 1H), 7.48 (dd, J = 8.0, 1.8 Hz, 1H), 7.45 (t, J = 7.6 Hz, 1H), 7.24 (dd, J = 7.8, 1.8 Hz, 1H), 7.12 (dd, J = 7.7, 1.7 Hz, 1H), 7.03 (dtd, J = 19.2, 7.5, 1.7 Hz, 2H), 3.54 (s, 2H), 2.44 (t, J = 5.5 Hz, 4H), 2.23 (d, J = 1.9 Hz, 3H), 1.59 (s, 3H), 1.58-1.51 (m, 3H), 1.17 (s, 6H). HPLC purity: 100%; LCMS Calculated for $C_{23}H_{29}FN_2O_3S$: 432.55; Observed: 431.0 $[M - H]^-$. |
| A-664 | 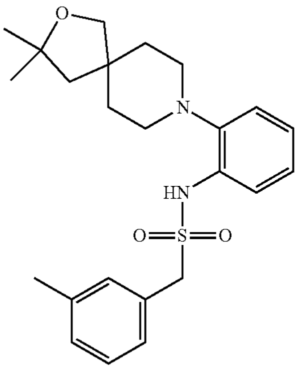 [SMILES: Cc1cccc(CS(=O)(=O)Nc2ccccc2N2CCC3(CC2)COC(C)(C)C3)c1] | Yield: 63.0 mg, 36.2%; Appearance: Light brown solid; $^{1}H$ NMR (400 MHz, DMSO-$d_6$) δ 7.83 (s, 1H), 7.39-7.32 (m, 1H), 7.17 (ddd, J = 7.4, 4.3, 2.8 Hz, 2H), 7.14-7.09 (m, 1H), 7.05 (ddd, J = 12.4, 7.6, 1.6 Hz, 2H), 7.00 (s, 1H), 6.97 (d, J = 7.4 Hz, 1H), 4.42 (s, 2H), 3.58 (s, 2H), 2.65 (t, J = 5.5 Hz, 4H), 2.30 (s, 3H), 1.61 (dd, J = 11.3, 5.8 Hz, 6H), 1.21 (d, J = 1.2 Hz, 6H). HPLC purity: 100%; LCMS Calculated for $C_{24}H_{32}N_2O_3S$: 428.59; Observed: 427.2 $[M - H]^-$. |
| A-665 | 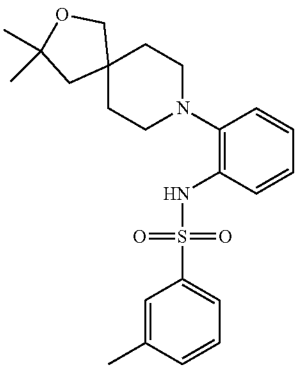 [SMILES: Cc1cccc(S(=O)(=O)Nc2ccccc2N2CCC3(CC2)COC(C)(C)C3)c1] | Yield: 52.1 mg, 30.1%; Appearance: Light brown solid; $^{1}H$ NMR (400 MHz, DMSO-$d_6$) δ 8.34 (s, 1H), 7.59 (s, 1H), 7.52 (dt, J = 6.7, 2.0 Hz, 1H), 7.41 (dd, J = 7.8, 1.9 Hz, 1H), 7.38-7.28 (m, 2H), 7.07 (dd, J = 7.5, 2.1 Hz, 1H), 7.01 (tdd, J = 11.1, 5.8, 2.1 Hz, 2H), 3.58 (d, J = 2.4 Hz, 2H), 2.41 (t, J = 5.3 Hz, 4H), 2.38 (d, J = 2.4 Hz, 3H), 1.80-1.52 (m, 6H), 1.22 (d, J = 2.4 Hz, 6H). HPLC purity: 100%; LCMS Calculated for $C_{23}H_{30}N_2O_3S$: 414.56; Observed: 413.3 $[M - H]^-$. |

-continued

| Compound No. | Structure | Analytical data |
|---|---|---|
| A-666 | 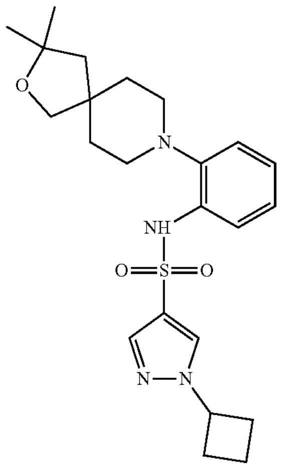 [SMILES: CC1(C)CC2(CCN(c3ccccc3NS(=O)(=O)c3cnn(C4CCC4)c3)CC2)CO1] | Yield: 40.8 mg, 23.5%; Appearance: Beige solid; $^1$H NMR (400 MHz, DMSO-$d_6$) δ 8.24 (s, 1H), 8.14 (s, 1H), 7.55 (s, 1H), 7.47-7.36 (m, 1H), 7.11 (t, J = 6.5 Hz, 1H), 7.06 (dd, J = 7.6, 1.8 Hz, 1H), 7.04-6.95 (m, 1H), 4.80 (p, J = 8.4 Hz, 1H), 3.61 (d, J = 21.2 Hz, 2H), 2.54 (d, J = 1.7 Hz, 1H), 2.52-2.43 (m, 5H), 2.43-2.26 (m, 2H), 1.82 (dt, J = 18.2, 9.2 Hz, 2H), 1.71 (p, J = 6.5, 5.4 Hz, 3H), 1.66 (s, 3H), 1.22 (d, J = 1.6 Hz, 6H). HPLC purity: 100%; LCMS Calculated for $C_{23}H_{32}N_4O_3S$: 444.59; Observed: 443.2 $[M - H]^-$. |
| A-667 | 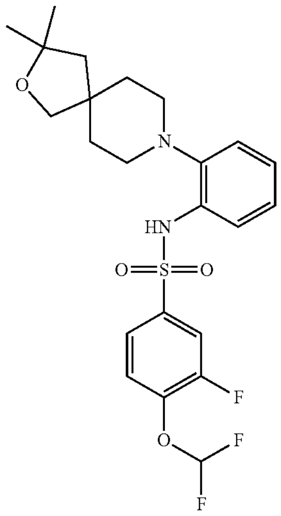 [SMILES: CC1(C)CC2(CCN(c3ccccc3NS(=O)(=O)c3ccc(OC(F)F)c(F)c3)CC2)CO1] | Yield: 78.9 mg, 4.56%; Appearance: Beige solid; $^1$H NMR (400 MHz, DMSO-$d_6$) δ 8.74 (s, 1H), 7.72 (dd, J = 9.8, 2.1 Hz, 1H), 7.68-7.56 (m, 1H), 7.44 (t, J = 8.0 Hz, 1H), 7.39-7.33 (m, 1H), 7.33-7.10 (m, 1H), 7.07 (d, J = 8.9 Hz, 1H), 7.05-6.96 (m, 2H), 3.58 (s, 2H), 2.49 (t, J = 3.2 Hz, 4H), 1.65 (d, J = 11.9 Hz, 6H), 1.22 (s, 6H). HPLC purity: 100%; LCMS Calculated for $C_{23}H_{27}F_3N_2O_4S$: 484.53; Observed: 483.1 $[M - H]^-$. |
| A-668 | 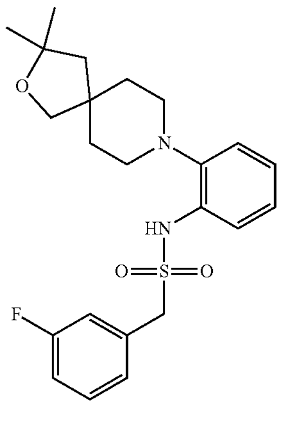 [SMILES: CC1(C)CC2(CCN(c3ccccc3NS(=O)(=O)Cc3cccc(F)c3)CC2)CO1] | Yield: 46.0 mg, 26.6%; Appearance: Grey solid; $^1$H NMR (400 MHz, DMSO-$d_6$) δ 7.92 (s, 1H), 7.34 (t, J = 7.4 Hz, 2H), 7.19 (dd, J = 7.4, 1.9 Hz, 1H), 7.06 (qd, J = 8.9, 4.6 Hz, 4H), 6.98 (d, J = 9.7 Hz, 1H), 4.53 (s, 2H), 3.59 (s, 2H), 2.69 (t, J = 5.5 Hz, 4H), 1.64 (d, J = 4.6 Hz, 6H), 1.22 (s, 6H). HPLC purity: 97.37%; LCMS Calculated for $C_{23}H_{29}FN_2O_3S$: 432.55; Observed: 431.1 $[M - H]^-$. |

-continued

| Compound No. | Structure | Analytical data |
| --- | --- | --- |
| A-669 | 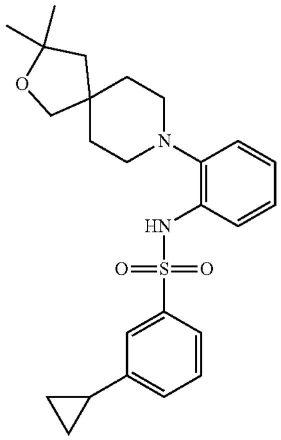 [SMILES: CC1(C)CC2(CCN(c3ccccc3NS(=O)(=O)c3cccc(C4CC4)c3)CC2)CO1] | Yield: 76.5 mg, 44.2%; Appearance: Grey solid; $^1H$ NMR (400 MHz, DMSO-$d_6$) δ 8.30 (s, 1H), 7.52-7.46 (m, 1H), 7.43 (d, J = 7.9 Hz, 1H), 7.40-7.35 (m, 1H), 7.31 (t, J = 7.7 Hz, 1H), 7.23 (d, J = 7.8 Hz, 1H), 7.06 (t, J = 6.2 Hz, 2H), 7.03-6.98 (m, 1H), 3.80-3.47 (m, 2H), 2.38 (t, J = 5.5 Hz, 4H), 1.93 (tt, J = 92, 5.4 Hz, 1H), 1.63 (d, J = 5.4 Hz, 6H), 1.34-1.11 (m, 6H), 1.07-0.90 (m, 2H), 0.62 (d, J = 5.2 Hz, 2H). HPLC purity: 100%; LCMS Calculated for $C_{25}H_{32}N_2O_3S$ 440.60; Observed: 439.2 $[M - H]^-$. |
| A-670 | 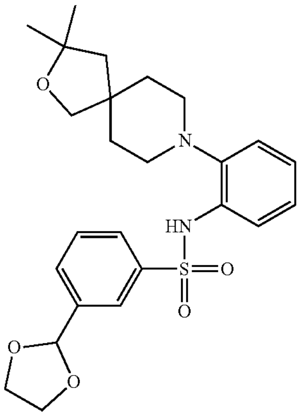 [SMILES: CC1(C)CC2(CCN(c3ccccc3NS(=O)(=O)c3cccc(C4OCCO4)c3)CC2)CO1] | Yield: 61.3 mg, 35.4%; Appearance: Light brown solid; $^1H$ NMR (400 MHz, DMSO-$d_6$) δ 8.44 (s, 1H), 7.86-7.76 (m, 1H), 7.73 (dd, J = 7.9, 1.7 Hz, 1H), 7.61 (d, J = 7.7 Hz, 1H), 7.48 (td, J = 7.8, 1.4 Hz, 1H), 7.44-7.34 (m, 1H), 7.13-6.93 (m, 3H), 5.74 (s, 1H), 3.99 (h, J = 2.5 Hz, 4H), 3.56 (s, 2H), 2.41 (t, J = 5.6 Hz, 4H), 1.64 (h, J = 7.0, 6.4 Hz, 6H), 1.21 (d, J = 1.4 Hz, 6H). HPLC purity: 100%; LCMS Calculated for $C_{25}H_{32}N_2O_5S$ 472.60; Observed: 471.2 $[M - H]^-$. |
| A-671 | 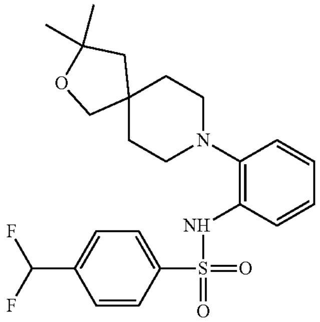 [SMILES: CC1(C)CC2(CCN(c3ccccc3NS(=O)(=O)c3ccc(C(F)F)cc3)CC2)CO1] | Yield: 64.1 mg, 37.0%; Appearance: Light Brown solid; $^1H$ NMR (400 MHz, DMSO-$d_6$) δ 8.64 (s, 1H), 7.90 (d, J = 8.0 Hz, 2H), 7.68 (d, J = 8.0 Hz, 2H), 7.36 (dd, J = 5.9, 3.7 Hz, 1H), 7.06 (q, J = 7.1, 6.1 Hz, 1H), 7.05-7.01 (m, 2H), 7.01-6.77 (m, 1H), 3.57 (s, 2H), 2.44 (d, J = 11.2 Hz, 4H), 1.72-1.47 (m, 6H), 1.21 (s, 6H). HPLC purity: 100%; LCMS Calculated for $C_{23}H_{28}F_2N_2O_3S$ 450.54; Observed: 449.1 $[M - H]^-$. |
| A-672 | 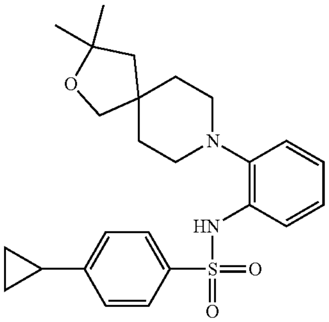 [SMILES: CC1(C)CC2(CCN(c3ccccc3NS(=O)(=O)c3ccc(C4CC4)cc3)CC2)CO1] | Yield: 53.6 mg, 31.0%; Appearance: Grey solid; $^1H$ NMR (400 MHz, DMSO-$d_6$) δ 8.27 (s, 1H), 7.68-7.56 (m, 2H), 7.39 (dt, J = 7.7, 1.8 Hz, 1H), 7.19-7.10 (m, 2H), 7.10-7.03 (m, 1H), 7.00 (ddt, J = 8.8, 7.1, 3.6 Hz, 2H), 3.58 (d, J = 1.6 Hz, 2H), 2.43 (d, J = 5.7 Hz, 4H), 1.94 (tt, J = 8.9, 5.5 Hz, 1H), 1.65 (d, J = 7.1 Hz, 6H), 1.22 (d, J = 1.6 Hz, 6H), 1.04 (dtd, J = 8.2, 4.6, 1.4 Hz, 2H), 0.73 (qd, J = 4.8, 2.3 Hz, 2H). HPLC purity: 97.82%; LCMS Calculated for $C_{25}H_{32}N_2O_3S$ 440.60; Observed: 439.2 $[M - H]^-$. |

-continued

| Compound No. | Structure | Analytical data |
|---|---|---|
| A-673 | 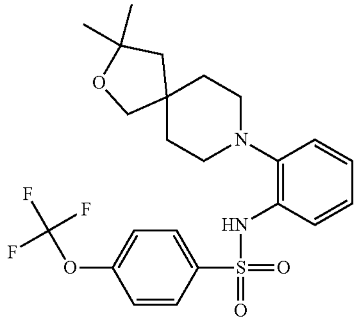 [SMILES: CC1(C)CC2(CCN(c3ccccc3NS(=O)(=O)c3ccc(OC(F)(F)F)cc3)CC2)CO1] | Yield: 64.1 mg, 37.0%; Appearance: Grey oil; $^1$H NMR (400 MHz, DMSO-$d_6$) δ 8.63 (s, 1H), 7.89 (dd, J = 8.6, 1.6 Hz, 2H), 7.45-7.28 (m, 3H), 7.05 (dddt, J = 10.1, 5.7, 4.1, 2.5 Hz, 3H), 3.56 (s, 2H), 2.43 (t, J = 5.6 Hz, 4H), 1.63 (hept, J = 6.8, 6.0 Hz, 6H), 1.21 (d, J = 1.5 Hz, 6H). HPLC purity: 100%; LCMS Calculated for $C_{23}H_{27}F_3N_2O_4S$ 484.53; Observed: 483.2 $[M - H]^-$. |
| A-691 | 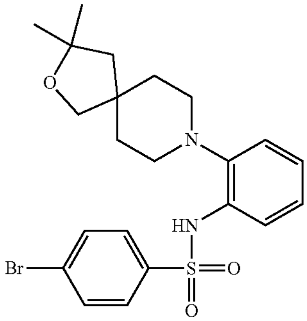 [SMILES: CC1(C)CC2(CCN(c3ccccc3NS(=O)(=O)c3ccc(Br)cc3)CC2)CO1] | Yield: 53.7 mg, 31.0%; Appearance: Violet solid; $^1$H NMR (600 MHz, DMSO-$d_6$) δ 8.93 (s, 1H), 7.75 (d, J = 8.2 Hz, 2H), 7.68 (d, J = 8.5 Hz, 2H), 7.32-7.22 (m, 1H), 7.12 (dd, J = 7.9, 1.6 Hz, 1H), 7.06 (td, J = 7.6, 1.6 Hz, 1H), 7.01 (td, J = 7.6, 1.5 Hz, 1H), 3.53 (s, 2H), 2.43 (d, J = 6.4 Hz, 4H), 1.58 (s, 2H), 1.53 (tq, J = 12.6, 6.5, 4.9 Hz, 4H), 1.17 (s, 6H). HPLC purity: 95.16%; LCMS Calculated for $C_{22}H_{27}BrN_2O_3S$ 479.43; Observed: 479.0 $[M - H]^-$. |
| A-674 | 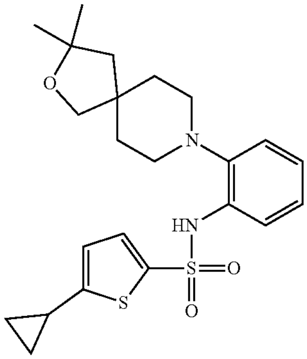 [SMILES: CC1(C)CC2(CCN(c3ccccc3NS(=O)(=O)c3ccc(C4CC4)s3)CC2)CO1] | Yield: 58.2 mg, 33.6%; Appearance: Grey solid; $^1$H NMR (400 MHz, DMSO-$d_6$) δ 8.36 (s, 1H), 7.44 (dt, J = 7.6, 2.0 Hz, 1H), 7.27 (dd, J = 3.9, 1.8 Hz, 1H), 7.17-7.11 (m, 1H), 7.06 (tt, J = 9.4, 6.4 Hz, 2H), 6.70 (dd, J = 4.0, 1.6 Hz, 1H), 3.59 (d, J = 1.8 Hz, 2H), 2.48 (s, 4H), 2.10 (ddt, J = 13.4, 8.8, 5.0 Hz, 1H), 1.78-1.53 (m, 6H), 1.22 (d, J = 1.7 Hz, 6H), 1.14-1.02 (m, 2H), 0.70 (qd, J = 5.5, 4.7, 3.1 Hz, 2H). HPLC purity: 100%; LCMS Calculated for $C_{23}H_30N_2O_3S_2$ 446.62; Observed: 445.2 $[M - H]^-$. |
| A-712 | 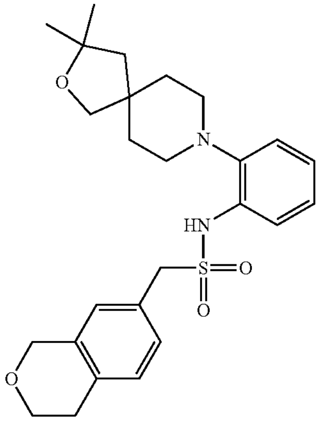 [SMILES: CC1(C)CC2(CCN(c3ccccc3NS(=O)(=O)Cc3ccc4c(c3)COCC4)CC2)CO1] | Yield: 11.9 mg, 7.58%; Appearance: Light brown solid; $^1$H NMR (600 MHz, DMSO-$d_6$) δ 7.99 (s, 1H), 7.27 (dd, J = 6.9, 2.4 Hz, 1H), 7.21 (dd, J = 6.8, 2.4 Hz, 1H), 7.13-7.04 (m, 3H), 7.03-6.94 (m, 1H), 6.83 (s, 1H), 4.54 (d, J = 4.6 Hz, 4H), 3.82 (t, J = 5.7 Hz, 2H), 3.55 (s, 2H), 2.72 (t, J = 5.7 Hz, 2H), 2.60 (t, J = 5.5 Hz, 4H), 1.60 (s, 2H), 1.56 (h, J = 7.6 Hz, 4H), 1.17 (s, 6H). HPLC purity: 100%; LCMS Calculated $C_{26}H_{34}N_2O_4S$ for 470.63; Observed: 469.0 $[M - H]^-$. |

-continued

| Compound No. | Structure | Analytical data |
|---|---|---|
| A-690 | 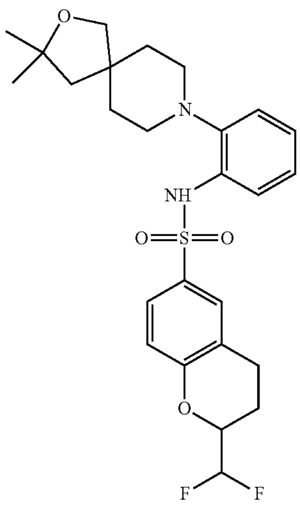 [SMILES: CC1(C)CC2(CCN(c3ccccc3NS(=O)(=O)c3ccc4c(c3)CCC(C(F)F)O4)CC2)CO1] | Yield: 86.1 mg, 49.8%; Appearance: Grey solid; $^1H$ NMR (500 MHz, DMSO-$d_6$) δ 8.55 (s, 1H), 7.59 (s, 1H), 7.44 (d, J = 8.8 Hz, 1H), 7.31 (d, J = 7.1 Hz, 1H), 7.22-7.09 (m, 1H), 7.10-6.96 (m, 2H), 6.91 (d, J = 8.8 Hz, 1H), 6.22 (t, J = 54.5 Hz, 1H), 4.52-4.39 (m, 1H), 3.57 (s, 2H), 2.82 (d, J = 17.9 Hz, 2H), 2.43 (d, J = 7.0 Hz, 4H), 2.08 (d, J = 13.5 Hz, 1H), 1.73 (dq, J = 11.4, 5.9 Hz, 1H), 1.61 (d, J = 8.0 Hz, 6H), 1.18 (s, 6H). HPLC purity: 100%; LCMS Calculated for $C_{26}H_{32}F_2N_2O_4S$ 506.61; Observed: 505.2 $[M-H]^-$. |
| A-713 | 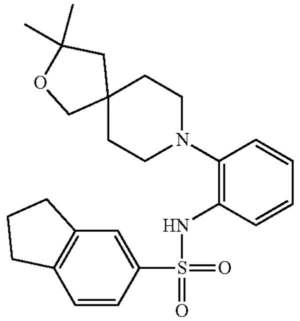 [SMILES: CC1(C)CC2(CCN(c3ccccc3NS(=O)(=O)c3ccc4c(c3)CCC4)CC2)CO1] | Yield: 45.6 mg, 29.0%; Appearance: Violet solid; $^1H$ NMR (600 MHz, DMSO-$d_6$) δ 8.59 (s, 1H), 7.64 (s, 1H), 7.47 (dd, J = 7.9, 1.8 Hz, 1H), 7.35-7.25 (m, 2H), 7.17-7.08 (m, 1H), 7.02 (qd, J = 7.4, 3.8 Hz, 2H), 3.55 (s, 2H), 2.84 (t, J = 7.5 Hz, 4H), 2.40 (t, J = 5.5 Hz, 4H), 2.07-1.91 (m, 2H), 1.69-1.38 (m, 6H), 1.17 (s, 6H). HPLC purity: 100%; LCMS Calculated for $C_{25}H_{32}N_2O_3S$ 440.60; Observed: 439.2 $[M-H]^-$. |
| A-714 | 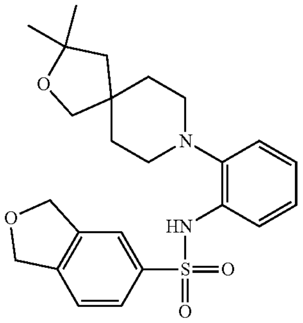 [SMILES: CC1(C)CC2(CCN(c3ccccc3NS(=O)(=O)c3ccc4c(c3)COC4)CC2)CO1] | Yield: 26.8 mg, 17.0%; Appearance: Beige solid; $^1H$ NMR (600 MHz, DMSO-$d_6$) δ 8.73 (s, 1H), 7.76 (s, 1H), 7.64 (dd, J = 7.9, 1.6 Hz, 1H), 7.43 (d, J = 8.0 Hz, 1H), 7.32-7.23 (m, 1H), 7.18-7.09 (m, 1H), 7.02 (qd, J = 7.4, 3.6 Hz, 2H), 4.97 (dd, J = 6.4, 2.0 Hz, 4H), 3.54 (s, 2H), 2.42 (t, J = 5.5 Hz, 4H), 1.59 (s, 2H), 1.57 (q, J = 5.5 Hz, 4H), 1.17 (s, 6H). HPLC purity: 100%; LCMS Calculated for $C_{24}H_{30}N_2O_4S$ 442.57; Observed: 441.2 $[M-H]^-$. |
| A-715 | 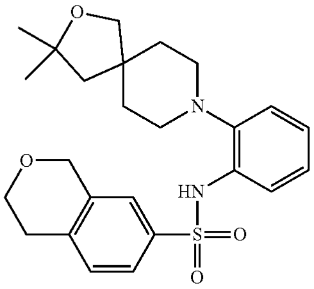 [SMILES: CC1(C)CC2(CCN(c3ccccc3NS(=O)(=O)c3ccc4c(c3)COCC4)CC2)CO1] | Yield: 18.2 mg, 11.5%; Appearance: Brown solid; $^1H$ NMR (600 MHz, DMSO-$d_6$) δ 8.64 (s, 1H), 7.49 (d, J = 7.9 Hz, 2H), 7.34-7.20 (m, 2H), 7.17-7.10 (m, 1H), 7.05-6.96 (m, 2H), 4.65 (s, 2H), 3.82 (t, J = 5.7 Hz, 2H), 3.55 (s, 2H), 2.78 (t, J = 5.8 Hz, 2H), 2.42 (t, J = 5.5 Hz, 4H), 1.59 (d, J = 7.0 Hz, 2H), 1.59-1.30 (m, 4H), 1.17 (s, 6H). HPLC purity: 100%; LCMS Calculated for $C_{25}H_{32}N_2O_4S$ 456.60; Observed: 455.2 $[M-H]^-$. |

-continued

| Compound No. | Structure | Analytical data |
|---|---|---|
| A-675 | 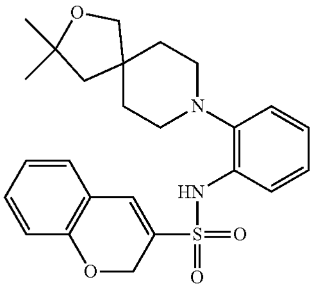 [SMILES: CC1(C)CC2(CCN(c3ccccc3NS(=O)(=O)C3=Cc4ccccc4OC3)CC2)CO1] | Yield: 32.6 mg, 18.8%; Appearance: Grey solid; $^1H$ NMR (400 MHz, DMSO-$d_6$) δ 8.63 (s, 1H), 7.43-7.31 (m, 1H), 7.28 (s, 1H), 7.28-7.18 (m, 2H), 7.20-7.10 (m, 1H), 7.09-6.99 (m, 2H), 6.93 (t, J = 7.5 Hz, 1H), 6.79 (d, J = 8.1 Hz, 1H), 4.90 (s, 2H), 3.60 (d, J = 1.5 Hz, 2H), 2.75 (t, J = 5.3 Hz, 4H), 1.77 (hept, J = 7.2, 6.2 Hz, 4H), 1.67 (s, 2H), 1.22 (d, J = 1.5 Hz, 6H). HPLC purity: 96.54%; LCMS Calculated for $C_{25}H_{30}N_2O_4S$ 454.59; Observed: 453.0 $[M-H]^-$. |
| A-676 | 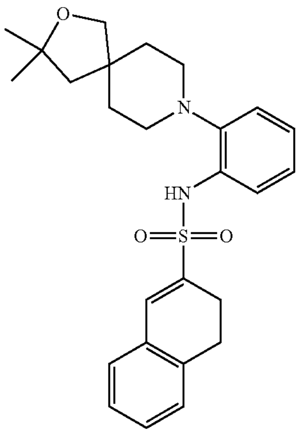 [SMILES: CC1(C)CC2(CCN(c3ccccc3NS(=O)(=O)C3=Cc4ccccc4CC3)CC2)CO1] | Yield: 60.4 mg, 34.9%; Appearance: Beige solid; $^1H$ NMR (400 MHz, DMSO-$d_6$) δ 8.20 (s, 1H), 7.44-7.32 (m, 2H), 7.28 (d, J = 7.3 Hz, 1H), 7.25-7.19 (m, 2H), 7.14 (dd, J = 13.2, 7.9 Hz, 2H), 7.08-6.93 (m, 2H), 3.62 (s, 2H), 2.81 (t, J = 8.3 Hz, 2H), 2.74 (t, J = 5.6 Hz, 4H), 2.60-2.51 (m, 2H), 1.77 (q, J = 6.0 Hz, 4H), 1.68 (s, 2H), 1.23 (s, 6H). HPLC purity: 98.76%; LCMS Calculated for $C_{26}H_{32}N_2O_3S$ 452.61; Observed: 451.2 $[M-H]^-$. |
| A-689 | 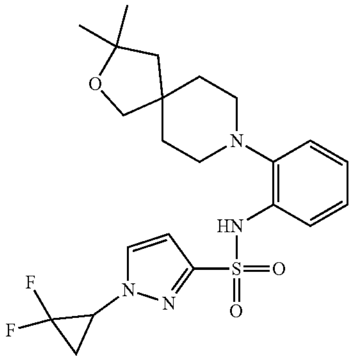 [SMILES: CC1(C)CC2(CCN(c3ccccc3NS(=O)(=O)c3ccn(C4CC4(F)F)n3)CC2)CO1] | Yield: 81.0 mg, 46.8%; Appearance: Light brown solid; $^1H$ NMR (600 MHz, DMSO-$d_6$) δ 8.82-8.65 (m, 1H), 8.05 (d, J =2.5 Hz, 1H), 7.33 (dd, J = 7.3, 2.1 Hz, 1H), 7.15 (dd, J = 7.3, 2.0 Hz, 1H), 7.01 (tt, J = 7.4, 5.6 Hz, 2H), 6.71 (d, J = 2.4 Hz, 1H), 4.77-4.57 (m, 1H), 3.57 (s, 2H), 2.56 (t, J = 5.4 Hz, 4H), 2.35 (q, J = 11.7, 11.2 Hz, 2H), 1.82-1.49 (m, 6H), 1.18 (s, 6H). HPLC purity: 100%; LCMS Calculated for $C_{22}H_{28}F_2N_4O_3S$ 466.55; Observed: 465.2 $[M-H]^-$. |
| A-677 | 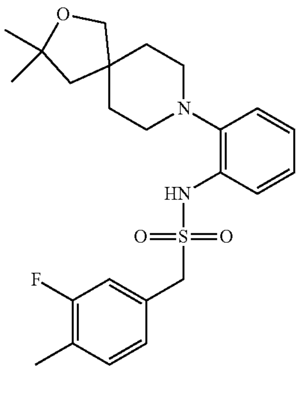 [SMILES: Cc1ccc(CS(=O)(=O)Nc2ccccc2N2CCC3(CC2)COC(C)(C)C3)cc1F] | Yield: 52.1 mg, 30.1%; Appearance: Light brown solid; $^1H$ NMR (400 MHz, DMSO-$d_6$) δ 7.85 (s, 1H), 7.38 (dt, J = 7.7, 1.6 Hz, 1H), 7.23-7.13 (m, 2H), 7.13-6.99 (m, 2H), 6.90 (dd, J = 13.8, 9.0 Hz, 2H), 4.46 (s, 2H), 3.58 (d, J = 1.4 Hz, 2H), 2.68 (t, J = 5.5 Hz, 4H), 2.26 (s, 3H), 1.63 (dd, J = 11.0, 4.9 Hz, 6H), 1.22 (d, J = 1.4 Hz, 6H). HPLC purity: 100%; LCMS Calculated for $C_{24}H_{31}FN_2O_3S$ 446.58; Observed: 445.0 $[M-H]^-$. |

-continued

| Compound No. | Structure | Analytical data |
|---|---|---|
| A-688 | 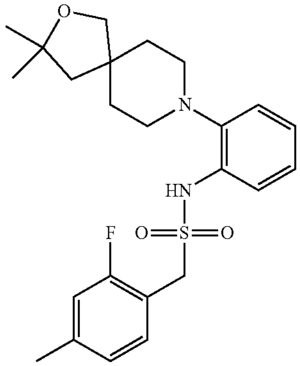 [SMILES: Cc1ccc(CS(=O)(=O)Nc2ccccc2N2CCC3(CC2)COC(C)(C)C3)c(F)c1] | Yield: 54.9 mg, 31.7%; Appearance: Grey solid; $^1H$ NMR (500 MHz, DMSO-$d_6$) δ 8.19 (s, 1H), 7.23 (q, J = 5.5, 4.7 Hz, 3H), 7.15-6.79 (m, 4H), 4.58 (d, J = 3.5 Hz, 2H), 3.57 (d, J = 3.5 Hz, 2H), 2.68 (q, J = 4.8 Hz, 4H), 2.29 (d, J = 3.4 Hz, 3H), 1.81-1.31 (m, 6H), 1.18 (d, J = 3.5 Hz, 6H). HPLC purity: 100%; LCMS Calculated for $C_{24}H_{31}FN_2O_3S$ 446.58; Observed: 445.2 $[M - H]^-$. |
| A-716 | 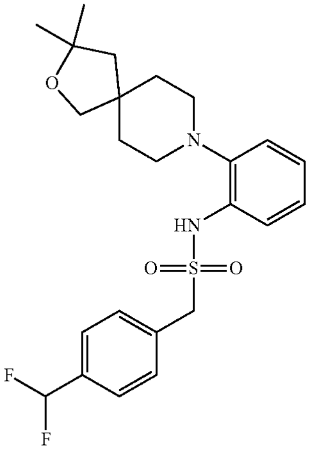 [SMILES: CC1(C)CC2(CCN(c3ccccc3NS(=O)(=O)Cc3ccc(C(F)F)cc3)CC2)CO1] | Yield: 24.1 mg, 15.3%; Appearance: Light brown solid; $^1H$ NMR (600 MHz, DMSO-$d_6$) δ 8.06 (s, 1H), 7.52 (d, J = 7.8 Hz, 2H), 7.37 (d, J = 7.8 Hz, 2H), 7.30-7.24 (m, 1H), 7.21 (dd, J = 5.9, 3.6 Hz, 1H), 7.05 (dd, J = 6.0, 3.6 Hz, 2H), 7.00 (t, J = 55.9 Hz, 1H), 4.69 (s, 2H), 3.54 (s, 2H), 2.62 (t, J = 5.4 Hz, 4H), 1.59 (s, 2H), 1.54 (dq, J = 13.2, 7.2, 6.4 Hz, 4H), 1.17 (d, J = 1.3 Hz, 6H). HPLC purity: 100%; LCMS Calculated for $C_{24}H_{30}F_2N_2O_3S$ 464.57; Observed: 463.2 $[M - H]^-$. |
| A-678 | 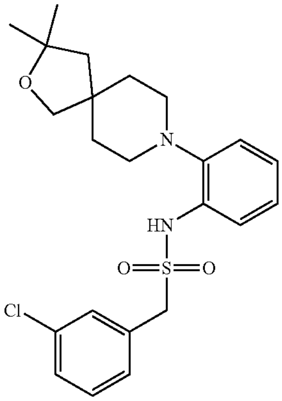 [SMILES: CC1(C)CC2(CCN(c3ccccc3NS(=O)(=O)Cc3cccc(Cl)c3)CC2)CO1] | Yield: 49.3 mg, 28.5%; Appearance: Grey solid; $^1H$ NMR (400 MHz, DMSO-$d_6$) δ 7.93 (s, 1H), 7.42-7.27 (m, 3H), 7.25-7.13 (m, 3H), 7.06 (tt, J = 9.1, 6.6 Hz, 2H), 4.52 (s, 2H), 3.72-3.37 (m, 2H), 2.70 (t, J = 5.5 Hz, 4H), 1.65 (d, J = 4.0 Hz, 6H), 1.22 (d, J = 1.4 Hz, 6H). HPLC purity: 100%; LCMS Calculated for $C_{23}H_{29}ClN_2O_3S$ 449.01; Observed: 447.2 $[M - H]^-$. |
| A-679 | 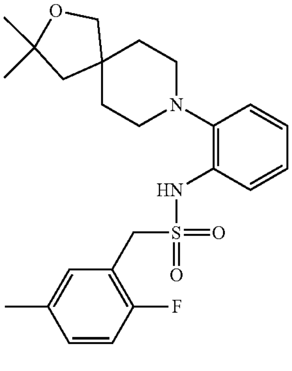 [SMILES: Cc1ccc(F)c(CS(=O)(=O)Nc2ccccc2N2CCC3(CC2)COC(C)(C)C3)c1] | Yield: 67.9 mg, 39.3%; Appearance: Grey solid; $^1H$ NMR (400 MHz, DMSO-$d_6$) δ 8.06 (s, 1H), 7.37-7.27 (m, 1H), 7.23-7.10 (m, 3H), 7.03 (dt, J = 6.1, 2.8 Hz, 2H), 6.96 (t, J = 9.1 Hz, 1H), 4.48 (d, J = 2.9 Hz, 2H), 3.60 (d, J = 3.1 Hz, 2H), 2.72 (t, J = 5.4 Hz, 4H), 2.31 (d, J = 3.0 Hz, 3H), 1.92-1.48 (m, 6H), 1.22 (d, J = 3.1 Hz, 6H). HPLC purity: 100%; LCMS Calculated for $C_{24}H_{31}FN_2O_3S$ 446.58; Observed: 445.2 $[M - H]^-$. |

-continued

| Compound No. | Structure | Analytical data |
|---|---|---|
| A-717 | 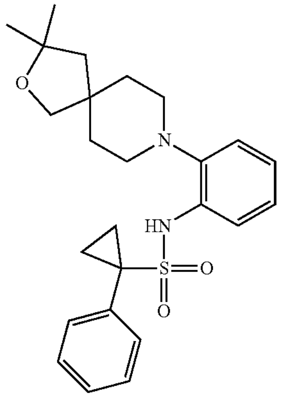 [SMILES: CC1(C)CC2(CCN(c3ccccc3NS(=O)(=O)C3(c4ccccc4)CC3)CC2)CO1] | Yield: 23.2 mg, 14.7%; Appearance: Light brown solid; $^1$H NMR (600 MHz, DMSO-$d_6$) δ 7.77 (s, 1H), 7.39-7.30 (m, 1H), 7.29 (d, J = 4.0 Hz, 4H), 7.22-7.16 (m, 1H), 7.12-7.06 (m, 1H), 6.99 (hept, J = 5.2 Hz, 2H), 3.51 (s, 2H), 2.55 (t, J = 5.4 Hz, 4H), 1.73-1.65 (m, 2H), 1.57 (s, 2H), 1.45 (q, J = 4.7 Hz, 4H), 1.36-1.27 (m, 2H), 1.16 (s, 6H). HPLC purity: 100%; LCMS Calculated for $C_{25}H_{32}N_2O_3S$ 440.60; Observed: 439.2 $[M - H]^-$. |
| A-718 | 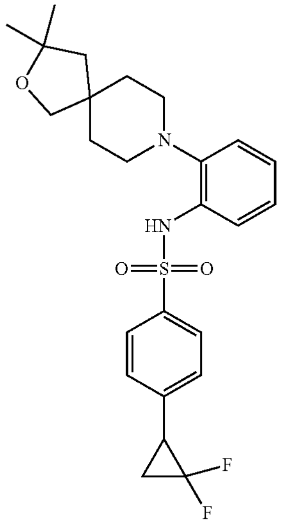 [SMILES: CC1(C)CC2(CCN(c3ccccc3NS(=O)(=O)c3ccc(C4CC4(F)F)cc3)CC2)CO1] | Yield: 33.2 mg, 21.1%; Appearance: Beige solid; $^1$H NMR (600 MHz, DMSO-$d_6$) δ 8.71 (s, 1H), 7.77-7.62 (m, 2H), 7.41 (d, J = 8.3 Hz, 2H), 7.36-7.21 (m, 1H), 7.22-7.09 (m, 1H), 7.09-6.95 (m, 2H), 3.53 (s, 2H), 3.07 (dt, J = 12.9, 9.6 Hz, 1H), 2.36 (q, J = 6.4, 5.7 Hz, 4H), 2.15-1.94 (m, 2H), 1.58 (s, 2H), 1.57-1.28 (m, 4H), 1.16 (s, 6H). HPLC purity: 100%; LCMS Calculated for $C_{25}H_{30}F_2N_2O_3S$ 476.58; Observed: 475.2 $[M - H]^-$. |
| A-687 | 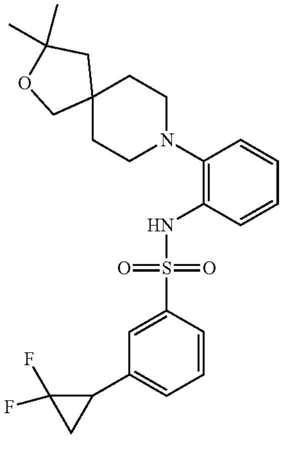 [SMILES: CC1(C)CC2(CCN(c3ccccc3NS(=O)(=O)c3cccc(C4CC4(F)F)c3)CC2)CO1] | Yield: 54.7 mg, 31.6%; Appearance: Violet solid; $^1$H NMR (600 MHz, DMSO-$d_6$) δ 8.72 (s, 1H), 7.66 (s, 1H), 7.62 (d, J = 7.0 Hz, 1H), 7.48 (d, J = 7.2 Hz, 2H), 7.37-7.25 (m, 1H), 7.17-7.07 (m, 1H), 7.07-6.92 (m, 2H), 3.53 (s, 2H), 3.09 (td, J = 12.5, 8.5 Hz, 1H), 2.42-2.30 (m, 4H), 2.08-1.94 (m, 1H), 1.94-1.80 (m, 1H), 1.57 (d, J = 9.9 Hz, 2H), 1.54 (dd, J = 12.8, 6.9 Hz, 4H), 1.16 (s, 6H). HPLC purity: 100%; LCMS Calculated for $C_{25}H_{30}F_2N_2O_3S$ 476.58; Observed: 475.2 $[M - H]^-$. |

-continued

| Compound No. | Structure | Analytical data |
|---|---|---|
| A-372 | 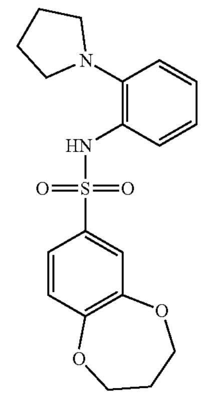 [SMILES: O=S(=O)(Nc1ccccc1N1CCCC1)c1ccc2c(c1)OCCCO2] | Yield: 21.7 mg, 13.8% ; Appearance: Violet solid; $^1$H NMR (500 MHz, DMSO-$d_6$) δ 8.79 (s, 1H), 7.25-7.19 (m, 2H), 7.00 (t, J = 7.7 Hz, 1H), 6.95 (d, J = 8.5 Hz, 1H), 6.80-6.71 (m, 2H), 6.60 (t, J = 7.4 Hz, 1H), 4.24 (dt, J = 20.7, 5.6 Hz, 4H), 3.19 (t, J = 6.3 Hz, 4H), 2.21 (p, J = 5.7 Hz, 2H), 1.92-1.85 (m, 4H); HPLC purity: 95.13%%; LCMS Calculated for $C_{19}H_{22}N_2O_4S$: 374,46; Observed: 374.15 [M − H]$^-$. |
| A-457 | 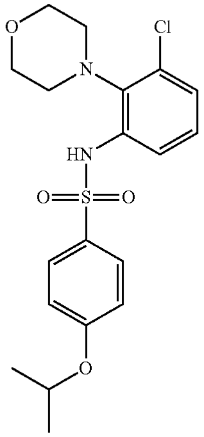 [SMILES: CC(C)Oc1ccc(S(=O)(=O)Nc2cccc(Cl)c2N2CCOCC2)cc1] | Yield: 59.3 mg, 29.4%; Appearance: Beige solid; $^1$H NMR (400 MHz, DMSO-$d_6$) δ 8.68 (s, 1H), 7.65-7.59 (m, 2H), 7.41 (dd, J = 8.1, 1.5 Hz, 1H), 7.12 (t, J = 8.1 Hz, 1H), 7.02 (dd, J = 8.1, 1.5 Hz, 1H), 6.93-6.88 (m, 2H), 4.65 (p, J = 6.0 Hz, 1H), 3.72-3.56 (m, 4H), 3.53-3.36 (m, 2H), 2.12 (d, J = 11.3 Hz, 2H), 1.30 (s, 3H), 1.29 (s, 3H); HPLC purity: 100%; LCMS Calculated for $C_{19}H_{23}ClN_2O_4S$: 410.92; Observed: 410.13 [M − H]$^-$. |
| A-608 | 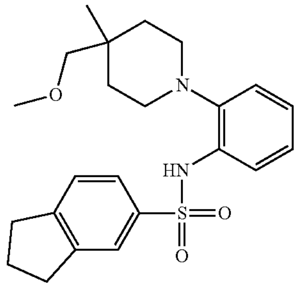 [SMILES: COCC1(C)CCN(c2ccccc2NS(=O)(=O)c2ccc3c(c2)CCC3)CC1] | Yield: 16.2 mg, 9.93%; Appearance: Brown solid; $^1$H NMR (600 MHz, DMSO-$d_6$) δ 8.54 (s, 1H), 7.63 (s, 1H), 7.47 (d, J = 9.2 Hz, 1H), 7.31 (d, J = 8.0 Hz, 1H), 7.29 (dd, J = 6.0, 3.6 Hz, 1H), 7.18 (dd, J = 5.9, 3.5 Hz, 1H), 7.01 (dd, J = 6.0, 3.5 Hz, 2H), 3.26 (s, 3H), 3.11 (s, 2H), 2.87-2.78 (m, 4H), 2.50-2.48 (m, 2H), 2.42-2.36 (m, 2H), 1.98 (p, J = 7.4 Hz, 2H), 1.59-1.51 (m, 2H), 1.32-1.25 (m, 2H), 0.92 (s, 3H); HPLC purity: 100%; LCMS Calculated for $C_{23}H_{30}N_2O_3S$: 414.56; Observed: 414.24 [M − H]$^-$. |

Example A42

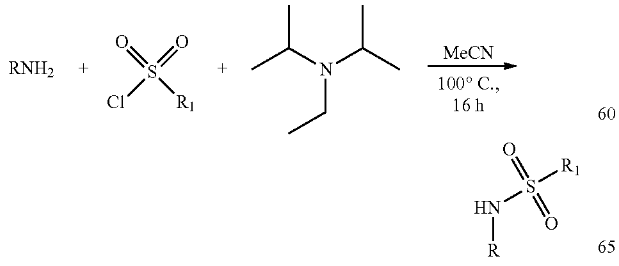

General Procedure for Synthesis of Aminobenzyl Series Compounds Method B

Sulfonyl chloride (1.1 eq) was added to the vial containing DIPEA (2.2 eq), aniline (1 eq) and acetonitrile (1 mL). The reaction mixture was heated at 50° C. with stirring for 16 h. After cooling to the room temperature the mixture was evaporated. The residue was dissolved in DMSO (2 mL), filtered from non-soluble impurities if there were any. The resulting filtrate was subjected to HPLC purification (deionized water/HPLC-grade methanol (acetonitrile)).

The following examples were prepared using method B:

| Compound No. | Structure | Analytical data |
| --- | --- | --- |
| A-417 | 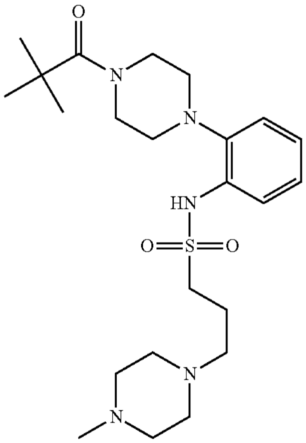 [SMILES: CN1CCN(CCCS(=O)(=O)Nc2ccccc2N2CCN(C(=O)C(C)(C)C)CC2)CC1] | Yield: 48.1 mg, 30.6%; Appearance: Orange oil; $^{1}$H NMR (400 MHz, DMSO-$d_6$) δ 8.35 (s, 1H), 7.39 (dd, J = 7.6, 1.8 Hz, 1H), 7.18 (dd, J = 7.4, 2.0 Hz, 1H), 7.09 (tt, J = 8.0, 6.4 Hz, 2H), 3.77 (t, J = 4.8 Hz, 4H), 3.23 (t, J = 7.7 Hz, 2H), 3.02-2.38 (m, 17H, and signals of solvent and water), 1.93 (s, 2H), 1.26 (s, 9H); HPLC purity: 100%; LCMS Calculated for $C_{23}H_{39}N_5O_3S$: 465.66; Observed: 465.33 $[M - H]^-$. |
| A-565 | 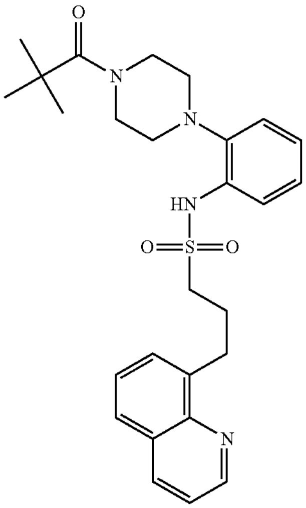 | Yield: 32.8 mg, 20.8%; Appearance: Violet solid; $^{1}$H NMR (400 MHz, DMSO-$d_6$) δ 8.72 (dd, J = 4.1, 1.8 Hz, 1H), 8.28 (dd, J = 8.4, 1.8 Hz, 1H), 8.06 (s, 1H), 7.95 (d, J = 7.6 Hz, 1H), 7.88 (d, J = 7.0 Hz, 1H), 7.61 (t, J = 7.7 Hz, 1H), 7.51-7.41 (m, 2H), 7.13-6.95 (m, 3H), 5.32 (s, 2H), 3.59 (s, 4H), 2.58 (t, J = 4.8 Hz, 4H), 1.23 (s, 9H); HPLC purity: 100%; LCMS Calculated for $C_{25}H_{30}N_4O_3S$: 466.6; Observed: 466.24 $[M - H]^-$. |
| A-566 | 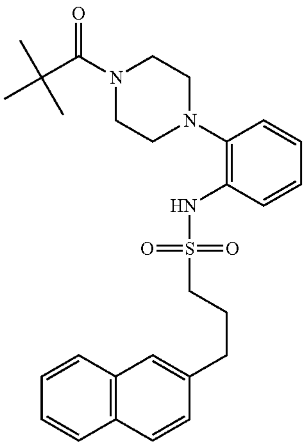 | Yield: 5.8 mg, 3.69% yield; Appearance: Beige solid; $^{1}$H NMR (600 MHz, DMSO-$d_6$) δ 8.30 (s, 1H), 7.92-7.86 (m, 2H), 7.86-7.81 (m, 1H), 7.79 (d, J = 1.9 Hz, 1H), 7.55-7.47 (m, 3H), 7.43 (dd, J = 8.4, 1.7 Hz, 1H), 131 (d, J = 2.2 Hz, 1H), 7.19 (dd, J = 13, 2.1 Hz, 1H), 7.11-7.03 (m, 3H), 4.78 (s, 2H), 3.45 (t, J = 4.7 Hz, 4H), 2.58 (t, J = 4.8 Hz, 4H), 1.13 (s, 9H); HPLC purity: 96.69%; LCMS Calculated for $C_{26}H_{31}N_3O_3S$: 465.61; Observed: 465.25 $[M - H]^-$. |

-continued

| Compound No. | Structure | Analytical data |
|---|---|---|
| A-595 | 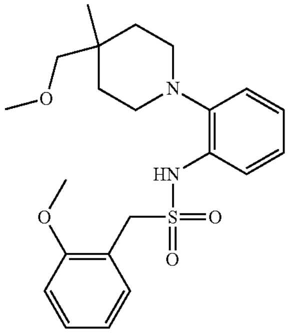 [SMILES: COCC1(C)CCN(c2ccccc2NS(=O)(=O)Cc2ccccc2OC)CC1] | Yield: 23.6 mg, 15.0%; Appearance: Brown oil; $^1H$ NMR (600 MHz, DMSO-$d_6$) δ 7.92 (s, 1H), 7.34-7.25 (m, 3H), 7.23 (dd, J = 7.6, 1.7 Hz, 1H), 7.10-7.01 (m, 2H), 6.97-6.88 (m, 2H), 4.59-4.56 (m, 2H), 3.52 (s, 3H), 3.09 (s, 2H), 2.72-2.59 (m, 4H), 1.55-1.48 (m, 2H), 1.32-1.25 (m, 2H), 0.93 (s, 3H); HPLC purity: 98.85%; LCMS Calculated for $C_{22}H_{30}N_2O_4S$: 418.55; Observed: 418.23 $[M - H]^-$. |
| A-582 | 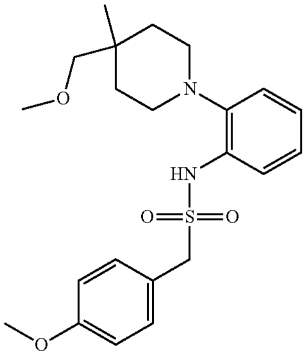 [SMILES: COCC1(C)CCN(c2ccccc2NS(=O)(=O)Cc2ccc(OC)cc2)CC1] | Yield: 35.5 mg, 22.6%; Appearance: Yellow oil; $^1H$ NMR (400 MHz, DMSO-$d_6$) δ 7.73 (s, 1H), 7.34 (dd, J = 7.8, 1.7 Hz, 1H), 7.20 (dd, J = 7.7, 1.8 Hz, 1H), 7.12-6.98 (m, 4H), 6.81 (d, J = 8.6 Hz, 2H), 4.39 (s, 2H), 3.77 (s, 3H), 3.31 (s, 3H), 3.12 (s, 2H), 2.77-2.63 (m, 4H), 1.61-1.49 (m, 2H), 1.34 (d, J = 13.1 Hz, 2H), 0.98 (s, 3H); HPLC purity: 96.7%; LCMS Calculated for $C_{22}H_{30}N_2O_4S$: 418.55; Observed: 418.23 $[M - H]^-$. |
| A-597 | 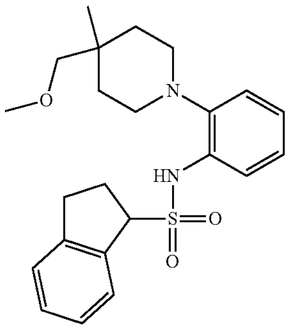 [SMILES: COCC1(C)CCN(c2ccccc2NS(=O)(=O)C2CCc3ccccc32)CC1] | Yield: 15.6 mg, 9.93%; Appearance: Brown solid; $^1H$ NMR (600 MHz, DMSO-$d_6$) δ 8.14 (s, 1H), 7.34-7.25 (m, 5H), 7.23-7.16 (m, 1H), 7.10-7.02 (m, 2H), 4.94 (dd, J = 9.0, 2.6 Hz, 1H), 3.25 (s, 3H), 3.12 (s, 2H), 3.01-2.92 (m, 1H), 2.89-2.81 (m, 1H), 2.78-2.69 (m, 3H), 2.71-2.64 (m, 1H), 2.55-2.49 (m, 1H), 2.45-2.38 (m, 1H), 1.64-1.52 (m, 2H), 1.37-1.30 (m, 2H), 0.95 (s, 3H); HPLC purity: 98.9%; LCMS Calculated for $C_{23}H_{30}N_2O_3S$: 414.56; Observed: 414.24 $[M - H]^-$. |

Example A43

General Procedure for Synthesis of Aminobenzyl Series Compounds—Method C

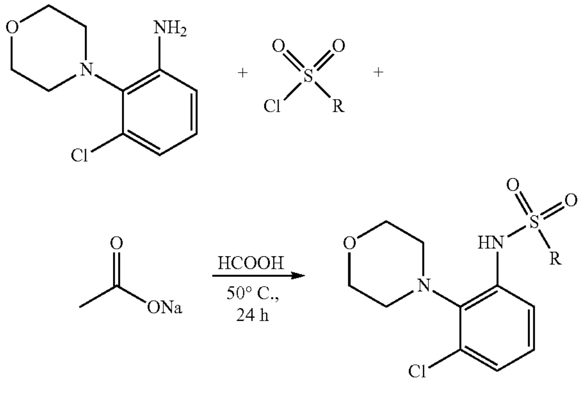

Sulfonyl chloride (1 eq) was added to the vial containing aniline (1 eq) and sodium acetate (1.1 eq) in acetic acid (0.5 mL). The reaction mixture was heated at 50° C. with stirring for 24 h. After cooling to the room temperature the mixture was evaporated. The residue was dissolved in DMSO (2 mL), filtered from non-soluble impurities if there were any. The resulting filtrate was subjected to HPLC purification (deionized water/HPLC-grade methanol (acetonitrile)).

The following example was prepared using method C:

| Compound No. | Structure | Analytical data |
|---|---|---|
| A-391 | 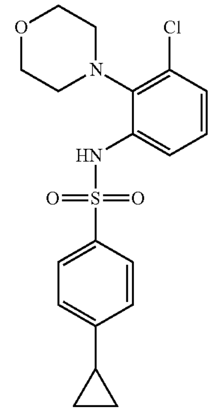 [SMILES: O=S(=O)(Nc1cccc(Cl)c1N1CCOCC1)c1ccc(C2CC2)cc1] | Yield: 32.8 mg, 15.2%; Appearance: Beige solid; $^1H$ NMR (400 MHz, DMSO-$d_6$) δ 8.99 (s, 1H), 7.58 (d, J = 8.5 Hz, 2H), 7.31 (dd, J = 6.6, 3.1 Hz, 1H), 7.22 (d, J = 8.1 Hz, 2H), 7.19-7.14 (m, 2H), 3.61 (t, J = 4.5 Hz, 4H), 3.31-3.22 (m, 2H), 2.13 (s, 2H), 1.96 (tt, J = 8.6, 5.0 Hz, 1H), 1.07-0.97 (m, 2H), 0.75-0.67 (m, 2H); HPLC purity: 100%; LCMS Calculated for $C_{19}H_{21}ClN_2O_3S$: 392.90; Observed: 392.12 $[M - H]^-$. |

Example A44

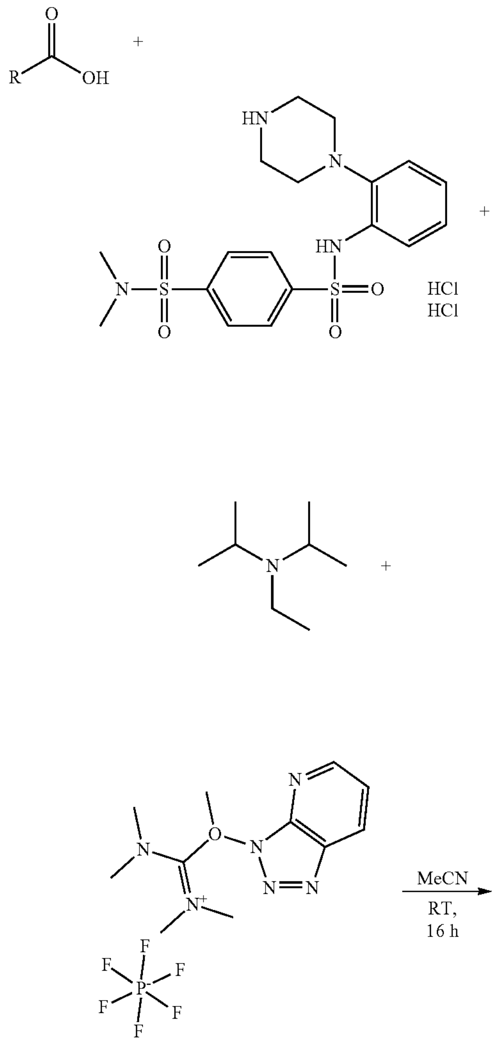

-continued

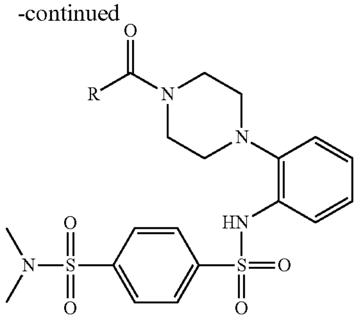

General Procedure for Synthesis of Aminobenzyl Series Compounds Method D

The vial was charged with amine (1 eq), acid (1.2-1.3 eq), and DIPEA (6.5 eq). Then HATU (1.16 eq) was added in one portion. The reaction mixture was stirred overnight at room temperature. The solvent was evaporated and the residue was dissolved in DMSO (2 mL), filtered from non-soluble impurities if there were any. The resulting filtrate was subjected to HPLC purification (deionized water/HPLC-grade methanol (acetonitrile)).

The following examples were prepared using method D:

| Compound No. | Structure | Analytical data |
|---|---|---|
| A-425 | 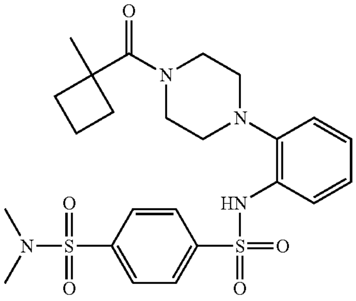 [SMILES: CN(C)S(=O)(=O)c1ccc(S(=O)(=O)Nc2ccccc2N2CCN(C(=O)C3(C)CCC3)CC2)cc1] | Yield: 49.3 mg, 14.3%; Appearance: Yellow solid; $^1$H NMR (400 MHz, DMSO-$d_6$) δ 9.47 (s, 1H), 7.96 (q, J = 8.4 Hz, 5H), 7.32 (d, J = 6.7 Hz, 1H), 7.18-7.07 (m, 3H), 3.41 (s, 2H), 3.24 (s, 2H), 2.63 (s, 6H), 2.46-2.33 (m, 6H), 1.98-1.84 (m, 1H), 1.77 (t, J = 10.9 Hz, 2H), 1.62 (d, J = 10.6 Hz, 1H), 1.34 (s, 3H); HPLC purity: 100%; LCMS Calculated for $C_{24}H_{32}N_4O_5S_2$: 520.66; Observed: 520.21 [M − H]$^-$. |
| A-426 | 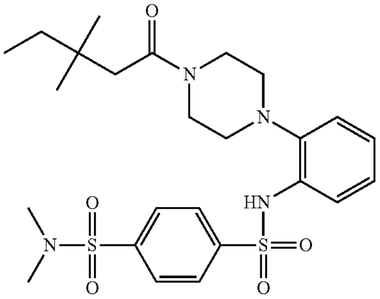 [SMILES: CCC(C)(C)CC(=O)N1CCN(c2ccccc2NS(=O)(=O)c2ccc(S(=O)(=O)N(C)C)cc2)CC1] | Yield: 71.4 mg, 45.5%; Appearance: Yellow solid; $^1$H NMR (400 MHz, DMSO-$d_6$) δ 9.25 (s, 1H), 8.03-7.83 (m, 4H), 7.39-7.32 (m, 1H), 7.10-7.03 (m, 3H), 3.53 (s, 4H), 2.68 (s, 6H), 2.58-2.52 (m, 2H, in the solvent signal), 2.44-2.37 (m, 2H), 2.16 (s, 2H), 1.37 (q, J = 7.5 Hz, 2H), 0.96 (s, 6H), 0.85 (t, J = 7.5 Hz, 3H); HPLC purity: 100%; LCMS Calculated for $C_{25}H_{36}N_4O_5S_2$: 536.71; Observed: 536.2 5 [M − H]$^-$. |
| A-427 | 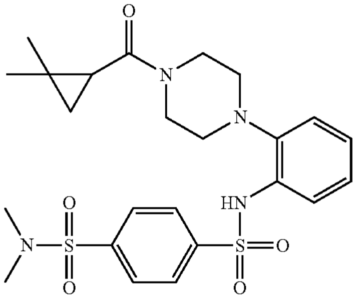 [SMILES: CN(C)S(=O)(=O)c1ccc(S(=O)(=O)Nc2ccccc2N2CCN(C(=O)C3CC3(C)C)CC2)cc1] | Yield: 72.8 mg, 46.6%; Appearance: Yellow solid; $^1$H NMR (400 MHz, DMSO-$d_6$) δ 9.48 (s, 1H), 8.03-7.91 (m, 4H), 7.31 (d, J = 7.5 Hz, 1H), 7.16-7.08 (m, 3H), 3.65-3.55 (m, 1H), 3.54-3.41 (m, 3H), 2.66-2.60 (m, 6H), 2.49-2.37 (m, 3H), 2.37-2.26 (m, 1H), 1.69 (t, J = 6.7 Hz, 1H), 1.15 (s, 3H), 0.95 (s, 3H), 0.94-0.87 (m, 1H), 0.67-0.59 (m, 1H); HPLC purity: 100%; LCMS Calculated for $C_{24}H_{32}N_4O_5S_2$: 520.66; Observed: 520.21 [M − H]$^-$. |
| A-428 | 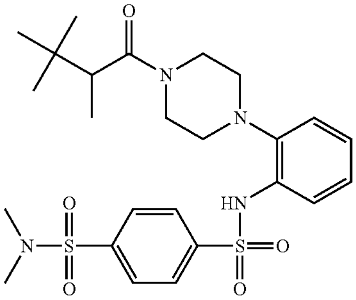 [SMILES: CC(C(=O)N1CCN(c2ccccc2NS(=O)(=O)c2ccc(S(=O)(=O)N(C)C)cc2)CC1)C(C)(C)C] | Yield: 57.7 mg, 36.7%; Appearance: Yellow solid; $^1$H NMR (400 MHz, DMSO-$d_6$) δ 9.26 (s, 1H), 8.00 (d, J = 8.2 Hz, 2H), 7.88 (d, J = 8.2 Hz, 2H), 7.35 (dd, J = 6.9, 2.4 Hz, 1H), 7.11-7.02 (m, 3H), 3.65-3.58 (m, 2H), 3.59-3.43 (m, 3H), 2.76-2.64 (m, 7H, ), 2.60-2.51 (m, 3H), 2.44-2.31 (m, 2H), 1.17-0.85 (m, 12H); HPLC purity: 97.77%; LCMS Calculated for $C_{25}H_{36}N_4O_5S_2$: 536.71; Observed: 536.25 [M − H]$^-$. |
| A-429 | 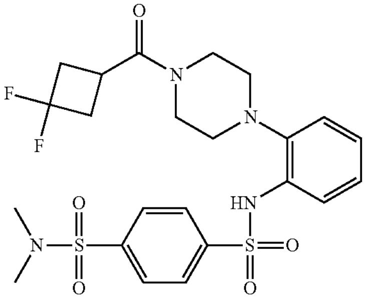 [SMILES: CN(C)S(=O)(=O)c1ccc(S(=O)(=O)Nc2ccccc2N2CCN(C(=O)C3CC(F)(F)C3)CC2)cc1] | Yield: 33.9 mg, 21.4%; Appearance: Yellow solid; $^1$H NMR (400 MHz, DMSO-$d_6$) δ 9.51 (s, 1H), 8.03-7.90 (m, 4H), 7.29 (d, J = 7.5 Hz, 1H), 7.17-7.06 (m, 3H), 3.48-3.43 (m, 2H), 3.43-3.36 (m, 2H), 3.29-3.20 (m, 1H), 2.78 (dt, J = 15.9, 9.5 Hz, 4H), 2.63 (s, 6H), 2.54 (s, 2H), 2.39 (t, J = 4.7 Hz, 2H); HPLC purity: 100%; LCMS Calculated for $C_{23}H_{28}F_2N_4O_5S_2$: 542.62; Observed: 542.17 [M − H]$^-$. |

-continued

| Compound No. | Structure | Analytical data |
|---|---|---|
| A-430 | 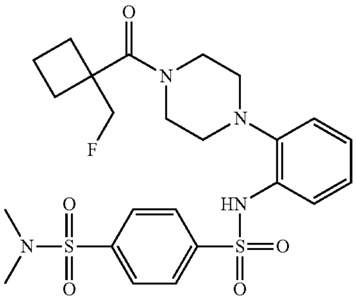 [SMILES: CN(C)S(=O)(=O)c1ccc(S(=O)(=O)Nc2ccccc2N2CCN(C(=O)C3(CF)CCC3)CC2)cc1] | Yield: 42.3 mg, 26.7%; Appearance: Beige solid; $^1$H NMR (400 MHz, DMSO-d$_6$) δ 9.25 (s, 1H), 7.98 (d, J = 8.5 Hz, 2H), 7.87 (d, J = 8.5 Hz, 2H), 7.36 (d, J = 6.8 Hz, 1H), 7.07 (dd, J = 6.3, 3.9 Hz, 3H), 4.62 (s, 1H), 4.50 (s, 1H), 3.51 (s, 2H), 3.31 (s, 2H), 2.68 (s, 6H), 2.46-2.36 (m, 6H), 2.06-1.98 (m, 2H), 2.00-1.87 (m, 1H), 1.79-1.72 (m, 1H); HPLC purity: 100%; LCMS Calculated for $C_{24}H_{31}FN_4O_5S_2$: 538.65; Observed: 538.2 [M − H]$^-$. |
| A-431 | 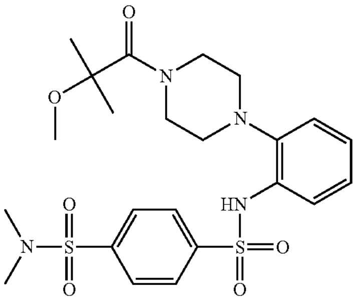 [SMILES: COC(C)(C)C(=O)N1CCN(c2ccccc2NS(=O)(=O)c2ccc(S(=O)(=O)N(C)C)cc2)CC1] | Yield: 61.8 mg, 39.6%; Appearance: Yellow solid; $^1$H NMR (400 MHz, DMSO-d$_6$) δ 9.25 (s, 1H), 7.99 (d, J = 8.2 Hz, 2H), 7.88 (d, J = 8.4 Hz, 2H), 7.41-7.33 (m, 1H), 7.12-7.04 (m, 3H), 3.95 (s, 2H), 3.55 (s, 2H), 3.18 (s, 3H), 3.02 (s, 3H), 2.68 (s, 6H), 2.55 (d, J = 10.4 Hz, 2H, in the solvent signal), 2.44 (d, J = 13.9 Hz, 2H, in the solvent signal), 1.35 (s, 6H); HPLC purity: 100%; LCMS Calculated for $C_{23}H_{32}N_4O_6S_2$: 524.65; Observed: 524.2 [M − H]$^-$. |
| A-432 | 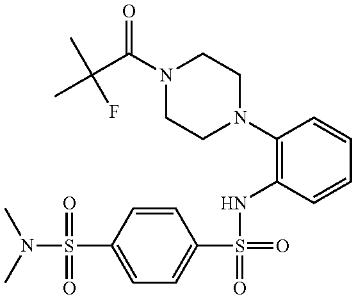 [SMILES: CN(C)S(=O)(=O)c1ccc(S(=O)(=O)Nc2ccccc2N2CCN(C(=O)C(C)(C)F)CC2)cc1] | Yield: 38.4 mg, 24.2%; Appearance: Yellow solid; $^1$H NMR (400 MHz, DMSO-d$_6$) δ 9.51 (s, 1H), 7.96 (q, J = 8.3 Hz, 5H), 7.37-7.30 (m, 1H), 7.18-7.08 (m, 3H), 3.67 (s, 2H), 3.49 (s, 2H), 2.62 (s, 6H), 1.54 (d, J = 21.9 Hz, 6H); HPLC purity: 100%; LCMS Calculated for $C_{22}H_{29}FN_4O_5S_2$: 512.62; Observed: 512.18 [M − H]$^-$. |
| A-487 | 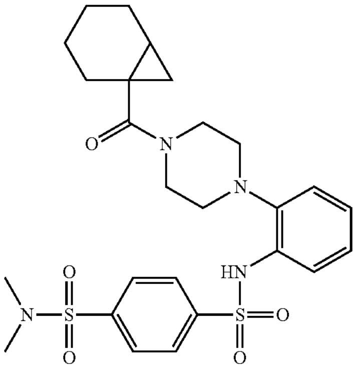 [SMILES: CN(C)S(=O)(=O)c1ccc(S(=O)(=O)Nc2ccccc2N2CCN(C(=O)C34CCCCC3C4)CC2)cc1] | Yield: 4.5 mg, 2.86%; Appearance: Yellow solid; $^1$H NMR (600 MHz, DMSO-d$_6$) δ 9.45 (s, 1H), 7.99-7.88 (m, 4H), 7.30 (dd, J = 7.7, 1.6 Hz, 1H), 7.16-7.06 (m, 3H), 3.44 (s, 4H), 2.60 (s, 6H), 2.37 (d, J = 20.2 Hz, 4H), 1.82-1.76 (m, 2H), 1.75-1.67 (m, 1H), 1.65-1.58 (m, 1H), 1.30-1.24 (m, 2H), 1.23-1.15 (m, 2H), 1.13-1.04 (m, 1H), 0.84 (dd, J = 9.4, 4.5 Hz, 1H), 0.47 (dd, J = 62, 4.5 Hz, 1H); HPLC purity: 100%; LCMS Calculated for $C_{26}H_{34}N_4O_5S_2$: 546.7; Observed: 546.23 [M − H]$^-$. |
| A-476 | 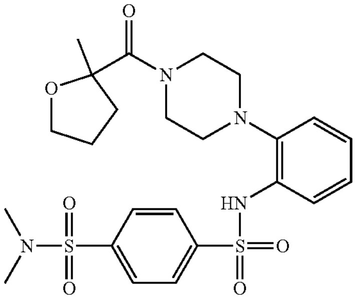 [SMILES: CN(C)S(=O)(=O)c1ccc(S(=O)(=O)Nc2ccccc2N2CCN(C(=O)C3(C)CCCO3)CC2)cc1] | Yield: 62.5 mg, 39.7%; Appearance: Yellow solid; $^1$H NMR (400 MHz, DMSO-d$_6$) δ 9.49 (s, 1H), 7.96 (q, J = 8.3, 7.8 Hz, 4H), 7.34 (d, J = 7.3 Hz, 1H), 7.18-7.09 (m, 3H), 3.97-3.80 (m, 2H), 3.69 (q, J = 7.5 Hz, 2H), 3.51 (s, 1H), 3.46-3.36 (m, 1H), 2.63 (s, 6H), 2.41 (s, 4H), 1.90-1.45 (m, 4H), 1.36 (s, 3H); HPLC purity: 100%; LCMS Calculated for $C_{24}H_{32}N_4O_6S_2$: 536.66; Observed: 536.2 [M − H]$^-$. |

-continued

| Compound No. | Structure | Analytical data |
|---|---|---|
| A-478 | 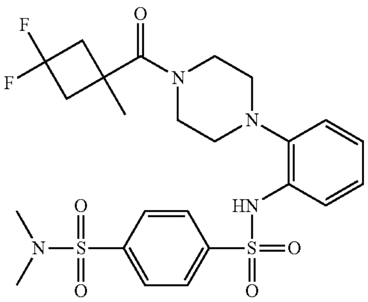 [SMILES: CN(C)S(=O)(=O)c1ccc(S(=O)(=O)Nc2ccccc2N2CCN(C(=O)C3(C)CC(F)(F)C3)CC2)cc1] | Yield: 18.5 mg, 11.7%; Appearance: Orange solid; $^{1}$H NMR (500 MHz, DMSO-$d_6$) δ 9.51 (s, 1H), 8.02-7.92 (m, 4H), 7.30 (dd, J = 7.7, 1.8 Hz, 1H), 7.14 (dddd, J = 19.8, 9.8, 7.6, 1.9 Hz, 3H), 3.45 (s, 2H), 3.29 (s, 2H, in the solvent signal), 3.02 (q, J = 14.3 Hz, 3H), 2.63 (s, 6H), 2.59-2.52 (m, 4H, in the solvent signal), 2.39 (s, 2H), 1.40 (s, 3H); HPLC purity: 100%; LCMS Calculated for $C_{24}H_{30}F_2N_4O_5S_2$: 556.64; Observed: 556., 19 [M − H]$^-$. |
| A-459 | 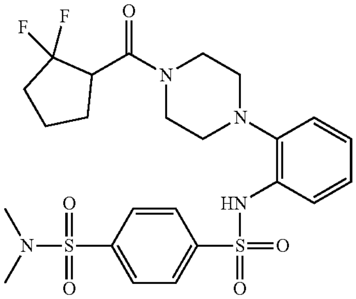 [SMILES: CN(C)S(=O)(=O)c1ccc(S(=O)(=O)Nc2ccccc2N2CCN(C(=O)C3CCCC3(F)F)CC2)cc1] | Yield: 38.4 mg, 24.2%; Appearance: Beige solid; $^{1}$H NMR (400 MHz, DMSO-$d_6$) δ 9.51 (s, 1H), 8.04-7.90 (m, 4H), 7.32 (d, J = 6.3 Hz, 1H), 7.17-7.07 (m, 3H), 3.65 (d, J = 14.2 Hz, 2H), 3.55 (s, 2H), 3.46 (s, 1H), 2.62 (s, 6H), 2.58-2.54 (m, 2H), 2.47-2.29 (m, 2H), 2.29-1.96 (m, 3H), 1.83 (s, 2H), 1.74-1.61 (m, 1H); HPLC purity: 95.3%; LCMS Calculated for $C_{24}H_{30}F_2N_4O_5S_2$: 556.64; Observed: 556.19 [M − H]$^-$. |
| A-460 | 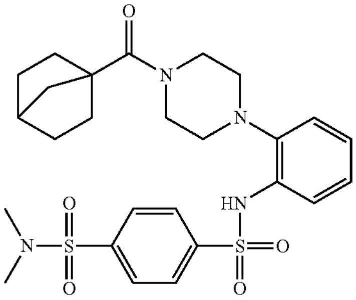 [SMILES: CN(C)S(=O)(=O)c1ccc(S(=O)(=O)Nc2ccccc2N2CCN(C(=O)C34CCC(CC3)C4)CC2)cc1] | Yield: 37.2 mg, 23.6%; Appearance: Beige solid; $^{1}$H NMR (400 MHz, DMSO-$d_6$) δ 9.49 (s, 1H), 8.03-7.91 (m, 4H), 7.32 (d, J = 7.1 Hz, 1H), 7.17-7.07 (m, 3H), 3.50 (s, 4H), 2.64 (d, J = 3.8 Hz, 6H), 2.40 (s, 4H), 2.10 (s, 1H), 1.66 (s, 6H), 1.57 (s, 2H), 1.34 (s, 2H); HPLC purity: 100%; LCMS Calculated for $C_{26}H_{34}N_4O_5S_2$: 546.7; Observed: 546.23 [M − H]$^-$. |
| A-448 | 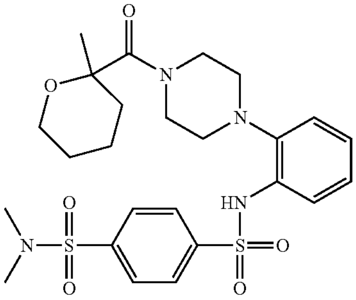 [SMILES: CN(C)S(=O)(=O)c1ccc(S(=O)(=O)Nc2ccccc2N2CCN(C(=O)C3(C)CCCCO3)CC2)cc1] | Yield: 16.5 mg, 8.04%; Appearance: Beige solid; $^{1}$H NMR (400 MHz, DMSO-$d_6$) δ 9.48 (s, 1H), 7.96 (q, J = 8.3 Hz, 4H), 7.33 (d, J = 6.7 Hz, 1H), 7.18-7.08 (m, 3H), 3.99 (s, 1H), 3.83-3.72 (m, 2H), 3.59-3.34 (m, 3H), 2.63 (s, 6H), 2.44 (s, 4H), 2.25 (d, J = 13.0 Hz, 1H), 1.62-1.35 (m, 4H), 1.27 (s, 3H), 1.19-1.09 (m, 1H); HPLC purity: 96.,97%; LCMS Calculated for $C_{25}H_{34}N_4O_6S_2$: 550.69; Observed: 550.22 [M − H]$^-$. |
| A-461 | 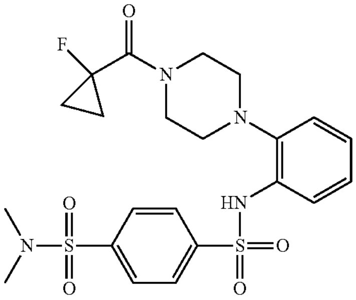 [SMILES: CN(C)S(=O)(=O)c1ccc(S(=O)(=O)Nc2ccccc2N2CCN(C(=O)C3(F)CC3)CC2)cc1] | Yield: 34.2 mg, 21.7%; Appearance: Beige solid; $^{1}$H NMR (400 MHz, DMSO-$d_6$) δ 9.54 (s, 1H), 7.97 (q, J = 8.3 Hz, 4H), 7.35 (d, J = 6.6 Hz, 1H), 7.19-7.10 (m, 3H), 3.58 (s, 4H), 2.62 (s, 6H), 2.49-2.41 (m, 4H, in the solvent signal), 1.34-1.09 (m, 4H); HPLC purity: 100%; LCMS Calculated for $C_{22}H_{27}FN_4O_5S_2$: 510.6; Observed: 510.16 [M − H]$^-$. |

-continued

| Compound No. | Structure | Analytical data |
| --- | --- | --- |
| A-462 | 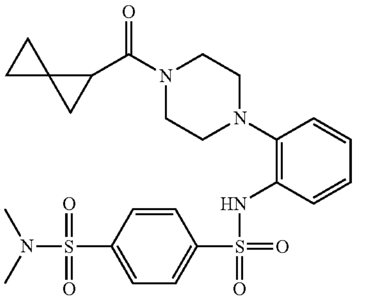 [SMILES: CN(C)S(=O)(=O)c1ccc(S(=O)(=O)Nc2ccccc2N2CCN(C(=O)C3CC34CC4)CC2)cc1] | Yield: 19.6 mg, 12.4%; Appearance: White solid; $^{1}H$ NMR (400 MHz, DMSO-$d_6$) δ 9.48 (s, 1H), 8.03-7.90 (m, 4H), 7.30 (d, J = 7.6 Hz, 1H), 7.20-7.04 (m, 3H), 3.49 (d, J = 45.0 Hz, 4H), 2.63 (s, 7H), 2.44-2.31 (m, 3H), 2.32-2.17 (m, 1H), 1.38 (t, J = 3.8 Hz, 1H), 1.21-1.14 (m, 1H), 0.93-0.86 (m, 1H), 0.85-0.73 (m, 2H), 0.70-0.63 (m, 1H); HPLC purity: 100%; LCMS Calculated for $C_{24}H_{30}N_4O_5S_2$: 518.65; Observed: 518.19 $[M-H]^-$. |
| A-463 | 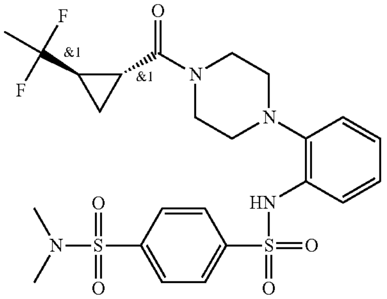 [SMILES: CN(C)S(=O)(=O)c1ccc(S(=O)(=O)Nc2ccccc2N2CCN(C(=O)[C@@H]3C[C@H]3C(C)(F)F)CC2)cc1] | Yield: 42.2 mg, 26.8%; Appearance: Yellow solid; $^{1}H$ NMR (400 MHz, DMSO-$d_6$) δ 9.47 (s, 1H), 7.99-7.87 (m, 4H), 7.28 (d, J = 7.5 Hz, 1H), 7.14-7.04 (m, 3H), 3.66 (s, 2H), 3.41 (s, 2H), 2.59 (s, 6H), 2.53 (s, 2H), 2.34 (s, 2H), 2.23-2.13 (m, 1H), 1.78 (s, 1H), 1.62 (t, J = 18.6 Hz, 3H), 1.05-0.98 (m, 1H), 0.99-0.91 (m, 1H); HPLC purity: 100%; LCMS Calculated for $C_{24}H_{30}F_2N_4O_5S_2$: 556.64; Observed: 556.19 $[M-H]^-$. |
| A-477 | 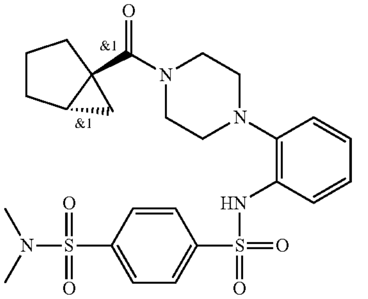 [SMILES: CN(C)S(=O)(=O)c1ccc(S(=O)(=O)Nc2ccccc2N2CCN(C(=O)[C@]34CCC[C@H]3C4)CC2)cc1] | Yield: 57.7 mg, 36.7%; Appearance: Yellow solid; $^{1}H$ NMR (400 MHz, DMSO-$d_6$) δ 9.26 (s, 1H), 7.99 (d, J = 8.4 Hz, 2H), 7.88 (d, J = 8.4 Hz, 2H), 7.37 (dd, J = 7.1, 2.4 Hz, 1H), 7.12-7.02 (m, 3H), 3.54 (s, 4H), 2.68 (s, 6H), 2.45 (d, J = 5.0 Hz, 4H), 1.95-1.66 (m, 5H), 1.59-1.52 (m, 1H), 1.32-1.22 (m, 1H), 0.74-0.62 (m, 2H); HPLC purity: 100%; LCMS Calculated for $C_{25}H_{32}N_4O_5S_2$: 532.67; Observed: 532.21 $[M-H]^-$. |
| A-449 | 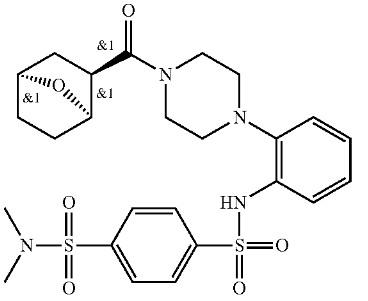 [SMILES: CN(C)S(=O)(=O)c1ccc(S(=O)(=O)Nc2ccccc2N2CCN(C(=O)[C@@H]3C[C@@H]4CC[C@H]3O4)CC2)cc1] | Yield: 43.4 mg, 27.6%; Appearance: Beige solid; $^{1}H$ NMR (400 MHz, DMSO-$d_6$) δ 9.52 (s, 1H), 8.04-7.91 (m, 4H), 7.30 (d, J = 7.5Hz, 1H), 7.16-7.06 (m, 3H), 4.65 (s, 1H), 4.52 (t, J = 5.1 Hz, 1H), 3.69-3.38 (m, 5H), 3.22-3.14 (m, 1H), 2.63 (s, 7H), 2.48-2.26 (m, 3H), 1.98 (dd, J = 11.5, 4.2 Hz, 1H), 1.71-1.66 (m, 1H), 1.58-1.53 (m, 1H), 1.48-1.40 (m, 2H); HPLC purity: 100%; LCMS Calculated for $C_{25}H_{32}N_4O_6S_2$: 548.67; Observed: 548.2 $[M-H]^-$. |

Example A45

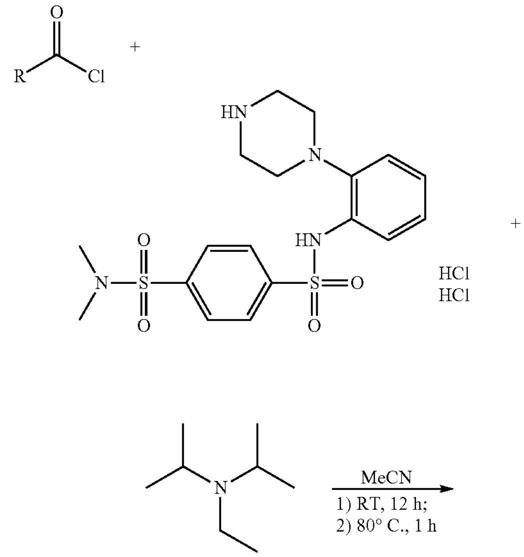

-continued

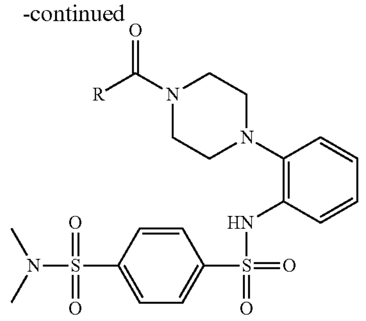

General Procedure for Synthesis of Aminobenzyl Series Compounds Method E

Amine (1.0 eq) was placed in a vial, dry acetonitrile (0.7 mL) and DIPEA (4.5 eq) were added followed by acid chloride (1.1 eq) addition. The reaction mixture was stirred for 12 h and then heated for 1 h at 80° C. After cooling to the room temperature the mixture was evaporated. The residue was dissolved in DMSO (2 mL), filtered from non-soluble impurities if there were any. The resulting filtrate was subjected to HPLC purification (deionized water/ HPLC-grade methanol (acetonitrile)).

The following examples were prepared using method E:

| Compound No. | Structure | Analytical data |
|---|---|---|
| A-444 | 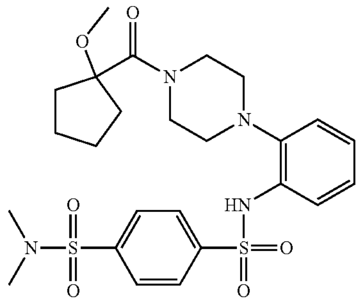 [SMILES: COC1(C(=O)N2CCN(c3ccccc3NS(=O)(=O)c3ccc(S(=O)(=O)N(C)C)cc3)CC2)CCCC1] | Yield: 59.7 mg, 34.5 Appearance: Beige solid; $^{1}H$ NMR (400 MHz, DMSO-$d_6$) δ 9.48 (s, 1H), 8.02-7.90 (m, 4H), 7.36-7.29 (m, 1H), 7.19-7.07 (m, 3H), 3.75 (s, 2H), 3.49 (s, 2H), 3.09 (s, 3H), 2.62 (s, 6H), 2.42 (s, 4H, in the solvent signal), 2.11-2.03 (m, 2H), 1.83-1.74 (m, 2H), 1.63-1.46 (m, 4H); HPLC purity: 100%; LCMS Calculated for $C_{25}H_{34}N_4O_6S_2$: 550.69; Observed: 550.22 $[M-H]^-$. |
| A-445 | 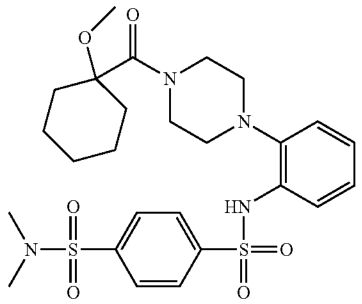 [SMILES: COC1(C(=O)N2CCN(c3ccccc3NS(=O)(=O)c3ccc(S(=O)(=O)N(C)C)cc3)CC2)CCCCC1] | Yield: 19.6 mg, 11.3%; Appearance: White solid; $^{1}H$ NMR (400 MHz, DMSO-$d_6$) δ 9.49 (s, 1H), 7.96 (q, J = 8.4 Hz, 4H), 7.33 (dd, J = 6.8, 1.9 Hz, 1H), 7.18-7.08 (m, 3H), 3.89 (s, 2H), 3.48 (s, 2H), 3.11 (s, 3H), 2.63 (s, 6H), 2.42 (s, 4H), 1.86 (d, J = 13.7 Hz, 2H), 1.69-1.39 (m, 7H), 1.21 (s, 1H); HPLC purity: 100%; LCMS Calculated for $C_{22}H_{27}BrFN_3O_3S$: 564.72; Observed: 564.24 $[M-H]^-$. |

-continued

| Compound No. | Structure | Analytical data |
|---|---|---|
| A-446 | 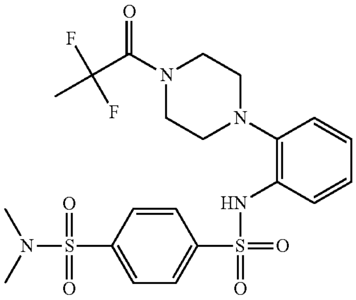 [SMILES: CN(C)S(=O)(=O)c1ccc(S(=O)(=O)Nc2ccccc2N2CCN(C(=O)C(C)(F)F)CC2)cc1] | Yield: 29.9 mg, 17.3%; Appearance: Yellow solid; $^1$H NMR (500 MHz, DMSO-$d_6$) δ 9.43 (s, 1H), 8.01-7.91 (m, 4H), 7.34 (dd, J = 6.4, 3.1 Hz, 1H), 7.19-7.08 (m, 3H), 3.62 (s, 2H), 3.53 (s, 1H), 2.62 (s, 6H), 2.48-2.42 (m, 4H, in the solvent signal), 1.80 (t, J = 20.1 Hz, 3H); HPLC purity: 100%; LCMS Calculated for $C_{21}H_{26}F_2N_4O_5S_2$: 516.58; Observed: 516.15 $[M - H]^-$. |
| A-458 | 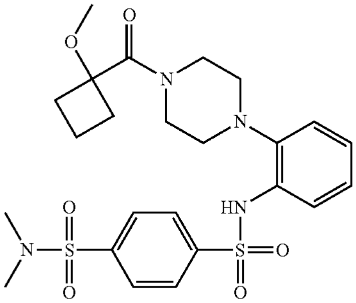 [SMILES: COC1(C(=O)N2CCN(c3ccccc3NS(=O)(=O)c3ccc(S(=O)(=O)N(C)C)cc3)CC2)CCC1] | Yield: 27.9 mg, 17.7%; Appearance: Beige solid; $^1$H NMR (400 MHz, DMSO-$d_6$) δ 9.46 (s, 1H), 8.02-7.90 (m, 4H), 7.33 (d, J = 7.2 Hz, 1H), 7.17-7.07 (m, 3H), 3.48 (s, 4H), 3.03 (s, 3H), 2.63 (s, 7H), 2.47-2.38 (m, 5H), 2.06 (q, J = 10.4 Hz, 2H), 1.78-1.68 (m, 1H), 1.52 (q, J = 9.1 Hz, 1H); HPLC purity: 100%; LCMS Calculated for $C_{24}H_{32}N_4O_6S_2$: 536.66; Observed: 536.2 $[M - H]^-$. |
| A-447 | 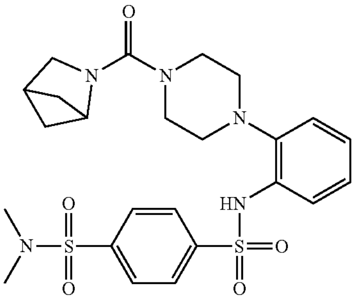 [SMILES: CN(C)S(=O)(=O)c1ccc(S(=O)(=O)Nc2ccccc2N2CCN(C(=O)N3CC4CC3C4)CC2)cc1] | Yield: 81.8 mg, 47.3%; Appearance: Beige solid; $^1$H NMR (400 MHz, DMSO-$d_6$) δ 9.41 (s, 1H), 8.03-7.91 (m, 4H), 7.30 (d, J = 7.6 Hz, 1H), 7.17-7.05 (m, 3H), 4.04 (d, J = 6.8 Hz, 1H), 3.34-3.27 (m, 4H, in the solvent signal), 3.22 (s, 2H), 2.79-2.72 (m, 1H), 2.63 (s, 6H), 2.45 (d, J = 4.9 Hz, 4H, in the solvent signal), 1.80 (s, 2H), 1.24-1.15 (m, 2H); HPLC purity: 100%; LCMS Calculated for $C_{24}H_{31}N_5O_5S_2$: 533.66; Observed: 533.2 $[M - H]^-$. |

Example A46: Synthesis of 4-(1-{[3-chloro-2-(morpholin-4-yl)phenyl]amino}-2,2,2-trifluoroethyl)-N,N-dimethylbenzene-1-sulfonamide (A-374)

-continued

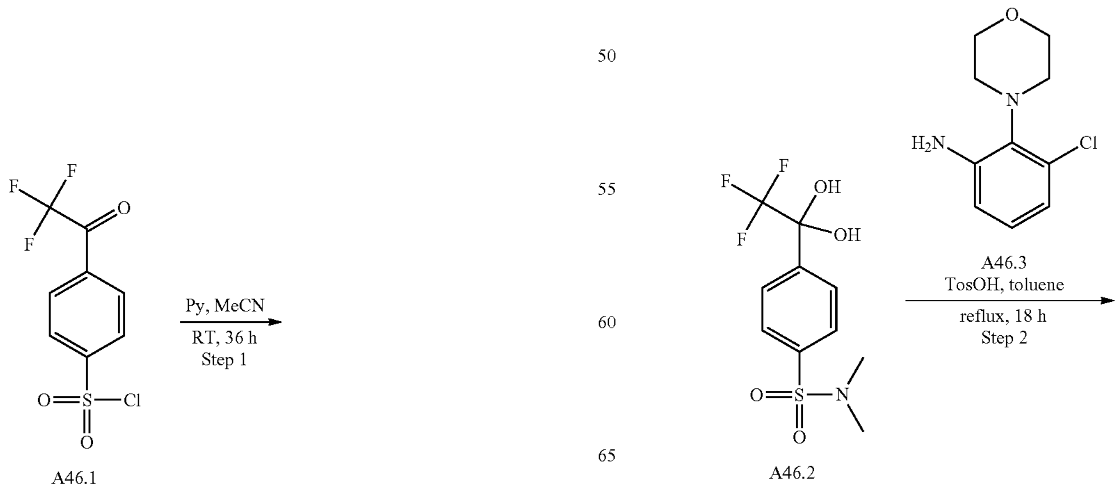

A46.1 A46.2

-continued

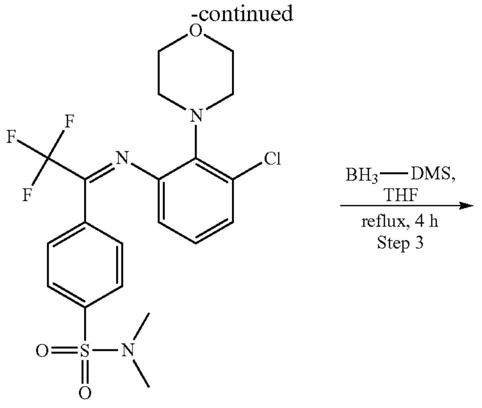

A46.4

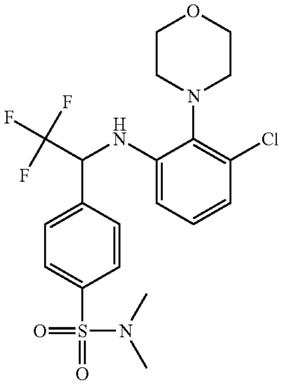

A374

Step-1: Synthesis of N,N-dimethyl-4-(2,2,2-trifluoro-1,1-dihydroxyethyl)benzenesulfonamide (A46.2)

Dimethylamine hydrochloride (0.298 g, 3.66 mmol) and pyridine (0.579 g, 7.32 mmol) were added at room temperature to a stirred solution of 4-(2,2,2-trifluoroacetyl)benzene-1-sulfonyl chloride (A46.1) (0.5 g, 1.83 mmol) in dry acetonitrile (5 mL). The resulting mixture was stirred at room temperature for 36 h. After completion of the reaction (TLC control), the reaction mixture was concentrated under reduced pressure, the residue was dissolved in water (10 mL) and chloroform (10 mL). The water layer was separated and extracted with chloroform (10 mL). The combined organic layers were washed with 1 M hydrogen chloride solution (10 mL×2), water (10 mL), dried over anhydrous sodium sulfate, filtered and concentrated under reduced pressure to afford N,N-dimethyl-4-(2,2,2-trifluoro-1,1-dihydroxyethyl)benzenesulfonamide (A46.2) (0.52 g, 1.73 mmol, 97% purity, 92.1% yield). This procedure was repeated to obtain enough material for next stages.

Step-2. Synthesis of (E)-4-(1-((3-chloro-2-morpholinophenyl)imino)-2,2,2-trifluoroethyl)-N,N-dimethylbenzenesulfonamide (A46.4)

Dry toluene (10 mL), 3-chloro-2-(morpholin-4-yl)aniline (A46.3) (0.808 g, 3.80 mmol), N,N-dimethyl-4-(2,2,2-trifluoro-1,1-dihydroxyethyl)benzenesulfonamide (A46.2) (0.95 g, 3.17 mmol), and 4-methylbenzenesulfonic acid hydrate (0.602 g, 3.17 mmol) were placed in a round-bottom flask equipped with Dean-Stark apparatus. The resulting mixture was stirred under reflux overnight. After cooling to room temperature the mixture was evaporated. The residue was dissolved with chloroform (10 mL), washed with saturated sodium hydrogencarbonate solution (10 mL×2), water (10 mL), dried over anhydrous sodium sulfate, filtered and evaporated to afford a crude (E)-4-(1-((3-chloro-2-morpholinophenyl)imino)-2,2,2-trifluoroethyl)-N,N-dimethylbenzenesulfonamide (A46.4) (0.7 g, 1.47 mmol, 95% purity, 44.3% yield).

Step-3. Synthesis of 4-(1-{[3-chloro-2-(morpholin-4-yl)phenyl]amino}-2,2,2-trifluoroethyl)-N,N-dimethylbenzene-1-sulfonamide (A-374)

Borane dimethylsulfide (0.334 g, 4.4 mmol) was added dropwise under Ar atmosphere to a stirred solution of (E)-4-(1-((3-chloro-2-morpholinophenyl)imino)-2,2,2-trifluoroethyl)-N,N-dimethylbenzene-sulfonamide (A46.4) (0.3 g, 0.630 mmol) in dry THF (5 mL). The resulting mixture was stirred under reflux for 4 h. After completion of the reaction (TLC control), the reaction mixture was cooled to room temperature and methanol (15 mL) was added dropwise. The resulting mixture was stirred for 15 min and then evaporated. The residue was diluted in 30% $K_2CO_3$ (20 mL) and ethyl acetate (15 mL). The water layer was separated and extracted with ethyl acetate (15 mL). The combined organic layers were dried over anhydrous sodium sulfate, filtered and concentrated under reduced pressure. The residue was purified by column chromatography to afford 4-(1-{[3-chloro-2-(morpholin-4-yl)phenyl]amino}-2,2,2-trifluoroethyl)-N,N-dimethylbenzene-1-sulfonamide (A-374). Yield: 300.0 mg, 94.6%; Appearance: Yellow oil; $^1$H NMR (400 MHz, Chloroform-d) δ 7.80 (d, J=8.0 Hz, 2H), 7.60 (d, J=8.0 Hz, 2H), 6.89 (t, J=8.1 Hz, 1H), 6.69 (dd, J=8.2, 1.4 Hz, 1H), 6.29 (d, J=8.0 Hz, 1H), 4.89 (q, J=7.0 Hz, 1H), 3.98 (d, J=11.0 Hz, 2H), 3.89-3.73 (m, 2H), 3.73-3.58 (m, 2H), 2.72 (s, 6H), 2.63 (d, J=11.2 Hz, 1H), 2.54 (d, J=11.8 Hz, 1H); HPLC purity: 100%; LCMS Calculated for $C_{20}H_{23}ClF_3N_3O_3S$: 477.93; Observed: 477.14 $[M-H]^-$.

Example A47: Synthesis of N-{3-chloro-2-[4-(4-chloro-2-fluorophenyl)piperidin-1-yl]phenyl}-2,3-dihydro-1H-indene-5-sulfonamide (A-373)

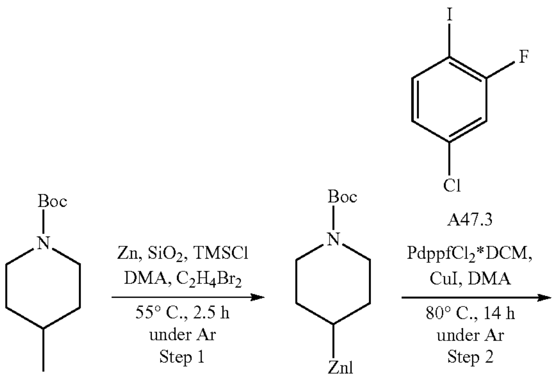

A47.1

A47.2

-continued

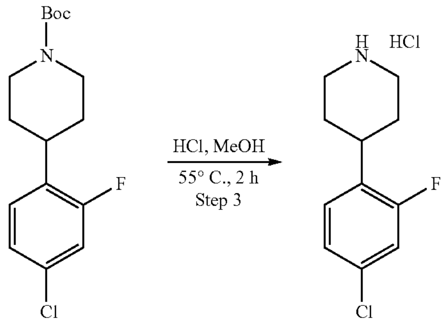

A47.4 A47.5

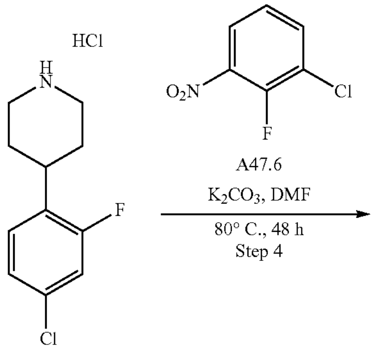

A47.5

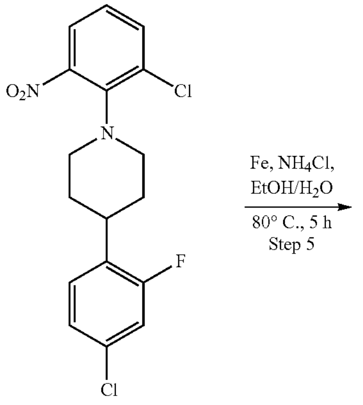

A47.7

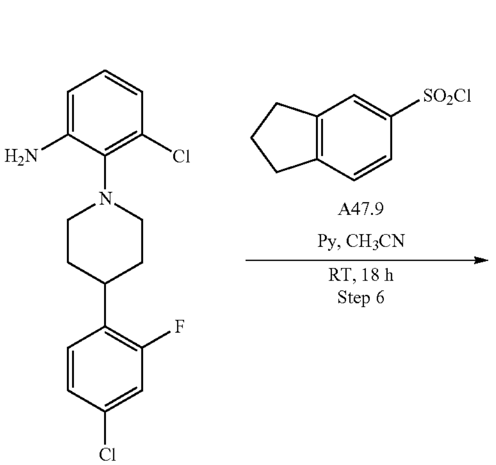

A47.8

-continued

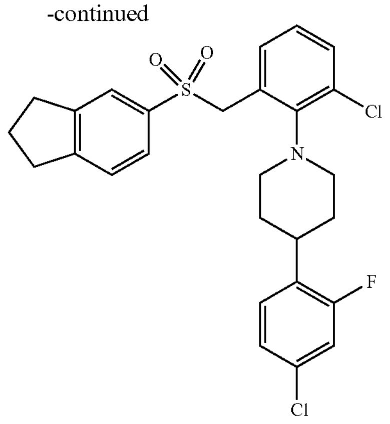

A-373

Step-1. Synthesis of {1-[(tert-butoxy)carbonyl]piperidin-4-yl}(iodo)zinc (A47.2)

Zinc powder (6.50 g, 99.5 mmol) and silica gel (1.2 g) were suspended in anhydrous DMA (32 mL) under Ar atmosphere, and then the 2 mL of 7:5 v/v mixture of TMSCl (0.998 g, 9.18 mmol)/1,2-dibromoethane was added at a rate to maintain the temperature below 60° C. The resulting slurry was stirred for additional 15 min before the solution of tert-butyl 4-iodopiperidine-1-carboxylate (A47.1) (25 g, 80.3 mmol) in dry DMA (40 mL) was added dropwise at a rate to maintain a temperature below 60° C. The mixture was stirred at 55° C. for 2.5 h and then allowed to sedimentate for 72 h. The organic layer was cannulated under Ar atmosphere and the concentration of {1-[(tert-butoxy)carbonyl]piperidin-4-yl}(iodo)zinc (A47.2) was determined by titration (0.69 M, 86 mL, 59.3 mmol, 74% yield).

Step-2. Synthesis of crude tert-butyl 4-(4-chloro-2-fluorophenyl)piperidine-1-carboxylate (A47.4)

4-chloro-2-fluoro-1-iodobenzene (A47.3) (10 g, 38.9 mmol), [1,1'-bis(diphenylphosphino)ferrocene]dichloropalladium(II)-dichloromethane complex (1.27 g, 1.56 mmol) and copper(I) iodide (0.6 g, 3.15 mmol) were added under Ar atmosphere to a stirred solution of {1-[(tert-butoxy)carbonyl]piperidin-4-yl}(iodo)zinc (0.69 M, 72 mL, 49.68 mmol) in dry DMA (72 mL). The resulting mixture was stirred at 80° C. for 14 h and cooled to room temperature. After the reaction was quenched with 25% $K_2CO_3$ solution (250 mL) and diluted with MTBE (180 mL). The organic layer was separated and the aqueous layer was extracted with MTBE (150 mL). The combined organic layers were washed with 5% $NH_4OH$ (150 mL), water (150 mL), dried over anhydrous $K_2CO_3$, filtered and concentrated under reduced pressure. The residue was purified by silica gel chromatography (ethyl acetate/hexane) to give crude tert-butyl 4-(4-chloro-2-fluorophenyl)piperidine-1-carboxylate (A47.4) (11.2 g, 26.7 mmol, 75% purity, 70% yield) that was used in next step without further purification.

Step-3. Synthesis of 4-(4-chloro-2-fluorophenyl)piperidine Hydrochloride (A47.5)

12 M HCl solution (130 mL) was added at room temperature to a stirred solution of crude tert-butyl 4-(4-chloro- 2-fluorophenyl)piperidine-1-carboxylate (A47.4) (11.2 g, 74% purity by LCMS) in methanol (130 mL). The resulting mixture was stirred for 2 h at 55° C. After completion (TLC control) of the reaction, the reaction mixture was extracted with chloroform (130 mL×2), water layer was separated and concentrated under reduced pressure. The residue was washed with acetonitrile (50 mL) to afford the crude 4-(4-chloro-2-fluorophenyl)piperidine hydrochloride (A47.5) (7.2 g, 0.959 mmol, 75% purity, 95.2% yield) which was used in the next step without further purification.

Step-4. Synthesis of 4-(4-chloro-2-fluorophenyl)-1-(2-chloro-6-nitrophenyl)piperidine (A47.7)

1-chloro-2-fluoro-3-nitrobenzene (A47.6) (0.921 g, 3.94 mmol) and potassium carbonate (1.23 g, 8.97 mmol) were added to a stirred solution of 4-(4-chloro-2-fluorophenyl) piperidine hydrochloride (0.9 g, 2.69 mmol, 75% purity) in dry DMF (10 mL). The reaction mixture was heated at 80° C. for 48 h. After completion of the reaction (TLC control), the reaction mixture was concentrated under reduced pressure, the residue was dissolved in water (20 mL) and ethyl acetate (15 mL). The water layer was separated and extracted with ethyl acetate (15 mL). The combined organic layers were dried over anhydrous sodium sulfate, filtered and concentrated under reduced pressure. The crude product was purified by silica gel column chromatography (chloroform) to afford 4-(4-chloro-2-fluorophenyl)-1-(2-chloro-6-nitrophenyl)piperidine (A47.7) (0.45 g, 1.21 mmol, 95% purity, 43% yield).

Step-5. Synthesis of 3-chloro-2-[4-(4-chloro-2-fluorophenyl)piperidin-1-yl]aniline (A47.8)

Iron powder (0.337 g, 6.05 mmol) and ammonium chloride (0.323 g, 6.05 mmol) were added to a stirred solution of 4-(4-chloro-2-fluorophenyl)-1-(2-chloro-6-nitrophenyl)piperidine (A47.7) (0.45 g, 1.21 mmol) in mixture of ethanol (15 mL) and water (4.5 mL) at room temperature. The resulting reaction mixture was heated at 80° C. for 5 h. After completion of the reaction (TLC control), the reaction mixture was cooled to room temperature, filtered, and the filtrate was evaporated. The residue was dissolved with water (10 mL) and chloroform (10 mL). The organic layer was separated, dried over anhydrous sodium sulfate, filtered, and evaporated under reduced pressure. The crude product was purified by silica gel column chromatography (chloroform) to afford 3-chloro-2-[4-(4-chloro-2-fluorophenyl)piperidin-1-yl]aniline (A47.8) (0.29 g, 0.854 mmol, 95% purity, 67% yield).

Step-6. Synthesis of N-{3-chloro-2-[4-(4-chloro-2-fluorophenyl)piperidin-1-yl]phenyl}-2,3-dihydro-1H-indene-5-sulfonamid (A-373)

Pyridine (0.168 g, 2.131 mmol) was added to a stirred solution of 3-chloro-2-[4-(4-chloro-2-fluorophenyl)piperidin-1-yl]aniline (A47.8) (0.29 g, 0.854 mmol) and 2,3-dihydro-1H-indene-5-sulfonyl chloride (A47.9) (0.203 g, 0.939 mmol) in dry acetonitrile (5 mL), at room temperature. The reaction was stirred at room temperature overnight. After completion of the reaction (TLC control), the reaction mixture was concentrated under reduced pressure to dryness. The residue was purified by prep HPLC (deionized water/HPLC-grade methanol) to afford N-{3-chloro-2-[4-(4-chloro-2-fluorophenyl)piperidin-1-yl]phenyl}-2,3-dihydro-1H-indene-5-sulfonamide (A-373). Yield: 116.0 mg, 24.8%; Appearance: White solid; $^1$H NMR (400 MHz, DMSO-$d_6$) δ 8.77 (s, 1H), 7.69 (s, 1H), 7.62-7.26 (m, 6H), 7.26-7.16 (m, 1H), 7.11 (d, J=8.0 Hz, 1H), 2.96-2.73 (m, 5H), 2.66 (s, 1H), 2.32-2.18 (m, 2H), 2.11-1.74 (m, 5H), 1.63 (d, J=11.9 Hz, 2H); HPLC purity: 100%; LCMS Calculated for $C_{26}H_{25}Cl_2FN_2O_2S$: 519.46; Observed: 518.14 $[M-H]^-$.

Example A48: Synthesis of N-{3-chloro-2-[4-(4-chloro-2-fluorophenyl)piperidin-1-yl]phenyl}-2,3-dihydro-1H-indene-5-sulfonamide (A-375)

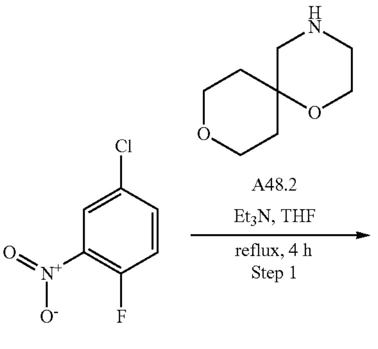

A48.1

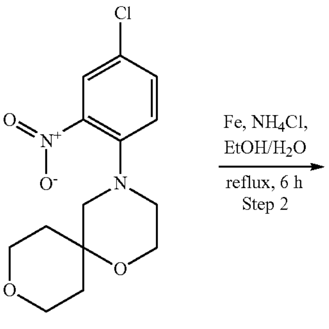

A48.3

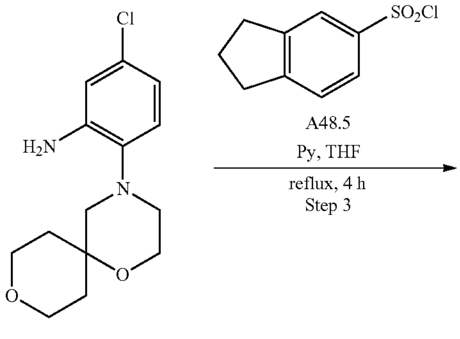

A48.4

-continued

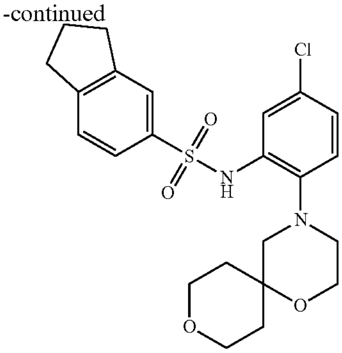

A-375

Step-1. Synthesis of 4-(4-chloro-2-nitrophenyl)-1,9-dioxa-4-azaspiro[5.5]undecane (A48.3)

4-chloro-1-fluoro-2-nitrobenzene (A48.1) (1 g, 5.69 mmol) was added to a stirred solution of 1,9-dioxa-4-azaspiro[5.5]undecane (A48.2) (0.9 g, 5.72 mmol) and triethylamine (0.863 g, 8.52 mmol) in dry THF (20 mL). The mixture was refluxed until the reaction completion (TLC control) and concentrated under the reduced pressure. The residue was dissolved in chloroform (15 mL), the organic layer was washed with water (15 mL), dried over anhydrous sodium sulfate, filtered and concentrated under reduced pressure. The chromatographic purification (hexane/ethyl acetate) of crude product afforded 4-(4-chloro-2-nitrophenyl)-1,9-dioxa-4-azaspiro[5.5]undecane (A48.3) as an oil (1.15 g, 3.67 mmol, 95% purity, 61.5% yield).

Step-2. Synthesis of 5-chloro-2-{1,9-dioxa-4-azaspiro[5.5]undecan-4-yl}aniline (A48.4)

Iron powder (1.03 g, 18.4 mmol) and ammonium chloride (0.98 g, 18.3 mmol) were added to a stirred solution of 4-(4-chloro-2-nitrophenyl)-1,9-dioxa-4-azaspiro[5.5]undecane (A48.3) (1.15 g, 3.67 mmol) in mixture of ethanol (25 mL) and water (25 mL) at room temperature. The resulting reaction mixture was heated at 80° C. for 6 h. After completion of the reaction (TLC control), the reaction mixture was cooled to room temperature, filtered, and the filtrate was evaporated. The residue was dissolved with water (10 mL) and ethyl acetate (10 mL). The organic layer was separated, dried over anhydrous sodium sulfate, filtered, and evaporated under reduced pressure to afford crude 5-chloro-2-{1,9-dioxa-4-azaspiro[5.5]undecan-4-yl}aniline (A48.4) (0.55 g, 1.94 mmol, 93.93% purity, 50.0% yield) that was used in next step without further purification.

Step-3. Synthesis of N-(5-chloro-2-{1,9-dioxa-4-azaspiro[5.5]undecan-4-yl}phenyl)-2,3-dihydro-1H-indene-5-sulfonamide (A-375)

2,3-dihydro-1H-indene-5-sulfonyl chloride (A48.5) (0.42 g, 1.93 mmol) was added to the mixture of 5-chloro-2-{1,9-dioxa-4-azaspiro[5.5]undecan-4-yl}aniline (A48.4) (0.55 g, 1.94 mmol) and pyridine (0.23 g, 2.9 mmol) in dry THF (20 mL). The reaction mixture was refluxed for 4 h and evaporated. The residue was subjected to HPLC purification (deionized water/HPLC-grade methanol, ammonia) that afforded N-(5-chloro-2-{1,9-dioxa-4-azaspiro[5.5]undecan-4-yl}phenyl)-2,3-dihydro-1H-indene-5-sulfonamide (A-375). Yield: 54.0 mg, 5.71%; Appearance: Yellow solid; $^1$H NMR (500 MHz, Chloroform-d) δ 7.71 (s, 1H), 7.60, J=4.4 Hz, 2H), 7.29 (d, J=8.1 Hz, 1H), 7.00 (s, 2H), 3.85-3.64 (m, 6H), 2.94 (t, J=7.4 Hz, 4H), 2.68-2.55 (m, 2H), 2.40 (s, 2H), 2.12 (p, J=7.4 Hz, 2H), 2.06-1.85 (m, 3H), 1.65-1.45 (m, 2H); HPLC purity: 98.13%; LCMS Calculated for $C_{23}H_{27}ClN_2O_4S$: 462.99; Observed: 462.17 $[M-H]^-$.

The following examples were prepared using standard chemical manipulations and procedures similar to those used for the preparation of the previous example.

| Compound No. | Structure | Analytical data |
| --- | --- | --- |
| A-376 | 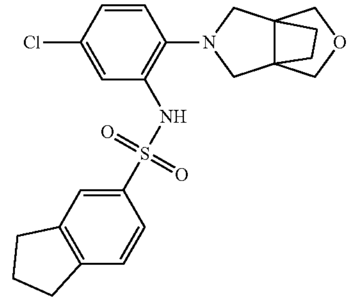 [SMILES: O=S(=O)(Nc1cc(Cl)ccc1N1CC23CCC2(COC3)C1)c1ccc2c(c1)CCC2] | Yield: 106.0 mg, 18.7%; Appearance: Light brown solid; $^1$H NMR (400 MHz, Chloroform-d) δ 7.91 (s, 1H), 7.68 (s, 1H), 7.62-7.56 (m, 1H), 7.56-7.52 (m, 1H), 7.24 (d, J = 2.7 Hz, 1H), 7.08 (dd, J = 8.5, 3.2 Hz, 1H), 6.96 (dt, J = 8.5, 2.7 Hz, 1H), 3.94-3.82 (m, 2H), 3.64-3.48 (m, 2H), 2.98-2.86 (m, 4H), 2.86-2.73 (m, 2H), 2.68-2.59 (m, 2H), 2.16-1.98 (m, 6H); HPLC purity: 100%; LCMS Calculated for $C_{23}H_{25}ClN_2O_3S$: 444.97; Observed: 444.16 $[M-H]^-$. |
| A-377 | 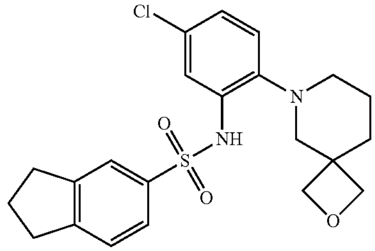 [SMILES: O=S(=O)(Nc1cc(Cl)ccc1N1CCCC2(COC2)C1)c1ccc2c(c1)CCC2] | Yield: 30.0 mg, 3.27%; Appearance: Yellow solid; $^1$H NMR (400 MHz, DMSO-$d_6$) δ 8.80 (s, 1H), 7.69 (s, 1H), 7.55 (dd, J = 7.8, 1.8 Hz, 1H), 7.40 (d, J = 8.0 Hz, 1H), 7.27 (d, J = 2.4 Hz, 1H), 7.21-7.09 (m, 2H), 4.33-4.21 (m, 4H), 2.89 (t, J = 7.5 Hz, 4H), 2.70 (s, 2H), 2.41 (t, J = 5.3 Hz, 2H), 2.03 (p, J = 7.5 Hz, 2H), 1.73-1.66 (m, 2H), 1.58-1.48 (m, 2H); HPLC purity: 97.79%; LCMS Calculated for $C_{22}H_{25}ClN_2O_3S$: 432.96; Observed: 432.16 $[M-H]^-$. |

-continued

| Compound No. | Structure | Analytical data |
|---|---|---|
| A-395 | 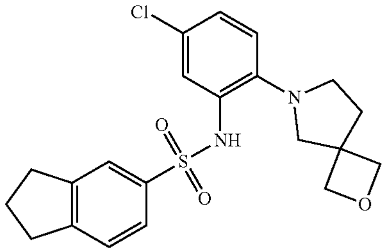 [SMILES: O=S(=O)(Nc1cc(Cl)ccc1N1CCC2(COC2)C1)c1ccc2c(c1)CCC2] | Yield: 30.0 mg, 3.27%; Appearance: Pink solid; $^1$H NMR (400 MHz, DMSO-$d_6$) δ 9.30 (s, 1H), 7.51 (s, 1H), 7.43 (q, J = 7.9 Hz, 2H), 7.08 (dd, J = 8.9, 2.6 Hz, 1H), 6.72 (d, J = 8.9 Hz, 1H), 6.65 (d, J = 2.6 Hz, 1H), 4.44 (q, J = 5.9 Hz, 4H), 3.34 (s, 2H, on the solvent signal), 3.15 (t, J = 6.8 Hz, 2H), 2.91 (q, J = 7.7 Hz, 4H), 2.13-1.99 (m, 4H); HPLC purity: 98.56%; LCMS Calculated for $C_{21}H_{23}ClN_2O_3S$: 418.94; Observed: 418.14 $[M - H]^-$. |
| A-396 | 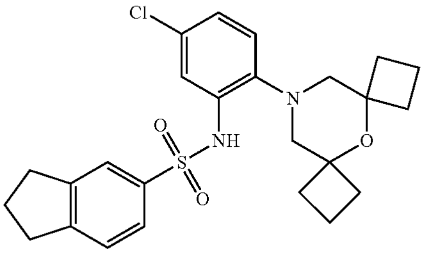 [SMILES: O=S(=O)(Nc1cc(Cl)ccc1N1CC2(CCC2)OC2(CCC2)C1)c1ccc2c(c1)CCC2] | Yield: 144.1 mg, 18.9%; Appearance: Brown solid; $^1$H NMR (400 MHz, DMSO-$d_6$) δ 8.73 (s, 1H), 7.66 (s, 1H), 7.58 (d, J = 7.9 Hz, 1H), 7.45 (d, J = 8.0 Hz, 1H), 7.26 (d, J = 8.6 Hz, 1H), 7.18 (d, J = 8.5 Hz, 1H), 7.07 (d, J = 2.4 Hz, 1H), 2.91 (q, J = 7.3 Hz, 4H), 2.72 (s, 4H), 2.16-2.00 (m, 6H), 1.96 (t, J = 9.7 Hz, 4H), 1.70 (q, J = 11.4, 10.8 Hz, 2H), 1.59-1.41 (m, 2H); HPLC purity: 100%; LCMS Calculated for $C_{25}H_{29}ClN_2O_3S$: 473.02; Observed: 472.2 $[M - H]^-$. |
| A-405 | 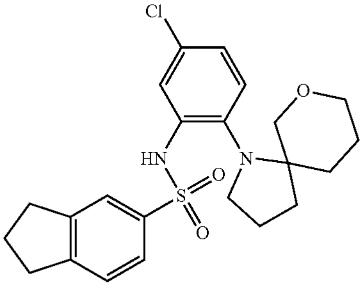 [SMILES: O=S(=O)(Nc1cc(Cl)ccc1N1CCCC12CCCOC2)c1ccc2c(c1)CCC2] | Yield: 104.0 mg, 11.1%; Appearance: Yellow solid; $^1$H NMR (500 MHz, Chloroform-d) δ 8.36 (s, 1H), 7.71 (s, 1H), 7.66-7.58 (m, 2H), 7.29 (d, J = 8.2 Hz, 1H), 6.99-6.91 (m, 2H), 3.72 (dt, J = 11.1, 2.9 Hz, 1H), 3.57 (d, J = 10.6 Hz, 1H), 2.99 (td, J = 11.4, 2.7 Hz, 2H), 2.92 (t, J = 7.4 Hz, 5H), 2.31 (dt, J = 12.9, 6.5 Hz, 1H), 2.10 (p, J = 7.5 Hz, 2H), 2.00-1.87 (m, 2H), 1.71 (q, J = 9.9 Hz, 1H), 1.52 (d, J = 12.5 Hz, 1H), 1.41 (d, J = 13.8 Hz, 1H), 1.17-1.00 (m, 1H); HPLC purity: 100%; LCMS Calculated for $C_{23}H_{27}ClN_2O_3S$: 446 99; Observed: 446.18 $[M - H]^-$. |
| A-436 | 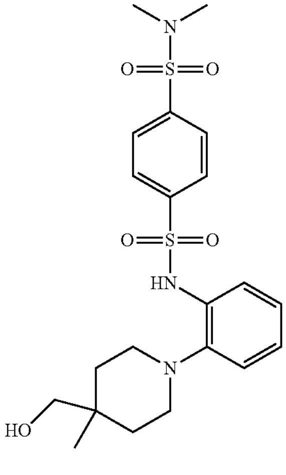 [SMILES: CN(C)S(=O)(=O)c1ccc(S(=O)(=O)Nc2ccccc2N2CCC(C)(CO)CC2)cc1] | Yield: 389.4 mg, 15.8%; Appearance: Grey solid; $^1$H NMR (400 MHz, DMSO-$d_6$) δ 9.09 (s, 1H), 8.00 (d, J = 8.4 Hz, 2H), 7.91 (d, J = 8.4 Hz, 2H), 7.26 (d, J = 7.8 Hz, 1H), 7.18 (d, J = 7.9 Hz, 1H), 7.14-7.00 (m, 2H), 4.51 (s, 1H), 3.19 (s, 2H), 2.61 (s, 6H), 2.48-2.39 (m, 4H), 1.57-1.46 (m, 2H), 1.21 (d, J = 13.0 Hz, 2H), 0.88 (s, 3H); HPLC purity: 100%; LCMS Calculated for $C_{21}H_{29}N_3O_5S_2$: 467.6; Observed: 467.18 $[M - H]^-$. |

-continued

| Compound No. | Structure | Analytical data |
|---|---|---|
| A-411 | 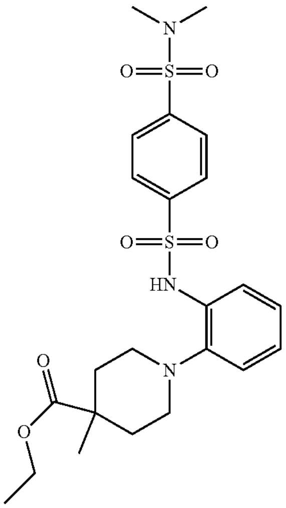 [SMILES: CCOC(=O)C1(C)CCN(c2ccccc2NS(=O)(=O)c2ccc(S(=O)(=O)N(C)C)cc2)CC1] | Yield: 900.0 mg, 46.7%; Appearance: Beige solid; $^1$H NMR (500 MHz, Chloroform-d) δ 8.12 (s, 1H), 7.97 (d, J = 8.0 Hz, 2H), 7.83 (d, J = 8.1 Hz, 2H), 7.58 (d, J = 8.0 Hz, 1H), 7.18-6.99 (m, 3H), 4.19 (q, J = 7.1 Hz, 2H), 2.71 (s, 6H), 2.52 (t, J = 12.9 Hz, 2H), 2.40 (d, J = 13.4 Hz, 2H), 2.18 (d, J = 13.3 Hz, 2H), 1.53 (d, J = 14.1 Hz, 3H), 1.32-1.24 (m, 6H); HPLC purity: 100%; LCMS Calculated for $C_{23}H_{31}N_3O_6S_2$: 509.64; Observed: 509.2 $[M-H]^-$. |
| A-416 | 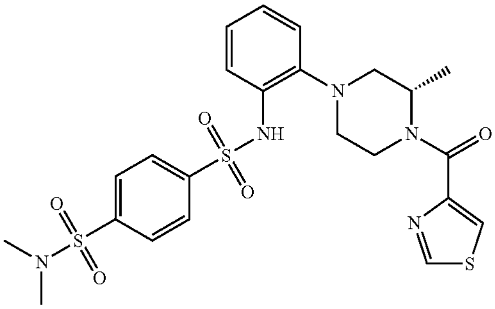 [SMILES: C[C@H]1CN(c2ccccc2NS(=O)(=O)c2ccc(S(=O)(=O)N(C)C)cc2)CCN1C(=O)c1cscn1] | Yield: 53.2 mg, 5.16%; Appearance: Yellow solid; $^1$H NMR (400 MHz, Chloroform-d) δ 8.78 (d, J = 2.2 Hz, 1H), 8.14 (s, 1H), 8.05-7.96 (m, 3H), 7.83 (d, J = 8.1 Hz, 2H), 7.52 (d, J = 8.0 Hz, 1H), 7.18-7.02 (m, 3H), 4.92 (s, 1H), 4.57 (d, J = 13.9 Hz, 1H), 3.46 (s, 4H), 2.95-2.82 (m, 2H), 2.70 (s, 6H), 2.63-2.46 (m, 2H), 1.54 (d, J = 6.8 Hz, 3H); HPLC purity: 98.02%; LCMS Calculated for $C_{23}H_{27}N_5O_5S_3$: 549.68; Observed: 549.13 $[M-H]^-$. |
| A-418 | 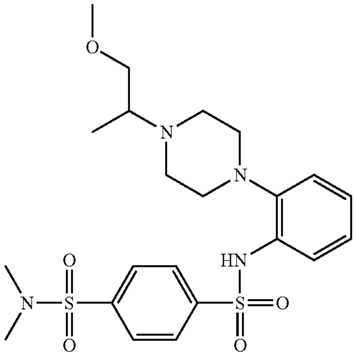 [SMILES: COCC(C)N1CCN(c2ccccc2NS(=O)(=O)c2ccc(S(=O)(=O)N(C)C)cc2)CC1] | Yield: 62.4 mg, 2.7%; Appearance: Orange solid; $^1$H NMR (400 MHz, Chloroform-d) δ 8.14 (s, 1H), 7.95 (d, J = 8.2 Hz, 2H), 7.80 (d, J = 8.1 Hz, 2H), 7.54 (d, J = 8.1 Hz, 1H), 7.18-6.98 (m, 3H), 3.46 (s, 1H), 3.36 (s, 4H), 2.88-2.72 (m, 1H), 2.68 (s, 10H), 2.56 (s, 4H), 1.07 (s, 3H); HPLC purity: 100%; LCMS Calculated for $C_{22}H_{32}N_4O_5S_2$: 496 64; Observed: 496.21 $[M-H]^-$. |

Example A49: Synthesis of N-(5-chloro-2-{6-fluoro-1-methyl-1,2-dihydrospiro[indole-3,4'-piperidin]-1'-yl}phenyl)-2,3-dihydro-1H-indene-5-sulfonamide (A-439)

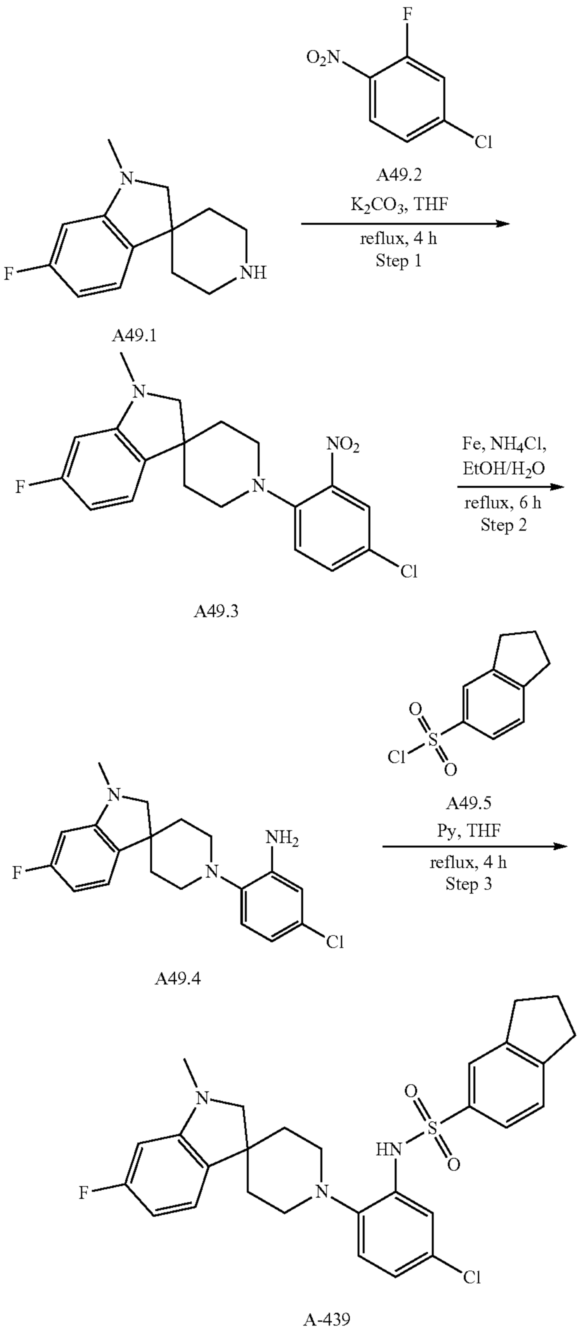

Step-1. Synthesis of 1'-(4-chloro-2-nitrophenyl)-6-fluoro-1-methyl-1,2-dihydrospiro[indole-3,4'-piperidine] (A49.3)

4-chloro-1-fluoro-2-nitrobenzene (A49.2) (0.39 g, 2.22 mmol) was added to a stirred solution of 6-fluoro-1-methylspiro[indoline-3,4'-piperidine]dihydrochloride (A49.1) (0.65 g, 2.22 mmol) and potassium carbonate (0.613, 4.43 mmol) in dry THF (20 mL). The mixture was refluxed until the reaction completion (TLC control) and concentrated under the reduced pressure. The residue was dissolved in chloroform (15 mL), the organic layer was washed with water, (15 mL), dried over anhydrous sodium sulfate, filtered and concentrated under reduced pressure. The HPLC purification (deionized water/HPLC-grade methanole) of crude product afforded 1'-(4-chloro-2-nitrophenyl)-6-fluoro-1-methyl-1,2-dihydrospiro[indole-3,4'-piperidine](A49.3) as a powder (0.23 g, 0.611 mmol, 95% purity, 26.1% yield).

Step-2. Synthesis of 5-chloro-2-{6-fluoro-1-methyl-1,2-dihydrospiro[indole-3,4'-piperidin]-1'-yl}aniline (A49.4)

Iron powder (0.17 g, 3.04 mmol) and ammonium chloride (0.16 g, 2.99 mmol) were added to a stirred solution of 1'-(4-chloro-2-nitrophenyl)-6-fluoro-1-methyl-1,2-dihydrospiro[indole-3,4'-piperidine] (A49.3) (0.23 g, 0.611 mmol) in mixture of ethanol (25 mL) and water (25 mL) at room temperature. The resulting reaction mixture was heated at 80° C. for 6 h. After completion of the reaction (TLC control), the reaction mixture was cooled to room temperature, filtered, and the filtrate was evaporated. The residue was dissolved with water (10 mL) and ethyl acetate (10 mL). The organic layer was separated, dried over anhydrous sodium sulfate, filtered, and evaporated under reduced pressure to afford 5-chloro-2-{6-fluoro-1-methyl-1,2-dihydrospiro[indole-3,4'-piperidin]-1'-yl}aniline (A49.4) (0.05 g, 0.144 mmol, 92.69% purity, 21.9% yield) that was used in next step without further purification.

Step-3. Synthesis of N-(5-chloro-2-{6-fluoro-1-methyl-1,2-dihydrospiro[indole-3,4'-piperidin]-1'-yl}phenyl)-2,3-dihydro-1H-indene-5-sulfonamide (A-439)

2,3-dihydro-1H-indene-5-sulfonyl chloride (A49.5) (0.03 g, 0.138 mmol) was added to the mixture of 5-chloro-2-{6-fluoro-1-methyl-1,2-dihydrospiro[indole-3,4'-piperidin]-1'-yl}aniline (0.05 g, 0.144 mmol) and pyridine (0.017 g, 0.214 mmol) in dry THF (20 mL). The reaction mixture was refluxed for 4 h and evaporated. The residue was subjected to HPLC purification (deionized water/HPLC-grade acetonitrile) that afforded N-(5-chloro-2-{6-fluoro-1-methyl-1,2-dihydrospiro[indole-3,4'-piperidin]-1'-yl}phenyl)-2,3-dihydro-1H-indene-5-sulfonamide (A-439). Yield: 11.9 mg, 14.9%; Appearance: Yellow solid; $^1H$ NMR (400 MHz, Chloroform-d) δ 7.97 (s, 1H), 7.68 (s, 1H), 7.62 (d, J=2.3 Hz, 1H), 7.58 (d, J=8.0 Hz, 1H), 7.21 (s, 1H), 7.07-6.90 (m, 3H), 6.45-6.33 (m, 1H), 6.16 (dd, J=10.2, 2.4 Hz, 1H), 3.26 (s, 2H), 2.94-2.80 (m, 3H), 2.74 (s, 3H), 2.57 (t, J=11.6 Hz, 2H), 2.52-2.38 (m, 2H), 2.04 (p, J=7.1 Hz, 2H), 1.96-1.82 (m, 2H), 1.72 (d, J=13.4 Hz, 2H); HPLC purity: 100%; LCMS Calculated for $C_{28}H_{29}ClFN_3O_2S$: 526.07; Observed: 525.21 $[M-H]^-$.

Example A50: Synthesis of N-(5-chloro-2-{7-oxa-1-azaspiro[4.4]nonan-1-yl}phenyl)-2,3-dihydro-1H-indene-5-sulfonamide (A-378)

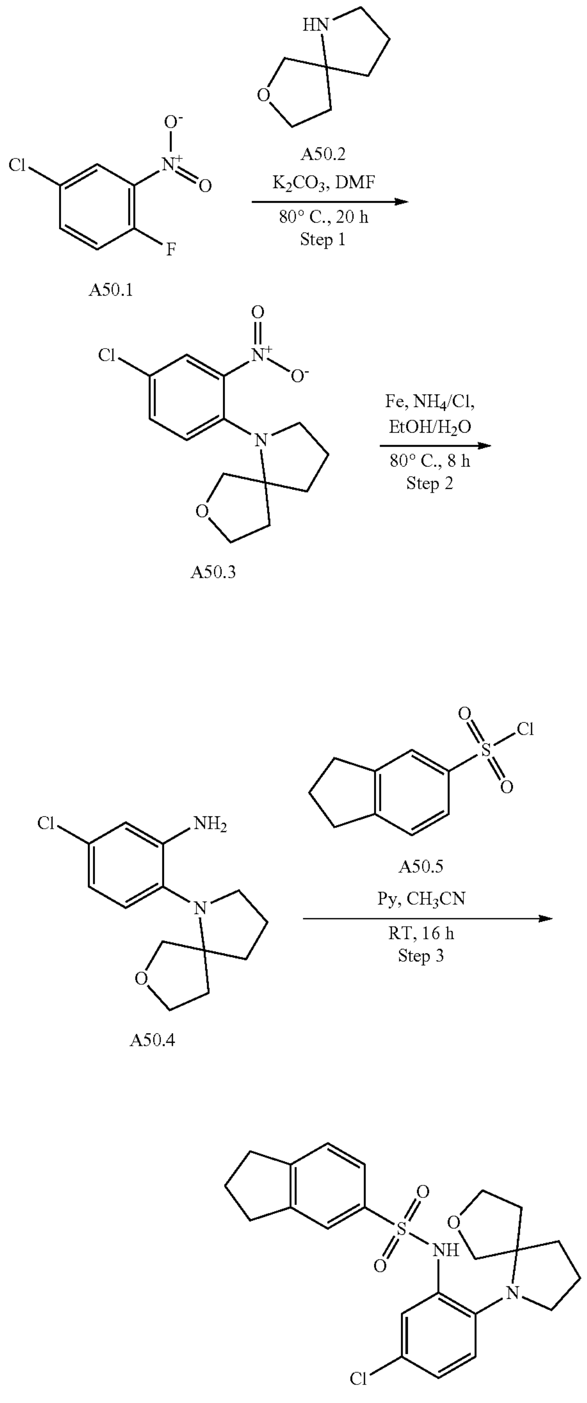

A-378

Step-1. Synthesis of 1-(4-chloro-2-nitrophenyl)-7-oxa-1-azaspiro[4.4]nonane (A50.3)

7-oxa-1-azaspiro[4.4]nonane (A50.2) (1 g, 7.86 mmol) and potassium carbon are (2.16 g, 15.7 mmol) were added to a stirred solution of 4-chloro-1-fluoro-2-nitrobenzene (A50.1) (1.51 g, 8.64 mmol) in dry DMF (10 mL). The reaction mixture was heated at 80° C. for 20 h. After completion of the reaction (TLC control), the reaction mixture was concentrated under reduced pressure, the residue was dissolved in water (20 mL) and chloroform (15 mL). The water layer was separated and extracted with chloroform (15 mL). The combined organic layers were dried over anhydrous sodium sulfate, filtered and concentrated under reduced pressure. The crude product was purified by column chromatography on silica gel (chloroform) to afford 1-(4-chloro-2-nitrophenyl)-7-oxa-1-azaspiro[4.4]nonane (A50.3) (0.8 g, 2.68 mmol, 95% purity, 34.2% yield).

Step-2. Synthesis of 5-chloro-2-{7-oxa-1-azaspiro[4.4]nonan-1-yl}aniline (A50.4)

Iron powder (0.787 g, 14.1 mmol) and ammonium chloride (0.754 g, 14.1 mmol) were added to a stirred solution of 1-(4-chloro-2-nitrophenyl)-7-oxa-1-azaspiro[4.4]nonane (A50.3) (0.8 g, 2.82 mmol) in mixture of ethanol (10 mL) and water (3 mL) at room temperature. The resulting reaction mixture was heated at 80° C. for 5 h. After completion of the reaction (TLC control), the reaction mixture was cooled to room temperature, filtered, and the filtrate was evaporated. The residue was dissolved with water (10 mL) and chloroform (10 mL). The organic layer was separated, dried over anhydrous sodium sulfate, filtered, and evaporated under reduced pressure. The crude product was purified by silica gel column chromatography (chloroform) to afford 5-chloro-2-{7-oxa-1-azaspiro[4.4]nonan-1-yl}aniline (A50.4) (0.76 g, 3.00 mmol, 84% purity, 89.6% yield).

Step-3. Synthesis of N-(5-chloro-2-{7-oxa-1-azaspiro[4.4]nonan-1-yl}phenyl)-2,3-dihydro-1H-indene-5-sulfonamide (A-378)

Pyridine (0.196 g, 2.49 mmol) was added to a stirred solution of 5-chloro-2-{7-oxa-1-azaspiro[4.4]nonan-1-yl}aniline (A50.4) (0.3 g, 0.997 mmol) and 2,3-dihydro-1H-indene-5-sulfonyl chloride (A50.5) (0.236 g, 1.09 mmol) in dry acetonitrile (5 mL) at room temperature. The reaction was stirred at room temperature overnight. After completion of the reaction (TLC control), the reaction mixture was concentrated under reduced pressure to dryness. The residue was purified by prep HPLC (deionized water/HPLC-grade methanol, ammonia) to afford N-(5-chloro-2-{7-oxa-1-azaspiro[4.4]nonan-1-yl}phenyl)-2,3-dihydro-1H-indene-5-sulfonamide (A-378). Yield: 220.0 mg, 48.4%; Appearance: Yellow solid; $^1H$ NMR (400 MHz, DMSO-$d_6$) δ 9.06 (s, 1H), 7.69 (s, 1H), 7.58 (d, J=7.9 Hz, 1H), 7.39 (d, J=7.9 Hz, 1H), 7.30 (d, J=2.5 Hz, 1H), 7.23 (d, J=8.7 Hz, 1H), 7.05 (d, J=8.6 Hz, 1H), 3.57 (q, J=8.1 Hz, 1H), 3.54-3.44 (m, 1H), 3.38 (d, J=8.7 Hz, 2H), 2.96 (t, J=6.6 Hz, 2H), 2.88 (t, J 7.5 Hz, 4H), 2.02 (p, J=7.4 Hz, 2H), 1.96-1.81 (m, 4H), 1.71-1.51 (m, 2H); HPLC purity: 6.9; LCMS Calculated for $C_{22}H_{25}ClN_2O_3S$: 432.96; Observed: 432.16 $[M-H]^-$.

The following examples were prepared using standard chemical manipulations and procedures similar to those used for the preparation of the previous example.

| Compound No. | Structure | Analytical data |
|---|---|---|
| A-397 | 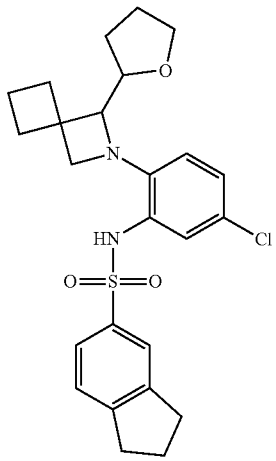 [SMILES: O=S(=O)(Nc1cc(Cl)ccc1N1CC2(CCC2)C1C1CCCO1)c1ccc2c(c1)CCC2] | Yield: 65.9 mg, 15.9%; Appearance: Light brown solid; $^1$H NMR (400 MHz, DMSO-$d_6$) δ 9.20 (s, 1H), 7.55 (s, 1H), 7.45 (dd, J = 8.1, 1.7 Hz, 1H), 7.40 (d, J = 7.9 Hz, 1H), 7.04 (dd, J = 8.8, 2.5 Hz, 1H), 6.84 (d, J = 8.9 Hz, 1H), 6.69 (d, J = 2.5 Hz, 1H), 4.16 (d, J = 7.9 Hz, 1H), 4.04-3.96 (m, 1H), 3.88 (d, J = 2.7 Hz, 1H), 3.62-3.47 (m, 2H), 3.39 (d, J = 7.9 Hz, 1H), 2.96-2.86 (m, 4H), 2.21 (q, J = 8.9, 7.9 Hz, 1H), 2.05 (dt, J = 12.9, 6.1 Hz, 3H), 1.84-1.50 (m, 8H); HPLC purity: 100%; LCMS Calculated for $C_{25}H_{29}ClN_2O_3S$: 473.03; Observed: 472.2 $[M-H]^-$. |
| A-379 | 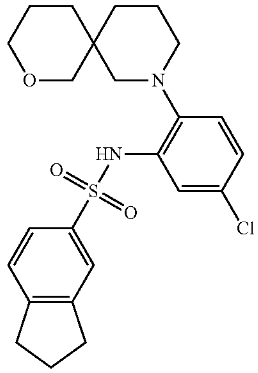 [SMILES: O=S(=O)(Nc1cc(Cl)ccc1N1CCCC2(CCCOC2)C1)c1ccc2c(c1)CCC2] | Yield: 207.4 mg, 48.7%; Appearance: Brown solid; $^1$H NMR (400 MHz, Chloroform-d) δ 7.88 (s, 1H), 7.69 (s, 1H), 7.60 (dd, J = 8.1, 1.7 Hz, 1H), 7.55 (d, J = 2.1 Hz, 1H), 7.22 (s, 1H), 7.00-6.85 (m, 2H), 3.78-3.61 (m, 2H), 3.60-3.50 (m, 1H), 3.41 (d, J = 11.2 Hz, 1H), 2.89 (t, J = 7.5 Hz, 4H), 2.59 (d, J = 11.2 Hz, 1H), 2.46 (t, J = 5.5 Hz, 2H), 2.44-2.31 (m, 1H), 2.07 (p, J = 7.6 Hz, 2H), 1.67-1.49 (m, 7H), 1.31 (s, 1H); HPLC purity: 100%; LCMS Calculated for $C_{24}H_{29}ClN_2O_3S$: 461.02; Observed: 460.2 $[M-H]^-$. |
| A-385 | 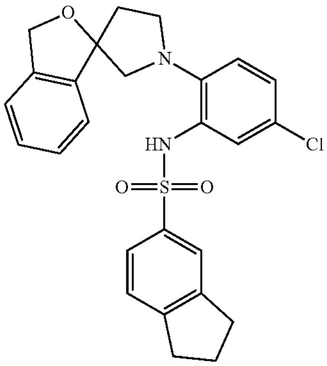 [SMILES: O=S(=O)(Nc1cc(Cl)ccc1N1CCC2(C1)OCc1ccccc12)c1ccc2c(c1)CCC2] | Yield: 36.4 mg, 7.2%; Appearance: Light brown solid; $^1$H NMR (400 MHz, DMSO-$d_6$) δ 9.26 (s, 1H), 7.46 (s, 1H), 7.41 (d, J = 8.0 Hz, 1H), 7.39-7.30 (m, 4H), 7.31-7.24 (m, 1H), 7.12 (dd, J = 8.9, 2.7 Hz, 1H), 6.79 (d, J = 8.9 Hz, 1H), 6.67 (d, J = 2.6 Hz, 1H), 5.08-4.85 (m, 2H), 3.62 (d, J = 10.9 Hz, 1H), 3.53 (q, J = 8.8 Hz, 1H), 3.44-3.33 (m, 2H), 3.13 (d, J = 10.9 Hz, 1H), 2.95-2.69 (m, 4H), 2.15-2.04 (m, 2H), 2.01 (t, J = 7.5 Hz, 2H); HPLC purity: 100%; LCMS Calculated for $C_{26}H_{25}ClN_2O_3S$: 481.01; Observed: 480.16 $[M-H]^-$. |
| A-433 | 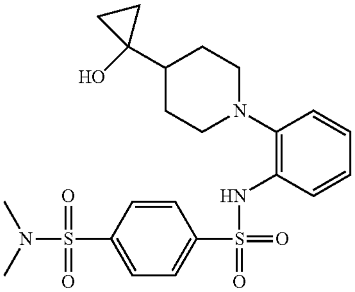 [SMILES: CN(C)S(=O)(=O)c1ccc(S(=O)(=O)Nc2ccccc2N2CCC(C3(O)CC3)CC2)cc1] | Yield: 609.7 mg, 68.6%; Appearance: Violet solid; $^1$H NMR (400 MHz, DMSO-$d_6$) δ 9.11 (s, 1H), 8.02 (d, J = 8.6 Hz, 2H), 7.91 (d, J = 8.2 Hz, 2H), 7.24 (d, J = 7.7 Hz, 1H), 7.17-6.91 (m, 3H), 4.99 (s, 1H), 2.61 (s, 8H), 2.42 (t, J = 11.3 Hz, 3H), 1.56 (q, J = 11.4 Hz, 4H), 1.00 (q, J = 8.9, 8.4 Hz, 1H), 0.56-0.47 (m, 2H), 0.41-0.31 (m, 2H); HPLC purity: 100%; LCMS Calculated for $C_{22}H_29N_3O_5S_2$: 479.61; Observed: 479.18 $[M-H]^-$. |

-continued

| Compound No. | Structure | Analytical data |
|---|---|---|
| A-420 | 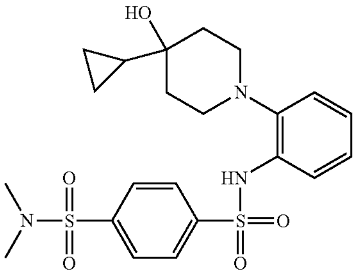 [SMILES: CN(C)S(=O)(=O)c1ccc(S(=O)(=O)Nc2ccccc2N2CCC(O)(C3CC3)CC2)cc1] | Yield: 399.5 mg, 44.9%; Appearance: Yellow solid; $^1$H NMR (400 MHz, DMSO-$d_6$) δ 9.14 (s, 1H), 8.00 (d, J = 8.5 Hz, 2H), 7.92 (d, J = 8.5 Hz, 2H), 7.30 (d, J = 7.3 Hz, 1H), 7.16-7.01 (m, 3H), 3.75 (s, 1H), 2.71 (t, J = 11.1 Hz, 2H), 2.61 (s, 6H), 2.30 (d, J = 11.1 Hz, 2H), 1.59 (t, J = 12.4 Hz, 2H), 1.37 (d, J = 12.8 Hz, 2H), 0.88-0.77 (m, 1H), 0.37-0.29 (m, 2H), 0.25-0.16 (m, 2H); HPLC purity: 100%; LCMS Calculated for $C_{22}H_{29}N_3O_5S_2$: 479.61; Observed: 479.18 [M − H]$^-$. |
| A-421 | 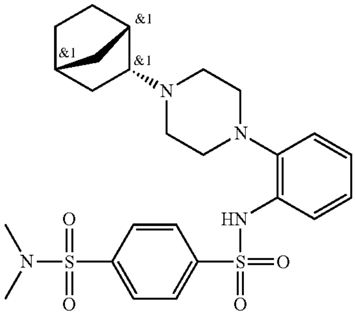 [SMILES: CN(C)S(=O)(=O)c1ccc(S(=O)(=O)Nc2ccccc2N2CCN([C@@H]3C[C@@H]4CC[C@H]3C4)CC2)cc1] | Yield: 272.3 mg, 28.2%; Appearance: Beige solid; $^1$H NMR (400 MHz, DMSO-$d_6$) δ 9.21 (s, 1H), 8.02-7.89 (m, 4H), 7.24 (d, J = 7.2 Hz, 1H), 7.19-7.01 (m, 3H), 2.62 (s, 6H), 2.58-2.54 (m, 4H), 2.37-2.19 (m, 5H), 2.13 (s, 1H), 2.07 (s, 1H), 1.66 (d, J = 11.5 Hz, 2H), 1.46-1.39 (m, 1H), 1.34 (d, J = 9.7 Hz, 1H), 1.28-1.20 (m, 2H), 1.19-1.11 (m, 1H), 0.80 (d, J = 12.1 Hz, 1H); HPLC purity: 100%; LCMS Calculated for $C_{25}H_{34}N_4O_4S_2$: 518.69; Observed: 518.24 [M − H]$^-$. |
| A-455 | 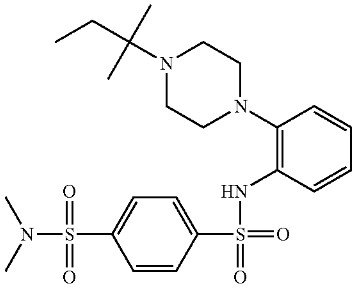 [SMILES: CCC(C)(C)N1CCN(c2ccccc2NS(=O)(=O)c2ccc(S(=O)(=O)N(C)C)cc2)CC1] | Yield: 330.0 mg, 38.3%; Appearance: Brown solid; $^1$H NMR (400 MHz, DMSO-$d_6$) δ 9.21 (s, 1H), 7.99 (d, J = 8.5 Hz, 2H), 7.92 (d, J = 8.3 Hz, 2H), 7.22 (d, J = 7.9 Hz, 1H), 7.11 (d, J = 4.2 Hz, 2H), 7.04 (dd, J = 8.1, 4.4 Hz, 1H), 2.61 (s, 6H), 2.57-2.50 (m, 4H), 2.47-2.42 (m, 4H), 1.39 (q, J = 7.4 Hz, 2H), 0.95 (s, 6H), 0.78 (t, J = 7.3 Hz, 3H); HPLC purity: 100%; LCMS Calculated for $C_{23}H_{34}N_4O_4S_2$: 494.67; Observed: 494.24 [M − H]$^-$. |
| A-464 | 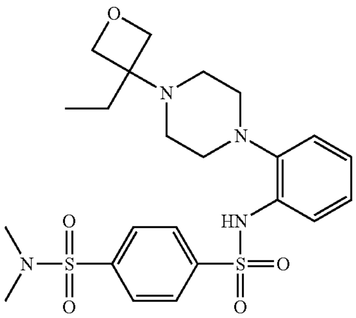 [SMILES: CCC1(N2CCN(c3ccccc3NS(=O)(=O)c3ccc(S(=O)(=O)N(C)C)cc3)CC2)COC1] | Yield: 351.2 mg, 36.3%; Appearance: Beige solid; $^1$H NMR (400 MHz, DMSO-$d_6$) δ 9.25 (s, 1H), 8.10-7.88 (m, 4H), 7.25 (d, J = 8.2 Hz, 1H), 7.14 (d, J = 4.0 Hz, 2H), 7.06 (dt, J = 8.6, 4.5 Hz, 1H), 4.44 (d, J = 6.3 Hz, 2H), 4.23 (d, J = 5.8 Hz, 2H), 2.61 (s, 6H), 2.59-2.51 (m, 7H), 2.41 (s, 4H), 1.70 (q, J = 7.2 Hz, 2H), 1.02 (t, J = 7.1 Hz, 3H); HPLC purity: 100%; LCMS Calculated for $C_{23}H_{32}N_4O_5S_2$: 508.65; Observed: 508.21 [M − H]$^-$. |
| A-475 | 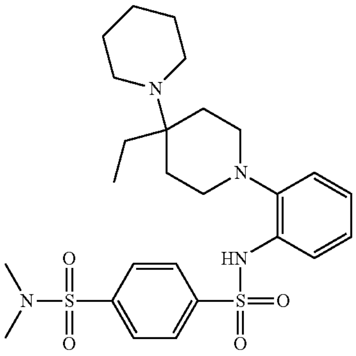 [SMILES: CCC1(N2CCCCC2)CCN(c2ccccc2NS(=O)(=O)c2ccc(S(=O)(=O)N(C)C)cc2)CC1] | Yield: 29.1 mg, 1.35%; Appearance: Yellow solid; $^1$H NMR (400 MHz, DMSO-$d_6$) δ 9.23 (s, 1H), 8.00 (d, J = 8.5 Hz, 2H), 7.91 (d, J = 8.2 Hz, 2H), 7.27 (d, J = 7.8 Hz, 1H), 7.16-7.07 (m, 2H), 7.07-7.00 (m, 1H), 2.77-2.67 (m, 2H), 2.60 (s, 6H), 2.48-2.44 (m, 4H), 2.31-2.23 (m, 2H), 1.65 (d, J = 13.8 Hz, 2H), 1.55-1.36 (m, 10H), 0.82 (t, J = 7.4 Hz, 3H); HPLC purity: 97.02%; LCMS Calculated for $C_{26}H_{38}N_4O_4S_2$: 534.73; Observed: 534.28 [M − H]$^-$. |

-continued

| Compound No. | Structure | Analytical data |
| --- | --- | --- |
| A-454 | 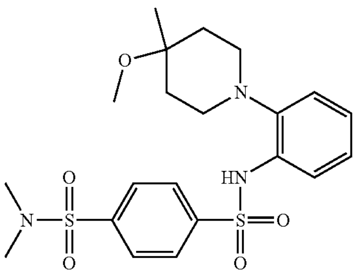 [SMILES: COC1(C)CCN(c2ccccc2NS(=O)(=O)c2ccc(S(=O)(=O)N(C)C)cc2)CC1] | Yield: 123.6 mg, 11.1%; Appearance: Brown solid; $^1$H NMR (400 MHz, DMSO-$d_6$) δ 9.21 (s, 1H), 8.00 (d, J = 8.5 Hz, 2H), 7.92 (d, J = 8.5 Hz, 2H), 7.28 (d, J = 7.5 Hz, 1H), 7.16-7.00 (m, 3H), 3.07 (s, 3H), 2.61 (s, 6H), 2.59 (d, J = 10.0 Hz, 2H), 2.29 (d, J = 11.2 Hz, 2H), 1.62 (d, J = 13.3 Hz, 2H), 1.58-1.46 (m, 2H), 1.10 (s, 3H); HPLC purity: 100%; LCMS Calculated for $C_{21}H_{29}N_3O_5S_2$: 467.6; Observed: 467.18 $[M - H]^-$. |
| A-422 | 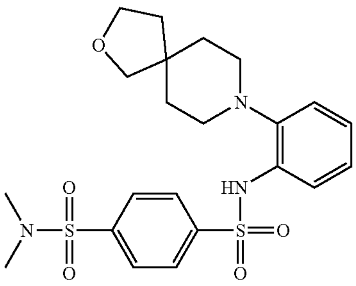 [SMILES: CN(C)S(=O)(=O)c1ccc(S(=O)(=O)Nc2ccccc2N2CCC3(CCOC3)CC2)cc1] | Yield: 270.8 mg, 30.4%; Appearance: Grey solid; $^1$H NMR (400 MHz, DMSO-$d_6$) δ 9.19 (s, 1H), 8.04-7.97 (m, 2H), 7.96-7.89 (m, 2H), 7.28 (dd, J = 7.8, 1.6 Hz, 1H), 7.19-7.08 (m, 3H), 7.08-7.01 (m, 1H), 3.72 (t, J = 7.1 Hz, 2H), 3.44 (s, 2H), 2.62 (s, 6H), 2.46 (dd, J = 12.8, 5.9 Hz, 4H), 1.69 (t, J = 7.1 Hz, 2H), 1.58-1.45 (m, 4H); HPLC purity: 100%; LCMS Calculated for $C_{22}H_{29}N_3O_5S_2$: 479.61; Observed: 479.18 $[M - H]^-$. |
| A-419 | 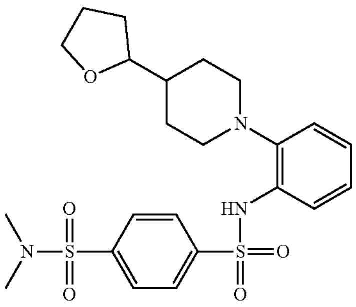 [SMILES: CN(C)S(=O)(=O)c1ccc(S(=O)(=O)Nc2ccccc2N2CCC(C3CCCO3)CC2)cc1] | Yield: 40.6 mg, 4.48%; Appearance: Beige solid; $^1$H NMR (400 MHz, DMSO-$d_6$) δ 9.16 (s, 1H), 8.00 (d, J = 8.4 Hz, 2H), 7.92 (d, J = 8.5 Hz, 2H), 7.27 (d, J = 7.8 Hz, 1H), 7.14-7.01 (m, 3H), 3.72 (dt, J = 8.0, 6.6 Hz, 1H), 3.66-3.55 (m, 1H), 3.52-3.44 (m, 1H), 2.62 (s, 6H), 2.57-2.50 (m, 2H), 2.41 (d, J = 10.9 Hz, 2H), 1.95-1.74 (m, 3H), 1.74-1.66 (m, 1H), 1.53-1.40 (m, 2H), 1.30 (s, 3H); HPLC purity: 100%; LCMS Calculated for $C_{23}H_{31}N_3O_5S_2$: 493.64; Observed: 493.2 $[M - H]^-$. |
| A-434 | 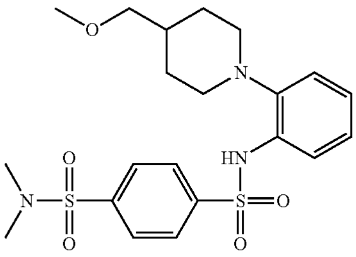 [SMILES: COCC1CCN(c2ccccc2NS(=O)(=O)c2ccc(S(=O)(=O)N(C)C)cc2)CC1] | Yield: 401.6 mg, 46.3%; Appearance: Beige solid; $^1$H NMR (400 MHz, DMSO-$d_6$) δ 9.14 (s, 1H), 8.00 (d, J = 10.3 Hz, 2H), 7.92 (d, J = 8.4 Hz, 2H), 7.28 (d, J = 7.8 Hz, 1H), 7.15-7.01 (m, 3H), 3.24 (s, 3H), 3.19 (d, J = 5.9 Hz, 2H), 2.62 (s, 6H), 2.54 (d, J = 3.6 Hz, 2H), 2.46-2.38 (m, 2H), 1.55 (d, J = 11.8 Hz, 3H), 1.25 (q, J = 11.9 Hz, 2H); HPLC purity: 100%; LCMS Calculated for $C_{21}H_{29}N_3O_5S_2$: 467.6; Observed: 467.18 $[M - H]^-$. |
| A-435 | 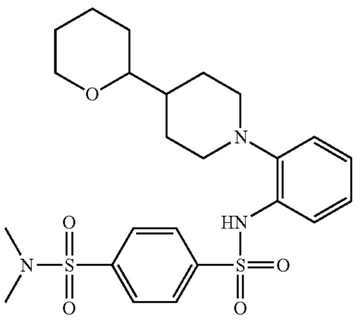 [SMILES: CN(C)S(=O)(=O)c1ccc(S(=O)(=O)Nc2ccccc2N2CCC(C3CCCCO3)CC2)cc1] | Yield: 483.3 mg, 51.3%; Appearance: Beige solid; $^1$H NMR (400 MHz, DMSO-$d_6$) δ 9.15 (s, 1H), 8.00 (d, J = 8.2 Hz, 2H), 7.92 (d, J = 8.2 Hz, 2H), 7.25 (d, J = 7.8 Hz, 1H), 7.14-7.00 (m, 3H), 3.89 (d, J = 11.2 Hz, 1H), 3.00 (d, J = 10.8 Hz, 1H), 2.62 (s, 8H), 2.46-2.35 (m, 2H), 1.91-1.00 (m, 11H); HPLC purity: 100%; LCMS Calculated for $C_{24}H_{33}N_3O_5S_2$: 507.66; Observed: 507.22 $[M - H]^-$. |

-continued

| Compound No. | Structure | Analytical data |
|---|---|---|
| A-549 | 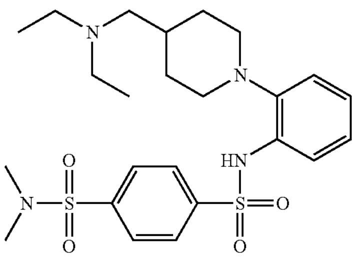 [SMILES: CCN(CC)CC1CCN(c2ccccc2NS(=O)(=O)c2ccc(S(=O)(=O)N(C)C)cc2)CC1] | Yield: 52.6 mg, 5.13%; Appearance: Beige solid; $^1H$ NMR (400 MHz, DMSO-$d_6$) δ 9.70 (s, 1H), 9.17 (s, 1H), 8.00 (d, J = 8.4 Hz, 2H), 7.93 (d, J = 8.4 Hz, 2H), 7.31-7.24 (m, 1H), 7.19-7.10 (m, 2H), 7.12-7.02 (m, 1H), 3.13 (dt, J = 12.7, 6.8 Hz, 4H), 2.93 (t, J = 5.7 Hz, 2H), 2.63 (d, J = 2.2 Hz, 6H), 2.46 (d, J = 10.9 Hz, 2H), 1.76 (d, J = 12.1 Hz, 3H), 1.32 (d, J = 12.1 Hz, 2H), 1.28-1.16 (m, 6H); HPLC purity: 100%; LCMS Calculated for $C_{24}H_{36}N_4O_4S_2$: 508.7; Observed: 508.26 $[M - H]^-$. |
| A-550 | 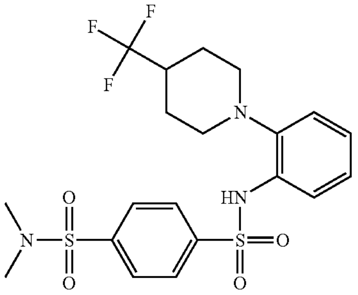 [SMILES: CN(C)S(=O)(=O)c1ccc(S(=O)(=O)Nc2ccccc2N2CCC(C(F)(F)F)CC2)cc1] | Yield: 96.8 mg, 9.19%; Appearance: Beige solid; $^1H$ NMR (400 MHz, DMSO-$d_6$) δ 9.42 (s, 1H), 8.01 (d, J = 8.7 Hz, 2H), 7.94 (d, J = 8.5 Hz, 2H), 7.28 (d, J = 7.5 Hz, 1H), 7.18-7.03 (m, 3H), 2.62 (s, 8H), 2.54 (d, J = 1.9 Hz, 2H), 2.30 (s, 1H), 1.71-1.59 (m, 4H); HPLC purity: 100%; LCMS Calculated for $C_{20}H_{24}F_3N_3O_4S_2$: 491.54; Observed: 491.14 $[M - H]^-$. |
| A-551 | 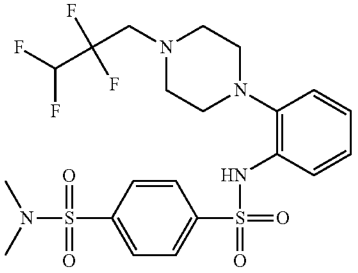 [SMILES: CN(C)S(=O)(=O)c1ccc(S(=O)(=O)Nc2ccccc2N2CCN(CC(F)(F)C(F)F)CC2)cc1] | Yield: 58.9 mg, 6.07%; Appearance: Yellow solid; $^1H$ NMR (400 MHz, DMSO-$d_6$) δ 9.29 (s, 1H), 8.03-7.89 (m, 4H), 7.25 (d, J = 7.9 Hz, 1H), 7.20-7.02 (m, 3H), 6.49 (t, J = 52.4 Hz, 1H), 3.00 (t, J = 15.2 Hz, 2H), 2.73-2.50 (m, 15H); HPLC purity: 100%; LCMS Calculated for $C_{21}H_{26}F_4N_4O_4S_2$: 538.58; Observed: 538.16 $[M - H]^-$. |
| A-450 | 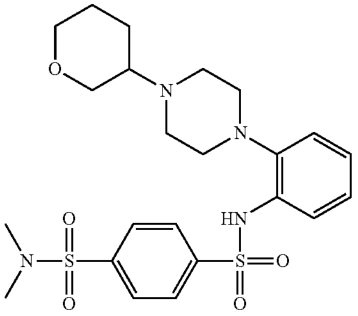 [SMILES: CN(C)S(=O)(=O)c1ccc(S(=O)(=O)Nc2ccccc2N2CCN(C3CCCOC3)CC2)cc1] | Yield: 226.6 mg, 28.2%; Appearance: Beige solid; $^1H$ NMR (400 MHz, DMSO-$d_6$) δ 9.25 (s, 1H), 8.07-7.83 (m, 4H), 7.23 (d, J = 7.7 Hz, 1H), 7.16-7.08 (m, 2H), 7.05 (td, J = 8.2, 7.1, 2.9 Hz, 1H), 3.88 (d, J = 11.0 Hz, 1H), 3.73 (d, J = 11.1 Hz, 1H), 3.33-3.31 (m, 3H), 3.25-3.09 (m, 2H), 2.62 (s, 6H), 2.49-2.44 (m, 3H), 2.37-2.25 (m, 1H), 1.91 (d, J = 12.0 Hz, 1H), 1.66 (d, J = 12.7 Hz, 1H), 1.55-1.45 (m, 1H), 1.44-1.32 (m, 1H); HPLC purity: 100%; LCMS Calculated for $C_{23}H_{32}N_4O_5S_2$: 508.65; Observed: 508.21 $[M - H]^-$. |
| A-456 | 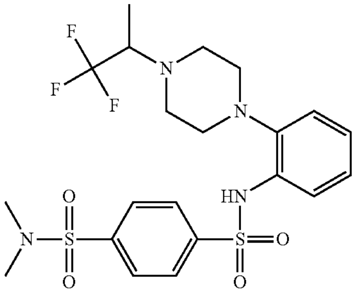 [SMILES: CC(N1CCN(c2ccccc2NS(=O)(=O)c2ccc(S(=O)(=O)N(C)C)cc2)CC1)C(F)(F)F] | Yield: 303.0 mg, 36.0%; Appearance: Beige solid; $^1H$ NMR (400 MHz, DMSO-$d_6$) δ 9.30 (s, 1H), 8.00 (d, J = 8.2 Hz, 2H), 7.92 (d, J = 8.2 Hz, 2H), 7.22 (d, J = 7.8 Hz, 1H), 7.17-7.10 (m, 2H), 7.10-7.01 (m, 1H), 3.51-3.42 (m, 1H), 2.70-2.59 (m, 10H), 2.58-2.51 (m, 5H), 1.18 (d, J = 7.0 Hz, 3H); HPLC purity: 96.33%; LCMS Calculated for $C_{21}H_{27}F_3N_4O_4S_2$: 520.59; Observed: 520.17 $[M - H]^-$. |

-continued

| Compound No. | Structure | Analytical data |
|---|---|---|
| A-452 | 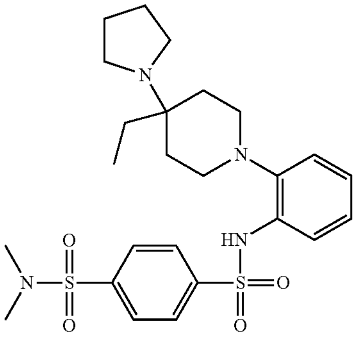 [SMILES: CCC1(N2CCCC2)CCN(c2ccccc2NS(=O)(=O)c2ccc(S(=O)(=O)N(C)C)cc2)CC1] | Yield: 85.0 mg, 5.93%; Appearance: Pink solid; $^1$H NMR (400 MHz, Chloroform-d) δ 7.94 (d, J = 8.1 Hz, 2H), 7.79 (d, J = 8.0 Hz, 2H), 7.56 (d, J = 8.1 Hz, 1H), 7.14 (s, 1H), 7.07 (d, J = 13.9 Hz, 2H), 2.64 (d, J = 29.1 Hz, 13H), 2.23 (s, 2H), 1.73-1.46 (m, 10H), 0.89 (d, J = 8.0 Hz, 3H); HPLC purity: 100%; LCMS Calculated for $C_{25}H_{36}N_4O_4S_2$: 520.71; Observed: 520.26 $[M-H]^-$. |
| A-451 | 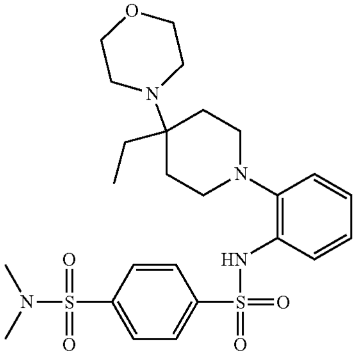 [SMILES: CCC1(N2CCOCC2)CCN(c2ccccc2NS(=O)(=O)c2ccc(S(=O)(=O)N(C)C)cc2)CC1] | Yield: 49.5 mg, 8.51%; Appearance: Yellow solid; $^1$H NMR (400 MHz, Chloroform-d) δ 8.19 (s, 1H), 7.98-7.91 (m, 2H), 7.79 (d, J = 8.2 Hz, 2H), 7.56 (dd, J = 7.9, 1.8 Hz, 1H), 7.21-7.14 (m, 1H), 7.14-7.01 (m, 2H), 3.66 (d, J = 4.5 Hz, 4H), 2.83 (d, J = 14.7 Hz, 2H), 2.68 (s, 6H), 2.56 (t, J = 4.5 Hz, 4H), 2.18 (s, 2H), 1.72 (d, J = 13.9 Hz, 2H), 1.57-1.38 (m, 4H), 0.89 (t, J = 7.6 Hz, 3H); HPLC purity: 100%; LCMS Calculated for $C_{25}H_{36}N_4O_5S_2$: 536.71; Observed: 536.25 $[M-H]^-$. |

Example A51: Synthesis of N4-[2-(4-cyclopentylpiperazin-1-yl)phenyl]-N1,N1-dimethylbenzene-1,4-disulfonamide (A-453)

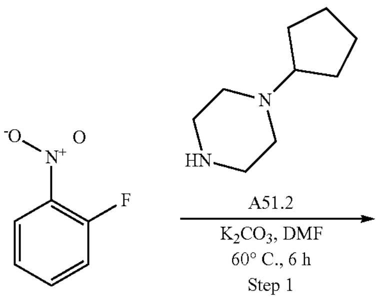

A51.1

-continued

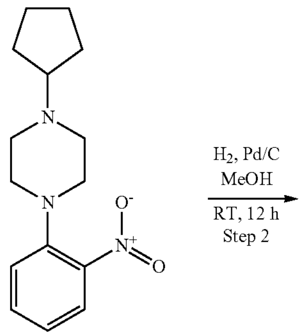

A51.3

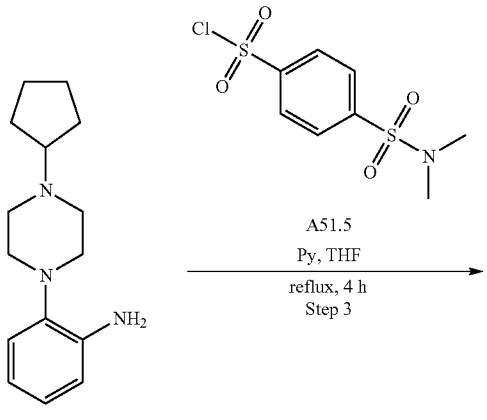

A51.4

-continued

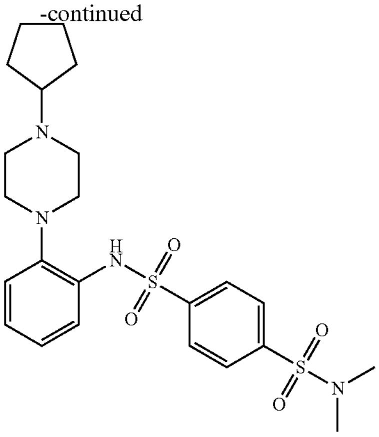

A-453

Step-1. Synthesis of 1-cyclopentyl-4-(2-nitrophenyl)piperazine (A51.3)

1-fluoro-2-nitrobenzene (A51.1) (1.83 g, 12.9 mmol) was added to a stirred solution of 1-cyclopentylpiperazine (A51.2) (2 g, 12.9 mmol) and potassium carbonate (2.69 g, 19.4 mmol) in dry DMF (20 mL). The mixture was stirred at 60° C. until the reaction completion (TLC control) and concentrated under the reduced pressure. The residue was dissolved in chloroform (15 mL), the organic layer was washed with water (15 mL), dried over anhydrous sodium sulfate, filtered and concentrated under reduced pressure to afford 1-cyclopentyl-4-(2-nitrophenyl)piperazine (1.12 g, 84.06 mmol, 85% purity, 26.8% yield) that was used in next step without further purification.

Step-2. Synthesis of 2-(4-cyclopentylpiperazin-1-yl)aniline (A51.4)

1-cyclopentyl-4-(2-nitrophenyl)piperazine (A51.3) (1.12 g, 4.06 mmol) was dissolved in methanol (100 mL) and treated with 10% Pd/C (0.1 g). The resulting mixture was hydrogenated at ambient pressure and room temperature until the reaction was completed (TLC control, overnight). The catalyst was filtered off and the filtrate was evaporated to afford 2-(4-cyclopentylpiperazin-1-yl)aniline (A51.4) (0.696 g, 2.83 mmol, 95% purity, 66.3% yield).

Step-3. Synthesis of N4-[2-(4-cyclopentylpiperazin-1-yl)phenyl]-N1,N1-dimethylbenzene-1,4-disulfonamide (A-453)

4-(N,N-dimethylsulfamoyl)benzenesulfonyl chloride (A51.5) (0.8 g, 3.69 mmol) was added to the mixture of 2-(4-cyclopentylpiperazin-1-yl)aniline (A51.4) (0.69 g, 2.48 mmol) and pyridine (0.33 g, 4.17 mmol) in dry THF (20 mL). The reaction mixture was refluxed for 4 h and evaporated. The residue was subjected to HPLC purification (deionized water/HPLC-grade methanol) that afforded the product as beige solid. The analytical data provided for this compound provisionally supports the proposed structure for N4-[2-(4-cyclopentylpiperazin-1-yl)phenyl]-N1,N1-dimethylbenzene-1,4-disulfonamide (A-453). Yield: 312.7 mg, 24.3%; Appearance: Beige solid; $^1$H NMR (400 MHz, Chloroform-d) δ 8.13 (s, 1H), 7.95 (d, J=8.3 Hz, 2H), 7.80 (d, J=8.3 Hz, 2H), 7.54 (d, J=8.6 Hz, 1H), 7.16-7.06 (m, 2H), 7.06-7.00 (m, 1H), 2.68 (m, 15H), 1.88 (t, J=12.3 Hz, 2H), 1.70 (t, J=7.9 Hz, 2H), 1.61-1.50 (m, 2H), 1.41 (s, 2H); HPLC purity: 98.02%; LCMS Calculated for $C_{23}H_{32}N_4O_4S_2$: 492.65; Observed: 492.22 $[M-H]^-$.

The following examples were prepared using standard chemical manipulations and procedures similar to those used for the preparation of the previous example.

| Compound No. | Structure | Analytical data |
|---|---|---|
| A-505 | 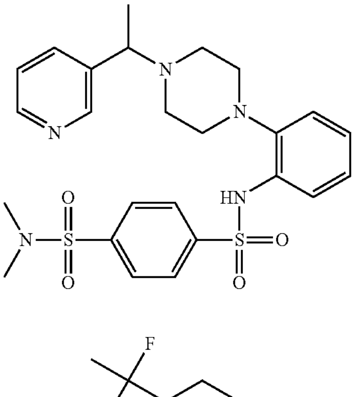 | Yield: 401.0 mg, 25.5%; Appearance: Light brown solid; $^1$H NMR (400 MHz, DMSO-$d_6$) δ 9.25 (s, 1H), 8.55-8.44 (m, 2H), 7.99-7.86 (m, 4H), 7.72 (d, J = 7.9 Hz, 1H), 7.38 (dd, J = 7.8, 4.7 Hz, 1H), 7.20 (d, J = 7.8 Hz, 1H), 7.12 (d, J = 4.3 Hz, 2H), 7.04 (dq, J = 8.6, 4.3 Hz, 1H), 3.53 (d, J = 7.0 Hz, 1H), 2.59 (s, 6H), 2.54 (s, 4H), 2.41 (s, 2H), 2.31 (s, 2H), 1.33 (d, J = 6.7 Hz, 3H); HPLC purity: 100%; LCMS Calculated for $C_{25}H_{31}N_5O_4S_2$: 529.67; Observed: 529.21 $[M - H]^-$. |
| A-506 | 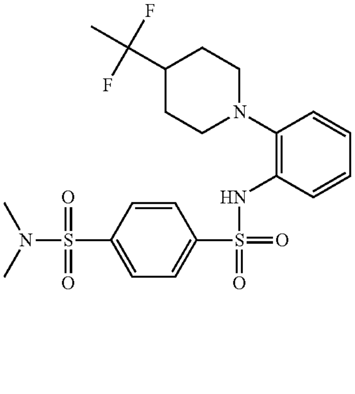 [SMILES: CN(C)S(=O)(=O)c1ccc(S(=O)(=O)Nc2ccccc2N2CCC(C(C)(F)F)CC2)cc1] | Yield: 112.8 mg, 8.84%; Appearance: Pink solid; $^1$H NMR (500 MHz, DMSO-$d_6$) δ 9.30 (s, 1H), 8.00 (d, J = 8.6 Hz, 2H), 7.92 (d, J = 8.1 Hz, 2H), 7.26 (d, J = 7.9 Hz, 1H), 7.11 (d, J = 4.3 Hz, 2H), 7.10-7.01 (m, 1H), 2.62 (s, 8H), 2.48-2.35 (m, 3H), 1.81 (t, J = 13.0 Hz, 1H), 1.66-1.44 (m, 7H); HPLC purity: 100%; LCMS Calculated for $C_{21}H_{27}F_2N_3O_4S_2$: 487.58; Observed: 487.17 $[M - H]^-$. |

-continued

| Compound No. | Structure | Analytical data |
| --- | --- | --- |
| A-494 | 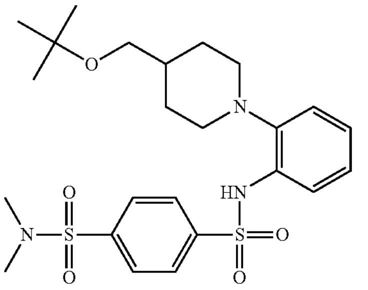 [SMILES: CN(C)S(=O)(=O)c1ccc(S(=O)(=O)Nc2ccccc2N2CCC(COC(C)(C)C)CC2)cc1] | Yield: 37.0 mg, 2.27%; Appearance: Brown solid; $^1$H NMR (400 MHz, DMSO-$d_6$) δ 9.11 (s, 1H), 8.00 (d, J = 8.5 Hz, 2H), 7.89 (d, J = 8.0 Hz, 2H), 7.25 (d, J = 6.2 Hz, 1H), 7.12-6.99 (m, 3H), 3.16 (s, 2H), 2.62 (d, J = 3.0 Hz, 8H), 2.41 (t, J = 11.6 Hz, 2H), 1.59 (d, J = 12.5 Hz, 2H), 1.40 (s, 1H), 1.22 (d, J = 12.9 Hz, 2H), 1.14 (d, J = 2.9 Hz, 9H); HPLC purity: 100%; LCMS Calculated for $C_{24}H_{35}N_3O_5S_2$: 509.68; Observed: 509.24 $[M - H]^-$. |
| A-495 | 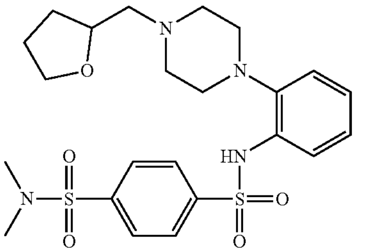 [SMILES: CN(C)S(=O)(=O)c1ccc(S(=O)(=O)Nc2ccccc2N2CCN(CC3CCCO3)CC2)cc1] | Yield: 145.5 mg, 7.53%; Appearance: Orange solid; $^1$H NMR (400 MHz, DMSO-$d_6$) δ 8.02-7.90 (m, 4H), 7.22 (d, J = 7.5Hz, 1H), 7.12 (d, J = 4.3 Hz, 2H), 7.04 (s, 1H), 3.90 (s, 1H), 3.73 (s, 1H), 3.59 (d, J = 7.6 Hz, 1H), 2.62 (q, J = 4.9, 3.5 Hz, 7H), 2.54 (s, 5H), 2.39 (s, 5H), 1.91 (s, 1H), 1.77 (s, 2H), 1.46 (s, 1H); HPLC purity: 100%; LCMS Calculated for $C_{23}H_{32}N_4O_5S_2$: 508.65; Observed: 508.21 $[M - H]^-$. |
| A-496 | 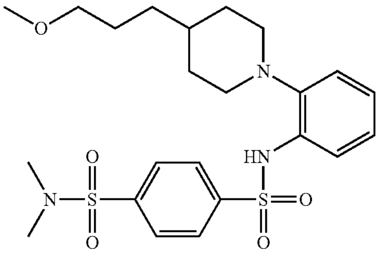 [SMILES: COCCCC1CCN(c2ccccc2NS(=O)(=O)c2ccc(S(=O)(=O)N(C)C)cc2)CC1] | Yield: 215.2 mg, 10.2%; Appearance: Violet solid; $^1$H NMR (400 MHz, DMSO-$d_6$) δ 9.11 (s, 1H), 7.98 (d, J = 8.4 Hz, 2H), 7.90 (d, J = 7.8 Hz, 2H), 7.25 (d, J = 7.8 Hz, 1H), 7.09 (d, J = 4.5 Hz, 2H), 7.03 (dt, J = 8.8, 4.5 Hz, 1H), 3.30-3.26 (m, 2H), 3.20 (s, 3H), 2.59 (s, 6H), 2.51 (s, 4H), 2.39 (t, J = 10.5 Hz, 2H), 1.56-1.44 (m, 4H), 1.29-1.09 (m, 5H); HPLC purity: 96.51%; LCMS Calculated for $C_{23}H_{33}N_3O_5S_2$: 495.65; Observed: 495.22 $[M - H]^-$. |
| A-611 | 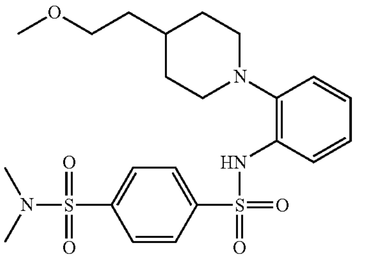 [SMILES: COCCC1CCN(c2ccccc2NS(=O)(=O)c2ccc(S(=O)(=O)N(C)C)cc2)CC1] | Yield: 176.4 mg, 7.42%; Appearance: Beige solid; $^1$H NMR (600 MHz, DMSO-$d_6$) δ 9.09 (s, 1H), 7.97 (d, J = 8.2 Hz, 2H), 7.89 (d, J = 8.2 Hz, 2H), 7.24 (d, J = 8.0 Hz, IH), 7.11-7.06 (m, 2H), 7.06-6.99 (m, 1H), 3.33 (d, J = 6.5 Hz, 2H), 3.19 (s, 3H), 2.59 (s, 6H), 2.52-2.49 (m, 2H), 2.43-2.35 (m, 2H), 1.52 (d, J = 12.5 Hz, 2H), 1.43 (q, J = 6.6 Hz, 2H), 1.37-1.31 (m, 1H), 1.25-1.15 (m, 2H); HPLC purity: 100%; LCMS Calculated for $C_{22}H_{31}N_3O_5S_2$: 481.63; Observed: 481.2 $[M - H]^-$. |
| A-562 | 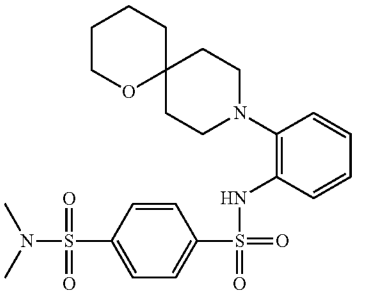 [SMILES: CN(C)S(=O)(=O)c1ccc(S(=O)(=O)Nc2ccccc2N2CCC3(CCCCO3)CC2)cc1] | Yield: 137.1 mg, 16.2%; Appearance: Pink solid; $^1$H NMR (400 MHz, DMSO-$d_6$) δ 9.21 (s, 1H), 8.01 (d, J = 8.1 Hz, 2H), 7.93 (d, J = 8.2 Hz, 2H), 7.27 (d, J = 7.8 Hz, 1H), 7.16-7.00 (m, 3H), 3.53 (t, J = 5.3 Hz, 2H), 2.62 (s, 8H), 2.35-2.26 (m, 2H), 1.75 (d, J = 13.2 Hz, 2H), 1.63-1.36 (m, 8H); HPLC purity: 100%; LCMS Calculated for $C_{23}H_{31}N_3O_5S_2$: 493.64; Observed: 493.2 $[M - H]^-$. |

-continued

| Compound No. | Structure | Analytical data |
| --- | --- | --- |
| A-584 | 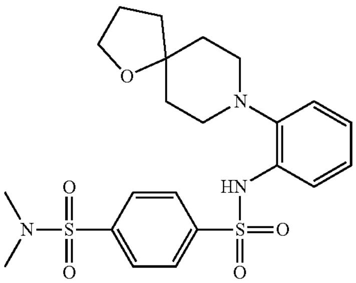 [SMILES: CN(C)S(=O)(=O)c1ccc(S(=O)(=O)Nc2ccccc2N2CCC3(CCCO3)CC2)cc1] | Yield: 291.9 mg, 22.5%; Appearance: Light brown solid; $^1$H NMR (600 MHz, DMSO-$d_6$) δ 9.19 (s, 1H), 7.98 (d, J = 8.4 Hz, 2H), 7.89 (d, J = 8.4 Hz, 2H), 7.25 (dd, J = 8.0, 1.4 Hz, 1H), 7.12-7.05 (m, 2H), 7.05-6.99 (m, 1H), 3.67 (t, J = 6.7 Hz, 2H), 2.59 (s, 8H), 2.36 (dt, J = 10.9, 4.9 Hz, 2H), 1.86-1.78 (m, 2H), 1.66-1.60 (m, 2H), 1.59-1.48 (m, 4H); HPLC purity: 100%; LCMS Calculated for $C_{22}H_{29}N_3O_5S_2$: 479.61; Observed: 479.18 $[M-H]^-$. |
| A-695 | 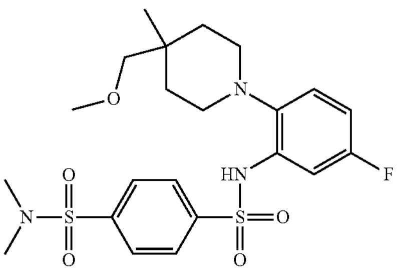 [SMILES: COCC1(C)CCN(c2ccc(F)cc2NS(=O)(=O)c2ccc(S(=O)(=O)N(C)C)cc2)CC1] | Yield: 718.6 mg, 28.7%; Appearance: Yellow solid; $^1$H NMR (400 MHz, DMSO-$d_6$) δ 9.28 (s, 1H), 8.01 (d, J = 8.2 Hz, 2H), 7.90 (d, J = 8.2 Hz, 2H), 7.26 (dd, J = 8.9, 5.9 Hz, 1H), 7.10 (dd, J = 10.3, 3.0 Hz, 1H), 6.93 (td, J = 8.5, 3.0 Hz, 1H), 3.24 (s, 3H), 3.08 (s, 2H), 2.58 (s, 6H), 2.42 (t, J = 10.1 Hz, 2H), 2.35-2.28 (m, 2H), 1.53-1.45 (m, 2H), 1.26-1.19 (m, 2H), 0.89 (s, 3H); HPLC purity: 100%; LCMS Calculated for $C_{22}H_{30}FN_3O_5S_2$: 499 62; Observed: 499.19 $[M-H]^-$. |
| A-694 | 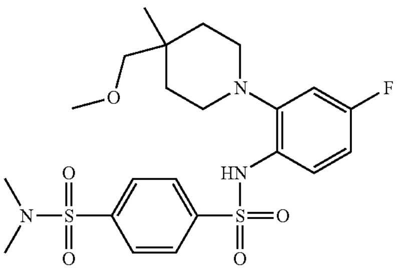 [SMILES: COCC1(C)CCN(c2cc(F)ccc2NS(=O)(=O)c2ccc(S(=O)(=O)N(C)C)cc2)CC1] | Yield: 210.5 mg, 7.74%; Appearance: Violet solid; $^1$H NMR (400 MHz, DMSO-$d_6$) δ 9.31 (s, 1H), 7.93 (s, 5H), 7.19 (dd, J = 8.9, 6.3 Hz, 1H), 6.98 (dd, J = 10.8, 2.9 Hz, 1H), 6.86 (td, J= 8.4, 2.8 Hz, 1H), 3.26 (s, 3H), 3.07 (s, 2H), 2.63 (s, 6H), 2.53 (t, J = 4.5 Hz, 4H), 1.45-1.33 (m, 2H), 1.23-1.12 (m, 2H), 0.89 (s, 3H); HPLC purity: 96.60%; LCMS Calculated for $C_{22}H_{30}FN_3O_5S_2$: 499 62; Observed: 499.19 $[M-H]^-$. |

Example A52: Synthesis of N4-{2-[4-(1,4-dioxan-2-yl)piperidin-1-yl]phenyl}-N1,N1-dimethylbenzene-1,4-disulfonamide (A-437)

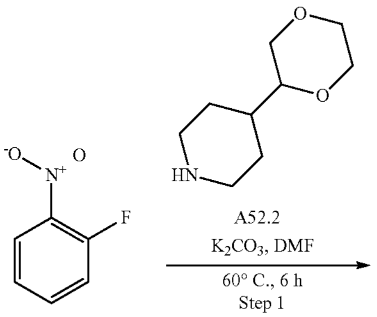

A52.1

-continued

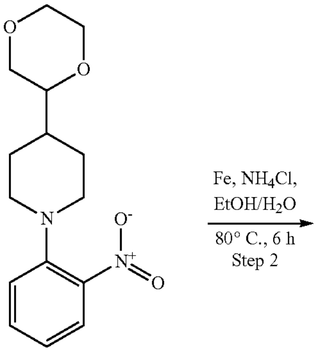

A52.3

-continued

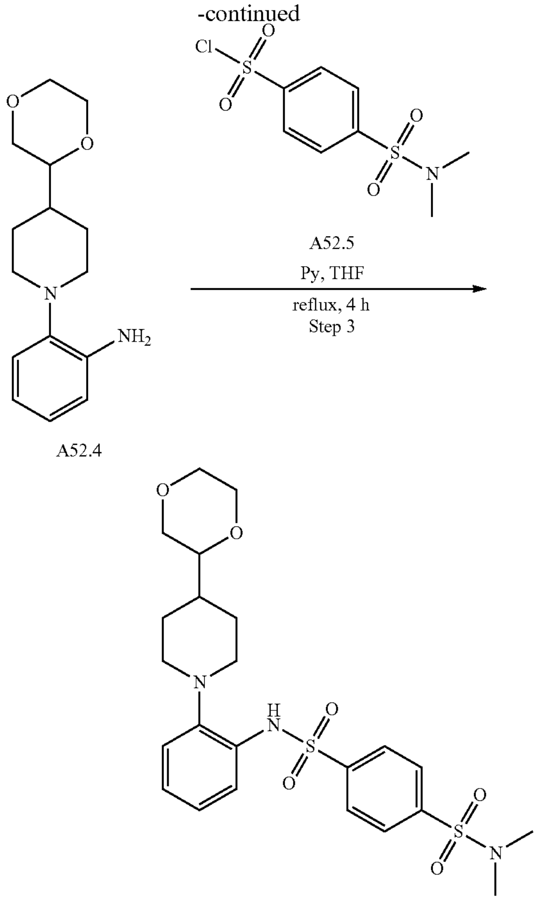

A52.4

A52.5

A-437

Step-1. Synthesis of 4-(1,4-dioxan-2-yl)-1-(2-nitrophenyl)piperidine (A52.3)

1-fluoro-2-nitrobenzene (A52.1) (1.65 g, 11.6 mmol) was added to a stirred solution of 4-(1,4-dioxan-2-yl)piperidine (A52.2) (2 g, 11.6 mmol) and potassium carbonate (2.42 g, 17.5 mmol) in dry DMF (20 mL). The mixture was stirred at 60° C. until the reaction completion (TLC control) and concentrated under the reduced pressure. The residue was dissolved in chloroform (15 mL), the organic layer was washed with water (15 mL), dried over anhydrous sodium sulfate, filtered and concentrated under reduced pressure. The chromatographic purification (chloroform/ethyl acetate) of crude product afforded 4-(1,4-dioxan-2-yl)-1-(2-nitrophenyl)piperidine as a powder (A52.3) (1.7 g, 5.81 mmol, 95% purity, 47.4% yield).

Step-2. Synthesis of 2-[4-(1,4-dioxan-2-yl)piperidin-1-yl]aniline (A52.4)

Iron powder (1.63 g, 29.1 mmol) and ammonium chloride (1.56 g, 29.1 mmol) were added at rt to a stirred solution of 4-(1,4-dioxan-2-yl)-1-(2-nitrophenyl)piperidine (A52.3) (1.7 g, 5.81 mmol) in a mixture of ethanol (25 mL) and water (25 mL) and the resulting reaction mixture was refluxed for 6 h. After the reaction completion (TLC control) the mixture was filtered through silica gel and the filtrate was evaporated. The residue was dissolved in water (25 mL) and ethyl acetate (25 mL). The organic layer was separated, washed with water (25 mL), dried over anhydrous sodium sulfate, filtered and evaporated under reduced pressure that afforded the crude 2-[4-(1,4-dioxan-2-yl)piperidin-1-yl]aniline (A52.4) (0.6 g, 2.28 mmol, 95% purity, 37.5% yield).

Step-3. Synthesis of N4-{2-[4-(1,4-dioxan-2-yl)piperidin-1-yl]phenyl}-N1,N1-dimethylbenzene-1,4-disulfonamide (A-437)

4-(N,N-dimethylsulfamoyl)benzenesulfonyl chloride (A52.5) (0.65 g, 2.99 mmol) was added to the mixture of 2-[4-(1,4-dioxan-2-yl)piperidin-1-yl]aniline (A52.4) (0.6 g, 2.28 mmol) and pyridine (0.27 g, 3.41 mmol) in dry THF (20 mL). The reaction mixture was refluxed for 4 h and evaporated. The residue was subjected to HPLC purification (deionized water/HPLC-grade methanol) that afforded N4-{2-[4-(1,4-dioxan-2-yl)piperidin-1-yl]phenyl}-N1,N1-dimethylbenzene-1,4-disulfonamide (A-437). Yield: 524.0 mg, 42.8%; Appearance: Beige solid; $^1$H NMR (400 MHz, Chloroform-d) δ 8.09 (s, 1H), 7.95 (d, J=8.2 Hz, 2H), 7.79 (d, J=8.2 Hz, 2H), 7.55 (d, J=8.0 Hz, 1H), 7.12-7.00 (m, 3H), 3.86-3.49 (m, 6H), 3.36 (d, J=6.1 Hz, 2H), 2.68 (s, 6H), 2.46 (d, J=12.4 Hz, 4H), 1.88 (s, 1H), 1.42 (s, 3H); HPLC purity: 100%; LCMS Calculated for $C_{23}H_{31}N_3O_6S_2$: 509.64; Observed: 509.19 $[M-H]^-$.

Example A53: Synthesis of N1,N1-dimethyl-N4-(2-{4-[(oxolan-3-yl)methyl]piperazin-1-yl}phenyl)benzene-1,4-disulfonamide (A-509)

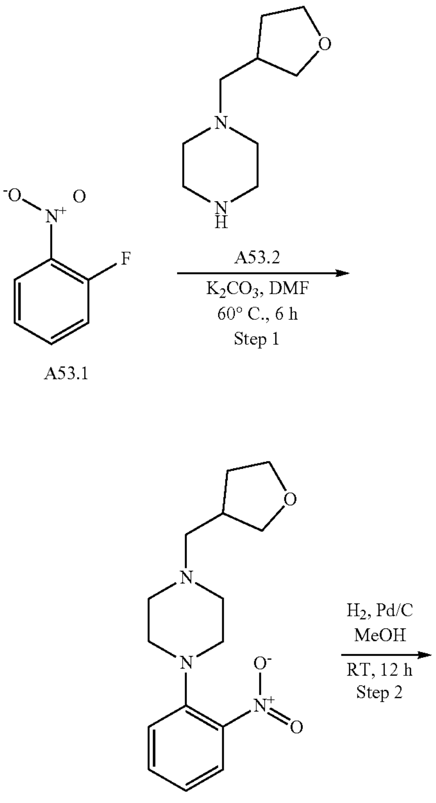

A53.2

A53.1

A53.3

-continued

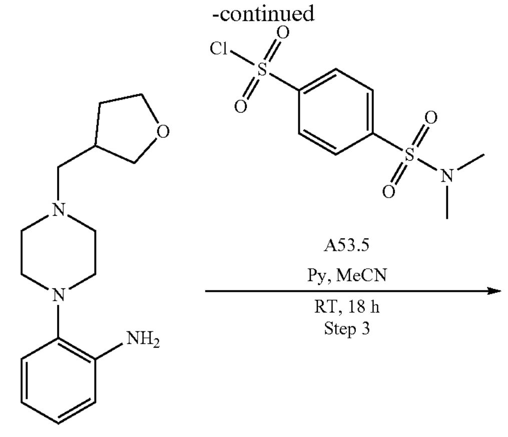

A53.4

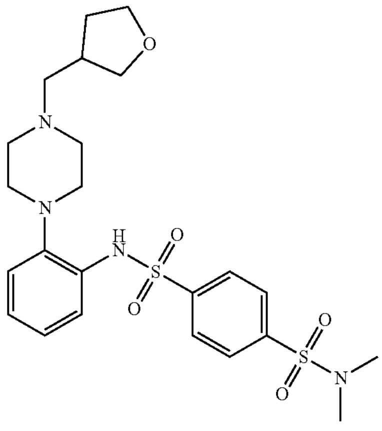

A-509

Step-1. Synthesis of 1-(2-nitrophenyl)-4-[(oxolan-3-yl)methyl]piperazine (A53.3)

1-fluoro-2-nitrobenzene (A53.1) (1.66 g, 11.7 mmol) was added to a stirred solution of 1-((tetrahydrofuran-3-yl) methyl)piperazine (A53.2) (2 g, 11.7 mmol) and potassium carbonate (2.44 g, 17.6 mmol) in dry DMF (20 mL). The mixture was stirred at 60° C. until the reaction completion (TLC control) and concentrated under the reduced pressure. The residue was dissolved in chloroform (15 mL), the organic layer was washed with water (15 mL), dried over anhydrous sodium sulfate, filtered and concentrated under reduced pressure to afford 1-(2-nitrophenyl)-4-[(oxolan-3-yl)methyl]piperazine (A53.3) (1.5 g, 5.14 mmol, 85% purity, 37.3% yield) that was used in next step without further purification.

Step-2. Synthesis of 2-{4-[(oxolan-3-yl)methyl] piperazin-1-1}aniline (A53.4)

1-(2-nitrophenyl)-4-[(oxolan-3-yl)methyl]piperazine (A53.3) (1.5 g, 5.14 mmol) was dissolved in methanol (100 mL) and treated with 10% Pd/C (0.1 g). The resulting mixture was hydrogenated at ambient pressure and room temperature until the reaction was completed (TLC control, overnight). The catalyst was filtered off and the filtrate was evaporated to afford 2-{4-[(oxolan-3-yl)methyl]piperazin-1-1}aniline (A53.4) (1.15 g, 4.39 mmol, 90% purity, 76.8% yield) that was used in next step without further purification.

Step-3. Synthesis of N1,N1-dimethyl-N4-(2-{4-[(oxolan-3-yl)methyl]piperazin-1-yl}phenyl)benzene-1,4-disulfonamide (A-509)

4-(dimethylsulfamoyl)benzene-1-sulfonyl chloride (A53.5) (1.25 g, 4.4 mmol) was added to the mixture of 2-{4-[(oxolan-3-yl)methyl]piperazin-1-yl}aniline (A53.4) (1.15 g, 4.4 mmol) and pyridine (0.52 g, 6.57 mmol) in dry acetonitrile (20 mL). The reaction mixture was stirred overnight and evaporated. The residue was subjected to HPLC purification (deionized water/HPLC-grade methanol, ammonia) that afforded N1,N1-dimethyl-N4-(2-{4-[(oxolan-3-yl)methyl]piperazin-1-yl}phenyl)benzene-1,4-disulfonamide (A-509). Yield: 156.0 mg, 6.63%; Appearance: Yellow solid; $^{1}$H NMR (500 MHz, DMSO-$d_6$) δ 9.22 (s, 1H), 7.98 (d, J=8.6 Hz, 2H), 7.92 (d, J=8.6 Hz, 2H), 7.22 (d, J=8.0 Hz, 1H), 7.15-7.08 (m, 2H), 7.08-7.01 (m, 1H), 3.70 (td, J=8.7, 4.2 Hz, 2H), 3.60 (q, J=7.5 Hz, 1H), 3.36 (d, J=7.2 Hz, 2H), 2.62 (d, J=1.7 Hz, 6H), 2.55 (t, J=5.1 Hz, 5H), 2.44-2.31 (m, 6H), 2.33-2.21 (m, 3H), 1.97-1.87 (m, 1H), 1.56-1.43 (in, 1H); HPLC purity: 100%; LCMS Calculated for $C_{23}H_{32}N_4O_5S_2$: 508.65; Observed: 508.21 $[M-H]^-$.

The following examples were prepared using standard chemical manipulations and procedures similar to those used for the preparation of the previous example.

| Compound No. | Structure | Analytical data |
| --- | --- | --- |
| A-510 | 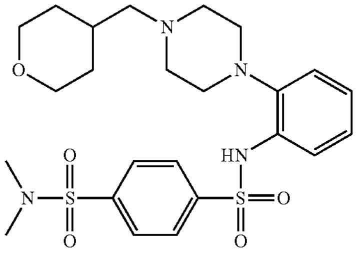 [SMILES: CN(C)S(=O)(=O)c1ccc(S(=O)(=O)Nc2ccccc2N2CCN(CC3CCOCC3)CC2)cc1] | Yield: 114.8 mg, 4.78%; Appearance: Yellow solid; $^{1}$H NMR (500 MHz, DMSO-$d_6$) δ 9.21 (s, 1H), 7.98 (d, J = 8.0 Hz, 2H), 7.91 (d, J = 8.2 Hz, 2H), 7.22 (d, J = 7.9 Hz, 1H), 7.11 (d, J = 4.4 Hz, 2H), 7.08-7.00 (m, 1H), 3.81 (dd, J = 11.2, 4.3 Hz, 2H), 3.26 (d, J = 11.5 Hz, 2H), 2.62 (s, 6H), 2.55 (t, J = 4.8 Hz, 4H), 2.34 (s, 4H), 2.14 (d, J = 7.2 Hz, 2H), 1.72 (d, J = 14.3 Hz, 1H), 1.58 (d, J = 13.1 Hz, 2H), 1.10 (qd, J = 12.2, 4.4 Hz, 2H); HPLC purity: 100%; LCMS Calculated for $C_{24}H_{34}N_4O_5S_2$: 522.68; Observed: 522.23 $[M-H]^-$. |

-continued

| Compound No. | Structure | Analytical data |
|---|---|---|
| A-523 | 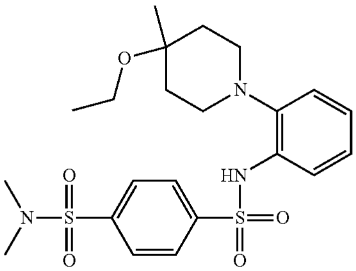 [SMILES: CCOC1(C)CCN(c2ccccc2NS(=O)(=O)c2ccc(S(=O)(=O)N(C)C)cc2)CC1] | Yield: 393.3 mg, 44.5%; Appearance: Pink solid; $^1$H NMR (400 MHz, DMSO-d$_6$) δ 9.20 (s, 1H), 8.04-7.97 (m, 2H), 7.96-7.88 (m, 2H), 7.27 (d, J = 7.9 Hz, 1H), 7.14-7.00 (m, 3H), 3.30 (t, J = 7.0 Hz, 2H), 2.61 (d, J = 2.0 Hz, 8H), 2.31 (d, J = 10.9 Hz, 2H), 1.63 (d, J = 13.1 Hz, 2H), 1.52 (t, J = 10.8 Hz, 2H), 1.14-1.03 (m, 6H); HPLC purity: 97.15%; LCMS Calculated for $C_{22}H_{31}N_3O_5S_2$: 481.63; Observed: 481.2 [M − H]$^-$. |
| A-545 | 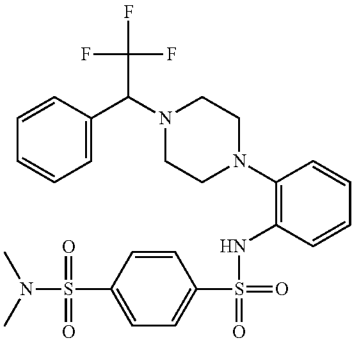 [SMILES: CN(C)S(=O)(=O)c1ccc(S(=O)(=O)Nc2ccccc2N2CCN(C(c3ccccc3)C(F)(F)F)CC2)cc1] | Yield: 575.9 mg, 53.6%; Appearance: Beige solid; $^1$H NMR (400 MHz, DMSO-d$_6$) δ 9.31 (s, 1H), 7.96-7.82 (m, 4H), 7.47 (dt, J = 12.0, 8.2 Hz, 5H), 7.19-6.98 (m, 4H), 4.58 (q, J = 9.6 Hz, 1H), 2.66-2.49 (m, 14H); HPLC purity: 100%; LCMS Calculated for $C_{26}H_{29}F_3N_4O_4S_2$: 582.66; Observed: 582.19 [M − H]$^-$. |
| A-544 | 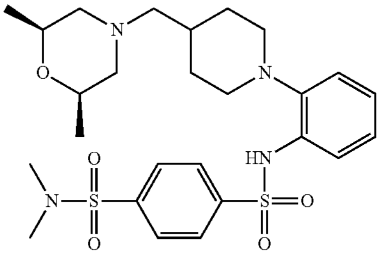 [SMILES: C[C@@H]1CN(CC2CCN(c3ccccc3NS(=O)(=O)c3ccc(S(=O)(=O)N(C)C)cc3)CC2)C[C@H](C)O1] | Yield: 218.2 mg, 28.7%; Appearance: Yellow solid; $^1$H NMR (400 MHz, DMSO-d$_6$) δ 9.12 (s, 1H), 7.99 (d, J = 8.1 Hz, 2H), 7.92 (d, J = 8.2 Hz, 2H), 7.27 (d, J = 7.9 Hz, 1H), 7.15-7.00 (m, 3H), 3.53 (t, J = 7.9 Hz, 2H), 2.69 (d, J = 11.0 Hz, 2H), 2.62 (s, 6H), 2.55 (d, J = 10.0 Hz, 2H), 2.42 (t, J = 11.2 Hz, 2H), 2.10 (d, J = 6.9 Hz, 2H), 1.57 (q, J = 11.7, 10.7 Hz, 5H), 1.14 (q, J = 10.5, 9.2 Hz, 2H), 1.04 (d, J = 6.2 Hz, 6H); HPLC purity: 100%; LCMS Calculated for $C_{26}H_{38}N_4O_5S_2$: 550.73; Observed: 550.27 [M − H]$^-$. |
| A-543 | 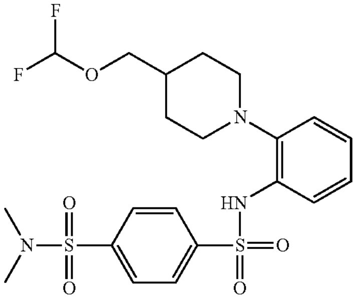 [SMILES: CN(C)S(=O)(=O)c1ccc(S(=O)(=O)Nc2ccccc2N2CCC(COC(F)F)CC2)cc1] | Yield: 199.2 mg, 24.0%; Appearance: Yellow solid; $^1$H NMR (400 MHz, DMSO-d$_6$) δ 9.17 (s, 1H), 7.98 (d, J = 8.5 Hz, 2H), 7.90 (d, J = 8.6 Hz, 2H), 7.25 (d, J = 7.8 Hz, 1H), 7.13-6.98 (m, 3H), 6.66 (t, J = 76.3 Hz, 1H), 3.69 (d, J = 6.2 Hz, 2H), 2.59 (s, 6H), 2.52 (d, J = 11.0 Hz, 2H), 2.41 (d, J = 11.3 Hz, 2H), 1.56 (d, J = 13.1 Hz, 3H), 1.37-1.26 (m, 2H); HPLC purity: 100%; LCMS Calculated for $C_{21}H_{27}F_2N_3O_5S_2$: 503.58; Observed: 503.16 [M − H]$^-$. |
| A-546 | 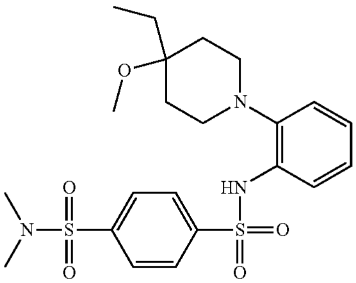 [SMILES: CCC1(OC)CCN(c2ccccc2NS(=O)(=O)c2ccc(S(=O)(=O)N(C)C)cc2)CC1] | Yield: 145.7 mg, 6.07%; Appearance: Beige solid; $^1$H NMR (400 MHz, DMSO-d$_6$) δ 9.22 (s, 1H), 8.00 (d, J = 8.2 Hz, 2H), 7.92 (d, J = 8.2 Hz, 2H), 7.28 (d, J = 7.8 Hz, 1H), 7.15-7.02 (m, 3H), 3.02 (s, 3H), 2.62 (s, 7H), 2.57 (s, 1H), 2.30 (d, J = 11.2 Hz, 2H), 1.61 (d, J = 13.3 Hz, 2H), 1.45 (q, J = 8.2 Hz, 4H), 0.78 (t, J = 7.4 Hz, 3H); HPLC purity: 100%; LCMS Calculated for $C_{22}H_{31}N_3O_5S_2$: 481.63; Observed: 481.2 [M − H]$^-$. |

-continued

| Compound No. | Structure | Analytical data |
|---|---|---|
| A-524 | 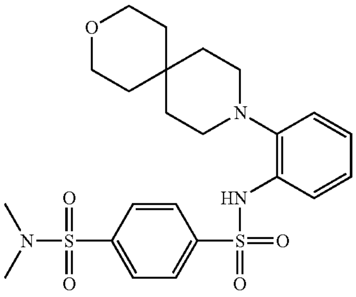 | Yield: 64.4 mg, 2.53%; Appearance: Orange solid; $^1$H NMR (400 MHz, DMSO-$d_6$) δ 9.17 (s, 2H), 8.00 (d, J = 7.8 Hz, 2H), 7.92 (d, J = 8.9 Hz, 2H), 7.26 (d, J = 8.1 Hz, 1H), 7.18 (d, J = 7.8 Hz, 1H), 7.14-7.00 (m, 2H), 3.53 (t, J = 5.5 Hz, 4H), 2.62 (d, J = 2.2 Hz, 6H), 2.47-2.44 (m, 4H), 1.45 (dd, J = 24.0, 6.3 Hz, 8H); HPLC purity: 100%; LCMS Calculated for $C_{23}H_{31}N_3O_5S_2$: 493.64; Observed: 493.2 $[M-H]^-$. |
| A-547 | 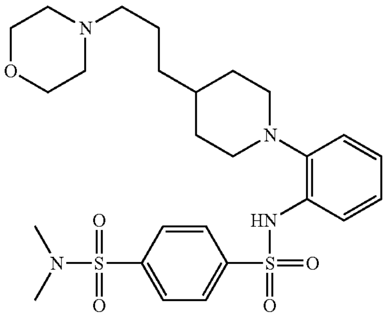 [SMILES: CN(C)S(=O)(=O)c1ccc(S(=O)(=O)Nc2ccccc2N2CCC(CCCN3CCOCC3)CC2)cc1] | Yield: 184.4 mg, 10.7%; Appearance: Red solid; $^1$H NMR (400 MHz, DMSO-$d_6$) δ 9.14 (s, 1H), 8.04-7.96 (m, 2H), 7.96-7.88 (m, 2H), 7.27 (d, J = 7.8 Hz, 1H), 7.14-7.00 (m, 3H), 3.57 (t, J = 4.6 Hz, 4H), 2.62 (s, 7H), 2.42 (t, J = 10.5 Hz, 2H), 2.33 (s, 4H), 2.24 (t, J = 7.4 Hz, 2H), 1.55 (d, J = 10.2 Hz, 2H), 1.43 (s, 2H), 1.22 (t, J = 6.9 Hz, 5H); HPLC purity: 100%; LCMS Calculated for $C_{26}H_{38}N_4O_5S_2$: 550.73; Observed: 550.27 $[M-H]^-$. |
| A-548 | 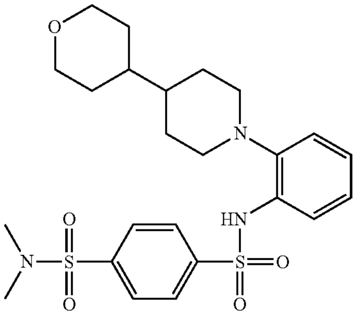 | Yield: 98.4 mg, 3.99%; Appearance: Pink solid; $^1$H NMR (400 MHz, DMSO-$d_6$) δ 9.17 (s, 1H), 7.99 (d, J = 8.3 Hz, 2H), 7.93 (d, J = 8.0 Hz, 2H), 7.27 (d, J = 7.8 Hz, 1H), 7.15-7.08 (m, 2H), 7.08-7.01 (m, 1H), 3.87 (d, J = 11.1 Hz, 2H), 3.26 (d, J = 11.0 Hz, 2H), 2.61 (d, J = 5.4 Hz, 8H), 2.39 (t, J = 11.0 Hz, 2H), 1.56 (s, 4H), 1.37-0.95 (m, 6H); HPLC purity: 100%; LCMS Calculated for $C_{24}H_{33}N_3O_5S_2$: 507.66; Observed: 507.22 $[M-H]^-$. |
| A-498 | 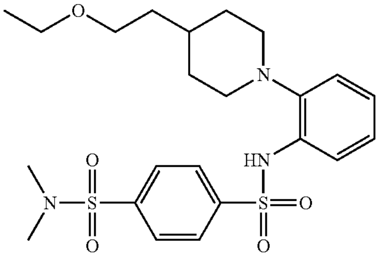 [SMILES: CCOCCC1CCN(c2ccccc2NS(=O)(=O)c2ccc(S(=O)(=O)N(C)C)cc2)CC1] | Yield: 163.2 mg, 7.04%; Appearance: Orange solid; $^1$H NMR (400 MHz, DMSO-$d_6$) δ 9.13 (s, 1H), 8.00 (d, J = 8.1 Hz, 2H), 7.92 (d, J = 8.2 Hz, 2H), 7.27 (d, J = 7.8 Hz, 1H), 7.12 (d, J = 4.3 Hz, 2H), 7.09-7.02 (m, 1H), 3.39 (t, J = 6.6 Hz, 4H), 2.61 (s, 6H), 2.42 (t, J = 11.1 Hz, 2H), 1.55 (d, J = 12.4 Hz, 2H), 1.44 (t, J = 6.6 Hz, 2H), 1.37 (s, 1H), 1.27-1.18 (m, 2H), 1.10 (t, J = 7.0 Hz, 3H); HPLC purity: 100%; LCMS Calculated for $C_{23}H_{33}N_3O_5S_2$: 495.65; Observed: 495.22 $[M-H]^-$. |
| A-525 | 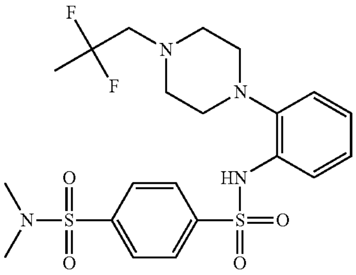 [SMILES: CN(C)S(=O)(=O)c1ccc(S(=O)(=O)Nc2ccccc2N2CCN(CC(C)(F)F)CC2)cc1] | Yield: 87.5 mg, 4.72%; Appearance: Orange solid; $^1$H NMR (400 MHz, DMSO-$d_6$) δ 9.27 (s, 1H), 7.98 (d, J = 8.4 Hz, 2H), 7.92 (d, J = 8.6 Hz, 2H), 7.23 (d, J = 7.6 Hz, 1H), 7.14 (d, J = 4.5 Hz, 2H), 7.10-7.03 (m, 1H), 2.72 (t, J = 13.9 Hz, 2H), 2.61 (s, 6H), 2.53 (s, 8H), 1.61 (t, J = 18.9 Hz, 3H); HPLC purity: 100%; LCMS Calculated for $C_{21}H_{28}F_2N_4O_4S_2$: 502.6; Observed: 502.18 $[M-H]^-$. |

-continued

| Compound No. | Structure | Analytical data |
|---|---|---|
| A-497 | 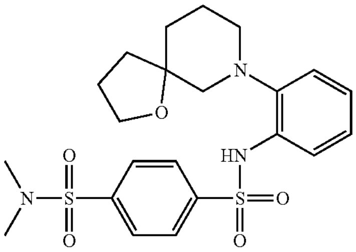 [SMILES: CN(C)S(=O)(=O)c1ccc(S(=O)(=O)Nc2ccccc2N2CCCC3(CCCO3)C2)cc1] | Yield: 384.6 mg, 44.2%; Appearance: Yellow solid; $^1$H NMR (400 MHz, DMSO-$d_6$) δ 9.19 (s, 1H), 7.98 (d, J = 8.1 Hz, 2H), 7.91 (d, J = 6.6 Hz, 2H), 7.37-7.30 (m, 1H), 7.08-7.00 (m, 3H), 3.97-3.90 (m, 1H), 3.80 (q, J = 7.7, 7.1 Hz, 1H), 2.78 (t, J = 8.9 Hz, 1H), 2.60 (s, 7H), 2.41 (d, J = 11.6 Hz, 1H), 1.94-1.84 (m, 2H), 1.82-1.38 (m, 6H); HPLC purity: 100%; LCMS Calculated for $C_{22}H_{29}N_3O_5S_2$: 479.61; Observed: 479.18 $[M - H]^-$. |
| A-507 | 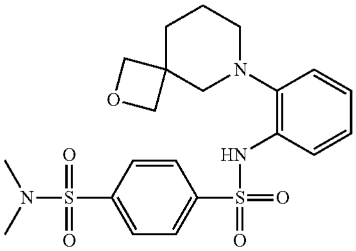 [SMILES: CN(C)S(=O)(=O)c1ccc(S(=O)(=O)Nc2ccccc2N2CCCC3(COC3)C2)cc1] | Yield: 350.0 mg, 40.9%; Appearance: Orange solid; $^1$H NMR (400 MHz, DMSO-$d_6$) δ 9.17 (s, 1H), 8.02 (d, J = 8.6 Hz, 2H), 7.94 (d, J = 8.5 Hz, 2H), 7.18-7.08 (m, 3H), 7.08-6.98 (m, 1H), 4.34-4.22 (m, 4H), 2.81 (s, 2H), 2.62 (s, 6H), 2.45 (d, J = 5.1 Hz, 2H), 1.70 (s, 2H), 1.49 (s, 2H); HPLC purity: 100%; LCMS Calculated for $C_{21}H_{27}N_3O_5S_2$: 465.58; Observed: 465.16 $[M - H]^-$. |
| A-508 | 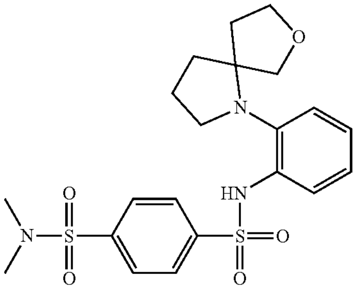 [SMILES: CN(C)S(=O)(=O)c1ccc(S(=O)(=O)Nc2ccccc2N2CCCC23CCOC3)cc1] | Yield: 414.9 mg, 48.6%; Appearance: White solid; $^1$H NMR (500 MHz, DMSO-$d_6$) δ 9.21 (s, 1H), 8.02 (d, J = 8.1 Hz, 2H), 7.92 (d, J = 8.1 Hz, 2H), 7.31 (dd, J = 6.6, 3.0 Hz, 1H), 7.24-7.18 (m, 1H), 7.08 (dd, J = 6.7, 3.1 Hz, 2H), 3.61-3.49 (m, 2H), 2.93 (q, J = 7.7 Hz, 1H), 2.89-2.81 (m, 1H), 2.61 (s, 6H), 1.93-1.80 (m, 4H), 1.67-1.56 (m, 2H); HPLC purity: 100%; LCMS Calculated for $C_{21}H_{27}N_3O_5S_2$: 465.58; Observed: 465.16 $[M - H]^-$. |
| A-499 | 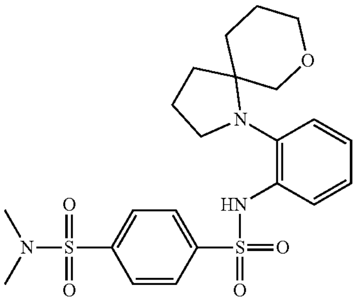 [SMILES: CN(C)S(=O)(=O)c1ccc(S(=O)(=O)Nc2ccccc2N2CCCC23CCCOC3)cc1] | Yield: 43.4 mg, 2.35%; Appearance: Light brown solid; $^1$H NMR (400 MHz, DMSO-$d_6$) δ 9.16 (s, 1H), 8.06 (d, J = 8.0 Hz, 2H), 7.93 (d, J = 7.1 Hz, 2H), 7.40 (d, J = 7.3 Hz, 1H), 7.25-7.20 (m, 1H), 7.19-7.11 (m, 1H), 7.10-7.01 (m, 1H), 3.62-3.48 (m, 2H), 2.97-2.79 (m, 4H), 2.61 (s, 6H), 2.06 (d, J = 11.6 Hz, 1H), 1.87-1.76 (m, 2H), 1.69-1.64 (m, 1H), 1.57-1.50 (m, 1H), 1.45-1.35 (m, 1H), 1.31-1.26 (m, 1H), 1.02-0.94 (m, 1H); HPLC purity: 100%; LCMS Calculated for $C_{22}H_{29}N_3O_5S_2$: 479.61; Observed: 479.18 $[M - H]^-$. |
| A-511 | 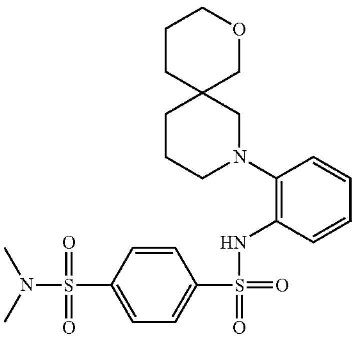 [SMILES: CN(C)S(=O)(=O)c1ccc(S(=O)(=O)Nc2ccccc2N2CCCC3(CCCOC3)C2)cc1] | Yield: 91.0 mg, 3.45%; Appearance: Yellow solid; $^1$H NMR (500 MHz, DMSO-$d_6$) δ 8.73 (s, 1H), 7.99 (d, J = 8.2 Hz, 2H), 7.92 (d, J = 8.1 Hz, 2H), 7.19 (d, J = 7.9 Hz, 1H), 7.17-7.08 (m, 2H), 7.03 (t, J = 7.6 Hz, 1H), 3.66-3.56 (m, 2H), 3.52-3.39 (m, 2H), 2.61 (s, 8H), 2.37 (d, J = 11.6 Hz, 2H), 1.59-1.37 (m, 7H), 1.18 (d, J = 9.3 Hz, 1H); HPLC purity: 100%; LCMS Calculated for $C_{23}H_{31}N_3O_5S_2$: 493.64; Observed: 493.2 $[M - H]^-$. |

-continued

| Compound No. | Structure | Analytical data |
|---|---|---|
| A-479 | 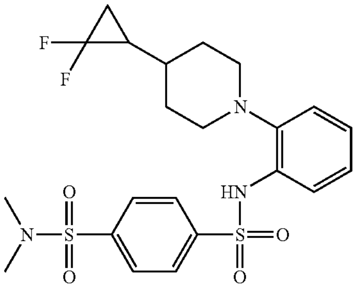 [SMILES: CN(C)S(=O)(=O)c1ccc(S(=O)(=O)Nc2ccccc2N2CCC(C3CC3(F)F)CC2)cc1] | Yield: 480.6 mg, 57.7%; Appearance: Beige solid; $^1$H NMR (400 MHz, DMSO-$d_6$) δ 9.18 (s, 1H), 8.00 (d, J = 8.4 Hz, 2H), 7.93 (d, J = 8.4 Hz, 2H), 7.30 (d, J = 7.8 Hz, 1H), 7.15-7.02 (m, 3H), 2.62 (s, 6H), 2.57-2.52 (m, 2H), 2.41 (t, J = 11.2 Hz, 2H), 1.65-1.34 (m, 6H), 1.20-1.04 (m, 2H); HPLC purity: 100%; LCMS Calculated for $C_{22}H_{27}F_2N_3O_4S_2$: 499.59; Observed: 499.17 $[M - H]^-$. |
| A-484 | 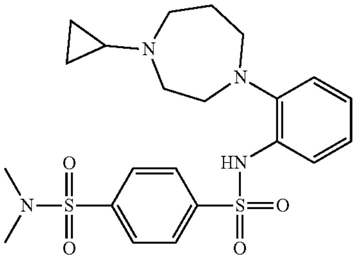 [SMILES: CN(C)S(=O)(=O)c1ccc(S(=O)(=O)Nc2ccccc2N2CCCN(C3CC3)CC2)cc1] | Yield: 186.0 mg, 21.3%; Appearance: Yellow solid; $^1$H NMR (400 MHz, DMSO-$d_6$) δ 10.58 (s, 1H), 7.95 (q, J = 8.0 Hz, 4H), 7.11-7.02 (m, 3H), 6.96-6.86 (m, 1H), 2.87 (d, J = 6.7 Hz, 4H), 2.82-2.71 (m, 4H), 2.63 (s, 6H), 1.90 (s, 1H), 1.74-1.64 (m, 2H), 0.42 (d, J = 6.7 Hz, 2H), 0.30 (s, 2H); HPLC purity: 96.15%; LCMS Calculated for $C_{22}H_{30}N_4O_4S_2$: 478.63; Observed: 478.2 $[M - H]^-$. |
| A-480 | 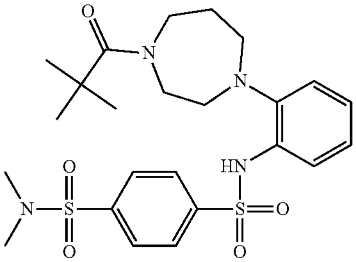 [SMILES: CN(C)S(=O)(=O)c1ccc(S(=O)(=O)Nc2ccccc2N2CCCN(C(=O)C(C)(C)C)CC2)cc1] | Yield: 191.6 mg, 19.2%; Appearance: Yellow solid; $^1$H NMR (400 MHz, DMSO-$d_6$) δ 9.30 (s, 1H), 8.00 (d, J = 8.5 Hz, 2H), 7.93 (d, J = 8.4 Hz, 2H), 7.16-7.04 (m, 3H), 7.00-6.91 (m, 1H), 3.61 (s, 2H), 3.55 (s, 2H), 2.81 (t, J = 12.2 Hz, 4H), 2.62 (s, 7H), 1.81 (s, 2H), 1.17 (s, 9H); HPLC purity: 100%; LCMS Calculated for $C_{24}H_{34}N_4O_5S_2$: 522.68; Observed: 522.23 $[M - H]^-$. |
| A-628 | 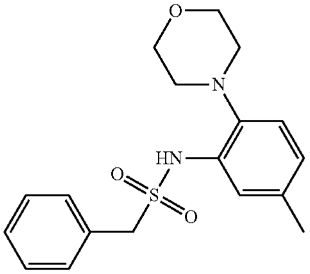 [SMILES: Cc1ccc(N2CCOCC2)c(NS(=O)(=O)Cc2ccccc2)c1] | Yield: 163.3 mg, 43.0%; Appearance: Green solid; $^1$H NMR (600 MHz, DMSO-$d_6$) δ 8.13 (s, 1H), 7.35-7.30 (m, 3H), 7.30-7.25 (m, 2H), 7.10 (d, J = 8.0 Hz, 1H), 6.91 (d, J = 1.9 Hz, 1H), 6.86 (dd, J = 8.0, 2.0 Hz, 1H), 4.60 (s, 2H), 3.65-3.60 (m, 4H), 2.69-2.65 (m, 4H), 2.18 (s, 3H); HPLC purity: 100%; LCMS Calculated for $C_{18}H_{22}N_2O_3S$: 346.45; Observed: 346.16 $[M - H]^-$. |
| A-681 | 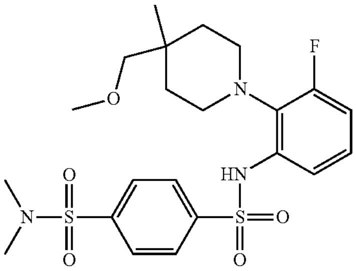 [SMILES: COCC1(C)CCN(c2c(F)cccc2NS(=O)(=O)c2ccc(S(=O)(=O)N(C)C)cc2)CC1] | Yield: 101.3 mg, 4.88%; Appearance: White solid; $^1$H NMR (400 MHz, DMSO-$d_6$) δ 9.26 (s, 1H), 8.01-7.89 (m, 4H), 7.26-7.13 (m, 2H), 7.04-6.94 (m, 1H), 3.27 (s, 3H), 3.11 (s, 2H), 2.71-2.63 (m, 2H), 2.60 (s, 6H), 2.43-2.31 (m, 2H), 1.50 (t, J = 11.4 Hz, 2H), 1.24 (d, J = 12.7 Hz, 2H), 0.92 (s, 3H); HPLC purity: 100%; LCMS Calculated for $C_{22}H_{30}FN_3O_5S_2$: 499.62; Observed: 499.19 $[M - H]^-$. |

Example A54: Synthesis of N4-{2-[4-(2-fluoroethyl)piperazin-1-yl]phenyl}-N1,N1-dimethylbenzene-1,4-disulfonamide (A-559)

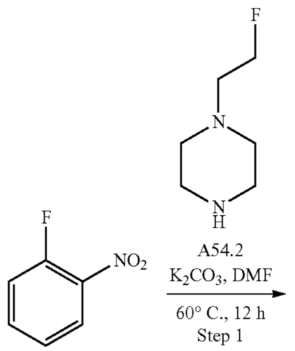

A54.1

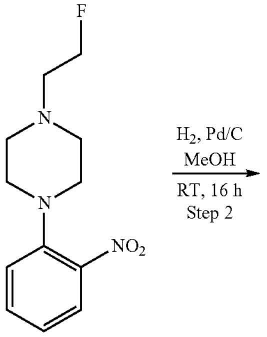

A54.3

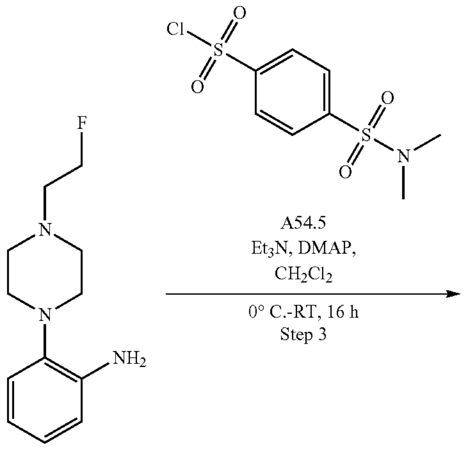

A54.4

-continued

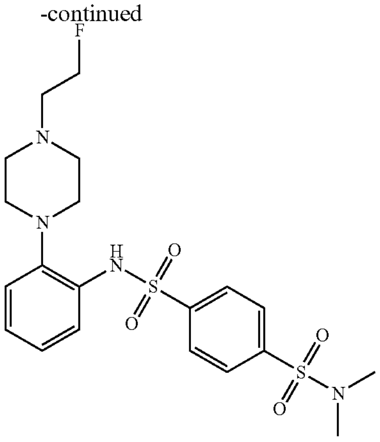

A-559

Step-1. Synthesis of 1-(2-fluoroethyl)-4-(2-nitrophenyl)piperazine (A54.3)

1-fluoro-2-nitrobenzene (A54.1) (0.5 g, 3.54 mmol) was added to a stirred solution of 1-(2-fluoroethyl)piperazine dihydrochloride (A54.2) (0.8 g, 3.89 mmol) and potassium carbonate (1.6 g, 11.6 mmol) in dry DMF (20 ml). The mixture was stirred at 60° C. until the reaction completion (TLC control) and concentrated under the reduced pressure. The residue was dissolved in chloroform (15 mL), the organic layer was washed with water, dried over anhydrous sodium sulfate, filtered and concentrated under reduced pressure to afford 1-(2-fluoroethyl)-4-(2-nitrophenyl)piperazine (A54.3) (0.75 g, 2.96 mmol, 83% purity, 69.4% yield) that was used in next step without further purification.

Step-2. Synthesis of 2-[4-(2-fluoroethyl)piperazin-1-yl]aniline (A54.4)

1-(2-fluoroethyl)-4-(2-nitrophenyl)piperazine (A54.3) (0.75 g, 2.96 mmol) was dissolved in methanol (10 mL) and treated with 5% Pd/C (0.1 g). The resulting mixture was hydrogenated at ambient pressure and room temperature until the reaction was completed (TLC control). The catalyst was filtered off and the filtrate was evaporated to afford 2-[4-(2-fluoroethyl)piperazin-1-yl]aniline (A54.4) (0.61 g, 2.73 mmol, 100% purity, 92.4% yield).

Step-3. Synthesis of N4-{2-[4-(2-fluoroethyl)piperazin-1-yl]phenyl}-N1,N1-dimethylbenzene-1,4-disulfonamide (A-559)

4-(dimethylsulfamoyl)benzene-1-sulfonyl chloride (A54.5) (0.397 g, 1.4 mmol) was added to an ice-cooled solution of 2-[4-(2-fluoroethyl)piperazin-1-yl]aniline (A54.4) (0.3 g, 1.34 mmol) and triethylamine (0.271 g, 2.68 mmol) in DCM (10 mL). After, DMAP (0.082 g, 0.670 mmol) was added and the reaction mixture was allowed to warm to room temperature and stirred until completion (overnight, NMR control). After the reaction mixture was diluted with water (10 mL), the organic layer was separated, dried over magnesium sulfate and concentrated in vacuo. The residue was subjected to HPLC purification (deionized water/HPLC-grade methanol) that afforded N4-{2-[4-(2-fluoroethyl)piperazin-1-yl]phenyl}-N1,N1-dimethylbenzene-1,4-disulfonamide (A-559). Yield: 36.6 mg, 5.5%;

Appearance: Beige solid; $^1$H NMR (400 MHz, DMSO-$d_6$) δ 9.28 (s, 1H), 7.99 (d, J=8.2 Hz, 2H), 7.92 (d, J=8.0 Hz, 2H), 7.23 (d, J=7.9 Hz, 1H), 7.17-7.11 (m, 2H), 7.11-7.04 (m, 1H), 4.63-4.56 (m, 1H), 4.51-4.41 (m, 1H), 2.67 (s, 1H), 2.62 (s, 7H), 2.56 (d, J=4.2 Hz, 4H), 2.48-2.43 (m, 4H); HPLC purity: 100%; LCMS Calculated for $C_{20}H_{27}FN_4O_4S_2$: 470.58; Observed: 470.17 [M−H]$^-$.

The following example was prepared using standard chemical manipulations and procedures similar to those used for the preparation of the previous example.

| Compound No. | Structure | Analytical data |
|---|---|---|
| A-552 | 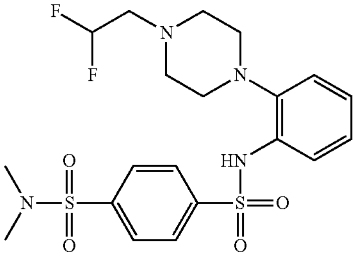 [SMILES: CN(C)S(=O)(=O)c1ccc(S(=O)(=O)Nc2ccccc2N2CCN(CC(F)F)CC2)cc1] | Yield: 76.1 mg, 11.9%; Appearance: Beige solid; $^1$H NMR (400 MHz, DMSO-$d_6$) δ 9.22 (s, 1H), 7.95 (d, J = 8.5 Hz, 2H), 7.88 (d, J = 8.5 Hz, 2H), 7.19 (d, J = 7.9 Hz, 1H), 7.14-7.07 (m, 2H), 7.08-6.98 (m, 1H), 6.09 (tt, J = 55.8, 4.4 Hz, 1H), 2.71 (td, J = 15.7, 4.3 Hz, 2H), 2.58 (s, 6H), 2.49-2.42 (m, 8H); HPLC purity: 98.24%; LCMS Calculated for $C_{20}H_{26}F_2N_4O_4S_2$: 488.57; Observed: 488.16 [M − H]$^-$. |

Example A55: Synthesis of N1,N1-dimethyl-N4-(2-{4-[(morpholin-4-yl)methyl]piperidin-1-yl}phenyl)benzene-1,4-disulfonamide (A-554)

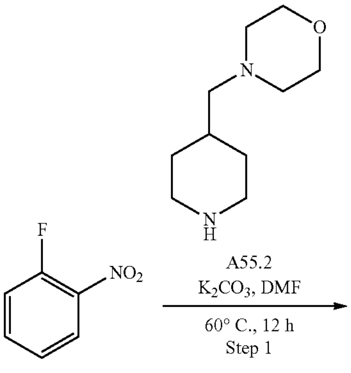

A55.1

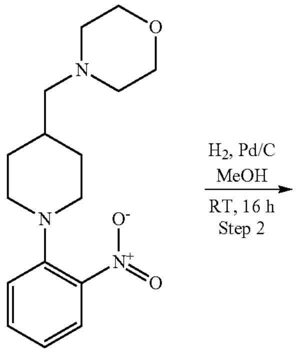

A55.3

-continued

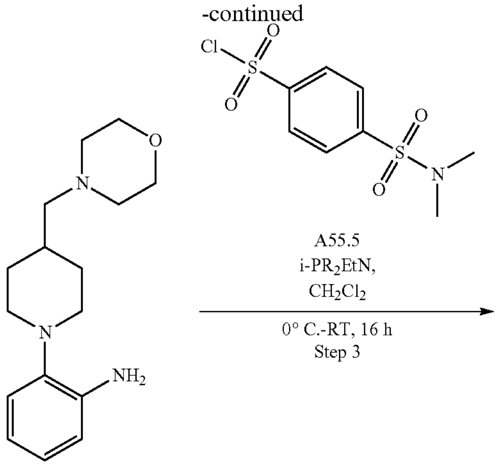

A55.4

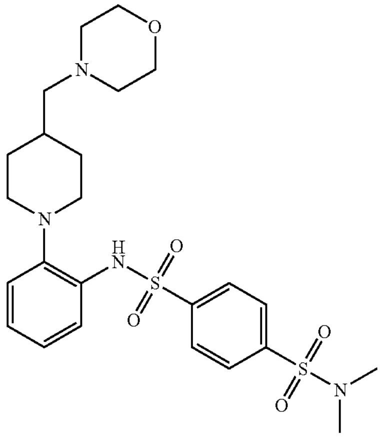

A-554

Step-1. Synthesis of 4-{[1-(2-nitrophenyl)piperidin-4-yl]methyl}morpholine (A55.3)

1-fluoro-2-nitrobenzene (A55.1) (0.39 g, 2.76 mmol) was added to a stirred solution of 4-[(piperidin-4-yl)methyl]morpholine (A55.2) (0.5 g, 2.71 mmol) and potassium carbonate (0.565 g, 4.08 mmol) in dry DMF (5 mL). The mixture was stirred at 60° C. until the reaction completion (TLC control) and concentrated under the reduced pressure. The residue was dissolved in EtOAc (15 mL), the organic layer was washed twice with water, dried over anhydrous sodium sulfate, filtered and concentrated under reduced pressure to obtain 4-{[1-(2-nitrophenyl)piperidin-4-yl]methyl}morpholine (A55.3) as oil (0.72 g, 2.35 mmol, 95% purity, 81.2% yield) which was used in the next step without further purification.

Step-2. Synthesis of 2-{4-[(morpholin-4-yl)methyl]piperidin-1-yl}aniline (A55.4)

4-{[1-(2-nitrophenyl)piperidin-4-yl]methyl}morpholine (A55.3) (0.72 g, 2.35 mmol) was dissolved in methanol (10 mL) and treated with 10% Pd/C (0.05 g). The resulting mixture was hydrogenated at 6 atm and room temperature until the reaction was completed (TLC control). The catalyst was filtered off and the filtrate was evaporated to afford 2-{4-[(morpholin-4-yl)methyl]piperidin-1-yl}aniline (A55.4) (0.53 g, 1.92 mmol, 95.9% purity, 77.7% yield).

Step-3. Synthesis of N1,N1-dimethyl-N4-(2-{4-[(morpholin-4-yl)methyl]piperidin-1-yl}phenyl)benzene-1,4-disulfonamide (A-554)

4-(dimethylsulfamoyl)benzene-1-sulfonyl chloride (A55.5) (0.27 g, 0.951 mmol) was added to the mixture of 2-{4-[(morpholin-4-yl)methyl]piperidin-1-yl}aniline (A55.4) (0.25 g, 0.907 mmol) and DIPEA (0.234 g, 1.81 mmol) in dry DCM (5 mL). The reaction mixture was stirred overnight, poured into water and extracted with DCM (10 mL×2). Combined organic layers were washed with sat aq $NaHCO_3$ solution (20 mL) and dried over anhydrous sodium sulfate, filtered and evaporated under reduced pressure. The residue was subjected to HPLC purification (deionized water/HPLC-grade acetonitrile) that afforded N1,N1-dimethyl-N4-(2-{4-[(morpholin-4-yl)methyl]piperidin-1-yl}phenyl)benzene-1,4-disulfonamide (A-554). Yield: 182.2 mg, 36.4%; Appearance: Yellow solid; $^1H$ NMR (400 MHz, DMSO-$d_6$) δ 9.12 (s, 1H), 8.00 (d, J=8.0 Hz, 2H), 7.92 (d, J=8.4 Hz, 2H), 7.27 (d, J=7.8 Hz, 1H), 7.15-7.09 (m, 2H), 7.09-7.01 (m, 1H), 3.56 (t, J=4.5 Hz, 4H), 2.62 (s, 6H), 2.57-2.53 (m, 2H), 2.42 (t, J=11.3 Hz, 2H), 2.32 (s, 4H), 2.13 (d, J=7.1 Hz, 2H), 2.07 (s, 2H), 1.64-1.55 (m, 2H), 1.52 (s, 1H), 1.22-1.11 (m, 2H); HPLC purity: 100%; LCMS Calculated for $C_{24}H_{34}N_4O_5S_2$: 522.68; Observed: 522.23 $[M-H]^-$.

The following examples were prepared using standard chemical manipulations and procedures similar to those used for the preparation of the previous example.

| Compound No. | Structure | Analytical data |
|---|---|---|
| A-553 | 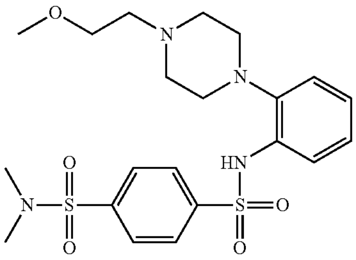 | Yield: 171.3 mg, 31.7%; Appearance: Beige solid; $^1H$ NMR (400 MHz, DMSO-$d_6$) δ 9.22 (s, 1H), 7.99 (d, J = 8.8 Hz, 2H), 7.92 (d, J = 8.5 Hz, 2H), 7.23 (d, J = 7.9 Hz, 1H), 7.17-7.10 (m, 2H), 7.10-7.01 (m, 1H), 3.43 (d, J = 5.7 Hz, 2H), 3.24 (d, J = 1.6 Hz, 3H), 2.62 (s, 6H), 2.58-2.52 (m, 5H), 2.43 (s, 3H); HPLC purity: 100%; LCMS Calculated for $C_{21}H_{30}N_4O_5S_2$: 482.61; Observed: 482.19 $[M-H]^-$. |
| A-560 | 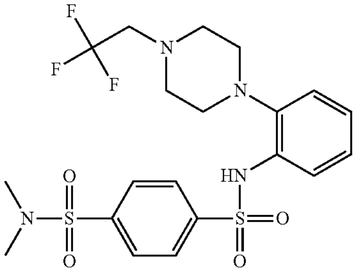 [SMILES: CN(C)S(=O)(=O)c1ccc(S(=O)(=O)Nc2ccccc2N2CCN(CC(F)(F)F)CC2)cc1] | Yield: 209.3 mg, 40.5%; Appearance: Pink solid; $^1H$ NMR (400 MHz, DMSO-$d_6$) δ 9.30 (s, 1H), 7.99 (d, J = 8.3 Hz, 2H), 7.93 (d, J = 8.3 Hz, 2H), 7.24 (d, J = 7.8 Hz, 1H), 7.20-7.09 (m, 2H), 7.07 (td, J = 7.2, 6.5, 2.3 Hz, 1H), 3.19 (q, J = 10.2 Hz, 2H), 2.63 (d, J = 5.6 Hz, 8H), 2.61-2.52 (m, 6H); HPLC purity: 100%; LCMS Calculated for $C_{20}H_{25}F_3N_4O_4S_2$: 506.56; Observed: 506.15 $[M-H]^-$. |
| A-585 | 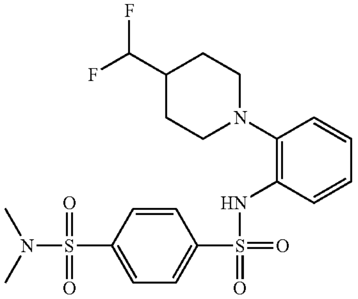 [SMILES: CN(C)S(=O)(=O)c1ccc(S(=O)(=O)Nc2ccccc2N2CCC(C(F)F)CC2)cc1] | Yield: 75.3 mg, 13.7%; Appearance: Beige solid; $^1H$ NMR (600 MHz, DMSO-$d_6$) δ 9.24 (s, 1H), 7.97 (d, J = 8.0 Hz, 2H), 7.90 (d, J = 8.5 Hz, 2H), 7.25 (d, J = 7.9 Hz, 1H), 7.10 (d, J = 4.4 Hz, 2H), 7.08-7.01 (m, 1H), 5.99-5.78 (m, 1H), 2.59 (s, 6H), 2.54 (d, J = 11.3 Hz, 2H), 2.43 (d, J = 11.2 Hz, 2H), 1.82-1.75 (m, 1H), 1.55 (d, J = 12.5 Hz, 2H), 1.52-1.42 (m, 2H); HPLC purity: 100%; LCMS Calculated for $C_{20}H_{25}F_2N_3O_4S_2$: 473.55; Observed: 473.15 $[M-H]^-$. |

-continued

| Compound No. | Structure | Analytical data |
|---|---|---|
| A-697 | 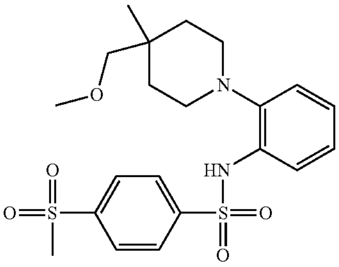 [SMILES: COCC1(C)CCN(c2ccccc2NS(=O)(=O)c2ccc(S(C)(=O)=O)cc2)CC1] | Yield: 40.0 mg, 9.84%; Appearance: Beige solid; $^1$H NMR (400 MHz, DMSO-$d_6$) δ 9.23 (s, 1H), 8.10 (d, J = 8.5 Hz, 2H), 8.03 (d, J = 8.1 Hz, 2H), 7.25-7.14 (m, 2H), 7.09 (t, J = 7.7 Hz, 1H), 7.03 (d, J = 7.7 Hz, 1H), 3.27 (d, J = 6.2 Hz, 6H), 3.10 (d, J = 3.5 Hz, 2H), 2.61-2.51 (m, 4H), 1.55-1.45 (m, 2H), 1.25 (d, J = 12.6 Hz, 2H), 0.92 (d, J = 3.4 Hz, 3H); HPLC purity: 97%; LCMS Calculated for $C_{21}H_{28}N_2O_5S_2$: 452.59; Observed: 452.17 $[M - H]^-$. |
| A-696 | 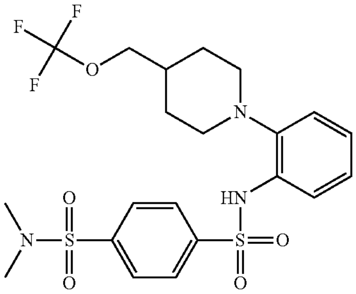 [SMILES: CN(C)S(=O)(=O)c1ccc(S(=O)(=O)Nc2ccccc2N2CCC(COC(F)(F)F)CC2)cc1] | Yield: 193.1 mg, 38.5%; Appearance: Beige solid; $^1$H NMR (400 MHz, DMSO-$d_6$) δ 9.20 (s, 1H), 8.04-7.97 (m, 2H), 7.92 (d, J = 8.2 Hz, 2H), 7.28 (d, J = 7.8 Hz, 1H), 7.17-7.10 (m, 2H), 7.11-7.02 (m, 1H), 3.97 (d, J = 6.3 Hz, 2H), 2.62 (s, 6H), 2.56 (d, J = 11.7 Hz, 2H), 2.45 (d, J = 9.4 Hz, 2H), 1.74-1.67 (m, 1H), 1.59 (d, J = 11.5 Hz, 2H), 1.43-1.28 (m, 2H); HPLC purity: 100%; LCMS Calculated for $C_{21}H_{26}F_3N_3O_5S_2$: 521.57; Observed: 521.15 $[M - H]^-$. |

Example A56: Synthesis of N1,N1-dimethyl-N4-{2-[4-(2-methylpropyl)-5-oxo-1,4-diazepan-1-yl]phenyl}benzene-1,4-disulfonamide (A-526)

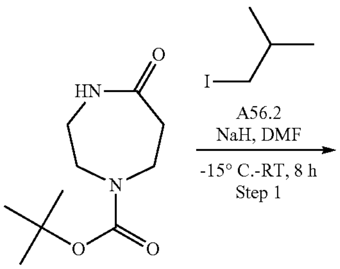

A56.1

-continued

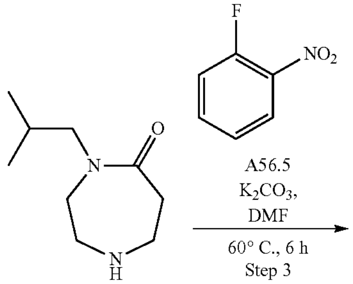

A56.4

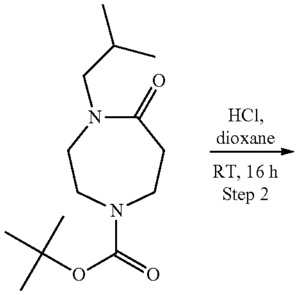

A56.3

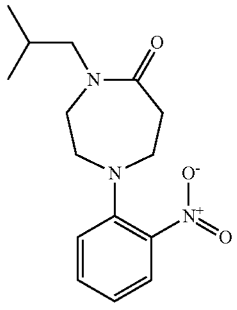
A56.6

-continued

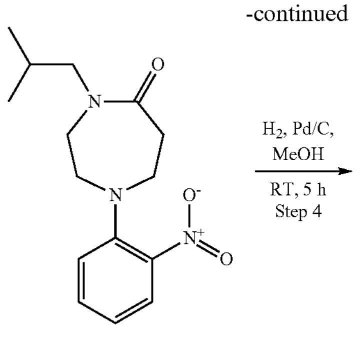

A56.6

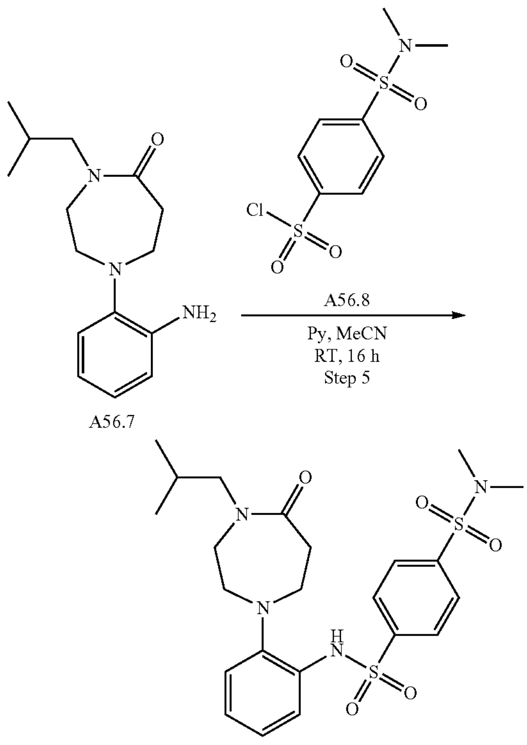

A56.7

A56.8

A-526

Step-1. Synthesis of tert-butyl 4-(2-methylpropyl)-5-oxo-1,4-diazepane-1-carboxylate (A56.3)

tert-butyl 5-oxo-1,4-diazepane-1-carboxylate (A56.1) (4 g, 18.6 mmol) solution in dry DMF (5 mL) was added dropwise to a suspension of NaH (60 w %, 0.9 g, 22.5 mmol) in dry DMF (10 mL) at −15° C. The mixture was stirred at this temperature for 20 minutes and 1-iodo-2-methylpropane (A56.2) (5 g, 27.1 mmol) was added. After the reaction mixture was allowed to warm up and stir for 8 h until the reaction completion. Than the mixture was quenched with water (15 mL) and the product was extracted with ethyl acetate (20 mL×2). The combined organic layers were dried over sodium sulfate, filtered and evaporated to afford tert-butyl 4-(2-methylpropyl)-5-oxo-1,4-diazepane-1-carboxylate (A56.3) (1.5 g, 5.54 mmol, 85% purity, 25.2% yield) that was used in next step without further purification.

Step-2. Synthesis of 4-(2-methylpropyl)-1,4-diazepan-5-one hydrochloride (A56.4)

Tert-butyl 4-(2-methylpropyl)-5-oxo-1,4-diazepane-1-carboxylate (A56.3) (1.5 g, 5.54 mmol) was dissolved in saturated HCl solution in dry dioxane (10 mL) at room temperature. The mixture was stirred overnight, evaporated to dryness, the residue was treated with ether (20 mL×2), formed precipitated was filtered, dried on air to afford 4-(2-methylpropyl)-1,4-diazepan-5-one hydrochloride (A564) (0.8 g, 3.87 mmol, 80% purity, 56.1% yield) that was used in next step without further purification.

Step-3. Synthesis of 4-(2-methylpropyl)-1-(2-nitrophenyl)-1,4-diazepan-5-one (A56.6)

1-fluoro-2-nitrobenzene (A56.5) (0.55 g, 3.89 mmol) was added to a stirred solution of 4-(2-methylpropyl)-1,4-diazepan-5-one hydrochloride (A56.4) (0.8 g, 3.87 mmol) and potassium carbonate (1.6 g, 11.5 mmol) in dry DMF (20 mL). The mixture was stirred at 60° C. until the reaction completion (TLC control) and concentrated under the reduced pressure. The residue was dissolved in ethyl acetate (15 mL), the organic layer was washed with water (15 mL), dried over anhydrous sodium sulfate, filtered and concentrated under reduced pressure. The chromatographic purification of residue (hexane/ethyl acetate) afforded 4-(2-methylpropyl)-1-(2-nitrophenyl)-1,4-diazepan-5-one (A56.6) (0.38 g, 1.3 mmol, 95% purity, 31.9% yield).

Step-4. Synthesis of 1-(2-aminophenyl)-4-(2-methylpropyl)-1,4-diazepan-5-one (A56.7)

4-(2-methylpropyl)-1-(2-nitrophenyl)-1,4-diazepan-5-one (A56.6) (0.38 g, 1.3 mmol) was dissolved in methanol (100 mL) and treated with 5% Pd/C (0.05 g). The resulting mixture was hydrogenated at ambient pressure and room temperature until the reaction was completed (TLC control). The catalyst was filtered off and the filtrate was evaporated to afford 1-(2-aminophenyl)-4-(2-methylpropyl)-1,4-diazepan-5-one (A56.7) (0.25 g, 0.956 mmol, 70% purity, 51.6% yield) that was used in next step without further purification.

Step-5. Synthesis of N1,N1-dimethyl-N4-{2-[4-(2-methylpropyl)-5-oxo-1,4-diazepan-1-yl]phenyl}benzene-1,4-disulfonamide (A-526)

4-(dimethylsulfamoyl)benzene-1-sulfonyl chloride (A56.8) (0.27 g, 0.951 mmol) was added to the mixture of 1-(2-aminophenyl)-4-(2-methylpropyl)-1,4-diazepan-5-one (A56.7) (0.25 g, 0.956 mmol) and pyridine (0.11 g, 1.39 mmol) in dry acetonitrile (20 mL). The reaction mixture was stirred overnight and evaporated. The residue was subjected to HPLC purification (deionized water/HPLC-grade methanol) that afforded N1,N1-dimethyl-N4-{2-[4-(2-methylpropyl)-5-oxo-1,4-diazepan-1-yl]phenyl}benzene-1,4-disulfonamide (A-526). Yield: 42.2 mg, 8.23%; Appearance: Yellow solid; $^1$H NMR (400 MHz, DMSO-$d_6$) δ 9.47 (s, 1H), 8.02-7.90 (m, 4H), 7.41-7.34 (m, 1H), 7.16-7.07 (m, 3H), 3.43 (s, 2H), 3.09 (d, J=7.3 Hz, 2H), 2.62 (s, 6H), 2.55 (d, J=13.7 Hz, 4H), 2.47-2.41 (m, 3H), 1.85-1.71 (m, 1H), 0.82 (dd, J=6.9, 2.5 Hz, 6H); HPLC purity: 100%; LCMS Calculated for $C_{23}H_{32}N_4O_5S_2$: 508.65; Observed: 508.21 $[M-H]^-$.

Example A57: Synthesis of N-{2-[4-(2,2-dimethylpropanoyl)piperazin-1-yl]phenyl}-2-methyl-1,3-benzothiazole-6-sulfonamide (A-600)

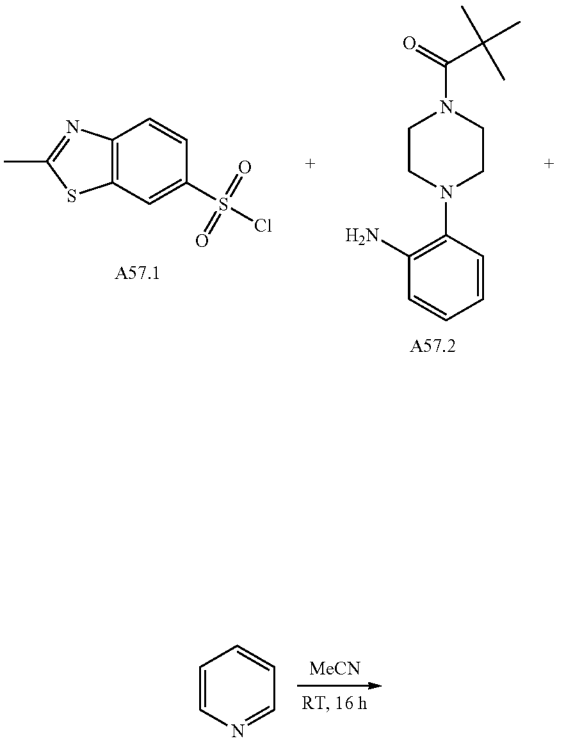

A57.1

A57.2

-continued

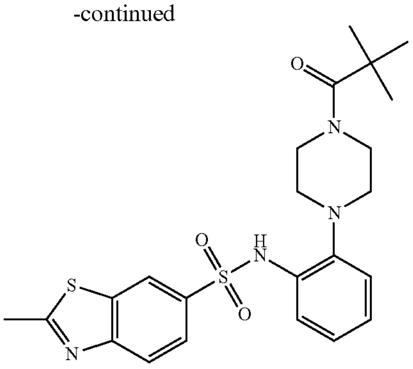

A-600

2-methyl-1,3-benzothiazole-6-sulfonyl chloride (A57.1) (0.5 g, 2.01 mmol) was added to the mixture of 1-[4-(2-aminophenyl)piperazin-1-yl]-2,2-dimethylpropan-1-one (A57.2) (0.53 g, 2.02 mmol) and pyridine (0.24 g, 3.03 mmol) in dry acetonitrile (20 mL). The reaction mixture was stirred overnight and evaporated. The residue was subjected to HPLC purification (deionized water/HPLC-grade methanol, ammonia) that afforded N-{2-[4-(2,2-dimethylpropanoyl)piperazin-1-yl]phenyl}-2-methyl-1,3-benzothiazole-6-sulfonamide (A-600). Yield: 137.2 mg, 13.6%; Appearance: Beige solid; $^1$H NMR (600 MHz, DMSO-$d_6$) δ 9.13 (s, 1H), 8.57 (d, J=1.9 Hz, 1H), 8.00 (d, J=8.6 Hz, 1H), 7.79 (dd, J=8.6, 1.9 Hz, 1H), 7.36-7.31 (m, 1H), 7.10-7.01 (m, 3H), 3.49 (t, J=4.7 Hz, 4H), 2.80 (s, 3H), 2.36 (t, J=4.8 Hz, 4H), 1.14 (s, 9H); HPLC purity: 100%; LCMS Calculated for $C_{23}H_{28}N_4O_3S_2$: 472.62; Observed: 472.19 $[M-H]^-$.

The following example was prepared using standard chemical manipulations and procedures similar to those used for the preparation of the previous example.

| Compound No. | Structure | Analytical data |
|---|---|---|
| A-583 | 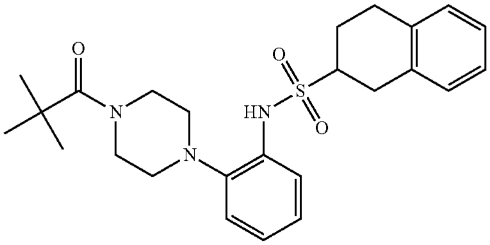 [SMILES: CC(C)(C)C(=O)N1CCN(c2ccccc2NS(=O)(=O)C2CCc3ccccc3C2)CC1] | Yield: 15.4 mg, 1.47%; Appearance: Light brown solid; $^1$H NMR (400 MHz, Chloroform-d) δ 7.83 (s, 1H), 7.59 (d, J = 8.1 Hz, 1H), 7.23-7.11 (m, 5H), 7.13-7.05 (m, 3H), 3.87 (s, 4H), 3.49 (d, J = 11.0 Hz, 1H), 3.30-3.12 (m, 2H), 3.06-2.96 (m, 1H), 2.88 (t, J = 5.1 Hz, 5H), 2.46 (d, J = 13.0 Hz, 1H), 2.05 (qd, J = 12.2, 5.6 Hz, 1H), 1.34 (s, 9H); HPLC purity: 100%; LCMS Calculated for $C_{25}H_{33}N_3O_3S$: 455.62; Observed: 455.27 $[M-H]^-$. |
| A-571 | 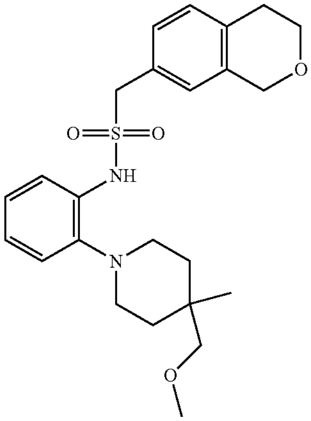 [SMILES: COCC1(C)CCN(c2ccccc2NS(=O)(=O)Cc2ccc3c(c2)COCC3)CC1] | Yield: 205.0 mg, 32.3%; Appearance: Beige solid; $^1$H NMR (600 MHz, DMSO-$d_6$) δ 7.93 (s, 1H), 7.30-7.24 (m, 2H), 7.09-7.01 (m, 3H), 6.99 (d, J = 7.0 Hz, 1H), 6.84 (s, 1H), 4.54 (d, J = 4.7 Hz, 4H), 3.82 (t, J = 5.7 Hz, 2H), 3.24 (s, 3H), 3.09 (s, 2H), 2.72 (t, J = 5.7 Hz, 2H), 2.70-2.63 (m, 3H), 2.64-2.57 (m, 2H), 1.55-1.47 (m, 2H), 1.31-1.24 (m, 2H), 0.93 (s, 3H); HPLC purity: 100%; LCMS Calculated for $C_{24}H_{32}N_2O_4S$: 444.59; Observed: 444.25 $[M-H]^-$. |

-continued

| Compound No. | Structure | Analytical data |
|---|---|---|
| A-609 | 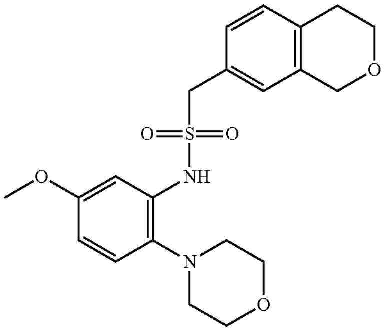 [SMILES: COc1ccc(N2CCOCC2)c(NS(=O)(=O)Cc2ccc3c(c2)COCC3)c1] | Yield: 150.4 mg, 35.4%; Appearance: White solid; $^1$H NMR (400 MHz, DMSO-$d_6$) δ 8.20 (s, 1H), 7.18 (d, J = 8.7 Hz, 1H), 7.06 (q, J = 7.8 Hz, 2H), 6.90 (s, 1H), 6.73 (d, J = 2.9 Hz, 1H), 6.61 (dd, J = 8.7, 2.8 Hz, 1H), 4.55 (d, J = 9.6 Hz, 4H), 3.81 (t, J = 5.7 Hz, 2H), 3.70-3.59 (m, 7H), 2.72 (t, J = 5.8 Hz, 2H), 2.61 (d, J = 4.6 Hz, 4H); HPLC purity: 100%; LCMS Calculated for C21H26N2O5S: 418.51; Observed: 418.18 $[M-H]^-$. |
| A-629 | 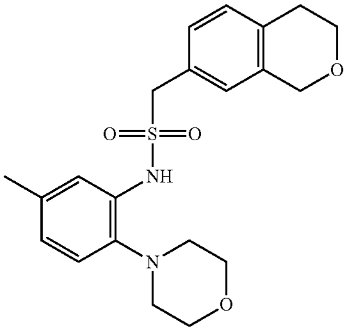 [SMILES: Cc1ccc(N2CCOCC2)c(NS(=O)(=O)Cc2ccc3c(c2)COCC3)c1] | Yield: 144.3 mg, 32.7%; Appearance: Yellow solid; $^1$H NMR (600 MHz, DMSO-$d_6$) δ 8.12 (s, 1H), 7.11-7.03 (m, 3H), 6.90 (s, 1H), 6.87 (s, 1H), 6.85 (dd, J = 8.1, 1.9 Hz, 1H), 4.54 (s, 4H), 3.81 (t, J = 5.7 Hz, 2H), 3.66-3.61 (m, 4H), 2.72 (t, J = 5.7 Hz, 2H), 2.68-2.63 (m, 4H), 2.17 (s, 3H); HPLC purity: 100%; LCMS Calculated for $C_{21}H_{26}N_2O_4S$: 402.51; Observed: 402.19 $[M-H]^-$. |

Example A58: Synthesis of N4-{2-[4-(2,2-difluoro-cyclohexyl)piperazin-1-yl]phenyl}-N1,N1-dimethyl-benzene-1,4-disulfonamide (A-626)

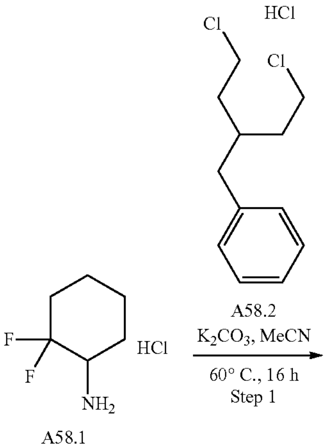

A58.1

-continued

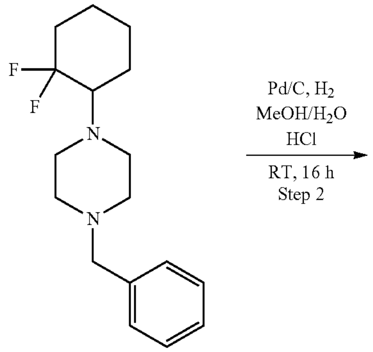

A58.3

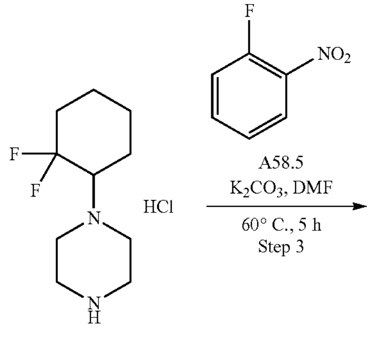

A58.4

-continued

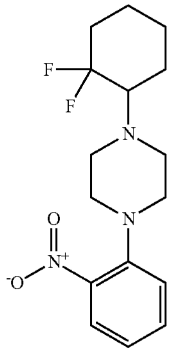

A58.6

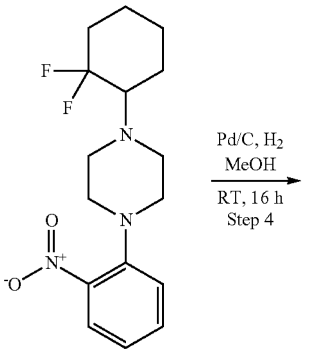

A58.6

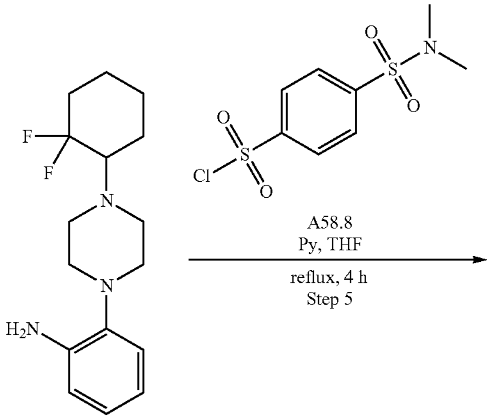

A58.7

-continued

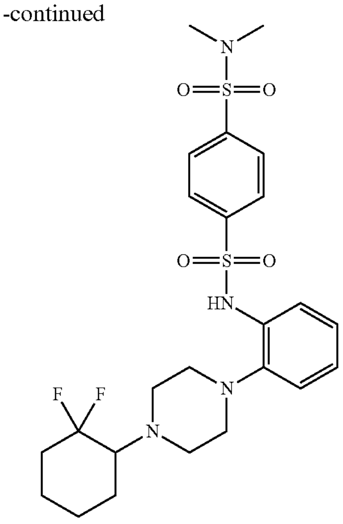

A-626

Step-1. Synthesis of 1-benzyl-4-(2,2-difluorocyclohexyl)piperazine (A58.3)

Benzylbis(2-chloroethyl)amine hydrochloride (A58.2) (7.9 g, 29.4 mmol) was added to a stirred solution of 2,2-difluorocyclohexan-1-amine hydrochloride (A58.1) (5 g, 29.1 mmol) and potassium carbonate (20 g, 145 mmol) in dry acetonitrile (250 mL). The mixture was stirred at 60° C. for 16 h and concentrated under the reduced pressure. The residue was dissolved in ethyl acetate (250 mL) and washed with water (250 mL), brine (250 mL), dried over sodium sulfate, filtered and concentrated under reduced pressure. The crude material was purified by flash chromatography (chloroform/methyl tert-butyl ether) to afford 1-benzyl-4-(2,2-difluorocyclohexyl)piperazine (A58.3) (0.9 g, 3.05 mmol, 95% purity, 9.98% yield).

Step-2. Synthesis of 1-(2,2-difluorocyclohexyl)piperazine Hydrochloride (A58.4)

1-benzyl-4-(2,2-difluorocyclohexyl)piperazine (A58.3) (0.9 g, 3.05 mmol) was dissolved in methanol (10 mL) and conc. aqueous HCl (10 mL) and treated with 10% Pd/C (0.1 g). The resulting mixture was hydrogenated at ambient pressure and room temperature until the reaction was completed. The catalyst was filtered off and the filtrate was evaporated to afford 1-(2,2-difluorocyclohexyl)piperazine hydrochloride (A58.4) (0.65 g, 2.7 mmol, 95% purity, 84% yield).

Step-3. Synthesis of 1-(2,2-difluorocyclohexyl)-4-(2-nitrophenyl)piperazine (A58.6)

1-fluoro-2-nitrobenzene (A58.5) (0.4 g, 2.83 mmol) was added to a stirred solution of 1-(2,2-difluorocyclohexyl) piperazine hydrochloride (A58.4) (0.65 g, 2.7 mmol) and potassium carbonate (0.932 g, 6.75 mmol) in dry DMF (20 mL). The mixture was stirred at 60° C. for 5 h and concentrated under the reduced pressure. The residue was dissolved in ethyl acetate (20 mL) and washed with water (40 mL), brine (40 mL), dried over sodium sulfate, filtered and concentrated under reduced pressure to afford 1-(2,2-difluorocyclohexyl)-4-(2-nitrophenyl)piperazine (A58.6) (0.85 g, 2.61 mmol, 67.85% purity, 65.6% yield) that was used in next step without further purification.

Step-4. Synthesis of 2-[4-(2,2-difluorocyclohexyl)piperazin-1-yl]aniline (A58.7)

1-(2,2-difluorocyclohexyl)-4-(2-nitrophenyl)piperazine (A58.6) (0.85 g, 2.61 mmol) was dissolved in methanol (25 mL) and treated with 10% Pd/C (0.1 g). The resulting mixture was hydrogenated at ambient pressure and room temperature until the reaction was completed. The catalyst was filtered off and the filtrate was evaporated to afford 2-[4-(2,2-difluorocyclohexyl)piperazin-1-yl]aniline (A58.7) (0.6 g, 2.03 mmol, 90% purity, 70.1% yield) that was used in next step without further purification.

Step-5. Synthesis of 2-[4-(2,2-difluorocyclohexyl)piperazin-1-yl]aniline (A-626)

4-(dimethylsulfamoyl)benzene-1-sulfonyl chloride (A58.8) (0.6 g, 2.11 mmol) was added to the mixture of 2-[4-(2,2-difluorocyclohexyl)piperazin-1-yl]aniline (A58.7) (0.6 g, 2.03 mmol) and pyridine (0.5 g, 6.32 mmol) in dry THF (20 mL). The reaction mixture was refluxed for 4 h and evaporated. The residue was diluted by saturated $NaHCO_3$ solution (20 mL) and ethyl acetate (20 mL). Organic layer was separated, washed with brine (20 mL), dried over sodium sulfate, filtered and evaporated under reduced pressure. The crude material was purified by HPLC (deionized water/HPLC-grade acetonitrile) to give N4-{2-[4-(2,2-difluorocyclohexyl)piperazin-1-yl]phenyl}-N1,N1-dimethylbenzene-1,4-disulfonamide (A-626). Yield: 335.4 mg, 28.9%; Appearance: Beige solid; $^1H$ NMR (600 MHz, DMSO-$d_6$) δ 9.21 (s, 1H), 7.97 (dd, J=8.5, 1.7 Hz, 2H), 7.89 (dd, J=8.5, 1.7 Hz, 2H), 7.19 (d, J=8.0 Hz, 1H), 7.14-7.07 (m, 2H), 7.02 (t, J=7.3 Hz, 1H), 2.81-2.73 (m, 1H), 2.73-2.65 (m, 4H), 2.59 (d, J=1.7 Hz, 6H), 2.56-2.48 (m, 6H), 1.95 (q, J=8.4 Hz, 1H), 1.77-1.68 (m, 2H), 1.64 (s, 2H), 1.54 (q, J=12.0 Hz, 1H), 1.31 (t, J=12.2 Hz, 2H); HPLC purity: 100%; LCMS Calculated for $C_{24}H_{32}F_2N_4O_4S_2$: 542.66; Observed: 542.22 $[M-H]^-$.

Example A59: Synthesis of N4-{2-[4-(4-chloro-2-fluorophenyl)piperidin-1-yl]phenyl}-N1-{2-[2-(2-methoxyethoxy)ethoxy]ethyl}-N1-methylbenzene-1,4-disulfonamide (A-587)

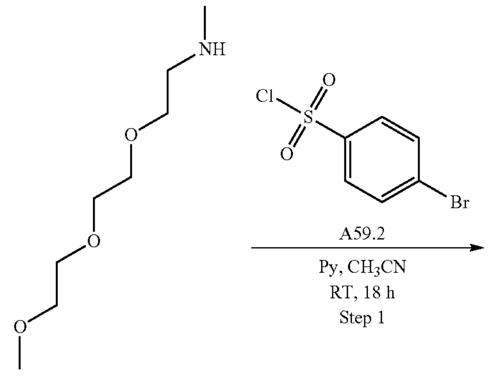

A59.1

-continued

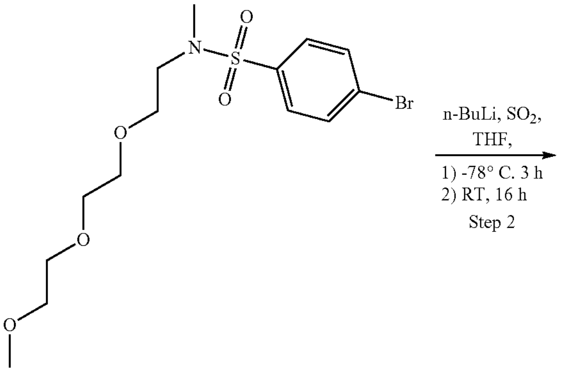

A59.3

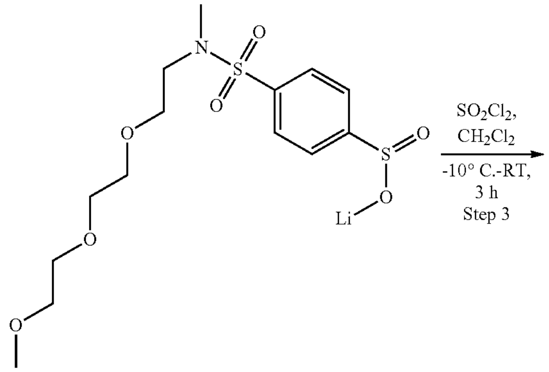

A59.4

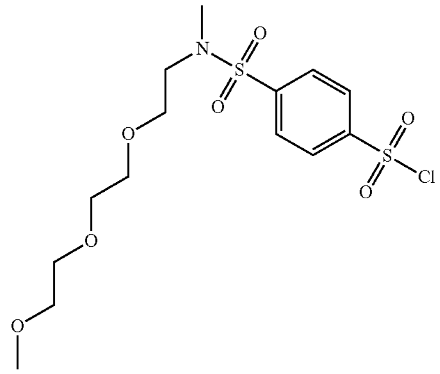

A59.5

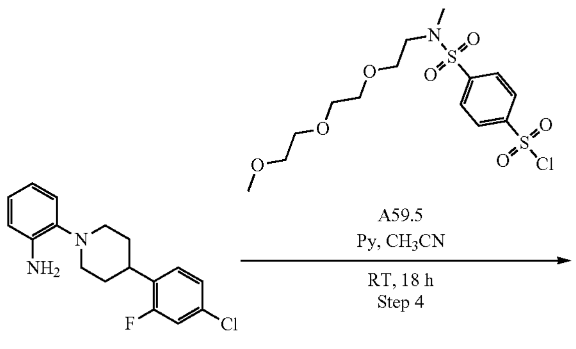

A59.6

-continued

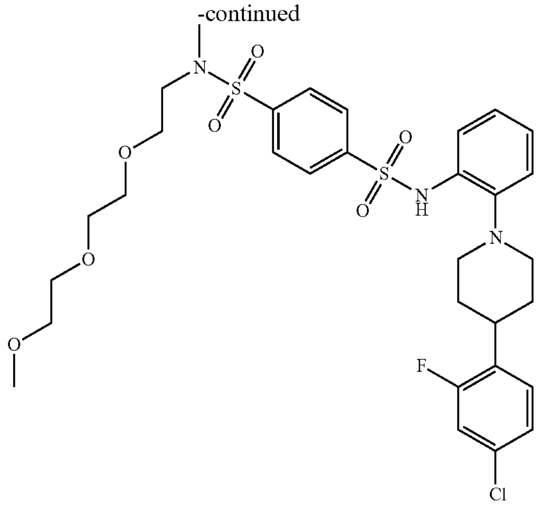

A-587

Step-1. Synthesis of 4-bromo-N-{2-[2-(2-methoxy-ethoxy)ethoxy]ethyl}-N-methylbenzene-1-sulfonamide (A59.3)

Pyridine (5.56 g, 70.4 mmol) and 4-bromobenzene-1-sulfonyl chloride (A59.2) (12.0 g, 47.0 mmol) were added to a solution of 2,5,8-trioxa-11-azadodecane (A59.1) (10 g, 56.4 mmol) in acetonitrile (250 mL). The reaction mixture was stirred at room temperature for 18 h and the reaction mixture has been evaporated. The residue was subjected to silica gel chromatography purification (hexane/methyl tert-butyl ether) that afforded 4-bromo-N-{2-[2-(2-methoxy-ethoxy)ethoxy]ethyl}-N-methylbenzene-1-sulfonamide as colorless oil (A59.3) (14 g, 35.3 mmol, 95% purity, 71.5% yield).

Step-2. Synthesis of lithio 4-({2-[2-(2-methoxy-ethoxy)ethoxy]ethyl}(methyl)sulfamoyl)benzene-1-sulfinate (A59.4)

n-butyllithium (16.9 mL, 2.5 M in hexane, 42.3 mmol) was added dropwise at −78° C. to a stirred solution of 4-bromo-N-{2-[2-(2-methoxyethoxy)ethoxy]ethyl}-N-methylbenzene-1-sulfonamide (A59.3) (14 g, 35.3 mmol) in dry THF (250 mL) at Ar atmosphere and the reaction mixture was stirred at −78° C. for 2 h. Solution of $SO_2$ (6.72 g, 105 mmol) in dry THF (100 mL) was added at −78° C., after the reaction mixture was allowed to warm up and stir overnight at room temperature. The suspension was concentrated under reduced pressure to give lithio 4-({2-[2-(2-methoxyethoxy)ethoxy]ethyl}(methyl)sulfamoyl)benzene-1-sulfinate as white solid (A59.4) (16 g, 41.3 mmol, 77% purity, 90.4% yield) that was used in the next step without further purification.

Step-3. Synthesis of 4-({2-[2-(2-methoxyethoxy)ethoxy]ethyl}(methyl)sulfamoyl)benzene-1-sulfonyl Chloride (A59.5)

Sulfuroyl dichloride (6.68 g, 49.5 mmol) was added dropwise at −10° C. to a stirred solution of lithio 4-({2-[2-(2-methoxyethoxy)ethoxy]ethyl}(methyl)sulfamoyl)benzene-1-sulfinate (A59.4) (16 g, 41.3 mmol) in dry dichloromethane (250 mL), the reaction mixture was allowed to warm up and stir for 2 h at room temperature. The organic layer was washed with water with ice (200 mL) and brine (200 mL), dried over anhydrous sodium sulfate, filtered and concentrated under reduced pressure. The residue was subjected to silica gel chromatography purification (hexane/methyl tert-butyl ether) that afforded 4-({2-[2-(2-methoxy-ethoxy)ethoxy]ethyl}(methyl)sulfamoyl)benzene-1-sulfonyl chloride as colorless oil (A59.5) (8.49 g, 20.4 mmol, 90% purity, 44.6% yield) that was used in next step without further purification.

Step-4. Synthesis of N4-{2-[4-(4-chloro-2-fluoro-phenyl)piperidin-1-yl]phenyl}-N1-{2-[2-(2-methoxy-ethoxy)ethoxy]ethyl}-N1-methylbenzene-1,4-disulfonamide (A-587)

Pyridine (0.0972 g, 0.0989 mmol) and 4-({2-[2-(2-methoxyethoxy)ethoxy]ethyl}(methyl)sulfamoyl)benzene-1-sulfonyl chloride (A59.5) (0.375 g, 0.902 mmol) were added to a solution of 2-[4-(4-chloro-2-fluorophenyl)piperidin-1-yl]aniline (A59.6) (0.25 g, 820 μmol) in acetonitrile (25 mL). The reaction mixture was stirred at room temperature for 18 h. The solvent was removed under reduced pressure and the residue was subjected to HPLC purification (deionized water/HPLC-grade acetonitrile) to afford N4-{2-[4-(4-chloro-2-fluorophenyl)piperidin-1-yl]phenyl}-N1-{2-[2-(2-methoxyethoxy)ethoxy]ethyl}-N1-methylbenzene-1,4-disulfonamide (A-587). Yield: 223.9 mg, 37.7%; Appearance: Beige solid; $^1$H NMR (600 MHz, DMSO-$d_6$) δ 9.20 (s, 1H), 7.98-7.90 (m, 4H), 7.40 (t, J=8.2 Hz, 1H), 7.38-7.26 (m, 3H), 7.17-7.04 (m, 3H), 3.47-3.41 (m, 4H), 3.42-3.35 (m, 6H), 3.19 (d, J=1.1 Hz, 3H), 3.10 (t, J=5.5 Hz, 2H), 2.83-2.75 (m, 1H), 2.68 (s, 3H), 2.59 (t, J=11.3 Hz, 3H), 2.52 (d, J=11.5 Hz, 3H), 1.81-1.71 (m, 2H), 1.57 (d, J=12.4 Hz, 2H); HPLC purity: 100%; LCMS Calculated for $C_{31}H_{39}ClFN_3O_7S_2$: 684.24; Observed: 683.23 $[M-H]^-$.

Example A60: Synthesis of N-{2-[4-(4-chloro-2-fluorophenyl)piperidin-1-yl]phenyl}-4-{2-[2-(2-methoxyethoxy)ethoxy]ethoxy}benzene-1-sulfonamide (A-588)

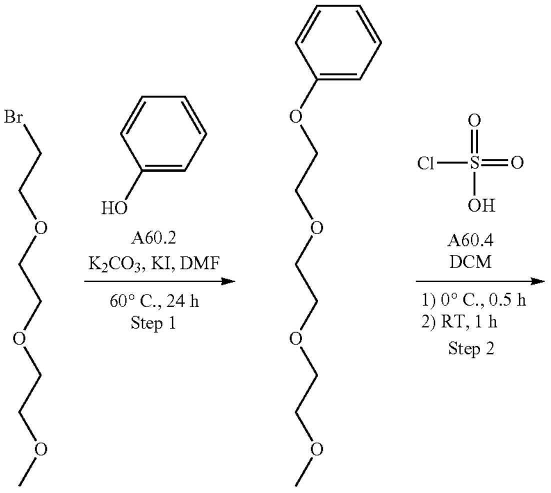

A60.1

A60.3

-continued

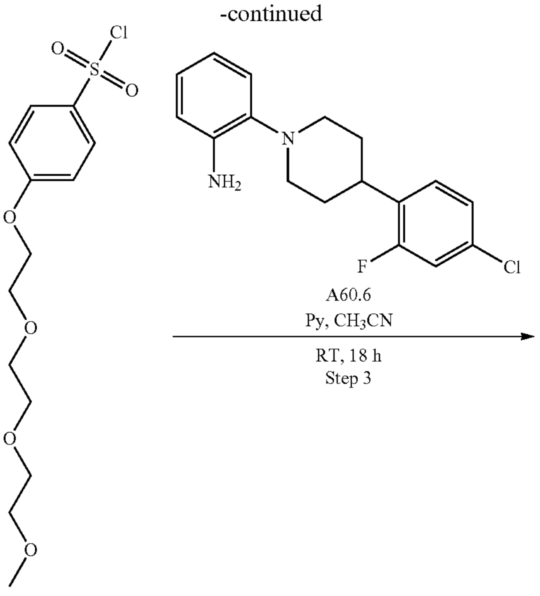

A60.5

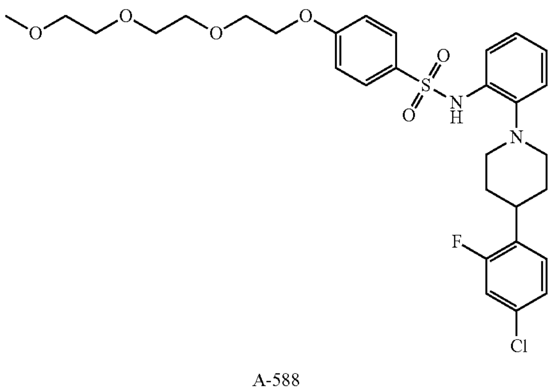

A-588

Step-1. Synthesis of {2-[2-(2-methoxyethoxy) ethoxy]ethoxy}benzene (A60.3)

1-bromo-2-(2-(2-methoxyethoxy)ethoxy)ethane (A60.1) (15 g, 66.0 mmol), potassium carbonate (25.0 g, 180 mmol), and potassium iodide (1 g, 6.02 mmol) were added to a stirred solution of the phenol (A60.2) (5.6 g, 59.5 mmol) in DMF (200 mL) and the mixture was stirred at 60° C. for 24 h. After water (400 mL) was added to the reaction mixture and the product was extracted with ethyl acetate (400 mL×3). The organic layer was washed with brine (500 mL), dried over anhydrous sodium sulfate, filtered and evaporated under reduced pressure to afford {2-[2-(2-methoxyethoxy) ethoxy]ethoxy}benzene (A60.3) (14 g, 59.5 mmol, 95% purity, 93.6% yield).

Step-2. Synthesis of 4-(2-(2-(2-methoxyethoxy) ethoxy)ethoxy)benzene-1-sulfonyl chloride (A60.5)

Sulfurochloridic acid (A60.4) (13.5 g, 116 mmol, 7.71 mL) was added dropwise under ice-cooling bath to the solution of (2-(2-(2-methoxyethoxy)ethoxy)ethoxy)benzene (A60.3) (14 g, 58.2 mmol) in DCM (200 mL). After the addition was completed, the mixture was warmed to room temperature and stirred for 1 h. The resulting mixture was poured into ice-water (30 mL) and then extracted with DCM (250 mL×3) for 3 times. Combined organic layers were washed with water (500 mL), brine (500 mL), dried over sodium sulfate, filtered and concentrated in vacuo to afford 4-(2-(2-(2-methoxyethoxy)ethoxy)ethoxy)benzene-1-sulfonyl chloride as an yellow oil (A60.5) (17 g, 50.1 mmol, 100% purity, 86.2% yield).

Step-3. Synthesis of N-(2-(4-(4-chloro-2-fluorophenyl)piperidin-1-yl)phenyl)-4-(2-(2-(2-methoxyethoxy)ethoxy)ethoxy)benzenesulfonamide (A-588)

4-(2-(2-(2-methoxyethoxy)ethoxy)ethoxy)benzene-1-sulfonyl chloride (A60.5) (0.28 g, 0.826 mmol) was added to the mixture of 2-(4-(4-chloro-2-fluorophenyl)piperidin-1-yl)aniline (A60.6) (0.276 g, 0.908 mmol) and pyridine (0.653 g, 8.26 mmol) in dry acetonitrile (20 mL). The reaction mixture was stirred at room temperature overnight and evaporated. The residue was subjected to HPLC purification (deionized water/HPLC-grade acetonitrile) to afford N-(2-(4-(4-chloro-2-fluorophenyl)piperidin-1-yl)phenyl)-4-(2-(2-(2-methoxyethoxy)ethoxy)ethoxy)benzenesulfonamide (A-588). Yield: 218.8 mg, 41.3%; Appearance: Beige solid; $^1H$ NMR (400 MHz, DMSO-$d_6$) δ 8.67 (s, 1H), 7.71 (d, J=8.6 Hz, 2H), 7.50 (t, J=8.3 Hz, 1H), 7.39 (dd, J=8.6, 3.0 Hz, 2H), 7.33 (dd, J=8.4, 2.1 Hz, 1H), 7.19 (dd, J=6.2, 3.3 Hz, 1H), 7.07 (t, J=7.3 Hz, 4H), 4.11 (t, J=4.4 Hz, 2H), 3.70 (t, J=4.5 Hz, 2H), 3.53 (dd, J=6.1, 3.6 Hz, 2H), 3.50-3.44 (m, 4H), 3.39 (dd, J=5.9, 3.6 Hz, 2H), 3.20 (s, 3H), 2.85 (t, J=12.3 Hz, 1H), 2.64 (t, J=11.2 Hz, 2H), 1.90 (tt, J=12.5, 7.0 Hz, 2H), 1.65 (dd, J=12.8, 3.6 Hz, 2H); HPLC purity: 100%; LCMS Calculated for $C_{30}H_{36}ClFN_2O_6S$: 607.13; Observed: 606.24 $[M-H]^-$.

The following example was prepared using standard chemical manipulations and procedures similar to those used for the preparation of the previous example.

| Compound No. | Structure | Analytical data |
|---|---|---|
| A-589 | 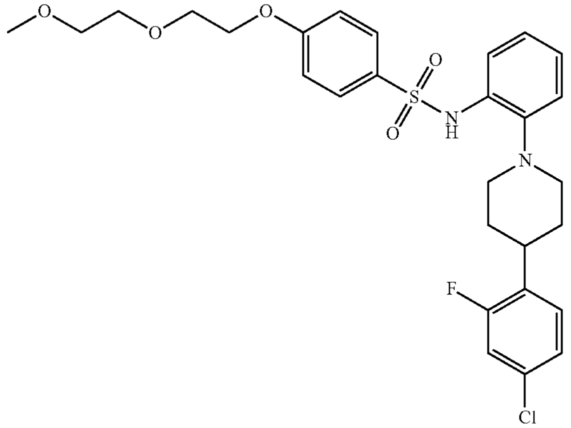 | Yield: 478.0 mg, 47.7%; Appearance: Beige solid; $^1$H NMR (600 MHz, DMSO-$d_6$) δ 7.96 (s, 1H), 7.31-7.22 (m, 2H), 7.20 (t, J = 7.5 Hz, 1H), 7.13 (d, J = 1.1 Hz, 1H), 7.09-7.03 (m, 2H), 7.03-6.98 (m, 2H), 4.56 (s, 2H), 3.24 (s, 3H), 3.09 (s, 2H), 2.73-2.59 (m, 4H), 2.22 (s, 3H), 1.55-1.48 (m, 2H), 1.32-1.25 (m, 2H), 0.93 (s, 3H); HPLC purity: 100%; LCMS Calculated for $C_{22}H_{30}N_2O_3S$: 402.55; Observed: 402.24 $[M-H]^-$. |

Example A61: Synthesis of 3-[({2-[4-(methoxymethyl)-4-methylpiperidin-1-yl]phenyl}sulfamoyl)methyl]-N,N-dimethylbenzene-1-sulfonamide (A-680)

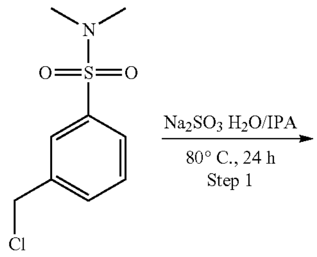

A61.1

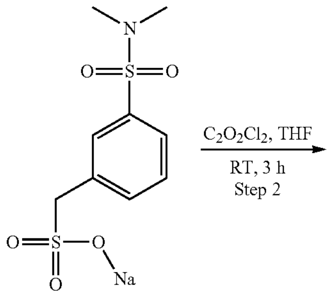

A61.2

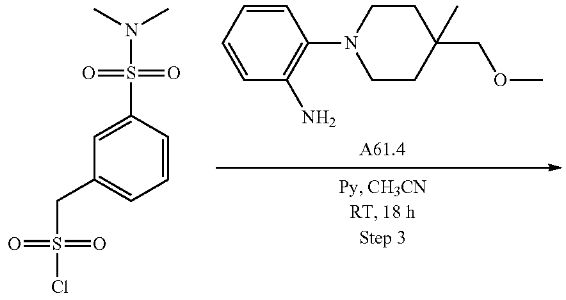

A61.3

-continued

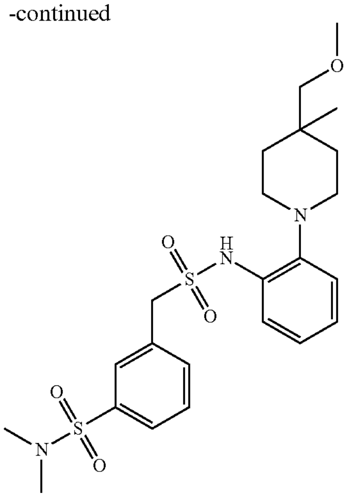

A-680

Step-1. Synthesis of sodium [3-(dimethylsulfamoyl)phenyl]methanesulfonate (A61.2)

3-(chloromethyl)-N,N-dimethylbenzene-1-sulfonamide (A61.1) (5.5 g, 23.5 mmol) and disodium sulfite (14.7 g, 117 mmol) in water/isopropanol mixture (50 mL/50 mL) were heated at 80° C. for 24 h. Then the reaction mixture was cooled to room temperature and evaporated to dryness under reduced pressure. The residue was refluxed in methanol (100 mL) for 15 min and filtered. Organics were evaporated, suspended with acetonitrile (30 mL), formed precipitate was filtered and dried under vacuum to give sodium [3-(dimethylsulfamoyl)phenyl]methanesulfonate as a white solid (A61.2) (5.5 g, 18.2 mmol, 90% purity, 69.9% yield) that was used in next step without further purification.

Step-2. Synthesis of [3-(dimethylsulfamoyl)phenyl]methanesulfonyl chloride (A61.3)

Oxalic dichloride (0.313 g, 2.47 mmol) was added at −10° C. to a suspension of sodium [3-(dimethylsulfamoyl)phenyl]methanesulfonate (A61.2) (0.5 g, 1.65 mmol) in THF (50 mL) and DMF (1 mL) was added. The bath temperature was maintained below 0° C. for 1 h, at which point the reaction was filtrated through SiO2, the precipitate was washed with THE (50 mL). The combined filtrate was evaporated under reduced pressure to afford [3-(dimethylsulfamoyl)phenyl] methanesulfonyl chloride as an yellow oil (A61.3) (0.4 g, 1.34 mmol, 93% purity, 75.7% yield) that was used in the next step without further purification.

Step-3. Synthesis of 3-[({2-[4-(methoxymethyl)-4-methylpiperidin-1-yl]phenyl}sulfamoyl)methyl]-N,N-dimethylbenzene-1-sulfonamide (A-680)

Pyridine (0.132 g, 1.67 mmol) and [3-(dimethylsulfamoyl)phenyl]methanesulfonyl chloride (A61.3) (0.4 g, 1.34 mmol) were added to a 2-[4-(methoxymethyl)-4-methylpiperidin-1-yl]aniline (A61.4) (0.260 g, 1.11 mmol) in acetonitrile (50 mL). The reaction mixture was stirred at room temperature for 18 h. The solvent was evaporated and the residue was subjected to HPLC purification (deionized water/HPLC-grade acetonitrile) that afforded 3-[({2-[4-(methoxymethyl)-4-methylpiperidin-1-yl]phenyl}sulfamoyl)methyl]-N,N-dimethylbenzene-1-sulfonamide (A-680). Yield: 325.9 mg, 56.1%; Appearance: White solid; $^1H$ NMR (400 MHz, DMSO-$d_6$) δ 8.12 (s, 1H), 7.81-7.75 (m, 1H), 7.77-7.69 (m, 1H), 7.69-7.59 (m, 2H), 7.27 (d, J=6.5 Hz, 1H), 7.10-6.95 (m, 3H), 4.85 (s, 2H), 3.27 (s, 3H), 3.13 (s, 2H), 2.83-2.62 (m, 4H), 2.50 (s, 6H), 1.70-1.54 (m, 2H), 1.34 (d, J=13.0 Hz, 2H), 0.96 (s, 3H); HPLC purity: 100%; LCMS Calculated for $C_{23}H_{33}N_3O_5S_2$: 495.65; Observed: 495.22 $[M-H]^-$.

The following example was prepared using standard chemical manipulations and procedures similar to those used for the preparation of the previous example.

-continued

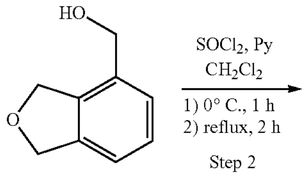

A62.2

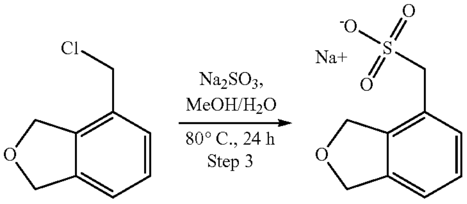

A62.3 A62.4

| Compound No. | Structure | Analytical data |
|---|---|---|
| A-627 | 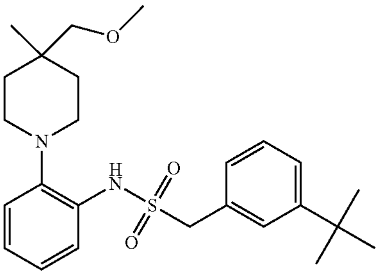 [SMILES: COCC1(C)CCN(c2ccccc2NS(=O)(=O)Cc2cccc(C(C)(C)C)c2)CC1] | Yield: 49.7 mg, 11.1%; Appearance: Brown oil; $^1H$ NMR (600 MHz, DMSO-$d_6$) δ 7.91 (s, 1H), 7.36-7.31 (m, 1H), 7.28-7.20 (m, 3H), 7.13-7.07 (m, 1H), 7.06-6.96 (m, 3H), 4.62 (s, 2H), 3.24 (s, 3H), 3.09 (s, 2H), 2.67-2.60 (m, 2H), 2.60-2.54 (m, 2H), 1.55-1.48 (m, 2H), 1.31-1.22 (m, 2H), 1.16 (s, 9H), 0.92 (s, 3H); HPLC purity:; LCMS Calculated for $C_{25}H_{36}N_2O_3S$: 444.63; Observed: 444.3 $[M-H]^-$. |

Example A62: Synthesis of 1-(1,3-dihydro-2-benzofuran-4-yl)-N-{2-[4-(methoxymethyl)-4-methylpiperidin-1-yl]phenyl}methanesulfonamide (A-607)

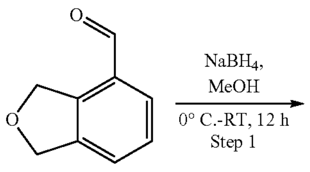

A62.1

-continued

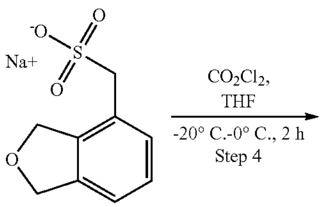

A62.4

-continued

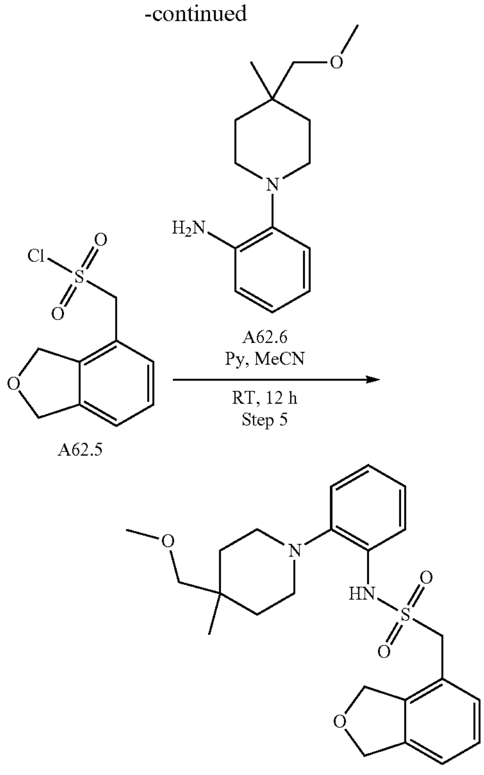

A62.5

A-607

Step-1. Synthesis of (1,3-dihydro-2-benzofuran-4-yl)methanol (A62.2)

$NaBH_4$ (1.21 g, 31.9 mmol) was added portionwise at 0° C. to a solution of 1,3-dihydroisobenzofuran-4-carbaldehyde (A62.1) (4.75 g, 32 mmol) in methanol (50 mL). Then, the reaction was warmed to r.t. and stirred for 12 h. After, the mixture was evaporated to dryness under reduced pressure. The residue was treated with ethyl acetate (100 mL) and the organic layer was washed with water (100 mL) and brine (100 mL), dried over sodium sulfate, filtered and evaporated to give (1,3-dihydro-2-benzofuran-4-yl)methanol (A62.2) (4 g, 26.6 mmol, 90% purity, 75% yield) which was used in the next step without further purification.

Step-2. Synthesis of 4-(chloromethyl)-1,3-dihydro-2-benzofuran (A62.3)

Thionyl chloride (4.92 g, 41.3 mmol, 3 mL) was added dropwise over 1 h at 0° C. to a solution of (1,3-dihydroisobenzofuran-4-yl)methanol (4 g, 26.6 mmol) in $CH_2Cl_2$ (40 mL) and pyridine (2.31 g, 29.2 mmol, 2.36 mL). Then, the reaction mixture was refluxed for 2 h, cooled to r.t. and poured in cold water (40 mL). The organic layer was separated, washed with brine (40 mL), dried over sodium sulfate, filtered and evaporated to afford 4-(chloromethyl)-1,3-dihydro-2-benzofuran as an yellow oil (A62.3) (4.4 g, 26 mmol, 90% purity, 88.3% yield) that was used in the next step without further purification.

Step-3. Synthesis of sodium (1,3-dihydro-2-benzofuran-4-yl)methanesulfonate (A62.4)

The mixture of 4-(chloromethyl)-1,3-dihydroisobenzofuran (A62.3) (4.4 g, 26 mmol) and disodium sulfite (10.5 g, 83.3 mmol) in water/methanol (50 mL/50 mL) were heated at 80° C. for 24 h. Then the reaction mixture was cooled to room temperature and evaporated to dryness under reduced pressure. The residue was refluxed in methanol (100 mL) for 15 min and filtered. The filtrate was evaporated under reduced pressure, the residue was suspended in acetonitrile (20 mL), filtered, and formed precipitate was dried in vacuum to obtain sodium (1,3-dihydro-2-benzofuran-4-yl) methanesulfonate as a white solid (A62.4) (6.2 g, 26.2 mmol, 93.54% purity, 94.2% yield) that was used in the next step without further purification.

Step-4. Synthesis of (1,3-dihydro-2-benzofuran-4-yl)methanesulfonyl chloride (A62.5)

Oxalyl chloride (7.4 g, 58.3 mmol, 5 mL) was added dropwise over 1 h at −20° C. to a suspension of sodium (1,3-dihydroisobenzofuran-4-yl)methanesulfonate (A62.4) (1.18 g, 4.99 mmol) in THE (15 mL) and DMF (1 mL). The bath temperature was maintained below 0° C. for 1 h, at which point the reaction was diluted with ethyl acetate (25 mL). The organic layer was separated, washed with brine (25 mL), dried over sodium sulfate, filtered and evaporated to give (1,3-dihydro-2-benzofuran-4-yl)methanesulfonyl chloride (A62.5) as an yellow oil (0.7 g, 3 mmol, 100% purity, 60.2% yield).

Step-5. Synthesis of 1-(1,3-dihydro-2-benzofuran-4-yl)-N-{2-[4-(methoxymethyl)-4-methylpiperidin-1-yl]phenyl}methanesulfonamide (A-607)

(1,3-dihydro-2-benzofuran-4-yl)methanesulfonyl chloride (A62.5) (0.32 g, 1.37 mmol) was added to the mixture of 2-[4-(methoxymethyl)-4-methylpiperidin-1-yl]aniline (A62.6) (0.23 g, 0.981 mmol) and pyridine (0.982 g, 12.4 mmol) in dry acetonitrile (10 mL). The reaction mixture was stirred for 12 h and evaporated. The residue was subjected to HPLC purification (deionized water/HPLC-grade acetonitrile) that afforded 1-(1,3-dihydro-2-benzofuran-4-yl)-N-{2-[4-(methoxymethyl)-4-methylpiperidin-1-yl] phenyl}methanesulfonamide (A-607). Yield: 208.8 mg, 47.0%; Appearance: Beige solid; $^1H$ NMR (600 MHz, DMSO-$d_6$) δ 8.09 (s, 1H), 7.30-7.22 (m, 3H), 7.18 (dd, J=7.4, 2.1 Hz, 1H), 7.12 (d, J=7.2 Hz, 1H), 7.09-7.00 (m, 2H), 4.95 (s, 2H), 4.92 (s, 2H), 4.57 (s, 2H), 3.24 (s, 3H), 3.10 (s, 2H), 2.73-2.62 (m, 4H), 1.58-1.50 (m, 2H), 1.33-1.26 (m, 2H), 0.93 (s, 3H); HPLC purity: 100%; LCMS Calculated for $C_{23}H_{30}N_2O_3S$: 414.56; Observed: 414.23 $[M-H]^-$.

Example A63: Synthesis of 1-(1,3-dihydro-2-benzofuran-5-yl)-N-{2-[4-(methoxymethyl)-4-methylpiperidin-1-yl]phenyl}methanesulfonamide (A-612)

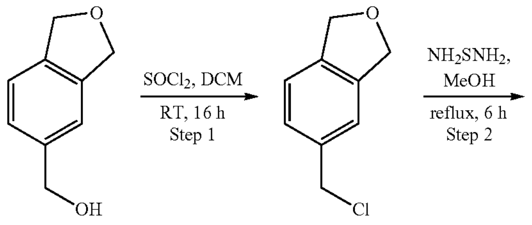

A63.1 A63.2

-continued

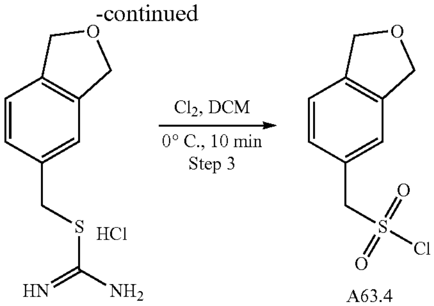

A63.3 A63.4

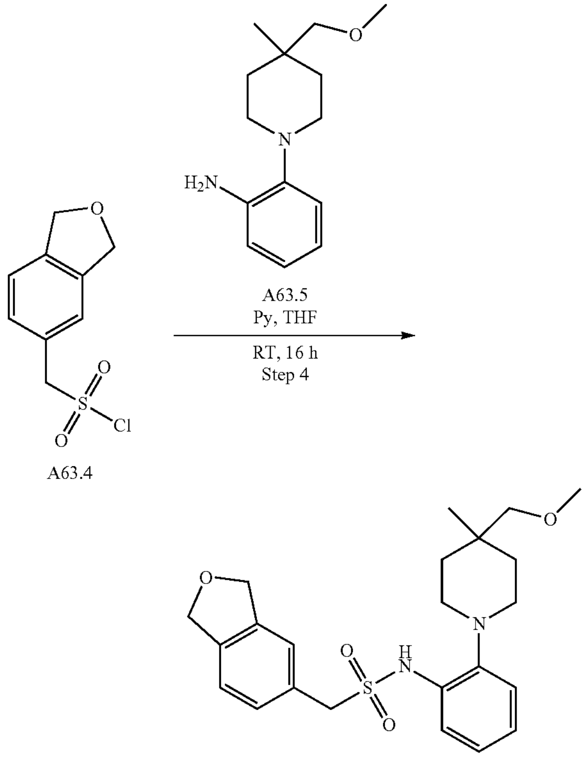

A63.5

A63.4

A-612

Step-1. Synthesis of 5-(chloromethyl)-1,3-dihydro-2-benzofuran (A63.2)

(1,3-dihydroisobenzofuran-5-yl)methanol (A63.1) (2 g, 13.3 mmol) was dissolved in anhydrous DCM (20 mL) and thionylchloride (1.75 g, 14.7 mmol) was added to this solution. The reaction mixture was stirred overnight at room temperature, then it was poured on water (20 mL), the organic layer was separated, washed with water (20 mL), dried over sodium sulfate, filtered and evaporated to afford crude 5-(chloromethyl)-1,3-dihydro-2-benzofuran (A63.2) (1.7 g, 10.0 mmol, 95% purity, 71.8% yield).

Step-2. Synthesis of {[(1,3-dihydro-2-benzofuran-5-yl) methyl]sulfanyl}methanimidamide hydrochloride (A63.3)

5-(chloromethyl)-1,3-dihydroisobenzofuran (A63.2) (1.7 g, 10 mmol) was added to a stirred solution of thiourea (0.76 g, 9.98 mmol) in dry methanol (20 mL). The mixture was refluxed until the reaction completion (TLC control, 6 h) and concentrated under the reduced pressure. The residue was washed with MTBE (20 mL×2) and dried on air to afford {[(1,3-dihydro-2-benzofuran-5-yl)methyl]sulfanyl}methanimidamide hydrochloride (A63.3) (1.3 g, 5.31 mmol, 90% purity, 47.9% yield) that was used in the next step without additional purification.

Step-3. Synthesis of (1,3-dihydro-2-benzofuran-5-yl)methanesulfonyl chloride (A63.4)

Gaseous chlorine was bubbled at room temperature through a stirred solution of (1,3-dihydroisobenzofuran-5-yl)methyl carbamimidothioate hydrochloride (A63.3) (1.3 g, 5.31 mmol) in acetic acid (20 mL) for 10 min. The water (50 mL) was added after and the precipitate was filtered, dried to afford (1,3-dihydro-2-benzofuran-5-yl)methanesulfonyl chloride (A63.4) (0.8 g, 3.43 mmol, 88% purity, 57.2% yield) that was used in the next step without further purification.

Step-4. Synthesis of 1-(1,3-dihydro-2-benzofuran-5-yl)-N-{2-[4-(methoxymethyl)-4-methylpiperidin-1-yl]phenyl}methanesulfonamide (A-612)

(1,3-dihydro-2-benzofuran-5-yl)methanesulfonyl chloride (A63.4) (0.2 g, 0.859 mmol) was added to the mixture of 2-[4-(methoxymethyl)-4-methylpiperidin-1-yl]aniline (A63.5) (0.2 g, 0.853 mmol) and pyridine (0.1 g, 1.26 mmol) in dry THF (20 mL). The reaction mixture was stirred overnight and evaporated. The residue was subjected to HPLC purification (deionized water/HPLC-grade methanol) that afforded 1-(1,3-dihydro-2-benzofuran-5-yl)-N-{2-[4-(methoxymethyl)-4-methylpiperidin-1-yl] phenyl}methanesulfonamide (A-612). Yield: 87.6 mg, 22.5%; Appearance: Light brown solid; $^1$H NMR (600 MHz, DMSO-$d_6$) δ 7.97 (s, 1H), 7.29-7.22 (m, 3H), 7.17-7.10 (m, 2H), 7.08-7.02 (m, 2H), 4.94 (s, 2H), 4.91 (s, 2H), 4.62 (s, 2H), 3.24 (s, 3H), 3.09 (s, 2H), 2.71-2.59 (m, 4H), 1.55-1.48 (m, 2H), 1.31-1.24 (m, 2H), 0.93 (s, 3H); HPLC purity: 100%; LCMS Calculated for $C_{23}H_{30}N_2O_4S$: 430.56; Observed: 430.23 $[M-H]^-$.

Example A64: Synthesis of N-{5-methoxy-2-[4-(methoxymethyl)-4-methylpiperidin-1-yl]phenyl}-2,3-dihydro-1H-indene-5-sulfonamide (A-630)

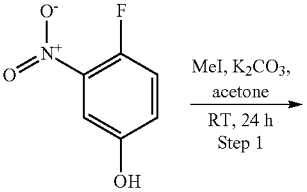

A64.1

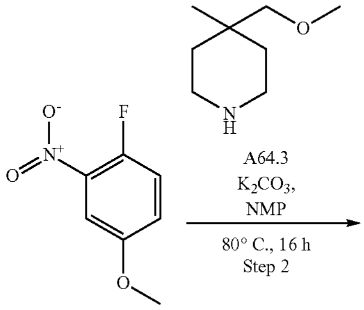

A64.3

A64.2

-continued

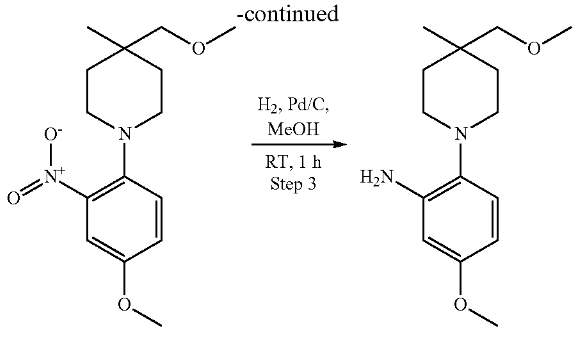

A64.4 A64.5

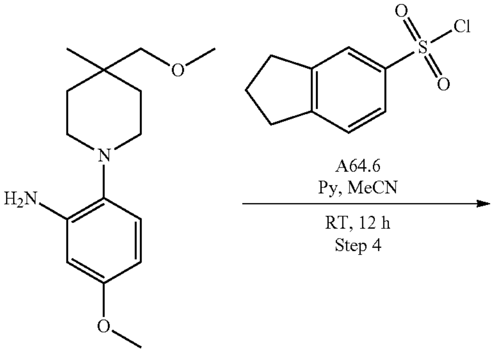

A64.5

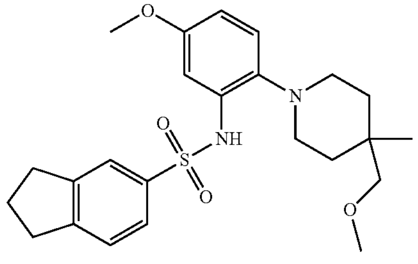

A-630

Step-1. Synthesis of 1-fluoro-4-methoxy-2-nitrobenzene (A64.2)

4-Fluoro-3-nitrophenol (A64.1) (5 g, 31.8 mmol) was dissolved in acetone (50 mL) and methyl iodide (6.77 g, 47.7 mmol) and potassium carbonate (6.59 g, 47.7 mmol) were added to this solution. The reaction mixture was stirred at room temperature for 24 hours and diluted with ethyl acetate (100 mL). The organic layer was separated, washed with 1N sodium hydroxide aqueous solution (100 mL), water (100 mL) and brine (100 mL), dried over sodium sulfate, and filtered. The filtrate was concentrated under reduced pressure to give 1-fluoro-4-methoxy-2-nitrobenzene as yellow oil (A64.2) (5.3 g, 30.9 mmol, 95% purity, 92.4% yield).

Step-2. Synthesis of 1-(4-methoxy-2-nitrophenyl)-4-(methoxymethyl)-4-methylpiperidine (A64.4)

1-fluoro-4-methoxy-2-nitrobenzene (A64.2) (1 g, 5.84 mmol) was added to a stirred solution of 4-(methoxymethyl)-4-methylpiperidine (A64.3) (0.836 g, 5.84 mmol) and $K_2CO_3$ (0.807 g, 5.83 mmol) in dry NMP (10 mL). The mixture was stirred until the reaction completion at 80° C. (TLC control, overnight). Then, it was cooled to room temperature, poured in water (20 mL) and extracted with ethyl acetate (15 mL×3). The organic layer was washed with water (40 mL) and brine (40 mL), dried over anhydrous sodium sulfate, filtered and concentrated under reduced pressure to afford 1-(4-methoxy-2-nitrophenyl)-4-(methoxymethyl)-4-methylpiperidine as orange oil (A64.4) (1.7 g, 5.77 mmol, 90% purity, 89.4% yield) that was used in the next step without further purification.

Step-3. Synthesis of 5-methoxy-2-[4-(methoxymethyl)-4-methylpiperidin-1-yl]aniline (A64.5)

1-(4-methoxy-2-nitrophenyl)-4-(methoxymethyl)-4-methylpiperidine (A64.4) (1.7 g, 5.77 mmol) was dissolved in methanol (50 mL) and treated with 10% Pd/C (0.2 g). The resulting mixture was hydrogenated at ambient pressure and room temperature for 1 h. The catalyst was filtered off and the filtrate was evaporated to afford 5-methoxy-2-[4-(methoxymethyl)-4-methylpiperidin-1-yl]aniline as a caramel oil (A64.5) (1.5 g, 5.67 mmol, 95% purity, 93.4% yield).

Step-4. Synthesis of N-{5-methoxy-2-[4-(methoxymethyl)-4-methylpiperidin-1-yl]phenyl}-2,3-dihydro-1H-indene-5-sulfonamide (A-630)

2,3-dihydro-1H-indene-5-sulfonyl chloride (A64.6) (0.41 g, 1.88 mmol) was added to the mixture of 5-methoxy-2-[4-(methoxymethyl)-4-methylpiperidin-1-yl]aniline (A64.5) (0.5 g, 1.89 mmol) and pyridine (0.982 g, 12.4 mmol) in dry acetonitrile (20 mL). The reaction mixture was stirred for 12 h and evaporated. The residue was subjected to HPLC purification (deionized water/HPLC-grade acetonitrile) that afforded N-{5-methoxy-2-[4-(methoxymethyl)-4-methylpiperidin-1-yl]phenyl}-2,3-dihydro-1H-indene-5-sulfonamide (A-630). Yield: 645.0 mg, 72.8%; Appearance: Pink solid; $^1$H NMR (600 MHz, DMSO-$d_6$) δ 8.52 (s, 1H), 7.64 (s, 1H), 7.47 (dd, J=7.9, 1.8 Hz, 1H), 7.32 (d, J=7.9 Hz, 1H), 7.16 (d, J=8.8 Hz, 1H), 6.89 (d, J=2.9 Hz, 1H), 6.58 (dd, J=8.8, 2.9 Hz, 1H), 3.65 (s, 3H), 3.26 (s, 3H), 3.11 (s, 2H), 2.83 (t, J=7.3 Hz, 4H), 2.43 (t, J=9.2 Hz, 2H), 2.30-2.23 (m, 2H), 1.98 (p, J=7.5 Hz, 2H), 1.59-1.51 (m, 2H), 1.31-1.24 (m, 2H), 0.92 (s, 3H); HPLC purity: 100%; LCMS Calculated for $C_{24}H_{32}N_2O_4S$: 444.59; Observed: 444.25 [M−H]$^-$.

Example A65: Synthesis of N4-{2-[4-(ethoxymethyl)-4-methylpiperidin-1-yl]phenyl}-N1,N1-dimethylbenzene-1,4-disulfonamide (A-719)

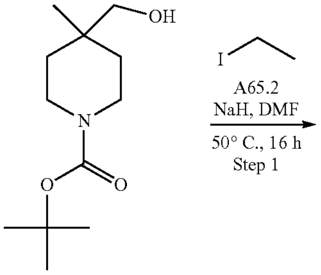

A65.1

-continued

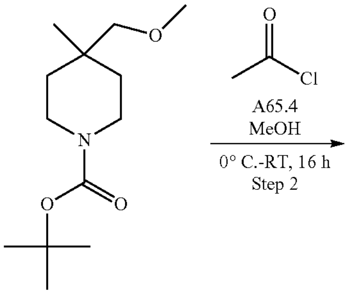

A65.3

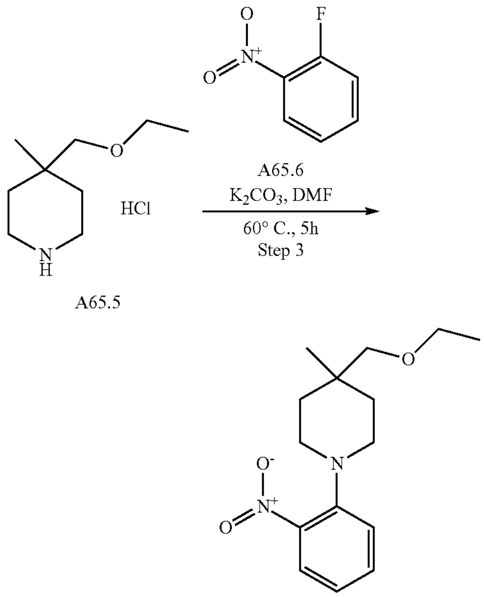

A65.5

A65.7

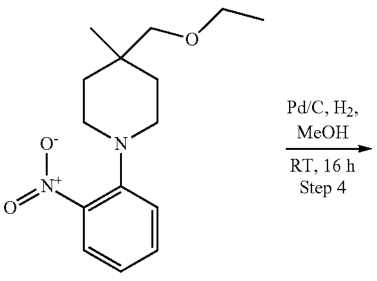

A65.7

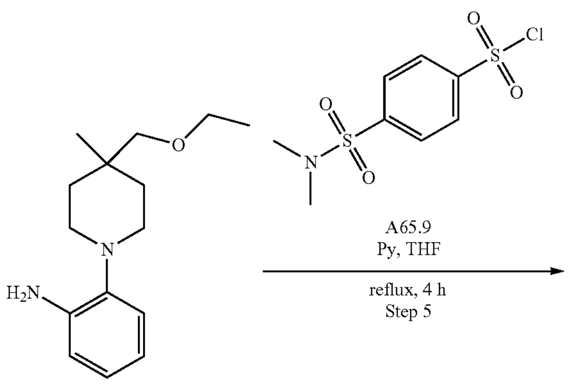

A65.8

-continued

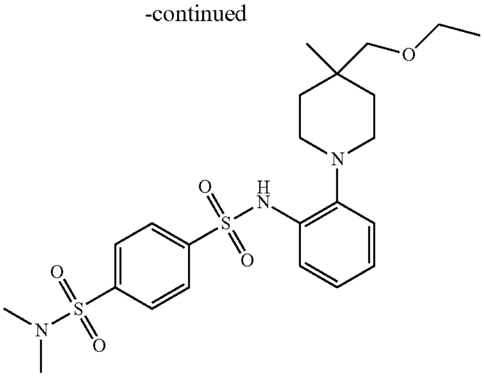

A-719

Step-1. Synthesis of tert-butyl 4-(ethoxymethyl)-4-methylpiperidine-1-carboxylate (A65.3)

Tert-butyl 4-(hydroxymethyl)-4-methylpiperidine-1-carboxylate (A65.1) (1.6 g, 6.97 mmol) was added to a suspension of sodium hydride (60% in mineral oil, 0.305 g, 7.66 mmol) in DMF (15 mL) and the mixture was stirred for 0.5 h at 50° C. Iodoethane (A65.2) (1.62 g, 10.4 mmol) was added dropwise after and the mixture was stirred at 50° C. overnight until completion. After the reaction mixture was diluted with water (25 mL) and ethyl acetate (25 mL). The organic layer was separated, washed with water (25 mL), brine (25 mL), dried over sodium sulfate, filtered and evaporated under reduced pressure to afford tert-butyl 4-(ethoxymethyl)-4-methylpiperidine-1-carboxylate (A65.3) (1.8 g, 6.99 mmol, 80% purity, 80.4% yield) that was used in next step without further purification.

Step-2. Synthesis of 4-(ethoxymethyl)-4-methylpiperidine hydrochloride (A65.5)

Acetyl chloride (A65.4) (5 g, 63.6 mmol) was added to methanol (25 g, 780 mmol) at 0° C. and the mixture was stirred for 1 h. After tert-butyl 4-(ethoxymethyl)-4-methylpiperidine-1-carboxylate (A65.3) (1.8 g, 6.99 mmol) was added and the reaction mixture was allowed to warm and stir at room temperature overnight. After the solvent was evaporated under reduced pressure, the residue was treated with mixture ether/hexane (20 mL, 1/5). The formed precipitate was filtered off, dried on air to afford 4-(ethoxymethyl)-4-methylpiperidine hydrochloride (A65.5) (1.5 g, 7.74 mmol, 85% purity, 94% yield) that was used in next step without further purification.

Step-3. Synthesis of 4-(ethoxymethyl)-4-methyl-1-(2-nitrophenyl)piperidine (A65.7)

1-fluoro-2-nitrobenzene (A65.6) (0.55 g, 3.89 mmol) was added to a stirred solution of 4-(ethoxymethyl)-4-methylpiperidine hydrochloride (A65.5) (0.75 g, 3.87 mmol) and potassium carbonate (1.33 g, 9.67 mmol) in dry DMF (20 mL). The mixture was stirred at 60° C. for 5 h and concentrated under the reduced pressure. The residue was dissolved in ethyl acetate (20 mL) and washed with water (40 mL), brine (40 mL), dried over sodium sulfate, filtered and concentrated under reduced pressure to afford 4-(ethoxymethyl)-4-methyl-1-(2-nitrophenyl)piperidine (A65.7) (0.8 g, 2.87 mmol, 62% purity, 46.3% yield) that was used in next step without further purification.

Step-4. Synthesis of 2-[4-(ethoxymethyl)-4-methylpiperidin-1-yl]aniline (A65.8)

4-(ethoxymethyl)-4-methyl-1-(2-nitrophenyl)piperidine (A65.7) (0.8 g, 2.87 mmol) was dissolved in methanol (25 mL) and treated with 10% Pd/C (0.1 g). The resulting mixture was hydrogenated at ambient pressure and room temperature until the reaction was completed. The catalyst was filtered off and the filtrate was evaporated to afford 2-[4-(ethoxymethyl)-4-methylpiperidin-1-yl]aniline (A65.8) (0.7 g, 2.81 mmol, 65.61% purity, 64.4% yield) that was used in next step without further purification.

Step-5. Synthesis of N4-{2-[4-(ethoxymethyl)-4-methylpiperidin-1-yl]phenyl}-N1,N1-dimethylbenzene-1,4-disulfonamide (A-719)

4-(dimethylsulfamoyl)benzene-1-sulfonyl chloride (A65.9) (0.84 g, 2.96 mmol) was added to the mixture of 2-[4-(ethoxymethyl)-4-methylpiperidin-1-yl]aniline (A65.8) (0.7 g, 2.81 mmol) and pyridine (0.5 g, 6.32 mmol) in dry THF (20 mL). The reaction mixture was refluxed for 4 h and evaporated. The residue was diluted with water (20 mL) and ethyl acetate (20 mL). Organic layer was separated, washed with brine (20 mL), dried over sodium sulfate, filtered and evaporated under reduced pressure. The crude material was purified by HPLC (deionized water/HPLC-grade acetonitrile) to give N4-{2-[4-(ethoxymethyl)-4-methylpiperidin-1-yl]phenyl}-N1,N1-dimethylbenzene-1,4-disulfonamide (A-719). Yield: 226.6 mg, 72.8%; Appearance: Light brown solid; $^1$H NMR (600 MHz, DMSO-$d_6$) δ 9.10 (s, 1H), 7.99-7.87 (m, 4H), 7.24 (d, J=6.5 Hz, 1H), 7.16 (d, J=7.9 Hz, 1H), 7.09 (t, J=7.0 Hz, 1H), 7.02 (t, J=8.1 Hz, 1H), 3.41 (q, J=7.0 Hz, 2H), 3.12 (s, 2H), 2.59 (s, 6H), 2.52-2.46 (m, 14H), 2.46-2.39 (m, 3H), 1.50-1.43 (m, 2H), 1.27-1.18 (m, 2H), 1.10 (t, J=7.0 Hz, 3H), 0.89 (s, 3H); HPLC purity: 100%; LCMS Calculated for $C_{23}H_{33}N_3O_5S_2$: 495.65; Observed: 495.22 $[M-H]^-$.

Example A66: Synthesis of N4-(2-{3,3-dimethyl-2-oxa-8-azaspiro[4.5]decan-8-yl}phenyl)-N1,N1-dimethylbenzene-1,4-disulfonamide (A-440)

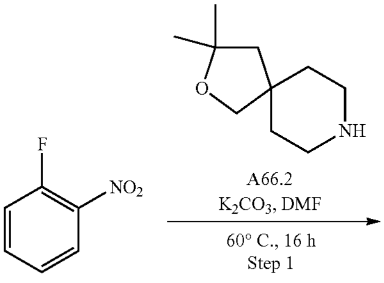

A66.1

-continued

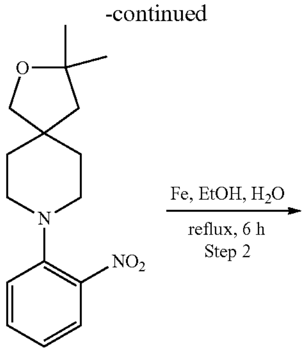

A66.3

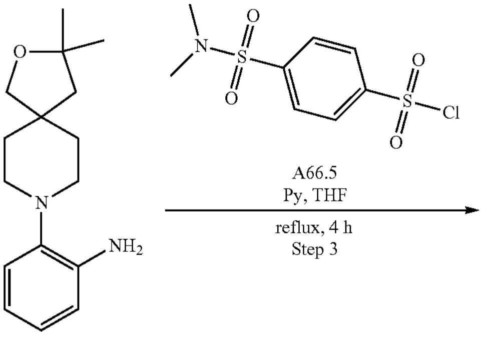

A66.4

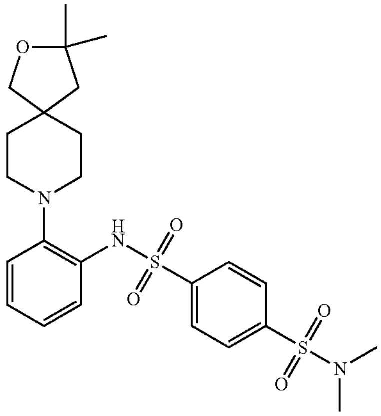

A-440

Step-1. Synthesis of 3,3-dimethyl-8-(2-nitrophenyl)-2-oxa-8-azaspiro[4.5]decane (A66.3)

1-fluoro-2-nitrobenzene (A66.1) (1.38 g, 9.78 mmol) was added to a stirred solution of 3,3-dimethyl-2-oxa-8-azaspiro[4.5]decane hydrochloride (A66.2) (2 g, 9.78 mmol) and potassium carbonate (2.8 g, 20.2 mmol) in dry DMF (20 mL). The mixture was stirred at 60° C. until the reaction completion (TLC control) and concentrated under the reduced pressure. The residue was dissolved in chloroform (15 mL), the organic layer was washed with water (15 mL), dried over anhydrous sodium sulfate, filtered and concentrated under reduced pressure. The residue was purified by flash chromatography (chloroform/acetonitrile) to give 3,3-dimethyl-8-(2-nitrophenyl)-2-oxa-8-azaspiro[4.5]decane (A66.3) (1.45 g, 4.99 mmol, 95% purity, 48.4% yield).

Step-2. Synthesis of 2-{3,3-dimethyl-2-oxa-8-azaspiro[4.5]decan-8-yl}aniline (A66.4)

Iron powder (1.4 g, 25 mmol) and ammonium chloride (1.34 g, 25 mmol) were added at room temperature to a stirred solution of 3,3-dimethyl-8-(2-nitrophenyl)-2-oxa-8-azaspiro[4.5]decane (A66.3) (1.45 g, 4.99 mmol) in a mixture of ethanol (25 mL)/water (25 mL) and the resulting reaction mixture was refluxed for 6 h. After the reaction completion (TLC control) the mixture was filtered through silica gel and the filtrate was evaporated under reduced pressure. The residue was dissolved in water (50 mL) and ethyl acetate (50 mL). The organic layer was separated, washed with water (50 mL), dried over anhydrous sodium sulfate, filtered and evaporated under reduced pressure that afforded the 2-{3,3-dimethyl-2-oxa-8-azaspiro[4.5]decan-8-yl}aniline (A66.4) (0.55 g, 2.11 mmol, 95% purity, 40.4% yield).

Step-3. Synthesis of N4-(2-{3,3-dimethyl-2-oxa-8-azaspiro[4.5]decan-8-yl}phenyl)-N1,N1-dimethylbenzene-1,4-disulfonamide (A-440)

2,3-dihydro-1H-indene-5-sulfonyl chloride (A66.5) (0.6 g, 2.76 mmol) was added to the mixture of 2-{3,3-dimethyl-2-oxa-8-azaspiro[4.5]decan-8-yl}aniline (A66.4) (0.718 g, 2.76 mmol) and pyridine (0.218 g, 2.76 mmol) in dry tetrahydrofuran (20 mL). The reaction mixture was refluxed for 4 h and evaporated under reduced pressure. The residue was subjected to HPLC purification (deionized water/HPLC-grade methanol) that afforded the N4-(2-{3,3-dimethyl-2-oxa-8-azaspiro[4.5]decan-8-yl}phenyl)-N1,N1-dimethylbenzene-1,4-disulfonamide (A-440). Yield: 129.3 mg, 8.71%; Appearance: Brown solid; $^1$H NMR (400 MHz, $CDCl_3$) δ 8.12 (s, 1H), 7.95 (d, J=8.1 Hz, 2H), 7.80 (d, J=8.1 Hz, 2H), 7.55 (d, J=7.9 Hz, 1H), 7.07 (q, J=11.3, 9.4 Hz, 3H), 3.67 (s, 2H), 2.68 (s, 6H), 2.44 (s, 4H), 1.66 (s, 6H), 1.26 (s, 6H); HPLC purity: 100%; LCMS Calculated for $C_{24}H_{33}N_3O_5S_2$: 507.67; Observed: 508.2[M+H]$^+$.

Example A67: Synthesis of N4-[2-(4-{[(2R,6S)-2,6-dimethylmorpholin-4-yl]methyl}piperidin-1-yl)phenyl]-N1,N1-dimethylbenzene-1,4-disulfonamide (A-544)

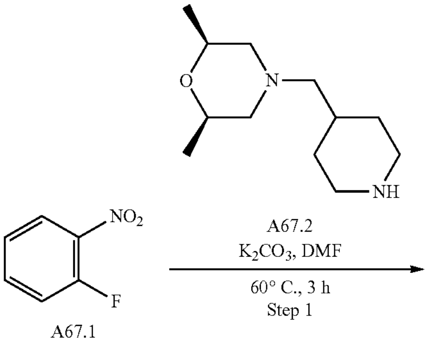

A67.1

-continued

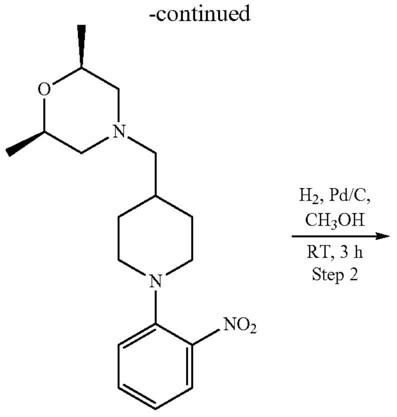

A67.3

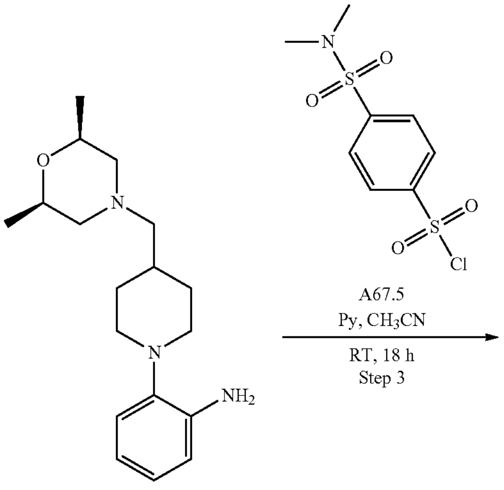

A67.4

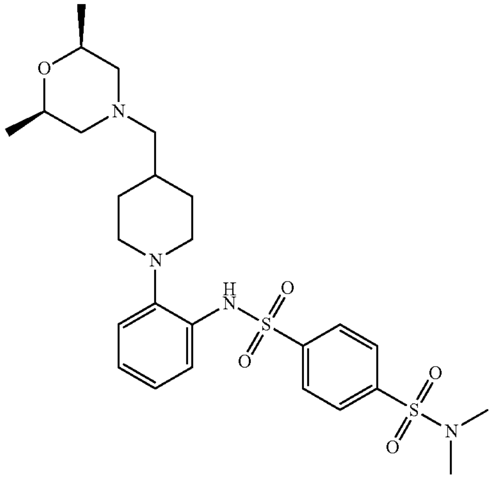

A-554

Step-1. Synthesis of (2R,6S)-2,6-dimethyl-4-{[1-(2-nitrophenyl)piperidin-4-yl]methyl}morpholine (A67.3)

1-fluoro-2-nitrobenzene (A67.1) (0.942 g, 6.66 mmol) was added to a stirred solution of (2R,6S)-2,6-dimethyl-4-[(piperidin-4-yl)methyl]morpholine (A67.2) (1.4 g, 6.6 mmol) and dipotassium carbonate (1.1 g, 8.03 mmol) in dry DMF (30 mL). The mixture was stirred until the reaction completion (TLC control) at 60° C. Then, it was cooled to room temperature, poured in water (30 mL) and extracted with ethyl acetate (25 mL×3). The organic layer was separated, washed with water (30 mL) and brine (30 mL), dried over anhydrous sodium sulfate, filtered and concentrated under reduced pressure to afford (2R,6S)-2,6-dimethyl-4-{[1-(2-nitrophenyl)piperidin-4-yl]methyl}morpholine as an orange solid (A67.3) (1.9 g, 5.69 mmol, 95% purity, 81% yield).

Step-2. Synthesis of 2-(4-{[(2R,6S)-2,6-dimethylmorpholin-4-yl]methyl}piperidin-1-yl)aniline (A67.4)

(2R,6S)-2,6-dimethyl-4-{[1-(2-nitrophenyl)piperidin-4-yl]methyl}morpholine (A67.3) (1.9 g, 5.69 mmol) was dissolved in methanol (100 mL). Pd/C (10 percent, 0.19 g) was added to the solution and then the black suspension was degassed three times and filled with $H_2$ (g). The suspension was shaken at room temperature for 3 h, filtered, the solids were washed with MeOH (50 mL) and combined filtrates were concentrated under reduced pressure to afford 2-(4-{[(2R,6S)-2,6-dimethylmorpholin-4-yl]methyl}piperidin-1-yl)aniline (A67.4) as beige oil (1.65 g, 5.43 mmol, 95% purity, 90.6% yield).

Step-3. Synthesis of N4-[2-(4-{[(2R,6S)-2,6-dimethylmorpholin-4-yl]methyl}piperidin-1-yl)phenyl]-N1,N1-dimethylbenzene-1,4-disulfonamide (A-544)

Pyridine (0.155 g, 1.96 mmol) and 4-(dimethylsulfamoyl)benzene-1-sulfonyl chloride (A67.5) (0.408 g, 1.44 mmol) were added to a solution of 2-(4-{[(2R,6S)-2,6-dimethylmorpholin-4-yl]methyl}piperidin-1-yl)aniline (A67.4) (0.4 g, 1.31 mmol) in acetonitrile (50 mL). The reaction mixture was stirred at room temperature for 18 h. The reaction mixture has been filtered through $SiO_2$, the filtrate was evaporated and the residue was subjected to HPLC purification (deionized water/HPLC-grade acetonitrile) that afforded N4-[2-(4-{[(2R,6S)-2,6-dimethylmorpholin-4-yl]methyl}piperidin-1-yl)phenyl]-N1,N1-dimethylbenzene-1,4-disulfonamide (A-544). Yield: 218.2 mg, 28.7%; Appearance: Yellow solid; $^1$H NMR (400 MHz, DMSO-$d_6$) δ 9.13 (s, 1H), 8.00 (dd, J=8.4, 2.6 Hz, 2H), 7.95-7.88 (m, 2H), 7.27 (d, J=8.3 Hz, 1H), 7.11 (s, 2H), 7.06 (s, 1H), 3.52 (d, J=8.9 Hz, 2H), 2.69 (d, J=11.0 Hz, 2H), 2.62 (d, J=2.6 Hz, 6H), 2.54 (d, J=2.5 Hz, 2H), 2.42 (t, J=11.3 Hz, 2H), 2.14-2.06 (m, 2H), 1.57 (q, J=11.6, 10.1 Hz, 5H), 1.14 (d, J=12.0 Hz, 2H), 1.04 (dd, J=6.3, 2.5 Hz, 6H); HPLC purity: 100%; LCMS Calculated for $C_{26}H_{38}N_4O_5S_2$: 550.73; Observed: 551.2[M+H]$^+$.

The following examples were prepared using standard chemical manipulations and procedures similar to those used for the preparation of the previous example.

| Compound No | Structure | Analytical Data |
|---|---|---|
| A-756 | 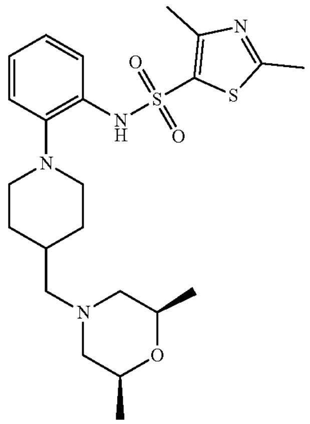 [SMILES: Cc1nc(C)c(S(=O)(=O)Nc2ccccc2N2CCC(CN3C[C@@H](C)O[C@@H](C)C3)CC2)s1] | Yield: 352 mg, 71%; Appearance: Brown oil; $^1$H NMR (400 MHz, DMSO-$d_6$) δ 7.30 (d, J = 7.9 Hz, 1H), 7.17 (d, J = 4.1 Hz, 2H), 7.08 (s, 1H), 4.10 (d, J = 5.3 Hz, 1H), 3.54 (d, J = 8.2 Hz, 2H), 3.16 (d, J = 5.0 Hz, 2H), 2.68 (t, J = 13.9 Hz, 5H), 2.58 (s, 3H), 2.31 (s, 3H), 2.12 (d, J = 6.9 Hz, 2H), 1.67 (d, J = 12.0 Hz, 2H), 1.56 (t, J = 10.5 Hz, 3H), 1.25-1.13 (m, 2H), 1.04 (d, J = 6.2 Hz, 6H); HPLC purity: 100%; LCMS Calculated for $C_{23}H_{34}N_4O_3S_2$: 478.67; Observed: 479.1 [M + H]$^+$. |
| A-757 | 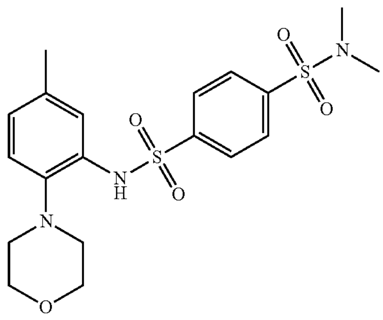 [SMILES: Cc1ccc(N2CCOCC2)c(NS(=O)(=O)c2ccc(S(=O)(=O)N(C)C)cc2)c1] | Yield: 432.7 mg, 57.4%; Appearance: Light brown solid; $^1$H NMR (400 MHz, DMSO-$d_6$) δ 9.35 (s, 1H), 8.00-7.90 (m, 4H), 7.12 (s, 1H), 7.05 (d, J = 8.1 Hz, 1H), 6.98 (d, J = 8.2 Hz, 1H), 3.52 (t, J = 4.5 Hz, 4H), 2.62 (s, 6H), 2.41 (s, 4H), 2.23 (s, 3H); HPLC purity: 100%; LCMS Calculated for $C_{19}H_{25}N_3O_5S_2$: 439.55; Observed: 440.2 [M + H]$^+$. |

-continued

| Compound No | Structure | Analytical Data |
|---|---|---|
| A-788 | 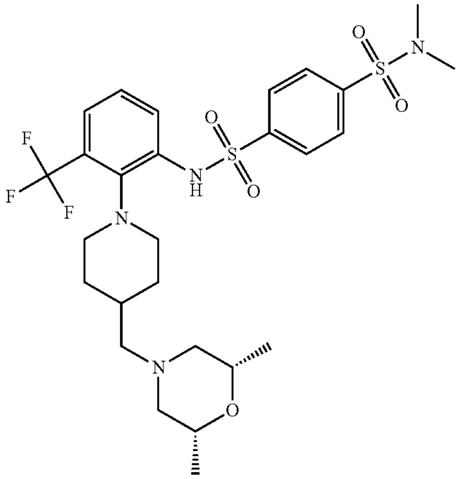 [SMILES: C[C@@H]1CN(CC2CCN(c3c(NS(=O)(=O)c4ccc(S(=O)(=O)N(C)C)cc4)cccc3C(F)(F)F)CC2)C[C@H](C)O1] | Yield: 28.2 mg, 12.4%; Appearance: Light brown solid; $^1$H NMR (400 MHz, $CDCl_3$) δ 8.03-7.96 (m, 2H), 7.91-7.80 (m, 3H), 7.37-7.32 (m, 1H), 7.24 (s, 1H), 3.70 (t, J = 8.5 Hz, 2H), 3.50 (s, 1H), 3.03 (t, J = 12.0 Hz, 2H), 2.72 (s, 8H), 2.63 (s, 2H), 2.47 (d, J = 12.1 Hz, 2H), 2.24 (d, J = 7.3 Hz, 2H), 1.87 (d, J = 12.9 Hz, 2H), 1.73 (t, J = 10.7 Hz, 3H), 1.24 (d, J = 12.1 Hz, 2H), 1.19 (d, J = 6.2 Hz, 6H); HPLC purity: 96.07; LCMS Calculated for $C_{27}H_{37}F_3N_4O_5S_2$: 618.73; Observed: 619.4 $[M + H]^+$. |
| A-792 | 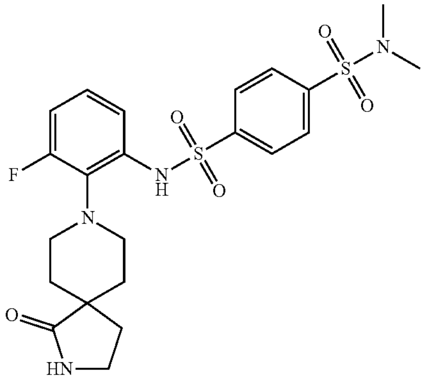 [SMILES: CN(C)S(=O)(=O)c1ccc(S(=O)(=O)Nc2cccc(F)c2N2CCC3(CCNC3=O)CC2)cc1] | Yield: 87.8 mg, 12.6%; Appearance: Brown solid; $^1$H NMR (400 MHz, DMSO-$d_6$) δ 9.49 (s, 1H), 8.00 (d, J = 8.2 Hz, 2H), 7.92 (d, J = 8.2 Hz, 2H), 7.55 (s, 1H), 7.18 (s, 2H), 6.96 (s, 1H), 3.15 (t, J = 6.9 Hz, 2H), 2.84 (t, J = 11.7 Hz, 2H), 2.37 (s, 2H), 1.97-1.80 (m, 4H), 1.24 (d, J = 12.0 Hz, 2H); HPLC purity: 100%; LCMS Calculated for $C_{22}H_{27}FN_4O_5S_2$: 510.6; Observed: 511.0 $[M + H]^+$. |
| A-796 | 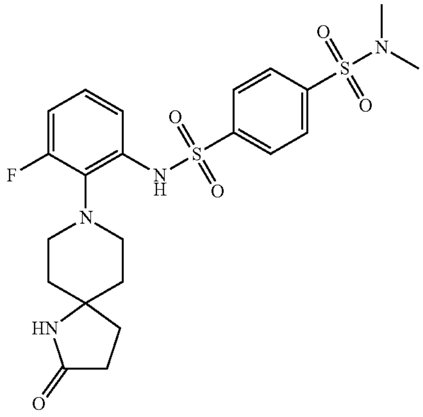 [SMILES: CN(C)S(=O)(=O)c1ccc(S(=O)(=O)Nc2cccc(F)c2N2CCC3(CCC(=O)N3)CC2)cc1] | Yield: 78.2 mg, 7.27%; Appearance: Yellow solid; $^1$H NMR (400 MHz, DMSO-$d_6$) δ 9.35 (s, 1H), 7.95 (q, J = 8.3 Hz, 5H), 7.25-7.14 (m, 2H), 7.04-6.93 (m, 1H), 2.69 (s, 2H), 2.61 (s, 6H), 2.54 (s, 2H), 2.18 (t, J = 7.9 Hz, 2H), 1.83 (t, J = 7.9 Hz, 2H), 1.66 (s, 2H), 1.55 (s, 2H); HPLC purity: 100%; LCMS Calculated for $C_{22}H_{27}FN_4O_5S_2$: 510.6; Observed: 511.0 $[M + H]^+$. |

-continued
| Compound No | Structure | Analytical Data |
|---|---|---|
| A-795 | 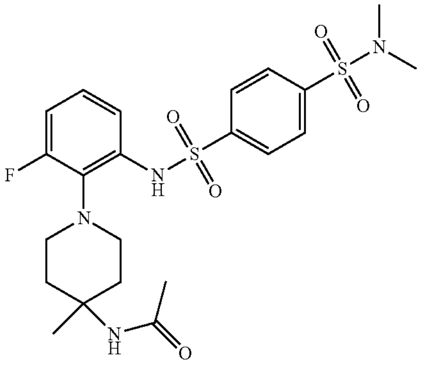 [SMILES: CC(=O)NC1(C)CCN(c2c(F)cccc2NS(=O)(=O)c2ccc(S(=O)(=O)N(C)C)cc2)CC1] | Yield: 46.2 mg, 8.67%; Appearance: White solid; $^1$H NMR (400 MHz, DMSO-$d_6$) δ 9.30 (s, 1H), 8.00-7.87 (m, 4H), 7.34-7.24 (m, 2H), 7.23-7.14 (m, 1H), 6.98 (dd, J = 12.3, 8.2 Hz, 1H), 2.82 (s, 2H), 2.60 (t, J = 2.1 Hz, 6H), 2.11 (s, 2H), 1.96 (d, J = 13.0 Hz, 2H), 1.79 (t, J = 2.4 Hz, 3H), 1.56 (d, J = 11.8 Hz, 2H), 1.33-1.19 (m, 3H); HPLC purity: 100%; LCMS Calculated for $C_{22}H_{29}FN_4O_5S_2$: 512.62; Observed: 513.0 [M + H]$^+$. |
Example A68: Synthesis of 4-(2-{[2-(4-benzylpiperazin-1-yl)phenyl]amino}propan-2-yl)-N,N-dimethylbenzene-1-sulfonamide (A-733)
-continued
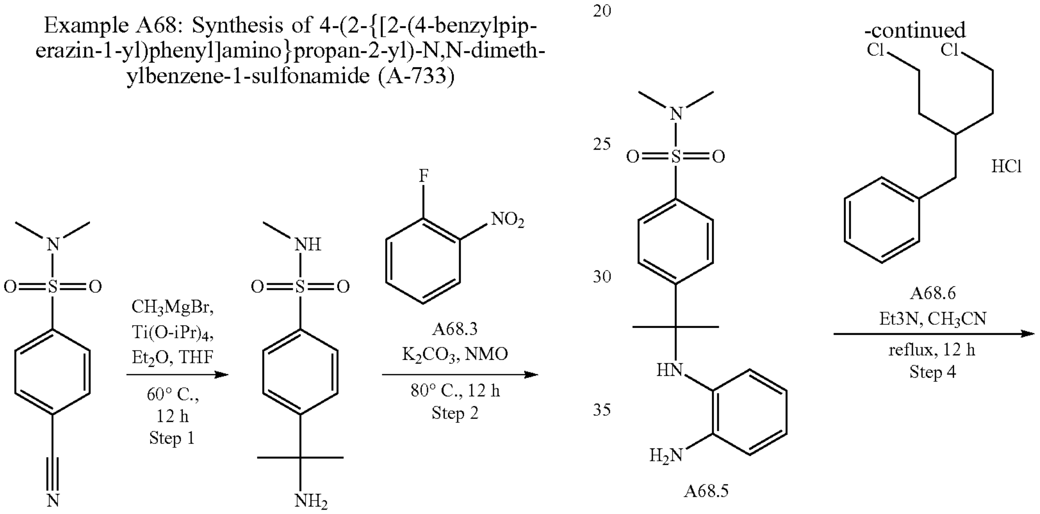
A68.1 A68.2 A68.5
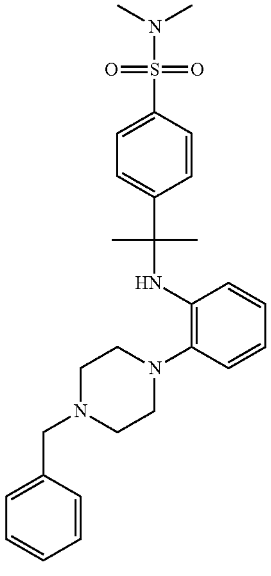
A-733
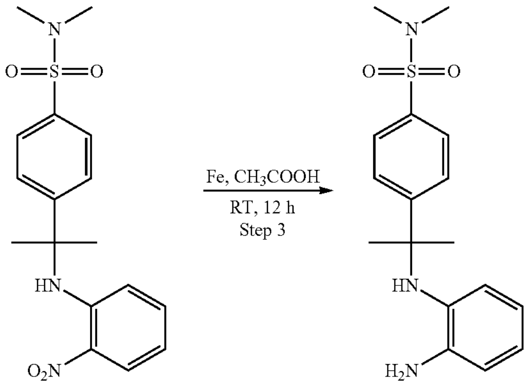
A68.4 A68.5

Step-1. Synthesis of 4-(2-aminopropan-2-yl)-N,N-dimethylbenzenesulfonamide (A68.2)

3 M methylmagnesium bromide (0.417 g, 3.49 mmol) solution in ether (139 mL) in ether was added dropwise to a solution of the 4-cyano-N,N-dimethylbenzenesulfonamide (A68.1) (25 g, 118 mmol) in THF (500 mL), the reaction mixture was stirred for 30 minutes, and tetrakis(propan-2-yloxy)titanium (36.6 g, 129 mmol) was added. The mixture was heated for 12 h keeping temperature at 60° C., cooled to room temperature and a 10% NaOH aqueous solution (400 mL) was then added slowly at 0° C. The reaction mixture was stirred for 30 minutes at room temperature and diluted with 5% $Na_2CO_3$ aqueous solution (400 mL). The product was extracted with ethyl acetate (100 mL×3). The combined ethyl acetate layers were concentrated under reduced pressure. The residue was subjected to flash chromatography (MTBE/methanol) to give 4-(2-aminopropan-2-yl)-N,N-dimethylbenzenesulfonamide (A68.1) as a white solid (6.42 g, 26.4 mmol, 95% purity, 21.3% yield).

Step-2. Synthesis of give N,N-dimethyl-4-(2-((2-nitrophenyl)amino)propan-2-yl)benzenesulfonamide (A68.4)

1-fluoro-2-nitrobenzene (A68.3) (3.72 g, 26.4 mmol) was added to a stirred solution of 4-(2-aminopropan-2-yl)-N,N-dimethylbenzenesulfonamide (A68.2) (6.42 g, 26.4 mmol) and potassium carbonate in dry NMP (20 mL). The mixture was stirred at 80° C. for 12 h. Then, it was cooled to room temperature, poured in water (100 mL) and extracted with ethyl acetate (100 mL×3). The organic layer was washed with water (100 mL), brine (100 mL), dried over anhydrous sodium sulfate, filtered and concentrated under reduced pressure. The residue was subjected to flash chromatography (hexane/MTBE) to give N,N-dimethyl-4-(2-((2-nitrophenyl)amino)propan-2-yl)benzenesulfonamide as an orange oil (A68.4) (0.754 g, 2.07 mmol, 95% purity, 7.46% yield).

Step-3. Synthesis of 4-{2-[(2-aminophenyl)amino]propan-2-yl}-N,N-dimethylbenzene-1-sulfonamide (A68.5)

Iron powder (0.5 g, 8.95 mmol) was added at room temperature to a stirred solution of N,N-dimethyl-4-(2-((2-nitrophenyl)amino)propan-2-yl)benzenesulfonamide (A68.4) (0.754 g, 2.07 mmol) in acetic acid (5 mL) and the resulting reaction mixture was stirred for 12 h at room temperature. After the reaction completion (TLC control) the mixture was filtered through silica gel and the filtrate was evaporated. The residue was partitioned between water (10 mL) and ethyl acetate (10 mL). The organic layer was washed with water (10 mL), dried over anhydrous sodium sulfate, filtered and evaporated under reduced pressure that afforded 4-{2-[(2-aminophenyl)amino]propan-2-yl}-N,N-dimethylbenzene-1-sulfonamide (A68.5) (0.6 g, 1.79 mmol, 90.84% purity, 78.9% yield) that was used in the next step without further purification.

Step-4. Synthesis of 4-(2-{[2-(4-benzylpiperazin-1-yl)phenyl]amino}propan-2-yl)-N,N-dimethylbenzene-1-sulfonamide (A-733)

A mixture of 4-(2-((2-aminophenyl)amino)propan-2-yl)-N,N-dimethylbenzenesulfonamide (A68.5) (0.5 g, 1.49 mmol), N-benzyl-2-chloro-N-(2-chloroethyl)ethanamine hydrochloride (A68.6) (0.48 g, 1.78 mmol) and triethylamine (0.527 g, 5.21 mmol) in acetonitrile (5 mL) was refluxed for 12 h. Then, it was cooled to room temperature and evaporated under reduced pressure. The residue was subjected to HPLC purification (deionized water/HPLC-grade acetonitrile) that afforded 4-(2-{[2-(4-benzylpiperazin-1-yl)phenyl]amino}propan-2-yl)-N,N-dimethylbenzene-1-sulfonamide (A-733). Yield: 96.5 mg, 12.4%; Appearance: Light brown solid; $^{1}H$ NMR (600 MHz, DMSO-$d_6$) δ 7.67 (s, 4H), 7.36-7.27 (m, 4H), 7.24 (tt, J=5.7, 2.6 Hz, 1H), 6.98 (dd, J=7.7, 1.4 Hz, 1H), 6.60 (td, J=7.7, 1.4 Hz, 1H), 6.47 (td, J=7.5, 1.3 Hz, 1H), 5.75 (dd, J=8.1, 1.3 Hz, 1H), 5.31 (s, 1H), 3.53 (s, 2H), 2.83 (s, 4H), 2.56 (s, 6H), 1.60 (s, 6H); HPLC purity: 96.62%; LCMS Calculated for $C_{28}H_{36}N_4O_2S$: 492.68; Observed: 493.2[M+H]+.

Example A69: Synthesis of N4-2-[4-(methoxymethyl)-4-(trifluoromethyl)piperidin-1-yl]phenyl-N1,N1-dimethylbenzene-1,4-disulfonamide (A-777)

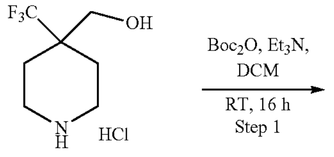

A69.1

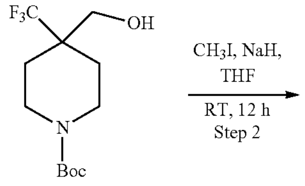

A69.2

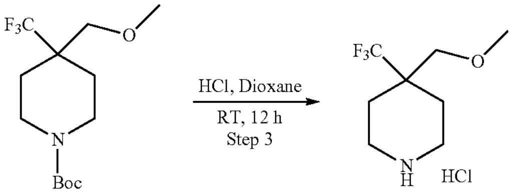

A69.3 A69.4

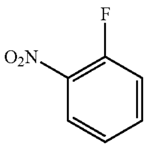

A69.5

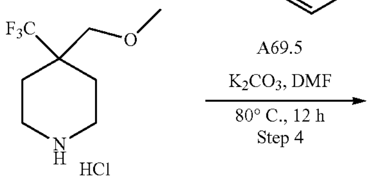

A69.4

-continued

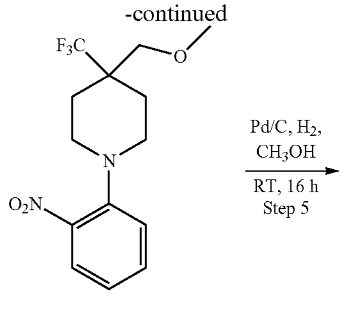

A69.6

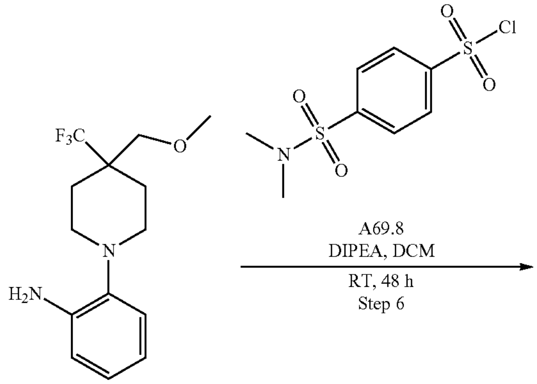

A69.7

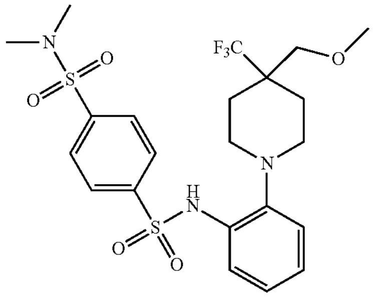

A-777

Step-1. Synthesis of tert-butyl 4-(hydroxymethyl)-4-(trifluoromethyl)piperidine-1-carboxylate (A69.2)

Triethylamine (3.46 g, 34.1 mmol, 4.77 mL) was added to a suspension of [4-(trifluoromethyl)piperidin-4-yl]methanol hydrochloride (A69.1) (3.0 g, 13.6 mmol) in dichloromethane (50 mL). Then di-tert-butyl dicarbonate (3.28 g, 15.00 mmol, 3.46 mL) was added dropwise at 0° C. The reaction mixture was stirred at room temperature for 48 hours, after washed with 1 M HCl aq. solution (30 mL), aq. potassium carbonate solution (30 mL). The organic layer was dried over anhydrous sodium sulfate, filtered and evaporated under reduced pressure to give tert-butyl 4-(hydroxymethyl)-4-(trifluoromethyl)piperidine-1-carboxylate (A69.2) (3.3 g, 11.6 mmol, 95% yield, 81.2% yield).

Step-2. Synthesis of tert-butyl 4-(methoxymethyl)-4-(trifluoromethyl)piperidine-1-carboxylate (A69.3)

tert-butyl 4-(methoxymethyl)-4-(trifluoromethyl)piperidine-1-carboxylate (A69.2) (1.0 g, 3.52 mmol) was added at 0° C. to a suspension of sodium hydride (0.168 g, 4.16 mmol) in THE (30 mL). After stirring for 30 min iodomethane (1.25 g, 8.80 mmol) was added at the same temperature. The reaction mixture was stirred at room temperature overnight, diluted with $NH_4Cl$ sat. aq. solution (25 mL). The product was extracted with ethyl acetate (20 mL×3), combined ethyl acetate layers were dried over sodium sulfate, filtered and evaporated under reduced pressure to give tert-butyl 4-(methoxymethyl)-4-(trifluoromethyl)piperidine-1-carboxylate (A69.3) (1.06 g, 3.51 mmol, 97.8% purity, 99% yield).

Step-3. Synthesis of 4-(methoxymethyl)-4-(trifluoromethyl)piperidine hydrochloride (A69.4)

2 M HCl solution in dioxane (10 mL) was added to tert-butyl 4-(methoxymethyl)-4-(trifluoromethyl)piperidine-1-carboxylate (A69.3) (1.07 g, 3.6 mmol) solution in dioxane (30 mL). The reaction mixture was stirred at room temperature overnight and then evaporated under reduced pressure to dryness. Crude material was crystalized from MTBE to give 4-(methoxymethyl)-4-(trifluoromethyl)piperidine hydrochloride (A69.4) (0.560 g, 2.39 mmol, 99.75% purity, 66.5% yield).

Step-4. Synthesis of 4-(methoxymethyl)-1-(2-nitrophenyl)-4-(trifluoromethyl)piperidine (A69.6)

4-(methoxymethyl)-4-(trifluoromethyl)piperidine hydrochloride (A69.4) (0.56 g, 2.39 mmol), 1-fluoro-2-nitrobenzene (A69.5) (0.337 g, 2.39 mmol) and potassium carbonate (0.825 g, 5.97 mmol) were mixed in DMF (30 mL) and heated at 80° C. overnight. After reaction completion (TLC control), the reaction mixture was cooled, diluted with water (30 mL) and extracted with ethyl acetate (20 mL×3). Combined ethyl acetate layers were washed with water (10 mL×7), dried over sodium sulfate and evaporated to give 4-(methoxymethyl)-1-(2-nitrophenyl)-4-(trifluoromethyl) piperidine (A69.6) (0.67 g, 2.1 mmol, 82.5% purity, 72.6% yield) that was used in next step without further purification.

Step-5. Synthesis of 2-[4-(methoxymethyl)-4-(trifluoromethyl)piperidin-1-yl]aniline (A69.7)

4-(Methoxymethyl)-1-(2-nitrophenyl)-4-(trifluoromethyl)piperidine (A69.6) (0.67 g, 2.1 mmol) was dissolved in methanol (20 mL) and treated with 10% Pd/C (0.07 g). The resulting mixture was hydrogenated at room temperature until the reaction was completed (LCMS control). The catalyst was filtered off and the filtrate was evaporated to afford 2-[4-(methoxymethyl)-4-(trifluoromethyl)piperidin-1-yl]aniline (A69.7) (0.6 g, 2.08 mmol, 100% purity, 99.1% yield).

Step-6. Synthesis of N4-2-[4-(methoxymethyl)-4-(trifluoromethyl)piperidin-1-yl]phenyl-N1,N1-dimethylbenzene-1,4-disulfonamide (A-777)

4-(dimethylsulfamoyl)benzene-1-sulfonyl chloride (A69.8) (0.283 g, 0.998 mmol) was added to a solution of 2-[4-(methoxymethyl)-4-(trifluoromethyl)piperidin-1-yl] aniline (A69.7) (0.262 g, 0.908 mmol) and pyridine (0.107 g, 1.36 mmol) in acetonitrile (10 mL) in one portion at 0° C. The reaction mixture was stirred at room temperature overnight, after evaporated under reduce pressure. The residue was subjected to HPLC purification (deionized water/HPLC-grade methanol) to give N4-2-[4-(methoxymethyl)-4-(trifluoromethyl)piperidin-1-yl]phenyl-N1,N1-dimethylbenzene-1,4-disulfonamide (A-777). Yield: 94.3 mg, 18.4%; Appearance: Violet solid; $^1H$ NMR (500 MHz, DMSO-$d_6$) δ 9.40 (s, 1H), 7.97-7.88 (m, 4H), 7.26 (dd, J=8.0, 1.6 Hz, 1H), 7.23-7.18 (m, 1H), 7.15-7.10 (m, 1H), 7.06 (t, J=7.6 Hz, 1H), 3.54 (s, 2H), 3.27 (s, 3H), 2.64 (d, J=12.6 Hz, 2H), 2.60 (s, 6H), 2.40 (d, J=12.1 Hz, 2H), 1.80 (td, J=12.6, 4.3 Hz, 2H), 1.55 (d, J=13.2 Hz, 2H); HPLC purity: 100%; LCMS Calculated for $C_{22}H_{28}F_3N_3O_5S_2$: 535.6; Observed: 536.2 $[M+H]^+$.

Example A70: Synthesis of N4-(2-{4-fluoro-4-[(trifluoromethoxy)methyl]piperidin-1-yl}phenyl)-N1,N1-dimethylbenzene-1,4-disulfonamide (A-798)

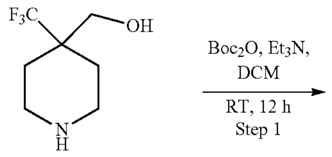

A70.1

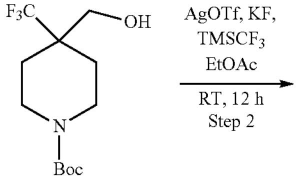

A70.2

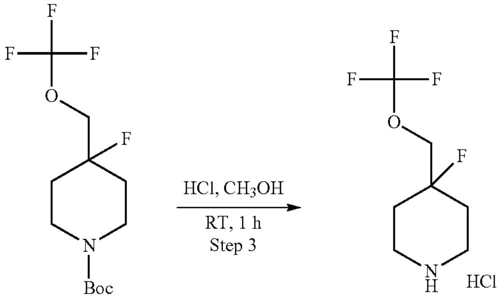

A70.3

A70.4

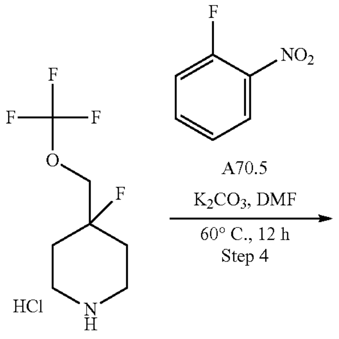

A70.4

-continued

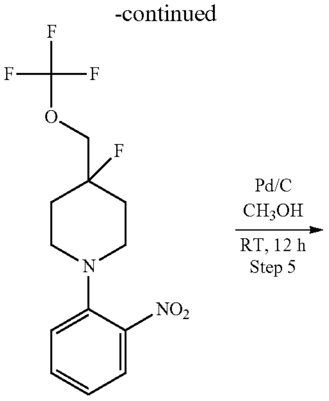

A70.6

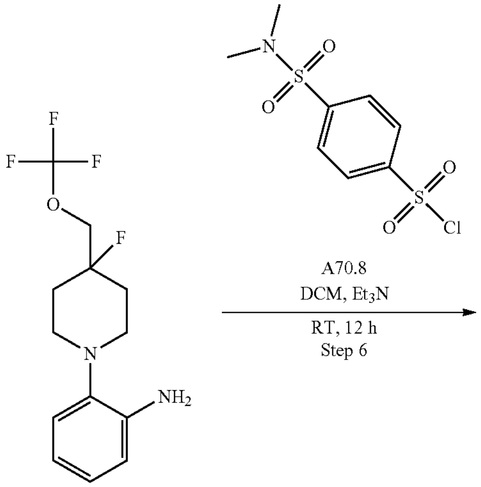

A70.7

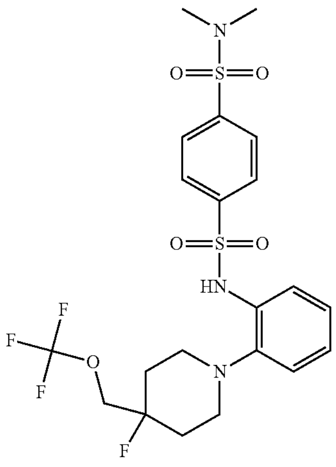

A-798

Step-1. Synthesis of tert-butyl 4-fluoro-4-(hydroxymethyl)piperidine-1-carboxylate (A70.2)

Di-tert-butyl dicarbonate (4.23 g, 19.4 mmol) was added to a stirred solution of (4-fluoropiperidin-4-yl)methanol hydrochloride (A70.1) (3.15 g, 18.5 mmol) and triethylamine (3.74 g, 37.0 mmol) in methanol (50 mL). The mixture was stirred at room temperature until the reaction completion (TLC control, overnight) and concentrated under the reduced pressure. The residue was dissolved in ethyl acetate (50 mL), this solution was washed with water (50 mL), dried over anhydrous sodium sulfate, filtered and concentrated under reduced pressure to afford tert-butyl 4-fluoro-4-(hydroxymethyl)piperidine-1-carboxylate (A70.2) (4 g, 17.1 mmol, 95% purity, 88.1% yield).

Step-2. Synthesis of tert-butyl 4-fluoro-4-[(trifluoromethoxy)methyl]piperidine-1-carboxylate (A70.3)

Tert-butyl 4-fluoro-4-(hydroxymethyl)piperidine-1-carboxylate (A70.2) (0.4 g, 1.71 mmol), AgOTf (0.878 g, 3.42 mmol), selectfluor (0.906 g, 2.56 mmol) and KF (0.298 g, 5.13 mmol) were dissolved in ethyl acetate (10 mL) under nitrogen atmosphere, then 2-fluoropyridine (0.332 g, 3.42 mmol) was added, followed by trimethyl(trifluoromethyl) silane (0.486 g, 3.42 mmol) addition in a dropwise manner for 30 min. After, the mixture was stirred at room temperature for 30 h. Then $NaHCO_3$ sat. aq. solution (40 mL) was added dropwise to reaction mixture and it was extracted with ethyl acetate (30 mL×2). The combined organic layers were washed with brine (30 mL), dried over anhydrous sodium sulfate, filtered and concentrated in vacuo to give tert-butyl 4-fluoro-4-[(trifluoromethoxy)methyl]piperidine-1-carboxylate (A70.3) (0.4 g, 1.32 mmol, 85% purity, 66.0% yield) that was used in next step without further purification.

Step-3. Synthesis of 4-fluoro-4-[(trifluoromethoxy)methyl]piperidine Hydrochloride (A70.4)

Tert-butyl 4-fluoro-4-[(trifluoromethoxy)methyl]piperidine-1-carboxylate (A70.3) (0.4 g, 1.32 mmol) was dissolved in 1 M HCl solution in methanol (10 mL). The reaction mixture was stirred for 1 h at room temperature and evaporated under reduced pressure. The product was treated with MTBE (10 mL), formed precipitate was filtered off, dried on air to give 4-fluoro-4-[(trifluoromethoxy)methyl]piperidine hydrochloride (A70.4) (0.317 g, 1.33 mmol, 90% purity, 99.7% yield).

Step-4. Synthesis of 4-fluoro-1-(2-nitrophenyl)-4-[(trifluoromethoxy)methyl]piperidine (A70.6)

1-fluoro-2-nitrobenzene (0.206 g, 1.46 mmol) was added to a stirred solution of 4-fluoro-4-[(trifluoromethoxy)methyl]piperidine hydrochloride (0.317 g, 1.33 mmol) and potassium carbonate (0.458 g, 3.32 mmol) in dry DMF (20 mL). The mixture was stirred at 60° C. until the reaction completion (TLC control) and concentrated under the reduced pressure. The residue was dissolved in chloroform (15 mL), the organic layer was washed with water (15 mL), dried over anhydrous sodium sulfate, filtered and concentrated under reduced pressure to afford 4-fluoro-1-(2-nitrophenyl)-4-[(trifluoromethoxy)methyl]piperidine (0.15 g, 0.465 mmol, 100% purity, 35% yield).

Step-5. Synthesis of 2-{4-fluoro-4-[(trifluoromethoxy)methyl]piperidin-1-yl}aniline (A70.7)

4-fluoro-1-(2-nitrophenyl)-4-[(trifluoromethoxy)methyl]piperidine (A70.6) (0.15 g, 0.465 mmol) was dissolved in methanol (10 mL) and treated with 5% Pd/C (0.05 g). The resulting mixture was hydrogenated at ambient pressure and room temperature until the reaction was completed (TLC control). The catalyst was filtered off and the filtrate was evaporated under reduced pressure to afford 2-{4-fluoro-4-[(trifluoromethoxy)methyl]piperidin-1-yl}aniline (A70.7) (0.12 g, 0.410 mmol, 98% purity, 86.6% yield).

Step-6. Synthesis of N4-(2-{4-fluoro-4-[(trifluoromethoxy)methyl]piperidin-1-yl}phenyl)-N1,N1-dimethylbenzene-1,4-disulfonamide (A-798)

4-(dimethylsulfamoyl)benzene-1-sulfonyl chloride (A70.8) (0.122 g, 0.430 mmol) was added to an ice-cooled solution of 2-{4-fluoro-4-[(trifluoromethoxy)methyl]piperidin-1-yl}aniline (A70.7) (0.12 g, 0.410 mmol) and pyridine (0.0972 g, 1.232 mmol) in dichloromethane (10 mL). The reaction mixture was allowed to warm to room temperature and stir until completion (overnight, NMR control). After the reaction mixture was diluted with water (10 mL), the organic layer was separated, dried over magnesium sulfate, filtered and concentrated in vacuo. The residue was subjected to HPLC purification (deionized water/HPLC-grade acetonitrile, ammonia) to give N4-(2-{4-fluoro-4-[(trifluoromethoxy)methyl]piperidin-1-yl}phenyl)-N1,N1-dimethylbenzene-1,4-disulfonamide (A-798). Yield: 58.3 mg, 25%; Appearance: Yellow solid; $^1H$ NMR (600 MHz, DMSO-$d_6$) δ 9.28 (s, 1H), 7.97 (d, J=8.4 Hz, 2H), 7.89 (d, J=8.4 Hz, 2H), 7.30 (dd, J=7.8, 1.6 Hz, 1H), 7.16 (dd, J=7.8, 1.6 Hz, 1H), 7.08 (dtd, J=15.2, 7.6, 1.6 Hz, 2H), 4.20 (d, J=21.4 Hz, 2H), 2.65-2.60 (m, 2H), 2.59 (s, 6H), 2.39 (dd, J=10.8, 5.0 Hz, 2H), 1.86-1.81 (m, 1H), 1.79-1.70 (m, 3H); HPLC purity: 100%; LCMS Calculated for $C_{21}H_{37}F_4N_3O_5S_2$: 539.56; Observed: 540.2[M+H]$^+$.

The following example was prepared using standard chemical manipulations and procedures similar to those used for the preparation of the previous example.

| Compound No. | Structure | Analytical Data |
| --- | --- | --- |
| A-784 | 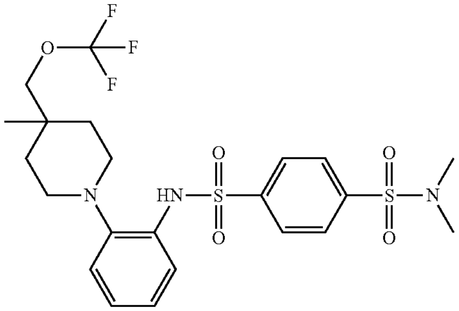 | Yield: 10.4 mg, 10.6%; Appearance: Beige solid; $^1H$ NMR (400 MHz, $CDCl_3$) δ 7.99 (dt, J = 8.5, 2.0 Hz, 2H), 7.84 (dt, J = 8.5, 2.0 Hz, 2H), 7.59 (dd, J = 7.9, 1.7 Hz, 1H), 7.19 - 7.02 (m, 3H), 3.77 (d, J = 1.7 Hz, 2H), 2.72 (q, J = 1.3 Hz, 6H), 2.66 - 2.58 (m, 2H), 2.43 (d, J = 12.0 Hz, 2H), 1.65 (t, J = 11.9 Hz, 2H), 1.49 (d, J = 13.8 Hz, 2H), 1.10 (d, J = 1.6 Hz, 3H). HPLC purity: 100%; LCMS Calculated for $C_{22}H_{28}F_3N_3O_5S_2$: 535.6; Observed: 536.2[M + H]$^+$. |

Example A71: Synthesis of N1,N1-dimethyl-N4-(2-{4-[(1,1,2-trifluoroethoxy)methyl]piperidin-1-yl}phenyl)benzene-1,4-disulfonamide (A797)

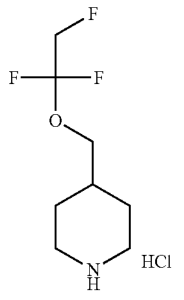

A71.1

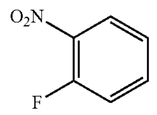

A71.2

$K_2CO_3$, DMF

60° C., 6 h

Step 1

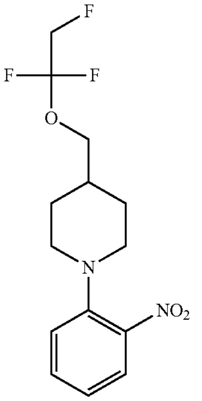

A71.3

Pd/C, $H_2$, $CH_3OH$

RT, 16 h

Step 2

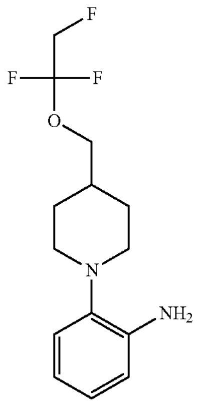

A71.4

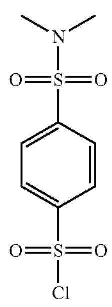

A71.5

Py, THF

RT, 16 h

Step 3

-continued

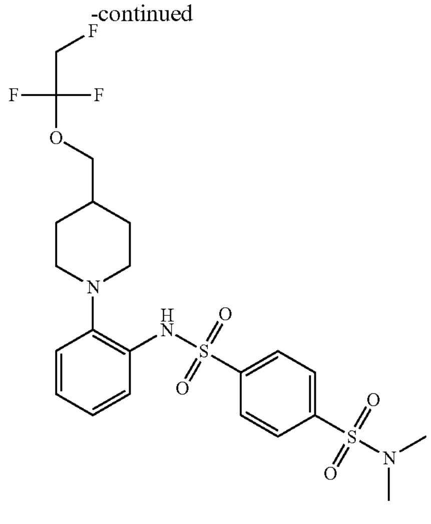

A-797

Step-1. Synthesis of 1-(2-nitrophenyl)-4-[(1,1,2-trifluoroethoxy)methyl]piperidine (A71.3)

1-fluoro-2-nitrobenzene (0.602 g, 4.27 mmol) was added to a stirred solution of 4-[(1,1,2-trifluoroethoxy)methyl]piperidine hydrochloride (1 g, 4.27 mmol) and potassium carbonate (1.46 g, 10.6 mmol) in dry DMF (20 mL). The reaction mixture was stirred at 60° C. until the reaction completion (TLC control) and concentrated under the reduced pressure. The residue was dissolved in chloroform (15 mL), the organic layer was separated, washed with water (15 mL), dried over anhydrous sodium sulfate, filtered and concentrated under reduced pressure to afford crude 1-(2-nitrophenyl)-4-[(1,1,2-trifluoroethoxy)methyl]piperidine (0.8 g, 2.51 mmol, 90% purity, 53.3% yield) that was used in the next step without further purification.

Step-2. Synthesis of 2-{4-[(1,1,2-trifluoroethoxy)methyl]piperidin-1-yl}aniline (A71.4)

10% Pd/C (0.05 g) was added to a stirred solution of 1-(2-nitrophenyl)-4-[(1,1,2-trifluoroethoxy)methyl]piperidine (A71.3) (0.8 g, 2.51 mmol) in methanol (20 mL). The resulting mixture was hydrogenated at ambient pressure and room temperature until the reaction was completed (TLC control). The catalyst was filtered off and the filtrate was evaporated under reduced pressure to afford 2-{4-[(1,1,2-trifluoroethoxy)methyl]piperidin-1-yl}aniline (A71.4) (0.5 g, 1.73 mmol, 90% purity, 62.2% yield) which was used in the next step without further purification.

Step-3. Synthesis of N1,N1-dimethyl-N4-(2-{4-[(1,1,2-trifluoroethoxy)methyl]piperidin-1-yl}phenyl)benzene-1,4-disulfonamide (A-797)

4-(dimethylsulfamoyl)benzene-1-sulfonyl chloride (A71.5) (0.49 g, 1.73 mmol) was added to the mixture of 2-{4-[(1,1,2-trifluoroethoxy)methyl]piperidin-1-yl}aniline (A71.4) (0.5 g, 1.73 mmol) and pyridine (0.204 g, 2.59 mmol) in dry tetrahydrofuran (20 mL). The reaction mixture was stirred overnight and evaporated under reduced pressure. The residue was subjected to HPLC purification (deionized water/HPLC-grade methanol) that afforded N1,N1-dimethyl-N4-(2-{4-[(1,1,2-trifluoroethoxy)methyl]

piperidin-1-yl}phenyl)benzene-1,4-disulfonamide (A-797). Yield: 152.3 mg, 15.5%; Appearance: Light brown solid; $^1$H NMR (600 MHz, DMSO-$d_6$) δ 7.99-7.93 (m, 2H), 7.91-7.83 (m, 2H), 7.27-7.23 (m, 1H), 7.10 (qd, J=8.0, 1.9 Hz, 2H), 7.04 (ddd, J=8.5, 6.6, 2.3 Hz, 1H), 4.74 (t, J=8.9 Hz, 1H), 4.66 (t, J=8.9 Hz, 1H), 3.78 (d, J=6.5 Hz, 2H), 2.59 (s, 6H), 2.52 (d, J=11.2 Hz, 2H), 2.45-2.40 (m, 2H), 1.59 (dd, J=27.1, 13.0 Hz, 3H), 1.30 (tt, J=12.1, 6.0 Hz, 2H); HPLC purity: 100%; LCMS Calculated for $C_{22}H_{28}F_3N_3O_5S_2$: 535.6; Observed: 536.0[M+H]$^+$.

Example A72: Synthesis of 3-fluoro-4-methanesulfonyl-N-{2-[4-(methoxymethyl)-4-methylpiperidin-1-yl]phenyl}benzene-1-sulfonamide (A-731)

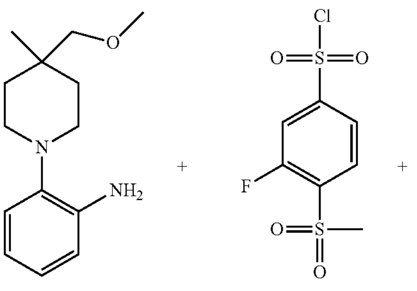

A72.1 + A72.2 +

-continued

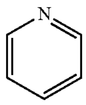

A72.3

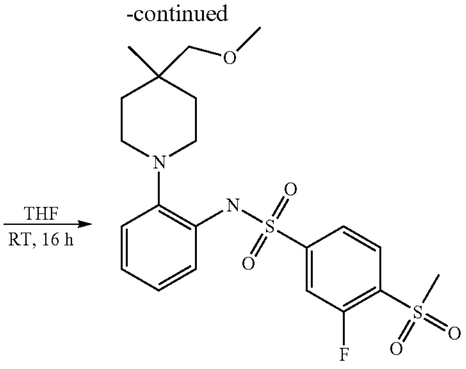

A-731

3-fluoro-4-methanesulfonylbenzene-1-sulfonyl chloride (A72.2) (0.5 g, 1.83 mmol) was added to the mixture of 2-[4-(methoxymethyl)-4-methylpiperidin-1-yl]aniline (A72.1) (0.428 g, 1.83 mmol) and pyridine (A72.3) (0.216 g, 2.74 mmol) in dry THF (20 ml). The reaction mixture was stirred overnight and evaporated under reduced pressure. The residue was subjected to HPLC purification (deionized water/HPLC-grade acetonitrile) that afforded the 3-fluoro-4-methanesulfonyl-N-{2-[4-(methoxymethyl)-4-methylpiperidin-1-yl]phenyl}benzene-1-sulfonamide (A-731). Yield: 98.6 mg, 10.8%; Appearance: White solid; $^1$H NMR (600 MHz, DMSO-$d_6$) δ 9.35 (s, 1H), 8.03 (dd, J=8.1, 6.8 Hz, 1H), 7.90 (dd, J=9.4, 1.6 Hz, 1H), 7.81 (dd, J=8.2, 1.6 Hz, 1H), 7.17 (ddd, J=7.9, 6.3, 1.5 Hz, 2H), 7.11 (td, J=7.6, 1.5 Hz, 1H), 7.01 (td, J=7.6, 1.4 Hz, 1H), 3.34 (s, 3H), 3.25 (s, 3H), 3.08 (s, 2H), 2.54 (dtd, J=15.6, 11.0, 10.2, 6.2 Hz, 4H), 1.47 (ddd, J=13.2, 9.0, 4.2 Hz, 2H), 1.23 (dt, J=13.1, 4.3 Hz, 2H), 0.90 (s, 3H); HPLC purity: 100%; LCMS Calculated for $C_{21}H_{27}FN_2O_5S_2$: 470.58; Observed: 471.2[M+H]$^+$.

The following examples were prepared using standard chemical manipulations and procedures similar to those used for the preparation of the previous example.

| Compound No. | Structure | Analytical Data |
|---|---|---|
| A-742 | 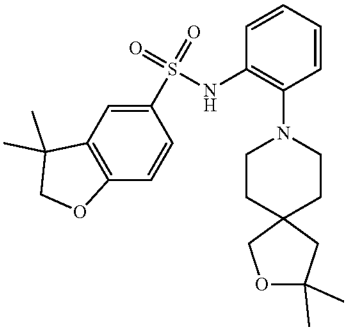 | Yield: 101.6 mg, 12.5%; Appearance: Blue solid; $^1$H NMR (600 MHz, DMSO-$d_6$) δ 8.41 (s, 1H), 7.54 - 7.48 (m, 2H), 7.38 (dd, J = 7.9, 1.6 Hz, 1H), 7.14 (dd, J = 7.7, 1.6 Hz, 1H), 7.07 - 6.98 (m, 2H), 6.84 (d, J = 8.4 Hz, 1H), 4.26 (s, 2H), 3.54 (s, 2H), 2.38 (t, J = 5.5 Hz, 4H), 1.63 - 1.50 (m, 6H), 1.18 (d, J = 17.6 Hz, 12H); HPLC purity: 100%; LCMS Calculated for $C_{26}H_{34}N_2O_4S$: 470.62; Observed: 471.2[M + H]$^+$. |

-continued

| Compound No. | Structure | Analytical Data |
|---|---|---|
| A-732 | 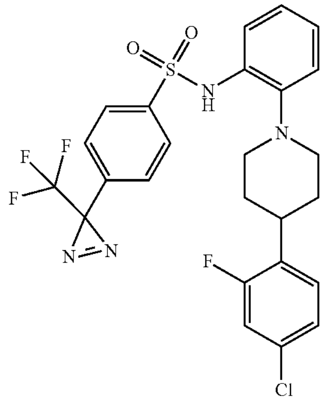 [SMILES: O=S(=O)(Nc1ccccc1N1CCC(c2ccc(Cl)cc2F)CC1)c1ccc(C2(C(F)(F)F)N=N2)cc1] | Yield: 221.6 mg, 46.3%; Appearance: Beige solid; $^1$H NMR (400 MHz, DMSO-$d_6$) δ 9.14 (s, 1H), 7.92 - 7.82 (m, 2H), 7.48 (d, J = 8.3 Hz, 2H), 7.45 - 7.36 (m, 2H), 7.36 - 7.30 (m, 2H), 7.20 - 7.06 (m, 3H), 2.81 (td, J = 11.8, 10.2, 5.8 Hz, 1H), 2.64 - 2.56 (m, 2H), 2.53 (s, 2H), 1.80 - 1.69 (m, 2H), 1.63 - 1.53 (m, 2H); HPLC purity: 100%; LCMS Calculated for $C_{25}H_{21}ClF_4N_4O_2S$: 552.97; Observed: 553.2 $[M + H]^+$. |
| A-759 | 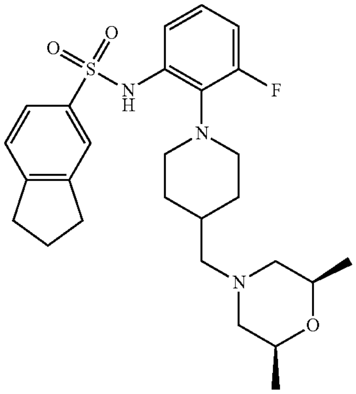 [SMILES: C[C@@H]1CN(CC2CCN(c3c(F)cccc3NS(=O)(=O)c3ccc4c(c3)CCC4)CC2)C[C@H](C)O1] | Yield: 235.7 mg, 45.9%; Appearance: Beige solid; $^1$H NMR (400 MHz, DMSO-$d_6$) δ 8.67 (s, 1H), 7.66 (s, 1H), 7.44 (d, J = 7.9 Hz, 1H), 7.34 (d, J = 8.0 Hz, 1H), 7.27 (d, J = 8.2 Hz, 1H), 7.16 (q, J = 7.6 Hz, 1H), 6.94 - 6.85 (m, 1H), 3.53 (t, J = 8.0 Hz, 2H), 2.90 - 2.67 (m, 8H), 2.32 (d, J = 10.8 Hz, 2H), 2.14 (d, J = 6.9 Hz, 2H), 2.01 (q, J = 7.5 Hz, 2H), 1.66 - 1.45 (m, 5H), 1.24 (d, J = 12.1 Hz, 2H), 1.04 (d, J = 6.2 Hz, 6H); HPLC purity: 100%; LCMS Calculated for $C_{27}H_{36}FN_3O_3S$: 501.66; Observed: 502.2$[M + H]^+$. |
| A-758 | 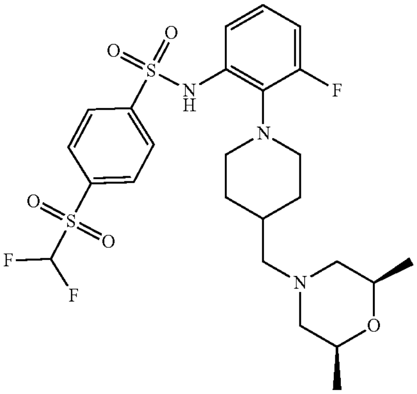 [SMILES: C[C@@H]1CN(CC2CCN(c3c(F)cccc3NS(=O)(=O)c3ccc(S(=O)(=O)C(F)F)cc3)CC2)C[C@H](C)O1] | Yield: 313 mg, 57.3%; Appearance: Beige solid; $^1$H NMR (400 MHz, DMSO-$d_6$) δ 9.39 (s, 1H), 8.21 - 8.15 (m, 2H), 8.14 - 8.06 (m, 2H), 7.53 - 7.35 (m, 1H), 7.27 - 7.17 (m, 2H), 7.04 - 6.93 (m, 1H), 3.59 - 3.49 (m, 2H), 2.81 - 2.67 (m, 4H), 2.29 (s, 2H), 2.09 (d, J = 6.5 Hz, 2H), 1.62 - 1.44 (m, 5H), 1.14 (d, J = 12.1 Hz, 2H), 1.04 (dd, J = 6.3, 4.1 Hz, 6H); HPLC purity: 100%; LCMS Calculated for $C_{25}H_{32}F_3N_3O_5S_2$: 575,.6; Observed: 576.2$[M + H]^+$. |
| A-771 | 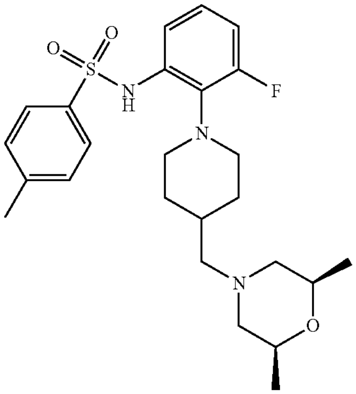 [SMILES: Cc1ccc(S(=O)(=O)Nc2cccc(F)c2N2CCC(CN3C[C@@H](C)O[C@@H](C)C3)CC2)cc1] | Yield: 131.9 mg, 28.2%; Appearance: Beige solid; $^1$H NMR (600 MHz, DMSO-$d_6$) δ 8.67 (s, 1H), 7.64 - 7.59 (m, 2H), 7.35 - 7.29 (m, 2H), 7.22 (d, J = 8.3 Hz, 1H), 7.13 (td, J = 8.3, 5.8 Hz, 1H), 6.86 (ddd, J = 12.1, 8.4, 1.3 Hz, 1H), 3.51 (dqd, J = 12.4, 6.1, 1.8 Hz, 2H), 2.79 (t, J = 11.4 Hz, 2H), 2.68 (d, J = 10.8 Hz, 2H), 2.34 (d, J = 11.1 Hz, 2H), 2.30 (s, 3H), 2.11 (d, J = 7.2 Hz, 2H), 1.61 (d, J = 12.5 Hz, 2H), 1.52 (t, J = 10.6 Hz, 3H), 1.22 (q, J = 10.6 Hz, 2H), 1.01 (d, J = 6.3 Hz, 6H); HPLC purity: 100%; LCMS Calculated for $C_{25}H_{34}FN_3O_3S$: 475.62; Observed: 476.2$[M + H]^+$. |

-continued

| Compound No. | Structure | Analytical Data |
|---|---|---|
| A-767 | 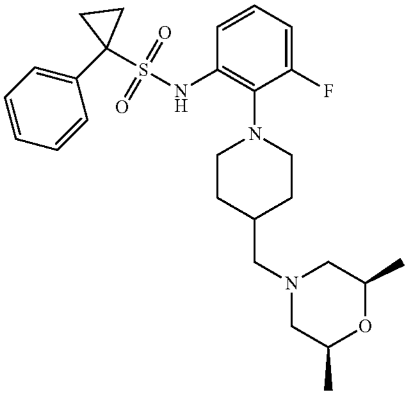 [SMILES: C[C@@H]1CN(CC2CCN(c3c(F)cccc3NS(=O)(=O)C3(c4ccccc4)CC3)CC2)C[C@H](C)O1] | Yield: 45.4 mg, 9.26%; Appearance: Light brown solid; $^1$H NMR (600 MHz, DMSO-$d_6$) δ 8.00 (s, 1H), 7.40 – 7.26 (m, 5H), 7.10 – 7.05 (m, 1H), 7.03 (d, J = 8.1 Hz, 1H), 6.83 (dd, J = 11.8, 8.3 Hz, 1H), 3.52 – 3.47 (m, 2H), 2.86 (t, J = 11.5 Hz, 2H), 2.65 (d, J = 10.9 Hz, 2H), 2.61 (d, J = 11.2 Hz, 2H), 2.02 (d, J = 7.1 Hz, 2H), 1.72 (q, J = 5.0 Hz, 2H), 1.61 (d, J = 13.0 Hz, 2H), 1.55 (s, 1H), 1.50 (t, J = 10.6 Hz, 2H), 1.33 (q, J = 5.0 Hz, 2H), 1.00 (d, J = 6.3 Hz, 6H), 0.85 (d, J = 11.8 Hz, 2H); HPLC purity: 100%; LCMS Calculated for $C_{27}H_3FN_3O_3S$: 501.66; Observed: 502.2[M + H]$^+$. |
| A-766 | 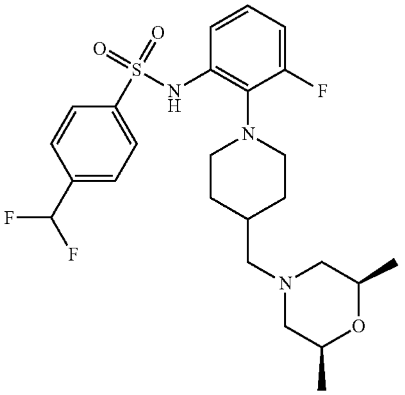 [SMILES: C[C@@H]1CN(CC2CCN(c3c(F)cccc3NS(=O)(=O)c3ccc(C(F)F)cc3)CC2)C[C@H](C)O1] | Yield: 302.5 mg, 57.8%; Appearance: White solid; $^1$H NMR (500 MHz, DMSO-$d_6$) δ 8.98 (s, 1H), 7.88 (d, J = 8.1 Hz, 2H), 7.74 (d, J = 8.1 Hz, 2H), 7.25 – 7.07 (m, 3H), 6.92 (ddd, J = 12.0, 8.3, 1.5 Hz, 1H), 3.51 (dtd, J = 12.2, 6.2, 2.1 Hz, 2H), 2.78 (t, J = 11.4 Hz, 2H), 2.69 (d, J = 10.9 Hz, 2H), 2.31 (d, J = 11.0 Hz, 2H), 2.10 (d, J = 6.8 Hz, 2H), 1.54 (q, J = 11.9, 10.4 Hz, 5H), 1.22 (t, J = 11.7 Hz, 2H), 1.02 (d, J = 6.2 Hz, 6H); HPLC purity: 100%; LCMS Calculated for $C_{25}H_{32}F_3N_3O_3S$: 511.6; Observed: 512.2[M + H]$^+$. |

Example A73: Synthesis of N-(2-{3,3-dimethyl-2-oxa-8-azaspiro[4.5]decan-8-yl}phenyl)-2-phenylethane-1-sulfonamide (A-743)

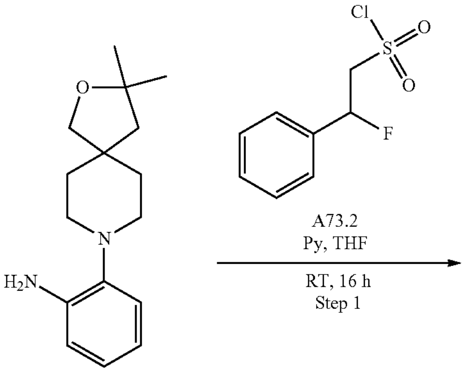

A73.1

-continued

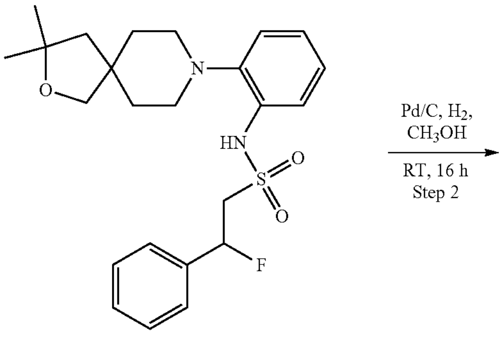

A73.3

-continued

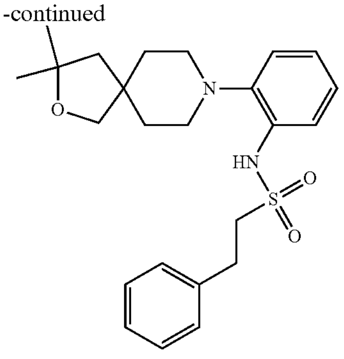

A743

Step-1. Synthesis of (1Z)—N-(2-{3,3-dimethyl-2-oxa-8-azaspiro[4.5]decan-8-yl}phenyl)-2-fluoro-2-phenylethene-1-sulfonamide (A73.3)

2-fluoro-2-phenylethene-1-sulfonyl chloride (A73.2) (0.5 g, 2.26 mmol) was added to the mixture of 2-{3,3-dimethyl-2-oxa-8-azaspiro[4.5]decan-8-yl}aniline (A73.1) (0.588 g, 2.26 mmol) and pyridine (0.267 g, 3.38 mmol) in dry tetrahydrofuran (20 mL). The reaction mixture was stirred overnight and evaporated under reduced pressure. The residue was subjected to HPLC purification (chloroform/ethylacetate) that afforded N-(2-{3,3-dimethyl-2-oxa-8-azaspiro[4.5]decan-8-yl}phenyl)-2-fluoro-2-phenylethene-1-sulfonamide (A73.3) (0.3 g, 0.674 mmol, 95% purity, 28.5% yield).

Step-2. Synthesis of N-(2-{3,3-dimethyl-2-oxa-8-azaspiro[4.5]decan-8-yl}phenyl)-2-phenylethane-1-sulfonamide (A-743)

10% Pd/C (0.007 g) was added at to a stirred solution of (1Z)—N-(2-{3,3-dimethyl-2-oxa-8-azaspiro[4.5]decan-8-yl}phenyl)-2-fluoro-2-phenylethene-1-sulfonamide (A73.3) (0.3 g, 0.674 mmol) in methanol (5 mL) and the reaction mixture was hydrogenated at 30 atm and room temperature. The reaction mixture was stirred overnight, filtered and the filtrate was evaporated under reduced pressure. The residue was subjected to HPLC purification (deionized water/HPLC-grade methanol) that afforded N-(2-{3,3-dimethyl-2-oxa-8-azaspiro[4.5]decan-8-yl}phenyl)-2-phenylethane-1-sulfonamide (A-743). Yield: 13.3 mg, 4.37%; Appearance: Light brown solid; $^{1}H$ NMR (400 MHz, $CDCl_3$) δ 7.89 (s, 1H), 7.55 (dd, J=8.1, 1.5 Hz, 1H), 7.34-7.12 (m, 6H), 7.10 (dt, J=7.6, 1.7 Hz, 3H), 3.75 (s, 2H), 3.44-3.36 (m, 2H), 3.18-3.07 (m, 2H), 2.78 (d, J=6.1 Hz, 4H), 1.87-1.75 (m, 4H), 1.31 (s, 6H); HPLC purity: 100%; LCMS Calculated for $C_{24}H_{32}N_2O_3S$: 428.6; Observed: 429.2[M+H]$^+$.

Example A74: Synthesis of N4-{2-[4-(1-methoxyethyl)-4-methylpiperidin-1-yl]phenyl}-N1,N1-dimethylbenzene-1,4-disulfonamide (A-741)

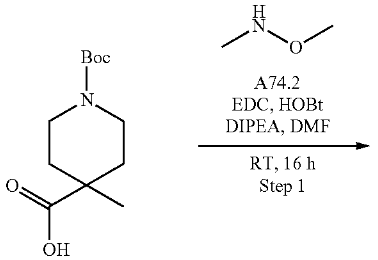

A74.1

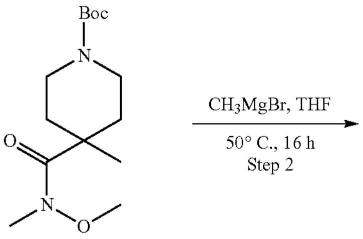

A74.3

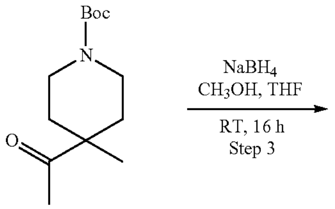

A74.4

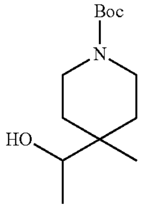

A74.5

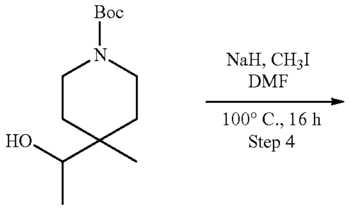

A74.5

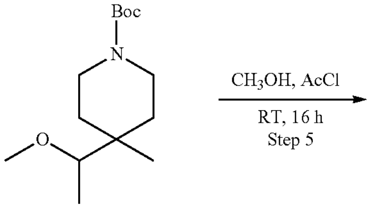

A74.6

-continued

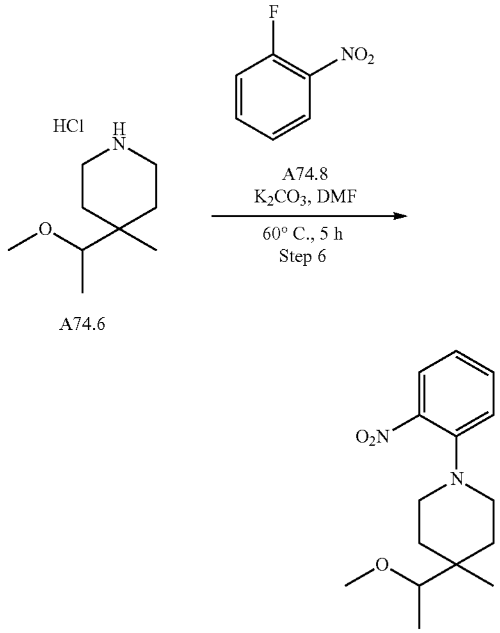

A74.6

A74.9

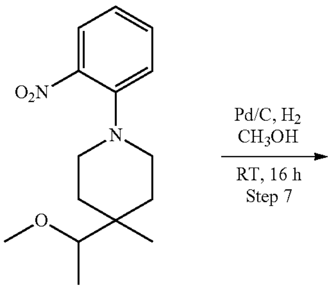

A74.9

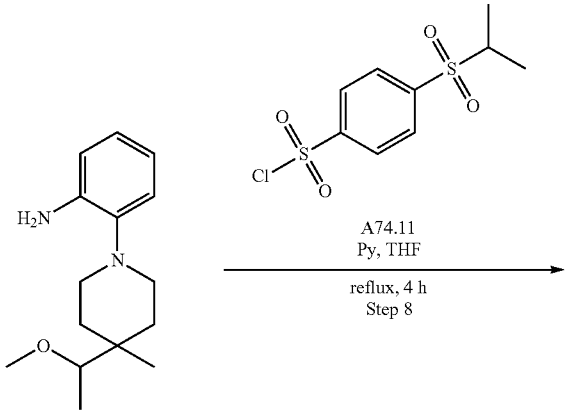

A74.10

-continued

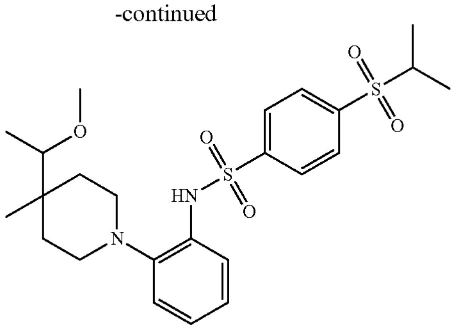

A-741

Step-1. Synthesis of tert-butyl 4-[methoxy(methyl)carbamoyl]-4-methylpiperidine-1-carboxylate (A74.3)

A solution of 1-[(tert-butoxy)carbonyl]-4-methylpiperidine-4-carboxylic acid (A74.1) (10 g, 41.1 mmol), methoxy(methyl)amine hydrochloride (A74.2) (4 g, 41.1 mmol), (3-{[(ethylimino)methylidene]amino}-propyl)dimethylamine hydrochloride (7.9 g, 41.2 mmol), 1H-1,2,3-benzotriazol-1-ol (5.55 g, 41.1 mmol) and ethylbis(propan-2-yl)amine (5.35 g, 41.3 mmol) in dry DMF (100 mL) was stirred at room temperature for 16 h and concentrated under the reduced pressure. The residue was dissolved in ethyl acetate (100 mL), washed with water (100 mL), brine (100 mL), dried over sodium sulfate, filtered and concentrated under reduced pressure to afford tert-butyl 4-[methoxy(methyl)carbamoyl]-4-methylpiperidine-1-carboxylate (A74.3) (10.8 g, 37.7 mmol, 74.65% purity, 68.8% yield) that was used in next step without further purification.

Step-2. Synthesis of tert-butyl 4-acetyl-4-methylpiperidine-1-carboxylate (A74.4)

3.2 M bromo(methyl)magnesium (4.86 g, 40.8 mmol) solution in 2-methyltetrahydrofuran (12.7 mL) was added to a stirred solution of tert-butyl 4-[methoxy(methyl)carbamoyl]-4-methylpiperidine-1-carboxylate (A74.3) (3.9 g, 13.6 mmol) in dry tetrahydrofuran (100 mL). The mixture was stirred at 50° C. for 16 h and quenched with $NH_4Cl$ sat. aq. solution (100 mL). The product was extracted with ethyl acetate (100 mL×2), combined organic layers were washed with water (100 mL), brine (100 mL), dried over sodium sulfate, filtered and concentrated under reduced pressure to obtain tert-butyl 4-acetyl-4-methylpiperidine-1-carboxylate (A74.4) (2.2 g, 9.11 mmol, 77% purity, 51.5% yield) that was used in next step without further purification.

Step-3. Synthesis of tert-butyl 4-(1-hydroxyethyl)-4-methylpiperidine-1-carboxylate (A74.5)

$NaBH_4$ (0.25 g, 6.6 mmol) was added to a stirred solution of tert-butyl 4-acetyl-4-methylpiperidine-1-carboxylate (A74.4) (1 g, 4.14 mmol) in mixture of tetrahydrofuran/methanol=1/1 (20 mL). The mixture was stirred at room temperature for 16 h and concentrated under reduced pressure. The residue was dissolved in ethyl acetate (30 mL), this solution was washed with water (30 mL), brine (30 mL), dried over sodium sulfate, filtered and concentrated under reduced pressure to obtain tert-butyl 4-(1-hydroxyethyl)-4- methylpiperidine-1-carboxylate (A74.5) (1 g, 4.1 mmol, 86.5% purity, 86.5% yield) that was used in the next step without further purification.

Step-4. Synthesis of tert-butyl 4-(1-methoxyethyl)-4-methylpiperidine-1-carboxylate (A74.6)

Sodium hydride (0.17 g, 60 w % in mineral oil, 4.25 mmol) was added to a solution of tert-butyl 4-(1-hydroxyethyl)-4-methylpiperidine-1-carboxylate (A74.5) (1 g, 4.1 mmol) in dry DMF (10 mL) and mixture was stirred for 0.5 h at 50° C. Then iodomethane (2.89 g, 20.4 mmol) was added dropwise and the mixture was stirred at 100° C. overnight. After, it was cooled to room temperature, diluted with water (100 mL) and extracted with ethyl acetate (100 mL). The organic layer was washed with water (100 mL), brine (100 mL), dried over sodium sulfate, filtered and evaporated under reduced pressure to give tert-butyl 4-(1-methoxyethyl)-4-methylpiperidine-1-carboxylate (A74.6) (1 g, 3.88 mmol, 50% purity, 47.6% yield) that was used in next step without further purification.

Step-5. Synthesis of 4-(1-methoxyethyl)-4-methylpiperidine Hydrochloride (A74.7)

Tert-butyl 4-(1-methoxyethyl)-4-methylpiperidine-1-carboxylate (A74.6) (1 g, 3.88 mmol) was added to HCl sat. solution in dioxane (30 mL) and the mixture was stirred at room temperature overnight. Then the solvent was evaporated under reduced pressure and the residue treated with ether (20 mL). Formed precipitate was filtered off, dried on air to give 4-(1-methoxyethyl)-4-methylpiperidine hydrochloride (A74.7) (0.75 g, 3.87 mmol, 38.6% purity, 38.4% yield) that was used in next step without further purification.

Step-6. Synthesis of 4-(1-methoxyethyl)-4-methyl-1-(2-nitrophenyl)piperidine (A74.9)

1-fluoro-2-nitrobenzene (A74.8) (0.55 g, 3.89 mmol) was added to a stirred solution of crude 4-(1-methoxyethyl)-4-methylpiperidine hydrochloride (A74.7) (0.55 g, 3.89 mmol) and potassium carbonate (1.33 g, 9.67 mmol) in dry DMF (20 mL). The mixture was stirred at 60° C. for 5 h and concentrated under the reduced pressure. The residue was dissolved in ethyl acetate (100 mL), washed with water (100 mL), brine (100 mL), dried over sodium sulfate, filtered and concentrated under reduced pressure. The crude material was purified by HPLC (deionized water/HPLC-grade acetonitrile) to give 4-(1-methoxyethyl)-4-methyl-1-(2-nitrophenyl)piperidine (A74.9) (0.286 g, 1.02 mmol, 86% purity, 22.8% yield).

Step-7. Synthesis of 2-[4-(1-methoxyethyl)-4-methylpiperidin-1-yl]aniline (A74.10)

4-(1-methoxyethyl)-4-methyl-1-(2-nitrophenyl)piperidine (A74.9) (0.286 g, 1.02 mmol) was dissolved in methanol (10 mL) and treated with 10% Pd/C (0.01 g). The resulting mixture was hydrogenated at ambient pressure and room temperature until the reaction was completed. The catalyst was filtered off and the filtrate was evaporated under reduced pressure to give 2-[4-(1-methoxyethyl)-4-methylpiperidin-1-yl]aniline (A74.10) (0.25 g, 1 mmol, 88% purity, 86.9% yield) that was used in next step without further purification.

Step-8. Synthesis of N4-{2-[4-(1-methoxyethyl)-4-methylpiperidin-1-yl]phenyl}-N1,N1-dimethylbenzene-1,4-disulfonamide (A-741)

4-(dimethylsulfamoyl)benzene-1-sulfonyl chloride (A74.11) (0.3 g, 1.05 mmol) was added to the mixture of 2-[4-(1-methoxyethyl)-4-methylpiperidin-1-yl]aniline (A74.10) (0.25 g, 1 mmol) and pyridine (0.237 g, 3 mmol) in dry tetrahydrofuran (5 mL). The reaction mixture was refluxed for 4 h, cooled to room temperature and evaporated under reduced pressure. The residue was purified by HPLC (deionized water/HPLC-grade acetonitrile) to give N4-{2-[4-(1-methoxyethyl)-4-methylpiperidin-1-yl]phenyl}-N1,N1-dimethylbenzene-1,4-disulfonamide (A-741). Yield: 135.3 mg, 25.8%; Appearance: Beige solid; $^1H$ NMR (400 MHz, DMSO-$d_6$) δ 9.11 (s, 1H), 8.00 (d, J=8.2 Hz, 2H), 7.92 (d, J=8.2 Hz, 2H), 7.25 (d, J=7.8 Hz, 1H), 7.19 (d, J=7.9 Hz, 1H), 7.12 (t, J=7.5 Hz, 1H), 7.05 (t, J=7.6 Hz, 1H), 3.01-2.93 (m, 1H), 2.62 (s, 9H), 2.41 (d, J=13.0 Hz, 2H), 1.50 (d, J=10.5 Hz, 2H), 1.38 (d, J=13.3 Hz, 1H), 1.13 (d, J=13.2 Hz, 1H), 1.00 (d, J=6.2 Hz, 3H), 0.83 (s, 3H); HPLC purity: 100%; LCMS Calculated for $C_{23}H_{33}N_3O_5S_2$: 495.66; Observed: 496.2[M+H]$^+$.

Example A75: Synthesis of 1-(3-methoxymethanesulfonylphenyl)-N-{2-[4-(methoxymethyl)-4-methylpiperidin-1-yl]phenyl}methanesulfonamide (A-744)

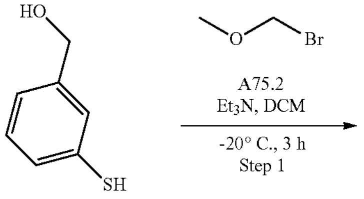

A75.1

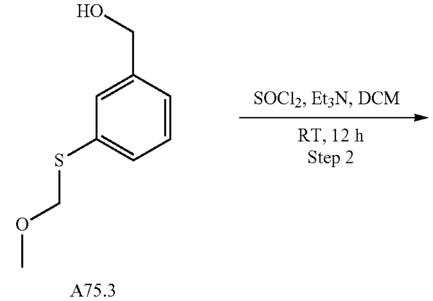

A75.3

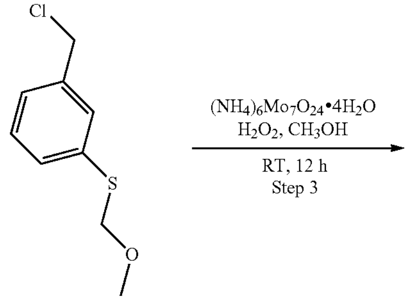

A75.4

-continued

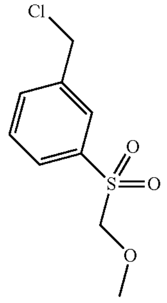

A75.5

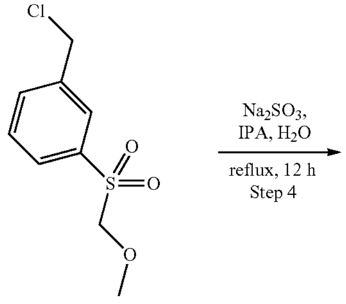

A75.5

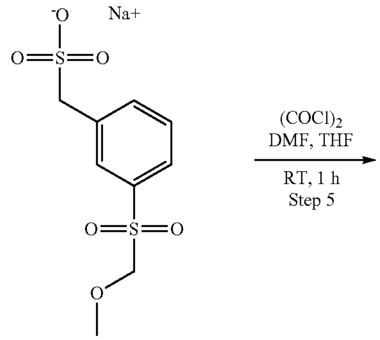

A75.6

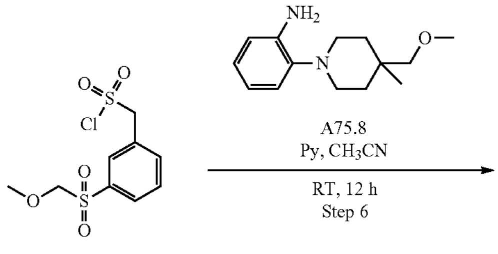

A75.7

-continued

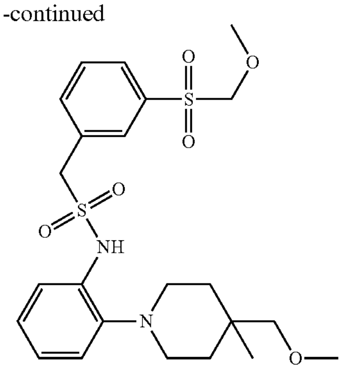

A-744

Step-1. Synthesis of {3-[(methoxymethyl)sulfanyl] phenyl}methanol (A75.3)

Bromo(methoxy)methane (A75.2) (9.79 g, 78.4 mmol) was added to a solution of (3-sulfanylphenyl)methanol (A75.1) (10 g, 71.3 mmol) and triethylamine (10.7 g, 106 mmol) in dichloromethane (150 mL) at −20° C. and the reaction mixture was stirred for 12 hours. After the solution was washed with 1 M hydrochloric acid aq. solution (150 mL), water (150 mL) and brine (150 mL). The organic layer was separated, dried over sodium sulfate, filtered and evaporated under reduced pressure to afford {3-[(methoxymethyl) sulfanyl]phenyl}methanol (A75.3) (3 g, 16.2 mmol, 90% purity, 20.6% yield) that was used in next step without further purification.

Step-2. Synthesis of 1-(chloromethyl)-3-[(methoxymethyl)sulfanyl]benzene (A75.4)

Thionyl chloride (2.11 g, 17.8 mmol) was added dropwise to a solution of (3-((methoxymethyl)thio)phenyl)methanol (A75.3) (3 g, 16.2 mmol) and triethylamine (2.44 g, 24.2 mmol) in dichloromethane (50 mL) at −10° C. The mixture was stirred for 12 hours at room temperature, washed with 1 M hydrochloric acid aq. solution (50 mL), water (50 mL), sodium bicarbonate sat. aq. solution (50 mL), and brine (50 mL). The organic layer was dried over sodium sulfate, filtered and evaporated under reduced pressure to afford 1-(chloromethyl)-3-[(methoxymethyl)sulfanyl]benzene (A75.4) (2 g, 9.86 mmol, 90% purity. 54.8% yield).

Step-3. Synthesis of 1-(chloromethyl)-3-methoxymethanesulfonylbenzene (A75.5)

Hexaammonium tris(dioxomolybdenumbis(olate))tetrakis(trioxomolybdenum) tetrahydrate (0.608 g, 0.492 mmol) and hydrogen peroxide (2.29 g, 23.6 mmol) were added to a solution of 1-(chloromethyl)-3-[(methoxymethyl)sulfanyl] benzene (A75.4) (2 g, 9.86 mmol) in methanol (50 mL) at 0° C. The solution was stirred overnight at room temperature and poured into brine (100 mL), the product was extracted with ethyl acetate (100 mL×3). The organic layer was dried over sodium sulfate, filtered and evaporated under reduced pressure to afford 1-(chloromethyl)-3-methoxymethanesulfonylbenzene (A75.5) (0.9 g, 3.83 mmol, 95% purity, 37% yield).

Step-4. Synthesis of sodium (3-methoxymethanesulfonylphenyl)methanesulfonate (A75.6)

Sodium sulfite (2.88 g, 22.9 mmol) was added to a solution of 1-(chloromethyl)-3-((methoxymethyl)sulfonyl) benzene (A75.5) (0.9 g, 3.83 mmol) in 2-propanol (25 mL) and water (100 mL). The mixture was stirred at 100° C. until the reaction completion (TLC control) and concentrated after under the reduced pressure. The residue was extracted with hot methanol (100 mL), filtered and the filtrate was concentrated under the reduced pressure to give sodium (3-methoxymethanesulfonylphenyl)methanesulfonate (A75.6) (1 g, 3.3 mmol, 60% purity, 52.1% yield) that was used in next step without purification.

Step-5. Synthesis of (3-methoxymethanesulfonylphenyl)methanesulfonyl chloride (A75.7)

Oxalyl chloride (0.209 g, 1.65 mmol) was added dropwise to a suspension of sodium (3-methoxymethanesulfonylphenyl)methanesulfonate (A75.6) (0.25 g, 0.827 mmol) and DMF (1 drop) in tetrahydrofuran (50 mL) at −20° C. Mixture stirring was continued for an hour, the solution was filtered and the filtrate was evaporated under reduced pressure to afford (3-methoxymethanesulfonylphenyl)methanesulfonyl chloride (A75.7) (0.25 g, 0.836 mmol, 85% purity, 85.8% yield) that was used in next step without further purification.

Step-6. Synthesis of 1-(3-methoxymethanesulfonylphenyl)-N-{2-[4-(methoxymethyl)-4-methylpiperidin-1-yl]phenyl}methanesulfonamide (A-744)

(3-methoxymethanesulfonylphenyl)methanesulfonyl chloride (A75.7) (0.25 g, 0.836 mmol) was added to the mixture of 2-[4-(methoxymethyl)-4-methylpiperidin-1-yl] aniline (A75.8) (0.195 g, 0.836 mmol) and pyridine (0.09 g, 1.13 mmol) in dry acetonitrile (20 mL). The reaction mixture was stirred for 12 h and evaporated under reduced pressure. The residue was subjected to HPLC purification (deionized water/HPLC-grade acetonitrile) that afforded the product 1-(3-methoxymethanesulfonylphenyl)-N-{2-[4-(methoxymethyl)-4-methylpiperidin-1-yl] phenyl}methanesulfonamide (A-744). Yield: 26 mg, 5.95%; Appearance: Light brown solid; $^1H$ NMR (400 MHz, DMSO-$d_6$) δ 8.17 (s, 1H), 7.94-7.87 (m, 2H), 7.71-7.63 (m, 2H), 7.29 (dd, J=7.6, 1.7 Hz, 1H), 7.18 (dd, J=7.6, 1.9 Hz, 1H), 7.11-6.99 (m, 2H), 4.84 (s, 2H), 4.75 (s, 2H), 3.46 (d, J=1.2 Hz, 3H), 3.13 (s, 2H), 2.81-2.68 (m, 4H), 1.60 (dt, J=13.5, 6.5 Hz, 2H), 1.34 (d, J=12.8 Hz, 2H), 0.96 (s, 3H); HPLC purity: 100%; LCMS Calculated for $C_{23}H_{32}N_2O_6S_2$: 496.64; Observed: 497.0[M+H]$^+$.

Example A76: Synthesis of 1-(4-methoxymethanesulfonylphenyl)-N-{2-[4-(methoxymethyl)-4-methylpiperidin-1-yl]phenyl}methanesulfonamide (A-747)

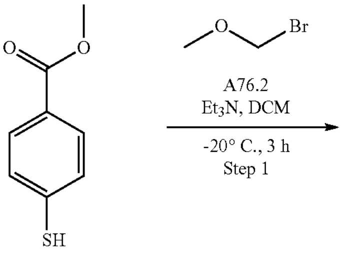

A76.1

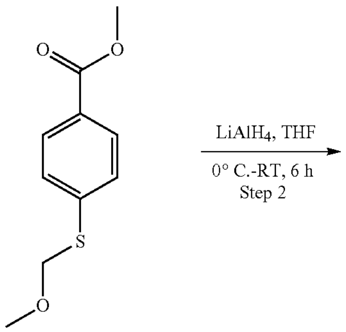

A76.3

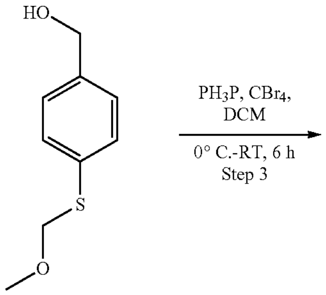

A76.4

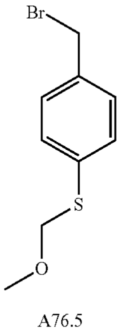

A76.5

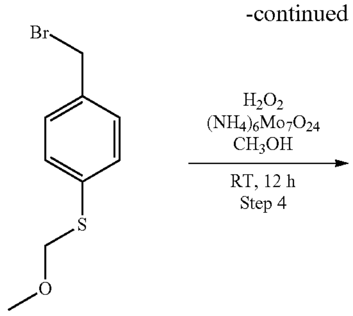

A76.5

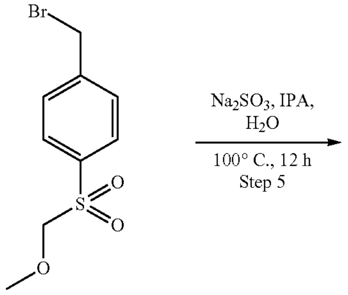

A76.6

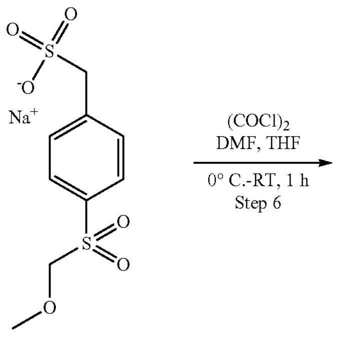

A76.7

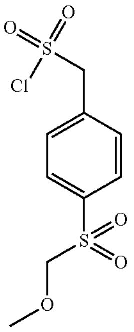

A76.8

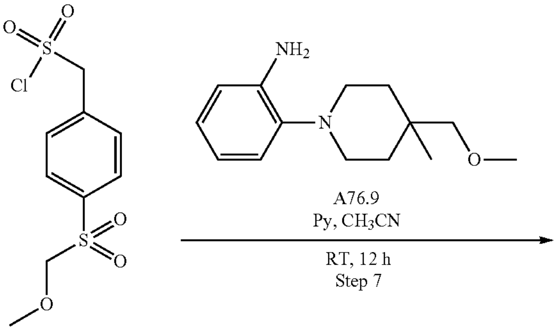

A76.8

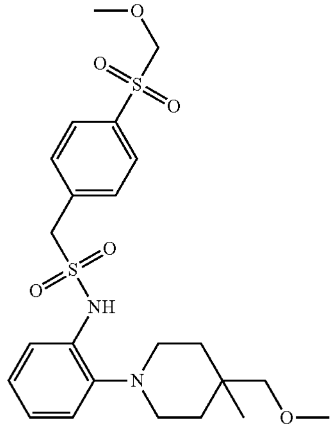

A-747

Step-1. Synthesis of methyl 4-[(methoxymethyl)-sulfanyl]benzoate (A76.3)

Bromo(methoxy)methane (A76.2) (8.16 g, 65.3 mmol) was added to a solution of methyl 4-mercaptobenzoate (A76.1) (10 g, 59.4 mmol) and triethylamine (9.01 g, 89.1 mmol) in dichloromethane (150 mL) at −20° C. and the reaction mixture was stirred for 12 hours. After the solution was washed with 1 M hydrochloric acid aq. solution (150 mL), water (150 mL) and brine (150 mL). The organic layer was separated, dried over sodium sulfate, filtered and evaporated under reduced pressure to afford methyl 4-[(methoxymethyl)-sulfanyl]benzoate (A76.3) (3 g, 14.1 mmol, 85% purity, 20.2% yield) that was used in next step without further purification.

Step-2. Synthesis of {4-[(methoxymethyl)sulfanyl]phenyl}methanol (A76.4)

A solution of methyl 4-((methoxymethyl)thio)benzoate (A76.3) (3 g, 14.1 mmol) in tetrahydrofuran (50 mL) was added dropwise at −5° C. to a suspension of lithium aluminum hydride (0.588 g, 15.5 mmol) in tetrahydrofuran (50 mL). After addition, the solution was warmed to room temperature and stirred for 12 hours. The solution was quenched with a mixture of water/tetrahydrofuran=1/1 (10 mL). The resulting mixture was filtered and filtrate evaporated under reduce pressure to give {4-[(methoxymethyl)sulfanyl]phenyl}methanol (A76.4) (2 g, 10.8 mmol, 85% purity, 65.6% yield) that was used in next step without further purification.

Step-3. Synthesis of 1-(bromomethyl)-4-[(methoxymethyl)sulfanyl]benzene (A76.5)

Triphenyl phosphine (2.83 g, 10.8 mmol) was added to a solution of tetrabromomethane (3.58 g, 10.8 mmol) in dichloromethane (50 mL) at −20° C. and the mixture was stirred for 20 minutes. (4-((methoxymethyl)sulfonyl)phenyl)methanol (A76.4) (2 g, 10.8 mmol) was added to the resulting solution and the reaction mixture was stirred for 12 h, diluted with hexane (150 mL), filtered and filtrate was evaporated under reduced pressure to give 1-(bromomethyl)-4-[(methoxymethyl)sulfanyl]benzene (A76.5) (2 g, 8.09 mmol, 85% purity, 63.9% yield) that was used in next step without further purification.

Step-4. Synthesis of 1-(bromomethyl)-4-methoxymethanesulfonylbenzene (A76.6)

Hexaammonium tris(dioxomolybdenumbis(olate))tetrakis(trioxomolybdenum) tetrahydrate (0.5 g, 0.404 mmol) and hydrogen peroxide (1.71 g, 17.7 mmol) were added to a solution of 1-(bromomethyl)-4-[(methoxymethyl)sulfanyl] benzene (A76.5) (2 g, 8.09 mmol) in methanol (50 mL). The solution was stirred overnight at room temperature and poured into brine (100 mL), the product was extracted with ethyl acetate (100 mL×3). The organic layer was dried over sodium sulfate, filtered and evaporated under reduced pressure to afford 1-(bromomethyl)-4-methoxymethanesulfonylbenzene (A76.6) (1.1 g, 3.94 mmol, 80% purity, 39.1% yield) that was used in next step without further purification.

Step-5. Synthesis of sodium (4-methoxymethanesulfonylphenyl)methanesulfonate (A76.7)

Sodium sulfite (3 g, 23.8 mmol) was added to a solution of 1-(bromomethyl)-4-methoxymethanesulfonylbenzene (A76.6) (1 g, 3.58 mmol) in 2-propanol (25 mL) and water (100 mL). The mixture was stirred at 100° C. until the reaction completion (TLC control) and concentrated after under the reduced pressure. The residue was extracted with hot methanol (100 mL), filtered and the filtrate was concentrated under the reduced pressure to give sodium (4-methoxymethanesulfonylphenyl)methanesulfonate (A76.7) (1.2 g, 3.96 mmol, 60% purity, 66.6% yield) that was used in next step without further purification.

Step-6. Synthesis of (4-methoxymethanesulfonylphenyl)methanesulfonyl chloride (A76.8)

Oxalyl chloride (0.507 g, 4 mmol) was added dropwise to a suspension of sodium (4-methoxymethanesulfonylphenyl) methanesulfonate (A76.7) (1.2 g, 4 mmol) and DMF (1 drop) in tetrahydrofuran (10 mL) at −20° C. Mixture stirring was continued for an hour, the solution was filtered, formed precipitate was washed with tetrahydrofuran. Combined filtrates were evaporated under reduced pressure to give (4-methoxymethanesulfonylphenyl)methanesulfonyl chloride (A76.8) (0.3 g, 1 mmol, 90% purity, 22.6% yield).

Step-7. Synthesis of 1-(4-methoxymethanesulfonylphenyl)-N-{2-[4-(methoxymethyl)-4-methylpiperidin-1-yl]phenyl}methanesulfonamide (A-747)

(4-methoxymethanesulfonylphenyl)methanesulfonyl chloride (A76.8) (0.3 g, 1 mmol) was added to the mixture of 2-[4-(methoxymethyl)-4-methylpiperidin-1-yl]aniline (0.234 g, 1 mmol) and pyridine (0.09 g, 1.13 mmol) in dry acetonitrile (20 mL). The reaction mixture was stirred for 12 h and evaporated under reduced pressure. The residue was subjected to HPLC purification (deionized water/HPLC-grade acetonitrile) that afforded the product 1-(4-methoxymethanesulfonylphenyl)-N-{2-[4-(methoxymethyl)-4-methylpiperidin-1-yl]phenyl}methanesulfonamide (A-747). Yield: 19.4 mg, 3.7%; Appearance: Yellow oil; $^1H$ NMR (600 MHz, DMSO-$d_6$) δ 8.17 (s, 1H), 7.87-7.84 (m, 2H), 7.56 (d, J=8.3 Hz, 2H), 7.27 (dd, J=7.8, 1.5 Hz, 1H), 7.17 (dd, J=7.9, 1.6 Hz, 1H), 7.05 (dtd, J=24.3, 7.6, 1.6 Hz, 2H), 4.79 (s, 4H), 3.48 (s, 3H), 3.24 (s, 3H), 3.10 (s, 2H), 2.70 (dt, J=9.0, 4.1 Hz, 4H), 1.56 (ddd, J=13.2, 8.7, 4.6 Hz, 2H), 1.31 (dt, J=13.4, 4.2 Hz, 2H), 0.93 (s, 3H); HPLC purity: 100%; LCMS Calculated for $C_{23}H_{32}N_2O_6S_2$: 496.64; Observed: 497.2[M+H]$^+$.

Example A77: Synthesis of N1,N1-dimethyl-N4-(2-((5R,7R)-3,3,7-trimethyl-2-oxa-8-azaspiro[4.5]decan-8-yl)phenyl)benzene-1,4-disulfonamide (A-799)

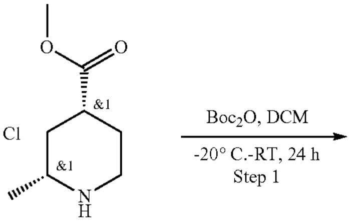

A77.1

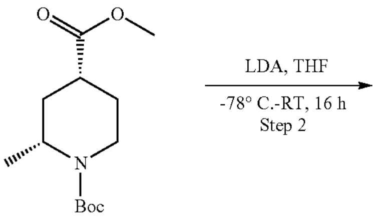

A77.2

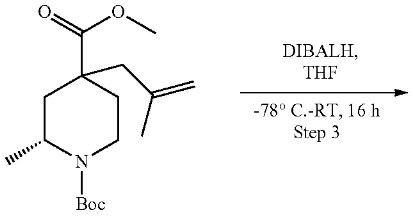

A77.3

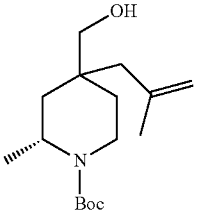

A77.4

-continued

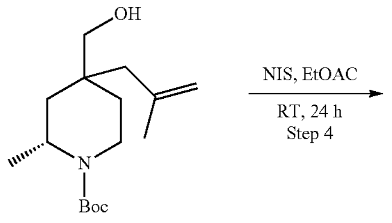

A77.4

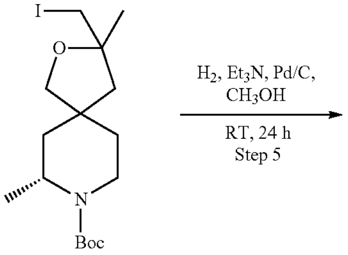

A77.5

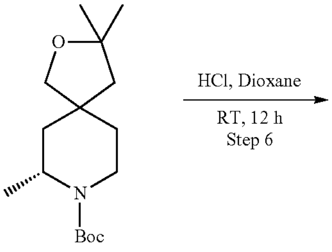

A77.6

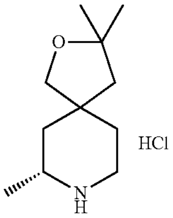

A77.7

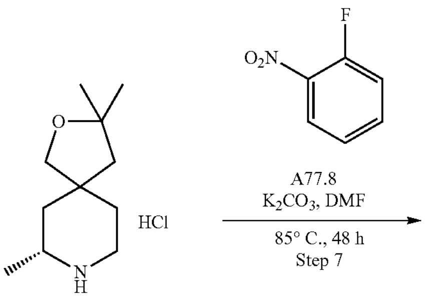

A77.7

-continued

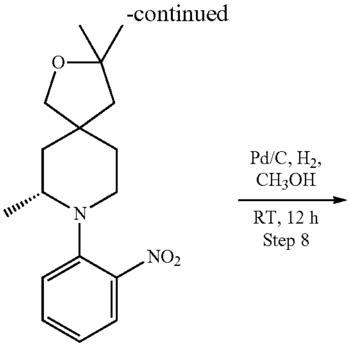

A77.9

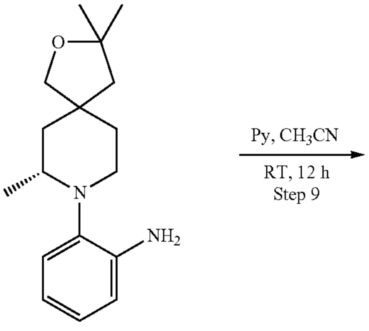

A77.10

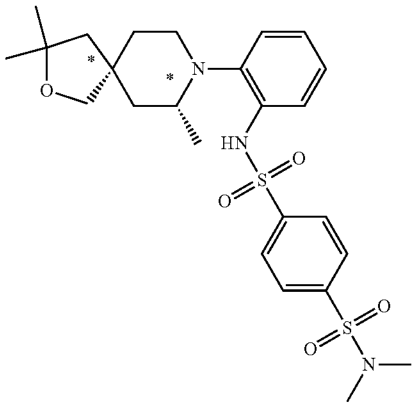

A-799 (cis)

Step-1. Synthesis of 1-tert-butyl 4-methyl (2R,4R)-2-methylpiperidine-1,4-dicarboxylate (A77.2)

Di-tert-butyl dicarbonate (12.3 g, 56.7 mmol) was added to a stirred solution of methyl (2R,4R)-2-methylpiperidine-4-carboxylate hydrochloride (A77.1) (10 g, 51.6 mmol) and triethylamine (13.0 g, 129 mmol, 17.9 mL) in dry dichloromethane (250 mL). The mixture was stirred at 0° C. until the reaction completion (TLC control). Organic layer was washed with water (50 mL), dried over anhydrous sodium sulfate, filtered and concentrated under reduced pressure to afford 1-tert-butyl 4-methyl (2R,4R)-2-methylpiperidine-1,4-dicarboxylate (A77.2) (13 g, 50.5 mmol, 95% purity, 93.1% yield).

Step-2. Synthesis of 1-tert-butyl 4-methyl (2R)-2-methyl-4-(2-methylprop-2-en-1-yl)piperidine-1,4-dicarboxylate (A77.3)

2.5 M butyllithium (3.39 g, 53.0 mmol) solution in hexane (21.2 mL) was added to a diisopropylamine solution (5.61 g, 55.5 mmol) in THE (250 mL) at −78° C. and the mixture was stirred at this temperature for 1 h, followed by addition of 1-tert-butyl 4-methyl (2R,4R)-2-methylpiperidine-1,4-dicarboxylate (A77.2) (13 g, 50.5 mmol) in THE (50 mL). The reaction mixture was stirred at −78° C. for 1 h and then gradually warmed to −20° C. over 2 h. 3-bromo-2-methylprop-1-ene (7.49 g, 55.5 mmol) was added to the mixture at −20° C. and the mixture was allowed to warm to room temperature over 2 h. The reaction was quenched with $NH_4Cl$ sat. aq. solution (250 mL) and the product was extracted with ethyl acetate (500 mL). The organic layer was washed with water (500 mL), brine (500 mL), dried over sodium sulfate, filtered and evaporated under reduced pressure. The residue was purified by flash chromatography (hexane/MTBE) to afford 1-tert-butyl 4-methyl (2R)-2-methyl-4-(2-methylprop-2-en-1-yl)piperidine-1,4-dicarboxylate as a colorless oil (A77.3) (10 g, 32.1 mmol, 95% purity, 60.5% yield).

Step-3. Synthesis of tert-butyl (2R,4R)-4-(hydroxymethyl)-2-methyl-4-(2-methylprop-2-en-1-yl) piperidine-1-carboxylate (A77.4)

1 M DIBAL-H (13 g, 92.1 mmol) solution in toluene (92.1 mL) was added dropwise at −78° C. to a 1-tert-butyl 4-methyl (2R,4R)-2-methyl-4-(2-methylprop-2-en-1-yl)piperidine-1,4-dicarboxylate (A77.3) (9 g, 28.8 mmol) solution in dry tetrahydrofuran (150 mL) followed by stirring for 5 h. The mixture was warmed to room temperature, quenched with $NH_4Cl$ sat. aq. solution (250 mL) and the product was extracted with ethyl acetate (200 mL×3). The organic layer was dried over sodium sulfate, filtered and concentrated under reduced pressure to give tert-butyl (2R,4R)-4-(hydroxymethyl)-2-methyl-4-(2-methylprop-2-en-1-yl)piperidine-1-carboxylate as pale yellow oil (A77.4) (4 g, 14.1 mmol, 95% purity, 46.5% yield).

Step-4. Synthesis of tert-butyl (5R,7R)-3-(iodomethyl)-3,7-dimethyl-2-oxa-8-azaspiro[4.5]decane-8-carboxylate (A77.5)

1-iodopyrrolidine-2,5-dione (4.11 g, 18.3 mmol) was added to a solution of tert-butyl (2R,4R)-4-(hydroxymethyl)-2-methyl-4-(2-methylprop-2-en-1-yl)piperidine-1-carboxylate (A77.4) (4 g, 14.1 mmol) in ethyl acetate (150 mL) at room temperature. The resulting mixture was stirred at room temperature overnight, quenched with $Na_2SO_3$ sat. aq. solution (50 mL), and diluted with water (100 mL). The product was extracted with ethyl acetate (200 mL×3), combined organic layers were dried over magnesium sulfate, filtered and concentrated in vacuo to afford tert-butyl (5R,7R)-3-(iodomethyl)-3,7-dimethyl-2-oxa-8-azaspiro[4.5]decane-8-carboxylate (A77.5) (3.7 g, 9.03 mmol, 90% purity, 57.7% yield).

Step-5. Synthesis of tert-butyl (5R,7R)-3,3,7-trimethyl-2-oxa-8-azaspiro[4.5]decane-8-carboxylate (A77.6)

Tert-butyl (5R,7R)-3-(iodomethyl)-3,7-dimethyl-2-oxa-8-azaspiro[4.5]decane-8-carboxylate (A77.5) (3.7 g, 9.03 mmol) was dissolved in methanol (100 mL), triethylamine (1 g, 9.93 mmol, 1.37 mL) was added to this solution and the reaction mixture was treated with 10% Pd/C (0.37 g). The resulting mixture was hydrogenated at ambient pressure and room temperature until the reaction was completed (TLC control). The catalyst was filtered off, the filtrate was evaporated under reduced pressure. The residue was dissolved in MTBE (150 mL), the solution was washed with water (150 mL), dried over sodium sulfate, filtered and evaporated under reduced pressure to afford tert-butyl (5R,7R)-3,3,7-trimethyl-2-oxa-8-azaspiro[4.5]decane-8-carboxylate (A77.6) (1.8 g, 6.35 mmol, 95% purity, 67% yield).

Step-6. Synthesis of (5R,7R)-3,3,7-trimethyl-2-oxa-8-azaspiro[4.5]decan-8-ium Chloride (A77.7)

A solution of tert-butyl (5R,7R)-3,3,7-trimethyl-2-oxa-8-azaspiro[4.5]decane-8-carboxylate (A77.6) (1.8 g, 6.35 mmol) in dioxane (10 mL) was added with sat. hydrochloric acid solution in dioxane (50 ml) at room temperature, the reaction mixture was stirred for 12 h at room temperature and evaporated to dryness. The residue was treated with MTBE (100 mL), formed precipitate was filtered off, dried on air to afford (5R,7R)-3,3,7-trimethyl-2-oxa-8-azaspiro[4.5]decan-8-ium chloride (A77.7) (1.38 g, 6.27 mmol, 95% purity, 94.2% yield).

Step-7. Synthesis of (5R,7R)-3,3,7-trimethyl-8-(2-nitrophenyl)-2-oxa-8-azaspiro[4.5]decane (A77.9)

(5R,7R)-3,3,7-trimethyl-2-oxa-8-azaspiro[4.5]decan-8-ium chloride (A77.7) (1.38 g, 6.27 mmol) was added to a stirred solution of 1-fluoro-2-nitrobenzene (A77.8) (884 mg, 6.27 mmol) and potassium carbonate (2.15 g mg, 15.6 mmol) in dry DMF (50 mL). The mixture was stirred at 90° C. until the reaction completion (TLC control) and concentrated under the reduced pressure. The residue was dissolved in ethyl acetate (150 mL), the organic layer was washed with water (150 mL), dried over anhydrous sodium sulfate, filtered and concentrated under reduced pressure to afford (5R,7R)-3,3,7-trimethyl-8-(2-nitrophenyl)-2-oxa-8-azaspiro[4.5]decane (A77.9) (1.15 g, 3.77 mmol, 64% purity, 38.7% yield) that was used in next step without further purification.

Step-8. Synthesis of 2-[(5R,7R)-3,3,7-trimethyl-2-oxa-8-azaspiro[4.5]decan-8-yl]aniline (A77.10)

(5R,7R)-3,3,7-trimethyl-8-(2-nitrophenyl)-2-oxa-8-azaspiro[4.5]decane (A77.9) (1.15 g, 2.41 mmol) was dissolved in methanol (50 mL) and the solution was treated with 10% Pd/C (0.1 g). The resulting mixture was hydrogenated at ambient pressure and room temperature until the reaction was completed (TLC control). The catalyst was filtered off and the filtrate was evaporated to afford 2-[(5R,7R)-3,3,7-trimethyl-2-oxa-8-azaspiro[4.5]decan-8-yl]aniline (A77.10) (0.65 g, 2.36 mmol, 95% purity, 93.3% yield).

Step-9. Synthesis of rac-N1,N1-dimethyl-N4-(2-((5R,7R)-3,3,7-trimethyl-2-oxa-8-azaspiro[4.5]decan-8-yl)phenyl)benzene-1,4-disulfonamide (A-799)

4-(dimethylsulfamoyl)benzene-1-sulfonyl chloride (0.397 g, 1.40 mmol) was added to the mixture of 3-fluoro-2-[(5R,7R)-3,3,7-trimethyl-2-oxa-8-azaspiro[4.5]decan-8-yl]aniline (0.375 g, 1.28 mmol) and pyridine (0.5 g, 6.32 mmol) in dry acetonitrile (20 mL). The reaction mixture was stirred at room temperature overnight and evaporated. The residue was subjected to HPLC purification (deionized water/HPLC-grade methanol) to afford the product as white solid (0.0295 g, 0.0546 mmol, 95% purity, 4.05% yield). The analytical data provided for this compound provisionally supports the proposed structure for N1,N1-dimethyl-N4-(2-((5R,7R)-3,3,7-trimethyl-2-oxa-8-azaspiro[4.5]decan-8-yl)phenyl)benzene-1,4-disulfonamide (A-799). Yield: 29.5 mg, 4.05%; Appearance: White solid; $^1H$ NMR (400 MHz, DMSO-$d_6$) δ 9.06 (s, 1H), 8.04 (d, J=8.1 Hz, 2H), 7.90 (d, J=8.1 Hz, 2H), 7.52 (d, J=8.0 Hz, 1H), 7.25 (d, J=7.7 Hz, 1H), 7.17 (t, J=7.7 Hz, 1H), 7.10 (t, J=7.6 Hz, 1H), 3.52-3.45 (m, 2H), 2.83 (s, 1H), 2.58 (s, 6H), 2.39 (d, J=12.0 Hz, 1H), 1.82 (d, J=11.4 Hz, 1H), 1.65 (dd, J=16.6, 4.1 Hz, 3H), 1.53 (d, J=12.6 Hz, 1H), 1.44 (d, J=11.6 Hz, 1H), 1.34 (d, J=12.5 Hz, 1H), 1.18 (d, J=8.7 Hz, 6H), 0.43 (d, J=5.9 Hz, 3H); HPLC purity: 100%; LCMS Calculated for $C_{25}H_{35}N_3O_5S_2$: 521.69; Observed: 522.2[M+H]$^+$.

Example A78: Synthesis of N4-(2-{4-[(2R,6S)-2,6-dimethylmorpholine-4-carbonyl]piperidin-1-yl}phenyl)-N1,N1-dimethylbenzene-1,4-disulfonamide (A-754)

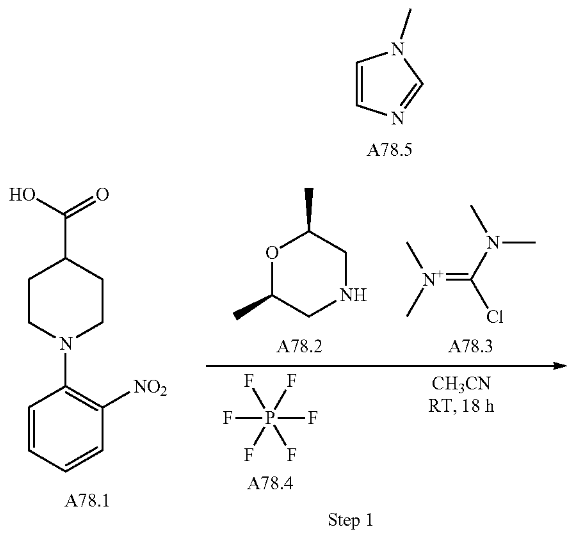

A78.5

A78.1 A78.2 A78.3 A78.4

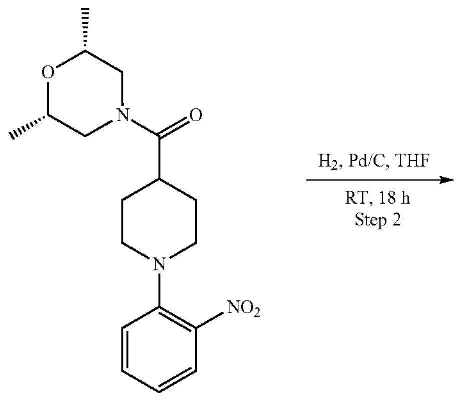

A78.6

-continued

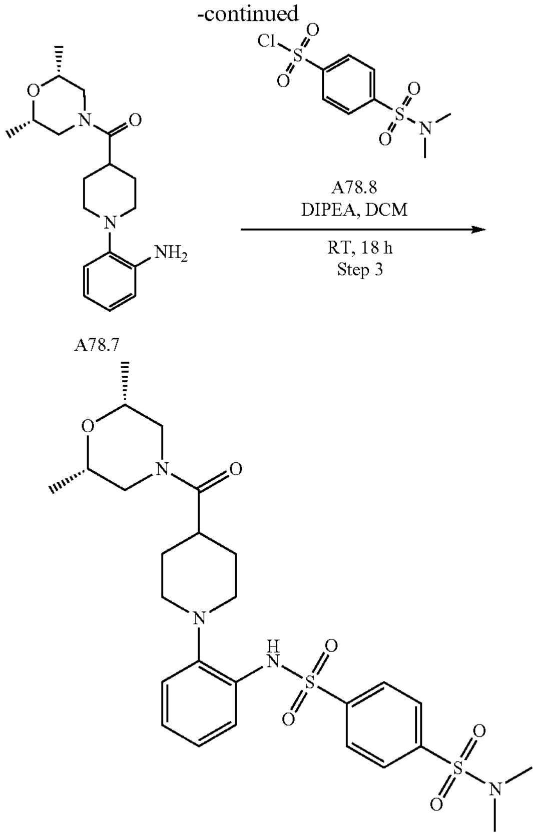

A78.7

A-754

Step-1. Synthesis of (2R,6S)-2,6-dimethyl-4-[1-(2-nitrophenyl)piperidine-4-carbonyl]morpholine (A78.6)

1-(2-Nitrophenyl)piperidine-4-carboxylic acid (A78.1) (1.0 g, 3.99 mmol), (2R,6S)-2,6-dimethylmorpholine (A78.2) (0.46 g, 3.99 mmol, 1.0 eq) and 1-methyl-1H-imidazole (A78.5) (1.6 g, 19.9 mmol, 5.0 eq) were dissolved in acetonitrile (20 mL) and [chloro(dimethylamino)methylidene]dimethylazanium (A78.3); hexafluoro-$\lambda^5$-phosphanide (A78.4) (1.68 g, 5.98 mmol) was added in a single portion. The reaction was stirred overnight. After completion, the reaction mixture was concentrated. Dichloromethane (20 mL) was added to the residue and the obtained solution was washed with brine (2×10 mL), dried over sodium sulfate, filtered and concentrated in vacuo to give crude (2R,6S)-2,6-dimethyl-4-[1-(2-nitrophenyl)piperidine-4-carbonyl]morpholine as oil (A78.6) (2.7 g, 3.49 mmol, 50.0% purity, 97.8% yield).

Step-2. Synthesis of 2-{4-[(2R,6S)-2,6-dimethylmorpholine-4-carbonyl]piperidin-1-yl}aniline (A78.7)

(2R,6S)-2,6-dimethyl-4-[1-(2-nitrophenyl)piperidine-4-carbonyl]morpholine (A78.6) (1.35 g, 3.88 mmol) was dissolved in THE (100 mL) and treated with 10% Pd/C (0.1 g). The resulting mixture was hydrogenated at ambient pressure and room temperature until the reaction was completed (LCMS control). The catalyst was filtered off and the filtrate was evaporated to afford product 2-{4-[(2R,6S)-2,6-dimethylmorpholine-4-carbonyl]piperidin-1-yl}aniline (A78.7) (1.0 g, 1.41 mmol, 64.8% purity, 52.6% yield).

Step-3. Synthesis of N4-(2-{4-[(2R,6S)-2,6-dimethylmorpholine-4-carbonyl]piperidin-1-yl}phenyl)-N1,N1-dimethylbenzene-1,4-disulfonamide (A-754)

4-(Dimethylsulfamoyl)benzene-1-sulfonyl chloride (A78.8) (0.282 g, 0.99 mmol) was added to the mixture of 2-4-[(2R,6S)-2,6-dimethylmorpholine-4-carbonyl]piperidin-1-ylaniline (A78.7) (0.5 g, 1.57 mmol) and ethylbis(propan-2-yl)amine (0.183 g, 1.41 mmol) in dry dichloromethane (5 mL). The reaction mixture was stirred overnight. After completion, it was diluted with water (20 mL) and extracted with dichloromethane (20 mL×2). Combined organic layers were dried over anhydrous sodium sulfate, filtered and concentrated in vacuo. The residue was subjected to HPLC purification (deionized water/HPLC-grade acetonitrile) to afford N4-(2-{4-[(2R,6S)-2,6-dimethylmorpholine-4-carbonyl]piperidin-1-yl}phenyl)-N1,N1-dimethylbenzene-1,4-disulfonamide (A-754). Yield: 105.7 mg, 11.2%; Appearance: Light brown solid; $^1$H NMR (600 MHz, DMSO-$d_6$) δ 9.30 (s, 1H), 8.00 (d, J=8.2 Hz, 2H), 7.89 (d, J=8.2 Hz, 2H), 7.21 (d, J=7.9 Hz, 1H), 7.06 (s, 2H), 7.00 (s, 1H), 4.26 (d, J=13.0 Hz, 1H), 3.82 (d, J=13.3 Hz, 1H), 3.50-3.30 (m, 4H), 2.66 (dt, J=15.1, 11.3 Hz, 3H), 2.59 (s, 6H), 2.53 (s, 3H), 2.19 (t, J=11.9 Hz, 1H), 1.81-1.69 (m, 2H), 1.50 (d, J=12.8 Hz, 2H), 1.07 (t, J=6.8 Hz, 6H); HPLC purity: 100%; LCMS Calculated for $C_{26}H_{36}N_4O_6S_2$: 564.72; Observed: 565.0[M+H]$^+$.

Example A79: Synthesis of N1,N1-dimethyl-N4-{2-[4-(morpholine-4-carbonyl)piperidin-1-yl]phenyl}benzene-1,4-disulfonamide (A-761)

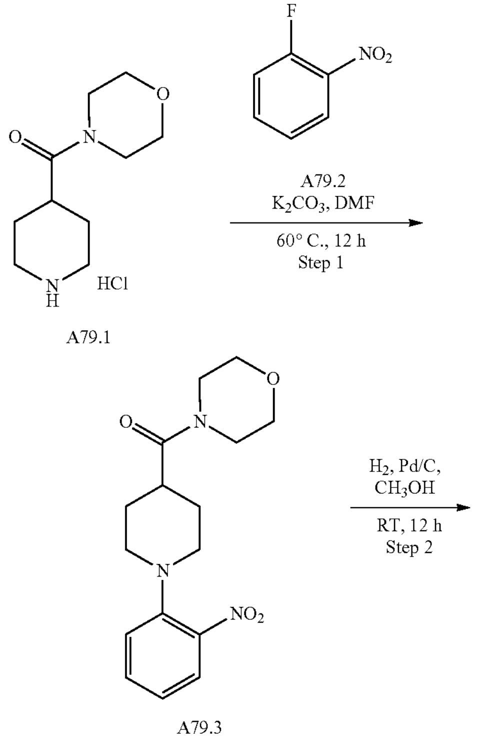

-continued

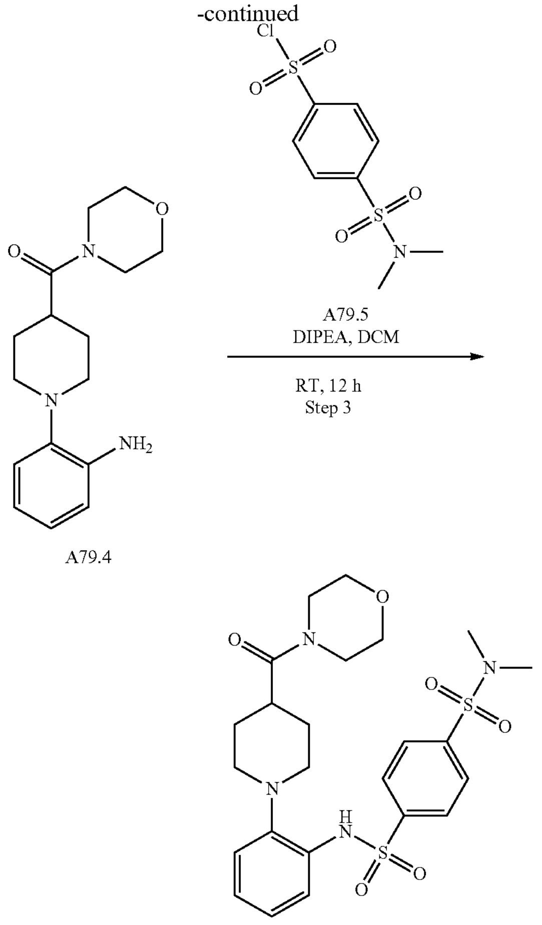

A-761

Step-1. Synthesis of 4-[1-(2-nitrophenyl)piperidine-4-carbonyl]morpholine (A79.3)

1-fluoro-2-nitrobenzene (A79.2) (0.3 g, 2.12 mmol) was added to a stirred solution of 4-(piperidine-4-carbonyl)morpholine hydrochloride (A79.1) (0.5242 g, 2.23 mmol) and potassium carbonate (0.735 g, 5.31 mmol) in dry DMF (5 mL). The mixture was stirred at 60° C. until the reaction completion (TLC control, overnight) and concentrated under the reduced pressure. The residue was dissolved in EtOAc (15 mL), the organic layer was washed twice with water (15 mL), dried over anhydrous sodium sulfate, filtered and concentrated under reduced pressure to obtain 4-[1-(2-nitrophenyl)piperidine-4-carbonyl]morpholine (A79.3) (0.67 g, 2.09 mmol, 95% purity, 89.3% yield).

Step-2. Synthesis of 2-[4-(morpholine-4-carbonyl)piperidin-1-yl]aniline (A79.4)

4-[1-(2-nitrophenyl)piperidine-4-carbonyl]morpholine (A79.3) (0.67 g, 2.09 mmol) was dissolved in methanol (10 mL) and treated with 10% Pd/C (0.075 g). The resulting mixture was hydrogenated at 6 atm and room temperature until the reaction was completed (TLC control). The catalyst was filtered off and the filtrate was evaporated to afford 2-[4-(morpholine-4-carbonyl)piperidin-1-yl]aniline (A79.4) (0.6 g, 2.07 mmol, 95% purity, 94.3% yield).

Step-3. Synthesis of N1,N1-dimethyl-N4-{2-[4-(morpholine-4-carbonyl)piperidin-1-yl]phenyl}benzene-1,4-disulfonamide (A-761)

4-(dimethylsulfamoyl)benzene-1-sulfonyl chloride (A79.5) (0.196 g, 0.69 mmol) was added to the mixture of 2-[4-(morpholine-4-carbonyl)piperidin-1-yl]aniline (A79.4) (0.2 g, 0.69 mmol) and DIPEA (0.135 g, 1.04 mmol) in dry DCM (5 mL). The reaction mixture was stirred overnight and poured into sat. aq. $NaHCO_3$ solution (10 mL). The organic layer was separated, the product was extracted from water layer with DCM (15 mL). Combined organic layers were dried over anhydrous sodium sulfate, filtered and evaporated under reduced pressure. The residue was subjected to HPLC purification (deionized water/HPLC-grade methanol) to give product as yellow solid (0.081 g, 0.150 mmol, 95% purity, 20.7% yield). The analytical data provided for this compound provisionally supports the proposed structure for N1,N1-dimethyl-N4-{2-[4-(morpholine-4-carbonyl)piperidin-1-yl]phenyl}benzene-1,4-disulfonamide (A-761). Yield: 81 mg, 20.7%; Appearance: Yellow solid; $^1H$ NMR (600 MHz, DMSO-$d_6$) δ 9.29 (s, 1H), 8.04-7.97 (m, 2H), 7.93-7.85 (m, 2H), 7.24-7.18 (m, 1H), 7.07 (q, J=5.3, 4.6 Hz, 2H), 7.02 (ddd, J=8.6, 6.0, 2.9 Hz, 1H), 3.52 (q, J=5.3, 4.8 Hz, 4H), 3.50-3.39 (m, 4H), 2.59 (s, 6H), 2.58-2.48 (m, 6H), 1.76 (qd, J=12.1, 4.1 Hz, 2H), 1.57-1.46 (m, 2H); HPLC purity: 100%; LCMS Calculated for $C_{24}H_{32}N_4O_6S_2$: 536.66; Observed: 537.0[M+H]$^+$.

The following example was prepared using standard chemical manipulations and procedures similar to those used for the preparation of the previous example.

Example A80: Synthesis of N4-{4-[4-(methoxymethyl)-4-methylpiperidin-1-yl]-1-methyl-1H-indazol-5-yl}-N1,N1-dimethylbenzene-1,4-disulfonamide (A-746)

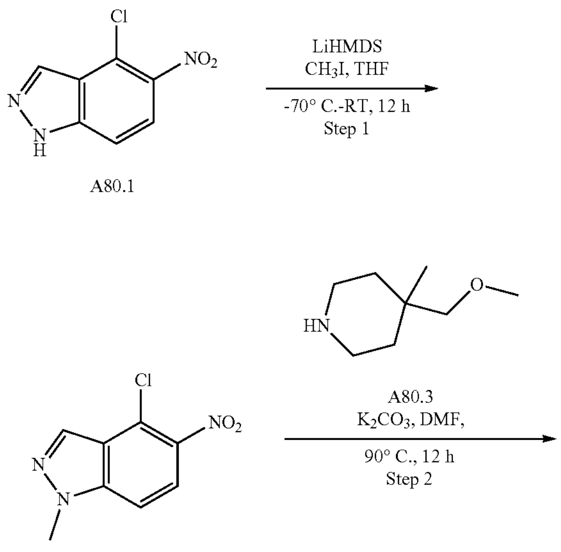

A80.1

A80.2

| Compound No. | Structure | Analytical Data |
| --- | --- | --- |
| A-755 | 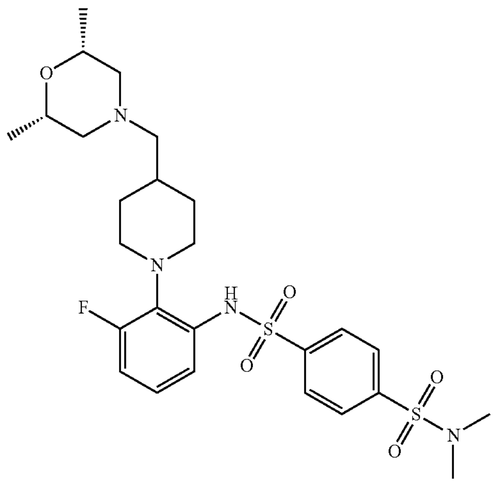 | Yield: 78 mg, 14.4%; Appearance: Yellow solid; $^1H$ NMR (600 MHz, DMSO-$d_6$) δ 9.16 (s, 1H), 7.94 (d, J = 8.4 Hz, 2H), 7.89 (d, J = 8.4 Hz, 2H), 7.21 (d, J = 8.2 Hz, 1H), 7.15 (d, J = 6.7 Hz, 1H), 6.95 (t, J = 10.0 Hz, 1H), 3.49 (dtd, J = 12.6, 6.3, 2.0 Hz, 2H), 2.76 (t, J = 11.5 Hz, 2H), 2.67 (d, J = 10.9 Hz, 2H), 2.58 (s, 6H), 2.28 (d, J = 10.7 Hz, 2H), 2.08 (d, J = 6.7 Hz, 2H), 1.52 (d, J = 11.2 Hz, 5H), 1.22 - 1.14 (m, 2H), 1.01 (d, J = 6.2 Hz, 6H); HPLC purity: 100%; LCMS Calculated for $C_{26}H_{37}FN_4O_5S_2$: 568.72; Observed: 569.2[M + H]$^+$. |

-continued

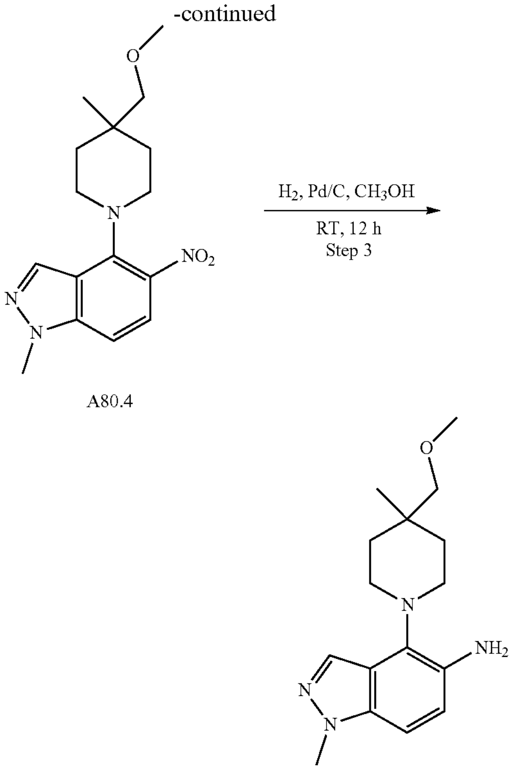

A80.4

A80.5

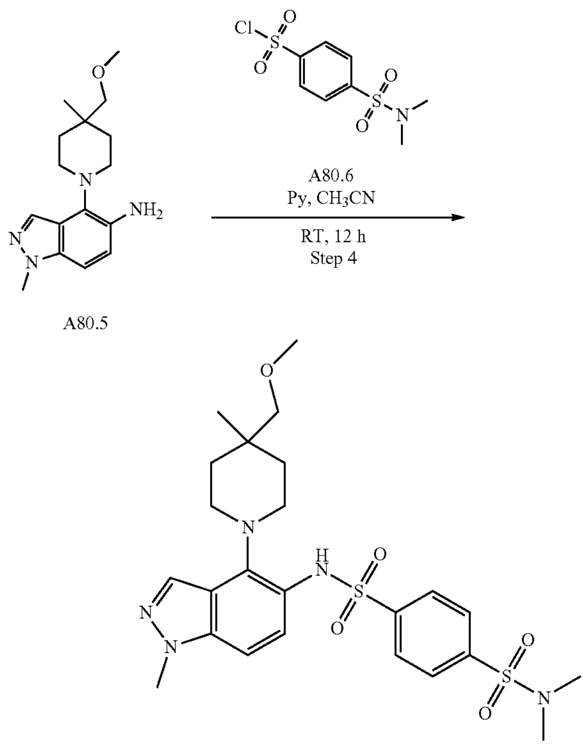

A80.5

A80.6

A-746

Step-1. Synthesis of 4-chloro-1-methyl-5-nitro-1H-indazole (A80.2)

Lithium hexamethyldisilazane (2.3 g, 13.8 mmol) was added to a solution of 4-chloro-5-nitro-1H-indazole (A80.1)

(2.5 g, 12.6 mmol) in tetrahydrofuran (100 mL) at −78° C., the mixture was stirred for 20 minutes and iodomethane (1.78 g, 12.6 mmol) was added. The solution was allowed to warm to room temperature, stir for 12 hours and evaporated under reduced pressure. The residue was diluted with water (100 mL) and extracted with ethyl acetate (100 mL). The organic layer was washed with brine (100 mL), dried with sodium sulfate, filtered and evaporated under reduced pressure. The residue was purified by flash chromatography (chloroform/MTBE) to give 4-chloro-1-methyl-5-nitro-1H-indazole (A80.2) (0.9 g, 4.25 mmol, 95% purity, 32.1% yield).

Step-2. Synthesis of 4-[4-(methoxymethyl)-4-methylpiperidin-1-yl]-1-methyl-5-nitro-1H-indazole (A80.4)

4-chloro-1-methyl-5-nitro-1H-indazole (A80.2) (0.8 g, 3.78 mmol) was added to a stirred solution of 4-(methoxymethyl)-4-methylpiperidine hydrochloride (A80.3) (0.745 g, 4.15 mmol) and potassium carbonate (1.58 g, 11.3 mmol) in dry DMF (25 mL). The mixture was stirred at 60° C. until the reaction completion (TLC control) and concentrated under the reduced pressure. The residue was dissolved in ethyl acetate (150 mL), the organic layer was washed with water (100 mL), dried over anhydrous sodium sulfate, filtered and concentrated under reduced pressure. The chromatographic purification (chloroform/acetonitrile) of crude product afforded 4-[4-(methoxymethyl)-4-methylpiperidin-1-yl]-1-methyl-5-nitro-1H-indazole (A80.4) (1 g, 3.14 mmol, 95% purity, 79.1% yield).

Step-3. Synthesis of 4-[4-(methoxymethyl)-4-methylpiperidin-1-yl]-1-methyl-1H-indazol-5-amine (A80.5)

4-[4-(methoxymethyl)-4-methylpiperidin-1-yl]-1-methyl-5-nitro-1H-indazole (A80.4) (1 g, 3.14 mmol) was dissolved in methanol (100 mL) and treated with 5% Pd/C (0.1 g). The resulting mixture was hydrogenated at ambient pressure and room temperature until the reaction was completed (TLC control). The catalyst was filtered off and the filtrate was evaporated to afford 4-[4-(methoxymethyl)-4-methylpiperidin-1-yl]-1-methyl-1H-indazol-5-amine (A80.5) (0.9 g, 3.12 mmol, 95% purity, 94.4% yield).

Step-4. Synthesis of N1-(4-(4-(methoxymethyl)-4-methylpiperidin-1-yl)-1-methyl-1H-indazol-5-yl)-N4,N4-dimethylbenzene-1,4-disulfonamide (A-746)

4-(dimethylsulfamoyl)benzene-1-sulfonyl chloride (A80.6) (0.391 g, 1.38 mmol) was added to the mixture of 4-[4-(methoxymethyl)-4-methylpiperidin-1-yl]-1-methyl-1H-indazol-5-amine (A80.5) (0.4 g, 1.38 mmol) and pyridine (0.150 g, 1.89 mmol) in dry acetonitrile (20 mL). The reaction mixture was stirred at room temperature for 18 h, filtered through silica, the filtrate was evaporated under reduced pressure and the residue was subjected to HPLC purification (deionized water/HPLC-grade methanol) that afforded N4-{4-[4-(methoxymethyl)-4-methylpiperidin-1-yl]-1-methyl-1H-indazol-5-yl}-N1,N1-dimethylbenzene-1,4-disulfonamide (A-746). Yield: 109.8 mg, 14%; Appearance: Yellow solid; $^{1}$H NMR (400 MHz, DMSO-$d_6$) δ 8.92 (s, 1H), 7.94-7.78 (m, 5H), 7.16 (s, 2H), 3.99 (d, J=2.0 Hz, 3H), 3.17 (s, 2H), 2.95 (d, J=10.9 Hz, 2H), 2.76 (d, J=8.1 Hz, 2H), 2.64 (d, J=1.9 Hz, 6H), 1.57 (d, J=11.5 Hz, 2H), 1.35

(s, 2H), 1.03 (s, 3H); HPLC purity: 100%; LCMS Calculated for $C_{24}H_{33}N_5O_5S_2$: 535.68; Observed: 536.2[M+H]$^+$.

Example A81: Synthesis of N4-{5-[4-(methoxymethyl)-4-methylpiperidin-1-yl]imidazo[1,2-a]pyridin-6-yl}-N1,N1-dimethylbenzene-1,4-disulfonamide (A-813)

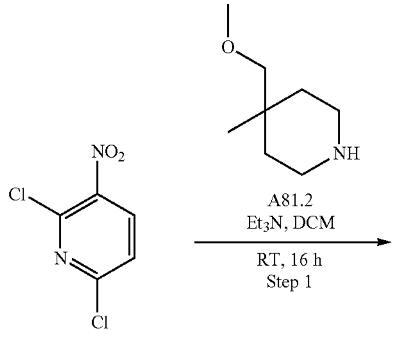

A81.1

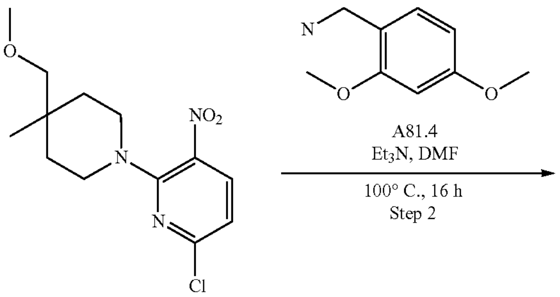

A81.3

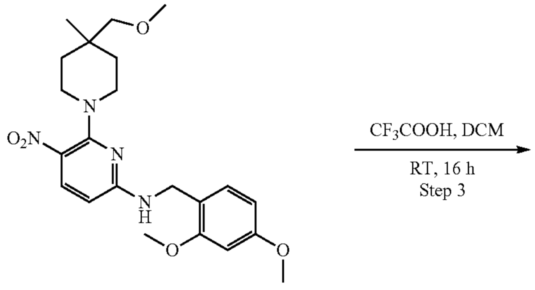

A81.5

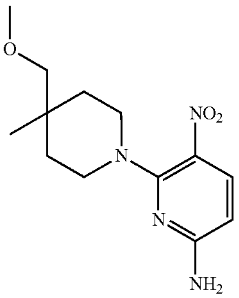

A81.6

-continued

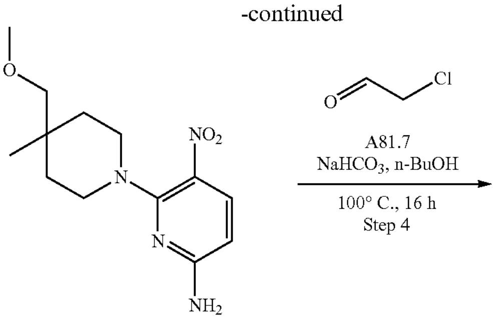

A81.6

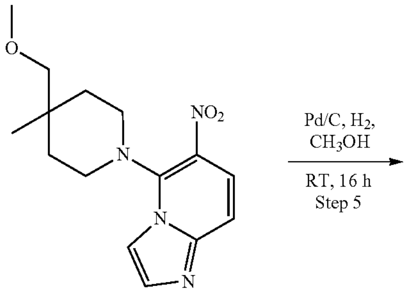

A81.8

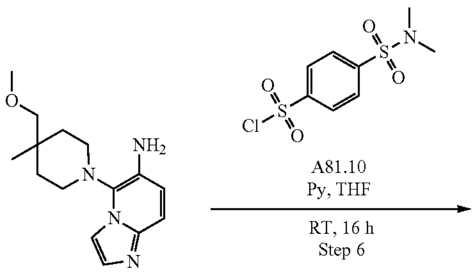

A81.9

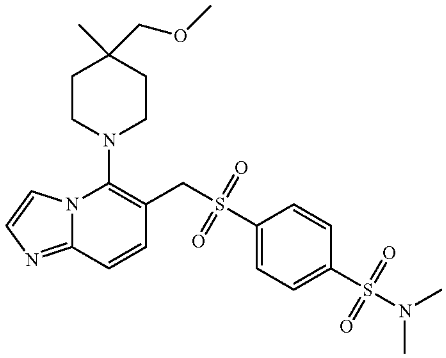

A-813

Step-1. Synthesis of 6-chloro-2-[4-(methoxymethyl)-4-methylpiperidin-1-yl]-3-nitropyridine (A81.3)

2,6-dichloro-3-nitropyridine (A81.1) (2.6 g, 13.4 mmol) was added to the mixture of 4-(methoxymethyl)-4-methylpiperidine (A81.2) (2 g, 13.9 mmol) and triethylamine (2 g, 19.7 mmol) in dry dichloromethane (50 mL). The reaction mixture was refluxed for 6 h, cooled to room temperature, washed with water (40 mL), brine (40 mL), dried over sodium sulfate, filtered and evaporated under reduced pressure to give 6-chloro-2-[4-(methoxymethyl)-4-methylpiperidin-1-yl]-3-nitropyridine (A81.3) (3.7 g, 12.3 mmol, 90.5% purity, 83.2% yield) that was used in next step without further purification.

Step-2. Synthesis of N-[(2,4-dimethoxyphenyl) methyl]-6-[4-(methoxymethyl)-4-methylpiperidin-1-yl]-5-nitropyridin-2-amine (A81.5)

6-chloro-2-[4-(methoxymethyl)-4-methylpiperidin-1-yl]-3-nitropyridine (A81.3) (3.7 g, 12.3 mmol), 1-(2,4-dimethoxyphenyl)methanamine (A81.4) (2.25 g, 13.5 mmol) and triethylamine (1.86 g, 18.4 mmol) were mixed in dry DMF (50 mL). The reaction mixture was stirred at 100° C. for 16 h, cooled to room temperature and concentrated under the reduced pressure. The residue was dissolved in ethyl acetate (50 mL), the solution was washed with water (40 mL), brine (40 mL), dried over sodium sulfate, filtered and concentrated under reduced pressure to give N-[(2,4-dimethoxyphenyl) methyl]-6-[4-(methoxymethyl)-4-methylpiperidin-1-yl]-5-nitropyridin-2-amine (A81.5) (5.8 g, 13.4 mmol, 90.3% purity, 98.8% yield) that was used in next step without further purification.

Step-3. Synthesis of 6-[4-(methoxymethyl)-4-methylpiperidin-1-yl]-5-nitropyridin-2-amine (A81.6)

N-[(2,4-dimethoxyphenyl)methyl]-6-[4-(methoxymethyl)-4-methylpiperidin-1-yl]-5-nitropyridin-2-amine (A81.5) (5.8 g, 13.4 mmol) was dissolved in dichloromethane (40 mL). Trifluoroacetic acid (15 g, 131 mmol) was added to the mixture, it was stirred at room temperature overnight and concentrated under the reduced pressure. The residue was dissolved in $NaHCO_3$ sat. aq. solution (50 mL) and extracted with ethyl acetate (40 mL×2). Combined organic layers were washed with brine (40 mL), dried over sodium sulfate, filtered and concentrated under reduced pressure to give 6-[4-(methoxymethyl)-4-methylpiperidin-1-yl]-5-nitropyridin-2-amine (A81.6) (4 g, 14.2 mmol, 86.6% purity, 92.2% yield) that was used in next step without further purification.

Step-4. Synthesis of 4-(methoxymethyl)-4-methyl-1-{6-nitroimidazo[1,2-a]pyridin-5-yl}piperidine (A81.8)

6-[4-(methoxymethyl)-4-methylpiperidin-1-yl]-5-nitropyridin-2-amine (A81.6) (2 g, 7.13 mmol), 2-chloroacetaldehyde (A81.7) (40% aqueous solution, 5 g, 25.4 mmol) and sodium hydrogen carbonate (1.2 g, 14.2 mmol) were mixed in n-butanol (50 mL). The mixture was stirred at 100° C. overnight and concentrated under reduced pressure. The residue was dissolved in ethyl acetate (50 mL), this solution was washed with water (50 mL), brine (40 mL), dried over sodium sulfate, filtered and concentrated under reduced pressure. Crude material was purified by flash chromatography (chloroform/ethyl acetate) to give 4-(methoxymethyl)-4-methyl-1-{6-nitroimidazo[1,2-a]pyridin-5-yl}piperidine (A81.8) (0.5 g, 1.64 mmol, 85% purity, 19.5% yield) that was used in next step without further purification.

Step-5. Synthesis of 5-[4-(methoxymethyl)-4-methylpiperidin-1-yl]imidazo[1,2-a]pyridin-6-amine (A81.9)

4-(methoxymethyl)-4-methyl-1-{6-nitroimidazo[1,2-a]pyridin-5-yl}piperidine (A81.8) (0.5 g, 1.39 mmol) was dissolved in methanol (15 mL) and treated with 10% Pd/C (0.05 g). The resulting mixture was hydrogenated at ambient pressure and room temperature until the reaction was completed. The catalyst was filtered off and the filtrate was evaporated to give 5-[4-(methoxymethyl)-4-methylpiperidin-1-yl]imidazo[1,2-a]pyridin-6-amine (A81.9) (0.3 g, 1.09 mmol, 100% purity, 78.7% yield).

Step-6. Synthesis of N4-{5-[4-(methoxymethyl)-4-methylpiperidin-1-yl]imidazo[1,2-a]pyridin-6-yl}-N1,N1-dimethylbenzene-1,4-disulfonamide (A-813)

4-(dimethylsulfamoyl)benzene-1-sulfonyl chloride (A81.10) (0.3 g, 1.09 mmol) was added to the solution of 5-[4-(methoxymethyl)-4-methylpiperidin-1-yl]imidazo[1,2-a]pyridin-6-amine (A81.9) (0.3 g, 1.05 mmol) in dry THF (15 mL). The reaction mixture was stirred at room temperature for 16 h and evaporated under reduced pressure. The crude material was purified by HPLC (deionized water/HPLC-grade methanol, ammonia) to give N4-{5-[4-(methoxymethyl)-4-methylpiperidin-1-yl]imidazo[1,2-a]pyridin-6-yl}-N1,N1-dimethylbenzene-1,4-disulfonamide (A-813). Yield: 7.8 mg, 1.3%; Appearance: Yellow solid; $^1$H NMR (400 MHz, $CD_3OD$) δ 7.97 (d, J=3.4 Hz, 4H), 7.70 (s, 1H), 7.60 (s, 1H), 7.04 (d, J=9.3 Hz, 1H), 6.47 (dd, J=22.9, 9.1 Hz, 1H), 3.71-3.48 (m, 3H), 3.41 (d, J=14.8 Hz, 3H), 3.21-3.12 (m, 3H), 2.74 (d, J=3.8 Hz, 6H), 2.67 (d, J=3.3 Hz, 2H), 1.82 (s, 2H), 1.61 (s, 1H), 1.50 (d, J=13.1 Hz, 1H), 1.15 (s, 2H), 1.09 (s, 1H); HPLC purity: 100%; LCMS Calculated for $C_{23}H_{31}N_5O_5S_2$: 521.65; Observed: 522.2[M+H]$^+$.

Example A82: Synthesis of N1,N1-dimethyl-N4-[7-(piperidin-1-yl)pyrazolo[1,5-a]pyridin-6-yl]benzene-1,4-disulfonamide (A-793)

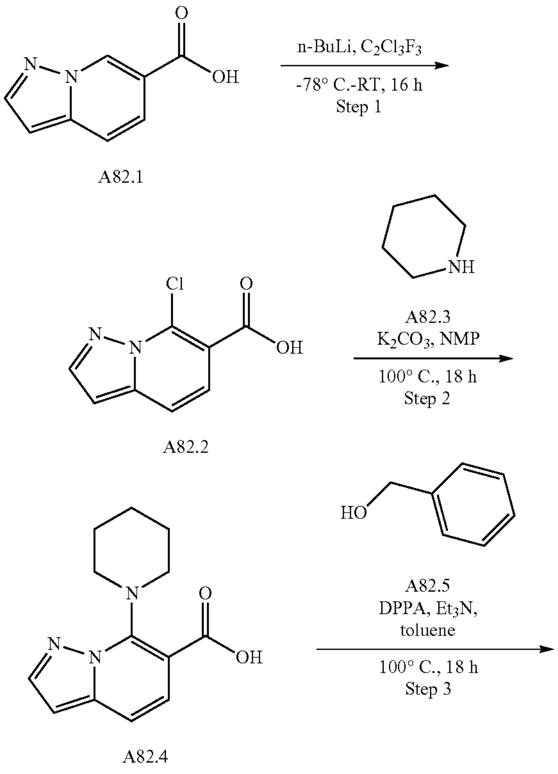

-continued

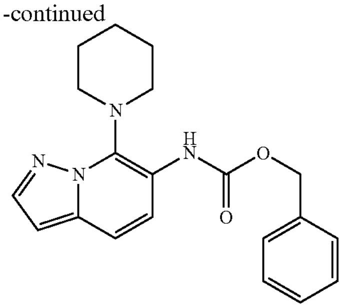

A82.6

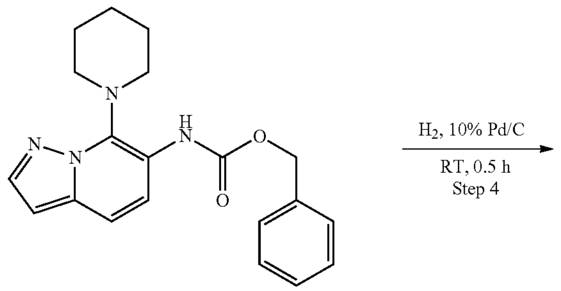

A82.6

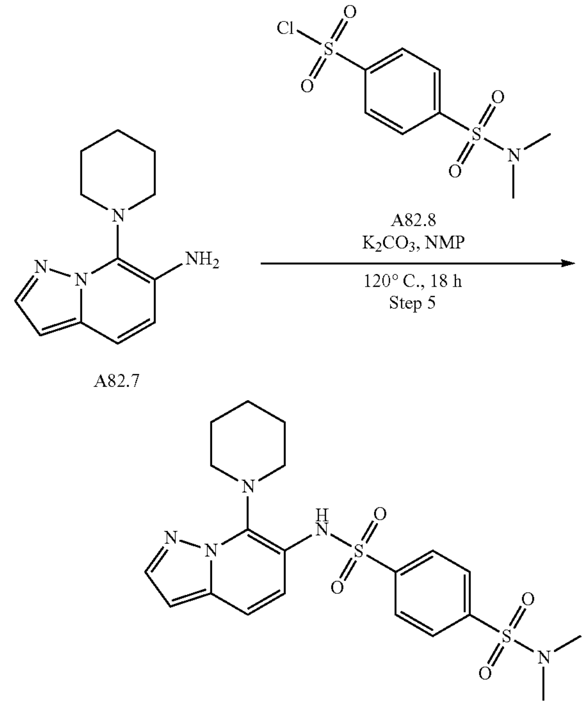

A82.7

A-793

Step-1. Synthesis of 7-chloropyrazolo[1,5-a]pyridine-6-carboxylic Acid (A82.2)

2.5 M n-butyllithium (7.36 g, 115 mmol) solution in hexane (46 mL) was added dropwise at −78° C. to a stirred solution of pyrazolo[1,5-a]pyridine-6-carboxylic acid (A82.1) (7.5 g, 46.2 mmol) in dry tetrahydrofuran (250 mL) under argon atmosphere and the reaction mixture was stirred at −70° C. for 4 h. Then 1,1,2-trichloro-1,2,2-trifluoroethane (25.8 g, 138 mmol) was added at −78° C., the reaction mixture was allowed to warm up and stir overnight at room temperature until completion. After the reaction mixture was poured in water (250 mL), acidified with $NaHSO_4$ sat. aq. solution to pH=4 and extracted with ethyl acetate (250 mL×3). The combined organic layer was washed with water (500 mL), brine (500 mL), dried over anhydrous sodium sulfate, filtered and concentrated under reduced pressure. The residue was purified by flash chromatography (acetonitrile/chloroform) that afforded 7-chloropyrazolo[1,5-a]pyridine-6-carboxylic acid as white solid (A82.2) (2.45 g, 12.4 mmol, 91% purity, 24.4% yield).

Step-2. Synthesis of 7-(piperidin-1-yl)pyrazolo[1,5-a]pyridine-6-carboxylic Acid (A82.4)

7-chloropyrazolo[1,5-a]pyridine-6-carboxylic acid (A82.2) (1.25 g, 6.35 mmol) was added to a stirred solution of piperidine (A82.3) (0.702 g, 8.25 mmol) and dipotassium carbonate (2.18 g, 15.8 mmol) in dry NMP (150 mL). The mixture was stirred at 120° C. for 18 h. Then, it was cooled to room temperature, poured in water (250 mL), acidified with $NaHSO_4$ sat. aq. solution to pH=5 and extracted with ethyl acetate (250 mL×3). The combined organic layer was washed with water (500 mL), brine (500 mL), dried over anhydrous sodium sulfate, filtered and concentrated under reduced pressure to give 7-(piperidin-1-yl)pyrazolo[1,5-a]pyridine-6-carboxylic acid as white solid (A82.4) (1.1 g, 4.48 mmol, 95% purity, 67% yield).

Step-3. Synthesis of Benzyl N-{7-[4-(methoxymethyl)-4-methylpiperidin-1-yl]pyrazolo[1,5-a]pyridin-6-yl}carbamate (A82.6)

{[azido(phenoxy)phosphoryl]oxy}benzene (1.49 g, 5.43 mmol was added to a stirred solution of 7-[4-(methoxymethyl)-4-methylpiperidin-1-yl]pyrazolo[1,5-a]pyridine-6-carboxylic acid (A82.4) (1.1 g, 3.62 mmol), phenylmethanol (A82.5) (1.16 g, 10.8 mmol) and triethylamine (0.549 g, 5.43 mmol) in dry toluene (100 mL). The mixture was stirred at 100° C. for 18 h. Then it was cooled to room temperature, poured in water (200 mL) and extracted with ethyl acetate (100 mL×3). The combined organic layer was washed with water (300 mL), brine (300 mL), dried over anhydrous sodium sulfate, filtered and concentrated under reduced pressure. The residue was subjected to HPLC purification (deionized water/HPLC-grade acetonitrile) that afforded benzyl N-{7-[4-(methoxymethyl)-4-methylpiperidin-1-yl]pyrazolo[1,5-a]pyridin-6-yl}carbamate (A82.6) as white solid (0.309 g, 0.756 mmol, 95% purity, 19.9% yield).

Step-4. Synthesis of 7-(piperidin-1-yl)pyrazolo[1,5-a]pyridin-6-amine (A82.7)

Benzyl N-[7-(piperidin-1-yl)pyrazolo[1,5-a]pyridin-6-yl]carbamate (A82.6) (0.1 g, 0.285 mmol) was dissolved in methanol/tetrahydrofuran=1/1 mixture (50 mL). 5% Pd/C (0.1 g) was added to the resulting orange solution wand the mixture was hydrogenated at ambient pressure and room temperature for 0.5 h, filtered. The filtrate was concentrated under reduced pressure to give 7-(piperidin-1-yl)pyrazolo[1,5-a]pyridin-6-amine as grey solid (A82.7) (0.055 g, 0.254 mmol, 86% purity, 76.7% yield) that was used in next step without further purification.

Step-5. Synthesis of N1,N1-dimethyl-N4-[7-(piperidin-1-yl)pyrazolo[1,5-a]pyridin-6-yl]benzene-1,4-disulfonamide (A-793)

Pyridine (0.0301 g, 381 mmol) and 4-(dimethylsulfamoyl)benzene-1-sulfonyl chloride (A82.8) (0.0791 g, 0.279 mmol) were added to 7-(piperidin-1-yl)pyrazolo[1,5-a]pyridin-6-amine (A82.7) (0.055 g, 0.254 mmol) solution in acetonitrile (10 mL). The reaction mixture was stirred at room temperature for 18 h and evaporated under reduced pressure. The residue was subjected to HPLC purification (deionized water/HPLC-grade acetonitrile) that afforded the product N1,N1-dimethyl-N4-[7-(piperidin-1-yl)pyrazolo[1,5-a]pyridin-6-yl]benzene-1,4-disulfonamide (A-793). Yield: 37.8 mg, 30.6%; Appearance: Brown solid; $^1H$ NMR (400 MHz, DMSO-$d_6$) δ 9.71 (s, 1H), 7.98 (d, J=2.2 Hz, 1H), 7.96-7.81 (m, 4H), 7.26 (dd, J=9.3, 1.9 Hz, 1H), 6.65 (d, J=9.1 Hz, 1H), 6.58 (d, J=2.1 Hz, 1H), 2.62 (s, 6H), 1.71-1.38 (m, 6H); HPLC purity: 100%; LCMS Calculated for $C_{20}H_{25}N_5O_4S_2$: 463.57; Observed: 464.2[M+H]$^+$.

Example A83: Synthesis of 4-[1-(2-{3,3-dimethyl-2-oxa-8-azaspiro[4.5]decan-8-yl}-3-fluorophenyl)ethanesulfonyl]-N,N-dimethylbenzene-1-sulfonamide (A-752)

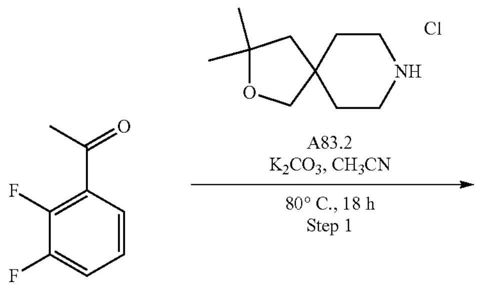

A83.1

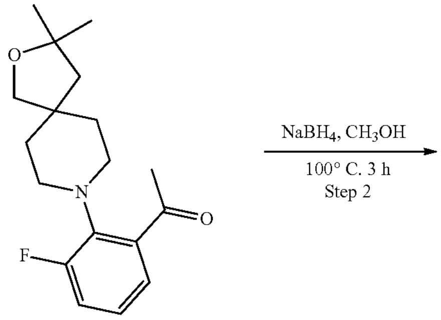

A83.3

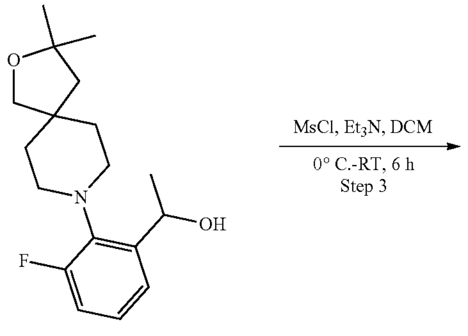

A83.4

-continued

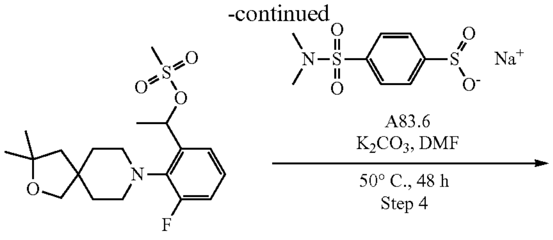

A83.5

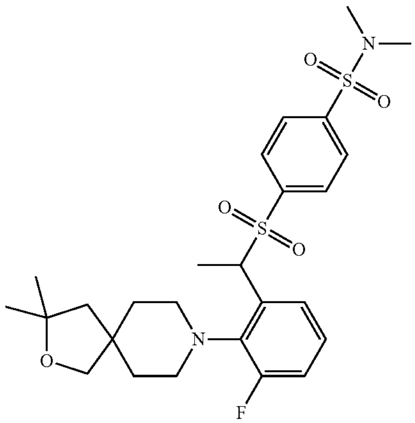

A-752

Step-1. Synthesis of 1-(2-{3,3-dimethyl-2-oxa-8-azaspiro[4.5]decan-8-yl}-3-fluorophenyl)ethan-1-one (A83.3)

1-(2,3-difluorophenyl)ethan-1-one (A83.1) (1.88 g, 12.1 mmol) was added to a stirred solution of 3,3-dimethyl-2-oxa-8-azaspiro[4.5]decane hydrochloride (A83.2) (2.5 g, 12.1 mmol) and dipotassium carbonate (4.17 g, 30.2 mmol) in dry NMP (100 mL). The mixture was stirred at 100° C. for 18 h. The reaction mixture cooled to room temperature, diluted with water (150 mL) and extracted with ethyl acetate (150 mL×3). The organic layer was washed with water (100 mL), brine (100 mL), dried over anhydrous sodium sulfate, filtered and concentrated under reduced pressure to give 1-(2-{3,3-dimethyl-2-oxa-8-azaspiro[4.5]decan-8-yl}-3-fluorophenyl)ethan-1-one as yellow oil (A83.3) (2.6 g, 8.51 mmol, 90% purity, 63.4% yield) that was used in the next step without further purification.

Step-2. Synthesis of give 1-(2-{3,3-dimethyl-2-oxa-8-azaspiro[4.5]decan-8-yl}-3-fluorophenyl)ethan-1-ol (A83.4)

Sodium boranuide (0.321 g, 8.51 mmol) was added to a stirred solution of 1-(2-{3,3-dimethyl-2-oxa-8-azaspiro[4.5]decan-8-yl}-3-fluorophenyl)ethan-1-one (A83.3) (2.6 g, 8.51 mmol) in dry methanol (150 mL) at 10° C. The mixture was stirred at room temperature for 3 h, diluted with water (150 mL) and extracted with ethyl acetate (100 mL×3). The organic layer was washed with water (100 mL), brine (100 mL), dried over anhydrous sodium sulfate, filtered and concentrated under reduced pressure to give 1-(2-{3,3-dimethyl-2-oxa-8-azaspiro[4.5]decan-8-yl}-3-fluorophenyl)ethan-1-ol as beige oil (A83.4) (2.3 g, 7.48 mmol, 95% purity, 83.5% yield).

Step-3. Synthesis of 1-(2-{3,3-dimethyl-2-oxa-8-azaspiro[4.5]decan-8-yl}-3-fluorophenyl)ethyl methanesulfonate (A83.5)

Methanesulfonyl chloride (0.222 g, 1.94 mmol) was added dropwise at 0° C. to a solution of 1-(2-{3,3-dimethyl-2-oxa-8-azaspiro[4.5]decan-8-yl}-3-fluorophenyl)ethan-1-ol (A83.4) (0.5 g, 1.62 mmol) and triethylamine (0.245 g, 2.43 mmol) in dichloromethane (10 mL). The solution was stirred for 6 h at room temperature, washed with brine (10 mL), dried over sodium sulfate, filtered and evaporated under reduced pressure to give 1-(2-{3,3-dimethyl-2-oxa-8-azaspiro[4.5]decan-8-yl}-3-fluorophenyl)ethyl methanesulfonate (A83.5) (0.7 g, 1.81 mmol, 80% purity, 89.5% yield) that was used in next step without further purification.

Step-4. Synthesis of 4-[1-(2-{3,3-dimethyl-2-oxa-8-azaspiro[4.5]decan-8-yl}-3-fluorophenyl)ethanesulfonyl]-N,N-dimethylbenzene-1-sulfonamide (A-752)

1-(2-{3,3-dimethyl-2-oxa-8-azaspiro[4.5]decan-8-yl}-3-fluorophenyl)ethyl methanesulfonate (A83.5) (0.624 g, 1.62 mmol) was added to a stirred solution of sodium 4-(dimethylsulfamoyl)benzene-1-sulfinate (A83.6) (0.526 g, 1.94 mmol) and dipotassium carbonate (0.335 g, 2.43 mmol) in dry DMF (50 mL). The mixture was stirred at 50° C. for 48 h. The reaction mixture was cooled to room temperature, diluted with water (100 mL) and extracted with ethyl acetate (2×150 mL). The organic layer was washed with water (100 mL), brine (100 mL), dried over anhydrous sodium sulfate, filtered and concentrated under reduced pressure. The residue was subjected to HPLC purification (deionized water/HPLC-grade acetonitrile) that afforded 4-[1-(2-{3,3-dimethyl-2-oxa-8-azaspiro[4.5]decan-8-yl}-3-fluorophenyl)ethanesulfonyl]-N,N-dimethylbenzene-1-sulfonamide (A-752). Yield: 152 mg, 16.5%; Appearance: Beige solid; $^1$H NMR (400 MHz, DMSO-$d_6$) δ 7.94-7.87 (m, 2H), 7.82-7.76 (m, 2H), 7.40 (t, J=7.4 Hz, 1H), 7.32 (td, J=8.2, 4.6 Hz, 1H), 7.18 (ddd, J=12.1, 8.2, 3.1 Hz, 1H), 5.40-5.33 (m, 1H), 3.64-3.57 (m, 1H), 3.56-3.50 (m, 1H), 2.89-2.78 (m, 2H), 2.62 (s, 6H), 2.57 (d, J=12.6 Hz, 1H), 1.65 (d, J=7.2 Hz, 4H), 1.60 (d, J=9.6 Hz, 3H), 1.50 (d, J=10.8 Hz, 2H), 1.36 (d, J=12.9 Hz, 1H), 1.19 (s, 6H); HPLC purity: 100%; LCMS Calculated for $C_{26}H_{35}FN_2O_5S_2$: 538.7; Observed: 539.2[M+H]$^+$.

The following example was prepared using standard chemical manipulations and procedures similar to those used for the preparation of the previous example as indicated in the table below.

| Compound No. | Structure | Analytical Data |
| --- | --- | --- |
| A-750 | 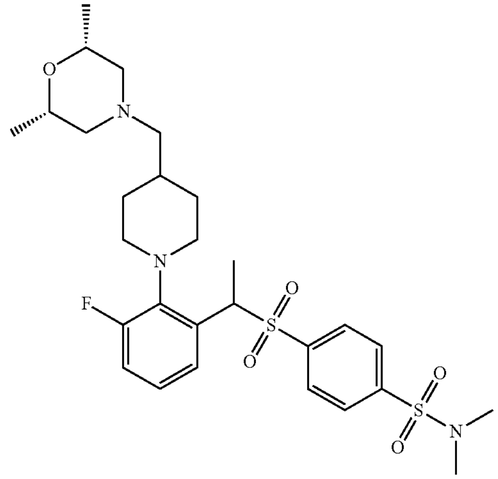 | Yield: 82.2 mg, 11.7%; Appearance: Yellow solid; $^1$H NMR (600 MHz, DMSO-$d_6$) δ 7.87 (d, J = 8.0 Hz, 2H), 7.75 (d, J = 8.0 Hz, 2H), 7.38 (d, J = 7.8 Hz, 1H), 7.28 (td, J = 8.0, 5.2 Hz, 1H), 7.15 (dd, J = 12.5, 8.2 Hz, 1H), 5.32 (t, J = 7.3 Hz, 1H), 3.50 (t, J = 8.1 Hz, 2H), 2.83 (t, J = 11.5 Hz, 1H), 2.76 (t, J = 11.8 Hz, 1H), 2.67 (td, J = 14.4, 12.7, 7.7 Hz, 3H), 2.59 (s, 6H), 2.14 – 2.07 (m, 2H), 1.66 (d, J = 10.6 Hz, 2H), 1.63 (d, J = 7.3 Hz, 3H), 1.52 (q, J = 9.6, 9.1 Hz, 4H), 1.16 (td, J = 12.2, 4.1 Hz, 1H), 1.01 (d, J = 6.2 Hz, 6H), 0.98 (d, J = 12.1 Hz, 1H); HPLC purity: 100%; LCMS Calculated for $C_{28}H_{40}FN_3O_5S_2$: 581.76; Observed: 582.4[M + H]$^+$. |

Example A84: Synthesis of N-[3-chloro-2-(piperidin-1-yl)phenyl]-4-[3-(trifluoromethyl)-3H-diazirin-3-yl]benzene-1-sulfonamide (A-749)

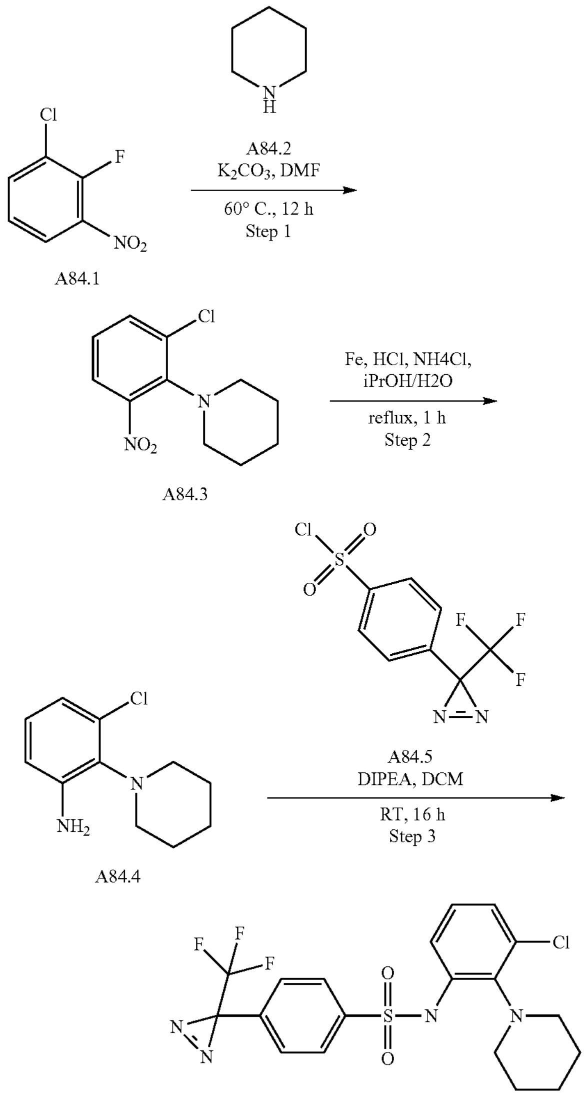

A84.1

A84.3

A84.4

A-749

Step-1. Synthesis of 1-(2-chloro-6-nitrophenyl)piperidine (A84.3)

1-chloro-2-fluoro-3-nitrobenzene (A84.1) (0.300 g, 1.7 mmol) was added to a stirred solution of piperidine (A84.2) (0.286 g, 3.4 mmol) and potassium carbonate (0.352 g, 2.55 mmol) in dry DMF (5 mL). The mixture was stirred at 60° C. until the reaction completion (TLC control) and concentrated under the reduced pressure. The residue was dissolved in ethyl acetate (15 mL), the organic layer was washed with water (15 mL×2), dried over anhydrous sodium sulfate, filtered and concentrated under reduced pressure to obtain crude 1-(2-chloro-6-nitrophenyl)piperidine as orange oil (A84.3) (0.37 g, 1.53 mmol, 95% purity, 85.8% yield).

Step-2. Synthesis of 3-chloro-2-(piperidin-1-yl)aniline (A84.4)

Iron powder (0.340 g, 6.112 mmol) and ammonium chloride (0.035 g) were added to a stirred solution of 1-(2-chloro-6-nitrophenyl)piperidine (A84.3) (0.37 g, 1.53 mmol) in a mixture of isopropanol (3.5 mL), water (0.35 mL) and conc. HCl (0.35 μL) and the resulting reaction mixture was refluxed for 1 h. After the reaction completion (TLC control) the mixture was filtered through silica, silica was washed with ethyl acetate (40 mL). The filtrate was partitioned between water (40 mL) and ethyl acetate (40 mL). The organic layer was washed with water (40 mL), dried over anhydrous sodium sulfate and evaporated under reduced pressure that afforded 3-chloro-2-(piperidin-1-yl) aniline (A84.4) (0.27 g, 1.28 mmol, 95% purity, 79.5% yield).

Step-3. Synthesis of N-(3-chloro-2-(piperidin-1-yl)phenyl)-4-(3-(trifluoromethyl)-3H-diazirin-3-yl)benzenesulfonamide (A-749)

4-(3-(trifluoromethyl)-3H-diazirin-3-yl)benzenesulfonyl chloride (A84.5) (0.398 g, 1.4 mmol) was added to the mixture of 3-chloro-2-(piperidin-1-yl)aniline (A84.4) (0.270 g, 1.28 mmol) and ethylbis(propan-2-yl)amine (0.248 g, 1.92 mmol) in dry dichloromethane (5 mL). The reaction mixture was stirred overnight and poured into $NaHCO_3$ sat. aq. solution (15 mL). The product was and extracted with dichloromethane (20 mL×2). Combined organic layer was dried over anhydrous sodium sulfate, filtered and evaporated under reduced pressure. Resulting solid was purified by HPLC (deionized water/HPLC-grade acetonitrile) to afford N-[3-chloro-2-(piperidin-1-yl)phenyl]-4-[3-(trifluoromethyl)-3H-diazirin-3-yl]benzene-1-sulfonamide (A-749). Yield: 239.6 mg, 38.6%; Appearance: Yellow solid; $^1$H NMR (600 MHz, DMSO-$d_6$) δ 9.07 (s, 1H), 7.83 (d, J=8.5 Hz, 2H), 7.47 (d, J=8.3 Hz, 2H), 7.21 (dd, J=7.8, 1.7 Hz, 1H), 7.16-7.05 (m, 2H), 3.10 (s, 2H), 2.26 (s, 2H), 1.59 (s, 1H), 1.51-1.44 (m, 3H), 1.26 (s, 1H); HPLC purity: 98.57%; LCMS Calculated for $C_{19}H_{18}ClF_3N_4O_2S$: 458.88; Observed: 459.2[M+H]$^+$.

Example A85: Synthesis of N-{2-[4-(methoxymethyl)-4-methylpiperidin-1-yl]phenyl}-4-[3-(trifluoromethyl)-3H-diazirin-3-yl]benzene-1-sulfonamide (A-740)

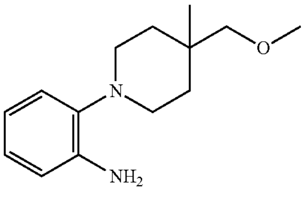

+

A85.1

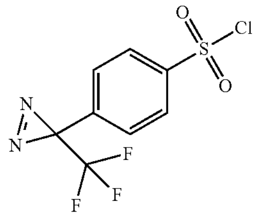

+

A85.2

-continued

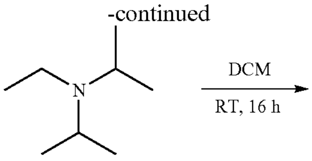

A85.3

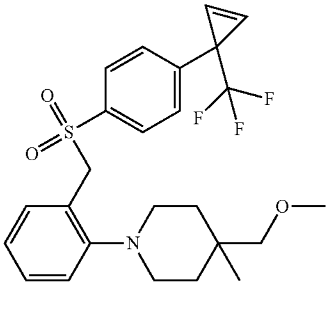

A-740

4-(3-(trifluoromethyl)-3H-diazirin-3-yl)benzenesulfonyl chloride (A85.2) (0.242 g, 0.853 mmol) was added to the mixture of 2-(4-(methoxymethyl)-4-methylpiperidin-1-yl) aniline (A85.1) (0.2 g, 0.853 mmol) and ethylbis(propan-2-yl)amine (A85.3) (0.164 g, 1.27 mmol) in dry dichloromethane (5 mL). The reaction mixture was stirred overnight and poured into $NaHCO_3$ sat. aq. solution (15 mL). The product was extracted with dichloromethane (20 mL). Combined organic layer was dried over anhydrous sodium sulfate, filtered and evaporated under reduced pressure. Resulting solid was purified by HPLC (deionized water/HPLC-grade acetonitrile) to afford N-{2-[4-(methoxymethyl)-4-methylpiperidin-11-yl]phenyl}-4-[3-(trifluoromethyl)-3H-diazirin-3-yl]benzene-Y-sulfonamide (A-740). Yield: 170.2 mg, 39.1%; Appearance: Yellow oil; $^1$H NMR (500 MHz, DMSO-$d_6$) δ 9.01 (s, 1H), 7.87-7.80 (m, 2H), 7.45 (dd, J=8.7, 2.9 Hz, 2H), 7.21 (dt, J=7.9, 2.1 Hz, 1H), 7.17 (dd, J=8.0, 1.8 Hz, 1H), 7.09 (ddd, J 10.3, 5.8, 2.2 Hz, 1H), 7.02 (tt, J 7.9, 2.2 Hz, 1H), 3.27 (s, 3H), 3.08 (d, J 3.1 Hz, 2H), 2.40 (dd, J=12.5, 4.9 Hz, 2H), 1.43 (tt, J=9.4, 3.8 Hz, 2H), 1.24-1.14 (m, 2H), 0.89 (d, J=3.1 Hz, 3H); HPLC purity: 98.45; LCMS Calculated for $C_{22}H_{25}F_3N_4O_3S$: 482.52; Observed: 483.2[M+H]$^+$.

The following examples were prepared using standard chemical manipulations and procedures similar to those used for the preparation of the previous example.

| Compound No. | Structure | Analytical Data |
|---|---|---|
| A-776 | 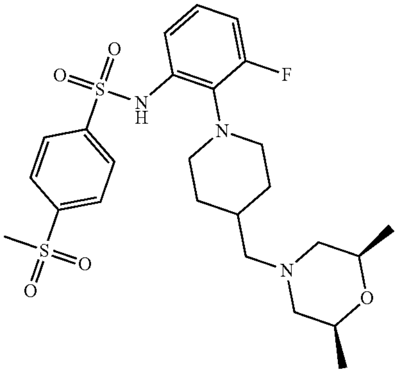 | Yield: 89 mg, 33.6%; Appearance: Beige solid; $^1$H NMR (600 MHz, DMSO-$d_6$) δ 9.20 (s, 1H), 8.11 - 8.06 (m, 2H), 8.01 - 7.96 (m, 2H), 7.21 - 7.12 (m, 2H), 6.96 - 6.91 (m, 1H), 3.54 - 3.47 (m, 2H), 3.24 (s, 3H), 2.78 (t, J = 11.5 Hz, 2H), 2.68 (d, J = 10.7 Hz, 2H), 2.36 - 2.31 (m, 2H), 2.08 (d, J = 6.8 Hz, 2H), 1.52 (h, J = 8.0, 7.3 Hz, 5H), 1.19 - 1.12 (m, 2H), 1.01 (d, J = 6.2 Hz, 6H); HPLC purity: 100%; LCMS Calculated for $C_{25}H_{34}FN_3O_5S_2$: 539.68; Observed: 540.0 [M + H]$^+$. |
| A-760 | 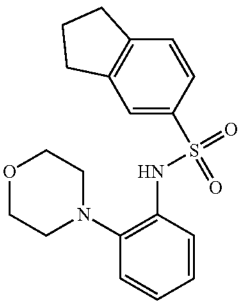 [SMILES: O=S(=O)(Nc1ccccc1N1CCOCC1)c1ccc2c(c1)CCC2] | Yield: 221.7 mg, 58.9%; Appearance: Light brown solid; $^1$H NMR (400 MHz, DMSO-δ 8.86 (s, 1H), 7.65 (s, 1H), 7.49 (dd, J = 7.8, 1.8 Hz, 1H), 7.35 - 7.29 (m, 2H), 7.16 (dt, J = 8.1, 3.0 Hz, 1H), 7.11 - 7.04 (m, 2H), 3.63 (t, J = 4.6 Hz, 4H), 2.86 (t, J = 7.3 Hz, 4H), 2.46 (d, J = 4.6 Hz, 4H), 2.01 (p, J = 7.4 Hz, 2H); HPLC purity: 100%; LCMS Calculated for $C_{19}H_{22}N_2O_3S$: 358.46; Observed: 359.0[M + H]$^+$. |

Example A86: Synthesis of N4-(2-{4-[(3,5-dimethylmorpholin-4-yl)methyl]piperidin-1-yl}-3-fluorophenyl)-N1,N1-dimethylbenzene-1,4-disulfonamide (A-763)

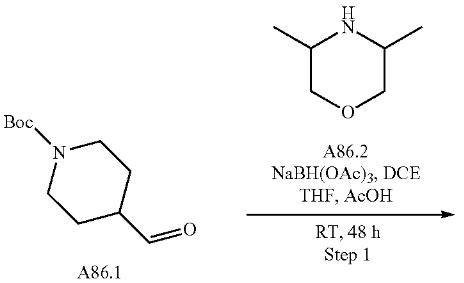

A86.1

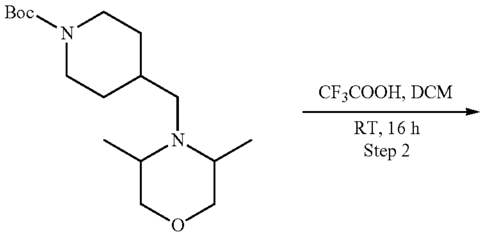

A86.3

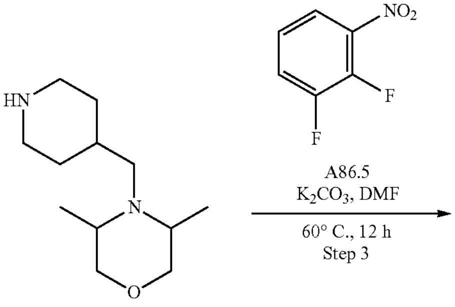

A86.4

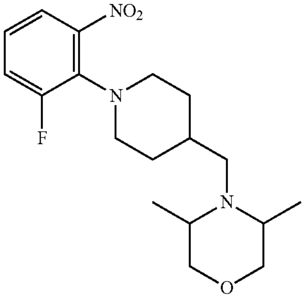

A86.6

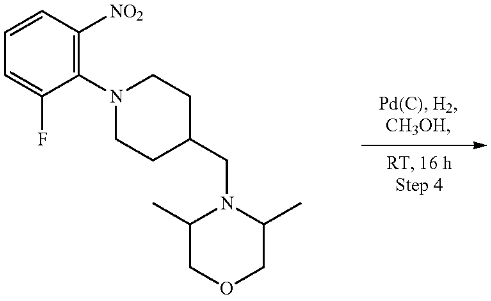

A86.6

-continued

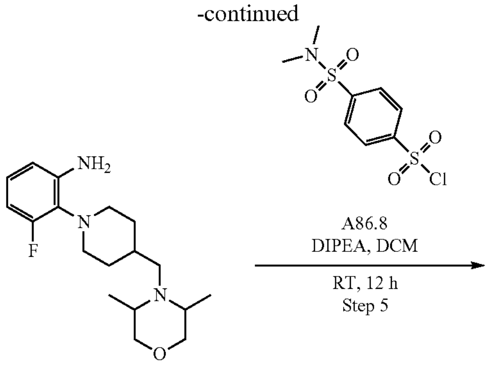

A86.7

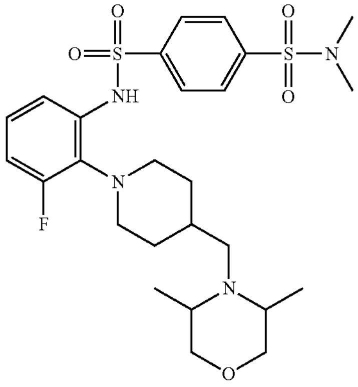

A-763

Step-1. Synthesis of tert-butyl 4-((3,5-dimethylmorpholino)methyl)piperidine-1-carboxylate (A86.3)

3,5-dimethylmorpholine (A86.2) (2.15 g, 18.7 mmol) and acetic acid (0.4 mL) were added to a solution of tert-butyl 4-formylpiperidine-1-carboxylate (A86.1) (2 g, 9.37 mmol) in DCE/THF (40 mL/4 mL). After the mixture was stirred for several minutes, and $NaBH(OAc)_3$ (3.96 g, 18.7 mmol) was added. The mixture was stirred at room temperature for 2 days and poured after into sat aq $NaHCO_3$ solution (50 mL). The product was extracted with EtOAc (50 mL×2). The combined organic layers were dried over sodium sulfate, filtered, and concentrated under reduced pressure. Flash column chromatography of residue (hexane/MTBE) afforded tert-butyl 4-((3,5-dimethylmorpholino)methyl)piperidine-1-carboxylate (A86.3) (1.2 g, 3.84 mmol, 100% purity, 41.0% yield).

Step-2. Synthesis of 3,5-dimethyl-4-[(piperidin-4-yl)methyl]morpholine (A86.4)

TFA (3 mL) was added in one portion to a stirred solution of tert-butyl 4-((3,5-dimethylmorpholino)methyl)piperidine-1-carboxylate (A86.3) (1.2 g, 3.84 mmol) in dichloromethane (5 mL). The resulting mixture was stirred overnight and evaporated. Crude residue was treated with 2 M NaOH aq. solution to pH=12 and the product was extracted with DCM (20 mL×3). Combined organic layers were dried over sodium sulfate, filtered and evaporated to afford 3,5-dimethyl-4-[(piperidin-4-yl)methyl]morpholine (A86.4) (0.55 g, 2.59 mmol, 95% purity, 64% yield).

Step-3. Synthesis of 4-{[1-(2-fluoro-6-nitrophenyl)piperidin-4-yl]methyl}-3,5-dimethylmorpholine (A86.6)

1,2-difluoro-3-nitrobenzene (A86.5) (0.186 g, 1.17 mmol) was added to a stirred solution of 3,5-dimethyl-4-(piperidin-4-ylmethyl)morpholine (0.250 g, 1.17 mmol) and potassium carbonate (0.241 g, 1.75 mmol) in dry DMF (5 mL). The mixture was stirred at 60° C. until the reaction completion (TLC control) and concentrated under the reduced pressure. The residue was dissolved in ethyl acetate (15 mL), the organic layer was washed twice with water (15 mL), dried over anhydrous sodium sulfate, filtered and concentrated under reduced pressure to obtain 4-{[1-(2-fluoro-6-nitrophenyl)piperidin-4-yl]methyl}-3,5-dimethylmorpholine as orange oil (A86.6) (0.31 g, 0.882 mmol, 100% purity, 75.4% yield).

Step-4. Synthesis of 2-{4-[(3,5-dimethylmorpholin-4-yl)methyl]piperidin-1-yl}-3-fluoroaniline (A86.7)

4-((1-(2-fluoro-6-nitrophenyl)piperidin-4-yl)methyl)-3,5-dimethylmorpholine (A86.6) (0.31 g, 0.882 mmol) was dissolved in methanol (10 mL) and treated with 10% Pd/C (0.05 g). The resulting mixture was hydrogenated at 6 atm and room temperature until the reaction was completed (TLC control). The catalyst was filtered off and the filtrate was evaporated to afford 2-{4-[(3,5-dimethylmorpholin-4-yl)methyl]piperidin-1-yl}-3-fluoroaniline (A86.7) (0.28 g, 0.871 mmol, 95% purity, 93.9% yield).

Step-5. Synthesis of N4-(2-{4-[(3,5-dimethylmorpholin-4-yl)methyl]piperidin-1-yl}-3-fluorophenyl)-N1,N1-dimethylbenzene-1,4-disulfonamide (A-763)

4-(N,N-dimethylsulfamoyl)benzenesulfonyl chloride (0.271 g, 0.958 mmol) was added to the mixture of 2-(4-((3,5-dimethylmorpholino)methyl)piperidin-1-yl)-3-fluoroaniline (0.28 g, 0.871 mmol) and DIPEA (0.168 g, 1.30 mmol) in dry DCM (5 mL). The reaction mixture was stirred overnight and poured into sat. aq. $NaHCO_3$ solution (15 mL). The product was extracted with dichloromethane (20 mL×2). Combined organic layers was dried over anhydrous sodium sulfate, filtered and evaporated under reduced pressure. Resulting solid was purified by HPLC (deionized water/HPLC-grade acetonitrile) to afford N4-(2-{4-[(3,5-dimethylmorpholin-4-yl)methyl]piperidin-1-yl}-3-fluorophenyl)-N1,N1-dimethylbenzene-1,4-disulfonamide as beige solid (0.0715 g, 0.125 mmol, 95% purity, 13.7% yield). The analytical data provided for this compound provisionally supports the proposed structure for N4-(2-{4-[(3,5-dimethylmorpholin-4-yl)methyl]piperidin-1-yl}-3-fluorophenyl)-N1,N1-dimethylbenzene-1,4-disulfonamide (A-763). Yield: 71.5 mg, 13.7%; Appearance: Beige solid; $^1H$ NMR (400 MHz, DMSO-$d_6$) δ 9.20 (s, 1H), 8.01-7.91 (m, 4H), 7.26-7.16 (m, 2H), 6.97 (t, J=10.2 Hz, 1H), 3.54 (dd, J=10.8, 3.1 Hz, 2H), 3.23 (s, 2H), 2.91-2.64 (m, 6H), 2.61 (d, J=2.6 Hz, 6H), 2.46-2.05 (m, 4H), 1.57 (dd, J=32.6, 12.3 Hz, 2H), 1.20 (dd, J=23.4, 11.6 Hz, 2H), 0.91 (dd, J=6.3, 2.7 Hz, 6H); HPLC purity: 100%; LCMS Calculated for $C_{26}H_{37}FN_4O_5S_2$: 568.72; Observed: 569.0[M+H]$^+$.

The following examples were prepared using standard chemical manipulations and procedures similar to those used for the preparation of the previous example.

| Compound No. | Structure | Analytical Data |
| --- | --- | --- |
| A-748 | 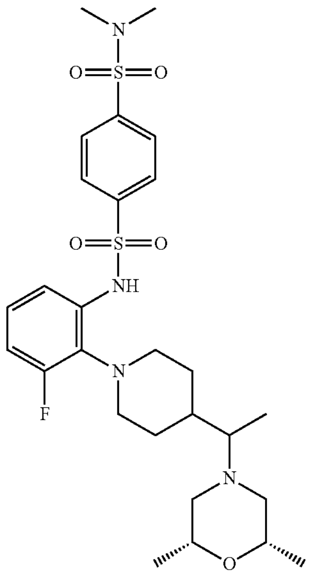 [SMILES: CC(C1CCN(c2c(F)cccc2NS(=O)(=O)c2ccc(S(=O)(=O)N(C)C)cc2)CC1)N1C[C@@H](C)O[C@@H](C)C1] | Yield: 157.3 mg, 32.2%; Appearance: Beige solid; $^1H$ NMR (400 MHz, DMSO-$d_6$) δ 9.19 (s, 1H), 8.00 - 7.91 (m, 4H), 7.25 - 7.14 (m, 2H), 7.02 - 6.92 (m, 1H), 3.54 (t, J = 8.0 Hz, 1H), 3.48 - 3.40 (m, 1H), 2.83 - 2.72 (m, 2H), 2.61 (s, 6H), 2.45 (d, J = 10.4 Hz, 2H), 2.36 - 2.29 (m, 2H), 2.25 - 2.17 (m, 1H), 2.10 (t, J = 10.4 Hz, 1H), 1.82 (d, J = 12.8 Hz, 1H), 1.72 (t, J = 10.5 Hz, 1H), 1.49 (d, J = 12.2 Hz, 1H), 1.32 (d, J = 10.2 Hz, 1H), 1.18 (d, J = 12.8 Hz, 2H), 1.03 (t, J = 6.4 Hz, 6H), 0.86 (d, J = 6.5 Hz, 3H); HPLC purity: 100%; LCMS Calculated for $C_{27}H_{39}FN_4O_5S_2$: 585.75; Observed: 583.2[M + H]$^+$. |

-continued

| Compound No. | Structure | Analytical Data |
|---|---|---|
| A-762 | 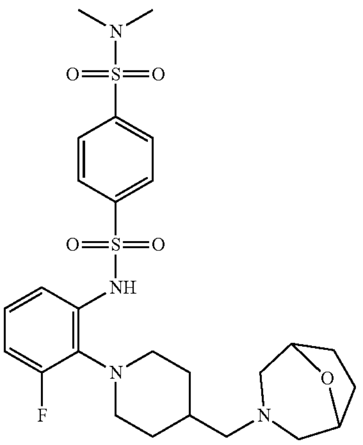 [SMILES: CN(C)S(=O)(=O)c1ccc(S(=O)(=O)Nc2cccc(F)c2N2CCC(CN3CC4CCC(C3)O4)CC2)cc1] | Yield: 46.9 mg, 16.7%; Appearance: Beige solid; $^1$H NMR (400 MHz, DMSO-$d_6$) δ 9.13 (s, 1H), 7.94 (d, J = 8.5 Hz, 2H), 7.88 (d, J = 8.5 Hz, 2H), 7.24 - 7.11 (m, 2H), 6.98 - 6.90 (m, 1H), 4.14 (s, 2H), 2.74 (t, J = 11.4 Hz, 2H), 2.57 (s, 6H), 2.25 (d, J = 11.1 Hz, 2H), 2.07 (t, J = 8.4 Hz, 4H), 1.77 (d, J = 6.6 Hz, 2H), 1.66 (d, J = 6.7 Hz, 2H), 1.50 (d, J = 13.0 Hz, 2H), 1.42 (s, 1H), 1.17 (t, J = 11.8 Hz, 2H); HPLC purity: 100%; LCMS Calculated for $C_{26}H_{35}FN_4O_5S_2$: 566.71; Observed: 567.2[M + H]$^+$. |
| A-787 | 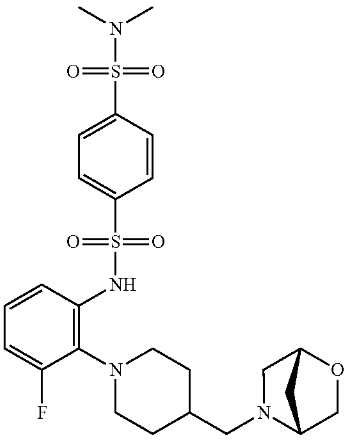 [SMILES: CN(C)S(=O)(=O)c1ccc(S(=O)(=O)Nc2cccc(F)c2N2CCC(CN3C[C@H]4C[C@@H]3CO4)CC2)cc1] | Yield: 8.3 mg, 1.43%; Appearance: Beige solid; $^1$H NMR (400 MHz, DMSO-$d_6$) δ 8.01 - 7.75 (m, 4H), 7.22 (d, J = 7.9 Hz, 1H), 7.15 (s, 1H), 4.30 (s, 1H), 3.82 (d, J = 7.4 Hz, 1H), 3.49 (d, J = 7.5 Hz, 1H), 2.77 (d, J = 9.8 Hz, 3H), 2.61 (d, J = 1.4 Hz, 6H), 2.43 (d, J = 5.7 Hz, 2H), 2.40 - 2.24 (m, 4H), 1.70 (d, J = 9.4 Hz, 1H), 1.66 - 1.49 (m, 3H), 1.22 (d, J = 13.1 Hz, 3H); HPLC purity: 100%; LCMS Calculated for $C_{25}H_{33}FN_4O_5S_2$: 552.68; Observed: 553.2[M + H]$^+$. |
| A-785 | 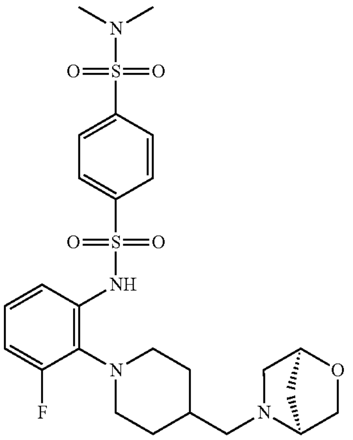 [SMILES: CN(C)S(=O)(=O)c1ccc(S(=O)(=O)Nc2cccc(F)c2N2CCC(CN3C[C@@H]4C[C@H]3CO4)CC2)cc1] | Yield: 21.7 mg, 3.75%; Appearance: Beige solid; $^1$H NMR (600 MHz, DMSO-$d_6$) δ 9.25 (s, 1H), 7.94 (d, J = 8.4 Hz, 2H), 7.89 (d, J = 8.3 Hz, 2H), 7.20 (d, J = 8.2 Hz, 1H), 7.18 - 7.12 (m, 1H), 6.93 (dd, J = 12.0, 8.3 Hz, 1H), 4.28 (s, 1H), 3.79 (d, J = 7.4 Hz, 1H), 3.46 (dd, J = 7.5, 1.7 Hz, 1H), 2.81 - 2.69 (m, 3H), 2.58 (s, 6H), 2.41 (d, J = 6.7 Hz, 1H), 2.36 - 2.26 (m, 4H), 1.67 (dd, J = 9.4, 2.1 Hz, 1H), 1.58 - 1.49 (m, 3H), 1.30 (s, 1H), 1.19 (dt, J = 13.2, 6.7 Hz, 2H); HPLC purity: 100%; LCMS Calculated for $C_{25}H_{33}FN_4O_5S_2$: 552.68; Observed: 553.2[M + H]$^+$. |

Example A87: Synthesis of N4-3-fluoro-2-[4-(3-oxa-6-azabicyclo[3.1.1]heptan-6-ylmethyl)piperidin-1-yl]phenyl-N1,N1-dimethylbenzene-1,4-disulfonamide (A-778)

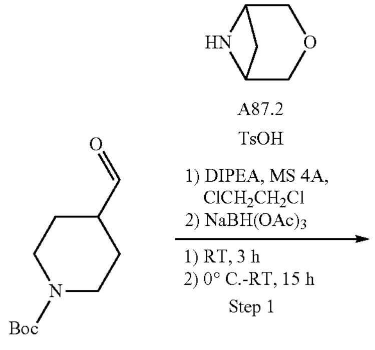

A87.1

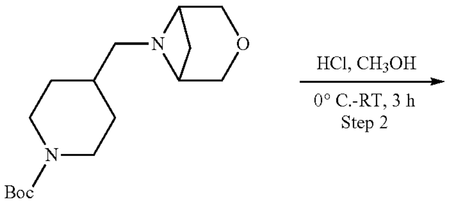

A87.3

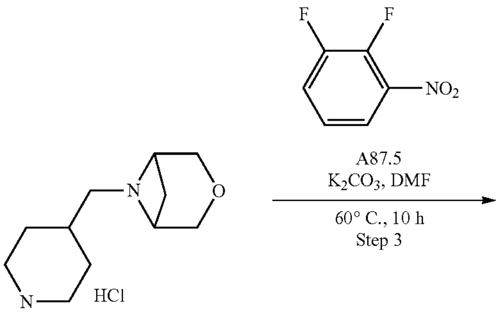

A87.4

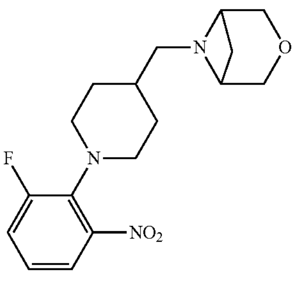

A87.6

-continued

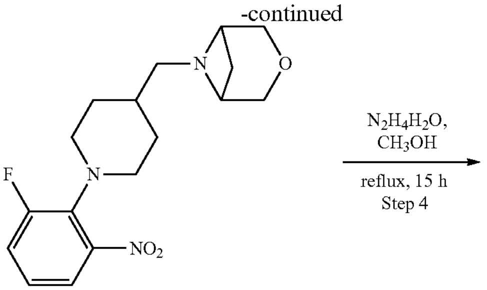

A87.6

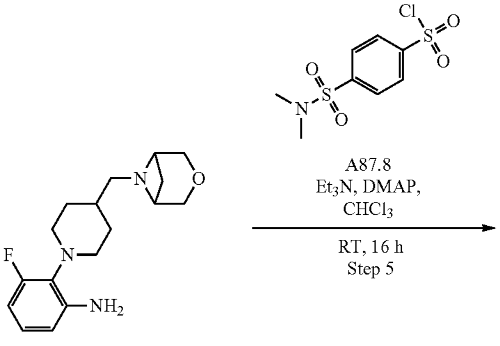

A87.7

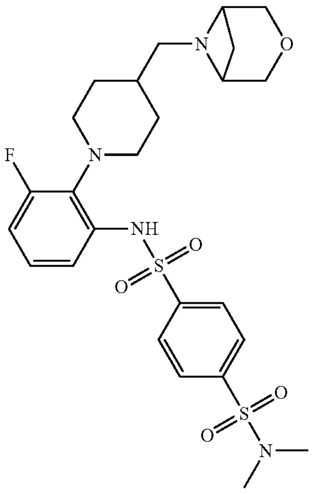

A-778

Step-1. Synthesis of tert-butyl 4-(3-oxa-6-azabicyclo[3.1.1]heptan-6-ylmethyl)piperidine-1-carboxylate (A87.3)

A mixture of 3-oxa-6-azabicyclo[3.1.1]heptane 4-methylbenzene-1-sulfonate (A87.2) (0.2 g, 0.737 mmol), tert-butyl 4-formylpiperidine-1-carboxylate (A87.1) (0.2 g, 0.937 mmol), ethylbis(propan-2-yl)amine (0.109 g, 0.843 mmol) and crushed 4 Å molecular sieves (0.3 g) in DCE (30 mL) in dichloroethane (30 mL) was stirred at room temperature for 5 h. Sodium bis(acetyloxy)boranuidyl acetate (2.15 g, 10.1 mmol) was added and the reaction mixture was stirred at room temperature for 16 hours. Then, the mixture was filtered through celite, celite was washed with dichloroethane (30 mL×2) and the combined filtrates were concentrated in vacuo. The residue was purified by flash chromatography (methanol/dichloromethane) to give tert-butyl 4-(3-oxa-6-azabicyclo[3.1.1]heptan-6-ylmethyl)piperidine-1-carboxylate (A87.3) (0.130 g, 0.438 mmol, 90% purity, 42.2% yield).

Step-2. Synthesis of 6-[(piperidin-4-yl)methyl]-3-oxa-6-azabicyclo[3.1.1]heptane Dihydrochloride (A87.4)

3N HCl solution in methanol (3 mL) was added dropwise to a solution of tert-butyl 4-({3-oxa-6-azabicyclo[3.1.1]heptan-6-yl}methyl)piperidine-1-carboxylate (A87.3) (0.13 g, 0.438 mmol) in methanol (5 mL) keeping the temperature at 0° C. The mixture was stirred at this temperature for 3 h and evaporated under reduced pressure to give 6-[(piperidin-4-yl)methyl]-3-oxa-6-azabicyclo[3.1.1]heptane dihydrochloride (A87.4) (0.1 g, 0.371 mmol, 100% purity, 85.4% yield).

Step-3. Synthesis of give 6-[1-(2-fluoro-6-nitrophenyl)piperidin-4-yl]methyl-3-oxa-6-azabicyclo[3.1.1]heptane (A87.6)

Potassium carbonate (0.206 g, 1.48 mmol) was added to the solution of 6-[(piperidin-4-yl)methyl]-3-oxa-6-azabicyclo[3.1.1]heptane dihydrochloride (A87.4) (0.1 g, 0.371 mmol) and 1,2-difluoro-3-nitrobenzene (A87.5) (0.0593 g, 0.372 mmol) in DMF (10 mL). Obtained mixture was stirred at 60° C. for 10 h, cooled to room temperature and poured into water (50 mL). The product was extracted with MTBE (15 mL×3). Combined organic layers were washed with water (15 mL×3) and brine (20 mL), dried over sodium sulfate, filtered and evaporated under reduced pressure to give 6-[1-(2-fluoro-6-nitrophenyl)piperidin-4-yl]methyl-3-oxa-6-azabicyclo[3.1.1]heptane as yellow crystals (A87.6) (0.09 g, 0.268 mmol, 95% purity, 59.7% yield).

Step-4. Synthesis of 3-fluoro-2-[4-(3-oxa-6-azabicyclo[3.1.1]heptan-6-ylmethyl)piperidin-1-yl]aniline (A87.7)

10% Pd/C (0.2 g) was added to a stirred solution 6-[1-(2-fluoro-6-nitrophenyl)piperidin-4-yl]methyl-3-oxa-6-azabicyclo[3.1.1]heptane (A87.6) (0.09 g, 0.268 mmol) in methanol (1 mL) followed by addition of hydrazine hydrate (0.2016 g, 4.09 mmol) dropwise to the mixture keeping the temperature below 40° C. After refluxing for 15 h the mixture was cooled to room temperature and filtered. The filtrate was evaporated under reduced pressure, the residue was dissolved in dichloromethane (50 mL). This solution was washed with water (50 mL×2), dried over sodium sulfate, filtered and evaporated under reduced pressure to give 3-fluoro-2-[4-(3-oxa-6-azabicyclo[3.1.1]heptan-6-ylmethyl)piperidin-1-yl]aniline as colorless oil (A87.7) (0.075 g, 0.245 mmol, 100% purity, 91.6% yield).

Step-5. Synthesis of N4-3-fluoro-2-[4-(3-oxa-6-azabicyclo[3.1.1]heptan-6-ylmethyl)piperidin-1-yl]phenyl-N1,N1-dimethylbenzene-1,4-disulfonamide (A-778)

4-(Dimethylsulfamoyl)benzene-1-sulfonyl chloride (A87.8) (0.0768 g, 0.27 mmol) was added to a solution of 3-fluoro-2-[4-({3-oxa-6-azabicyclo[3.1.1]heptan-6-yl}methyl)piperidin-1-yl]aniline (A87.7) (0.0752 g, 0.246 mmol), triethylamine (0.062 g, 0.612 mmol) and N,N-dimethylpyridin-4-amine (0.003 g, 0.0245 mmol) in chloroform (5 mL) and the reaction mixture was stirred at room temperature overnight. The solvent was evaporated under reduced pressure and residue was subjected to HPLC purification (deionized water/HPLC-grade acetonitrile) to afford the product N4-3-fluoro-2-[4-(3-oxa-6-azabicyclo[3.1.1]heptan-6-ylmethyl)piperidin-1-yl]phenyl-N1,N1-dimethylbenzene-1,4-disulfonamide (A-778). Yield: 8 mg, 5.62%; Appearance: Beige solid; $^1$H NMR (500 MHz, DMSO-$d_6$) δ 7.97-7.88 (m, 4H), 7.23-7.15 (m, 2H), 6.97 (d, J=10.9 Hz, 1H), 4.12 (s, 2H), 3.62 (s, 2H), 2.74 (d, J=11.4 Hz, 2H), 2.60 (s, 6H), 2.27 (d, J=11.0 Hz, 2H), 1.72 (s, 1H), 1.56 (d, J=11.8 Hz, 2H), 1.28 (s, 3H); HPLC purity: 98.09%; LCMS Calculated for $C_{25}H_{33}FN_4O_5S_2$: 552.68; Observed: 553.0[M+H]$^+$.

The following example was prepared using standard chemical manipulations and procedures similar to those used for the preparation of the previous example.

| Compound No. | Structure | Analytical Data |
|---|---|---|
| A-790 | 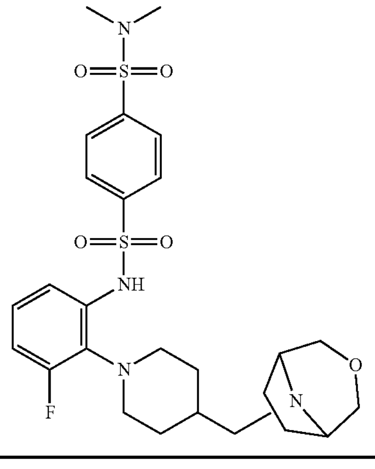 | Yield: 40.3 mg, 7.18%; Appearance: Beige solid; $^1$H NMR (400 MHz, DMSO-$d_6$) δ 9.19 (s, 1H), 7.99 - 7.90 (m, 4H), 7.27 - 7.17 (m, 2H), 6.97 (t, J = 9.8 Hz, 1H), 3.49 (d, J = 10.1 Hz, 2H), 3.39 (d, J = 10.2 Hz, 2H), 2.98 (s, 2H), 2.78 (t, J = 11.4 Hz, 2H), 2.61 (d, J = 1.7 Hz, 6H), 2.30 (d, J = 11.7 Hz, 2H), 2.10 (d, J = 7.3 Hz, 2H), 1.81 (s, 2H), 1.66 (dd, J = 20.0, 10.1 Hz, 4H), 1.38 (s, 1H), 1.22 (t, J = 12.1 Hz, 2H) HPLC purity: 100%; LCMS Calculated for $C_{26}H_{35}FN_4O_5S_2$: 566.71; Observed: 567.2[M + H]$^+$ |

Example A88: Synthesis of N4-{3-fluoro-2-[4-({6-oxa-3-azabicyclo[3.1.1]heptan-3-yl}methyl)piperidin-1-yl]phenyl}-N1,N1-dimethylbenzene-1,4-disulfonamide (A-791)

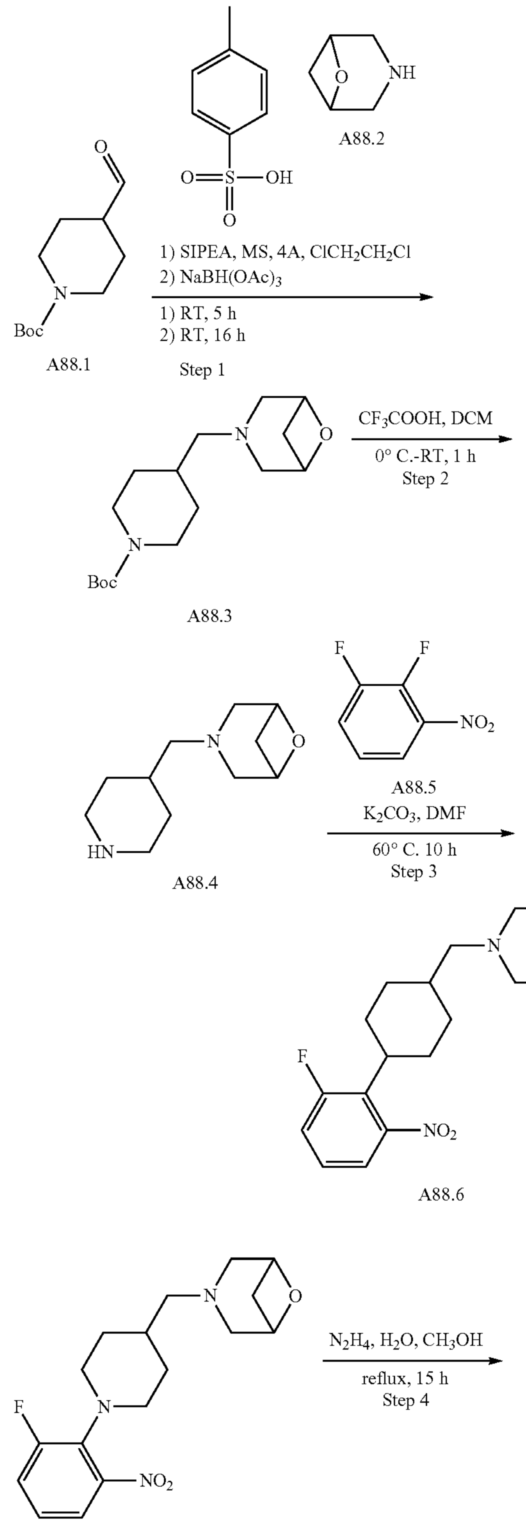

A88.1, A88.2, A88.3, A88.4, A88.5, A88.6, A88.6

-continued

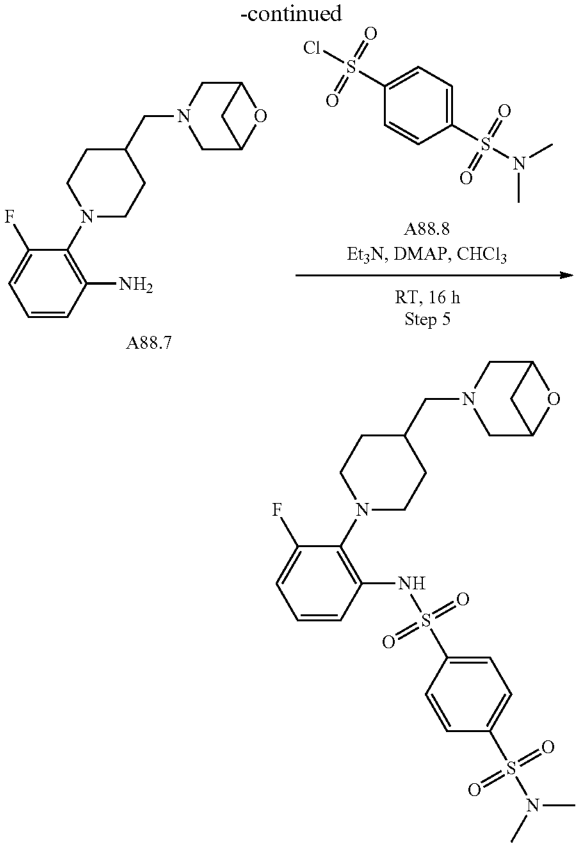

A88.7, A88.8, A-791

Step-1. Synthesis of tert-butyl 4-(6-oxa-3-azabicyclo[3.1.1]heptan-3-ylmethyl)piperidine-1-carboxylate (A88.3)

A mixture of 4-methylbenzene-1-sulfonic acid; 6-oxa-3-azabicyclo[3.1.1]heptane (A88.2) (0.5 g, 1.84 mmol), tert-butyl 4-formylpiperidine-1-carboxylate (A88.1) (0.392 g, 1.84 mmol), ethylbis(propan-2-yl)amine (0.262 g, 2.02 mmol) and crushed 4 Å molecular sieves (0.3 g) in DCE (30 mL) was stirred at ambient temperature for 5 hours. Sodium bis(acetyloxy)boranuidyl acetate (0.781 g, 3.68 mmol) was added and the reaction was stirred at room temperature for further 16 hours. Then the mixture was filtered through celite, celite was washed with DCM (30 mL×2) and the combined filtrates were concentrated in vacuo to give tert-butyl 4-(6-oxa-3-azabicyclo[3.1.1]heptan-3-ylmethyl)piperidine-1-carboxylate as colorless oil (A88.3) (0.4 g, 1.34 mmol, 95% purity, 69.7% yield).

Step-2. Synthesis of 3-[(piperidin-4-yl)methyl]-6-oxa-3-azabicyclo[3.1.1]heptane; bis(trifluoroacetic Acid) (A88.4)

Trifluoroacetic acid (7.39 g, 64.8 mmol, 5.0 mL) was added to the stirred solution of tert-butyl 4-(6-oxa-3-azabicyclo[3.1.1]heptan-3-ylmethyl)piperidine-1-carboxylate (A88.3) (0.400 g, 1.34 mmol) in dichloromethane (5 mL). The resulting mixture was stirred at room temperature for 4 h, then the solvent was evaporated in vacuo affording 3-[(piperidin-4-yl)methyl]-6-oxa-3-azabicyclo[3.1.1]heptane; bis(trifluoroacetic acid) as white solid (A88.4) (0.6 g, 1.41 mmol, 90% purity, 95% yield) that was used in next step without further purification.

Step-3. Synthesis of 3-[1-(2-fluoro-6-nitrophenyl) piperidin-4-yl]methyl-6-oxa-3-azabicyclo[3.1.1] heptane (A88.6)

Potassium carbonate (0.781 g, 5.65 mmol) was added to the solution of 3-[(piperidin-4-yl)methyl]-6-oxa-3-azabicyclo[3.1.1]heptane; bis(trifluoroacetic acid) (A88.4) (0.6 g, 1.41 mmol) and 1,2-difluoro-3-nitrobenzene (A88.5) (0.224 g, 1.41 mmol) in DMF (10 mL). Obtained mixture was stirred at 60° C. for 10 h, then poured into water (50 mL) and extracted with MTBE (15 mL×3). Combined organic layers were washed with water (15 mL×3) and brine (20 mL), dried over sodium sulfate, filtered and evaporated to give 3-[1-(2-fluoro-6-nitrophenyl)piperidin-4-yl]methyl-6-oxa-3-azabicyclo[3.1.1]heptane as yellow oil (A88.6) (0.42 g, 1.25 mmol, 85.4% purity, 75.8% yield) that was used in next step without further purification.

Step-4. Synthesis of 3-fluoro-2-[4-(6-oxa-3-azabicyclo[3.1.1]heptan-3-ylmethyl)piperidin-1-yl]aniline (A88.7)

10% Palladium (0.013 g, 0.125 mmol) was added to a stirred solution 3-[1-(2-fluoro-6-nitrophenyl)piperidin-4-yl]methyl-6-oxa-3-azabicyclo[3.1.1]heptane (A88.6) (0.42 g, 1.25 mmol) in methanol (5 mL) followed by addition of hydrazine hydrate (0.939 g, 18.76 mmol, 1.57 mL) dropwise to the mixture keeping the temperature below 40° C. After refluxing for 15 h the mixture was cooled to room temperature and filtered. The filtrate was evaporated under reduced pressure, the residue was dissolved in DCM (50 mL). This solution was washed with water (50 mL×2), dried over sodium sulfate, filtered and evaporated under reduced pressure to give 3-fluoro-2-[4-(6-oxa-3-azabicyclo[3.1.1]heptan-3-ylmethyl)piperidin-1-yl]aniline as white crystals (A88.7) (0.34 g, 1.11 mmol, 95.0% purity, 84.6% yield).

Step-5. Synthesis of N4-{3-fluoro-2-[4-({6-oxa-3-azabicyclo[3.1.1]heptan-3-yl}methyl)piperidin-1-yl] phenyl}-N1,N1-dimethylbenzene-1,4-disulfonamide (A-791)

Solution of 3-fluoro-2-[4-(6-oxa-3-azabicyclo[3.1.1]heptan-3-ylmethyl)piperidin-1-yl]aniline (A88.7) (0.15 g, 0.491 mmol), 4-(Dimethylsulfamoyl)benzene-1-sulfonyl chloride (A88.8) (0.153 g, 0.539 mmol), pyridine (96.96 mg, 1.23 mmol, 100.0 μl, 2.5 eq) and N,N-dimethylpyridin-4-amine (0.0599 g, 0.049 mmol) in chloroform (15 mL) was stirred at room temperature overnight and evaporated under reduced pressure to dryness. The residue was subjected to HPLC purification (deionized water/HPLC-grade acetonitrile) to give product N4-{3-fluoro-2-[4-({6-oxa-3-azabicyclo[3.1.1]heptan-3-yl}methyl)piperidin-1-yl]phenyl}-N1,N1-dimethylbenzene-1,4-disulfonamide (A-791). Yield: 84.3 mg, 16.3%; Appearance: Orange solid; $^1$H NMR (600 MHz, DMSO-$d_6$) δ 7.94 (d, J=8.2 Hz, 2H), 7.88 (d, J=8.2 Hz, 2H), 7.20 (d, J=8.2 Hz, 1H), 7.12 (d, J=7.0 Hz, 1H), 6.91 (d, J=11.1 Hz, 1H), 4.07 (d, J=10.6 Hz, 2H), 3.55 (d, J=10.6 Hz, 2H), 3.36 (d, J=6.1 Hz, 2H), 2.75 (t, J=11.0 Hz, 2H), 2.58 (s, 6H), 2.42 (d, J=6.0 Hz, 2H), 2.28 (d, J=10.8 Hz, 2H), 1.66 (d, J=7.9 Hz, 1H), 1.55 (d, J=11.3 Hz, 2H), 1.30-1.19 (m, 3H); HPLC purity: 95.59%; LCMS Calculated for $C_{25}H_{33}FN_4O_5S_2$: 552.68; Observed: 553.2[M+H]$^+$.

The following examples were prepared using standard chemical manipulations and procedures similar to those used for the preparation of the previous example.

| Compound No. | Structure | Analytical Data |
|---|---|---|
| A-774 | 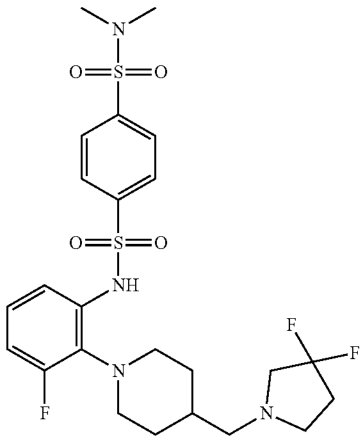 [SMILES: CN(C)S(=O)(=O)c1ccc(S(=O)(=O)Nc2cccc(F)c2N2CCC(CN3CCC(F)(F)C3)CC2)cc1] | Yield: 77.7 mg, 20.9%; Appearance: Yellow solid; $^1$H NMR (400 MHz, $CDCl_3$) δ 8.44 (s, 1H), 7.98 − 7.92 (m, 2H), 7.84 (d, J = 8.4 Hz, 2H), 7.43 (d, J = 8.2 Hz, 1H), 7.13 (td, J = 8.4, 5.7 Hz, 1H), 6.78 (ddd, J = 11.6, 8.4, 1.3 Hz, 1H), 3.00 (t, J = 11.9 Hz, 2H), 2.88 (t, J = 13.3 Hz, 2H), 2.72 (s, 8H), 2.35 (dd, J = 19.0, 7.5 Hz, 4H), 2.26 (dt, J = 14.5, 7.1 Hz, 2H), 1.82 (d, J = 13.0 Hz, 2H), 1.22 (dd, J = 22.9, 11.1 Hz, 2H); HPLC purity: 100%; LCMS Calculated for $C_{24}H_{31}F_3N_4O_4S_2$: 560.65; Observed: 561.2[M + H]$^+$. |

-continued

| Compound No. | Structure | Analytical Data |
|---|---|---|
| A-773 | 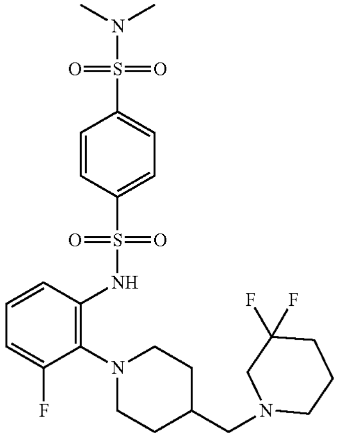 [SMILES: CN(C)S(=O)(=O)c1ccc(S(=O)(=O)Nc2cccc(F)c2N2CCC(CN3CCCC(F)(F)C3)CC2)cc1] | Yield: 73 mg, 22%; Appearance: Light brown solid; $^1$H NMR (400 MHz, DMSO-$d_6$) δ 9.18 (s, 1H), 7.99 - 7.85 (m, 4H), 7.26 - 7.15 (m, 2H), 6.98 (t, J = 10.1 Hz, 1H), 2.79 (t, J = 11.3 Hz, 2H), 2.60 (s, 6H), 2.46 (s, 1H), 2.34 (d, J = 19.1 Hz, 6H), 2.22 (d, J = 6.6 Hz, 2H), 1.85 (s, 2H), 1.69 - 1.43 (m, 5H), 1.20 (d, J = 10.8 Hz, 2H); HPLC purity: 100%; LCMS Calculated for $C_{25}H_{33}F_3N_4O_4S_2$: 574.68; Observed: 575.2[M + H]$^+$. |
| A-789 | 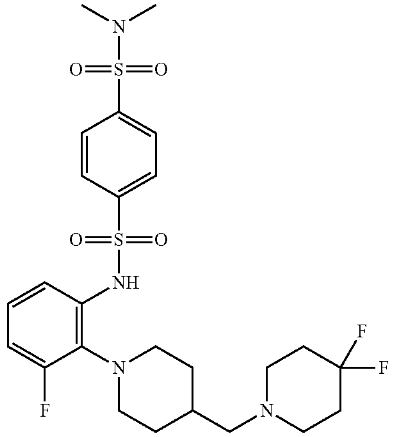 [SMILES: CN(C)S(=O)(=O)c1ccc(S(=O)(=O)Nc2cccc(F)c2N2CCC(CN3CCC(F)(F)CC3)CC2)cc1] | Yield: 83.2 mg, 12.6%; Appearance: Yellow solid; $^1$H NMR (600 MHz, DMSO-$d_6$) δ 9.16 (s, 1H), 7.95 (d, J = 8.3 Hz, 2H), 7.90 (d, J = 8.3 Hz, 2H), 7.21 (d, J = 8.2 Hz, 1H), 7.16 (td, J = 8.2, 5.6 Hz, 1H), 6.99 - 6.93 (m, 1H), 2.77 (t, J = 11.5 Hz, 2H), 2.58 (s, 6H), 2.43 (s, 4H), 2.29 (d, J = 11.0 Hz, 2H), 2.18 (d, J = 7.0 Hz, 2H), 1.99 - 1.85 (m, 4H), 1.53 (d, J = 12.9 Hz, 2H), 1.48 (d, J = 11.6 Hz, 1H), 1.21 - 1.12 (m, 2H); HPLC purity: 100%; LCMS Calculated for $C_{25}H_{33}F_3N_4O_4S_2$: 574.68; Observed: 575.2[M + H]$^+$. |

Example A89: Synthesis of N-[2-(4-{[(2R,6S)-2,6-dimethylmorpholin-4-yl]methyl}piperidin-1-yl)-3-fluorophenyl]-2,2-dimethyl-2,3-dihydro-1-benzofuran-6-sulfonamide (A-780)

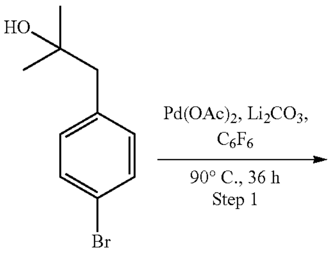

A89.1

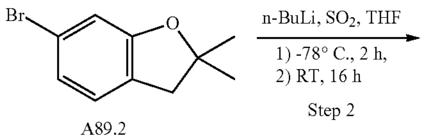

A89.2

-continued

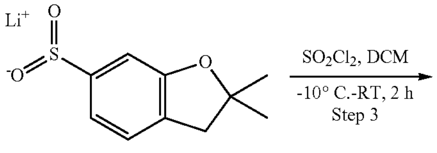

A89.3

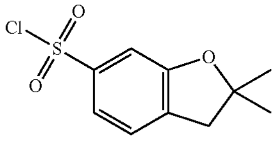

A89.4

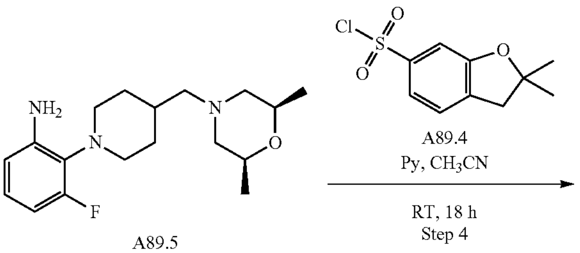

A89.5

-continued

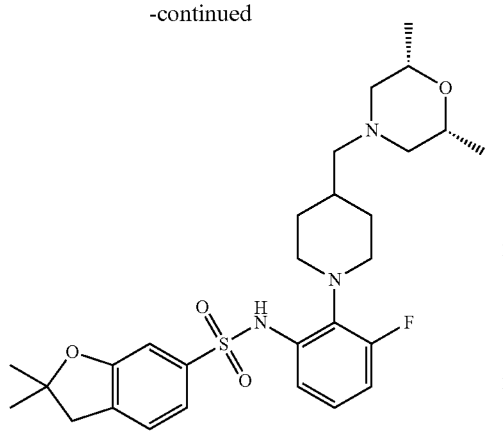

A-780

Step-1. Synthesis of 6-bromo-2,2-dimethyl-2,3-dihydro-1-benzofuran (A89.2)

A mixture of 1-(4-bromophenyl)-2-methylpropan-2-ol (A89.1) (5 g, 21.8 mmol), $Pd(OAc)_2$ (0.489 g, 2.18 mmol), $Li_2CO_3$ (3.22 g, 43.6 mmol), and Iodobenzene diacetate (10.5 g, 32.6 mmol) in hexafluorobenzene (20 mL) was stirred at 90° C. for 36 h. After cooling to room temperature, the reaction mixture was diluted with MTBE (250 mL). This solution was washed with water (100 mL×2), brine (50 ml), dried over anhydrous sodium sulfate, filtered and concentrated under reduced pressure. The residue was subjected to flash chromatography (hexane/MTBE) that afforded 6-bromo-2,2-dimethyl-2,3-dihydro-1-benzofuran as colorless oil (A89.2) (1.5 g, 6.60 mmol, 95% purity, 28.6% yield).

Step-2. Synthesis of lithium 2,2-dimethyl-2,3-dihydrobenzofuran-6-sulfinate (A89.3)

2.5 M n-butyllithium (0.507 g, 7.92 mmol) solution in hexane (3.16 mL) was added dropwise at −78° C. to a stirred solution of 6-bromo-2,2-dimethyl-2,3-dihydro-1-benzofuran (A89.2) (1.5 g, 6.60 mmol) in dry tetrahydrofuran (100 mL) under argon atmosphere and the reaction mixture was stirred at −78° C. for 2 h. $SO_2$ (1.26 g, 19.7 mmol) solution in dry tetrahydrofuran (50 mL) was added at −78° C. after and the reaction mixture was allowed to warm up and stir overnight at room temperature. The suspension was concentrated under reduced pressure to give lithium 2,2-dimethyl-2,3-dihydro-1-benzofuran-6-sulfinate as white solid (A89.3) (1.7 g, 7.79 mmol, 80% purity, 94.4% yield) that was used in the next step without further purification.

Step-3. Synthesis of 2,2-dimethyl-2,3-dihydro-1-benzofuran-6-sulfonyl chloride (A89.4)

Sulfuroyl dichloride (1.11 g, 8.25 mmol) was added dropwise at −10° C. to a stirred solution of lithium 2,2-dimethyl-2,3-dihydro-1-benzofuran-6-sulfinate (A89.3) (1.44 g, 6.60 mmol) in dry dichloromethane (100 mL), the reaction mixture was allowed to warm up and stir for 2 h at room temperature. The organic layer was washed with water with ice (100 mL) and brine (50 mL), dried over anhydrous sodium sulfate, filtered and concentrated under reduced pressure that afforded 2,2-dimethyl-2,3-dihydro-1-benzofuran-6-sulfonyl chloride as colorless oil (A89.4) (1.6 g, 6.48 mmol, 79% purity, 77.7% yield) that was used in next step without further purification.

Step-4. Synthesis of N-[2-(4-{[(2R,6S)-2,6-dimethylmorpholin-4-yl]methyl}piperidin-1-yl)-3-fluorophenyl]-2,2-dimethyl-2,3-dihydro-1-benzofuran-6-sulfonamide (A-780)

Pyridine (0.183 g, 2.32 mmol) and 2,2-dimethyl-2,3-dihydro-1-benzofuran-6-sulfonyl chloride (A89.4) (0.458 g, 1.86 mmol) were added to a solution of 2-(4-{[(2R,6S)-2,6-dimethylmorpholin-4-yl]methyl}piperidin-1-yl)-3-fluoroaniline (A89.5) (0.5 g, 1.55 mmol) in acetonitrile (55 mL). The reaction mixture was stirred at room temperature for 18 h. The solvent was removed under reduced pressure and the residue was subjected to HPLC purification (deionized water/HPLC-grade acetonitrile, ammonia) to afford N-[2-(4-{[(2R,6S)-2,6-dimethylmorpholin-4-yl]methyl}piperidin-1-yl)-3-fluorophenyl]-2,2-dimethyl-2,3-dihydro-1-benzofuran-6-sulfonamide (A-780). Yield: 167.6 mg, 19.2%; Appearance: Beige solid; $^1H$ NMR (600 MHz, DMSO-$d_6$) δ 8.67 (s, 1H), 7.25 (dd, J=8.3, 2.5 Hz, 2H), 7.15 (td, J=8.2, 5.7 Hz, 1H), 7.06 (dd, J=7.7, 1.7 Hz, 1H), 7.02 (d, J=1.7 Hz, 1H), 6.90-6.86 (m, 1H), 3.50 (dtt, J=12.6, 6.6, 3.2 Hz, 2H), 2.99 (s, 2H), 2.78 (t, J=11.4 Hz, 2H), 2.71-2.64 (m, 2H), 2.28 (d, J=10.9 Hz, 2H), 2.10 (d, J=7.1 Hz, 2H), 1.58 (d, J=12.8 Hz, 2H), 1.52 (t, J=10.6 Hz, 3H), 1.35 (s, 6H), 1.24-1.17 (m, 2H), 1.01 (d, J=6.2 Hz, 6H); HPLC purity: 100%; LCMS Calculated for $C_{26}H_{38}FN_5O_4S_2$: 531.68; Observed: 532.4$[M+H]^+$.

Example A90: Synthesis of N-(2-(4-(((2S,6R)-2,6-dimethylmorpholino)methyl)piperidin-1-yl)-3-fluorophenyl)-4-(N,N-dimethylsulfamimidoyl)benzenesulfonamide (A-769

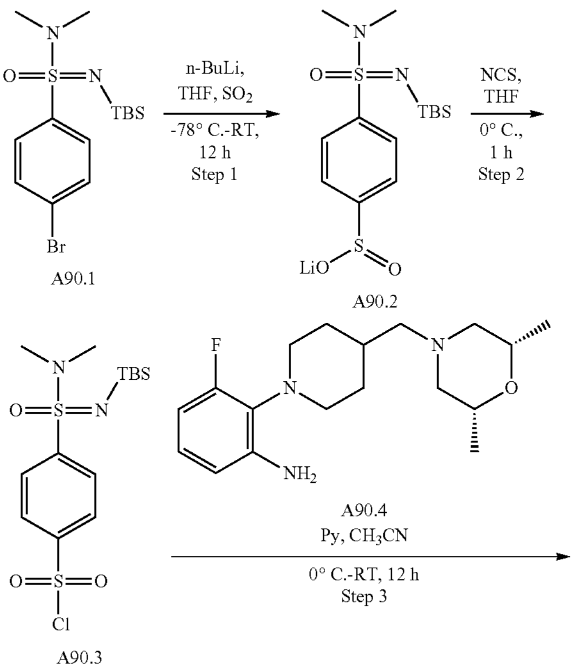

-continued

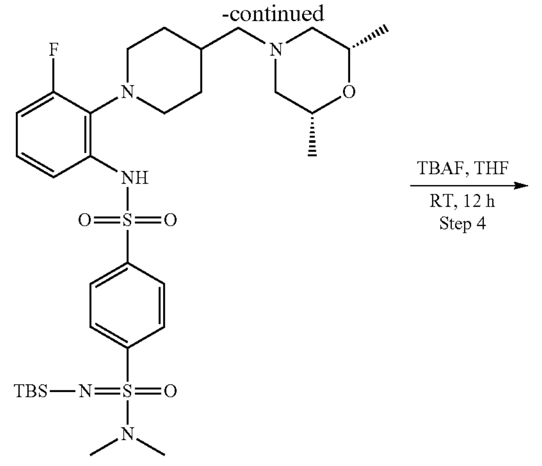

A90.5

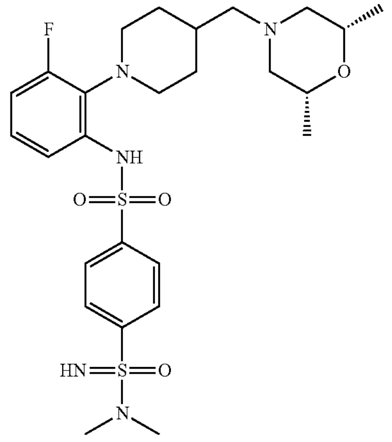

A-769

Step-1&2. Synthesis of 4-[(tert-butyldimethylsilyl) dimethyl-S-aminosulfonimidoyl]benzene-1-sulfonyl chloride (A90.3)

2.5 M n-butyllithium (0.382 g, 5.97 mmol) in hexane (2.38 mL) was added to a solution of 4-bromo-N'-(tert-butyldimethylsilyl)-N,N-dimethylbenzenesulfonimidamide (A90.1) (1.88 g, 4.98 mmol) in anhydrous tetrahydrofuran (20 mL) at −78° C. under argon atmosphere and the mixture was stirred for 1 h at −78° C. After the solution of $SO_2$ (0.954 g, 14.9 mmol) in tetrahydrofuran (20 mL) was added to the resulting mixture at the same temperature. Then the cooling bath was removed and the mixture was allowed to warm to room temperature and stir for 12 h. The solution was evaporated in vacuo, the residue was dissolved in dichloromethane (20 mL) and N-chlorosuccinimide (0.797 g, 5.97 mmol) was added maintaining the reaction mixture temperature at 0° C. The mixture was stirred for 30 minutes, diluted with ethyl acetate (20 mL) and water (20 mL). The organic layer was separated, dried over sodium sulfate, filtered and the filtrate was evaporated in vacuo to give 4-[(tert-butyldimethylsilyl)dimethyl-S-aminosulfonimidoyl]benzene-1-sulfonyl chloride as a dark resin (A90.3) (1.76 g, 4.43 mmol, 58.66% purity, 52.2% yield) that was used in the next step without further purification.

Step-3. Synthesis of 4-(N'-(tert-butyldimethylsilyl)-N,N-dimethylsulfamimidoyl)-N-(2-(4-(((2S,6R)-2,6-dimethylmorpholino)methyl)piperidin-1-yl)-3-fluorophenyl)benzenesulfonamide (A90.5)

4-[(tert-butyldimethylsilyl)dimethyl-S-aminosulfonimidoyl]benzene-1-sulfonyl chloride (A90.3) (0.7 g, 1.76 mmol) was added to the mixture of 2-(4-{[(2R,6S)-2,6-dimethylmorpholin-4-yl]methyl}piperidin-1-yl)-3-fluoroaniline (A90.4) (0.565 g, 1.76 mmol) and pyridine (0.982 g, 12.4 mmol) in dry acetonitrile (20 mL). The reaction mixture was stirred for 12 h and evaporated in vacuo to give 4-(N'-(tert-butyldimethylsilyl)-N,N-dimethylsulfamimidoyl)-N-(2-(4-(((2S,6R)-2,6-dimethylmorpholino)methyl) piperidin-1-yl)-3-fluorophenyl)benzenesulfonamide as a dark resin (A90.5) (1.2 g, 1.75 mmol, 20% purity, 20% yield) that was used in the next step without further purification.

Step-4. Synthesis of N-(2-(4-(((2S,6R)-2,6-dimethylmorpholino)methyl)piperidin-1-yl)-3-fluorophenyl)-4-(N,N-dimethylsulfamimidoyl)benzenesulfonamide (A-769)

1 M TBAF (0.266 g, 1.02 mmol) solution in tetrahydrofuran (1.02 mL) was added to a solution of N-(tert-butyldimethylsilyl)-4-{[2-(4-{[(2R,6S)-2,6-dimethylmorpholin-4-yl]methyl}piperidin-1-yl)-3-fluorophenyl]-sulfamoyl}-N, N-dimethylbenzene-1-sulfonimidamide (A90.5) (0.7 g, 1.02 mmol) in dry tetrahydrofuran (20 mL) under argon atmosphere. The reaction mixture was stirred for 12 h at room temperature and evaporated in vacuo. The residue was subjected to HPLC purification (deionized water/HPLC-grade acetonitrile) that afforded the product N-(2-(4-(((2S, 6R)-2,6-dimethylmorpholino)methyl)piperidin-1-yl)-3-fluorophenyl)-4-(N,N-dimethylsulfamimidoyl)benzenesulfonamide (A-769). Yield: 8.4 mg, 1.37%; Appearance: Beige solid; $^1H$ NMR (400 MHz, $CDCl_3$) δ 8.49 (s, 1H), 8.03-7.92 (m, 4H), 7.42 (d, J=8.2 Hz, 1H), 7.11 (td, J=8.3, 5.5 Hz, 1H), 6.81-6.71 (m, 1H), 3.69 (d, J=8.4 Hz, 2H), 3.00 (d, J=9.5 Hz, 2H), 2.69 (d, J=1.1 Hz, 8H), 2.58 (s, 1H), 2.40 (dd, J=25.9, 11.4 Hz, 2H), 2.21 (d, J=7.2 Hz, 2H), 1.81 (d, J=13.0 Hz, 2H), 1.72 (t, J=10.7 Hz, 2H), 1.18 (d, J=6.2 Hz, 8H); HPLC purity: 100%; LCMS Calculated for $C_{26}H_{38}FN_5O_4S_2$: 567.74; Observed: 568.2[M+H]$^+$.

Example A91: Synthesis of 4-(azetidine-1-sulfonyl)-N-[2-(4-{[(2R,6S)-2,6-dimethylmorpholin-4-yl] methyl}piperidin-1-yl)-3-fluorophenyl]benzene-1-sulfonamide (A-765)

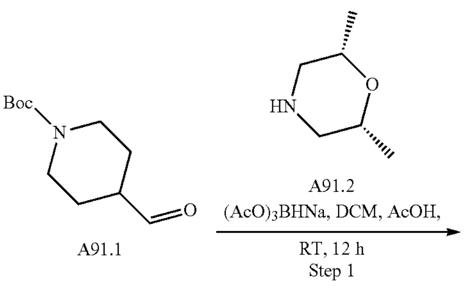

A91.1

A91.2

-continued

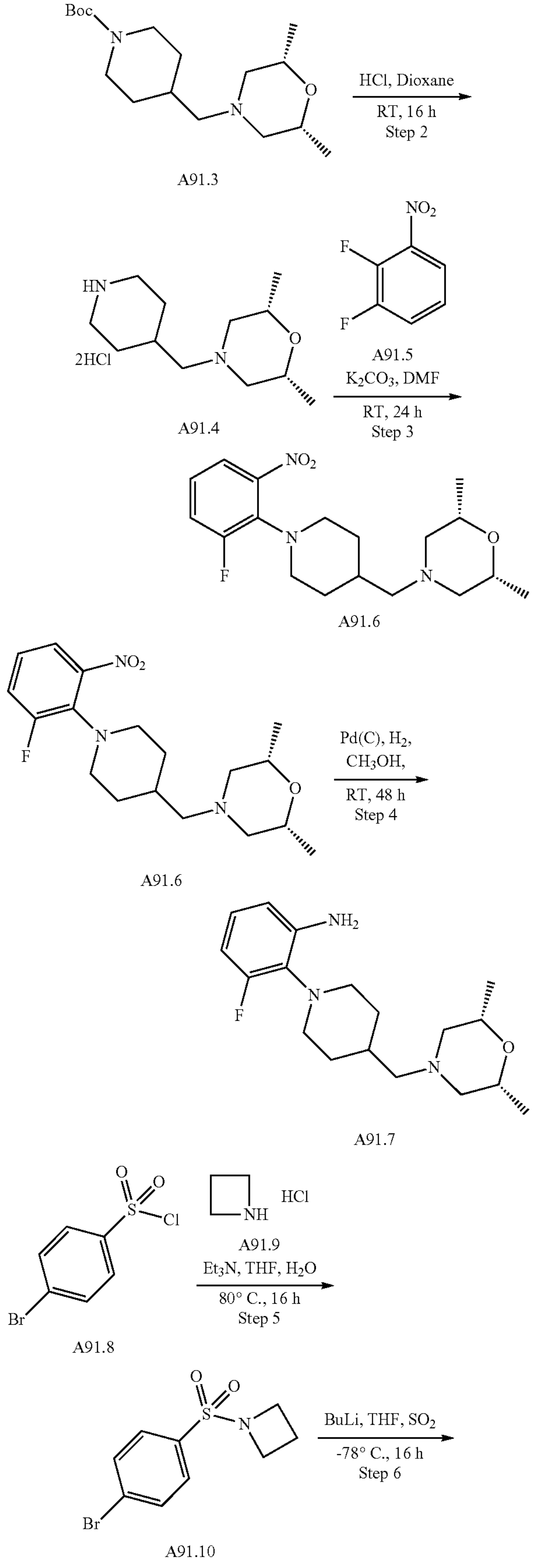

-continued

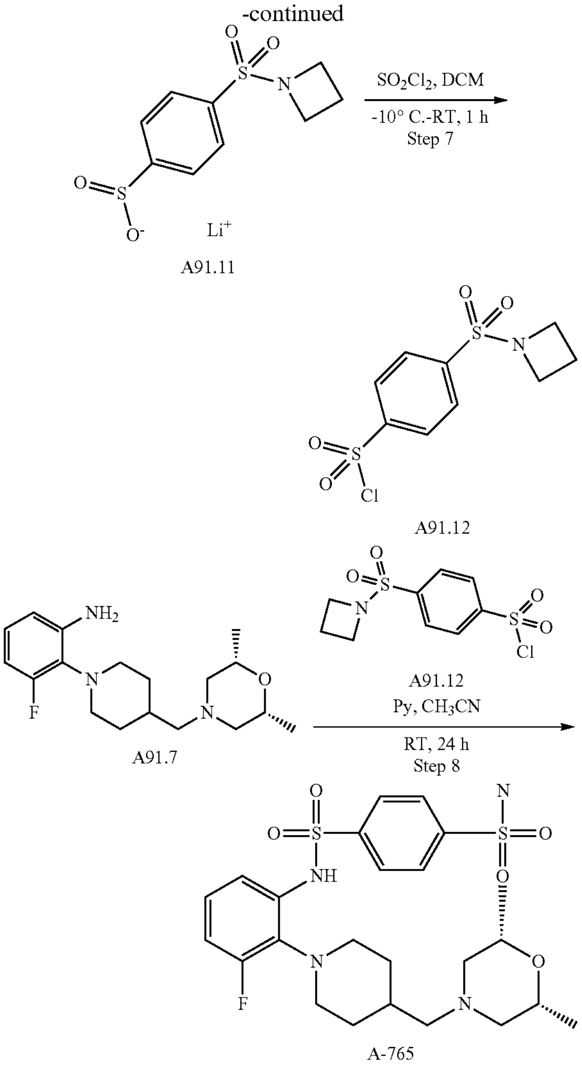

Step-1. Synthesis of tert-butyl 4-{[(2R,6S)-2,6-dimethylmorpholin-4-yl]methyl}piperidine-1-carboxylate (A91.3)

(2R,6S)-2,6-dimethylmorpholine (A91.2) (27.7 g, 240 mmol) and glacial acetic acid (15 mL) were added to a solution of tert-butyl 4-formylpiperidine-1-carboxylate (A91.1) (51.1 g, 240 mmol) in dry 1,2-dichloroethane (1 L). The mixture was stirred for 6 h at room temperature and sodium triacetoxyborohydride (66.1 g, 312 mmol) was added to it. The resulting mixture was stirred for 12 h until reaction completion (LCMS control), diluted with water (0.4 L). The product was extracted with dichloromethane (1 L), the organic layer was washed with 50% sodium bicarbonate aq. solution (250 mL), brine (250 mL), dried over sodium sulfate, filtered and evaporated under reduced pressure to give tert-butyl 4-{[(2R,6S)-2,6-dimethylmorpholin-4-yl]methyl}piperidine-1-carboxylate as white crystals (A91.3) (59 g, 188 mmol, 95% purity, 74.7% yield).

Step-2. Synthesis of (2R,6S)-2,6-dimethyl-4-[(piperidin-4-yl)methyl]morpholine dihydrochloride (A91.4)

Tert-butyl 4-{[(2R,6S)-2,6-dimethylmorpholin-4-yl]methyl}piperidine-1-carboxylate (A91.3) (59 g, 188 mmol)

was added to a sat. HCl solution in dioxane (500 mL) at room temperature. The solution was stirred overnight, the precipitate was filtered, washed with MTBE (100 mL×3) and dried on air to give (2R,6S)-2,6-dimethyl-4-[(piperidin-4-yl)methyl]morpholine dihydrochloride (A91.4) (45 g, 157 mmol, 95% purity, 79.6% yield).

Step-3. Synthesis of (2R,6S)-4-{[1-(2-fluoro-6-nitrophenyl)piperidin-4-yl]methyl}-2,6-dimethylmorpholine (A91.6)

1,2-difluoro-3-nitrobenzene (A91.5) (10.07 g, 62.8 mmol) was added to a stirred solution of (2R,6S)-2,6-dimethyl-4-[(piperidin-4-yl)methyl]morpholine dihydrochloride (A91.4) (15.5 g, 54.3 mmol) and potassium carbonate (30.2 g, 218 mmol) in dry DMF (500 mL). The mixture was stirred at 100° C. until the reaction completion (TLC control, 24 h) and concentrated under the reduced pressure. The residue was dissolved in ethyl acetate (1000 mL), the organic layer was washed with water (500 mL), dried over anhydrous sodium sulfate, filtered and concentrated under reduced pressure. The chromatographic purification (chloroform/acetonitrile) of crude product afforded (2R,6S)-4-{[1-(2-fluoro-6-nitrophenyl)piperidin-4-yl]methyl}-2,6-dimethylmorpholine as a powder (A91.6) (18 g, 51.2 mmol, 95% purity, 90% yield).

Step-4. Synthesis of (2R,6S)-4-{[1-(2-fluoro-6-nitrophenyl)piperidin-4-yl]methyl}-2,6-dimethylmorpholine (A91.7)

(2R,6S)-4-{[1-(2-fluoro-6-nitrophenyl)piperidin-4-yl]methyl}-2,6-dimethylmorpholine (A91.6) (18 g, 51.2 mmol) was dissolved in methanol (300 mL) and treated with 10% Pd/C (1.8 g). The resulting mixture was hydrogenated at ambient pressure and room temperature until the reaction was completed (TLC control), 2 days. The catalyst was filtered off and the filtrate was evaporated to afford 2-(4-{[(2R,6S)-2,6-dimethylmorpholin-4-yl]methyl}piperidin-1-yl)-3-fluoroaniline (A91.7) (16 g, 49.7 mmol, 80% purity by LCMS, 78.0% yield) that was used in next step without further purification.

Step-5. Synthesis of 1-(4-bromobenzenesulfonyl)azetidine (A91.10)

A solution of 4-bromobenzene-1-sulfonyl chloride (A91.8) (10 g, 39.1 mmol) in tetrahydrofuran (200 mL) was added dropwise to a solution of azetidine hydrochloride (A91.9) (7.31 g, 7.31 g) and triethylamine (15.7 g, 156 mmol, 21.6 mL) in water (100 mL) at 0° C. The solution was stirred for 12 hours at room temperature and evaporated. The resulting mass was suspended in water (200 mL) and extracted with ethyl acetate (200 mL). The organic layer was washed with water (200 mL), 5% aq solution of hydrochloric acid (200 mL), brine (200 mL), dried over sodium sulfate and evaporated under reduced pressure to afford 1-(4-bromobenzenesulfonyl)azetidine as white powder (A91.10) (10 g, 36.2 mmol, 95% purity, 88.7% yield).

Step-6. Synthesis of lithium-4-(azetidine-1-sulfonyl)benzene-1-sulfinate (A91.11)

2.5 M solution of n-butyllithium (2.54 g, 39.8 mmol, 15.9 mL) in hexane was added dropwise for 30 min to a solution of 1-(4-bromobenzenesulfonyl)azetidine (A91.10) (10 g, 36.2 mmol) in tetrahydrofuran (250 mL) maintained under nitrogen atmosphere at −78° C. The resulting solution was stirred at −78° C. for 2 h. Sulfur dioxide (23 g, 362 mmol) solution in tetrahydrofuran (200 mL) was added to the solution at −78° C. for 30 sec. After, ether (200 mL) was added and the precipitate was collected by filtration. The solid was washed with ether (100 mL×2) and dried in vacuum to give lithium-4-(azetidine-1-sulfonyl)benzene-1-sulfinate as a white solid (A91.11) (9 g, 33.6 mmol, 90% purity, 83.7% yield).

Step-7. Synthesis of 4-(azetidine-1-sulfonyl)benzene-1-sulfonyl Chloride (A91.12)

Sulfuroyl dichloride (2.76 g, 20.5 mmol) was added dropwise to a suspension of lithium-4-(azetidine-1-sulfonyl)benzene-1-sulfinate (A91.11) (5 g, 18.7 mmol) in dichloromethane (100 mL) at −15° C. The solution was stirred for 30 minutes at this temperature, washed with sodium bicarbonate (100 mL), water (100 mL), brine (100 mL), dried over sodium sulfate, filtered and evaporated under reduced pressure to give 4-(azetidine-1-sulfonyl)benzene-1-sulfonyl chloride as white powder (A91.12) (2.5 g, 8.45 mmol, 70% purity, 31.6% yield) that was used in next step without further purification.

Step-8. Synthesis of 4-(azetidine-1-sulfonyl)-N-[2-(4-{[(2R,6S)-2,6-dimethylmorpholin-4-yl]methyl}piperidin-1-yl)-3-fluorophenyl]benzene-1-sulfonamide (A-765)

4-(azetidine-1-sulfonyl)benzene-1-sulfonyl chloride (A91.12) (0.5 g, 1.69 mmol) was added to the mixture of 2-(4-{[(2R,6S)-2,6-dimethylmorpholin-4-yl]methyl}piperidin-1-yl)-3-fluoroaniline (A91.7) (0.543 g, 1.68 mmol) and pyridine (1.39 g, 17.5 mmol) in dry acetonitrile (40 mL). The reaction mixture was stirred at room temperature overnight and evaporated. The residue was subjected to HPLC purification (deionized water/HPLC-grade acetonitrile, ammonia) to afford 4-(azetidine-1-sulfonyl)-N-[2-(4-{[(2R,6S)-2,6-dimethylmorpholin-4-yl]methyl}piperidin-1-yl)-3-fluorophenyl]benzene-1-sulfonamide (A-765). Yield: 80 mg, 7.79%; Appearance: White solid; $^1$H NMR (400 MHz, DMSO-$d_6$) δ 9.23 (s, 1H), 7.99 (q, J=8.3 Hz, 4H), 7.20 (dt, J=22.1, 7.9 Hz, 2H), 6.96 (t, J=10.2 Hz, 1H), 3.67 (t, J=7.7 Hz, 4H), 3.51 (t, J=8.4 Hz, 2H), 2.80 (t, J=11.4 Hz, 2H), 2.69 (d, J=11.1 Hz, 2H), 2.33 (d, J=10.5 Hz, 2H), 2.11 (d, J=6.5 Hz, 2H), 1.98 (p, J=7.6 Hz, 2H), 1.54 (t, J=10.9 Hz, 5H), 1.22 (d, J=12.5 Hz, 2H), 1.03 (d, J=6.2 Hz, 6H); HPLC purity: 100%; LCMS Calculated for $C_{27}H_{37}FN_4O_5S_2$: 580.74; Observed: 581.2[M+H]$^+$.

Example A92: Synthesis of 4-(1-cyclopropylethyl)-N-[2-(4-{[(2R,6S)-2,6-dimethylmorpholin-4-yl]methyl}piperidin-1-yl)phenyl]benzene-1-sulfonamide, (A-779)

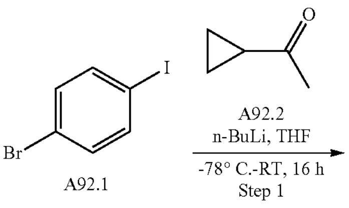

-continued

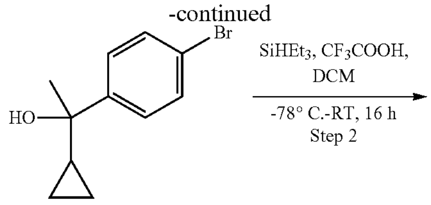

A92.3

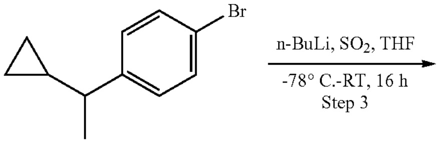

A92.4

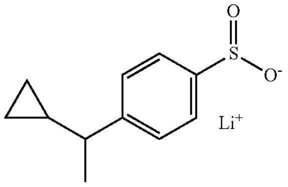

A92.5

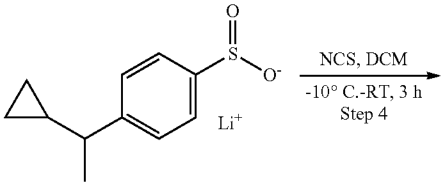

A92.5

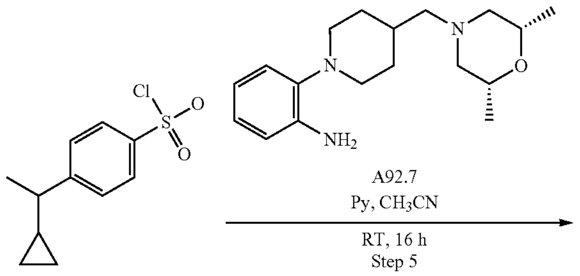

A92.6

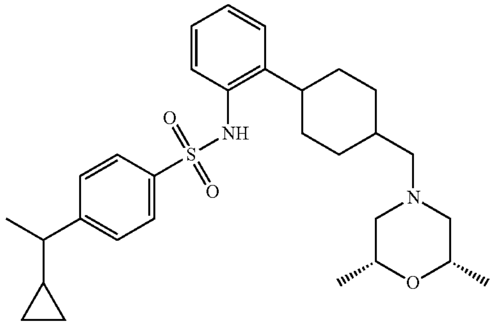

A-779

Step-1. Synthesis of 1-(4-bromophenyl)-1-cyclopropylethan-1-ol (A92.3)

2.5 M n-butyllithium (6.72 g, 105 mmol) solution in hexane (41.9 mL) was added dropwise at −78° C. to a stirred solution of 1-bromo-4-iodobenzene (A92.1) (25 g, 88.3 mmol) in dry tetrahydrofuran (500 mL) under argon atmosphere and the reaction mixture was stirred at −78° C. for 2 h. Then, the solution of 1-cyclopropylethan-1-one (A92.2) (11.1 g, 132 mmol) in dry tetrahydrofuran (50 mL) was added at −78° C., after the reaction mixture was allowed to warm up and stir overnight at room temperature. Then, it was poured in water (500 mL) and extracted with ethyl acetate (250 mL×3). The organic layer was washed with water (250 mL), brine (250 mL), dried over anhydrous sodium sulfate, filtered and concentrated under reduced pressure. The residue was subjected to flash chromatography purification (hexane/methyl tert-butyl ether) that afforded 1-(4-bromophenyl)-1-cyclopropylethan-1-ol as colorless oil (A92.3) (17 g, 70.5 mmol, 95% purity, 75.9% yield).

Step-2. Synthesis of 1-bromo-4-(1-cyclopropylethyl)benzene (A92.4)

Triethylsilane (10.6 g, 91.6 mmol) and trifluoroacetic acid (16.0 g, 141 mmol) were added to a solution of 1-(4-bromophenyl)-1-cyclopropylethan-1-ol (A92.3) (17 g, 70.5 mmol) in dichloromethane (500 mL) at −78° C. and the reaction mixture was allowed to warm up to room temperature and stir for 2 h. The organic layer was washed with 10% aq. solution of $NaHCO_3$ and brine (200 mL), dried over anhydrous sodium sulfate, filtered and concentrated under reduced pressure. The residue was subjected to flash chromatography purification (hexane/methyl tert-butyl ether) that afforded 1-bromo-4-(1-cyclopropylethyl)benzene as colorless oil (A92.4) (7.3 g, 32.4 mmol, 95% purity, 43.8% yield).

Step-3. Synthesis of lithium 4-(1-cyclopropylethyl)benzene-1-sulfinate (A92.5)

2.5 M n-butyllithium (2.48 g, 38.8 mmol) solution in hexane (15.5 mL) was added dropwise at −78° C. to a stirred solution of 1-bromo-4-(1-cyclopropylethyl)benzene (A92.4) (7.3 g, 32.4 mmol) in dry tetrahydrofuran (250 mL) under argon atmosphere and the reaction mixture was stirred at −78° C. for 2 h. Solution of $SO_2$ (6.22 g, 97.1 mmol) in dry tetrahydrofuran (100 mL) was added at −78° C., after the reaction mixture was allowed to warm up to room temperature and stir overnight. The suspension was concentrated under reduced pressure to give lithium 4-(1-cyclopropylethyl)benzene-1-sulfinate as white solid (A92.5) (7.55 g, 34.9 mmol, 87.49% purity, 94.2% yield) that was used in the next step without further purification.

Step-4. Synthesis of 4-(1-cyclopropylethyl)benzene-1-sulfonyl chloride (A92)

1-chloropyrrolidine-2,5-dione (5.18 g, 38.8 mmol) was added dropwise at −10° C. to a stirred solution of lithium 4-(1-cyclopropylethyl)benzene-1-sulfinate (A92.5) (7.00 g, 32.4 mmol) in dry dichloromethane (250 mL). The reaction mixture was allowed to warm up to room temperature and stir for 2 h. The organic layer was washed with water with ice (200 mL) and brine (200 mL), dried over anhydrous sodium sulfate, filtered and concentrated under reduced pressure that afforded 4-(1-cyclopropylethyl)benzene-1-sulfonyl chloride as colorless oil (A92.6) (7.5 g, 30.6 mmol, 74% purity, 70.0% yield) that was used in next step without further purification.

Step-5. Synthesis of 4-(1-cyclopropylethyl)-N-[2-(4-{[(2R,6S)-2,6-dimethylmorpholin-4-yl]methyl}piperidin-1-yl)phenyl]benzene-1-sulfonamide (A-779)

Pyridine (0.117 g, 1.48 mmol) and 4-(1-cyclopropylethyl)benzene-1-sulfonyl chloride (A) (0.313 g, 1.28 mmol) were added to a solution of 2-(4-{[(2R,6S)-2,6-dimethylmorpholin-4-yl]methyl}piperidin-1-yl)aniline (0.3 g, 0.988 mmol) in acetonitrile (25 mL). The reaction mixture was stirred at room temperature for 18 h. The solvent was removed under reduced pressure and the residue was subjected to HPLC purification (deionized water/HPLC-grade acetonitrile, ammonia) to afford 4-(1-cyclopropylethyl)-N-[2-(4-{[(2R,6S)-2,6-dimethylmorpholin-4-yl]methyl}piperidin-1-yl)phenyl]benzene-1-sulfonamide (A-779). Yield: 134.8 mg, 25.3%; Appearance: White solid; $^1$H NMR (500 MHz, DMSO-$d_6$) δ 8.52 (s, 1H), 7.67-7.63 (m, 2H), 7.41 (d, J=8.1 Hz, 2H), 7.38-7.34 (m, 1H), 7.11-7.08 (m, 1H), 7.05 (t, J=4.7 Hz, 2H), 3.51 (t, J=8.2 Hz, 2H), 2.67 (d, J=10.8 Hz, 2H), 2.38 (d, J=8.5 Hz, 4H), 2.10 (d, J=7.0 Hz, 2H), 2.01 (q, J=8.1, 7.7 Hz, 1H), 1.62-1.49 (m, 5H), 1.21 (d, J=7.0 Hz, 4H), 1.17 (s, 1H), 1.02 (d, J=6.2 Hz, 6H), 0.88 (dd, J=8.9, 4.6 Hz, 1H), 0.47 (dd, J=9.2, 4.3 Hz, 1H), 0.29 (dq, J=8.7, 4.8, 4.3 Hz, 1H), 0.17 (dt, J=9.6, 4.7 Hz, 1H), 0.06 (s, 1H); HPLC purity: 100%; LCMS Calculated for $C_{29}H_{41}N_3O_3S$: 511.72; Observed: 512.4[M+H]$^+$.

Example A93: Synthesis of 4-(cyclopropyldifluoromethyl)-N-[2-(4-{[(2R,6S)-2,6-dimethylmorpholin-4-yl]methyl}piperidin-1-yl)-3-fluorophenyl]benzene-1-sulfonamide (A-814)

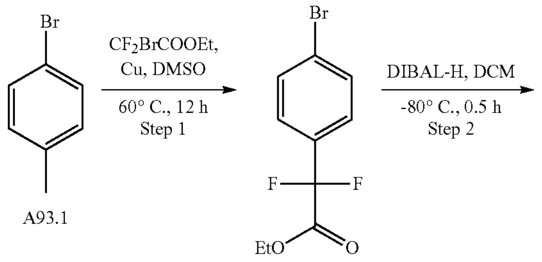

A93.1 A93.2

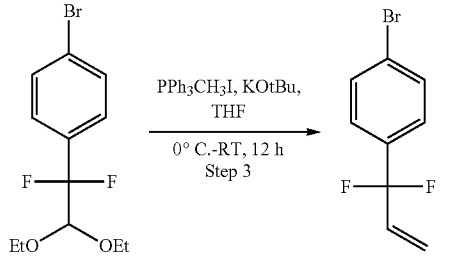

A93.3 A93.4

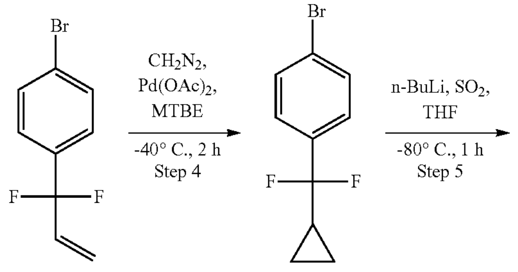

A93.4 A93.5

-continued

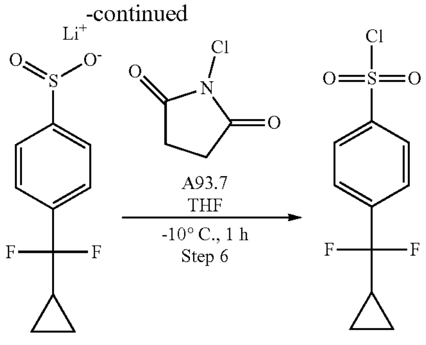

A93.6 A93.8

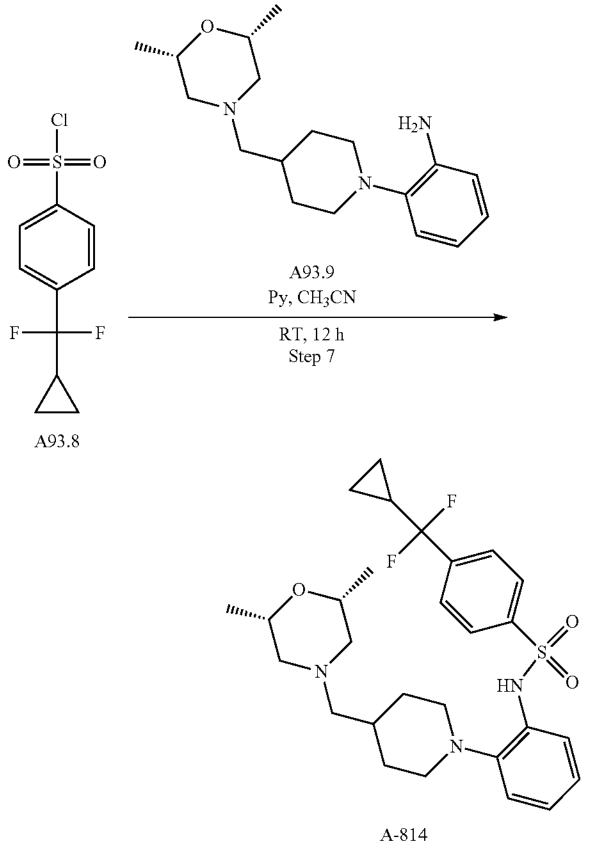

A93.8

A-814

Step-1. Synthesis of Ethyl 2-(4-bromophenyl)-2,2-difluoroacetate (A93.2)

1-bromo-4-iodobenzene (A93.1) (47.2 g, 166 mmol) and ethyl 2-bromo-2,2-difluoroacetate (36.9 g, 182 mmol) were added under argon atmosphere to a suspension of activated copper powder (27.3 g, 431 mmol) in DMSO (500 mL) and the mixture was stirred at 60° C. for 12 h. After, the mixture was poured into a mixture of ice (400 g) and $NH_4Cl$ sat. aq. solution (300 mL), the product was extracted with MTBE (500 mL×3). The combined MTBE layers were washed with $NH_4Cl$ saturated aq. solution (500 mL), brine (500 mL), dried over sodium sulfate, filtered and evaporated under reduced pressure. The residue was purified by column chromatography (hexane/chloroform) to afford ethyl 2-(4-bromophenyl)-2,2-difluoroacetate as a light-yellow oil (A93.2) (31.3 g, 112 mmol, 95% purity, 67.6% yield).

Step-2. Synthesis of 2-(4-bromophenyl)-1-ethoxy-2,2-difluoroethanol (A93.3)

1 M DIBAL (18.2 g, 128 mmol) solution in cyclohexane (128 mL) was added dropwise at −78° C. under argon atmosphere to a solution of ethyl 2-(4-bromophenyl)-2,2-difluoroacetate (A93.2) (29.9 g, 107 mmol) in dry dichloromethane (250 mL). The reaction mixture was stirred at −78° C. for 15 min and poured in 10% HCl aq/solution (250 mL). The mixture was extracted with dichloromethane (250 mL×2), combined organic layer was washed with brine (250 mL), dried over sodium sulfate, filtered and evaporated under reduced pressure to obtain 2-(4-bromophenyl)-1-ethoxy-2,2-difluoroethanol as a white solid (A93.3) (30.1 g, 107 mmol, 98.61% purity, 98.6% yield).

Step-3. Synthesis of 1-bromo-4-(1,1-difluoroallyl)benzene (A93.4)

Methyltriphenylphosphoniumiodide (151 g, 374 mmol) was suspended in dry tetrahydrofuran (500 mL) under argon atmosphere and (tert-butoxy)potassium (41.9 g, 374 mmol) was added at 0° C. over 30 min. The mixture was stirred at 0° C. for 1 h. Then, 2-(4-bromophenyl)-1-ethoxy-2,2-difluoroethanol (A93.3) (30.1 g, 107 mmol) was added to it and the mixture was stirred at room temperature for 12 h. After the reaction was diluted with water (500 mL), the product was extracted with MTBE (500 mL×2). The combined organic layer was washed with brine (500 mL), dried over sodium sulfate, filtered and evaporated in vacuo. The crude product was purified by flash chromatography (hexane/chloroform) to give 1-bromo-4-(1,1-difluoroallyl)benzene as a colorless oil (A93.4) (12.51 g, 53.6 mmol, 90% purity, 44.9% yield).

Step-4. Synthesis of 1-bromo-4-(cyclopropyldifluoromethyl)benzene (A93.5)

0.8 M diazomethane (5.36 g, 127.5 mmol) solution in MTBE (159 mL) was added at −40° C. to a mixture of 1-bromo-4-(1,1-difluoroallyl)benzene (A93.4) (12.51 g, 53.6 mmol) and $Pd(OAc)_2$ (0.0572 g, 0.254 mmol) in dry MTBE (200 mL). The mixture was stirred at −40° C. until the evolution of gas was ceased (for 2 h), filtered and the filtrate was concentrated in vacuo. The residue was purified by flash chromatography (hexane/MTBE) to give 1-bromo-4-(cyclopropyldifluoromethyl)benzene as a colorless oil (A93.5) (4.9 g, 19.8 mmol, 91% purity, 33.7% yield).

Step-5& 6. Synthesis of 4-(cyclopropyldifluoromethyl)benzene-1-sulfonyl chloride (A93.8)

2 M n-Butyllithium (1.51 g, 23.7 mmol) in hexane (9.47 mL) was added to a solution of 1-bromo-4-(cyclopropyldifluoromethyl)benzene (A93.5) (4.9 g, 19.8 mmol) in anhydrous tetrahydrofuran (50 mL) at −78° C. under argon atmosphere and the mixture was stirred for 1 h at this temperature. The solution of $SO_2$ (3.8 g, 59.4 mmol) in tetrahydrofuran (50 mL) was added to the resulting mixture at −78° C. Then the mixture was allowed to warm to room temperature and stir for 12 h. The solution was evaporated in vacuo and the residue was dissolved in dichloromethane (20 mL) and N-chlorosuccinimide (A93.7) (3.16 g, 23.7 mmol) was added portionwise maintaining the mixture temperature at 0° C. The mixture was stirred for 30 minutes, diluted with water (50 mL) and extracted with ethyl acetate (50 mL×2). The organic layer was dried over sodium sulfate, filtered and the filtrate was evaporated in vacuo to give 4-(cyclopropyldifluoromethyl)benzene-1-sulfonyl chloride as a dark resin (A93.8) (5.3 g, 19.8 mmol, 76.62% purity, 76.8% yield) which was used in the next step without further purification.

Step-7. Synthesis of 4-(cyclopropyldifluoromethyl)-N-(2-(4-(((2S,6R)-2,6-dimethylmorpholino)-methyl)piperidin-1-yl)-3-fluorophenyl)benzenesulfonamide (A-814)

4-(cyclopropyldifluoromethyl)benzene-1-sulfonyl chloride (A93.8) (0.53 g, 1.98 mmol) was added to the mixture of 2-(4-{[(2R,6S)-2,6-dimethylmorpholin-4-yl]methyl}piperidin-1-yl)-3-fluoroaniline (A93.9) (0.636 g, 1.98 mmol) and pyridine (0.982, 12.4 mmol) in dry acetonitrile (20 mL). The reaction mixture was stirred for 12 h and evaporated in vacuo. The residue was subjected to HPLC purification (deionized water/HPLC-grade methanol, ammonia) that afforded 4-(cyclopropyldifluoromethyl)-N-[2-(4-{[(2R,6S)-2,6-dimethylmorpholin-4-yl]methyl}piperidin-1-yl)-3-fluorophenyl]benzene-1-sulfonamide (A-814). Yield: 147.7 mg, 12.8%; Appearance: Light brown oil; $^1H$ NMR (400 MHz, DMSO-$d_6$) δ 8.90 (s, 1H), 7.87 (d, J=8.2 Hz, 2H), 7.73 (d, J=8.2 Hz, 2H), 7.35-7.26 (m, 1H), 7.18-7.00 (m, 3H), 3.58-3.49 (m, 2H), 2.68 (d, J=11.0 Hz, 2H), 2.41 (t, J=11.1 Hz, 2H), 2.10 (d, J=6.9 Hz, 2H), 2.07 (s, 1H), 1.74-1.64 (m, 1H), 1.57 (q, J=11.8, 10.5 Hz, 5H), 1.18 (d, J=17.8 Hz, 2H), 1.04 (d, J=6.2 Hz, 6H), 0.73-0.56 (m, 4H); HPLC purity: 96.4%; LCMS Calculated for $C_{28}H_{37}FN_3O_3S$: 533.67; Observed: 534.0[M+H]+.

Example A94: Synthesis of 1-(cyclopropylmethyl)-N-[2-(4-[(2R,6S)-2,6-dimethylmorpholin-4-yl]methylpiperidin-1-yl)phenyl]-1H-pyrazole-4-sulfonamide (A-772)

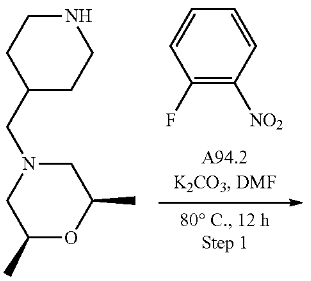

A94.1

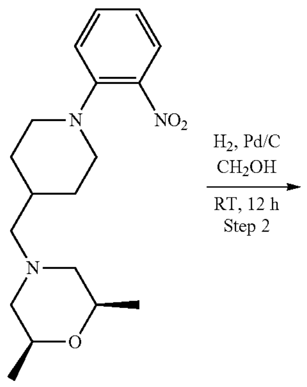

A94.3

-continued

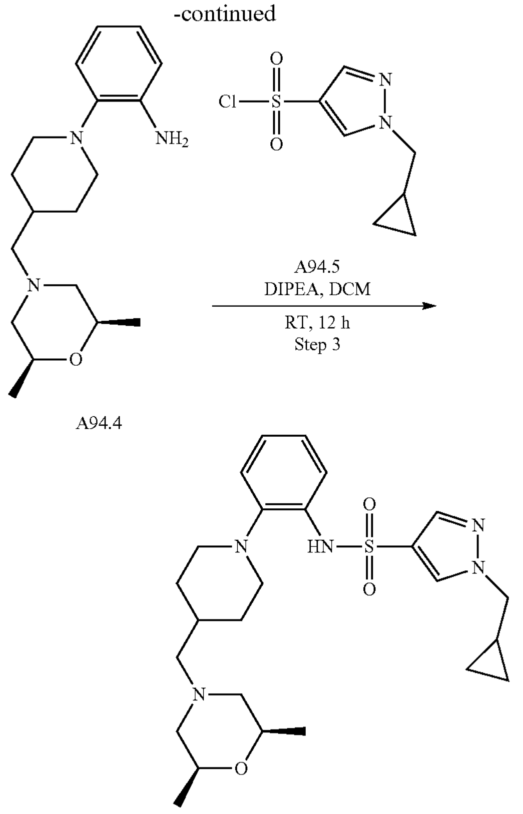

A94.4

A-772

Step-1. Synthesis of (2R,6S)-2,6-dimethyl-4-{[1-(2-nitrophenyl)piperidin-4-yl]methyl}morpholine (A94.3)

(2R,6S)-2,6-dimethyl-4-[(piperidin-4-yl)methyl]morpholine dihydrochloride (A94.1) (1.0 g, 3.50 mmol), 1-fluoro-2-nitrobenzene (A94.2) (0.493 g, 3.50 mmol) and dipotassium carbonate (1.7 g, 12.27 mmol) were mixed in DMF (30 mL), heated to 80° C. and stirred at this temperature overnight. Completion of reaction was controlled by LCMS. Reaction mixture was cooled to room temperature, diluted with water (40 mL) and the product was extracted with ethyl acetate (30 mL×3). Combined ethyl acetate layer was washed with water (20 mL×7), dried over anhydrous sodium sulfate, filtered, and evaporated under reduced pressure to afford (2R,6S)-2,6-dimethyl-4-[1-(2-nitrophenyl)piperidin-4-yl]methylmorpholine (A94.3) (1.0 g, 2.99 mmol, 100% purity, 86.2% yield).

Step-2. Synthesis of 2-(4-[(2R,6S)-2,6-dimethylmorpholin-4-yl]methylpiperidin-1-yl)aniline (A94.4)

(2R,6S)-2,6-dimethyl-4-[1-(2-nitrophenyl)piperidin-4-yl]methylmorpholine (A94.3) (1 g, 2.99 mmol) was dissolved in methanol (50 mL) and treated with 10% Pd/C (0.1 g). The resulting mixture was hydrogenated at ambient pressure and room temperature until the reaction was completed (LCMS control). The catalyst was filtered off and the filtrate was evaporated under reduced pressure to afford 2-(4-[(2R,6S)-2,6-dimethylmorpholin-4-yl]methylpiperidin-1-yl)aniline (A94.4) (0.96 g, 3.16 mmol, 93.43% purity, 98.7% yield).

Step-3. Synthesis of 1-(cyclopropylmethyl)-N-[2-(4-{[(2R,6S)-2,6-dimethylmorpholin-4-yl]methyl}piperidin-1-yl)phenyl]-1H-pyrazole-4-sulfonamide (A-772)

Ethylbis(propan-2-yl)amine (0.261 g, 2.04 mmol) was added to a solution of 2-(4-[(2R,6S)-2,6-dimethylmorpholin-4-yl]methylpiperidin-1-yl)aniline (A94.4) (0.413 g, 1.35 mmol) in dichloromethane (20 mL). Then 1-(cyclopropylmethyl)-1H-pyrazole-4-sulfonyl chloride (A94.5) (0.297 g, 1.35 mmol) was added in one portion. Reaction mixture was stirring at room temperature overnight and evaporated under reduced pressure. Crude product was purified by HPLC (deionized water/HPLC-grade methanol, ammonia) to give 1-(cyclopropylmethyl)-N-[2-(4-[(2R,6S)-2,6-dimethylmorpholin-4-yl]methylpiperidin-1-yl)phenyl]-1H-pyrazole-4-sulfonamide (A-772). Yield: 398.5 mg, 57.4%; Appearance: Beige solid; $^1$H NMR (600 MHz, DMSO-$d_6$) δ 8.32 (s, 1H), 8.26 (s, 1H), 7.69 (s, 1H), 7.37 (dd, J=7.6, 2.0 Hz, 1H), 7.14 (dd, J=7.4, 2.0 Hz, 1H), 7.05 (pd, J=7.4, 1.8 Hz, 2H), 3.92 (d, J=7.2 Hz, 2H), 3.51 (dtt, J=12.5, 6.2, 3.3 Hz, 2H), 2.70-2.66 (m, 2H), 2.54 (d, J=11.4 Hz, 2H), 2.12 (d, J=7.3 Hz, 2H), 1.71-1.67 (m, 2H), 1.59 (td, J=7.4, 3.7 Hz, 1H), 1.54 (dd, J=11.3, 10.1 Hz, 2H), 1.29-1.21 (m, 2H), 1.11 (tt, J=7.6, 4.6 Hz, 1H), 1.01 (d, J=6.3 Hz, 6H), 0.46-0.39 (m, 2H), 0.28-0.22 (m, 2H); HPLC purity: 100%; LCMS Calculated for $C_{25}H_{37}N_5O_3S$: 487.66; Observed: 488.2[M+H]$^+$.

Example A95: Synthesis of 2-cyclopropyl-N-[2-(4-{[(2R,6S)-2,6-dimethylmorpholin-4-yl]methyl}piperidin-1-yl)phenyl]-4-methyl-1,3-thiazole-5-sulfonamide (A-768)

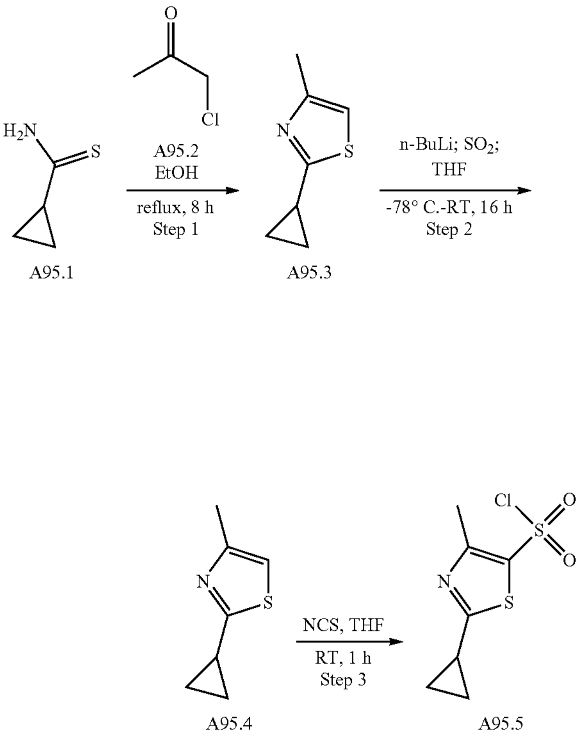

A95.1 A95.3 A95.4 A95.5

-continued

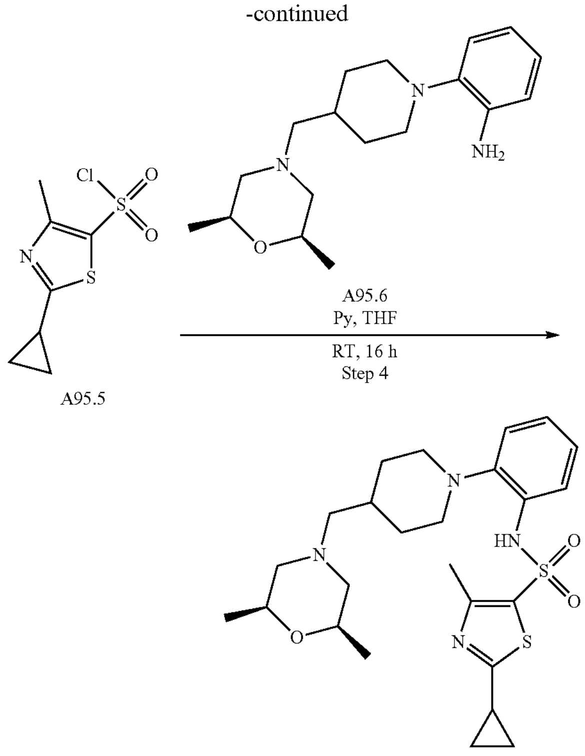

A95.5

A-768

Step-1. Synthesis of 2-cyclopropyl-4-methylthiazole (A95.3)

The solution of cyclopropanecarbothioamide (A95.1) (3 g, 29.6 mmol) and 1-chloropropan-2-one (A95.2) (2.73 g, 29.6 mmol) in ethanol (10 mL) was refluxed for 8 h, the reaction mixture was cooled to room temperature and evaporated to dryness. The residue was treated with $NaHCO_3$ sat. aq. solution (10 mL), the product was extracted with ethyl acetate (10 mL×2). Combined organic layer was washed with water (10 mL), dried over sodium sulfate, filtered and evaporated in vacuo. The residue was distilled (bp=60° C. at 1 mm Hg) to give 2-cyclopropyl-4-methylthiazole (A95.3) (3 g, 21.5 mmol, 95% purity, 69.1% yield).

Step-2. Synthesis of lithium 2-cyclopropyl-4-methylthiazole-5-sulfinate (A95.4)

2.5 M n-BuLi (1.71 g, 26.8 mmol) solution in hexane (10.7 mL) was added dropwise to the solution of 2-cyclopropyl-4-methylthiazole (A95.3) (3 g, 21.5 mmol) in tetrahydrofuran (30 mL) at −78° C., the mixture was stirred at the same temperature for 1 h, and the gaseous $SO_2$ was bubbled through the mixture for 10 min. Then the mixture was allowed to warm to room temperature and stir overnight. The solvents were evaporated under reduced pressure to give crude lithium 2-cyclopropyl-4-methylthiazole-5-sulfinate (A95.4) (3 g, 14.3 mmol) that was used in the next step without further purification.

Step-3. Synthesis of 2-cyclopropyl-4-methyl-1,3-thiazole-5-sulfonyl Chloride (A95.5)

1-chloropyrrolidine-2,5-dione (3.75 g, 28 mmol) was added portionwise to the solution of lithium 2-cyclopropyl-4-methylthiazole-5-sulfinate (A95.4) (3 g, 14.3 mmol) in tetrahydrofuran (100 mL) at 0° C., the mixture was stirred for 1 h, then water (100 mL) was added. The product was extracted with MTBE (100 mL×2), combined organic layer were washed with water (100 mL), dried over sodium sulfate, evaporated and purified by flash chromatography (hexane/chloroform) to give 2-cyclopropyl-4-methyl-1,3-thiazole-5-sulfonyl chloride (A95.5).

Step-4. Synthesis of 2-cyclopropyl-N-[2-(4-{[(2R,6S)-2,6-dimethylmorpholin-4-yl]methyl}piperidin-1-yl)phenyl]-4-methyl-1,3-thiazole-5-sulfonamide (A-768)

2-cyclopropyl-4-methyl-1,3-thiazole-5-sulfonyl chloride (A95.5) (0.5 g, 2.10 mmol) was added to the mixture of 2-(4-{[(2R,6S)-2,6-dimethylmorpholin-4-yl]methyl}piperidin-1-yl)aniline (A95.6) (0.637 g, 2.10 mmol) and pyridine (0.25 g, 3.15 mmol) in dry tetrahydrofuran (20 mL). The reaction mixture was stirred overnight and evaporated under reduced pressure. The residue was subjected to HPLC purification (deionized water/HPLC-grade methanol) that afforded the product 2-cyclopropyl-N-[2-(4-{[(2R,6S)-2,6-dimethylmorpholin-4-yl]methyl}piperidin-1-yl)phenyl]-4-methyl-1,3-thiazole-5-sulfonamide (A-768). Yield: 139 mg, 12.5%; Appearance: Light brown solid; $^1$H NMR (400 MHz, DMSO-$d_6$) δ 9.08 (s, 1H), 7.31 (d, J=7.9 Hz, 1H), 7.17 (d, J=4.0 Hz, 2H), 7.11-7.06 (m, 1H), 3.54 (ddd, J=10.0, 6.1, 2.0 Hz, 2H), 2.70 (d, J=11.0 Hz, 2H), 2.63 (d, J=11.2 Hz, 2H), 2.54 (s, 1H), 2.37 (tt, J=8.1, 4.7 Hz, 1H), 2.24 (s, 3H), 2.12 (d, J=7.1 Hz, 2H), 1.65 (d, J=12.9 Hz, 2H), 1.56 (t, J=10.6 Hz, 3H), 1.20-1.09 (m, 4H), 1.04 (d, J=6.3 Hz, 6H), 0.98-0.92 (m, 2H); HPLC purity: 100%; LCMS Calculated for $C_{25}H_{36}N_4O_3S_2$: 504.71; Observed: 505.2[M+H]$^+$.

Example A96: Synthesis of N1,N1-dimethyl-N4-[2-(morpholin-4-yl)phenyl]benzene-1,4-disulfonamide (A-815)

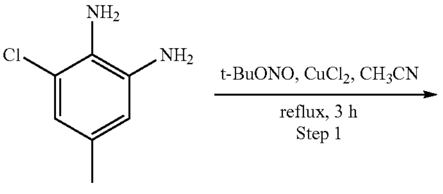

A96.1

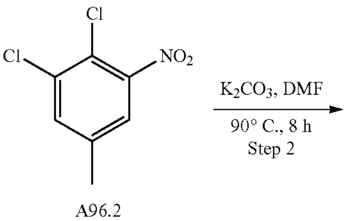

A96.2

-continued

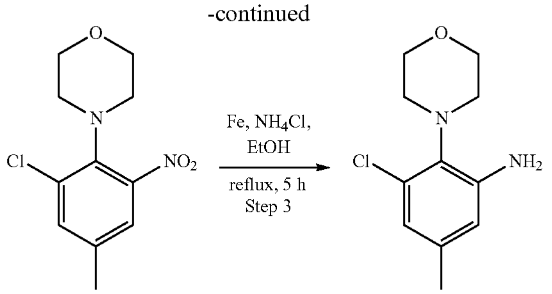

A96.3 A96.4

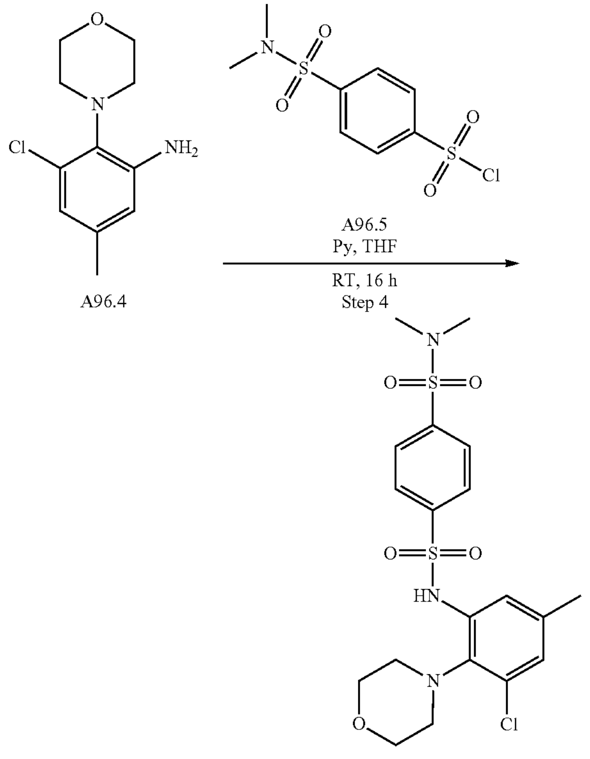

A96.4 A96.5

A-815

Step-1. Synthesis of 1,2-dichloro-5-methyl-3-nitrobenzene (A96.2)

The solution of 2-chloro-4-methyl-6-nitroaniline (A96.1) (5 g, 26.7 mmol), tert-butyl nitrite (4.12 g, 40 mmol)) and copper (II) chloride (4.66 g, 34.6 mmol)) in acetonitrile (50 mL) was refluxed for 4 h, cooled to room temperature, filtered through silica pad and filtrate was evaporated to dryness. The residue was dissolved in ethyl acetate (50 mL), this solution was washed with water (50 mL), dried over sodium sulfate, filtered and evaporated under reduced pressure to give 1,2-dichloro-5-methyl-3-nitrobenzene (A96.2) (3 g, 14.5 mmol, 90% purity, 49% yield) which was used in the next step without purification.

Step-2. Synthesis of 4-(2-chloro-4-methyl-6-nitrophenyl)morpholine (A96.3)

1,2-dichloro-5-methyl-3-nitrobenzene (A96.2) (3 g, 14.5 mmol) was added to a stirred solution of morpholine (1.9 g, 21.8 mmol) and potassium carbonate (3 g, 21.8 mmol) in dry DMF (20 mL). The mixture was stirred at 60° C. until the reaction completion (TLC control) and concentrated under the reduced pressure. The residue was dissolved in chloroform (15 mL), the organic layer was washed with water (15 mL), dried over anhydrous sodium sulfate, filtered and concentrated under reduced pressure to give 4-(2-chloro-4-methyl-6-nitrophenyl)morpholine (A96.3) (2.8 g, 10.9 mmol, 90% purity, 45% yield) that was used in the next step without purification.

Step-3. Synthesis of 3-chloro-5-methyl-2-(morpholin-4-yl)aniline (A96.4)

Iron powder (6.08 g, 109 mmol)) and ammonium chloride (5.83 g, 109 mmol) were added at room temperature to a stirred solution of 4-(2-chloro-4-methyl-6-nitrophenyl)morpholine (A96.3) (2.8 g, 10.9 mmol)) in a mixture of ethanol (50 mL) and water (50 mL) and the resulting reaction mixture was refluxed for 6 h. After the reaction completion (TLC control) the mixture was filtered through silica and the filtrate was evaporated. The residue was treated with water (50 mL) and ethyl acetate (50 mL). The organic layer was separated, washed with water (50 mL), dried over anhydrous sodium sulfate, filtered and evaporated under reduced pressure that afforded crude 3-chloro-5-methyl-2-(morpholin-4-yl)aniline (A96.4) (1.6 g, 7.05 mmol, 90% purity, 58.2% yield) which was used in the next step without further purification.

Step-4. Synthesis of N4-[3-chloro-5-methyl-2-(morpholin-4-yl)phenyl]-N1,N1-dimethylbenzene-1,4-disulfonamide (A-815)

4-(dimethylsulfamoyl)benzene-1-sulfonyl chloride (A96.5) (0.62 g, 2.2 mmol) was added to the mixture of 3-chloro-5-methyl-2-(morpholin-4-yl)aniline (A96.4) (0.5 g, 2.2 mmol)) and pyridine (0.261 g, 3.3 mmol) in dry tetrahydrofuran (20 mL). The reaction mixture was stirred overnight and evaporated under reduced pressure. The residue was subjected to HPLC purification (deionized water/HPLC-grade methanol) that afforded N4-[3-chloro-5-methyl-2-(morpholin-4-yl)phenyl]-N1,N1-dimethylbenzene-1,4-disulfonamide (A-815). Yield: 230.8 mg, 21.0%; Appearance: Yellow solid; $^1H$ NMR (400 MHz, DMSO-$d_6$) δ 9.91 (s, 1H), 7.97-7.92 (m, 2H), 7.89 (d, J=8.6 Hz, 2H), 6.95 (s, 1H), 6.79 (d, J=3.0 Hz, 1H), 3.69 (t, J=4.4 Hz, 4H), 2.91 (t, J=4.4 Hz, 4H), 2.62 (s, 6H), 1.94 (s, 3H); HPLC purity: 100%; LCMS Calculated for $C_{19}H_{24}ClN_3O_5S_2$: 473.99; Observed: 474.0[M+H]$^+$.

Example A97: Synthesis of N1,N1-dimethyl-N4-[2-(morpholin-4-yl)phenyl]benzene-1,4-disulfonamide (A-770)

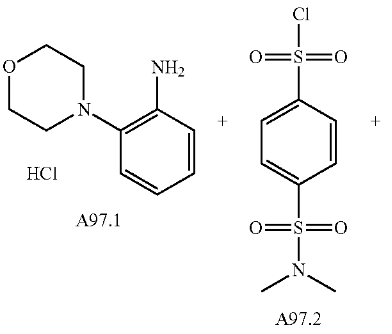

A97.1 A97.2

-continued

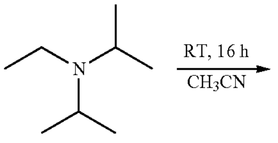

A97.3

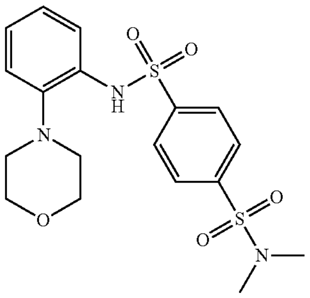

A-770

4-(dimethylsulfamoyl)benzene-1-sulfonyl chloride (A97.2) (0.354 g, 1.24 mmol) was added to the mixture 2-(morpholin-4-yl)aniline dihydrochloride (A97.1) (0.3 g, 1.19 mmol) and ethylbis(propan-2-yl)amine (A97.3) (0.23 g, 1.77 mmol) in dry acetonitrile (5 mL). The reaction mixture was stirred overnight. After completion, it was concentrated in vacuo. The residue was subjected to HPLC purification (deionized water/HPLC-grade methanol, ammonia) to afford N1,N1-dimethyl-N4-[2-(morpholin-4-yl)phenyl]benzene-1,4-disulfonamide (A-770). Yield: 26.7 mg, 4.99%; Appearance: Light brown solid; $^1H$ NMR (600 MHz, DMSO-$d_6$) δ 9.40 (s, 1H), 7.96 (d, J=8.4 Hz, 2H), 7.90 (d, J=8.4 Hz, 2H), 7.25-7.22 (m, 1H), 7.13 (dd, J=7.0, 1.8 Hz, 2H), 7.06 (ddd, J=8.5, 6.4, 2.4 Hz, 1H), 3.58-3.47 (m, 4H), 2.59 (s, 6H); HPLC purity: 100%; LCMS Calculated for $C_{18}H_{23}N_3O_5S_2$: 425.52; Observed: 426.2[M+H]$^+$.

Example A98: Synthesis of N4-[2-(4-{[(2R,6S)-2,6-dimethylmorpholin-4-yl]methyl}-4-methylpiperidin-1-yl)-3-fluorophenyl]-N1,N1-dimethylbenzene-1,4-disulfonamide (A-781)

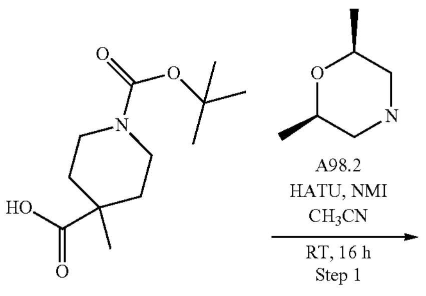

A98.2

A98.1

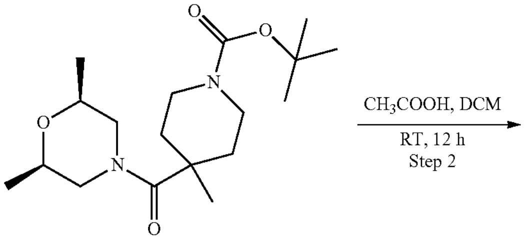

A98.3

-continued

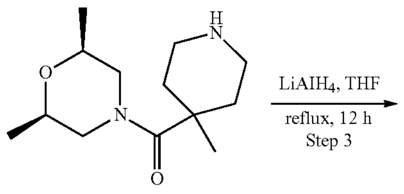

A98.4

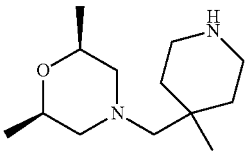

A98.5

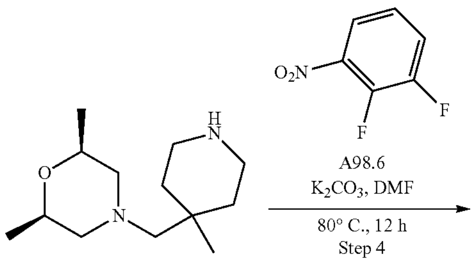

A98.6

A98.5

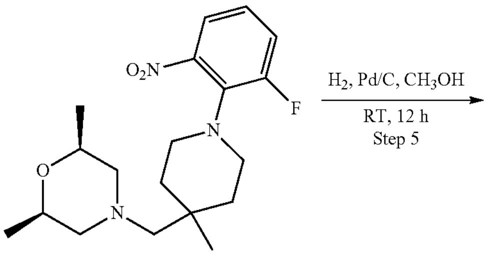

A98.7

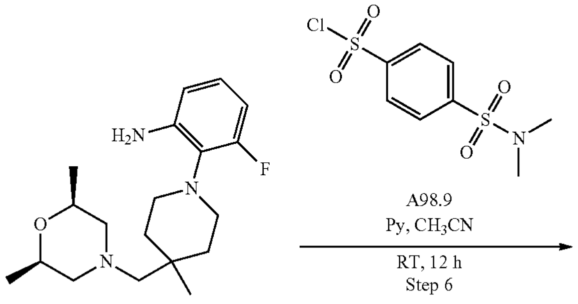

A98.9

A98.8

-continued

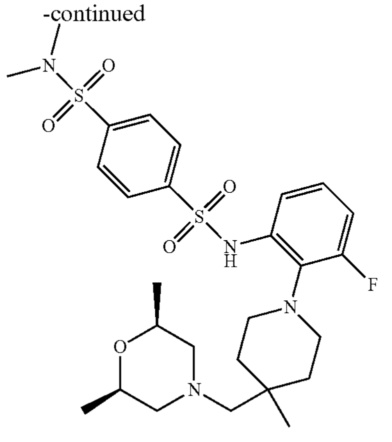

A-781

Step-1. Synthesis of tert-butyl 4-[(2R,6S)-2,6-dimethylmorpholine-4-carbonyl]-4-methylpiperidine-1-carboxylate (A98.3)

1-[(tert-butoxy)carbonyl]-4-methylpiperidine-4-carboxylic acid (A98.1) (2.0 g, 8.22 mmol), (2R,6S)-2,6-dimethylmorpholine (A98.2) (0.946 g, 8.22 mmol, 1.02 mL) and 1-methyl-1H-imidazole (2.01 g, 24.6 mmol, 1.97 mL) were dissolved in acetonitrile (20 mL) and [chloro(dimethylamino)methylidene]dimethylazanium; hexafluoro-$\lambda^5$-phosphanide (3.45 g, 12.3 mmol) was added in a single portion. The reaction was stirred overnight at room temperature and concentrated under reduced pressure. Dichloromethane (20 mL) was added to the residue and the obtained solution was washed with brine (10 mL 2 mL), dried over sodium sulfate, filtered and concentrated in vacuo to give crude tert-butyl 4-[(2R,6S)-2,6-dimethylmorpholine-4-carbonyl]-4-methylpiperidine-1-carboxylate (A98.3) (3.4 g, 50.44% purity, 5.03 mmol, 61.2% yield).

Step-2. Synthesis of (2R,6S)-2,6-dimethyl-4-(4-methylpiperidine-4-carbonyl)morpholine (A98.4)

TFA (15 mL) was added in one portion to a stirred solution of tert-butyl 4-[(2R,6S)-2,6-dimethylmorpholine-4-carbonyl]-4-methylpiperidine-1-carboxylate (A98.3) (3.4 g, 9.98 mmol) in dichloromethane (45 mL). The resulting mixture was stirred overnight and evaporated under reduced pressure. The residue was partitioned between ethyl acetate (20 mL) and saturated aqueous solution of potassium carbonate (40 mL). The organic layer was separated, washed with brine (20 mL), dried over sodium sulfate, filtered and concentrated in vacuo to give crude (2R,6S)-2,6-dimethyl-4-(4-methylpiperidine-4-carbonyl)morpholine (A98.4) (2 g, 8.32 mmol, 86.06% purity, 71.9% yield) that was used in the next step without purification.

Step-3. Synthesis of (2R,6S)-2,6-dimethyl-4-[(4-methylpiperidin-4-yl)methyl]morpholine (A98.5)

$LiAH_4$ (0.563 g, 16.6 mmol) was suspended in dry tetrahydrofuran (20 mlL, and (2R,6S)-2,6-dimethyl-4-(4-methylpiperidine-4-carbonyl)morpholine (A98.4) (2 g, 8.32 mmol) solution in tetrahydrofuran (10 mL) was added under ice-cooling dropwise keeping the temperature of mixture below 0° C. After the mixture was refluxed for 16 h, cooled to room temperature, and quenched with 2.0 M NaOH aq. solution (20 mL). The resulting mixture was stirred at room temperature for 15 min, the precipitate was filtered off and washed with THE (10 mL). The combined filtrates were concentrated under reduced pressure to give (2R,6S)-2,6-dimethyl-4-[(4-methylpiperidin-4-yl)methyl]morpholine (A98.5) (1.14 g, 5.03 mmol, 90% purity, 54.2% yield) that was used in next step without further purification.

Step-4. Synthesis of (2R,6S)-4-{[1-(2-fluoro-6-nitrophenyl)-4-methylpiperidin-4-yl]methyl}-2,6-dimethylmorpholine (A98.7)

1,2-difluoro-3-nitrobenzene (A98.6) (0.8 g, 5.03 mmol) was added to a stirred solution of (2R,6S)-2,6-dimethyl-4-[(4-methylpiperidin-4-yl)methyl]morpholine (A98.5) (1.14 g, 5.03 mmol) and potassium carbonate (1.04 g, 7.54 mmol) in dry DMF (30 mL). The mixture were heated to 80° C. and stirred at this temperature till completion (overnight, TLC control). After the reaction mixture was cooled to room temperature, diluted with water (50 mL) and the product was extracted with ethyl acetate (30 mL×3). Combined ethyl acetate layers were washed with water (20 mL×7), dried over anhydrous sodium sulfate, filtered and evaporated under reduced pressure to afford (2R,6S)-4-{[1-(2-fluoro-6-nitrophenyl)-4-methylpiperidin-4-yl]methyl}-2,6-dimethylmorpholine as an orange solid (A98.7) (1.2 g, 3.28 mmol, 92.25% purity, 60.1% yield).

Step-5. Synthesis of 2-(4-{[(2R,6S)-2,6-dimethylmorpholin-4-yl]methyl}-4-methylpiperidin-1-yl)-3-fluoroaniline (A98.8)

10% Pd/C (0.1 g) was added to the solution of (2R,6S)-4-{[1-(2-fluoro-6-nitrophenyl)-4-methylpiperidin-4-yl]methyl}-2,6-dimethylmorpholine (A98.7) (1.2 g, 3.28 mmol) in methanol (20 mL). The resulting mixture was hydrogenated at ambient pressure and room temperature until the reaction was completed (LCMS control, overnight). The catalyst was filtered off and the filtrate was evaporated to afford 2-(4-{[(2R,6S)-2,6-dimethylmorpholin-4-yl]methyl}-4-methylpiperidin-1-yl)-3-fluoroaniline (A98.8) (0.9 g, 2.68 mmol, 73.58% purity, 60.1% yield) that was used in next step without further purification.

Step-6. Synthesis of N4-[2-(4-{[(2R,6S)-2,6-dimethylmorpholin-4-yl]methyl}-4-methylpiperidin-1-yl)-3-fluorophenyl]-N1,N1-dimethylbenzene-1,4-disulfonamide (A-781)

Pyridine (0.136 g, 1.72 mmol, 140.0 μl) was added to the mixture of 2-(4-{[(2R,6S)-2,6-dimethylmorpholin-4-yl]methyl}-4-methylpiperidin-1-yl)-3-fluoroaniline (A98.8) (0.387 g, 1.15 mmol) and 4-(dimethylsulfamoyl)benzene-1-sulfonyl chloride (A98.9) (0.357 g, 1.26 mmol) in dry acetonitrile (5 mL). The reaction mixture was stirred overnight. After completion, it was concentrated in vacuo. The residue was subjected to HPLC purification (deionized water/HPLC-grade acetonitrile) to afford N4-[2-(4-{[(2R,6S)-2,6-dimethylmorpholin-4-yl]methyl}-4-methylpiperidin-1-yl)-3-fluorophenyl]-N1,N1-dimethylbenzene-1,4-disulfonamide (A-781). Yield: 127.8 mg, 18%; Appearance: Beige solid; $^1H$ NMR (400 MHz, DMSO-$d_6$) δ 9.23 (s, 1H), 7.97 (d, J=8.3 Hz, 2H), 7.91 (d, J=8.3 Hz, 2H), 7.25-7.17 (m, 2H), 6.99 (ddd, J=12.3, 8.0, 1.6 Hz, 1H), 3.56 (dd, J=9.0, 5.9 Hz, 2H), 2.74 (d, J=27.9 Hz, 2H), 2.60 (s, 8H), 2.29 (s, 2H), 2.11 (s, 2H), 1.90 (t, J=10.6 Hz, 2H), 1.44 (t, J=10.4 Hz, 2H), 1.20 (d, J=12.9 Hz, 2H), 1.03 (d, J=6.2 Hz, 6H), 0.89 (s, 3H);

HPLC purity: 100%; LCMS Calculated for $C_{27}H_{39}FN_4O_5S_2$: 582.75; Observed: 583.2[M+H]+.

Example A99: Synthesis of N4-[2-(4-{[(2R,6S)-2,6-dimethylmorpholin-4-yl]methyl}-4-fluoropiperidin-1-yl)-3-fluorophenyl]-N1,N1-dimethylbenzene-1,4-disulfonamide (A-794)

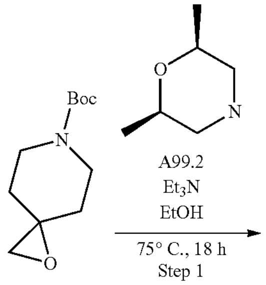

A99.1

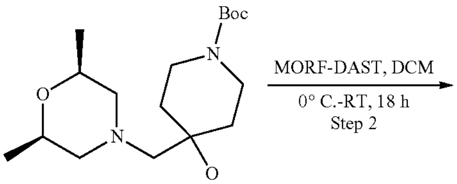

A99.3

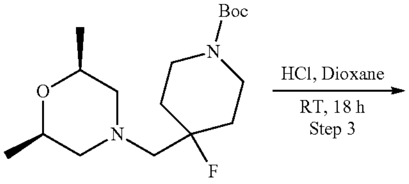

A99.4

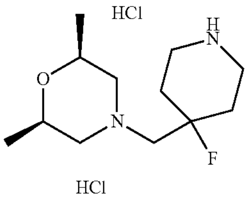

A99.5

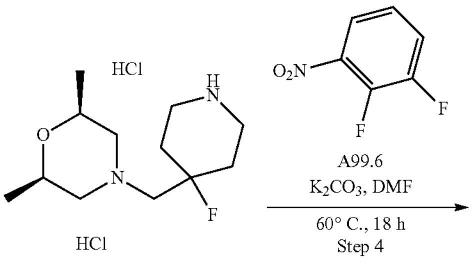

A99.5

-continued

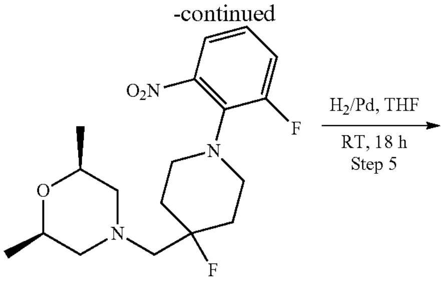

A99.7

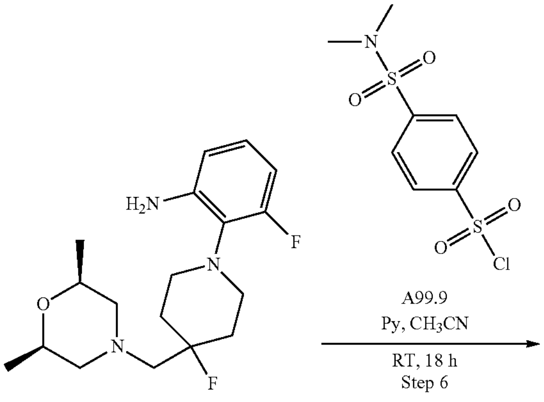

A99.8

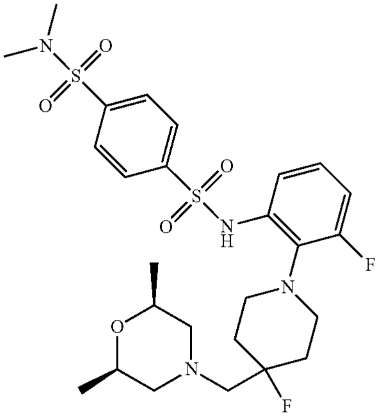

A-794

Step-1. Synthesis of tert-butyl 4-[(2R,6S)-2,6-dimethylmorpholin-4-yl]methyl-4-hydroxypiperidine-1-carboxylate (A99.3)

tert-butyl 1-oxa-6-azaspiro[2.5]octane-6-carboxylate (A99.1) (1 g, 4.68 mmol), rac-(2R,6S)-2,6-dimethylmorpholine (A99.2) (1.07 g, 9.36 mmol) and triethylamine (1.41 g, 14 mmol) were mixed in ethanol (10 mL) and stirred at 75° C. overnight. After the reaction mixture was cooled to room temperature and evaporated to dryness to give crude tert-butyl 4-[(2R,6S)-2,6-dimethylmorpholin-4-yl]methyl-4-hydroxypiperidine-1-carboxylate (A99.3) (1.6 g, 4.87 mmol, 80.0% purity, 83.6% yield) that was used in next step without further purification.

Step-2. Synthesis of tert-butyl 4-{[(2R,6S)-2,6-dimethylmorpholin-4-yl]methyl}-4-fluoropiperidine-1-carboxylate (A99.4)

4-morpholinylsulfur trifluoride (1.7 g, 9.74 mmol, 2.0 eq) was added at 0° C. to a solution of tert-butyl 4-[(2R,6S)-2, 6-dimethylmorpholin-4-yl]methyl-4-hydroxypiperidine-1-carboxylate (A99.3) (1.6 g, 4.87 mmol) in anhydrous dichloromethane (10 mL). After the mixture was allowed to warm to room temperature and stir overnight. After the reaction was quenched by ice water (20 mL) and the organic layer was separated, dried over anhydrous sodium sulfate, filtered and evaporated under reduced pressure. The residue was purified by HPLC (deionized water/HPLC-grade acetonitrile) to give tert-butyl 4-{[(2R,6S)-2,6-dimethylmorpholin-4-yl]methyl}-4-fluoropiperidine-1-carboxylate (A99.4) (0.58 g, 1.75 mmol, 95% purity, 34.4% yield).

Step-3. Synthesis of (2R,6S)-4-[(4-fluoropiperidin-4-yl)methyl]-2,6-dimethylmorpholine Dihydrochloride (A99.5)

tert-butyl 4-{[(2R,6S)-2,6-dimethylmorpholin-4-yl]methyl}-4-fluoropiperidine-1-carboxylate (A99.4) (0.58 g, 1.75 mmol) was dissolved in MTBE (10 mL) and 2 M HCl solution in dioxane was added (5 mL). The reaction mixture was stirred at room temperature overnight, evaporated under reduced pressure to give (2R,6S)-4-[(4-fluoropiperidin-4-yl)methyl]-2,6-dimethylmorpholine dihydrochloride (A99.5) (0.45 g, 1.48 mmol, 95% purity, 80.5% yield).

Step-4. Synthesis of (2R,6S)-4-{[4-fluoro-1-(2-fluoro-6-nitrophenyl)piperidin-4-yl]methyl}-2,6-dimethylmorpholine (A99.7)

1,2-difluoro-3-nitrobenzene (A99.6) (0.115 g, 0.728 mmol), (2R,6S)-4-[(4-fluoropiperidin-4-yl)methyl]-2,6-dimethylmorpholine dihydrochloride (A99.5) (0.201 g, 0.662 mmol) and potassium carbonate (0.319 g, 2.31 mmol) were mixed in DMF (10 mL), heated to 80° C. and stirred at this temperature till completion (overnight, TLC control). After the reaction mixture was cooled to room temperature, diluted with water (20 mL) and the product was extracted with ethyl acetate (10 mL×3). Combined ethyl acetate layers were washed with water (5 mL×7), dried over anhydrous sodium sulfate, filtered and evaporated under reduced pressure to afford (2R,6S)-4-{[4-fluoro-1-(2-fluoro-6-nitrophenyl)piperidin-4-yl]methyl}-2,6-dimethylmorpholine as an orange solid (A99.7) (0.2 g, 0.541 mmol, 100% purity, 81.9% yield).

Step-5. Synthesis of 2-(4-{[(2R,6S)-2,6-dimethylmorpholin-4-yl]methyl}-4-fluoropiperidin-1-yl)-3-fluoroaniline (A99.8)

10% Pd/C (0.05 g) was added to the solution of (2R,6S)-4-{[4-fluoro-1-(2-fluoro-6-nitrophenyl)piperidin-4-yl]methyl}-2,6-dimethylmorpholine (A99.7) (0.2 g, 0.541 mmol) in methanol (10 mL). The resulting mixture was hydrogenated at ambient pressure and room temperature until the reaction was completed (LCMS control, overnight). The catalyst was filtered off and the filtrate was evaporated to afford 2-(4-{[(2R,6S)-2,6-dimethylmorpholin-4-yl]methyl}-4-fluoropiperidin-1-yl)-3-fluoroaniline (A99.8) (0.18 g, 0.530 mmol, 99.14% purity, 97.2% yield).

Step-6. Synthesis of N4-[2-(4-{[(2R,6S)-2,6-dimethylmorpholin-4-yl]methyl}-4-fluoropiperidin-1-yl)-3-fluorophenyl]-N1,N1-dimethylbenzene-1,4-disulfonamide (A-794)

Pyridine (0.0627 g, 0.795 mmol, 70.0 µl) was added to the mixture of 2-(4-{[(2R,6S)-2,6-dimethylmorpholin-4-yl]methyl}-4-fluoropiperidin-1-yl)-3-fluoroaniline (A99.8) (0.18 g, 0.53 mmol) and 4-(dimethylsulfamoyl)benzene-1-sulfonyl chloride (A99.9) (0.165 g, 0.583 mmol) in dry acetonitrile (5 mL). The reaction mixture was stirred overnight. After completion, it was concentrated in vacuo. The residue was subjected to HPLC purification (deionized water/HPLC-grade methanol, ammonia) to afford N4-[2-(4-{[(2R,6S)-2,6-dimethylmorpholin-4-yl]methyl}-4-fluoropiperidin-1-yl)-3-fluorophenyl]-N1,N1-dimethylbenzene-1,4-disulfonamide (A-794). Yield: 24.7 mg, 7.54%; Appearance: Beige solid; $^1$H NMR (400 MHz, DMSO-$d_6$) δ 9.41 (s, 1H), 7.99-7.88 (m, 4H), 7.27-7.17 (m, 2H), 6.99 (dd, J=12.1, 8.2 Hz, 1H), 3.59-3.51 (m, 2H), 2.93 (s, 2H), 2.75 (d, J=11.2 Hz, 2H), 2.62 (d, J=2.1 Hz, 6H), 2.44 (d, J=24.4 Hz, 2H), 2.22 (s, 2H), 1.76 (dd, J=23.0, 12.9 Hz, 6H), 1.04 (dd, J=6.3, 2.0 Hz, 6H); HPLC purity: 100%; LCMS Calculated for $C_{26}H_{36}F_2N_4O_5S_2$: 586.72; Observed: 587.2[M+H]$^+$.

Example A100: Synthesis of N4-[2-(4-{[(2R,6S)-2,6-dimethyloxan-4-yl]oxy}piperidin-1-yl)-3-fluorophenyl]-N1,N1-dimethylbenzene-1,4-disulfonamide (A-817)

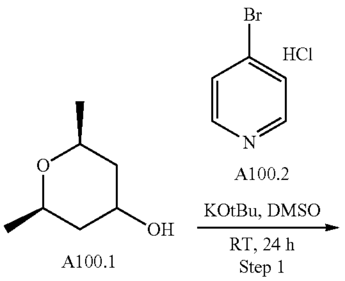

A100.2

A100.1

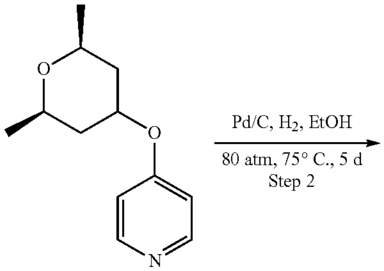

A100.3

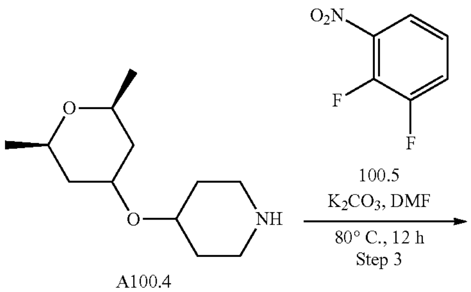

100.5

A100.4

-continued

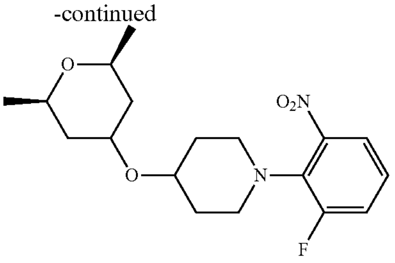

A100.6

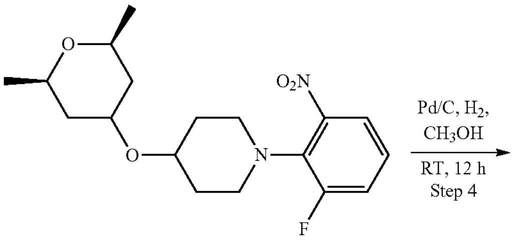

A100.6

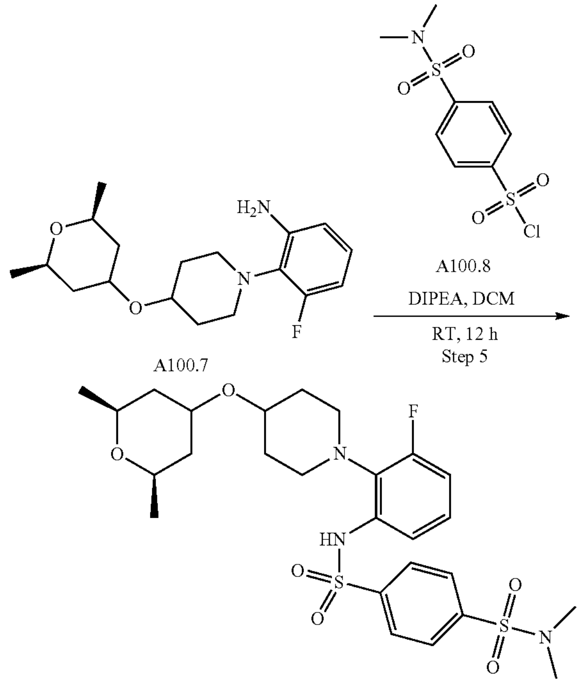

A100.7

A-817

Step-1. Synthesis of 4-{[(2R,6S)-2,6-dimethyloxan-4-yl]oxy}pyridine (A100.3)

Potassium tert-butylate (4.78 g, 42.6 mmol) was added at 0° C. to (2R,6S)-2,6-dimethyloxan-4-ol (A100.1) (1.85 g, 2.3 mmol) solution in DMSO (50 mL) and the mixture was stirred for 1 hour at room temperature. After it was cooled to 0° C. and 4-bromopyridine hydrochloride (A100.2) (2.39 g, 21.3 mmol) was added. The mixture was warmed to room temperature and stirred for 16 h. After monitoring by TLC, the reaction mixture was concentrated under reduced pressure. The residue was taken up in water (200 mL) and extracted with dichloromethane (200 mL×2). The combined organic layers were washed with water (100 mL), brine (100 mL), dried over sodium sulfate, concentrated under reduced pressure to give 4-{[(2R,6S)-2,6-dimethyloxan-4-yl]oxy}pyridine (A100.3) (3.1 g, 14.9 mmol, 90% purity, 94.8% yield) that was used in next step without further purification.

Step-2. Synthesis of 4-{[(2R,6S)-2,6-dimethyloxan-4-yl]oxy}piperidine (A100.4)

10% Pd/C (1.5 g) was added to a solution of 4-{[(2R,6S)-2,6-dimethyloxan-4-yl]oxy}pyridine (A100.3) (3.1 g, 14.9 mmol) in ethanol (50 mL) and the mixture was hydrogenated at 80 bar and 70° C. for 3 days. After the mixture was cooled to room temperature, palladium was filtered off and the filtrate was concentrated under reduced pressure to give 4-{[(2R,6S)-2,6-dimethyloxan-4-yl]oxy}piperidine (A100.4) (2.5 g, 11.7 mmol, 85% purity, 66.8% yield) that was used in next step without further purification.

Step-3. Synthesis of 4-{[(2R,6S)-2,6-dimethyloxan-4-yl]oxy}-1-(2-fluoro-6-nitrophenyl)piperidine (A100.6)

1,2-difluoro-3-nitrobenzene (A100.5) (0.205 g, 1.29 mmol) was added to a stirred solution of 4-{[(2R,6S)-2,6-dimethyloxan-4-yl]oxy}piperidine (A100.4) (0.305 g, 1.42 mmol) and potassium carbonate (0.445 g, 3.22 mmol) in dry DMF (5 mL). The mixture was stirred at 60° C. until the reaction completion (TLC control) and concentrated under the reduced pressure. The residue was dissolved in ethyl acetate (15 mL), the organic layer was washed with water (15 mL×2), dried over anhydrous sodium sulfate, filtered and concentrated under reduced pressure to obtain crude 4-{[(2R,6S)-2,6-dimethyloxan-4-yl]oxy}-1-(2-fluoro-6-nitrophenyl)piperidine as an orange oil (A100.6) (0.41 g, 1.16 mmol, 95% purity, 85.6% yield).

Step-4. Synthesis of 2-(4-{[(2R,6S)-2,6-dimethyloxan-4-yl]oxy}piperidin-1-yl)-3-fluoroaniline (A100.7)

4-{[(2R,6S)-2,6-dimethyloxan-4-yl]oxy}-1-(2-fluoro-6-nitrophenyl)piperidine (A100.6) (0.41 g, 1.16 mmol) was dissolved in methanol (10 mL) and treated with 10% Pd/C (0.05 g). The resulting mixture was hydrogenated at 6 atm and room temperature until the reaction was completed (TLC control). The catalyst was filtered off and the filtrate was evaporated to afford 2-(4-{[(2R,6S)-2,6-dimethyloxan-4-yl]oxy}piperidin-1-yl)-3-fluoroaniline (A100.7) (0.29 g, 0.899 mmol, 95% purity, 73.5% yield).

Step-5. Synthesis of N4-[2-(4-{[(2R,6S)-2,6-dimethyloxan-4-yl]oxy}piperidin-1-yl)-3-fluorophenyl]-N1,N1-dimethylbenzene-1,4-disulfonamide (A-817)

4-(N,N-dimethylsulfamoyl)benzenesulfonyl chloride (A100.8) (0.255 g, 0.899 mmol) was added to the mixture of 2-(4-{[(2R,6S)-2,6-dimethyloxan-4-yl]oxy}piperidin-1-yl)-3-fluoroaniline (A100.7) (0.29 g, 0.899 mmol) and ethylbis(propan-2-yl)amine (0.173 g, 1.34 mmol) in dry dichloromethane (5 mL). The reaction mixture was stirred overnight, poured into $NaHCO_3$ sat. aq. solution (15 mL) and extracted with dichloromethane (20 mL). Organic layer was dried over anhydrous sodium sulfate, filtered and evaporated under reduced pressure. Resulting solid was purified by HPLC (deionized water/HPLC-grade methanol) to afford N4-[2-(4-{[(2R,6S)-2,6-dimethyloxan-4-yl]oxy}piperidin-1-yl)-3-fluorophenyl]-N1,N1-dimethylbenzene-1,4-disulfonamide (A-817). Yield: 84.8 mg, 15.7%;

Appearance: Orange solid; $^{1}H$ NMR (400 MHz, DMSO-$d_6$) δ 9.35 (s, 1H), 8.02-7.89 (m, 4H), 7.25-7.15 (m, 2H), 6.96 (t, J=10.1 Hz, 1H), 3.59-3.36 (m, 6H), 2.61 (d, J=1.5 Hz, 6H), 1.87 (dd, J=13.1, 4.2 Hz, 2H), 1.70 (s, 2H), 1.52 (d, J=10.1 Hz, 2H), 1.15-1.01 (m, 6H), 0.92 (q, J=11.4 Hz, 2H); HPLC purity: 100%; LCMS Calculated for $C_{26}H_{36}FN_3O_6S_2$: 569.71; Observed: 570.4[M+H]$^+$.

Example A101: Synthesis of N4-[2-(4-[(2R,6S)-2,6-dimethylmorpholin-4-yl]methyl-4-methoxypiperidin-1-yl)-3-fluorophenyl]-N1,N1-dimethylbenzene-1,4-disulfonamide (A-786)

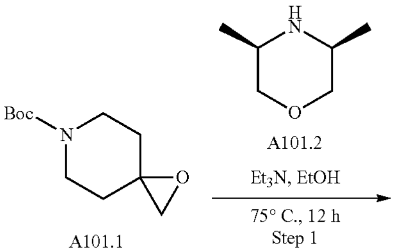

A101.1 A101.2

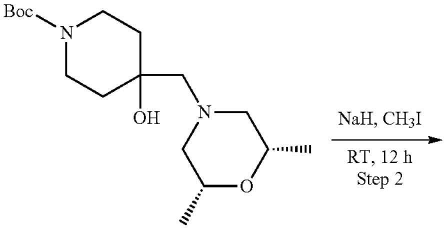

A101.3

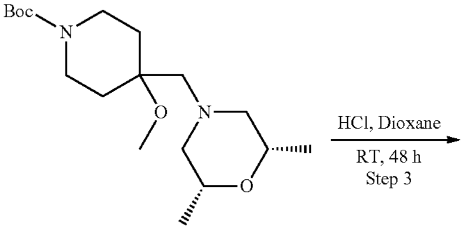

A101.4

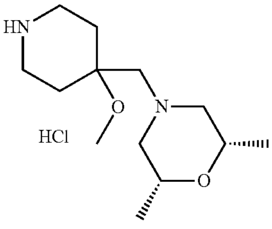

A101.5

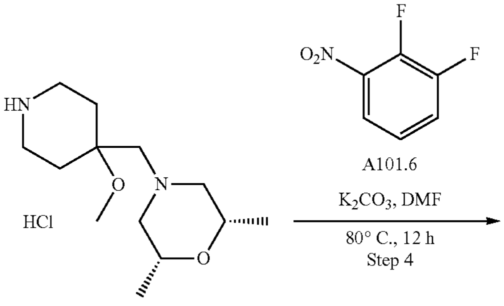

A101.5 A101.6

-continued

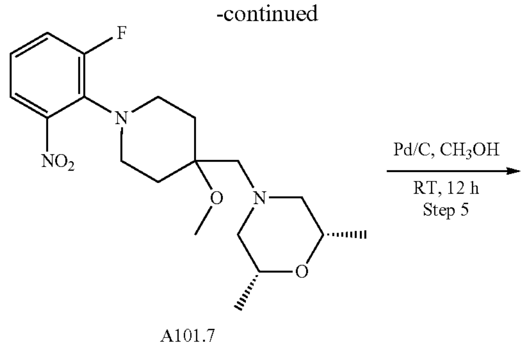

A101.7

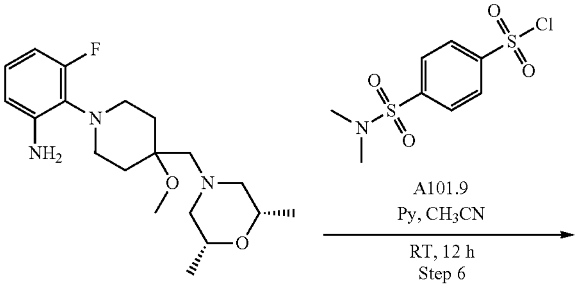

A101.8 A101.9

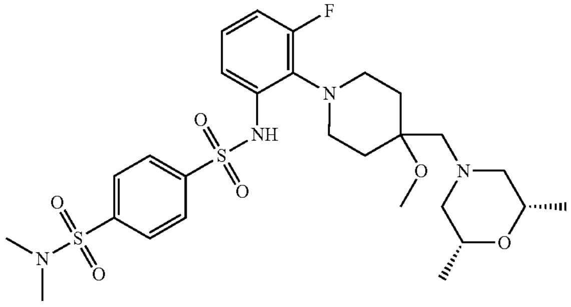

A-786

Step-1. Synthesis of 4-[(2R,6S)-2,6-dimethylmorpholin-4-yl]methyl-4-hydroxypiperidine-1-carboxylate (A101.3)

Tert-butyl 1-oxa-6-azaspiro[2.5]octane-6-carboxylate (A101.1) (1 g, 4.68 mmol), rac-(2R,6S)-2,6-dimethylmorpholine (A101.2) (1.07 g, 9.36 mmol) and triethylamine (1.41 g, 14.05 mmol) were mixed together in ethanol (20 mL) and stirred at 75° C. overnight. Reaction mixture was cooled to room temperature, evaporated under reduced pressure to give crude tert-butyl 4-[(2R,6S)-2,6-dimethylmorpholin-4-yl]methyl-4-hydroxypiperidine-1-carboxylate (A101.3) (1.45 g, 4.41 mmol, 88.73% purity, 83.6% yield) which was used in next step without further purification.

Step-2. Synthesis of tert-butyl 4-[(2R,6S)-2,6-dimethylmorpholin-4-yl]methyl-4-methoxypiperidine-1-carboxylate (A101.4)

tert-butyl-4-[(2R,6S)-2,6-dimethylmorpholin-4-yl]methyl-4-hydroxypiperidine-1-carboxylate (A101.3) (1.45 g, 4.43 mmol) was added at 0° C. to suspension of sodium hydride (0.211 g, 8.86 mmol) in tetrahydrofuran (50 mL). After 30 min of stirring at this temperature, iodomethane (1.57 g, 11.08 mmol) was added. The reaction mixture was stirred at room temperature overnight, cooled to 0° C. and diluted with $NH_4Cl$ sat. aq. solution (20 mL). The product was extracted with ethyl acetate (20 mL×3), combined ethyl acetate layers were dried under sodium sulfate, filtered and evaporated under reduce pressure to give crude tert-butyl 4-[(2R,6S)-2,6-dimethylmorpholin-4-yl]methyl-4-methoxypiperidine-1-carboxylate (A101.4) (1.54 g, 4.49 mmol, 70.0% purity, 70.8% yield) that was used in next step without further purification.

Step-3. Synthesis of give (2R,6S)-4-[(4-methoxypiperidin-4-yl)methyl]-2,6-dimethylmorpholine dihydrochloride (A101.5)

15 mL of HCl sat. solution in dioxane was added to solution of tert-butyl 4-[(2R,6S)-2,6-dimethylmorpholin-4-yl]methyl-4-methoxypiperidine-1-carboxylate (A101.4) (1.54 g, 4.5 mmol) in dioxane (40 mL). The reaction mixture was stirred at room temperature overnight and evaporated under reduced pressure. The residue was washed with MTBE (30 mL×2), dried on air to give (2R,6S)-4-[(4-methoxypiperidin-4-yl)methyl]-2,6-dimethylmorpholine dihydrochloride (A101.5) (1.05 g, 3.33 mmol, 95% purity, 70.7% yield).

Step-4. Synthesis of (2R,6S)-4-[1-(2-fluoro-6-nitrophenyl)-4-methoxypiperidin-4-yl]methyl-2,6-dimethylmorpholine (A101.7)

(2R,6S)-4-[(4-methoxypiperidin-4-yl)methyl]-2,6-dimethylmorpholine dihydrochloride (A101.5) (0.5 g, 1.58 mmol), 1,2-difluoro-3-nitrobenzene (A101.6) (0.251 g, 1.58 mmol) and dipotassium carbonate (0.764 g, 5.53 mmol) were mixed in DMF (50 mL), heated to 80° C. and stirred at this temperature overnight. Then the reaction mixture was cooled to room temperature, diluted with water (40 mL) and extracted with ethyl acetate (30 mL×3). Combined ethyl acetate layers were washed with water (15 mL×7), dried over sodium sulfate, filtered and evaporated under reduced pressure to afford crude (2R,6S)-4-[1-(2-fluoro-6-nitrophenyl)-4-methoxypiperidin-4-yl]methyl-2,6-dimethylmorpholine (A101.7) (0.68 g, 1.78 mmol, 87.63% purity, 98.8% yield) that was used in next step without further purification.

Step-5. Synthesis of 2-(4-[(2R,6S)-2,6-dimethylmorpholin-4-yl]methyl-4-methoxypiperidin-1-yl)-3-fluoroaniline (A101.8)

(2R,6S)-4-[1-(2-fluoro-6-nitrophenyl)-4-methoxypiperidin-4-yl]methyl-2,6-dimethylmorpholine (A101.7) (0.68 g, 1.78 mmol) was dissolved in MeOH (30 mL) and treated with 10% Pd/C (0.07 g). The resulting mixture was hydrogenated at ambient pressure and room temperature until the reaction was completed (TLC control). The catalyst was filtered off and the filtrate was evaporated to afford 2-(4-[(2R,6S)-2,6-dimethylmorpholin-4-yl]methyl-4-methoxypiperidin-1-yl)-3-fluoroaniline (A101.8) (0.42 mg, 1.2 mmol, 83.7% purity, 56.1% yield) which was used in next step without further purification.

Step-6. Synthesis of N4-[2-(4-{[(2R,6S)-2,6-dimethylmorpholin-4-yl]methyl}-4-methoxypiperidin-1-yl)-3-fluorophenyl]-N1,N1-dimethylbenzene-1,4-disulfonamide (A-786)

4-(dimethylsulfamoyl)benzene-1-sulfonyl chloride (A101.9) (0.177 g, 0.625 mmol) was added in one portion to a solution of 2-(4-[(2R,6S)-2,6-dimethylmorpholin-4-yl]methyl-4-methoxypiperidin-1-yl)-3-fluoroaniline (A101.8) (0.2 g, 0.569 mmol) and pyridine (0.0674 g, 0.853 mmol) in acetonitrile (10 mL). Reaction mixture was stirred at room temperature overnight and evaporated under reduced pressure. The residue was purified by HPLC (deionized water/HPLC-grade acetonitrile, ammonia) to give N4-[2-(4-[(2R,6S)-2,6-dimethylmorpholin-4-yl]methyl-4-methoxypiperidin-1-yl)-3-fluorophenyl]-N1,N1-dimethylbenzene-1,4-disulfonamide (A-786). Yield: 31.4 mg, 8.76%; Appearance: Yellow solid; $^1$H NMR (600 MHz, DMSO-$d_6$) δ 9.28 (s, 1H), 7.97-7.93 (m, 2H), 7.89 (d, J=8.3 Hz, 2H), 7.21 (d, J=8.2 Hz, 1H), 7.16 (s, 1H), 6.94 (s, 1H), 3.54-3.48 (m, 2H), 3.05 (s, 3H), 2.83 (d, J=10.7 Hz, 2H), 2.77-2.73 (m, 2H), 2.58 (s, 6H), 2.27 (s, 2H), 2.13 (s, 2H), 1.75 (t, J=10.6 Hz, 2H), 1.63 (d, J=13.4 Hz, 2H), 1.57-1.49 (m, 2H), 1.01 (d, J=6.2 Hz, 6H); HPLC purity: 100%; LCMS Calculated for $C_{27}H_{39}FN_4O_6S_2$: 598.75; Observed: 599.0 $[M+H]^+$.

Example A102: Synthesis of N4-(2-{1,7-diazaspiro[3.5]nonan-7-yl}-3-fluorophenyl)-N1,N1-dimethylbenzene-1,4-disulfonamide (A-816)

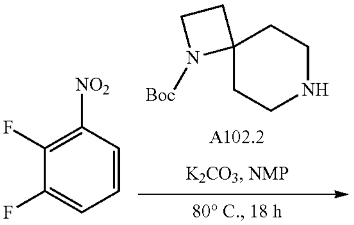

A102.2

A102.1

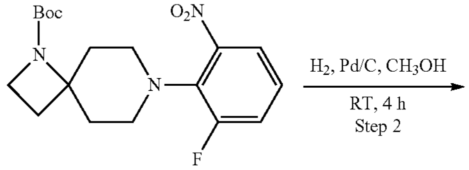

A102.3

SHRINK

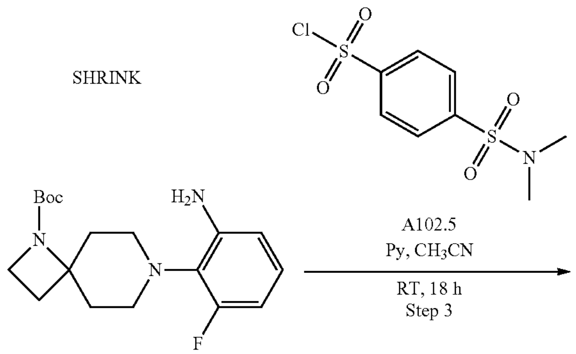

A102.5

A102.4

-continued

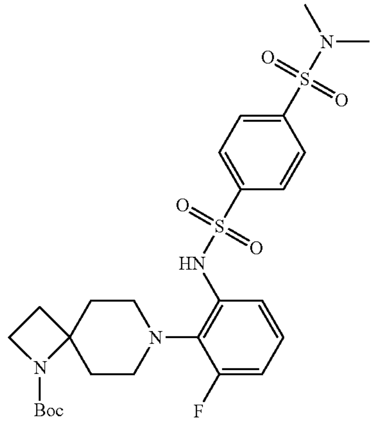

A102.6

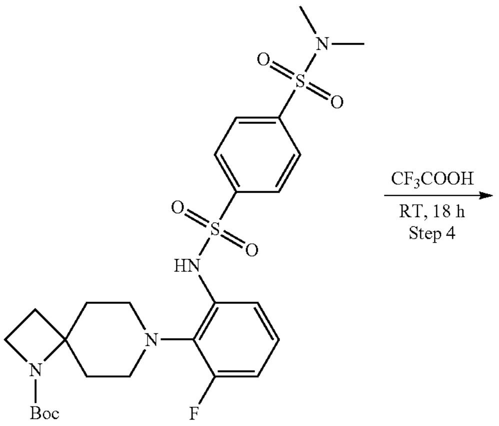

A102.6

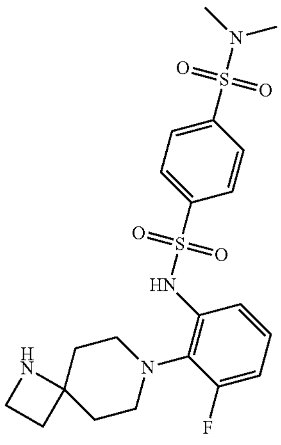

A-816

-continued

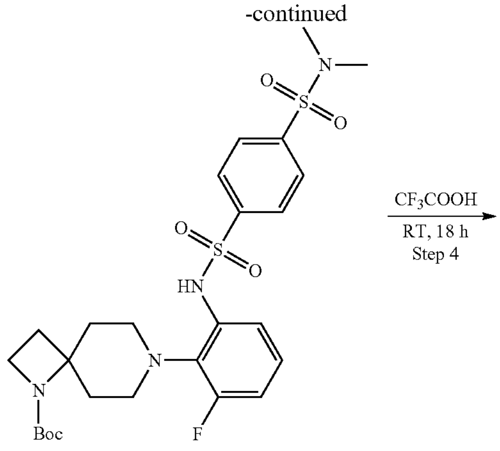

A102.6

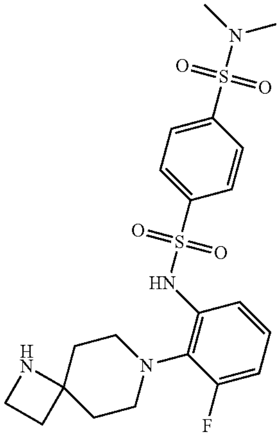

A-816

Step-1. Synthesis of tert-butyl 7-(2-fluoro-6-nitrophenyl)-1,7-diazaspiro[3.5]nonane-1-carboxylate (A102.3)

1,2-difluoro-3-nitrobenzene (A102.1) (0.994 g, 6.25 mmol) was added to a stirred solution of tert-butyl 1,7-diazaspiro[3.5]nonane-1-carboxylate (A102.2) (1.7 g, 7.51 mmol) and dipotassium carbonate (1.29 g, 9.38 mmol) in dry DMF (100 mL). The mixture was stirred at 80° C. for 18 h. Then, it was cooled to room temperature, poured in water (200 mL) and extracted with ethyl acetate (100 mL×3). The organic layer was washed with water (100 mL), brine (100 mL), dried over anhydrous sodium sulfate, filtered and concentrated under reduced pressure to obtain tert-butyl 7-(2-fluoro-6-nitrophenyl)-1,7-diazaspiro[3.5]nonane-1-carboxylate (A102.3) (2.2 g, 6.02 mmol, 95% purity, 91.6% yield).

Step-2. Synthesis of tert-butyl 7-(2-amino-6-fluorophenyl)-1,7-diazaspiro[3.5]nonane-1-carboxylate (A102.4)

tert-butyl 7-(2-fluoro-6-nitrophenyl)-1,7-diazaspiro[3.5]nonane-1-carboxylate (A102.3) (2.2 g, 6.02 mmol) was dissolved in methanol (100 mL). 10% Pd/C (0.3 g) was added to the solution and the mixture was hydrogenated at ambient pressure and room temperature for 4 h. Then it was filtered, the solid washed with methanol (50 mL) and combined filtrates were concentrated under reduced pressure to afford tert-butyl 7-(2-amino-6-fluorophenyl)-1,7-diazaspiro[3.5]nonane-1-carboxylate as white solid (A102.4) (1.95 g, 5.81 mmol, 91.57% purity, 88.5% yield) that was used in next step without further purification.

Step-3. Synthesis of tert-butyl 7-{2-[4-(dimethylsulfamoyl)benzenesulfonamido]-6-fluorophenyl}-1,7-diazaspiro[3.5]nonane-1-carboxylate (A102.6)

Pyridine (0.688 g, 8.71 mmol) and 4-(dimethylsulfamoyl) benzene-1-sulfonyl chloride (A102.5) (1.81 g, 6.39 mmol) were added to tert-butyl 7-(2-amino-6-fluorophenyl)-1,7-diazaspiro[3.5]nonane-1-carboxylate (A102.4) (1.95 g, 5.81 mmol) in acetonitrile (100 mL). The reaction mixture was stirred at room temperature for 18 h and evaporated. The residue was purified by flash chromatography (chloroform/acetonitrile) that afforded tert-butyl 7-{2-[4-(dimethylsulfamoyl)benzenesulfonamido]-6-fluorophenyl}-1,7-diazaspiro[3.5]nonane-1-carboxylate as white solid (A102.6) (1.5 g, 2.57 mmol, 95% purity, 42.0% yield).

Step-4. Synthesis of N4-(2-{1,7-diazaspiro[3.5]nonan-7-yl}-3-fluorophenyl)-N1,N1-dimethylbenzene-1,4-disulfonamide (A-816)

tert-butyl 7-{2-[4-(dimethylsulfamoyl)benzenesulfonamido]-6-fluorophenyl}-1,7-diazaspiro[3.5]nonane-1-carboxylate (A102.6) (1 g, 1.71 mmol) was added to trifluoroacetic acid (50 mL). The mixture was stirred at room temperature overnight. Then, it was concentrated under reduced pressure and the residue was subjected to HPLC purification (deionized water/HPLC-grade acetonitrile, ammonia) that afforded N4-(2-{1,7-diazaspiro[3.5]nonan-7-yl}-3-fluorophenyl)-N1,N1-dimethylbenzene-1,4-disulfonamide (A-816). Yield: 35.1 mg, 4.03%; Appearance: Beige solid; $^1$H NMR (400 MHz, DMSO-$d_6$) δ 7.90-7.85 (m, 2H), 7.78-7.70 (m, 2H), 6.93 (d, J=8.2 Hz, 1H), 6.69 (d, J=8.6 Hz, 1H), 6.37 (t, J=9.7 Hz, 1H), 5.48 (s, 1H), 3.10 (s, 2H), 2.89 (t, J=7.6 Hz, 2H), 2.59 (d, J=2.1 Hz, 6H), 2.54 (d, J=1.8 Hz, 2H), 2.23 (s, 2H), 2.00 (s, 2H); HPLC purity: 97.36%; LCMS Calculated for $C_{21}H_{27}FN_4O_4S_2$: 482.59; Observed: 483.4[M+H]$^+$.

Example A103: Synthesis of N-(2-(2-methyl-3,4-dihydro-2H-spiro[isoquinoline-1,4'-piperidin]-1'-yl)phenyl)-4-(methylsulfonyl)benzenesulfonamide (A-441)

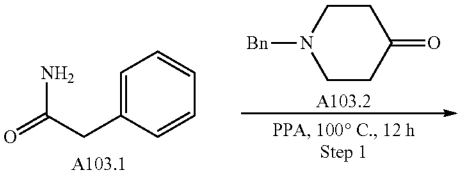

A103.1

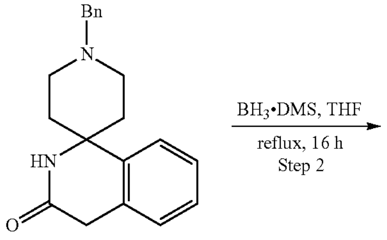

A103.3

-continued

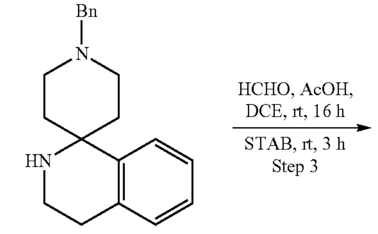

A103.4

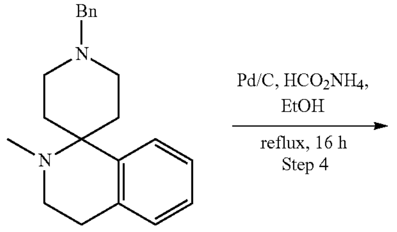

A103.5

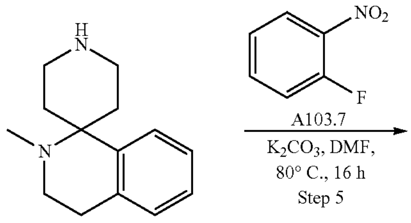

A103.6

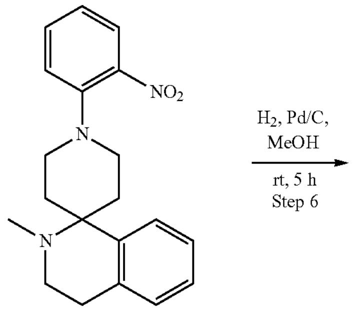

A103.8

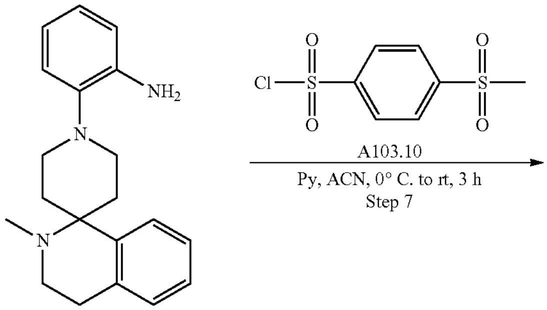

A103.9

-continued

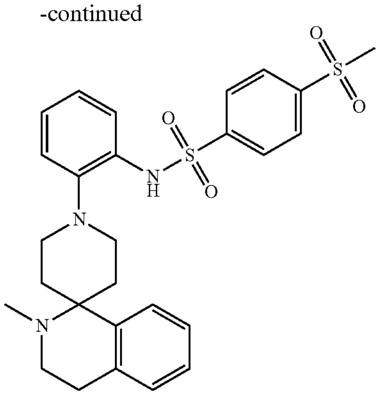

A-441

Step-1. Synthesis of 1'-benzyl-2H-spiro[isoquinoline-1,4'-piperidin]-3(4H)-one (A103.3)

A mixture of 2-phenylacetamide (A103.1) (5 g, 36 mmol, 1 eq) and 1-benzylpiperidin-4-one (A103.2) (10.5 g, 55 mmol, 1.5 eq) in polyphosphoric acid (100 g) was heated at 100° C. for 16 h. The progress of the reaction was monitored by TLC. After completion of reaction, the reaction mixture was cooled to 50° C. and slowly poured into ice-water mixture. The mixture was basified with 36% aqueous sodium hydroxide to pH 7 to 8 and stirred for 10 min. The resultant precipitate was filtered out, washed with water and dried under reduced pressure to afford 1'-benzyl-2H-spiro[isoquinoline-1,4'-piperidin]-3(4H)-one (A103.3) (8 g, crude). This compound was used in the next step without further purification. LCMS: 307.17 $[M+H]^+$.

Step-2. Synthesis of 1'-benzyl-3,4-dihydro-2H-spiro[isoquinoline-1,4'-piperidine] (A103.4)

To a stirred solution of 1'-benzyl-2H-spiro[isoquinoline-1,4'-piperidin]-3(4H)-one (A103.3) (2 g, 6.5 mmol, 1 eq) in THE (30 mL) was added a 2 M solution of borane dimethylsulfide (6.52 mL, 13 mmol, 2 eq) and the reaction mixture was refluxed for 16 h. The progress of the reaction was monitored by TLC. After completion of reaction, the reaction mixture was cooled to room temperature, 10% aqueous HCl was added and stirred for 5 min, followed by addition of methanol and refluxed for 1 h. The reaction mixture was cooled to room temperature, poured into 10% aqueous sodium hydroxide solution and extracted with DCM. The combined organic layers were dried over anhydrous $Na_2SO_4$, filtered and concentrated under reduced pressure. The crude product was purified by column chromatography on silica gel to afford 1'-benzyl-3,4-dihydro-2H-spiro[isoquinoline-1,4'-piperidine] (A103.4) (1.52 g, 80%). LCMS: 293.19 $[M+H]^+$.

Step-3. Synthesis of 1'-benzyl-2-methyl-3,4-dihydro-2H-spiro[isoquinoline-1,4'-piperidine] (A103.5)

A solution of 1'-benzyl-3,4-dihydro-2H-spiro[isoquinoline-1,4'-piperidine] (A103.4) (1 g, 3.4 mmol, 1 eq) and a 37% aqueous formaldehyde solution (4 mL) in methanol (15 mL) was stirred at room temperature for 16 h. Sodium triacetoxyborohydride (2.17 g, 10 mmol, 3 eq) was then added to the reaction mixture and stirred for 3 h. The progress of the reaction was monitored by TLC. After completion of reaction, the reaction mixture was basified with saturated aqueous $NaHCO_3$ solution to pH 8. The reaction mixture was concentrated under reduced pressure, and the residue was treated with water and extracted with DCM. The combined organic layers were dried over anhydrous $Na_2SO_4$, filtered, concentrated and purified by combiflash chromatography on silica gel to afford 1'-benzyl-2-methyl-3,4-dihydro-2H-spiro[isoquinoline-1,4'-piperidine] (A103.5) (900 mg, 86%). LCMS: 307.21 $[M+H]^+$.

Step-4. Synthesis of 2-methyl-3,4-dihydro-2H-spiro[isoquinoline-1,4'-piperidine] (A103.6)

A stirred solution of 1'-benzyl-2-methyl-3,4-dihydro-2H-spiro[isoquinoline-1,4'-piperidine] (A103.5) (1.3 g, 4.2 mmol, 1 eq) in ethanol was purged with nitrogen for 5 min. 10% Palladium on carbon (400 mg, 30% w/w) and ammonium formate (2.67 g, 42 mmol, 10 eq) were then added to the reaction mixture under nitrogen atmosphere. The reaction mixture was refluxed for 16 h. The progress of the reaction was monitored by TLC. After completion of reaction, the reaction mixture was cooled to room temperature, filtered through a pad of Celite and the Celite pad was washed with methanol. The filtrate was concentrated under reduced pressure to dryness to afford 2-methyl-3,4-dihydro-2H-spiro[isoquinoline-1,4'-piperidine] (A103.6) (1 g, crude). This compound was used in the next step without further purification. LCMS: 271.16 $[M+H]^+$.

Step-5. Synthesis of 2-methyl-1'-(2-nitrophenyl)-3,4-dihydro-2H-spiro[isoquinoline-1,4'-piperidine] (A103.8)

To a stirred solution of 2-methyl-3,4-dihydro-2H-spiro[isoquinoline-1,4'-piperidine](A103.6) (1 g, 4.6 mmol, 1 eq) in DMF or DMSO/$CH_3CN$ (10 mL) were added potassium carbonate/DIPEA (1.28 g, 9.2 mmol, 2 eq) and 2-fluoro nitrobenzene (A103.7) (0.649 g, 4.6 mmol, 1 eq) and the reaction mixture was stirred at 80° C. for 16 h. The progress of the reaction was monitored by TLC. After completion of the reaction, the reaction mixture was cooled to room temperature, diluted with cold water and extracted with ethyl acetate. The combined organic layers were dried over anhydrous $Na_2SO_4$, filtered and concentrated under reduced pressure. The crude product was purified by Combiflash chromatography on silica gel to afford 2-methyl-1'-(2-nitrophenyl)-3,4-dihydro-2H-spiro[isoquinoline-1,4'-piperidine] (A103.8) (1.1 g, 71%).

Step-6. Synthesis of 2-(2-methyl-3,4-dihydro-2H-spiro[isoquinoline-1,4'-piperidin]-1'-yl)aniline (A103.9)

An autoclave was charged with a solution of 2-methyl-1'-(2-nitrophenyl)-3,4-dihydro-2H-spiro[isoquinoline-1,4'-piperidine] (A103.8) (500 mg, 1.4 mmol, 1 eq) in a mixture of methanol (15 mL) and DCM (5 mL) and purged with nitrogen for 5 min. 10% Palladium on carbon (200 mg, 50% moisture, 20% w/w) was then added to the reaction mixture under nitrogen atmosphere. The reaction mixture was purged with hydrogen and stirred at room temperature for 5 h. The progress of the reaction was monitored by TLC. After completion of reaction, the reaction mixture was filtered through a pad of Celite and the Celite pad was washed with methanol. The filtrate was concentrated under reduced pressure to dryness to afford 2-(2-methyl-3,4-dihydro-2H-spiro

[isoquinoline-1,4'-piperidin]-1'-yl)aniline (A103.9) (450 mg, crude). This compound was used in the next step without further purification.

Step-7. Synthesis of N-(2-(2-methyl-3,4-dihydro-2H-spiro[isoquinoline-1,4'-piperidin]-1'-yl)phenyl)-4-(methylsulfonyl)benzenesulfonamide (A-441)

To a stirred solution of 2-(2-methyl-3,4-dihydro-2H-spiro[isoquinoline-1,4'-piperidin]-1'-yl)aniline (A103.9) (250 mg, 0.813 mmol, 1 eq) in acetonitrile (5 mL) was added pyridine (0.2 mL, 2.44 mmol, 3 eq) at 0° C. and the reaction mixture was stirred for 10 min. 4-(methylsulfonyl)benzene-sulfonyl chloride (A103.10) (248 mg, 0.976 mmol, 1.2 eq) was added to the reaction mixture at 0° C. The reaction mixture was allowed to attain room temperature and stirred for 3 h. The progress of the reaction was monitored by TLC.

After completion of reaction, the reaction mixture was diluted with ethyl acetate and washed with water. The organic layer was dried over anhydrous $Na_2SO_4$, filtered and concentrated under reduced pressure. The crude product was purified by preparative SFC to afford the titled compound (A-441). Yield: 80 mg, 18.7%; Appearance: White solid; $^1H$ NMR (400 MHz, DMSO-$d_6$) δ 9.34 (bs,/1H), 8.13-8.04 (m, 4H), 7.40 (d, J=8.0 Hz, 1H), 7.32 (d, J=7.2 Hz, 1H), 7.24 (t, J=7.2 Hz, 1H), 7.20-7.03 (m, 5H), 3.21 (s, 3H), 3.12-3.06 (m, 2H), 2.97-2.88 (m, 2H), 2.76-2.70 (m, 2H), 2.33-2.27 (m, 2H), 2.19 (s, 3H), 2.08-1.98 (m, 2H), 1.82 (d, J=13.2 Hz, 2H); HPLC purity: 99.57%; LCMS calculated for $C_{27}H_{31}N_3O_4S_2$: 525.18; Observed: 526.25 $[M+H]^+$.

The following examples were prepared using standard chemical manipulations and procedures similar to those used for the preparation of the previous example.

| Compound No. | Structure | Yields/Analytical data |
| --- | --- | --- |
| A-348 | 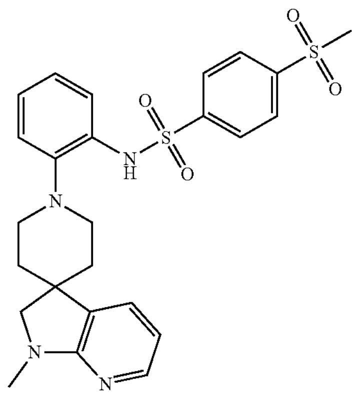 | Yield: 45 mg, 12.9%; Appearance: White solid; $^1H$ NMR (400 MHz, DMSO-$d_6$) δ 9.30 (bs, 1H), 8.12 (d, J = 8.4 Hz, 2H), 8.04 (d, J = 8.4 Hz, 2H), 7.81 (d, J = 4.0 Hz, 1H), 7.35 - 7.30 (m, 2H), 7.24 - 7.20 (m, 1H), 7.19 - 7.13 (m, 1H), 7.11 - 8.06 (m, 1H), 6.55 - 6.50 (m, 1H), 3.23 (s, 3H), 2.85 (s, 3H), 2.64 - 2.56 (m, 2H), 1.88 - 1.78 (m, 2H), 1.53 (d, J = 12.8 Hz, 2H), (s, 2H merged with the moisture peak, m, 2H merged with the solvent peak); HPLC purity: 99.79%; LCMS calculated for $C_{25}H_{28}N_4O_4S_2$: 512.16; Observed: 513.25 $[M + H]^+$. |
| A-398 | 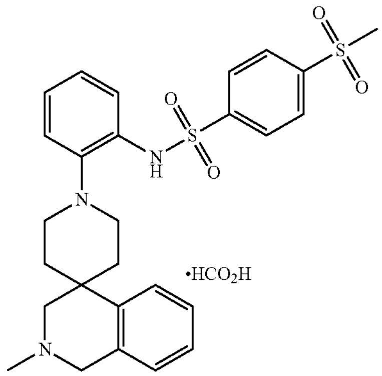 | Yield: 14 mg, 2.73%; Appearance: White solid; $^1H$ NMR (400 MHz, DMSO-$d_6$) δ 9.50 (bs, 1H), 8.16 (s, 1H, formate salt), 8.10 (d, J = 8.8 Hz, 2H), 8.06 (d, J = 8.4 Hz, 2H), 7.58 (d, J = 8.0 Hz, 1H), 7.34 - 7.25 (m, 3H), 7.17 - 7.04 (m, 3H), 7.02 (d, J = 7.6 Hz, 1H), 3.45 (s, 2H), 3.20 (s, 3H), 2.75 (t, J = 11.6 Hz, 2H), 2.62 (s, 2H), 2.39 - 2.31 (m, 2H), 2.35 (s, 3H), 2.11 - 2.02 (m, 2H), 1.55 (d, J = 13.2 Hz, 2H); HPLC purity: 97.94%; LCMS calculated for $C_{27}H_{31}N_3O_4S_2$: 525.18; Observed: 526.25 $[M + H]^+$. |
| A-402 | 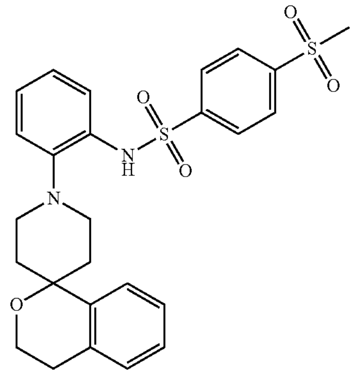 [SMILES: CS(=O)(=O)c1ccc(S(=O)(=O)Nc2ccccc2N2CCC3(CC2)OCCc2ccccc23)cc1] | Yield: 200 mg, 57%; Appearance: Off white solid; $^1H$ NMR (400 MHz, DMSO-$d_6$) δ 9.36 (bs, 1H), 8.12 (d, J = 8.4 Hz, 2H), 8.06 (d, J = 8.0 Hz, 2H), 7.40 - 7.32 (m, 2H), 7.29 (t, J = 7.6 Hz, 1H), 7.20 - 7.05 (m, 5H), 3.85 - 3.79 (m, 2H), 3.22 (s, 3H), 2.85 (t, J = 11.2 Hz, 2H), 2.77 - 2.71 (m, 2H), 2.30 (d, J = 10.4 Hz, 2H), 2.14-2.03 (m, 2H), 1.69 (d, J = 13.2 Hz, 2H); HPLC purity: 99.86%; LCMS calculated for $C_{26}H_{28}N_2O_5S_2$: 512.14; Observed: 513.20 $[M + H]^+$. |

-continued

| Compound No. | Structure | Yields/Analytical data |
|---|---|---|
| A-481 | 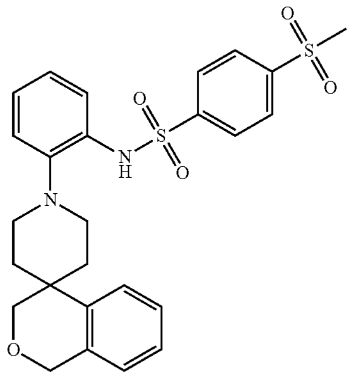 [SMILES: CS(=O)(=O)c1ccc(S(=O)(=O)Nc2ccccc2N2CCC3(CC2)COCc2ccccc23)cc1] | Yield: 260 mg, 74.7%; Appearance: Off white solid; $^{1}H$ NMR (400 MHz, DMSO-$d_6$) δ 9.37 (bs, 1H), 8.11 (d, J = 8.4 Hz, 2H), 8.06 (d, J = 8.4 Hz, 2H), 7.62 (d, J = 7.6 Hz, 1H), 7.36 - 7.26 (m, 3H), 7.20 - 7.05 (m, 3H), 7.01 (d, J = 12 Hz, 1H), 4.69 (s, 2H), 3.90 (s, 2H), 3.20 (s, 3H), 2.74 (t, J = 12.0 Hz, 2H), 2.35 (d, J = 11.2 Hz, 2H), 2.13 - 2.04 (m, 2H), 1.52 (d, J = 12.8 Hz, 2H); HPLC purity: 99.64%; LCMS calculated for $C_{26}H_{28}N_2O_5S_2$: 512.14; Observed: 513.25 $[M + H]^+$. |
| A-492 | 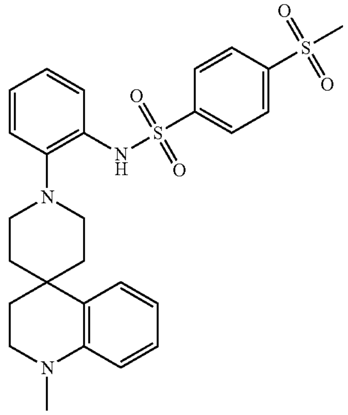 [SMILES: CN1CCC2(CCN(c3ccccc3NS(=O)(=O)c3ccc(S(C)(=O)=O)cc3)CC2)c2ccccc21] | Yield: 6 mg, 7%; Appearance: Off white solid; $^{1}H$ NMR (400 MHz, $CDCl_3$) δ 8.20 (bs, 1H), 8.06 - 7.97 (m, 4H), 7.61 (dd, J = 1.2, 8.0 Hz, 1H), 7.36 (d, J = 7.2 Hz, 1H), 7.20 - 7.06 (m, 4H), 6.78 (t, J = 12 Hz, 1H), 6.65 (d, J = 8.4 Hz, 1H), 3.18 (t, J = 6.0 Hz, 2H), 3.03 (s, 3H), 2.90 (s, 3H), 2.85 (t, J = 11.2 Hz, 2H), 2.33 (d, J = 11.6 Hz, 2H), 2.17 - 2.07 (m, 2H), 2.04 - 1.98 (m, 2H), 1.70 (d, J = 13.2 Hz, 2H); HPLC purity: 97.78%; LCMS calculated for $C_{27}H_{31}N_3O_4S_2$: 525.18; Observed: 526.25 $[M + H]^+$. |
| A-470 | 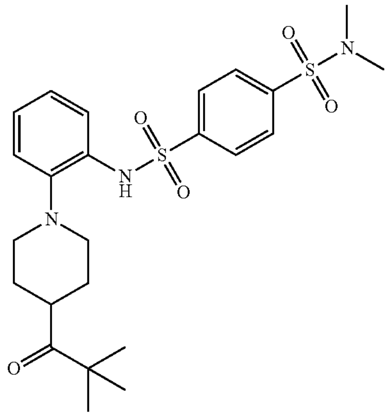 [SMILES: CN(C)S(=O)(=O)c1ccc(S(=O)(=O)Nc2ccccc2N2CCC(C(=O)C(C)(C)C)CC2)cc1] | Yield: 100 mg, 25.6; Appearance: Off white solid; $^{1}H$ NMR (400 MHz, DMSO-$d_6$) δ 9.36 (bs, 1H), 8.03 (d, J = 7.6 Hz, 2H), 7.92 (d, J = 8.4 Hz, 2H), 7.24 (d, J = 7.6 Hz, 1H), 7.14 - 7.02 (m, 3H), 3.03 - 2.94 (m, 1H), 2.61 (s, 6H), 2.59 - 2.52 (m, 4H), 1.79 - 1.65 (m, 2H), 1.49 (d, J = 12.0 Hz, 2H), 1.11 (s, 9H); HPLC purity: 99.73%; LCMS Calculated for $C_{24}H_{33}N_3O_5S_2$: 507.19; Observed: 508.25 $[M + H]^+$. |

-continued

| Compound No. | Structure | Yields/Analytical data |
|---|---|---|
| A-352 | 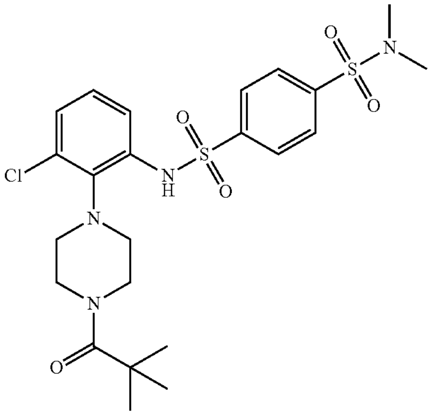 [SMILES: CN(C)S(=O)(=O)c1ccc(S(=O)(=O)Nc2cccc(Cl)c2N2CCN(C(=O)C(C)(C)C)CC2)cc1] | Yield: 60 mg, 33%; Appearance: Off white solid; $^1$H NMR (400 MHz, DMSO-$d_6$) δ 9.63 (s, 1H), 7.97 (s, 4H), 7.27 - 7.14 (m, 3H), 3.87 - 3.78 (m, 2H), 3.20 - 3.19 (m, 2H), 2.64 (s, 6H), 2.34 - 2.24 (m, 2H), 1.19 (s, 9H), (2H merged with the moisture peak); HPLC purity: 99.79%; LCMS Calculated for $C_{23}H_{31}ClN_4O_5S_2$: 542.14; Observed: 543.25 $[M + H]^+$. |
| A-353 | 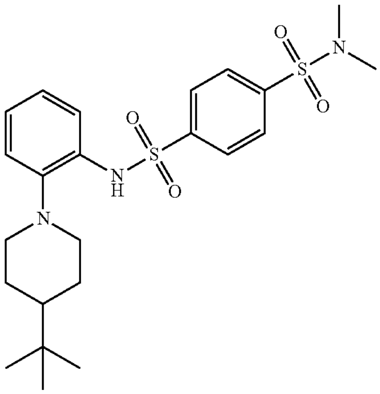 [SMILES: CN(C)S(=O)(=O)c1ccc(S(=O)(=O)Nc2ccccc2N2CCC(C(C)(C)C)CC2)cc1] | Yield: 100 mg, 30%; Appearance: Off white solid; $^1$H NMR (400 MHz, DMSO-$d_6$) δ 9.18 (bs, 1H), 7.99 (d, J = 8.4 Hz, 2H), 7.92 (d, J = 8.0 Hz, 2H), 7.25 (d, J = 8.0 Hz, 1H), 7.12 - 7.07 (m, 2H), 7.07 - 7.00 (M, 1H), 2.62 (s, 8H), 2.39 (t, J = 11.6 Hz, 2H), 1.52 (d, J = 12.0 Hz, 2H), 1.35 - 1.22 (m, 2H), 1.02 - 0.92 (m, 1H), 0.86 (s, 9H); HPLC purity: 99 40%; LCMS Calculated for $C_{23}H_{33}N_3O_4S_2$ 479.19; Observed: 480.70 $[M + H]^+$. |
| A-361 | 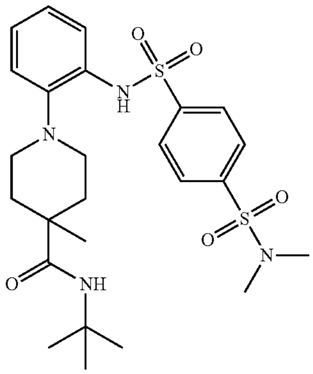 [SMILES: CN(C)S(=O)(=O)c1ccc(S(=O)(=O)Nc2ccccc2N2CCC(C)(C(=O)NC(C)(C)C)CC2)cc1] | Yield: 460 mg, 71%; Appearance: White solid; $^1$H NMR (400 MHz, DMSO-$d_6$) δ 9.19 (bs, 1H), 8.02 (d, J = 8.0 Hz, 2H), 7.92 (d, J = 8.0 Hz, 2H), 7.24 (d, J = 7.6 Hz, 1H), 7.13 - 7.00 (m, 3H), 6.67 (s, 1H), 2.62 (s, 6H), 2.50 - 2.38 (m, 4H), 2.04 - 1.95 (m, 2H), 1.44 - 1.34 (m, 2H), 1.27 (s, 9H), 1.09 (s, 3H); HPLC purity: 99.76%; LCMS Calculated for $C_{25}H_{36}N_4O_5S_2$ 536.21; Observed: 537.55 $[M + H]^+$. |

-continued

| Compound No. | Structure | Yields/Analytical data |
| --- | --- | --- |
| A-360 | 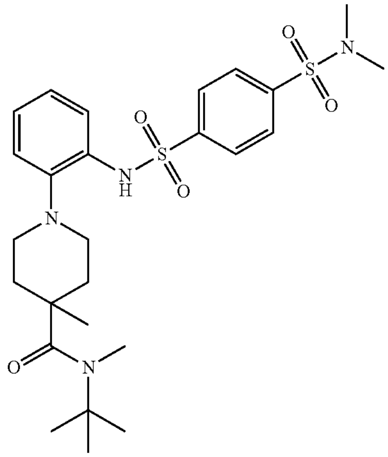 [SMILES: CN(C(=O)C1(C)CCN(c2ccccc2NS(=O)(=O)c2ccc(S(=O)(=O)N(C)C)cc2)CC1)C(C)(C)C] | Yield: 47 mg, 17%; Appearance: White solid; $^1$H NMR (400 MHz, DMSO-$d_6$) δ 9.23 (bs, 1H), 8.0 (d, J = 8.8 Hz, 2H), 7.92 (d, J = 8.8 Hz, 2H), 7.27 (dd, J = 1.6, 8.0 Hz, 1H), 7.14 - 7.07 (m, 1H), 7.07 - 6.97 (m, 2H), 2.84 (s, 3H), 2.63 (s, 6H), 2.47 - 2.35 (m, 4H), 2.10 (d, J = 13.2 Hz, 2H), 1.51 - 1.42 (m, 2H), 1.31 (s, 9H), 1.18 (s, 3H); HPLC purity: 99.94%; LCMS Calculated for $C_{26}H_{38}N_4O_5S_2$: 550.23; Observed: 551.35 [M + H]$^+$. |
| A-354 | 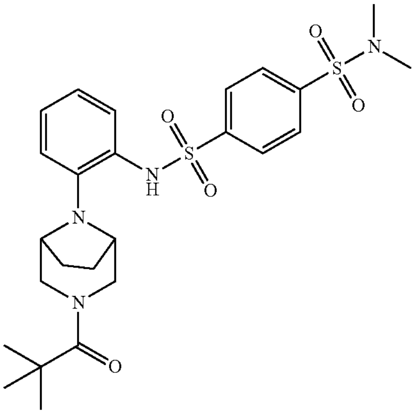 [SMILES: CN(C)S(=O)(=O)c1ccc(S(=O)(=O)Nc2ccccc2N2C3CCC2CN(C(=O)C(C)(C)C)C3)cc1] | Yield: 120 mg, 16.1%; Appearance: Off white solid; $^1$H NMR (400 MHz, DMSO-$d_6$) δ 9.44 (s, 1H), 8.04 (d, J = 8.4 Hz, 2H), 7.96 (d, J = 8.4 Hz, 2H), 7.08 (t, J = 8.0 Hz, 1H), 6.96 (d, J = 8.0 Hz, 1H), 6.91 (d, J = 7.6 Hz, 1H), 6.86 (d, J = 7.6 Hz, 1H), 3.92 (d, J = 11.6 Hz, 2H), 3.71 (s, 2H), 3.10 (d, J = 11.6 Hz, 2H), 2.64 (s, 6H), 1.79 - 1.72 (m, 2H), 1.56 - 1.50 (m, 2H), 1.20 (s, 9H); HPLC purity: 97 18%; LCMS Calculated for $C_{25}H_{34}N_4O_5S_2$ 534.20; Observed: 535.25 [M + H]$^+$. |
| A-407 | 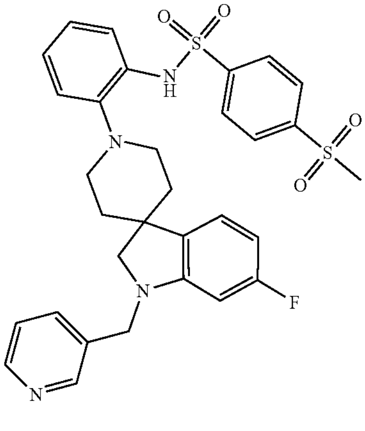 [SMILES: CS(=O)(=O)c1ccc(S(=O)(=O)Nc2ccccc2N2CCC3(CC2)CN(Cc2cccnc2)c2cc(F)ccc23)cc1] | Yield: 56 mg, 17.6%; Appearance: Off white solid; $^1$H NMR (400 MHz, DMSO-$d_6$) δ 9.27 (bs, 1H), 8.55 (s, 1H), 8.49 (d, J = 4.4 Hz, 1H), 8.12 (d, J = 8.8 Hz, 2H), 8.04 (d, J = 8.4 Hz, 2H), 7.72 (d, J = 7.6 Hz, 1H), 7.38 (dd, J = 4.8, 7.6 Hz, 1H), 7.31 (d, J = 7.6 Hz, 1H), 7.20 - 7.04 (m, 4H), 6.49 (d, J = 10.8 Hz, 1H), 6.44 - 6.36 (m, 1H), 4.39 (s, 2H), 3.30 (s, 2H), 3.23 (s, 3H), 2.55 - 2.42 (m, 4H), 1.90 - 1.80 (m, 2H), 1.50 (d, J = 12.8 Hz, 2H); HPLC purity: 99.62%; LCMS Calculated for $C_{31}H_{31}FN_4O_4S_2$: 606.18; Observed: 607.30 [M + H]$^+$. |

-continued

| Compound No. | Structure | Yields/Analytical data |
|---|---|---|
| A-403 | 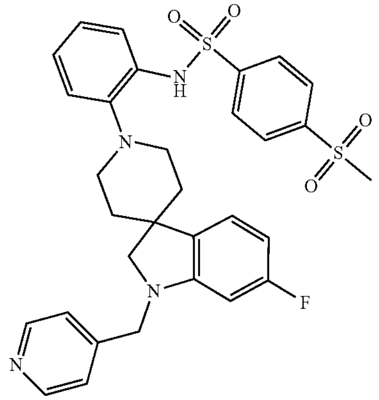 [SMILES: CS(=O)(=O)c1ccc(S(=O)(=O)Nc2ccccc2N2CCC3(CC2)CN(Cc2ccncc2)c2cc(F)ccc23)cc1] | Yield: 40 mg, 12.9%; Appearance: White solid; $^1$H NMR (400 MHz, DMSO-$d_6$) δ 9.30 (bs, 1H), 8.54 - 8.50 (m, 2H), 8.12 (d, J = 8.8 Hz, 2H), 8.04 (d, J = 8.8 Hz, 2H), 7.34 - 7.28 (m, 3H), 7.20 - 7.04 (m, 4H), 6.43 - 6.35 (m, 2H), 4.40 (s, 2H), 3.24 (s, 3H), 2.58 - 2.40 (m, 4H), 1.93 - 1.82 (m, 2H), 1.54 (d, J = 12.8 Hz, 2H), (2H merged with the moisture peak); HPLC purity: 98.54%; LCMS calculated for $C_{31}H_{31}FN_4O_4S_2$: 606.18; Observed: 607.30 $[M + H]^+$. |
| A-466 | 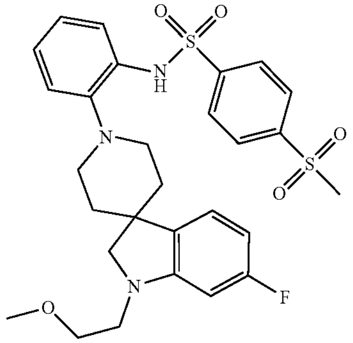 [SMILES: COCCN1CC2(CCN(c3ccccc3NS(=O)(=O)c3ccc(S(C)(=O)=O)cc3)CC2)c2ccc(F)cc21] | Yield: 67.7 mg, 21.1%; Appearance: Pale brown solid; $^1$H NMR (400 MHz, DMSO-$d_6$) δ 9.28 (bs, 1H), 8.12 (d, J = 8.4 Hz, 2H), 8.04 (d, J = 8.4 Hz, 2H), 7.32 (d, J = 8.0 Hz, 1H), 7.24 - 7.00 (m, 4H), 6.37 - 6.28 (m, 2H), 3.52 (t, J = 5.2 Hz, 2H), 3.40 (s, 2H), 3.29 (m, 2H), 3.27 (s, 3H), 3.23 (s, 3H), 2.62 - 2.52 (m, 2H), 2.50 - 2.44 (m, 2H), 1.88 - 1.78 (m, 2H), 1.48 (d, J = 13.2 Hz, 2H); HPLC purity: 99 61%; LCMS calculated for $C_{28}H_{32}FN_3O_5S_2$: 573.18; Observed: 574.20 $[M + H]^+$. |
| A-467 | 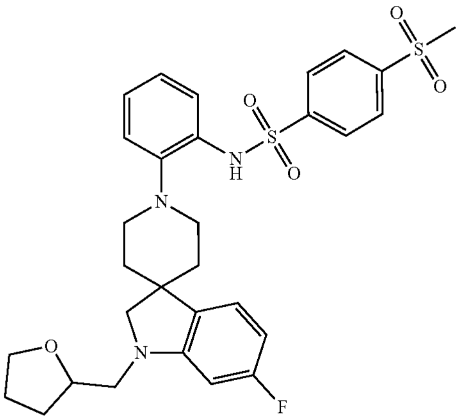 [SMILES: CS(=O)(=O)c1ccc(S(=O)(=O)Nc2ccccc2N2CCC3(CC2)CN(CC2CCCO2)c2cc(F)ccc23)cc1] | Yield: 120 mg, 38.2%; Appearance: Off white solid; $^1$H NMR (400 MHz, DMSO-$d_6$) δ 9.28 (bs, 1H), 8.12 (d, J = 8.4 Hz, 2H), 8.04 (d, J = 8.4 Hz, 2H), 7.32 (d, J = 7.2 Hz, 1H), 7.22 (d, J = 7.6 Hz, 1H), 7.15 (t, J = 7.2 Hz, 1H), 7.10 - 7.04 (m, 1H), 7.02 (t, 6.8 Hz, 1H), 6.35 - 6.29 (m, 2H), 4.08 - 4.00 (m, 1H), 3.76 (q, J = 6.8 Hz, 1H), 3.63 (q, J = 6.4 Hz, 1H), 3.48 - 3.40 (m, 2H), 3.23 (s, 3H), 3.19 (d, J = 3.6 Hz, 1H), 3.15 - 3.08 (m, 1H), 2.61 - 2.43 (m, 4H), 2.00 - 1.90 (m, 1H), 1.90 - 1.73 (m, 4H), 1.57 - 1.43 (m, 3H); HPLC purity: 99.81%; LCMS Calculated for $C_{30}H_{34}FN_3O_5S_2$ 599.19; Observed: 599.80 $[M + H]^+$. |
| A-423 | 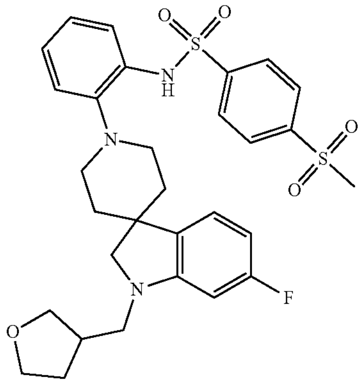 [SMILES: CS(=O)(=O)c1ccc(S(=O)(=O)Nc2ccccc2N2CCC3(CC2)CN(CC2CCOC2)c2cc(F)ccc23)cc1] | Yield: 120 mg, 38.2%; Appearance: Off white solid; $^1$H NMR (400 MHz, DMSO-$d_6$) δ 9.28 (bs, 1H), 8.12 (d, J = 8.8 Hz, 2H), 8.04 (d, J = 8.8 Hz, 2H), 7.32 (d, J = 8.0 Hz, 1H), 7.23 (d, J = 8.0 Hz, 1H), 7.15 (t, J = 6.4 Hz, 1H), 7.11 - 7.00 (m, 2H), 6.37 - 6.30 (m, 2H), 3.82 - 3.73 (m, 2H), 3.65 (q, J = 8.0 Hz, 1H), 3.41 - 3.35 (m, 2H), 3.23 (s, 3H), 3.08 - 3.04 (m, 2H), 2.69 - 2.53 (m, 3H), 2.50 - 2.43 (m, 2H), 2.02 - 1.93 (m, 1H), 1.90 - 1.76 (m, 2H), 1.61 - 1.51 (m, 1H), 1.48 (bd, J = 12.4 Hz, 2H), ($^1$H merged with the moisture peak); HPLC purity: 98.05%; LCMS Calculated for $C_{30}H_{34}FN_3O_5S_2$: 599.19; Observed: 600.10 $[M + H]^+$. |

-continued

| Compound No. | Structure | Yields/Analytical data |
|---|---|---|
| A-468 | 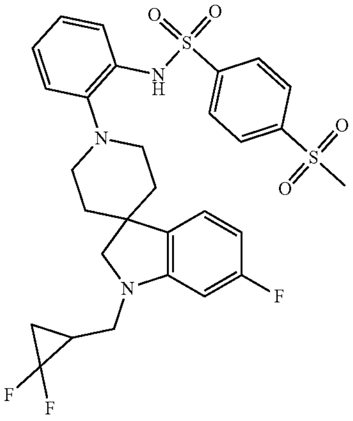 [SMILES: CS(=O)(=O)c1ccc(S(=O)(=O)Nc2ccccc2N2CCC3(CC2)CN(CC2CC2(F)F)c2cc(F)ccc23)cc1] | Yield: 100 mg, 21.4%; Appearance: Off white solid; $^1$H NMR (400 MHz, DMSO-$d_6$) δ 9.20 (bs, 1H), 8.12 (d, J = 8.4 Hz, 2H), 8.05 (d, J = 8.4 Hz, 2H), 7.32 (dd, J = 1.6, 8.0 Hz, 1H), 7.12 (d, J = 8.0 Hz, 1H), 7.18 - 7.12 (m, 1H), 7.10 - 7.04 (m, 2H), 6.43 - 6.35 (m, 2H), 3.43 - 3.34 (m, 3H), 3.30 (s, 2H), 3.23 (s, 3H), 3.18 - 3.11 (m, 1H), 2.64 - 2.50 (m, 2H), 2.00 - 1.78 (m, 3H), 1.69 - 1.59 (m, 1H), 1.50 (bd, J = 12.4 Hz, 2H), 1.37 - 1.27 (m, 1H); HPLC purity: 99.86%; LCMS Calculated for $C_{29}H_{30}F_3N_3O_4S_2$: 605.16; Observed: 605.95 $[M + H]^+$. |
| A-469 | 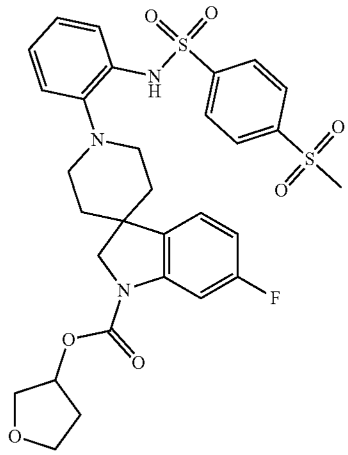 [SMILES: CS(=O)(=O)c1ccc(S(=O)(=O)Nc2ccccc2N2CCC3(CC2)CN(C(=O)OC2CCOC2)c2cc(F)ccc23)cc1] | Yield: 136.6 mg, 35.6%; Appearance: White solid; $^1$H NMR (400 MHz, DMSO-$d_6$) δ 9.29 (bs, 1H), 8.12 (d, J = 8.4 Hz, 2H), 8.05 (d, J = 8.4 Hz, 2H), 7.47 (bs, 1H), 7.35 - 7.23 (m, 3H), 7.17 - 7.06 (m, 2H), 6.91 - 6.84 (m, 1H), 5.32 (bs, 1H), 3.90 - 3.72 (m, 6H), 3.22 (s, 3H), 2.64 - 2.54 (m, 2H), 2.50 - 2.43 (m, 2H), 2.25 - 2.14 (m, 1H), 2.08-1.98 (m, 1H), 1.91 (t, J = 11.6 Hz, 2H), 1.53 (d, J = 12.8 Hz, 2H); HPLC purity: 96.48%; LCMS calculated for $C_{30}H_{32}FN_3O_7S_2$: 629.17; Observed: 630.25 $[M + H]^+$. |
| A-442 | 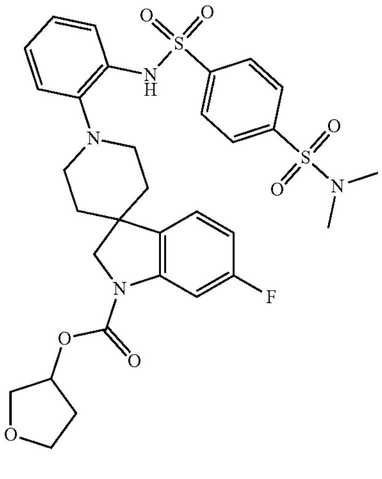 [SMILES: CN(C)S(=O)(=O)c1ccc(S(=O)(=O)Nc2ccccc2N2CCC3(CC2)CN(C(=O)OC2CCOC2)c2cc(F)ccc23)cc1] | Yield: 209.6 mg, 43.6%; Appearance: Off white solid; $^1$H NMR (400 MHz, DMSO-$d_6$) δ 9.27 (s, 1H), 8.03 (d, J = 8.0 Hz, 2H), 7.93 (d, J = 8.0 Hz, 2H), 7.47 (bs, 1H), 7.37 - 7.30 (m, 2H), 7.28 - 7.23 (m, 1H), 7.18 - 8.08 (m, 2H), 6.91 - 6.83 (m, 1H), 5.32 (bs, 1H), 3.90 - 3.72 (m, 6H), 2.64 - 2.54 (m, 2H), 2.58 (s, 6H), 2.50 - 2.40 (m, 2H), 2.25 - 2.13 (m, 1H), 2.09 - 1.98 (m, 1H), 1.98 - 1.87 (m, 2H), 1.50 (d, J = 12.4 Hz, 2H); HPLC purity: 99.62%; LCMS calculated for $C_{31}H_{35}FN_4OS_2$: 658.19; Observed: 659.25 $[M + H]^+$. |

-continued

| Compound No. | Structure | Yields/Analytical data |
|---|---|---|
| A-408 | 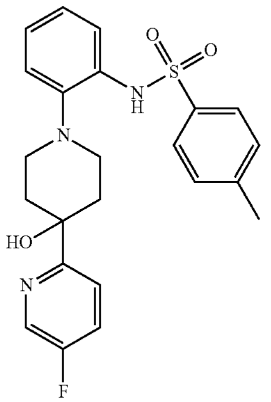 [SMILES: Cc1ccc(S(=O)(=O)Nc2ccccc2N2CCC(O)(c3ccc(F)cn3)CC2)cc1] | Yield: 90 mg, 39%; Appearance: Off white solid; $^1$H NMR (400 MHz, DMSO-$d_6$) δ 8.80 (bs, 1H), 8.56 (s, 1H), 7.80 - 7.73 (m, 2H), 7.70 (d, J = 7.6 Hz, 2H), 7.34 (d, J = 7.6 Hz, 2H), 7.29 (d, J = 6.8 Hz, 1H), 7.19 (d, J = 6.8 Hz, 1H), 7.09 - 7.00 (m, 2H), 5.25 (s, 1H), 2.94 (t, J = 11.2 Hz, 2H), 2.46 - 2.30 (m, 4H), 2.32 (s, 3H), 1.55 (d, J = 13.2 Hz, 2H); HPLC purity: 98.74%; LCMS Calculated for $C_{23}H_{24}FN_3O_3S$: 441 15; Observed: 442.20 [M + H]$^+$. |
| A-409 | 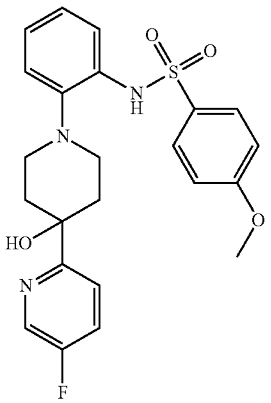 [SMILES: COc1ccc(S(=O)(=O)Nc2ccccc2N2CCC(O)(c3ccc(F)cn3)CC2)cc1] | Yield: 95 mg, 40%; Appearance: Off white solid; $^1$H NMR (400 MHz, DMSO-$d_6$) δ 8.70 (bs, 1H), 8.56 (s, 1H), 7.79 - 7.70 (m, 4H), 7.34 - 7.29 (m, 1H), 7.21 - 7.17 (m, 1H), 7.08 - 7.02 (m, 4H), 5.26 (s, 1H), 3.77 (s, 3H), 2.95 (t, J = 11.2 Hz, 2H), 2.46 - 2.30 (m, 4H), 1.56 (d, J = 12.4 Hz, 2H); HPLC purity: 99.38%; LCMS Calculated for $C_{23}H_{24}FN_3O_4S$: 457.15; Observed: 458.25 [M + H]$^+$. |
| A-414 | 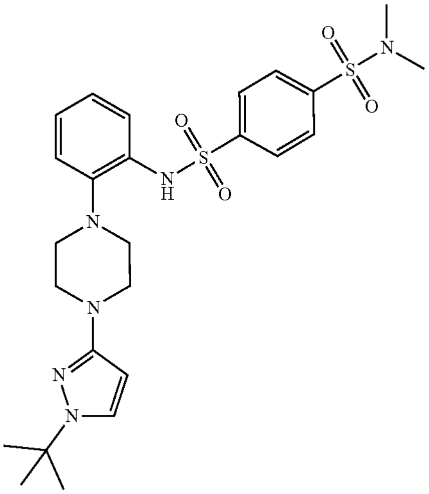 [SMILES: CN(C)S(=O)(=O)c1ccc(S(=O)(=O)Nc2ccccc2N2CCN(c3ccn(C(C)(C)C)n3)CC2)cc1] | Yield: 10 mg, 5.4%; Appearance: White solid; $^1$H NMR (400 MHz, $CDCl_3$) δ 8.18 (bs, 1 H), 7.98 (d, J = 8.0 Hz, 2H), 7.83 (d, J = 7.6 Hz, 2H), 7.61 (d, J = 8.0 Hz, 1H), 7.34 (s, 1H), 7.19 - 7.06 (m, 3H), 5.66 (s, 1H), 3.32 - 3.23 (m, 4H), 2.77 - 2.64 (m, 4H), 2.71 (s, 6H), 1.54 (s, 9H); HPLC purity: 98.07%; LCMS Calculated for $C_{25}H_{34}N_6O_4S_2$: 546.21; Observed: 547.20 [M + H]$^+$. |

-continued

| Compound No. | Structure | Yields/Analytical data |
|---|---|---|
| A-482 | 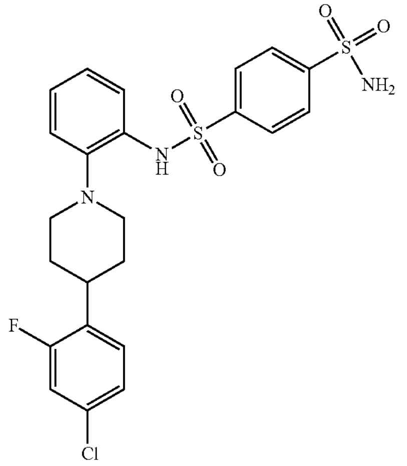 [SMILES: NS(=O)(=O)c1ccc(S(=O)(=O)Nc2ccccc2N2CCC(c3ccc(Cl)cc3F)CC2)cc1] | Yield: 200 mg, 21.7%; Appearance: Pale yellow solid; $^1$H NMR (400 MHz, DMSO-$d_6$) δ 9.13 (bs, 1H), 8.03 – 7.92 (m, 4H), 7.57 (s, 2H), 7.47 (t, J = 8.4 Hz, 1H), 7.38 (d, J = 10.4 Hz, 1H), 7.35 – 7.30 (m, 2H), 7.23 – 7.05 (m, 3H), 2.89 – 2.79 (m, 1H), 2.68 – 2.50 (m, 4H), 1.92 – 1.80 (m, 2H), 1.68 – 1.60 (m, 2H); HPLC purity: 98.43%; LCMS calculated for $C_{23}H_{23}ClFN_3O_4S_2$: 523.08; Observed: 524.20 $[M + H]^+$. |
| A-424 | 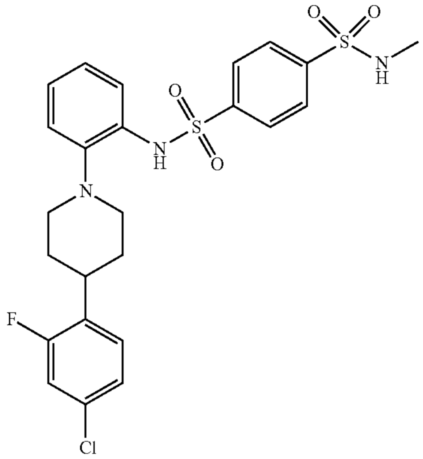 [SMILES: CNS(=O)(=O)c1ccc(S(=O)(=O)Nc2ccccc2N2CCC(c3ccc(Cl)cc3F)CC2)cc1] | Yield: 98.4 mg, 24.7%; Appearance: Gray solid; $^1$H NMR (400 MHz, DMSO-$d_6$) δ 9.18 (br s, 1H), 8.00 (d, J = 8.4 Hz, 2H), 7.92 (d, J = 8.4 Hz, 2H), 7.70 – 7.65 (m, 1H), 7.45 (t, J = 8.0 Hz, 1H), 7.40 – 7.29 (m, 3H), 7.20 – 7.06 (m, 3H), 2.87 – 2.77 (m, 1H), 2.65 – 2.56 (m, 2H), 2.55 – 2.50 (m, 2H), 2.37 (d, J = 4.8 Hz, 3H), 1.88 – 1.75 (m, 2H), 1.60 (d, J = 11.6 Hz, 2H); HPLC purity: 99.56%; LCMS calculated for $C_{24}H_{25}ClFN_3O_4S_2$: 537.10; Observed: 538.15 $[M + H]^+$. |
| A-637 | 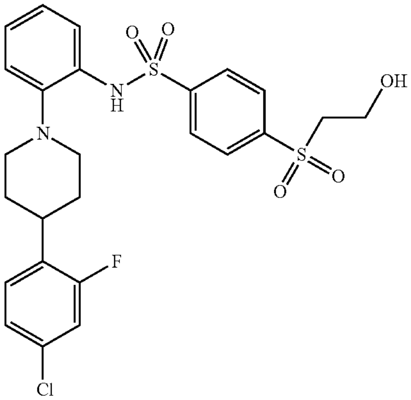 [SMILES: O=S(=O)(CCO)c1ccc(S(=O)(=O)Nc2ccccc2N2CCC(c3ccc(Cl)cc3F)CC2)cc1] | Yield: 0.5 g, 18%; Appearance: White solid; $^1$H NMR (400 MHz, DMSO-$d_6$) δ 1.56-1.67 (m, 2H) 1.70-1.87 (m, 2H) 2.55-2.71 (m, 4H) 2.82 (t, J = 11.25 Hz, 1H) 3.41-3.53 (m, 2H) 3.65 (q, J = 5.87 Hz, 2H) 4.80 – 4.89 (m, 1H) 7.05 – 7.22 (m, 3H) 7.27 – 7.49 (m, 4H) 7.98 – 8.11 (m, 4H) 9.17 – 9.32 (m, 1H); HPLC purity: 98.82%; LCMS Calculated for $C_{25}H_{26}ClFN_2O_5S_2$ 553.06; Observed: 553.07 $[M + H]^+$. |

-continued

| Compound No. | Structure | Yields/Analytical data |
|---|---|---|
| A-701 | 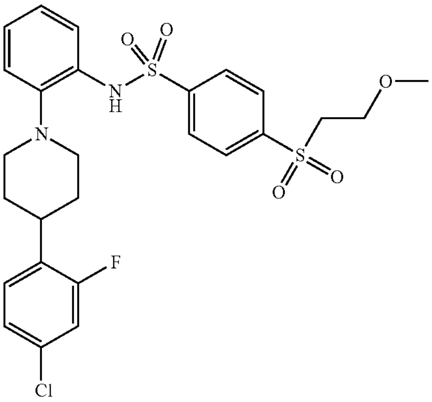 [SMILES: COCCS(=O)(=O)c1ccc(S(=O)(=O)Nc2ccccc2N2CCC(c3ccc(Cl)cc3F)CC2)cc1] | Yield: 0.165 g, 26%; Appearance: White solid; $^1$H NMR (400 MHz, DMSO-$d_6$) δ 9.25 (bs, 1H), 8.07 (q, J = 7.84 Hz, 4H), 7.47 – 7.36 (m, 2H), 7.32-7.30 (m, 2H), 7.19 – 7.05 (m, 3H), 3.64 – 3.61 (m, 2H), 3.57 – 3.54 (m, 2H), 2.95 (s, 3H), 2.85 – 2.79 (m, 1H), 2.65 – 2.60 (m, 4H), 1.86 – 1.78 (m, 2H), 1.64 – 1.61 (m, 2H); HPLC purity: 98.80%; LCMS Calculated for $C_{26}H_{28}ClFN_2O_5S_2$ 566.11; Observed: 566.95 $[M + H]^+$. |
| A-502 | 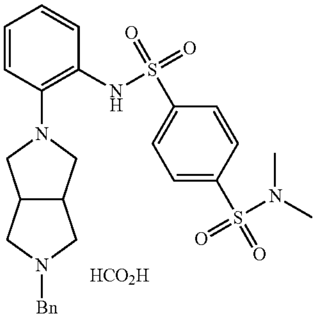 [SMILES: CN(C)S(=O)(=O)c1ccc(S(=O)(=O)Nc2ccccc2N2CC3CN(Cc4ccccc4)CC3C2)cc1 ; "HCO2H"] | Yield: 0.06 g, 59%; Appearance: White solid; $^1$H NMR (400 MHz, DMSO-$d_6$) δ 8.16 (s, 1H), 7.99 – 7.82 (m, 4H), 7.34 – 7.28 (m, 4H), 7.27 – 7.21 (m, 1H), 7.10 (t, J = 7.2 Hz, 1H), 6.97 (d, J = 8.4 Hz, 1H), 6.90 (d, J = 7.6 Hz, 1H), 6.85 (t, J = 8.0 Hz, 1H), 3.59 (s, 2H), 3.12 (t, J = 7.2 Hz, 2H), 2.75 – 2.70 (m, 2H), 2.68 – 2.58 (m, 2H), 2.62 (s, 6H), 2.57 – 2.50 (m, 2H), 2.46 – 2.40 (m, 2H); HPLC purity: 97.51%; LCMS calculated for $C_{27}H_{32}N_4O_4S_2$: 540.19; Observed: 541.30 $[M + H]^+$. |
| A-483 | 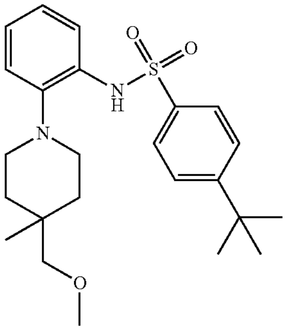 [SMILES: COCC1(C)CCN(c2ccccc2NS(=O)(=O)c2ccc(C(C)(C)C)cc2)CC1] | Yield: 120 mg, 32.7%; Appearance: White solid; $^1$H NMR (400 MHz, DMSO-$d_6$) δ 8.59 (br s, 1H), 7.67 (d, J = 8.8 Hz, 2H), 7.54 (d, J = 8.4 Hz, 2H), 7.37 – 7.32 (m, 1H), 7.23 – 7.18 (m, 1H), 7.09 – 7.03 (m, 2H), 3.28 (s, 3H), 3.12 (s, 2H), 2.50 – 2.43 (m, 2H), 2.37 – 2.30 (m, 2H), 1.56 – 1.48 (m, 2H), 1.30 – 1.20 (m, 2H), 1.24 (s, 9H), 0.93 (s, 3H); HPLC purity: 97.99%; LCMS calculated for $C_{24}H_{34}N_2O_3S$: 430.23; Observed: 431.35 $[M + H]^+$. |
| A-489 | 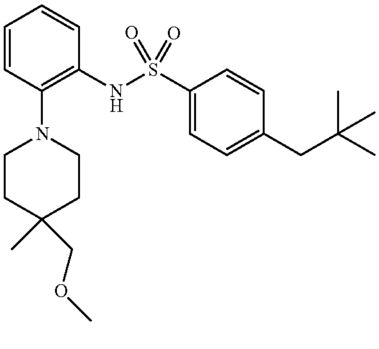 [SMILES: COCC1(C)CCN(c2ccccc2NS(=O)(=O)c2ccc(CC(C)(C)C)cc2)CC1] | Yield: 80 mg, 28.2%; Appearance: Colorless oil; $^1$H NMR (400 MHz, DMSO-$d_6$) δ 8.54 (s, 1H), 7.64 (d, J = 7.6 Hz, 2H), 7.41 – 7.36 (m, 1H), 7.27 (d, J = 8.0 Hz, 2H), 7.23 – 7.18 (m, 1H), 7.09 – 7.03 (m, 2H), 3.27 (s, 3H), 3.12 (s, 2H), 2.47 – 2.41 (m, 2H), 2.37 – 2.30 (m, 2H), 1.60 – 1.50 (m, 2H), 1.31 – 1.23 (m, 2H), 0.93 (s, 3H), 0.80 (s, 9H), (2H merged with the solvent peak); HPLC purity: 99.68%; LCMS calculated for $C_{25}H_{36}N_2O_3S$: 444.24; Observed: 445.60 $[M + H]^+$. |

-continued

| Compound No. | Structure | Yields/Analytical data |
|---|---|---|
| A-555 | 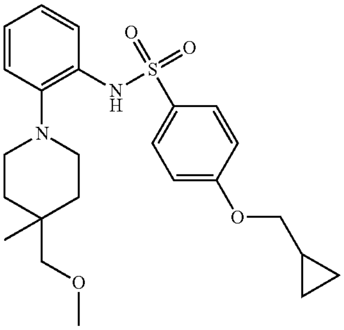 [SMILES: COCC1(C)CCN(c2ccccc2NS(=O)(=O)c2ccc(OCC3CC3)cc2)CC1] | Yield: 110 mg, 17.5%; Appearance: White solid; $^1$H NMR (400 MHz, DMSO-$d_6$) δ 8.48 (br s, 1H), 7.69 (d, J = 8.8 Hz, 2H), 7.34 - 7.24 (m, 1H), 7.23 - 7.18 (m, 1H), 7.06 - 6.99 (m, 4H), 3.85 (d, J = 6.8 Hz, 2H), 3.29 (s, 3H), 3.14 (s, 2H), 2.57 - 2.40 (m, 4H), 1.64 - 1.53 (m, 2H), 1.35 - 1.29 (m, 2H), 1.23 - 1.13 (m, 1H), 0.95 (s, 3H), 0.58 - 0.50 (m, 2H), 0.32 - 0.27 (m, 2H); HPLC purity: 99.35%; LCMS calculated for $C_{24}H_{32}N_2O_4S$: 444 21; Observed: 445.20 $[M + H]^+$. |
| A-518 | 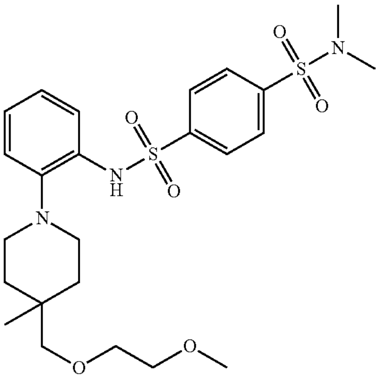 [SMILES: COCCOCC1(C)CCN(c2ccccc2NS(=O)(=O)c2ccc(S(=O)(=O)N(C)C)cc2)CC1] | Yield: 400 mg, 53%; Appearance: White solid; $^1$H NMR (400 MHz, DMSO-$d_6$) δ 9.13 (bs, 1H), 7.99 (d, J = 8.0 Hz, 2H), 7.91 (d, J = 8.4 Hz, 2H), 7.27 (d, J = 7.6 Hz, 1H), 7.20 - 7.00 (m, 3H), 3.55 - 3.43 (m, 4H), 3.27 (s, 3H), 3.19 (s, 2H), 2.61 (s, 6H), 2.50 - 2.40 (m, 2H), 1.54 - 1.45 (m, 2H), 1.30 - 1.20 (m, 2H), 0.92 (s, 3H), (2H merged with the solvent peak); HPLC purity: 99.85%; LCMS calculated for $C_{24}H_{35}N_3O_6S_2$: 525.20; Observed: 526.15 $[M + H]^+$. |
| A-519 | 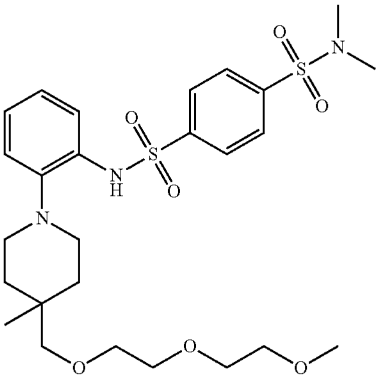 [SMILES: COCCOCCOCC1(C)CCN(c2ccccc2NS(=O)(=O)c2ccc(S(=O)(=O)N(C)C)cc2)CC1] | Yield: 86 mg, 9.76%; Appearance: White solid; $^1$H NMR (400 MHz, DMSO-$d_6$) δ 9.12 (bs, 1H), 7.99 (d, J = 8.4 Hz, 2H), 7.90 (d, J = 8.4 Hz, 2H), 7.27 (d, J = 7.6 Hz, 1H), 7.19 (d, J = 7.6 Hz, 1H), 7.12 (t, J = 7.2 Hz, 1H), 7.05 (t, J = 7.2Hz, 1H), 3.58 - 3.50 (m, 6H), 3.44 (t, J = 4.4 Hz, 2H), 3.24 (s, 3H), 3.20 (s, 2H), 2.61 (s, 6H), 2.55 - 2.40 (m, 4H), 1.54 - 1.45 (m, 2H), 1.30 - 1.21 (m, 2H), 0.92 (s, 3H); HPLC purity: 99.77%; LCMS calculated for $C_{26}H_{39}N_3O_7S_2$: 569.22; Observed: 570.35 $[M + H]^+$. |
| A-520 | 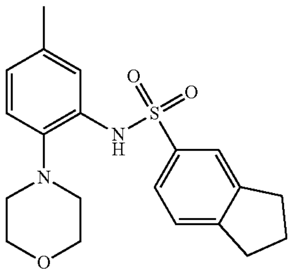 [SMILES: Cc1ccc(N2CCOCC2)c(NS(=O)(=O)c2ccc3c(c2)CCC3)c1] | Yield: 169 mg, 29%; Appearance: White solid; $^1$H NMR (400 MHz, DMSO-$d_6$) δ 8.75 (s, 1H), 7.66 (s, 1H), 1.49 (d, J = 8.0 Hz, 1H), 7.34 (d, J = 8.0 Hz, 1H), 7.12 (s, 1H), 7.07 (d, J = 8.4 Hz, 1H), 6.91 (d, J = 8.0 Hz, 1H), 3.64 - 3.60 (m, 4H), 2.90 - 2.84 (m, 4H), 2.42 - 2.37 (m, 4H), 2.24 (s, 3H), 2.06 - 1.98 (m, 2H); HPLC purity: 99.97%; LCMS calculated for $C_{20}H_{24}N_2O_3S$: 372.15; Observed: 373.20 $[M + H]^+$. |

-continued

| Compound No. | Structure | Yields/Analytical data |
|---|---|---|
| A-521 | 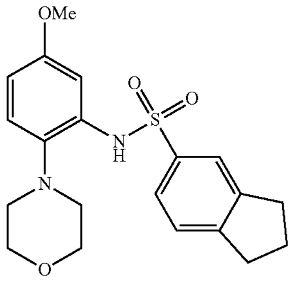 [SMILES: COc1ccc(N2CCOCC2)c(NS(=O)(=O)c2ccc3c(c2)CCC3)c1] | Yield: 786 mg, 13.7%; Appearance: White solid; $^1$H NMR (400 MHz, DMSO-$d_6$) δ 8.80 (s, 1H), 7.67 (s, 1H), 7.50 (d, J = 7.6 Hz, 1H), 7.34 (d, J = 7.6 Hz, 1H), 7.13 (d, J = 8.8 Hz, 1H), 6.93 (d, J = 6.4 Hz, 1H), 6.65 (dd, J = 3.2, 8.8 Hz, 1H), 3.69 (s, 3H), 3.65 - 3.60 (m, 4H), 2.89 - 2.82 (m, 4H), 2.38 - 2.33 (m, 4H), 2.04 - 1.95 (m, 2H); HPLC purity: 99.93%; LCMS calculated for $C_{20}H_2N_2O_4S$: 388.15; Observed: 389.20 $[M + H]^+$. |
| A-699 | 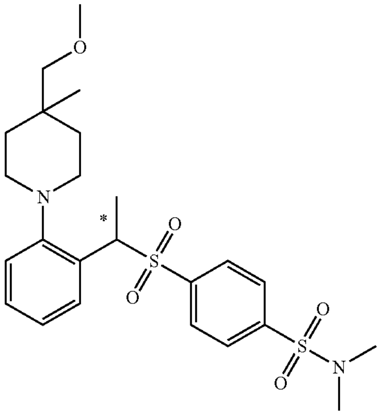 Eanantiomer 2 | Yield: 10.01 mg, 22%; Appearance: Off white solid; $^1$H NMR (400 MHz, DMSO-$d_6$) δ 7.76 (d, J = 7.2 Hz, 2H), 7.63 (d, J = 7.6 Hz, 2H), 7.56 (d, J = 6.8 Hz, 1H), 7.27 (t, J = 7.2 Hz, 1H), 7.18 (t, J = 7.2 Hz, 1H), 6.98 (d, J = 7.6 Hz, 1H), 5.13 - 5.04 (m, 1H), 3.29 (s, 3H), 3.13 (bs, 2H), 2.60 (s, 6H), 1.73 (d, J = 6.8 Hz, 3H), 1.61 - 1.34 (m, 3H), 1.30 - 1.20 (m, 2H), 0.92 (s, 3H), (3H merged with the solvent peak); HPLC purity: 98.45%; LCMS calculated for $C_{24}H_{34}N_2O_5S_2$: 494.19; Observed: 496.39 $[M + H]^+$. Chiral HPLC details: Method: Mobile Phase: A) CO2 B) MEOH + 0.1% TFA; Gradient: 25-30% B in 5 min, hold 30% Btill 9 min, 30-25% B at 10min, hold 25% B till 12 Min. Column: YMC CHIRALART CELLULOSE-SC(250 × 4.6 mm, 5u); Wavelength: 249 nm; Flow: 3 mL/min: retention time: 6.0. |
| A-586 | 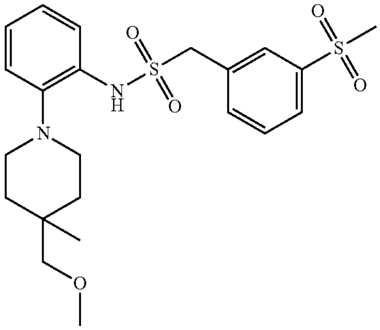 [SMILES: COCC1(C)CCN(c2ccccc2NS(=O)(=O)Cc2cccc(S(C)(=O)=O)c2)CC1] | Yield: 280 mg; 57%; Appearance: Off white solid; $^1$H NMR (400 MHz, DMSO-$d_6$) δ 8.20 (s, 1H), 7.96 - 7.90 (m, 2H), 7.69 - 7.64 (m, 2H), 7.28 (d, J = 8.0 Hz, 1H), 7.15 (d, J = 7.2 Hz, 1H), 7.10 - 7.00 (m, 2H), 4.83 (s, 2H), 3.27 (s, 3H), 3.14 (s, 2H), 3.12 (s, 3H), 2.79 - 2.69 (m, 4H), 1.64 - 1.54 (m, 2H), 1.39 - 1.30 (m, 2H), 0.97 (s, 3H); HPLC purity: 99.13%; LCMS calculated for $C_{22}H_{30}N_2O_5S_2$: 466.16; Observed: 467.90 $[M + H]^+$; |
| A-570 | 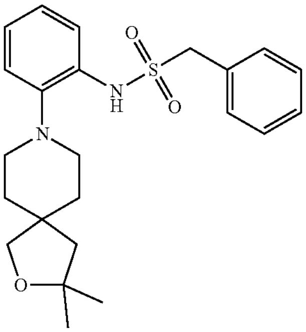 [SMILES: CC1(C)CC2(CCN(c3ccccc3NS(=O)(=O)Cc3ccccc3)CC2)CO1] | Yield: 100 mg; 32%; Appearance: White solid; $^1$H NMR (400 MHz, DMSO-$d_6$) δ 8.04 (s, 1H), 7.37 - 7.32 (m, 3H), 7.28 - 7.22 (m, 4H), 7.10 - 7.04 (m, 2H), 4.62 (s, 2H), 3.57 (s, 2H), 2.66 (t, J = 4.8 Hz, 4H), 1.63 (s, 2H), 1.61 - 1.53 (m, 4H), 1.19 (s, 6H); HPLC purity: 99 47%; LCMS calculated for $C_{23}H_{30}N_2O_3S$: 414.20; Observed: 415.10 $[M + H]^+$. |

-continued

| Compound No. | Structure | Yields/Analytical data |
|---|---|---|
| A-639 | 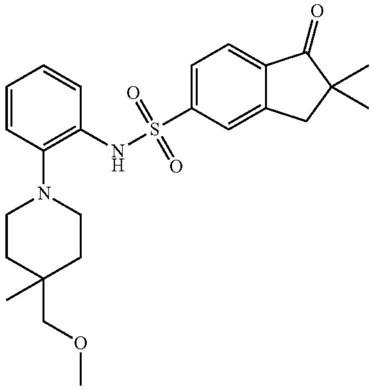 [SMILES: COCC1(C)CCN(c2ccccc2NS(=O)(=O)c2ccc3c(c2)CC(C)(C)C3=O)CC1] | Yield: 0.074 g, 25%; Appearance: Off white solid; $^{1}$H NMR (400 MHz, DMSO-$d_6$) δ 9.05 (bs, 1H), 7.98 (s, 1H), 7.79 – 7.74 (m, 2H), 7.29-7.27 (m, 2H), 7.20 – 7.18 (m, 2H), 7.12 – 7.02 (m, 2H), 3.26 (s, 3H), 3.08 (s, 2H), 3.04 (s, 2H), 2.56 – 2.53 (m, 1H), 2.47 – 2.42 (m, 2H), 1.50 – 1.44 (m, 2H), 1.23 – 1.20 (m, 6H), 0.90 (s, 3H); HPLC purity: 97.15%; LCMS Calculated for $C_{25}H_{32}N_2O_4S$: 456.60; Observed: 456.9 $[M + H]^+$. |
| A-638 | 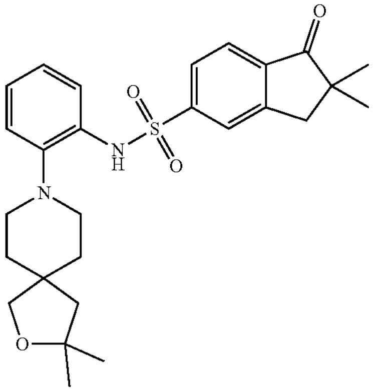 [SMILES: CC1(C)CC2(CCN(c3ccccc3NS(=O)(=O)c3ccc4c(c3)CC(C)(C)C4=O)CC2)CO1] | Yield: 0.114 g, 41%; Appearance: Off white solid; $^{1}$H NMR (400 MHz, DMSO-$d_6$) δ 9.05 (bs, 1H), 7.99 (s, 1H), 7.79 – 7.75 (m, 2H), 7.30 – 7.28 (m, 1H), 7.15-7.03 (m, 3H), 3.53 (s, 2H), 3.04 (s, 2H), 2.46 (t, J = 5.4 Hz, 4H), 1.58 (s, 2H), 1.56 – 1.48 (m, 4H), 1.17 (s, 6H), 1.13 (s, 6H); HPLC purity: 99.73%; LCMS Calculated for $C_{27}H_{34}N_2O_4S$: 482.64; Observed: 483.2 $[M + H]^+$. |
| A-730 | 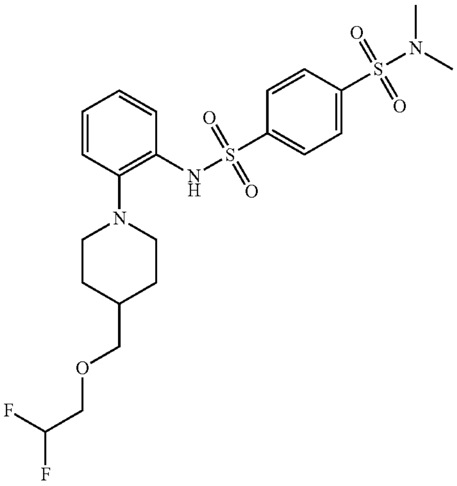 [SMILES: CN(C)S(=O)(=O)c1ccc(S(=O)(=O)Nc2ccccc2N2CCC(COCC(F)F)CC2)cc1] | Yield: 0.03 g, 8%; Appearance: White solid; $^{1}$H NMR (400 MHz, DMSO-$d_6$) δ 9.15 (bs, 1H), 8.00 – 7.98 (m, 2H), 7.92 – 7.90 (m, 2H), 7.27-7.29 (m, 1H), 7.11 – 7.05 (m, 3H), 6.14 (s, 1H), 3.70 – 3.63 (m, 2H), 3.37 – 3.31 (m, 2H), 2.61 (s, 6H), 2.60 – 2.49 (m, 2H), 2.43 – 2.40 (m, 2H), 1.57 (d, J = 10 Hz, 3H), 1.25 – 1.23 (m, 2H); HPLC purity: 99 54%; LCMS Calculated for $C_{22}H_{29}F_2N_3O_5S_2$ 517.61; Observed: 518.05 $[M + H]^+$. |

-continued

| Compound No. | Structure | Yields/Analytical data |
|---|---|---|
| A-703 | 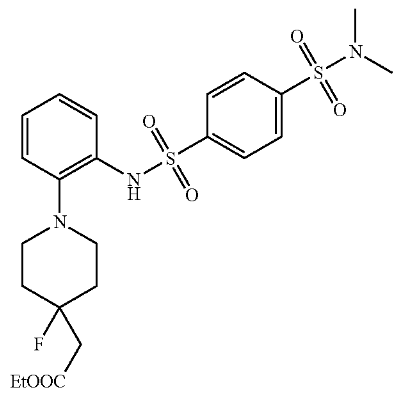 [SMILES: CCOC(=O)CC1(F)CCN(c2ccccc2NS(=O)(=O)c2ccc(S(=O)(=O)N(C)C)cc2)CC1] | Yield: 2.0 g, 44%; Appearance: Off white solid; $^1$H NMR (400 MHz, DMSO-$d_6$) δ 9.33 (s, 1H), 8.00 – 7.98 (m, 2H), 7.93 – 7.90 (m, 2H), 7.31-7.29 (m, 1H), 7.17 – 7.06 (m, 3H), 4.12 (q, J = 7.2 Hz, 2H), 2.73 (s, 1H), 2.68 – 2.61 (m, 9H), 2.41 (d, J = 11.2 Hz, 2H), 1.94 – 1.84 (m, 4H), 1.23 (t, J = 12 Hz, 3H); HPLC purity: 97.82%; LCMS Calculated for $C_{23}H_3FN_3O_6S_2$ 527.63; Observed: 528.0 [M + H]$^+$. |
| A-722 | 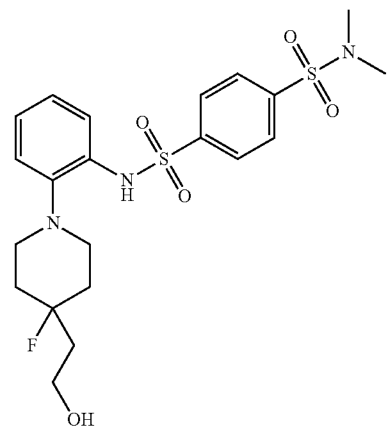 [SMILES: CN(C)S(=O)(=O)c1ccc(S(=O)(=O)Nc2ccccc2N2CCC(F)(CCO)CC2)cc1] | Yield: 0.05 g, 13%; Appearance: White solid; $^1$H NMR (400 MHz, DMSO-$d_6$) δ 9.31 (bs, 1H), 8.01 – 7.98 (m, 2H), 7.93 – 7.91 (m, 2H), 7.30-7.28 (m, 1H), 7.15 – 7.04 (m, 3H), 4.51 (t, J = 5 Hz, 1H), 3.59 (q, J = 6.24 Hz, 2H), 2.66 – 2.61 (m, 8H), 2.38 (d, J = 10.8 Hz, 2H), 1.86 – 1.65 (m, 6H); HPLC purity: 97.82%; LCMS Calculated for $C_{21}H_{28}FN_3O_5S_2$ 485.59; Observed: 486.15 [M + H]$^+$. |
| A-472 | 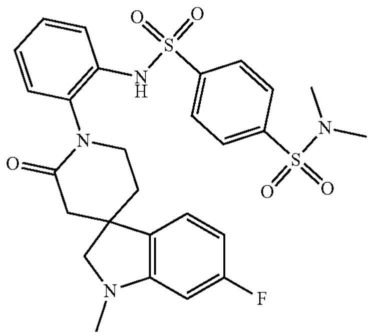 [SMILES: CN1CC2(CCN(c3ccccc3NS(=O)(=O)c3ccc(S(=O)(=O)N(C)C)cc3)C(=O)C2)c2ccc(F)cc21] | Yield: 50 mg, 9.61%; Appearance: White solid; $^1$H NMR (400 MHz, DMSO-$d_6$) δ 9.41 (s, 1H), 8.05 (d, J = 8.4 Hz, 2H), 7.93 (d, J = 8.0 Hz, 2H), 7.63 – 7.57 (m, 1H), 7.34 – 7.28 (m, 2H), 7.18 (t, J = 8.0 Hz, 1H), 7.10 (t, J = 7.6 Hz, 1H), 7.02 – 6.98 (m, 1H), 6.89 – 6.82 (m, 1H), 3.13 (s, 3H), 3.02 – 2.92 (m, 2H), 2.73 – 2.64 (m, 2H), 2.58 (s, 6H), 1.91 – 1.82 (m, 2H), 1.78 – 1.68 (m, 2H); HPLC purity: 99.59%; LCMS calculated for $C_{27}H_{29}FN_4O_5S_2$: 572.16; Observed: 573.25 [M + H]$^{+.}$ |
| A-473 | 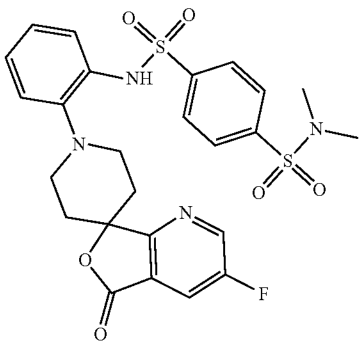 [SMILES: CN(C)S(=O)(=O)c1ccc(S(=O)(=O)Nc2ccccc2N2CCC3(CC2)OC(=O)c2cc(F)cnc23)cc1] | Yield: 48 mg, 17.9%; Appearance: 1.6 Hz, 1H), 8.34 (dd, J = 2.8, 8.0 Hz, 1H), 8.05 (d, J = 8.4 Hz, 2H), 7.94 (d, J = 8.4 Hz, 2H), 7.30 – 7.24 (m, 2H), 7.16 (t, J = 8.0 Hz, 1H), 7.11 – 7.05 (m, 1H), 2.90 – 2.82 (m, 2H), 2.76 – 2.69 (m, 2H), 2.59 (s, 6H), 2.46 – 2.40 (m, 2H), 1.72 (d, J = 13.2 Hz, 2H); HPLC purity: 99.44%; LCMS Calculated for $C_{25}H_{25}FN_4O_6S_2$: 560.12; Observed: 561.15 [M + H]$^+$. |

-continued

| Compound No. | Structure | Yields/Analytical data |
| --- | --- | --- |
| A-401 | 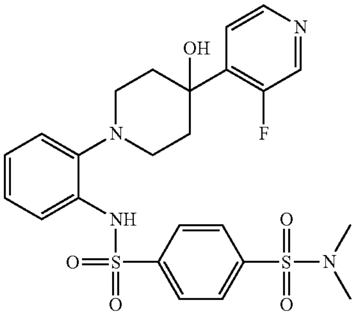 [SMILES: CN(C)S(=O)(=O)c1ccc(S(=O)(=O)Nc2ccccc2N2CCC(O)(c3ccncc3F)CC2)cc1] | Yield: 600 mg, 41%; Appearance: White solid; $^1H$ NMR (400 MHz, DMSO-$d_6$) δ 1.50-1.60 (m, 2H) 2.19 - 2.28 (m, 2H) 2.35 (d, J = 10.76 Hz, 2H) 2.58 (s, 6H) 2.95 (t, J = 11.25 Hz, 2H) 5.43 (s, 1H) 7.03 - 7.22 (m, 3H) 7.27 - 7.35 (m, 1H) 7.55 - 7.62 (m, 1H) 7.88 - 7.94 (m, 2H) 7.95 - 7.99 (m, 2H) 8.43 (s, 1H) 8.48 - 8.51 (m, 1H) 9.26 (s, 1H); HPLC purity: 99.93%; LCMS calculated for $C_{24}H_{27}FN_4O_5S_2$: 534.14; Observed: 535.18 $[M + H]^+$. |
| A-355 | 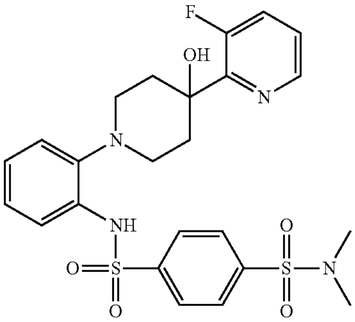 [SMILES: CN(C)S(=O)(=O)c1ccc(S(=O)(=O)Nc2ccccc2N2CCC(O)(c3ncccc3F)CC2)cc1] | Yield: 200 mg, 19%; Appearance: White solid; $^1H$ NMR (400 MHz, DMSO-$d_6$) δ 1.80 (d, J = 12.23 Hz, 2H) 2.21 - 2.35 (m, 3H) 2.60 (s, 6H) 2.93 (t, J = 10.52 Hz, 2H) 5.25 (s, 1H) 7.01 - 7.21 (m, 4H) 7.22-7.35 (m, 1H) 7.38-7.47 (m, 1 H) 7.70 (dd, J = 11.74, 8.31 Hz, 1 H) 7.91 (d, J = 8.31 Hz, 2 H) 8.01 (d, J = 8.31 Hz, 2 H) 8.40 (d, J = 3.91 Hz, 1 H) 9.30 (s, 1 H); HPLC purity: 99.02%; LCMS calculated for $C_{24}H_{27}FN_4O_5S_2$: 534.14; Observed: 535.25 $[M + H]^+$. |
| A-412 | 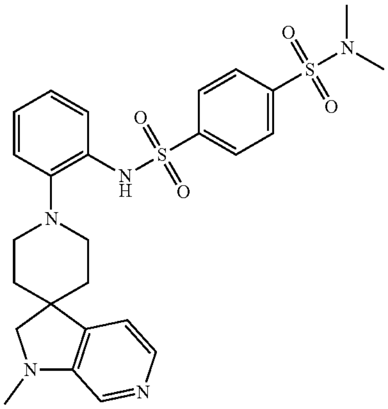 | Yield: 50 mg, 7%; Appearance: White solid; $^1H$ NMR (400 MHz, DMSO-$d_6$) δ 1.45-1.58 (m, 2H) 1.76-1.94 (m, 2H) 2.58 (s, 6H) 2.77 (s, 3H) 3.24 (s, 2H) 7.03-7.17 (m, 2H) 7.19-7.23 (m, 2H) 7.34 (d, J = 1.83 Hz, 1H) 7.84 (s, 1H) 7.86-7.95 (m, 2H) 7.97-8.05 (m, 3H) 9.30 (brs, 1H) 4H's are merged in solvent peak; HPLC purity: 99.28%; LCMS calculated for $C_{26}H_{31}N_5O_4S_2$: 541.18; Observed: 542.25 $[M + H]^+$. |
| A-724 | 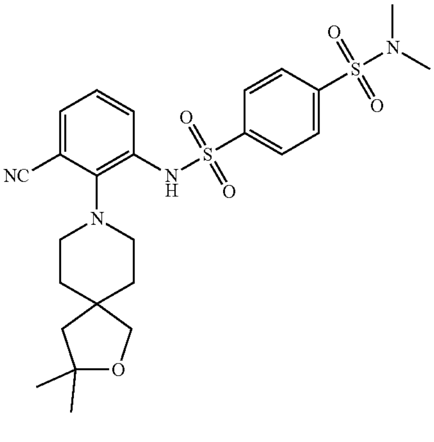 [SMILES: CN(C)S(=O)(=O)c1ccc(S(=O)(=O)Nc2cccc(C#N)c2N2CCC3(CC2)COC(C)(C)C3)cc1] | Yield: 80 mg, 11%; Appearance: Off white solid; $^1H$ NMR (400 MHz, DMSO-$d_6$) δ ppm 1.18 (s, 6H) 1.52 - 1.66 (m, 6H) 2.62 (s, 6H) 2.79 - 2.90 (m, 2H) 2.91 - 3.00 (m, 2H) 3.56 (s, 2H) 7.11 - 7.18 (m, 1H) 7.20 - 7.27 (m, 1H) 7.56 - 7.59 (m, 1H) 7.92-7.98 (m, 4H) 9.72 (s, 1H); HPLC purity: 99.57%; LCMS calculated for $C_{25}H_{32}N_4O_5S_2$: 532.18; Observed: 533.10 $[M + H]^+$. |

-continued

| Compound No. | Structure | Yields/Analytical data |
| --- | --- | --- |
| A-653 | 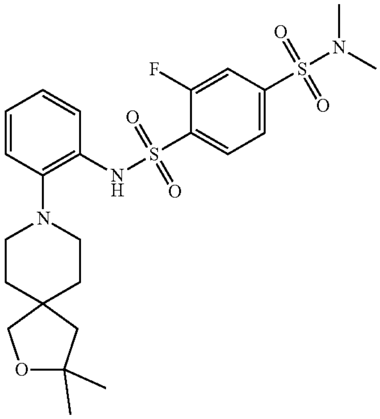 [SMILES: CN(C)S(=O)(=O)c1ccc(S(=O)(=O)Nc2ccccc2N2CCC3(CC2)COC(C)(C)C3)c(F)c1] | Yield: 50 mg, 12%; Appearance: White solid; $^{1}H$ NMR (400 MHz, DMSO-$d_6$) δ 1.18 (s, 6H) 1.38-1.65 (m, 6H) 2.52-2.60 (m, 2H) 2.66 (s, 6H) 3.54 (s, 2H) 6.99-7.07 (m, 1H) 7.09-7.17 (m, 1H) 7.18-7.21 (m, 1 H) 7.24 (d, J = 7.83 Hz, 1H) 7.70 (d, J = 8.31 Hz, 1 H) 7.84 (d, J = 9.29 Hz, 1 H) 7.92 – 8.03 (m, 1 H) 9.48 (s, 1H) 2H's are merged in solvent peak; HPLC purity: 98.31%; LCMS calculated for $C_{24}H_{32}FN_3O_5S_2$: 525.18; Observed: 526.45 $[M + H]^+$. |
| A-652 | 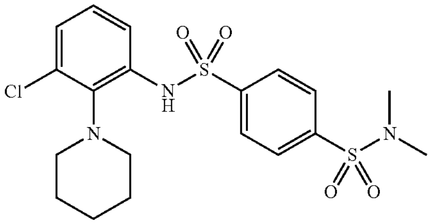 [SMILES: CN(C)S(=O)(=O)c1ccc(S(=O)(=O)Nc2cccc(Cl)c2N2CCCCC2)cc1] | Yield: 0.9 g, 49%; Appearance: Off white solid; $^{1}H$ NMR (400 MHz, DMSO-$d_6$) δ 1.10-1.20 (m, 2H) 1.48-1.56 (m, 4H) 2.24-2.32 (m, 2H) 2.61 (s, 6H) 3.06-3.15 (m, 2H) 7.11 – 7.26 (m, 3H) 7.9-7.98 (m, 4H) 9.23 (s, 1H); HPLC purity: 99.34%; LCMS calculated for $C_{19}H_{24}ClN_3O_4S_2$: 457.09; Observed: 458.30 $[M + H]^+$. |
| A-615 | 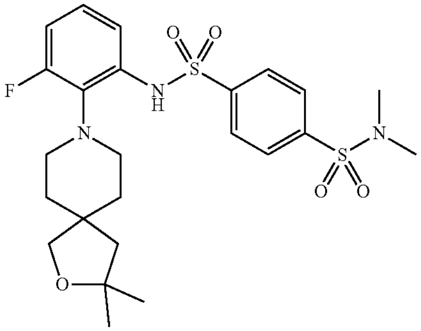 [SMILES: CN(C)S(=O)(=O)c1ccc(S(=O)(=O)Nc2cccc(F)c2N2CCC3(CC2)COC(C)(C)C3)cc1] | Yield: 100 mg, 9%; Appearance: White solid; $^{1}H$ NMR (400 MHz, DMSO-$d_6$) δ ppm 1.18 (s, 6H) 1.44 – 1.64 (m, 6H) 2.44 (s, 2H) 2.61 (s, 6H) 3.53 (s, 2H) 6.94-7.02 (m, 1H) 7.12 – 7.28 (m, 2H) 7.90 – 7.95 (m, 2H) 7.95-8.02 (m, 2H) 9.29 (brs, 1H) 2H's are merged in solvent peak; HPLC purity: 98.95%; LCMS calculated for $C_{24}H_{32}FN_3O_5S_2$: 525.18; Observed: 526.2 $[M + H]^+$. |
| A-702 | 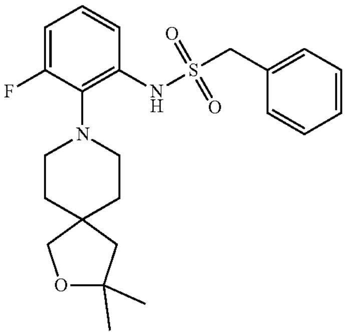 [SMILES: CC1(C)CC2(CCN(c3c(F)cccc3NS(=O)(=O)Cc3ccccc3)CC2)CO1] | Yield: 35 mg, 11%; Appearance: White solid; $^{1}H$ NMR (400 MHz, DMSO-$d_6$) δ 1.19 (s, 6H) 1.52-1.58 (m, 2H) 1.62 (s, 2H) 2.78 (s, 4H) 3.32 (s, 2H) 3.55 (s, 2H) 4.67 (s, 2H) 6.83 – 6.95 (m, 1H) 7.12-7.20 (m, 2H) 7.27 (d, J = 2.93 Hz, 2H) 7.35 (d, J = 2.93 Hz, 3H) 8.27 (s, 1H); HPLC purity: 99.64%; LCMS calculated for $C_{23}H_{29}FN_2O_3S$: 432.19; Observed: 433.1 $[M + H]^+$. |

-continued

| Compound No. | Structure | Yields/Analytical data |
| --- | --- | --- |
| A-685 | 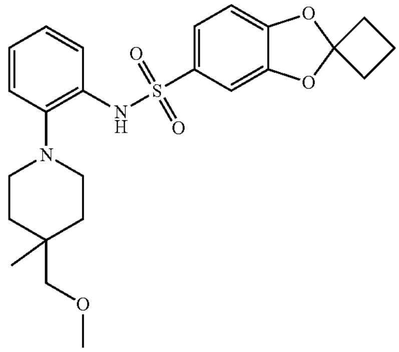 [SMILES: COCC1(C)CCN(c2ccccc2NS(=O)(=O)c2ccc3c(c2)OC2(CCC2)O3)CC1] | Yield: 158 mg, 40%; Appearance: White solid; $^1$H NMR (400 MHz, DMSO-$d_6$) δ 0.95 (s, 3H) 1.22-1.37 (m, 2H) 1.57 (t, J = 9.05 Hz, 2H) 1.78 (dt, J =l 5.65, 7.83 Hz, 2H) 2.35 - 2.47 (m, 2H) 2.51-2.64 (m, 6H) 3.14 (s, 2H) 3.29 (s, 3H) 6.98 (d, J = 7.83 Hz, 1H) 7.01-7.11 (m, 2H) 7.13-7.23 (m, 1H) 7.25 (s, 1H) 7.27 (s, 2H) 8.60 (s, 1H); HPLC purity: 98 59%; LCMS calculated for $C_{24}H_{30}N_2O_5S$: 458.19; Observed: 459.15 $[M + H]^+$. |
| A-723 | 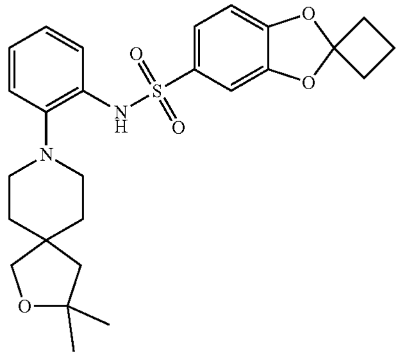 [SMILES: CC1(C)CC2(CCN(c3ccccc3NS(=O)(=O)c3ccc4c(c3)OC3(CCC3)O4)CC2)CO1] | Yield: 35 mg, 9%; Appearance: White solid; $^1$H NMR (400 MHz, DMSO-$d_6$) δ ppm 1.18 (s, 6H) 1.44 - 1.64 (m, 6H) 2.44 (s, 2H) 2.61 (s, 6H) 3.53 (s, 2H) 6.94-7.02 (m, 1H) 7.12 - 7.28 (m, 2H) 7.90 - 7.95 (m, 2H) 7.95-8.02 (m, 2H) 9.29 (brs, 1H) 2H's are merged in solvent peak; HPLC purity: 99.68%; LCMS calculated for $CH_{32}N_2O_5S$: 484.20; Observed: 485.25 $[M + H]^+$. |
| A-655 | 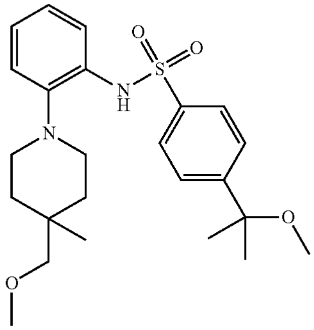 [SMILES: COCC1(C)CCN(c2ccccc2NS(=O)(=O)c2ccc(C(C)(C)OC)cc2)CC1] | Yield: 35 mg, 9%; Appearance: Sticky White solid; $^1$H NMR (400 MHz, DMSO-$d_6$) δ 0.92 (s, 3H) 1.18-1.31 (m, 2H) 1.40 (s, 6H) 1.46-1.59 (m, 2H) 2.27-2.38 (m, 2H) 2.44 (d, J = 8.80 Hz, 2H) 2.94 (s, 3H) 3.15 (m, 2H) 3.28 (s, 3H) 7.06 (dd, J = 5.62, 3.67 Hz, 2H) 7.15 - 7.24 (m, 1H) 7.32 - 7.41 (m, 1H) 7.52 (d, J = 8.31 Hz, 2H) 7.72 (d, J = 8.31 Hz, 2H) 8.65 (s, 1H); HPLC purity: 99.68%; LCMS calculated for $C_{24}H_{34}N_2O_4S$: 446.22; Observed: 447.45 $[M + H]^+$. |
| A-656 | 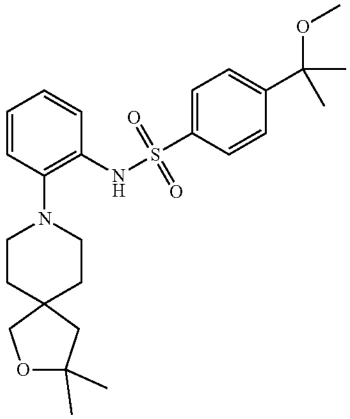 [SMILES: COC(C)(C)c1ccc(S(=O)(=O)Nc2ccccc2N2CCC3(CC2)COC(C)(C)C3)cc1] | Yield: 22 mg, 6%; Appearance: Sticky white solid; $^1$H NMR (400 MHz, DMSO-$d_6$) δ 1.18 (s, 6H) 1.40 (s, 6H) 1.48 - 1.56 (m, 4H) 1.60 (s, 2H) 2.27-2.39 (m, 4H) 2.94 (s, 3H) 3.55 (s, 2H) 7.00 - 7.10 (m, 2H) 7.10 - 7.17 (m, 1H) 7.34 - 7.39 (m, 1H) 7.53 (d, J = 8.31 Hz, 2H) 7.72 (d, J = 8.80 Hz, 2H) 8.71 (s, 1H); HPLC purity: 99.27%; LCMS calculated for $C_{26}H_{36}N_2O_4S$: 472.24; Observed: 473.30 $[M + H]^+$. |

-continued

| Compound No. | Structure | Yields/Analytical data |
|---|---|---|
| A-704 | 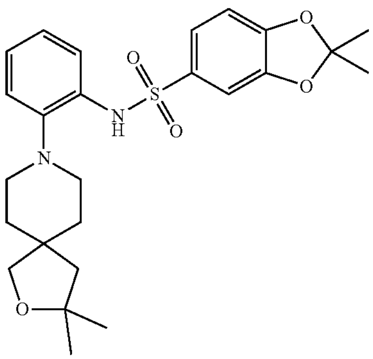 [SMILES: CC1(C)CC2(CCN(c3ccccc3NS(=O)(=O)c3ccc4c(c3)OC(C)(C)O4)CC2)CO1] | Yield: 50 mg, 14%; Appearance: White solid; $^1$H NMR (400 MHz, DMSO-$d_6$) δ 1.19 (s, 6H) 1.53 – 1.69 (m, 12H) 2.45 (t, J = 5. 14 Hz, 4H) 3.57 (s, 2H) 6.93 (d, J = 8.80 Hz, 1H) 7.06 (dd, J = 5.87, 3.91 Hz, 2H) 7.16 (dd, J = 5.87, 3.42 Hz, 1H) 7.20 – 7.25 (m, 2H) 7.28 – 7.38 (m, 1H) 8.61 (s, 1H); HPLC purity: 99.36%; LCMS calculated for $C_{25}H_{32}N_2O_5S$: 472.20; Observed: 473.20 $[M + H]^+$. |
| A-721 | 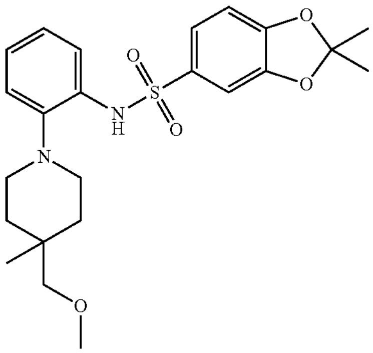 [SMILES: COCC1(C)CCN(c2ccccc2NS(=O)(=O)c2ccc3c(c2)OC(C)(C)O3)CC1] | Yield: 30 mg, 8%; Appearance: White solid; $^1$H NMR (400 MHz, DMSO-$d_6$) δ 0.95 (s, 3H) 1.21-1.38 (m, 2H) 1.52-1.60 (s, 2H) 1.64 (s, 6H) 2.39 – 2.61 (m, 4H) 3.14 (s, 2H) 3.28 (s, 3H) 6.93 (d, J = 7.83 Hz, 1H) 7.00 – 7.10 (m, 2 H) 7.17 – 7.27 (m, 3H) 7.29 – 7.36 (m, 1H) 8.56 (s, 1H).; HPLC purity: 99.53%; LCMS calculated for $C_{23}H_{30}N_2O_5S$: 446.19; Observed: 447.20 $[M + H]^+$. |
| A-633 | 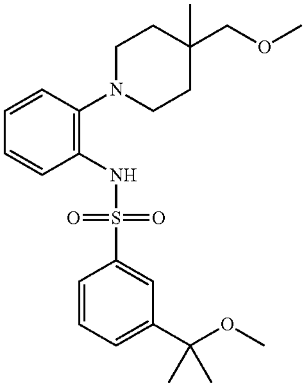 [SMILES: COCC1(C)CCN(c2ccccc2NS(=O)(=O)c2cccc(C(C)(C)OC)c2)CC1] | Yield: 57 mg, 15%; Appearance: White solid; $^1$H NMR (400 MHz, DMSO-$d_6$) $^1$H NMR (400 MHz, DMSO-$d_6$) δ 0.92 (s, 3H) 1.18-1.31 (m, 2H) 1.34 (s, 6H) 1.47-1.60 (m, 2H) 2.25 – 2.35 (m, 2H) 2.38 – 2.47 (m, 2H) 2.83 (s, 3H) 3.12 (s, 2H) 3.27 (s, 3H) 7.03 – 7.12 (m, 2H) 7.17 – 7.25 (m, 1H) 7.37 – 7.42 (m, 1H) 7.51 – 7.55 (m, 1H) 7.57 – 7.65 (m, 2H) 7.71 (d, J = 7.83 Hz, 1H) 8.60 (s, 1H); HPLC purity: 99.47%; LCMS calculated for $C_{24}H_{34}N_2O_4S$: 446.22; Observed: 447.0 $[M + H]^+$. |
| A-634 | 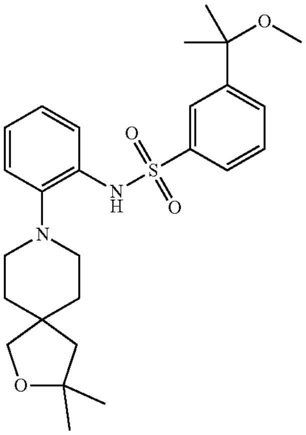 [SMILES: COC(C)(C)c1cccc(S(=O)(=O)Nc2ccccc2N2CCC3(CC2)COC(C)(C)C3)c1] | Yield: 27 mg, 7%; Appearance: Off white solid; $^1$H NMR (400 MHz, DMSO-$d_6$) δ 1.18 (s, 6H) 1.34 (s, 6H) 1.47-1.58 (m, 4H) 1.60 (s, 2H) 2.35 (t, J = 5.14 Hz, 4 H) 2.83 (s, 3H) 3.55 (s, 2H) 7.00-7.11 (m, 2H) 7.12 – 7.18 (m, 1H) 7.40 (dd, J = 7.34, 1.96 Hz, 1H) 7.48 – 7.57 (m, 1H) 7.61 (d, J = 12.23 Hz, 2H) 7.72 (d, J = 7.83 Hz, 1 H) 8.66 (s, 1H); HPLC purity: 99.82%; LCMS calculated for $C_{26}H_{36}N_2O_4S$: 472.24; Observed: 473.15 $[M + H]^+$. |

-continued

| Compound No. | Structure | Yields/Analytical data |
|---|---|---|
| A-635 | 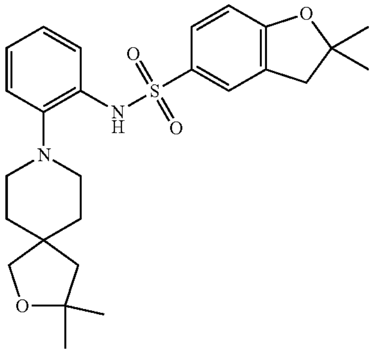 [SMILES: CC1(C)CC2(CCN(c3ccccc3NS(=O)(=O)c3ccc4c(c3)CC(C)(C)O4)CC2)CO1] | Yield: 0.116 g; 32%; Appearance: Off white solid; $^{1}$H NMR (400 MHz, DMSO-$d_6$) δ 8.45 (s, 1H), 7.63 (s, 1H), 7.48 (bd, J = 8.4 Hz, 1H), 7.36 (bd, J = 8.4 Hz, 1H), 7.18 – 7.15 (m, 1H), 7.05 (bs, 2H), 6.78 – 6.76 (m, 1H), 3.57 (s, 2H), 3.00 (s, 2H), 2.43 (bs, 4H), 1.63 (s, 6H), 1.61 – 1.39 (m, 6H), 1.19 (s, 6H); HPLC purity: 98.93%; LCMS calculated for $C_{26}H_{34}N_2O_4S$: 470.63; Observed: 471.1 $[M + H]^+$. |
| A-613 | 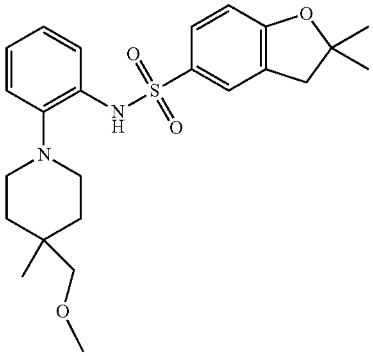 [SMILES: COCC1(C)CCN(c2ccccc2NS(=O)(=O)c2ccc3c(c2)CC(C)(C)O3)CC1] | Yield: 0.016 g, 8%; Appearance: Off white solid; $^{1}$H NMR (400 MHz, DMSO-$d_6$) δ 7.97 (s, 1H), 7.60 (m, 3H), 7.14 – 7.08 (m, 2H), 7.04 – 7.00 (m, 1H), 6.68 – 6.66 (m, 1H), 3.39 (s, 3H), 3.18 (s, 2H), 2.97 (s, 2H), 2.63 – 2.58 (m, 2H), 2.46 – 2.44 (m, 2H), 1.67 – 1.61 (m, 2H), 1.49 – 1.39 (m, 8H), 1.03 (s, 3H); HPLC purity: 97.98%; LCMS calculated for $C_{24}H_{32}N_2O_4S$: 444.59; Observed: 445.0 $[M + H]^+$. |
| A-640 | 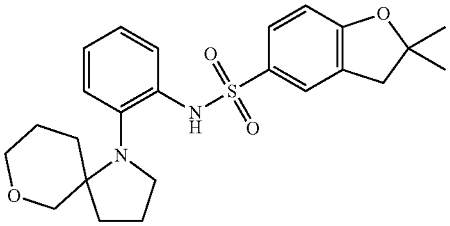 [SMILES: CC1(C)Cc2cc(S(=O)(=O)Nc3ccccc3N3CCCC34CCCOC4)ccc2O1] | Yield: 0.042 g, 37%; Appearance: Off white solid; $^{1}$H NMR (400 MHz, DMSO-$d_6$) δ 8.60 (s, 1H), 7.66 (s, 1H), 7.54 – 7.53 (bd, J = 7.2 Hz, 1H), 7.45 – 7.43 (bd, J = 7.6 Hz, 1H), 7.21 – 7.19 (bd, J = 8 Hz, 1H), 7.16 – 7.12 (m, 1H), 7.02 – 6.98 (m, 1H), 6.79 – 6.77 (m, 1H), 3.60 – 3.53 (m, 2H), 3.00 (s, 2H), 2.91 – 2.84 (m, 3H), 2.78 – 2.76 (m, 1H), 2.12 – 2.07 (m, 1H), 1.84 – 1.83 (m, 2H), 1.72 – 1.67 (m, 1H), 1.54 – 1.51 (m, 1H), 1.38 (s, 8H), 0.97 – 0.94 (m, 1H); HPLC purity: 99.04%; LCMS calculated for $C_{24}H_{30}N_2O_4S$: 442.57; Observed: 442.8 $[M + H]^+$. |
| A-654 | 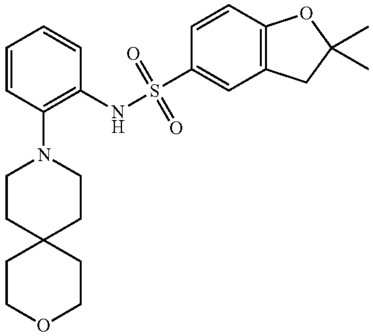 [SMILES: CC1(C)Cc2cc(S(=O)(=O)Nc3ccccc3N3CCC4(CCOCC4)CC3)ccc2O1] | Yield: 0.06 g, 32%; Appearance: Off white solid; $^{1}$H NMR (400 MHz, DMSO-$d_6$) δ 1.31-1.50 (m, 10H) 1.50 – 1.61 (m, 4H) 3.01 (s, 2H) 3.46 – 3.61 (m, 4H) 6.70 – 6.81 (m, 1H) 6.99 – 7.10 (m, 2H) 7.16 – 7.24 (m, 1H) 7.35 (d, J = 6.36 Hz, 1H) 7.47 (d, J = 1.83 Hz, 1H) 7.59-7.68 (m, 1H) 8.36 – 8.49 (m, 1H) 4H's are merged in solvent peak; HPLC purity: 99.72%; LCMS calculated for $C_{25}H_{32}N_2O_4S$: 456.60; Observed: 456.9 $[M + H]^+$. |

-continued

| Compound No. | Structure | Yields/Analytical data |
|---|---|---|
| A-632 | 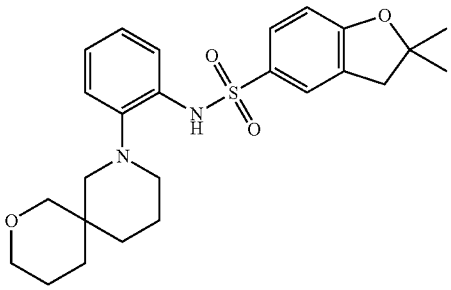 [SMILES: CC1(C)Cc2cc(S(=O)(=O)Nc3ccccc3N3CCCC4(CCCOC4)C3)ccc2O1] | Yield: 0.062 g, 33.51%; Appearance: Off white solid; $^1$H NMR (400 MHz, DMSO-$d_6$) δ 1.13-1.18 (m, 2H) 1.39 (s, 6H) 1.43-1.69 (m, 4H) 2.34 (d, J = 10.27 Hz, 1H) 2.58 (d, J = 10.27 Hz, 1H) 3.01 (s, 2H) 3.30 (s, 4H) 3.38-3.56 (m, 2H) 3.63-3.71 (m, 2H) 6.70-6.85 (m, 1H) 6.99-7.12 (s, 2H) 7.12-7.17 (m, 1H) 7.34 (d, J = 5.87 Hz, 1H) 7.51 (d, J = 7.34 Hz, 1H) 7.58-7.68 (m, 1H) 8.04-8.12 (m, 1H); HPLC purity: 98.25%; LCMS calculated for $C_{25}H_{32}N_2O_4S$: 456.60; Observed: 457.1 $[M + H]^+$. |
| A-636 | 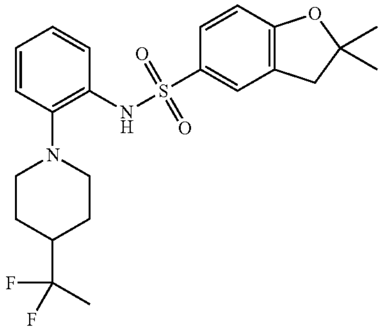 [SMILES: CC1(C)Cc2cc(S(=O)(=O)Nc3ccccc3N3CCC(C(C)(F)F)CC3)ccc2O1] | Yield: 0.074 g, 26%; Appearance: Off white solid; $^1$H NMR (400 MHz, DMSO-$d_6$) δ 1.39 (s, 6H) 1.49-1.70 (m, 8H) 1.75-1.93 (m, 2H) 3.01 (s, 2H) 6.78 (d, J = 8.31 Hz, 1H) 7.01-7.10 (m, 2H) 7.11-7.17 (m, 1H) 7.28-7.37 (m, 1H) 7.43-7.52 (m, 1H) 7.64 (s, 1H) 8.60 (s, 1H). 2H's merged in solvent peak; HPLC purity: 99.12%; LCMS calculated for $C_{23}H_{28}N_2O_3S$: 450.54; Observed: 450.8 $[M + H]^+$. |
| A-631 | 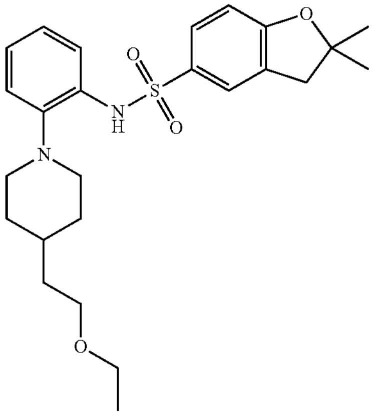 [SMILES: CCOCCC1CCN(c2ccccc2NS(=O)(=O)c2ccc3c(c2)CC(C)(C)O3)CC1] | Yield: 0.05 g, 9.02%; Appearance: Colourless sticky solid; $^1$H NMR (400 MHz, DMSO-$d_6$) δ 1.09 (t, J = 6.85 Hz, 3H) 1.20-1.41 (m, 8H) 1.43-1.51 (m, 3H) 1.53-1.66 (m, 2H) 2.45 (d, J = 6.36 Hz, 4H) 2.99 (s, 2H) 3.34-3.47 (m, 4H) 6.70-6.79 (m, 1H) 6.98-7.08 (m, 2H) 7.13 (d, J = 5.38 Hz, 1H) 7.35 (d, J = 7.83 Hz, 1H) 7.39-7.49 (m, 1H) 7.62 (s, 1H) 8.39 (s, 1H); HPLC purity: 99.80%; LCMS calculated for $C_{25}H_{34}N_2O_4S$: 458.62; Observed: 459.50 $[M + H]^+$. |
| A-614 | 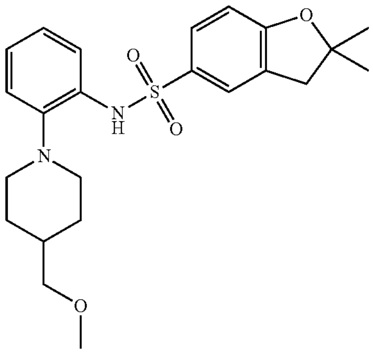 [SMILES: COCC1CCN(c2ccccc2NS(=O)(=O)c2ccc3c(c2)CC(C)(C)O3)CC1] | Yield: 11.31 mg, 3.55%; Appearance: Off white solid; $^1$H NMR (400 MHz, DMSO-$d_6$) δ 1.24-1.36 (m, 2H) 1.39 (s, 6H) 1.55-1.66 (m, 4H) 3.00 (s, 2H) 3.23 (d, J = 5.38 Hz, 2H) 3.25 (s, 3H) 6.77 (d, J = 8.31 Hz, 1H) 6.98-7.08 (m, 2H) 7.10-7.16 (m, 1H) 7.35 (d, J = 6.85 Hz, 1H) 7.47 (d, J = 7.34 Hz, 1H) 7.62 (s, 1H) 8.43 (s, 1H). 3H's are merged in solvent peak; HPLC purity: 97.73%; LCMS calculated for $C_{23}H_{30}N_2O_4S$: 430.56; Observed: 431.1 $[M + H]^+$. |

-continued

| Compound No. | Structure | Yields/Analytical data |
|---|---|---|
| A-686 | 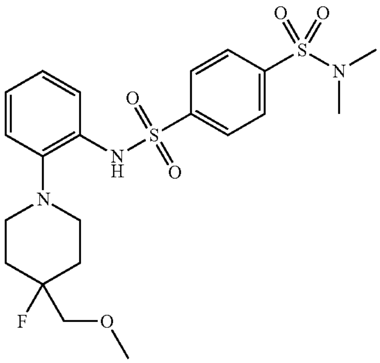 [SMILES: COCC1(F)CCN(c2ccccc2NS(=O)(=O)c2ccc(S(=O)(=O)N(C)C)cc2)CC1] | Yield: 0.043 g, 7%; Appearance: White solid; $^1$H NMR (400 MHz, DMSO-$d_6$) δ ppm 1.61-1.75 (m, 2H) 1.75 - 1.85 (m, 2H) 2.35-2.45 (m, 4H) 2.62 (s, 6H) 3.36 - 3.47 (m, 2H) 6.99 - 7.20 (m, 2H) 7.23 - 7.32 (m, 2H) 7.81 - 7.94 (m, 2 H) 7.96-8.04 (m, 2H) 9.33 (s, 1H). 3H' are merged in solvent peak; HPLC purity: 98.76%; LCMS calculated for $C_{21}H_{28}FN_3O_5S_2$: 485.59; Observed: 486.1 $[M + H]^+$. |
| A-438 | 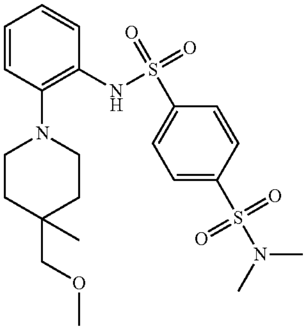 [SMILES: COCC1(C)CCN(c2ccccc2NS(=O)(=O)c2ccc(S(=O)(=O)N(C)C)cc2)CC1] | Yield: 7.6 g, 71%; Appearance: Off white solid; $^1$H NMR (400 MHz, DMSO-$d_6$) δ 0.92 (s, 3H), 1.19-1.29 (m, 2H), 1.45-1.55 (m, 2H), 2.39-2.50 (m, 4H), 2.61 (s, 6H), 3.11 (s, 2H), 3.27 (s, 3H), 7.00-7.06 (m, 1H), 7.12 (t, J = 7.34 Hz, 1H), 7.15-7.21 (m, 1H), 7.26 (d, J = 7.83 Hz, 1H), 7.87-7.94 (m, 2H), 7.96-8.02 (m, 2H), 9.06-9.21 (m, 1H); HPLC purity : 99.87%; LCMS calculated for $C_{22}H_{31}N_3O_5S_2$: 481.17; Observed: 482.35 $[M + H]^+$. |
| A-727 | 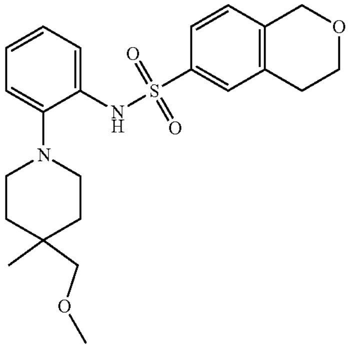 [SMILES: COCC1(C)CCN(c2ccccc2NS(=O)(=O)c2ccc3c(c2)CCOC3)CC1] | Yield: 0.040 g, 18.18%; Appearance: Off white sticky solid; $^1$H NMR (400 MHz, DMSO-$d_6$) δ 0.95 (s, 3H) 1.31 (d, 13.20 Hz, 2H) 1.52-1.63 (m, 2H) 2.43 (d, J = 6.85 Hz, 2H) 2.52-2.60 (m, 2H) 2.79 (t, J = 5.38 Hz, 2H) 3.14 (s, 2H) 3.29 (s, 3H) 3.85 (t, J = 5.62 Hz, 2H) 4.68 (s, 2H) 7.01-7.08 (m, 2H) 7.13-7.22 (m, 2H) 7.26-7.33 (m, 1H) 7.51 (d, J = 7.82 Hz, 1H) 7.60 (s, 1H) 8.63 (s, 1H); HPLC purity: 99.25%; LCMS calculated for $C_{23}H_{30}N_2O_4S$: 430.56; Observed: 431.08 $[M + H]^+$. |
| A-726 | 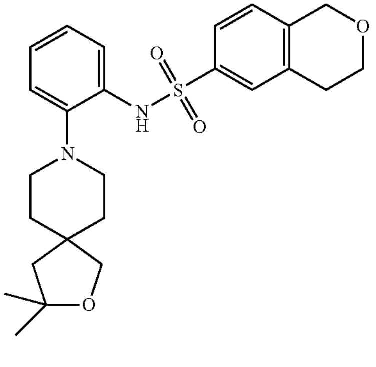 [SMILES: CC1(C)CC2(CCN(c3ccccc3NS(=O)(=O)c3ccc4c(c3)CCOC4)CC2)CO1] | Yield: 0.042 g; 16%; Appearance: Off white solid; $^1$H NMR (400 MHz, DMSO-$d_6$) δ 1.19 (s, 6H) 1.50-1.68 (m, 6H) 2.35-2.46 (m, 4H) 2.71-2.85 (m, 2H) 3.57 (s, 2H) 3.85 (s, 2H) 4.68 (s, 2H) 6.99-7.09 (m, 2H) 7.18 (d, J = 7.82 Hz, 2H) 7.31 (s, 1H) 7.51 (d, J = 6.85 Hz, 1H) 7.56-7.66 (m, 1H) 8.68 (s, 1H); HPLC purity: 97.19%; LCMS calculated for $C_{25}H_{32}N_2O_4S$: 456.60; Observed: 457.05 $[M + H]^+$. |

-continued

| Compound No. | Structure | Yields/Analytical data |
|---|---|---|
| A-683 | 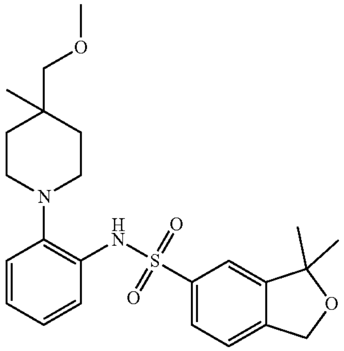 [SMILES: COCC1(C)CCN(c2ccccc2NS(=O)(=O)c2ccc3c(c2)C(C)(C)OC3)CC1] | Yield: 0.085 g, 44.97%; Appearance: Off white solid; $^1$H NMR (400 MHz, DMSO-$d_6$) δ 0.93 (s, 3H) 1.19-1.31 (m, 2H) 1.35 (s, 6H) 1.47-1.60 (m, 2H) 2.33-2.44 (m, 2H) 3.12 (s, 2H) 3.27 (s, 3H) 4.95 (s, 2H) 7.01-7.09 (m, 2H) 7.17-7.24 (m, 1H) 7.30-7.37 (m, 1H) 7.42 (d, J = 7.83 Hz, 1H) 7.60 (s, 1H) 7.65-7.73 (m, 1H) 8.61 (brs, 1H), 2H's are merged in to solvent peak; HPLC purity: 98.97%; LCMS calculated for $C_{24}H_{32}N_2O_4S$: 444.59; Observed: 445.25 $[M + H]^+$. |
| A-682 | 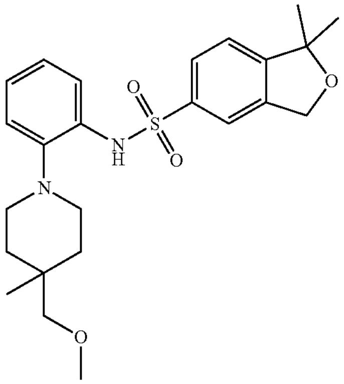 [SMILES: COCC1(C)CCN(c2ccccc2NS(=O)(=O)c2ccc3c(c2)COC3(C)C)CC1] | Yield: 0.05 g, 24%; Appearance: Off white semisolid; $^1$H NMR ((400 MHz, DMSO-$d_6$) δ 0.93 (s, 3H) 1.25 (d, J = 13.21 Hz, 2H) 1.38 (s, 6H) 1.42 - 1.56 (m, 2H) 2.30-2.39 (m, 2H) 2.46 (d, J = 9.29 Hz, 2H) 3.12 (s, 2H) 3.28 (s, 3H) 4.94 (s, 2H) 7.02-7.11 (m, 2H) 7.21 (dd, J = 6.60, 2.69 Hz, 1H) 7.30-7.37 (m, 1H) 7.41 (d, J = 8.31 Hz, 1H) 7.61 (d, J = 8.31 Hz, 1H) 7.70 (s, 1H) 8.66 (s, 1H); HPLC purity: 96.83%; LCMS calculated for $C_{24}H_{32}N_2O_4S$: 444.59; Observed: 445.55 $[M + H]^+$. |
| A-700 | 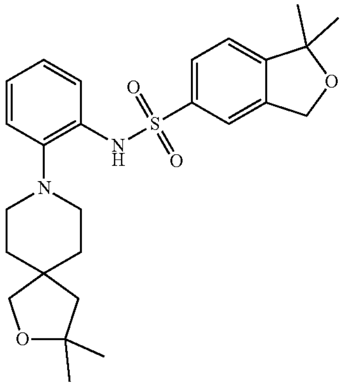 [SMILES: CC1(C)CC2(CCN(c3ccccc3NS(=O)(=O)c3ccc4c(c3)COC4(C)C)CC2)CO1] | Yield: 0.04 g; 11%; Appearance: Off white solid; $^1$H NMR (400 MHz, DMSO-$d_6$) δ 1.18 (s, 6H) 1.38 (s, 6H) 1.46-1.56 (m, 4H) 1.57-1.64 (m, 2H) 2.28-2.41 (m, 4H) 3.55 (s, 2H) 4.94 (s, 2H) 6.98-7.09 (m, 2H) 7.12-7.19 (m, 1H) 7.30-7.37 (m, 1H) 7.41 (d, J = 7.83 Hz, 1H) 7.62 (d, J = 7.83 Hz, 1H) 7.70 (s, 1H) 8.72 (brs, 1H); HPLC purity: 98.22%; LCMS calculated for $C_{26}H_{34}N_2O_4S$: 470.63; Observed: 471.1 $[M + H]^+$. |
| A-720 | 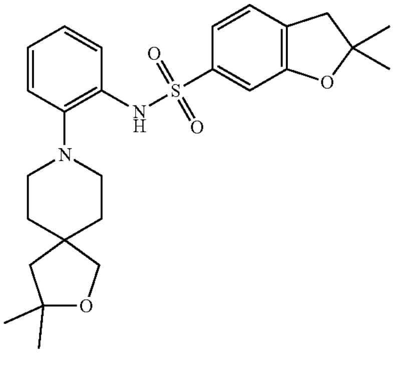 | Yield: 0.061 g, 17%; Appearance: Off white solid; $^1$H NMR (400 MHz, CHLOROFORM-d) δ 1.30 (s, 6 H) 1.38 - 1.50 (m, 6 H) 1.62 - 1.77 (m, 4 H) 2.49 (br t, J = 5.14 Hz, 4 H) 2.99 (s, 2 H) 3.72 (s, 2 H) 4.77 (s, 2 H) 6.96 - 7.05 (m, 1 H) 7.06 - 7.31 (m, 4 H) 7.59 (br d, J = 1.82 Hz, 1 H). 2H's merged in to solvent peak; HPLC purity: 99.80%; LCMS calculated for $C_{26}H_{34}N_2O_4S$: 470.63; Observed: 471.1 $[M + H]^+$. |

-continued

| Compound No. | Structure | Yields/Analytical data |
| --- | --- | --- |
| A-605 | 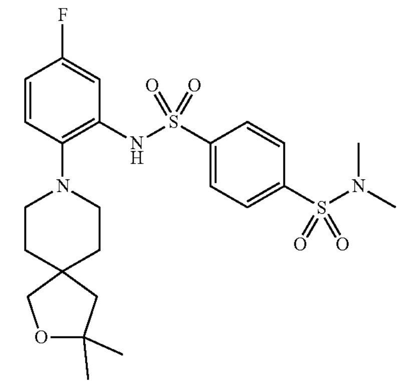 [SMILES: CN(C)S(=O)(=O)c1ccc(S(=O)(=O)Nc2cc(F)ccc2N2CCC3(CC2)COC(C)(C)C3)cc1] | Yield: 0.2 g, 35%; Appearance: Off white solid; $^1$H NMR (400 MHz, DMSO-$d_6$) δ 9.39 (bs, 1H), 8.04 - 8.02 (m, 2H), 7.94 - 7.92 (m, 2H), 7.23 (q, J = 4.8 Hz , 1H), 7.15 - 7.12 (m, 1H), 6.97 - 6.93 (m, 1H), 3.53 (s, 2H), 2.61 (s, 6H), 2.34 (bs, 4H), 1.58 (s, 2H), 1.54 - 1.49 (m, 4H), 1.17 (s, 6H); HPLC purity: 99.72%; LCMS Calculated for $C_{24}H_{32}FN_3O_5S_2$ 525.65; Observed: 526.25 $[M + H]^+$. |
| A-606 | 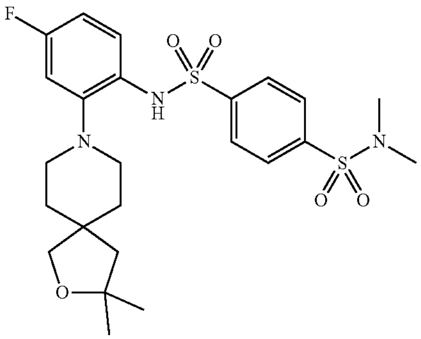 [SMILES: CN(C)S(=O)(=O)c1ccc(S(=O)(=O)Nc2ccc(F)cc2N2CCC3(CC2)COC(C)(C)C3)cc1] | Yield: 0.11 g, 39%; Appearance: White solid; $^1$H NMR (400 MHz, DMSO-$d_6$) δ 9.31 (bs, 1H), 7.91 (s, 4H), 7.19 (q, J = 5.6 Hz , 1H), 6.93 - 6.82 (m, 2H), 3.48 (s, 2H), 2.61 (s, 6H), 2.45 (s, 4H, merged in solvent peak) 1.54 (s, 2H), 1.42 (bd, J = 3.2 Hz, 4H), 1.15 (s, 6H); HPLC purity: 99.82%; LCMS Calculated for $C_{24}H_{32}FN_3O_5S_2$: 525.65; Observed: 526.25 $[M + H]^+$. |
| A-735 | 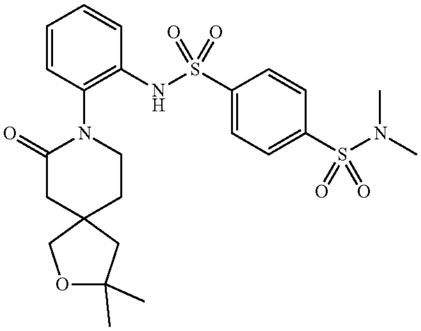 [SMILES: CN(C)S(=O)(=O)c1ccc(S(=O)(=O)Nc2ccccc2N2CCC3(COC(C)(C)C3)CC2=O)cc1] | Yield: 100 mg, 21%; Appearance: Off white solid; $^1$H NMR (400 MHz, $DMSO_6$) δ 9.66 (d, J = 13.2 Hz, 1H), 7.98 (q, J = 10 Hz, 4H), 7.22 - 7.15 (m, 4H), 3.64-3.56 (m, 2H), 3.37 (bs, 1H), 2.90 (bs, 1H), 2.63 (s, 6H), 2.45 - 2.31 (m, 2H), 1.80 - 1.63 (m, 4H), 1.22 (s, 3H), 1.20 (s, 3H). HPLC purity: 99.54%; LCMS calculated for $C_{24}H_{31}N_3O_6S_2$: 521.17; Observed: 522.20 $[M + H]^+$. |
| A-734 | 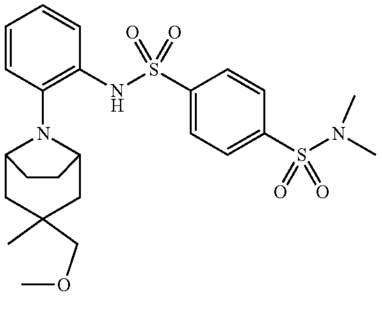 [SMILES: COCC1(C)CC2CCC(C1)N2c1ccccc1NS(=O)(=O)c1ccc(S(=O)(=O)N(C)C)cc1] | Yield: 15 mg, 5%; Appearance: White solid; : $^1$H NMR (400 MHz, $DMSO_6$) δ 9.17 (s, 1H), 7.98 (q, J = 5.2 Hz, 4H), 7.06 (t, J = 7.2 Hz, 1H), 6.89 (d, J = 10 Hz, 2H), 6.77 (t, J = 7.2 Hz, 1H), 3.72 (s, 2H), 3.27 (s, 3H), 3.16 (s, 2H), 2.63 (s, 6H), 1.79 - 1.78 (m, 2H), 1.60-1.53 (m, 6H), 0.86 (s, 3H). HPLC purity: 99.37%; LCMS calculated for $C_{24}H_{33}N_3O_5S_2$: 507.19; Observed: 575.45 $[M + H]^+$. |

-continued

| Compound No. | Structure | Yields/Analytical data |
| --- | --- | --- |
| A-738 | 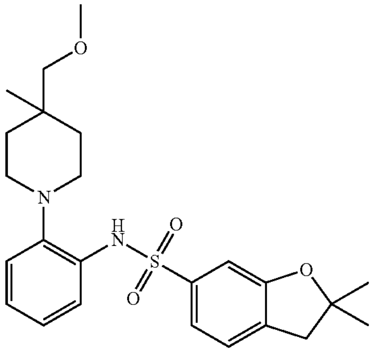 [SMILES: COCC1(C)CCN(c2ccccc2NS(=O)(=O)c2ccc3c(c2)OC(C)(C)C3)CC1] | Yield: 93 mg, 49%; Appearance: Off white solid; $^1$H NMR (400 MHz, $DMSO_6$) δ 8.6 (s, 1H), 7.34 − 7.28 (m, 2H), 7.24 − 7.18 (m, 2H), 7.08 − 7.03 (m, 3H), 3.28 (s, 3H), 3.13 (s, 2H), 3.02 (s, 2H), 2.51 (s, 2H), 2.48 − 2.38 (m, 2H), 1.61 − 1.53 (m, 2H), 1.38 (s, 6H), 1.35 − 1.28 (m, 2H), 0.94 (s, 3H). HPLC purity: 98.85%; LCMS calculated for $C_{24}H_{32}N_2O_4S$: 444.21; Observed: 445.15 $[M + H]^+$. |
| A-739 | 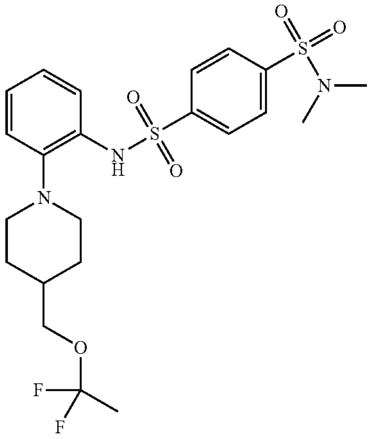 [SMILES: CN(C)S(=O)(=O)c1ccc(S(=O)(=O)Nc2ccccc2N2CCC(COC(C)(F)F)CC2)cc1] | Yield: 15 mg, 13%; Appearance: Off white solid; $^1$H NMR (400 MHz, $DMSO_6$) δ 9.17 (s, 1H), 8.01 (d, J = 8.4 Hz, 2H), 7.92 (d, J = 8.4 Hz, 2H), 7.27 (d, J = δ Hz, 1H), 7.12 − .05 (m, 3H), 3.69 (d, J = 5.6 Hz, 2H), 2.61 (s, 6H), 2.58 − 2.53 (m, 2H), 2.44 − 2.41 (m 2H), 1.79 (t,J = 13.2 Hz, 3H), 1.59 (d, J = 9.6 Hz, 3H), 1.34-1.29 (m, 2H); HPLC purity: 97.41%; LCMS calculated for $C_{22}H_{29}F_2N_3O_5S_2$ 517.15; Observed: 518.0 $[M + H]^+$. |
| A-745 | 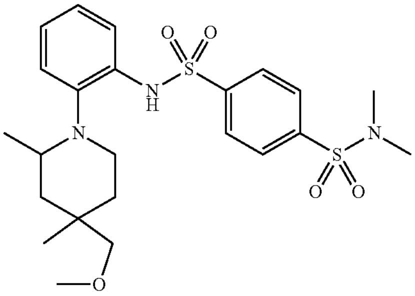 | Yield: 100 mg, 33%; Appearance: White solid; $^1$H NMR (400 MHz, $DMSO_6$) δ 9.01 (s, 1H), 8.05 (d, J = 8 Hz, 2H), 7.90 (d, J = 8.4 Hz, 2H), 7.50 (d, J = 7.6 Hz, 1H), 7.35 (d, J = 7.2 Hz, 1H), 7.18 − 7.08 (m, 2H), 3.28 (s, 3H), 3.04 (s, 2H), 3.01 − 2.99 (m, 1H), 2.57 (s, 7H), 1.82 (d, J = 10.8 Hz, 1H), 1.61 − 1.55 (m, 1H), 1.39 − 1.30 (m, 2H), 1.13 (d, J = 12 Hz, 1H), 0.97 (s, 3H), 0.41 (d, J = 6Hz, 3H) HPLC purity: 98.72%; LCMS calculated for $C_{23}H_{33}N_3O_5S_2$: 495.19; Observed: 496.20 $[M + H]^+$. |
| A-809 | 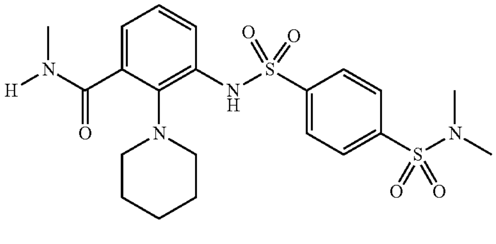 [SMILES: CNC(=O)c1cccc(NS(=O)(=O)c2ccc(S(=O)(=O)N(C)C)cc2)c1N1CCCCC1] | Yield: 46 mg; 22%; Appearance: White solid; $^1$H NMR (400 MHz, DMSO-$d_6$) δ 8.97 (s, 1H), 8.25 (s, 1H), 8.02 (d, J = 6.4 Hz, 2H), 7.95 (d, J = 6.4 Hz, 2H), 7.28 (d, J = 6.4 Hz, 1H), 7.11 (t, J = 6.0 Hz, 1H), 6.99 (d, J = 6.0 Hz, 1H), 2.74 − 2.68 (m, 4H), 2.65 (s, 9H), 1.56 − 1.38 (m, 6H); HPLC purity: 99.72%; LCMS calculated for $C_{21}H_{28}N_4O_5S_2$: 480.60; Observed: 481.2 $[M + H]^+$. |
| A-812 | 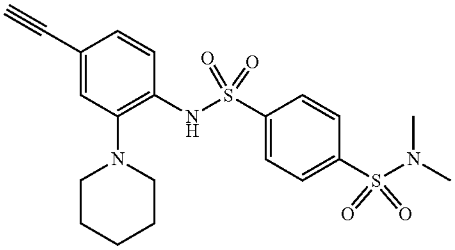 [SMILES: C#Cc1ccc(NS(=O)(=O)c2ccc(S(=O)(=O)N(C)C)cc2)c(N2CCCCC2)c1] | Yield: 70 mg; 18%; Appearance: White solid; $^1$H NMR (400 MHz, $CDCl_3$) δ 8.2 (brs, 1H), 7.97 (d, J = 8.8 Hz, 2H), 7.82 (d, J = 8.4 Hz, 2H), 7.55 (d, J = 8.4 Hz, 1H), 7.23 − 7.20 (m, 2H), 3.03 (s, 1H), 2.70 (s, 6H), 2.46 (t, J = 5.6 Hz, 4H), 1.64-1.54 (m, 6H), HPLC purity: 98.7%; LCMS calculated for $C_{21}H_{25}N_3O_4S_2$: 447.13; Observed: 448.2 $[M + H]^+$ |

-continued

| Compound No. | Structure | Yields/Analytical data |
|---|---|---|
| A-753 | 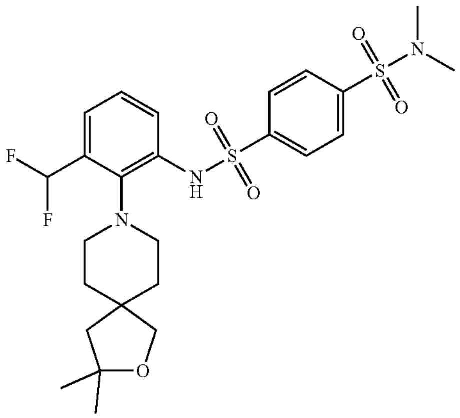 [SMILES: CN(C)S(=O)(=O)c1ccc(S(=O)(=O)Nc2cccc(C(F)F)c2N2CCC3(CC2)COC(C)(C)C3)cc1] | Yield: 0.045 g, 13%; Appearance: Off white solid; $^1$H NMR (400 MHz, DMSO$_6$) δ 9.64 (s, 1H), 8.02 (q, J = 8.52 Hz, 4H), 7.44 (d, J = 7.6 Hz, 1H), 7.26 - 6.98 (m, 3H), 3.61 - 3.54 (m, 2H), 3.07 - 2.96 (m, 2H), 2.71 (bs, 2H), 2.64 (s, 6H), 1.62 - 1.60 (m, 6H), 1.21 (s, 6H); HPLC purity: 97.16%; LCMS calculated for $C_{25}H_{33}F_2N_3O_5S_2$: 557.18; Observed: 558.00 [M + H]$^+$. |
| A-764 | 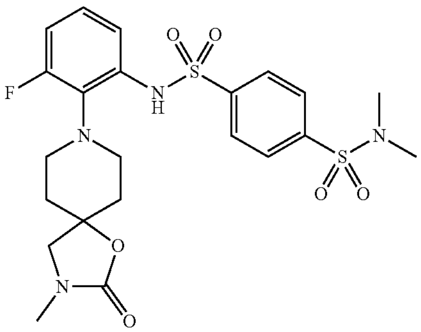 [SMILES: CN1CC2(CCN(c3c(F)cccc3NS(=O)(=O)c3ccc(S(=O)(=O)N(C)C)cc3)CC2)OC1=O] | Yield: 0.155 g, 33%; Appearance: Off white solid; $^1$H NMR (400 MHz, DMSO$_6$) δ 9.49 (s, 1H), 7.99 - 7.92 (m, 4H), 7.26 - 7.19 (m, 2H), 7.02 - 6.97 (m, 1H), 3.31 (s, 3H), 2.88 - 2.75 (m, 4H), 2.61 (s, 6H), 2.38 (bs, 2H), 1.84 - 1.77 (m, 4H); HPLC purity: 99.55%; LCMS calculated for $C_{22}H_{27}FN_4O_6S_2$: 526.14 Observed: 527.00 [M + H]$^+$. |
| A-736 | 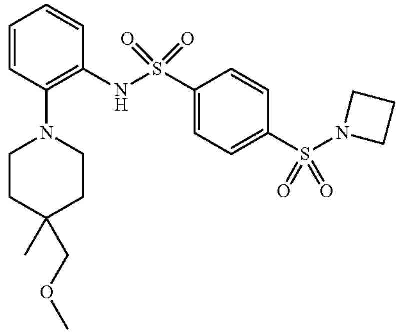 [SMILES: COCC1(C)CCN(c2ccccc2NS(=O)(=O)c2ccc(S(=O)(=O)N3CCC3)cc2)CC1] | Yield: 0.009 g, 2%; Appearance: Off white solid; $^1$H NMR (400 MHz, DMSO-d$_6$) δ 9.19 (s, 1H), 8.05 (d, J = 7.6 Hz, 2H), 7.97 (d, J = 8 Hz, 2H), 7.27 (d, J = 7.6 Hz, 1H), 7.22-7.04 (m, 3H), 3.69 (t, J = 8 Hz, 4H), 3.27 (s, 3H), 3.10 (s, 2H), 1.99 - 1.96 (m, 2H), 1.53-1.47 (m, 2H), 1.27 - 1.23 (m, 2H), 0.91 (s, 3H). 4H's are merged in to solvent peak; HPLC purity: 99.84%; LCMS calculated for $C_{23}H_{31}N_3O_5S_2$: 493.17; Observed: 494.25 [M + H]$^+$. |
| A-868 | 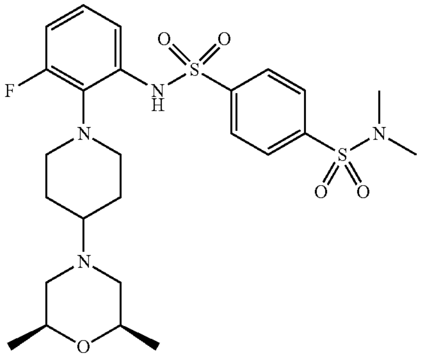 [SMILES: C[C@@H]1CN(C2CCN(c3c(F)cccc3NS(=O)(=O)c3ccc(S(=O)(=O)N(C)C)cc3)CC2)C[C@H](C)O1] | Yield: 0.1 g, 13.88%; Appearance: White solid; $^1$H NMR (400 MHz, DMSO$_6$) δ 9.30 (brs, 1 H), 7.96 (d, J = 14.18 Hz, 4 H), 7.25 - 7.13 (m, 2 H), 7.0 - 6.92 (m, 1 H), 3.58 - 3.48 (m, 2 H), 2.87 - 2.69 (m, 4 H), 2.61 (s, 6 H), 2.40 - 2.32 (m, 2 H), 2.20 - 2.12 (m, 1 H), 1.81 (t, J = 9.54 Hz, 2 H), 1.62 - 1.51 (m, 4 H), 1.07 (d, J = 4.40 Hz, 6 H); HPLC purity: 99.75%; LCMS calculated for $C_{25}H_{35}FNO_5S_2$: 554.20 Observed: 555.25 [M + H]$^+$. |

Example A104: Synthesis of N1-(2-(4-(tert-butyl)-4-hydroxypiperidin-1-yl)phenyl)-N4,N4-dimethyl-benzene-1,4-disulfonamide (A-471)

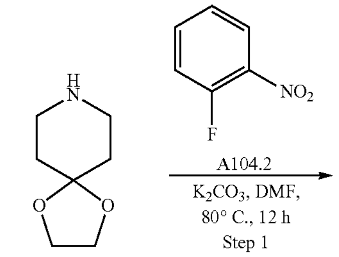

A104.1

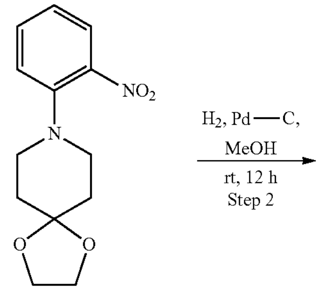

A104.3

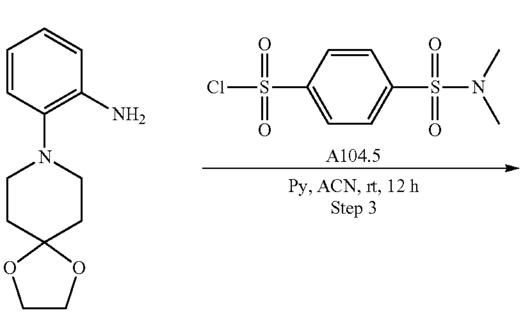

A104.4

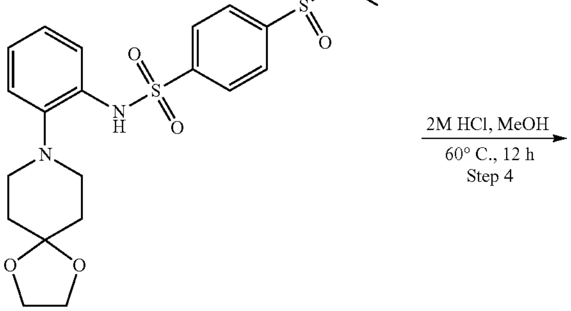

A104.6

-continued

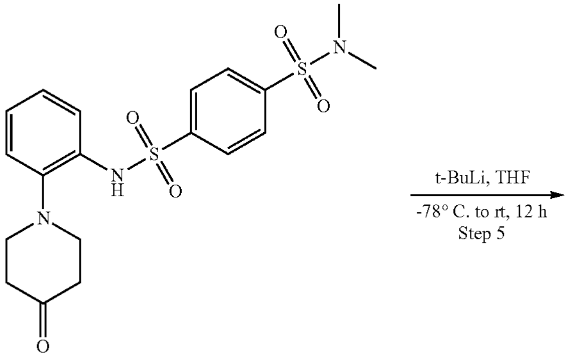

A104.7

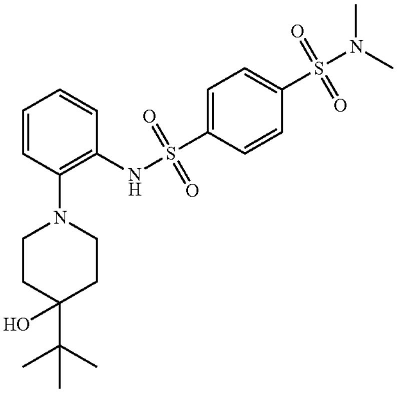

A-471

Step-1. Synthesis of 8-(2-nitrophenyl)-1,4-dioxa-8-azaspiro[4.5]decane (A104.3)

To a stirred solution of 1,4-dioxa-8-azaspiro[4.5]decane (A104.1) (5 g, 34.9 mmol, 1 eq) in DMF (50 mL), potassium carbonate (14.4 g, 105 mmol, 3 eq) and 1-fluoro-2-nitrobenzene (A104.2) (5.42 g, 38.4 mmol, 1.1 eq) were added at room temperature. The reaction mixture was stirred at 80° C. for 12 h. The progress of the reaction was monitored by TLC. After completion of the reaction, the reaction mixture was cooled to room temperature, diluted with ice-cold water and extracted with ethyl acetate. The combined organic layers were washed with cold water and brine, dried over anhydrous $Na_2SO_4$, filtered and concentrated under reduced pressure to dryness. The crude product was purified by column chromatography on silica gel to afford 8-(2-nitrophenyl)-1,4-dioxa-8-azaspiro[4.5]decane (A104.3) (9.08 g, 98.5%). LCMS: 265.11 $[M+H]^+$.

Step-2. Procedure for the synthesis of 2-(1,4-dioxa-8-azaspiro[4.5]decan-8-yl)aniline (A104.4)

A stirred solution of 8-(2-nitrophenyl)-1,4-dioxa-8-azaspiro[4.5]decane (A104.3) (9.08 g, 34.3 mmol, 1 eq) in methanol (50 mL) was purged with nitrogen for 5 min. 10% Palladium on carbon (2 g, 22% w/w) was added to the reaction mixture under nitrogen atmosphere. The reaction mixture was purged with hydrogen and hydrogenated at room temperature for 12 h. The progress of the reaction was monitored by TLC. After completion of the reaction, the reaction mixture was filtered through a pad of Celite and the Celite pad was washed with methanol. The filtrated was concentrated under reduced pressure to dryness to afford 2-(1,4-dioxa-8-azaspiro[4.5]decan-8-yl)aniline (A104.4) (7.7 g, crude which was used in the next step without further purification. LCMS: 235.14 $[M+H]^+$.

Step-3. Procedure for the synthesis of N1-(2-(1,4-dioxa-8-azaspiro[4.5]decan-8-yl)phenyl)-N4,N4-dimethylbenzene-1,4-disulfonamide (A104.6)

To a stirred solution of 2-(1,4-dioxa-8-azaspiro[4.5]decan-8-yl)aniline (A104.4) (1.5 g, 6.4 mmol, 1 eq) in acetonitrile (20 mL), pyridine (1.51 mL, 19.2 mmol, 3 eq) followed by 4-(N,N-dimethylsulfamoyl)benzenesulfonyl chloride (A104.5) (2 g, 7 mmol, 1.1 eq) were added at room temperature and stirred for 12 h. The progress of the reaction was monitored by TLC. After completion of the reaction, the reaction mixture was diluted with water and extracted with ethyl acetate. The combined organic layers were washed with brine, dried over anhydrous $Na_2SO_4$, filtered and concentrated under reduced pressure to dryness. The crude product was purified by column chromatography on silica gel to afford N1-(2-(1,4-dioxa-8-azaspiro[4.5]decan-8-yl)phenyl)-N4,N4-dimethylbenzene-1,4-disulfonamide (A104.6) (2.5 g, 81.4%). LCMS: 482.13 $[M+H]^+$.

Step-4. Procedure for the synthesis of N1,N1-dimethyl-N4-(2-(4-oxopiperidin-1-yl)phenyl)benzene-1,4-disulfonamide (A104.7)

To a stirred solution of N1-(2-(1,4-dioxa-8-azaspiro[4.5]decan-8-yl)phenyl)-N4,N4-dimethylbenzene-1,4-disulfonamide (A104.6) (2.8 g, 5.8 mmol, 1 eq) in methanol (14 mL), 2 M aqueous HCl (14 mL) was added and the reaction mixture was stirred at 60° C. for 12 h. The progress of the reaction was monitored by TLC. After completion of the reaction, the reaction mixture was concentrated under reduced pressure. The residue was dissolved in saturated aqueous $NaHCO_3$ solution and extracted with ethyl acetate. The combined organic layers were washed with brine, dried over anhydrous $Na_2SO_4$, filtered and concentrated under reduced pressure to dryness. The crude product was purified by column chromatography on silica gel to afford N1,N1-dimethyl-N4-(2-(4-oxopiperidin-1-yl)phenyl)benzene-1,4-disulfonamide (A104.7) (2 g, 78.7%). LCMS: 438.11 $[M+H]^+$.

Step-5. Procedure for the synthesis of N1-(2-(4-(tert-butyl)-4-hydroxypiperidin-1-yl)phenyl)-N4,N4-dimethylbenzene-1,4-disulfonamide (A-471)

To a stirred solution N1,N1-dimethyl-N4-(2-(4-oxopiperidin-1-yl)phenyl)benzene-1,4-disulfonamide (A104.7) (250 mg, 0.57 mmol, 1 eq) in THE (5 mL) was added a 1.7 M solution of tert-butyl lithium in pentane (1 mL, 1.7 mmol, 1.7 mmol, 3 eq) at −78° C. under an argon atmosphere. The reaction mixture was warmed to room temperature and stirred for 12 h. The progress of the reaction was monitored by TLC. After completion of the reaction, the reaction mixture was slowly quenched with saturated aqueous $NH_4Cl$ solution and extracted with ethyl acetate. The combined organic layers were washed with brine, dried over anhydrous $Na_2SO_4$, filtered and concentrated under reduced pressure to dryness. The crude product was purified by combiflash chromatography on silica gel followed by reverse phase preparative HPLC to afford N1-(2-(4-(tert-butyl)-4-hydroxypiperidin-1-yl)phenyl)-N4,N4-dimethylbenzene-1,4-disulfonamide (A-471). Yield: 35 mg, 6.18%; Appearance: White solid; $^1H$ NMR (400 MHz, DMSO-$d_6$) δ 9.20 (bs, 1H), 7.97 (d, J=7.6 Hz, 2H), 7.91 (d, J=8.0 Hz, 2H), 7.27 (d, J=8.0 Hz, 1H), 7.14-7.00 (m, 3H), 3.80 (s, 1H), 2.76 (t, J=11.2 Hz, 2H), 2.61 (s, 6H), 2.33-2.24 (m, 2H), 1.69-1.60 (m, 2H), 1.32 (d, J=12.8 Hz, 2H), 0.88 (s, 9H); HPLC purity: 99.72%; LCMS Calculated for $C_{23}H_{33}N_3O_5S_2$: 495.19; Observed: 496.25 $[M+H]^+$.

Example A105: Synthesis of 4-((2-(4-benzylpiperazin-1-yl)benzyl)sulfonyl)-N,N-dimethylbenzenesul fonamide (A-406) and 4-((1-(2-(4-benzylpiperazin-1-yl)phenyl)ethyl)sulfonyl)-N,N-dimethylbenzene-sulfonamide (A-465)

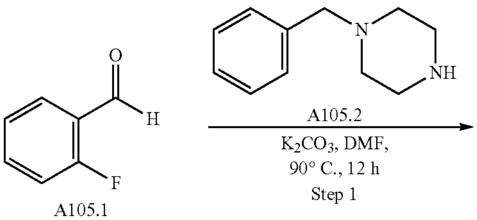

A105.1

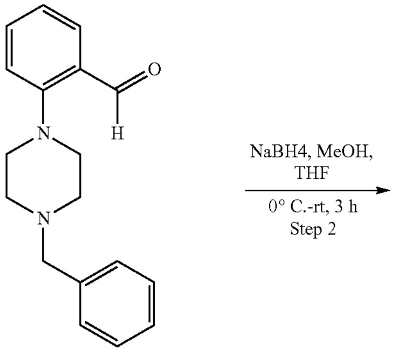

A105.3

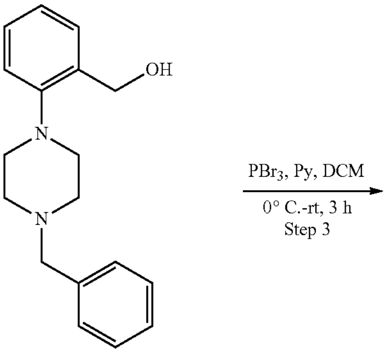

A105.4

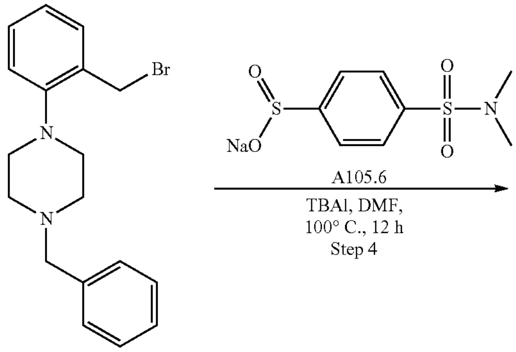

A105.5

-continued

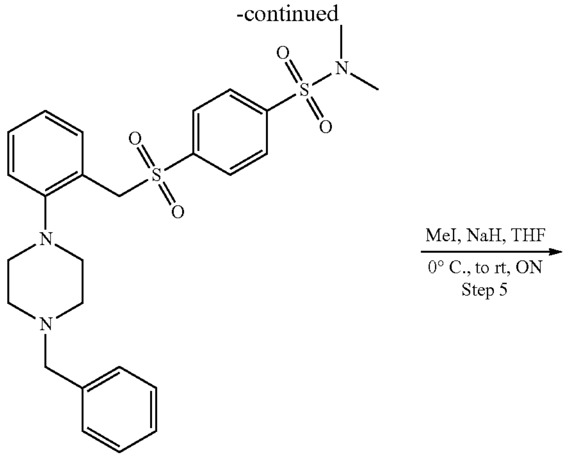

A-406

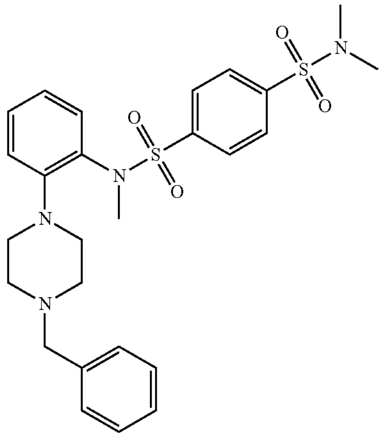

A-465

Step-1. Procedure for the synthesis of 2-(4-benzylpiperazin-1-yl)benzaldehyde (A105.3)

To a stirred solution of 2-fluorobenzaldehyde (A105.1) (5 g, 40.3 mmol, 1 eq) and 1-benzylpiperazine (A105.2) (7.8 g, 44 mmol, 1.1 eq) in DMF (50 mL) was added potassium carbonate (16.67 g, 120 mmol, 3 eq) at room temperature and the reaction mixture was stirred at 90° C. for 12 h. The progress of the reaction was monitored by TLC. After completion of the reaction, the reaction mixture was cooled to room temperature, diluted with cold water and extracted with ethyl acetate. The combined organic layers were washed with cold water and brine, dried over anhydrous $Na_2SO_4$, filtered and concentrated under reduced pressure. The crude product was purified by flash column chromatography on silica gel to afford 2-(4-benzylpiperazin-1-yl) benzaldehyde (A105.3) (4.35 g, 38%). LCMS: 281.16 $[M+H]^+$.

Step-2. Procedure for the Synthesis of (2-(4-benzylpiperazin-1-yl)phenyl)methanol (A105.4)

To a stirred solution of 2-(4-benzylpiperazin-1-yl)benzaldehyde (A105.3) (4.3 g, 15.3 mmol, 1 eq) in a mixture of methanol (25 mL) and THE (25 mL) was added sodium borohydride (0.87 g, 23 mmol, 1.5 eq) in portions at 0° C. The reaction mixture was warmed to room temperature and stirred for 3 h. The progress of the reaction was monitored by TLC. After completion of the reaction, the reaction mixture was quenched with saturated aqueous $NH_4Cl$ solution and extracted with ethyl acetate. The combined organic layers were washed with water and brine, dried over anhydrous $Na_2SO_4$, filtered and concentrated under reduced pressure to dryness to afford the titled (2-(4-benzylpiperazin-1-yl)phenyl)methanol (A105.4) (4 g, crude). This compound was used in the next step without further purification. LCMS: 283.17 $[M+H]^+$.

Step-3. Procedure for the Synthesis of 1-benzyl-4-(2-(bromomethyl)phenyl)piperazine (A105.5)

To a stirred solution of (2-(4-benzylpiperazin-1-yl)phenyl)methanol (A105.4) (3 g, 10.6 mmol, 1 eq) in DCM (60 ML) was added pyridine (1.71 mL, 21.2 mmol, 2 eq) followed by phosphorous tribromide (4.31 g, 15.9 mmol, 1.5 eq) dropwise at 0° C. The reaction mixture was warmed to room temperature and stirred for 3 h. The progress of the reaction was monitored by TLC. After completion of the reaction, the reaction mixture was quenched with saturated aqueous $NaHCO_3$ solution and extracted with DCM. The combined organic layers were washed with water and brine, dried over anhydrous $Na_2SO_4$, filtered and concentrated under reduced pressure to dryness to afford 1-benzyl-4-(2-(bromomethyl)phenyl)piperazine (A105.5) (3.5 g, crude). This compound was used in the next step without further purification. LCMS: 345.09 $[M+H]^+$.

Step-4. Procedure for the Synthesis of 4-((2-(4-benzylpiperazin-1-yl)benzyl)sulfonyl)-N,N-dimethylbenzenesulfonamide (A-406)

To a stirred solution of 1-benzyl-4-(2-(bromomethyl)phenyl)piperazine (A105.5) (3 g, 8.7 mmol, 1 eq) and sodium 4-(N,N-dimethylsulfamoyl)benzenesulfinate (A105.6) (2.35 g, 8.7 mmol, 1 eq) in DMF (60 mL) was added TBAI (0.32 g, 0.87 mmol, 0.1 eq) and the reaction mixture was stirred at 100° C. for 12 h. The progress of the reaction was monitored by TLC. After completion of the reaction, the reaction mixture was cooled to room temperature and diluted with ice-cold water. The resultant precipitate was filtered out, washed water and dried under reduced pressure. The crude product was purified by flash column chromatography on silica gel to afford 4-((2-(4-benzylpiperazin-1-yl)benzyl)sulfonyl)-N,N-dimethylbenzenesulfonamide (A-406). Yield: 1.5 g, 33%; Appearance: White solid; $^1H$ NMR (400 MHz, DMSO-$d_6$) δ 7.87 (d, J=8.0 Hz, 2H), 7.74 (d, J=8.4 Hz, 2H), 7.42 (d, J=7.6 Hz, 1H), 7.16-7.22 (m, 6H), 7.15 (t, J=7.6 Hz, 1H), 7.07 (d, J=8.0 Hz, 1H), 4.75 (s, 2H), 3.49 (s, 2H), 2.61 (s, 6H), 2.48-2.25 (m, 8H); HPLC purity: 99.67%; LCMS Calculated for $C_{26}H_{31}N_3O_4S_2$: 513.18; Observed: 514.30 $[M+H]^+$.

The following examples were prepared using standard chemical manipulations and procedures similar to those used for the preparation of the previous example.

| Compound No. | Structure | Yields/Analytical data |
|---|---|---|
| A-493 | 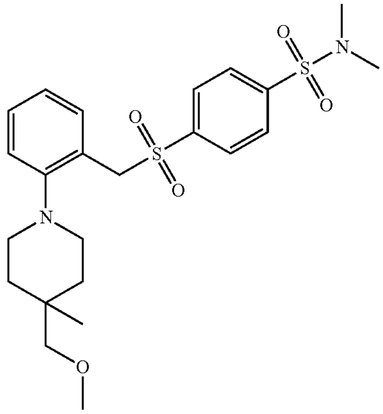 [SMILES: COCC1(C)CCN(c2ccccc2CS(=O)(=O)c2ccc(S(=O)(=O)N(C)C)cc2)CC1] | Yield: 600 mg, 39%; Appearance: Off white solid; $^1$H NMR (400 MHz, DMSO-$d_6$) δ 7.85 (d, J = 8.0 Hz, 2H), 7.73 (d, J = 8.0 Hz, 2H), 7.43 (d, J = 7.6 Hz, 1H), 7.30 (t, J = 6.8 Hz, 1H), 7.13 (t, J = 7.2 Hz, 1H), 7.08 (d, J = 8.0 Hz, 1H), 4.73 (s, 2H), 3.28 (s, 3H), 3.11 (s, 2H), 2.62 (s, 6H), 2.46-2.39 (m, 2H), 2.33-2.25 (m, 2H), 1.44-1.35 (m, 2H), 1.23-1.16 (m, 2H), 0.91 (s, 3H); HPLC purity: 99.95%; LCMS calculated for $C_{23}H_{32}N_2O_5S_2$: 480.18; Observed: 480.80 [M + H]$^+$. |
| A-598 | 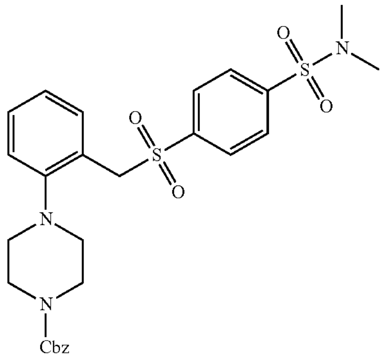 [SMILES: CN(C)S(=O)(=O)c1ccc(S(=O)(=O)Cc2ccccc2N2CCN(C(=O)OCc3ccccc3)CC2)cc1] | Appearance: White solid; $^1$H NMR (400 MHz, DMSO-$d_6$) δ 7.90 (d, J = 8.0 Hz, 2H), 7.83 (d, J = 8.0 Hz, 2H), 7.44 (d, J = 7.2 Hz, 1H), 7.42-7.30 (m, 6H), 7.21-7.16 (m, 1H), 7.10 (d, J = 7.6 Hz, 1H), 5.09 (s, 2H), 4.80 (s, 2H), 3.38 (bs, 4H), 2.63 (s, 6H), 2.43-2.37 (m, 4H); HPLC purity: 99.76%; LCMS calculated for $C_{27}H_{31}N_3O_6S_2$: 557.17; Observed: 558.10 [M + H]$^+$. |
| A-599 | 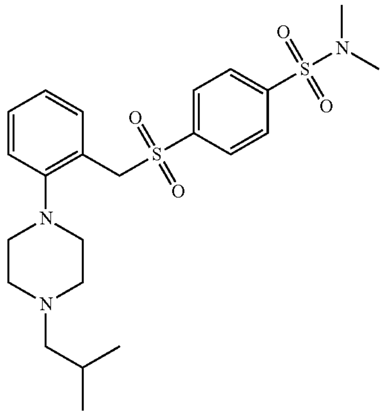 [SMILES: CC(C)CN1CCN(c2ccccc2CS(=O)(=O)c2ccc(S(=O)(=O)N(C)C)cc2)CC1] | Yield: 15 mg, 13%; Appearance: White solid; $^1$H NMR (400 MHz, DMSO-$d_6$) δ 7.87 (d, J = 8.4 Hz, 2H), 7.74 (d, J = 8.4 Hz, 2H), 7.43 (d, J = 8.4 Hz, 1H), 7.32 (t, J = 7.2 Hz, 1H), 7.16 (t, J = 7.2 Hz, 1H), 7.07 (d, J = 8.0 Hz, 1H), 4.75 (s, 2H), 2.63 (s, 6H), 2.47-2.39 (m, 4H), 2.36-2.20 (m, 4H), 2.06 (d, J = 7.2 Hz, 2H), 1.79-1.69 (m, 1H), 0.85 (d, J = 6.4 Hz, 6H); HPLC purity: 99.73%; LCMS calculated for $C_{23}H_{33}N_3O_4S_2$: 479.19; Observed: 480.25 [M + H]$^+$. |

Step-5. Procedure for the synthesis of 4-((1-(2-(4-benzylpiperazin-1-yl)phenyl)ethyl)sulfonyl)-N,N-dimethylbenzenesulfonamide (A-465)

To a stirred solution of 4-((2-(4-benzylpiperazin-1-yl)benzyl)sulfonyl)-N,N-dimethylbenzenesulfonamide (A-406) (300 mg, 0.58 mmol, 1 eq) in THF (10 mL) was added a 60% suspension of sodium hydride in mineral oil (210 mg, 1.75 mmol, 3 eq) at 0° C. and the reaction mixture was stirred at the same temperature for 30 min. Methyl iodide (0.072 mL, 1.16 mmol, 2 eq) was then added dropwise to the reaction mixture at 0° C. The reaction mixture was warmed to room temperature and stirred for overnight. The progress of the reaction was monitored by TLC. After completion of the reaction, the reaction mixture was quenched with saturated aqueous $NH_4Cl$ solution and extracted with ethyl acetate. The combined organic layers were washed with brine, dried over anhydrous $Na_2SO_4$, filtered and concentrated under reduced pressure. The crude product was purified by flash column chromatography on silica gel followed by reverse phase preparative HPLC to afford the titled compound (A-465). Yield: 30 mg, 10%; Appearance: Off white solid; $^1$H NMR (400 MHz, DMSO-$d_6$) δ 7.78 (d, J=8.4 Hz, 2H), 7.64 (d, J=8.0 Hz, 2H), 7.56 (d, J=7.6 Hz, 1H), 7.37-7.29 (m, 4H), 7.28-7.17 (m, 3H), 6.96 (d, J=8.4 Hz, 1H), 5.12 (q, J=7.6 Hz, 1H), 3.53 (q, J=12.8 Hz, 2H), 2.73-2.64 (m, 2H), 2.58 (s, 6H), 1.72 (d, J=7.2 Hz, 3H), (6H merged with the solvent/moisture peaks); HPLC purity: 99.58%; LCMS Calculated for $C_{27}H_{33}N_3O_4S_2$: 527.19; Observed: 528.25 [M+H]$^+$.

The following examples were prepared using standard chemical manipulations and procedures similar to those used for the preparation of the previous example.

| Compound No. | Structure | Yields/Analytical data |
|---|---|---|
| A-474 | 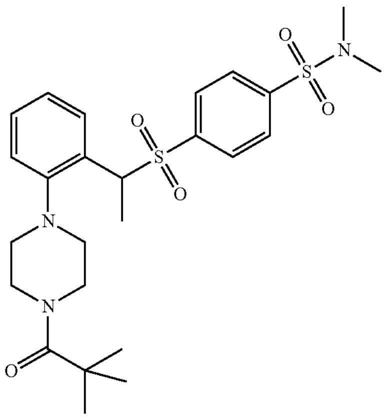 [SMILES: CC(c1ccccc1N1CCN(C(=O)C(C)(C)C)CC1)S(=O)(=O)c1ccc(S(=O)(=O)N(C)C)cc1] | Yield: 15 mg, 29%; Appearance: Off white solid; $^1$H NMR (400 MHz, DMSO-$d_6$) δ 7.83 (d, J = 8.4 Hz, 2H), 7.74 (d, J = 8.4 Hz, 2H), 7.58 (d, J = 7.2 Hz, 1H), 7.33-7.20 (m, 2H), 6.99 (d, J = 7.6 Hz, 1H), 5.22 (q, J = 6.8 Hz, 1H), 2.71-2.59 (m, 2H), 2.62 (s, 6H), 1.72 (d, J = 7.2 Hz, 3H), 1.20 (s, 9H), (6H merged with the solvent/moisture peaks); HPLC purity: 99.31%; LCMS Calculated for $C_{25}H_{35}N_3O_5S_2$: 521.20; Observed: 522.48 $[M + H]^+$. |
| A-491 | 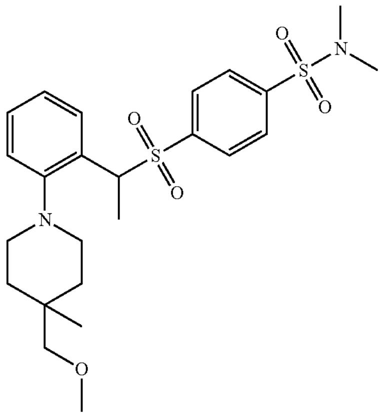 [SMILES: COCC1(C)CCN(c2ccccc2C(C)S(=O)(=O)c2ccc(S(=O)(=O)N(C)C)cc2)CC1] | Yield: 60 mg, 27%; Appearance: Off white solid; $^1$H NMR (400 MHz, DMSO-$d_6$) δ 7.76 (d, J = 7.2 Hz, 2H), 7.63 (d, J = 7.6 Hz, 2H), 7.56 (d, J = 6.8 Hz, 1H), 7.27 (t, J = 7.2 Hz, 1H), 7.18(t, J = 7.2 Hz, 1H), 6.98 (d, J = 7.6 Hz, 1H), 5.13-5.04 (m, 1H), 3.29 (s, 3H), 3.13 (bs, 2H), 2.60 (s, 6H), 1.73 (d, J = 6.8 Hz, 3H), 1.61-1.34 (m, 3H), 1.30-1.20 (m, 2H), 0.92 (s, 3H), (3H merged with the solvent peak); HPLC purity: 98.45%; LCMS calculated for $C_{24}H_{34}N_2O_5S_2$: 494.19; Observed: 496.39 $[M + H]^+$. |
| A-556 | 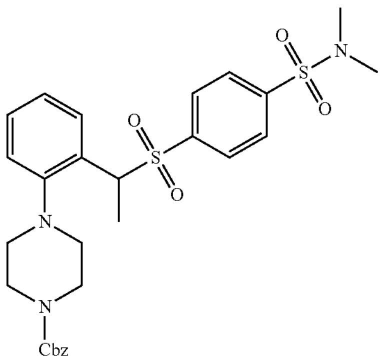 [SMILES: CC(c1ccccc1N1CCN(C(=O)OCc2ccccc2)CC1)S(=O)(=O)c1ccc(S(=O)(=O)N(C)C)cc1] | Yield: 80 mg, 19%; Appearance: White solid; $^1$H NMR (400 MHz, $CDCl_3$) δ 7.72 (d, J = 8.4 Hz, 2H), 7.69-7.63 (m, 3H), 7.42-7.27 (m, 6H), 7.25-7.20 (m, 1H), 6.89 (d, J = 8.0 Hz, 1H), 5.23 (q, J = 7.2 Hz, 1H), 5.15 (s, 2H), 4.09 (bs, 2H), 3.04 (bs, 2H), 2.85-2.40 (m, 4H), 2.69 (s, 6H), 1.80 (d, J = 7.6 Hz, 3H); HPLC purity: 99 81%; LCMS calculated for $C_{28}H_{33}N_3O_6S_2$: 571.18; Observed: 572.10 $[M + H]^+$. |

-continued

| Compound No. | Structure | Yields/Analytical data |
|---|---|---|
| A-604 | 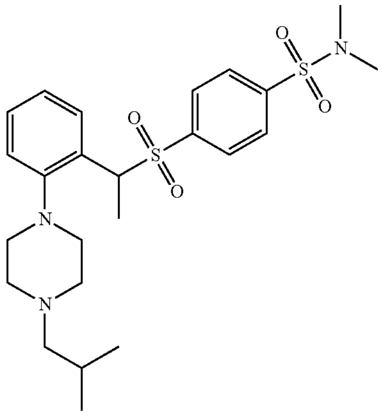 [SMILES: CC(C)CN1CCN(c2ccccc2C(C)S(=O)(=O)c2ccc(S(=O)(=O)N(C)C)cc2)CC1] | Yield: 25 mg, 16%; Appearance: White solid; $^1$H NMR (400 MHz, $DMSO_6$) δ 7.79 (d, J = 8.0 Hz, 2H), 7.63 (d, J = 8.4 Hz, 2H), 7.57 (d, J = 7.2 Hz, 1H), 7.28 (t, J = 7.2 Hz, 1H), 7.20 (t, J = 7.2 Hz, 1H), 6.96 (d, J = 8.0 Hz, 1H), 5.12 (q, J = 7.2 Hz, 1H), 2.72-2.63 (m, 2H), 2.60 (s, 6H), 2.40 (bs, 4H), 2.10 (d, J = 7.2 Hz, 2H), 1.80-1.70 (m, 1H), 1.73 (d, J = 7.2 Hz, 3H), 0.86 (d, J = 6.4 Hz, 6H), (2H merged with the solvent peak); HPLC purity: 97.70%; LCMS calculated for $C_{24}H_{35}N_3O_4S_2$: 493.21; Observed: 494.30 $[M + H]^+$. |
| A-603 | 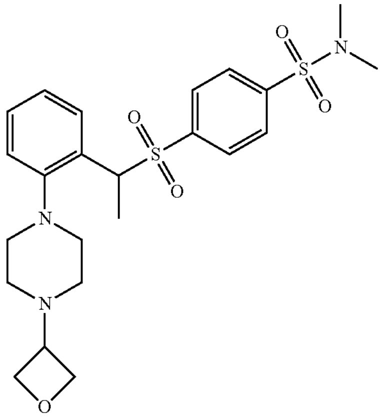 [SMILES: CC(c1ccccc1N1CCN(C2COC2)CC1)S(=O)(=O)c1ccc(S(=O)(=O)N(C)C)cc1] | Yield: 25 mg, 12%; Appearance: White solid; $^1$H NMR (400 MHz, $CDCl_3$) δ 7.71-7.61 (m, 5H), 7.32-7.27 (m, 1H), 7.22 (t, J = 7.6 Hz, 1H), 6.92 (d, J = 8.0 Hz, 1H), 5.19 (q, J = 7.6 Hz, 1H), 4.69 (q, J = 6.8 Hz, 2H), 4.60 (t, J = 5.6 Hz, 2H), 3.53 (quint, J = 5.6 Hz, 1H), 2.90-2.50 (m, 5H), 2.68 (s, 6H), 2.20 (bs, 3H), 1.83 (d, J = 7.2 Hz, 3H); HPLC purity: 99.89%; LCMS calculated for $C_{23}H_{31}N_3O_5S_2$: 493.17; Observed: 494.20 $[M + H]^+$. |
| A-737 | 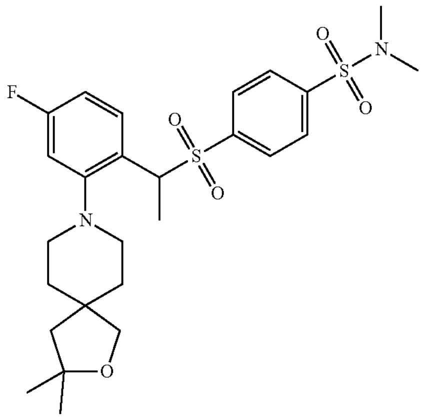 [SMILES: CC(c1ccc(F)cc1N1CCC2(CC1)COC(C)(C)C2)S(=O)(=O)c1ccc(S(=O)(=O)N(C)C)cc1] | Yield: 0.05 g, 16.12%; Appearance: White solid; $^1$H NMR (400 MHz, $DMSO_6$) δ 7.90 (q, J = 9.4 Hz, 4H), 7.19 (t, J = 8.8 Hz, 1H), 6.75 (d, J = 8.8 Hz, 1H), 6.51 (d, J = 14.4 Hz, 1H), 4.76 (q, J = 7.2 Hz, 1H), 3.55 (s, 2H), 3.18-3.13 (m, 4H), 2.60 (s, 6H), 1.61-1.56 (m, 9H), 1.19 (s, 6H); HPLC purity: 95.51%; LCMS calculated for $C_{26}H_{35}FN_2O_5S_2$: 538.20 Observed: 539.25 $[M + H]^+$. |

Example A106: Synthesis of 4-((3-(1-(2,6-difluorophenyl)piperidin-4-yl)-4,5,6,7-tetrahydro-1H-pyrazolo[4,3-b]pyridin-1-yl)sulfonyl)-N,N-dimethylbenzenesulfonamide (A-503)

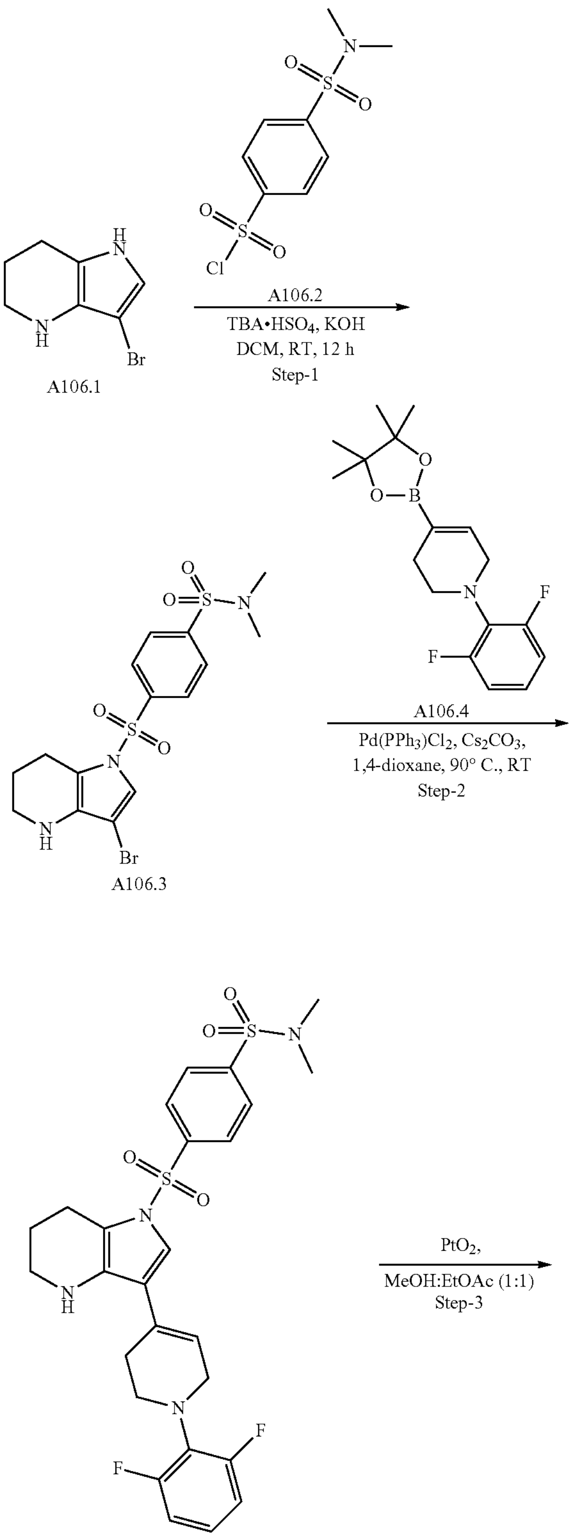

A106.1

A106.3

A106.5

-continued

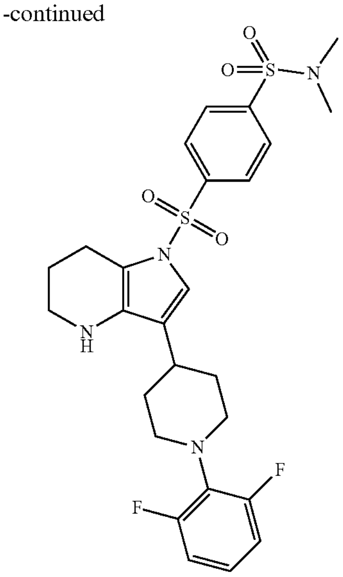

A-503

Step-1. Synthesis of 4-((3-bromo-4,5,6,7-tetrahydro-1H-pyrazolo[4,3-b]pyridin-1-yl)sulfonyl)-N,N-dimethylbenzenesulfonamide (A106.3)

To a stirred solution of 3-bromo-4,5,6,7-tetrahydro-1H-pyrazolo[4,3-b]pyridine (A106.1) (0.7 g, 3.48 mmol, 1 eq) in DCM (15 mL) was added $TBA.HSO_4$ (0.177 g, 0.522 mmol, 0.15 eq) and KOH (0.39 g, 6.96 mmol, 2 eq) followed by 4-(N,N-dimethylsulfamoyl)benzenesulfonyl chloride (A106.2) (1.08 g, 3.83 mmol, 1.1 eq). The reaction mixture was stirred at room temperature for 12 h. The progress of the reaction was monitored by TLC. After completion of reaction, the reaction mixture was diluted with water and extracted with ethyl acetate. The combined organic layer was washed with brine, dried over anhydrous $Na_2SO_4$, filtered and concentrated under reduced pressure to dryness. The crude product was purified by flash column chromatography on silica gel to afford 4-((3-bromo-4,5,6,7-tetrahydro-1H-pyrazolo[4,3-b]pyridin-1-yl)sulfonyl)-N,N-dimethylbenzenesulfonamide (A106.3) (0.5 g, 33%). LCMS: 451.0 (bromo pattern).

Step-2. Synthesis of 4-((3-(1-(2,6-difluorophenyl)-1,2,3,6-tetrahydropyridin-4-yl)-4,5,6,7-tetrahydro-1H-pyrazolo[4,3-b]pyridin-1-yl)sulfonyl)-N,N-dimethylbenzenesulfonamide (A106.5)

To a stirred solution of 4-((3-bromo-4,5,6,7-tetrahydro-1H-pyrazolo[4,3-b]pyridin-1-yl)sulfonyl)-N,N-dimethylbenzenesulfonamide (A106.3) (0.5 g, 1.12 mmol, 1 eq), 1-(2,6-difluorophenyl)-4-(4,4,5,5-tetramethyl-1,3,2-dioxaborolan-2-yl)-1,2,3,6-tetrahydropyridine (A106.4) (0.387 g, 1.17 mmol, 1.05 eq), in 1,4-Dioxane (10 mL) was added $Cs_2CO_3$ (2 M in $H_2O$, 1 mL, 2.008 mmol, 1.8 eq) and KOH (0.39 g, 6.96 mmol, 2 eq) followed by $Pd(PPh_3)_2C_{12}$ (1.08 g, 3.83 mmol, 1.1 eq), after degassing with argon for 20 minutes. The reaction mixture was stirred 90° C. for 12 h. The progress of the reaction was monitored by TLC. After completion of reaction, the reaction mixture was diluted with water and extracted with ethyl acetate. The combined organic layer was washed with brine, dried over anhydrous $Na_2SO_4$, filtered and concentrated under reduced pressure to dryness. The crude product was purified by flash column chromatography on silica gel to afford 4-((3-(1-(2,6-difluorophenyl)-1,2,3,6-tetrahydropyridin-4-yl)-4,5,6,7-tetrahydro-1H-pyrazolo[4,3-b]pyridin-1-yl)sulfonyl)-N,N-dimethylbenzenesulfonamide (A106.5) (0.3 g, 48%).

Step-3. Synthesis of 4-((3-(1-(2,6-difluorophenyl)piperidin-4-yl)-4,5,6,7-tetrahydro-1H-pyrazolo[4,3-b]pyridin-1-yl)sulfonyl)-N,N-dimethylbenzenesulfonamide (A-503)

To a stirred solution of 4-((3-(1-(2,6-difluorophenyl)-1,2,3,6-tetrahydropyridin-4-yl)-4,5,6,7-tetrahydro-1H-pyrazolo[4,3-b]pyridin-1-yl)sulfonyl)-N,N-dimethylbenzenesulfonamide (A106.5) (0.2 g, 0.355 mmol, 1 eq) in MeOH:EtOAc (1:1, 10 mL) was added $PtO_2$ (0.1 g) under N2 atmosphere. The reaction mixture was hydrogenated (100 psi) at room temperature for 12 h. The progress of the reaction was monitored by TLC. After completion of reaction, the reaction mixture was filtered through celite and the celite bed was washed with EtOAc. The filtrate was concentrated under reduced pressure to dryness. The crude product was purified by prep-HPLC to afford 4-((3-(1-(2,6-difluorophenyl)piperidin-4-yl)-4,5,6,7-tetrahydro-1H-pyrazolo[4,3-b]pyridin-1-yl)sulfonyl)-N,N-dimethylbenzenesulfonamide (A-503). Yield: 0.04 g, 20%; Appearance: White solid; $^1H$ NMR (400 MHz, DMSO-$d_6$) δ 8.03-8.01 (m, 2H), 7.95-7.93 (m, 2H), 7.04-7.01 (m, 3H), 4.85 (s, 1H), 3.18-3.15 (m, 2H), 3.04-2.98 (m, 4H), 2.87-2.84 (m, 2H), 2.61 (s, 7H), 1.79-1.75 (m, 4H), 1.65-1.53 (m, 2H); HPLC purity: 99.26%; LCMS Calculated for $C_{25}H_{29}F_2N_5O_4S_2$: 565.65; Observed: 566.20 $[M+H]^+$.

The following examples were prepared using standard chemical manipulations and procedures similar to those used for the preparation of the previous example.

| Compound No. | Structure | Yields/Analytical data |
|---|---|---|
| A-504 | 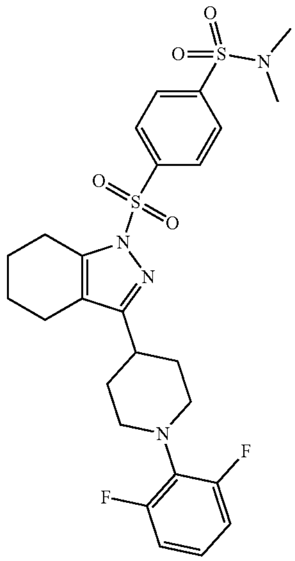 [SMILES: CN(C)S(=O)(=O)c1ccc(S(=O)(=O)n2nc(C3CCN(c4c(F)cccc4F)CC3)c3c2CCCC3)cc1] | Yield: 0.004 g, 3%; Appearance: White solid; (400 MHz, CHLOROFORM-d) δ 1.78-1.91 (m, 4 H) 1.94-2.09 (m, 2 H) 2.41-2.50 (m, 2 H) 2.66-2.72 (m, 1H) 2.77 (s, 6 H) 2.92 (br t, J = 5.62 Hz, 2 H) 3.20 (br t, J = 11.49 Hz, 2 H) 3.30-3.41 (m, 2 H) 6.81-6.89 (m, 2 H) 6.92-7.01 (m, 1 H) 7.92 (d, J = 8.31 Hz, 2 H) 8.13 (d, J = 8.80 Hz, 2 H). 2H's are merged in to solvent peak; HPLC purity: 99%; LCMS Calculated for $C_{26}H_{30}F_2N_4O_4S_2$: 564.67; Observed: 565.20 $[M + H]^+$. |
| A-533 | 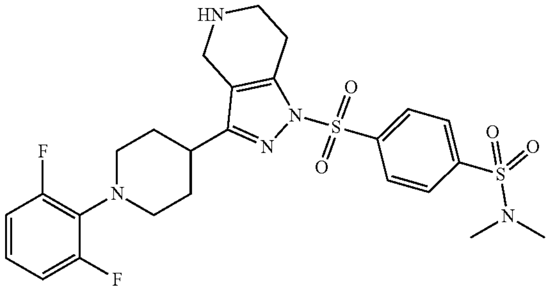 [SMILES: CN(C)S(=O)(=O)c1ccc(S(=O)(=O)n2nc(C3CCN(c4c(F)cccc4F)CC3)c3c2CCNC3)cc1] | Yield: 0.02 g, 12%; Appearance: Off white solid; $^1H$ NMR (400 MHz, DMSO-$d_6$) 1.63-1.72 (m, 2H) 1.73-1 83 (m, 2H) 2.64 (s, 6H) 2.65-2.77 (m, 1H) 2.81-2.88 (m, 2H) 2.90-2.98 (m, 2H) 3.03-3.13 (m, 2H) 3.14-3.23 (m, 2H) 3.62-3.68 (m, 2H) 6.97-7.12 (m, 4H) 8.00 (d, J = 8.31 Hz, 2 H) 8.14 (d, J = 8.31 Hz, 2 H); HPLC purity: 97%; LCMS Calculated for $C_{25}H_{29}F_2N_5O_4S_2$: 565.65; Observed: 566.4 $[M + H]^+$. |

Example A107: Synthesis of N,N-dimethyl-4-(2,2,2-trifluoro-1-((2-(4-(methoxymethyl)-4-methylpiperidin-1-yl)phenyl)amino)ethyl)benzenesulfonamide (A-684)

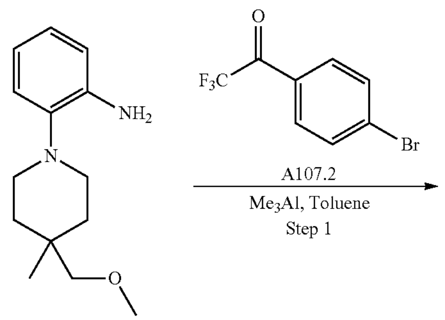

A107.1

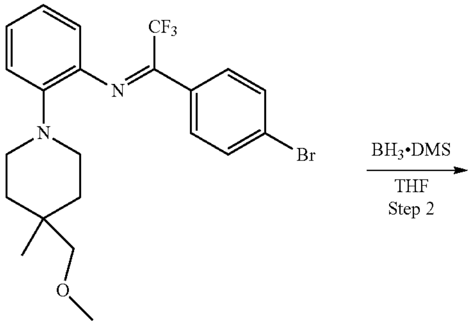

A107.3

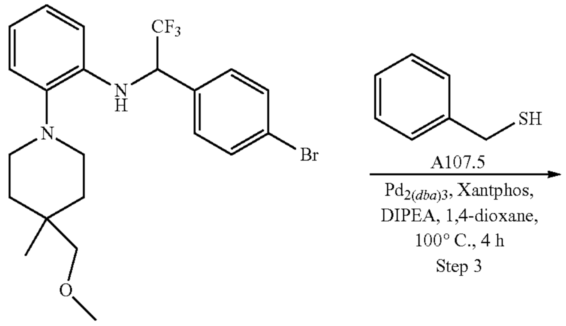

A107.4

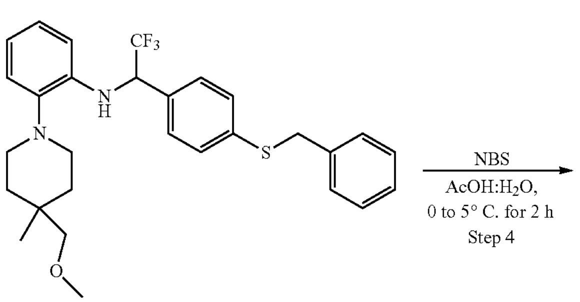

A107.6

-continued

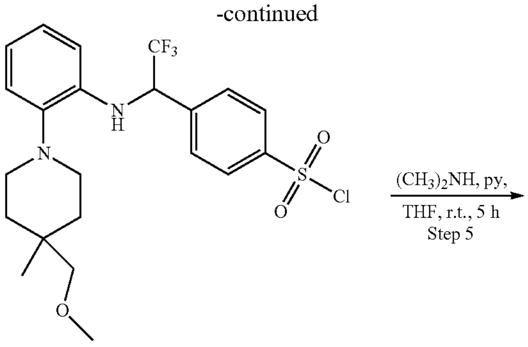

A107.7

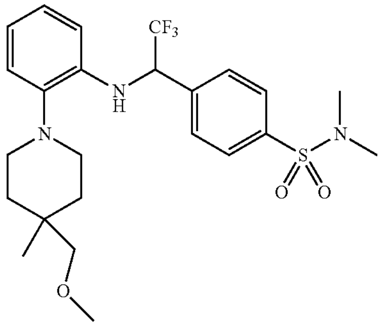

A-684

Step-1. Synthesis of (Z)-1-(4-bromophenyl)-2,2,2-trifluoro-N-(2-(4-(methoxymethyl)-4-methylpiperidin-1-yl)phenyl)ethan-1-imine (A107.3)

To a stirred solution of 2-(4-(methoxymethyl)-4-methylpiperidin-1-yl)aniline (A107.1) (0.5 g, 2.134 mmol, 1 eq) in dry toluene (5 mL) was added trimethylaluminium (4.2 mL, 8.54 mmol, 4 eq) under argon atmosphere at 0° C. and stirred for 15 minutes at the same temperature. To the resultant reaction mixture was added a solution of 1-(4-bromophenyl)-2,2,2-trifluoroethan-1-one (A107.2) (0.65 g, 2.56 mmol, 1.2 eq) in toluene and stirred at 90° C. for 12 h in a sealed tube. After completion of the reaction, the reaction mixture was quenched with ice cold water, basified with saturated $NaHCO_3$ solution and extracted with ethyl acetate (2×25 mL). The combined organic layers were dried over anhydrous $Na_2SO_4$, filtered and concentrated under reduced pressure to dryness. The crude product was purified by column chromatography on silica gel using (EtOAc/n-Hexane: 2-5%) as eluent to afford (Z)-1-(4-bromophenyl)-2,2,2-trifluoro-N-(2-(4-(methoxymethyl)-4-methylpiperidin-1-yl)phenyl)ethan-1-imine (A107.3) (0.5 g, 50%) as a yellow semisolid. LCMS: 470.95 $[M+H]^+$.

Step-2. Synthesis of N-(1-(4-bromophenyl)-2,2,2-trifluoroethyl)-2-(4-(methoxymethyl)-4-methylpiperidin-1-yl)aniline (A107.4)

To a stirred solution of (Z)-1-(4-bromophenyl)-2,2,2-trifluoro-N-(2-(4-(methoxymethyl)-4-methylpiperidin-1-yl)

phenyl)ethan-1-imine (A107.3) (0.5 g, 1.065 mmol, 1 eq) in THF (10 mL) was added Borane.DMS, 1 M solution in THE (2.1 mL, 4.26 mmol, 4 eq). The reaction mixture was stirred at reflux temperature for 5 h. The progress of the reaction was monitored by TLC. After completion of the reaction, the reaction mixture was slowly quenched with MeOH, concentrated under reduced pressure, diluted with water and extracted with ethyl acetate. The combined organic layers were dried over anhydrous $Na_2SO_4$, filtered and concentrated under reduced pressure to dryness to afford N-(1-(4-bromophenyl)-2,2,2-trifluoroethyl)-2-(4-(methoxymethyl)-4-methylpiperidin-1-yl)aniline (A107.4) (0.45 g, 89.6%). This compound was used in the next step without further purification. LCMS: 472.95 $[M+H]^+$.

Step-3. Synthesis of N-(1-(4-benzylthio)phenyl)-2,2,2-trifluoroethyl)-2-(4-(methoxymethyl)-4-methylpiperidin-1-yl)aniline (A107.6)

To a stirred solution of N-(1-(4-bromophenyl)-2,2,2-trifluoroethyl)-2-(4-(methoxymethyl)-4-methylpiperidin-1-yl) aniline (A107.4) (0.45 g, 0.954 mmol, 1 eq), benzyl mercaptan (A107.5) (0.166 g, 1.336 mmol, 1.4 eq) and DIPEA (0.44 mL, 2.38 mmol, 2.5 eq) in 1,4-Dioxane (10 mL) were added $Pd_2(dba)_3$ (0.026 g, 0.029 mmol, 0.03 eq) and xantphos (0.039 g, 0.067 mmol, 0.07 eq) and the mixture was degassed for 15 minutes using argon. The resulting reaction mixture was stirred at 100° C. for 15 h. The progress of the reaction was monitored by TLC. After completion of the reaction, the reaction mixture was diluted with water and extracted with ethyl acetate. The combined organic layers were dried over anhydrous $Na_2SO_4$, filtered and concentrated under reduced pressure to dryness. The crude product was purified by combiflash using (EtOAc/n-hexane: 1-5%) as eluent to afford N-(1-(4-benzylthio)phenyl)-2,2,2-trifluoroethyl)-2-(4-(methoxymethyl)-4-methylpiperidin-1-yl)aniline (A107.6) (0.5 g, crude) as a yellow oil. LCMS: 515.1 $[M+H]^+$.

Step-4. Synthesis of 4-(2,2,2-trifluoro-1-((2-(4-(methoxymethyl)-4-methylpiperidin-1-yl)phenyl) amino)ethyl)benzenesulfonyl chloride (A107.7)

To a stirred solution of N-(1-(4-benzylthio)phenyl)-2,2,2-trifluoroethyl)-2-(4-(methoxymethyl)-4-methylpiperidin-1-yl)aniline (A107.6) (0.5 g, 0.97 mmol, 1 eq) in AcOH:$H_2O$ (1:1, 10 mL) was added NBS (0.35 g, 1.95 mmol, 2 eq) and stirred at 0° C. for 1 h. To the resultant reaction mixture was added NBS (0.35 g, 1.95 mmol, 2 eq) again and stirred at 0° C. for 1 h. After completion of the reaction, the reaction mixture was concentrated under reduced pressure, diluted with $H_2O$, basified with saturated solution of $NaHCO_3$, extracted with ethyl acetate. The combined organic layers were dried over anhydrous $Na_2SO_4$, filtered and concentrated under reduced pressure to dryness to afford 4-(2,2,2-trifluoro-1-((2-(4-(methoxymethyl)-4-methylpiperidin-1-yl) phenyl)amino)ethyl)benzenesulfonyl chloride (A107.7) (0.4 g, crude) as yellow semisolid. This compound was used in the next step without further purification.

Step-5. Synthesis of N,N-dimethyl-4-(2,2,2-trifluoro-1-((2-(4-(methoxymethyl)-4-methylpiperidin-1-yl)phenyl)amino)ethyl)benzenesulfonamide (A-684)

To a stirred solution of 4-(2,2,2-trifluoro-1-((2-(4-(methoxymethyl)-4-methylpiperidin-1-yl)phenyl)amino) ethyl)benzenesulfonyl chloride (A107.7) (0.4 mg, 0.81 mmol, 1 eq) in THE (5 mL), pyridine (0.128 g, 1.628 mmol, 2 eq) followed dimethylamine in THE (2 M, 200 mg, 0.74 mmol, 1 eq) were added at 0° C. and the reaction mixture was stirred at room temperature for 5 h. The progress of the reaction was monitored by TLC. After completion of reaction, the reaction mixture was diluted with water (20 mL) and extracted with ethyl acetate (2×20 mL). The combined organic layers were washed with water and brine, dried over anhydrous $Na_2SO_4$, filtered and concentrated under reduced pressure. The crude product was purified by column chromatography on silica gel using (EtOAc/n-hexane: 20-30%) as eluent followed by recrystallization with MeOH and dried to afford N,N-dimethyl-4-(2,2,2-trifluoro-1-((2-(4-(methoxymethyl)-4-methylpiperidin-1-yl)phenyl)amino) ethyl)benzenesulfonamide (A-684). Yield: 29 mg, 7.9%; Appearance: White solid; $^1H$ NMR (400 MHz, DMSO-$d_6$) δ 7.83-7.77 (m, 4H), 7.12 (d, J=7.2 Hz, 1H), 6.92-6.88 (m, 1H), 6.80-6.78 (m, 1H), 6.71 (t, J=7.4 Hz, 1H), 5.85-5.83 (m, 1H), 5.78-5.76 (m, 1H), 3.29 (s, 3H), 3.18 (s, 2H), 2.82-2.80 (s, 2H), 2.66-2.63 (m, 2H), 2.60 (s, 6H), 1.66-1.61 (m, 2H), 1.43 (bs, 2H), 1.00 (s, 3H); HPLC purity: 99.78%; LCMS calculated for $C_{24}H_{32}F_3N_3O_3S$: 499.59; Observed: 500.1 $[M+H]^+$.

Example A108: Syntheses of N1-(2-(4-(2-hydroxy-propan-2-yl)-4-methylpiperidin-1-yl)phenyl)-N4,N4-dimethylbenzene-1,4-disulfonamide (A-522), N1-(2-(4-(1-hydroxycyclopropyl)-4-methylpiperidin-1-yl)phenyl)-N4,N4-dimethylbenzene-1,4-disulfonamide (A-558), and N1-(2-(4-(1-hydroxyethyl)-4-methylpiperidin-1-yl)phenyl)-N4,N4-dimethylbenzene-1,4-disulfonamide (A-557)
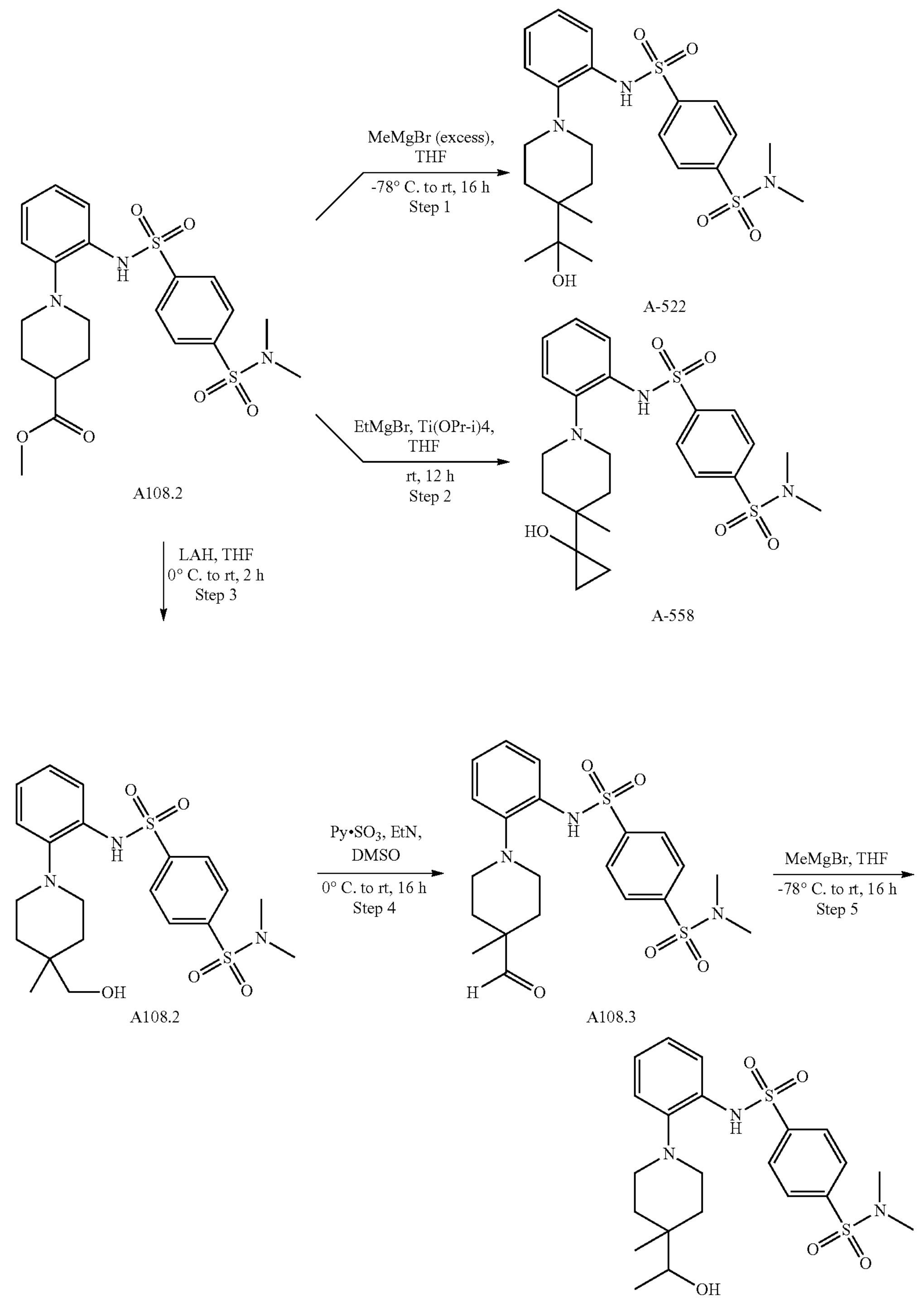
A108.2
A-522
A-558
A108.2
A108.3
A-557

Step-1. Synthesis of N1-(2-(4-(2-hydroxypropan-2-yl)-4-methylpiperidin-1-yl)phenyl)-N4,N4-dimethylbenzene-1,4-disulfonamide (A-522)

To a stirred solution of methyl 1-(2-((4-(N,N-dimethylsulfamoyl)phenyl)sulfonamido)phenyl)-4-methylpiperidine-4-carboxylate (A108.1) (100 mg, 0.2 mmol, 1 eq) in THE (5 mL) was added a 1.4 M solution of methylmagnesium bromide solution in THE (1.44 mL, 2 mmol, 10 eq) at −78° C. The reaction mixture was warmed to room temperature and stirred for 16 h. The progress of the reaction was monitored by TLC. After completion of the reaction, the reaction mixture was quenched with cold water. The resultant solid was filtered out and dried under reduced pressure. The crude product was purified by reverse phase preparative HPLC to afford N1-(2-(4-(2-hydroxypropan-2-yl)-4-methylpiperidin-1-yl)phenyl)-N4,N4-dimethylbenzene-1,4-disulfonamide (A-522). Yield: 35 mg, 35%; Appearance: White solid; $^{1}H$ NMR (400 MHz, DMSO-$d_6$) δ 9.02 (br s, 1H), 7.98 (d, J=8.8 Hz, 2H), 7.90 (d, J=8.4 Hz, 2H), 7.25 (d, J=6.8 Hz, 1H), 7.19 (d, J=7.6 Hz, 1H), 7.10 (t, J=7.2 Hz, 1H), 7.03 (t, J=7.6 Hz, 1H), 4.06 (s, 1H), 2.67-2.56 (m, 2H), 2.60 (s, 6H), 2.40-2.32 (m, 2H), 1.90-1.80 (m, 2H), 1.15-1.05 (m, 2H), 1.07 (s, 6H), 0.88 (s, 3H); HPLC purity: 99.68%; LCMS calculated for $C_{23}H_{33}N_3O_5S_2$: 495.19; Observed: 496.40 $[M+H]^+$.

Step-2. Synthesis of N1-(2-(4-(1-hydroxycyclopropyl)-4-methylpiperidin-1-yl)phenyl)-N4,N4-dimethylbenzene-1,4-disulfonamide (A-558)

To a stirred solution of methyl 1-(2-((4-(N,N-dimethylsulfamoyl)phenyl)sulfonamido)phenyl)-4-methylpiperidine-4-carboxylate (A108.1) (200 mg, 0.4 mmol, 1 eq) in THE (15 mL) was added titanium tetraisopropoxide (0.735 mL, 2.4 mmol, 6 eq) and the reaction mixture was stirred at room temperature for 5 min. To the resulting reaction mixture, a 3 M solution of ethylmagnesium bromide solution in THF (0.404 mL, 1.2 mmol, 3 eq) was added at room temperature and stirred for 12 h. The progress of the reaction was monitored by TLC. After completion of the reaction, the reaction mixture was quenched with 1N aqueous HCl and extracted with ethyl acetate. The combined organic layers were washed with water and brine, dried over anhydrous $Na_2SO_4$, filtered and concentrated under reduced pressure. The crude product was purified by Combiflash chromatography on silica gel to afford N1-(2-(4-(1-hydroxycyclopropyl)-4-methylpiperidin-1-yl)phenyl)-N4,N4-dimethylbenzene-1,4-disulfonamide (A-558). Yield: 20 mg, 10%; Appearance: White solid; $^{1}H$ NMR (400 MHz, DMSO-$d_6$) δ 9.10 (br s, 1H), 8.00 (d, J=7.6 Hz, 2H), 7.91 (d, J=8.4 Hz, 2H), 7.26 (d, J=7.6 Hz, 1H), 7.20 (d, J=7.6 Hz, 1H), 7.11 (t, J=8.0 Hz, 1H), 7.04 (t, J=7.2 Hz, 1H), 4.95 (s, 1H), 2.67-2.59 (m, 2H), 2.61 (s, 6H), 2.37 (d, J=11.2 Hz, 2H), 1.60-1.50 (m, 2H), 1.18 (d, J=12.8 Hz, 2H), 0.96 (s, 3H), 0.63-0.59 (m, 2H), 0.47-0.42 (m, 2H); HPLC purity: 99.71%; LCMS calculated for $C_{23}H_{31}N_3O_5S_2$: 493.17; Observed: 492.20 $[M+H]^+$.

Step-3. Synthesis of N1-(2-(4-(hydroxymethyl)-4-methylpiperidin-1-yl)phenyl)-N4,N4-dimethylbenzene-1,4-disulfonamide (A108.2)

To a stirred solution of compound 1-(2-((4-(N,N-dimethylsulfamoyl)phenyl)sulfonamido)phenyl)-4-methylpiperidine-4-carboxylate (A108.1) (800 mg, 1.61 mmol, 1 eq) in THE (10 mL) was added a 2 M solution of lithium aluminium hydride (0.88 mL, 1.77 mmol, 1.1 eq) at 0° C. The reaction mixture was warmed to room temperature and stirred for 2 h. The progress of the reaction was monitored by TLC. After completion of reaction, the reaction mixture was quenched with saturated aqueous $Na_2SO_4$ solution, filtered through a pad of Celite and the Celite pad was washed with ethyl acetate. The filtrate was concentrated under reduced pressure. The crude product was purified by combiflash chromatography on silica gel to afford N1-(2-(4-(hydroxymethyl)-4-methylpiperidin-1-yl)phenyl)-N4, N4-dimethylbenzene-1,4-disulfonamide (A108.2) (750 mg, 88.3%). LCMS: 468.15 $[M+H]^+$.

Step-4. Synthesis of N1-(2-(4-formyl-4-methylpiperidin-1-yl)phenyl)-N4,N4-dimethylbenzene-1,4-disulfonamide (A108.3)

To a stirred solution of N1-(2-(4-(hydroxymethyl)-4-methylpiperidin-1-yl)phenyl)-N4,N4-dimethylbenzene-1,4-disulfonamide (A108.2) (750 mg, 1.6 mmol, 1 eq) in DMSO (5 mL), pyridine sulfur trioxide (1.27 g, 8 mmol, 5 eq) and triethyl amine (1.21 mL, 8 mmol, 5 eq) at 0° C. The reaction mixture was warmed to room temperature and stirred for 16 h. The progress of the reaction was monitored by TLC. After completion of reaction, the reaction mixture was quenched with water and extracted with ethyl acetate. The combined organic layers were washed with water and brine, dried over anhydrous $Na_2SO_4$, filtered and concentrated under reduced pressure. The crude product was purified by combiflash chromatography on silica gel to afford N1-(2-(4-formyl-4-methylpiperidin-1-yl)phenyl)-N4,N4-dimethylbenzene-1,4-disulfonamide (A108.3) (600 mg, 80.3%). LCMS: 466.14 $[M+H]^+$.

Step-5. Synthesis of NJ-(2-(4-(1-hydroxyethyl)-4-methylpiperidin-1-yl)phenyl)-N4,N4-dimethylbenzene-1,4-disulfonamide (A-557)

To a stirred solution of compound (A108.3) (200 mg, 0.429 mmol, 1 eq) in THE (2 mL) was added a 1.4 M solution of methyl magnesium bromide solution in THF (0.46 mL, 0.64 mmol, 1.5 eq) at −78° C. The reaction mixture was warmed to room temperature and stirred for 16 h. The progress of the reaction was monitored by TLC. After completion of reaction, the reaction mixture was quenched with saturated aqueous $NH_4Cl$ solution and extracted with ethyl acetate. The combined organic layers were washed with brine, dried over anhydrous $Na_2SO_4$, filtered and concentrated under reduced pressure. The crude product was purified by reverse phase preparative HPLC to afford the titled compound (A-557). Yield: 30 mg, 14.6%; Appearance: Off white solid; 1H NMR (400 MHz, DMSO-$d_6$) δ 9.07 (bs, 1H), 8.00 (d, J=8.4 Hz, 2H), 7.91 (d, J=8.8 Hz, 2H), 7.25 (d, J=8.0 Hz, 1H), 7.18 (d, J=7.2 Hz, 1H), 7.10 (t, J=8.0 Hz, 1H), 7.04 (t, J=7.6 Hz, 1H), 4.35 (d, J=5.2 Hz, 1H), 2.61 (s, 6H), 2.60-2.50 (m, 2H), 2.46-2.35 (m, 2H), 1.60-1.48 (m, 2H), 1.35 (d, J=12.4 Hz, 1H), 1.10 (d, J=13.2 Hz, 1H), 0.99 (d, J=6.4 Hz, 3H), 0.81 (s, 3H), (1H merged with the moisture peak); HPLC purity: 98.93%; LCMS calculated for $C_{22}H_{31}N_3O_5S_2$: 481.17; Observed: 482.40 $[M+H]^+$.

Example A109: Synthesis of 4-((1-(2-(4-((4,4-difluoropiperidin-1-yl)methyl)piperidin-1-yl)-3-fluorophenyl)ethyl)sulfonyl)-N,N-dimethylbenzenesulfonamide (A-801, A-803 & A-804)

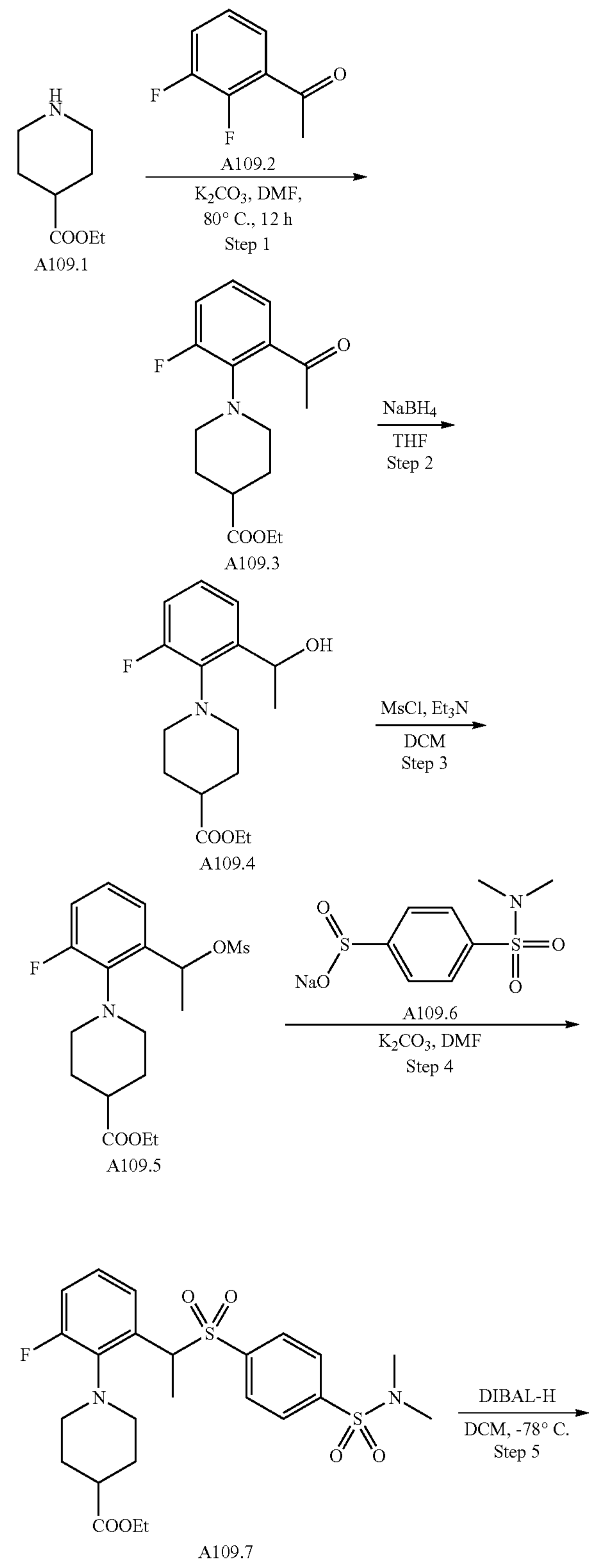

A109.1, A109.2, A109.3, A109.4, A109.5, A109.6, A109.7

-continued

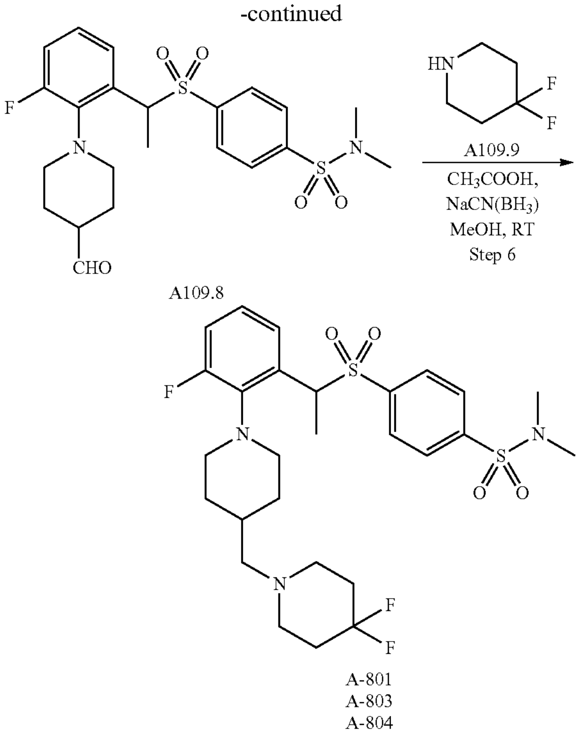

A109.8, A109.9

A-801
A-803
A-804

Step-1. Synthesis of ethyl 1-(2-acetyl-6-fluorophenyl)piperidine-4-carboxylate (A109.3)

To a stirred solution of ethyl piperidine-4-carboxylate (A109.1) (0.6 g, 3.84 mmol, 1.2 eq) and 1-(2,3-difluorophenyl)ethan-1-one (A109.2) (0.5 g, 3.2 mmol, 1 eq) in DMF (15 mL) was added potassium carbonate (0.88 g, 6.41 mmol, 2 eq) at room temperature and the reaction mixture was stirred at 80° C. for 12 h. The progress of the reaction was monitored by TLC. After completion of the reaction, the reaction mixture was cooled to room temperature, diluted with cold water and extracted with ethyl acetate. The combined organic layers were washed with cold water and brine, dried over anhydrous $Na_2SO_4$, filtered and concentrated under reduced pressure. The crude product was purified by column chromatography on silica gel to afford ethyl 1-(2-acetyl-6-fluorophenyl)piperidine-4-carboxylate (A109.3) (0.6 g, 53.5%) as colorless oil. LCMS: 294.2 $[M+H]^+$.

Step-2. Synthesis of ethyl 1-(2-fluoro-6-(1-hydroxyethyl)phenyl)piperidine-4-carboxylate (A109.4)

To a stirred solution of ethyl 1-(2-acetyl-6-fluorophenyl) piperidine-4-carboxylate (A109.3) (0.6 g, 2.04 mmol, 1 eq) in THF (25 mL) was added sodium borohydride (0.077 g, 2.04 mmol, 1 eq) in portions at 0° C. The reaction mixture was warmed to room temperature and stirred for 8 h. The progress of the reaction was monitored by TLC. After completion of the reaction, the reaction mixture was quenched with ice water and extracted with ethyl acetate. The combined organic layers were washed with water and brine, dried over anhydrous $Na_2SO_4$, filtered and concentrated under reduced pressure. The crude product was purified by combiflash chromatography to afford ethyl 1-(2-fluoro-6-(1-hydroxyethyl)phenyl)piperidine-4-carboxylate (A109.4) (0.5 g, 83.3%) as a thick liquid. LCMS: 295.65 $[M+H]^+$.

Step-3. Synthesis of ethyl 1-(2-fluoro-6-(1-((methylsulfonyl)oxy)ethyl)phenyl)piperidine-4-carboxylate (A109.5)

To a stirred solution of ethyl 1-(2-fluoro-6-(1-hydroxyethyl)phenyl)piperidine-4-carboxylate (A109.4) (0.5 g, 1.69 mmol, 1 eq) in DCM (15 mL), triethyl amine (0.46 mL, 3.38 mmol, 2 eq) and methanesulfonyl chloride (0.16 mL, 2.03 mmol, 1.2 eq) were added at 0° C. and the reaction mixture was stirred at same temperature for 3 h. The progress of the reaction was monitored by TLC. After completion of reaction, the reaction mixture was diluted with water and extracted with dichloromethane. The combined organic layers were washed with saturated solution of $NaHCO_3$, separated, dried over anhydrous $Na_2SO_4$, filtered and concentrated under reduced pressure to dryness to afford ethyl 1-(2-fluoro-6-(1-((methylsulfonyl)oxy)ethyl)phenyl)piperidine-4-carboxylate (A109.5) (0.5 g, crude) as a yellow oil. This compound was used in the next step without further purification. LCMS: No ionization.

Step-4. Synthesis of ethyl 1-(2-(1-((4-(N,N-dimethylsulfamoyl)phenyl)sulfonyl)ethyl)-6-fluorophenyl) piperidine-4-carboxylate (A109.7)

To a stirred solution of ethyl 1-(2-fluoro-6-(1-((methylsulfonyl)oxy)ethyl)phenyl)piperidine-4-carboxylate (A109.5) (0.5 g, 1.34 mmol, 1 eq) and sodium 4-(N,N-dimethylsulfamoyl)benzenesulfinate (A109.6) (0.36 g, 1.34 mmol, 1 eq) in DMF (25 mL) was added potassium carbonate (0.36 g, 2.68 mmol, 2 eq) at room temperature and the reaction mixture was stirred at 50° C. for 8 h. The progress of the reaction was monitored by TLC. After completion of the reaction, the reaction mixture was cooled to room temperature, diluted with cold water and extracted with ethyl acetate. The combined organic layers were washed with cold water and brine, dried over anhydrous $Na_2SO_4$, filtered and concentrated under reduced pressure. The crude product was purified by combiflash chromatography to afford ethyl 1-(2-(1-((4-(N,N-dimethylsulfamoyl)phenyl) sulfonyl)ethyl)-6-fluorophenyl)piperidine-4-carboxylate (A109.7) (0.28 g, 40%) as an off-white solid. LCMS: 527.33 $[M+H]^+$.

Step-5. Synthesis of 4-((1-(3-fluoro-2-(4-formylpiperidin-1-yl)phenyl)ethyl)sulfonyl)-N,N-dimethylbenzenesulfonamide (A109.8)

To a stirred solution of ethyl 1-(2-(1-((4-(N,N-dimethylsulfamoyl)phenyl)sulfonyl)ethyl)-6-fluorophenyl)piperidine-4-carboxylate (A109.7) (0.28 g, 0.53 mmol, 1 eq) in DCM (15 mL), was added DIBAL (0.22 g, 1.59 mmol, 3 eq) at −78° C. The reaction mixture was stirred at same temperature for 2 h. After completion of the reaction, the reaction mixture was quenched with 1N HCl and extracted with dichloromethane. The combined organic layers were washed with brine, separated, dried over anhydrous $Na_2SO_4$, filtered and concentrated under reduced pressure. The crude product was purified by combiflash chromatography to afford 4-((1-(3-fluoro-2-(4-formylpiperidin-1-yl)phenyl) ethyl)sulfonyl)-N,N-dimethylbenzenesulfonamide (A109.8) (0.2 g, 91%) as an off-white solid. LCMS: 483.18 $[M+H]^+$.

Step-6. Synthesis of 4-((1-(2-(4-((4,4-difluoropiperidin-1-yl)methyl)piperidin-1-yl)-3-fluorophenyl) ethyl)sulfonyl)-N,N-dimethylbenzenesulfonamide (A-801, A-803 & A-804)

To a stirred solution of 4-((1-(3-fluoro-2-(4-formylpiperidin-1-yl)phenyl)ethyl)sulfonyl)-N,N-dimethylbenzenesulfonamide (A109.8) (0.2 g, 0.41 mmol, 1 eq) in MeOH (10 mL) was added 4,4-difluoropiperidine (A109.9) (0.05 g, 0.41 mmol, 1 eq) and the reaction mixture was stirred at room temperature for 30 min. Sodium cyanoborohydride (0.052 g, 0.82 mmol, 2 eq) was added at 0° C. and the reaction mixture was stirred at room temperature for 2 h. The progress of the reaction was monitored by TLC. After completion of reaction, the reaction mixture was quenched with water and extracted with ethyl acetate. The combined organic layers were dried over anhydrous $Na_2SO_4$, filtered and concentrated under reduced pressure to dryness. The crude product was purified by combiflash chromatography, followed by reverse phase preparative HPLC to afford 4-((1-(2-(4-((4,4-difluoropiperidin-1-yl)methyl)piperidin-1-yl)-3-fluorophenyl)ethyl)sulfonyl)-N,N-dimethylbenzenesulfonamide (A-801) (350 mg). The compound A-801 (329 mg) was given for chiral separation to afford titled compounds A-803 and A-804.

A-801: Yield: 0.35 g, 73%; Appearance: Off-white solid; $^1H$ NMR (400 MHz, $DMSO_6$) δ 7.90 (d, J=8 Hz, 2H), 7.78 (d, J=8.4 Hz, 2H), 7.44-7.38 (m, 1H), 7.34-7.28 (m, 1H), 7.22-7.14 (m, 1H), 5.38-5.32 (m, 1H), 2.90-2.76 (m, 2H), 2.72-2.66 (m, 1H), 2.61 (s, 6H), 2.48-2.42 (m, 4H), 2.24 (d, J=7.2 Hz, 2H), 2.00-1.86 (m, 4H), 1.76-1.64 (m, 5H), 1.58-1.46 (m, 2H) 1.24-1.14 (m, 1H), 1.04-0.98 (m, 1H). HPLC purity: 99.55%; LCMS calculated for $C_{27}H_{36}F_3N_3O_4S_2$: 587.21 Observed: 588.1 $[M+H]^+$.

A-803: Yield: 0.048 g, 13.7%; Appearance: Off-white solid; 1H NMR (400 MHz, $DMSO_6$) δ 7.89 (d, J=7.2 Hz, 2H), 7.77 (d, J=6.8 Hz, 2H), 7.41 (d, J=6.4 Hz, 1H), 7.34-7.26 (m, 1H), 7.19-7.14 (m, 1H), 5.35-5.33 (m, 1H), 2.86-2.76 (m, 2H), 2.72-2.68 (m, 1H), 2.61 (s, 6H), 2.48-2.40 (m, 4H), 2.24 (d, J=4.8 Hz, 2H), 2.00-1.86 (m, 4H), 1.74-1.62 (m, 5H), 1.58-1.42 (m, 2H), 1.24-1.14 (m, 1H), 1.02-0.99 (m, 1H); HPLC purity: 99.79%; LCMS calculated for $C_{27}H_{36}F_3N_3O_4S_2$:587.21 Observed: 588.1 $[M+H]^+$. Method for chiral sepn: Column: DIACEL CHIRALPAK-IG, 250 mm*4.6 mm, 5 u; Mobile Phase: A: n-HEXANE: MTBE (60:40)+0.1% TFA B: ETHANOL, Flow rate: 1.00 mL/min, Isocratic: 10% B, Ret. Time: 12.48.

A-804: Yield: 0.05 g, 14.2%; Appearance: Off-white solid; $^1H$ NMR (400 MHz, $DMSO_6$) δ 7.90 (d, J=7.6 Hz, 2H), 7.78 (d, J 8 Hz, 2H), 7.41 (d, J=7.2 Hz, 1H), 7.33-7.28 (m, 1H), 7.20-7.16 (m, 1H), 5.35-5.33 (m, 1H), 2.86-2.76 (m, 2H), 2.69-2.66 (m, 1H), 2.61 (s, 6H), 2.48-2.39 (m, 4H), 2.24 (d, J=5.6 Hz, 2H), 2.00-1.86 (m, 4H), 1.71-1.65 (m, 5H) 1.55-1.48 (m, 2H), 1.23-1.17 (m, 1H), 1.02-0.99 (m, 1H); HPLC purity: 95.15%; LCMS calculated for $C_{27}H_{36}F_3N_3O_4S_2$: 587.21; Observed: 588.1 $[M+H]^+$. Method for chiral sepn: Column: DIACEL CHIRALPAK-IG, 250 mm*4.6 mm, 5 u; Mobile Phase: A: n-HEXANE: MTBE (60:40)+0.1% TFA B: ETHANOL, Flow rate: 1.00 mL/min, Isocratic: 10% B, Ret. Time: 17.61.

The following examples were prepared using standard chemical manipulations and procedures similar to those used for the preparation of the previous example.

| Compound No. | Structure | Yields/Analytical data |
|---|---|---|
| A-802 | 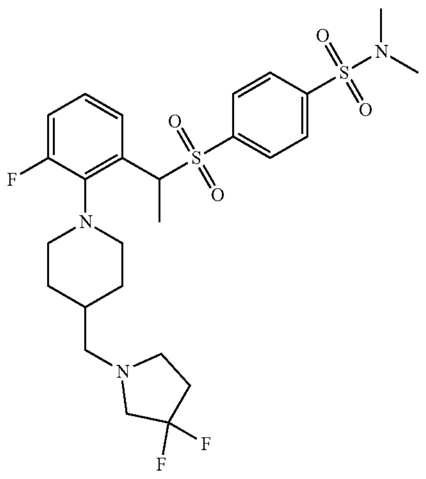 [SMILES: CC(c1cccc(F)c1N1CCC(CN2CCC(F)(F)C2)CC1)S(=O)(=O)c1ccc(S(=O)(=O)N(C)C)cc1] | Yield: 0.202 g, 34.2%; Appearance: Off-white solid; $^1$H NMR (400 MHz, DMSO$_6$) δ 7.90 (d, J = 8.4 Hz, 2H), 7.78 (d, J = 7.6 Hz, 2H), 7.42 (d, J = 8 Hz, 1H), 7.33-7.28 (m, 1H), 7.20-7.15 (m, 1H), 5.37 (q, J = 7.2 Hz, 1H), 2.87-2.68 (m, 4H), 2.66-2.65 (m, 3H), 2.61 (s, 6H), 2.33 (d, J = 6.8 Hz, 2H), 2.27-2.16 (m, 2H), 1.70-1.65 (m, 5H), 1.57-1.54 (m, 1H), 1.48-1.40 (m, 1H), 1.20-1.17 (m, 1H), 1.03-1.00 (m, 1H); HPLC purity: 99.86%; LCMS calculated for $C_{26}H_{34}F_3N_3O_4S_2$: 573.19 Observed: 574.1 [M + H]$^+$. |
| A-805 | 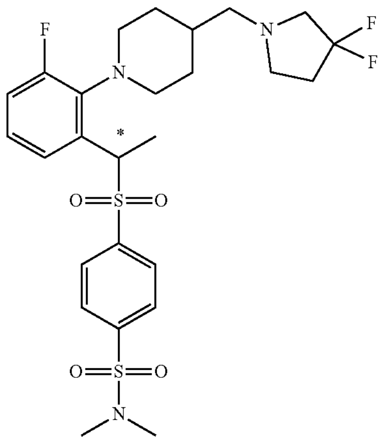 Enantiomer 1 | Yield: 0.042 g, 23.3%; Appearance: Off-white solid; $^1$H NMR (400 MHz, DMSO$_6$) δ 7.90 (d, J = 8.4 Hz, 2H), 7.78 (d, J = 8.4 Hz, 2H), 7.42 (d, J = 7.6 Hz, 1H), 7.33-7.28 (m, 1H), 7.20-7.15 (m, 1H), 5.37 (q, J = 7.2 Hz, 1H), 2.878-2.76 (m, 4H), 2.68 (t, J = 7.2 Hz, 3H), 2.61 (s, 6H), 2.33 (d, J = 6.8 Hz, 2H), 2.27-2.18 (m, 2H), 1.70-1.65 (m, 5H), 1.57-1.53 (m, 1H), 1.48-1.40 (m, 1H), 1.20-1.18 (m, 1H), 1.03-1.00 (m, 1H) ; HPLC purity: 99.37%; LCMS calculated for $C_{26}H_{34}F_3N_3O_4S_2$: 573.19 Observed: 574.1 [M + H]$^+$. Method for Chiral sepn: Column: DIACEL CHIRALPAK-IG, 250 mm * 4.6 mm, 5u, Mobile Phase: A: n-HEXANE + 0.1% TFA, B: ETHANOL, Flow rate: 1.0 mL/min, Isocratic: 8% B, Ret. Time: 9.48. |
| A-806 | 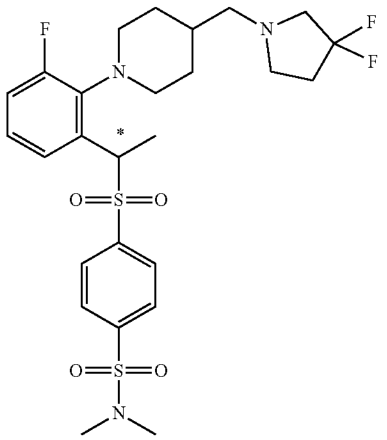 Enantiomer 2 | Yield: 0.022 g, 12.2%; Appearance: Off-white solid; $^1$H NMR (400 MHz, DMSO$_6$) δ 7.90 (d, J = 8.4 Hz, 2H), 7.78 (d, J = 8.4 Hz, 2H), 7.42 (d, J = 8 Hz, 1H), 7.33-7.28 (m, 1H), 7.20-7.15 (m, 1H), 5.37 (q, J = 6.8 Hz 1H), 2.87-2.77 (m, 4H), 2.68 (t, J = 7.20 Hz, 3H), 2.61 (s, 6H), 2.33 (d, J = 6.8 Hz, 2H), 2.28-2.17 (m, 2H), 1.72-1.65 (m, 5H), 1.57-1.54 (m, 1H), 1.50-1.38 (m, 1H), 1.23-1.18 (m, 1H), 1.03-1.00 (m, 1H) ; HPLC purity: 99.75%; LCMS calculated for $C_{26}H_{34}F_3N_3O_4S_2$: 573.19 Observed: 574.11 [M + H]$^+$. Method for Chiral sepn: Column: DIACEL CHIRALPAK-IG, 250 mm * 4.6 mm, 5u, Mobile Phase: A: n-HEXANE + 0.1 % TFA, B: ETHANOL, Flow rate: 1.0 mL/min, Isocratic: 8% B, Ret. Time: 11.63. |

-continued

| Compound No. | Structure | Yields/Analytical data |
|---|---|---|
| A-782 | 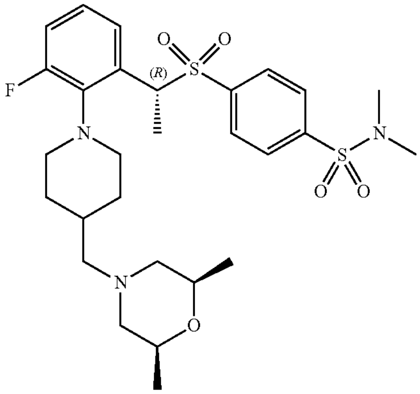 | Yield: 0.025 g, 13.8%; Appearance: White solid; $^1$H NMR (400 MHz, DMSO$_6$) δ 7.90 (d, J = 8.4 Hz, 2H), 7.78 (d, J = 8 Hz, 2H), 7.41 (d, J = 8 Hz, 1H), 7.31-7.29 (m, 1H), 7.22-7.14 (m, 1H), 5.35 (q, J = 7.2 Hz, 1H), 3.58-3.50 (m, 2H), 2.79-2.65 (m, 5H), 2.61 (s, 6H), 2.16-2.10 (m, 2H), 1.70-1.62 (m, 5H), 1.60-1.53 (m, 4H), 1.04 (d, J = 5.2 Hz, 6H). HPLC purity: 99.80%; LCMS calculated for $C_{28}H_{40}N_3O_5FS_2$: 581.24; Observed: 582.2 [M + H]$^+$. Method of chiral sepn: Column: DIACEL CHIRAL-PAK-IG, 250 mm * 4.6 mm , 5u, Mobile Phase: A: n-HEXANE + 0.1% TFA B: ETHANOL, Flow rate: 1.0 mL/min, Isocratic: 20% B, Ret. Time: 19.64 |
| A-783 | 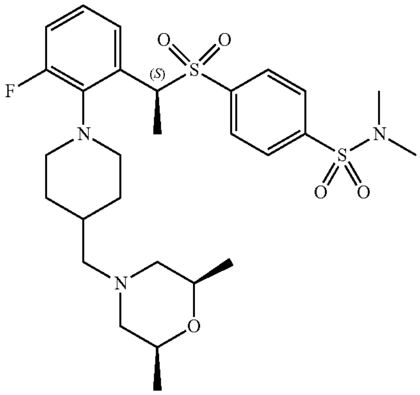 | Yield: 0.028 g, 15.5%; Appearance: White solid; $^1$H NMR (400 MHz, DMSO$_6$) δ 7.90 (d, J = 8.4 Hz, 2H), 7.78 (d, J = 8.4 Hz, 2H), 7.42 (d, J = 8 Hz, 1H), 7.31-7.29 (m, 1H), 7.12-7.14 (m, 1H), 5.35 (q, J = 7.2 Hz, 1H), 3.58-3.48 (m, 2H), 2.90-2.64 (m, 5H), 2.61 (s, 6H), 2.14 (d, J = 6 Hz, 2H), 1.72-1.62 (m, 5H), 1.58-1.48 (m, 4H), 1.04 (d, J = 6.4 Hz, 6H). HPLC purity: 99 80%; LCMS calculated for $C_{28}H_{40}N_3O_5FS_2$: 581.24; Observed: 582.36 [M + H]$^+$. Method of chiral sepn: Column: DIACEL CHIRAL-PAK-IG, 250 mm * 4.6 mm , 5u, Mobile Phase: A: n-HEXANE + 0.1% TFA B: ETHANOL, Flow rate: 1.0 mL/min, Isocratic: 20% B, Ret. Time: 25.52 |
| A-800 | 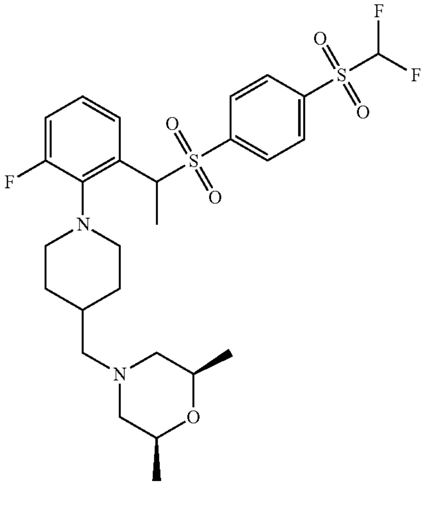 [SMILES: CC(c1cccc(F)c1N1CCC(CN2C[C@@H](C)O[C@@H](C)C2)CC1)S(=O)(=O)c1ccc(S(=O)(=O)C(F)F)cc1] | Yield: 0.2 g, 32%; Appearance: Off-white solid; $^1$H NMR (400 MHz, DMSO$_6$) δ 8.13 (d, J = 8.4 Hz, 2H), 7.90 (d, J = 8.4 Hz, 2H), 7.42-7.40 (m, 1H), 7.32-7.27(m, 1H), 7.19-7.13 (m, 1H), 5.36 (q, J = 7.04 Hz, 1H), 3.53-3.49 (m, 2H), 2.83-2.63 (m, 4H), 2.12 (d, J = 6.2 Hz, 2H), 1.66 (d, J = 7.2 Hz, 4H), 1.57-1.46 (m, 5H), 1.17-1.14 (m, 1H), 1.03 (d, J = 6 Hz, 6H), 0.95-0.93 (m, 1H). HPLC purity: 98 72%; LCMS calculated for $C_{27}H_{35}F_3N_2O_5S_2$: 588.19; Observed: 589.1 [M + H]$^+$. |

-continued

| Compound No. | Structure | Yields/Analytical data |
|---|---|---|
| A-807 | 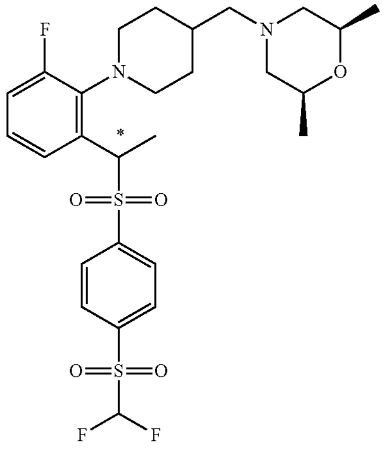 Enantiomer 1 | Yield: 26 mg; Appearance: Off white solid; $^1$H NMR (400 MHz, DMSO$_6$) δ 8.15 (d, J = 7.6 Hz, 2H), 7.91 (d, J = 8 Hz, 2H), 7.44-7.41 (m, 1H), 7.33-7.28 (m, 1H), 7.20-7.15 (m, 1H), 5.36 (q, J = 7.2 Hz, 1H), 3.53 (bs, 2H), 2.82-2.67 (m, 4H), 2.13 (d, J = 6 Hz, 2H), 1.68 (d, J = 7.2 Hz, 4H), 1.55-1.48 (m, 5H), 1.22-1.16 (m, 1H), 1.04 (d, J = 6 Hz, 6H), 0.97-0.94 (m, 1H). HPLC purity: 99.29%; Chiral HPLC purity: 98.87%; LCMS calculated for $C_{27}H_{35}$ $F_3N_2O_5S_2$: 588.19; Observed: 589.1 [M + H]$^+$. Method for chiral sepn: Column: DIACEL CHIRALPAK-IG, 250 mm * 4.6 mm, 5u, Mobile Phase: A: n-HEXANE + 0.1% TFA, B: Iso-Propyl-Alcohol, Flow rate: 1.00 mL/min, Isocratic: 20% B, Ret. Time: 17.37 |
| A-808 | 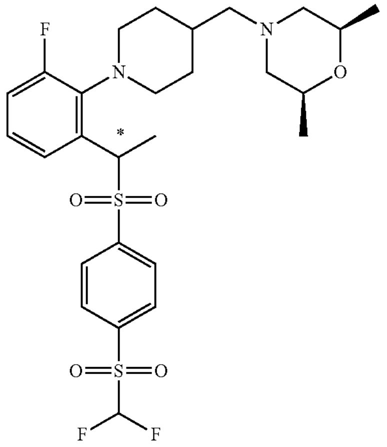 Enantiomer 2 | Yield: 17 mg; Appearance: Off white solid; $^1$H NMR (400 MHz, DMSO$_6$) δ 8.15 (d, J = 8.4 Hz, 2H), 7.91 (d, J = 8.4 Hz, 2H), 7.54-7.15 (m, 3H), 5.36 (q, J = 7 Hz, 1H), 3.58-3.50 (m, 2H), 2.82-2.68 (m, 4H), 2.14 (d J = 6.4 Hz, 2H), 1.68 (d, J = 7.2 Hz, 4H), 1.56-1.48 (m, 5H), 1.23-1.16 (m, 1H), 1.05 (d, J = 6.4 Hz, 6H), 0.97-0.94 (m, 1H). HPLC purity: 98.99%; Chiral HPLC purity: 97.36%; LCMS calculated for $C_{27}H_{35}F_3N_2O_5S_2$: 588.19; Observed: 589.1 [M + H]$^+$. Method for chiral sepn: Column: DIACEL CHIRALPAK-IG, 250 mm * 4.6 mm, 5u, Mobile Phase: A: n-HEXANE + 0.1% TFA, B: Iso-Propyl-Alcohol, Flow rate: 1.00 mL/min, Isocratic: 20% B, Ret. Time: 25.72. |
| A-839 | 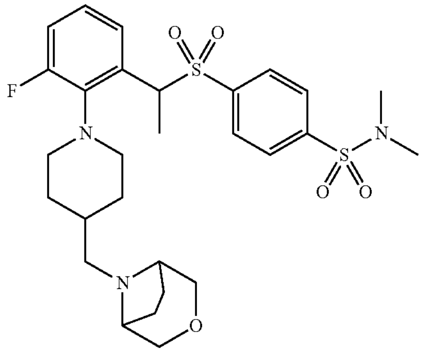 [SMILES: CC(c1cccc(F)c1N1CCC(CN2C3CCC2COC3)CC1)S(=O)(=O)c1ccc(S(=O)(=O)N(C)C)cc1] | Yield: 940 mg. 98%; Appearance: Off-white solid; $^1$H NMR (400 MHz, DMSO-d$_6$) δ 7.88 (d, J = 7.34 Hz, 2 H), 7.76 (d, J = 7.34 Hz, 2 H), 7.41 (d, J = 7.34 Hz, 1 H), 7.34-7.24 (m, 1 H), 7.20-7.14 (m, 1 H), 5.36-5.32 (m, 1 H), 3.48 (d, J = 9.78 Hz, 2 H), 3.37 (d, J = 9.78 Hz, 2 H), 2.96 (bs, 2 H), 2.90-2.73 (m, 2 H), 2.69-2.66 (m, 1 H), 2.61 (s, 6 H), 2.16-2.06 (m, 2 H), 1.84-1.75 (m, 3 H), 1.72-1.62 (m, 6 H), 1.61-1.54 (m, 1 H), 1.47-1.30 (m, 1 H), 1.25-1.14 (m, 1 H), 1.01 (d, J = 10.76 Hz, 1 H): HPLC purity: 99.83%; LCMS calculated for $C_{28}H_{38}FN_3O_5S_2$: 579.22 Observed: 580.1 [M + H]$^+$. |

-continued

| Compound No. | Structure | Yields/Analytical data |
|---|---|---|
| A-832 | 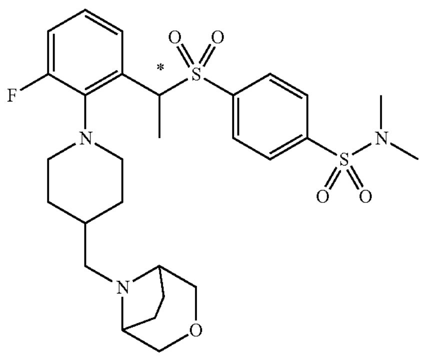 Enantiomer 1 | Yield: 12.82 mg, 12%; Appearance: Off-white solid; $^1$H NMR (400 MHz, DMSO-$d_6$) δ 7.90 (d, J = 7.34 Hz, 2 H), 7.78 (d, J = 7.34 Hz, 2 H), 7.42 (d, J = 7.34 Hz, 1 H), 7.34-7.28 (m, 1 H), 7.21-7.15 (m, 1 H), 5.25-5.44 (m, 1 H), 3.50 (d, J = 9.78 Hz, 2 H), 3.40 (d, J = 9.78 Hz, 2 H), 3.00-2.95 (m, 2 H), 2.88-2.74 (m, 2 H), 2.71-2.67 (m, 1 H), 2.62 (s, 6 H), 2.17-2.06 (m, 2 H), 1.85-1.75 (m, 3 H), 1.70-1.64 (m, 6 H), 1.62-1.57 (m, 1 H), 1.44-1.34 (m 1 H), 1.25-1.14 (m, 1 H), 1.10-0.96 (m, 1 H); HPLC purity: 99.53%; LCMS calculated for $C_{28}H_{38}FN_3O_5S_2$: 579.22 Observed: 580.1 [M + H]$^+$. Column: YMC CHIRAL ART CELLULOSE-SC, 250 mm * 4.6 mm , 5u; Mobile Phase: A: n-HEXANE + 0.1 % TFA; B: DCM:MEOH(50:50); Flow rate: 1.00 mL/min; Isocratic: 20% B; Retention time: 24.377 |
| A-855 | 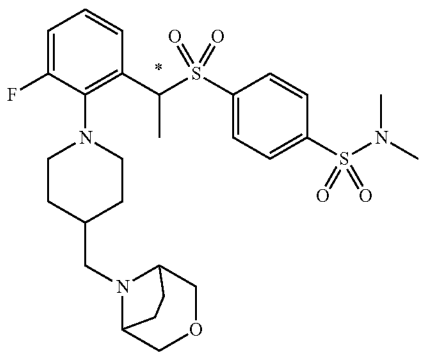 Enantiomer 2 | Yield: 9.13 mg, 1%; Appearance: Off-white solid; $^1$H NMR (400 MHz, DMSO-$d_6$) δ 7.90 (d, J = 8 Hz, 2 H), 7.78 (d, J = 8 Hz, 2 H), 7.43 (d, J = 7.6 Hz, 1 H), 7.34-7.28 (m, 1 H), 7.20-7.15 (m, 1 H), 5.38-5.34 (m, 1 H), 3.51 (d, J = 9.6 Hz, 2 H), 3.41 (d, J = 9.6 Hz, 2 H), 3.01-2.96 (m, 2 H), 2.90-2.74 (m, 2 H), 2.72-2.68 (m, 1 H), 2.62 (s, 6 H), 2.15-2.09 (m, 2 H), 1.86-1.76 (m, 3 H), 1.72-1.65 (m, 6H), 1.64-1.57 (m, 1 H), 1.44-1.34 (m, 1 H), 1.24-1.19 (m, 1 H), 1.02-0.99 (m, 1 H); HPLC purity: 98 41%; LCMS calculated for $C_{28}H_{28}FN_3O_5S_2$: 579.22 Observed: 580.1 [M + H]$^+$. METHOD: Column: YMC CHIRAL ART CELLULOSE-SC, 250 mm * 4.6 mm, 5u; Mobile Phase: A: n-HEXANE + 0.1% TFA; B: DCM: MEOH(50:50); Flow rate: 1.00 mL/min; Isocratic: 20% B; Ret. Time: 26.374. |
| A-837 | 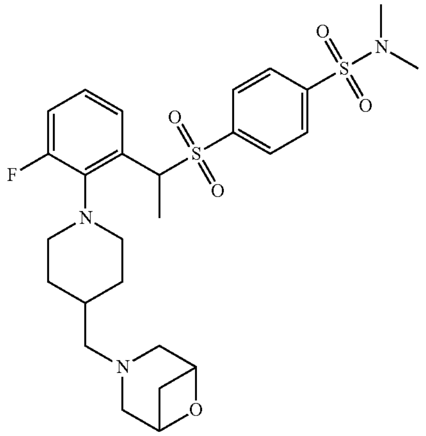 [SMILES: CC(c1cccc(F)c1N1CCC(CN2CC3CC(C2)O3)CC1)S(=O)(=O)c1ccc(S(=O)(=O)N(C)C)cc1] | Yield: 0.4 g. 69%; Appearance: Off white solid; $^1$H NMR (400 MHz, DMSO-$d_6$) δ 7.88 (d, J = 8.31 Hz, 2 H), 7.77 (d, J = 8.31 Hz, 2 H), 7.41 (d, J = 7.82 Hz, 1 H), 7.32-7.27 (m, 1 H), 7.19-7.14 (m, 1 H), 5.37 (q, J = 7.01 Hz, 1 H), 4.41 (d, J = 5.87 Hz, 2 H), 3.30-2.88 (m, 2 H), 2.84-2.76 (m, 3 H), 2.69 (d, J = 11.74 Hz, 1 H), 2.61 (s, 6 H), 2.57-2.52 (m, 2 H), 2.43-2.37 (m, 2 H), 2.20-2.15 (m, 1 H), 1.74-1.70 (m, 1 H), 1.66 (d, J = 7.34 Hz, 3 H), 1.56 (d, J = 11.25 Hz, 2H), 1.24-1.18 (m, 1 H), 1.04-0.99 (m, 1 H).; HPLC purity: 98.44%; LCMS calculated for $C_{27}H_{36}F_3N_3O_5S_2$: 565.21 Observed: 566.1 [M + H]$^+$. |

-continued

| Compound No. | Structure | Yields/Analytical data |
|---|---|---|
| A-848 | 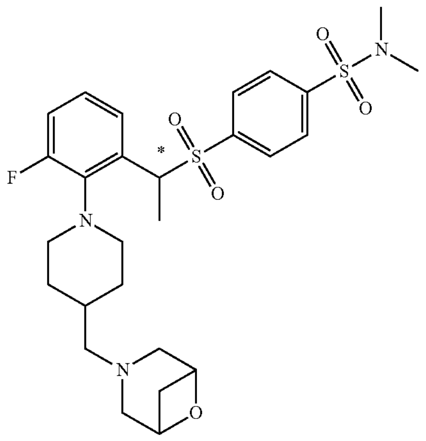 Enantiomer 1 | Yield: 0.0426 g, 12%; Appearance: Off white solid; $^1$H NMR (400 MHz, DMSO-$d_6$) δ 7.90 (d, J = 8 Hz, 2 H), 7.80 (d, J = 8.4 Hz, 2 H), 7.42 (d, J = 7.2 Hz, 1 H), 7.34-7.27 (m, 1 H), 7.21-7.14 (m, 1 H), 5.41-5.33 (m, 1 H), 4.42 (d, J = 5.2 Hz, 2 H), 3.03 (dd, J = 10,51, 5.14 Hz, 2 H), 2.95-2.76 (m, 3 H), 2.72-2.67 (m, 1 H), 2.62 (s, 6 H), 2.58-2.56 (m, 2 H), 2.44 (d, J = 6.8 Hz, 2 H), 2.20 (d, J = 7.2 Hz, 1 H), 1.70-1.80 (m, 2 H), 1.67 (d, J = 7.34 Hz, 3 H), 1.60-1.52 (m, 2 H), 1.28-1.18 (m, 1 H), 1.05 (d, J = 10.27 Hz, 1 H); HPLC purity: 99.68%; LCMS calculated for $C_{27}H_{36}F_3N_3O_5S_2$: 565.21 Observed: 566.1 [M + H]$^+$. METHOD: Column: YMC CHIRAL ART CELLULOSE-SC, 250 mm * 4.6 mm , 5u; Mobile Phase: A: n-HEXANE + 0. 1% Iso-propyl-amine; B: DCM:MEOH (50:50); Flow rate: 1.00 mL/min; Isocratic: 20% B; Ret. Time: 24.387. |
| A-849 | 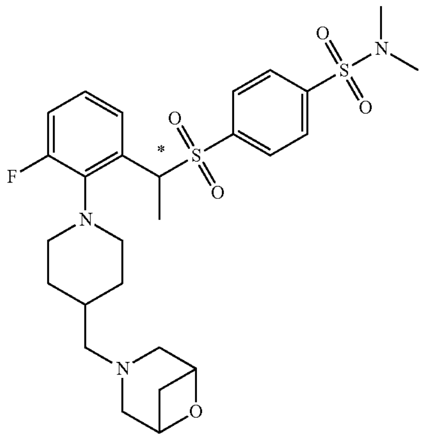 Enantiomer 2 | Yield: 0.021 g. 6%; Appearance: Off white solid: $^1$H NMR (400 MHz, $DMSO_6$) δ 7.91 (d, J = 8.31 Hz, 2 H), 7.79 (d, J = 8.31 Hz, 2 H), 7.42 (d, J = 7.82 Hz, 1 H), 7.37-7.25 (m, 1 H), 7.24-7.11 (m, 1 H), 5.37 (q, J = 7.2 Hz, 1 H), 4.42 (d, J = 5.87 Hz, 2 H), 3.03 (dd, J = 10.51, 5.14 Hz, 2 H), 2.95-2.76 (m, 3 H), 2.74-2.66 (m, 1 H), 2.62 (s, 6 H), 2.60-2.55 (m, 2 H), 2.44 (d, J = 6.85 Hz, 2 H), 2.19 (d, J = 7.6 Hz, 1 H), 1.79-1.70 (m, 2 H), 1.67 (d, J = 7.34 Hz, 3 H), 1.60-1.52 (m, 2 H), 1.28-1.18 (m, 1 H), 1.05 (d, J = 10.8 Hz, 1 H): HPLC purity: 96.86%; LCMS calculated for $C_{27}H_{36}F_3N_3O_5S_2$: 565.21 Observed: 566.1 [M + H]$^+$. METHOD: Column: YMC CHIRAL ART CELLULOSE-SC, 250 mm * 4.6 mm , 5u; Mobile Phase: A: n-HEXANE + 0.1% Iso-propyl-amine; B: DCM:MEOH (50:50) Flow rate: 1.00 mL/min; Isocratic: 20% B; Ret. Time: 27.739. |
| A-860 | 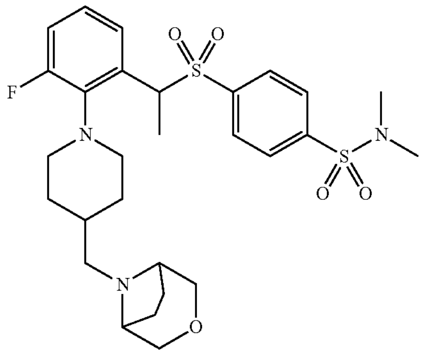 | Yield: 0.25 g. 35.5%: Appearance: White solid: $^1$H NMR (400 MHz, CHLOROFORM-d) δ 7.78 (d, J = 2.93 Hz, 4 H), 7.47 (d, J = 7.82 Hz, 1 H), 7.22-7.15 (m, 1 H), 6.98 (dd, J = 11.25, 8.80 Hz, 1 H), 5.51-5.45 (m, 1 H), 4.24 (d, J = 10 Hz, 2 H), 3.72 (d, J = 10.27 Hz, 2 H), 3.51-3.42 (m, 2 H), 2.93 (t, J = 11.00 Hz, 2 H), 2.70 (s, 6 H), 2.64 (d, J = 7.83 Hz, 2 H), 2.58-2.50 (m, 2 H), 1.84 (d, J = 8.31 Hz, 1 H), 1.75 (d, J = 6.85 Hz, 6 H), 1.47-1.35 (m, 1 H), 1.30-1.23 (m, 1 H), 1.09-0.98 (m, 1 H): HPLC purity: 96.95%; LCMS calculated for $C_{27}H_{36}FN_3O_5S_2$: 565.21 Observed: 566.1 [M + H]$^+$. |

-continued

| Compound No. | Structure | Yields/Analytical data |
|---|---|---|
| A-869 | 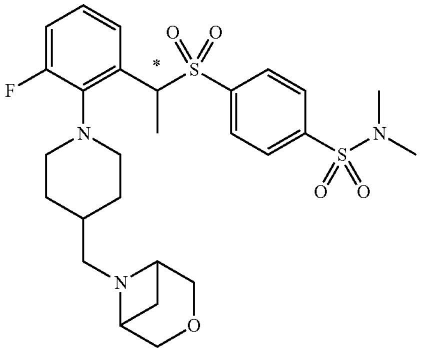 Enantiomer 1 | Yield: 0.042 g, 5.97%; Appearance: White solid; $^{1}$H NMR (400 MHz, $DMSO_6$) δ 8.17 (s, 1 H), 7.89 (d, J = 8.4 Hz, 2 H), 7.78 (d, J = 8 Hz, 2 H), 7.42 (d, J = 7.34 Hz, 1 H), 7.36-7.26 (m, 1 H), 7.21-7.15 (m, 1 H), 5.36 (d, J = 6.85 Hz, 1 H), 4.11 (d, J = 10.27 Hz, 2 H), 3.63-3.55 (m, 3 H), 3.45-3.40 (m, 4 H), 2.87-2.68 (m, 3 H), 2.62 (s, 6 H), 1.75-1.65 (m, 6 H), 1.58 (d, J = 11.25 Hz, 1 H), 1.37-1.21 (m, 2 H), 1.10-1.01 (m, 1 H); HPLC purity: 100.00%; LCMS calculated for $C_{27}H_{36}FN_3O_5S_2$: 565.21 Observed: 566.1 $[M + H]^+$. Method: Mobile Phase: A) CO2 B) MEOH + 0.1% NH3; Gradient: 35-50% B in 5 min, hold 50% B till 9 min, 50-35% B at 10 min, hold 35% B till 12 Min. Column: DIACEL CH1RALPAK-IG(250 4.6 mm, 5u); Wavelength: 241 nm; Flow: 5 mL/min; Ret. Time: 5.66. |
| A-870 | 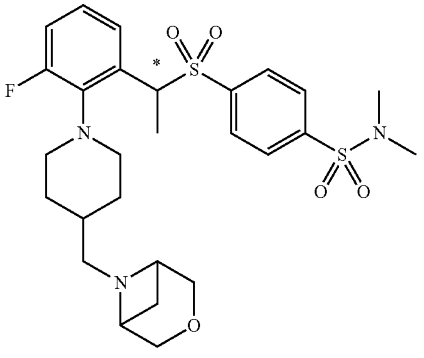 Enantiomer 2 | Yield: 0.019 g, 2.70%; Appearance: White solid; $^{1}$H NMR (400 MHz, $DMSO_6$) δ 8.17 (s, 1 H), 7.89 (d, J = 8.4 Hz, 2 H), 7.78 (d, J = 8 Hz, 2 H), 7.42 (d, J = 7.34 Hz, 1 H), 7.36-7.26 (m, 1 H), 7.21-7.15 (m, 1 H), 5.35 (d, J = 7.2 Hz, 1 H), 4.11 (d, J = 10.27 Hz, 2 H), 3.63-3.55 (m, 3 H), 3.45-3.40 (m, 4 H), 2.87-2.68 (m, 3 H), 2.62 (s, 6 H), 1.75-1.65 (m, 6 H), 1.58 (d, J = 11.25 Hz, 1 H), 1.37-1.20 (m, 2 H), 1.10-1.01 (m, 1 H); HPLC purity: 96.11%; LCMS calculated for $C_{27}H_{36}FN_3O_5S_2$: 565.21 Observed: 566.1 $[M + H]^+$. Method: Mobile Phase: A) CO2 B) MEOH + 0.1% NH3; Gradient: 35-50% B in 5 min, hold 50% B till 9 min, 50-35% B at 10 min, hold 35% B till 12 Min. Column: DIACEL CHIRALPAK-IG (250 × 4.6 mm, 5u); Wavelength: 241 nm; Flow: 5 mL/min; Ret. Time: 6.03. |
| A-859 | 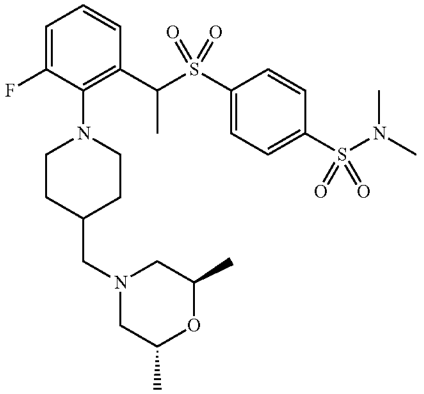 [SMILES: CC(c1cccc(F)c1N1CCC(CN2C[C@@H](C)O[C@H](C)C2)CC1)S(=O)(=O)c1ccc(S(=O)(=O)N(C)C)cc1] | Yield: 0 234 g, 38.3%; Appearance: Off white solid; $^{1}$H NMR (400 MHz, $DMSO_6$) δ 7.89 (d, J = 8.31 Hz, 2 H), 7.78 (br d, J = 4.89 Hz, 2 H), 7.45-7.38 (m, 1 H), 7.36-7.27 (m, 1 H), 7.22-7.12 (m, 1 H), 5.35 (d, J = 7.34 Hz, 1 H), 3.94-3.84 (m, 2 H), 2.88-2.67 (m, 3 H), 2.61 (s, 6 H), 2.40-2.30 (m, 2 H), 2.19-1.98 (m, 4 H), 1.66 (d, J = 4.89 Hz, 4 H), 1.59-1.42 (m, 2 H), 1.12 (d, J = 5.38 Hz, 6 H), 1.07-0.93 (m, 1 H), HPLC purity: 99.83%; LCMS calculated for $C_{28}H_{40}FN_3O_5S_2$: 581.24 Observed: 582.2 $[M + H]^+$. |

Example A110: Syntheses of Rel-N-(2-(4-((2,6-dimethylmorpholino)methyl)piperidin-1-yl)-3-fluorophenyl)-4-(N,N-dimethylsulfamidimidoyl)benzenesulfonamide (A-810 & A-811)

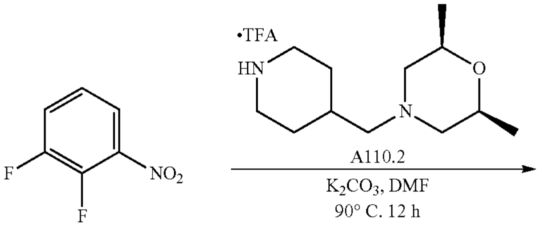

A110.1

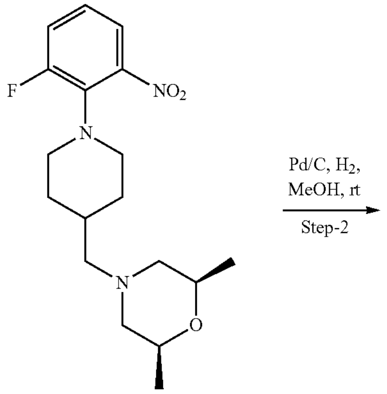

A110.3

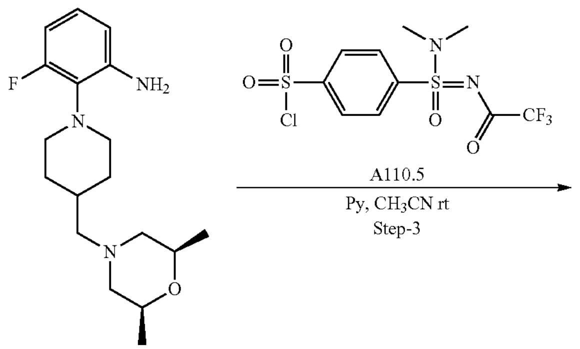

A110.4

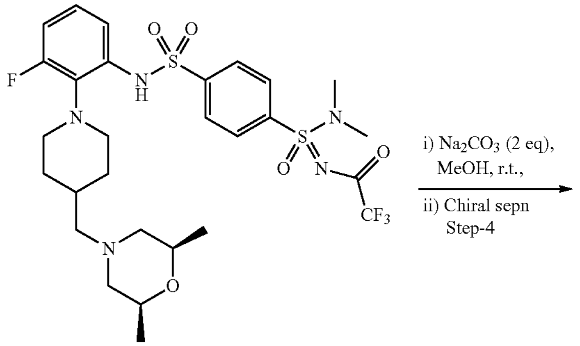

A110.6

-continued

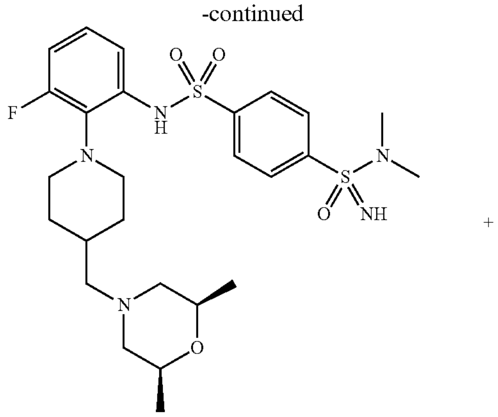

+

A-810

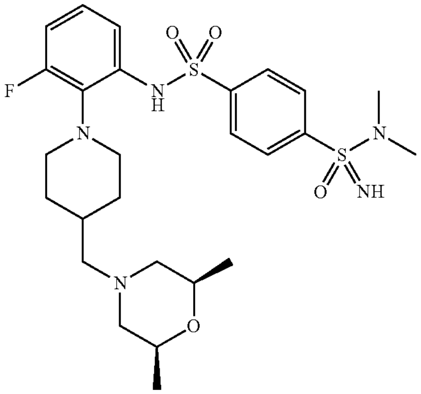

A-811

Step-1. Synthesis of Rel-4-((1-(2-fluoro-6-nitrophenyl)piperidin-4-yl)methyl)-2,6-dimethylmorpholine (A110.3)

To a stirred solution of 1,2-difluoro-3-nitrobenzene (A110.1) (1 g, 6.4 mmol, 1 eq) and Rel-(2S,6R)-2,6-dimethyl-4-(piperidin-4-ylmethyl)morpholine (A110.2) (2 g, 6.4 mmol, 1 eq) in DMF (20 mL) was added potassium carbonate (2.67 g, 19.41 mmol, 3 eq) at room temperature and the reaction mixture was stirred at 90° C. for 12 h. The progress of the reaction was monitored by TLC. After completion of the reaction, the reaction mixture was cooled to room temperature, diluted with cold water and extracted with ethyl acetate. The combined organic layers were washed with cold water and brine, dried over anhydrous $Na_2SO_4$, filtered and concentrated under reduced pressure. The crude product was purified by column chromatography on silica gel to afford Rel-4-((1-(2-fluoro-6-nitrophenyl)piperidin-4-yl)methyl)-2,6-dimethylmorpholine (A110.3) (1.2 g, 54.5%) as yellow solid LCMS: 352.0 $[M+H]^+$.

Step-2. Synthesis of Rel-2-(4-((2,6-dimethylmorpholino)methyl)piperidin-1-yl)-3-fluoroaniline (A110.4)

An autoclave was charged with a solution of Rel-4-((1-(2-fluoro-6-nitrophenyl)piperidin-4-yl)methyl)-2,6-dimethylmorpholine (A110.3) (1.2 g, 3.41 mmol, 1 eq) in MeOH (12 mL) and purged with nitrogen for 5 min. 20% Palladium on carbon (0.24 g, 20% w/w) was then added to the reaction mixture under nitrogen atmosphere. The reaction mixture was purged with hydrogen and stirred at room temperature for 6 h under hydrogen atmosphere at 100 psi. The progress of the reaction was monitored by TLC. After completion of the reaction, the reaction mixture was filtered through a pad of Celite and the Celite pad was washed with methanol. The filtrate was concentrated under reduced pressure to afford Rel-2-(4-((2,6-dimethylmorpholino)methyl)piperidin-1-yl)-3-fluoroaniline (A110.4) (0.95 g, 95%) as a colorless semi solid. LCMS: 322.15 $[M+H]^+$.

Step-3. Synthesis of Rel-N-((dimethylamino)(4-(N-(2-(4-((2,6-dimethylmorpholino)methyl)piperidin-1-yl)-3-fluorophenyl)sulfamoyl)phenyl)(oxo)-$\lambda^6$-6-sulfaneylidene)-2,2,2-trifluoroacetamide (A110.6)

To a stirred solution of Rel-2-(4-((2,6-dimethylmorpholino)methyl)piperidin-1-yl)-3-fluoroaniline (A110.4) (0.3 g, 0.93 mmol, 1 eq) in acetonitrile (10 mL), pyridine (0.147 g, 1.86 mmol, 2 eq) was added at 0° C. 4-(N,N-dimethyl-N'-(2,2,2-trifluoroacetyl)sulfamidimidoyl)benzenesulfonyl chloride (A110.5) (0.42 g, 1.12 mmol, 1.2 eq) was added and the reaction mixture was stirred at room temperature for 12 h. The progress of the reaction was monitored by TLC. After completion of reaction, the reaction mixture was diluted with water and extracted with ethyl acetate. The combined organic layers were dried over anhydrous $Na_2SO_4$, filtered, concentrated under reduced pressure and purified by combiflash to afford Rel-N-((dimethylamino)(4-(N-(2-(4-((2,6-dimethylmorpholino)methyl)piperidin-1-yl)-3-fluorophenyl)sulfamoyl)phenyl)(oxo)-$\lambda^6$-sulfaneylidene)-2,2,2-trifluoroacetamide (A110.6) (0.19 g, 30.6%) as an off-white solid.

Step-4. Synthesis of Rel-N-(2-(4-((2,6-dimethylmorpholino)methyl)piperidin-1-yl)-3-fluorophenyl)-4-(N,N-dimethylsulfamidimidoyl)benzenesulfonamide (A-810 & A-811)

To a stirred solution of Rel-N-((dimethylamino)(4-(N-(2-(4-((2,6-dimethylmorpholino)methyl)piperidin-1-yl)-3-fluorophenyl)sulfamoyl)phenyl)(oxo)-$\lambda^6$-sulfaneylidene)-2,2,2-trifluoroacetamide (A110.6) (0.18 g, 0.27 mmol, 1 eq) in MeOH (5 mL) sodium carbonate (0.06 g, 0.54 mmol, 2 eq) was added and the reaction mixture was stirred at room temperature for 2 h. The progress of the reaction was monitored by TLC. After completion of the reaction, the reaction mixture was concentrated under reduced pressure. The residue was diluted with water and extracted with ethyl acetate. The combined organic layers were dried over anhydrous $Na_2SO_4$, filtered and concentrated under reduced pressure. The crude product was purified by trituration with methanol, filtered, dried and purified by chiral HPLC to afford Rel-N-(2-(4-((2,6-dimethylmorpholino)methyl)piperidin-1-yl)-3-fluorophenyl)-4-(N,N-dimethylsulfamidimidoyl)benzenesulfonamide (A-810 & A-811).

A-810: Yield: 0.025 g, 16.2%; Appearance: White solid; $^1H$ NMR (400 MHz, $DMSO_6$) δ 9.07 (s, 1H), 7.92 (s, 4H), 7.25-7.18 (m, 2H), 6.98-6.90 (m, 1H), 4.66 (s, 1H), 3.54 (t, J=6.4 Hz, 2H), 2.82 (t, J=10.4 Hz, 2H), 2.71 (d, J=10.8 Hz, 2H), 2.53 (s, 6H), 2.36-2.24 (m, 2H), 2.12 (d, J=6.4 Hz, 2H), 1.58-1.51 (m, 5H), 1.04 (d, J=6.4 Hz, 6H). HPLC purity: 98.84%; LCMS calculated for $C_{26}H_{38}N_5O_4FS_2$: 567.23; Observed: 568.8 $[M+H]^+$. Method for chiral sepn: Column: YMC CHIRAL ART CELLULOSE SC, 250 mm*4.6 mm, 5 u, Mobile Phase: A: n-HEXANE+MTBE (50:50)+0.1% Iso-propyl-amine, B: DCM:MEOH (50:50), Flow rate: 1.00 mL/min, Isocratic: 10% B, Ret. Time: 8.685

A-811: Yield: 0.015 g, 9.7%; Appearance: White solid; $^1H$ NMR (400 MHz, $DMSO_6$) δ 9.07 (s, 1H), 7.91 (s, 4H), 7.24-7.08 (m, 2H), 6.94-6.84 (m, 1H), 4.64 (s, 1H), 3.58-3.48 (m, 2H), 2.86-2.76 (m, 2H), 2.71 (d, J=10.4 Hz, 2H), 2.53 (s, 6H), 2.38-2.28 (m, 2H), 2.12 (d, J=6.4 Hz, 2H), 1.58-1.50 (m, 5H), 1.04 (d, J=6.4 Hz, 6H). HPLC purity: 99.14%; LCMS calculated for $C_{26}H_{38}N_5O_4FS_2$: 567.23; Observed: 568.1 $[M+H]^+$. Method for chiral sepn: Column: YMC CHIRAL ART CELLULOSE SC, 250 mm*4.6 mm, 5 u, Mobile Phase: A: n-HEXANE+MTBE (50:50)+0.100 Iso-propyl-amine, B: DCM:MEOH (50:50), Flow rate: 1.00 mL/min, Isocratic: 10% B, Ret. Time: 10.12.

The following examples were prepared using standard chemical manipulations and procedures similar to those used for the preparation of the previous example.

| Compound No. | Structure | Yields/Analytical data |
|---|---|---|
| A-841 | 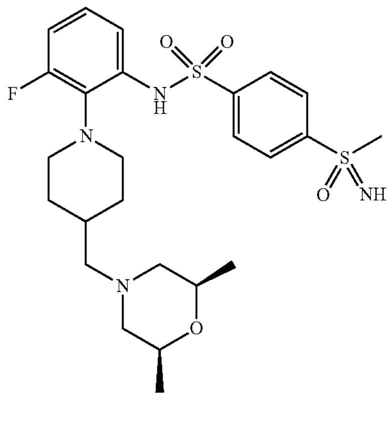 | $^1H$ NMR (400 MHz, $DMSO_6$) δ 8.13 (bs, 1 H), 8.10-8.04 (m, 2 H), 7.99-7.93 (m, 2 H), 7.22-7.12 (m, 2 H), 6.97-6.90 (m, 1 H), 4.45 (bs, 1 H), 3.56-3.49 (m, 3 H), 3.07 (s, 3 H), 2.83-2.77 (m, 2 H), 2.72 (d, J = 6.36 Hz, 2 H), 2.45-2.31 (m, 2 H), 2.11 (d, J = 6.4 Hz, 2H), 1.60-1.50 (m, 5 H), 1.27-1.15 (m, 2 H), 1.03 (d, J = 5.6 Hz, 6 H); HPLC purity: 99.49%; LCMS calculated for $C_{25}H_{35}FN_4O_4S_2$: 538.21 Observed: 539.1 $[M + H]^+$. |

-continued

| Compound No. | Structure | Yields/Analytical data |
|---|---|---|
| A-846 | 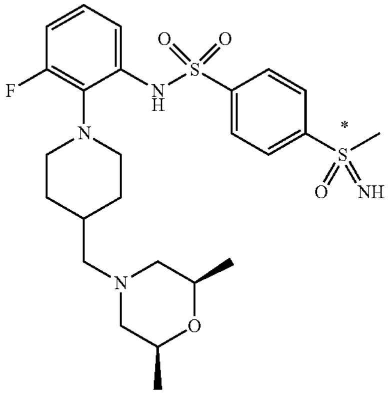 [SMILES: C[C@@H]1CN(CC2CCN(c3c(F)cccc3NS(=O)(=O)c3ccc(S(C)(=N)=O)cc3)CC2)C[C@H](C)O1] Enantiomer 1 | Yield: 30 mg; 3.5%; Appearance: Off white solid; $^1$H NMR (400 MHz, DMSO-$d_6$) δ 9.13 (br s, 1 H), 8.09 (d, J = 7.82 Hz, 2 H), 7.97 (d, J = 8.4 Hz, 2 H), 7.24-7.16 (m, 2 H), 6.95 (dd, J = 11.25, 8.80 Hz, 1 H), 4.45 (br s, 1 H), 3.56-3.53 (m, 2 H), 3.09 (s, 3 H), 2.82 (t, J = 10.76 Hz, 2 H), 2.72 (d, J = 10.76 Hz, 2 H), 2.42-2.37 (m, 2 H), 2.13 (d, J = 5.38 Hz, 2 H), 1.61-1.58 (m, 5 H), 1.22-1.99 (m, 2 H), 1.05 (d, J = 5.87 Hz, 6 H); HPLC purity: 99.27%; Chiral HPLC purity: 99.76%; LCMS calculated for $C_{25}H_{35}FN_4O_4S_2$: 538.70; Observed: 539.1 $[M + H]^+$. Column: YMC CHIRAL ART CELLULOSE-SC, 250 mm * 4.6 mm, 5u; Mobile Phase: A: n-HEXANE + 0.1% Iso-propyl-amine; B: DCM: MeOH(50:50); Flow rate: 1.00 mL/min; Isocratic: 25% B; Ret. Time: 12.437. |
| A-847 | 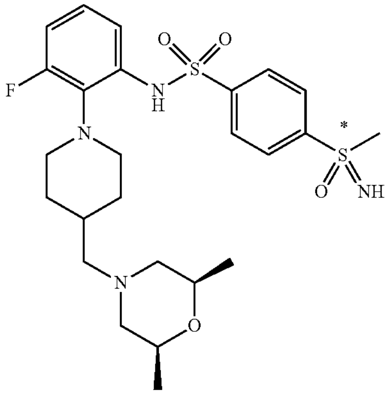 Enantiomer 2 | Yield: 28 mg; 3.3%; Appearance: White solid; $^1$H NMR (400 MHz, DMSO-$d_6$) δ 9.12 (br s, 1 H), 8.09 (d, J = 8.31 Hz, 2 H), 7.98 (d, J = 8.31 Hz, 2 H), 7.23-7.16 (m, 2 H), 6.97-6.92 (m, 1 H), 4.45 (br s, 1 H), 3.56-3.53 (m, 2 H), 3.09 (s, 3 H), 2.83 (t, J = 10.51 Hz, 2 H), 2.71 (d, J = 10.27 Hz, 2 H), 2.49-2.37 (m, 2 H), 2.13 (d, J = 6.36 Hz, 2 H), 1.61-1.53 (m, 5 H), 1.21 (d, J = 11.25 Hz, 2 H), 1.05 (d, J = 6.36 Hz, 6 H); HPLC purity: 99.60%; Chiral HPLC purity: 99.04%; LCMS calculated for $C_{25}H_{35}FN_4O_4S_2$: 538.70; Observed: 539.1 $[M + H]^+$. Column: YMC CHIRAL ART CELLULOSE-SC, 250 mm * 4.6 mm, 5u; Mobile Phase: A: n-HEXANE + 0.1% Iso-propyl-amine; B: DCM:MeOH (50:50); Flow rate. 1.00 mL/min; Isocratic: 25% B, Ret. Time: 13.884. |
| A-867 | 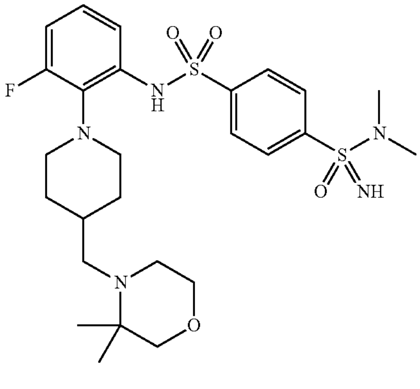 [SMILES: CN(C)S(=N)(=O)c1ccc(S(=O)(=O)Nc2cccc(F)c2N2CCC(CN3CCOCC3(C)C)CC2)cc1] | Yield: 0.040 g, 22%); Appearance: White solid; $^1$H NMR (400 MHz, $DMSO_6$) δ 9.25 (brs, 1H), 8.14 (s, 1H), 7.93 (bs, 4 H), 7.26 (d, J = 7.82 Hz, 1 H), 7.22-7.16 (m, 1 H), 7.01-6.92 (m, 1 H), 4.67 (s, 1 H), 3.60-3.51 (m, 2 H), 3.20 (s, 3 H), 2.81-2.70 (m, 2 H), 2.54 (s, 4 H), 2.46-2.40 (m, 2 H), 2.38-2.22 (m, 2 H), 2.16 (d, J = 4.4 Hz, 2 H), 1.66-1.54 (m, 2 H), 1.42-1.30 (m, 1 H), 1.29-1.17 (m, 2 H), 0.94 (s, 6 H). 2 exchangeable proton not seen; HPLC purity: 99.88%; LCMS calculated for $C_{26}H_{38}FN_5O_4S_2$: 567.23 Observed: 568.1 $[M + H]^+$. |

-continued

| Compound No. | Structure | Yields/Analytical data |
|---|---|---|
| A-858 | 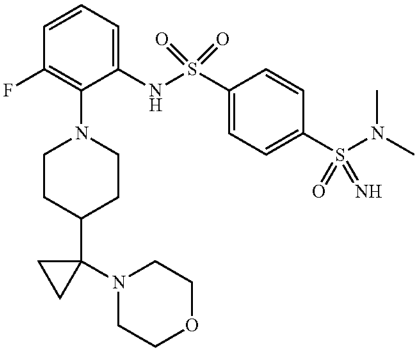 [SMILES: CN(C)S(=N)(=O)c1ccc(S(=O)(=O)Nc2cccc(F)c2N2CCC(C3(N4CCOCC4)CC3)CC2)cc1] | Yield: 0.2 g, 48%; Appearance: White solid; $^1$H NMR (400 MHz, DMSO$_6$) δ 9.11 (br s, 1 H), 7.92 (s, 4 H), 7.29-7.11 (m, 2 H), 7.00-6.91 (m, 1 H), 4.66 (s, 1 H), 3.52 (bs, 4 H), 2.75-2.88 (m, 2 H), 2.53 (s, 6 H), 2.27 (t, J = 10.76 Hz, 2 H), 1.49-1.22 (m, 5 H), 0.60-0.52 (m, 2 H), 0.49-0.41 (m, 2 H). 4 H's are merged into solvent peak; HPLC purity: 99.55%; LCMS calculated for $C_{26}H_{36}FN_5O_4S_2$: 565.22 Observed: 566.1 $[M + H]^+$. |
| A-844 | 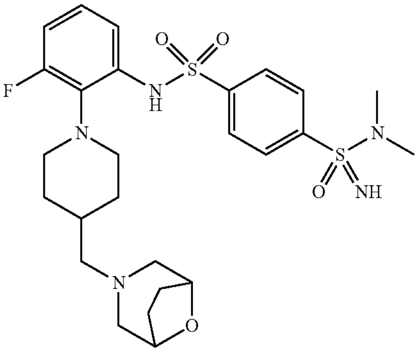 [SMILES: CN(C)S(=N)(=O)c1ccc(S(=O)(=O)Nc2cccc(F)c2N2CCC(CN3CC4CCC(C3)O4)CC2)cc1] | Yield: 0.2 g, 49.18%; Appearance: Off-white solid; $^1$H NMR (400 MHz, DMSO$_6$) δ 9.05 (bs, 1 H), 7.93 (s, 4 H), 7.29-7.22 (m, 1 H), 7.21-7.14 (m, 1 H), 6.96 (dd, J = 1.25, 8.80 Hz, 1 H), 4.66 (s, 1 H), 4.22-4.14 (m, 2 H), 2.78 (t, J = 10.76 Hz, 2 H), 2.53 (s, 6 H), 2.38-2.22 (m, 3 H), 2.16-2.04 (m, 4 H), 1.84-1.78 (m, 2 H), 1.74-1.65 (m, 3 H), 1.57 (d, J = 12.23 Hz, 2 H), 1.51-1.42 (m, 1 H), 1.30-1.16 (m, 2 H); HPLC purity: 98.6%; LCMS calculated for $C_{26}H_{36}FN_5O_4S_2$: 565.22 Observed: 566.1 $[M + H]^+$. |
| A-852 | 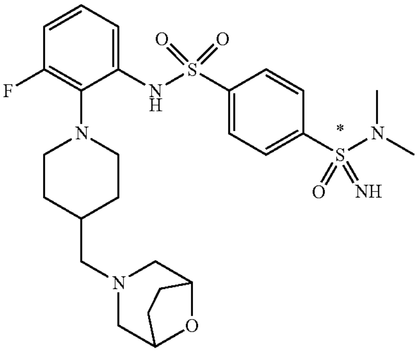<br>enantiomer 1 | Yield: 0.018 g; Appearance: White solid; $^1$H NMR (400 MHz, DMSO$_6$) δ 9.05 (bs, 1H), 8.93-9.13 (m, 1 H), 7.91 (bs, 4 H), 7.26-7.14 (m, 2 H), 7.00-6.89 (m, 1 H), 4.65 (bs, 1 H), 4.21-4.14 (m, 2 H), 2.84-2.72 (m, 2 H), 2.37-2.22 (m, 2 H), 2.16-2.05 (m, 4 H), 1.79 (d, J = 5.87 Hz, 2 H), 1.74-1.62 (m, 2 H), 1.56 (d, J = 11.74 Hz, 2 H), 1.50-1.42 (m, 1 H), 1.30-1.16 (m, 2 H). 7H's are merged into solvent peak; HPLC purity: 96.78%; LCMS calculated for $C_{26}H_{36}FN_5O_4S_2$: 565.22 Observed: 566.1 $[M + H]^+$. METHOD: Column : YMC CHIRAL ART CELLULOSE-SC, 250 mm * 4.6 mm, 5u; Mobile Phase: A: n-HEXANE + 0.1% Iso-propyl-amine; B: DCM:MEOH (50:50)Flow rate: 1.00 mL/min; Isocratic: 25% B; Ret. Time: 16.399. |
| A-853 | 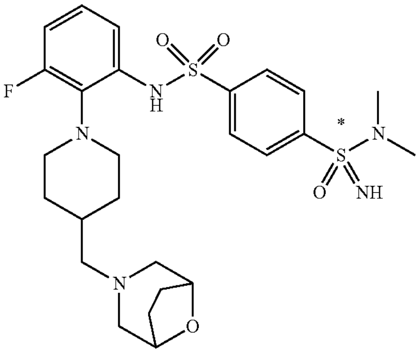<br>enantiomer 2 | Yield: 0.017 g; Appearance: Off-white solid; $^1$H NMR (400 MHz, DMSO$_6$) δ 9.04 (bs, 1 H), 7.91 (bs, 4 H), 7.25-7.14 (m, 2 H), 6.99-6.84 (m, 1 H), 4.65 (bs, 1 H), 4.20-4.12 (m, 2 H), 2.77 (t, J = 10.03 Hz, 2 H), 2.39-2.22 (m, 2 H), 2.15-2.05 (m, 4 H), 1.82-1.75 (m, 2 H), 1.74-1.64 (m, 2 H), 1.60-1.40 (m, 3 H), 1.28-1.12 (m, 2 H). 8H's are merged into solvent peak; HPLC purity: 97.34%; LCMS calculated for $C_{26}H_{36}FN_5O_4S_2$: 565.22 Observed: 566.1 $[M + H]^+$. METHOD: Column: YMC CHIRAL ART CELLULOSE-SC, 250 mm * 4.6 mm , 5u; Mobile Phase: A: n-HEXANE + 0.1% Iso-propyl-amine; B: DCM:MEOH(50:50); Flow rate: 1.00 mL/min; Isocratic: 25% B, Ret. Time: 18.274. |

Example A111: Synthesis of 4-((1-(3-cyano-2-(4-((2,6-dimethylmorpholino)methyl)piperidin-1-yl)phenyl)ethyl)sulfonyl)-N,N-dimethylbenzenesulfonamide (A-842, A-854 and A-845)

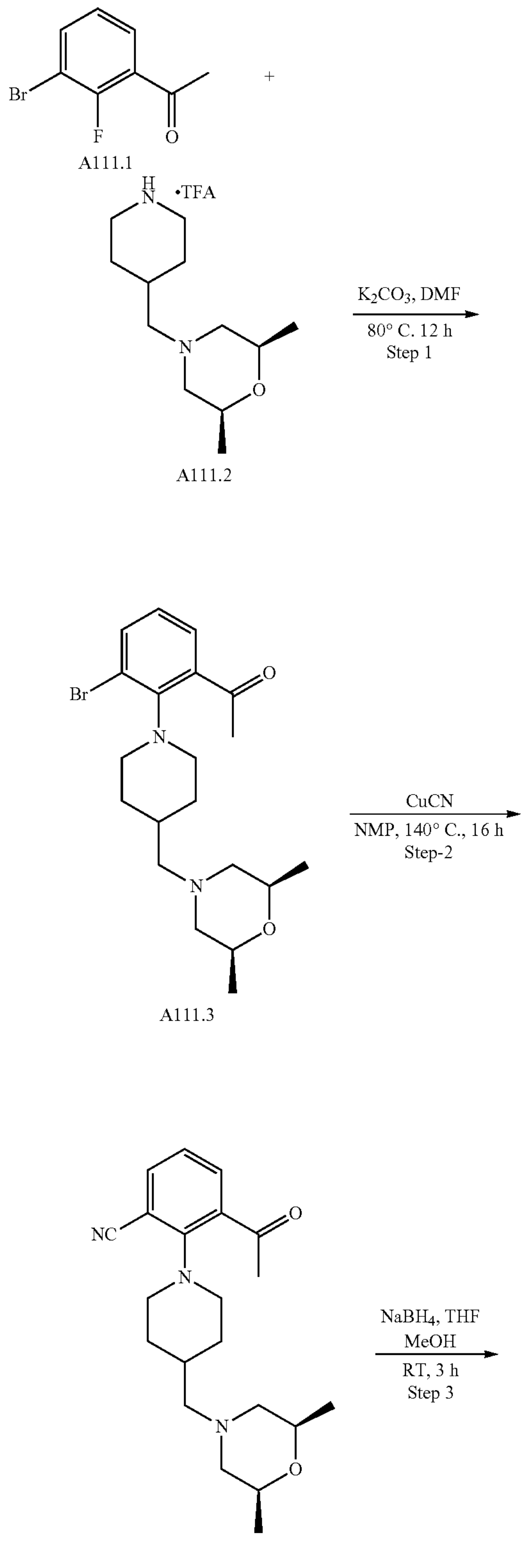

A111.1

A111.2

A111.3

A111.4

-continued

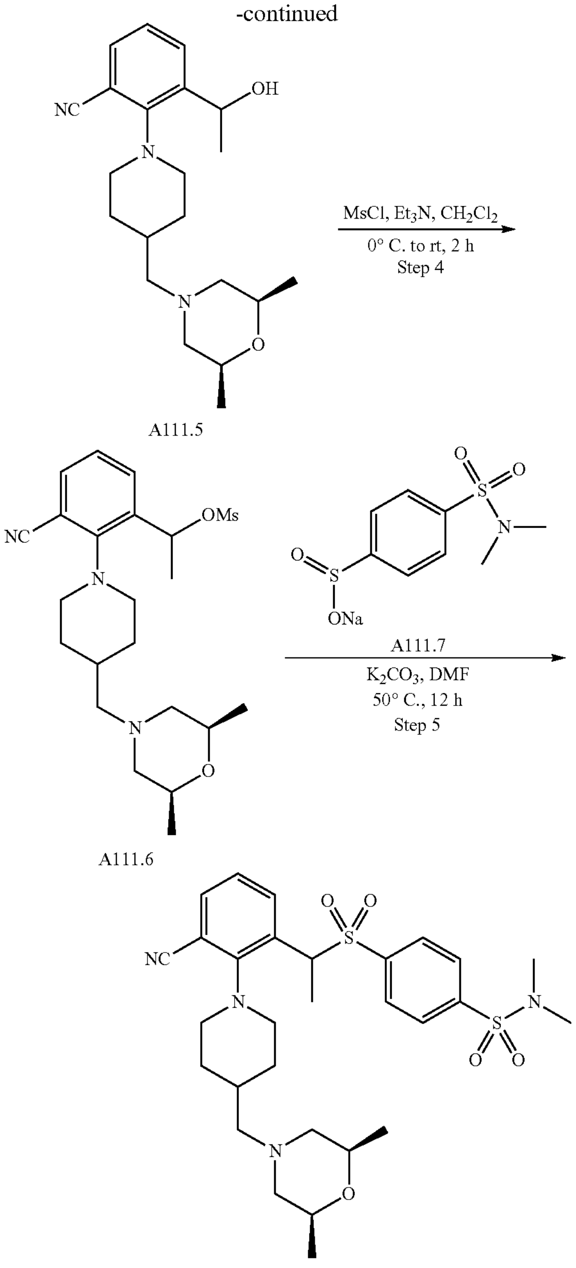

A111.5

A111.6

A-842, A-854 and A-845

Step-1. Synthesis of 1-(3-bromo-2-(4-((2,6-dimethylmorpholino)methyl)piperidin-1-yl)phenyl)ethan-1-one (A111.3)

To a stirred solution of cis-2,6-dimethyl-4-(piperidin-4-ylmethyl)morpholine trifluoroacetate salt (A111.2) (7.0 g, 21.4 mmol, 1 eq), 1-(3-bromo-2-fluorophenyl)ethan-1-one (A111.1) (4.65 g, 21.4 mmol, 1 eq) in DMF (40 mL) was added $K_2CO_3$ (11.85 g, 84.0 mmol, 4 eq). The reaction mixture was stirred at 80° C. for 12 h. The progress of the reaction was monitored by TLC. After completion of the reaction, the reaction mixture was diluted with water and extracted with ethyl acetate. The combined organic layers were dried over anhydrous $Na_2SO_4$, filtered and concentrated under reduced pressure to dryness. The crude product was purified by flash column chromatography to afford 1-(3-bromo-2-(4-((2,6-dimethylmorpholino)methyl)piperidin-1-yl)phenyl)ethan-1-one (A111.3) (3.5 g, 39%). LCMS: 411.0 $[M+H]^+$.

Step-2. Synthesis of 3-acetyl-2-(4-((2,6-dimethylmorpholino)methyl)piperidin-1-yl)benzonitrile (A111.4)

To a stirred solution of 1-(3-bromo-2-(4-((2,6-dimethylmorpholino)methyl)piperidin-1-yl)phenyl)ethan-1-one (A111.3) (3.5 g, 8.5 mmol, 1 eq) in NMP (10 mL) was added CuCN (3.5 g, 8.5 mmol, 1 eq) at room temperature. The reaction mixture was stirred at 140° C. for 12 h. The progress of the reaction was monitored by TLC. After completion of reaction, the reaction mixture was allowed to cool to room temperature, diluted with water and extracted with ethyl acetate. The combined organic layers were dried over anhydrous $Na_2SO_4$, filtered and concentrated under reduced pressure to dryness. The crude was purified by flash column chromatography to afford 3-acetyl-2-(4-((2,6-dimethylmorpholino)methyl)piperidin-1-yl)benzonitrile (A111.4) (1.7 g, 55%). LCMS: 355.84 $[M+H]^+$.

Step-3. Synthesis of 2-(4-((2,6-dimethylmorpholino)methyl)piperidin-1-yl)-3-(1-hydroxyethyl)benzonitrile (A111.5)

To a stirred solution of 3-acetyl-2-(4-((2,6-dimethylmorpholino)methyl)piperidin-1-yl)benzonitrile (A111.4) (1.7 g, 4.78 mmol, 1 eq) in THE (30 mL) and MeOH (10 mL) was added $NaBH_4$ (0.35 g, 9.57 mmol, 2 eq) at 0° C. The resulting reaction mixture was stirred at room temperature for 3 h. The progress of the reaction was monitored by TLC. After completion of the reaction, the reaction mixture was quenched with ice cold water and extracted with ethyl acetate. The combined organic layers were dried over anhydrous $Na_2SO_4$, filtered and concentrated under reduced pressure to dryness to afford 2-(4-((2,6-dimethylmorpholino)methyl)piperidin-1-yl)-3-(1-hydroxyethyl)benzonitrile (A111.5) (1.2 g, 70%). This compound was used in the next step without further purification. LCMS: 357.90 $[M+H]^+$.

Step-4. Synthesis of 1-(3-cyano-2-(4-((2,6-dimethylmorpholino)methyl)piperidin-1-yl)phenyl)ethyl methanesulfonate (A111.6)

To a stirred solution of 2-(4-((2,6-dimethylmorpholino)methyl)piperidin-1-yl)-3-(1-hydroxyethyl)benzonitrile (A111.5) (1.0 g, 2.8 mmol, 1 eq) in DCM (50 mL) was added $Et_3N$ (1.17 mL, 8.4 mmol, 3 eq) followed by MsCl (0.32 mL, 4.2 mmol, 1.5 eq) and catalytic quantity of DMAP at 0° C. The resulting reaction mixture was stirred at room temperature for 2 h. The progress of the reaction was monitored by TLC. After completion of the reaction, the reaction mixture was quenched with water and extracted DCM. The combined organic layers were dried over anhydrous $Na_2SO_4$, filtered and concentrated under reduced pressure to dryness to afford 1-(3-cyano-2-(4-((2,6-dimethylmorpholino)methyl)piperidin-1-yl)phenyl)ethyl methanesulfonate (A111.6) (1.2 g, crude). This compound was used in the next step without further purification.

Step-5. Synthesis of 4-((1-(3-cyano-2-(4-((2,6-dimethylmorpholino)methyl)piperidin-1-yl)phenyl)ethyl)sulfonyl)-N,N-dimethylbenzenesulfonamide (A-842, A-854 and A-845)

To a stirred solution of 1-(3-cyano-2-(4-((2,6-dimethylmorpholino)methyl)piperidin-1-yl)phenyl)ethyl methanesulfonate (A111.6) (1.2 g, 2.7 mmol, 1 eq), sodium 4-(N,N-dimethylsulfamoyl)benzenesulfinate (A111.7) (0.89 g, 3.3 mmol, 1.2 eq) in DMF (20 mL) was added $K_2CO_3$ (1.14 g, 8.2 mmol, 3 eq). The reaction mixture was stirred at 70° C. for 12 h in a sealed tube. The progress of the reaction was monitored by TLC. After completion of the reaction, the reaction mixture was diluted with water and extracted with ethyl acetate. The combined organic layers were dried over anhydrous $Na_2SO_4$, filtered and concentrated under reduced pressure to dryness. The crude product was purified by flash column chromatography followed by reverse phase preparative HPLC to afford 4-((1-(3-cyano-2-(4-((2,6-dimethylmorpholino)methyl)piperidin-1-yl)phenyl)ethyl)sulfonyl)-N,N-dimethylbenzenesulfonamide (A-842) (0.38 g, 23%). A-842 (200 mg) was further purified by chiral separation to afford A-854 and A-845.

A-842: Yield: 0.38 g, 23%; Appearance: Off-white solid; $^1H$ NMR (400 MHz, DMSO-$d_6$) $^1H$ NMR (400 MHz, CHLOROFORM-d) δ 7.94-7.90 (m, 3H), 7.79-7.75 (m, 3H), 7.48 (t, J=7.8 Hz, 1H), 5.27 (q, J=7.2 Hz, 1H), 3.56-3.52 (m, 2H), 2.97-2.92 (m, 1H), 2.77-2.69 (m, 3H), 2.64 (s, 6H), 2.17 (d, J=6.8 Hz, 2H), 1.87-1.85 (m, 1H), 1.76-1.64 (m, 4H), 1.61-1.53 (m, 4H), 1.24-1.17 (m, 1H), 1.06 (d, J=6.0 Hz, 6H); HPLC purity: 99.46%; LCMS calculated for $C_{29}H_{40}N_4O_5S_2$: 588.24 Observed: 589.1 $[M+H]^+$.

A-854: Yield: 0.03 g; Appearance: Off-white solid; $^1H$ NMR (400 MHz, DMSO-$d_6$) δ 7.92 (d, J=6.4 Hz, 3H), 7.76 (d, J=6.4 Hz, 3H), 7.46 (t, J=7.38 Hz, 1H), 5.25 (d, J=6.8 Hz, 1H), 3.60-3.48 (m, 2H), 3.25-3.15 (m, 2H), 2.95 (t, J=11.2 Hz, 1H), 2.78-2.69 (m, 3H), 2.64 (s, 6H), 2.16 (d, J=4.8 Hz, 2H), 1.86 (d, J=8.39 Hz, 1H), 1.76-1.51 (m, 8H), 1.26-1.15 (m, 1H), 1.05 (d, J=5.6 Hz, 6H); HPLC purity: 98.99%; LCMS calculated for $C_{29}H_{40}N_4O_5S_2$: 588.24 Observed: 589.1 $[M+H]^+$. METHOD: Column: YMC CHIRAL ART CELLULOSE-SC, 250 mm*4.6 mm, 5 u; Mobile Phase: A: n-HEXANE+0.1% TFA; B:DCM:MEOH (50:50); Flow rate: 1.00 mL/min; Isocratic: 20% B; Ret. Time: 18.472

A-845: Yield: 0.021 g; Appearance: White solid; $^1H$ NMR (400 MHz, DMSO-$d_6$) δ 7.96-7.88 (m, 3H), 7.81-7.73 (m, 3H), 7.46 (t, J=7.6 Hz, 1H), 7.2 (d, J=7.12 Hz, 1H), 3.58-3.48 (m, 2H), 3.24-3.20 (m, 1H), 2.96-2.90 (m, 1H), 2.80-2.68 (m, 3H), 2.63 (s, 6H), 2.16 (d, J=6.4 Hz, 2H), 1.92-1.79 (m, 1H), 1.77-1.71 (m, 1H), 1.68 (d, J=6.8 Hz, 3H), 1.64-1.51 (m, 3H), 1.27-1.19 (m, 1H), 1.05 (d, J=5.6 Hz, 6H); HPLC purity: 97.28%; LCMS calculated for $C_{29}H_{40}N_4O_5S_2$: 588.24 Observed: 589.1 $[M+H]^+$. METHOD: Column: YMC CHIRAL ART CELLULOSE-SC, 250 mm*4.6 mm, Su; Mobile Phase: A: n-HEXANE+0.1% TFA; B:DCM:MEOH (50:50); Flow rate: 1.00 mL/min; Isocratic: 20% B; Ret. Time: 19.642.

Example A112: Synthesis of trans-N-(2-(4-((3,5-dimethylmorpholino)methyl)piperidin-1-yl)-3-fluorophenyl)-4-(methylsulfonyl)benzenesulfonamide (A-838)

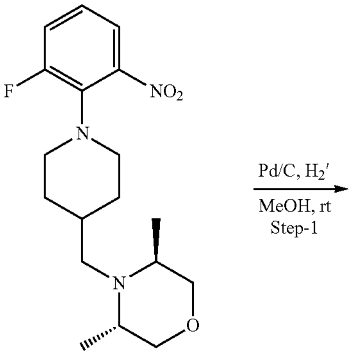

A112.1

Step-1. Synthesis of rel-2-(4-((3,5-dimethylmorpholino)methyl)piperidin-1-yl)-3-fluoroaniline (A112.2)

To a stirred solution of rel-4-((1-(2-fluoro-6-nitrophenyl)piperidin-4-yl)methyl)-3,5-dimethylmorpholine (A112.1) (0.28 g, 0.8 mmol, 1 eq) in MeOH (5 mL) was added Pd/C (20%, 0.2 g) under nitrogen atmosphere. The resulting reaction mixture was hydrogenated at room temperature for 2 h. The progress of the reaction was monitored by TLC. After completion of the reaction, the reaction mixture was filtered through celite and concentrated under reduced pressure to afford rel-2-(4-((3,5-dimethylmorpholino)methyl)piperidin-1-yl)-3-fluoroaniline (A112.2) (0.26 g, crude). This compound was used in the next step without further purification. LCMS: 322.20 $[M+H]^+$.

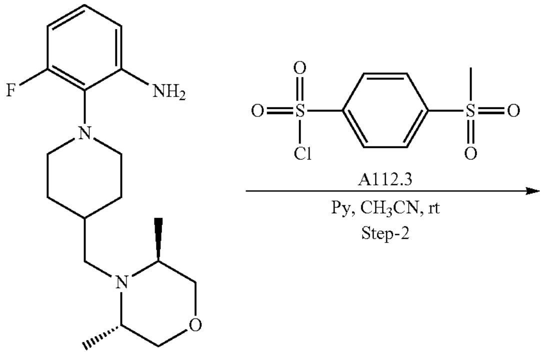

A112.2

Step-2. Synthesis of rel-N-(2-(4-((3,5-dimethylmorpholino)methyl)piperidin-1-yl)-3-fluorophenyl)-4-(methylsulfonyl)benzenesulfonamide (A-838)

To a stirred solution of rel-2-(4-((3,5-dimethylmorpholino)methyl)piperidin-1-yl)-3-fluoroaniline (A112.2) (0.26 g, 0.81 mmol, 1 eq) and 4-(methylsulfonyl)benzenesulfonyl chloride (A112.3) (0.25 g, 0.98 mmol, 1.2 eq) in acetonitrile (5 mL) was added pyridine (0.13 g, 1.62 mmol, 2 eq) at 0° C. and the reaction mixture was stirred at room temperature for 4 h. The progress of the reaction was monitored by TLC. After completion of reaction, the reaction mixture was quenched with water and extracted with ethyl acetate. The combined organic layers were dried over anhydrous $Na_2SO_4$, filtered and concentrated under reduced pressure to dryness. The crude product was purified by flash column chromatography by using (EtOAc/n-hexane: 20%) as eluent followed by reverse phase preparative HPLC to afford rel-N-(2-(4-((3,5-dimethylmorpholino)methyl)piperidin-1-yl)-3-fluorophenyl)-4-(methylsulfonyl)benzenesulfonamide (A-838). Yield: 0.035 g, 8%; Appearance: Off white solid; $^1H$ NMR (400 MHz, DMSO-$d_6$) δ 9.21 (bs, 1H), 8.09 (d, J=7.6 Hz, 2H), 8.01 (d, J=8 Hz, 2H), 7.20-7.13 (m, 1H), 6.99-6.89 (m, 1H), 3.58-3.50 (m, 2H), 3.26 (s, 3H), 3.23-3.20 (m, 1H), 2.84-2.68 (m, 4H), 2.45-2.38 (m, 2H), 2.32 (d, J=9.78 Hz, 1H), 1.61 (d, J=12.4, 1H), 1.54 (d, J=11.6, 1H), 1.42-1.32 (m, 1H), 1.24-1.12 (m, 3H), 0.90 (d, J=5.87 Hz, 6H); HPLC purity: 97.11%; LCMS calculated for $C_{25}H_{34}FN_3O_5S_2$:539.19, Observed: 540.95 $[M+H]^+$.

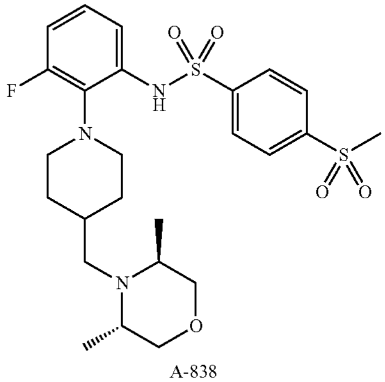
A-838

The following example was prepared using standard chemical manipulations and procedures similar to those used for the preparation of the previous example.

| Compound No. | Structure | Yields/Analytical data |
|---|---|---|
| A-866 | 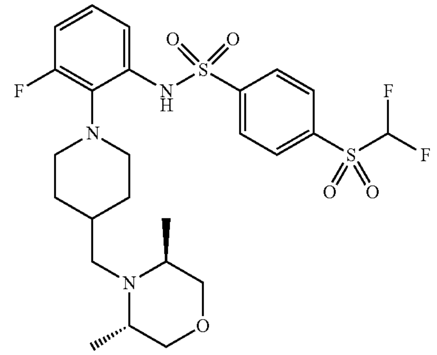 [SMILES: C[C@H]1COC[C@H](C)N1CC1CCN(c2c(F)cccc2NS(=O)(=O)c2ccc(S(=O)(=O)C(F)F)cc2)CC1] | Yield: 0.25 g, 23%; Appearance: Off white solid; $^1$H NMR (400 MHz, DMSO-$d_6$) δ 9.43 (brs, 1H), 8.28-8.21 (m, 2 H), 8.20-8.13 (m, 2 H), 7.59-7.19 (t, 3 H), 7.10-7.00 (m, 1 H), 3.61 (d, J = 8.80 Hz, 2 H), 3.34-3.25 (m, 2 H), 2.89-2.70 (m, 4 H), 2.49-2.37 (m, 2 H), 2.34-2.24 (m, 1 H), 2.22-2.12 (m, 1 H), 1.64 (d, J = 11.74 Hz, 1 H), 1.55 (d, J = 10.27 Hz, 1 H), 1.48-1.36 (m, 1 H), 1.34-1.14 (m, 2H), 0.97 (d, J = 5.38 Hz, 6 H); HPLC purity: 98.38%; LCMS calculated for $C_{25}H_{32}F_3N_3O_5S_2$: 575.17, Observed: 576.0 [M + H]$^+$. |

Example A113: Synthesis of N1-(5-fluoro-4-(piperidin-1-yl)pyridin-3-yl)-$N^4$,$N^4$-dimethylbenzene-1,4-disulfonamide (A-856)

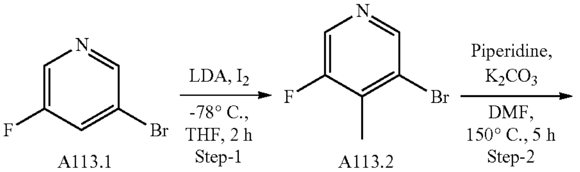

A113.1 A113.2

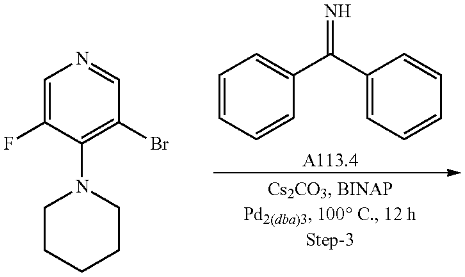

A113.3

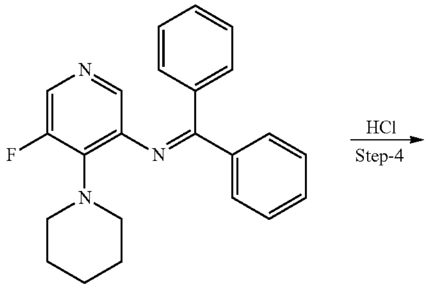

A113.5

-continued

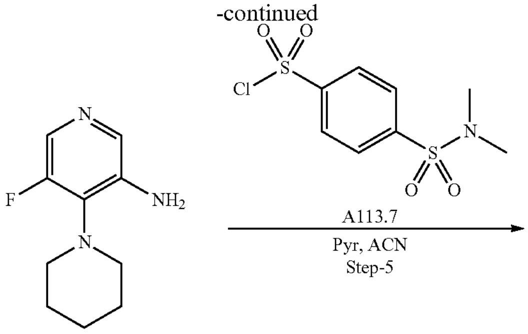

A113.6

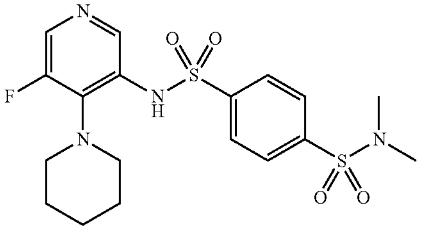

A-856

Step-1. Synthesis of 3-bromo-5-fluoro-4-iodopyridine (A113.2)

To a stirred solution of 3-bromo-5-fluoropyridine (A113.1) (4.0 g, 22.72 mmol, 1 eq) in THF (10 mL) was added LDA (1 M in THF, 34 mL, 34 mmol, 1.5 eq) at −78° C. followed by the addition of iodine (6.9 gm in THF, 27.2 mmol, 1.2 eq) at the same temperature after stirring for 15 minutes. The reaction mixture was stirred at −78° C. for 2 h. The progress of the reaction was monitored by TLC. After completion of the reaction, the reaction mixture slowly quenched with saturated $NH_4Cl$ solution and extracted with ethyl acetate. The combined organic layers were dried over anhydrous $Na_2SO_4$, filtered and concentrated under reduced pressure to dryness. The crude product was purified by flash column chromatography to afford 3-bromo-5-fluoro-4-iodopyridine (A113.2) (6.1 g, 89.70%). LCMS: 301.65 [M+H]$^+$.

Step-2. Synthesis of 3-bromo-5-fluoro-4-(piperidin-1-yl)pyridine (A113.3)

To a stirred solution of 3-bromo-5-fluoro-4-iodopyridine (A113.2) (5.1 g, 16.94 mmol, 1 eq), piperidine (1.7 g, 20.33 mmol, 1.2 eq) in DMF (60 mL) was added $K_2CO_3$ (4.6 g, 33.8 mmol, 2 eq). The reaction mixture was stirred at 150° C. for 5 h. The progress of the reaction was monitored by TLC. After completion of the reaction, the reaction mixture was diluted with water and extracted with ethyl acetate. The combined organic layers were dried over anhydrous $Na_2SO_4$, filtered and concentrated under reduced pressure to dryness. The crude product was purified by flash column chromatography to afford 3-bromo-5-fluoro-4-(piperidin-1-yl)pyridine (A113.3) (2.0 g, 45.76%). LCMS: 259.1 $[M+H]^+$.

Step-3. Synthesis of N-(5-fluoro-4-(piperidin-1-yl) pyridine-3-yl)-1,1-diphenylmethanimine (A113.5)

To a stirred solution of 3-bromo-5-fluoro-4-(piperidin-1-yl)pyridine (A113.3) (1.8 g, 6.97 mmol, 1 eq) in toluene (25 mL) was added diphenylmethanimine (A113.4) (1.5 g, 8.37 mmol, 1.2 eq), cesium carbonate (4.5 g, 13.95 mmol, 2 eq) at room temperature, degassed for 20 minutes by using nitrogen gas followed by the addition of tris(dibenzylideneacetone)dipalladium(0) (0.32 g, 0.35 mmol, 0.05 eq) and BINAP (0.433 g, 0.7 mmol, 0.1 eq) under a nitrogen atmosphere. The resulting reaction mixture was stirred at 100° C. for 12 h. The progress of the reaction was monitored by TLC. After completion of the reaction, the reaction mixture was quenched with ice cold water and extracted with ethyl acetate. The combined organic layers were dried over anhydrous $Na_2SO_4$, filtered and concentrated under reduced pressure to dryness. The crude product was purified by column chromatography on silica gel to afford N-(5-fluoro-4-(piperidin-1-yl)pyridine-3-yl)-1,1-diphenylmethanimine (A113.5) (1.4 g, 56%). LCMS: 359.76 $[M+H]^+$.

Step-4. Synthesis of 5-fluoro-4-(piperidin-1-yl)pyridine-3-amine (A113.6)

To a stirred solution of N-(5-fluoro-4-(piperidin-1-yl) pyridine-3-yl)-1,1-diphenylmethanimine (A113.5) (0.7 g, 1.95 mmol, 1 eq) in THE (10 mL) was added aqueous HCl (2 M, 2.9 mL, 5.85 mmol, 3 eq) at 0° C. The reaction mixture was stirred at room temperature for 5 h. The progress of the reaction was monitored by TLC. After completion of reaction, the reaction mixture was quenched by using saturated sodiumbicarbonate solution and extracted with ethylacetate. The combined organic layers were dried over anhydrous $Na_2SO_4$, filtered and concentrated under reduced pressure to dryness. The crude product was purified by column chromatography on silica gel to afford to afford 5-fluoro-4-(piperidin-1-yl)pyridine-3-amine (A113.6) (0.3 g, 78.94%). LCMS: 195.68 $[M+H]^+$.

Step-5. Synthesis of N-(5-fluoro-4-(piperidin-1-yl) pyridin-3-yl)-N4,N4-dimethylbenzene-1,4-disulfonamide (A-856)

To a stirred solution of 5-fluoro-4-(piperidin-1-yl)pyridine-3-amine (A113.6) (0.3 g, 1.54 mmol, 1 eq) and 4-(N,N-dimethylsulfamoyl)benzenesulfonyl chloride (A113.7) (0.653 g, 2.31 mmol, 1.5 eq) in acetonitrile (10 mL) was added pyridine (0.243 g, 3.08 mmol, 2 eq) and the reaction mixture was stirred at room temperature for 12 h. The progress of the reaction was monitored by TLC. After completion of reaction, the reaction mixture was concentrated under reduced pressure, quenched with water and extracted with ethyl acetate. The combined organic layers were dried over anhydrous $Na_2SO_4$, filtered and concentrated under reduced pressure to dryness. The crude product was purified by combiflash followed by preparative HPLC to afford N1-(5-fluoro-4-(piperidin-1-yl)pyridin-3-yl)-$N^4$,N4-dimethylbenzene-1,4-disulfonamide (A-856). Yield: 0.065 g, 9.5%; Appearance: Off white solid; 1H NMR (400 MHz, DMSO-$d_6$) δ 9.98 (bs, 1H), 8.19 (d, J=2.93 Hz, 1H), 8.00-7.89 (m, 4H), 7.63 (s, 1H), 3.05-2.98 (m, 4H), 2.64 (s, 6H), 1.55-1.48 (m, 6H); HPLC purity: 99.40%; LCMS calculated for $C_{18}H_{23}FN_4O_4S_2$: 442.11 Observed: 442.9 $[M+H]^+$.

Example A114: Synthesis of 4-(((R)-1-(2-(4,4-difluoropiperidin-1-yl)-3-fluorophenyl)ethyl)sulfonyl)-N,N-dimethylbenzenesulfonimidamide (A-884)

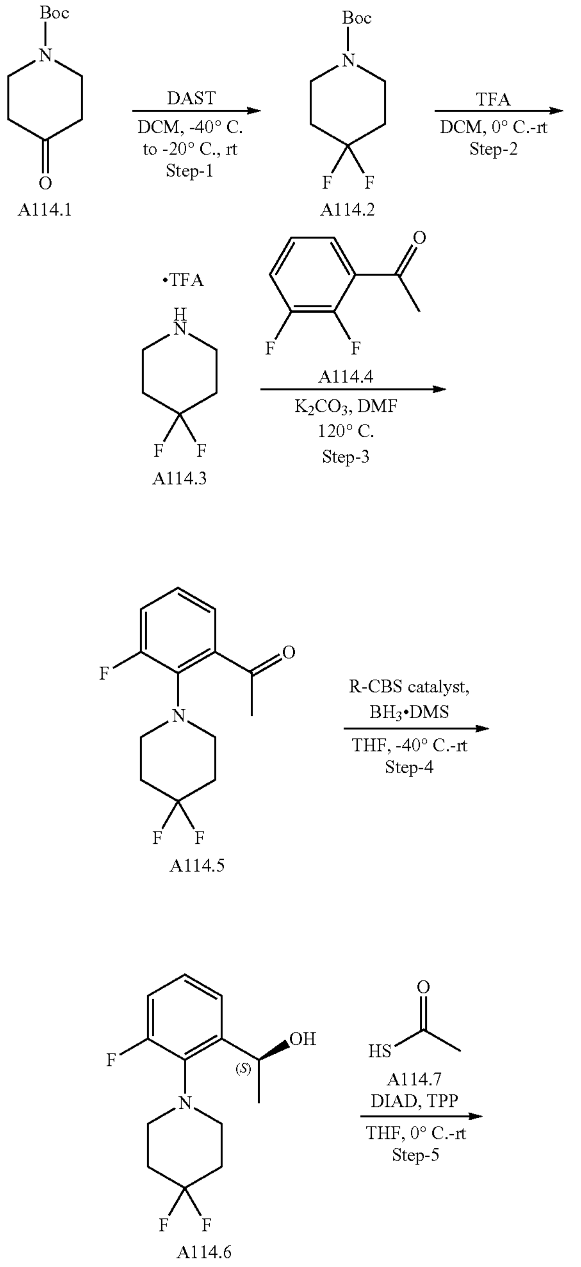

-continued

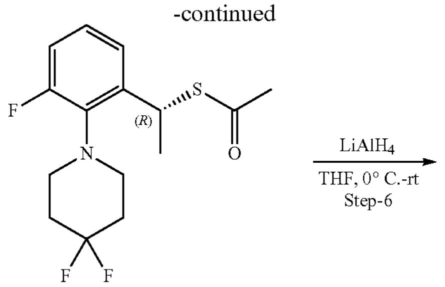

A114.8

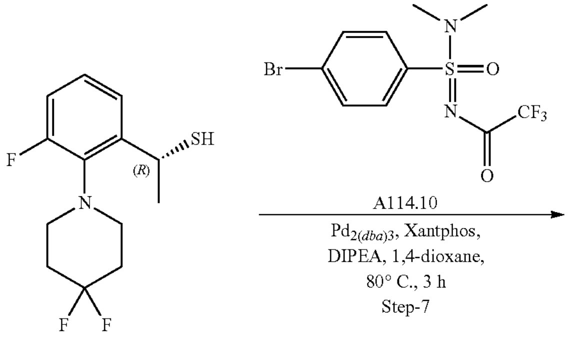

A114.9

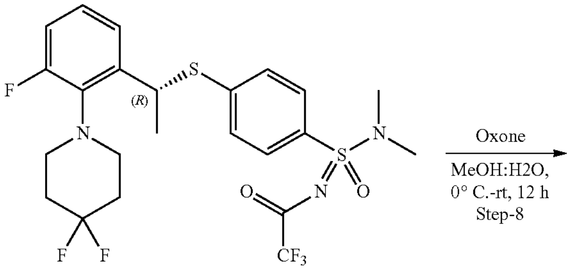

A114.11

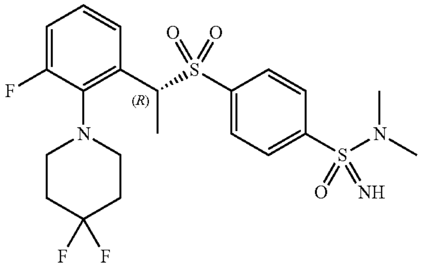

A-884

Step-1. Synthesis of tert-butyl 4,4-difluoropiperidine-1-carboxylate (A114.2)

To a stirred solution of tert-butyl 4-oxopiperidine-1-carboxylate (A114.1) (3.0 g, 15.06 mmol, 1 eq) in DCM (30 mL) was added DAST (5.2 mL, 45.19 mmol, 3 eq) at −40° C. The resulting reaction mixture was stirred at −40° C. for 2 h and then at room temperature for 1 h. The progress of the reaction was monitored by TLC. After completion of the reaction, the reaction mixture was quenched with saturated $NaHCO_3$ solution and extracted with DCM. The combined organic layer was dried over anhydrous $Na_2SO_4$, filtered and concentrated under reduced pressure. The crude product was purified by column chromatography on silica gel to afford tert-butyl 4,4-difluoropiperidine-1-carboxylate (A114.2) (2.5 g, 75%) as an off white solid.

Step-2. Synthesis of 4,4-difluoropiperidine TFA Salt (A114.3)

To a stirred solution of tert-butyl 4,4-difluoropiperidine-1-carboxylate (A114.2) (1.5 g, 6.78 mmol, 1 eq) in DCM (15 mL) was added TFA (7.5 mL) at 0° C. The reaction mixture was stirred at room temperature for 2 h. After completion of the reaction, the reaction mixture was concentrated under reduced pressure to afford 4,4-difluoropiperidine TFA Salt (A114.3) (3.0 g, crude). This compound was used in the next step without further purification.

Step-3. Synthesis of 1-(2-(4,4-difluoropiperidin-1-yl)-3-fluorophenyl)ethan-1-one (A114.5)

To a stirred solution of 4,4-difluoropiperidine TFA Salt (A114.3) (2.0 g, 8.50 mmol, 1 eq) and 1-(2,3-difluorophenyl)ethan-1-one (A114.4) (1.46 g, 9.35 mmol, 1.1 eq) in DMF (20 mL) was added $K_2CO_3$ (2.35 g, 17.01 mmol, 2 eq). The reaction mixture was stirred at 120° C. for 12 h in a sealed tube. The progress of the reaction was monitored by TLC. After completion of reaction, the reaction mixture was allowed to cool to room temperature, diluted with water and extracted with ethyl acetate. The combined organic layers were dried over anhydrous $Na_2SO_4$, filtered and concentrated under reduced pressure to dryness. The crude was purified by column chromatography to afford 1-(2-(4,4-difluoropiperidin-1-yl)-3-fluorophenyl)ethan-1-one (A114.5) (1.0 g, 46%) as a pale brown oil. LCMS: 258.11 $[M+H]^+$.

Step-4. Synthesis of (S)-1-(2-(4,4-difluoropiperidin-1-yl)-3-fluorophenyl)ethan-1-ol (A114.6)

To a stirred solution of 1-(2-(4,4-difluoropiperidin-1-yl)-3-fluorophenyl)ethan-1-one (A114.5) (1.0 g, 3.88 mmol, 1 eq) in THE (20 mL) was added (R)-2-Methyl-CBS-oxazaborolidine (1 M in Toluene, 0.8 mL, 0.77 mmol, 0.2 eq) at −40° C. The reaction mixture was allowed to stir for 5 min, and then $BH_3$.DMS (2 M in THF, 3.9 mL, 7.77 mmol, 2.0 eq) was added dropwise at −40° C. The reaction mixture was stirred at −40° C. for 1 h and then at the same temperature for 30 min. The progress of the reaction was monitored by TLC. After completion of the reaction, the reaction mixture was cooled to 0° C. and quenched with dropwise addition of MeOH and water. The resulting solution was extracted with ethyl acetate. The combined organic layers were dried over anhydrous $Na_2SO_4$, filtered and concentrated under reduced pressure to dryness. The crude was purified by column chromatography to afford (S)-1-(2-(4,4-difluoropiperidin-1-yl)-3-fluorophenyl)ethan-1-ol (A114.6) (0.85 g, 85%) as an off white solid. LCMS: 260.12 $[M+H]^+$.

Step-5. Synthesis of (R)—S-(1-(2-(4,4-difluoropiperidin-1-yl)-3-fluorophenyl)ethyl) ethanethioate (A114.8)

To a stirred solution of Triphenyl phosphine (1.72 g, 6.56 mmol, 2 eq) in THE (20 mL) was added DIAD (1.2 mL, 6.23 mmol, 1.9 eq) dropwise at 0° C. The reaction mixture was allowed to stir at 0° C. for 30 min. and then a mixture of (S)-1-(2-(4,4-difluoropiperidin-1-yl)-3-fluorophenyl)ethan-1-ol (A114.6) (850 mg, 3.28 mmol, 1 eq) and ethanethioic S-acid (A114.7) (0.45 mL, 5.90 mmol, 1.8 eq) dissolved in THE (5 mL) were added at 0° C. The reaction mixture was warmed to room temperature and stirred for 1 h. The progress of the reaction was monitored by TLC. After completion of the reaction, the reaction mixture was diluted with EtOAc and washed with water. The organic layer was dried over anhydrous $Na_2SO_4$, filtered and concentrated under reduced pressure to dryness. The crude was purified by column chromatography to afford (R)—S-(1-(2-(4,4-difluoropiperidin-1-yl)-3-fluorophenyl)ethyl) ethanethioate (A114.8) (700 mg, 67%) as an yellow oil. LCMS: 318.11 $[M+H]^+$.

Step-6. Synthesis of (R)-1-(2-(4,4-difluoropiperidin-1-yl)-3-fluorophenyl)ethane-1-thiol (A114.9)

To a stirred solution of (R)—S-(1-(2-(4,4-difluoropiperidin-1-yl)-3-fluorophenyl)ethyl) ethanethioate (A114.8) (700 mg, 2.20 mmol, 1 eq) in THE (15 mL) was added a 1 M solution of lithium aluminium hydride (4.4 mL, 4.41 mmol, 2 eq) dropwise at 0° C. The reaction mixture was warmed to room temperature and stirred for 1 h. The progress of the reaction was monitored by TLC. After completion of reaction, the reaction mixture was quenched with EtOAc and ice-water. The resulting solution was then extracted with EtOAc, dried over anhydrous $Na_2SO_4$, filtered and concentrated under reduced pressure to dryness. The crude was purified by column chromatography to afford (R)-1-(2-(4,4-difluoropiperidin-1-yl)-3-fluorophenyl)ethane-1-thiol (A114.9) (535 mg, 88%) as a pale yellow oil. LCMS: 276.10 $[M+H]^+$.

Step-7. Synthesis of N-((4-(((R)-1-(2-(4,4-difluoropiperidin-1-yl)-3-fluorophenyl)ethyl)thio)phenyl)(dimethylamino)(oxo)-16-sulfaneylidene)-2,2,2-trifluoroacetamide (A114.11)

A pyrex tube was charged with (R)-1-(2-(4,4-difluoropiperidin-1-yl)-3-fluorophenyl)ethane-1-thiol (A114.9) (524.5 mg, 1.90 mmol, 1.05 eq), N-((4-bromophenyl)(dimethylamino)(oxo)-16-sulfaneylidene)-2,2,2-trifluoroacetamide (A114.10) (650 mg, 1.81 mmol, 1 eq), and DIPEA (0.63 mL, 3.63 mmol, 2 eq) in 1,4-dioxane (20 mL). The tube was sealed with a septum and the reaction mixture was purged with argon for 15 min. Tris(dibenzylideneacetone)dipalladium(0) (49.9 mg, 0.05 mmol, 0.03 eq) and Xantphos (63 mg, 0.10 mmol, 0.06 eq) were added to the reaction mixture under an argon atmosphere. The tube was then fitted with a screw cap and the reaction mixture was heated at 80° C. for 5 h. The progress of the reaction was monitored by TLC. After completion of the reaction, the reaction mixture was cooled to room temperature and diluted with water. The resulting solution was extracted in ethyl acetate. The combined organic layers were washed with water and brine, dried over anhydrous $Na_2SO_4$, filtered and concentrated under reduced pressure to dryness. The crude product was purified by column chromatography on silica gel to afford N-((4-(((R)-1-(2-(4,4-difluoropiperidin-1-yl)-3-fluorophenyl)ethyl)thio)phenyl)(dimethylamino)(oxo)-16-sulfaneylidene)-2,2,2-trifluoroacetamide (A114.11) (900 mg, 90%) as a pale brown semi-solid. LCMS: 604.25 $[M+H]^+$.

Step-8. Synthesis of 4-(((R)-1-(2-(4,4-difluoropiperidin-1-yl)-3-fluorophenyl)ethyl)sulfonyl)-N,N-dimethylbenzenesulfonimidamide (A-884)

To a stirred solution of N-((4-(((R)-1-(2-(4,4-difluoropiperidin-1-yl)-3-fluorophenyl)ethyl)thio)phenyl)(dimethylamino)(oxo)-16-sulfaneylidene)-2,2,2-trifluoroacetamide (A114.11) (400 mg, 0.72 mmol, 1 eq) in MeOH:$H_2O$ (6.4 mL: 1.6 mL) was added oxone (667 mg, 2.16 mmol, 3 eq) at 0° C. The reaction mixture was warmed to room temperature and stirred for 12 h. The progress of the reaction was monitored by TLC. After completion of reaction, the reaction mixture was quenched with ice-water. The resulting precipitate was filtered and washed with aqueous saturated $NaHCO_3$ solution and water. The obtained solid was dried under vacuum and purified by reverse phase preparative HPLC followed by Chiral HPLC to afford 4-(((R)-1-(2-(4,4-difluoropiperidin-1-yl)-3-fluorophenyl)ethyl)sulfonyl)-N,N-dimethylbenzenesulfonimidamide (A-884). Yield: 13.4 mg, 4%; Appearance: White solid; $^1H$ NMR (400 MHz, DMSO-$d_6$) δ 7.94 (d, J=8.31 Hz, 2H), 7.83 (d, J=8.4 Hz, 2H), 7.40-7.34 (m, 2H), 7.24-7.19 (m, 1H), 5.45-5.43 (m, 1H), 4.63 (br s, 1H), 3.03-3.00 (m, 2H), 2.90-2.80 (m, 1H), 2.56 (s, 6H), 2.35-2.09 (m, 1H), 2.10-1.82 (m, 4H), 1.63 (br d, J=7.34 Hz, 3H); HPLC purity: 99.62%; Chiral HPLC purity: 98.27%; LCMS calculated for $C_2H_6F_3N_3O_3S_2$: 489.57; Observed: 490.25 $[M+H]^+$. Column: YMC CHIRAL ART CELLULOSE-SC, 250 mm*4.6 mm, 5 u; Mobile Phase: A: n-HEXANE+MTBE (50:50)+0.1% Iso-propylamine; B:DCM:MEOH (50:50); Flow rate: 1.00 mL/min; Isocratic: 10% B; Ret. Time: 11.590.

Example A115: Synthetic Scheme for Synthesis of rel-N'-(2-(4-((2,6-dimethylmorpholino)methyl)piperidin-1-yl)-3-fluorophenyl)-N4,N4-dimethylbenzene-1,4-disulfonamide (A-843)

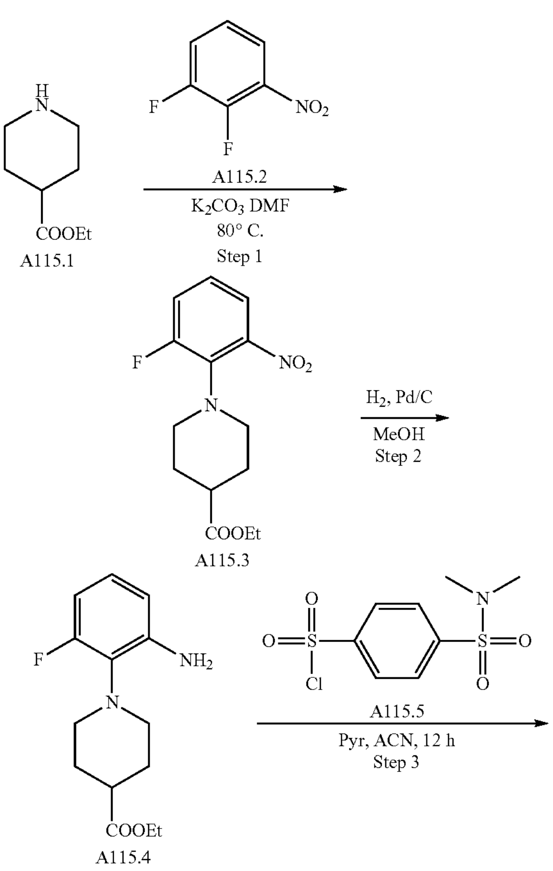

-continued

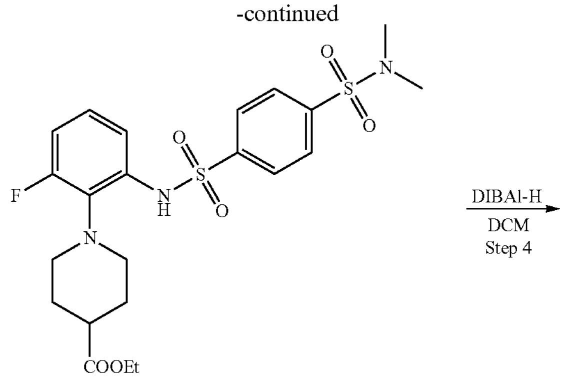

A115.6

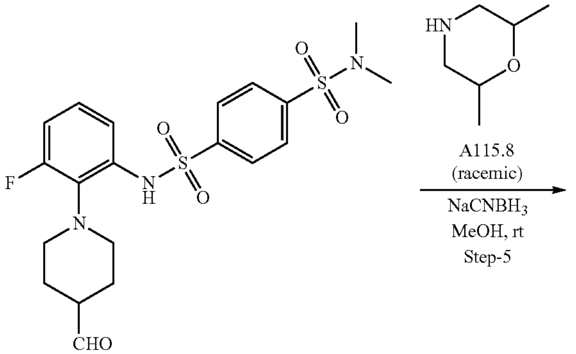

A115.7

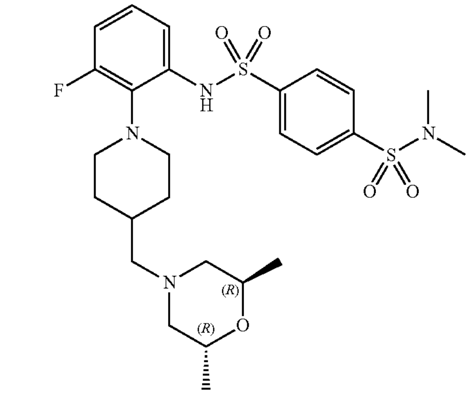

A-843

+

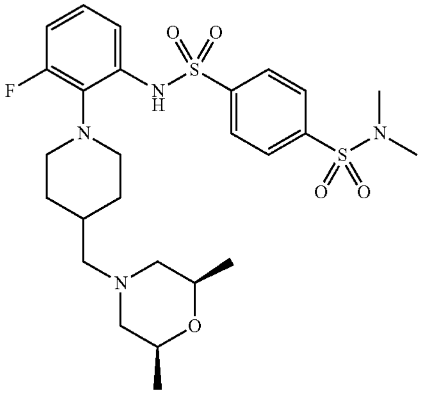

A-755

Step-1. Synthesis of Ethyl 1-(2-fluoro-6-nitrophenyl)piperidine-4-carboxylate (A115.3)

To a stirred solution of ethyl piperidine-4-carboxylate (A115.1) (11.8 g, 75.06 mmol, 1.2 eq) and 1,2-difluoro-3-nitrobenzene (A115.2) (10.0 g, 62.9 mmol, 1 eq) in DMF (50 mL) was added $K_2CO_3$ (17.3 g, 125.8 mmol, 2 eq). The reaction mixture was stirred at 80° C. for 12 h. The progress of the reaction was monitored by TLC. After completion of reaction, the reaction mixture was allowed to cool to room temperature, diluted with water and extracted with ethyl acetate. The combined organic layers were dried over anhydrous $Na_2SO_4$, filtered and concentrated under reduced pressure to dryness. The crude was purified by column chromatography to afford ethyl 1-(2-fluoro-6-nitrophenyl) piperidine-4-carboxylate (A115.3) (12 g, 66.6%). LCMS: 297.18 $[M+H]^+$.

Step-2. Synthesis of ethyl 1-(2-amino-6-fluorophenyl)piperidine-4-carboxylate (A115.4)

An autoclave was charged with a solution of ethyl 1-(2-fluoro-6-nitrophenyl)piperidine-4-carboxylate (A115.3) (12.0 g, 40.54 mmol, 1 eq) in methanol (100 mL) and the reaction mixture was purged with nitrogen for 5 min. 20% Palladium on carbon (1.0 g, 20% w/w) was added to the reaction mixture under nitrogen atmosphere. The reaction mixture was purged with hydrogen and stirred at room temperature for 12 h under hydrogen atmosphere (100 psi). The progress of the reaction was monitored by TLC. After completion of the reaction, the reaction mixture was filtered through a pad of Celite and the Celite pad was washed with ethyl acetate. The filtrate was concentrated under reduced pressure to dryness to afford ethyl 1-(2-amino-6-fluorophenyl)piperidine-4-carboxylate (A115.4) (10.0 g, crude, 93.4%). This compound was used in the next step without further purification. LCMS: 266.79 $[M+H]^+$.

Step-3. Synthesis of Ethyl 1-(2-((4-(N,N-dimethylsulfamoyl)phenyl)sulfonamido)-6-fluorophenyl) piperidine-4-carboxylate (A15.6)

To a stirred solution of ethyl 1-(2-amino-6-fluorophenyl) piperidine-4-carboxylate (A115.4) (1.0 g, 3.76 mmol, 1 eq) and 4-(N,N-dimethylsulfamoyl)benzenesulfonyl chloride (A115.5) (1.28 g, 4.14 mmol, 1.1 eq) in acetonitrile (25 mL) was added pyridine (0.6 mL, 7.52 mmol, 2 eq) and the reaction mixture was stirred at room temperature for 12 h. The progress of the reaction was monitored by TLC. After completion of reaction, the reaction mixture was diluted with water and extracted with ethyl acetate. The combined organic layers were dried over anhydrous $Na_2SO_4$, filtered and concentrated under reduced pressure to dryness. The crude product was purified by combiflash chromatography on silica gel to afford ethyl 1-(2-((4-(N,N-dimethylsulfamoyl)phenyl)sulfonamido)-6-fluorophenyl)piperidine-4-carboxylate (A115.6) (1.2 g, 62.5%). LCMS: 514.1 $[M+H]^+$.

Step-4. Synthesis of N'-(3-fluoro-2-(4-formylpiperidin-1-yl)phenyl)-N4,N4-dimethylbenzene-1,4-disulfonamide (A115.7)

To a stirred solution of ethyl 1-(2-((4-(N,N-dimethylsulfamoyl)phenyl)sulfonamido)-6-fluorophenyl)piperidine-4-carboxylate (A115.6) (1.0 g, 1.95 mmol, 1 eq) in DCM (50 mL) was added DIBAL-H (1 M, 10 mL, 5.85 mmol, 3 eq) at −78° C. and the reaction mixture was stirred at the same temperature for 2 h. The progress of the reaction was monitored by TLC. After completion of reaction, the reaction mixture was quenched with 1N HCl and extracted with DCM. The combined organic layers were dried over anhydrous $Na_2SO_4$, filtered and concentrated under reduced pressure to dryness. The crude product was purified by combiflash chromatography on silica gel to afford N1-(3-fluoro-2-(4-formylpiperidin-1-yl)phenyl)-N4,N4-dimethylbenzene-1,4-disulfonamide (A115.7) (0.8 g, 87.9%).

Step-5. Synthesis of rel-N'-(2-(4-((2,6-dimethylmorpholino)methyl)piperidin-1-yl)-3-fluorophenyl)-N4, N4-dimethylbenzene-1,4-disulfonamide (A-843)

To a stirred solution of N1-(3-fluoro-2-(4-formylpiperidin-1-yl)phenyl)-N4,$N^4$-dimethylbenzene-1,4-disulfonamide (A115.7) (0.5 g, 1.04 mmol, 1 eq) in MeOH (20 mL) was added 2,6-dimethylmorpholine (A115.8) (0.14 g, 1.25 mmol, 1.2 eq) at room temperature, stirred for 30 minutes followed by addition of $NaCNBH_3$ (0.134 g, 2.1 mmol, 2 eq) at 0° C. and stirred at room temperature for 12 h. The progress of the reaction was monitored by TLC. After completion of reaction, the reaction mixture was quenched with water and extracted with ethyl acetate. The combined organic layers were dried over anhydrous $Na_2SO_4$, filtered and concentrated under reduced pressure to dryness to obtain the crude product, which was purified by combiflash chromatography followed by reverse phase preparative HPLC to afford rel-N1-(2-(4-((2,6-dimethylmorpholino)methyl)piperidin-1-yl)-3-fluorophenyl)-N4,N4-dimethylbenzene-1,4-disulfonamide (A-843) (0.075 g, 12.5%) and A-755 (0.125 g, 20.8%). A-843: Yield: 0.075 g, 12.5%; Appearance: Off white solid; $^1H$ NMR (400 MHz, DMSO-$d_6$)$^1H$ NMR (400 MHz, DMSO-$d_6$) δ 9.17 (s, 1H), 7.98-7.90 (m, 4H), 7.26-7.15 (m, 2H), 7.02-6.94 (m, 1H), 3.90-3.85 (m, 2H), 2.79 (br t, J=10.27 Hz, 2H), 2.60 (s, 6H), 2.36-2.25 (m, 3H), 2.15-2.02 (m, 4H), 1.59-1.48 (m, 3H), 1.27-1.15 (m, 2H), 1.12 (d, J=6.36 Hz, 6H); HPLC purity: 99.57%; LCMS calculated for $C_{26}H_{37}FN_4O_5S_2$: 568.22 Observed: 569.20 $[M+H]^+$.

Example A116: Synthesis of N-(2-(4-(1-((2S,6R)-2,6-dimethylmorpholino)ethyl)piperidin-1-yl)-3-fluorophenyl)-4-(N,N-dimethylsulfamidimidoyl)benzenesulfonamide, Isomer-I (A-871) and Isomer-II (A-872)

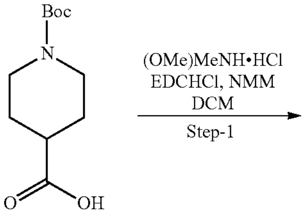

A116.1

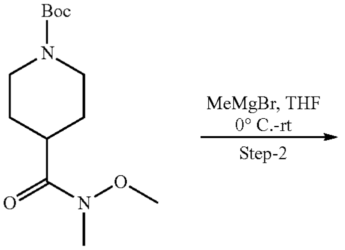

A116.2

-continued

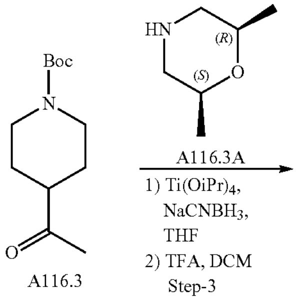

A116.3

Step-3

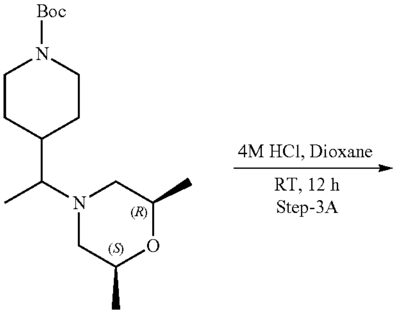

A116.4

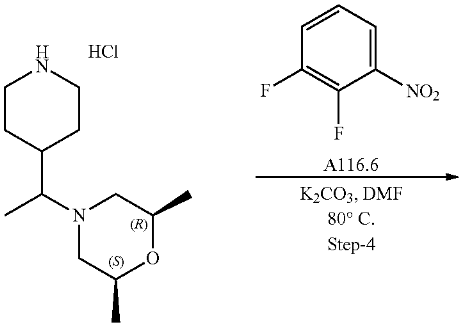

A116.5

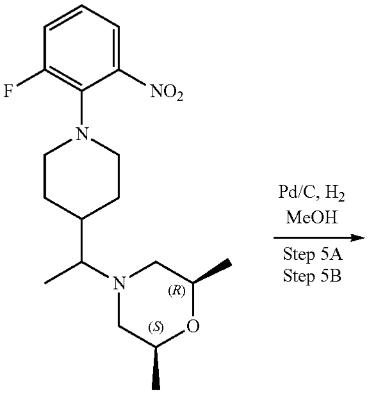

A116.7A Pk-I
A116.7B Pk-II
Chiral separation of 7A & 7B

-continued

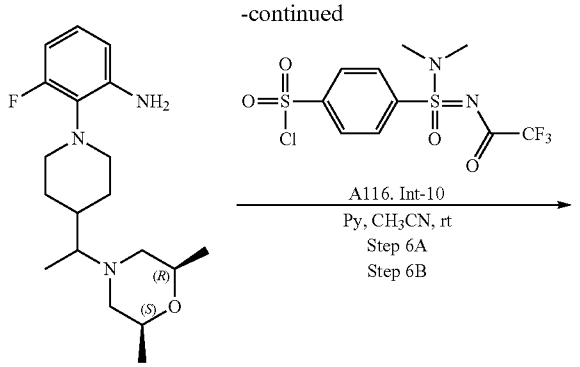

A116.8A
A116.8B

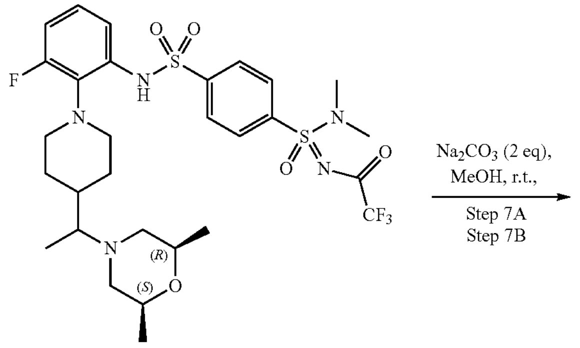

A116.9A
A116.9B

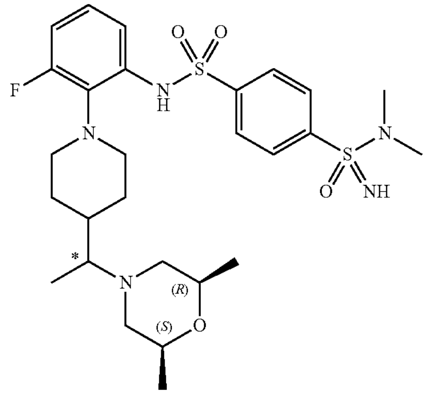

A-871
A-872

Step-1. Synthesis of Synthesis of tert-butyl 4-(methoxy(methyl)carbamoyl)piperidine-1-carboxylate (A116.2)

To a stirred solution of compound A116.1 (6.0 g, 26.2 mmol, 1 eq) in DCM (50 mL) was added N,O-dimethoxy-hydroxyamine (3.3 g, 34.0 mmol, 1.3 eq) and EDC.HCl (11.91 g, 62 mmol, 2.4 eq) at 0° C. followed by the addition of NMM (3.93 g, 39.0 mmol, 1.5 eq). The reaction mixture was stirred at room temperature for 16 h. The progress of the reaction was monitored by TLC. After completion of reaction, the reaction mixture was diluted with water and extracted with DCM. The combined organic layers were dried over anhydrous $Na_2SO_4$, filtered and concentrated under reduced pressure to dryness. The crude product was purified by flash column chromatography to afford title compound A116.2 (6.72 g, 94.38%). LCMS: No ionization.

Step-2. Synthesis of tert-butyl 4-acetylpiperidine-1-carboxylate (A116.3)

To a stirred solution of compound A116.2 (6.6 g, 24.26 mmol, 1 eq) in THF (40 mL) was added methyl magnesium bromide (3 M, 48 mL) −5° C. in 30 minutes. The reaction mixture was stirred at room temperature for 12 h. The progress of the reaction was monitored by TLC. After completion of reaction, the reaction mixture was slowly quenched with saturated $NH_4Cl$ solution (50 mL) at 0° C. and extracted with ethyl acetate. The combined organic layers were dried over anhydrous $Na_2SO_4$, filtered and concentrated under reduced pressure to dryness to afford crude of the titled compound A116.3 (4.68 g, 85.09%). LCMS: No ionization.

Step-3. Synthesis of tert-butyl 4-(1-((2S,6R)-2,6-dimethylmorpholino)ethyl)piperidine-1-carboxylate (A116.4)

To a stirred solution of compound A116.3 (3.5 g, 15.41 mmol, 1 eq) in THE (100 mL) was added compound A116.3A (2.1 g, 18.5 mmol, 1.2 eq) and titanium isopropoxide (13.1 g, 46.23 mmol, 3 eq) at 0° C. and stirred at room temperature for 1 h. To the resultant reaction mixture was added $NaCNBH_3$ (2.4 g, 38.52 mmol, 2.5 eq) portionwise at 0° C. and the reaction mixture was stirred at room temperature for 12 h. The progress of the reaction was monitored by TLC. After completion of reaction, the reaction mixture was concentrated under reduced pressure, quenched with cold water and extracted with ethyl acetate. The combined organic layers were dried over anhydrous $Na_2SO_4$, filtered and concentrated under reduced pressure to dryness. The crude product was purified by flash column chromatography to afford the titled compound A116.4 (2.5 g, 50%). LCMS: 327.1 $[M+H]^+$.

Step-3A. Synthesis of (2S,6R)-2,6-dimethyl-4-(1-(piperidin-4-yl)ethyl)morpholine Hydrochloride (A116.5)

To a stirred solution of compound A116.4 (2.5 g, 7.67 mmol, 1 eq) in dioxane (15 mL) was added 4 M HCl in dioxane (20 mL). The reaction mixture was stirred at room temperature for 12 h. The progress of the reaction was monitored by TLC. After completion of reaction, the reaction mixture was concentrated under reduced pressure to dryness to afford the titled compound A116.5 (2.0 g, 76.9%, crude). This compound was used in the next step without further purification. LCMS: No ionization.

Step-4. Synthesis of (2S,6R)-4-(1-(1-(2-fluoro-6-nitrophenyl)piperidin-4-yl)ethyl)-2,6-dimethylmorpholine (A116.7A & A116.7B)

To a stirred solution of compound A116.5 (2.0 g, 5.88 mmol, 1 eq), compound A116.6 (1.02 g, 6.47 mmol, 1.1 eq) in DMF (20 mL) was added $K_2CO_3$ (1.62 g, 11.77 mmol, 2 eq). The reaction mixture was stirred at 80° C. for 12 h. The progress of the reaction was monitored by TLC. After completion of the reaction, the reaction mixture was diluted with water and extracted with ethyl acetate. The combined organic layers were dried over anhydrous $Na_2SO_4$, filtered and concentrated under reduced pressure to dryness. The crude product was purified by flash column chromatography to afford title compound A116.7 (racemic compound) (2.0 g, 95.2%). LCMS: 366.1 $[M+H]^+$. The compound A116.7 (racemic compound) (2.0 g) was given for chiral separation to afford titled compounds A116.7A Pk-I (RT=? min, 1.0 g), LCMS: 366.2 $[M+H]^+$; A116.7B Pk-II (RT=? min, 1.0 g), LCMS: 366.2 $[M+H]^+$.

Step-5A. Synthesis of 2-(4-(1-((2S,6R)-2,6-dimethylmorpholino)ethyl)piperidin-1-yl)-3-fluoroaniline (A116.8A)

To a stirred solution of compound A116.7A (1.0 g, 2.74 mmol, 1 eq) in MeOH (15 mL) was added Pd/C (20%, 0.1 g) under nitrogen atmosphere. The resulting reaction mixture was hydrogenated (50 psi) at room temperature for 2 h. The progress of the reaction was monitored by TLC. After completion of the reaction, the reaction mixture was filtered through celite and concentrated under reduced pressure to afford the crude of the titled compound A116.8A (0.9 g, crude). This compound was used in the next step without further purification. LCMS: 336.2 $[M+H]^+$.

Step-5B. Synthesis of 2-(4-(1-((2S,6R)-2,6-dimethylmorpholino)ethyl)piperidin-1-yl)-3-fluoroaniline (A116.8B)

To a stirred solution of compound A116.7B (1.0 g, 2.74 mmol, 1 eq) in MeOH (15 mL) was added Pd/C (20%, 0.1 g) under nitrogen atmosphere. The resulting reaction mixture was hydrogenated (50 psi) at room temperature for 2 h. The progress of the reaction was monitored by TLC. After completion of the reaction, the reaction mixture was filtered through celite and concentrated under reduced pressure to afford the crude of the titled compound A116.8B (0.9 g, crude). This compound was used in the next step without further purification. LCMS: 336.2 $[M+H]^+$.

Step-6A. Synthesis of N-((dimethylamino)(4-(N-(2-(4-(1-((2S,6R)-2,6-dimethylmorpholino)ethyl)piperidin-1-yl)-3-fluorophenyl)sulfamoyl)phenyl)(oxo)-λ6-sulfaneylidene)-2,2,2-trifluoroacetamide (A116.9A)

To a stirred solution of compound A116.8A (0.5 g, 1.49 mmol, 1 eq) and compound A116.Int-10 (0.676 g, 1.79 mmol, 1.2 eq) in acetonitrile (10 mL) was added pyridine (0.235 mg, 2.98 mmol, 2 eq) at 0° C. and the reaction mixture was stirred at room temperature for 12 h. The progress of the reaction was monitored by TLC. After completion of reaction, the reaction mixture was quenched with water and extracted with ethyl acetate. The combined organic layers were dried over anhydrous $Na_2SO_4$, filtered and concentrated under reduced pressure to dryness. The crude product was purified by flash column chromatography to afford the titled compound A116.9A (0.35 g, 35%). LCMS: 678.1 $[M+H]^+$.

Step-6B. Synthesis of N-((dimethylamino)(4-(N-(2-(4-(1-((2S,6R)-2,6-dimethylmorpholino)ethyl)piperidin-1-yl)-3-fluorophenyl)sulfamoyl)phenyl)(oxo)-26-sulfaneylidene)-2,2,2-trifluoroacetamide (A116.9B)

To a stirred solution of compound A116.8B (0.4 g, 1.1 mmol, 1 eq) and compound A116.Int-10 (0.496 g, 1.3 mmol, 1.1 eq) in acetonitrile (5 mL) was added pyridine (0.173 g, 2.2 mmol, 2 eq) at 0° C. and the reaction mixture was stirred at room temperature for 12 h. The progress of the reaction was monitored by TLC. After completion of reaction, the reaction mixture was quenched with water and extracted with ethyl acetate. The combined organic layers were dried over anhydrous $Na_2SO_4$, filtered and concentrated under reduced pressure to dryness. The crude product was purified by flash column chromatography to afford the titled compound A116.9B (0.4 g, 49.5%). LCMS: 678.05 $[M+H]^+$.

Step-7A. Synthesis of N-(2-(4-(1-((2S,6R)-2,6-dimethylmorpholino)ethyl)piperidin-1-yl)-3-fluorophenyl)-4-(N,N-dimethylsulfamidimidoyl)benzenesulfonamide (A-871)

To a stirred solution of the mixture of the compound A116.9A (0.35 g, 0.52 mmol, 1 eq) in MeOH (10 mL) was added $Na_2CO_3$ (0.11 g, 1.032 mmol, 2 eq) at 0° C. and the reaction mixture was stirred at room temperature for 2 h. The progress of the reaction was monitored by TLC. After completion of reaction, the reaction mixture was quenched with water and extracted with ethyl acetate. The combined organic layers were dried over anhydrous $Na_2SO_4$, filtered and concentrated under reduced pressure to dryness. The crude product was purified by combiflash to afford the titled compound, racemic mixture, A-871 (170 mg, 56.6%), out of which 150 mg was given for chiral separation to afford A-871A (0.053 g) and A-871B (0.051 g). A-871: Yield: 170 mg, 56.6%; Appearance: Off white solid; $^1H$ NMR (400 MHz, DMSO-$d_6$) δ 9.07 (bs, 1H), 7.93 (bs, 4H), 7.28-7.14 (m, 2H), 6.98-6.91 (m, 1H), 4.67 (bs, 1H), 3.59-3.50 (m, 1H), 3.49-3.40 (m, 1H), 2.85-2.73 (m, 2H), 2.54 (s, 6H), 2.40-2.30 (m, 1H), 2.39-2.29 (m, 1H), 2.28-2.17 (m, 1H), 1.89-1.81 (m, 1H), 1.73 (t, J=10.2 Hz, 1H), 2.58-2.50 (m, 1H), 1.39-1.17 (m, 4H), 1.04 (s, 6H), 0.87 (d, J=5.87 Hz, 3H); HPLC purity: 95.52%; LCMS calculated for $C_{27}H_{40}FN_5O_4S_2$: 581.25, Observed: 582.2 $[M+H]^+$.

Step-7B. Synthesis of N-(2-(4-(1-((2S,6R)-2,6-dimethylmorpholino)ethyl)piperidin-1-yl)-3-fluorophenyl)-4-(N,N-dimethylsulfamidimidoyl)benzenesulfonamide (A-872)

To a stirred solution of the mixture of the compound A116.9B (0.4 g, 0.59 mmol, 1 eq) in MeOH (10 mL) was added $Na_2CO_3$ (0.125 g, 1.18 mmol, 2 eq) at 0° C. and the reaction mixture was stirred at room temperature for 2 h. The progress of the reaction was monitored by TLC. After completion of reaction, the reaction mixture was quenched with water and extracted with ethyl acetate. The combined organic layers were dried over anhydrous $Na_2SO_4$, filtered and concentrated under reduced pressure to dryness. The crude product was purified by combiflash to afford the titled compound A-872 (200 mg, 58.3%), out of which 170 mg which was given for chiral separation to afford the compounds A-872A (0.048 g) and A-872B (0.036 g). A-872: Yield: 200 mg, 58.3%; Appearance: Off white solid; $^1H$ NMR (400 MHz, DMSO-$d_6$) δ 9.06 (bs, 1H), 7.93 (bs, 4H), 7.28-7.14 (m, 2H), 7.00-6.9-(m, 1H), 4.67 (s, 1H), 3.59-3.51 (m, 1H), 3.50-3.41 (m, 1H), 2.85-2.73 (m, 2H), 2.54 (s, 6H), 2.40-2.30 (m, 2H), 2.39-2.29 (m, 1H), 2.18-2.06 (m, 1H), 1.89-1.81 (m, 1H), 1.73 (t, J=10.2 Hz, 1H), 2.58-2.50 (m, 1H), 1.39-1.17 (m, 3H), 1.04 (t, J=5.62 Hz, 6H), 0.87 (d, J=6.36 Hz, 3H); HPLC purity: 96.63%; LCMS calculated for $C_{27}H_{40}FN_5O_4S_2$: 581.25, Observed: 582.1 $[M+H]^+$.

Example A117: Synthesis of N-(2-(4-(((3S,5S)-3,5-dimethylmorpholino)methyl)piperidin-1-yl)-3-fluorophenyl)-4-(N,N-dimethylsulfamidimidoyl)benzenesulfonamide (A-840, A-833, A-834, A-835, and A-836)

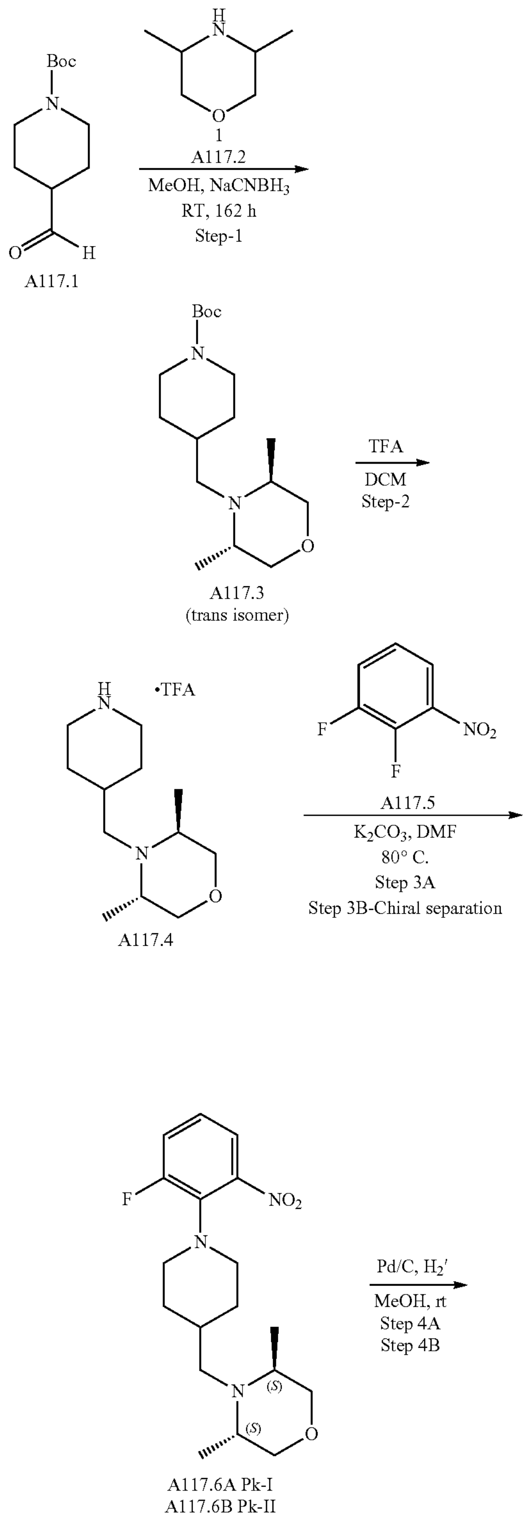

-continued

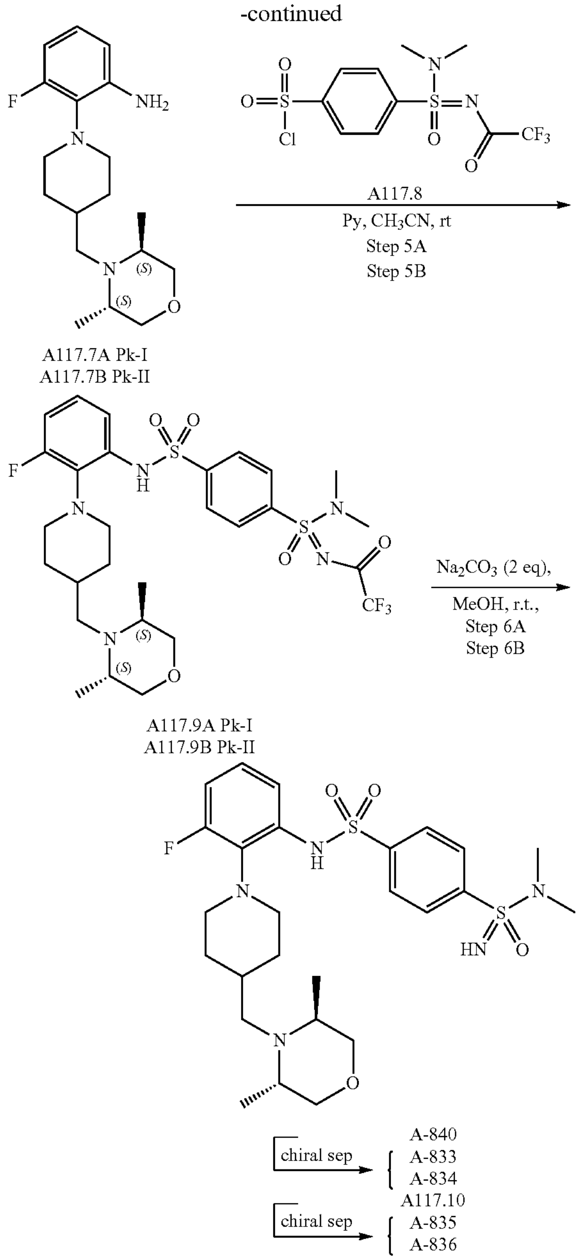

Step-1. Synthesis of trans-tert-butyl 4-((3,5-dimethylmorpholino)methyl)piperidine-1-carboxylate (A117.3)

To a stirred solution of tert-butyl 4-formylpiperidine-1-carboxylate (A117.1) (5.0 g, 23.4 mmol, 1 eq) in MeOH (100 mL) was added 3,5-dimethylmorpholine (A117.2) (4.0 g, 35.0 mmol, 1.5 eq) at room temperature and stirred at room temperature for 1 h. To the resultant reaction mixture was added $NaCNBH_3$ (3.69 g, 58.6 mmol, 2.5 eq) portion-wise at 0° C. and the reaction mixture was stirred at room temperature for 12 h. The progress of the reaction was monitored by TLC. After completion of reaction, the reaction mixture was concentrated under reduced pressure, quenched with cold water and extracted with ethyl acetate. The combined organic layers were dried over anhydrous $Na_2SO_4$, filtered and concentrated under reduced pressure to dryness. The crude product was purified by flash column chromatography to afford trans-tert-butyl 4-((3,5-dimethylmorpholino)methyl)piperidine-1-carboxylate (A117.3) (0.80 g, 9%) as a colourless oil. LCMS: NA.

Step-2. Synthesis of trans-3,5-dimethyl-4-(piperidin-4-ylmethyl)morpholine.TFA salt (A117.4)

To a stirred solution of rel-tert-butyl 4-(((3S,5S)-3,5-dimethylmorpholino)methyl)piperidine-1-carboxylate (A117.3) (0.8 g, 2.56 mmol, 1 eq) in DCM (10 mL) was added TFA (5 mL) at 0° C. The reaction mixture was stirred at room temperature for 3 h. The progress of the reaction was monitored by TLC. After completion of reaction, the reaction mixture was concentrated under reduced pressure to dryness to afford trans-(3,5-dimethyl-4-(piperidin-4-ylmethyl)morpholine TFA salt (A117.4) (0.8 g, crude). This compound was used in the next step without further purification.

Step-3A & 3B: Procedure for the Synthesis of trans-4-((1-(2-fluoro-6-nitrophenyl)piperidin-4-yl)methyl)-3,5-dimethylmorpholine (A117.6)

To a stirred solution of trans-3,5-dimethyl-4-(piperidin-4-ylmethyl)morpholine TFA salt (A117.4) (0.8 g, 2.4 mmol, 1 eq), 1,2-difluoro-3-nitrobenzene (A117.5) (0.43 g, 2.6 mmol, 1.1 eq) in DMF (20 mL) was added $K_2CO_3$ (1.01 g, 7.36 mmol, 3 eq). The reaction mixture was stirred at 80° C. for 12 h. The progress of the reaction was monitored by TLC. After completion of the reaction, the reaction mixture was diluted with water and extracted with ethyl acetate. The combined organic layers were dried over anhydrous $Na_2SO_4$, filtered and concentrated under reduced pressure to dryness. The crude product was purified by flash column chromatography to afford trans-4-((1-(2-fluoro-6-nitrophenyl)piperidin-4-yl)methyl)-3,5-dimethylmorpholine (A117.6) (0.65 g, 75%). LCMS: 352.0 $[M+H]^+$. Trans-4-((1-(2-fluoro-6-nitrophenyl)piperidin-4-yl)methyl)-3,5-dimethylmorpholine (A117.6) (0.65 g) was further purified by chiral Prep. HPLC to afford individual enantiomers of A117.6A Pk-I (0.25 g) and A117.6B Pk-II (0.28 g).

Step-4A. Synthesis of 2-(4-(((3S,5S)-3,5-dimethylmorpholino)methyl)piperidin-1-yl)-3-fluoroaniline (A117.7A Pk-I)

To a stirred solution of compound A117.6A Pk-I (0.25 g, 0.7 mmol, 1 eq) in MeOH (20 mL) was added Pd/C (20%, 0.1 g) under nitrogen atmosphere. The resulting reaction mixture was hydrogenated (50 psi) at room temperature for 2 h. The progress of the reaction was monitored by TLC. After completion of the reaction, the reaction mixture was filtered through celite and concentrated under reduced pressure to afford the crude of the titled compound A117.7A Pk-I (0.22 g, crude). This compound was used in the next step without further purification. LCMS: 321.72 $[M+H]^+$.

Step-4B. Synthesis of 2-(4-(((3S,5S)-3,5-dimethylmorpholino)methyl)piperidin-1-yl)-3-fluoroaniline (A117.7B Pk-II)

To a stirred solution of compound A117.6B Pk-II (0.29 g, 0.8 mmol, 1 eq) in MeOH (20 mL) was added Pd/C (20%, 0.12 g) under nitrogen atmosphere. The resulting reaction mixture was hydrogenated (50 psi) at room temperature for 2 h. The progress of the reaction was monitored by TLC. After completion of the reaction, the reaction mixture was filtered through celite and concentrated under reduced pressure to afford the crude of the titled compound A117.7B Pk-II (0.25 g, crude). This compound was used in the next step without further purification. LCMS: 322.25 $[M+H]^+$.

Step-5A. Synthesis of N-((dimethylamino)(4-(N-(2-(4-(((3S,5S)-3,5-dimethylmorpholino)methyl)piperidin-1-yl)-3-fluorophenyl)sulfamoyl)phenyl)(oxo)-26-sulfaneylidene)-2,2,2-trifluoroacetamide, (A117.9A Pk-I)

To a stirred solution of compound A117.7A Pk-I (0.5 g, 1.56 mmol, 1 eq) and compound A117.8 (0.71 g, 1.87 mmol, 1.2 eq) in acetonitrile (10 mL) was added pyridine (0.36 mL, 4.67 mmol, 3 eq) at 0° C. and the reaction mixture was stirred at room temperature for 12 h. The progress of the reaction was monitored by TLC. After completion of reaction, the reaction mixture was quenched with water and extracted with ethyl acetate. The combined organic layers were dried over anhydrous $Na_2SO_4$, filtered and concentrated under reduced pressure to dryness. The crude product was purified by flash column chromatography by using (EtOAc/n-Hexane: 20-30%) as eluent to afford the titled compound A117.9A Pk-I (0.35 g, 35%) as a yellow solid. LCMS: 664.0 $[M+H]^+$.

Step-5B. Synthesis of N-((dimethylamino)(4-(N-(2-(4-(((3S,5S)-3,5-dimethylmorpholino)methyl)piperidin-1-yl)-3-fluorophenyl)sulfamoyl)phenyl)(oxo)-26-sulfaneylidene)-2,2,2-trifluoroacetamide, (A117.9B Pk-II)

To a stirred solution of compound A117.7B Pk-II (0.5 g, 1.56 mmol, 1 eq) and compound A117.8 (0.71 g, 1.87 mmol, 1.2 eq) in acetonitrile (10 mL) was added pyridine (0.36 mL, 4.67 mmol, 3 eq) at 0° C. and the reaction mixture was stirred at room temperature for 12 h. The progress of the reaction was monitored by TLC. After completion of reaction, the reaction mixture was quenched with water and extracted with ethyl acetate. The combined organic layers were dried over anhydrous $Na_2SO_4$, filtered and concentrated under reduced pressure to dryness. The crude product was purified by flash column chromatography by using (EtOAc/n-Hexane: 20-30%) as eluent to afford the titled compound A117.9B Pk-II (0.27 g, 27%). LCMS: 664.0 $[M+H]^+$.

Step-6A. Synthesis of N-(2-(4-(((3S,5S)-3,5-dimethylmorpholino)methyl)piperidin-1-yl)-3-fluorophenyl)-4-(N,N-dimethylsulfamidimidoyl)benzenesulfonamide (A-840, A-833, and A-834)

To a stirred solution of the mixture of the compound A117.9A Pk-I (0.35 g, 0.53 mmol, 1 eq) in MeOH (10 mL) was added $Na_2CO_3$ (0.112 g, 1.054 mmol, 2 eq) at 0° C. and the reaction mixture was stirred at room temperature for 2 h. The progress of the reaction was monitored by TLC. After completion of reaction, the reaction mixture was quenched with water and extracted with ethyl acetate. The combined organic layers were dried over anhydrous $Na_2SO_4$, filtered and concentrated under reduced pressure to dryness. The crude product was purified by combiflash to afford the titled compound A-840 (35 mg, 23%), which was further purified by chiral prep.HPLC to afford titled compounds A-833 (0.018 g) and A-834 (0.015 g).

A-833: Yield: 0.018 g; Appearance: Off white solid; $^1$H NMR (400 MHz, DMSO-$d_6$) δ 9.07 (s, 1H), 7.96-7.89 (m, 4H), 7.26-7.23 (m, 1H), 7.17 (d, J=5.87 Hz, 1H), 6.98-6.90 (m, 1H), 4.67 (s, 1H), 3.54 (dd, J=10.51, 2.20 Hz, 1H), 3.26-3.20 (m, 2H), 2.85-2.65 (m, 3H), 2.54 (s, 6H), 2.44-2.41 (m, 1H), 2.38-2.28 (m, 2H), 2.14 (dd, J=12.47, 5.14 Hz, 1H), 1.66-1.54 (m, 2H), 1.45-1.32 (m, 1H), 1.30-1.14 (m, 2H), 0.91 (d, J=6.36 Hz, 6H); HPLC purity: 97.36%; LCMS calculated for $C_{26}H_{38}FN_5O_4S_2$: 567.23, Observed: 568.1 $[M+H]^+$.

METHOD, Column: YMC CHIRAL ART CELLULOSE-SC, 250 mm*4.6 mm, 5μ, Mobile Phase: A: n-HEXANE+0.1% Iso-propyl-amine; B:DCM:MEOH (50:50), Flow rate: 1.00 mL/min, Isocratic: 25% B, Ret. Time: 13.141

A-834: Yield: 0.015; Appearance: Off white solid; $^1$H NMR (400 MHz, DMSO-$d_6$) δ 9.07 (s, 1H), 7.96-7.89 (m, 4H), 7.27-7.22 (m, 1H), 7.21-7.14 (m, 1H), 6.98-6.90 (m, 1H), 4.67 (s, 1H), 3.55 (dd, J=10.76, 1.96 Hz, 1H), 3.25-3.20 (m, 2H), 2.86-2.68 (m, 3H), 2.54 (s, 6H), 2.47-2.25 (m, 3H), 2.14 (dd, J=12.47, 5.14 Hz, 1H), 1.64 (d, J=12.4 Hz, 1H), 1.55 (d, J=12.0 Hz, 1H), 1.45-1.32 (m, 1H), 1.32-1.15 (m, 2H), 0.91 (d, J=5.87 Hz, 6H); HPLC purity: 98.44%; LCMS calculated for $C_{26}H_{38}FN_5O_4S_2$: 567.23, Observed: 568.2 $[M+H]^+$.

METHOD, Column: YMC CHIRAL ART CELLULOSE-SC, 250 mm*4.6 mm, 5μ, Mobile Phase: A: n-HEXANE+0.1% Iso-propyl-amine; B:DCM:MEOH (50:50), Flow rate: 1.00 mL/min, Isocratic: 25% B, Ret. Time: 14.668

Step-6B. Synthesis of N-(2-(4-(((3S,5S)-3,5-dimethylmorpholino)methyl)piperidin-1-yl)-3-fluorophenyl)-4-(N,N-dimethylsulfamidimidoyl)benzenesulfonamide (A-835 and A-836)

To a stirred solution of the mixture of the compound A117.9B Pk-II (0.25 g, 0.38 mmol, 1 eq) in MeOH (5 mL) was added $Na_2CO_3$ (0.080 g, 0.75 mmol, 2 eq) at 0° C. and the reaction mixture was stirred at room temperature for 2 h. The progress of the reaction was monitored by TLC. After completion of reaction, the reaction mixture was quenched with water and extracted with ethyl acetate. The combined organic layers were dried over anhydrous $Na_2SO_4$, filtered and concentrated under reduced pressure to dryness. The crude product was purified by combiflash to afford the titled compound A117.10 (150 mg, 70%), which was further purified by chiral prep.HPLC to afford titled compounds A-835 (0.013 g) and A-836 (0.009 g).

A-836: Yield: 0.013 g; Appearance: Off white solid; $^1$H NMR (400 MHz, DMSO-$d_6$) δ 9.07 (s, 1H), 7.98-7.88 (m, 4H), 7.28-7.22 (m, 1H), 7.21-7.15 (m, 1H), 6.98-6.90 (m, 1H), 4.67 (bs, 1H), 3.58-3.51 (m, 1H), 3.25-3.18 (m, 2H), 2.84-2.59 (m, 3H), 2.52 (s, 6H), 2.47-2.25 (m, 3H), 2.17-2.12 (m, 1H), 1.64 (d, J=11.6 Hz, 1H), 1.55 (d, J=11.2 Hz, 1H), 1.32-1.46 (m, 1H), 1.30-1.12 (m, 2H), 0.91 (d, J=5.87 Hz, 6H); HPLC purity: 99.23%; LCMS calculated for $C_{26}H_{38}FN_5O_4S_2$: 567.23, Observed: 568.1 $[M+H]^+$.

METHOD, Column: YMC CHIRAL ART CELLULOSE-SC, 250 mm*4.6 mm, 5 u, Mobile Phase: A: n-HEXANE+0.1% Iso-propyl-amine; B:DCM:MEOH (50:50), Flow rate: 1.00 mL/min, Isocratic: 30% B, Ret. Time: 10.356

A-836: Yield: 0.009 g; Appearance: Off white solid; $^1$H NMR (400 MHz, DMSO-$d_6$) δ 9.07 (s, 1H), 7.98-7.88 (m, 4H), 7.26-7.21 (m, 1H), 7.20-7.14 (m, 1H), 6.98-6.90 (m, 1H), 4.67 (s, 1H), 3.54 (dd, J=10.51, 2.20 Hz, 2H), 3.27-3.19 (m, 1H), 2.82-2.69 (m, 3H) 2.53 (s, 6H), 2.46-2.30 (m, 3H), 2.14 (dd, J=12.72, 5.38 Hz, 1H), 1.68-1.52 (m, 2H), 1.45-1.34 (m, 1H), 1.30-1.12 (m, 2H), 0.91 (d, J=6.36 Hz, 6H); HPLC purity: 99.24%; LCMS calculated for $C_{26}H_{38}FN_5O_4S_2$: 567.23, Observed: 568.2 $[M+H]^+$.

METHOD, Column: YMC CHIRAL ART CELLULOSE-SC, 250 mm*4.6 mm, 5 u, Mobile Phase:A: n-HEXANE+0.1% Iso-propyl-amine; B:DCM:MEOH (50:50), Flow rate: 1.00 mL/min, Isocratic: 30% B, Ret. Time: 11.523

Example A118

The following compounds were prepared according to methods described herein using standard chemical transformations known to one of skill in the art.

| Compound No. | Structure | Analytical data |
|---|---|---|
| A-956 | 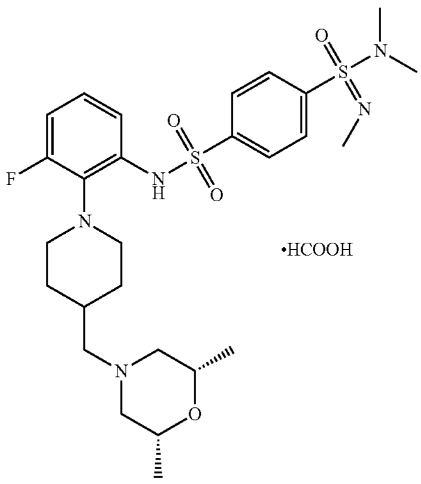 [SMILES: CN=S(=O)(c1ccc(S(=O)(=O)Nc2cccc(F)c2N2CCC(CN3C[C@@H](C)O[C@@H](C)C3)CC2)cc1)N(C)C ; "·HCOOH"] •HCOOH | Appearance: Off white solid; $^1$H NMR (400 MHz, DMSO-$d_6$) δ 9.20 (br s, 1 H), 7.93 (s, 4 H), 7.24-7.19 (m, 2 H), 6.98-6.95 (m, 1 H), 3.33-3.50 (m, 2 H), 2.82-2.75 (m, 2 H), 2.70-7.62 (m, 5 H), 2.54 (s, 6 H), 2.36-2.29 (m, 2 H), 2.16-7.10 (m, 2 H), 1.61-1.52 (m, 5H), 1.28-1.17 (m, 2 H), 1.03 (s, 6 H) 2H's are merged in solvent peak; HPLC purity: 99.76%; LCMS calculated for $C_{28}H_{42}FN_5O_6S_2$: 627.26, for free base 581.25; Observed: 582.1 $[M + H]^+$. |

-continued

| Compound No. | Structure | Analytical data |
|---|---|---|
| A-957 | 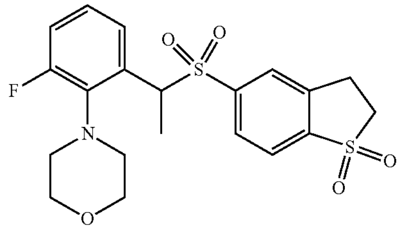 [SMILES: CC(c1cccc(F)c1N1CCOCC1)S(=O)(=O)c1ccc2c(c1)CCS2(=O)=O] | Appearance: Off white solid; $^1$H NMR (400 MHz, DMSO-$d_6$) δ 7.96-7.94 (m, 2H), 7.63 (d, J = 8.0 Hz, 1 H), 7.40-7.33 (m, 2 H), 7.27-7.22 (m, 1 H), 5.43 (q, J = 7.6 Hz, 1 H), 3.78-3.57 (m, 5 H), 3.43-3.38 (m, 3 H), 3.12-2.98 (m, 2 H), 2.59-2.56 (m, 1 H), 1.76-1.73 (m, 1 H), 1.61 (d, J = 7.2 Hz, 3 H); HPLC purity: 95.86%; LCMS calculated for $C_{20}H_{22}FNO_5S_2$: 439.09, Observed: 440.1 $[M + H]^+$. |
| A-958 | 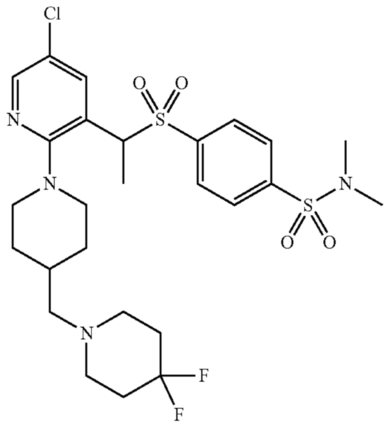 [SMILES: CC(c1cc(Cl)cnc1N1CCC(CN2CCC(F)(F)CC2)CC1)S(=O)(=O)c1ccc(S(=O)(=O)N(C)C)cc1] | Appearance: Off white solid; $^1$H NMR (400 MHz, DMSO-$d_6$) δ 8.21 (d, J = 2.4 Hz, 1 H), 7.95 (d, J = 2.4 Hz, 1 H), 7.82 (d, J = 8.0 Hz, 2 H), 7.67 (d, J = 8.4 Hz, 2 H), 4.71 (q, J = 7.2 Hz, 1 H), 2.90-2.87 (m, 1H), 2.62 (s, 6 H), 2.61-2.45 (m, 4H), 2.37-2.32 (m, 2H), 2.24-2.17 (m, 3 H), 1.96-1.88 (m, 4 H), 1.81 (d, J = 7.2 Hz, 3 H), 1.71-1.50 (m, 3 H), 1.31-1.23 (m, 1 H), 0.95-0.87 (m, 1H); HPLC purity: 99.03%; LCMS calculated for: 604.18 Observed: 605.2 $[M + H]^+$; HPLC purity: 99.03%; LCMS calculated for $C_{26}H_{33}ClF_2N_4O_4S_2$: 604.18, Observed: 605.2 $[M + H]^+$. |
| A-959 | 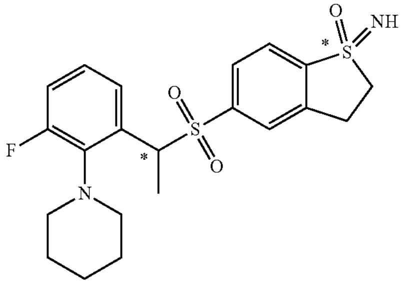<br>Diastereomer 3 | Appearance: Off white solid; $^1$H NMR (400 MHz, DMSO-$d_6$) δ 7.78-7.73 (m, 2 H), 7.49 (d, J = 8.0 Hz, 1 H), 7.41 (d, J = 7.6 Hz, 1 H), 7.35-7.28 (m, 1 H), 7.21-7.15 (m, 1 H), 5.33 (q, J = 6.8 Hz, 1 H), 4.84 (s, 1H), 3.53-3.49 (m, 2 H), 2.88-2.60 (m, 4 H), 1.45-1.79 (m, 8 H), 1.43-1.09 (m, 3 H); HPLC purity: 98.19%; LCMS calculated for $C_{21}H_{25}FN_2O_3S_2$: 436.13, Observed: 437.2 $[M + H]^+$. |
| A-960 | 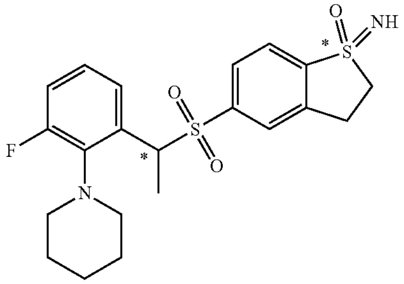<br>Diastereomer 4 | Appearance: Off white solid; $^1$H NMR (400 MHz, DMSO-$d_6$) δ 7.78-7.73 (m, 2 H), 7.49 (d, J = 8.0 Hz, 1 H), 7.41 (d, J = 7.6 Hz, 1 H), 7.35-7.28 (m, 1 H), 7.21-7.15 (m, 1 H), 5.33 (q, J = 6.8 Hz, 1 H), 4.84 (s, 1H), 3.53-3.49 (m, 2 H), 2.88-2.60 (m, 4 H), 1.45-1.79 (m, 8 H), 1.43-1.09 (m, 3 H); HPLC purity: 97.97%; LCMS calculated for $C_{21}H_{25}FN_2O_3S_2$: 436.13, Observed: 437.1 $[M + H]^+$. |

-continued

| Compound No. | Structure | Analytical data |
|---|---|---|
| A-961 | 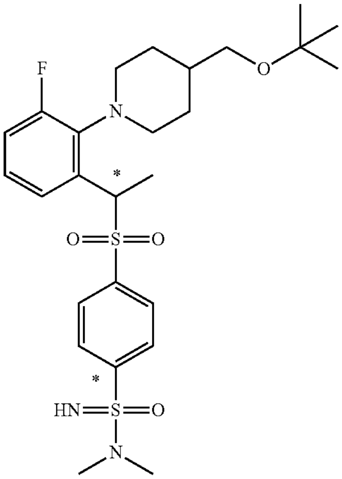 Diastereomer 4 | Appearance: White solid; 1H NMR (400 MHz, DMSO-d6) δ 7.88 (d, J = 6.8 Hz, 2H), 7.735 (d, J = 6.8 Hz, 2H), 7.40 (d, J = 6.4 Hz, 1H), 7.32-7.26 (m, 1H), 7.2-7.12 (m, 1H), 5.40-5.25 (m, 1H), 4.69 (br s, 1H), 3.30-3.15 (m, 2H), 2.90-2.60 (m, 3H), 2.55 (s, 6H), 1.8-1.6 (m, 5H), 1.52 (d, J = 9.6 Hz, 1H), 1.49-1.30 (m, 1H), 1.30-1.10 (11H); HPLC purity: 97.22%; LCMS calculated for $C_{26}H_{18}FN_3O_4S_2$: 539.23, Observed: 540.1 $[M + H]^+$. |
| A-962 | 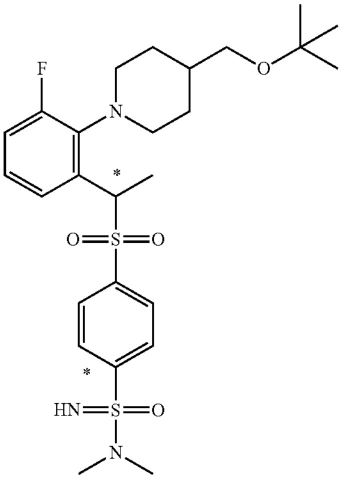 Diastereomer 3 | Appearance: White solid; 1H NMR (400 MHz, DMSO-d6) δ 7.88 (d, J = 6.8 Hz, 2H), 7.735 (d, J = 6.8 Hz, 2H), 7.40 (d, J = 6.4 Hz, 1H), 7.32-7.26 (m, 1H), 7.2-7.12 (m, 1H), 5.40-5.25 (m, 1H), 4.69 (brs, 1H), 3.30-3.15 (m, 2H), 2.90-2.60 (m, 3H), 2.55 (s, 6H), 1.8-1.6 (m, 5H), 1.52 (d, J = 9.6 Hz, 1H), 1.49-1.30 (m, 1H), 1.30-1.10 (m, 11H); HPLC purity: 98.78%; LCMS calculated for $C_{26}H_{38}FN_3O_4S_2$: 539.23, Observed: 540.1 $[M + H]^+$. |
| A-963 | 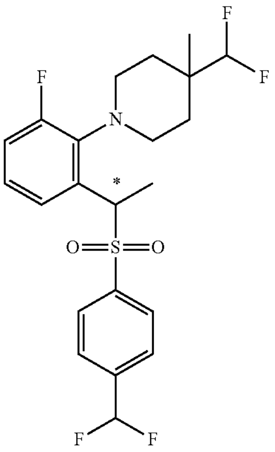 Enantiomer 1 | Appearance: White solid; 1H NMR (400 MHz, DMSO-d6) δ 7.80-7.69 (m, 4H), 7.42-6.99 (m, 4H), 5.81 (t, J = 56 8 Hz, 1H), 5.32-5.25 (m, 1H), 3.10-2.90 (m, 2H), 2.60-2.50 (m, 1 H), 1 75-1.42 (m, 6H), 1.30 (d, J = 13.2 Hz, 1H), 1.175 (d, J = 12.4 Hz, 1H), 1.0 (s, 3H); HPLC purity: 99.81%; LCMS calculated for $C_{22}H_{24}F_5NO_2S$: 461.14, Observed: 462.0 $[M + H]^+$. |

-continued

| Compound No. | Structure | Analytical data |
|---|---|---|
| A-964 | 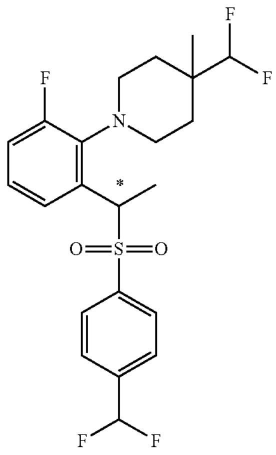 Enantiomer 2 | Appearance: White solid; 1H NMR (400 MHz, DMSO-d6) δ 7.80-7.69 (m, 4H), 7.42-6.99 (m, 4H), 5.81 (t, J = 56.8 Hz, 1H), 5.32-5.25 (m, 1H), 3.10-2.90 (m, 2H), 2.60-2.50 (m, 1H), 1.75-1.42 (m, 6H), 1.30 (d, J = 13.2 Hz, 1H), 1.175 (d, J = 12.4 Hz, 1H), 1.0 (s, 3H); HPLC purity: 99.70%; LCMS calculated for $C_{22}H_{24}F_5NO_2S$: 461.14, Observed: 462.0 $[M + H]^+$. |
| A-965 | 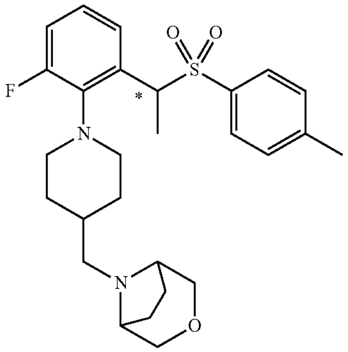 [SMILES: Cc1ccc(S(=O)(=O)C(C)c2cccc(F)c2N2CCC(CN3C4CCC3COC4)CC2)cc1] | Appearance: Off white solid; $^1H$ NMR (400 MHz, DMSO-$d_6$) δ 7.43 (br d, J = 8.00 Hz, 2 H), 7.41-7.33 (m, 3 H), 7.18-7.15 (m, 1 H), 7.20-7.10 (m, 1 H), 5.28 (q, J = 8 Hz, 1 H), 3.59-3.48 (m, 2 H), 3.40 (br d, J = 8 Hz, 2 H), 2.98 (br s, 2 H), 2.83 (br t, J = 12 Hz, 2 H), 2.70-2.65 (m, 1 H), 2.36 (s, 3 H), 2.18-2.04 (m, 2 H), 1.90-1.78 (m, 4 H), 1.72-1.64 (m, 3 H), 1.58 (d, J = 8.0 Hz, 3H), 1.40-1.38 (m, 1 H), 1.24-1.12 (m, 1 H) 1.08-0.98 (m, 1 H); HPLC purity: 96.67%; LCMS calculated for $C_{27}H_{35}FN_2O_3S$: 486.24, Observed: 487.3 $[M + H]^+$. |
| A-966 | 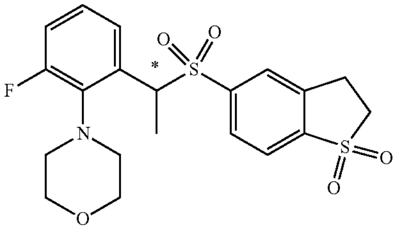 Enantiomer 1 | Appearance: Off white solid; $^1H$ NMR (400 MHz, DMSO-$d_6$) δ 7.96-7.94 (m, 2H), 7.63 (d, J = 8.0 Hz, 1 H), 7.40-7.33 (m, 2 H), 7.27-7.22 (m, 1 H), 5.43 (q, J = 7.2 Hz, 14.4 Hz, 1 H), 3.78-3.57 (m, 5 H), 3.43-3.38 (m, 3 H), 3.12-2.98 (m, 2 H), 2.59-2.56 (m, 1 H), 1.76-1.73 (m, 1 H), 1.61 (d, J = 7.2 Hz, 3 H); HPLC purity: 98.04%; LCMS calculated for $C_{20}H_{22}FNO_5S_2$: 439.09, Observed: 440.0 $[M + H]^+$. |
| A-967 | 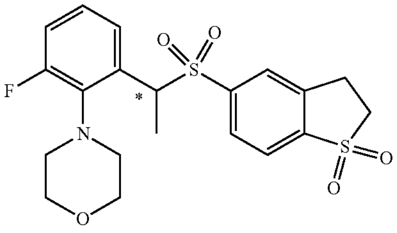 Enantiomer 2 | Appearance: Off white solid; $^1H$ NMR (400 MHz, DMSO-$d_6$) δ 7.96-7.94 (m, 2H), 7.63 (d, J = 8.0 Hz, 1 H), 7.40-7.35 (m, 2 H), 7.27-7.22 (m, 1 H), 5.43 (q, J = 7.2 Hz, 1 H), 3.74-3.57 (m, 5 H), 3.43-3.31 (m, 3 H), 3.12-2.98 (m, 2 H), 2.59-2.55 (m, 1 H), 1.76-1.70 (m, 1 H), 1.61 (d, J = 7.25 Hz, 3 H); HPLC purity: 98.43%; LCMS calculated for $C_{20}H_{22}FNO_5S_2$: 439.09, Observed: 440.1 $[M + H]^+$. |

-continued

| Compound No. | Structure | Analytical data |
|---|---|---|
| A-971 | 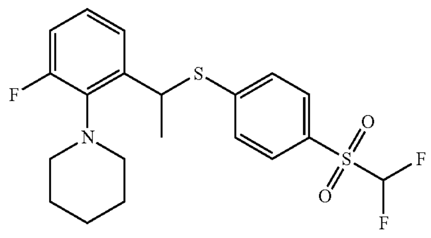 [SMILES: CC(Sc1ccc(S(=O)(=O)C(F)F)cc1)c1cccc(F)c1N1CCCCC1] | Appearance: White solid; 1H NMR (400 MHz, $CDCl_3$) δ 7.74 (d, J = 7.2 Hz, 2H), 7.46 (d, J = 8.4 Hz, 2H), 7.31 (d, J = 7.6 Hz, 1H), 7.15-7.04 (m, 1H), 6.92 (t, J = 10.4 Hz, 1H), 6.14 (t, J = 53.6 Hz, 1H), 5.50-5.40 (m, 1H), 3.32-3.22 (br t, 1H), 3.16-3.06 (m, 1H), 2.98-2.82 (m, 2H), 1.845 (d, J = 11.6 Hz, 1H), 1.73 (br s, 3 H), 1.68-1.58 (m, 4H), 1.45-1.34 (m, 1H); HPLC purity: 99.45%; LCMS calculated for $C_{20}H_{22}F_3NO_2S_2$: 429.10, Observed: 430.0 $[M + H]^+$. |
| A-972 | 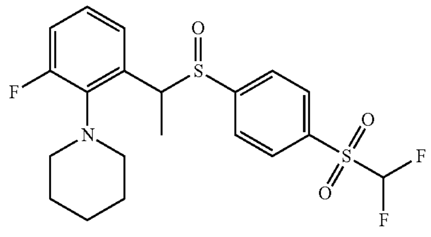 [SMILES: CC(c1cccc(F)c1N1CCCCC1)S(=O)c1ccc(S(=O)(=O)C(F)F)cc1] | Appearance: White solid; 1H NMR (400 MHz, $CDCl_3$) δ 7.99 (d, J = 8.4 Hz, 2H), 7.63 (d, J = 8 Hz, 2H), 7.22-7.18 (m, 2H), 7.05-6.99 (m, 1H), 6.20 (t, J = 53.2 Hz, 1H), 4.85 (q, J = 7.2 Hz, 1H), 3.05-2.90 (m, 2H), 2.69 (d, J = 11.2 Hz, 1H), 1.86 (d, J = 11.2 Hz, 1H), 1.76 (d, J = 11.6 Hz, 1H), 1.70-1.55 (m, 4H), 1.54-1.48 (m, 2H), 1.30-1.15 (m, 2H); HPLC purity: 99.32%; LCMS calculated for $C_{20}H_{22}F_3NO_3S_2$: 445.10, Observed: 445.9 $[M + H]^+$. |
| A-973 | 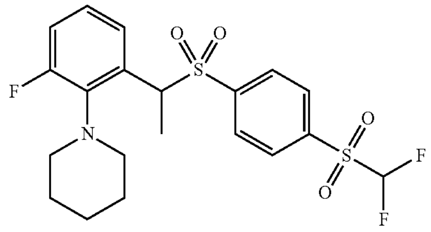 [SMILES: CC(c1cccc(F)c1N1CCCCC1)S(=O)(=O)c1ccc(S(=O)(=O)C(F)F)cc1] | Appearance: White solid; 1H NMR (400 MHz, $CDCl_3$) δ 8.0 (d, J = 8.4 Hz, 2H), 7.85 (d, J = 8 Hz, 2H), 7.50 (d, J = 8 Hz, 1H), 7.26-7.19 (m, 1H), 7.02-6.97 (m, 1H), 6.20 (t, J = 53.6 Hz, 1H), 5.49 (q, J = 7.4 Hz, 1H), 2.92-2.84 (m, 2H), 2.58 (d, J = 10.8 Hz, 1H), 1.78-1.70 (m, 4H), 1.68-1 60 (m, 1H), 1.55-1.46 (m, 3H), 1.30-1.15 (m, 2H); HPLC purity: 99.80%; LCMS calculated for $C_{20}H_{22}F_3NO_4S_2$: 461.09, Observed: 461.9 $[M + H]^+$. |
| A-974 | 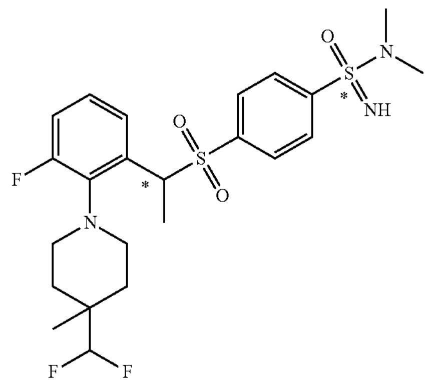 Diastereomer 3 | Appearance: White solid; 1H NMR (400 MHz, DMSO-d6) δ 7.91 (d, J = 8 Hz, 2H), 7.78 (d, J = 8 Hz, 2H), 7.40 (d, J = 8 Hz, 1H), 7.36-7.30 (m, 1H), 7.23-7.18 (m, 1H), 5.84 (t, J = 56.8 Hz, 1H), 5.35 (q, J = 7.2 Hz, 1H), 4.75 (brs, 1H), 3.10-2.92 (m, 2H), 2.62-2.50 (m, 7H), 1.80-1.5 (m, 6H), 1.31 (d, J = 12.8 Hz, 1H), 1.20 (d, J = 12.8 Hz, 1H), 1.0 (s, 3H); HPLC purity: 98.62%; LCMS calculated for $C_{23}H_{30}F_3N_3O_3S_2$: 517.17, Observed: 518.1 $[M + H]^+$. |

-continued

| Compound No. | Structure | Analytical data |
|---|---|---|
| A-975 | 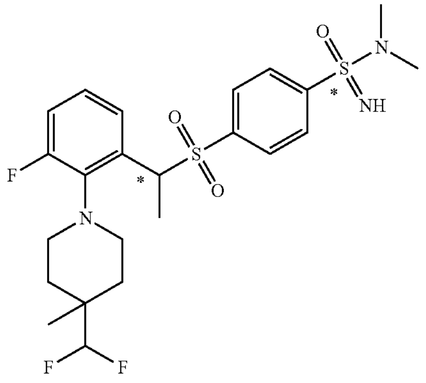 Diastereomer 4 | Appearance: White solid; 1H NMR (400 MHz, DMSO-d6) δ 7.91 (d, J = 8 Hz, 2H), 7.78 (d, J = 8 Hz, 2H), 7.40 (d, J = 8Hz, 1H), 7.36-7.30 (m, 1H), 7.23-7.18 (m, 1H), 5.84 (t, J = 56 8 Hz, 1H), 5.35 (q, J = 7.2 Hz, 1H), 4.70 (brs, 1H), 3.07-2.95 (m, 2H), 2.62-2.50 (m, 7H), 1.80-1.5 (m, 6H), 1.31 (d, J = 12.8 Hz, 1H), 1.20 (d, J = 12.8 Hz, 1H), 1.0 (s, 3H); HPLC purity: 99.07%; LCMS calculated for $C_{23}H_{30}F_3N_3O_3S_2$: 517.17, Observed: 518.3 [M + H ]$^+$. |
| A-976 | 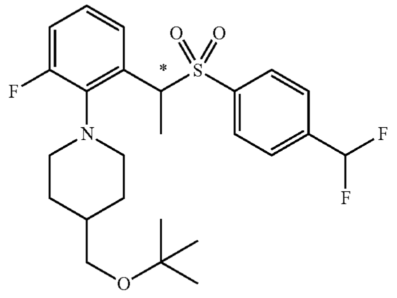 Enantiomer 1 | Appearance: White solid; $^1$H NMR (400 MHz, DMSO-$d_6$) δ 7.73 (d, J = 8.0 Hz, 2H), 7.68 (d, J = 8 Hz, 2H), 7.41 (d, J = 7.6 Hz, 1H), 7.33-6.90 (m, 3 H), 5.45-5.35 (m, 1 H), 3.19-3.16 (m, 2 H), 2.75-2.62 (m, 3 H), 1.69-1.61 (m, 5 H), 1.48 (d, J = 12.4 Hz, 1H), 1.82-1.72 (m, 1 H), 1.25-1.09 (m, 10 H), 1.08-0.94 (m, 1 H); HPLC purity: 99.69%; LCMS calculated for $C_{25}H_{32}F_3NO_3S$: 483.21, Observed: 484.2 [M + H]$^+$. |
| A-977 | 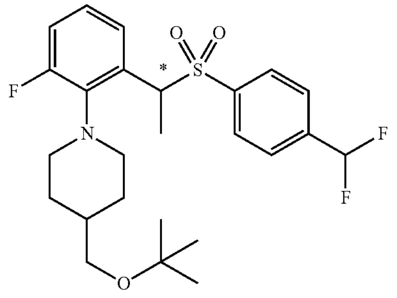 Enantiomer 2 | Appearance: White solid; $^1$H NMR (400 MHz, DMSO-$d_6$) δ 7.73 (d, J = 8.0 Hz, 2H), 7.68 (d, J = 8 Hz, 2H), 7.41 (d, J = 7.6 Hz, 1H), 7.33-6.90 (m, 3 H), 5.45-5.35 (m, 1 H), 3.19-3.16 (m, 2H), 2.75-2.62 (m, 3 H), 1.69-1.61 (m, 5 H), 1.48 (d, J = 12.4 Hz, 1H), 1.82-1.72 (m, 1 H), 1.25-1.09 (m, 10 H), 1.08-0.94 (m, 1 H); HPLC purity: 98.88%; LCMS calculated for $C_{25}H_32F_3NO_3S$: 483.21, Observed: 484.1 [M + H]$^+$. |
| A-978 | 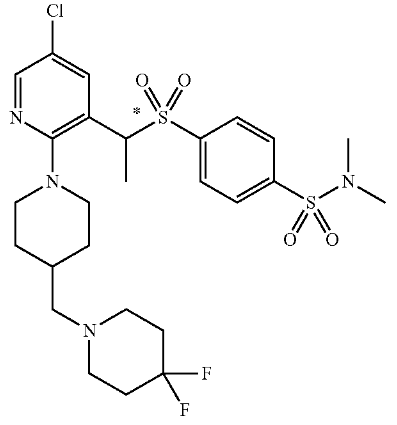 Enantiomer 1 | Appearance: Off white solid; $^1$H NMR (400 MHz, DMSO-$d_6$) δ 8.21 (d, J = 2.4 Hz, 1 H), 7.95 (d, J = 2.4 Hz, 1 H), 7.82 (d, J = 8.0 Hz, 2 H), 7.67 (d, J = 8.4 Hz, 2 H), 4.71 (q, J = 7.2 Hz, 1 H), 2.90-2.87 (m, 1H), 2.62 (s, 6 H), 2.61-2.45 (m, 4 H), 2.37-2.32 (m, 2 H), 2.24-2.17 (m, 3 H), 1.96-1.88 (m, 4 H), 1.81 (d, J = 7.2 Hz, 3 H), 1.71-1.50 (m, 3 H), 1.28-1.22 (m, 1 H), 0.95-0.89 (m, 1 H); HPLC purity: 97.72%; LCMS calculated for: 604.18 Observed: 605.2 [M + H]$^+$; HPLC purity: 97.72%; LCMS calculated for $C_{26}H_{35}ClF_2N_4O_4S_2$: 604.18, Observed: 605.2 [M + H]$^+$. |

-continued

| Compound No. | Structure | Analytical data |
|---|---|---|
| A-979 | 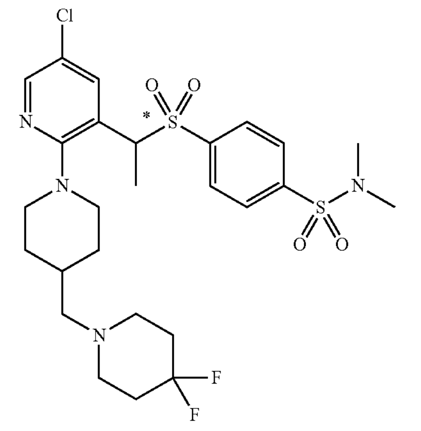 Enantiomer 2 | Appearance: Off white solid; $^1$H NMR (400 MHz, DMSO-$d_6$) δ 8.21 (d, J = 2.4 Hz, 1 H), 7.95 (d, J = 2.4 Hz, 1 H), 7.82 (d, J = 8.4 Hz, 2 H), 7.67 (d, J = 8.8 Hz, 2 H), 4.71 (q, J = 6.8 Hz, 1 H), 2.90-2.87 (m, 1 H), 2.62 (s, 6 H), 2.61-2.45 (m, 4 H), 2.37-2.32 (m, 2 H), 2.24-2.17 (m, 3 H), 1.96-1 88 (m, 4 H), 1.81 (d, J = 7.2 Hz, 3 H), 1.71-1.50 (m, 3 H), 1.28-1.22 (m, 1 H), 0.95-0.89 (m, 1H); HPLC purity: 97.73%; LCMS calculated for $C_{26}H_{35}ClF_2N_4O_4S_2$: 604.18, Observed: 605.2 $[M + H]^+$. |
| A-980 | 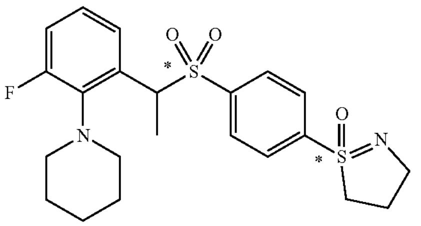 Diastereomer 2 | Appearance: Off white solid; $^1$H NMR (400 MHz, DMSO-$d_6$) δ 8.03 (d, J = 8 Hz, 2 H), 7.80 (d, J = 8 Hz, 2 H), 7.41-7.18 (m, 3 H), 5.39-5.32 (m, 1 H), 3.88-3.81 (m, 1 H), 3.69-3.62 (m, 1 H), 3.49-3.32 (m, 2 H), 2.88-2.55 (m, 3 H), 2.30-2.19 (m, 2 H), 1.79-0.86 (m, 10 H); HPLC purity: 99.66%; LCMS calculated for $C_{22}H_{27}FN_2O_3S_2$: 450.14, Observed: 451.2 $[M + H]^+$. |
| A-981 | 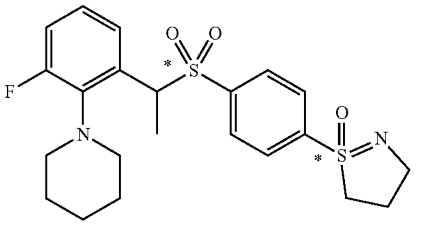 Diastereomer 1 | Appearance: Off white solid; $^1$H NMR (400 MHz, DMSO-$d_6$) δ 8.03 (d, J = 8 Hz, 2 H), 7.80 (d, J = 8 Hz, 2 H), 7.41-7.18 (m, 3 H), 5.40-5.30 (m, 1 H), 3.88-3.80 (m, 1 H), 3.68-3.60 (m, 1 H), 3.49-3.35 (m, 2 H), 2.88-2.55 (m, 3 H), 2.30-2.25 (m, 2 H), 1.78-1.16 (m, 10 H); HPLC purity: 99.78%; LCMS calculated for $C_{22}H_{27}FN_2O_3S_2$: 450.14, Observed: 451.2 $[M + H]^+$. |
| A-982 | 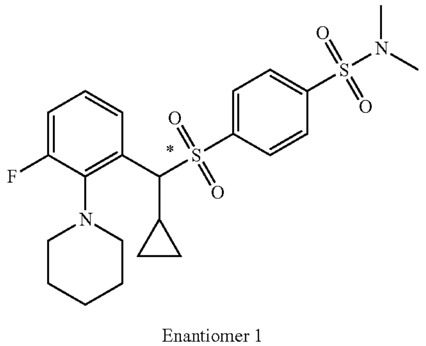 [SMILES: CN(C)S(=O)(=O)c1ccc(S(=O)(=O)C(c2cccc(F)c2N2CCCCC2)C2CC2)cc1] Enantiomer 1 | Appearance: Off white solid; $^1$H NMR (400 MHz, DMSO-$d_6$) δ 8.01-7.89 (m, 4 H), 7.50 (dd, J = 7.83 Hz, 0.98 Hz, 1 H), 7.37-7.35 (m, 1 H), 7.24-7.21 (m, 1 H), 4.63 (d, J = 10.88 Hz, 1 H), 2.99-2.79 (m, 2 H), 2.69-2.61 (m, 7 H), 2.18 (br d, J = 10.39 Hz, 1H), 1.73 (br d, J = 12.23 Hz, 1 H), 1.63-1.39(m, 5 H), 1.30-1.17 (m, 1 H), 0.70-0.61 (m, 1 H), 0.55-0.46 (m, 1 H), 0.22-0.11 (m, 1 H), 0.12-0.02 (m, 1 H); HPLC purity: 100.00%; LCMS calculated for $C_{23}H_{29}FN_2O_4S_2$: 480.16; Observed: 481.2 $[M + H]^+$. |

-continued

| Compound No. | Structure | Analytical data |
|---|---|---|
| A-983 | 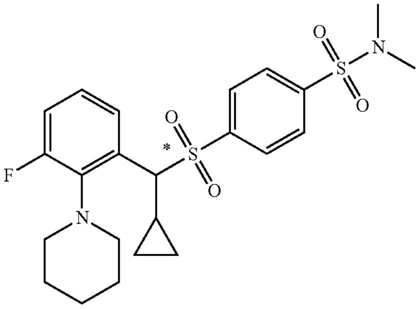<br>Enantiomer 2 | Appearance: Off white solid; $^1$H NMR (400 MHz, DMSO-$d_6$) δ 8.03-7.88 (m, 4 H), 7.50 (dd, J = 7.89, 1.04 Hz, 1 H), 7.37-7.34 (m, 1 H), 7.24-7.21 (m, 1 H), 4.63 (d, J = 10.88 Hz, 1 H), 2.97-2.80 (m, 2 H), 2.64 (s, 7 H), 2.19 (br d, J = 10.03 Hz, 1H), 1.73 (br d, J = 12.96 Hz, 1 H), 1.64-1.40 (m, 5 H), 1.28-1.19 (m, 1 H), 0.70-0.60 (m, 1 H), 0.55-0.46 (m, 1 H), 0.18-0.14 (m, 1 H), 0.12-0.03 (m, 1 H); HPLC purity: 97.10%; LCMS calculated for $C_{23}H_{29}FN_2O_4S_2$: 480.16; Observed: 481.2 $[M + H]^+$. |
| A-986 | 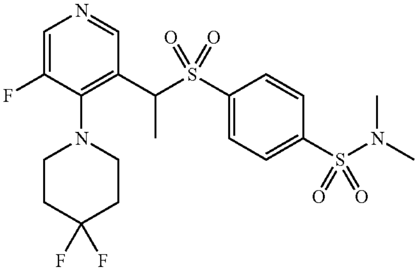 [SMILES: CC(c1cncc(F)c1N1CCC(F)(F)CC1)S(=O)(=O)c1ccc(S(=O)(=O)N(C)C)cc1] | Appearance: White solid; $^1$H NMR (400 MHz, $CDCl_3$) δ 8.53 (s, 1H), 8.43 (d, J = 3.2 Hz, 1H), 7.93-7.86 (m, 4 H), 5.16-5.08 (m, 1 H), 3.40-2.60(m, 10H), 2.17-2.00 (m, 4 H), 1.78 (d, J = 7.6 Hz, 3 H); HPLC purity: 97.73%; LCMS calculated for $C_{20}H_{24}F_3N_3O_4S_2$: 491.12, Observed: 490.0 $[M - H]^-$. |
| A-987 | 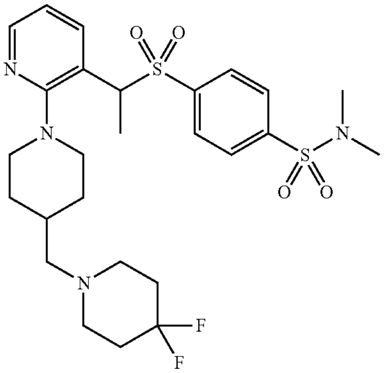 [SMILES: CC(c1cccnc1N1CCC(CN2CCC(F)(F)CC2)CC1)S(=O)(=O)c1ccc(S(=O)(=O)N(C)C)cc1] | Appearance: Off white solid; $^1$H NMR (400 MHz, DMSO-$d_6$) δ 8.16 (br d, J = 3.55 Hz, 1 H), 7.91 (br d, J = 7.09 Hz, 1 H), 7.77 (br d, J = 7.82 Hz, 2 H), 7.62 (br d, J = 7.83 Hz, 2 H), 7.18-7.08 (m, 1 H), 4.77 (br d, J = 6.85 Hz, 1 H), 2.88 (br d, J = 11.98 Hz, 1 H), 2.61 (s, 6 H), 2.58-2.30 (m, 4 H), 2.25 (br d, J = 6.60 Hz, 2 H), 2.16 (br d, J = 11.86 Hz, 1 H), 2.01-1.87 (m, 5 H), 1.80 (d, J = 6.97 Hz, 3 H), 1.75-1.56 (m, 2 H), 1.54-1.46 (m, 1 H), 1.34-1.14 (m, 2 H), 1.02-0.89 (m, 1 H); HPLC purity: 99.89%, LCMS calculated for $C_{26}H_{36}F_2N_4O_4S_2$: 570.21; Observed: 571.3 $[M + H]^+$. |
| A-988 | 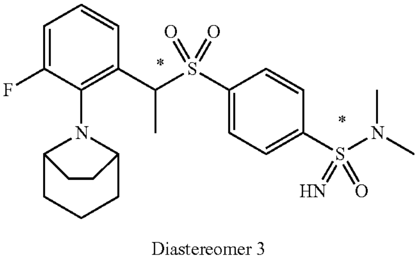 [SMILES: CC(c1cccc(F)c1N1C2CCCC1CC2)S(=O)(=O)c1ccc(S(=N)(=O)N(C)C)cc1]<br>Diastereomer 3 | Appearance: Off white solid; $^1$H NMR (400 MHz, DMSO-$d_6$) δ 7.84 (d, J = 8.4 Hz, 2 H), 7.66 (d, J = 8.4 Hz, 2 H), 7.39 (d, J = 8.0 Hz, 1 H), 7.09-6.99 (m, 2 H), 5.24 (q, J = 7.2 Hz, 1 H), 4.69 (bs, 1H), 3.30-3.22 (m, 2 H), 2.53 (s, 6 H), 2.01-1.95 (m, 1 H), 1.84-1.76 (m, 1 H), 1.74 (d, J = 7.2 Hz, 3H), 1.79-1.48 (m, 7 H), 1.49-1.36 (m, 1 H); HPLC purity: 98.33%; LCMS calculated for $C_{23}H_{30}FN_3O_3S_2$: 479.17 Observed: 480.1 $[M + H]^+$. |
| A-989 | 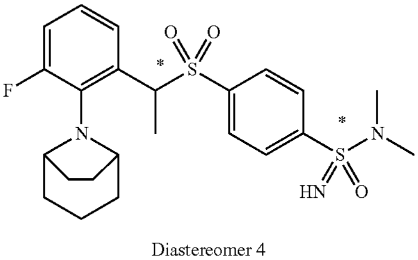 [SMILES: CC(c1cccc(F)c1N1C2CCCC1CC2)S(=O)(=O)c1ccc(S(=N)(=O)N(C)C)cc1]<br>Diastereomer 4 | Appearance: Off white solid; $^1$H NMR (400 MHz, DMSO-$d_6$) δ 7.83 (d, J = 8.4 Hz, 2 H), 7.67 (d, J = 8.4 Hz, 2 H), 7.39 (d, J = 7.6 Hz, 1 H), 7.09-6.84 (m, 2 H), 5.24 (q, J = 7.2 Hz, 1 H), 4.70 (bs, 1H), 3.31-3.22 (m, 2 H), 2.66 (s, 6H), 2.01-1.95 (m, 1 H), 1.84-1.76 (m, 1 H), 1.74 (d, J = 7.2 Hz, 3H), 1.79-1.48 (m, 7 H) 1.49-1.36 (m, 1 H); HPLC purity: 97.71%; LCMS calculated for $C_{23}H_{30}FN_3O_3S_2$: 479.17 Observed: 480.1 $[M + H]^+$. |

-continued

| Compound No. | Structure | Analytical data |
|---|---|---|
| A-990 | 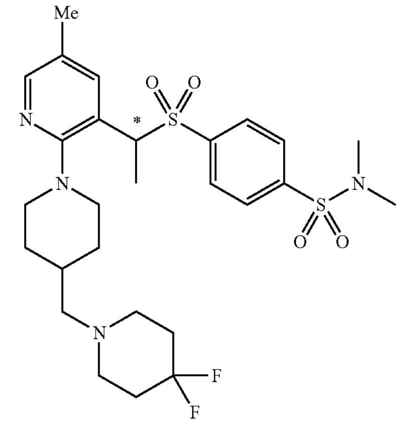 Enantiomer 1 | Appearance: Off white solid; $^1H$ NMR (400 MHz, DMSO-$d_6$) δ 8.01 (d, J = 1.6 Hz, 1 H), 7.78 (d, J = 8.8 Hz, 2 H), 7.72 (d, J = 2 Hz, 1 H), 7.63 (d, J = 8.4 Hz, 2 H), 4.79 (q, J = 14.0 Hz, 1 H), 2.81 (br d J = 12.4 Hz, 1 H), 2.68-2.61 (m, 7 H), 2.45 (br s, 4 H), 2.32-2.23 (m, 6 H), 2.05 (br d J = 12.4 Hz, 1 H), 1.97-1.90 (m, 4 H), 1.77 (d, J = 7.2 Hz, 3 H), 1.69 (br d J = 12.4 Hz, 1 H), 1.58 (br d J = 12.4 Hz, 1 H), 1.49-1.47 (m, 1 H), 1.27-1.23 (m, 1 H), 0.90-1.02 (m, 1 H); HPLC purity: 99.90%; LCMS calculated for $C_{27}H_{38}F_2N_4O_4S_2$: 584.23; Observed: 585.2 $[M + H]^+$. |
| A-991 | 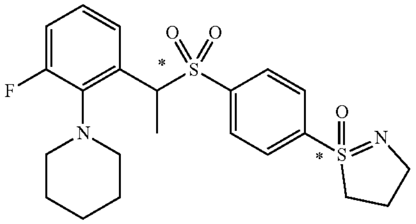 diastereomer 3 | Appearance: Off white solid; $^1H$ NMR (400 MHz, DMSO-$d_6$) δ 8.01 (d, J = 8.8 Hz, 2 H), 7.80 (d, J = 8.8 Hz, 2 H), 7.40 (dd, J = 8.0, 2.4 Hz, 1 H), 7.34-7.28 (m, 1H), 7.22-7.16 (m, 1 H), 5.36 (q, J = 8.0 Hz, 1 H), 3.86-3.81 (m, 1H), 3.67-3.62 (m, 1H), 3.41 (t, J = 8.0 Hz, 2H), 2.85-2.76 (m, 2H), 2.68-2.63 (m, 1 H), 2.30-2.18 (m, 2 H), 1.82-1.68 (m, 2H), 1.63 (d, J = 8.0 Hz, 3H), 1.57-1.46 (m, 3 H), 1.39-1.30 (m, 1 H), 1.24-1.13 (m, 1 H); HPLC purity: 99.73%; LCMS calculated for $C_{22}H_{27}FN_2O_3S_2$; 450.14 Observed: 451.0 $[M + H]^+$. |
| A-992 | 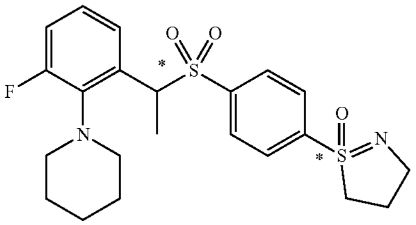 diastereomer 4 | Appearance: Off white solid; $^1H$ NMR (400 MHz, DMSO-$d_6$) δ 8.02 (d, J = 8.4 Hz, 2 H), 7.79 (d, J = 8.4 Hz, 2 H), 7.40 (d, J = 7.2 Hz, 1 H), 7.34-7.28 (m, 1 H), 7.22-7.16 (m, 1 H), 5.36 (q, J = 8.0 Hz, 1 H), 3.86-3.79 (m, 1 H), 3.67-3.62 (m, 1H), 3.44-3.31 (m, 2H), 2.85-2.76 (m, 2H), 2.68-2.64 (m, 1 H), 2.30-2.18 (m, 2 H), 1.77-1.68 (m, 2H), 1.62 (d, J = 7.2 Hz, 3H), 1.57-1.46 (m, 3 H), 1.39-1.30 (m, 1 H), 1.24-1.16 (m, 1 H), HPLC purity: 99.78%; LCMS calculated for $C_{22}H_{27}FN_2O_3S_2$: 450.14 Observed: 451.1 $[M + H]^+$. |
| A-993 | 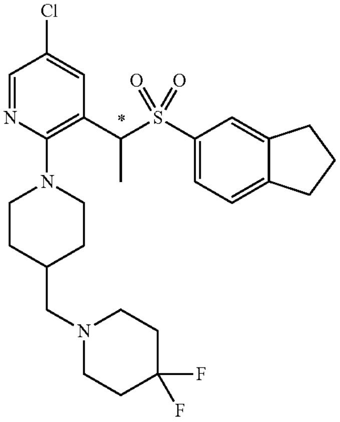 Enantiomer 1 | Appearance: Off white solid; $^1H$ NMR (400 MHz, DMSO-$d_6$) δ 8.22 (d, J = 2.57 Hz, 1 H), 7.89 (d, J = 2.57 Hz, 1 H), 7.31-7.24 (m, 2 H), 7.11-7.03 (m, 1 H), 4.58 (q, J = 7.21 Hz, 1 H), 2.90-2.77 (m, 5 H), 2.63-2.54 (m, 1 H), 2.34-2.27 (m, 5 H), 2.21 (d, J = 7.09 Hz, 3 H), 2.05-1.86 (m, 6 H), 1.73 (d, J = 7.21 Hz, 3 H), 1.67-1.59 (m, 2 H), 1.51-1.48 (m, 1 H), 1.24-1.13 (m, 1 H), 0.89-0.77 (m, 1 H); HPLC purity: 98.19%; LCMS calculated for $C_{27}H_{34}ClF_2N_3O_2S$: 537.20; Observed 538.2 $[M + H]^+$. |

-continued

| Compound No. | Structure | Analytical data |
|---|---|---|
| A-994 | 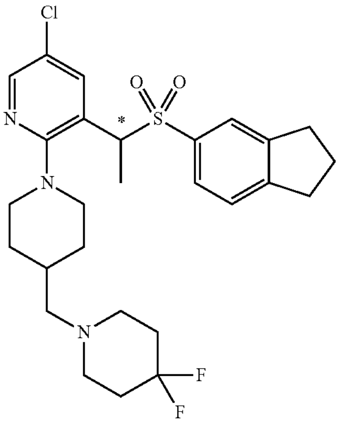 Enantiomer 2 | Appearance: Off white solid; $^1$H NMR (400 MHz, DMSO-$d_6$) δ 8.23 (d, J = 2.50 Hz, 1 H), 7.90 (d, J = 2.63 Hz, 1 H), 7.29-7.25 (m, 2 H), 7.07 (dd, J = 8.0, 1.2 Hz, 1H), 4.58 (d, J = 7.38 Hz, 1 H), 2.89-2.80 (m, 5 H), 2.62-2.58 (m, 1 H), 2.52-2.46 (m, 4 H), 2.39-2.24 (m, 2 H), 2.23 (d, J = 7.2 Hz, 2H), 2.03-1.89 (m, 6 H), 1.73 (d, J = 7.25 Hz, 3 H), 1.71-1.56 (m, 3 H), 1.24-1.11 (m, 1 H), 0.88-0.80 (m, 1 H); HPLC purity: 99.76%; LCMS calculated for $C_{27}H_{34}ClF_2N_3O_2S$: 537.20; Observed: 538.2 $[M + H]^+$. |
| A-995 | 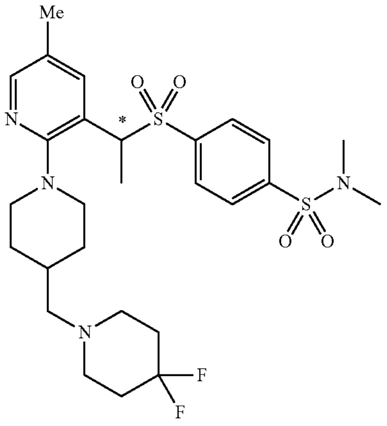 Enantiomer 2 | Appearance: Off white solid; $^1$H NMR (400 MHz, DMSO-$d_6$) δ 8.01 (d, J = 1.6 Hz, 1 H), 7.78 (d, J = 8.8 Hz, 2 H), 7.72 (d, J = 2 Hz, 1 H), 7.63 (d, J = 8.4 Hz, 2 H), 4.79 (d, J = 14.0 Hz, 1 H), 2.81 (br d) J = 12.4 Hz, 1 H), 2.68-2.61 (m, 7 H), 2.45 (br s, 4 H), 2.32-2.23 (m, 6 H), 2.05 (br d J = 12.4 Hz, 1 H), 1.97-1.90 (m, 4 H), 1.77 (d, J = 7.2 Hz, 3 H), 1.69 (br d J = 12.4 Hz, 1 H), 1.58 (br d J = 12.4 Hz, 1 H), 1.49-1.47 (m, 1 H), 1.27-1.23 (m, 1 H), 1.02-0.90 (m, 1 H); HPLC purity: 96.77%; LCMS calculated for $C_{27}H_{38}F_2N_4O_4S_2$: 584.23; Observed: 585.2 $[M + H]^+$. HPLC purity: 99.76%; LCMS calculated for $C_{27}H_{34}ClF_2N_3O_2S$: 537.20; Observed 538.2 $[M + H]^+$. |
| A-996 | 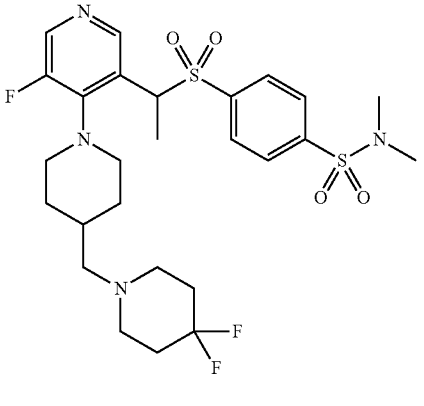 [SMILES: CC(c1cncc(F)c1N1CCC(CN2CCC(F)(F)CC2)CC1)S(=O)(=O)c1ccc(S(=O)(=O)N(C)C)cc1] | Appearance: Off white solid; $^1$H NMR (400 MHz, $CDCl_3$) δ 8.64 (s, 1H), 8.34 (d, J = 3.2 Hz, 1H) 7.85-7.79 (m, 4 H), 5.18-5.08 (m, 1 H), 3.08-2.88 (m, 2 H), 2.81-2.72 (m, 8 H), 2.58-2.51 (m, 5 H), 2.29-2.55 (m, 2 H), 2.42-2.25 (m, 1 H), 2.05-1.96 (m, 4 H), 1.85-1.72 (m, 6 H); HPLC purity: 97.64%; LCMS calculated for $C_{26}H_{35}F_3N_4O_4S_2$: 588.21, Observed: 589.25 $[M - H]^-$. |

-continued

| Compound No. | Structure | Analytical data |
|---|---|---|
| A-997 | 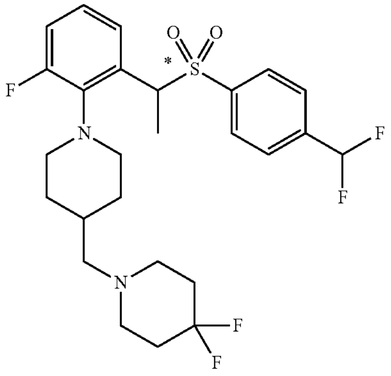 Enantiomer 1 | Appearance: Off white solid; $^1H$ NMR (400 MHz, DMSO-$d_6$) δ 7.74 (d, J = 8.0 Hz, 2H), 7.68 (d, J = 7.6 Hz, 2H), 7.41 (d, J = 8.0 Hz, 1H), 7.32-6.99 (m, 3 H), 5.33-5.28 (m, 1 H), 2.84-2.75 (m, 2H), 2.70-2.68 (m, 1 H), 2.50-2.42 (m, 4 H), 2.24 (d, J = 7.2 Hz, 2H), 2.00-1.86 (m, 4 H), 1.74-1.66 (m, 2 H), 1.63 (d, J = 6.8 Hz, 3H), 1.56-1.42 (m, 2 H), 1.23-1.15 (m, 1 H), 1.06-0.71 (m, 1 H); HPLC purity: 100%; LCMS calculated for $C_{26}H_{31}F_5N_2O_2S$: 530.20, Observed: 531.1 $[M + H]^+$. |
| A-998 | 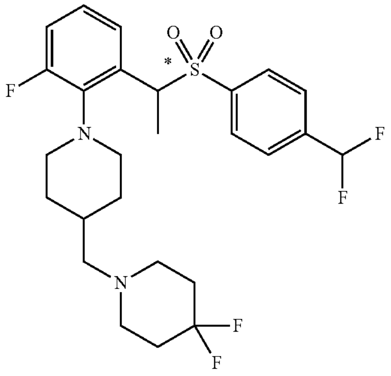 Enantiomer 2 | Appearance: Off white solid; $^1H$ NMR (400 MHz, DMSO-$d_6$) δ 7.74 (d, J = 8.0 Hz, 2H), 7.68 (d, J = 7.6 Hz, 2H), 7.41 (d, J = 8.0 Hz, 1H), 7.32-6.99 (m, 3H), 5.33-5.28 (m, 1H), 2.84-2.75 (m, 2 H), 2.70-2.68 (m, 1 H), 2.50-2.42 (m, 4 H), 2.24 (d, J = 7.2 Hz, 2H), 2.00-1.86 (m, 4 H), 1.74-1.66 (m, 2 H), 1.63 (d, J = 6.8 Hz, 3H), 1.56-1.42 (m, 2 H), 1.23-1.15 (m, 1 H), 1.06-0.71 (m, 1 H); HPLC purity: 98.91%; LCMS calculated for $C_{26}H_{31}F_5N_2O_2S$: 530.20, Observed: 531.1 $[M + H]^+$. |
| A-999 | 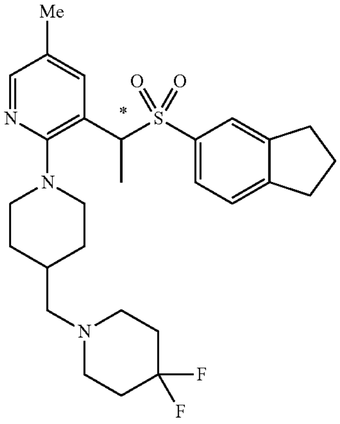 Enantiomer 1 | Appearance: Off white solid; $^1H$ NMR (400 MHz, DMSO-$d_6$) δ 8.04 (s, 1H), 7.70 (s, 1 H), 7.29 (s, 1 H), 7.26 (d, J = 8.0 Hz, 1 H), 7.07 (d, J = 7.6 Hz, 1 H), 4.70 (q, J = 14.4 hz, 1 H), 2.89-2.79 (m, 5 H), 2.71-2.55 (m, 2 H), 2.69-2.62 (m, 4 H), 2.38-2.12 (m, 6 H), 2.03-1.91 (m, 6 H), 1.70 (d, J = 7.2 Hz, 4 H), 1.61 (br d J = 12.0 Hz, 1 H), 1.49 (br s, 1 H), 1.25-1.18 (m, 1 H), 0.93-0.85 (m, 1 H); HPLC purity: 98.73%; LCMS calculated for $C_{28}H_{37}F_2N_3O_2S$: 517.26; Observed: 518.2 $[M + H]^+$. |

-continued

| Compound No. | Structure | Analytical data |
|---|---|---|
| A-1000 | 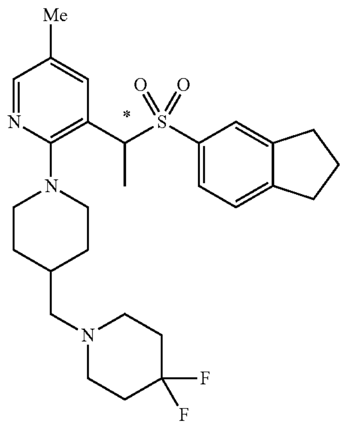 Enantiomer 2 | Appearance: Off white solid; $^1$H NMR (400 MHz, DMSO-$d_6$) δ 8.04 (s, 1 H), 7.70 (s, 1 H), 7.29 (s, 1 H), 7.26 (d, J = 8.0 Hz, 1 H), 7.07 (d, J = 7.6 Hz, 1 H), 4.70 (q, J = 14.4 Hz, 1 H), 2.89-2.79 (m, 5 H), 2.71-2.55 (m, 2 H), 2.52-2.40 (m, 3 H), 2.39-2.13 (m, 7 H), 2.03-1.91 (m, 6 H), 1.70 (d, J = 7.2 Hz, 4 H), 1.61 (br d J = 12.0 Hz, 1 H), 1.49 (br s 1 H), 1.25-1.18 (m, 1 H), 0.93-0.85 (m, 1 H); HPLC purity: 99.36%; LCMS calculated for $C_{28}H_{37}F_2N_3O_2S$: 517.26; Observed: 518.2 $[M + H]^+$. |

Example A119

The following compounds were prepared according to methods described herein using standard chemical transformations known to one of skill in the art.

| Compound No. | Structure | Analytical data |
|---|---|---|
| A-828 | 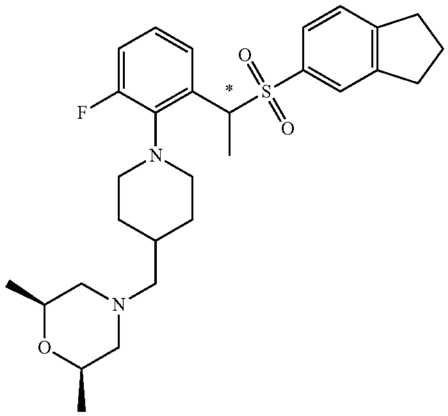 Enantiomer 1 | Yield: 0.038 g, 6.13%; Appearance: Off white solid; $^1$H NMR (400 MHz, DMSO-$d_6$) δ 7.46 (s, 1 H), 7.41-7.37 (m, 1 H), 7.33-7.25 (m, 2 H), 7.19-7.11 (m, 2 H), 5.25 (q, J = 7.17 Hz, 1 H), 3.56-3.49 (m, 2 H), 2.92-2.78 (m, 6 H), 2.72-2.62 (m, 3 H), 2.12 (d, J = 6.85 Hz, 2 H), 2.08-2.98 (m, 2H), 1.79 (d, J = 10.76 Hz, 1 H), 1.69 (d, J = 11.74 Hz, 1 H), 1.62-1.49 (m, 7H), 1.18-1.11 (m, 1 H), 1.04 (d, J = 6.36 Hz, 6 H), 0.98-0.94 (m, 1 H); HPLC purity: 99.23%; LCMS calculated for $C_{29}H_{39}FN_2O_3S$: 514.27 Observed: 515.1 $[M + H]^+$. |

-continued

| Compound No. | Structure | Analytical data |
|---|---|---|
| A-871A | 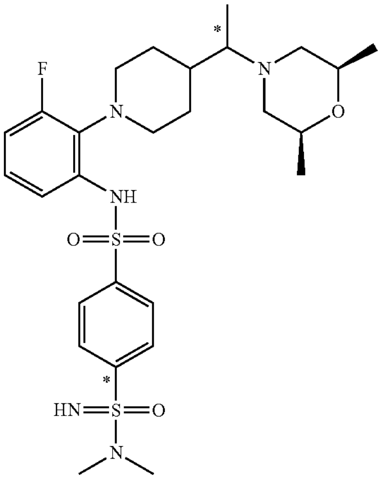 Diastereomer 1 | Appearance: Off white solid; $^1$H NMR (400 MHz, DMSO-$d_6$) δ 9.09 (brs, 1 H), 8.01-7.80 (m, 4 H), 7.27-7.08 (m, 2 H), 6.97-6.80 (m, 1 H), 4.65 (s, 1 H) 3.60-3.49 (m, 1 H), 3.47-3.38 (m, 1 H), 2.90-2.73 (m, 2 H), 2.54 (s, 6 H), 2.42-2.29 (m, 3 H), 2.29-2.15 (m, 1H), 2.14-2.02 (m, 1 H), 1.92-1.79 (m, 1 H), 1.77-1.64 (m, 1 H), 1.60-1.44 (m, 1 H), 1.40-1.13 (m, 4 H), 1.04 (d, J = 5.62 Hz, 6 H), 0.86 (d, J = 5.87 Hz, 3 H); HPLC purity: 100%; LCMS calculated for $C_{27}H_{40}FN_5O_4S_2$: 581.25, Observed: 582.1 $[M + H]^+$. |
| A-871B | 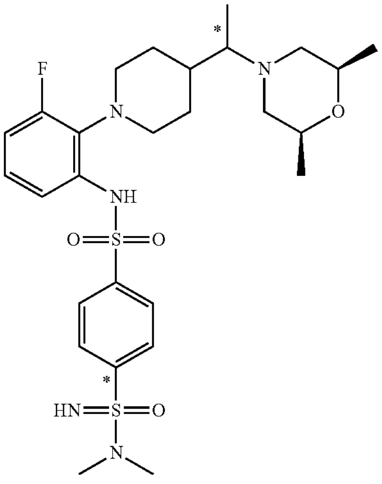 Diastereomer 2 | Appearance: Off white solid; $^1$H NMR (400 MHz, DMSO-$d_6$) δ 9.06 (brs, 1 H), 8.04-7.83 (m, 4 H), 7.29-7.10 (m, 2 H), 7.01-6.88 (m, 1 H), 4.66 (s, 1 H), 3.59-3.49 (m, 1 H), 3.49-3.39 (m, 1 H), 2.88-2.72 (m, 2 H), 2.54 (s, 6 H), 2.39-2.28 (m, 3 H), 2.24 (d, J = 7.34 Hz, 1 H), 2.15-2.01 (m, 1H), 1.86 (d, J = 11.25 Hz, 1H), 1.77-1.64 (m, 1 H), 1.58-1.43 (m, 1 H), 1.40-1.12 (m, 4 H), 1.04 (d, J = 6.11 Hz, 6 H), 0.86 (d, J = 6.36 Hz, 3 H); HPLC purity: 99.32%; LCMS calculated for $C_{27}H_{40}FN_5O_4S_2$: 581.25, Observed: 582.1 $[M + H]^+$. |
| A-872A | 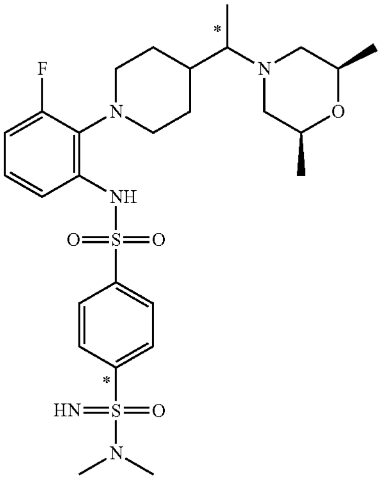 Diastereomer 3 | Appearance: Off white solid; $^1$H NMR (400 MHz, DMSO-$d_6$) δ 9.05 (s, 1H), 8.00-7.86 (m, 4 H), 7.28-7.08 (m, 2 H), 7.00-6.87 (m, 1 H), 4.66 (s, 1 H), 3.60-3.49 (m, 1 H), 3.49-3.39 (m, 1 H), 2.82-2.72 (m, 2 H), 2.54 (s, 6 H), 2.40-2.28 (m, 3 H), 2.27-2.16 (m, 1 H), 2.16-2.01 (m, 1 H), 1.92-1.78 (m, 1 H), 1.78-1.65 (m, 1 H), 1.57-1.44 (m, 1 H), 1.42-1.15 (m, 4 H), 1.04 (d, J = 6. 11 Hz, 6 H), 0.86 (d, J = 6.36 Hz, 3 H); HPLC purity: 96.45%; LCMS calculated for $C_{27}H_{40}FN_5O_4S_2$: 581.25, Observed: 582.1 $[M + H]^+$. |

-continued

| Compound No. | Structure | Analytical data |
|---|---|---|
| A-872B | 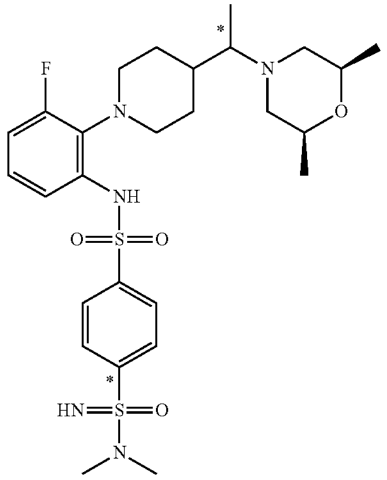 Diastereomer 4 | Appearance: Off white solid; $^1$H NMR (400 MHz, DMSO-$d_6$) δ 9.06 (s, 1 H), 8.00-7.85 (m, 4 H), 7.30-7.07 (m, 2 H), 7.02-6.83 (m, 1 H), 4.66 (s, 1 H), 3.62-3.50 (m, 1 H), 3.49-3.38 (m, 1 H), 2.87-2.72 (m, 2 H), 2.54 (s, 6 H), 2.41-2.29 (m, 3 H), 2.27-2.16 (m, 1 H), 2.10 (t, J = 10.27 Hz, 1 H), 1.85 (d, J = 11.25 Hz, 1 H), 1.73 (t, J = 10.27 Hz, 1 H), 1.53 (d, J = 10.76 Hz, 1 H), 1.39-1.15 (m, 4 H) 1.04 (d, J = 6.11 Hz, 6 H), 0.86 (d, J = 6.36 Hz, 3 H); HPLC purity: 98.50%; LCMS calculated for $C_{27}H_{40}FN_5O_4S_2$: 581.25, Observed: 582.1 [M + H]$^+$. |
| A-885 | 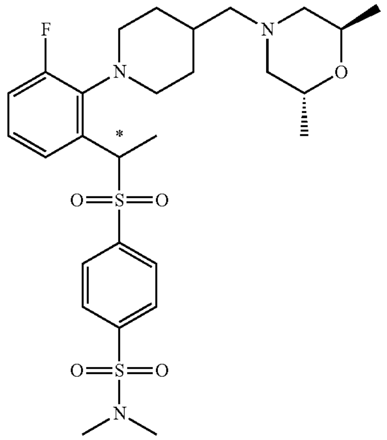 Diastereomer 4 | Appearance: Off white solid; $^1$H NMR (400 MHz, DMSO-$d_6$) δ 7.96-7.83 (m, 2H), 7.78 (d, J = 7.82 Hz, 2 H), 7.46-7.35 (m, 1 H), 7.33-7.24 (m, 1 H), 7.21-7.07 (m, 1 H), 5.43-5.26 (m, 1 H), 3.95-3.82 (m, 2 H), 2.94-2.65 (m, 5 H), 2.62 (s, 6 H), 2.40-2.25 (m, 2 H), 2.18-1.98 (m, 5 H), 1.65 (s, 3 H), 1.57-1.39 (m, 1 H), 1.26-1.15 (m, 1 H), 1.13 (d, J = 5.87 Hz, 6 H), 1.05-0.91 (m, 1 H); HPLC purity: 95.50%; LCMS calculated for $C_{26}H_{40}FN_3O_5S_2$: 581.24 Observed: 582.6 [M + H]$^+$. |
| A-890 | 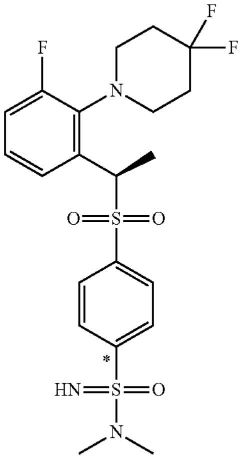 Diastereomer 1 | Appearance: Off white solid; $^1$H NMR (400 MHz, DMSO-$d_6$) δ 7.94 (d, J = 8.31 Hz, 2 H), 7.88-7.74 (m, 2 H), 7.45-7.29 (m, 2 H), 7.26-7.12 (m, 1 H), 5.51-5.36 (m, 1 H), 4.75 (s, 1 H), 3.10-2.89 (m, 3 H), 2.87-2.75 (m, 1 H), 2.56 (s, 6 H), 2.35-1.83 (m, 4 H), 1.62, 1.64 (s, 3 H); HPLC purity: 97.56%; LCMS calculated for $C_{21}H_{26}F_3N_3O_3S_2$: 489.14 Observed: 490.20 [M + H]$^+$. |

-continued

| Compound No. | Structure | Analytical data |
|---|---|---|
| A-892 | 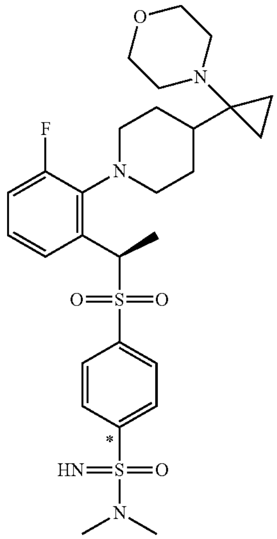 Diastereomer 1 | Appearance: Off white solid; $^1$H NMR (400 MHz, DMSO-$d_6$) δ 7.92 (d, J = 6.36 Hz, 2 H), 7.78 (d, J = 6.85 Hz, 2 H), 7.46-7.35 (m, 1 H), 7.34-7.24 (m, 1 H), 7.18 (d, J = 9.78 Hz, 1 H), 5.43-5.29 (m, 1 H), 4.71 (s, 1 H), 3.63-3.46 (m, 4 H), 2.98-2.75 (m, 2 H), 2.75-2.64 (m, 1 H), 2.56 (s, 6 H), 2.01-1.83 (m, 1 H), 1.71-1.52 (m, 4H), 1.51-1.33 (m, 2H), 1.30-1.12 (m, 2 H), 0.54-0.70 (m, 2 H), 0.52-0.32 (m, 2 H). 4H's are merged in to solvent peak; HPLC purity: 100%; LCMS calculated for $C_{26}H_{39}FN_4O_4S_2$: 578.24 Observed: 579.1 $[M + H]^+$. |
| A-893 | 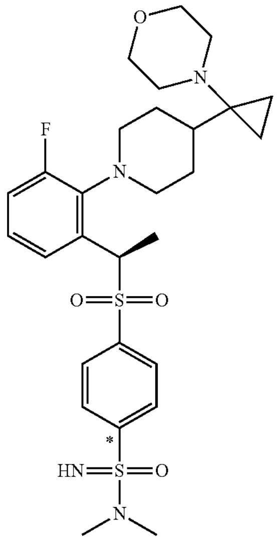 Diastereomer 2 | Appearance: Off white solid; $^1$H NMR (400 MHz, DMSO-$d_6$) δ ppm 7.93 (d, J = 7.82 Hz, 2 H), 7.84-7.70 (m, 2 H), 7.39 (d, J = 7.34 Hz, 1 H), 7.30 (d, J = 4.89 Hz, 1 H), 7.22-7.08 (m, 1 H), 5.42-5.28 (m, 1 H), 4.68 (s, 1 H), 3.60-3.46 (m, 4 H), 2.93-2.74 (m, 3 H), 2.70 (d, J = 11.74 Hz, 2 H), 2.56 (s, 6 H), 1.95 (d, J = 9.29 Hz, 2 H), 1.62, 1.64 (s, 3 H), 1.58-1.52 (m, 1 H), 1.50-1.33 (m, 2 H), 1.31-1.09 (m, 3 H). 4H's are merged in to solvent peak; HPLC purity: 97.56%; LCMS calculated for $C_{26}H_{39}FN_4O_4S_2$: 578.24 Observed: 579.1 $[M + H]^+$. |

-continued

| Compound No. | Structure | Analytical data |
|---|---|---|
| A-894 | 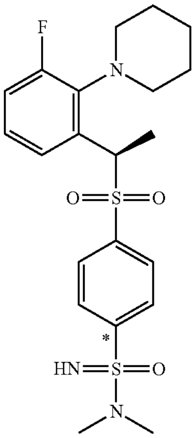 Diastereomer 1 | Appearance: Off white solid; $^1$H NMR (400 MHz, DMSO-$d_6$) δ 7.90 (d, J = 8.31 Hz, 2 H), 7.78-7.64 (m, 2 H), 7.40 (d, J = 7.82 Hz, 1 H), 7.33-7.23 (m, 1 H), 7.22-7.09 (m, 1 H), 5.45-5.28 (m, 1 H), 4.71 (brs, 1 H), 2.88-2.70 (m, 2 H), 2.70-2.61 (m, 1 H), 2.54 (s, 6 H), 1.72 (d, J = 9.78 Hz, 2 H), 1.65, 1.63 (s, 3 H), 1.59-1.48 (m, 2 H), 1.46-1.30 (m, 2 H), 1.26-1.08 (m, 1 H); HPLC purity: 99.94%; LCMS calculated for $C_{21}H_{28}FN_3O_3S_2$: 453.16 Observed: 454.1 $[M + H]^+$. |
| A-895 | 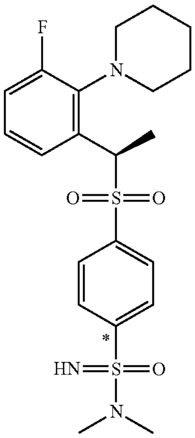 Diastereomer 2 | Appearance: Off white solid; $^1$H NMR (400 MHz, DMSO-$d_6$) δ 7.90 (d, J = 8.31 Hz, 2 H), 7.74 (d, J = 7.82 Hz, 2 H), 7.40 (d, J = 7.34 Hz, 1 H), 7.29 (d, J = 4.89 Hz, 1 H), 7.20-7.09 (m, 1 H), 5.45-5.27 (m, 1 H), 4.66 (s, 1 H), 2.88-2.71 (m, 2 H), 2.70-2.60 (m, 1 H), 2.54 (s, 6 H), 1.78-1.67 (m, 2 H), 1.63, 1.65 (s, 3 H) 1.59-1.31 (m, 4 H), 1.25-1.07 (m, 1H); HPLC purity: 96.49%; LCMS calculated for $C_{21}H_{28}FN_3O_3S_2$: 453.16 Observed: 454.1 $[M + H]^+$. |
| A-901 | 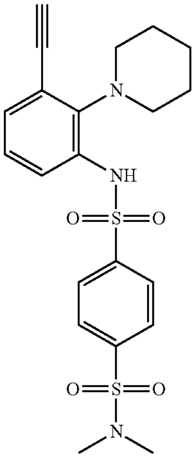 [SMILES: C#Cc1cccc(NS(=O)(=O)c2ccc(S(=O)(=O)N(C)C)cc2)c1N1CCCCC1] | Yield: 30 mg; 17% Appearance: white solid; $^1$H NMR (500 MHz, $CDCl_3$) δ 1.28 (br d, J = 17.39 Hz, 1H), 1.55 (s, 2 H), 1.68 (br d, J = 11.59 Hz, 2 H), 1.80 (br d, J = 10.43 Hz, 1 H), 2.21 (br d, J = 8.69 Hz, 2 H), 2.70 (s, 6 H), 3.31 (s, 1 H), 3.41 (br t, J = 11.59 Hz, 2H), 7.18-7.09 (m, 2 H), 7.67 (br d, J = 7.53 Hz, 1 H), 7.81 (d, J = 8.11 Hz, 2 H), 7.93 (d, J = 8.11 Hz, 2 H), 8.77 (br s, 1 H); HPLC purity: 99.59%; LCMS calculated for $C_{21}H_{25}N_3O_4S_2$: 447.57; Observed: 448.1 $[M + H]^+$. |

-continued

| Compound No. | Structure | Analytical data |
|---|---|---|
| A-902 | 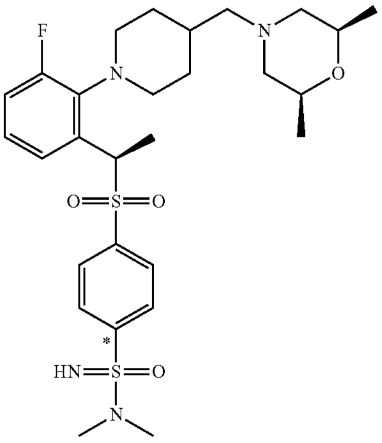<br>Diastereomer 3 | Appearance: White solid; $^1$H NMR (400 MHz, DMSO-$d_6$) δ 7.94-7.82 (m, 2 H), 7.73 (d, J = 7.82 Hz, 2 H), 7.41 (d, J = 7.34 Hz, 1 H), 7.34-7.23 (m, 1 H), 7.20-7.08 (m, 1 H), 5.42-5.26 (m, 1 H), 4.72 (s, 1 H), 3.61-3.45 (m, 2 H), 2.90-2.75 (m, 2 H), 2.74-2.64 (m, 3 H), 2.54 (s, 6 H), 2.21-2.04 (m, 2 H), 1.77-1.70 (m, 1 H), 1.64, 1,66 (s, 3 H), 1.58-1.41 (m, 4 H), 1.30-1.10 (m, 2 H) 1.04 (d, J = 5.87 Hz, 6 H), 0.92-0.82 (m, 1 H); HPLC purity: 100%; LCMS calculated for $C_{26}H_{41}FN_4O_4S_2$: 580.26 Observed: 581.1 $[M + H]^+$. |
| A-903 | 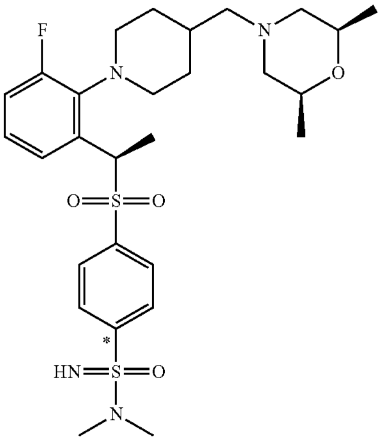<br>Diastereomer 4 | Appearance: White solid; $^1$H NMR (400 MHz, DMSO-$d_6$) δ 8.00-7.81 (m, 2 H), 7.77-7.61 (m, 2 H), 7.41 (d, J = 6.36 Hz, 1 H), 7.35-7.22 (m, 1 H), 7.21-7.08 (m, 1 H), 5.41-5.23 (m, 1 H), 4.72 (s, 1 H), 3.59-3.46 (m, 2 H), 2.92-2.62 (m, 6 H), 2.54 (s, 6 H), 2.18-2.08 (m, 2 H), 1.79-1.45 (m, 8 H), 1.28-1.11 (m, 2 H), 1.04 (br d, J = 4.32 Hz, 6 H); HPLC purity: 96.70%; LCMS calculated for $C_{26}H_{41}FN_4O_4S_2$: 580.26 Observed: 581.1 $[M + H]^+$. |
| A-904 | 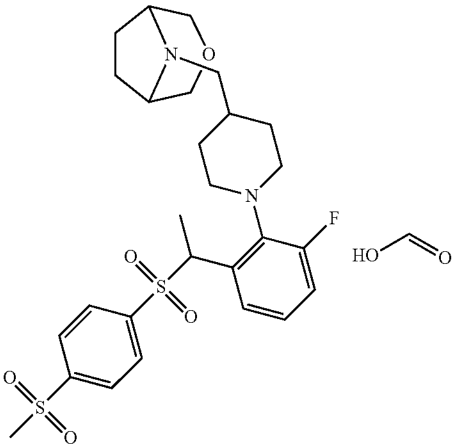 | Appearance: Off white solid; $^1$H NMR (400 MHz, DMSO-$d_6$) δ 8.10 (d, J = 7.34 Hz, 2 H), 7.81 (d, J = 7.34 Hz, 2 H), 7.40 (d, J = 6.85 Hz, 1 H), 7.31 (d, J = 4.89 Hz, 1 H), 7.22-7.11 (m, 1 H), 5.34 (d, J = 6.36 Hz, 1 H), 3.52 (d, J = 9.29 Hz, 3H), 3.40 (d, J = 9.29 Hz, 5H), 3.27 (s, 3 H), 3.01 (s, 2 H), 2.91-2.75 (m, 2 H), 2.75-2.63 (m, 2 H), 2.12 (dd, J = 15.89, 6.11 Hz, 2 H), 1.89-1.74 (m, 2 H), 1.75-1.49 (m, 5 H), 1.40-1.31 (m, 1 H), 1.28-1.10 (m, 1 H), 1.02-0.93 (m, 1 H); HPLC purity: 99.30%; LCMS calculated for $C_{28}H_{37}FN_2O_7S_2$: 596.20, for free base 550.20; Observed: 551.1 $[M + H]^+$. |

-continued

| Compound No. | Structure | Analytical data |
|---|---|---|
| A-905 | 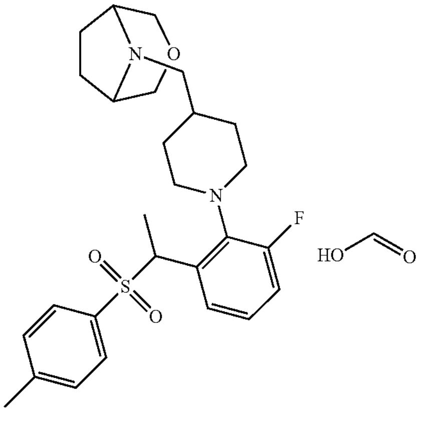 | Appearance: Off white solid; $^{1}H$ NMR (400 MHz, DMSO-$d_6$) δ 8.19-8.06 (m, 1 H), 7.50-7.21 (m, 6H), 7.20-7.05 (m, 1 H), 5.35-5.19 (q, 1 H), 3.59-3.46 (m, 4H), 3.05-2.90 (m, 2H), 2.88-2.76 (m, 2 H), 2.72-2.59 (m, 1 H), 2.36 (s, 3 H), 2.20-2.01 (m, 2 H), 1.94-1.74 (m, 4 H), 1.70 (d, J = 5.87 Hz, 2 H), 1.58 (d, J = 5.87 Hz, 5H), 1.44-1.30 (m, 1 H), 1.23-1.10 (m, 1 H), 1.03 (d, J = 9.78 Hz, 1 H); HPLC purity: 98.06%; LCMS calculated for $C_{28}H_{37}FN_2O_5S$: 532.24, for free base 486.24; Observed: 487.2 $[M + H]^+$. |
| A-906 | 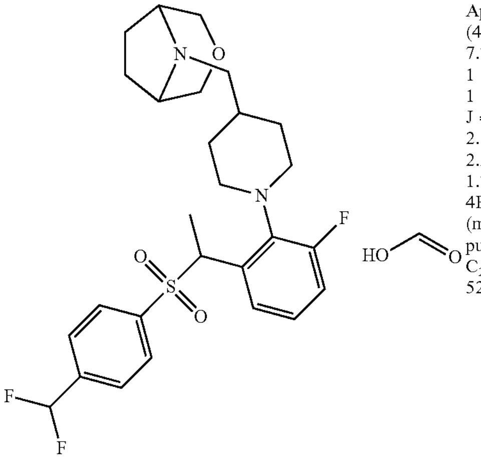 | Appearance: Off white solid; $^{1}H$ NMR (400 MHz, DMSO-$d_6$) δ 8.14 (br s, 1H), 7.78-7.57 (m, 4 H), 7.41 (d, J = 7.34 Hz, 1 H), 7.34-6.99 (m, 3H), 5.37-5.21 (m, 1 H), 3.53 (d, J = 9.78 Hz, 3 H), 3.41 (d, J = 9.78 Hz, 2 H), 3.07-2.94 (m, 2 H), 2.89-2.73 (m, 2 H), 2.72-2.59 (m, 1 H), 2.24-2.03 (m, 2 H), 1.91-1.75 (m, 3 H), 1.71 (d, J = 5.87 Hz, 3 H), 1.65-1.48 (m, 4H), 1.39 (d, J = 2.45 Hz, 1 H), 1.26-1.11 (m, 1 H), 1.05-0.91 (m, 1 H); HPLC purity: 96.61%; LCMS calculated for $C_{28}H_{35}F_3N_2O_3S$: 568.22 Observed: 523.1 $[M + H]^+$. |
| A-911 | 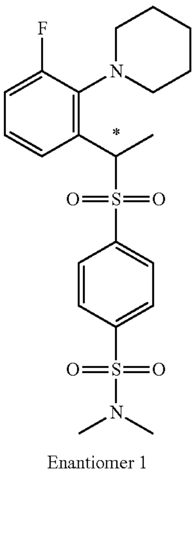 [SMILES: CC(c1cccc(F)c1N1CCCCC1)S(=O)(=O)c1ccc(S(=O)(=O)N(C)C)cc1]<br>Enantiomer 1 | Appearance: Off white solid; $^{1}H$ NMR (400 MHz, DMSO-$d_6$) δ 7.99-7.84 (m, 2H), 7.83-7.69 (m, 2H), 7.41 (d, J = 6.85 Hz, 1 H), 7.31 (d, J = 4.89 Hz, 1H), 7.23-7.07 (m, 1 H), 5.45-5.28 (m, 1H), 2.90-2.71 (m, 2 H), 2.62 (s, 7H), 1.77-1.60 (m, 4 H), 1.57 (brs, 2 H) 1.47-1.09 (m, 3 H), 1 proton merged in solvent; HPLC purity: 98.70%; LCMS Calculated for $C_{21}H_{27}FN_2O_4S_2$: 454.14 Observed: 455.1 $[M + H]^+$. |

-continued

| Compound No. | Structure | Analytical data |
|---|---|---|
| A-912 | 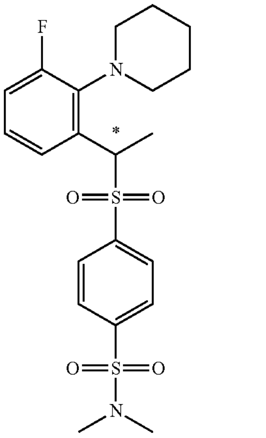 Enantiomer 2 | Appearance: Off white solid; $^1$H NMR (400 MHz, DMSO-$d_6$) δ 7.91 (d, J = 7.82 Hz, 2 H), 7.79 (d, J = 7.82 Hz, 2 H), 7.41 (d, J = 6.85 Hz, 1 H), 7.31 (d, J = 4.89 Hz, 1 H), 7.23-7.09 (m, 1 H), 5.37 (d, J = 7.34 Hz, 1 H), 2.89-2.72 (m, 3 H), 2.62 (s, 6 H), 1.66 (d, J = 6.85 Hz, 4 H), 1.61-1.50 (m, 2 H), 1.49-1.27 (m, 2 H), 1.27-1.09 (m, 2 H); HPLC purity: 98.66%; LCMS calculated for $C_{21}H_{27}FN_2O_4S_2$: 454.14 Observed: 455.1 $[M + H]^+$. |
| A-913 | 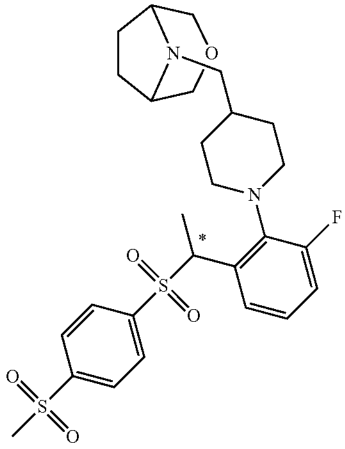 Enantiomer 1 | Appearance: Off white solid; $^1$H NMR (400 MHz, DMSO-$d_6$) δ 8.16-8.02 (m, 2 H), 7.88-7.72 (m, 2 H), 7.46-7.23 (m, 2 H), 7.22-7.10 (m, 1 H), 5.44-5.26 (m, 1 H), 3.50 (d, J = 9.29 Hz, 2 H), 3.40 (d, J = 9.29 Hz, 2 H), 3.04-2.92 (m, 2 H), 2.92-2.62 (m, 5 H), 2.12 (dd, J = 15.89, 6.11 Hz, 2 H), 1.89-1.49 (m, 8 H), 1.45-1.31 (m, 1H), 1.28-1.10 (m, 1 H), 0.97 (d, J = 10.27 Hz, 1 H). 3H's are merged in to solvent peak; HPLC purity: 95.73%; LCMS calculated for $C_{27}H_{35}FN_2O_5S_2$: 550.20 Observed: 551.6 $[M + H]^+$. |
| A-914 | 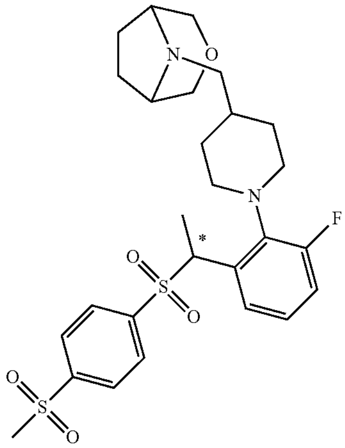 Enantiomer 2 | Appearance: Off white solid; $^1$H NMR (400 MHz, DMSO-$d_6$) δ 8.10 (d, J = 6.36 Hz, 2 H), 7.81 (d, J = 6.36 Hz, 2 H), 7.45-7.37 (m, 1 H), 7.35-7.23 (m, 1 H), 7.19 (d, J = 8.80 Hz, 1 H), 5.34 (d, J = 5.87 Hz, 1 H), 3.50 (d, J = 9.29 Hz, 2 H), 3.40 (d, J = 8.80 Hz, 2 H), 3.19-3.09 (m, 1 H), 3.04-2.92 (m, 2 H), 2.91-2.61 (m, 3 H), 2.20-2.01 (m, 2 H), 1.90-1.49 (m, 9 H), 1.45-1.30 (m, 1H), 1.26-1.09 (m, 1 H), 0.97 (d, J = 11.25 Hz, 1 H), 3H's are merged in to solvent peak; HPLC purity: 97.57%; LCMS calculated for $C_{27}H_{35}FN_2O_5S_2$: 550.20 Observed: 551.6 $[M + H]^+$. |

-continued

| Compound No. | Structure | Analytical data |
|---|---|---|
| A-920 | 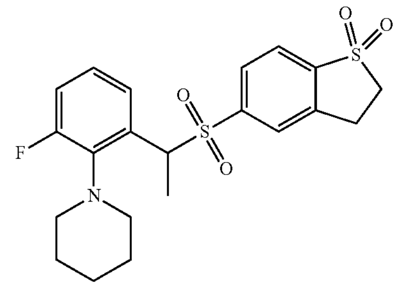 [SMILES: CC(c1cccc(F)c1N1CCCCC1)S(=O)(=O)c1ccc2c(c1)CCS2(=O)=O] | Yield: 70 mg, 43%; Appearance: White solid $^1$H NMR (400 MHz, DMSO-$d_6$) δ 9.93-7.87 (m, 2H), 7.54-7.50 (m, 1H), 7.41 (dd, J = 7.83, 1.10 Hz, 1 H), 7.33-7.30 (m, 1H), 7.23-7.17 (m, 1H), 5.35 (q, J = 7.25 Hz, 1H), ), 3.7--3.64 (m, 2H), 3.42-3.36 (m, 2H), 2.87-2.74 (m, 2H), 2.68-2.65 (m, 1H), 1.73 (br d, J = 8.68 Hz, 2 H), 1.64 (d, J = 7.21 Hz, 3 H); 1.59-1.46 (m, 3H); 1.36-1.14 (m, 2 H); HPLC purity: 96.10%; LCMS calculated for $C_{21}H_{24}FNO_4S_2$: 437.54; Observed: 438.1 $[M + H]^+$. |
| A-921 | 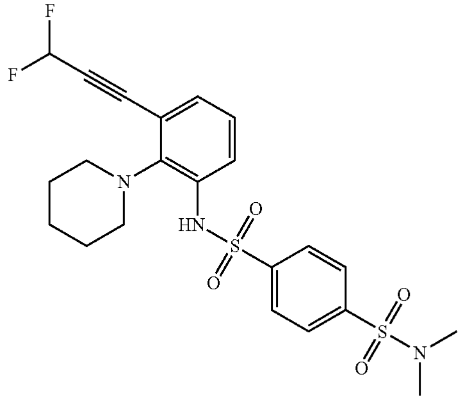 [SMILES: CN(C)S(=O)(=O)c1ccc(S(=O)(=O)Nc2cccc(C#CC(F)F)c2N2CCCCC2)cc1] | Appearance: Off white solid; 1H NMR (400 MHz, DMSO-$d_6$) δ 9.37 (s, 1 H), 7.98-7.89 (m, 4 H), 7.35-6.83 (m, 4 H), 2.80 (br s, 4 H), 2.62 (s, 6 H), 1.58-1.41 (m, 6 H); HPLC purity: 98.91%; LCMS calculated for $C_{22}H_{25}F_2N_3O_4S_2$: 497.58 Observed: 498.2 $[M + H]^+$. |
| A-922 | 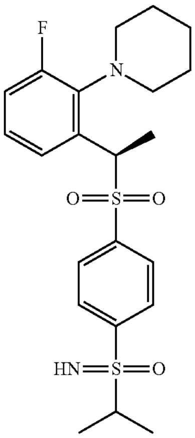 [SMILES: CC(C)S(=N)(=O)c1ccc(S(=O)(=O)[C@H](C)c2cccc(F)c2N2CCCCC2)cc1] | Appearance: Off white solid; $^1$H NMR (400 MHz, DMSO-$d_6$) δ 8.08-7.89 (m, 2 H), 7.85-7.71 (m, 2 H), 7.41 (d, J = 6.36 Hz, 1 H), 7.30 (d, J = 4.40 Hz, 1 H), 7.18 (d, J = 10.76 Hz, 1 H), 4.52-4.37 (m, 1 H), 2.88-2.59 (m, 4 H), 1.81-1.30 (m, 10 H), 1.28-1.14 (m, 1 H), 1.15-1.0 (m, 6 H); HPLC purity: 98.60%; LCMS calculated for $C_{22}H_{29}FN_2O_3S_2$: 452.16 Observed: 452.69 $[M + H]^+$. |

-continued

| Compound No. | Structure | Analytical data |
|---|---|---|
| A-923 | 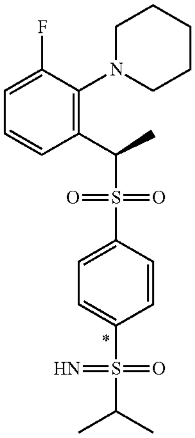 Diastereomer 3 | Appearance: Off white solid; $^1$H NMR (400 MHz, DMSO-$d_6$) δ 7.99 (d, J = 5.38 Hz, 2 H), 7.85-7.66 (m, 2 H), 7.40 (br s, 1 H), 7.34-7.22 (m, 1 H), 7.18 (d, J = 9.29 Hz, 1 H), 5.39 (d, J = 4.89 Hz, 1 H), 4.43 (s, 1 H), 2.78 (brs, 2 H), 2.67 (brs, 2 H) 1.79-1.27 (m, 9H), 1.21 (d, J = 15.65 Hz, 1 H), 1.09 (s, 6 H); HPLC purity: 100%; LCMS calculated for $C_{22}H_{29}FN_2O_3S_2$: 452.16 Observed: 453.1 $[M + H]^+$. |
| A-924 | 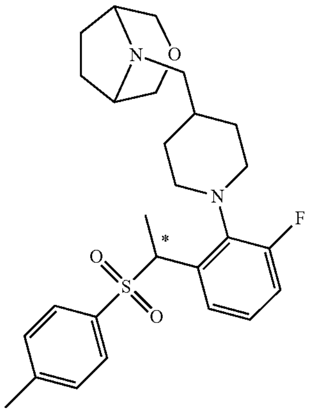 Enantiomer 1 | Appearance: Off white solid; $^1$H NMR (400 MHz, DMSO-$d_6$) δ 7.43 (br d, J = 8.00 Hz, 2 H), 7.41-7.32 (m, 3 H), 7.31-7.24 (m, 1 H), 7.14 (br dd, J = 12.01, 8.38 Hz, 1 H), 5.28 (q, J = 7.05 Hz, 1 H), 3.50 (br d, J = 9.63 Hz, 2 H), 2.98 (br s, 2 H), 2.83 (br t, 2H), 2.68 (br d, J = 12.26 Hz, 1 H), 2.36 (s, 4 H), 2.18-2.04 (m, 2 H), 1.90-1.78 (m, 4 H), 1.72-1.56 (m, 6 H), 1.38 (br d, J = 3.38 Hz, 1 H), 1.26-1.12 (m, 2 H), 1.08-0.97 (m, 1 H); HPLC purity: 100%; LCMS calculated for $C_{27}H_{35}FN_2O_3S$: 486.65 Observed: 487.3 $[M + H]^+$. |
| A-925 | 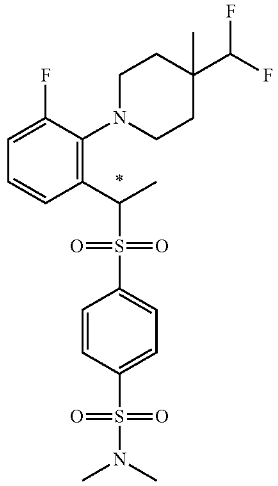 Enantiomer 1 | Appearance: Off white solid; $^1$H NMR (400 MHz, DMSO-$d_6$) δ 7.91 (d, J = 7.34 Hz, 2 H), 7.86-7.71 (m, 2 H), 7.47-7.11 (m, 3 H), 6.01-5.64 (m, 1 H), 5.35 (d, J = 6.36 Hz, 1 H), 3.13-2.86 (m, 3 H), 2.62 (s, 6 H), 1.80-1.46 (m, 6 H), 1.36-1.12 (m, 2 H), 1.01 (s, 3 H); HPLC purity: 100%; LCMS calculated for $C_{23}H_{29}F_3N_2O_4S_2$: 518.15 Observed: 519.1 $[M + H]^+$. |

-continued

| Compound No. | Structure | Analytical data |
|---|---|---|
| A-926 | 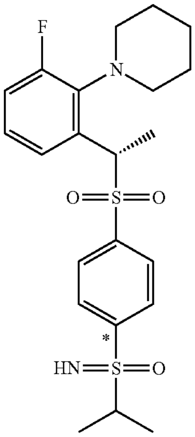 diastereomer 1 | Appearance: White solid; $^1$H NMR (400 MHz, DMSO-$d_6$) δ 8.08-7.91 (m, 2 H), 7.79 (d, J = 5.87 Hz, 2 H), 7.41 (d, J = 5.38 Hz, 1 H), 7.30 (d, J = 4.89 Hz, 1 H), 7.22-7.05 (m, 1 H), 5.39 (d, J = 5.87 Hz, 1 H), 4.48 (s, 1 H), 2.92-2.60 (m, 4 H), 1.82-1.31 (m, 9 H), 1.23-1.15 (m, 1 H), 1.15-0.99 (m, 6H); HPLC purity: 96.41%; LCMS calculated for $C_{22}H_{29}FN_2O_3S_2$: 452.16 Observed: 453.1 $[M + H]^+$. |
| A-927 | 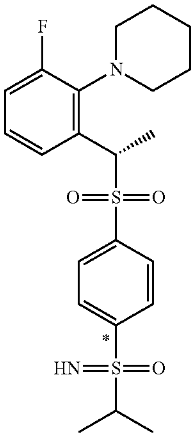 diastereomer 2 | Appearance: White solid; $^1$H NMR (400 MHz, DMSO-$d_6$) δ 8.06-7.89 (m, 2 H), 7.78 (d, J = 6.85 Hz, 2 H), 7.47-7.35 (m, 1 H), 7.30 (d, J = 3.42 Hz, 1 H), 7.18 (d, J = 11.25 Hz, 1 H), 5.48-5.30 (m, 1 H), 4.43 (s, 1 H), 3.55-3.38 (m, 2 H), 2.88-2.71 (m, 1 H), 2.70-2.60 (m, 1 H), 1.80-1.28 (m, 9 H), 1.18-1.06 (m, 6 H), 1.04-0.92 (m, 1 H); HPLC purity: 94.87%; LCMS calculated for $C_{22}H_{29}FN_2O_3S_2$: 452.16 Observed: 453.1 $[M + H]^+$. |
| A-928 | 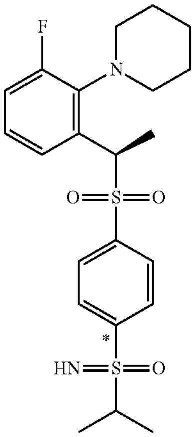 diastereomer 4 | Appearance: White sticky solid; $^1$H NMR (400 MHz, DMSO-$d_6$) δ 8.08-7.89 (m, 2 H), 7.79 (d, J = 6.36 Hz, 2 H), 7.40 (brs, 1 H), 7.30 (d, J = 3.91 Hz, 1 H), 7.18 (d, J = 9.78 Hz, 1 H), 5.47-5.26 (m, 1 H), 4.48 (s, 1 H) 3.53-3.40 (m, 1 H), 2.80 (d, J = 5.87 Hz, 2 H), 2.72-2.61 (m, 1 H), 1.85-1.31 (m, 8 H), 1.23-1.15 (m, 1H), 1.15-1.05 (m, 6 H), 1.04-0.94 (m, 1 H); HPLC purity: 99.30%; LCMS calculated for $C_{22}H_{29}FN_2O_3S_2$: 452.16 Observed: 453.1 $[M + H]^+$. |

-continued

| Compound No. | Structure | Analytical data |
|---|---|---|
| A-929 | 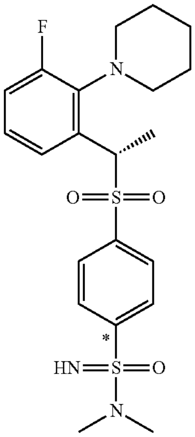 diastereomer 1 | Appearance: White solid; $^1$H NMR (400 MHz, DMSO-$d_6$) δ 7.91 (d, J = 8.31 Hz, 2 H), 7.75 (d, J = 8.31 Hz, 2 H), 7.41 (d, J = 7.83 Hz, 1 H), 7.33-7.24 (m, 1 H), 7.20-7.08 (m, 1 H), 5.38 (q, J = 7.01 Hz, 1 H), 4.71 (s, 1 H), 2.87-2.72 (m, 2 H), 2.69-2.61 (m, 1 H), 2.55 (s, 6 H), 1.76-1.68 (m, 2 H), 1.65 (d, J = 6.36 Hz, 3 H), 1.60-1.28 (m, 4 H), 1.25-1.10 (m, 1 H); HPLC purity: 99.66%; LCMS calculated for $C_{21}H_{28}FN_3O_3S_2$: 453.16 Observed: 454.1 $[M + H]^+$. |
| A-930 | 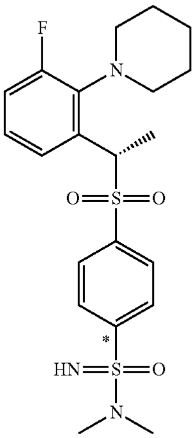 diastereomer 2 | Appearance: Off white solid; $^1$H NMR (400 MHz, DMSO-$d_6$) δ 7.91 (d, J = 8.31 Hz, 2 H), 7.75 (d, J = 8.31 Hz, 2 H), 7.41 (d, J = 7.83 Hz, 1 H), 7.33-7.24 (m, 1 H), 7.20-7.08 (m, 1 H), 5.38 (q, J = 7.01 Hz, 1 H), 4.71 (s, 1 H), 2.87-2.72 (m, 2 H), 2.69-2.61 (m, 1 H), 2.55 (s, 6 H), 1.76-1.68 (m, 2 H), 1.65 (d, J = 6.36 Hz, 3 H), 1.60-1.28 (m, 4 H), 1.25-1.10 (m, 1H); HPLC purity: 100%; LCMS calculated for $C_{21}H_{28}FN_3O_3S_2$: 453.16 Observed: 454.1 $[M + H]^+$. |
| A-931 | 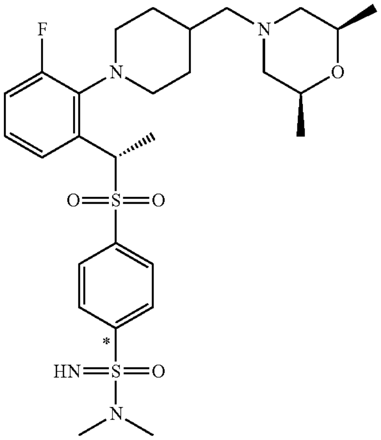 diastereomer 1 | Appearance: Off white solid; $^1$H NMR (400 MHz, DMSO-$d_6$) δ 7.95-7.82 (m, 2 H), 7.78-7.62 (m, 2 H), 7.41 (d, J = 7.34 Hz, 1 H), 7.30 (d, J = 5.38 Hz, 1 H), 7.21-7.07 (m, 1 H), 5.41-5.25 (m, 1 H), 4.67 (s, 1 H), 3.62-3.45 (m, 3 H), 2.93-2.62 (m, 6 H), 2.55 (s, 6 H), 2.18-2.05 (m, 2 H), 1.79-1.43 (m, 8 H), 1.24-1.12 (m, 1 H), 1.04 (d, J = 5.38 Hz, 6 H); HPLC purity: 97.59%; LCMS calculated for $C_{28}H_{41}FN_4O_4S_2$: 580.26 Observed: 581.6 $[M + H]^+$. |

-continued

| Compound No. | Structure | Analytical data |
|---|---|---|
| A-932 | 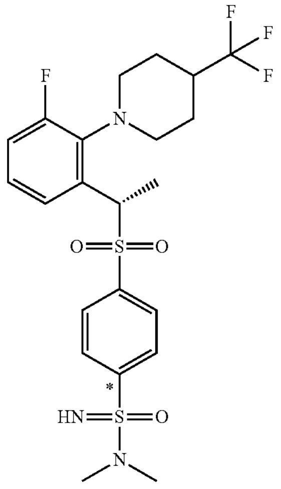 diastereomer 1 | Appearance: Off white solid; $^1$H NMR (400 MHz, DMSO-$d_6$) δ 7.93 (d, J = 7.34 Hz, 2 H), 7.77 (d, J = 7.83 Hz, 2 H), 7.43-7.29 (m, 2 H), 7.25-7.11 (m, 1 H), 5.42-5.29 (m, 1 H), 4.70 (s, 1 H), 3.58-3.41 (m, 2 H), 2.99-2.74 (m, 3 H), 2.56 (s, 6 H), 2.36 (d, J = 18.10 Hz, 1 H), 1.94-1.69 (m, 2 H), 1.66 (d, J = 6.36 Hz, 3 H), 1.51-1.32 (m, 1H); HPLC purity: 95.41%; LCMS calculated for $C_{22}H_{27}F_4N_3O_3S_2$: 521.14 Observed: 522.1 $[M + H]^+$. |
| A-933 | 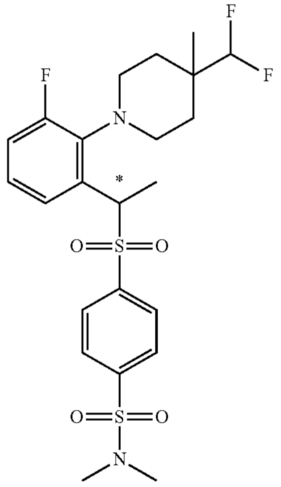 enantiomer 2 | Appearance: White solid; $^1$H NMR (400 MHz, DMSO-$d_6$) δ 7.86-7.76 (m, 2 H), 7.97-7.87 (m, 2 H), 7.47-7.28 (m, 2 H), 7.25-7.11 (m, 1 H), 6.02-5.61 (m, 1 H), 5.42-5.25 (m, 1 H), 3.56-3.40 (m, 1 H), 3.12-2.87 (m, 2 H), 2.62 (s, 6 H), 1.78-1.43 (m, 6 H), 1.36-1.13 (m, 2 H), 1.09-0.93 (m, 3 H); HPLC purity: 94.19%; LCMS calculated for $C_{23}H_{29}F_3N_2O_4S_2$: 518.15 Observed: 519.0 $[M + H]^+$. |
| A-935 | 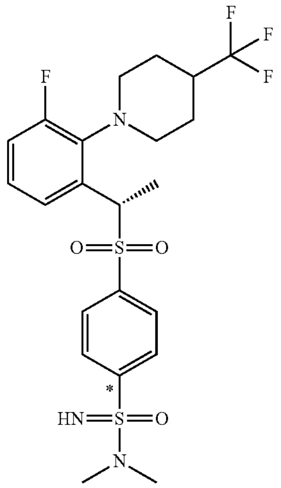 diastereomer 2 | Appearance: White solid; $^1$H NMR (400 MHz, DMSO-$d_6$) δ 8.0-7.83 (m, 2 H), 7.77 (d, J = 7.34 Hz, 2 H), 7.45-7.27 (m, 2 H), 7.21 (d, J = 9.78 Hz, 1 H), 5.41-5.24 (m, 1 H), 4.71 (s, 1 H), 3.0-2.71 (m, 3 H), 2.56 (s, 6 H), 2.42-2.27 (m, 2H), 1.99-1.85 (m, 1 H), 1.78 (br d, J = 8.80 Hz, 1 H), 1.66-1.52 (m, 4H), 1.49-1.33 (m, 1 H); HPLC purity: 96.37%; LCMS calculated for $C_{22}H_{27}F_4N_3O_3S_2$: 521.14 Observed: 522.1 $[M + H]^+$. |

-continued

| Compound No. | Structure | Analytical data |
|---|---|---|
| A-936 | 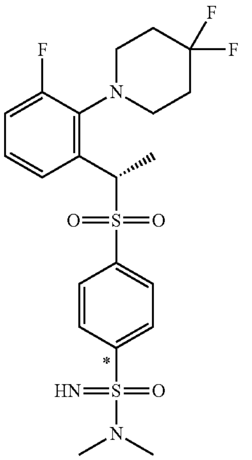 Diastereomer 2 | Appearance: White solid; $^1H$ NMR (400 MHz, DMSO-$d_6$) δ 7.94 (d, J = 8.31 Hz, 2 H), 7.83 (d, J = 8.31 Hz, 2 H), 7.42-7.28 (m, 2 H), 7.22 (dd, J = 11.74, 8.31 Hz, 1 H), 5.43 (q, J = 6.85 Hz, 1 H), 4.70 (s, 1 H), 3.09-2.93 (m, 2 H), 2.81 (d, J = 7.82 Hz, 1 H), 2.56 (s, 6 H), 2.35-2.11 (m, 1 H), 2.08-1.83 (m, 4 H), 1.63 (d, J = 6.85 Hz, 3 H); HPLC purity: 98.00%; LCMS calculated for $C_{21}H_{26}F_3N_3O_3S_2$: 489.14 Observed: 490.1 $[M + H]^+$. |
| A-937 | 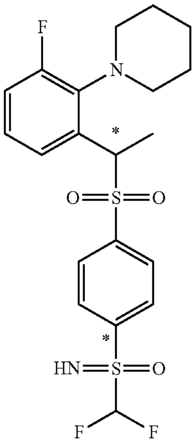 Diastereomer 1 | Appearance: Off white solid; $^1H$ NMR (400 MHz, DMSO-$d_6$) δ 8.10 (d, J = 8.51 Hz, 2H), 7.85 (d, J = 8.50 Hz, 2 H), 7.43 (d, J = 7.00 Hz, 1 H), 7.31 (td, J = 8.00, 5.38 Hz, 1 H), 7.19-7.16 (m, 1 H), 7.10-6.80 (m, 1 H), 5.95 (s, 1 H), 5.37 (q, J = 7.25 Hz, 1 H), 2.81-2.70 (m, 2 H), 2.68-2.60 (m, 1 H), 1.74-1.64 (m, 4 H), 1.60-1.50 (m, 3 H), 1.43-1.08 (m, 3 H); HPLC purity: 95.26%; LCMS calculated for $C_{20}H_{23}F_3N_2O_3S_2$: 460.53 Observed: 461.2 $[M + H]^+$. |
| A-938 | 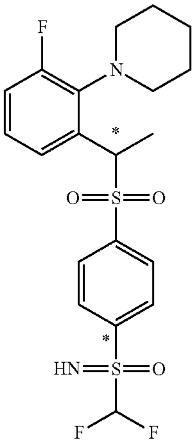 Diastereomer 2 | Appearance: Off white solid; $^1H$ NMR (400 MHz, DMSO-$d_6$) δ 8.10 (d, J = 8.50 Hz, 2 H), 7.85 (d, J = 8.50 Hz, 2 H), 7.43 (dd, J = 7.88, 1.00 Hz, 1 H), 7.31 (td, J = 8.04, 5.44 Hz, 1 H), 7.22-7.13 (m, 1 H), 7.09-6.79 (m, 1 H), 5.92 (s, 1 H), 5.37 (q, J = 7.17 Hz, 1 H), 2.75 (br dd, J = 10.26, 6.50 Hz, 2 H), 2.67 (br s, 1 H), 1.73-1.64 (m, 4 H), 1.56 (br d, J = 7.50 Hz, 3 H), 1.46-1.38 (m, 1 H), 1.37-1.26 (m, 1 H), 1.22-1.09 (m, 1 H); ; HPLC purity: 98.64%; LCMS calculated for $C_{20}H_{23}F_3N_2O_3S_2$: 460.53 Observed: 461.2 $[M + H]^+$. |

-continued

| Compound No. | Structure | Analytical data |
|---|---|---|
| A-939 | 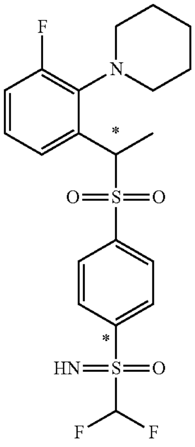 Diastereomer 3 | Appearance: Off white solid; $^1$H NMR (400 MHz, DMSO-$d_6$) δ 8.10 (d, J = 8.44 Hz, 2 H), 7.85 (d, J = 8.44 Hz, 2 H), 7.43 (d, J = 6.97 Hz, 1 H), 7.31 (td, J = 8.01, 5.38 Hz, 1 H), 7.19-7.16 (m, 1 H), 7.10-6.80 (m, 1 H), 5.95 (s, 1 H), 5.37 (q, J = 7.21 Hz, 1 H), 2.82-2.60 (m, 3 H), 1.74-1.63 (m, 4 H), 1.60-1.49 (m, 3 H), 1.43-1.09 (m, 3 H); HPLC purity: 99.70%; LCMS calculated for $C_{20}H_{23}F_3N_2O_3S_2$: 460.53 Observed: 461.1 $[M + H]^+$. |
| A-940 | 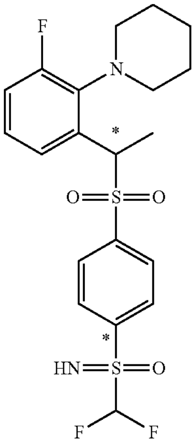 Diastereomer 4 | Appearance: Off white solid; $^1$H NMR (400 MHz, DMSO-$d_6$) δ 8.10 (d, J = 8.31 Hz, 2 H), 7.85 (d, J = 8.31 Hz, 2 H), 7.43 (d, J = 7.46 Hz, 1 H), 7.32-7.29 (m, 1 H), 7.17 (dd, J = 11.98, 8.68 Hz, 1 H), 7.09-6.79 (m, 1 H), 5.92 (s, 1 H), 5.37 (q, J = 7.17 Hz, 1 H), 2.80-2.61 (m, 3 H), 1.66 (br d, J = 7.21 Hz, 4 H), 1.56 (br s, 3 H), 1.46-1.09 (m, 3 H); HPLC purity: 98.56%; LCMS calculated for $C_{20}H_{23}F_3N_2O_3S_2$: 460.53 Observed: 461.1 $[M + H]^+$. |
| A-941 | 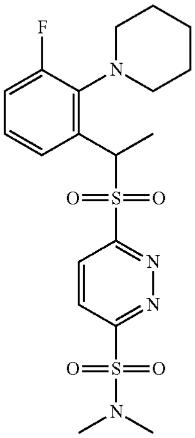 [SMILES: CC(c1cccc(F)c1N1CCCCC1)S(=O)(=O)c1ccc(S(=O)(=O)N(C)C)nn1] | Appearance: Off white solid; $^1$H NMR (400 MHz, DMSO-$d_6$) δ 8.49-8.30 (m, 2 H), 7.49-7.15 (m, 3 H), 5.97 (q, J = 7.21 Hz, 1 H), 2.99-2.86 (m, 8 H), 2.82-2.65 (m, 2 H), 1.77 (br d, J = 12.51 Hz, 1 H), 1.68-1.53 (m, 7 H), 1.33-1.19 (m, 1 H); HPLC purity: 99.66%; LCMS calculated for $C_{19}H_{25}FN_4O_4S_2$: 456.13 Observed: 457.1 $[M + H]^+$. |

-continued

| Compound No. | Structure | Analytical data |
|---|---|---|
| A-942 | 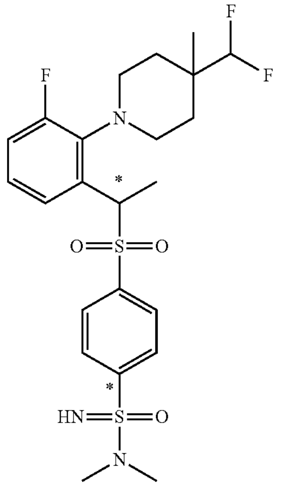 Diastereomer 1 | Appearance: White solid; $^{1}H$ NMR (400 MHz, DMSO-$d_6$) δ 7.92 (d, J = 6.85 Hz, 2 H), 7.78 (d, J = 7.34 Hz, 2 H), 7.40 (d, J = 6.36 Hz, 1 H), 7.35-7.26 (m, 1 H), 7.25-7.10 (m, 1 H), 6.01-5.62 (m, 1 H), 5.35 (d, J = 6.36 Hz, 1 H), 4.68 (s, 1 H), 3.11-2.89 (m, 2 H), 2.61-2.53 (m, 6 H), 1.77-1.46 (m, 6 H), 1.35-1.10 (m, 3 H), 1.07-0.94 (m, 3 H); HPLC purity: 96.63%; LCMS calculated for $C_{23}H_{30}F_3N_3O_3S_2$: 517.17 Observed: 518.1 $[M + H]^+$. |
| A-943 | 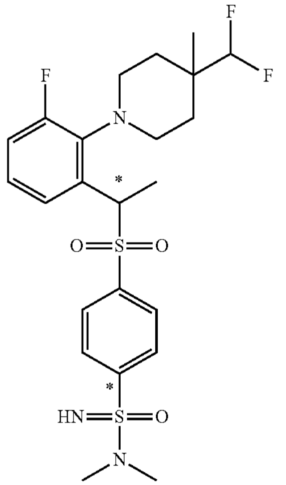 Diastereomer 2 | Appearance: White solid; $^{1}H$ NMR (400 MHz, DMSO-$d_6$) δ 7.97-7.84 (m, 2 H), 7.83-7.67 (m, 2 H), 7.47-7.36 (m, 1 H), 7.35-7.24 (m, 1 H), 7.23-7.11 (m, 1 H), 6.02-5.63 (m, 1 H), 5.42-5.27 (m, 1 H), 4.72 (s, 1 H), 3.12-2.87 (m, 3 H), 2.55 (s, 6 H), 1.78-1.48 (m, 6 H), 1.32 (d, J = 12.23 Hz, 1 H), 1.25-1.12 (m, 1 H), 1.07-0.94 (m, 3 H); HPLC purity: 97.90%; LCMS calculated for $C_{23}H_{30}F_3N_3O_3S_2$: 517.17 Observed: 518.5 $[M + H]^+$. |
| A-944 | 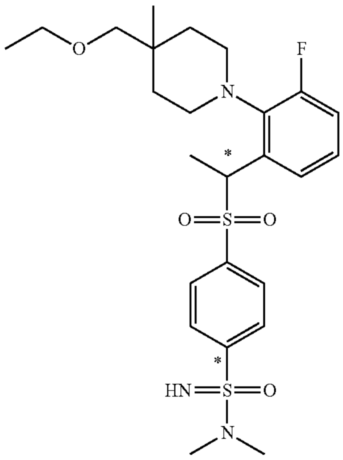 Diastereomer 1 | Appearance: White solid; $^{1}H$ NMR (400 MHz, DMSO-$d_6$) δ 7.90 (d, J = 6.85 Hz, 2 H), 7.81-7.63 (m, 2 H), 7.45-7.39 (m, 1 H), 7.35-7.26 (m, 1 H), 7.23-7.05 (m, 1 H), 5.44-5.27 (m, 1 H), 4.65 (s, 1 H), 3.97-3.85 (m, 1 H), 3.54-3.38 (m, 2 H), 3.16-2.82 (m, 4 H), 2.54 (s, 6 H), 1.71-1.49 (m, 4 H), 1.49-1.33 (m, 3 H), 1.28 (d, J = 12.23 Hz, 1 H), 1.19-1.04 (m, 3 H), 1.01-0.84 (m, 3 H); HPLC purity: 95.12%; LCMS calculated for $C_{25}H_{36}FN_3O_4S_2$: 525.21 Observed: 526.1 $[M + H]^+$. |

-continued

| Compound No. | Structure | Analytical data |
|---|---|---|
| A-945 | 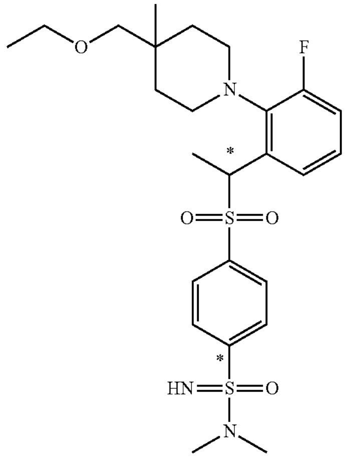 Diastereomer 2 | Appearance: Off white solid; $^{1}$H NMR (400 MHz, DMSO-$d_6$) δ 7.90 (d, J = 7.82 Hz, 2 H), 7.76 (d, J = 7.83 Hz, 2 H), 7.40 (d, J = 6.85 Hz, 1 H), 7.34-7.24 (m, 1 H), 7.22-7.08 (m, 1 H), 5.41-5.28 (m, 1 H), 4.71 (s, 1 H), 3.52-3.37 (m, 2 H), 3.14-2.89 (m, 4 H), 2.54 (s, 6 H), 1.69-1.57 (m, 4 H), 1.57-1.47 (m, 1 H), 1.43 (d, J = 8.31 Hz, 2 H), 1.31-1.19 (m, 2 H), 1.18-1.06 (m, 3 H), 1.0-0.86 (m, 3 H); HPLC purity: 94.01%; LCMS calculated for $C_{25}H_{36}FN_3O_4S_2$: 525.21 Observed: 526.1 $[M + H]^+$. |
| A-946 | 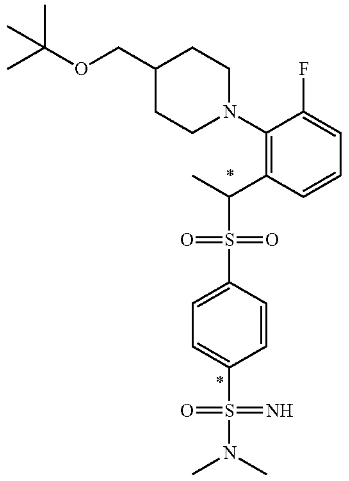 Diastereomer 1 | Appearance: White solid; $^{1}$H NMR (400 MHz, DMSO-$d_6$) δ 7.98-7.82 (m, 2 H), 7.73 (d, J = 7.34 Hz, 2 H), 7.46-7.34 (m, 1 H), 7.30 (d, J = 4.89 Hz, 1 H), 7.22-7.07 (m, 1 H), 5.42-5.25 (m, 1 H), 4.66 (s, 1 H), 3.20 (d, J = 5.38 Hz, 3 H), 2.93-2.62 (m, 4 H), 2.55 (s, 6 H), 1.83-1.58 (m, 5 H), 1.68-1.48 (m, 1 H), 1.45-1.30 (m, 1 H), 1.14 (s, 9 H); HPLC purity: 98.48%; LCMS calculated for $C_{26}H_{38}FN_3O_4S_2$: 539.23 Observed: 540.1 $[M + H]^+$. |
| A-947 | 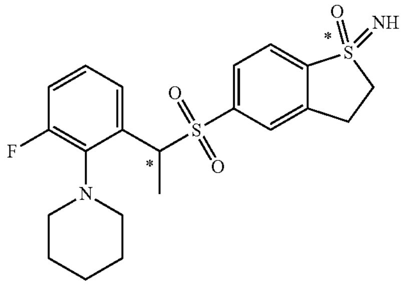 Diastereomer 1 | Yield: 46 mg (46%); Appearance: off white solid; $^{1}$H NMR (400 MHz, DMSO-$d_6$) δ 7.80-7.72 (m, 2H), 7.49 (d, J = 8.07 Hz, 1H), 7.41 (d, J = 6.97 Hz, 1H), 7.33-7.29 (m, 1H), 7.20-7.16 (m, 1H), 5.33 (q, J = 7.17 Hz, 1H), 4.85 (br s, 1H), 3.54-3.48 (m, 2H), 3.28 (br s, 1H), 2.84-2.75 (m, 2H), 2.69-2.61 (m, 1H), 1.77-1.45 (m, 8H), 1.37-1.26 (m, 2H), 1.25-1.14 (m, 1H); HPLC purity: 98.7%; LCMS calculated for $C_{21}H_{25}FN_2O_3S_2$: 436.56; Observed: 437.1 $[M + H]^+$. |

-continued

| Compound No. | Structure | Analytical data |
|---|---|---|
| A-948 | 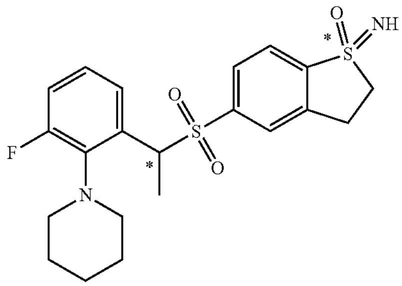<br>Diastereomer 2 | Yield: 34 mg (34%); Appearance: off white solid; $^1H$ NMR (400 MHz, DMSO-$d_6$) δ 7.81-7.71 (m, 2H), 7.49-7.45 (m, 1H), 7.41 (dd, J = 7.82, 1.06 Hz, 1H), 7.32-7.29 (m, 1H), 7.20-7.16 (m, 1H), 5.33 (q, J = 7.17 Hz, 1H), 4.82 (s, 1H), 3.54-3.47 (m, 2H), 3.35 (br s, 1H), 3.28 (br s, 1H), 2.84-2.74 (m, 2H), 2.69-2.62 (m, 1H), 1.72 (br t, J = 9.69 Hz, 2H), 1.63 (d, J = 7.25 Hz, 3H), 1.60-1.47 (m, 3H), 1.37-1.12 (m, 2H); HPLC purity: 97.60%; LCMS calculated for $C_{21}H_{25}FN_2O_3S_2$: 436.56; Observed: 437.1 $[M + H]^+$. |
| A-949 | 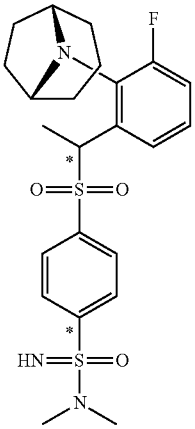<br>Diastereomer 1 | Appearance: Off white solid; $^1H$ NMR (400 MHz, $CD_3OD$) δ 7.90 (d, J = 8.51 Hz, 2 H), 7.72 (d, J = 8.50 Hz, 2 H), 7.49 (d, J = 7.75 Hz, 1 H), 7.06-7.03 (m, 1 H), 6.94-6.90 (m, 1 H), 5.43 (q, J = 7.25 Hz, 1 H), 3.37-3.34 (m, 1 H), 3.22-3.18 (m, 1 H), 2.68 (s, 6 H), 2.15-2.05 (m, 1 H), 2.01-1.90 (m, 1 H), 1.84-1.79 (m, 3H), 1.79-1.58 (m, 7 H), 1.50-1.40 (m, 1 H), 1 proton merged in solvent; HPLC purity: 98.10%; LCMS calculated for $C_{23}H_{30}FN_3O_3S_2$: 479.63 Observed: 480.2 $[M + H]^+$. |
| A-950 | 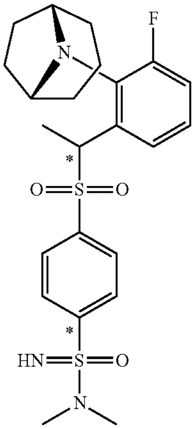<br>Diastereomer 2 | Appearance: Off white solid; $^1H$ NMR (400 MHz, DMSO-$d_6$) δ 7.86 (br d, J = 7.82 Hz, 2 H), 7.68 (br d, J = 7.70 Hz, 2 H), 7.41 (br d, J = 6.97 Hz, 1 H), 6.98-7.12 (m, 2 H), 5.26 (br d, J = 6.97 Hz, 1 H), 4.68 (br s, 1 H), 3.16-3.27 (m, 2 H), 2.55-2.70 (m, 6 H), 1.98 (br d, J = 4.77 Hz, 1 H), 1.76 (br d, J = 6.72 Hz, 5 H), 1.69-1.62 (m, 4 H), 1.59-1.48 (m, 3 H); HPLC purity: 98.37%; LCMS calculated for $C_{23}H_{30}FN_3O_3S_2$: 479.63 Observed: 480.2 $[M + H]^+$. |

-continued

| Compound No. | Structure | Analytical data |
|---|---|---|
| A-951 | 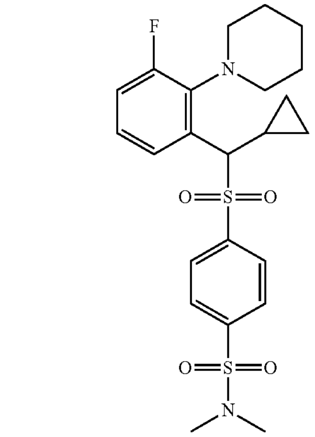 [SMILES: CN(C)S(=O)(=O)c1ccc(S(=O)(=O)C(c2cccc(F)c2N2CCCCC2)C2CC2)cc1] | Yield: 160 mg (30%); Appearance: off white solid; $^1$H NMR (400 MHz, DMSO-$d_6$) δ 7.96 (q, J = 8.64 Hz, 4H), 7.52-7.47 (m, 1H), 7.37-7.34 (m, 1H), 7.24-7.21 (m, 1H), 4.63 (d, J = 10.88 Hz, 1H), 2.99-2.78 (m, 2H), 2.63 (s, 6H), 2.19 (br d, J = 10.39 Hz, 1H), 1.73 (br d, J = 12.35 Hz, 1H), 1.64-1.39 (m, 5H), 1.31-1.16 (m, 2H), 0.72-0.45 (m, 2H), 0.18-0.14 (m, 1H), -0.01 to -0.12 (m, 1H); HPLC purity: 97.60%; LCMS calculated for $C_{23}H_{29}FN_2O_4S_2$: 480.61; Observed: 481.2 $[M + H]^+$. |
| A-952 | 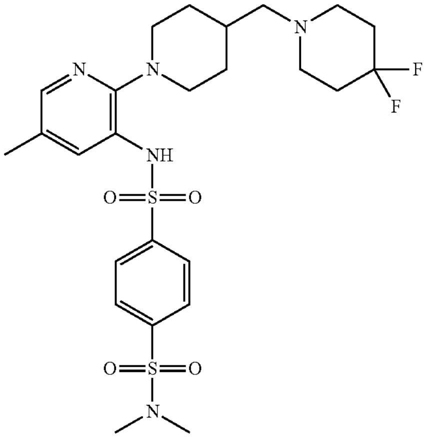 [SMILES: Cc1cnc(N2CCC(CN3CCC(F)(F)CC3)CC2)c(NS(=O)(=O)c2ccc(S(=O)(=O)N(C)C)cc2)c1] | Yield: 0.15 g (29%); Appearance: off white solid; $^1$H NMR (400 MHz, DMSO-$d_6$) δ 9.71-9.46 (m, 1H), 8.01-7.89 (m, 5H), 7.23 (d, J = 1.71 Hz, 1H), 3.16 (br d, J = 11.13 Hz, 2H), 2.64 (s, 6H), 2.45 (br s, 5H), 2.19-2.10 (m, 5H), 2.0-1.85 (m, 5H), 1.61-1.44 (m, 3H), 1.07-0.91 (m, 2H); HPLC purity: 99.26%; LCMS calculated for $C_{25}H_{35}F_2N_5O_4S_2$: 571.70; Observed: 572.2 $[M + H]^+$. |
| A-953 | 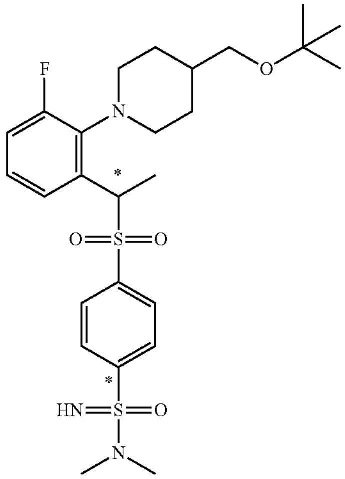 Diastereomer 2 | Appearance: White solid; $^1$H NMR (400 MHz, DMSO-$d_6$) δ 7.95-7.80 (m, 2 H), 7.78-7.63 (m, 2 H), 7.41 (d, J = 7.34 Hz, 1 H), 7.34-7.22 (m, 1 H), 7.20-7.06 (m, 1 H), 5.40-5.26 (m, 1 H), 4.70 (s, 1 H), 3.22-3.09 (m, 2 H), 2.91-2.61 (m, 3 H), 2.55 (s, 6 H), 1.78-1.59 (m, 5 H), 1.56-1.18 (m, 4 H), 1.14 (s, 9 H); HPLC purity: 96.82%; LCMS calculated for $C_{26}H_{38}FN_3O_4S_2$: 539.23 Observed: 540.1 $[M + H]^+$. |

-continued

| Compound No. | Structure | Analytical data |
|---|---|---|
| A-954 | 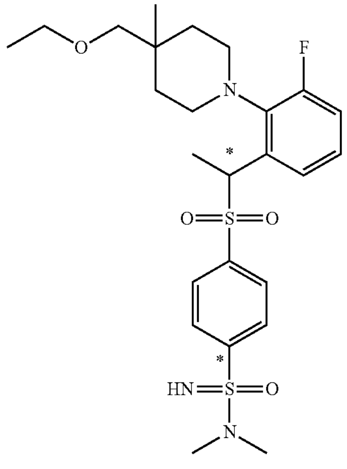 Diastereomer 3 | Appearance: White solid; $^1$H NMR (400 MHz, DMSO-$d_6$) δ 7.90 (d, J = 7.82 Hz, 2 H), 7.80-7.63 (m, 2 H), 7.47-7.35 (m, 1 H), 7.31 (d, J = 4.40 Hz, 1 H), 7.23-7.08 (m, 1 H), 5.44-5.25 (m, 1 H), 4.71 (s, 1 H), 3.56-3.38 (m, 2 H), 3.17-2.85 (m, 4 H), 2.55 (s, 6 H), 1.70-1.52 (m, 4 H), 1.49-1.34 (m, 2 H), 1.32-1.03 (m, 6 H), 1.0-0.87 (m, 3 H); HPLC purity: 99.70%; LCMS calculated for $C_{25}H_{36}FN_3O_4S_2$: 525.21 Observed: 526.1 $[M + H]^+$. |
| A-955 | 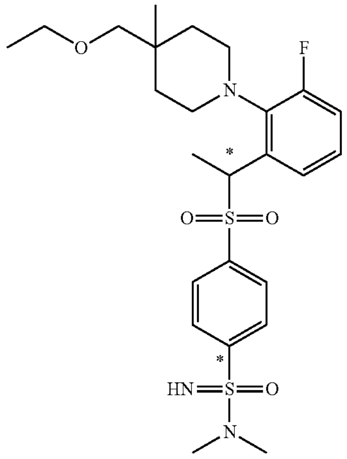 Diastereomer 4 | Appearance: White solid; $^1$H NMR (400 MHz, DMSO-$d_6$) δ 7.97-7.82 (m, 2 H), 7.80-7.66 (m, 2 H), 7.47-7.36 (m, 1 H), 7.31 (d, J = 4.89 Hz, 1 H), 7.23-7.08 (m, 1 H), 5.44-5.26 (m, 1 H), 4.67 (s, 1 H), 3.53-3.40 (m, 2 H), 3.14-2.88 (m, 4 H), 2.55 (s, 6 H), 1.73-1.35 (m, 6 H), 1.34-1.21 (m, 2 H), 1.18-1.03 (m, 4 H), 1.0-0.86 (m, 3 H); HPLC purity: 98.96%; LCMS calculated for $C_{25}H_{36}FN_3O_4S_2$: 525.21 Observed: 526.1 $[M + H]^+$. |
| A-1001 | 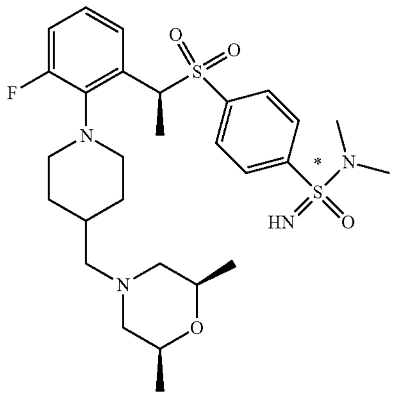 Diastereomer 2 | Appearance: Off-white solid; $^1$H NMR (400 MHz, $CDCl_3$) δ 8.00 (d, J = 8.4 Hz, 2 H), 7.82 (d, J = 7.6 Hz, 2 H), 7.39 (d, J = 8.0 Hz, 1H), 7.24-7.18 (m, 1 H), 7.06-6.98 (m, 1 H), 5.46-5.37 (m, 1 H), 4.18-4.06 (m, 2H), 3.51 (d, J = 11.6 Hz, 2 H), 3.09-2.91 (m, 4 H), 2.70 (s, 7 H), 2.40-2.21 (m, 3 H), 1.78-1.71 (m, 2 H), 1.66 (d, J = 7.2 Hz, 3 H), 1.46-1.28 (m, 2 H), 1.26-1.22 (m, 7 H), 1 H merged in solvent peak; HPLC purity: 99.71%; LCMS calculated for $C_{28}H4_1FN_4O_4S_2$: 580.26 Observed: 581.1 $[M + H]^+$. |

-continued

| Compound No. | Structure | Analytical data |
|---|---|---|
| A-1002 | 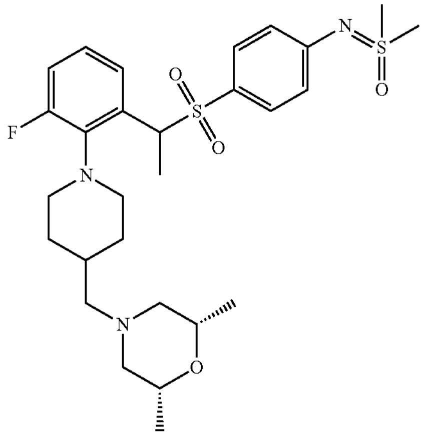 [SMILES: CC(c1cccc(F)c1N1CCC(CN2C[C@@H](C)O[C@@H](C)C2)CC1)S(=O)(=O)c1ccc(N=S(C)(C)=O)cc1] | Appearance: Off-white solid; $^1$H NMR (400 MHz, DMSO-$d_6$) δ 7.38 (d, J = 8.0 Hz, 1H), 7.30-7.23 (m, 3H), 7.17-7.10 (m, 1 H), 6.93 (d, J = 8.4 Hz, 2 H), 5.28-5.18 (m, 1 H), 3.58-3.48 (m, 2 H), 3.28 (s, 6 H), 2.82 (t, J = 11 Hz, 2 H), 2.64-2.62 (m, 3 H), 2.12 (d, J = 6.4 Hz, 2 H), 1.88 (d, J = 10.4 Hz, 1 H), 1.69 (bd, J = 11.6 Hz, 1 H), 1.60-1.50 (m, 7 H), 1.19-1.11 (m, 1H), 1.04 (d, J = 6.4 Hz, 6 H), 1.01-0.98 (m, 1 H); HPLC purity: 95.95%; LCMS calculated for $C_{28}H_{40}FN_3O_4S_2$: 565.24 Observed: 566.1 $[M + H]^+$. |

Analytical Instrumentation and Purification:

NMR Instrument Details: Varian 400 MHz, Probe-1: Auto XID Probe 2: ATB.

LCMS Instrument Details: Shimadzu LCMS-2010EV system coupled to SPD-M20A PDA and ELS detectors. Softa model 400.

LCMS Method 1—Acidic Conditions

Column: X-Select C18 CSH (3.0*50) mm 2.5μ; Make: Waters

Mobile Phase A: 0.05% formic acid in water:Acetonitrile (95:5); pH=3.5

Mobile Phase B: 0.05% formic acid in Acetonitrile

Column oven temperature: 5° C.

Flow rate: 1.2 ml/minute

PDA: 210 nm Maxplot

Gradient program:

| Time(min) | A % | B % |
|---|---|---|
| 0.0 | 100 | 0 |
| 2.0 | 2 | 98 |
| 3.0 | 2 | 98 |
| 3.2 | 100 | 0 |
| 4.0 | 100 | 0 |

MS Parameters

Mode: Dual (+/−)

Detector voltage: 1.5 KV

Scan rang: 80-2000 amu

Scan speed: 2000

LCMS Method 2—Basic Conditions

Column: X-Select C18 CSH (3.0*50) mm 2.5 μm; Make: Waters

Mobile Phase A: 5 mM Ammonium Bicarb; pH=8.8

Mobile Phase B: Acetonitrile

Column oven temperature: 5° C.

Flow rate: 1.2 ml/minute

PDA: 210 nm Maxplot

Gradient program:

| Time(min) | A % | B % |
|---|---|---|
| 0.0 | 100 | 0 |
| 2.0 | 2 | 98 |
| 3.0 | 2 | 98 |
| 3.2 | 100 | 0 |
| 4.0 | 100 | 0 |

MS Parameters

Mode: Dual (+/−)

Detector voltage: 1.5 KV

Scan rang: 80-2000 amu

Scan speed: 2000

HPLC Method 1—Acidic Conditions

Column: X-Select CSH $C_{18}$ (4.6*150) mm; 5μ; Make: Waters

Mobile Phase: A—0.1% Formic acid in water:Acetonitrile (95:05); pH=3.5

B—Acetonitrile

Flow Rate: 1.0. mL/minute

PDA: 210 nm maxplot

Gradient program:

| Time(min) | A % | B % |
|---|---|---|
| 0.0 | 95 | 5 |
| 1.0 | 95 | 5 |
| 8.0 | 0 | 100 |
| 12.0 | 0 | 100 |
| 14.0 | 95 | 5 |
| 18.0 | 95 | 5 |

HPLC Method 2—Basic Conditions

Column: Xbridge C18 (4.6*150) mm, 5μ; Make: Waters

Mobile Phase A—0.1% $NH_3$ in water; pH=9.5

B—Acetonitrile

Flow Rate: 1.2. mL/minute

PDA: 210 nm maxplot

Gradient program:

| Time(min) | A % | B % |
|---|---|---|
| 0.0 | 98 | 2 |
| 6.0 | 0 | 85 |
| 8.0 | 0 | 85 |
| 9.0 | 0 | 100 |
| 12.0 | 0 | 100 |
| 14.0 | 98 | 2 |
| 18.0 | 98 | 2 |

Biological Activity

For the TFEB nuclear translocation assay, HeLa wt or HeLa TRPML1 KO cells were plated at 2700 cells/well into black-walled, 384-well Cell carrier Ultra tissue culture treated plates in complete media and incubated overnight. The next day, cells are treated for 2 hrs with compounds and incubated at 37° C. Cells were then fixed for 30 minutes at room temperature in 4% final PFA and washed five times with 90 μL PBS. PBS is aspirated from the wells and the cells are blocked with 7.5 μL blocking buffer (1:1 PBS/Odyssey block buffer containing 0.1% triton x-100 and 1% goat serum). After 30-60 minutes of block, 7.5 μL of primary anti-TFEB (rabbit) antibody is added for a final dilution of 1:200 antibody in 15 μL blocking buffer. Plates are incubated overnight at 4° C. The following day, plates are washed again into PBS, 90 μL with 5 washes, all PBS is aspirated from the wells and the cells are incubated for 1 hr in 1:1000 goat-anti rabbit Alexa 488 secondary antibody, also containing 10 μg/mL Hoechst 33342. After the 1 hr room temperature incubation, plates are washed a final time into PBS, sealed with foil and imaged with an automated epifluorescence microscopy (PerkinElmer Operetta CLS). Four different fields were imaged per well using ×20 magnification for DAPI and FITC filter sets. Images were quantified using PerkinElmer Harmony software, briefly: apply flatfield correction (basic/advanced) for input images. Use the Find Nuclei building block with channel set at Hoechst to find the nuclei. Use the Find cytoplasm building block with channel set to Alexa 488 to find the cytoplasm. Use select cell region with Channel set at Alexa 488 and region of interest as Nuclei and define outer border at 0 μm and inner at 45 μm to cover complete nuclei. Use select cell region with Channel set at Alexa 488 and region of interest as ring region and define outer border at −5 μm and inner at 0 μm to define a ring around the nucleus. Use the find calculate intensity parameter to calculate intensity of the nuclear region and the ring region. Define results as Number of nuclei and ratio of A/B where A is Intensity of Nuclei and B is intensity of the ring region.

Table 1 shows the activity of selected compounds of this invention in TFEB assays. The compound numbers correspond to the compound numbers above in Tables A or B. Compounds having an activity designated as "++++" provided an $AC_{50}$ of ≤2.00 μM; compounds having an activity designated as "+++" provided an $AC_{50}$ of 2.01-8.00 μM; compounds having an activity designated as "++" provided an $AC_{50}$ of 8.01-9.99 μM; and compounds having an activity designated as "+" provided an $AC_{50}$ of ≥10.00 μM.

TABLE 1

| Compound | TFEB $AC_{50}$ (μM) |
|---|---|
| A-1 | ++++ |
| A-2 | ++++ |
| A-3 | ++++ |
| A-4 | ++++ |
| A-5 | +++ |
| A-6 | + |
| A-7 | ++++ |
| A-8 | + |
| A-9 | ++++ |
| A-10 | ++++ |
| A-11 | ++++ |
| A-12 | ++++ |
| A-13 | ++++ |
| A-14 | +++ |
| A-15 | + |
| A-16 | +++ |
| A-17 | +++ |
| A-18 | ++++ |
| A-19 | ++++ |
| A-20 | ++++ |
| A-21 | +++ |
| A-22 | +++ |
| A-23 | ++++ |
| A-24 | ++++ |
| A-25 | ++++ |
| A-26 | ++++ |
| A-27 | +++ |
| A-28 | ++++ |
| A-29 | + |
| A-30 | ++++ |
| A-31 | ++++ |
| A-32 | ++++ |
| A-33 | + |
| A-34 | ++++ |
| A-35 | + |
| A-36 | ++++ |
| A-37 | +++ |
| A-38 | ++++ |
| A-39 | +++ |
| A-40 | +++ |
| A-41 | + |
| A-42 | + |
| A-43 | ++++ |
| A-44 | ++++ |
| A-45 | +++ |
| A-46 | + |
| A-47 | ++++ |
| A-48 | + |
| A-49 | + |
| A-50 | +++ |
| A-51 | +++ |
| A-52 | ++++ |
| A-53 | +++ |
| A-54 | + |
| A-55 | ++++ |
| A-56 | +++ |
| A-57 | +++ |
| A-58 | + |
| A-59 | + |
| A-60 | +++ |
| A-61 | + |
| A-62 | ++ |
| A-63 | +++ |
| A-64 | + |
| A-65 | + |
| A-66 | + |
| A-67 | + |
| A-68 | + |
| A-69 | +++ |
| A-70 | ++++ |
| A-71 | + |
| A-72 | ++++ |
| A-73 | ++++ |
| A-74 | +++ |
| A-75 | + |
| A-76 | + |
| A-77 | ++++ |
| A-78 | + |

TABLE 1-continued

| Compound | TFEB AC50 (μM) |
|---|---|
| A-79 | + |
| A-80 | +++ |
| A-81 | + |
| A-82 | + |
| A-83 | ++++ |
| A-84 | + |
| A-85 | + |
| A-86 | + |
| A-87 | + |
| A-88 | +++ |
| A-89 | ++++ |
| A-90 | +++ |
| A-91 | + |
| A-92 | ++++ |
| A-93 | + |
| A-94 | +++ |
| A-96 | + |
| A-97 | + |
| A-98 | ++++ |
| A-99 | ++++ |
| A-100 | ++++ |
| A-101 | +++ |
| A-102 | +++ |
| A-103 | ++++ |
| A-104 | ++++ |
| A-105 | + |
| A-106 | + |
| A-107 | + |
| A-108 | ++++ |
| A-109 | ++++ |
| A-110 | + |
| A-111 | + |
| A-112 | ++++ |
| A-113 | ++++ |
| A-114 | + |
| A-115 | ++++ |
| A-116 | + |
| A-117 | + |
| A-118 | +++ |
| A-119 | ++++ |
| A-120 | ++++ |
| A-121 | ++++ |
| A-122 | + |
| A-123 | +++ |
| A-124 | ++++ |
| A-128 | + |
| A-129 | + |
| A-130 | + |
| A-131 | ++++ |
| A-132 | ++++ |
| A-133 | + |
| A-134 | + |
| A-135 | + |
| A-136 | ++++ |
| A-137 | +++ |
| A-138 | ++++ |
| A-139 | + |
| A-140 | ++++ |
| A-141 | ++++ |
| A-142 | +++ |
| A-143 | ++++ |
| A-144 | + |
| A-145 | + |
| A-146 | ++++ |
| A-147 | +++ |
| A-148 | ++++ |
| A-149 | ++++ |
| A-150 | ++++ |
| A-151 | +++ |
| A-152 | + |
| A-153 | +++ |
| A-154 | ++++ |
| A-155 | +++ |
| A-156 | +++ |
| A-157 | ++++ |
| A-158 | ++++ |
| A-159 | +++ |
| A-160 | +++ |

TABLE 1-continued

| Compound | TFEB AC50 (μM) |
|---|---|
| A-161 | +++ |
| A-162 | +++ |
| A-163 | + |
| A-164 | + |
| A-165 | +++ |
| A-166 | +++ |
| A-167 | +++ |
| A-168 | + |
| A-169 | + |
| A-170 | ++++ |
| A-171 | +++ |
| A-172 | +++ |
| A-173 | ++++ |
| A-174 | +++ |
| A-175 | ++++ |
| A-176 | + |
| A-177 | + |
| A-178 | ++++ |
| A-179 | ++++ |
| A-180 | ++ |
| A-181 | +++ |
| A-182 | ++++ |
| A-183 | ++++ |
| A-184 | ++++ |
| A-185 | ++++ |
| A-186 | + |
| A-187 | + |
| A-188 | + |
| A-189 | ++++ |
| A-190 | ++++ |
| A-191 | +++ |
| A-192 | + |
| A-193 | + |
| A-194 | + |
| A-195 | +++ |
| A-196 | ++++ |
| A-197 | + |
| A-198 | ++++ |
| A-199 | + |
| A-200 | +++ |
| A-201 | +++ |
| A-202 | + |
| A-203 | +++ |
| A-204 | ++++ |
| A-205 | ++++ |
| A-206 | + |
| A-207 | ++++ |
| A-208 | ++++ |
| A-209 | ++++ |
| A-210 | ++++ |
| A-211 | ++++ |
| A-212 | ++++ |
| A-213 | ++++ |
| A-214 | ++++ |
| A-215 | ++++ |
| A-216 | ++++ |
| A-217 | ++++ |
| A-218 | ++++ |
| A-219 | + |
| A-220 | + |
| A-221 | ++++ |
| A-222 | ++++ |
| A-223 | +++ |
| A-224 | + |
| A-225 | +++ |
| A-226 | ++++ |
| A-227 | + |
| A-228 | ++++ |
| A-229 | ++++ |
| A-230 | + |
| A-231 | ++++ |
| A-232 | + |
| A-233 | + |
| A-234 | + |
| A-235 | + |
| A-236 | + |
| A-237 | + |
| A-238 | + |

TABLE 1-continued

| Compound | TFEB $AC_{50}$ (μM) |
|---|---|
| A-239 | + |
| A-240 | + |
| A-241 | + |
| A-242 | + |
| A-243 | ++++ |
| A-244 | + |
| A-245 | ++++ |
| A-246 | ++++ |
| A-247 | ++++ |
| A-248 | + |
| A-249 | + |
| A-250 | + |
| A-251 | ++++ |
| A-252 | ++++ |
| A-253 | ++++ |
| A-254 | ++++ |
| A-255 | + |
| A-256 | + |
| A-257 | ++++ |
| A-258 | ++++ |
| A-259 | + |
| A-260 | + |
| A-261 | + |
| A-262 | + |
| A-263 | + |
| A-264 | + |
| A-265 | + |
| A-266 | + |
| A-267 | + |
| A-268 | ++++ |
| A-269 | + |
| A-270 | + |
| A-271 | ++++ |
| A-272 | + |
| A-273 | + |
| A-274 | + |
| A-275 | + |
| A-276 | + |
| A-277 | + |
| A-278 | + |
| A-279 | + |
| A-280 | + |
| A-281 | + |
| A-282 | +++ |
| A-283 | + |
| A-284 | + |
| A-285 | + |
| A-286 | + |
| A-287 | + |
| A-288 | ++++ |
| A-289 | + |
| A-290 | + |
| A-291 | ++++ |
| A-292 | ++++ |
| A-293 | + |
| A-294 | + |
| A-295 | +++ |
| A-296 | +++ |
| A-297 | + |
| A-298 | ++++ |
| A-299 | + |
| A-300 | +++ |
| A-301 | ++++ |
| A-302 | + |
| A-303 | ++ |
| A-304 | ++++ |
| A-305 | +++ |
| A-306 | + |
| A-307 | +++ |
| A-308 | +++ |
| A-309 | +++ |
| A-310 | ++++ |
| A-311 | +++ |
| A-312 | + |
| A-313 | ++++ |
| A-314 | + |
| A-315 | + |
| A-316 | +++ |

TABLE 1-continued

| Compound | TFEB $AC_{50}$ (μM) |
|---|---|
| A-317 | +++ |
| A-318 | +++ |
| A-319 | ++++ |
| A-320 | + |
| A-321 | + |
| A-322 | ++ |
| A-323 | +++ |
| A-324 | + |
| A-325 | + |
| A-326 | + |
| A-327 | + |
| A-328 | + |
| A-329 | + |
| A-330 | + |
| A-331 | ++++ |
| A-332 | +++ |
| A-333 | + |
| A-334 | +++ |
| A-335 | + |
| A-336 | ++++ |
| A-337 | ++ |
| A-338 | +++ |
| A-339 | +++ |
| A-340 | + |
| A-341 | ++++ |
| A-342 | ++ |
| A-343 | +++ |
| A-344 | +++ |
| A-345 | +++ |
| A-346 | ++++ |
| A-347 | ++++ |
| A-348 | ++ |
| A-349 | + |
| A-350 | +++ |
| A-351 | + |
| A-352 | +++ |
| A-353 | ++++ |
| A-354 | + |
| A-355 | +++ |
| A-356 | +++ |
| A-357 | + |
| A-358 | + |
| A-359 | ++++ |
| A-360 | ++++ |
| A-361 | ++++ |
| A-362 | ++++ |
| A-363 | + |
| A-364 | + |
| A-365 | + |
| A-366 | + |
| A-367 | +++ |
| A-368 | +++ |
| A-369 | + |
| A-370 | ++++ |
| A-371 | ++++ |
| A-372 | +++ |
| A-390 | ++++ |
| A-391 | +++ |
| A-392 | +++ |
| A-393 | ++ |
| A-394 | +++ |
| A-395 | + |
| A-396 | ++++ |
| A-397 | +++ |
| A-398 | +++ |
| A-399 | ++++ |
| A-400 | +++ |
| A-401 | + |
| A-402 | +++ |
| A-403 | +++ |
| A-404 | +++ |
| A-405 | +++ |
| A-406 | +++ |
| A-407 | ++++ |
| A-408 | + |
| A-409 | + |
| A-410 | +++ |
| A-411 | ++++ |

TABLE 1-continued

| Compound | TFEB $AC_{50}$ (μM) |
|---|---|
| A-412 | ++++ |
| A-413 | ++ |
| A-414 | ++++ |
| A-415 | ++++ |
| A-416 | +++ |
| A-417 | +++ |
| A-418 | +++ |
| A-419 | ++++ |
| A-420 | +++ |
| A-421 | ++++ |
| A-422 | ++++ |
| A-423 | ++++ |
| A-424 | +++ |
| A-425 | +++ |
| A-426 | ++++ |
| A-427 | +++ |
| A-428 | ++++ |
| A-429 | +++ |
| A-430 | +++ |
| A-431 | +++ |
| A-432 | +++ |
| A-433 | +++ |
| A-434 | ++++ |
| A-435 | ++++ |
| A-436 | +++ |
| A-437 | +++ |
| A-438 | ++++ |
| A-439 | ++++ |
| A-440 | ++++ |
| A-441 | +++ |
| A-442 | ++++ |
| A-443 | +++ |
| A-444 | ++++ |
| A-445 | ++++ |
| A-446 | +++ |
| A-447 | +++ |
| A-448 | ++++ |
| A-449 | +++ |
| A-450 | ++ |
| A-451 | ++++ |
| A-452 | ++ |
| A-453 | +++ |
| A-454 | ++++ |
| A-455 | +++ |
| A-456 | ++++ |
| A-457 | +++ |
| A-458 | +++ |
| A-459 | +++ |
| A-460 | ++++ |
| A-461 | +++ |
| A-462 | +++ |
| A-463 | +++ |
| A-464 | +++ |
| A-465 | ++++ |
| A-466 | ++++ |
| A-467 | ++++ |
| A-468 | ++++ |
| A-469 | ++++ |
| A-470 | ++++ |
| A-471 | ++++ |
| A-472 | ++++ |
| A-473 | +++ |
| A-474 | +++ |
| A-475 | ++++ |
| A-476 | +++ |
| A-477 | +++ |
| A-478 | +++ |
| A-479 | ++++ |
| A-480 | +++ |
| A-481 | ++++ |
| A-482 | +++ |
| A-483 | ++++ |
| A-484 | +++ |
| A-485 | +++ |
| A-486 | +++ |
| A-487 | ++++ |
| A-488 | ++ |
| A-489 | +++ |

TABLE 1-continued

| Compound | TFEB $AC_{50}$ (μM) |
|---|---|
| A-490 | + |
| A-491 | ++++ |
| A-492 | ++++ |
| A-493 | ++++ |
| A-494 | ++++ |
| A-495 | ++ |
| A-496 | ++++ |
| A-497 | ++++ |
| A-498 | ++++ |
| A-499 | ++++ |
| A-500 | +++ |
| A-501 | +++ |
| A-502 | ++++ |
| A-503 | ++++ |
| A-504 | ++++ |
| A-505 | +++ |
| A-506 | ++++ |
| A-507 | +++ |
| A-508 | +++ |
| A-509 | +++ |
| A-510 | ++++ |
| A-511 | ++++ |
| A-512 | +++ |
| A-513 | +++ |
| A-514 | ++++ |
| A-515 | +++ |
| A-516 | +++ |
| A-517 | +++ |
| A-518 | ++++ |
| A-519 | ++++ |
| A-520 | ++++ |
| A-521 | ++++ |
| A-522 | +++ |
| A-523 | ++++ |
| A-524 | ++++ |
| A-525 | ++++ |
| A-526 | +++ |
| A-527 | +++ |
| A-528 | +++ |
| A-529 | +++ |
| A-530 | +++ |
| A-531 | ++++ |
| A-532 | ++++ |
| A-533 | +++ |
| A-534 | +++ |
| A-535 | +++ |
| A-536 | ++ |
| A-537 | ++ |
| A-538 | ++++ |
| A-539 | ++++ |
| A-540 | ++++ |
| A-541 | ++++ |
| A-542 | ++++ |
| A-543 | ++++ |
| A-544 | ++++ |
| A-545 | ++++ |
| A-546 | ++++ |
| A-547 | ++++ |
| A-548 | ++++ |
| A-549 | +++ |
| A-550 | ++++ |
| A-551 | ++++ |
| A-552 | ++++ |
| A-553 | +++ |
| A-554 | ++++ |
| A-555 | +++ |
| A-556 | ++++ |
| A-557 | +++ |
| A-558 | +++ |
| A-559 | +++ |
| A-560 | ++++ |
| A-561 | +++ |
| A-562 | ++++ |
| A-563 | + |
| A-564 | ++++ |
| A-565 | ++ |
| A-566 | +++ |
| A-567 | + |

TABLE 1-continued

| Compound | TFEB $AC_{50}$ (μM) |
|---|---|
| A-568 | ++ |
| A-569 | ++ |
| A-570 | ++++ |
| A-571 | +++ |
| A-572 | +++ |
| A-573 | ++ |
| A-574 | +++ |
| A-575 | ++ |
| A-576 | + |
| A-577 | +++ |
| A-578 | +++ |
| A-579 | +++ |
| A-580 | ++ |
| A-581 | +++ |
| A-582 | +++ |
| A-583 | + |
| A-584 | ++++ |
| A-585 | ++++ |
| A-586 | ++ |
| A-587 | +++ |
| A-588 | ++++ |
| A-589 | ++++ |
| A-590 | +++ |
| A-591 | + |
| A-592 | ++ |
| A-593 | +++ |
| A-594 | +++ |
| A-595 | +++ |
| A-596 | +++ |
| A-597 | ++ |
| A-598 | ++++ |
| A-599 | +++ |
| A-600 | + |
| A-601 | +++ |
| A-602 | +++ |
| A-603 | +++ |
| A-604 | ++++ |
| A-605 | ++++ |
| A-606 | +++ |
| A-607 | +++ |
| A-608 | ++++ |
| A-609 | ++ |
| A-610 | +++ |
| A-611 | ++++ |
| A-612 | +++ |
| A-613 | ++++ |
| A-614 | ++++ |
| A-615 | ++++ |
| A-616 | +++ |
| A-617 | +++ |
| A-618 | +++ |
| A-619 | +++ |
| A-620 | ++++ |
| A-621 | ++++ |
| A-622 | +++ |
| A-623 | +++ |
| A-624 | +++ |
| A-625 | ++++ |
| A-626 | ++++ |
| A-627 | +++ |
| A-628 | +++ |
| A-629 | +++ |
| A-630 | ++++ |
| A-631 | ++++ |
| A-632 | ++++ |
| A-633 | +++ |
| A-634 | +++ |
| A-635 | +++ |
| A-636 | ++++ |
| A-637 | + |
| A-638 | +++ |
| A-639 | + |
| A-640 | +++ |
| A-641 | ++ |
| A-642 | ++++ |
| A-643 | ++++ |
| A-644 | +++ |
| A-645 | ++ |

TABLE 1-continued

| Compound | TFEB $AC_{50}$ (μM) |
|---|---|
| A-646 | +++ |
| A-647 | ++ |
| A-648 | ++++ |
| A-649 | +++ |
| A-650 | ++++ |
| A-651 | ++++ |
| A-652 | ++++ |
| A-653 | +++ |
| A-654 | ++++ |
| A-655 | +++ |
| A-656 | +++ |
| A-657 | ++ |
| A-658 | ++++ |
| A-659 | +++ |
| A-660 | ++ |
| A-661 | +++ |
| A-662 | ++++ |
| A-663 | ++++ |
| A-664 | ++++ |
| A-665 | +++ |
| A-666 | +++ |
| A-667 | +++ |
| A-668 | +++ |
| A-669 | ++++ |
| A-670 | +++ |
| A-671 | ++++ |
| A-672 | ++++ |
| A-673 | +++ |
| A-674 | ++++ |
| A-675 | ++++ |
| A-676 | +++ |
| A-677 | ++++ |
| A-678 | ++++ |
| A-679 | ++++ |
| A-680 | ++ |
| A-681 | ++++ |
| A-682 | +++ |
| A-683 | +++ |
| A-684 | +++ |
| A-685 | ++++ |
| A-686 | ++++ |
| A-687 | ++++ |
| A-688 | +++ |
| A-689 | + |
| A-690 | +++ |
| A-691 | +++ |
| A-692 | +++ |
| A-693 | +++ |
| A-694 | ++++ |
| A-695 | ++++ |
| A-696 | ++++ |
| A-697 | +++ |
| A-698 | ++++ |
| A-699 | +++ |
| A-700 | +++ |
| A-701 | ++++ |
| A-702 | ++++ |
| A-703 | ++++ |
| A-704 | ++++ |
| A-705 | ++ |
| A-706 | ++++ |
| A-707 | +++ |
| A-708 | ++++ |
| A-709 | +++ |
| A-710 | ++ |
| A-711 | ++++ |
| A-712 | +++ |
| A-713 | ++++ |
| A-714 | ++ |
| A-715 | ++++ |
| A-716 | +++ |
| A-717 | +++ |
| A-718 | ++++ |
| A-719 | ++++ |
| A-720 | +++ |
| A-721 | ++++ |
| A-722 | + |
| A-723 | ++++ |

TABLE 1-continued

| Compound | TFEB $AC_{50}$ (μM) |
|---|---|
| A-724 | ++++ |
| A-725 | ++ |
| A-726 | +++ |
| A-727 | +++ |
| A-728 | +++ |
| A-729 | +++ |
| A-730 | ++++ |
| A-731 | + |
| A-732 | +++ |
| A-733 | +++ |
| A-734 | ++++ |
| A-735 | + |
| A-736 | ++++ |
| A-737 | + |
| A-738 | ++++ |
| A-739 | ++++ |
| A-740 | ++ |
| A-741 | ++++ |
| A-742 | ++++ |
| A-743 | + |
| A-744 | + |
| A-745 | + |
| A-746 | ++++ |
| A-747 | + |
| A-748 | ++++ |
| A-749 | +++ |
| A-750 | ++++ |
| A-751 | + |
| A-752 | ++++ |
| A-753 | ++++ |
| A-754 | +++ |
| A-755 | ++++ |
| A-756 | +++ |
| A-757 | ++++ |
| A-758 | ++++ |
| A-759 | ++++ |
| A-760 | +++ |
| A-761 | + |
| A-762 | ++++ |
| A-763 | ++++ |
| A-764 | +++ |
| A-765 | ++++ |
| A-766 | ++++ |
| A-767 | ++++ |
| A-768 | ++++ |
| A-769 | ++++ |
| A-770 | + |
| A-771 | ++++ |
| A-772 | ++ |
| A-773 | ++++ |
| A-774 | ++++ |
| A-775 | ++ |
| A-776 | ++++ |
| A-777 | ++++ |
| A-778 | ++++ |
| A-779 | ++++ |
| A-780 | ++++ |
| A-781 | ++++ |
| A-782 | ++++ |
| A-783 | ++++ |
| A-784 | ++++ |
| A-785 | ++++ |
| A-786 | ++++ |
| A-788 | ++++ |
| A-789 | ++++ |
| A-790 | ++++ |
| A-791 | + |
| A-792 | + |
| A-793 | +++ |
| A-794 | ++++ |
| A-795 | ++ |
| A-796 | + |
| A-797 | ++++ |
| A-798 | ++++ |
| A-799 | ++++ |
| A-800 | ++++ |
| A-801 | ++++ |
| A-802 | ++++ |

TABLE 1-continued

| Compound | TFEB $AC_{50}$ (μM) |
|---|---|
| A-803 | ++++ |
| A-804 | ++++ |
| A-805 | ++++ |
| A-806 | ++++ |
| A-807 | ++++ |
| A-808 | ++++ |
| A-809 | + |
| A-810 | ++++ |
| A-811 | ++++ |
| A-812 | ++++ |
| A-813 | + |
| A-814 | ++++ |
| A-815 | + |
| A-816 | + |
| A-817 | ++++ |
| A-818 | ++++ |
| A-819 | + |
| A-820 | + |
| A-821 | ++++ |
| A-822 | +++ |
| A-823 | + |
| A-824 | ++++ |
| A-825 | ++++ |
| A-826 | ++++ |
| A-827 | + |
| A-828 | ++++ |
| A-829 | ++++ |
| A-830 | ++++ |
| A-831 | ++++ |
| A-832 | ++++ |
| A-833 | ++++ |
| A-834 | ++++ |
| A-835 | ++++ |
| A-836 | +++ |
| A-837 | ++++ |
| A-838 | ++++ |
| A-839 | ++++ |
| A-840 | ++++ |
| A-841 | +++ |
| A-842 | ++++ |
| A-843 | ++++ |
| A-844 | ++++ |
| A-845 | +++ |
| A-846 | +++ |
| A-847 | + |
| A-848 | ++++ |
| A-849 | +++ |
| A-850 | +++ |
| A-851 | ++++ |
| A-852 | ++++ |
| A-853 | ++++ |
| A-854 | ++++ |
| A-855 | +++ |
| A-856 | + |
| A-857 | ++++ |
| A-858 | ++++ |
| A-859 | ++++ |
| A-860 | +++ |
| A-861 | ++++ |
| A-862 | ++++ |
| A-863 | ++++ |
| A-864 | ++++ |
| A-865 | ++++ |
| A-866 | ++++ |
| A-867 | ++++ |
| A-868 | ++++ |
| A-869 | +++ |
| A-870 | + |
| A-871 | ++++ |
| A-871A | ++++ |
| A-871B | ++++ |
| A-872 | ++++ |
| A-872A | ++++ |
| A-872B | ++++ |
| A-873 | + |
| A-874 | +++ |
| A-875 | + |
| A-876 | + |

TABLE 1-continued

| Compound | TFEB $AC_{50}$ (μM) |
|---|---|
| A-877 | ++++ |
| A-878 | ++++ |
| A-879 | ++++ |
| A-880 | ++++ |
| A-881 | ++++ |
| A-882 | ++++ |
| A-883 | ++++ |
| A-885 | ++++ |
| A-886 | ++++ |
| A-887 | ++++ |
| A-888 | +++ |
| A-889 | +++ |
| A-890 | +++ |
| A-891 | + |
| A-892 | ++ |
| A-893 | + |
| A-894 | +++ |
| A-895 | + |
| A-896 | ++++ |
| A-897 | ++++ |
| A-898 | + |
| A-899 | + |
| A-900 | + |
| A-901 | ++++ |
| A-902 | + |
| A-903 | + |
| A-904 | +++ |
| A-905 | ++++ |
| A-906 | ++++ |
| A-907 | ++++ |
| A-908 | +++ |
| A-909 | +++ |
| A-910 | +++ |
| A-911 | ++++ |
| A-912 | ++++ |
| A-913 | ++++ |
| A-914 | + |
| A-915 | + |
| A-916 | + |
| A-917 | +++ |
| A-918 | ++++ |
| A-919 | ++++ |
| A-920 | + |
| A-921 | ++++ |
| A-922 | + |
| A-923 | + |
| A-924 | ++++ |
| A-925 | ++++ |
| A-926 | + |
| A-927 | + |
| A-928 | +++ |
| A-929 | ++++ |
| A-930 | +++ |
| A-931 | ++++ |
| A-932 | ++++ |
| A-933 | ++++ |
| A-934 | + |
| A-935 | ++++ |
| A-936 | ++++ |
| A-937 | +++ |
| A-938 | + |
| A-939 | +++ |
| A-940 | ++++ |
| A-941 | +++ |
| A-946 | ++++ |
| A-952 | ++++ |
| A-956 | ++++ |
| A-957 | + |
| A-958 | ++++ |
| A-959 | + |
| A-960 | + |
| A-961 | + |
| A-962 | ++++ |
| A-963 | +++ |
| A-964 | ++++ |
| A-965 | + |
| A-966 | + |
| A-967 | + |

TABLE 1-continued

| Compound | TFEB $AC_{50}$ (μM) |
|---|---|
| A-968 | ++++ |
| A-969 | ++++ |
| A-970 | ++++ |
| A-971 | +++ |
| A-972 | +++ |
| A-973 | ++++ |
| A-974 | ++++ |
| A-975 | + |
| A-976 | ++++ |
| A-977 | +++ |
| A-978 | ++++ |
| A-979 | +++ |
| A-980 | + |
| A-981 | + |
| A-982 | ++++ |
| A-983 | ++++ |
| A-984 | ++++ |
| A-985 | ++++ |
| A-986 | + |
| A-987 | ++++ |
| A-988 | + |
| A-989 | ++ |
| A-990 | ++++ |
| A-991 | +++ |
| A-992 | + |
| A-993 | ++++ |
| A-994 | ++++ |
| A-995 | + |
| A-996 | ++++ |
| A-997 | ++++ |
| A-998 | +++ |
| A-999 | ++++ |
| A-1000 | + |
| A-1001 | ++++ |
| A-1002 | + |

The invention claimed is:

1. A compound of Formula IIb-1 or IId:

IIb-1

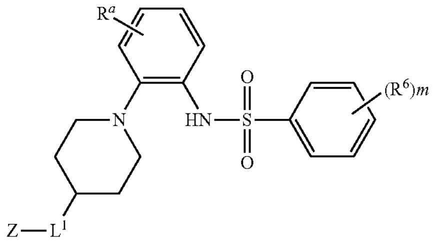

IId

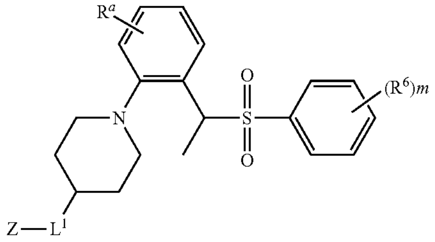

or a pharmaceutically acceptable salt thereof, wherein $L^1$ is —C(O)—$NR^3$—, —$NR^3$—C(O)—, or an optionally substituted bivalent moiety selected from $C_{1-6}$ alkylenyl, —$NR^3$-$C_{0-6}$ alkylenyl, —C(O)—$C_{0-6}$ alkylenyl, —$C_{1-6}$ alkylenyl-C(O)—, and —$C_{1-6}$ alkylenyl-O—C(O)—;

Z is 4- to 16-membered monocyclic or polycyclic heterocyclyl comprising 1 to 4 heteroatoms selected from N, O, and S, wherein Z is substituted with $(R^2)_q$;

each $R^a$ is independently H, halo, —CN, or an optionally substituted group selected from $C_{1-6}$ aliphatic, —$C_{3-6}$ cycloaliphatic, and —O—$C_{1-6}$ aliphatic;

each $R^2$ is independently selected from halo, oxo, —CN, —OH, —O—$R^{2a}$, —C(O)—$R^{2a}$, —C(O)O—$R^{2a}$, and an optionally substituted group selected from —$C_{1-6}$ aliphatic, —$C_{6-12}$ aryl, and 5- to 12-membered monocyclic or bicyclic heteroaryl comprising 1 to 4 heteroatoms selected from N, O, and S;

each $R^{2a}$ is independently H or an optionally substituted group selected from $C_{1-6}$ aliphatic, $C_{3-12}$ cycloaliphatic, and 4- to 12-membered monocyclic or bicyclic heterocyclyl comprising 1 to 4 heteroatoms selected from N, O, and S;

each $R^3$ is independently selected from H and optionally substituted-$C_{1-6}$ aliphatic;

each $R^5$ is —$N(R^3)_2$ or an optionally substituted group selected from —$C_{1-6}$ aliphatic, —P(O)($C_{1-6}$ aliphatic)$_2$, —$C_{3-12}$ cycloaliphatic, and 5- to 12-membered monocyclic or polycyclic heterocyclyl comprising 1 to 4 heteroatoms selected from N, O, and S;

each $R^6$ is independently selected from halo, —$SF_5$, —S(O)—$R^5$, $S(O)_2$—$R^5$, —S(O)(NH)—$R^5$, —$S(O)_2$—(NH)—$R^5$, —S(O)—$N(R^5)_2$, —$S(O)_2$—N$(R^5)_2$, —CN, —C(O)—NH($R^5$), —C(O)—$N(R^5)_2$, —P(O)$(R^5)_2$, —O—$R^5$, or an optionally substituted group selected from —$C_{1-6}$ aliphatic, -S—$C_{1-6}$ aliphatic, —$C_{0-6}$ alkylenyl —C(O)—$R^5$, —$C_{0-6}$ alkylenyl-C(O)O—$R^5$, —$C_{6-12}$ aryl, —$C_{3-12}$ cycloaliphatic, and 4- to 7-membered monocyclic heterocyclyl comprising 1 to 4 heteroatoms selected from N, O, and S;

m is 0, 1, 2, 3, or 4; and q is 2.

2. The compound of claim 1, wherein each $R^6$ is independently halo, —S(O)—$R^5$, —$S(O)_2$—$R^5$, —S(O)(NH)—$R^5$, or an optionally substituted —O—$C_{1-6}$ aliphatic.

3. The compound of claim 1, wherein $R^6$ is —S(O)—$R^5$, —$S(O)_2$—$R^5$, or optionally substituted —$C_{1-6}$ aliphatic.

4. A pharmaceutical composition comprising a compound of claim 1, and a pharmaceutically acceptable carrier, adjuvant, or vehicle.

5. The compound of claim 1, wherein the compound is selected from:

| Structure | Compound No. |
|---|---|
| 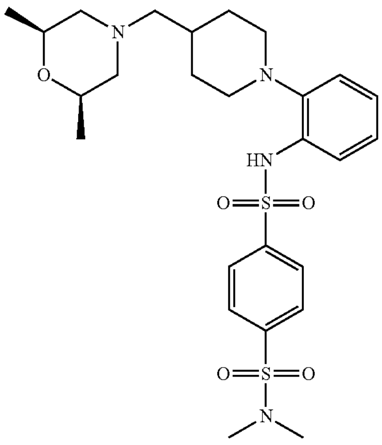 [SMILES: C[C@@H]1CN(CC2CCN(c3ccccc3NS(=O)(=O)c3ccc(S(=O)(=O)N(C)C)cc3)CC2)C[C@H](C)O1] | A-544 |

-continued

| Structure | Compound No. |
|---|---|
| 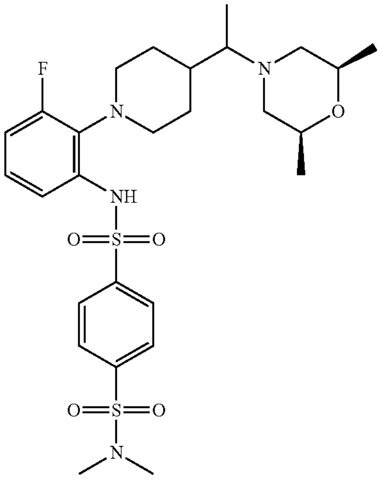 [SMILES: CC(C1CCN(c2c(F)cccc2NS(=O)(=O)c2ccc(S(=O)(=O)N(C)C)cc2)CC1)N1C[C@@H](C)O[C@@H](C)C1] | A-748 |
| 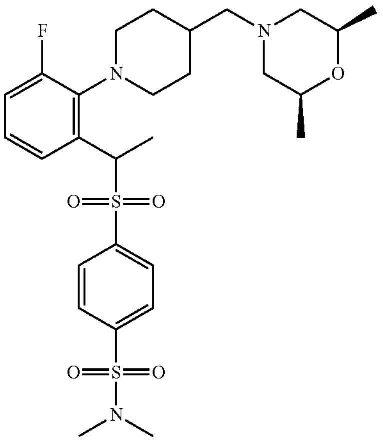 | A-750 |
| 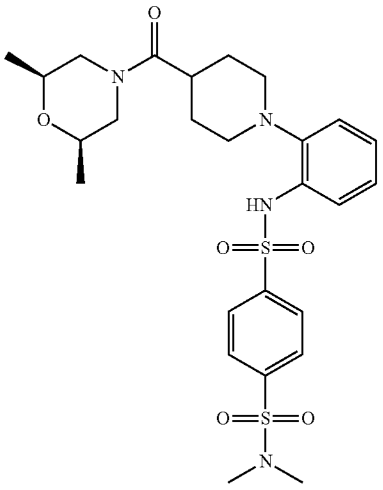 [SMILES: C[C@@H]1CN(C(=O)C2CCN(c3ccccc3NS(=O)(=O)c3ccc(S(=O)(=O)N(C)C)cc3)CC2)C[C@H](C)O1] | A-754 |

-continued
| Structure | Compound No. |
|---|---|
| 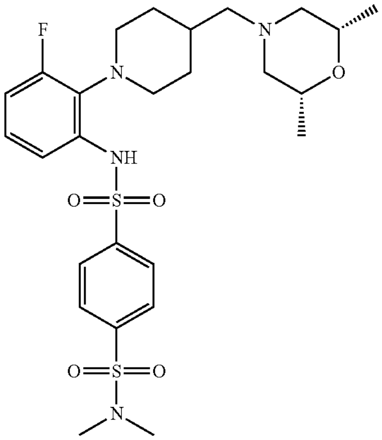 | A-755 |
| 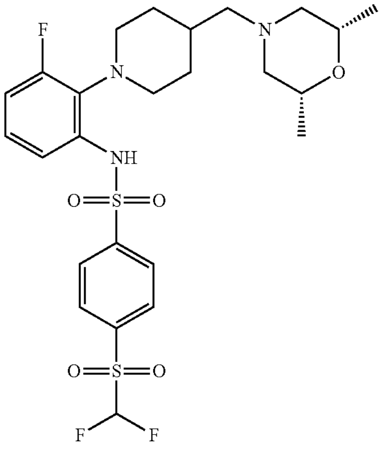 [SMILES: C[C@@H]1CN(CC2CCN(c3c(F)cccc3NS(=O)(=O)c3ccc(S(=O)(=O)C(F)F)cc3)CC2)C[C@H](C)O1] | A-758 |
| 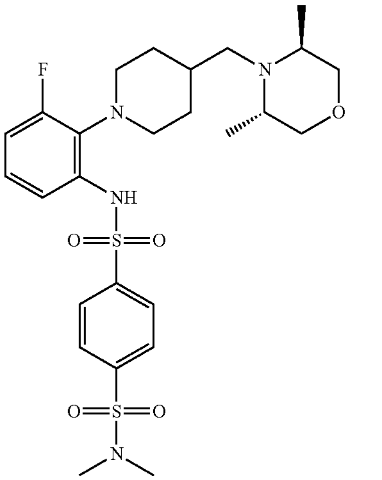 [SMILES: C[C@H]1COC[C@H](C)N1CC1CCN(c2c(F)cccc2NS(=O)(=O)c2ccc(S(=O)(=O)N(C)C)cc2)CC1] | A-763 |
-continued
| Structure | Compound No. |
|---|---|
| 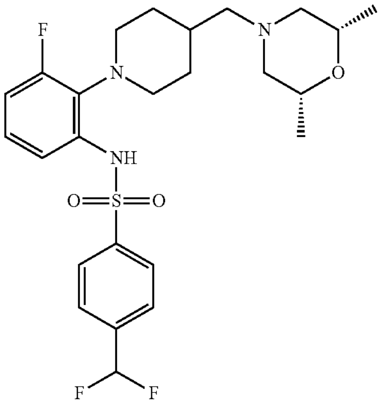 [SMILES: C[C@@H]1CN(CC2CCN(c3c(F)cccc3NS(=O)(=O)c3ccc(C(F)F)cc3)CC2)C[C@H](C)O1] | A-766 |
| 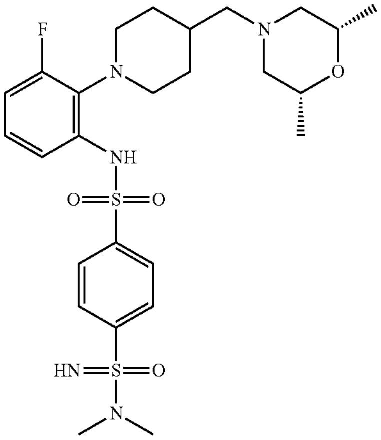 [SMILES: C[C@@H]1CN(CC2CCN(c3c(F)cccc3NS(=O)(=O)c3ccc(S(=N)(=O)N(C)C)cc3)CC2)C[C@H](C)O1] | A-769 |
| 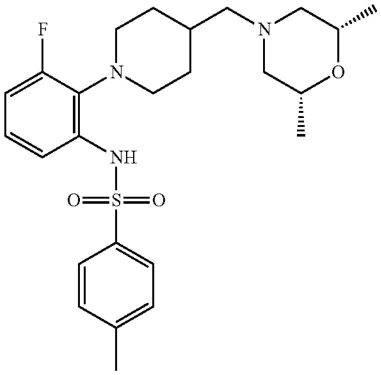 [SMILES: Cc1ccc(S(=O)(=O)Nc2cccc(F)c2N2CCC(CN3C[C@@H](C)O[C@@H](C)C3)CC2)cc1] | A-771 |

-continued
| Structure | Compound No. |
|---|---|
| 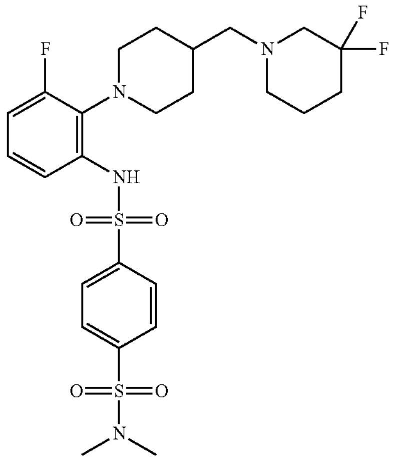 [SMILES: CN(C)S(=O)(=O)c1ccc(S(=O)(=O)Nc2cccc(F)c2N2CCC(CN3CCCC(F)(F)C3)CC2)cc1] | A-773 |
| 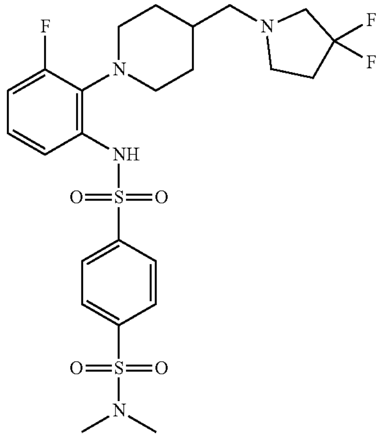 [SMILES: CN(C)S(=O)(=O)c1ccc(S(=O)(=O)Nc2cccc(F)c2N2CCC(CN3CCC(F)(F)C3)CC2)cc1] | A-774 |
| 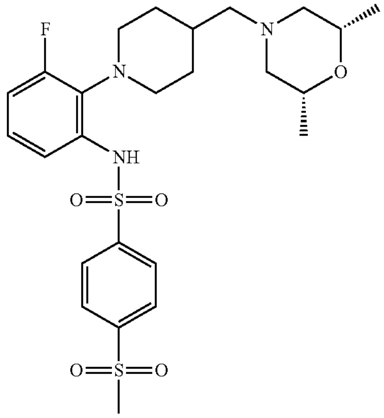 [SMILES: C[C@@H]1CN(CC2CCN(c3c(F)cccc3NS(=O)(=O)c3ccc(S(C)(=O)=O)cc3)CC2)C[C@H](C)O1] | A-776 |
-continued
| Structure | Compound No. |
|---|---|
| 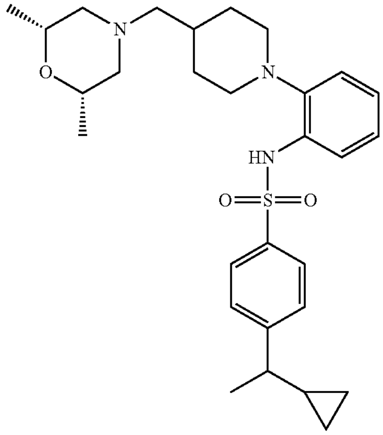 [SMILES: CC(c1ccc(S(=O)(=O)Nc2ccccc2N2CCC(CN3C[C@@H](C)O[C@@H](C)C3)CC2)cc1)C1CC1] | A-779 |
| 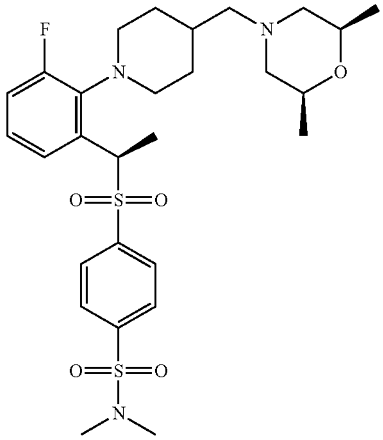 [SMILES: C[C@@H]1CN(CC2CCN(c3c(F)cccc3[C@@H](C)S(=O)(=O)c3ccc(S(=O)(=O)N(C)C)cc3)CC2)C[C@H](C)O1] | A-782 |
| 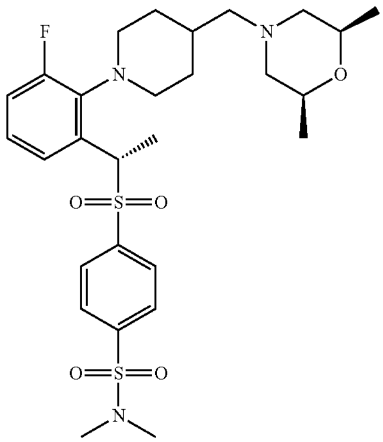 | A-783 |

-continued
| Structure | Compound No. |
|---|---|
| 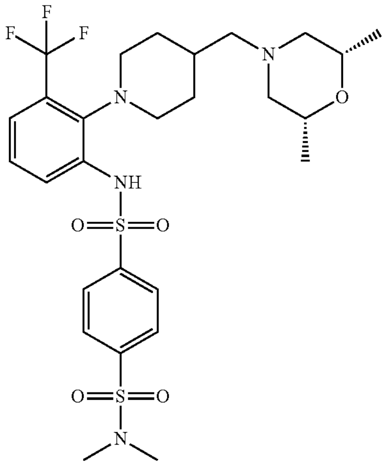 [SMILES: C[C@@H]1CN(CC2CCN(c3c(NS(=O)(=O)c4ccc(S(=O)(=O)N(C)C)cc4)cccc3C(F)(F)F)CC2)C[C@H](C)O1] | A-788 |
| 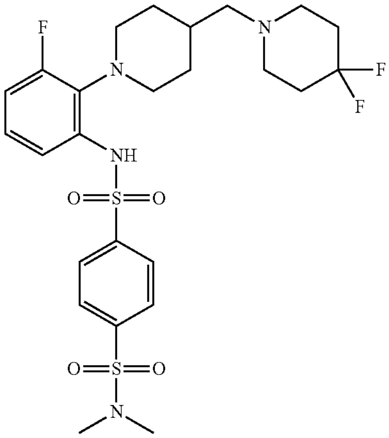 [SMILES: CN(C)S(=O)(=O)c1ccc(S(=O)(=O)Nc2cccc(F)c2N2CCC(CN3CCC(F)(F)CC3)CC2)cc1] | A-789 |
| 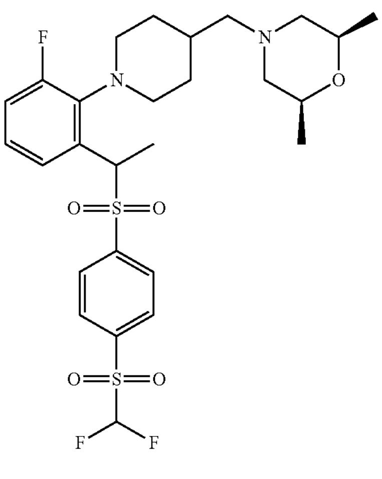 [SMILES: CC(c1cccc(F)c1N1CCC(CN2C[C@@H](C)O[C@@H](C)C2)CC1)S(=O)(=O)c1ccc(S(=O)(=O)C(F)F)cc1] | A-800 |
-continued
| Structure | Compound No. |
|---|---|
| 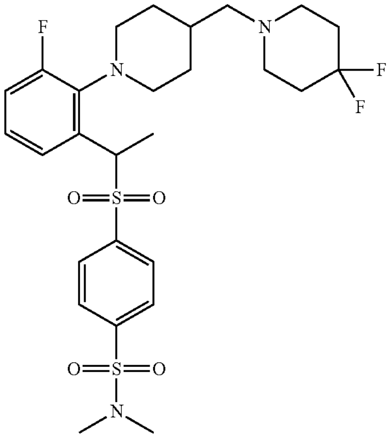 | A-801 |
| 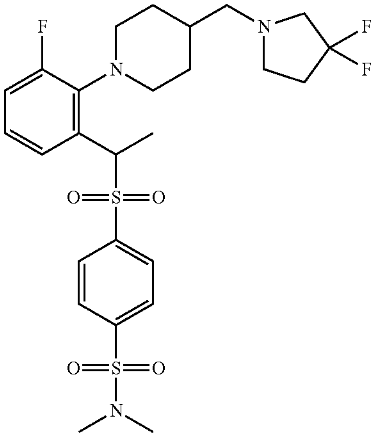 | A-802 |
| 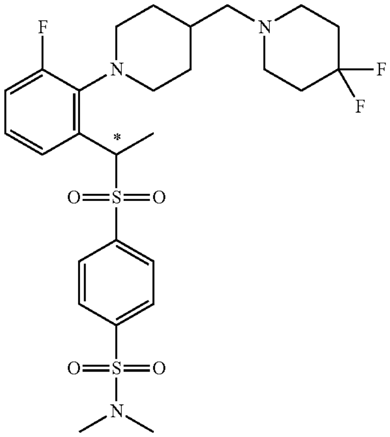 Enantiomer 1 | A-803 |

-continued
| Structure | Compound No. |
|---|---|
| 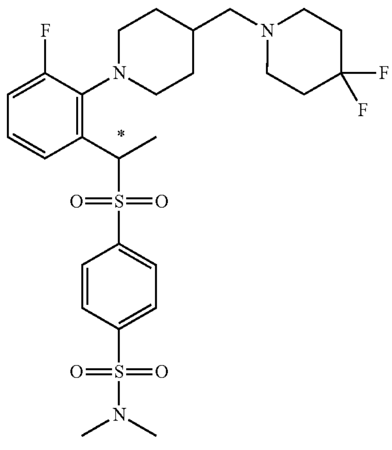 [SMILES: CC(c1cccc(F)c1N1CCC(CN2CCC(F)(F)CC2)CC1)S(=O)(=O)c1ccc(S(=O)(=O)N(C)C)cc1]<br>Enantiomer 2 | A-804 |
| 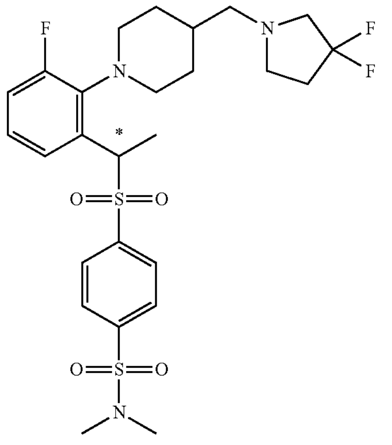<br>Enantiomer 1 | A-805 |
| 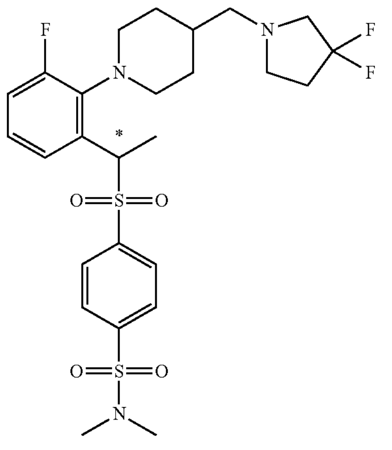 [SMILES: CC(c1cccc(F)c1N1CCC(CN2CCC(F)(F)C2)CC1)S(=O)(=O)c1ccc(S(=O)(=O)N(C)C)cc1]<br>Enantiomer 2 | A-806 |
-continued
| Structure | Compound No. |
|---|---|
| 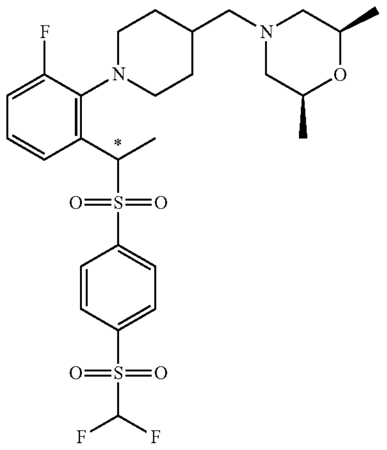<br>Enantiomer 1 | A-807 |
| 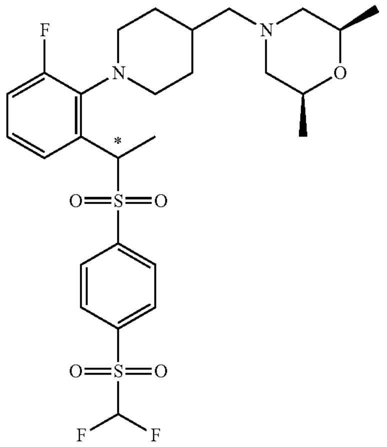<br>Enantiomer 2 | A-808 |
| 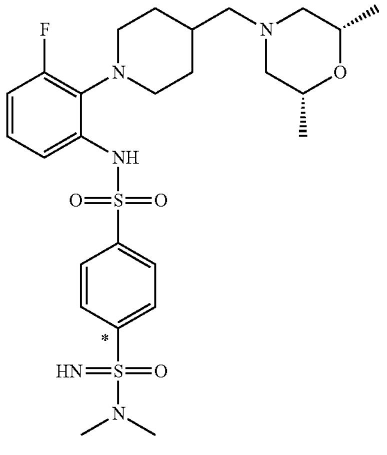<br>Enantiomer 1 | A-810 |

-continued
| Structure | Compound No. |
| --- | --- |
| 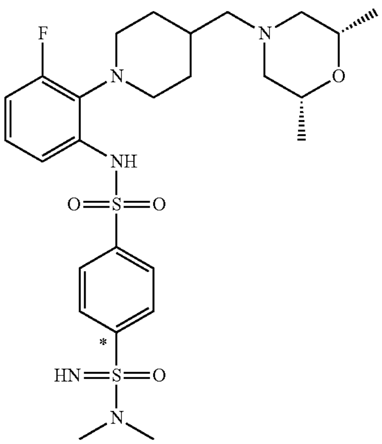 Enantiomer 2 | A-811 |
| 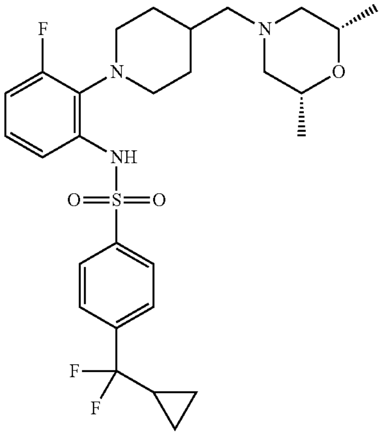 [SMILES: C[C@@H]1CN(CC2CCN(c3c(F)cccc3NS(=O)(=O)c3ccc(C(F)(F)C4CC4)cc3)CC2)C[C@H](C)O1] | A-814 |
| 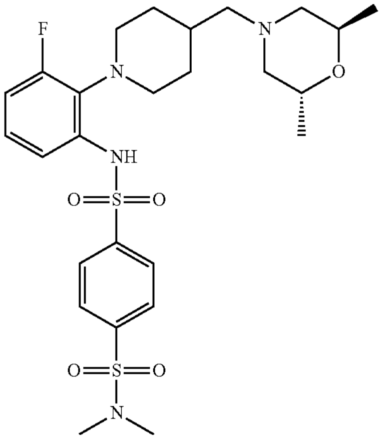 [SMILES: C[C@@H]1CN(CC2CCN(c3c(F)cccc3NS(=O)(=O)c3ccc(S(=O)(=O)N(C)C)cc3)CC2)C[C@@H](C)O1] | A-818 |
-continued
| Structure | Compound No. |
| --- | --- |
| 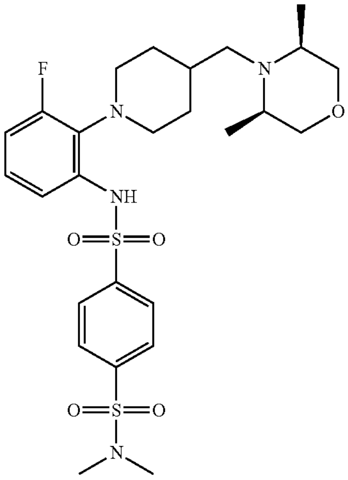 [SMILES: C[C@@H]1COC[C@H](C)N1CC1CCN(c2c(F)cccc2NS(=O)(=O)c2ccc(S(=O)(=O)N(C)C)cc2)CC1] | A-824 |
| 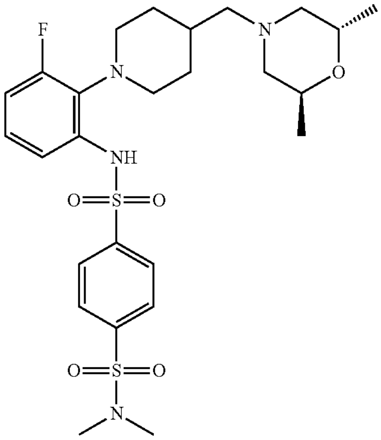 [SMILES: C[C@H]1CN(CC2CCN(c3c(F)cccc3NS(=O)(=O)c3ccc(S(=O)(=O)N(C)C)cc3)CC2)C[C@H](C)O1] | A-826 |
| 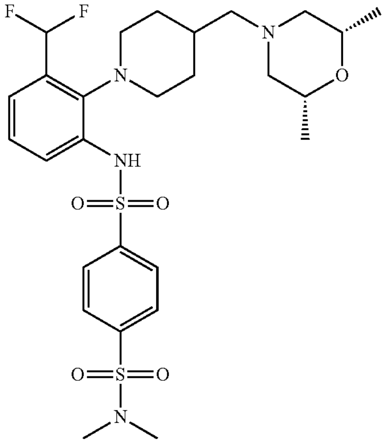 [SMILES: C[C@@H]1CN(CC2CCN(c3c(NS(=O)(=O)c4ccc(S(=O)(=O)N(C)C)cc4)cccc3C(F)F)CC2)C[C@H](C)O1] | A-831 |

-continued
| Structure | Compound No. |
| --- | --- |
| 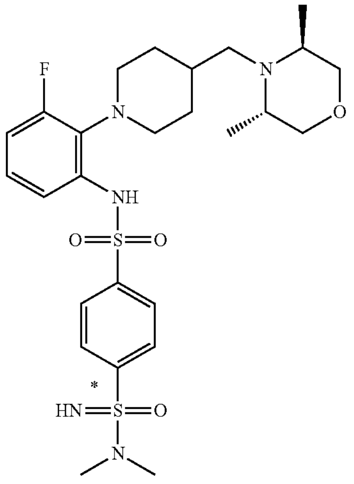 Diastereomer 1 | A-833 |
| 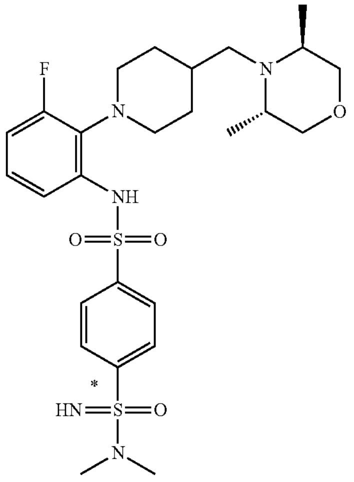 Diastereomer 2 | A-834 |
| 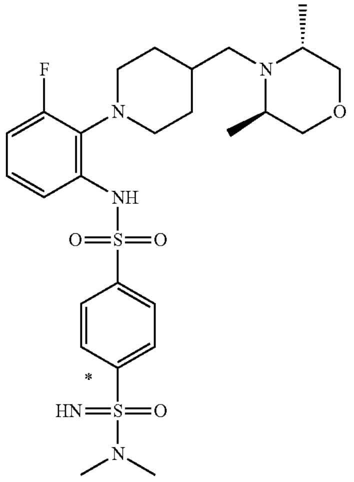 diastereomer 3 | A-835 |
-continued
| Structure | Compound No. |
| --- | --- |
| 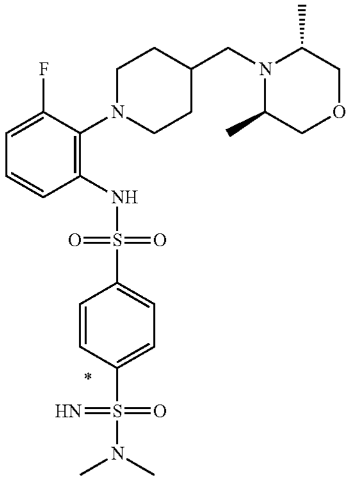 diastereomer 4 | A-836 |
| 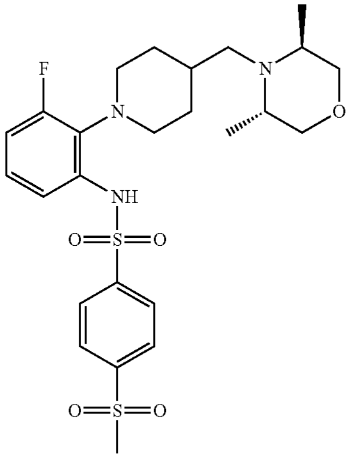 [SMILES: C[C@H]1COC[C@H](C)N1CC1CCN(c2c(F)cccc2NS(=O)(=O)c2ccc(S(C)(=O)=O)cc2)CC1] | A-838 |
| 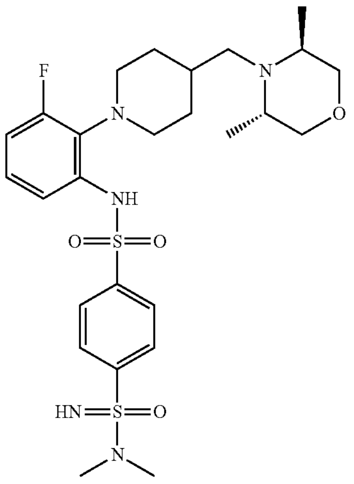 | A-840 |

-continued
| Structure | Compound No. |
|---|---|
| 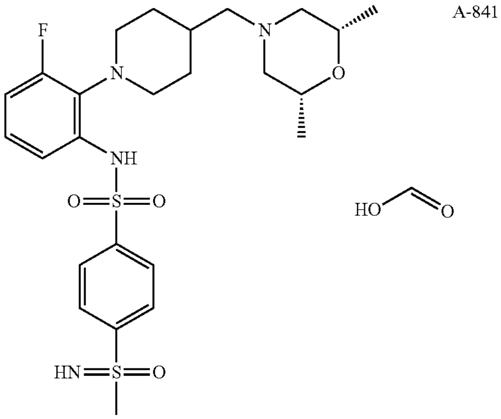 | A-841 |
| 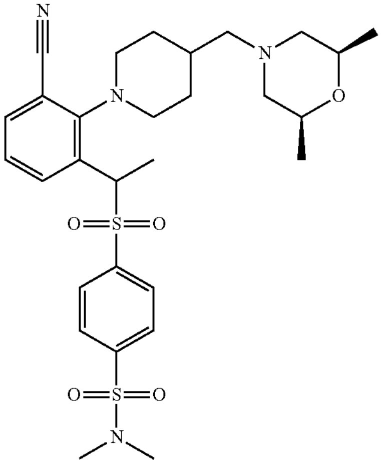 [SMILES: CC(c1cccc(C#N)c1N1CCC(CN2C[C@@H](C)O[C@@H](C)C2)CC1)S(=O)(=O)c1ccc(S(=O)(=O)N(C)C)cc1] | A-842 |
| 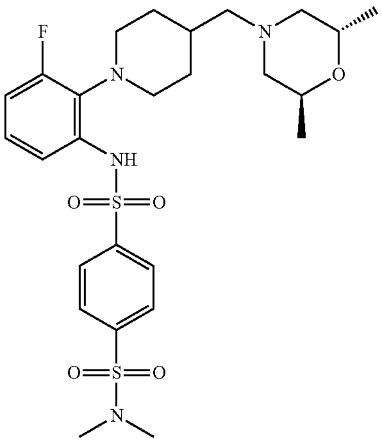 Trans, racemic | A-843 |
-continued
| Structure | Compound No. |
|---|---|
| 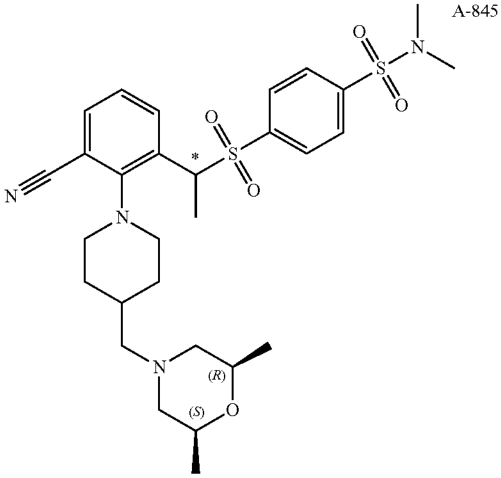 Enantiomer 2 | A-845 |
| 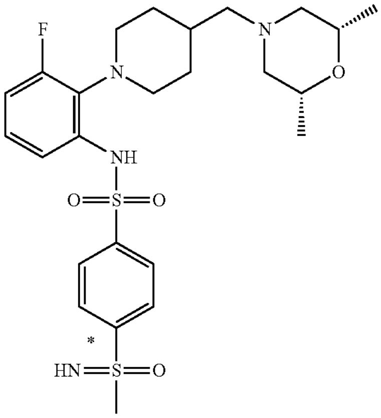 Enantiomer 1 | A-846 |
| 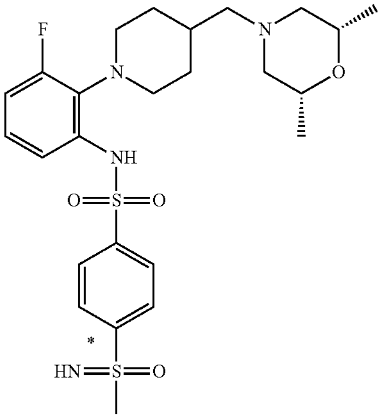 Enantiomer 2 | A-847 |

-continued
| Structure | Compound No. |
|---|---|
| 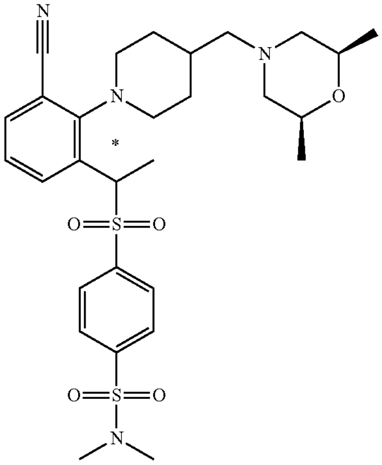<br>Enantiomer 1 | A-854 |
| 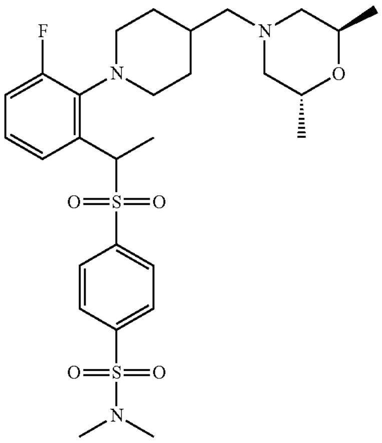 [SMILES: CC(c1cccc(F)c1N1CCC(CN2C[C@@H](C)O[C@H](C)C2)CC1)S(=O)(=O)c1ccc(S(=O)(=O)N(C)C)cc1] | A-859 |
| 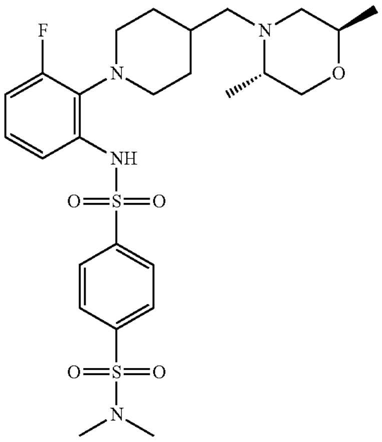 [SMILES: C[C@@H]1CN(CC2CCN(c3c(F)cccc3NS(=O)(=O)c3ccc(S(=O)(=O)N(C)C)cc3)CC2)[C@@H](C)CO1] | A-862 |
-continued
| Structure | Compound No. |
|---|---|
| 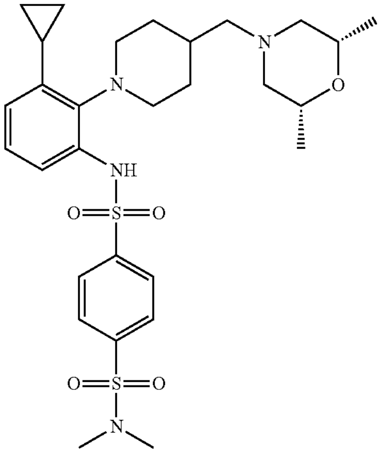 [SMILES: C[C@@H]1CN(CC2CCN(c3c(NS(=O)(=O)c4ccc(S(=O)(=O)N(C)C)cc4)cccc3C3CC3)CC2)C[C@H](C)O1] | A-863 |
| 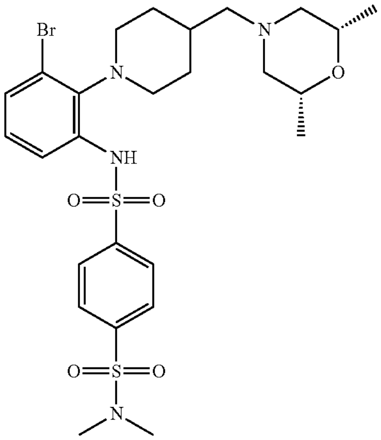 [SMILES: C[C@@H]1CN(CC2CCN(c3c(Br)cccc3NS(=O)(=O)c3ccc(S(=O)(=O)N(C)C)cc3)CC2)C[C@H](C)O1] | A-864 |
| 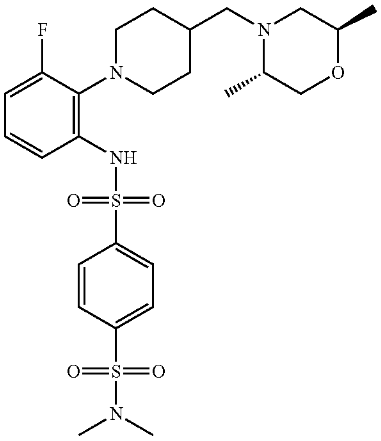 [SMILES: C[C@@H]1CN(CC2CCN(c3c(F)cccc3NS(=O)(=O)c3ccc(S(=O)(=O)N(C)C)cc3)CC2)[C@@H](C)CO1] | A-865 |

-continued
| Structure | Compound No. |
|---|---|
| 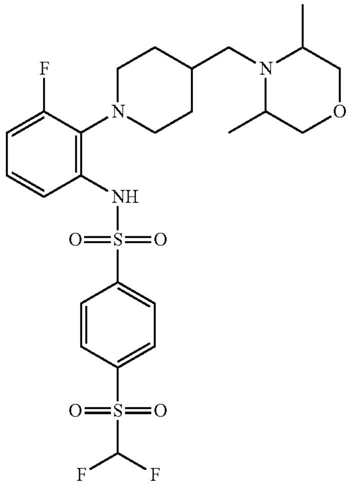 [SMILES: CC1COCC(C)N1CC1CCN(c2c(F)cccc2NS(=O)(=O)c2ccc(S(=O)(=O)C(F)F)cc2)CC1] | A-866 |
| 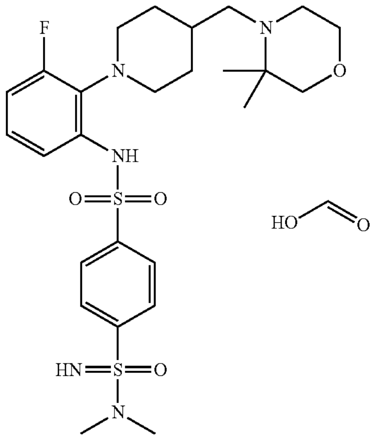 [SMILES: CN(C)S(=N)(=O)c1ccc(S(=O)(=O)Nc2cccc(F)c2N2CCC(CN3CCOCC3(C)C)CC2)cc1 ; O=CO] | A-867 |
| 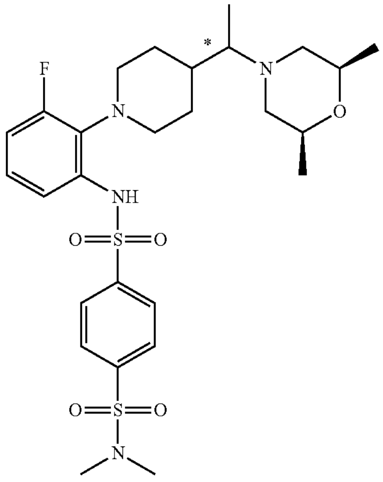 Isomer 1 | A-871 |
-continued
| Structure | Compound No. |
|---|---|
| 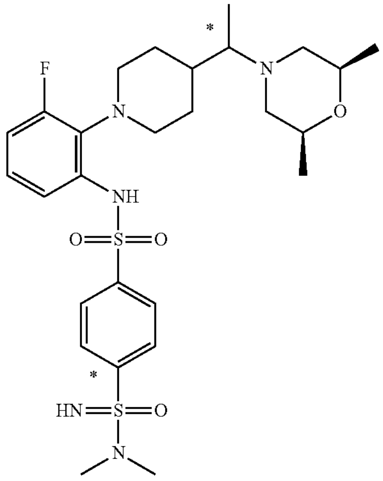 Diastereomer 1 | A-871A |
| 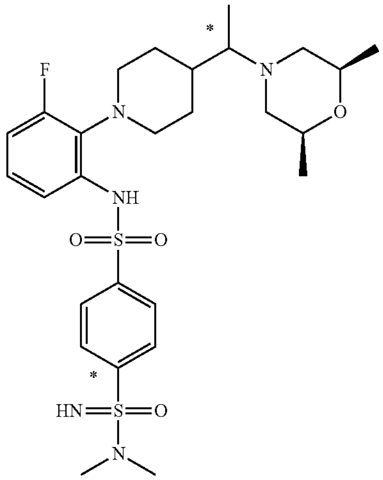 Diastereomer 2 | A-871B |
| 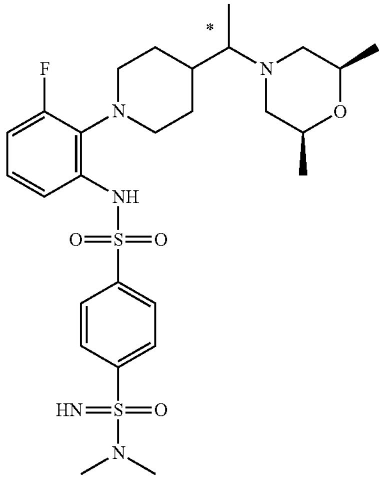 Isomer 2 | A-872 |

-continued
| Structure | Compound No. |
|---|---|
| 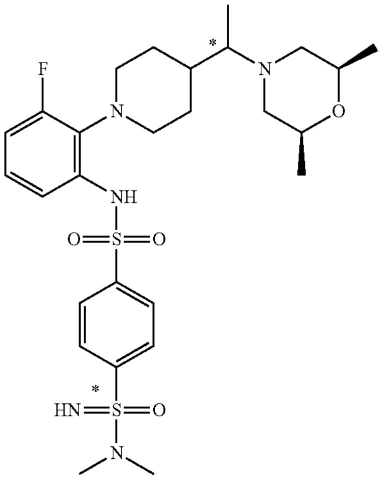 Diastereomer 3 | A-872A |
| 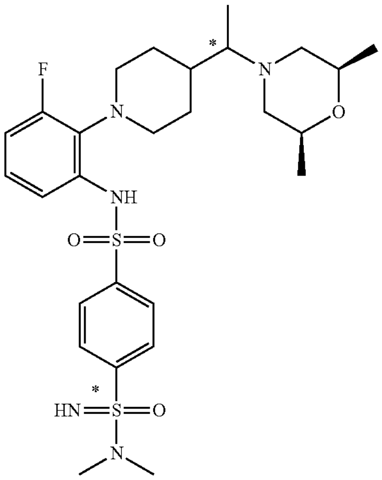 Diastereomer 4 | A-872B |
| 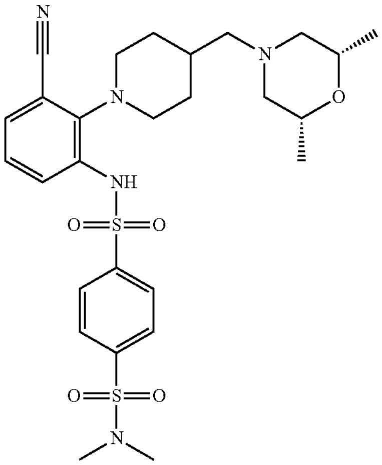 [SMILES: C[C@@H]1CN(CC2CCN(c3c(C#N)cccc3NS(=O)(=O)c3ccc(S(=O)(=O)N(C)C)cc3)CC2)C[C@H](C)O1] | A-878 |
-continued
| Structure | Compound No. |
|---|---|
| 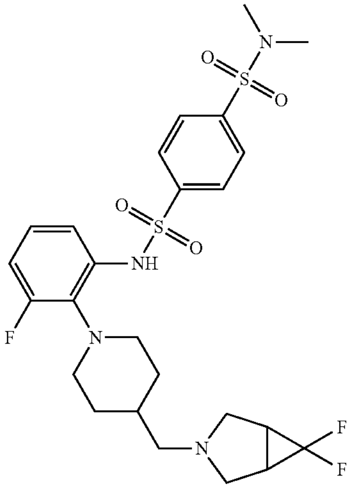 [SMILES: CN(C)S(=O)(=O)c1ccc(S(=O)(=O)Nc2cccc(F)c2N2CCC(CN3CC4C(C3)C4(F)F)CC2)cc1] | A-883 |
| 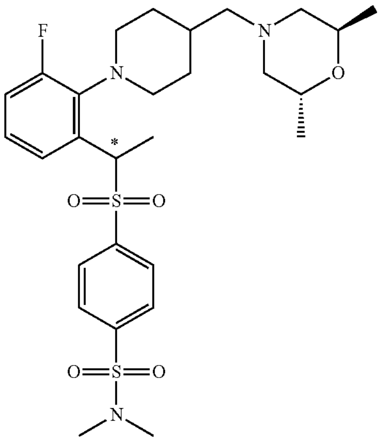 Diastereomer 4 | A-885 |
| 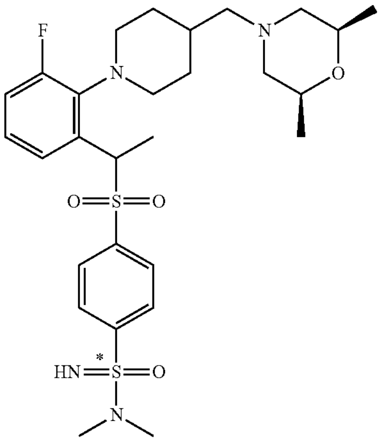 Diastereomer 3 | A-902 |

-continued
| Structure | Compound No. |
|---|---|
| 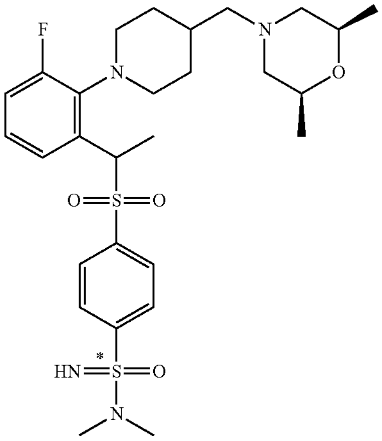 Diastereomer 4 | A-903 |
| 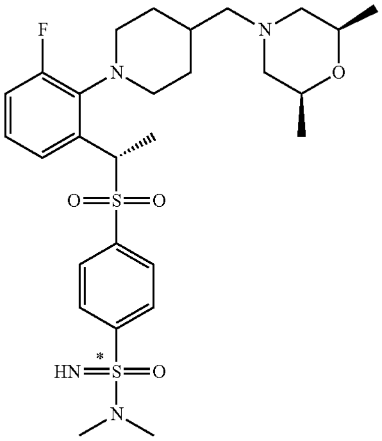 Diastereomer 1 | A-931 |
| 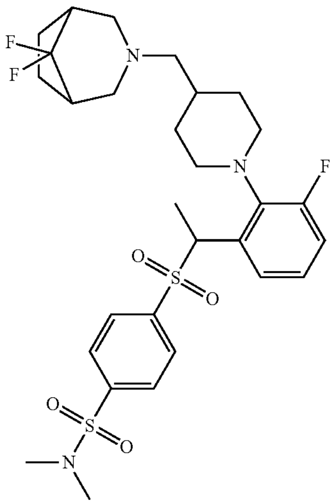 [SMILES: CC(c1cccc(F)c1N1CCC(CN2CC3CCC(C2)C3(F)F)CC1)S(=O)(=O)c1ccc(S(=O)(=O)N(C)C)cc1] | A-985 |
-continued
| Structure | Compound No. |
|---|---|
| 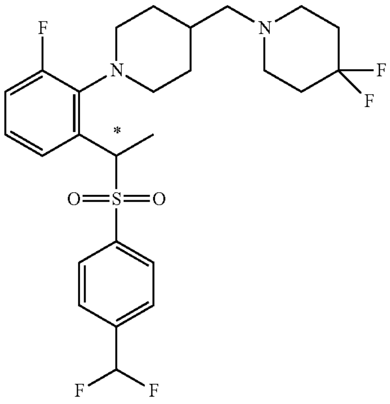 Enantiomer 1 | A-997 |
| 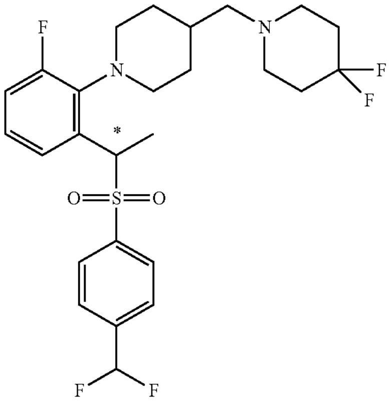 Enantiomer 2 | A-998 |
| 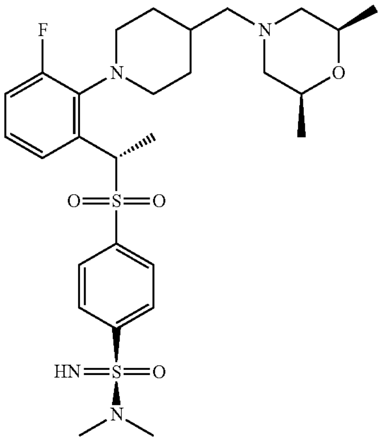 [SMILES: C[C@@H]1CN(CC2CCN(c3c(F)cccc3[C@H](C)S(=O)(=O)c3ccc([S@@](=N)(=O)N(C)C)cc3)CC2)C[C@H](C)O1] | A-1001 |
or a pharmaceutically acceptable salt thereof.

6. The compound of claim 1, wherein Z is selected from:
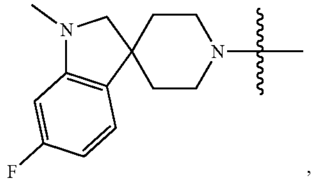
,
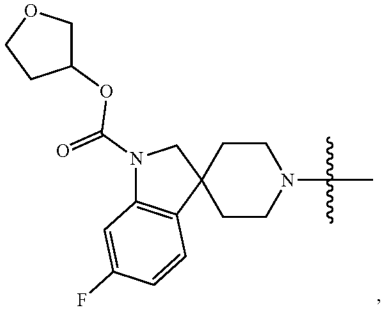
,
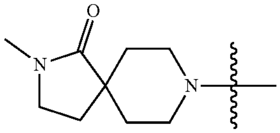
,
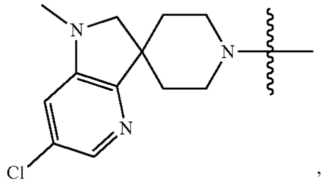
,
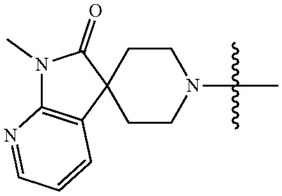
,
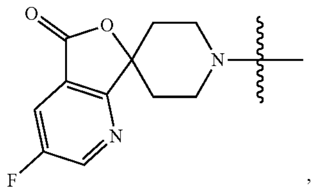
,
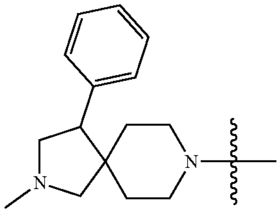
,
-continued
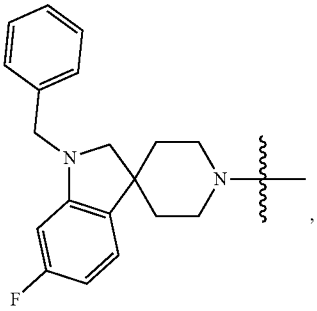
,
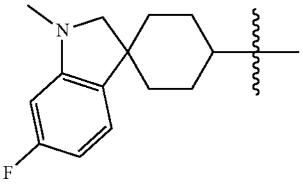
,
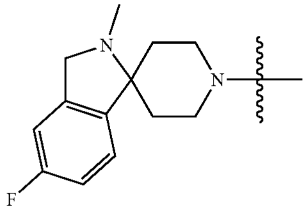
,
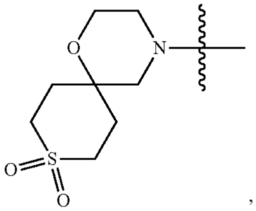
,
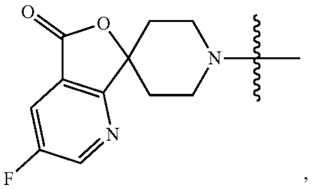
,
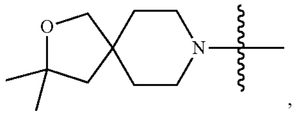
,
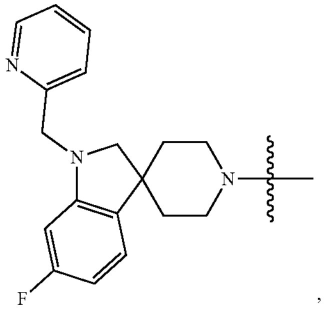
,
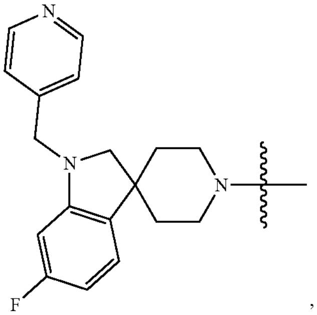
, -continued

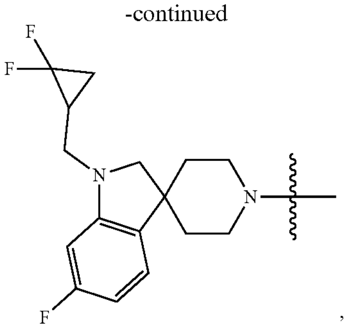

,

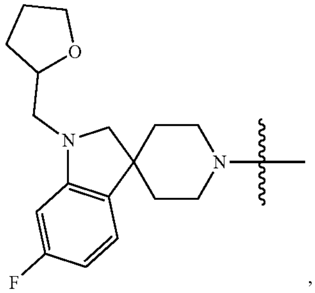

,

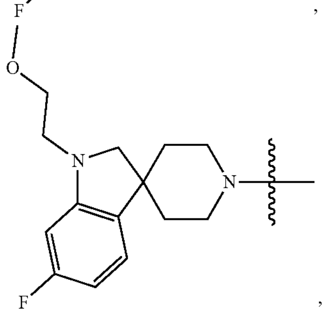

,

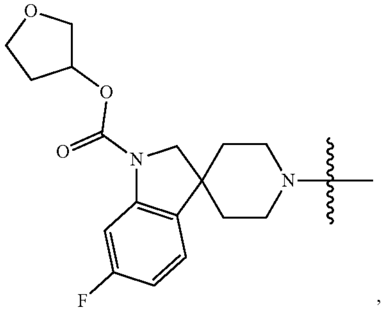

,

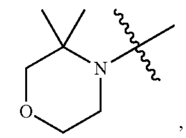

,

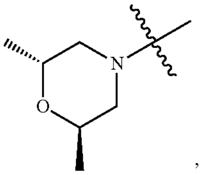

,

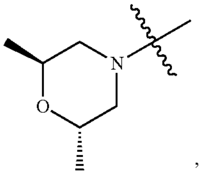

,

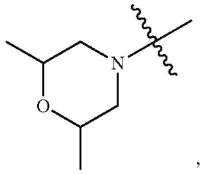

,

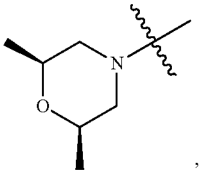

,

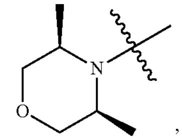

,

-continued

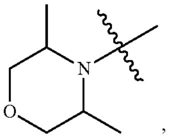

,

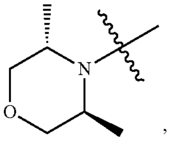

,

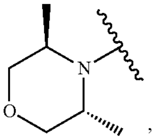

,

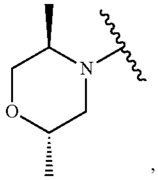

,

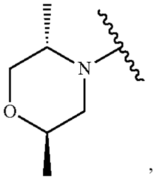

,

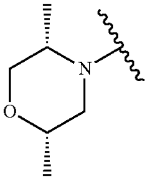

,

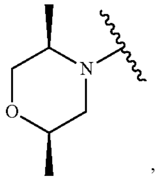

,

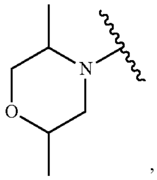

,

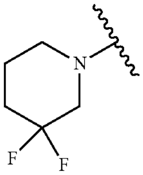

,

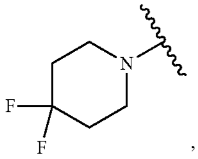

,

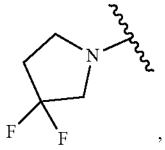

,

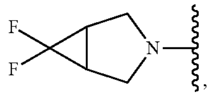

,

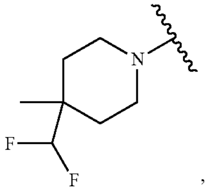

, and

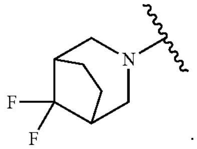

.

7. The compound of claim 1, wherein m is 1.

8. The compound of claim 3, wherein $R^6$ is —$S(O)_2$—$R^5$.

9. The compound of claim 1, wherein $L^1$ is $C_{1-6}$ alkylenyl.

10. The compound of claim 1, wherein Z is 4- to 6-membered monocyclic heterocyclyl comprising 1 to 4 heteroatoms selected from N, O, and S.

11. The compound of claim 1, wherein $R^a$ is H.

12. The compound of claim 1, wherein each $R^2$ is —$C_{1-6}$ aliphatic.

13. The compound of claim 1, wherein $R^5$ is —$N(R^3)_2$.

14. The compound of claim 1, wherein each $R^3$ is —$C_{1-6}$ aliphatic.

15. A compound having the structure:
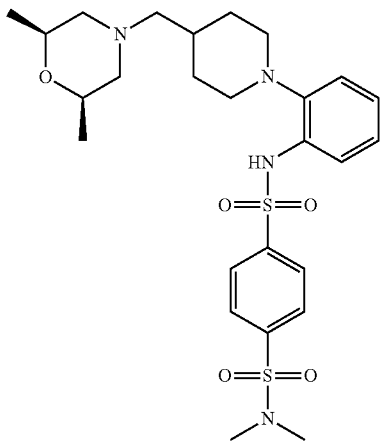 [SMILES: C[C@@H]1CN(CC2CCN(c3ccccc3NS(=O)(=O)c3ccc(S(=O)(=O)N(C)C)cc3)CC2)C[C@H](C)O1]
or a pharmaceutically acceptable salt thereof.
16. A compound having the structure:
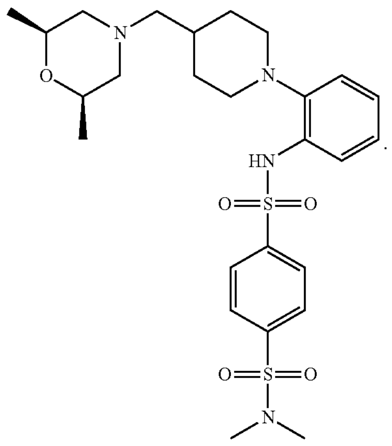 [SMILES: C[C@@H]1CN(CC2CCN(c3ccccc3NS(=O)(=O)c3ccc(S(=O)(=O)N(C)C)cc3)CC2)C[C@H](C)O1]
* * * * *